US007704995B2

(12) United States Patent
Buhr et al.

(10) Patent No.: US 7,704,995 B2
(45) Date of Patent: Apr. 27, 2010

(54) PROTEIN KINASE MODULATORS AND METHODS OF USE

(75) Inventors: Chris A. Buhr, Redwood City, CA (US); Tae-Gon Baik, Foster City, CA (US); Sunghoon Ma, Foster City, CA (US); Zerom Tesfai, Castro Valley, CA (US); Longcheng Wang, Palo Alto, CA (US); Erick Wang Co, Redwood City, CA (US); Sergey Epshteyn, Fremont, CA (US); Abigail R Kennedy, San Leandro, CA (US); Baili Chen, Palo Alto, CA (US); Larisa Dubenko, San Francisco, CA (US); Neel Kumar Anand, San Mateo, CA (US); Tsze H. Tsang, El Cerrito, CA (US); John M. Nuss, Danville, CA (US); Csaba J Peto, Alameda, CA (US); Kenneth D. Rice, Mill Valley, CA (US); Mohamed Abdulkader Ibrahim, Mountain View, CA (US); Kevin Luke Schnepp, Elk Grove, CA (US); Xian Shi, San Francisco, CA (US); James William Leahy, San Leandro, CA (US); Jeff Chen, San Francisco, CA (US); Lisa Esther Dalrymple, San Francisco, CA (US); Timothy Patrick Forsyth, San Mateo, CA (US); Tai Phat Huynh, Oakland, CA (US); Grace Mann, Brisbane, CA (US); Larry Wayne Mann, Redwood City, CA (US); Craig Stacy Takeuchi, Burlingame, CA (US); Peter Lamb, Oakland, CA (US); David J. Matthews, San Francisco, CA (US); Nicole Miller, San Francisco, CA (US)

(73) Assignee: Exelixis, Inc., South San Francisco, CA (US)

( * ) Notice: Subject to any disclaimer, the term of this patent is extended or adjusted under 35 U.S.C. 154(b) by 666 days.

(21) Appl. No.: 10/513,081

(22) PCT Filed: May 2, 2003

(86) PCT No.: PCT/US03/13869

§ 371 (c)(1),
(2), (4) Date: Jul. 27, 2005

(87) PCT Pub. No.: WO03/093297

PCT Pub. Date: Nov. 13, 2003

(65) Prior Publication Data

US 2006/0211709 A1  Sep. 21, 2006

(51) Int. Cl.
C07D 279/16 (2006.01)
C07D 279/12 (2006.01)
C07D 417/12 (2006.01)
C07D 265/36 (2006.01)
C07D 413/12 (2006.01)
C07D 403/12 (2006.01)
C07D 401/12 (2006.01)
C07D 405/12 (2006.01)
C07D 409/12 (2006.01)
C07D 411/12 (2006.01)
C07D 419/12 (2006.01)
C07D 241/18 (2006.01)
C07D 241/20 (2006.01)
A61K 31/55 (2006.01)
A61K 31/497 (2006.01)
A61K 31/5355 (2006.01)
A61K 31/541 (2006.01)
C07D 305/12 (2006.01)
C07D 307/79 (2006.01)
A61K 31/44 (2006.01)
A61P 35/00 (2006.01)

(52) U.S. Cl. .................. 514/217.05; 514/252.11; 514/252.13; 514/255.05; 514/255.06; 514/235.8; 514/227.8; 514/230.5; 514/352; 544/405; 544/407; 544/295; 544/120; 544/58.6; 544/60; 544/105; 540/598; 549/310; 546/309; 546/311

(58) Field of Classification Search ............ 514/255.04, 514/217.05, 252.11, 252.13, 255.06, 235.8, 514/227.8, 230.5, 255.05; 540/598; 544/120, 544/295, 405, 407, 359, 58.6, 60, 105
See application file for complete search history.

(56) References Cited

U.S. PATENT DOCUMENTS 3,313,813 A * 4/1967 Cragoe, Jr. .................. 544/407
3,555,024 A * 1/1971 Cragoe et al. ............... 544/405
6,992,087 B2 * 1/2006 Verhoest et al. ......... 514/255.05

FOREIGN PATENT DOCUMENTS

DE             31894        * 4/1965

(Continued)

OTHER PUBLICATIONS

Yamamoto, et al., Chemical & Pharmaceutical Bulletin (1997), 45(8), 1282-1286.*

(Continued)

Primary Examiner—Mark L Berch
Assistant Examiner—Cecilia M Jaisle
(74) Attorney, Agent, or Firm—Robert L. Bernstein; McDonnell Boehnen Hulbert & Berghoff LLP

(57) ABSTRACT

This invention relates to compounds for modulating protein kinase enzymatic activity for modulating cellular activities such as proliferation, differentiation, programmed cell death, migration and chemoinvasion, and to pharmaceutical compositions containing such compounds. Even more specifically, the invention relates to compounds that inhibit, regulate and/or modulate kinases, particularly Checkpoint Kinases, even more particularly Checkpoint Kinase 1, or Chk1. Methods of therapeutically or prophylactically using the compounds and compositions to treat kinase-dependent diseases and conditions are also an aspect of the invention, and include methods of treating cancer, as well as other disease states associated with unwanted angiogenesis and/or cellular proliferation, by administering effective amounts of such compounds.

35 Claims, No Drawings

FOREIGN PATENT DOCUMENTS

| | | | |
|---|---|---|---|
| WO | WO9743267 | | 11/1997 |
| WO | WO0012488 | | 3/2000 |
| WO | WO 0076980 | * | 12/2000 |
| WO | WO 0248152 | * | 6/2002 |
| WO | WO02/066470 A1 | | 8/2002 |
| WO | WO03004472 | | 1/2003 |
| WO | WO03004475 | | 1/2003 |
| WO | WO03045924 | | 6/2003 |
| WO | WO03051851 | | 6/2003 |
| WO | WO2004055005 | | 7/2004 |
| WO | WO2004055006 | | 7/2004 |
| WO | WO2004055009 | | 7/2004 |
| WO | WO2004/080982 A1 | | 9/2004 |

OTHER PUBLICATIONS

De Meester, et al., J. Het. Chem. (1987), 24(4), 1109-.*
De Meester, et al., J. Het. Chem. (1987), 24(2), 441-51.*
Asher, et al., J. Biol. Chem. (1987), 262(18), 8566-73.*
Lutz, et al., Croatica Chemica Acta (1986), 59(1), 199-220.*
Nakamura, et al., Agricultural and Biological Chemistry (1984), 48(4), 1009-16.*
Hirano, et al., J. Het. Chem. (1982), 19(6), 1409-13.*
Keir, et al., Journal of the Chemical Society, Perkin Transactions 1: Organic and Bio-Organic Chemistry (1972-1999) (1977), (11), 1321-5.*
Kobayashi, et al., Chemische Berichte (1976), 109(9), 3194-2.*
Ambrogi, et al., Arzneimittel-Forschung (1971), 21(2), 200-4.*
Bicking, et al., Journal of Medicinal Chemistry (1967), 10(4), 598-602.*
Taylor, et al., Journal of the American Chemical Society (1960), 82, 6058-64.*
Boon, et al., Journal of the Chemical Society (1957) 2159-61.*
Dick, et al., Journal of the Chemical Society (1956) 2131-6.*
Taylor, et al., J. American Chemical Society (1956), 78, 210-13.*
Taylor, et al., J. American Chemical Society (1953), 75, 1904-8.*
Taylor, et al., J. American Chemical Society (1952), 74, 1651-5.*
Dai, et al., Blood, 2008, 112: 2439-2449.*
Tse, et al., Clin. Cancer Res. 2007;13(2), Jan 15, 2007, 591-602.*
Xiao, Biomarkers, vol. 13, #6, Sep. 2008, 579-598(18) (Abstract).*
Kortmansky, et al., J. Clin. Oncol., vol. 23, #9, Mar. 20, 2005, 1-10.*
Supplementary European Search Report for parallel European Patent Application No. EP03728690.3, completed by The Hague on Jul. 22, 2009.

* cited by examiner

PROTEIN KINASE MODULATORS AND METHODS OF USE

BACKGROUND OF THE INVENTION

1. Field of the Invention

This invention relates to compounds for modulating protein kinase enzymatic activity for modulating cellular activities such as proliferation, differentiation, programmed cell death, migration and chemoinvasion, and to pharmaceutical compositions containing such compounds. Even more specifically, the invention relates to compounds that inhibit, regulate and/or modulate kinases, particularly Checkpoint Kinases, even more particularly Checkpoint Kinase 1, or Chk1. Methods of therapeutically or prophylactically using the compounds and compositions to treat kinase-dependent diseases and conditions are also an aspect of the invention, and include methods of treating cancer, as well as other disease states associated with unwanted angiogenesis and/or cellular proliferation, by administering effective amounts of such compounds.

2. Summary of Related Art

Cells reproduce by duplicating their contents and then dividing in two. This cell division cycle is the fundamental means by which all living things are propagated. In unicellular species, such as bacteria and yeasts, each cell division produces an additional organism. In multicellular species many rounds of cell division are required to make a new individual, and cell division is needed in the adult body too, to replace cells that are lost by wear and tear or by programmed cell death. Thus an adult human must manufacture many millions of new cells each second simply to maintain the status quo, and if all cell division is halted—for example, by a large dose of ionizing radiation—the individual will die within a few days.

The cell division cycle is the subject of a control system that coordinates the cycle as a whole. A multitude of genes, proteins and other cellular machinery directly or indirectly regulate progression of a cell through the cell division cycle. Regulatory elements can either help stimulate an increase in cell numbers or help to inhibit it. Uncontrolled cell proliferation is the insignia of cancer, and can be manifested by a deregulation of the cell division cycle in one of two ways—making stimulatory genes hyperactive or inhibitory genes inactive.

It can be understood, therefore, that agents that modulate the cell cycle, and thus hyperproliferation, could be used to treat various disease states associated with uncontrolled or unwanted cell proliferation. In addition to oncological indications, altered cell cycle division signaling is implicated in numerous other pathological diseases. These include, but are not limited to antiparasitics (See, Gray et al., *Curr. Med. Chem.* 6, 859-875 (1999)); potential antivirals (See, Schang et al., *J. Virol.* 74, 2107-2120 (2000)); cardiovascular maladies such as artherosclerosis or restenosis (See Braun-Dullaeus et al., *Circulation,* 98, 82-89 (1998)); and states of inflammation and immunological disorders, such as arthritis (See, Taniguchi et al., *Nature Med.,* 5, 760-767(1999)) or psoriasis.

Mechanisms of cell proliferation are under active investigation at cellular and molecular levels. At the cellular level, de-regulation of signaling pathways, loss of cell cycle controls, unbridled angiogenesis or stimulation of inflammatory pathways are under scrutiny, while at the molecular level, these processes are modulated by various proteins, among which protein kinases are prominent suspects. Overall abatement of proliferation may also result from programmed cell death, or apoptosis, which is also regulated via multiple pathways, some involving proteolytic enzyme proteins. Among the candidate regulatory proteins, protein kinases are a family of enzymes that catalyze phosphorylation of proteins, in particular the hydroxyl group of specific tyrosine, serine, or threonine residues in proteins. The consequences of this seemingly simple activity are staggering, and typically, such phosphorylation dramatically perturbs the function of the protein, and thus protein kinases are pivotal in the regulation of a wide variety of cellular processes, including metabolisim, cell proliferation, cell differentiation, and cell survival. Of the many different cellular functions in which the activity of protein kinases is known to be required, some processes represent attractive targets for therapeutic intervention for certain disease states. Two examples are cell-cycle control and angiogenesis, in which protein kinases play a pivotal role; these processes are essential for the growth of solid tumors as well as for other diseases.

CDKs constitute a class of enzymes that play critical roles in regulating the transitions between different phases of the cell cycle, such as the progression from a quiescent stage in $G_1$ (the gap between mitosis and the onset of DNA replication for a new round of cell division) to S (the period of active DNA synthesis), or the progression from $G_2$ to M phase, in which active mitosis and cell-division occur. See, e.g., the articles compiled in *Science,* vol. 274 (1996), pp. 1643-1677; and *Ann. Rev. Cell Dev. Biol.,* vol. 13 (1997), pp. 261-291. CDK complexes are formed through association of a regulatory cyclin subunit (e.g., cyclin A, B1, B2, D1, D2, D3, and E) and a catalytic kinase subunit (e.g., cdc2 (CDK1), CDK2, CDK4, CDK5, and CDK6). As the name implies, the CDKs display an absolute dependence on the cyclin subunit in order to phosphorylate their target substrates, and different kinase/cyclin pairs function to regulate progression through specific portions of the cell cycle.

The D cyclins are sensitive to extracellular growth signals and become activated in response to mitogens during the $G_1$ phase of the cell cycle. CDK4/cyclin D plays an important role in cell cycle progression by phosphorylating, and thereby inactivating, the retinoblastoma protein (Rb). Hypophosphorylated Rb binds to a family of transcriptional regulators, but upon hyperphosphorylation of Rb by CDK4/cyclin D, these transcription factors are released to activate genes whose products are responsible for S phase progression. Rb phosphorylation and inactivation by CDK4/cyclin D permit passage of the cell beyond the restriction point of the $G_1$ phase, whereupon sensitivity to extracellular growth or inhibitory signals is lost and the cell is committed to cell division. During late $G_1$, Rb is also phosphorylated and inactivated by CDK2/cyclin E, and recent evidence indicates that CDK2/cyclin E can also regulate progression into S phase through a parallel pathway that is independent of Rb phosphorylation (see Lukas et al., "Cyclin E-induced S Phase Without Activation of the pRb/E2F Pathway," *Genes and Dev.,* vol. 11 (1997), pp. 1479-1492).

The progression from $G_1$ to S phase, accomplished by the action of CDK4/cyclin D and CDK2/cyclin E, is subject to a variety of growth regulatory mechanisms, both negative and positive. Growth stimuli, such as mitogens, cause increased synthesis of cyclin D1 and thus increased functional CDK4. By contrast, cell growth can be "reined in," in response to DNA damage or negative growth stimuli, by the induction of endogenous inhibitory proteins. These naturally occurring protein inhibitors include $p21^{WAF1/CIP1}$, $p27^{KIP1}$, and the $p16^{INK4}$ family, the latter of which inhibit CDK4 exclusively (see Harper, "Cyclin Dependent Kinase Inhibitors," *Cancer Surv.,* vol. 29 (1997), pp.

91-107). Aberrations in this control system, particularly those that affect the function of CDK4 and CDK2, are implicated in the advancement of cells to the highly proliferative state characteristic of malignancies, such as familial melanomas, esophageal carcinomas, and pancreatic cancers (see, e.g., Hall and Peters, "Genetic Alterations of Cyclins, Cyclin-Dependent Kinases, and CDK Inhibitors in Human Cancer," *Adv. Cancer Res.*, vol. 68 (1996), pp. 67-108; and Kamb et al., "A Cell Cycle Regulator Potentially Involved in Genesis of Many Tumor Types," *Science*, vol. 264 (1994), pp. 436-440).

Over-expression of cyclin D1 is linked to esophageal, breast, and squamous cell carcinomas (see, e.g., DelSal et al., "Cell Cycle and Cancer: Critical Events at the $G_1$ Restriction Point," *Critical Rev. Oncogenesis*, vol. 71 (1996), pp. 127-142). Genes encoding the CDK4-specific inhibitors of the p16 family frequently have deletions and mutations in familial melanoma, gliomas, leukemias, sarcomas, and pancreatic, non-small cell lung, and head and neck carcinomas (see Nobori et al., "Deletions of the Cyclin-Dependent Kinase-4 Inhibitor Gene in Multiple Human Cancers," *Nature*, vol. 368 (1994), pp. 753-756). Amplification and/or overexpression of cyclin E has also been observed in a wide variety of solid tumors, and elevated cyclin E levels have been correlated with poor prognosis. In addition, the cellular levels of the CDK inhibitor p27, which acts as both a substrate and inhibitor of CDK2/cyclin E, are abnormally low in breast, colon, and prostate cancers, and the expression levels of p27 are inversely correlated with the stage of disease (see Loda et al., "Increased Proteasome-dependent Degradation of the Cyclin-Dependent Kinase Inhibitor p27 in Aggressive Colorectal Carcinomas," Nature Medicine, vol. 3 (1997), pp. 231-234). Recently there is evidence that CDK4/cyclin D might sequester p27, as reviewed in Sherr, et al., Genes Dev., Vol. 13 (1999), pp. 1501-1512. The p21 proteins also appear to transmit the p53 tumor-suppression signal to the CDKs; thus, the mutation of p53 in approximately 50% of all human cancers may indirectly result in deregulation of CDK activity.

In at least one instance modulation of protein kinase activity as been used as a treatment for an oncological condition. For example, modulation of protein kinase activity for the treatment of chronic myeloid leukemia (CML) and gastrointestinal stroma cancers has been demonstrated successfully with the FDA approval of Gleevec® (imatinib mesylate, produced by Novartis Pharmaceutical Corporation of East Hanover, N.J.). Gleevec is a selective Abl kinase inhibitor.

Another series of protein kinases are those that play an important role as a checkpoint in cell cycle progression. See, e.g., Melo et al., *Current Opinion in Cell Biology* 2002, 14:237-245 (2003). Proliferation of eukaryotic cells is controlled by cell cycle checkpoint pathways, which mediate progression through critical transitions of the cell cycle (reviewed by Walworth (2000), *Curr. Opin. Cell Biol.* 12, 697-704). Checkpoints prevent cell cycle progression at inappropriate times, such as in response to DNA damage, and maintain the metabolic balance of cells while the cell is arrested, and in some instances can induce apoptosis (programmed cell death) when the requirements of the checkpoint have not been met. See, e.g., O'Connor, *Cancer Surveys*, 29, 151-182 (1997); Nurse, *Cell*, 91, 865-867 (1997); Hartwell et al., *Science*, 266, 1821-1828 (1994); Hartwell et al., *Science*, 246, 629-634 (1989). Checkpoint control can occur in the G1 phase (prior to DNA synthesis) and in G2, prior to entry into mitosis.

One series of checkpoints monitors the integrity of the genome and, upon sensing DNA damage, these "DNA damage checkpoints" block cell cycle progression in $G_1$ & $G_2$ phases, and slow progression through S phase. O'Connor, *Cancer Surveys*, 29, 151-182 (1997); Hartwell et al., *Science*, 266, 1821-1828 (1994). This action enables DNA repair processes to complete their tasks before replication of the genome and subsequent separation of this genetic material into new daughter cells takes place. Importantly, the most commonly mutated gene in human cancer, the p53 tumor suppressor gene, produces a DNA damage checkpoint protein that blocks cell cycle progression in $G_1$ phase and/or induces apoptosis (programmed cell death) following DNA damage. Hartwell et al., *Science*, 266, 1821-1828 (1994). The p53 tumor suppressor has also been shown to strengthen the action of a DNA damage checkpoint in $G_2$ phase of the cell cycle. See, e.g., Bunz et al., *Science*, 28, 1497-1501 (1998); Winters et al., *Oncogene*, 17, 673-684 (1998); Thompson, *Oncogene*, 15, 3025-3035 (1997).

Given the pivotal nature of the p53 tumor suppressor pathway in human cancer, therapeutic interventions that exploit vulnerabilities in p53-defective cancer have been actively sought. One emerging vulnerability lies in the operation of the $G_2$ checkpoint in p53 defective cancer cells. Cancer cells, because they lack $G_1$ checkpoint control, are particularly vulnerable to abrogation of the last remaining barrier protecting them from the cancer killing effects of DNA-damaging agents: the Gsub.2 checkpoint. The $G_2$ checkpoint is regulated by a control system that has been conserved from yeast to humans. Important in this conserved system is a kinase, CHK1, which transduces signals from the DNA-damage sensory complex to inhibit activation of the cyclin B/Cdc2 kinase, which promotes mitotic entry. See, e.g., Peng et al., *Science*, 277, 1501-1505 (1997); Sanchez et al., *Science*, 277, 1497-1501 (1997). Inactivation of CHK1 has been shown to both abrogate $G_2$ arrest induced by DNA damage inflicted by either anticancer agents or endogenous DNA damage, as well as result in preferential killing of the resulting checkpoint defective cells. See, e.g., Nurse, *Cell*, 91, 865-867 (1997); Weinert, *Science*, 277, 1450-1451 (1997); Walworth et al., *Nature*, 363, 368-371 (1993); and AI-Khodairy et al., *Molec. Biol. Cell.*, 5, 147-160 (1994).

Selective manipulation of checkpoint control in cancer cells could afford broad utilization in cancer chemotherapeutic and radiotherapy regimens and may, in addition, offer a common hallmark of human cancer "genomic instability" to be exploited as the selective basis for the destruction of cancer cells. A number of factors place CHK1 as a pivotal target in DNA-damage checkpoint control. The elucidation of inhibitors of this and functionally related kinases such as CDS1/CHK2, a kinase recently discovered to cooperate with CHK1 in regulating S phase progression (see Zeng et al., *Nature*, 395, 507-510 (1998); Matsuoka, *Science*, 282, 1893-1897 (1998)), could provide valuable new therapeutic entities for the treatment of cancer.

Another group of kinases are the tyrosine kinases. Tyrosine kinases can be of the receptor type (having extracellular, transmembrane and intracellular domains) or the non-receptor type (being wholly intracellular). At least one of the non-receptor protein tyrosine kinases, namely, LCK is believed to mediate the transduction in T-cells of a signal from the interaction of a cell-surface protein (Cd4) with a cross-linked anti-Cd4 antibody. A more detailed discussion of non-receptor tyrosine kinases is provided in Bolen, *Oncogene*, 8, 2025-2031 (1993), which is incorporated herein by reference.

Receptor-type tyrosine kinases are comprised of a large number of transmembrane receptors with diverse biological activity. In fact, about 20 different subfamilies of receptor-type tyrosine kinases have been identified. One tyrosine kinase subfamily, designated the HER subfamily, is comprised of EGFR (HER1), HER2, HER3, and BER4. Ligands of this subfamily of receptors identified so far include epithelial growth factor, TGF-alpha, amphiregulin, HB-EGF, betacellulin and heregulin. Another subfamily of these receptor-type tyrosine kinases is the insulin subfamily, which includes INS-R, IGF-R, and IR-R. The PDGF subfamily includes the PDGF-alpha and beta receptors, CSFIR, c-kit and FLK-II. Then there is the FLK family, which is comprised of the kinase insert domain receptor (KDR), fetal liver kinase-1 (FLK-1), fetal liver kinase-4 (FLK-4) and the fms-like tyrosine kinase-1 (flt-1). The PDGF and FLK families are usually considered together due to the similarities of the two groups. For a detailed discussion of the receptor-type tyrosine kinases, see Plowman et al., *DN&P* 7(6): 334-339, 1994, which is hereby incorporated by reference.

The non-receptor type of tyrosine kinases is also comprised of numerous subfamilies, including Src, Frk, Btk, Csk, Abl, Zap70, Fes/Fps, Fak, Jak, Ack, and LIMK. Each of these subfamilies is further sub-divided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. For a more detailed discussion of the non-receptor type of tyrosine kinases, see Bolen, *Oncogene*, 8:2025-2031 (1993), which is hereby incorporated by reference.

In addition to its role in cell-cycle control, protein kinases also play a crucial role in angiogenesis, which is the mechanism by which new capillaries are formed from existing vessels. When required, the vascular system has the potential to generate new capillary networks in order to maintain the proper functioning of tissues and organs. In the adult, however, angiogenesis is fairly limited, occurring only in the process of wound healing and neovascularization of the endometrium during menstruation. See Merenmies, J., Parada, L. F., Henkemeyer, M., *Cell Growth & Differentiation*, 8, 3-10 (1997). On the other hand, unwanted angiogenesis is a hallmark of several diseases, such as retinopathies, psoriasis, rheumatoid arthritis, age-related macular degeneneration, and cancer (solid tumors). Folkman, *Nature Med.*, 1, 27-31 (1995). Protein kinases which have been shown to be involved in the angiogenic process include three members of the growth factor receptor tyrosine kinase family: VEGF-R2 (vascular endothelial growth factor receptor 2, also know as KDR (kinase insert domain receptor) and as FLK-1); FGF-R (fibroblast growth factor receptor); and TEK (also known as Tie-2).

VEGF-R2, which is expressed only on endothelial cells, binds the potent angiogenic growth factor VEGF and mediates the subsequent signal transduction through activation of its intracellular kinase activity. Thus, it is expected that direct inhibition of the kinase activity of VEGF-R2 will result in the reduction of angiogenesis even in the presence of exogenous VEGF (see Strawn et al., *Cancer Research*, 56, 3540-3545 (1996)), as has been shown with mutants of VEGF-R2 which fail to mediate signal transduction. Millauer et al., *Cancer Research*, 56, 1615-1620 (1996). Furthermore, VEGF-R2 apppears to have no function in the adult beyond that of mediating the angiogenic activity of VEGF. Therefore, a selective inhibitor of the kinase activity of VEGF-R2 would be expected to exhibit little toxicity.

Similarly, FGF-R binds the angiogenic growth factors aFGF and bFGF and mediates subsequent intracellular signal transduction. Recently, it has been suggested that growth factors such as bFGF may play a critical role in inducing angiogenesis in solid tumors that have reached a certain size. Yoshiji et al., *Cancer Research*, 57, 3924-3928 (1997). Unlike VEGF-R2, however, FGF-R is expressed in a number of different cell types throughout the body and may or may not play important roles in other normal physiological processes in the adult. Nonetheless, systemic administration of a small molecule inhibitor of the kinase activity of FGF-R has been reported to block bFGF-induced angiogensis in mice without apparent toxicity. Mohammad et al., *EMBO Journal*, 17, 5996-5904(1998).

TEK (also known as Tie-2) is another receptor tyrosine kinase expressed only on endothelial cells which has been shown to play a role in angiogenesis. The binding of the factor angiopoietin-1 results in autophosphorylation of the kinase domain of TEK and results in a signal transduction process which appears to mediate the interaction of endothelial cells with peri-endothelial support cells, thereby facilitating the maturation of newly formed blood vessels. The factor angiopoietin-2, on the other hand, appears to antagonize the action of angiopoietin-1 on TEK and disrupts angiogenesis. Maisonpierre et al., *Science*, 277, 55-60 (1997).

As a result of the above-described developments, it has been proposed to treat angiogenesis by the use of compounds inhibiting the kinase activity of VEGF-R2, FGF-R, and/or TEK. For example, WIPO International Publication No. WO 97/34876 discloses certain cinnoline derivatives that are inhibitors of VEGF-R2, which may be used for the treatment of disease states associated with abnormal angiogenesis and/or increased vascular permeability such as cancer, diabetes, psoriasis, rheumatoid arthritis, Kaposi's sarcoma, haemangioma, acute and chronic nephropathies, atheroma, arterial restinosis, autoimmune diseases, acute inflammation and ocular diseases with retinal vessel proliferation.

In addition to the protein kinases identified above, many other protein kinases have been considered to be therapeutic targets, and numerous publications disclose inhibitors of kinase activity, as reviewed in the following: McMahon et al., *Oncologist*, 5, 3-10 (2000); Garcia-Echeverria et al., *Med. Res. Rev.*, 20, 28-57 (2000); Holash et al., *Oncogene*, 18, 5356-5362. (1999); Stover et al., *Curr. Opin. Drug Disc. Dev.*, 2, 274-285 (1999); Toledo et al., Curr Med. Chem., 6, 775-805 (1999); Thomas et al., *J. Biol. Chem.*, 274, 36684-36692 (1992); Cohen, *Curr. Op. Chem. Biol.*, 10, 544-549 (1999); Adams et al., *Curr. Opin. Drug Disc. Dev.*, 2, 96-109 (1999); McMahon et al., *Curr. Opin. Drug Disc. Dev.*, 1, 131-146 (1998); and Strawn et al., *Exp. Opin. Invest. Drugs*, 7, 553-573 (1998).

It can be understood, therefore, that there is a need, for effective inhibitors of protein kinases in order to treat or prevent disease states associated with abnormal cell proliferation. Moreover, as would be understood by those skilled in the art, it is desirable for kinase inhibitors to possess both high affinity for the target kinase as well as high selectivity versus other protein kinases. Small-molecule compounds that may be readily synthesized and are potent inhibitors of cell proliferation are those, for example, that are inhibitors of one or more protein kinases, such as CHK1, CHK2, VEGF, CDKs or CDK/cyclin complexes and both receptor and non-receptor tyrosine kinases.

SUMMARY OF THE INVENTION

Based on the aforementioned evidence, we contemplated that highly specific inhibitors of protein kinase, such as Chk1 kinase, will have a synergistic cytotoxic effect with DNA damaging agents in many kinds of tumor cells, whilst not causing excessive toxicity in non-tumor cells. Thus, one aspect of the invention is selective protein kinase modulators, particularly inhibitors like Chk1. Methods of the invention include both use of such compounds in a synergistic fashion as mention, and also as single agents for cancer therapy.

We have unexpectedly found that analogs of 3-amino-pyrazine-2-carboxamide and related compounds effectively inhibit protein kinases such as Chk1 kinase. The compounds disclosed herein are useful for inhibiting the protein kinase and, therefore, useful for studying the role of protein kinase in various biological pathways as well as to augment the efficacy of cancer therapeutics, including DNA damaging agents. Accordingly, the invention also comprises pharmaceutical compositions comprising the compounds of the invention, as well as methods of using compounds of the invention to inhibit protein kinase and thereby modulate kinase dependent diseases or conditions.

In another aspect, the invention provides methods of screening for modulators of kinase activity. The methods comprise combining a composition of the invention, a kinase, and at least one candidate agent and determining the effect of the candidate agent on the kinase activity.

In yet another aspect, the invention also provides pharmaceutical kits comprising one or more containers filled with one or more of the ingredients of pharmaceutical compounds and/or compositions of the present invention, including, one or more kinase enzyme activity modulators as described herein. Such kits can also include, for example, other compounds and/or compositions (e.g., diluents, permeation enhancers, lubricants, and the like), a device(s) for administering the compounds and/or compositions, and written instructions in a form prescribed by a governmental agency regulating the manufacture, use or sale of pharmaceuticals or biological products, which instructions can also reflects approval by the agency of manufacture, use or sale for human administration.

In still yet another aspect, the invention also provides a diagnostic agent comprising a compound of the invention and, optionally, pharmaceutically acceptable adjuvants and excipients.

These and other features and advantages of the present invention will be described in more detail below.

DETAILED DESCRIPTION OF THE INVENTION

The compounds set forth in the detailed description are useful as pharmaceuticals in mammals, especially humans, for modulating protein kinase enzymatic activity for modulating cellular activities such as uncontrolled, abnormal, or unwanted proliferation, differentiation, programmed cell death, migration and chemoinvasion. It is appreciated, however, that in some cases the cells may not be in a hyper or hypo-proliferative and/or migratory state (abnormal state) and still require treatment. For example, during wound healing, the cells may be proliferating "normally," but proliferation and migration enhancement may be desired. Alternatively, reduction in "normal" cell proliferation and/or migration rate may be desired. Furthermore, such compounds may be used to prevent de-differentiation of post-mitotic tissue and/or cells.

Diseases or disorders associated with uncontrolled, abnormal, and/or unwanted cellular activities, especially cellular proliferation include, but are not limited to the conditions set forth in the background and to the following:

a variety of cancers, including, but not limited to carcinoma, hematopoietic tumors of lymphoid lineage, hematopoietic tumors of myeloid lineage, tumors of mesenchymal origin, tumors of the central and peripheral nervous system ad other tumors including melanoma, seminoma and Kaposi's sarcoma and the like, and those further discussed below;

a disease process which features abnormal cellular proliferation, e.g., benign prostatic hyperplasia, familial adenomatosis polyposis, neuro-fibromatosis, pulmonary fibrosis, hypertrophic scar formation, transplantation rejection, nodosum, endotoxic shock, and a variety of cardiovascular indications, including, but not limited to atherosclerosis, dysregulated vascularization including ischemic coronary artery disease, myocardioinfarction, ischemia, pulmonary hypertension, stroke, emphysema, anemia, and restenosis following angioplasty or vascular surgery;

an immune and/or inflammatory disorder, especially those involving immunological defects associated with aberrant B & T cell development. Such disorders can include, but are not limited to, acquired immunodeficiency syndrome (AIDS), Addison's disease, adult respiratory distress syndrome, allergies, ankylosing spondylitis, amyloidosis, asthma, autoimmune hemolytic anemia, autoimmune thyroiditis, Crohn's disease, episodic lymphopenia with lymphocytotoxins, erythroblastosis fetalis, Goodpasture's syndrome, Graves' disease, Hashimoto's thyroiditis, hypereosinophilia, irritable bowel syndrome and other interbowel diseases, Lupus, myasthenia gravis, myocardial or pericardial inflammation, pancreatitis, polymyositis, psoriasis, Reiter's syndrome, scleroderma, systemic analphylaxis, lucerative colitis, nephritis (including glomerulonephritis), gout, arthritis (such as rheumatoid arthritis and osteoarthritis), erythema, dermatitis, dermatomyositis, bronchitis, cholecystitis, and gastritis;

a disorder of carbohydrate metabolism, including but not limited to diabetic (including diabetes mellitus, diabetic retinopathy);

a parasitic, fungal and/or viral infection, including but not limited to herpes virus, poxvirus, Epstein-Barr virus, Sindbis virus and adenovirus, HIV, human papilloma virus; and a neurodegenerative disorder, including but not limited to, Alzheimer's disease, amyotrophic lateral sclerosis, retinitis pignientosa, Parkinson's disease, AIDS-related dementia, spinal muscular atrophy and cerebellar degeneration, myelodysplastic syndromes, degenerative diseases of the musculoskeletal system (including but not limited to osteroporosis), cystic fibrosis, macular degeneration, and multiple sclerosis.

The present invention comprises compounds for modulating protein kinase activity, more particularly Checkpoint kinase activity, even more particularly Chk1 and Chk2, even still more particularly Chk1, of Formula I,

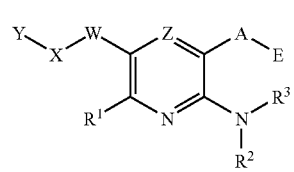

or a pharmaceutically acceptable salt, hydrate, or prodrug thereof, wherein, $R^1$ is independently selected from —H, halogen, —CN, —NH$_2$, —CF$_3$, —NO$_2$, —OR$^4$, —N(R$^4$)R$^5$, —S(O)$_{0-2}$R$^5$, —SO$_2$N(R$^4$)R$^5$, —CO$_2$R$^4$, —C(O)N(R$^4$)R$^5$, —N(R$^4$)SO$_2$R$^5$, —N(R$^4$)C(O)R$^5$, —N(R$^4$)CO$_2$R$^5$, —C(O)R$^4$, optionally substituted lower alkyl, optionally substituted aryl, optionally substituted lower arylalkyl, optionally substituted heterocyclyl, and optionally substituted lower heterocyclylalkyl;

$R^2$ and $R^3$ are each independently selected from —H, optionally substituted alkyl, optionally substituted aryl, optionally substituted lower arylalkyl, optionally substituted heterocyclyl, and optionally substituted lower heterocyclylalkyl; or R² and R³, together with the nitrogen to which they are attached, are combined to form an optionally substituted five- to seven-membered heterocyclyl, said five- to seven-membered heterocyclyl optionally containing at least one additional heteroatom selected from N, O, S, and P;

R⁴ is —H or R⁵;

R⁵ is selected from optionally substituted lower alkyl, optionally substituted aryl, optionally substituted lower arylalkyl, optionally substituted heterocyclyl, and optionally substituted lower heterocyclylalkyl; or R⁴ and R⁵, when taken together with a common nitrogen to which they are attached, form an optionally substituted five- to seven-membered heterocyclyl, said optionally substituted five- to seven-membered heterocyclyl optionally containing at least one additional heteroatom selected from N, O, S, and P;

Z is —N═ or —C(H)═;

A is selected from —C(═O)—, —C(═S)—, —C(═NR⁶)—, and —R⁷, when A is —R⁷, E does not exist;

R⁶ is selected from —H, —NO₂, —N(R²)R³, —NC(═NR²)N(R²)R³, —CN, —OR⁴, optionally substituted lower alkyl, optionally substituted heteroalicyclylalkyl, optionally substituted aryl, optionally substituted arylalkyl and optionally substituted heteroalicyclic;

R⁷ is optionally substituted five- to seven-membered heterocyclyl, said five- to seven-membered heterocyclyl optionally containing at least one additional heteroatom selected from N, O, S, and P;

E is selected from —N(R⁸)R⁹—, —NN(R²)R³—, —NNC(═O)N(R²)R³—, —OR⁴, and —R¹⁰;

R⁸ is —H or optionally substituted alkyl;

R⁹ is selected from —H, optionally substituted heteroalicyclylalkyl, optionally substituted heteroarylalkyl, and optionally substituted heteroalicyclic; or R⁸ and R⁹, together with the nitrogen to which they are attached, are combined to form an optionally substituted five- to seven-membered heteroalicyclyl, said five- to seven-membered heteroalicyclyl optionally containing at least one additional heteroatom selected from N, O, S, and P;

R¹⁰ is selected from —H, optionally substituted heteroalicyclylalkyl, optionally substituted heteroalicyclic, optionally substituted arylalkyl, optionally substituted aryl, and optionally substituted alkyl;

W is either an optionally substituted six- to ten-membered arylene or an optionally substituted five- to ten-membered heteroarylene;

X is selected from a single bond, —(CH₂)₀₋₃C(═O)N(R⁴)(CH₂)₀₋₃—, —(CH₂)₀₋₃CO₂(CH₂)₀₋₃—, —(CH₂)₀₋₃SO₂N(R⁴)(CH₂)₀₋₃—, —N(R⁴)(CH₂)₂₋₃O—, —(CH₂)₀₋₃N(R⁴)C(═O)N(R⁴)(CH₂)₀₋₂—, —(CH₂)₀₋₃C(═O)N(R⁴)(CH₂)₂₋₃O—, —(CH₂)₀₋₃S(O)₀₋₂(CH₂)₀₋₃—, —N(R⁴)(CH₂)₂₋₃N(R⁴)—, —(CH₂)₀₋₃C(═O)N(R⁴)(CH₂)₁₋₃C(═O)—, —(CH₂)₀₋₃OC(═O)N(R⁴)(CH₂)₀₋₃—, —C(═O)N(R⁴)N(R⁴)—, —(CH₂)₀₋₃CO₂(CH₂)₂₋₃N(R⁴)—, —(CH₂)₀₋₃N(R⁴)C(═O)(CH₂)₀₋₃O—, —(CH₂)₀₋₃N(R⁴)(CH₂)₀₋₃—, —C(═O)N(R⁴)(CH₂)₂₋₃N(R⁴)—, —O(CH₂)₂₋₃O—, —(CH₂)₀₋₃C(═O)N(R⁴)(CH₂)₂₋₃S(O)₀₋₂—, —(CH₂)₀₋₃N(R⁴)C(═O)(CH₂)₀₋₃S(O)₀₋₂—, —(CH₂)₀₋₃O(CH₂)₀₋₃—, optionally substituted alkoxyl, and optionally substituted lower alkylene, wherein any —CH₂— in X is optionally substituted; and Y is selected from —H, optionally substituted lower alkyl, optionally substituted aryl, and optionally substituted heterocyclyl;

provided the compound is not:

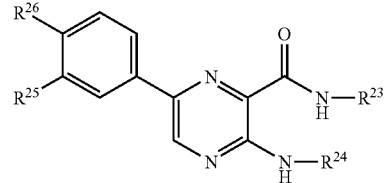

wherein R²³, R²⁴, and R²⁵ are —H; and R²⁶ is —H, —Cl, —CH₃, or —OCH₃; or wherein R²³ is —C(NH)NH₂; R²⁴ is —CH₃; R²⁵ is H; and R²⁶ is —Cl; or wherein R²³ is —H, methyl, ethyl, propyl, isopropyl, butyl, t-butyl, 1-methylpropyl, hydroxyethyl; and R²⁴, R²⁵, and R²⁶ are H; or wherein R²³ is —H; R²⁴ is butyl; and R²⁵ and R²⁶ are methoxy; or wherein R²³ 1-methylpropyl; R²⁴ is —CHO; R²⁵ is —H; and R²⁶ is —Cl; or wherein R²³ is —H; R²⁴ is —CH₃; and R²⁵ and R²⁶ are —H.

In one example, the compound is according to paragraph [0039], wherein Z is ═N—.

In another example, the compound is according to paragraph [0040], wherein R¹ is —H.

In another example, the compound is according to paragraph [0041]; wherein R² is —H and R³ is either —H or lower alkyl.

In another example, the compound is according to paragraph [0042], wherein R² and R³ are —H.

In another example, the compound is according to paragraph [0043], wherein A is R⁷, and R⁷ is either

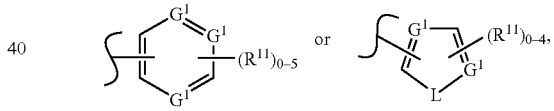

wherein each G¹ is independently ═N— or ═C(R¹¹)—, L is selected from —O—, —S(O)₀₋₂—, and —NR¹¹, wherein each R¹¹ is independently selected from —H, halogen, —CN, —NH₂, —CF₃, —NO₂, —OR⁴, —N(R⁴)R⁵, —S(O)₀₋₂R⁵, —SO₂N(R⁴)R⁵, —CO₂R⁴, —C(O)N(R⁴)R⁵, —N(R⁴)SO₂R⁵, —N(R⁴)C(O)R⁵, —N(R⁴)CO₂R⁵, —C(O)R⁴, optionally substituted lower alkyl, optionally substituted aryl, optionally substituted lower arylalkyl, optionally substituted heterocyclyl, and optionally substituted lower heterocyclylalkyl; or optionally two R¹¹'s form a ring system fused with the existing ring of R⁷, said ring system substituted with 0 to 3 additional of R¹¹ and said ring system optionally containing between 1 and 3 heteroatoms.

In another example, the compound is according to paragraph [0044], wherein R⁷ is selected from

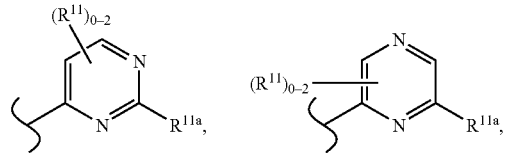

-continued

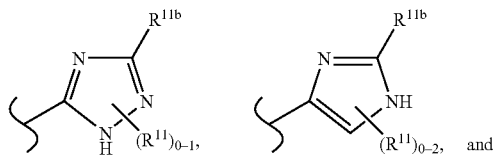

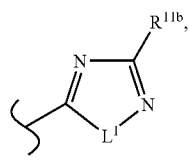

wherein $R^{11a}$ is selected from —H, lower alkyl, and —$NR^4R^5$; and $R^{11b}$ is selected from optionally substituted alkyl, optionally substituted aryl, optionally substituted arylalkyl, optionally substituted heteroaryl, optionally substituted heteroarylalkyl, and optionally substituted heteroalicyclic; and L is selected from —O—, —S(O)$_{0-2}$—.

In another example, the compound is according to paragraph [0045], wherein $R^{11b}$ is selected from optionally substituted alkyl,

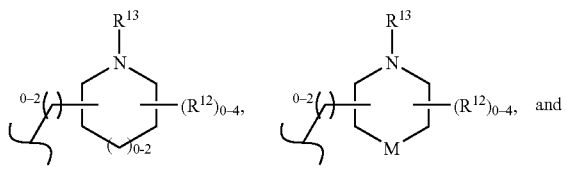

wherein each $R^{12}$ is independently selected from —H, halogen, oxo, —CN, —$NH_2$, —$CF_3$, —$NO_2$, —$OR^4$, —$N(R^4)R^5$, —$S(O)_{0-2}R^5$, —$SO_2N(R^4)R^5$, —$CO_2R^4$, —$C(O)N(R^4)R^5$, —$N(r^4)SO_2R^5$, —$N(R^4)C(O)R^5$, —$N(R^4)CO_2R^5$, —$C(O)R^4$, optionally substituted lower alkyl, optionally substituted aryl, optionally substituted lower arylalkyl, optionally substituted heterocyclyl, and optionally substituted lower heterocyclylalkyl; $R^{13}$ is selected from —H, lower alkyl, and acyl; Q is either =N— or =$C(R^{12})$—; and M is selected from —O—, —$S(O)_{0-2}$—, and —$NR^{13}$.

In another example, the compound is according to paragraph [0046], wherein W is

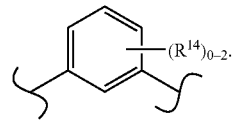

wherein each $G^2$ is independently =N— or =$C(R^{14})$—, wherein each $R^{14}$ is independently selected from —H, halogen, —CN, —$NH_2$, —$CF_3$, —$NO_2$, —$OR^4$, —$N(R^4)R^5$, —$S(O)_{0-2}R^5$, —$SO_2N(R^4)R^5$, —$CO_2R^4$, —$C(O)N(R^4)R^5$, —$N(R^4)SO_2R^5$, —$N(R^4)C(O)R^5$, —$N(R^4)CO_2R^5$, —$C(O)R^4$, optionally substituted lower alkyl, optionally substituted aryl, optionally substituted lower arylalkyl, optionally substituted heterocyclyl, and optionally substituted lower heterocyclylalkyl.

In another example, the compound is according to paragraph [0047], wherein W is

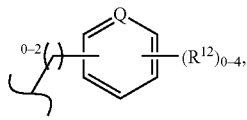

In another example, the compound is according to paragraph [0048], wherein X is selected from —$(CH_2)_{0-3}C(=O)N(R^4)(CH_2)_{0-3}$—, —$(CH_2)_{0-3}SO_2N(R^4)(CH_2)_{0-3}$—, —$N(R^4)(CH_2)_{2-3}O$—, —$(CH_2)_{0-3}N(R^4)C(=O)N(R^4)(CH_2)_{0-3}$—, —$C(=O)N(R^4)N(R^4)$—, —$(CH_2)_{0-3}C(=O)N(R^4)(CH_2)_{2-3}O$—, —$N(R^4)(CH_2)_{2-3}N(R^4)$—, —$(CH_2)_{0-3}N(R^4)(CH_2)_{0-3}$—, —$(CH_2)_{0-3}C(=O)N(R^4)(CH_2)_{1-3}C(=O)$—, —$O(CH_2)_{2-3}O$—, —$(CH_2)_{0-3}OC(=O)N(R^4)(CH_2)_{0-3}$—, —$(CH_2)_{0-3}O(CH_2)_{0-3}$—, —$(CH_2)_{0-3}CO_2(CH_2)_{2-3}N(R^4)$—, —$CH_2)_{0-3}N(R^4)C(=O)(CH_2)_{0-3}O$—, —$C(=O)N(R^4)(CH_2)_{2-3}N(R^4)$—, optionally substituted alkoxyl, and optionally substituted lower alkylene.

In another example, the compound is according to paragraph [0049], wherein X is selected from —$C(=O)N(H)(CH_2)_{1-2}$—, —$(CH_2)_{1-2}C(=O)N(H)$—, —$C(=O)N(H)$—, —$SO_2N(H)(CH_2)_{1-2}$—, —$(CH_2)_{1-2}SO_2N(H)$—, —$SO_2N(H)$—, —$N(H)C(=O)N(H)(CH_2)_{1-2}$—, —$N(H)C(=O)N(H)$—, —$(CH_2)_{0-2}N(R^4)(CH_2)_{0-2}$—, —$(CH_2)_{0-2}O(CH_2)_{0-2}$—, —$C(=O)N(H)N(H)$—, —$N(R^4)(CH_2)_{2-3}N(R^4)$—, —$OCH_2C(=O)N(H)CH_2$—, —$(CH_2)_{1-2}N(H)C(=O)N(H)$—, —$OCH_2CH_2O$—, —$N(R^4)CH_2C(=O)N(H)CH_2$—, —$(CH_2)_{0-1}C(=O)N(H)(CH_2)_{1-2}C(=O)$—, optionally substituted alkoxyl, and optionally substituted lower alkylene.

In another example, the compound is according to paragraph [0050], wherein Y is selected from optionally substituted cycloalkyl, optionally substituted phenyl, and optionally substituted five- to six-membered heterocyclyl.

In another example, the compound is according to paragraph [0051], wherein Y is selected from Table 1.

TABLE 1

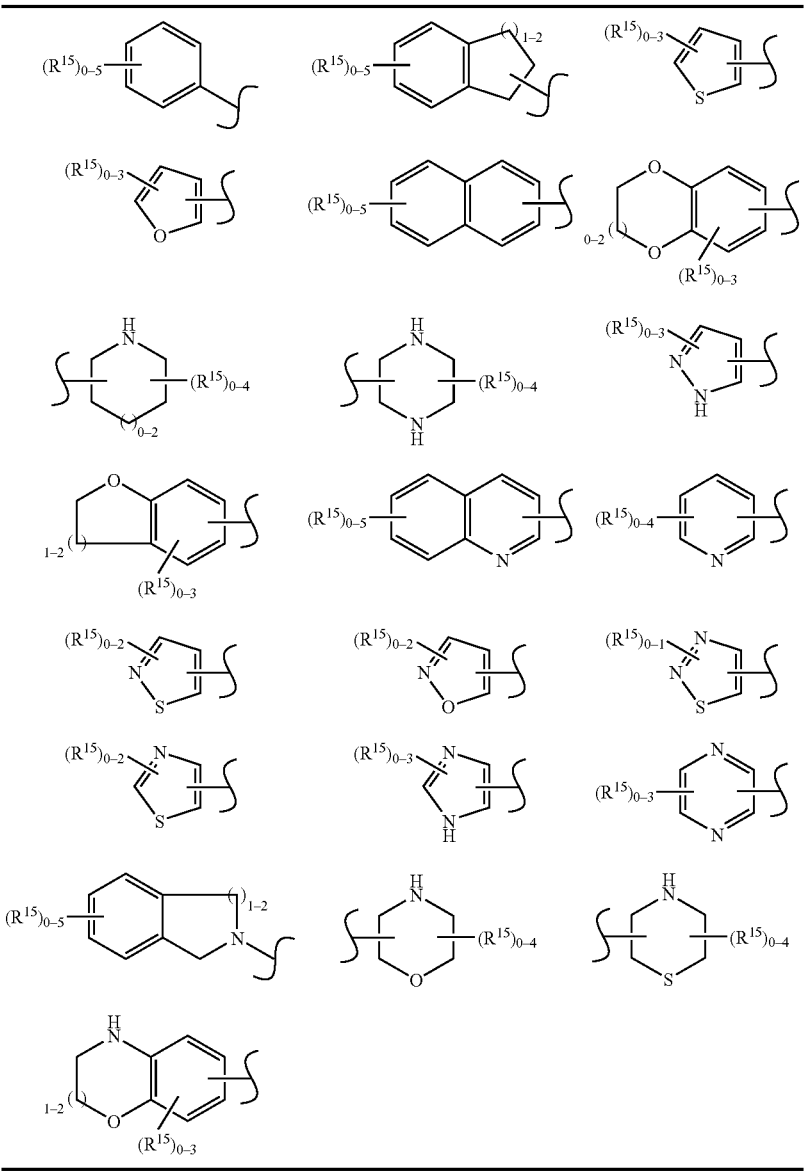

wherein each $R^{15}$ is independently selected from —H, halogen, oxo, —CN, —NH$_2$, —CF$_3$, —NO$_2$, —OR$^4$, —N(R$^4$)R$^5$, —S(O)$_{0-2}$R$^5$, —SO$_2$N(R$^4$)R$^5$, —CO$_2$R$^4$, —C(O)N(R$^4$)R$^5$, —N(R$^4$)SO$_2$R$^5$, —N(R$^4$)C(O)R$^5$, —N(R$^4$)CO$_2$R$^5$, —C(O)R$^4$, optionally substituted lower alkyl, optionally substituted aryl, optionally substituted lower arylalkyl, optionally substituted heterocyclyl, and optionally substituted lower heterocyclylalkyl.

In another example, the compound is according to paragraph [0052], wherein $R^{11b}$ is selected from optionally substituted alkyl, optionally substituted phenyl, optionally substituted pyridyl, and optionally substituted heteroalicyclic.

In another example, the compound is according to paragraph [0053], wherein $R^7$ is

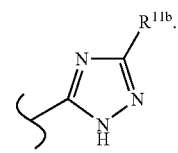

In another example, the compound is according to paragraph [0054], wherein $R^{11b}$ is selected from optionally substituted morpholine, optionally substituted pyrrolidine, optionally substituted piperidine, and optionally substituted azepane.

In another example, the compound is according to paragraph [0055], wherein $R^{11b}$ is 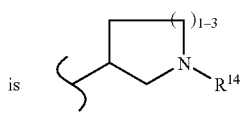

where R¹⁴ is either —H or lower alkyl.

In another example, the compound is according to paragraph [0054], wherein $R^{11b}$ is a pyridine.

In another example, the compound is according to paragraph [0057], wherein $R^{11b}$ is a pyridine bearing a 2-amino group.

In another example, the compound is according to paragraph [0042], wherein A is —C(=O)— or —C(=NR⁶)—.

In another example, the compound is according to paragraph [0059], wherein A is —C(=O)—.

In another example, the compound is according to paragraph [0060], wherein E is selected from Table 2.

wherein each $R^{16}$ is independently selected from —H, optionally substituted lower alkyl, —CO₂R⁴, and —C(=O)R⁴; or optionally two of $R^{16}$, together with the nitrogen or nitrogens to which they are attached, form a heterocyclic ring; each $R^{17}$ is independently selected from —H, halogen, oxo, —CN, —NH₂, —CF₃, —NO₂, —OR⁴, —N(R⁴)R⁵, —S(O)₀₋₂R⁵, —SO₂N(R⁴)R⁵, —CO₂R⁴, —C(O)N(R⁴)R⁵, —N(R⁴)SO₂R⁵, —N(R⁴)C(O)R⁵, —N(R⁴)CO₂R⁵, —(O)R⁴, optionally substituted lower alkyl, optionally substituted aryl, optionally substituted lower arylalkyl, optionally substituted heterocyclyl, and optionally substituted lower heterocyclylalkyl; $R^{18}$ is optionally substituted lower alkyl; $J^1$ is a saturated bridged ring system containing at least one nitrogen ring atom, said saturated bridged ring system having a geometry selected from the group consisting of [4.4.0], [4.3.0], [4.2.0], [4.1.0], [3.3.0], [3.2.0], and [3.1.0]; and $J^2$ is a saturated bridged ring system containing at least one nitrogen ring atom, said saturated bridged ring system having a geometry selected from the group consisting of [4.4.0], [4.3.0], [4.2.0],

TABLE 2

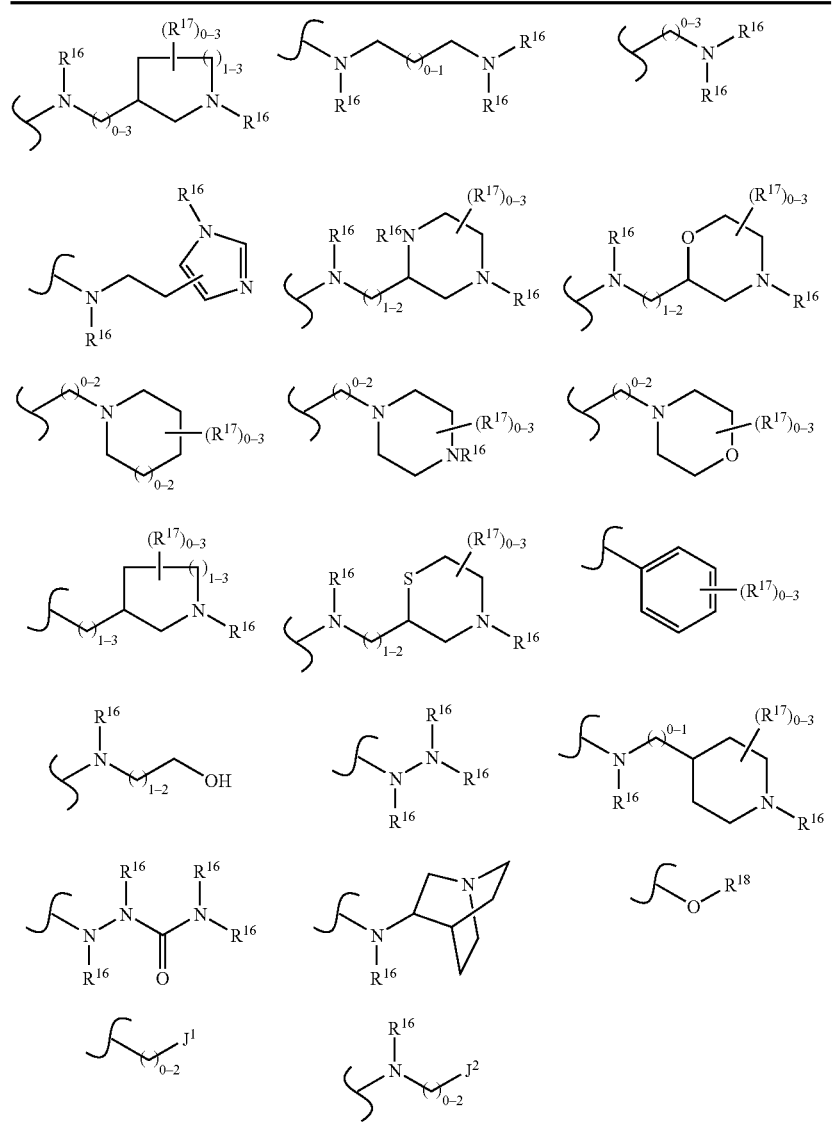

[4.1.0], [3.3.0], [3.2.0], and [3.1.0], wherein the nitrogen bearing $R^{16}$ and any nitrogen in $J^2$ must have at least two carbons between them.

In another example, the compound is according to paragraph [0061], wherein W is

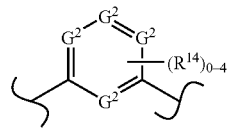

wherein each $G^2$ is independently =N— or =C($R^{14}$)—, wherein each $R^{14}$ is independently selected from —H, halogen, —CN, —NH$_2$, —CF$_3$, —NO$_2$, —OR$^4$, —N(R$^4$)R$^5$, —S(O)$_{0-2}$R$^5$, —SO$_2$N(R$^4$)R$^5$, —CO$_2$R$^4$, —C(O)N(R$^4$)R$^5$, —N($^4$)SO$_2$R$^5$, —N(R$^4$)C(O)R$^5$, —N(R$^4$)CO$_2$R$^5$, —C(O)R$^4$, optionally substituted lower alkyl, optionally substituted aryl, optionally substituted lower arylalkyl, optionally substituted heterocyclyl, and optionally substituted lower heterocyclylalkyl.

In another example, the compound is according to paragraph [0062], wherein W is

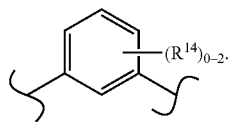

In another example, the compound is according to paragraph [0063], wherein X is selected from —(CH$_2$)$_{0-3}$C(=O)N(R$^4$)(CH$_2$)$_{0-3}$—, —(CH$_2$)$_{0-3}$SO$_2$N(R$^4$)(CH$_2$)$_{0-3}$—, —N(R$^4$)(CH$_2$)$_{2-3}$O, —(CH$_2$)$_{0-3}$N(R$^4$)C(=O)N(R$^4$) (CH$_2$)$_{0-3}$—, —C(=O)N(R$^4$)N(R$^4$)—, —(CH$_2$)$_{0-3}$C(=O)N (R$^4$)(CH$_2$)$_{2-3}$O—, —N(R$^4$)(CH$_2$)$_{2-3}$N(R$^4$)—, —(CH$_2$)$_{0-3}$N (R$^4$)(CH$_2$)$_{0-3}$—, —(CH$_2$)$_{0-3}$C(=O)N(R$^4$)(CH$_2$)$_{1-3}$C (=O)—, —O(CH$_2$)$_{2-3}$O—, —(CH$_2$)$_{0-3}$OC(=O)N(R$^4$) (CH$_2$)$_{0-3}$—, —(CH$_2$)$_{0-3}$O(CH$_2$)$_{0-3}$—, —(CH$_2$)$_{0-3}$CO$_2$ (CH$_2$)$_{2-3}$N(R$^4$)—, —(CH$_2$)$_{0-3}$N(R$^4$)C(=O)(CH$_2$)$_{0-3}$O—, —C(=O)N(R$^4$)(CH$_2$)$_{2-3}$N(R$^4$)—, optionally substituted alkoxyl, and optionally substituted lower alkylene.

In another example, the compound is according to paragraph [0064], wherein X is selected from —C(=O)N(H) (CH$_2$)$_{1-2}$—, —(CH$_2$)$_{1-2}$C(=O)N(H)—, —C(=O)N(H)—, —SO$_2$N(H)(CH$_2$)$_{1-2}$—, —(CH$_2$)$_{1-2}$SO$_2$N(H)—, —SO$_2$N (H)—, —N(H)C(=O)N(H)(CH$_2$)$_{1-2}$—, —N(H)C(=O)N (H)—, —(CH$_2$)$_{0-2}$N(R$^4$)(CH$_2$)$_{0-2}$—, —(CH$_2$)$_{0-2}$O(CH$_2$)$_{0-2}$, —C(=O)N(H)N(H)—, —N(R$^4$)(CH$_2$)$_{2-3}$N(R$^4$)—, —OCH$_2$C(=O)N(H)CH$_2$—, —(CH$_2$)$_{1-2}$N(H)C(=O)N (H)—, —OCH$_2$CH$_2$O—, —N(R$^4$)CH$_2$C(=O)N(H)CH$_2$—, —(CH$_2$)$_{0-1}$C(=O)N(H)(CH$_2$)$_{1-2}$C(=O)—, optionally substituted alkoxyl, and optionally substituted lower alkylene.

In another example, the compound is according to paragraph [0065], wherein Y is selected from optionally substituted cycloalkyl, optionally substituted phenyl, and optionally substituted five- to six-membered heterocyclyl.

In another example, the compound is according to paragraph [0066], wherein Y is selected from Table 3.

TABLE 3

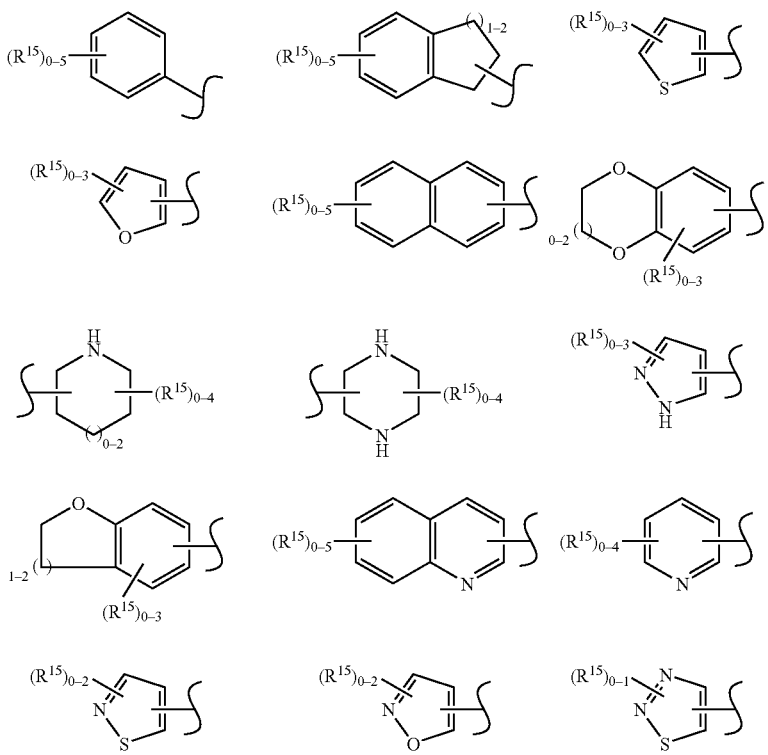

TABLE 3-continued

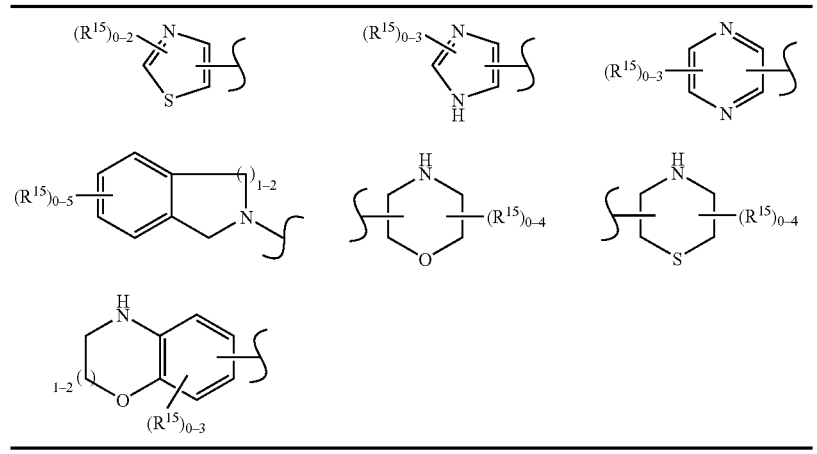

wherein each $R^{15}$ is independently selected from —H, halogen, oxo, —CN, —NH$_2$, —CF$_3$, —NO$_2$, —OR$^4$, —N(R$^4$)R$^5$, —S(O)$_{0-2}$R$^5$, —SO$_2$N(R$^4$)R$^5$, —CO$_2$R$^4$, —C(O)N(R$^4$)R$^5$, —N(R$^4$)SO$_2$R$^5$, —N(R$^4$)C(O)R$^5$, —N(R$^4$)CO$_2$R$^5$, —C(O)R$^4$, optionally substituted lower alkyl, optionally substituted aryl, optionally substituted lower arylalkyl, optionally substituted heterocyclyl, and optionally substituted lower heterocyclylalkyl.

In another example, the compound is according to paragraph [0067], wherein E is either

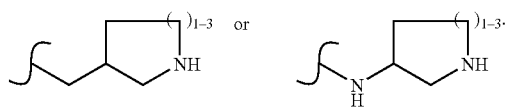

In another example, the compound is according to paragraph [0068], wherein E is either

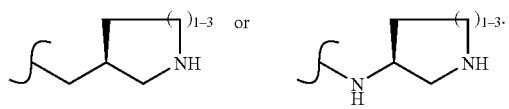

In another example, the compound is according to paragraph [0069], wherein $R^2$ and $R^3$ are —H.

In another example, the compound is according to paragraph [0070], wherein A is —C(=NR$^6$)—.

In another example, the compound is according to paragraph [0071], wherein E is selected from —H, lower alkyl, and a group listed in Table 4,

TABLE 4

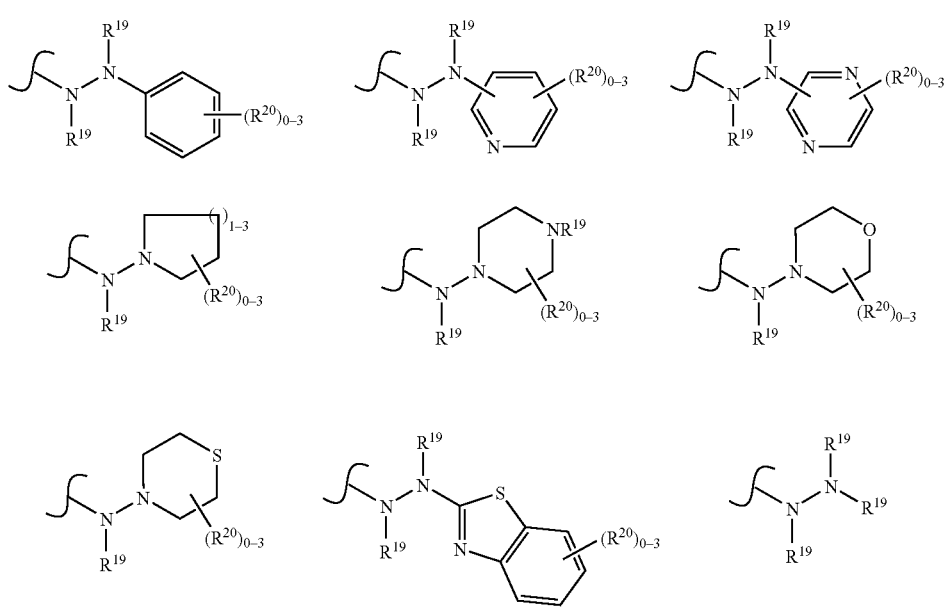

TABLE 4-continued

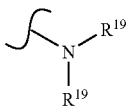

$R^6$ is selected from —H, —OH, lower alkyl, —NO$_2$, —CN, lower alkoxy, and a group listed in Table 5,

TABLE 5

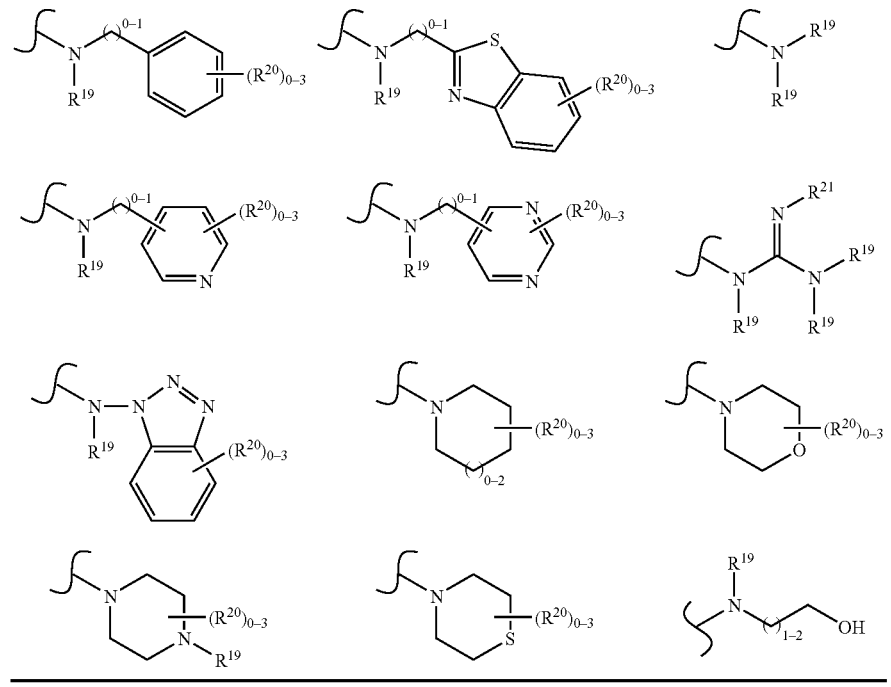

wherein each $R^{19}$ is independently either —H or lower alkyl;

each $R^{20}$ is independently selected from —H, halogen, oxo, —CN, —NH$_2$, —CF$_3$, —NO$_2$, —OR$^4$, —N(R$^4$)R$^5$, —S(O)$_{0-2}$R$^5$, —SO$_2$N(R$^4$)R$^5$, —CO$_2$R$^4$, —C(O)N(R$^4$)R$^5$, —N(R$^4$)SO$_2$R$^5$, —N(R$^4$)C(O)R$^5$, —N(R$^4$)CO$_2$R$^5$, —C(O)R$^4$, optionally substituted lower alkyl, optionally substituted aryl, optionally substituted lower arylalkyl, optionally substituted heterocyclyl, and optionally substituted lower heterocyclylalkyl;

and $R^{21}$ is selected from —H, —OH, lower alkyl, —NO$_2$, —CN, lower alkoxy.

In another example, the compound is according to paragraph [0072], wherein W is

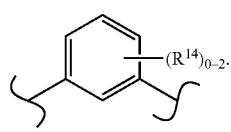

In another example, the compound is according to paragraph [0073], wherein X is selected from —(CH$_2$)$_{0-3}$C(=O)N(R$^4$)(CH$_2$)$_{0-3}$—, —(CH$_2$)$_{0-3}$SO$_2$N(R$^4$)(CH$_2$)$_{0-3}$—, —N(R$^4$)(CH$_2$)$_{2-3}$O, —(CH$_2$)$_{0-3}$N(R$^4$)C(=O)N(R$^4$)(CH$_2$)$_{0-3}$—, —C(=O)N(R$^4$)N(R$^4$)—, —(CH$_2$)$_{0-3}$C(=O)N(R$^4$)(CH$_2$)$_{2-3}$O—, —N(R$^4$)(CH$_2$)$_{2-3}$N(R$^4$)—, —(CH$_2$)$_{0-3}$N(R$^4$)(CH$_2$)$_{0-3}$—, —(CH$_2$)$_{0-3}$C(=O)N(R$^4$)(CH$_2$)$_{1-3}$C(=O)—, —O(CH$_2$)$_{2-3}$O—, —(CH$_2$)$_{0-3}$OC(=O)N(R$^4$)(CH$_2$)$_{0-3}$—, —(CH$_2$)$_{0-3}$O(CH$_2$)$_{0-3}$—, —(CH$_2$)$_{0-3}$CO$_2$(CH$_2$)$_{2-3}$N(R$^4$)—, —(CH$_2$)$_{0-3}$N(R$^4$)C(=O)(CH$_2$)$_{0-3}$O—, —C(=O)N(R$^4$)(CH$_2$)$_{2-3}$N(R$^4$)—, optionally substituted alkoxyl, and optionally substituted lower alkylene.

In another example, the compound is according to paragraph [0074], wherein X is selected from —C(=O)N(H)(CH$_2$)$_{1-2}$—, —(CH$_2$)$_{1-2}$C(=O)N(H)—, —C(=O)N(H)—, —SO$_2$N(H)(CH$_2$)$_{1-2}$—, —(CH$_2$)$_{1-2}$SO$_2$N(H)—, —SO$_2$N(H)—, —N(H)C(=O)N(H)(CH$_2$)$_{1-2}$—, —N(H)C(=O)N(H)—, —(CH$_2$)$_{0-2}$N(R$^4$)(CH$_2$)$_{0-2}$—, —(CH$_2$)$_{0-2}$O(CH$_2$)$_{0-2}$—, —C(=O)N(H)N(H)—, —N(R$^4$)(CH$_2$)$_{2-3}$N(R$^4$)—, —OCH$_2$C(=O)N(H)CH$_2$—, —(CH$_2$)$_{1-2}$N(H)C(=O)N(H)—, —OCH$_2$CH$_2$O—, —N(R$^4$)CH$_2$C(=O)N(H)CH$_2$—, —(CH$_2$)$_{0-1}$C(=O)N(H)(CH$_2$)$_{1-2}$C(=O)—, optionally substituted alkoxyl, and optionally substituted lower alkylene.

In another example, the compound is according to paragraph [0075], wherein Y is selected from optionally substituted cycloalkyl, optionally substituted phenyl, and optionally substituted five- to six-membered heterocyclyl.

In another example, the compound is according to paragraph [0076], wherein Y is selected from Table 6.

TABLE 6
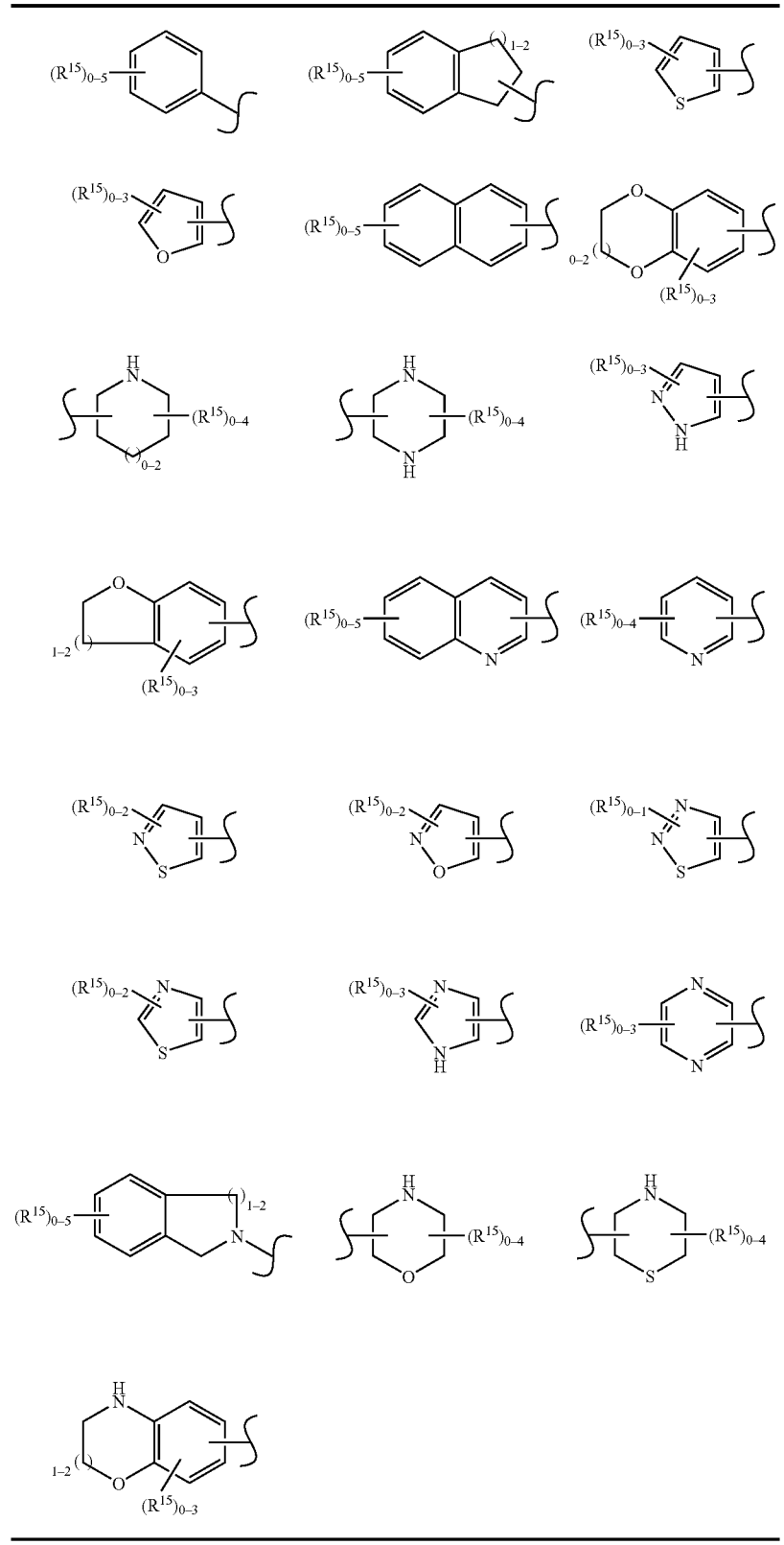

wherein each $R^{15}$ is independently selected from —H, halogen, oxo, —CN, —NH$_2$, —CF$_3$, —NO$_2$, —OR$^4$, —N(R$^4$)R$^5$, —S(O)$_{0-2}$R$^5$, —SO$_2$N(R$^4$)R$^5$, —CO$_2$R$^4$, —C(O)N(R$^4$)R$^5$, —N(R$^4$)SO$_2$R$^5$, —N(R$^4$)C(O)R$^5$, —N(R$^4$)CO$_2$R$^5$, —C(O)R$^4$, optionally substituted lower alkyl, optionally substituted aryl, optionally substituted lower arylalkyl, optionally substituted heterocyclyl, and optionally substituted lower heterocyclylalkyl.

In another example, the compound is according to paragraph [0039], of formula II,

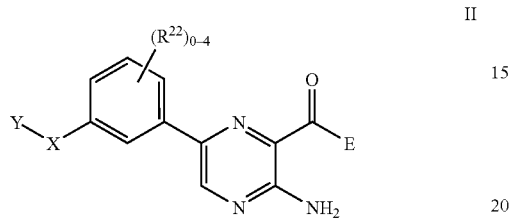

wherein E is selected from Table 7,

TABLE 7

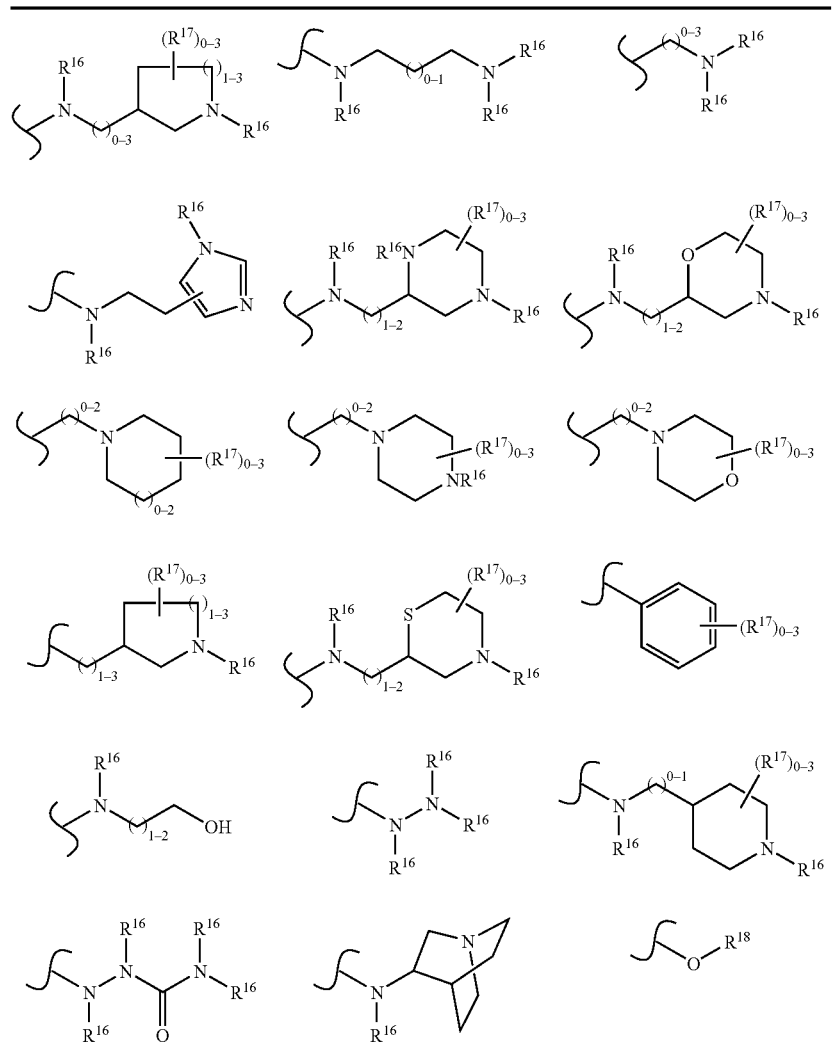

TABLE 7-continued

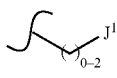 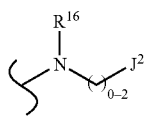

wherein each $R^{16}$ is independently selected from —H, optionally substituted lower alkyl, —$CO_2R^4$, and —C(=O)$R^4$, or optionally two of $R^{16}$, together with the nitrogen or nitrogens to which they are attached, form a heterocyclic ring;

each $R^{17}$ is independently selected from —H, halogen, oxo, —CN, —$NH_2$, —$CF_3$, —$NO_2$, —$OR^4$, —$N(R^4)R^5$, —$S(O)_{0-2}R^5$, —$SO_2N(R^4)R^5$, —$CO_2R^4$, —$C(O)N(R^4)R^5$, —$N(R^4)SO_2R^5$, —$N(R^4)C(O)R^5$, optionally substituted lower arylalkyl, optionally substituted heterocyclyl, and optionally substituted lower heterocyclylalkyl;

$R^{18}$ is optionally substituted lower alkyl;

$J^1$ is a saturated bridged ring system containing at least one nitrogen ring atom, said saturated bridged ring system having a geometry selected from the group consisting of [4.4.0], [4.3.0], [4.2.0], [4.1.0], [3.3.0], [3.2.0], and [3.1.0];

$J^2$ is a saturated bridged ring system containing at least one nitrogen ring atom, said saturated bridged ring system having a geometry selected from the group consisting of [4.4.0], [4.3.0], [4.2.0], [4.1.0], [3.3.0], [3.2.0], and [3.1.0], wherein the nitrogen bearing $R^{16}$ and any nitrogen in $J^2$ must have at least two carbons between them.

X is selected from —C(=O)N(H)($CH_2$)$_{1-2}$—, —($CH_2$)$_{1-2}$C(=O)N(H)—, —C(=O)N(H)—, —$SO_2$N(H)($CH_2$)$_{1-2}$—, —($CH_2$)$_{1-2}SO_2$N(H)—, —$SO_2$N(H)—, —N(H)C(=O)N(H)($CH_2$)$_{1-2}$—, —N(H)C(=O)N(H)—, —($CH_2$)$_{0-2}$N($R^4$)($CH_2$)$_{0-2}$—, —($CH_2$)$_{0-2}$O($CH_2$)$_{0-2}$—, —C(=O)N(H)N(H)—, —($R^4$)($CH_2$)$_{2-3}$N($R^4$)—, —$OCH_2$C(=O)N(H)$CH_2$—, —($CH_2$)$_{1-2}$N(H)C(=O)N(H)—, —$OCH_2CH_2$O—, —N($R^4$)$CH_2$C(=O)N(H)$CH_2$—, —($CH_2$)$_{0-1}$C(=O)N(H)($CH_2$)$_{1-2}$C(=O)—, optionally substituted alkoxyl, and optionally substituted lower alkylene;

Y is selected from Table 8,

TABLE 8

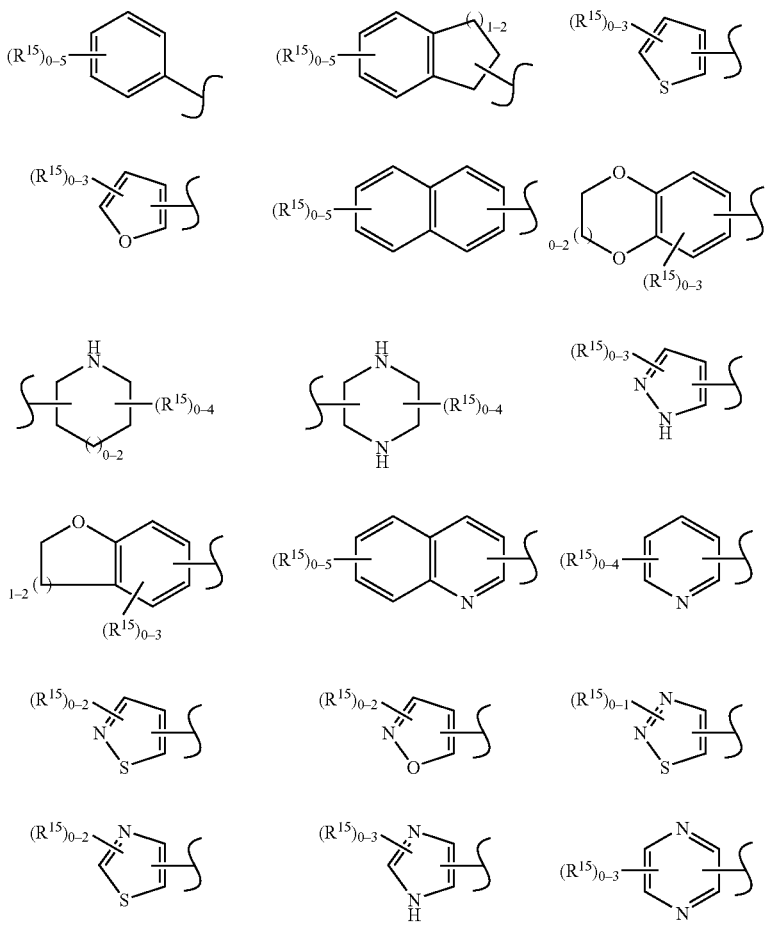

TABLE 8-continued

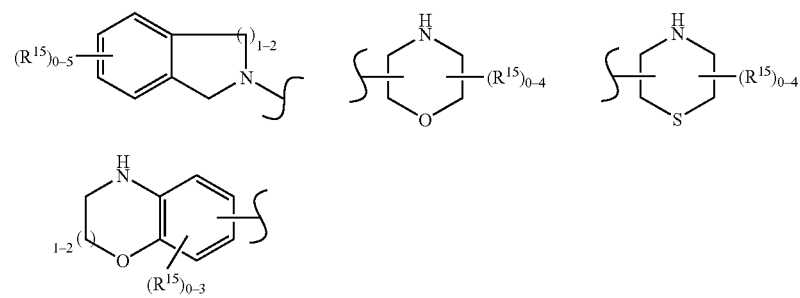

wherein each R[15] is independently selected from —H, halogen, oxo, —CN, —NH$_2$, —CF$_3$, —NO$_2$, —OR$^4$, —N(R$^4$)R$^5$, —S(O)$_{0-2}$R$^5$, —SO$_2$N(R$^4$)R$^5$, —CO$_2$R$^4$, —C(O)N(R$^4$)R$^5$, —N(R$^4$)SO$_2$R$^5$, —N(R$^4$)C(O)R$^5$, —N(R$^4$)CO$_2$R$^5$, —C(O)R$^4$, optionally substituted lower alkyl, optionally substituted aryl, optionally substituted lower arylalkyl, optionally substituted heterocyclyl, and optionally substituted lower heterocyclylalkyl; and, each R[22] is independently selected from —H, halogen, —CN, —NH$_2$, —CF$_3$, —NO$_2$, —OR$^4$, —N(R$^4$)R$^5$, —S(O)$_{0-2}$R$^5$, —SO$_2$N(R$^4$)R$^5$, —CO$_2$R$^4$, —C(O)N(R$^4$)R$^5$, —N(R$^4$)SO$_2$R$^5$, —N(R$^4$)C(O)R$^5$, —N(R$^4$)CO$_2$R$^5$, —C(O)R$^4$, optionailly substituted lower alkyl, optionally substituted aryl, optionally substituted lower arylalkyl, optionally substituted heterocyclyl, and optionally substituted lower heterocyclylalkyl.

In another example, the compound is according to paragraph [0039], of formula

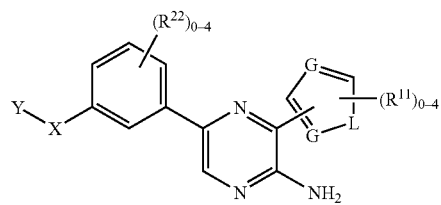

III wherein, each G is independently =N— or =C(R[11])—;

L is selected from —O—, —S(O)$_{0-2}$—, and —NR[11]; each R[11] is independently selected from —H, halogen, —CN, —NH$_2$, —CF$_3$, —NO$_2$, —OR$^4$, —N(R$^4$)R$^5$, —S(O)$_{0-2}$R$^5$, —SO$_2$N($^4$)R$^5$, —CO$_2$R$^4$, —C(O)N($^4$)R$^5$, —N(R$^4$)SO$_2$R$^5$, —N(R$^4$)C(O)R$^5$, —N(R$^4$)CO$_2$R$^5$, —C(O)R$^4$, optionally substituted lower alkyl, optionally substituted aryl, optionally substituted lower arylalkyl, optionally substituted heterocyclyl, and optionally substituted lower heterocyclylalkyl; or optionally two R[11]'s form a ring system fused with the existing ring of R$^7$, said ring system substituted with 0 to 3 additional of R[11] and said ring system optionally containing between 1 and 3 heteroatoms;

X is selected from —C(=O)N(H)(CH$_2$)$_{1-2}$—, —(CH$_2$)$_{1-2}$C(=O)N(H)—, —C(=O)N(H)—, —SO$_2$N(R)(CH$_2$)$_{1-2}$—, —(CH$_2$)$_{1-2}$SO$_2$N(H)—, —SO$_2$N(H)—, —N(H)C(=O)N(H)(CH$_2$)$_{1-2}$—, —N(H)C(=O)N(H)—, —(CH$_2$)$_{0-2}$N(R$^4$)(CH$_2$)$_{0-2}$—, —(CH$_2$)$_{0-2}$O(CH$_2$)$_{0-2}$, —C(=O)N(H)N(H)—, —N(R$^4$)(CH$_2$)$_{2-3}$N(R$^4$)—, —OCH$_2$C(=O)N(H)CH$_2$—, —(CH$_2$)$_{1-2}$N(H)C(=O)N(H)—, —OCH$_2$CH$_2$O, —N(R$^4$)CH$_2$C(=O)N(H)CH$_2$—, —(CH$_2$)$_{0-1}$C(=O)N(H)(CH$_2$)$_{1-2}$C(=O)—, optionally substituted alkoxyl, and optionally substituted lower alkylene;

Y is selected from Table 9,

TABLE 9

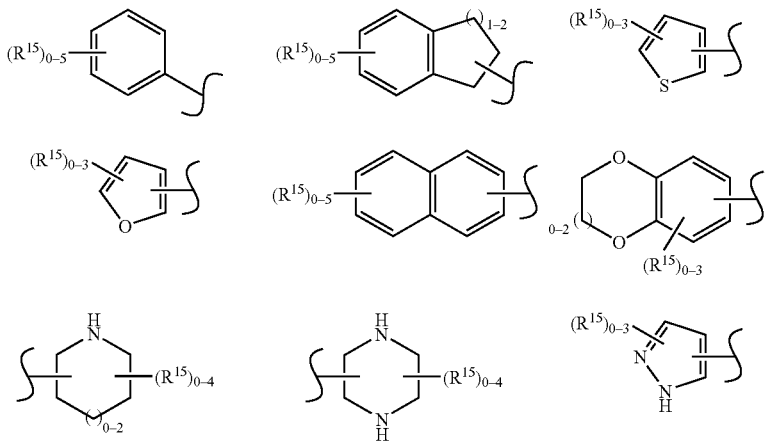

TABLE 9-continued

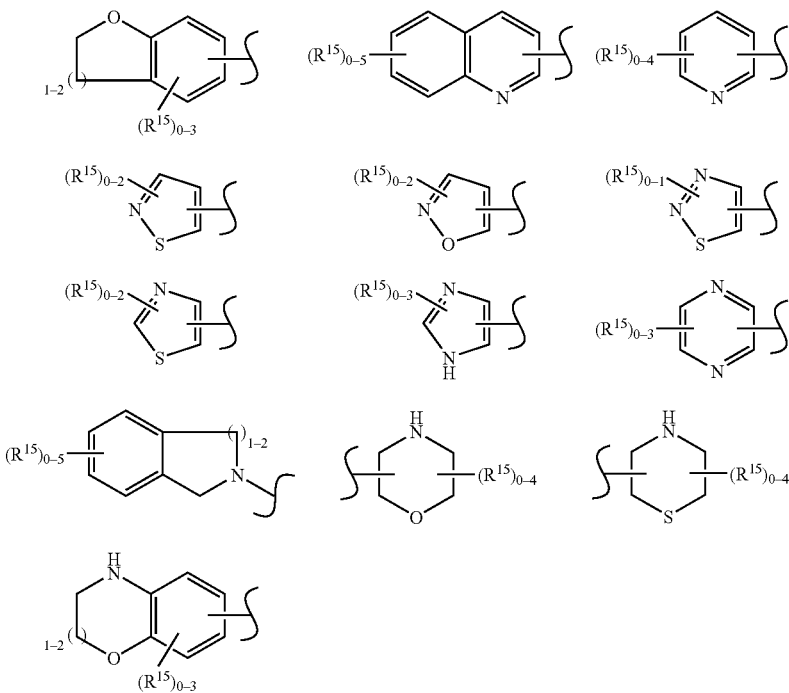

wherein each $R^{15}$ is independently selected from —H, halogen, oxo, —CN, —NH$_2$, —CF$_3$, —NO$_2$, —OR$^4$, —N(R$^4$)R$^5$, —S(O)$_{0-2}$R$^5$, —SO$_2$N(R$^4$)R$^5$, —CO$_2$R$^4$, —C(O)N(R$^4$)R$^5$, —N(R$^4$)SO$_2$R$^5$, —N(R$^4$)C(O)R$^5$, —N(R$^4$)CO$_2$R$^5$, —C(O)R$^4$, optionally substituted lower alkyl, optionally substituted aryl, optionally substituted lower arylalkyl, optionally substituted heterocyclyl, and optionally substituted lower heterocyclylalkyl; and, each $R^{22}$ is independently selected from —H, halogen, —CN, —NH$_2$, —CF$_3$, —NO$_2$, —OR$^4$, —N(R$^4$)R$^5$, —S(O)$_{0-2}$R$^5$, —SO$_2$N(R$^4$)R$^5$, —CO$_2$R$^4$, —C(O)N(R$^4$)R$^5$, —N(R$^4$)SO$_2$R$^5$, —N(R$^4$)C(O)R$^5$, —N(R$^4$)CO$_2$R$^5$, —C(O)R$^4$, optionally substituted lower alkyl, optionally substituted aryl, optionaaly substituted lower arylalkyl, optionally substituted heterocyclyl, and optionally substituted lower heterocyclylalkyl.

In another example, the compound is according to paragraph [0039], wherein the copound is selected from Table 10.

TABLE 10

| # | Name |
|---|------|
| 1 | 3-amino-6-phenyl-N-(2-phenylethyl)pyrazine-2-carboxamide |
| 2 | 3-amino-6-phenyl-N-(phenylmethyl)pyrazine-2-carboxamide |
| 3 | 3-amino-6-(3-chlorophenyl)pyrazine-2-carboxamide |
| 4 | 3-amino-N-[(1R)-2,3-dihydro-1H-inden-1-yl]-6-phenylpyrazine-2-carboxamide |
| 5 | 3-amino-N-[(1S)-2,3-dihydro-1H-inden-1-yl]-6-phenylpyrazine-2-carboxamide |
| 6 | 3-amino-N-(2,3-dihydro-1H-inden-2-yl)-6-phenylpyrazine-2-carboxamide |
| 7 | 3-amino-6-(2-chlorophenyl)pyrazine-2-carboxamide |
| 8 | 3-amino-N-cyclopentyl-6-phenylpyrazine-2-carboxamide |
| 9 | 3-amino-N,N-dimethyl-6-phenylpyrazine-2-carboxamide |
| 10 | 3-amino-6-[3-(methyloxy)phenyl]pyrazine-2-carboxamide |
| 11 | 5-phenyl-3-(pyrrolidin-1-ylcarbonyl)pyrazin-2-amine |
| 12 | 3-amino-N-(cyclopropylmethyl)-6-phenylpyrazine-2-carboxamide |
| 13 | 3-amino-6-phenyl-N-(tetrahydrofuran-2-ylmethyl)pyrazine-2-carboxamide |
| 14 | 3-amino-N-cyclohexyl-6-phenylpyrazine-2-carboxamide |
| 15 | 6-phenyl-N-propyl-3-(propylamino)pyrazine-2-carboxamide |
| 16 | 3-amino-6-(2-methylphenyl)pyrazine-2-carboxamide |
| 17 | 3-amino-6-[2-(methyloxy)phenyl]pyrazine-2-carboxamide |
| 18 | 3-amino-6-(2,4-difluorophenyl)pyrazine-2-carboxamide |
| 19 | 3-amino-6-(3-fluorophenyl)pyrazine-2-carboxamide |
| 20 | 3-amino-N-cyclopropyl-6-phenylpyrazine-2-carboxamide |
| 21 | 3-amino-6-(3,4-difluorophenyl)pyrazine-2-carboxamide |
| 22 | 3-amino-6-(4-fluorophenyl)-N-methylpyrazine-2-carboxamide |
| 23 | 3-amino-6-[4-(ethyloxy)phenyl]pyrazine-2-carboxamide |
| 24 | 3-amino-6-[3-(ethyloxy)phenyl]pyrazine-2-carboxamide |

TABLE 10-continued

| # | Name |
|---|------|
| 25 | 3-amino-6-(1,3-benzodioxol-5-yl)pyrazine-2-carboxamide |
| 26 | 3-amino-6-naphthalen-1-ylpyrazine-2-carboxamide |
| 27 | 3-amino-6-naphthalen-2-ylpyrazine-2-carboxamide |
| 28 | 3-amino-6-{3-[(trifluoromethyl)oxy]phenyl}pyrazine-2-carboxamide |
| 29 | 3-amino-6-[3-(aminocarbonyl)phenyl]pyrazine-2-carboxamide |
| 30 | 6-[3-(acetylamino)phenyl]-3-aminopyrazine-2-carboxamide |
| 31 | 3-amino-6-biphenyl-4-ylpyrazine-2-carboxamide |
| 32 | 3-amino-6-[4-(dimethylamino)phenyl]pyrazine-2-carboxamide |
| 33 | 3-amino-6-(3-methylphenyl)pyrazine-2-carboxamide |
| 34 | methyl 3-[5-amino-6-(aminocarbonyl)pyrazin-2-yl]benzoate |
| 35 | 3-amino-6-{3-[(phenylmethyl)oxy]phenyl}pyrazine-2-carboxamide |
| 36 | 3-amino-6-(3-hydroxyphenyl)pyrazine-2-carboxamide |
| 37 | 3-amino-6-(1-benzofuran-2-yl)pyrazine-2-carboxamide |
| 38 | 3-(methylamino)-6-phenylpyrazine-2-carboxamide |
| 39 | 6-phenyl-3-[(phenylmethyl)amino]pyrazine-2-carboxamide |
| 40 | 6-phenyl-3-(propylamino)pyrazine-2-carboxamide |
| 41 | 3-amino-6-biphenyl-3-ylpyrazine-2-carboxamide |
| 42 | 3-[5-amino-6-(aminocarbonyl)pyrazin-2-yl]benzoic acid |
| 43 | 3-amino-6-{4-[(phenylmethyl)oxy]phenyl}pyrazine-2-carboxamide |
| 44 | 3-amino-N-methyl-6-{3-[(phenylmethyl)oxy]phenyl}pyrazine-2-carboxamide |
| 45 | 3-amino-6-(3-hydroxyphenyl)-N-methylpyrazine-2-carboxamide |
| 46 | 3-amino-N-[2-(methyloxy)ethyl]-6-phenylpyrazine-2-carboxamide |
| 47 | N-[2-(acetylamino)ethyl]-3-amino-6-phenylpyrazine-2-carboxamide |
| 48 | 3-amino-6-phenylpyrazine-2-carbohydrazide |
| 49 | 3-amino-N-hydroxy-6-phenylpyrazine-2-carboxamide |
| 50 | 3-amino-6-[3-(ethyloxy)phenyl]-N-methylpyrazine-2-carboxamide |
| 51 | 3-amino-6-(3-aminophenyl)-N-methylpyrazine-2-carboxamide |
| 52 | 3-amino-6-[4-(ethyloxy)phenyl]-N-methylpyrazine-2-carboxamide |
| 53 | 3-amino-N-methyl-6-(3-methylphenyl)pyrazine-2-carboxamide |
| 54 | 3-amino-N-methyl-6-[4-(methyloxy)phenyl]pyrazine-2-carboxamide |
| 55 | 3-amino-6-biphenyl-3-yl-N-methylpyrazine-2-carboxamide |
| 56 | 6-[3-(acetylamino)phenyl]-3-amino-N-methylpyrazine-2-carboxamide |
| 57 | 3-amino-6-[3-(hydroxymethyl)phenyl]-N-methylpyrazine-2-carboxamide |
| 58 | 3-amino-6-[4-(hydroxymethyl)phenyl]-N-methylpyrazine-2-carboxamide |
| 59 | 3-amino-N-methyl-6-{3-[(1E)-N-methylethanimidoyl]phenyl}pyrazine-2-carboxamide |
| 60 | 3-amino-N-methyl-6-[3-(methyloxy)phenyl]pyrazine-2-carboxamide |
| 61 | 3-amino-6-(4-fluoro-3-methylphenyl)-N-methylpyrazine-2-carboxamide |
| 62 | 3-amino-N-methyl-6-pyridin-3-ylpyrazine-2-carboxamide |
| 63 | 6-[4-(acetylamino)phenyl]-3-amino-N-methylpyrazine-2-carboxamide |
| 64 | 3-amino-N-methyl-6-{3-[(methylamino)carbonyl]phenyl}pyrazine-2-carboxamide |
| 65 | 6-(3-acetylphenyl)-3-amino-N-methylpyrazine-2-carboxamide |
| 66 | 3-amino-N-methyl-6-(5-pyridin-3-yl-1,2,4-oxadiazol-3-yl)pyrazine-2-carboxamide |
| 67 | 3-amino-6-(5-cyclopentyl-1,2,4-oxadiazol-3-yl)-N-methylpyrazine-2-carboxamide |
| 68 | 3-amino-6-(5-cyclohexyl-1,2,4-oxadiazol-3-yl)-N-methylpyrazine-2-carboxamide |
| 69 | 3-amino-N-methyl-6-(5-phenyl-1,2,4-oxadiazol-3-yl)pyrazine-2-carboxamide |
| 70 | 3-amino-N-methyl-6-[5-(phenylmethyl)-1,2,4-oxadiazol-3-yl]pyrazine-2-carboxamide |
| 71 | 3-amino-N-methyl-6-(5-methyl-1,2,4-oxadiazol-3-yl)pyrazine-2-carboxamide |
| 72 | 3-amino-N-methyl-6-[5-(2-phenylethyl)-1,2,4-oxadiazol-3-yl]pyrazine-2-carboxamide |
| 73 | 3-amino-N-methyl-6-(5-pyridin-4-yl-1,2,4-oxadiazol-3-yl)pyrazine-2-carboxamide |
| 74 | 3-amino-6-[5-(1,1-dimethylethyl)-1,2,4-oxadiazol-3-yl]-N-methylpyrazine-2-carboxamide |
| 75 | 3-amino-6-(5-furan-2-yl-1,2,4-oxadiazol-3-yl)-N-methylpyrazine-2-carboxamide |
| 76 | 3-amino-6-[4-(dimethylamino)phenyl]-N-methylpyrazine-2-carboxamide |
| 77 | 3-amino-N-methyl-6-{4-[(methylsulfonyl)amino]phenyl}pyrazine-2-carboxamide |
| 78 | 3-amino-6-(3,5-dimethylphenyl)-N-methylpyrazine-2-carboxamide |
| 79 | 6-(4-acetylphenyl)-3-amino-N-methylpyrazine-2-carboxamide |
| 80 | 3-amino-6-[3,4-bis(methyloxy)phenyl]-N-methylpyrazine-2-carboxamide |
| 81 | 3-amino-N-methyl-6-{3-[(phenylcarbonyl)amino]phenyl}pyrazine-2-carboxamide |
| 82 | 3-amino-N-methyl-6-{3-[(methylsulfonyl)amino]phenyl}pyrazine-2-carboxamide |
| 83 | 3-amino-N-methyl-6-[3-(1H-tetrazol-5-yl)phenyl]pyrazine-2-carboxamide |
| 84 | 3-amino-N-methyl-6-(3-{[(phenylmethyl)amino]carbonyl}phenyl)pyrazine-2-carboxamide |
| 85 | 3-amino-6-[3-(aminocarbonyl)phenyl]-N-methylpyrazine-2-carboxamide |
| 86 | 3-amino-6-{3-[(dimethylamino)carbonyl]phenyl}-N-methylpyrazine-2-carboxamide |
| 87 | 3-amino-N-methyl-6-[4-(methylsulfonyl)phenyl]pyrazine-2-carboxamide |
| 88 | 3-amino-6-(3-aminophenyl)-N-ethylpyrazine-2-carboxamide |
| 89 | 3-amino-6-[3-({[(4-fluorophenyl)amino]carbonyl}amino)phenyl]-N-methylpyrazine-2-carboxamide |
| 90 | 3-amino-N-methyl-6-{3-[({[4-(methyloxy)phenyl]amino}carbonyl)amino]phenyl}pyrazine-2-carboxamide |

TABLE 10-continued

| # | Name |
|---|---|
| 91 | 6,6'-[(oxomethanediyl)bis(iminobenzene-3,1-diyl)]bis(3-amino-N-methylpyrazine-2-carboxamide) |
| 92 | 3-{5-amino-6-[(methylamino)carbonyl]pyrazin-2-yl}benzoic acid |
| 93 | 3-amino-N-methyl-6-{3-[(4-methylpiperazin-1-yl)carbonyl]phenyl}pyrazine-2-carboxamide |
| 94 | 3-amino-N-methyl-6-(3-{[(2-phenylethyl)amino]carbonyl}phenyl)pyrazine-2-carboxamide |
| 95 | 3-amino-N-methyl-6-{3-[({[4-(methyloxy)phenyl]methyl}amino)carbonyl]phenyl}pyrazine-2-carboxamide |
| 96 | 3-amino-6-(3-{[(1R)-2,3-dihydro-1H-inden-1-ylamino]carbonyl}phenyl)-N-methylpyrazine-2-carboxamide |
| 97 | 3-amino-6-(3-{[(1S)-2,3-dihydro-1H-inden-1-ylamino]carbonyl}phenyl)-N-methylpyrazine-2-carboxamide |
| 98 | 3-amino-6-[3-({[(4-chlorophenyl)methyl]amino}carbonyl)phenyl]-N-methylpyrazine-2-carboxamide |
| 99 | 3-amino-N-methyl-6-(3-{[methyl(phenylmethyl)amino]carbonyl}phenyl)pyrazine-2-carboxamide |
| 100 | 3-amino-6-[3-({[(2,4-dichlorophenyl)methyl]amino}carbonyl)phenyl]-N-methylpyrazine-2-carboxamide |
| 101 | 3-amino-N-methyl-6-[3-({[(4-methylphenyl)methyl]amino}carbonyl)phenyl]pyrazine-2-carboxamide |
| 102 | 3-amino-N-methyl-6-{3-[({[4-(trifluoromethyl)phenyl]methyl}amino)carbonyl]phenyl}pyrazine-2-carboxamide |
| 103 | 3-amino-6-[3-({[(4-fluorophenyl)methyl]amino}carbonyl)phenyl]-N-methylpyrazine-2-carboxamide |
| 104 | 3-amino-6-{3-[(2,3-dihydro-1H-inden-2-ylamino)carbonyl]phenyl}-N-methylpyrazine-2-carboxamide |
| 105 | 3-amino-N-methyl-6-[3-({[3-(methyloxy)phenyl]carbonyl}amino)phenyl]pyrazine-2-carboxamide |
| 106 | 3-amino-N-methyl-6-[3-({[4-(methyloxy)phenyl]carbonyl}amino)phenyl]pyrazine-2-carboxamide |
| 107 | 3-amino-N-methyl-6-{3-[({[3-(methyloxy)phenyl]methyl}amino)carbonyl]phenyl}pyrazine-2-carboxamide |
| 108 | 3-amino-N-methyl-6-{3-[({(1R)-1-[4-(methyloxy)phenyl]ethyl}amino)carbonyl]phenyl}pyrazine-2-carboxamide |
| 109 | 3-amino-N-methyl-6-{3-[({[2-(trifluoromethyl)phenyl]methyl}amino)carbonyl]phenyl}pyrazine-2-carboxamide |
| 110 | 3-amino-6-[3-({[(3-fluorophenyl)methyl]amino}carbonyl)phenyl]-N-methylpyrazine-2-carboxamide |
| 111 | 3-amino-6-(3-{[(4-chlorophenyl)carbonyl]amino}phenyl)-N-methylpyrazine-2-carboxamide |
| 112 | 3-amino-6-[3-({[1-(4-fluorophenyl)ethyl]amino}carbonyl)phenyl]-N-methylpyrazine-2-carboxamide |
| 113 | 3-amino-6-{3-[({[2,3-bis(methyloxy)phenyl]methyl}amino)carbonyl]phenyl}-N-methylpyrazine-2-carboxamide |
| 114 | 3-amino-6-(3-{[bis(phenylmethyl)amino]carbonyl}phenyl)-N-methylpyrazine-2-carboxamide |
| 115 | 3-amino-6-{3-[({[2,4-bis(methyloxy)phenyl]methyl}amino)carbonyl]phenyl}-N-methylpyrazine-2-carboxamide |
| 116 | 3-amino-6-(3-{[ethyl(pyridin-4-ylmethyl)amino]carbonyl}phenyl)-N-methylpyrazine-2-carboxamide |
| 117 | 3-amino-N-methyl-6-(3-{4-(phenylmethyl)piperazin-1-yl]carbonyl}phenyl)pyrazine-2-carboxamide |
| 118 | 3-amino-N-methyl-6-[3-({[1-(phenylmethyl)piperidin-4-yl]amino}carbonyl)phenyl]pyrazine-2-carboxamide |
| 119 | 3-amino-N-methyl-6-(3-{[(4-methylphenyl)carbonyl]amino}phenyl)pyrazine-2-carboxamide |
| 120 | 3-amino-N-methyl-6-[3-({[(5-methylpyrazin-2-yl)methyl]amino}carbonyl)phenyl]pyrazine-2-carboxamide |
| 121 | 3-amino-N-methyl-6-(3-{[(pyridin-2-ylmethyl)amino]carbonyl}phenyl)pyrazine-2-carboxamide |
| 122 | 3-amino-N-methyl-6-(3-{[(pyridin-3-ylmethyl)amino]carbonyl}phenyl)pyrazine-2-carboxamide |
| 123 | 3-amino-N-methyl-6-(3-{[(pyridin-4-ylmethyl)amino]carbonyl}phenyl)pyrazine-2-carboxamide |
| 124 | 3-amino-6-{3-[(furan-2-ylcarbonyl)amino]phenyl}-N-methylpyrazine-2-carboxamide |
| 125 | 3-amino-6-[3-({[(3-chlorophenyl)methyl]amino}carbonyl)phenyl]-N-methylpyrazine-2-carboxamide |
| 126 | 3-amino-6-(3-{[(cyclohexylmethyl)amino]carbonyl}phenyl)-N-methylpyrazine-2-carboxamide |
| 127 | 3-amino-N-methyl-6-(3-{[(2-phenylpropyl)amino]carbonyl}phenyl)pyrazine-2-carboxamide |
| 128 | 3-amino-6-[3-({[(2-chlorophenyl)methyl]amino}carbonyl)phenyl]-N-methylpyrazine-2-carboxamide |
| 129 | 3-amino-6-[3-({[2-(2-chlorophenyl)ethyl]amino}carbonyl)phenyl]-N-methylpyrazine-2-carboxamide |

TABLE 10-continued

| # | Name |
|---|---|
| 130 | 3-amino-N-methyl-6-{3-[({2-[2-(methyloxy)phenyl]ethyl}amino)carbonyl]phenyl}pyrazine-2-carboxamide |
| 131 | 3-amino-6-[3-({[2-(4-fluorophenyl)ethyl]amino}carbonyl)phenyl]-N-methylpyrazine-2-carboxamide |
| 132 | 3-amino-N-methyl-6-[3-({[2-(2-thienyl)ethyl]amino}carbonyl)phenyl]pyrazine-2-carboxamide |
| 133 | 3-amino-6-{3-[(cyclohexylamino)carbonyl]phenyl}-N-methylpyrazine-2-carboxamide |
| 134 | 1,1-dimethylethyl 4-({[(3-{5-amino-6-[(methylamino)carbonyl]pyrazin-2-yl}phenyl)carbonyl]amino}methyl)piperidine-1-carboxylate |
| 135 | 3-amino-N-methyl-6-(3-{[(piperidin-4-ylmethyl)amino]carbonyl}phenyl)pyrazine-2-carboxamide |
| 136 | 3-amino-N-methyl-6-{3-[5-phenyl-1,2,4-oxadiazol-3-yl]phenyl}pyrazine-2-carboxamide |
| 137 | 3-amino-N-methyl-6-{3-[5-(phenylmethyl)-1,2,4-oxadiazol-3-yl]phenyl}pyrazine-2-carboxamide |
| 138 | 3-amino-N-methyl-6-{3-[5-(2-phenylethyl)-1,2,4-oxadiazol-3-yl]phenyl}pyrazine-2-carboxamide |
| 139 | 3-amino-6-(3-{[(1,1-dimethylethyl)amino]carbonyl}phenyl)-N-methylpyrazine-2-carboxamide |
| 140 | 3-amino-6-[3-({[(1R,2S)-2-hydroxy-2,3-dihydro-1H-inden-1-yl]amino}carbonyl)phenyl]-N-methylpyrazine-2-carboxamide |
| 141 | 3-amino-6-[3-({[(1S,2R)-2-hydroxy-2,3-dihydro-1H-inden-1-yl]amino}carbonyl)phenyl]-N-methylpyrazine-2-carboxamide |
| 142 | 3-amino-N-methyl-6-{3-[(phenylamino)carbonyl]phenyl}pyrazine-2-carboxamide |
| 143 | 3-amino-6-[3-(1,3-dihydro-2H-isoindol-2-ylcarbonyl)phenyl]-N-methylpyrazine-2-carboxamide |
| 144 | 3-amino-N-methyl-6-[3-({[(1R)-1-phenylethyl]amino}carbonyl)phenyl]pyrazine-2-carboxamide |
| 145 | 3-amino-N-methyl-6-[3-({[(1S)-1-phenylethyl]amino}carbonyl)phenyl]pyrazine-2-carboxamide |
| 146 | 3-amino-N-methyl-6-[3-({[(1R)-1-phenylpropyl]amino}carbonyl)phenyl]pyrazine-2-carboxamide |
| 147 | 3-amino-N-methyl-6-[3-({[(1S)-1-phenylpropyl]amino}carbonyl)phenyl]pyrazine-2-carboxamide |
| 148 | 3-amino-N-methyl-6-[3-({[(1R,2S)-2-phenylcyclopropyl]amino}carbonyl)phenyl]pyrazine-2-carboxamide |
| 149 | phenylmethyl 4-{5-amino-6-[(methylamino)carbonyl]pyrazin-2-yl}benzoate |
| 150 | 3-amino-N-methyl-6-(4-{[(phenylmethyl)amino]carbonyl}phenyl)pyrazine-2-carboxamide |
| 151 | 3-amino-N-methyl-6-(4-{[(2-phenylethyl)amino]carbonyl}phenyl)pyrazine-2-carboxamide |
| 152 | 3-amino-6-[4-({[(2,4-dichlorophenyl)methyl]amino}carbonyl)phenyl]-N-methylpyrazine-2-carboxamide |
| 153 | 3-amino-N-methyl-6-[4-({[(4-methylphenyl)methyl]amino}carbonyl)phenyl]pyrazine-2-carboxamide |
| 154 | 3-amino-6-(4-{[(1S)-2,3-dihydro-1H-inden-1-ylamino]carbonyl}phenyl)-N-methylpyrazine-2-carboxamide |
| 155 | 3-amino-6-(3-{[(4-chlorophenyl)acetyl]amino}phenyl)-N-methylpyrazine-2-carboxamide |
| 156 | 3-amino-N-methyl-6-(3-({[3-(phenyloxy)phenyl]carbonyl}amino)phenyl]pyrazine-2-carboxamide |
| 157 | 3-amino-6-{3-[(diphenylacetyl)amino]phenyl}-N-methylpyrazine-2-carboxamide |
| 158 | 3-amino-N-methyl-6-{3-[(phenylacetyl)amino]phenyl}pyrazine-2-carboxamide |
| 159 | 3-amino-N-methyl-6-{3-[(3-phenylpropanoyl)amino]phenyl}pyrazine-2-carboxamide |
| 160 | 3-amino-N-methyl-6-(3-{[(1R)-1,2,3,4-tetrahydronaphthalen-1-ylamino]carbonyl}phenyl)pyrazine-2-carboxamide |
| 161 | 3-amino-N-methyl-6-(3-{[(1S)-1,2,3,4-tetrahydronaphthalen-1-ylamino]carbonyl}phenyl)pyrazine-2-carboxamide |
| 162 | 3-amino-N-methyl-6-{3-[({[3,4,5-tris(methyloxy)phenyl]methyl}amino)carbonyl]phenyl}pyrazine-2-carboxamide |
| 163 | 3-amino-N-methyl-6-{3-[({(1R,2R)-2-[(phenylmethyl)oxy]cyclopentyl}amino)carbonyl]phenyl}pyrazine-2-carboxamide |
| 164 | 3-amino-N-methyl-6-{3-[({(1S,2S)-2-[(phenylmethyl)oxy]cyclopentyl}amino)carbonyl]phenyl}pyrazine-2-carboxamide |
| 165 | 3-amino-6-(3-cyanophenyl)-N-methylpyrazine-2-carboxamide |
| 166 | 3-amino-6-{3-[(cyclopentylcarbonyl)amino]phenyl}-N-methylpyrazine-2-carboxamide |
| 167 | 3-amino-6-(3-{[(4-cyanophenyl)carbonyl]amino}phenyl)-N-methylpyrazine-2-carboxamide |
| 168 | 3-amino-N-methyl-6-[3-({[(phenylmethyl)amino]carbonyl}amino)phenyl]pyrazine-2-carboxamide |
| 169 | 3-amino-N-methyl-6-(3-{[(naphthalen-2-ylmethyl)amino]carbonyl}phenyl)pyrazine-2-carboxamide |
| 170 | 3-amino-N-methyl-6-(3-{[(tetrahydrofuran-2-ylmethyl)amino]carbonyl}phenyl)pyrazine-2-carboxamide |

TABLE 10-continued

| # | Name |
|---|---|
| 171 | 3-amino-6-[3-({[(2-chloro-6-fluorophenyl)methyl]amino}carbonyl)phenyl]-N-methylpyrazine-2-carboxamide |
| 172 | 3-amino-6-{3-[({[3-fluoro-5-(trifluoromethyl)phenyl]methyl}amino)carbonyl]phenyl}-N-methylpyrazine-2-carboxamide |
| 173 | 3-amino-6-{3-[({2-[3,5-bis(methyloxy)phenyl]ethyl}amino)carbonyl]phenyl}-N-methylpyrazine-2-carboxamide |
| 174 | 3-amino-N-methyl-6-{3-[(2-phenylethyl)oxy]phenyl}pyrazine-2-carboxamide |
| 175 | 3-amino-N-methyl-6-(3-{[2-(4-methylpiperidin-1-yl)ethyl]oxy}phenyl)pyrazine-2-carboxamide |
| 176 | 3-amino-6-[3-({2-[4-(2-hydroxyethyl)piperidin-1-yl]ethyl}oxy)phenyl]-N-methylpyrazine-2-carboxamide |
| 177 | 3-amino-6-(3-{[2-(3-hydroxypyrrolidin-1-yl)ethyl]oxy}phenyl)-N-methylpyrazine-2-carboxamide |
| 178 | 3-amino-6-[3-({2-[ethyl(phenylmethyl)amino]ethyl}oxy)phenyl]-N-methylpyrazine-2-carboxamide |
| 179 | 3-amino-6-(3-{[2-(diethylamino)ethyl]oxy}phenyl)-N-methylpyrazine-2-carboxamide |
| 180 | 3-amino-6-(3-{[(biphenyl-2-ylmethyl)amino]carbonyl}phenyl)-N-methylpyrazine-2-carboxamide |
| 181 | 3-amino-N-methyl-6-(3-{[2-(4-phenylpiperazin-1-yl)ethyl]oxy}phenyl)pyrazine-2-carboxamide |
| 182 | 3-amino-6-(3-{[(biphenyl-4-ylmethyl)amino]carbonyl}phenyl)-N-methylpyrazine-2-carboxamide |
| 183 | 3-amino-N-methyl-6-[3-({2-[methyl(phenylmethyl)amino]ethyl}oxy)phenyl]pyrazine-2-carboxamide |
| 184 | 3-amino-N-methyl-6-{3-[({[4-(phenyloxy)phenyl]methyl}amino)carbonyl]phenyl}pyrazine-2-carboxamide |
| 185 | 3-amino-N-methyl-6-{3-[(2-morpholin-4-ylethyl)oxy]phenyl}pyrazine-2-carboxamide |
| 186 | 3-amino-6-[3-({2-[(cyclopropylmethyl)(propyl)amino]ethyl}oxy)phenyl]-N-methylpyrazine-2-carboxamide |
| 187 | 3-amino-N-methyl-6-[3-({2-[4-(phenylmethyl)piperidin-1-yl]ethyl}oxy)phenyl]pyrazine-2-carboxamide |
| 188 | 3-amino-N-methyl-6-{3-[(2-piperidin-1-ylethyl)oxy]phenyl}pyrazine-2-carboxamide |
| 189 | 3-amino-N-methyl-6-{3-[({[3-(phenyloxy)phenyl]methyl}amino)carbonyl]phenyl}pyrazine-2-carboxamide |
| 190 | 3-amino-6-(3-{[2-(4-ethylpiperazin-1-yl)ethyl]oxy}phenyl)-N-methylpyrazine-2-carboxamide |
| 191 | 3-amino-N-methyl-6-{3-[(2-pyrrolidin-1-ylethyl)oxy]phenyl}pyrazine-2-carboxamide |
| 192 | 3-amino-N-methyl-6-(3-{[2-(4-methylpiperazin-1-yl)ethyl]oxy}phenyl)pyrazine-2-carboxamide |
| 193 | 3-amino-6-[3-({2-[4-(2-hydroxyethyl)piperazin-1-yl]ethyl}oxy)phenyl]-N-methylpyrazine-2-carboxamide |
| 194 | 3-amino-6-(3-{[2-(3,4-dihydroisoquinolin-2(1H)-yl)ethyl]oxy}phenyl)-N-methylpyrazine-2-carboxamide |
| 195 | ethyl 4-{2-[(3-{5-amino-6-[(methylamino)carbonyl]pyrazin-2-yl}phenyl)oxy]ethyl}piperazine-1-carboxylate |
| 196 | 3-amino-N-methyl-6-[3-({[(3S)-1-(phenylmethyl)pyrrolidin-3-yl]amino}carbonyl)phenyl]pyrazine-2-carboxamide |
| 197 | 3-amino-N-methyl-6-[3-({[(3R)-1-(phenylmethyl)pyrrolidin-3-yl]amino}carbonyl)phenyl]pyrazine-2-carboxamide |
| 198 | 3-amino-N-methyl-6-[3-({[2-(phenyloxy)ethyl]amino}carbonyl)phenyl]pyrazine-2-carboxamide |
| 199 | 3-amino-N-methyl-6-{3-[({2-[4-(phenylmethyl)piperazin-1-yl]ethyl}amino)carbonyl]phenyl}pyrazine-2-carboxamide |
| 200 | 3-amino-N-methyl-6-{3-[({[1-(phenylmethyl)piperidin-4-yl]methyl}amino)carbonyl]phenyl}pyrazine-2-carboxamide |
| 201 | 3-amino-6-(3-{[(furan-3-ylmethyl)amino]carbonyl}phenyl)-N-methylpyrazine-2-carboxamide |
| 202 | 3-amino-6-(3-{[(2,3-dihydro-1,4-benzodioxin-2-ylmethyl)amino]carbonyl}phenyl)-N-methylpyrazine-2-carboxamide |
| 203 | 3-amino-6-(3-{[(furan-2-ylmethyl)amino]carbonyl}phenyl)-N-methylpyrazine-2-carboxamide |
| 204 | 3-amino-N-methyl-6-{3-[({[4-(phenylmethyl)morpholin-2-yl]methyl}amino)carbonyl]phenyl}pyrazine-2-carboxamide |
| 205 | 3-amino-6-(3-{[(2,3-dihydro-1,4-benzodioxin-6-ylmethyl)amino]carbonyl}phenyl)-N-methylpyrazine-2-carboxamide |
| 206 | 3-amino-6-(3-{[(2,3-dihydro-1,4-benzodioxin-6-ylmethyl)amino]carbonyl}phenyl)-N-methylpyrazine-2-carboxamide |
| 207 | 3-amino-6-(3-{[(2,3-dihydro-1-benzofuran-5-ylmethyl)amino]carbonyl}phenyl)-N-methylpyrazine-2-carboxamide |
| 208 | 3-amino-6-[3-({[(6-fluoro-4H-1,3-benzodioxin-8-yl)methyl]amino}carbonyl)phenyl]-N-methylpyrazine-2-carboxamide |

TABLE 10-continued

| # | Name |
|---|------|
| 209 | 3-amino-6-(3-{[(2,4-dichlorophenyl)acetyl]amino}phenyl)-N-methylpyrazine-2-carboxamide |
| 210 | 3-amino-6-(3-{[(3,4-dichlorophenyl)acetyl]amino}phenyl)-N-methylpyrazine-2-carboxamide |
| 211 | 3-amino-N-methyl-6-[3-({[4-(trifluoromethyl)phenyl]acetyl}amino)phenyl]pyrazine-2-carboxamide |
| 212 | 3-amino-6-[3-({[(3,5-dimethylphenyl)methyl]amino}carbonyl)phenyl]-N-methylpyrazine-2-carboxamide |
| 213 | 3-amino-6-[3-({[(5-chloro-2-methylphenyl)methyl]amino}carbonyl)phenyl]-N-methylpyrazine-2-carboxamide |
| 214 | 3-amino-6-[3-({[(2,4-dimethylphenyl)methyl]amino}carbonyl)phenyl]-N-methylpyrazine-2-carboxamide |
| 215 | 3-amino-6-[3-({[(2,3-difluorophenyl)methyl]amino}carbonyl)phenyl]-N-methylpyrazine-2-carboxamide |
| 216 | 3-amino-N-methyl-6-{3-[({[4-(methylthio)phenyl]methyl}amino)carbonyl]phenyl}pyrazine-2-carboxamide |
| 217 | 3-amino-N-methyl-6-(3-{[(2-methylpropyl)amino]carbonyl}phenyl)pyrazine-2-carboxamide |
| 218 | 3-amino-N-methyl-6-(3-{[({3-[(trifluoromethyl)oxy]phenyl}methyl)amino]carbonyl}phenyl)pyrazine-2-carboxamide |
| 219 | 3-amino-6-(3-{[(cyclopropylmethyl)amino]carbonyl}phenyl)-N-methylpyrazine-2-carboxamide |
| 220 | 3-amino-6-{3-[(cyclopentylamino)carbonyl]phenyl}-N-methylpyrazine-2-carboxamide |
| 221 | 3-amino-N-methyl-6-(3-{[(4-methylphenyl)amino]carbonyl}phenyl)pyrazine-2-carboxamide |
| 222 | 3-amino-N-methyl-6-[3-({[4-(methyloxy)phenyl]amino}carbonyl)phenyl]pyrazine-2-carboxamide |
| 223 | 3-amino-6-(3-{[(1,3-benzodioxol-5-ylmethyl)amino]carbonyl}phenyl)-N-methylpyrazine-2-carboxamide |
| 224 | 3-amino-6-(3-{[(biphenyl-3-ylmethyl)amino]carbonyl}phenyl)-N-methylpyrazine-2-carboxamide |
| 225 | 3-amino-N-methyl-6-(3-{[(1-methyl-1-phenylethyl)amino]carbonyl}phenyl)pyrazine-2-carboxamide |
| 226 | 3-amino-6-[3-({[(2,4-difluorophenyl)methyl]amino}carbonyl)phenyl]-N-methylpyrazine-2-carboxamide |
| 227 | 3-amino-N-methyl-6-(3-{[({4-[(trifluoromethyl)oxy]phenyl}methyl)amino]carbonyl}phenyl)pyrazine-2-carboxamide |
| 228 | 3-amino-6-{3-[({[4-fluoro-3-(trifluoromethyl)phenyl]methyl}amino)carbonyl]phenyl}-N-methylpyrazine-2-carboxamide |
| 229 | 3-amino-6-{3-[({[4-chloro-3-(trifluoromethyl)phenyl]methyl}amino)carbonyl]phenyl}-N-methylpyrazine-2-carboxamide |
| 230 | 3-amino-6-[3-({[(4-aminophenyl)methyl]amino}carbonyl)phenyl]-N-methylpyrazine-2-carboxamide |
| 231 | 3-amino-6-[3-({[(2-aminophenyl)methyl]amino}carbonyl)phenyl]-N-methylpyrazine-2-carboxamide |
| 232 | 3-amino-6-[3-({[(3-aminophenyl)methyl]amino}carbonyl)phenyl]-N-methylpyrazine-2-carboxamide |
| 233 | 3-amino-N-methyl-6-pyrimidin-5-ylpyrazine-2-carboxamide |
| 234 | 3-amino-N-methyl-6-[3-(methylsulfonyl)phenyl]pyrazine-2-carboxamide |
| 235 | 3-amino-N-methyl-6-[4-(tetrahydro-2H-pyran-2-yloxy)phenyl]pyrazine-2-carboxamide |
| 236 | 3-amino-6-(4-hydroxyphenyl)-N-methylpyrazine-2-carboxamide |
| 237 | 3-amino-6-{3-[({[4-(aminosulfonyl)phenyl]methyl}amino)carbonyl]phenyl}-N-methylpyrazine-2-carboxamide |
| 238 | 3-amino-6-{3-[({[4-(dimethylamino)phenyl]methyl}amino)carbonyl]phenyl}-N-methylpyrazine-2-carboxamide |
| 239 | 3-amino-6-[3-({[(3-bromophenyl)methyl]amino}carbonyl)phenyl]-N-methylpyrazine-2-carboxamide |
| 240 | 3-amino-6-(4-chloro-3-{[(phenylmethyl)amino]carbonyl}phenyl)-N-methylpyrazine-2-carboxamide |
| 241 | methyl 3-{5-amino-6-[(cyclopropylamino)carbonyl]pyrazin-2-yl}benzoate |
| 242 | methyl 3-{5-amino-6-[(ethylamino)carbonyl]pyrazin-2-yl}benzoate |
| 243 | 3-amino-6-[3-({[(2,3-dimethylphenyl)methyl]amino}carbonyl)phenyl]-N-methylpyrazine-2-carboxamide |
| 244 | 3-amino-6-{3-[({[4-hydroxy-3-(methyloxy)phenyl]methyl}amino)carbonyl]phenyl}-N-methylpyrazine-2-carboxamide |
| 245 | 3-amino-6-[3-({[(4-chloro-2-methylphenyl)methyl]amino}carbonyl)phenyl]-N-methylpyrazine-2-carboxamide |
| 246 | 3-amino-6-{3-[({[2-(ethyloxy)phenyl]methyl}amino)carbonyl]phenyl}-N-methylpyrazine-2-carboxamide |
| 247 | 3-amino-6-{3-[({[2-chloro-6-(phenyloxy)phenyl]methyl}amino)carbonyl]phenyl}-N-methylpyrazine-2-carboxamide |

TABLE 10-continued

| # | Name |
|---|---|
| 248 | 3-amino-6-[3-({[(2,5-dichlorophenyl)methyl]amino}carbonyl)phenyl]-N-methylpyrazine-2-carboxamide |
| 249 | 3-amino-6-{3-[({[2,6-bis(methyloxy)phenyl]methyl}amino)carbonyl]phenyl}-N-methylpyrazine-2-carboxamide |
| 250 | 3-amino-6-[3-({[(2-chloro-6-methylphenyl)methyl]amino}carbonyl)phenyl]-N-methylpyrazine-2-carboxamide |
| 251 | 3-amino-N-methyl-6-[3-({[(2,4,5-trifluorophenyl)methyl]amino}carbonyl)phenyl]pyrazine-2-carboxamide |
| 252 | 3-amino-6-(3-{[(2,2-dimethylpropyl)amino]carbonyl}phenyl)-N-methylpyrazine-2-carboxamide |
| 253 | 3-amino-6-(3-{[(cyclopentylmethyl)amino]carbonyl}phenyl)-N-methylpyrazine-2-carboxamide |
| 254 | 3-amino-6-{3-[({[3,5-bis(methyloxy)phenyl]methyl}amino)carbonyl]phenyl}-N-methylpyrazine-2-carboxamide |
| 255 | 3-amino-N-methyl-6-{3-[({[4-(methylsulfonyl)phenyl]methyl}amino)carbonyl]phenyl}pyrazine-2-carboxamide |
| 256 | 3-amino-6-[3-({[(5-bromo-2-fluorophenyl)methyl]amino}carbonyl)phenyl]-N-methylpyrazine-2-carboxamide |
| 257 | 3-amino-6-[3-({[(3-bromo-4-fluorophenyl)methyl]amino}carbonyl)phenyl]-N-methylpyrazine-2-carboxamide |
| 258 | 3-amino-N-methyl-6-{3-[({[2,4,6-tris(methyloxy)phenyl]methyl}amino)carbonyl]phenyl}pyrazine-2-carboxamide |
| 259 | 3-amino-N-methyl-6-[3-({[(3-methylphenyl)methyl]amino}carbonyl)phenyl]pyrazine-2-carboxamide |
| 260 | 3-amino-6-[3-({[(4-bromo-2-fluorophenyl)methyl]amino}carbonyl)phenyl]-N-methylpyrazine-2-carboxamide |
| 261 | 3-amino-6-[3-({[(2,5-dimethylphenyl)methyl]amino}carbonyl)phenyl]-N-methylpyrazine-2-carboxamide |
| 262 | 3-amino-6-{3-[({[3,5-bis(trifluoromethyl)phenyl]methyl}amino)carbonyl]phenyl}-N-methylpyrazine-2-carboxamide |
| 263 | 3-amino-6-(3-{[(2,2-diphenylethyl)amino]carbonyl}phenyl)-N-methylpyrazine-2-carboxamide |
| 264 | 3-amino-N-methyl-6-(3-thienyl)pyrazine-2-carboxamide |
| 265 | 3-amino-N-methyl-6-(3-{[(phenylmethyl)amino]sulfonyl}phenyl)pyrazine-2-carboxamide |
| 266 | 5,5'-diamino-N,N'-dimethyl-2,2'-bipyrazine-6,6'-dicarboxamide |
| 267 | 3-amino-6-(1H-indol-5-yl)-N-methylpyrazine-2-carboxamide |
| 268 | 3-amino-N-methyl-6-(2-thienyl)pyrazine-2-carboxamide |
| 269 | 3-amino-N-methyl-6-pyridin-4-ylpyrazine-2-carboxamide |
| 270 | 3-amino-N-cyclopropyl-6-(3-{[(phenylmethyl)amino]carbonyl}phenyl)pyrazine-2-carboxamide |
| 271 | 3-amino-6-[3-({[(2-chloro-6-fluorophenyl)methyl]amino}carbonyl)phenyl]-N-cyclopropylpyrazine-2-carboxamide |
| 272 | 3-amino-N-ethyl-6-(3-{[(phenylmethyl)amino]carbonyl}phenyl)pyrazine-2-carboxamide |
| 273 | 3-amino-6-[3-({[(2-chloro-6-fluorophenyl)methyl]amino}carbonyl)phenyl]-N-ethylpyrazine-2-carboxamide |
| 274 | 3-amino-6-[3-({[(2,3-dichlorophenyl)methyl]amino}carbonyl)phenyl]-N-methylpyrazine-2-carboxamide |
| 275 | 3-amino-6-[3-({[(4-chloro-2-fluorophenyl)methyl]amino}carbonyl)phenyl]-N-methylpyrazine-2-carboxamide |
| 276 | 3-amino-6-[3-({[(3,5-dichlorophenyl)methyl]amino}carbonyl)phenyl]-N-methylpyrazine-2-carboxamide |
| 277 | 3-amino-6-[3-({[(5-chloro-2-fluorophenyl)methyl]amino}carbonyl)phenyl]-N-methylpyrazine-2-carboxamide |
| 278 | 3-amino-6-{3-[(cyclopropylamino)carbonyl]phenyl}-N-methylpyrazine-2-carboxamide |
| 279 | 3-amino-6-[3-({[(3,4-dichlorophenyl)methyl]amino}carbonyl)phenyl]-N-methylpyrazine-2-carboxamide |
| 280 | 3-amino-6-[3-({[(4'-fluorobiphenyl-2-yl)methyl]amino}carbonyl)phenyl]-N-methylpyrazine-2-carboxamide |
| 281 | 3-amino-N-methyl-6-[3-({[(2,3,4-trifluorophenyl)methyl]amino}carbonyl)phenyl]pyrazine-2-carboxamide |
| 282 | 3-amino-6-[3-({[(3-chloro-2,6-difluorophenyl)methyl]amino}carbonyl)phenyl]-N-methylpyrazine-2-carboxamide |
| 283 | 3-amino-6-[3-({[(3-chloro-2,6-difluorophenyl)methyl]amino}carbonyl)phenyl]-N-methylpyrazine-2-carboxamide |
| 284 | 3-amino-6-{3-[(9H-fluoren-9-ylamino)carbonyl]phenyl}-N-methylpyrazine-2-carboxamide |
| 285 | 3-amino-N-methyl-6-[3-({[(2-methylphenyl)methyl]amino}carbonyl)phenyl]pyrazine-2-carboxamide |
| 286 | 3-amino-6-[3-({[(3,4-dimethylphenyl)methyl]amino}carbonyl)phenyl]-N-methylpyrazine-2-carboxamide |
| 287 | 3-amino-6-[3-({[(5-fluoro-2-methylphenyl)methyl]amino}carbonyl)phenyl]-N-methylpyrazine-2-carboxamide |
| 288 | 3-amino-6-[3-({[(3,4-difluorophenyl)methyl]amino}carbonyl)phenyl]-N-methylpyrazine-2-carboxamide |

TABLE 10-continued

| # | Name |
|---|---|
| 289 | 3-amino-6-[3-({[(2-fluorophenyl)methyl]amino}carbonyl)phenyl]-N-methylpyrazine-2-carboxamide |
| 290 | 3-amino-N-methyl-6-{3-[({[4-(4-methylpiperazin-1-yl)phenyl]methyl}amino)carbonyl]phenyl}pyrazine-2-carboxamide |
| 291 | 3-amino-6-(4-fluoro-3-{[(phenylmethyl)amino]carbonyl}phenyl)-N-methylpyrazine-2-carboxamide |
| 292 | 3-amino-N-methyl-6-[3-({[(2,4,6-trichlorophenyl)methyl]amino}carbonyl)phenyl]pyrazine-2-carboxamide |
| 293 | 3-amino-6-[3-({[(3-chloro-2-methylphenyl)methyl]amino}carbonyl)phenyl]-N-methylpyrazine-2-carboxamide |
| 294 | 3-amino-6-{3-[({[2,5-bis(methyloxy)phenyl]methyl}amino)carbonyl]phenyl}-N-methylpyrazine-2-carboxamide |
| 295 | 3-amino-6-[3-({[(3-fluoro-4-methylphenyl)methyl]amino}carbonyl)phenyl]-N-methylpyrazine-2-carboxamide |
| 296 | 3-amino-6-[3-({[(2-chloro-6-fluoro-3-methylphenyl)methyl]amino}carbonyl)phenyl]-N-methylpyrazine-2-carboxamide |
| 297 | 3-amino-6-[3-({[(2-chloro-3,6-difluorophenyl)methyl]amino}carbonyl)phenyl]-N-methylpyrazine-2-carboxamide |
| 298 | 3-amino-6-[3-({[(2,3-difluoro-4-methylphenyl)methyl]amino}carbonyl)phenyl]-N-methylpyrazine-2-carboxamide |
| 299 | 3-amino-6-[3-({[(4-fluoro-3-methylphenyl)methyl]amino}carbonyl)phenyl]-N-methylpyrazine-2-carboxamide |
| 300 | 3-amino-6-[3-({[(3-chloro-2-fluorophenyl)methyl]amino}carbonyl)phenyl]-N-methylpyrazine-2-carboxamide |
| 301 | 3-amino-6-[3-({[(6-chloro-2-fluoro-3-methylphenyl)methyl]amino}carbonyl)phenyl]-N-methylpyrazine-2-carboxamide |
| 302 | 3-amino-6-[3-({[(4-iodophenyl)methyl]amino}carbonyl)phenyl]-N-methylpyrazine-2-carboxamide |
| 303 | 3-amino-6-[3-({[(3-chloro-4-methylphenyl)methyl]amino}carbonyl)phenyl]-N-methylpyrazine-2-carboxamide |
| 304 | 3-amino-6-[3-({[(4-bromophenyl)methyl]amino}carbonyl)phenyl]-N-methylpyrazine-2-carboxamide |
| 305 | 3-amino-6-[3-({[(2-bromophenyl)methyl]amino}carbonyl)phenyl]-N-methylpyrazine-2-carboxamide |
| 306 | 3-amino-N-methyl-6-[3-({[(2,3,6-trifluorophenyl)methyl]amino}carbonyl)phenyl]pyrazine-2-carboxamide |
| 307 | 3-amino-N-methyl-6-[3-({[(2,3,6-trifluorophenyl)methyl]amino}carbonyl)phenyl]pyrazine-2-carboxamide |
| 308 | 3-amino-N-methyl-6-(3-{[(phenylcarbonyl)amino]methyl}phenyl)pyrazine-2-carboxamide |
| 309 | 3-amino-6-[3-({[(4-chlorophenyl)carbonyl]amino}methyl)phenyl]-N-methylpyrazine-2-carboxamide |
| 310 | 3-amino-6-[3-({[(2,5-difluorophenyl)carbonyl]amino}methyl)phenyl]-N-methylpyrazine-2-carboxamide |
| 311 | 3-amino-N-methyl-6-(3-{[(naphthalen-2-ylcarbonyl)amino]methyl}phenyl)pyrazine-2-carboxamide |
| 312 | 3-amino-N-methyl-6-(3-{[(phenylmethyl)thio]methyl}phenyl)pyrazine-2-carboxamide |
| 313 | 3-amino-N-methyl-6-(3-{[(phenylmethyl)sulfonyl]methyl}phenyl)pyrazine-2-carboxamide |
| 314 | 3-amino-N-methyl-6-(3-{[(phenylmethyl)oxy]methyl}phenyl)pyrazine-2-carboxamide |
| 315 | 3-amino-N-methyl-6-(3-{[(phenylmethyl)amino]methyl}phenyl)pyrazine-2-carboxamide |
| 316 | 3-amino-N-methyl-6-[3-({[(3,4,5-trifluorophenyl)methyl]amino}carbonyl)phenyl]pyrazine-2-carboxamide |
| 317 | 9H-fluoren-9-ylmethyl (3-{5-amino-6-[(methylamino)carbonyl]pyrazin-2-yl}phenyl)carbamate |
| 318 | phenylmethyl (3-{5-amino-6-[(methylamino)carbonyl]pyrazin-2-yl}phenyl)carbamate |
| 319 | ethyl (3-{5-amino-6-[(methylamino)carbonyl]pyrazin-2-yl}phenyl)carbamate |
| 320 | 3-amino-6-[3-({[(3,4-dichlorophenyl)carbonyl]amino}methyl)phenyl]-N-methylpyrazine-2-carboxamide |
| 321 | 1,1-dimethylethyl (3-{5-amino-6-[(methylamino)carbonyl]pyrazin-2-yl}phenyl)carbamate |
| 322 | (1R,2S,5R)-5-methyl-2-(1-methylethyl)cyclohexyl (3-{5-amino-6-[(methylamino)carbonyl]pyrazin-2-yl}phenyl)carbamate |
| 323 | 3-amino-6-[3-({[(4-hydroxyphenyl)methyl]amino}carbonyl)phenyl]-N-methylpyrazine-2-carboxamide |
| 324 | 3-amino-N-methyl-6-(3-{[({4-[(2-morpholin-4-ylethyl)oxy]phenyl}methyl)amino]carbonyl}phenyl)pyrazine-2-carboxamide |
| 325 | 3-amino-N-methyl-6-{3-[({[2-(methyloxy)phenyl]methyl}amino)carbonyl]phenyl}pyrazine-2-carboxamide |
| 326 | 3-amino-6-[3-({[(3-hydroxyphenyl)methyl]amino}carbonyl)phenyl]-N-methylpyrazine-2-carboxamide |
| 327 | 3-amino-6-[3-({[(2-hydroxyphenyl)methyl]amino}carbonyl)phenyl]-N-methylpyrazine-2-carboxamide |

TABLE 10-continued

| # | Name |
|---|------|
| 328 | 3-amino-N-methyl-6-{3-[(2-phenylhydrazino)carbonyl]phenyl}pyrazine-2-carboxamide |
| 329 | 3-amino-N-(2-hydroxyethyl)-6-(3-methylphenyl)pyrazine-2-carboxamide |
| 330 | 3-amino-N-methyl-6-(3-{[(phenylacetyl)amino]methyl}phenyl)pyrazine-2-carboxamide |
| 331 | 3-amino-6-[3-({[(4-chlorophenyl)acetyl]amino}methyl)phenyl]-N-methylpyrazine-2-carboxamide |
| 332 | 3-amino-6-(3-{[(biphenyl-4-ylcarbonyl)amino]methyl}phenyl)-N-methylpyrazine-2-carboxamide |
| 333 | 3-amino-6-{3-[({[2-chloro-5-(trifluoromethyl)phenyl]carbonyl}amino)methyl]phenyl}-N-methylpyrazine-2-carboxamide |
| 334 | N-[(3-{5-amino-6-[(methylamino)carbonyl]pyrazin-2-yl}phenyl)methyl]-1H-indole-2-carboxamide |
| 335 | 3-amino-6-[3-({[(3-hydroxypyridin-2-yl)carbonyl]amino}methyl)phenyl]-N-methylpyrazine-2-carboxamide |
| 336 | 3-amino-6-(3-{[(1H-indol-3-ylacetyl)amino]methyl}phenyl)-N-methylpyrazine-2-carboxamide |
| 337 | 3-amino-6-[3-({[[(2,5-difluorophenyl)methyl]amino}carbonyl)phenyl]-N-methylpyrazine-2-carboxamide |
| 338 | 3-amino-6-[3-({[[(2,6-difluorophenyl)methyl]amino}carbonyl)phenyl]-N-methylpyrazine-2-carboxamide |
| 339 | 3-amino-6-[3-({[[(3,5-difluorophenyl)methyl]amino}carbonyl)phenyl]-N-methylpyrazine-2-carboxamide |
| 340 | 3-amino-6-[3-({[(3-iodophenyl)methyl]amino}carbonyl)phenyl]-N-methylpyrazine-2-carboxamide |
| 341 | 3-amino-N-methyl-6-[3-({[(2-morpholin-4-ylphenyl)methyl]amino}carbonyl)phenyl]pyrazine-2-carboxamide |
| 342 | 3-amino-N-methyl-6-(3-{[({3-[(2-morpholin-4-ylethyl)oxy]phenyl}methyl)amino]carbonyl}phenyl)pyrazine-2-carboxamide |
| 343 | 3-amino-N-methyl-6-[3-({[(4-morpholin-4-ylphenyl)methyl]amino}carbonyl)phenyl]pyrazine-2-carboxamide |
| 344 | 3-amino-N-methyl-6-[3-({[(3-morpholin-4-ylphenyl)methyl]amino}carbonyl)phenyl]pyrazine-2-carboxamide |
| 345 | 3-amino-N-methyl-6-{3-[({[4-(1-methylethyl)phenyl]methyl}amino)carbonyl]phenyl}pyrazine-2-carboxamide |
| 346 | 3-amino-N-methyl-6-(3-{[({[4-(1-methylethyl)phenyl]oxy}acetyl)amino]methyl}phenyl)pyrazine-2-carboxamide |
| 347 | 3-amino-6-{3-[({[[(4-aminophenyl)thio]acetyl}amino)methyl]phenyl}-N-methylpyrazine-2-carboxamide |
| 348 | 3-amino-N-methyl-6-(4-(methyloxy)-3-{[(phenylmethyl)amino]carbonyl}phenyl)pyrazine-2-carboxamide |
| 349 | 3-amino-N-methyl-6-(5-{[(phenylmethyl)amino]carbonyl}pyridin-3-yl)pyrazine-2-carboxamide |
| 350 | 3-amino-6-[3-({[(4-iodophenyl)carbonyl]amino}methyl)phenyl]-N-methylpyrazine-2-carboxamide |
| 351 | 3-amino-N-methyl-6-[3-({[(4-pentylphenyl)carbonyl]amino}methyl)phenyl]pyrazine-2-carboxamide |
| 352 | 3-amino-6-(3-{[(1,3-benzodioxol-5-ylcarbonyl)amino]methyl}phenyl)-N-methylpyrazine-2-carboxamide |
| 353 | 3-amino-6-{3-[({[4-(1,1-dimethylethyl)phenyl]methyl}amino)carbonyl]phenyl}-N-methylpyrazine-2-carboxamide |
| 354 | 3-amino-N-methyl-6-(3-{[({1-[5-(trifluoromethyl)pyrimidin-2-yl]piperidin-4-yl}carbonyl)amino]methyl}phenyl)pyrazine-2-carboxamide |
| 355 | 3-amino-N-methyl-6-[3-({[(2-piperidin-1-ylphenyl)methyl]amino}carbonyl)phenyl]pyrazine-2-carboxamide |
| 356 | 3-amino-N-methyl-6-{3-[({[2-(methylthio)phenyl]methyl}amino)carbonyl]phenyl}pyrazine-2-carboxamide |
| 357 | 1,1-dimethylethyl (3R)-3-{[(3-{5-amino-6-[(methylamino)carbonyl]pyrazin-2-yl}phenyl)carbonyl]amino}pyrrolidine-1-carboxylate |
| 358 | 3-amino-N-methyl-6-(3-{[(3R)-pyrrolidin-3-ylamino]carbonyl}phenyl)pyrazine-2-carboxamide |
| 359 | 3-{[(4-chlorophenyl)methyl]amino}-6-{3-[({(3R)-1-[(4-chlorophenyl)methyl]pyrrolidin-3-yl}amino)carbonyl]phenyl}-N-methylpyrazine-2-carboxamide |
| 360 | 3-amino-6-{3-[({(3R)-1-[(2,4-dichlorophenyl)methyl]pyrrolidin-3-yl}amino)carbonyl]phenyl}-N-methylpyrazine-2-carboxamide |
| 361 | N-methyl-3-({[3-(methyloxy)phenyl]methyl}amino)-6-(3-{[((3R)-1-{[3-(methyloxy)phenyl]methyl}pyrrolidin-3-yl)amino]carbonyl}phenyl)pyrazine-2-carboxamide |
| 362 | 3-amino-6-{3-[({(3R)-1-[(2,6-dichlorophenyl)methyl]pyrrolidin-3-yl}amino)carbonyl]phenyl}-N-methylpyrazine-2-carboxamide |
| 363 | N-methyl-3-[(phenylmethyl)amino]-6-(3-{[[(3R)-1-(phenylmethyl)pyrrolidin-3-yl]amino}carbonyl]phenyl)pyrazine-2-carboxamide |
| 364 | 1,1-dimethylethyl 3-({[(3-{5-amino-6-[(methylamino)carbonyl]pyrazin-2-yl}phenyl)carbonyl]amino}methyl)pyrrolidine-1-carboxylate |

TABLE 10-continued

| # | Name |
|---|---|
| 365 | 1,1-dimethylethyl 2-({[(3-{5-amino-6-[(methylamino)carbonyl]pyrazin-2-yl}phenyl)carbonyl]amino}methyl)pyrrolidine-1-carboxylate |
| 366 | 3-amino-N-methyl-6-(3-{[(pyrrolidin-3-ylmethyl)amino]carbonyl}phenyl)pyrazine-2-carboxamide |
| 367 | 3-amino-N-methyl-6-(3-{[(pyrrolidin-2-ylmethyl)amino]carbonyl}phenyl)pyrazine-2-carboxamide |
| 368 | 3-amino-6-(2-fluoro-5-{[(phenylmethyl)amino]carbonyl}phenyl)-N-methylpyrazine-2-carboxamide |
| 369 | 3-amino-6-{3-[(1,3-benzodioxol-5-ylacetyl)amino]phenyl}-N-methylpyrazine-2-carboxamide |
| 370 | 3-amino-6-[3-({[(2-chloro-4-fluorophenyl)methyl]amino}carbonyl)phenyl]-N-methylpyrazine-2-carboxamide |
| 371 | 3-amino-6-{3-[({[3,4-bis(methyloxy)phenyl]methyl}amino)carbonyl]phenyl}-N-methylpyrazine-2-carboxamide |
| 372 | 3-amino-N-methyl-6-{3-[(phenylmethyl)amino]phenyl}pyrazine-2-carboxamide |
| 373 | 3-amino-N-methyl-6-(3-{[({2-[(2-morpholin-4-ylethyl)oxy]phenyl}methyl)amino]carbonyl}phenyl)pyrazine-2-carboxamide |
| 374 | 3-amino-N-methyl-6-{3-[({[4-(1-methylethyl)phenyl]carbonyl}amino)methyl]phenyl}pyrazine-2-carboxamide |
| 375 | 3-amino-6-[3-({[(4-butylphenyl)methyl]amino}carbonyl)phenyl]-N-methylpyrazine-2-carboxamide |
| 376 | 3-amino-N-methyl-6-{3-[({[4-(1,2,3-thiadiazol-4-yl)phenyl]methyl}amino)carbonyl]phenyl}pyrazine-2-carboxamide |
| 377 | 3-amino-N-methyl-6-{3-[({[4-(2-thienyl)phenyl]methyl}amino)carbonyl]phenyl}pyrazine-2-carboxamide |
| 378 | 3-amino-6-{3-[({[4-(1,1-dimethylethyl)phenyl]carbonyl}amino)methyl]phenyl}-N-methylpyrazine-2-carboxamide |
| 379 | 3-amino-N-methyl-6-{3-[({[4-(1H-pyrazol-1-yl)phenyl]methyl}amino)carbonyl]phenyl}pyrazine-2-carboxamide |
| 380 | 3-amino-6-(3-{[(3,4-dihydro-2H-1,4-benzoxazin-6-ylmethyl)amino]carbonyl}phenyl)-N-methylpyrazine-2-carboxamide |
| 381 | 3-amino-6-[3-({[(2-amino-6-fluorophenyl)methyl]amino}carbonyl)phenyl]-N-methylpyrazine-2-carboxamide |
| 382 | 3-amino-6-(3-{[(biphenyl-4-ylmethyl)amino]methyl}phenyl)-N-methylpyrazine-2-carboxamide |
| 383 | 3-amino-6-(3-{[(biphenyl-2-ylmethyl)amino]methyl}phenyl)-N-methylpyrazine-2-carboxamide |
| 384 | 3-amino-6-(3-{[(biphenyl-3-ylmethyl)amino]methyl}phenyl)-N-methylpyrazine-2-carboxamide |
| 385 | 3-amino-N-methyl-6-{3-[({[1-(phenylmethyl)pyrrolidin-2-yl]methyl}amino)carbonyl]phenyl}pyrazine-2-carboxamide |
| 386 | 3-amino-6-(3-{[(3,4-dihydro-2H-1,4-benzoxazin-6-ylmethyl)amino]methyl}phenyl)-N-methylpyrazine-2-carboxamide |
| 387 | 3-amino-6-[3-({[(2,4-difluorophenyl)methyl]amino}methyl)phenyl]-N-methylpyrazine-2-carboxamide |
| 388 | 3-amino-6-[3-({[(2,5-difluorophenyl)methyl]amino}methyl)phenyl]-N-methylpyrazine-2-carboxamide |
| 389 | 3-amino-6-[3-({[(2,3-difluorophenyl)methyl]amino}methyl)phenyl]-N-methylpyrazine-2-carboxamide |
| 390 | 3-amino-N-methyl-6-[3-({[(2-pyridin-4-ylphenyl)methyl]amino}carbonyl)phenyl]pyrazine-2-carboxamide |
| 391 | 3-amino-N-methyl-6-[3-({[(2-pyridin-3-ylphenyl)methyl]amino}carbonyl)phenyl]pyrazine-2-carboxamide |
| 392 | 3-amino-N-methyl-6-{3-[({[4-(methylsulfonyl)phenyl]methyl}amino)methyl]phenyl}pyrazine-2-carboxamide |
| 393 | 3-amino-6-(3-{[(2,2-diphenylethyl)amino]methyl}phenyl)-N-methylpyrazine-2-carboxamide |
| 394 | 3-amino-N-methyl-6-{3-[({[1-(phenylmethyl)pyrrolidin-3-yl]methyl}amino)carbonyl]phenyl}pyrazine-2-carboxamide |
| 395 | 3-amino-N-methyl-6-{3-[({[3-(phenyloxy)phenyl]methyl}amino)methyl]phenyl}pyrazine-2-carboxamide |
| 396 | 3-amino-6-[3-({[(4-aminophenyl)methyl]amino}methyl)phenyl]-N-methylpyrazine-2-carboxamide |
| 397 | 3-amino-N-methyl-6-{3-[({[4-(phenyloxy)phenyl]methyl}amino)methyl]phenyl}pyrazine-2-carboxamide |
| 398 | 3-amino-6-{3-[({[2,6-bis(methyloxy)phenyl]methyl}amino)methyl]phenyl}-N-methylpyrazine-2-carboxamide |
| 399 | 3-amino-6-[3-({[(2-fluorophenyl)methyl]amino}methyl)phenyl]-N-methylpyrazine-2-carboxamide |
| 400 | 3-amino-6-[5-({[(2,6-difluorophenyl)methyl]amino}carbonyl)pyridin-3-yl]-N-methylpyrazine-2-carboxamide |
| 401 | 3-amino-6-(5-{[(biphenyl-2-ylmethyl)amino]carbonyl}pyridin-3-yl)-N-methylpyrazine-2-carboxamide |
| 402 | 3-amino-6-[3-({[(2,6-difluorophenyl)methyl]amino}methyl)phenyl]-N-methylpyrazine-2-carboxamide |
| 403 | 3-amino-6-(3-{[(2,3-dihydro-1,4-benzodioxin-6-ylmethyl)amino]methyl}phenyl)-N-methylpyrazine-2-carboxamide |

TABLE 10-continued

| # | Name |
|---|---|
| 404 | 3-amino-N-methyl-6-[3-({[(2-piperidin-1-yl)phenyl]methyl}amino}methyl)phenyl]pyrazine-2-carboxamide |
| 405 | 3-amino-6-{3-[({[4-fluoro-2-(trifluoromethyl)phenyl]methyl}amino)carbonyl]phenyl}-N-methylpyrazine-2-carboxamide |
| 406 | 3-amino-N-methyl-6-{3-[({[6-(trifluoromethyl)pyridin-3-yl]methyl}amino)carbonyl]phenyl}pyrazine-2-carboxamide |
| 407 | 3-amino-6-[3-(1H-benzimidazol-2-yl)phenyl]-N-methylpyrazine-2-carboxamide |
| 408 | 3-amino-6-[3-({[(2,5-dichlorophenyl)methyl]amino}methyl)phenyl]-N-methylpyrazine-2-carboxamide |
| 409 | 3-amino-6-[3-({[(3,5-dichlorophenyl)methyl]amino}methyl)phenyl]-N-methylpyrazine-2-carboxamide |
| 410 | 3-amino-N-methyl-6-{3-[(2-phenylethyl)amino]phenyl}pyrazine-2-carboxamide |
| 411 | 3-amino-6-(5-{[(2,3-dihydro-1,4-benzodioxin-6-ylmethyl)amino]carbonyl}pyridin-3-yl)-N-methylpyrazine-2-carboxamide |
| 412 | 3-amino-N-methyl-6-[3-({[2-(phenylamino)ethyl]amino}carbonyl)phenyl]pyrazine-2-carboxamide |
| 413 | 3-amino-6-[3-({[(4-ethylphenyl)methyl]amino}carbonyl)phenyl]-N-methylpyrazine-2-carboxamide |
| 414 | 3-amino-N-methyl-6-[3-({[(4-pyridin-3-ylphenyl)methyl]amino}carbonyl)phenyl]pyrazine-2-carboxamide |
| 415 | 3-amino-6-{3-[(2,3-dihydro-1H-inden-2-ylamino)methyl]phenyl}-N-methylpyrazine-2-carboxamide |
| 416 | 3-amino-6-[3-(1,3-dihydro-2H-isoindol-2-ylmethyl)phenyl]-N-methylpyrazine-2-carboxamide |
| 417 | 3-amino-6-(3-{[(1R)-2,3-dihydro-1H-inden-1-ylamino]methyl}phenyl)-N-methylpyrazine-2-carboxamide |
| 418 | 3-amino-6-(3-{[(1S)-2,3-dihydro-1H-inden-1-ylamino]methyl}phenyl)-N-methylpyrazine-2-carboxamide |
| 419 | 3-amino-N-methyl-6-[3-({[(3,4,5-trifluorophenyl)methyl]amino}methyl)phenyl]pyrazine-2-carboxamide |
| 420 | 3-amino-N-methyl-6-[3-({[(1R)-1-phenylethyl]amino}methyl)phenyl]pyrazine-2-carboxamide |
| 421 | 3-amino-6-[3-({[(1R,2S)-2-hydroxy-2,3-dihydro-1H-inden-1-yl]amino}methyl)phenyl]-N-methylpyrazine-2-carboxamide |
| 422 | 3-amino-N-methyl-6-{3-[({[4-(2-thienyl)phenyl]methyl}amino)methyl]phenyl}pyrazine-2-carboxamide |
| 423 | 3-amino-N-methyl-6-[3-({[(3-(1,2,3-thiadiazol-4-yl)phenyl]methyl}amino)methyl]phenyl}pyrazine-2-carboxamide |
| 424 | 3-amino-N-methyl-6-[3-({[(4-propylphenyl)methyl]amino}carbonyl)phenyl]pyrazine-2-carboxamide |
| 425 | 3-amino-6-[3-({[(4-chloro-2-fluorophenyl)methyl]amino}methyl)phenyl]-N-methylpyrazine-2-carboxamide |
| 426 | 3-amino-N-methyl-6-{3-[({[3-(trifluoromethyl)phenyl]methyl}amino)methyl]phenyl}pyrazine-2-carboxamide |
| 427 | 3-amino-N-methyl-6-[3-({[(1S)-1-phenylethyl]amino}methyl)phenyl]pyrazine-2-carboxamide |
| 428 | 3-amino-6-[3-({[(1R)-2-hydroxy-1-phenylethyl]amino}methyl)phenyl]-N-methylpyrazine-2-carboxamide |
| 429 | methyl (2S)-{[(3-{5-amino-6-[(methylamino)carbonyl]pyrazin-2-yl}phenyl)methyl]amino}(phenyl)ethanoate |
| 430 | 3-amino-6-(3-{[2-(2,5-difluorophenyl)hydrazino]carbonyl}phenyl)-N-methylpyrazine-2-carboxamide |
| 431 | 3-amino-N-methyl-6-(3-{[2-(2,3,5,6-tetrafluoro-4-methylphenyl)hydrazino]carbonyl}phenyl)pyrazine-2-carboxamide |
| 432 | 3-amino-6-(3-{[2-(2-fluorophenyl)hydrazino]carbonyl}phenyl)-N-methylpyrazine-2-carboxamide |
| 433 | 3-amino-6-(3-{[2-(2,4-difluorophenyl)hydrazino]carbonyl}phenyl)-N-methylpyrazine-2-carboxamide |
| 434 | 3-amino-N-methyl-6-(3-{[2-(2,3,5,6-tetrafluorophenyl)hydrazino]carbonyl}phenyl)pyrazine-2-carboxamide |
| 435 | 3-amino-N-methyl-6-[3-({[(5-methylpyrazin-2-yl)methyl]amino}methyl)phenyl]pyrazine-2-carboxamide |
| 436 | 3-amino-N-methyl-6-(3-{[(1S)-1,2,3,4-tetrahydronaphthalen-1-ylamino]methyl}phenyl)pyrazine-2-carboxamide |
| 437 | 3-amino-N-methyl-6-[3-({[(3S)-1-(phenylmethyl)pyrrolidin-3-yl]amino}methyl)phenyl]pyrazine-2-carboxamide |
| 438 | 3-amino-N-methyl-6-[3-({[(3R)-1-(phenylmethyl)pyrrolidin-3-yl]amino}methyl)phenyl]pyrazine-2-carboxamide |
| 439 | 3-amino-6-(3-{[ethyl(phenylmethyl)amino]methyl}phenyl)-N-methylpyrazine-2-carboxamide |
| 440 | 3-amino-N-methyl-6-[3-({[(1S,2S)-2-phenylcyclopropyl]amino}methyl)phenyl]pyrazine-2-carboxamide |
| 441 | 3-Amino-6-(3-benzylcarbamoyl-phenyl)-pyrazine-2-carboxylic acid methylamide |
| 442 | 3-amino-N-methyl-6-[3-(4-phenyl-1H-imidazol-2-yl)phenyl]pyrazine-2-carboxamide |

TABLE 10-continued

| # | Name |
|---|---|
| 443 | 3-amino-N-methyl-6-[3-({[(4-propylphenyl)methyl]amino}methyl)phenyl]pyrazine-2-carboxamide |
| 444 | 3-amino-6-[3-({[(5-bromo-2-fluorophenyl)methyl]amino}methyl)phenyl]-N-methylpyrazine-2-carboxamide |
| 445 | 3-amino-N-methyl-6-(3-{[(2R)-1,2,3,4-tetrahydronaphthalen-2-ylamino]methyl}phenyl)pyrazine-2-carboxamide |
| 446 | 3-amino-N-methyl-6-(3-{[(1-methyl-1-phenylethyl)amino]methyl}phenyl)pyrazine-2-carboxamide |
| 447 | 3-amino-6-{3-[(9H-fluoren-9-ylamino)methyl]phenyl}-N-methylpyrazine-2-carboxamide |
| 448 | 3-amino-N-methyl-6-{3-[(naphthalen-1-ylamino)methyl]phenyl}pyrazine-2-carboxamide |
| 449 | 3-amino-6-[3-({[(3-fluorobiphenyl-4-yl)methyl]amino}methyl)phenyl]-N-methylpyrazine-2-carboxamide |
| 450 | 3-amino-6-{3-[({[2-fluoro-4-(2-thienyl)phenyl]methyl}amino)methyl]phenyl}-N-methylpyrazine-2-carboxamide |
| 451 | 3-amino-6-[3-({[(2-fluoro-4-furan-2-ylphenyl)methyl]amino}methyl)phenyl]-N-methylpyrazine-2-carboxamide |
| 452 | 3-amino-N-methyl-6-{3-[(naphthalen-2-ylamino)methyl]phenyl}pyrazine-2-carboxamide |
| 453 | 3-amino-6-[3-({[(1S,2R)-2-hydroxy-2,3-dihydro-1H-inden-1-yl]amino}methyl)phenyl]-N-methylpyrazine-2-carboxamide |
| 454 | 3-amino-N-methyl-6-(3-{[(2S)-1,2,3,4-tetrahydronaphthalen-2-ylamino]methyl}phenyl)pyrazine-2-carboxamide |
| 455 | methyl 3-amino-6-(3-{[(4,7-difluoro-2,3-dihydro-1H-inden-1-yl)amino]methyl}phenyl)pyrazine-2-carboxylate |
| 456 | 3-amino-6-(3-{[(5-bromo-2,3-dihydro-1H-inden-2-yl)amino]methyl}phenyl)-N-methylpyrazine-2-carboxamide |
| 457 | 3-amino-6-{3-[({[2-fluoro-5-(2-thienyl)phenyl]methyl}amino)methyl]phenyl}-N-methylpyrazine-2-carboxamide |
| 458 | 3-amino-6-[3-({[(4-ethenyl-2-fluorophenyl)methyl]amino}methyl)phenyl]-N-methylpyrazine-2-carboxamide |
| 459 | 3-amino-6-(3-{[(4,7-difluoro-3-methyl-2,3-dihydro-1H-inden-1-yl)amino]methyl}phenyl)-N-methylpyrazine-2-carboxamide |
| 460 | 3-amino-N-methyl-6-[3-({[(1S,2R)-2-(methyloxy)-2,3-dihydro-1H-inden-1-yl]amino}methyl)phenyl]pyrazine-2-carboxamide |
| 461 | 3-amino-6-(3-{[(5-bromo-2,3-dihydro-1H-inden-1-yl)amino]methyl}phenyl)-N-methylpyrazine-2-carboxamide |
| 462 | 3-amino-6-[3-({[(2S)-6-bromo-1,2,3,4-tetrahydronaphthalen-2-yl]amino}methyl)phenyl]-N-methylpyrazine-2-carboxamide |
| 463 | 3-amino-6-[3-({[(2R)-6-bromo-1,2,3,4-tetrahydronaphthalen-2-yl]amino}methyl)phenyl]-N-methylpyrazine-2-carboxamide |
| 464 | 3-amino-6-(3-{[(5-fluoro-2,3-dihydro-1H-inden-1-yl)amino]methyl}phenyl)-N-methylpyrazine-2-carboxamide |
| 465 | 3-amino-6-[3-({[(2S)-5-bromo-2,3-dihydro-1H-inden-2-yl]amino}methyl)phenyl]-N-methylpyrazine-2-carboxamide |
| 466 | 3-amino-6-(3-{[(4-fluoro-2,3-dihydro-1H-inden-2-yl)amino]methyl}phenyl)-N-methylpyrazine-2-carboxamide |
| 467 | 3-amino-6-(3-{[(4-fluoro-1-hydroxy-2,3-dihydro-1H-inden-2-yl)amino]methyl}phenyl)-N-methylpyrazine-2-carboxamide |
| 468 | 3-amino-N-methyl-6-[3-({[(1R,2S)-2-(methyloxy)-2,3-dihydro-1H-inden-1-yl]amino}methyl)phenyl]pyrazine-2-carboxamide |
| 469 | 3-amino-6-(3-{[(4,7-difluoro-2,3-dihydro-1H-inden-1-yl)amino]methyl}phenyl)-N-methylpyrazine-2-carboxamide |
| 470 | 3-amino-6-(3-{[(6-bromo-4-fluoro-2,3-dihydro-1H-inden-1-yl)amino]methyl}phenyl)-N-methylpyrazine-2-carboxamide |
| 471 | 3-amino-N-methyl-6-(3-{[(3-oxo-2,3-dihydro-1H-inden-1-yl)amino]methyl}phenyl)pyrazine-2-carboxamide |
| 472 | 3-amino-6-(3-{[(5-furan-2-yl-2,3-dihydro-1H-inden-1-yl)amino]methyl}phenyl)-N-methylpyrazine-2-carboxamide |
| 473 | 3-amino-6-(3-{[(4-fluoro-2,3-dihydro-1H-inden-1-yl)amino]methyl}phenyl)-N-methylpyrazine-2-carboxamide |
| 474 | 3-amino-6-(3-{[(4,6-difluoro-2,3-dihydro-1H-inden-1-yl)amino]methyl}phenyl)-N-methylpyrazine-2-carboxamide |
| 475 | 3-amino-6-(3-{[(6-fluoro-2,3-dihydro-1H-inden-1-yl)amino]methyl}phenyl)-N-methylpyrazine-2-carboxamide |
| 476 | 3-amino-6-(3-{[(5,6-difluoro-2,3-dihydro-1H-inden-1-yl)amino]methyl}phenyl)-N-methylpyrazine-2-carboxamide |
| 477 | 3-amino-6-(3-{[(5-chloro-2,3-dihydro-1H-inden-1-yl)amino]methyl}phenyl)-N-methylpyrazine-2-carboxamide |
| 478 | 3-amino-N-methyl-6-[3-({[5-(2-thienyl)-2,3-dihydro-1H-inden-1-yl]amino}methyl)phenyl]pyrazine-2-carboxamide |
| 479 | 3-amino-6-(3-{[(5,7-difluoro-2,3-dihydro-1H-inden-1-yl)amino]methyl}phenyl)-N-methylpyrazine-2-carboxamide |
| 480 | 3-amino-6-(3-{[(5-furan-3-yl-2,3-dihydro-1H-inden-1-yl)amino]methyl}phenyl)-N-methylpyrazine-2-carboxamide |

TABLE 10-continued

| # | Name |
|---|------|
| 481 | 3-amino-N-methyl-6-[3-({[5-(3-thienyl)-2,3-dihydro-1H-inden-1-yl]amino}methyl)phenyl]pyrazine-2-carboxamide |
| 482 | 3-amino-6-[3-({[(1S)-4-fluoro-2,3-dihydro-1H-inden-1-yl]amino}methyl)phenyl]-N-methylpyrazine-2-carboxamide |
| 483 | 3-amino-6-[3-({[(1S)-5,7-difluoro-2,3-dihydro-1H-inden-1-yl]amino}methyl)phenyl]-N-methylpyrazine-2-carboxamide |
| 484 | 3-amino-6-(3-{[(7-bromo-4-fluoro-2,3-dihydro-1H-inden-1-yl)amino]methyl}phenyl)-N-methylpyrazine-2-carboxamide |
| 485 | 3-amino-6-(3-{[(6-chloro-2,3-dihydro-1H-inden-1-yl)amino]methyl}phenyl)-N-methylpyrazine-2-carboxamide |
| 486 | 3-amino-6-(3-{[(4,6-dichloro-2,3-dihydro-1H-inden-1-yl)amino]methyl}phenyl)-N-methylpyrazine-2-carboxamide |
| 487 | 3-amino-6-(3-{[(4-chloro-2,3-dihydro-1H-inden-1-yl)amino]methyl}phenyl)-N-methylpyrazine-2-carboxamide |
| 488 | 3-amino-6-(3-{[(1S)-2,3-dihydro-1H-inden-1-ylamino]methyl}phenyl)-N-ethylpyrazine-2-carboxamide |
| 489 | 3-amino-6-(3-{[(5,7-difluoro-2,3-dihydro-1H-inden-1-yl)amino]methyl}phenyl)-N-ethylpyrazine-2-carboxamide |
| 490 | 3-amino-N-methyl-6-[3-({[(1S)-5-(2-thienyl)-2,3-dihydro-1H-inden-1-yl]amino}methyl)phenyl]pyrazine-2-carboxamide |
| 491 | 3-amino-N-methyl-6-(3-{[(5-phenyl-2,3-dihydro-1H-inden-1-yl)amino]methyl}phenyl)pyrazine-2-carboxamide |
| 492 | 3-amino-6-(3-{[(4-bromo-2,3-dihydro-1H-inden-1-yl)amino]methyl}phenyl)-N-methylpyrazine-2-carboxamide |
| 493 | 3-amino-N-methyl-6-(3-{[(4-phenyl-2,3-dihydro-1H-inden-1-yl)amino]methyl}phenyl)pyrazine-2-carboxamide |
| 494 | 3-amino-N-methyl-6-[3-({[4-(2-thienyl)-2,3-dihydro-1H-inden-1-yl]amino}methyl)phenyl]pyrazine-2-carboxamide |
| 495 | 3-amino-N-methyl-6-[3-({[6-(2-thienyl)-2,3-dihydro-1H-inden-1-yl]amino}methyl)phenyl]pyrazine-2-carboxamide |
| 496 | 3-amino-N-methyl-6-[3-({[5-(4-methyl-2-thienyl)-2,3-dihydro-1H-inden-1-yl]amino}methyl)phenyl]pyrazine-2-carboxamide |
| 497 | 3-amino-N-methyl-6-[3-({[(2R)-6-phenyl-1,2,3,4-tetrahydronaphthalen-2-yl]amino}methyl)phenyl]pyrazine-2-carboxamide |
| 498 | 3-amino-N-methyl-6-naphthalen-2-ylpyrazine-2-carboxamide |
| 499 | 3-amino-N-methyl-6-{3-[({(1S,2S)-2-[(phenylmethyl)oxy]cyclopentyl}amino)methyl]phenyl}pyrazine-2-carboxamide |
| 500 | 3-amino-6-{3-[(cyclopentylamino)methyl]phenyl}-N-methylpyrazine-2-carboxamide |
| 501 | 3-amino-6-(3-{[(6-bromo-2,3-dihydro-1H-inden-1-yl)amino]methyl}phenyl)-N-methylpyrazine-2-carboxamide |
| 502 | 3-amino-6-(3-{[(7-fluoro-2,3-dihydro-1H-inden-1-yl)amino]methyl}phenyl)-N-methylpyrazine-2-carboxamide |
| 503 | 3-amino-N-methyl-6-quinolin-3-ylpyrazine-2-carboxamide |
| 504 | 3-amino-6-[3-(1H-imidazol-1-ylmethyl)phenyl]-N-methylpyrazine-2-carboxamide |
| 505 | 3-amino-N-methyl-6-{3-[({5-[(2-morpholin-4-ylethyl)oxy]-2,3-dihydro-1H-inden-1-yl}amino)methyl]phenyl}pyrazine-2-carboxamide |
| 506 | 3-amino-N-methyl-6-{3-[({(1R,2R)-2-[(phenylmethyl)oxy]cyclopentyl}amino)methyl]phenyl}pyrazine-2-carboxamide |
| 507 | 3-amino-6-{3-[(2,3-dihydro-1-benzofuran-3-ylamino)methyl]phenyl}-N-methylpyrazine-2-carboxamide |
| 508 | 3-amino-6-{3-[({5-[(cyanomethyl)oxy]-2,3-dihydro-1H-inden-1-yl}amino)methyl]phenyl}-N-methylpyrazine-2-carboxamide |
| 509 | 2-amino-5-(3-{[(1S)-2,3-dihydro-1H-inden-1-ylamino]methyl}phenyl)-N-methylpyridine-3-carboxamide |
| 510 | 3-amino-N-methyl-6-[3-({[5-(4-methylphenyl)-2,3-dihydro-1H-inden-1-yl]amino}methyl)phenyl]pyrazine-2-carboxamide |
| 511 | 3-amino-6-[3-({[2-(dimethylamino)-1-phenylethyl]amino}methyl)phenyl]-N-methylpyrazine-2-carboxamide |
| 512 | 3-amino-N-methyl-6-[3-({[5-(1H-1,2,4-triazol-1-yl)-2,3-dihydro-1H-inden-1-yl]amino}methyl)phenyl]pyrazine-2-carboxamide |
| 513 | 3-amino-6-(3-{[(5-hydroxy-2,3-dihydro-1H-inden-1-yl)amino]methyl}phenyl)-N-methylpyrazine-2-carboxamide |
| 514 | 3-amino-N-methyl-6-{3-[({4-[(2-morpholin-4-ylethyl)oxy]-2,3-dihydro-1H-inden-1-yl}amino)methyl]phenyl}pyrazine-2-carboxamide |
| 515 | 3-amino-6-(3-{[(4-hydroxy-2,3-dihydro-1H-inden-1-yl)amino]methyl}phenyl)-N-methylpyrazine-2-carboxamide |
| 516 | 3-amino-N-methyl-6-{1-[(phenylmethyl)amino]isoquinolin-7-yl}pyrazine-2-carboxamide |
| 517 | 3-amino-N-methyl-6-(3-{[(2-morpholin-4-yl-1-phenylethyl)amino]methyl}phenyl)pyrazine-2-carboxamide |
| 518 | 3-amino-N-methyl-6-(3-{[(1-phenyl-2-pyrrolidin-1-ylethyl)amino]methyl}phenyl)pyrazine-2-carboxamide |
| 519 | 2-amino-5-(3-{[(6-bromo-2,3-dihydro-1H-inden-1-yl)amino]methyl}phenyl)-N-methylpyridine-3-carboxamide |
| 520 | 2-amino-5-(3-{[(4,6-difluoro-2,3-dihydro-1H-inden-1-yl)amino]methyl}phenyl)-N-methylpyridine-3-carboxamide |

TABLE 10-continued

| # | Name |
|---|------|
| 521 | 2-amino-5-(3-{[(7-bromo-4-fluoro-2,3-dihydro-1H-inden-1-yl)amino]methyl}phenyl)-N-methylpyridine-3-carboxamide |
| 522 | 2-amino-5-(3-{[(4-chloro-2,3-dihydro-1H-inden-1-yl)amino]methyl}phenyl)-N-methylpyridine-3-carboxamide |
| 523 | 2-amino-5-(3-{[(5,6-difluoro-2,3-dihydro-1H-inden-1-yl)amino]methyl}phenyl)-N-methylpyridine-3-carboxamide |
| 524 | 2-amino-5-(3-{[(5,7-difluoro-2,3-dihydro-1H-inden-1-yl)amino]methyl}phenyl)-N-methylpyridine-3-carboxamide |
| 525 | 3-amino-6-{1-[(1S)-2,3-dihydro-1H-inden-1-ylamino]isoquinolin-7-yl}-N-methylpyrazine-2-carboxamide |
| 526 | 3-amino-6-{3-[(1S)-2,3-dihydro-1H-inden-1-ylamino]-2,3-dihydro-1H-inden-5-yl}-N-methylpyrazine-2-carboxamide |
| 527 | 3-amino-6-[3-({[6-(3-hydroxypropyl)-2,3-dihydro-1H-inden-1-yl]amino}methyl)phenyl]-N-methylpyrazine-2-carboxamide |
| 528 | 5-(3-{[(1S)-2,3-dihydro-1H-inden-1-ylamino]methyl}phenyl)-3-(1,3-oxazol-5-yl)pyrazin-2-amine |
| 529 | 3-amino-6-(3-{[(1S)-2,3-dihydro-1H-inden-1-ylamino]methyl}phenyl)pyrazine-2-carbohydrazide |
| 530 | 3-amino-6-(3-{[(1S)-2,3-dihydro-1H-inden-1-ylamino]methyl}phenyl)pyrazine-2-carboxamide |
| 531 | 1-[3-amino-6-(3-{[(1S)-2,3-dihydro-1H-inden-1-ylamino]methyl}phenyl)pyrazin-2-yl]ethanone |
| 532 | 3-amino-6-{3-[(2,3-dihydro-1H-inden-1-ylamino)methyl]phenyl}-N-(naphthalen-2-ylmethyl)pyrazine-2-carboxamide |
| 533 | 3-amino-N-cyclohexyl-6-{3-[(2,3-dihydro-1H-inden-1-ylamino)methyl]phenyl}pyrazine-2-carboxamide |
| 534 | 3-amino-6-(3-{[(1S)-2,3-dihydro-1H-inden-1-ylamino]methyl}phenyl)-N-(pyridin-4-ylmethyl)pyrazine-2-carboxamide |
| 535 | {3-[5-amino-6-(4H-1,2,4-triazol-3-yl)pyrazin-2-yl]phenyl}methanol |
| 536 | 5-(3-{[(1S)-2,3-dihydro-1H-inden-1-ylamino]methyl}phenyl)-3-(4H-1,2,4-triazol-3-yl)pyrazin-2-amine |
| 537 | 3-amino-6-(3-{[(1S)-2,3-dihydro-1H-inden-1-ylamino]methyl}phenyl)-N-(2,2,2-trifluoroethyl)pyrazine-2-carboxamide |
| 538 | 3-amino-6-(3-{[(1S)-2,3-dihydro-1H-inden-1-ylamino]methyl}phenyl)-N-(5-hydroxypentyl)pyrazine-2-carboxamide |
| 539 | 3-amino-6-(3-{[(1S)-2,3-dihydro-1H-inden-1-ylamino]methyl}phenyl)-N-(4-hydroxybutyl)pyrazine-2-carboxamide |
| 540 | 3-amino-6-(3-{[(1S)-2,3-dihydro-1H-inden-1-ylamino]methyl}phenyl)-N-(2-pyrrolidin-1-ylethyl)pyrazine-2-carboxamide |
| 541 | 3-amino-6-(3-{[(1S)-2,3-dihydro-1H-inden-1-ylamino]methyl}phenyl)-N-(2-piperidin-1-ylethyl)pyrazine-2-carboxamide |
| 542 | 3-amino-6-(3-{[(1S)-2,3-dihydro-1H-inden-1-ylamino]methyl}phenyl)-N-(2-morpholin-4-ylethyl)pyrazine-2-carboxamide |
| 543 | 3-amino-N-(cyclopropylmethyl)-6-(3-{[(1S)-2,3-dihydro-1H-inden-1-ylamino}methyl}phenyl)pyrazine-2-carboxamide |
| 544 | 3-amino-6-(3-{[(1S)-2,3-dihydro-1H-inden-1-ylamino]methyl}phenyl)-N-(phenylmethyl)pyrazine-2-carboxamide |
| 545 | 3-amino-6-(3-{[(1S)-2,3-dihydro-1H-inden-1-ylamino]methyl}phenyl)-N-(2-phenylethyl)pyrazine-2-carboxamide |
| 546 | [3-amino-6-(3-{[(1S)-2,3-dihydro-1H-inden-1-ylamino]methyl}phenyl)pyrazin-2-yl](phenyl)methanone |
| 547 | 3-amino-6-(3-{[(1S)-2,3-dihydro-1H-inden-1-ylamino]methyl}phenyl)-N-(2-hydroxyethyl)pyrazine-2-carboxamide |
| 548 | 3-amino-N-cyclopropyl-6-(3-{[(1S)-2,3-dihydro-1H-inden-1-ylamino]methyl}phenyl)pyrazine-2-carboxamide |
| 549 | 5-(3-{[(1S)-2,3-dihydro-1H-inden-1-ylamino]methyl}phenyl)-3-(pyrrolidin-1-ylcarbonyl)pyrazin-2-amine |
| 550 | {3-[5-amino-6-(5-methyl-4H-1,2,4-triazol-3-yl)pyrazin-2-yl]phenyl}methanol |
| 551 | {3-[5-amino-6-(5-phenyl-4H-1,2,4-triazol-3-yl)pyrazin-2-yl]phenyl}methanol |
| 552 | (3-{5-amino-6-[5-(phenylmethyl)-4H-1,2,4-triazol-3-yl]pyrazin-2-yl}phenyl)methanol |
| 553 | 3-amino-6-(3-{[(1S)-2,3-dihydro-1H-inden-1-ylamino]methyl}phenyl)-N'-methylpyrazine-2-carbohydrazide |
| 554 | 3-amino-6-(3-{[(1S)-2,3-dihydro-1H-inden-1-ylamino]methyl}phenyl)-N,N-dimethylpyrazine-2-carboxamide |
| 555 | 5-(3-{[(1S)-2,3-dihydro-1H-inden-1-ylamino]methyl}phenyl)-3-[5-(phenylmethyl)-4H-1,2,4-triazol-3-yl]pyrazin-2-amine |
| 556 | 3-amino-6-(3-{[(1S)-2,3-dihydro-1H-inden-1-ylamino]methyl}phenyl)-N-[2-(dimethylamino)ethyl]pyrazine-2-carboxamide |
| 557 | 5-(3-{[(1S)-2,3-dihydro-1H-inden-1-ylamino]methyl}phenyl)-3-(3-phenyl-1H-1,2,4-triazol-5-yl)pyrazin-2-amine |
| 558 | 3-amino-6-(3-{[(1S)-2,3-dihydro-1H-inden-1-ylamino]methyl}phenyl)-N-[2-(1H-imidazol-4-yl)ethyl]pyrazine-2-carboxamide |
| 559 | 3-amino-6-(3-{[(1S)-2,3-dihydro-1H-inden-1-ylamino]methyl}phenyl)-N-[2-(methylamino)ethyl]pyrazine-2-carboxamide |
| 560 | 3-{5-amino-6-[(3-fluorophenyl)carbonyl]pyrazin-2-yl}-N-(phenylmethyl)benzamide |

TABLE 10-continued

| # | Name |
|---|------|
| 561 | 3-amino-6-(3-{[(1S)-2,3-dihydro-1H-inden-1-ylamino]methyl}phenyl)-N-(3-hydroxypropyl)pyrazine-2-carboxamide |
| 562 | 1,1-dimethylethyl 4-({[3-amino-6-(3-{[(phenylmethyl)amino]carbonyl}phenyl)pyrazin-2-yl]carbonyl}amino)piperidine-1-carboxylate |
| 563 | 1,1-dimethylethyl 4-[({[3-amino-6-(3-{[(phenylmethyl)amino]carbonyl}phenyl)pyrazin-2-yl]carbonyl}amino)methyl]piperidine-1-carboxylate |
| 564 | 3-amino-6-(3-{[(phenylmethyl)amino]carbonyl}phenyl)-N-piperidin-4-ylpyrazine-2-carboxamide |
| 565 | 3-amino-6-(3-{[(phenylmethyl)amino]carbonyl}phenyl)-N-(piperidin-4-ylmethyl)pyrazine-2-carboxamide |
| 566 | 3-[5-amino-6-(morpholin-4-ylcarbonyl)pyrazin-2-yl]-N-(phenylmethyl)benzamide |
| 567 | 1,1-dimethylethyl 3-({[3-amino-6-(3-{[(phenylmethyl)amino]carbonyl}phenyl)pyrazin-2-yl]carbonyl}amino)pyrrolidine-1-carboxylate |
| 568 | 3-amino-6-(3-{[(phenylmethyl)amino]carbonyl}phenyl)-N-pyrrolidin-3-ylpyrazine-2-carboxamide |
| 569 | (3-{5-amino-6-[5-(1,1-dimethylethyl)-4H-1,2,4-triazol-3-yl]pyrazin-2-yl}phenyl)methanol |
| 570 | {3-[5-amino-6-(5-furan-2-yl-4H-1,2,4-triazol-3-yl)pyrazin-2-yl]phenyl}methanol |
| 571 | [3-(5-amino-6-{5-[3-(methyloxy)phenyl]-4H-1,2,4-triazol-3-yl}pyrazin-2-yl)phenyl]methanol |
| 572 | 2-({3-amino-6-[3-(hydroxymethyl)phenyl]pyrazin-2-yl}carbonyl)-N-phenylhydrazinecarboxamide |
| 573 | 3-{5-amino-6-[(4-methylpiperazin-1-yl)carbonyl]pyrazin-2-yl}-N-(phenylmethyl)benzamide |
| 574 | 3-(5-amino-6-{[4-(4-fluorophenyl)piperazin-1-yl]carbonyl}pyrazin-2-yl)-N-(phenylmethyl)benzamide |
| 575 | 3-(5-amino-6-{[4-(phenylmethyl)piperazin-1-yl]carbonyl}pyrazin-2-yl)-N-(phenylmethyl)benzamide |
| 576 | methyl N-{[3-amino-6-(3-{[(phenylmethyl)amino]carbonyl}phenyl)pyrazin-2-yl]carbonyl}glycinate |
| 577 | N-{[3-amino-6-(3-{[(phenylmethyl)amino]carbonyl}phenyl)pyrazin-2-yl]carbonyl}glycine |
| 578 | 3-{5-amino-6-[(3,5-difluorophenyl)carbonyl]pyrazin-2-yl}-N-(phenylmethyl)benzamide |
| 579 | 3-[5-amino-6-(biphenyl-4-ylcarbonyl)pyrazin-2-yl]-N-(phenylmethyl)benzamide |
| 580 | {3-[5-amino-6-(3-pyridin-3-yl-1H-1,2,4-triazol-5-yl)pyrazin-2-yl]phenyl}methanol |
| 581 | (3-{5-amino-6-[3-(4-chlorophenyl)-1H-1,2,4-triazol-5-yl]pyrazin-2-yl}phenyl)methanol |
| 582 | 5-(3-{[(1S)-2,3-dihydro-1H-inden-1-ylamino]methyl}phenyl)-3-[5-(1,1-dimethylethyl)-4H-1,2,4-triazol-3-yl]pyrazin-2-amine |
| 583 | (3-{5-amino-6-[3-(2-thienyl)-1H-1,2,4-triazol-5-yl]pyrazin-2-yl}phenyl)methanol |
| 584 | 5-(3-{[(1S)-2,3-dihydro-1H-inden-1-ylamino]methyl}phenyl)-3-{3-[3-(methyloxy)phenyl]-1H-1,2,4-triazol-5-yl}pyrazin-2-amine |
| 585 | 3-amino-6-(3-{[(1S)-2,3-dihydro-1H-inden-1-ylamino]methyl}phenyl)-N-[3-(dimethylamino)propyl]pyrazine-2-carboxamide |
| 586 | 3-amino-6-(3-{[(1S)-2,3-dihydro-1H-inden-1-ylamino]methyl}phenyl)-N-[3-(1H-imidazol-1-yl)propyl]pyrazine-2-carboxamide |
| 587 | 3-{5-amino-6-[(4-chloro-3-fluorophenyl)carbonyl]pyrazin-2-yl}-N-(phenylmethyl)benzamide |
| 588 | 3-(5-amino-6-{[2,4-bis(methyloxy)phenyl]carbonyl}pyrazin-2-yl)-N-(phenylmethyl)benzamide |
| 589 | 3-(5-amino-6-{[4-(dimethylamino)phenyl]carbonyl}pyrazin-2-yl)-N-(phenylmethyl)benzamide |
| 590 | methyl 1-{[3-amino-6-(3-{[(phenylmethyl)amino]carbonyl}phenyl)pyrazin-2-yl]carbonyl}-L-prolinate |
| 591 | methyl 1-{[3-amino-6-(3-{[(phenylmethyl)amino]carbonyl}phenyl)pyrazin-2-yl]carbonyl}piperidine-3-carboxylate |
| 592 | 1,1-dimethylethyl 4-{[3-amino-6-(3-{[(phenylmethyl)amino]carbonyl}phenyl)pyrazin-2-yl]carbonyl}piperazine-1-carboxylate |
| 593 | 3-[5-amino-6-(piperazin-1-ylcarbonyl)pyrazin-2-yl]-N-(phenylmethyl)benzamide |
| 594 | N-{[3-amino-6-(3-{[(phenylmethyl)amino]carbonyl}phenyl)pyrazin-2-yl]carbonyl}glutamic acid |
| 595 | 5-(3-{[(1S)-2,3-dihydro-1H-inden-1-ylamino]methyl}phenyl)-3-{5-[(methyloxy)methyl]-4H-1,2,4-triazol-3-yl}pyrazin-2-amine |
| 596 | 5-(3-{[(1S)-2,3-dihydro-1H-inden-1-ylamino]methyl}phenyl)-3-(3-pyridin-3-yl-1H-1,2,4-triazol-5-yl)pyrazin-2-amine |
| 597 | 3-amino-6-(3-{[(1S)-2,3-dihydro-1H-inden-1-ylamino]methyl}phenyl)-N-[3-(methylamino)propyl]pyrazine-2-carboxamide |
| 598 | 3-amino-6-(3-{[(1S)-2,3-dihydro-1H-inden-1-ylamino]methyl}phenyl)-N-(3-pyrrolidin-1-ylpropyl)pyrazine-2-carboxamide |
| 599 | 3-(5-amino-6-{(1E)-N-[4-(methyloxy)phenyl]ethanehydrazonoyl}pyrazin-2-yl)-N-(phenylmethyl)benzamide |

TABLE 10-continued

| # | Name |
|---|------|
| 600 | 3-(5-amino-6-{(1E)-N-[4-(1-methylethyl)phenyl]ethanehydrazonoyl}pyrazin-2-yl)-N-(phenylmethyl)benzamide |
| 601 | 3-{5-amino-6-[(1E)-N-1,3-benzothiazol-2-ylethanehydrazonoyl]pyrazin-2-yl}-N-(phenylmethyl)benzamide |
| 602 | 3-{5-amino-6-[(1E)-N-(4-methylphenyl)ethanehydrazonoyl]pyrazin-2-yl}-N-(phenylmethyl)benzamide |
| 603 | 3-{5-amino-6-[(1E)-N-(4-chlorophenyl)ethanehydrazonoyl]pyrazin-2-yl}-N-(phenylmethyl)benzamide |
| 604 | 3-{5-amino-6-[(1E)-N-methyl-N-phenylethanehydrazonoyl]pyrazin-2-yl}-N-(phenylmethyl)benzamide |
| 605 | 3-{5-amino-6-[(1E)-N-(2-hydroxyethyl)ethanehydrazonoyl]pyrazin-2-yl}-N-(phenylmethyl)benzamide |
| 606 | {3-[5-amino-6-(3-pyridin-4-yl-1H-1,2,4-triazol-5-yl)pyrazin-2-yl]phenyl}methanol |
| 607 | {3-[5-amino-6-(3-piperidin-4-yl-1H-1,2,4-triazol-5-yl)pyrazin-2-yl]phenyl}methanol |
| 608 | 3-[5-amino-6-(2-aminopyrimidin-4-yl)pyrazin-2-yl]-N-(phenylmethyl)benzamide |
| 609 | 3-{5-amino-6-[2-(dimethylamino)pyrimidin-4-yl]pyrazin-2-yl}-N-(phenylmethyl)benzamide |
| 610 | ethyl N-{[3-amino-6-(3-{[(phenylmethyl)amino]carbonyl}phenyl)pyrazin-2-yl]carbonyl}-L-tyrosinate |
| 611 | N-{[3-amino-6-(3-{[(phenylmethyl)amino]carbonyl}phenyl)pyrazin-2-yl]carbonyl}-D-tyrosine |
| 612 | 1,1-dimethylethyl [3-({[3-amino-6-(3-{[(phenylmethyl)amino]carbonyl}phenyl)pyrazin-2-yl]carbonyl}amino)propyl]carbamate |
| 613 | 3-amino-N-(3-aminopropyl)-6-(3-{[(phenylmethyl)amino]carbonyl}phenyl)pyrazine-2-carboxamide |
| 614 | 1-{[3-amino-6-(3-{[(phenylmethyl)amino]carbonyl}phenyl)pyrazin-2-yl]carbonyl}piperidine-3-carboxylic |
| 615 | 1,1-dimethylethyl [2-({[3-amino-6-(3-{[(phenylmethyl)amino]carbonyl}phenyl)pyrazin-2-yl]carbonyl}amino)ethyl]carbamate |
| 616 | 3-amino-N-(2-aminoethyl)-6-(3-{[(phenylmethyl)amino]carbonyl}phenyl)pyrazine-2-carboxamide |
| 617 | 1,1-dimethylethyl (1-{[3-amino-6-(3-{[(phenylmethyl)amino]carbonyl}phenyl)pyrazin-2-yl]carbonyl}piperidin-4-yl)carbamate |
| 618 | 3-{5-amino-6-[(4-aminopiperidin-1-yl)carbonyl]pyrazin-2-yl}-N-(phenylmethyl)benzamide |
| 619 | 3-{5-amino-6-[imino(2-phenylhydrazino)methyl]pyrazin-2-yl}-N-(phenylmethyl)benzamide |
| 620 | 3-{5-amino-6-[imino(morpholin-4-ylamino)methyl]pyrazin-2-yl}-N-(phenylmethyl)benzamide |
| 621 | 3-(5-amino-6-{imino[(4-methylpiperazin-1-yl)amino]methyl}pyrazin-2-yl)-N-(phenylmethyl)benzamide |
| 622 | 3-{5-amino-6-[imino(piperidin-1-ylamino)methyl]pyrazin-2-yl}-N-(phenylmethyl)benzamide |
| 623 | 3-{5-amino-6-[(azepan-1-ylamino)(imino)methyl]pyrazin-2-yl}-N-(phenylmethyl)benzamide |
| 624 | 3-{5-amino-6-[imino({(2R)-2-[(methyloxy)methyl]pyrrolidin-1-yl}amino)methyl]pyrazin-2-yl}-N-(phenylmethyl)benzamide |
| 625 | {3-[5-amino-6-(3-piperidin-3-yl-1H-1,2,4-triazol-5-yl)pyrazin-2-yl]phenyl}methanol |
| 626 | 3-{5-amino-6-[(1E)-N-morpholin-4-ylethanimidoyl]pyrazin-2-yl}-N-(phenylmethyl)benzamide |
| 627 | 4-((2E)-2-{1-[3-amino-6-(3-{[(phenylmethyl)amino]carbonyl}phenyl)pyrazin-2-yl]ethylidene}hydrazino)benzoic acid |
| 628 | ethyl ((2E)-2-{1-[3-amino-6-(3-{[(phenylmethyl)amino]carbonyl}phenyl)pyrazin-2-yl]ethylidene}hydrazino)acetate |
| 629 | 3-{5-amino-6-[(1E)-N,N-dimethylethanehydrazonoyl]pyrazin-2-yl}-N-(phenylmethyl)benzamide |
| 630 | 3-(5-amino-6-{(1E)-N-[4-(methylsulfonyl)phenyl]ethanehydrazonoyl}pyrazin-2-yl)-N-(phenylmethyl)benzamide |
| 631 | 3-{5-amino-6-[(1E)-N-(4-cyanophenyl)ethanehydrazonoyl]pyrazin-2-yl}-N-(phenylmethyl)benzamide |
| 632 | 3-{5-amino-6-[(1E)-N-pyridin-2-ylethanehydrazonoyl]pyrazin-2-yl}-N-(phenylmethyl)benzamide |
| 633 | 3-(5-amino-6-{(1E)-N-[amino(imino)methyl]ethanehydrazonoyl}pyrazin-2-yl)-N-(phenylmethyl)benzamide |
| 634 | 3-[5-amino-6-((1E)-N-{4-[(trifluoromethyl)oxy]phenyl}ethanehydrazonoyl)pyrazin-2-yl]-N-(phenylmethyl)benzamide |
| 635 | 3-(5-Amino-6-{1-[(4-nitro-phenyl)-hydrazono]-ethyl}-pyrazin-2-yl)-N-benzyl-benzamide |
| 636 | 3-(5-amino-6-{(1E)-N-[4-(trifluoromethyl)pyrimidin-2-yl]ethanehydrazonoyl}pyrazin-2-yl)-N-(phenylmethyl)benzamide |

TABLE 10-continued

| # | Name |
|---|---|
| 637 | 3-{5-amino-6-[(1E)-N-1H-1,2,3-benzotriazol-1-ylethanimidoyl]pyrazin-2-yl}-N-(phenylmethyl)benzamide |
| 638 | 3-{5-amino-6-[(1E)-N-methylethanehydrazonoyl]pyrazin-2-yl}-N-(phenylmethyl)benzamide |
| 639 | 5-(3-{[(1S)-2,3-dihydro-1H-inden-1-ylamino]methyl}phenyl)-3-(3-piperidin-4-yl-1H-1,2,4-triazol-5-yl)pyrazin-2-amine |
| 640 | 3-(5-amino-6-{(1E)-N-[4-(trifluoromethyl)phenyl]ethanehydrazonoyl}pyrazin-2-yl)-N-(phenylmethyl)benzamide |
| 641 | 3-{5-amino-6-[(1E)-N-phenylethanehydrazonoyl]pyrazin-2-yl}-N-(phenylmethyl)benzamide |
| 642 | 3-{5-amino-6-[(1E)-N-(4-methylpiperazin-1-yl)ethanimidoyl]pyrazin-2-yl}-N-(phenylmethyl)benzamide |
| 643 | {3-[5-amino-6-(3-pyrrolidin-3-yl-1H-1,2,4-triazol-5-yl)pyrazin-2-yl]phenyl}methanol |
| 644 | 3-amino-6-(3-{[(1S)-2,3-dihydro-1H-inden-1-ylamino]carbonyl}phenyl)-N-[(3S)-pyrrolidin-3-yl]pyrazine-2-carboxamide |
| 645 | 3-amino-6-(3-{[(1S)-2,3-dihydro-1H-inden-1-ylamino]carbonyl}phenyl)-N-[(3R)-pyrrolidin-3-yl]pyrazine-2-carboxamide |
| 646 | 3-amino-6-(3-{[(1S)-2,3-dihydro-1H-inden-1-ylamino]carbonyl}phenyl)-N-[(3S)-1-(furan-2-ylcarbonyl)pyrrolidin-3-yl]pyrazine-2-carboxamide |
| 647 | N-[3-(acetylamino)propyl]-3-amino-6-(3-{[(phenylmethyl)amino]carbonyl}phenyl)pyrazine-2-carboxamide |
| 648 | 3-amino-N-{3-[(furan-2-ylcarbonyl)amino]propyl}-6-(3-{[(phenylmethyl)amino]carbonyl}phenyl)pyrazine-2-carboxamide |
| 649 | 3-amino-6-(3-{[(1S)-2,3-dihydro-1H-inden-1-ylamino]carbonyl}phenyl)-N-[(3S)-1-(pyridin-4-ylcarbonyl)pyrrolidin-3-yl]pyrazine-2-carboxamide |
| 650 | 3-amino-6-(3-{[(phenylmethyl)amino]carbonyl}phenyl)-N-{3-[(pyridin-4-ylcarbonyl)amino]propyl}pyrazine-2-carboxamide |
| 651 | N-[3-({[3-amino-6-(3-{[(phenylmethyl)amino]carbonyl}phenyl)pyrazin-2-yl]carbonyl}amino)propyl]quinoxaline-2-carboxamide |
| 652 | 3-amino-6-(3-{[(phenylmethyl)amino]carbonyl}phenyl)-N-[3-({[6-(trifluoromethyl)pyridin-3-yl]carbonyl}amino)propyl]pyrazine-2-carboxamide |
| 653 | 3-amino-6-(3-{[(phenylmethyl)amino]carbonyl}phenyl)-N-{3-[(quinolin-8-ylsulfonyl)amino]propyl}pyrazine-2-carboxamide |
| 654 | 3-amino-6-(3-{[(phenylmethyl)amino]carbonyl}phenyl)-N-{3-[(pyridin-2-ylsulfonyl)amino]propyl}pyrazine-2-carboxamide |
| 655 | 3-amino-N-[3-({[(3,5-dimethylisoxazol-4-yl)amino]carbonyl}amino)propyl]-6-(3-{[(phenylmethyl)amino]carbonyl}phenyl)pyrazine-2-carboxamide |
| 656 | 3-[5-amino-6-(2-methylpyrimidin-4-yl)pyrazin-2-yl]-N-(phenylmethyl)benzamide |
| 657 | 3-{5-amino-6-[2-(methylamino)pyrimidin-4-yl]pyrazin-2-yl}-N-(phenylmethyl)benzamide |
| 658 | 3-amino-6-(3-{[(phenylmethyl)amino]carbonyl}phenyl)-N-{2-[(pyridin-4-ylcarbonyl)amino]ethyl}pyrazine-2-carboxamide |
| 659 | 3-amino-N-{2-[(furan-2-ylcarbonyl)amino]ethyl}-6-(3-{[(phenylmethyl)amino]carbonyl}phenyl)pyrazine-2-carboxamide |
| 660 | N,N'-cyclohexane-1,2-diylbis[3-amino-6-(3-{[(phenylmethyl)amino]carbonyl}phenyl)pyrazine-2-carboxamide] |
| 661 | N-[2-(acetylamino)ethyl]-3-amino-6-(3-{[(phenylmethyl)amino]carbonyl}phenyl)pyrazine-2-carboxamide |
| 662 | 3-amino-6-(3-{[(phenylmethyl)amino]carbonyl}phenyl)-N-{2-[(quinolin-8-ylsulfonyl)amino]ethyl}pyrazine-2-carboxamide |
| 663 | N-[2-({[3-amino-6-(3-{[(phenylmethyl)amino]carbonyl}phenyl)pyrazin-2-yl]carbonyl}amino)ethyl]quinoxaline-2-carboxamide |
| 664 | 3-amino-N-(2-{[(2-chloropyridin-3-yl)carbonyl]amino}ethyl)-6-(3-{[(phenylmethyl)amino]carbonyl}phenyl)pyrazine-2-carboxamide |
| 665 | 3-amino-6-(3-{[(phenylmethyl)amino]carbonyl}phenyl)-N-{2-[(pyridin-2-ylsulfonyl)amino]ethyl}pyrazine-2-carboxamide |
| 666 | 3-amino-N-[2-({[(3,5-dimethylisoxazol-4-yl)amino]carbonyl}amino)ethyl]-6-(3-{[(phenylmethyl)amino]carbonyl}phenyl)pyrazine-2-carboxamide |
| 667 | 3-amino-6-(3-{[(phenylmethyl)amino]carbonyl}phenyl)pyrazine-2-carboxamide |
| 668 | 3-[5-amino-6-(imino{2-[4-(trifluoromethyl)pyrimidin-2-yl]hydrazino}methyl)pyrazin-2-yl]-N-(phenylmethyl)benzamide |
| 669 | 3-{5-amino-6-[[2-(1,3-benzothiazol-2-yl)hydrazino](imino)methyl]pyrazin-2-yl}-N-(phenylmethyl)benzamide |
| 670 | 3-[5-amino-6-(1,5-diphenyl-1H-1,2,4-triazol-3-yl)pyrazin-2-yl]-N-(phenylmethyl)benzamide |
| 671 | 3-[5-amino-6-(1,5-dimethyl-1H-1,2,4-triazol-3-yl)pyrazin-2-yl]-N-(phenylmethyl)benzamide |
| 672 | 3-[5-amino-6-(1-methyl-5-phenyl-1H-1,2,4-triazol-3-yl)pyrazin-2-yl]-N-(phenylmethyl)benzamide |
| 673 | 3-[5-amino-6-((1E)-N-{(2R)-2-[(methyloxy)methyl]pyrrolidin-1-yl}ethanimidoyl)pyrazin-2-yl]-N-(phenylmethyl)benzamide |
| 674 | 3-{5-amino-6-[(1E)-N-azepan-1-ylethanimidoyl]pyrazin-2-yl}-N-(phenylmethyl)benzamide |
| 675 | 3-(5-amino-6-{(E)-[(phenylmethyl)hydrazono]methyl}pyrazin-2-yl)-N-(phenylmethyl)benzamide |

TABLE 10-continued

| # | Name |
|---|---|
| 676 | 3-[5-amino-6-((E)-{[amino(imino)methyl]hydrazono}methyl)pyrazin-2-yl]-N-(phenylmethyl)benzamide |
| 677 | 3-(5-amino-6-{(E)-[(2-hydroxyethyl)hydrazono]methyl}pyrazin-2-yl)-N-(phenylmethyl)benzamide |
| 678 | 3-{5-amino-6-[(E)-(pyridin-2-ylhydrazono)methyl]pyrazin-2-yl}-N-(phenylmethyl)benzamide |
| 679 | 3-(5-amino-6-{(E)-[(4-cyanophenyl)hydrazono]methyl}pyrazin-2-yl)-N-(phenylmethyl)benzamide |
| 680 | 3-(5-amino-6-{(E)-[(4-methylphenyl)hydrazono]methyl}pyrazin-2-yl)-N-(phenylmethyl)benzamide |
| 681 | 3-{5-amino-6-[(E)-(hydroxyimino)methyl]pyrazin-2-yl}-N-(phenylmethyl)benzamide |
| 682 | {3-[5-amino-6-(3-pyridin-2-yl-1H-1,2,4-triazol-5-yl)pyrazin-2-yl]phenyl}methanol |
| 683 | 5-(3-{[(1R)-2,3-dihydro-1H-inden-1-ylamino]methyl}phenyl)-3-(3-piperidin-3-yl-1H-1,2,4-triazol-5-yl)pyrazin-2-amine |
| 684 | 3-amino-N-[3-({[4-(dimethylamino)phenyl]carbonyl}amino)propyl]-6-(3-{[(phenylmethyl)amino]carbonyl}phenyl)pyrazine-2-carboxamide |
| 685 | 3-amino-6-(3-{[(1S)-2,3-dihydro-1H-inden-1-ylamino]methyl}phenyl)-N-[(3S)-pyrrolidin-3-yl]pyrazine-2-carboxamide |
| 686 | 1,1-dimethylethyl 4-[(3S)-3-({[3-amino-6-(3-{[(phenylmethyl)amino]carbonyl}phenyl)pyrazin-2-yl]carbonyl}amino)pyrrolidin-1-yl]piperidine-1-carboxylate |
| 687 | 3-amino-6-(3-{[(phenylmethyl)amino]carbonyl}phenyl)-N-[(3S)-1-piperidin-4-ylpyrrolidin-3-yl]pyrazine-2-carboxamide |
| 688 | 1,1-dimethylethyl (2R)-2-{[(3S)-3-({[3-amino-6-(3-{[(phenylmethyl)amino]carbonyl}phenyl)pyrazin-2-yl]carbonyl}amino)pyrrolidin-1-yl]methyl}pyrrolidine-1-carboxylate |
| 689 | 3-amino-6-(3-{[(phenylmethyl)amino]carbonyl}phenyl)-N-{(3S)-1-[(2R)-pyrrolidin-2-ylmethyl]pyrrolidin-3-yl}pyrazine-2-carboxamide |
| 690 | 3-amino-N-((3S)-1-{[4-(dimethylamino)phenyl]methyl}pyrrolidin-3-yl)-6-(3-{[(phenylmethyl)amino]carbonyl}phenyl)pyrazine-2-carboxamide |
| 691 | 3-amino-N-{2-[({[4-(dimethylamino)phenyl]amino}carbonyl)amino]ethyl}-6-(3-{[(phenylmethyl)amino]carbonyl}phenyl)pyrazine-2-carboxamide |
| 692 | 3-amino-N-[2-({[4-(dimethylamino)phenyl]carbonyl}amino)ethyl]-6-(3-{[(phenylmethyl)amino]carbonyl}phenyl)pyrazine-2-carboxamide |
| 693 | 3-{5-amino-6-[imino(2-pyridin-2-ylhydrazino)methyl]pyrazin-2-yl}-N-(phenylmethyl)benzamide |
| 694 | 3-[5-amino-6-(morpholin-4-ylmethyl)pyrazin-2-yl]-N-(phenylmethyl)benzamide |
| 695 | ethyl 1-{[3-amino-6-(3-{[(phenylmethyl)amino]carbonyl}phenyl)pyrazin-2-yl]methyl}piperidine-4-carboxylate |
| 696 | 3-amino-6-(3-{[(phenylmethyl)amino]carbonyl}phenyl)-N-[(3S)-1-(pyridin-2-ylmethyl)pyrrolidin-3-yl]pyrazine-2-carboxamide |
| 697 | methyl N-{[3-amino-6-(3-{[(phenylmethyl)amino]carbonyl}phenyl)pyrazin-2-yl]carbonyl}threoninate |
| 698 | {3-[5-amino-6-(3-piperidin-2-yl-1H-1,2,4-triazol-5-yl)pyrazin-2-yl]phenyl}methanol |
| 699 | 3-(ethylamino)-N-[(3S)-1-ethylpyrrolidin-3-yl]-6-(3-{[(phenylmethyl)amino]carbonyl}phenyl)pyrazine-2-carboxamide |
| 700 | 3-amino-N-[(3S)-1-ethylpyrrolidin-3-yl]-6-(3-{[(phenylmethyl)amino]carbonyl}phenyl)pyrazine-2-carboxamide |
| 701 | 3-[5-amino-6-(1-methyl-5-piperidin-2-yl-1H-1,2,4-triazol-3-yl)pyrazin-2-yl]-N-(phenylmethyl)benzamide |
| 702 | 3-[5-amino-6-(5-methyl-1-pyridin-2-yl-1H-1,2,4-triazol-3-yl)pyrazin-2-yl]-N-(phenylmethyl)benzamide |
| 703 | {3-[5-amino-6-(3-morpholin-2-yl-1H-1,2,4-triazol-5-yl)pyrazin-2-yl]phenyl}methanol |
| 704 | 5-(3-{[(1S)-2,3-dihydro-1H-inden-1-ylamino]methyl}phenyl)-3-{3-[(3S)-piperidin-3-yl]-1H-1,2,4-triazol-5-yl}pyrazin-2-amine |
| 705 | 5-(3-{[(1S)-2,3-dihydro-1H-inden-1-ylamino]methyl}phenyl)-3-{3-[(3R)-piperidin-3-yl]-1H-1,2,4-triazol-5-yl}pyrazin-2-amine |
| 706 | 3-amino-6-(3-{[(1S)-2,3-dihydro-1H-inden-1-ylamino]carbonyl}phenyl)-N-[(3S)-1-ethylpyrrolidin-3-yl]pyrazine-2-carboxamide |
| 707 | 6-(3-{[(1S)-2,3-dihydro-1H-inden-1-ylamino]carbonyl}phenyl)-3-(ethylamino)-N-[(3S)-1-ethylpyrrolidin-3-yl]pyrazine-2-carboxamide |
| 708 | 3-amino-6-[3-({[(1S,2R)-2-hydroxy-2,3-dihydro-1H-inden-1-yl]amino}carbonyl)phenyl]-N-[(3S)-pyrrolidin-3-yl]pyrazine-2-carboxamide |
| 709 | 1,1-dimethylethyl (3S)-3-({[3-amino-6-(3-{[(1S)-2,3-dihydro-1H-inden-1-ylamino]carbonyl}phenyl)pyrazin-2-yl]carbonyl}amino)pyrrolidine-1-carboxylate |
| 710 | 1,1-dimethylethyl (3S)-3-[({3-amino-6-[3-({[(1R)-1-phenylethyl]amino}carbonyl)phenyl]pyrazin-2-yl}carbonyl)amino]pyrrolidine-1-carboxylate |
| 711 | 1,1-dimethylethyl (3S)-3-[({3-amino-6-[3-(3,4-dihydroisoquinolin-2(1H)-ylcarbonyl)phenyl]pyrazin-2-yl}carbonyl)amino]pyrrolidine-1-carboxylate |
| 712 | 1,1-dimethylethyl (3S)-3-({[3-amino-6-(3-{[(2-phenylethyl)amino]carbonyl}phenyl)pyrazin-2-yl]carbonyl}amino)pyrrolidine-1-carboxylate |

TABLE 10-continued

| # | Name |
|---|------|
| 713 | 1,1-dimethylethyl (3S)-3-[({3-amino-6-[3-({[(1S)-1-phenylethyl]amino}carbonyl)phenyl]pyrazin-2-yl}carbonyl)amino]pyrrolidine-1-carboxylate |
| 714 | 3-amino-6-[3-(3,4-dihydroisoquinolin-2(1H)-ylcarbonyl)phenyl]-N-[(3S)-pyrrolidin-3-yl]pyrazine-2-carboxamide |
| 715 | 3-amino-6-(3-{[(2-phenylethyl)amino]carbonyl}phenyl)-N-[(3S)-pyrrolidin-3-yl]pyrazine-2-carboxamide |
| 716 | 3-amino-6-[3-({[(1R)-1-phenylethyl]amino}carbonyl)phenyl]-N-[(3S)-pyrrolidin-3-yl]pyrazine-2-carboxamide |
| 717 | 3-amino-6-[3-({[(1S)-1-phenylethyl]amino}carbonyl)phenyl]-N-[(3S)-pyrrolidin-3-yl]pyrazine-2-carboxamide |
| 718 | 3-{5-amino-6-[(2-ethylhydrazino)(imino)methyl]pyrazin-2-yl}-N-(2,3-dihydro-1H-inden-1-yl)benzamide |
| 719 | 3-{5-amino-6-[imino(2-methylhydrazino)methyl]pyrazin-2-yl}-N-[(1S)-2,3-dihydro-1H-inden-1-yl]benzamide |
| 720 | 3-{5-amino-6-[imino(2-phenylhydrazino)methyl]pyrazin-2-yl}-N-[(1S)-2,3-dihydro-1H-inden-1-yl]benzamide |
| 721 | phenylmethyl 3-{3-[3-amino-6-(3-{[(1S)-2,3-dihydro-1H-inden-1-ylamino]carbonyl}phenyl)pyrazin-2-yl]-1-methyl-1H-1,2,4-triazol-5-yl}piperidine-1-carboxylate |
| 722 | phenylmethyl 3-{3-[3-amino-6-(3-{[(1S)-2,3-dihydro-1H-inden-1-ylamino]carbonyl}phenyl)pyrazin-2-yl]-1-ethyl-1H-1,2,4-triazol-5-yl}piperidine-1-carboxylate |
| 723 | 5-(3-{[(1S)-2,3-dihydro-1H-inden-1-ylamino]methyl}phenyl)-3-(3-pyridin-4-yl-1H-1,2,4-triazol-5-yl)pyrazin-2-amine |
| 724 | [3-(5-amino-6-{3-[(3R)-piperidin-3-yl]-1H-1,2,4-triazol-5-yl}pyrazin-2-yl)phenyl]methanol |
| 725 | [3-(5-amino-6-{3-[(3S)-piperidin-3-yl]-1H-1,2,4-triazol-5-yl}pyrazin-2-yl)phenyl]methanol |
| 726 | 3-amino-6-[3-({[(1R,2S)-2-hydroxy-2,3-dihydro-1H-inden-1-yl]amino}carbonyl)phenyl]-N-[(3S)-pyrrolidin-3-yl]pyrazine-2-carboxamide |
| 727 | 3-amino-N-[(3S)-1-ethylpyrrolidin-3-yl]-6-[3-({[(1S,2R)-2-hydroxy-2,3-dihydro-1H-inden-1-yl]amino}carbonyl)phenyl]pyrazine-2-carboxamide |
| 728 | 1,1-dimethylethyl 3-({[3-amino-6-(3-{[(1S)-2,3-dihydro-1H-inden-1-ylamino]carbonyl}phenyl)pyrazin-2-yl]carbonyl}amino)piperidine-1-carboxylate |
| 729 | 3-amino-6-(3-{[(1S)-2,3-dihydro-1H-inden-1-ylamino]carbonyl}phenyl)-N-piperidin-3-ylpyrazine-2-carboxamide |
| 730 | 3-amino-6-(3-{[(1S)-2,3-dihydro-1H-inden-1-ylamino]carbonyl}phenyl)-N-(1-ethylpiperidin-3-yl)pyrazine-2-carboxamide |
| 731 | 3-amino-N-[(3S)-1-ethylpyrrolidin-3-yl]-6-[3-({[(1R,2S)-2-hydroxy-2,3-dihydro-1H-inden-1-yl]amino}carbonyl)phenyl]pyrazine-2-carboxamide |
| 732 | (3-{5-amino-6-[5-(1-ethylpiperidin-3-yl)-4H-1,2,4-triazol-3-yl]pyrazin-2-yl}phenyl)methanol |
| 733 | 5-(3-{[(1S)-2,3-dihydro-1H-inden-1-ylamino]methyl}phenyl)-3-[5-(1-ethylpiperidin-3-yl)-4H-1,2,4-triazol-3-yl]pyrazin-2-amine |
| 734 | 3-[5-amino-6-(1-ethyl-5-piperidin-3-yl-1H-1,2,4-triazol-3-yl)pyrazin-2-yl]-N-[(1R)-2,3-dihydro-1H-inden-1-yl]benzamide |
| 735 | 3-[5-amino-6-(1-methyl-5-piperidin-3-yl-1H-1,2,4-triazol-3-yl)pyrazin-2-yl]-N-[(1S)-2,3-dihydro-1H-inden-1-yl]benzamide |
| 736 | (3-{5-amino-6-[3-(1-methylpiperidin-3-yl)-1H-1,2,4-triazol-5-yl]pyrazin-2-yl}phenyl)methanol |
| 737 | 5-(3-{[(1S)-2,3-dihydro-1H-inden-1-ylamino]methyl}phenyl)-3-[3-(1-methylpiperidin-3-yl)-1H-1,2,4-triazol-5-yl]pyrazin-2-amine |
| 738 | 1,1-dimethylethyl (3S)-3-{[(3-amino-6-{3-[({[4-(methyloxy)phenyl]methyl}amino)carbonyl]phenyl}pyrazin-2-yl)carbonyl]amino}pyrrolidine-1-carboxylate |
| 739 | 1,1-dimethylethyl (3S)-3-({[3-amino-6-(3-{[({4-[(trifluoromethyl)oxy]phenyl}methyl)amino]carbonyl}phenyl)pyrazin-2-yl]carbonyl}amino)pyrrolidine-1-carboxylate |
| 740 | 1,1-dimethylethyl (3S)-3-[({3-amino-6-[3-({[(2-chloro-6-fluorophenyl)methyl]amino}carbonyl)phenyl]pyrazin-2-yl}carbonyl)amino]pyrrolidine-1-carboxylate |
| 741 | 1,1-dimethylethyl (3S)-3-{[(3-amino-6-{3-[({[4-(methylthio)phenyl]methyl}amino)carbonyl]phenyl}pyrazin-2-yl)carbonyl]amino}pyrrolidine-1-carboxylate |
| 742 | 1,1-dimethylethyl (3S)-3-{[(3-amino-6-{3-[(2,3-dihydro-1H-inden-2-ylamino)carbonyl]phenyl}pyrazin-2-yl)carbonyl]amino}pyrrolidine-1-carboxylate |
| 743 | 3-amino-6-{3-[({[4-(methyloxy)phenyl]methyl}amino)carbonyl]phenyl}-N-[(3S)-pyrrolidin-3-yl]pyrazine-2-carboxamide |
| 744 | 3-amino-N-[(3S)-pyrrolidin-3-yl]-6-(3-{[({4-[(trifluoromethyl)oxy]phenyl}methyl)amino]carbonyl}phenyl)pyrazine-2-carboxamide |
| 745 | 3-amino-6-{3-[(2,3-dihydro-1H-inden-2-ylamino)carbonyl]phenyl}-N-[(3S)-pyrrolidin-3-yl]pyrazine-2-carboxamide |
| 746 | 3-amino-6-[3-({[(2-chloro-6-fluorophenyl)methyl]amino}carbonyl)phenyl]-N-[(3S)-pyrrolidin-3-yl]pyrazine-2-carboxamide |

TABLE 10-continued

| # | Name |
|---|---|
| 747 | 3-amino-6-{3-[({[4-(methylthio)phenyl]methyl}amino)carbonyl]phenyl}-N-[(3S)-pyrrolidin-3-yl]pyrazine-2-carboxamide |
| 748 | 3-{5-amino-6-[imino(2-pyridin-4-ylhydrazino)methyl]pyrazin-2-yl}-N-[(1R)-2,3-dihydro-1H-inden-1-yl]benzamide |
| 749 | phenylmethyl (3R)-3-{3-[3-amino-6-(3-{[(1S)-2,3-dihydro-1H-inden-1-ylamino]carbonyl}phenyl)pyrazin-2-yl]-1-ethyl-1H-1,2,4-triazol-5-yl}piperidine-1-carboxylate |
| 750 | 3-amino-6-(3-{(1S)-1-[(1S)-2,3-dihydro-1H-inden-1-ylamino]ethyl}phenyl)-N-methylpyrazine-2-carboxamide |
| 751 | 3-amino-6-[3-({[(1R,2S)-2-hydroxy-2,3-dihydro-1H-inden-1-yl]amino}carbonyl)phenyl]-N-[2-(1H-imidazol-4-yl)ethyl]pyrazine-2-carboxamide |
| 752 | 1,1-dimethylethyl (3S)-3-[({[3-amino-6-(3-{[(1S)-2,3-dihydro-1H-inden-1-ylamino]carbonyl}phenyl)pyrazin-2-yl]carbonyl}amino)methyl]pyrrolidine-1-carboxylate |
| 753 | 3-amino-6-(3-{[(1S)-2,3-dihydro-1H-inden-1-ylamino]carbonyl}phenyl)-N-[(3R)-pyrrolidin-3-ylmethyl]pyrazine-2-carboxamide |
| 754 | phenylmethyl (3R)-3-{3-[3-amino-6-(3-{[(1S)-2,3-dihydro-1H-inden-1-ylamino]carbonyl}phenyl)pyrazin-2-yl]-1-methyl-1H-1,2,4-triazol-5-yl}piperidine-1-carboxylate |
| 755 | 3-(5-amino-6-{5-[(3S)-piperidin-3-yl]-4H-1,2,4-triazol-3-yl}pyrazin-2-yl)-N-[(1S)-2,3-dihydro-1H-inden-1-yl]benzamide |
| 756 | 1,1-dimethylethyl (3S)-3-[({3-amino-6-[3-({[(4-chlorophenyl)methyl]amino}carbonyl)phenyl]pyrazin-2-yl}carbonyl)amino]pyrrolidine-1-carboxylate |
| 757 | 1,1-dimethylethyl (3S)-3-({[3-amino-6-(3-{[(pyridin-2-ylmethyl)amino]carbonyl}phenyl)pyrazin-2-yl]carbonyl}amino)pyrrolidine-1-carboxylate |
| 758 | 1,1-dimethylethyl (3S)-3-({[3-amino-6-(3-{[(pyridin-3-ylmethyl)amino]carbonyl}phenyl)pyrazin-2-yl]carbonyl}amino)pyrrolidine-1-carboxylate |
| 759 | 1,1-dimethylethyl (3S)-3-{[(3-amino-6-{3-[(3,4-dihydro-2H-chromen-4-ylamino)carbonyl]phenyl}pyrazin-2-yl)carbonyl]amino}pyrrolidine-1-carboxylate |
| 760 | 3-amino-6-[3-({[(4-chlorophenyl)methyl]amino}carbonyl)phenyl]-N-[(3S)-pyrrolidin-3-yl]pyrazine-2-carboxamide |
| 761 | 3-amino-6-(3-{[(pyridin-2-ylmethyl)amino]carbonyl}phenyl)-N-[(3S)-pyrrolidin-3-yl]pyrazine-2-carboxamide |
| 762 | 3-amino-6-(3-{[(pyridin-3-ylmethyl)amino]carbonyl}phenyl)-N-[(3S)-pyrrolidin-3-yl]pyrazine-2-carboxamide |
| 763 | dimethyl 5-{5-amino-6-[(methylamino)carbonyl]pyrazin-2-yl}benzene-1,3-dicarboxylate |
| 764 | 3-amino-6-(3-{[(1S)-2,3-dihydro-1H-inden-1-ylamino]carbonyl}phenyl)-N-[(3S)-piperidin-3-yl]pyrazine-2-carboxamide |
| 765 | 3-amino-6-(3-{[(1S)-2,3-dihydro-1H-inden-1-ylamino]carbonyl}phenyl)-N-[(3R)-piperidin-3-yl]pyrazine-2-carboxamide |
| 766 | 3-amino-6-[3-({[(1R,2S)-2-hydroxy-2,3-dihydro-1H-inden-1-yl]amino}carbonyl)phenyl]-N-piperidin-3-ylpyrazine-2-carboxamide |
| 767 | 3-amino-6-(3-{[(1S)-2,3-dihydro-1H-inden-1-ylamino]carbonyl}phenyl)-N-[2-(1H-imidazol-4-yl)ethyl]pyrazine-2-carboxamide |
| 768 | 3-amino-N-azepan-4-yl-6-(3-{[(1S)-2,3-dihydro-1H-inden-1-ylamino]carbonyl}phenyl)pyrazine-2-carboxamide |
| 769 | 1,1-dimethylethyl (3S)-3-{[({3-amino-6-[3-({[(1R,2S)-2-hydroxy-2,3-dihydro-1H-inden-1-yl]amino}carbonyl)phenyl]pyrazin-2-yl}carbonyl)amino]methyl}pyrrolidine-1-carboxylate |
| 770 | 1,1-dimethylethyl 4-({[3-amino-6-(3-{[(1S)-2,3-dihydro-1H-inden-1-ylamino]carbonyl}phenyl)pyrazin-2-yl]carbonyl}amino)azepane-1-carboxylate |
| 771 | 3-[5-amino-6-(5-{2-[(phenylmethyl)oxy]ethyl}-1H-1,2,4-triazol-3-yl)pyrazin-2-yl]-N-[(1S)-2,3-dihydro-1H-inden-1-yl]benzamide |
| 772 | 3-amino-6-(3-{[(1S)-2,3-dihydro-1H-inden-1-ylamino]carbonyl}-4-fluorophenyl)-N-methylpyrazine-2-carboxamide |
| 773 | 3-[5-amino-6-(1-phenyl-5-piperidin-3-yl-1H-1,2,4-triazol-3-yl)pyrazin-2-yl]-N-[(1S)-2,3-dihydro-1H-inden-1-yl]benzamide |
| 774 | 3-{5-amino-6-[amino(imino)methyl]pyrazin-2-yl}-N-[(1S)-2,3-dihydro-1H-inden-1-yl]benzamide |
| 775 | 3-(5-amino-6-{5-[(3S)-piperidin-3-yl]-4H-1,2,4-triazol-3-yl}pyrazin-2-yl)-N-[(1R,2S)-2-hydroxy-2,3-dihydro-1H-inden-1-yl]benzamide |
| 776 | 1,1-dimethylethyl (3S)-3-({[3-amino-6-(3-{[(1S)-2,3-dihydro-1H-inden-1-ylamino]carbonyl}phenyl)pyrazin-2-yl]carbonyl}amino)piperidine-1-carboxylate |
| 777 | 1,1-dimethylethyl (3S)-3-[({3-amino-6-[3-({[(1R,2S)-2-hydroxy-2,3-dihydro-1H-inden-1-yl]amino}carbonyl)phenyl]pyrazin-2-yl}carbonyl)amino]piperidine-1-carboxylate |
| 778 | 3-amino-6-{3-[(3,4-dihydro-2H-chromen-4-ylamino)carbonyl]phenyl}-N-[(3S)-pyrrolidin-3-yl]pyrazine-2-carboxamide |
| 779 | 3-amino-6-{3-[(2,3-dihydro-1-benzofuran-3-ylamino)carbonyl]phenyl}-N-[(3S)-pyrrolidin-3-yl]pyrazine-2-carboxamide |
| 780 | 3-amino-6-[3-({[(1R,2S)-2-hydroxy-2,3-dihydro-1H-inden-1-yl]amino}carbonyl)phenyl]-N-[(3R)-pyrrolidin-3-ylmethyl]pyrazine-2-carboxamide |

TABLE 10-continued

| # | Name |
|---|---|
| 781 | 1,1-dimethylethyl 4-[({3-amino-6-[3-({[(1R,2S)-2-hydroxy-2,3-dihydro-1H-inden-1-yl]amino}carbonyl)phenyl]pyrazin-2-yl}carbonyl)amino]azepane-1-carboxylate |
| 782 | 3-amino-N-azepan-4-yl-6-[3-({[(1R,2S)-2-hydroxy-2,3-dihydro-1H-inden-1-yl]amino}carbonyl)phenyl]pyrazine-2-carboxamide |
| 783 | 3-amino-N-azepan-4-yl-6-{3-[(3aR,8aS)-8,8a-dihydro-3aH-indeno[1,2-d][1,3]oxazol-2-yl]phenyl}pyrazine-2-carboxamide |
| 784 | 1,1-dimethylethyl (3R)-3-[(({3-amino-6-(3-{[(1S)-2,3-dihydro-1H-inden-1-ylamino]carbonyl}phenyl)pyrazin-2-yl]carbonyl}amino)methyl]pyrrolidine-1-carboxylate |
| 785 | 3-amino-6-(3-{[(1S)-2,3-dihydro-1H-inden-1-ylamino]carbonyl}phenyl)-N-[(3S)-pyrrolidin-3-ylmethyl]pyrazine-2-carboxamide |
| 786 | 1,1-dimethylethyl (3R)-3-{[({3-amino-6-[3-({[(1R,2S)-2-hydroxy-2,3-dihydro-1H-inden-1-yl]amino}carbonyl)phenyl]pyrazin-2-yl}carbonyl)amino]methyl}pyrrolidine-1-carboxylate |
| 787 | 3-amino-6-[3-({[(1R,2S)-2-hydroxy-2,3-dihydro-1H-inden-1-yl]amino}carbonyl)phenyl]-N-[(3S)-pyrrolidin-3-ylmethyl]pyrazine-2-carboxamide |
| 788 | 3-amino-6-(3-{[(1S)-2,3-dihydro-1H-inden-1-ylamino]carbonyl}-5-fluorophenyl)-N-methylpyrazine-2-carboxamide |
| 789 | 3-{5-amino-6-[(methylamino)carbonyl]pyrazin-2-yl}-5-[(methyloxy)carbonyl]benzoic acid |
| 790 | methyl 3-{5-amino-6-[(methylamino)carbonyl]pyrazin-2-yl}-5-{[(1S)-2,3-dihydro-1H-inden-1-ylamino]carbonyl}benzoate |
| 791 | 5-{5-amino-6-[(methylamino)carbonyl]pyrazin-2-yl}-N-[(1S)-2,3-dihydro-1H-inden-1-yl]-N'-pyrrolidin-3-ylbenzene-1,3-dicarboxamide |
| 792 | 3-[5-amino-6-(5-phenyl-1-pyridin-2-yl-1H-1,2,4-triazol-3-yl)pyrazin-2-yl]-N-(phenylmethyl)benzamide |
| 793 | 3-[5-amino-6-(5-methyl-1-pyridin-4-yl-1H-1,2,4-triazol-3-yl)pyrazin-2-yl]-N-[(1S)-2,3-dihydro-1H-inden-1-yl]benzamide |
| 794 | 1,1-dimethylethyl (3R)-3-({[3-amino-6-(3-{[(1S)-2,3-dihydro-1H-inden-1-ylamino]carbonyl}phenyl)pyrazin-2-yl]carbonyl}amino)piperidine-1-carboxylate |
| 795 | 1,1-dimethylethyl (3R)-3-[({3-amino-6-[3-({[(1R,2S)-2-hydroxy-2,3-dihydro-1H-inden-1-yl]amino}carbonyl)phenyl]pyrazin-2-yl}carbonyl)amino]piperidine-1-carboxylate |
| 796 | 3-amino-6-(3-{[(1S)-2,3-dihydro-1H-inden-1-ylamino]carbonyl}phenyl)-N-[(3S)-piperidin-3-yl]pyrazine-2-carboxamide |
| 797 | 5-{5-amino-6-[(methylamino)carbonyl]pyrazin-2-yl}-N-[(1R)-2,3-dihydro-1H-inden-1-yl]-N'-[(3R)-pyrrolidin-3-yl]benzene-1,3-dicarboxamide |
| 798 | (3-{5-amino-6-[3-(2-aminopyridin-4-yl)-1H-1,2,4-triazol-5-yl]pyrazin-2-yl}phenyl)methanol |
| 799 | 3-[5-amino-6-(1,5-dimethyl-1H-1,2,4-triazol-3-yl)pyrazin-2-yl]-N-[(1S)-2,3-dihydro-1H-inden-1-yl]benzamide |
| 800 | 1,1-dimethylethyl (3S)-3-({[3-amino-6-(3-{[(1-methyl-1-phenylethyl)amino]carbonyl}phenyl)pyrazin-2-yl]carbonyl}amino)pyrrolidine-1-carboxylate |
| 801 | 3-amino-6-(3-{[(1-methyl-1-phenylethyl)amino]carbonyl}phenyl)-N-[(3S)-pyrrolidin-3-yl]pyrazine-2-carboxamide |
| 802 | 3-amino-6-(3-{[(1S)-2,3-dihydro-1H-inden-1-ylamino]sulfonyl}phenyl)pyrazine-2-carboxamide |
| 803 | 3-amino-6-(3-{[(1S)-2,3-dihydro-1H-inden-1-ylamino]sulfonyl}phenyl)-N-piperidin-3-ylpyrazine-2-carboxamide |
| 804 | 3-amino-6-(3-{[(1S)-2,3-dihydro-1H-inden-1-ylamino]carbonyl}phenyl)-N-[(3S)-1-methylpyrrolidin-3-yl]pyrazine-2-carboxamide |
| 805 | 3-amino-6-[3-({[(1R,2S)-2-hydroxy-2,3-dihydro-1H-inden-1-yl]amino}carbonyl)phenyl]-N-[(3S)-1-methylpyrrolidin-3-yl]pyrazine-2-carboxamide |
| 806 | 3-amino-6-[3-({[(1R,2S)-2-hydroxy-2,3-dihydro-1H-inden-1-yl]amino}methyl)phenyl]-N-[(3S)-pyrrolidin-3-yl]pyrazine-2-carboxamide |
| 807 | 3-amino-6-[3-({[(1R,2S)-2-hydroxy-2,3-dihydro-1H-inden-1-yl]amino}carbonyl)phenyl]-N-[(3S)-piperidin-3-yl]pyrazine-2-carboxamide |
| 808 | 3-amino-N-[(3S)-pyrrolidin-3-yl]-6-(3-{[(1S)-1,2,3,4-tetrahydronaphthalen-1-ylamino]methyl}phenyl)pyrazine-2-carboxamide |
| 809 | N-[3-(5-amino-6-{5-[(3S)-piperidin-3-yl]-4H-1,2,4-triazol-3-yl}pyrazin-2-yl)phenyl]-2-(2,4-dichlorophenyl)acetamide |
| 810 | 1,1-dimethylethyl (3S)-3-({[3-amino-6-(3-{[(1R)-2,3-dihydro-1H-inden-1-ylamino]sulfonyl}phenyl)pyrazin-2-yl]carbonyl}amino)pyrrolidine-1-carboxylate |
| 811 | 3-amino-6-(3-hydroxyphenyl)-N-[(3S)-pyrrolidin-3-yl]pyrazine-2-carboxamide |
| 812 | 3-amino-6-(3-{[(1R)-2,3-dihydro-1H-inden-1-ylamino]sulfonyl}phenyl)-N-[(3S)-pyrrolidin-3-yl]pyrazine-2-carboxamide |
| 813 | 3-[5-amino-6-(1-pyridin-4-yl-1H-1,2,4-triazol-3-yl)pyrazin-2-yl]-N-[(1S)-2,3-dihydro-1H-inden-1-yl]benzamide |
| 814 | 3-amino-N-[(3S)-pyrrolidin-3-yl]-6-[3-({[(3,4,5-trifluorophenyl)methyl]amino}carbonyl)phenyl]pyrazine-2-carboxamide |
| 815 | 3-amino-N-[(3S)-pyrrolidin-3-yl]-6-[3-({[(2,3,6-trifluorophenyl)methyl]amino}carbonyl)phenyl]pyrazine-2-carboxamide |
| 816 | 3-amino-N-[(3S)-pyrrolidin-3-yl]-6-[3-({[(2,3,5-trifluorophenyl)methyl]amino}carbonyl)phenyl]pyrazine-2-carboxamide |

TABLE 10-continued

| # | Name |
|---|------|
| 817 | 3-amino-6-[3-({[(3-bromo-4-fluorophenyl)methyl]amino}carbonyl)phenyl]-N-[(3S)-pyrrolidin-3-yl]pyrazine-2-carboxamide |
| 818 | 3-{5-amino-6-[3-(1-methylpiperidin-3-yl)-1H-1,2,4-triazol-5-yl]pyrazin-2-yl}-N-[(2-chloro-6-fluorophenyl)methyl]benzamide |
| 819 | 3-amino-N-1-azabicyclo[2.2.2]oct-3-yl-6-(3-{[(1S)-2,3-dihydro-1H-inden-1-ylamino]methyl}phenyl)pyrazine-2-carboxamide |
| 820 | 3-(5-amino-6-{3-[(3S)-piperidin-3-yl]-1H-1,2,4-triazol-5-yl}pyrazin-2-yl)-N-[(4-chloro-2-fluorophenyl)methyl]benzamide |
| 821 | 3-(5-amino-6-{3-[(3S)-piperidin-3-yl]-1H-1,2,4-triazol-5-yl}pyrazin-2-yl)-N-[(2-chlorophenyl)methyl]benzamide |
| 822 | 1,1-dimethylethyl (3S)-3-[({3-amino-6-[3-({[(2,4-dichlorophenyl)methyl]amino}carbonyl)phenyl]pyrazin-2-yl}carbonyl)amino]pyrrolidine-1-carboxylate |
| 823 | 1,1-dimethylethyl (3S)-3-[({3-amino-6-[3-({[(3,4-dichlorophenyl)methyl]amino}carbonyl)phenyl]pyrazin-2-yl}carbonyl)amino]pyrrolidine-1-carboxylate |
| 824 | 5-(3-{[(1S)-2,3-dihydro-1H-inden-1-ylamino]methyl}phenyl)-3-(4-piperidin-3-yl-1,3-thiazol-2-yl)pyrazin-2-amine |
| 825 | 3-amino-6-[3-({[(2,4-dichlorophenyl)methyl]amino}carbonyl)phenyl]-N-[(3S)-pyrrolidin-3-yl]pyrazine-2-carboxamide |
| 826 | 3-amino-6-[3-({[(3,4-dichlorophenyl)methyl]amino}carbonyl)phenyl]-N-[(3S)-pyrrolidin-3-yl]pyrazine-2-carboxamide |
| 827 | 3-(5-amino-6-{3-[(3S)-piperidin-3-yl]-1H-1,2,4-triazol-5-yl}pyrazin-2-yl)-N-[(2,6-difluorophenyl)methyl]benzamide |
| 828 | 3-(5-amino-6-{3-[(3S)-piperidin-3-yl]-1H-1,2,4-triazol-5-yl}pyrazin-2-yl)-N-[(2-chloro-6-fluorophenyl)methyl]benzamide |
| 829 | 3-(5-amino-6-{3-[(3S)-piperidin-3-yl]-1H-1,2,4-triazol-5-yl}pyrazin-2-yl)-N-[(2,5-dichlorophenyl)methyl]benzamide |
| 830 | 3-(5-amino-6-{3-[(3S)-piperidin-3-yl]-1H-1,2,4-triazol-5-yl}pyrazin-2-yl)-N-[(3,4-dichlorophenyl)methyl]benzamide |
| 831 | 3-amino-6-{3-[({[4-(methyloxy)phenyl]methyl}amino)carbonyl]phenyl}-N-[(3S)-piperidin-3-yl]pyrazine-2-carboxamide |
| 832 | 3-amino-6-[3-({[(2,4-dichlorophenyl)methyl]amino}carbonyl)phenyl]-N-[(3S)-piperidin-3-yl]pyrazine-2-carboxamide |
| 833 | 1,1-dimethylethyl (3S)-3-{[(3-amino-6-{3-[({[(1,1-dimethylethyl)oxy]carbonyl}amino)methyl]phenyl}pyrazin-2-yl)carbonyl]amino}piperidine-1-carboxylate |
| 834 | 3-(5-amino-6-{5-[(3S)-piperidin-3-yl]-4H-1,2,4-triazol-3-yl}pyrazin-2-yl)-N-[(2-fluorophenyl)methyl]benzamide |
| 835 | 3-(5-amino-6-{5-[(3S)-piperidin-3-yl]-4H-1,2,4-triazol-3-yl}pyrazin-2-yl)-N-[(3-fluorophenyl)methyl]benzamide |
| 836 | 3-(5-amino-6-{5-[(3S)-piperidin-3-yl]-4H-1,2,4-triazol-3-yl}pyrazin-2-yl)-N-[(4-fluorophenyl)methyl]benzamide |
| 837 | 3-(5-amino-6-{5-[(3S)-piperidin-3-yl]-4H-1,2,4-triazol-3-yl}pyrazin-2-yl)-N-[(3-chlorophenyl)methyl]benzamide |
| 838 | 3-(5-amino-6-{5-[(3S)-piperidin-3-yl]-4H-1,2,4-triazol-3-yl}pyrazin-2-yl)-N-[(4-chlorophenyl)methyl]benzamide |
| 839 | 3-amino-6-[3-(aminomethyl)phenyl]-N-[(3S)-piperidin-3-yl]pyrazine-2-carboxamide |
| 840 | 3-amino-6-(3-hydroxyphenyl)-N-[(3S)-piperidin-3-yl]pyrazine-2-carboxamide |
| 841 | 1,1-dimethylethyl (3S)-3-[({3-amino-6-[3-(aminomethyl)phenyl]pyrazin-2-yl}carbonyl)amino]piperidine-1-carboxylate |
| 842 | 3-amino-6-[3-({[(4-fluorophenyl)methyl]amino}carbonyl)phenyl]-N-[(3S)-piperidin-3-yl]pyrazine-2-carboxamide |
| 843 | 3-amino-N-[(3S)-piperidin-3-yl]-6-(3-{[({4-[(trifluoromethyl)oxy]phenyl}methyl)amino]carbonyl}phenyl)pyrazine-2-carboxamide |
| 844 | 3-amino-6-(3-{[(biphenyl-4-ylmethyl)amino]carbonyl}phenyl)-N-[(3S)-piperidin-3-yl]pyrazine-2-carboxamide |
| 845 | 3-amino-N-[(3S)-piperidin-3-yl]-6-{3-[({[4-(1,2,3-thiadiazol-5-yl)phenyl]methyl}amino)carbonyl]phenyl}pyrazine-2-carboxamide |
| 846 | 3-amino-N-[(3S)-piperidin-3-yl]-6-{3-[({2-[(trifluoromethyl)oxy]phenyl}methyl)amino]carbonyl}phenyl)pyrazine-2-carboxamide |
| 847 | 3-amino-6-(3-{[(biphenyl-2-ylmethyl)amino]carbonyl}phenyl)-N-[(3S)-piperidin-3-yl]pyrazine-2-carboxamide |
| 848 | 3-amino-6-[3-({[(2,4-difluorophenyl)methyl]amino}carbonyl)phenyl]-N-[(3S)-piperidin-3-yl]pyrazine-2-carboxamide |
| 849 | 3-amino-6-[3-({[(4-chloro-2-fluorophenyl)methyl]amino}carbonyl)phenyl]-N-[(3S)-piperidin-3-yl]pyrazine-2-carboxamide |
| 850 | 3-amino-6-{3-[({[4-fluoro-3-(trifluoromethyl)phenyl]methyl}amino)carbonyl]phenyl}-N-[(3S)-piperidin-3-yl]pyrazine-2-carboxamide |
| 851 | 3-amino-6-(3-{[(naphthalen-2-ylmethyl)amino]carbonyl}phenyl)-N-[(3S)-piperidin-3-yl]pyrazine-2-carboxamide |
| 852 | 3-amino-6-{3-[({[4-(dimethylamino)phenyl]methyl}amino)carbonyl]phenyl}-N-[(3S)-piperidin-3-yl]pyrazine-2-carboxamide |

TABLE 10-continued

| # | Name |
|---|------|
| 853 | 3-amino-6-(3-{[(1,3-benzodioxol-5-ylmethyl)amino]carbonyl}phenyl)-N-[(3S)-piperidin-3-yl]pyrazine-2-carboxamide |
| 854 | 3-amino-N-[(3S)-piperidin-3-yl]-6-{3-[({[4-(2-thienyl)phenyl]methyl}amino)carbonyl]phenyl}pyrazine-2-carboxamide |
| 855 | 3-amino-6-{3-[({[2-(methyloxy)phenyl]methyl}amino)carbonyl]phenyl}-N-[(3S)-piperidin-3-yl]pyrazine-2-carboxamide |
| 856 | 3-amino-6-{3-[({[2,4-bis(methyloxy)phenyl]methyl}amino)carbonyl]phenyl}-N-[(3S)-piperidin-3-yl]pyrazine-2-carboxamide |
| 857 | 3-amino-6-[3-({[(4-chloro-2-methylphenyl)methyl]amino}carbonyl)phenyl]-N-[(3S)-piperidin-3-yl]pyrazine-2-carboxamide |
| 858 | 3-amino-6-[3-({[(2,3-difluoro-4-methylphenyl)methyl]amino}carbonyl)phenyl]-N-[(3S)-piperidin-3-yl]pyrazine-2-carboxamide |
| 859 | 3-amino-6-{3-[({[4-(methylsulfonyl)phenyl]methyl}amino)carbonyl]phenyl}-N-[(3S)-piperidin-3-yl]pyrazine-2-carboxamide |
| 860 | 3-amino-6-(3-{[(2,3-dihydro-1,4-benzodioxin-6-ylmethyl)amino]carbonyl}phenyl)-N-[(3S)-piperidin-3-yl]pyrazine-2-carboxamide |
| 861 | 3-amino-6-[3-({[(4-chlorophenyl)methyl]amino}carbonyl)phenyl]-N-[(3S)-piperidin-3-yl]pyrazine-2-carboxamide |
| 862 | 3-amino-6-[3-({[(5-chloro-2-fluorophenyl)methyl]amino}carbonyl)phenyl]-N-[(3S)-piperidin-3-yl]pyrazine-2-carboxamide |
| 863 | 3-amino-N-[(3R)-1-azabicyclo[2.2.2]oct-3-yl]-6-(3-{[(1S)-2,3-dihydro-1H-inden-1-ylamino]methyl}phenyl)pyrazine-2-carboxamide |
| 864 | 3-amino-6-{3-[({[4-(methylthio)phenyl]methyl}amino)carbonyl]phenyl}-N-[(3S)-piperidin-3-yl]pyrazine-2-carboxamide |
| 865 | 3-(5-amino-6-{3-[(3S)-piperidin-3-yl]-1H-1,2,4-triazol-5-yl}pyrazin-2-yl)-N-[(2,4-difluorophenyl)methyl]benzamide |
| 866 | 3-amino-6-(3-{[(1,2-diphenylethyl)amino]carbonyl}phenyl)-N-[(3S)-piperidin-3-yl]pyrazine-2-carboxamide |
| 867 | 3-(5-amino-6-{3-[(3S)-piperidin-3-yl]-1H-1,2,4-triazol-5-yl}pyrazin-2-yl)-N-[(3,4-difluorophenyl)methyl]benzamide |
| 868 | 3-amino-6-[3-({[(3,5-difluorophenyl)methyl]amino}carbonyl)phenyl]-N-[(3S)-piperidin-3-yl]pyrazine-2-carboxamide |
| 869 | methyl 4-[({[3-(5-amino-6-{[(3S)-piperidin-3-ylamino]carbonyl}pyrazin-2-yl)phenyl]carbonyl}amino)methyl]benzoate |
| 870 | 3-amino-6-[3-({[(4-bromophenyl)methyl]amino}carbonyl)phenyl]-N-[(3S)-piperidin-3-yl]pyrazine-2-carboxamide |
| 871 | 3-amino-6-[3-({[(4-bromo-2-fluorophenyl)methyl]amino}carbonyl)phenyl]-N-[(3S)-piperidin-3-yl]pyrazine-2-carboxamide |
| 872 | 3-amino-6-[3-({[(2-bromophenyl)methyl]amino}carbonyl)phenyl]-N-[(3S)-piperidin-3-yl]pyrazine-2-carboxamide |
| 873 | 3-amino-6-{3-[({[4-fluoro-2-(trifluoromethyl)phenyl]methyl}amino)carbonyl]phenyl}-N-[(3S)-piperidin-3-yl]pyrazine-2-carboxamide |
| 874 | 3-amino-6-{3-[({[2-fluoro-3-(trifluoromethyl)phenyl]methyl}amino)carbonyl]phenyl}-N-[(3S)-piperidin-3-yl]pyrazine-2-carboxamide |
| 875 | 3-amino-N-[(3S)-piperidin-3-yl]-6-[3-({[(3R)-pyrrolidin-3-ylmethyl]amino}carbonyl)phenyl]pyrazine-2-carboxamide |
| 876 | 3-amino-N-[(3S)-piperidin-3-yl]-6-(3-{[(3R)-pyrrolidin-3-ylamino]carbonyl}phenyl)pyrazine-2-carboxamide |
| 877 | 3-amino-N-[(3S)-piperidin-3-yl]-6-(3-{[(2-piperidin-1-ylethyl)amino]carbonyl}phenyl)pyrazine-2-carboxamide |
| 878 | 3-amino-6-(3-{[(2-phenylethyl)amino]carbonyl}phenyl)-N-[(3S)-piperidin-3-yl]pyrazine-2-carboxamide |
| 879 | 3-amino-6-[3-({[(2-methyloxy)ethyl]amino}carbonyl)phenyl]-N-[(3S)-piperidin-3-yl]pyrazine-2-carboxamide |
| 880 | 3-amino-6-[3-({[(4-iodophenyl)methyl]amino}carbonyl)phenyl]-N-[(3S)-piperidin-3-yl]pyrazine-2-carboxamide |
| 881 | 3-amino-6-[3-({[(2-chlorophenyl)methyl]amino}carbonyl)phenyl]-N-[(3S)-piperidin-3-yl]pyrazine-2-carboxamide |
| 882 | 3-amino-6-[3-({[(4-fluorophenyl)carbonyl]amino}methyl)phenyl]-N-[(3S)-piperidin-3-yl]pyrazine-2-carboxamide |
| 883 | 3-amino-N-[(3S)-piperidin-3-yl]-6-(3-[({4-[(trifluoromethyl)oxy]phenyl}carbonyl)amino]methyl}phenyl)pyrazine-2-carboxamide |
| 884 | 3-amino-6-[3-({[(4-chlorophenyl)carbonyl]amino}methyl)phenyl]-N-[(3S)-piperidin-3-yl]pyrazine-2-carboxamide |
| 885 | 3-amino-6-(3-{[[(4-chlorophenyl)acetyl]amino}phenyl)-N-[(3S)-piperidin-3-yl]pyrazine-2-carboxamide |
| 886 | 3-amino-6-(3-{[[(2,6-dichlorophenyl)acetyl]amino}phenyl)-N-[(3S)-piperidin-3-yl]pyrazine-2-carboxamide |
| 887 | 3-amino-6-(3-{[(pentafluorophenyl)acetyl]amino}phenyl)-N-[(3S)-piperidin-3-yl]pyrazine-2-carboxamide |
| 888 | 3-amino-6-(3-{[[(2-chloro-4-fluorophenyl)acetyl]amino}phenyl)-N-[(3S)-piperidin-3-yl]pyrazine-2-carboxamide |
| 889 | 3-amino-6-[3-({[4-(methylthio)phenyl]acetyl}amino)phenyl]-N-[(3S)-piperidin-3-yl]pyrazine-2-carboxamide |

TABLE 10-continued

| # | Name |
|---|---|
| 890 | 3-amino-6-(3-{[(2,4-dichlorophenyl)acetyl]amino}phenyl)-N-[(3S)-piperidin-3-yl]pyrazine-2-carboxamide |
| 891 | 3-amino-6-[3-({[4-(4-chlorophenyl)-2-thienyl]carbonyl}amino)phenyl]-N-[(3S)-piperidin-3-yl]pyrazine-2-carboxamide |
| 892 | 3-amino-6-[3-({[(4-bromophenyl)carbonyl]amino}methyl)phenyl]-N-[(3S)-piperidin-3-yl]pyrazine-2-carboxamide |
| 893 | 3-amino-6-(3-{[(naphthalen-2-ylcarbonyl)amino]methyl}phenyl)-N-[(3S)-piperidin-3-yl]pyrazine-2-carboxamide |
| 894 | 3-amino-6-(3-{[2-(4-phenylpiperazin-1-yl)ethyl]oxy}phenyl)-N-[(3S)-piperidin-3-yl]pyrazine-2-carboxamide |
| 895 | N-[(3-{5-amino-6-[(3R)-piperidin-3-ylacetyl]pyrazin-2-yl}phenyl)methyl]-N'-(4-bromophenyl)urea |
| 896 | N-[(3-{5-amino-6-[(3R)-piperidin-3-ylacetyl]pyrazin-2-yl}phenyl)methyl]-N'-naphthalen-2-ylurea |
| 897 | 3-amino-6-(3-{[(2,4-difluorophenyl)acetyl]amino}phenyl)-N-[(3S)-piperidin-3-yl]pyrazine-2-carboxamide |
| 898 | 3-amino-6-(3-{[(2-fluorophenyl)acetyl]amino}phenyl)-N-[(3S)-piperidin-3-yl]pyrazine-2-carboxamide |
| 899 | 3-amino-6-{3-[({5-[2-chloro-5-(trifluoromethyl)phenyl]furan-2-yl}carbonyl)amino]phenyl}-N-[(3S)-piperidin-3-yl]pyrazine-2-carboxamide |
| 900 | 3-amino-6-[3-({[4-(dimethylamino)naphthalen-1-yl]carbonyl}amino)phenyl]-N-[(3S)-piperidin-3-yl]pyrazine-2-carboxamide |
| 901 | 3-amino-N-[(3S)-piperidin-3-yl]-6-[3-({[4-(1,2,3-thiadiazol-5-yl)phenyl]carbonyl}amino)phenyl]pyrazine-2-carboxamide |
| 902 | 3-amino-6-(3-{[(1,3-dimethyl-1H-pyrazol-5-yl)carbonyl]amino}phenyl)-N-[(3S)-piperidin-3-yl]pyrazine-2-carboxamide |
| 903 | 3-amino-6-{3-[({[4-(dimethylamino)phenyl]carbonyl}amino)methyl]phenyl}-N-[(3S)-piperidin-3-yl]pyrazine-2-carboxamide |
| 904 | 3-amino-6-{3-[(2-hydroxyethyl)oxy]phenyl}-N-[(3S)-piperidin-3-yl]pyrazine-2-carboxamide |
| 905 | 3-amino-6-(3-{[(2,3-dihydro-1-benzofuran-5-ylsulfonyl)amino]methyl}phenyl)-N-[(3S)-piperidin-3-yl]pyrazine-2-carboxamide |
| 906 | 3-amino-6-(3-{[(3,4-dihydro-2H-1,5-benzodioxepin-7-ylsulfonyl)amino]methyl}phenyl)-N-[(3S)-piperidin-3-yl]pyrazine-2-carboxamide |
| 907 | 3-amino-N-[(3S)-piperidin-3-yl]-6-(3-{[(quinolin-7-ylsulfonyl)amino]methyl}phenyl)pyrazine-2-carboxamide |
| 908 | 3-amino-6-[3-({[(biphenyl-4-ylamino)carbonyl]amino}methyl)phenyl]-N-[(3S)-piperidin-3-yl]pyrazine-2-carboxamide |
| 909 | 3-amino-6-(3-{[(4-bromo-2-fluorophenyl)carbonyl]amino}phenyl)-N-[(3S)-piperidin-3-yl]pyrazine-2-carboxamide |
| 910 | N-[3-(5-amino-6-{[(3S)-piperidin-3-ylamino]carbonyl}pyrazin-2-yl)phenyl]quinoline-3-carboxamide |
| 911 | 3-amino-6-[3-({[6-(methyloxy)-1-benzofuran-3-yl]acetyl}amino)phenyl]-N-[(3S)-piperidin-3-yl]pyrazine-2-carboxamide |
| 912 | 3-amino-N-[(3S)-piperidin-3-yl]-6-[3-({[4'-(trifluoromethyl)biphenyl-2-yl]carbonyl}amino)phenyl]pyrazine-2-carboxamide |
| 913 | 3-amino-6-[3-({[3,5-bis(trifluoromethyl)phenyl]acetyl}amino)phenyl]-N-[(3S)-piperidin-3-yl]pyrazine-2-carboxamide |
| 914 | 3-amino-6-{3-[({[(2,4-difluorophenyl)amino]carbonyl}amino)methyl]phenyl}-N-[(3S)-piperidin-3-yl]pyrazine-2-carboxamide |
| 915 | 3-amino-N-[(3S)-piperidin-3-yl]-6-{3-[({[2-(trifluoromethyl)phenyl]sulfonyl}amino)methyl]phenyl}pyrazine-2-carboxamide |
| 916 | 3-amino-N-[(3S)-piperidin-3-yl]-6-(3-{[({4-[(trifluoromethyl)oxy]phenyl}sulfonyl)amino]methyl}phenyl)pyrazine-2-carboxamide |
| 917 | 3-amino-N-[(3S)-piperidin-3-yl]-6-(3-{[({2-[(trifluoromethyl)oxy]phenyl}sulfonyl)amino]methyl}phenyl)pyrazine-2-carboxamide |
| 918 | 3-amino-N-[(3S)-piperidin-3-yl]-6-{3-[({[4-(trifluoromethyl)phenyl]sulfonyl}amino)methyl]phenyl}pyrazine-2-carboxamide |
| 919 | 3-amino-N-[(3S)-piperidin-3-yl]-6-{3-[({[({2-[(trifluoromethyl)oxy]phenyl}amino)carbonyl]amino}methyl)phenyl]pyrazine-2-carboxamide |
| 920 | 3-amino-6-(3-{[({[2-(methylthio)phenyl]amino}carbonyl)amino]methyl}phenyl)-N-[(3S)-piperidin-3-yl]pyrazine-2-carboxamide |
| 921 | 3-amino-6-{3-[({[(3-bromo-5-methylphenyl)amino]carbonyl}amino)methyl]phenyl}-N-[(3S)-piperidin-3-yl]pyrazine-2-carboxamide |
| 922 | 3-amino-6-{3-[({[(2-bromophenyl)amino]carbonyl}amino)methyl]phenyl}-N-[(3S)-piperidin-3-yl]pyrazine-2-carboxamide |
| 923 | 5-[3-(aminomethyl)phenyl]-3-{3-[(3S)-piperidin-3-yl]-1H-1,2,4-triazol-5-yl}pyrazin-2-amine |
| 924 | 3-amino-6-{3-[({[4-(4-methylpiperazin-1-yl)phenyl]methyl}amino)carbonyl]phenyl}-N-[(3S)-piperidin-3-yl]pyrazine-2-carboxamide |
| 925 | 3-amino-6-[3-({[2-(4-fluorophenyl)ethyl]amino}carbonyl)phenyl]-N-[(3S)-piperidin-3-yl]pyrazine-2-carboxamide |

TABLE 10-continued

| # | Name |
|---|---|
| 926 | 3-amino-6-(3-{[(2-morpholin-4-ylethyl)amino]carbonyl}phenyl)-N-[(3S)-piperidin-3-yl]pyrazine-2-carboxamide |
| 927 | 3-amino-N-[(3S)-piperidin-3-yl]-6-[3-({[(2R)-pyrrolidin-2-ylmethyl]amino}carbonyl)phenyl]pyrazine-2-carboxamide |
| 928 | 3-amino-N-[(3S)-piperidin-3-yl]-6-(3-{[(2S)-pyrrolidin-2-ylamino]carbonyl}phenyl)pyrazine-2-carboxamide |
| 929 | 3-amino-6-{3-[(cyclopentylamino)carbonyl]phenyl}-N-[(3S)-piperidin-3-yl]pyrazine-2-carboxamide |
| 930 | 3-amino-N-[(3S)-piperidin-3-yl]-6-[3-({[({4-[(trifluoromethyl)oxy]phenyl}amino)carbonyl]amino}methyl)phenyl]pyrazine-2-carboxamide |
| 931 | 3-amino-N-[(3S)-piperidin-3-yl]-6-(3-{[({[4-(trifluoromethyl)phenyl]amino}carbonyl)amino]methyl}phenyl)pyrazine-2-carboxamide |
| 932 | 3-amino-6-{3-[({[4-(methyloxy)phenyl]carbonyl}amino)methyl]phenyl}-N-[(3S)-piperidin-3-yl]pyrazine-2-carboxamide |
| 933 | 3-amino-6-(3-{[(biphenyl-4-ylcarbonyl)amino]methyl}phenyl)-N-[(3S)-piperidin-3-yl]pyrazine-2-carboxamide |
| 934 | 3-amino-6-(3-{[(furan-2-ylcarbonyl)amino]methyl}phenyl)-N-[(3S)-piperidin-3-yl]pyrazine-2-carboxamide |
| 935 | 3-amino-6-[3-({[(2,3-dihydro-1,4-benzodioxin-6-ylamino)carbonyl]amino}methyl)phenyl]-N-[(3S)-piperidin-3-yl]pyrazine-2-carboxamide |
| 936 | 3-amino-6-(3-{[(2,3-dihydro-1-benzofuran-5-ylcarbonyl)amino]methyl}phenyl)-N-[(3S)-piperidin-3-yl]pyrazine-2-carboxamide |
| 937 | 3-amino-6-(3-{[(2,3-dihydro-1,4-benzodioxin-6-ylsulfonyl)amino]methyl}phenyl)-N-[(3S)-piperidin-3-yl]pyrazine-2-carboxamide |
| 938 | 3-amino-N-[(3S)-piperidin-3-yl]-6-(3-{[(2-thienylcarbonyl)amino]methyl}phenyl)pyrazine-2-carboxamide |
| 939 | 3-amino-6-(3-{[(2,3-dihydro-1,4-benzodioxin-2-ylcarbonyl)amino]methyl}phenyl)-N-[(3S)-piperidin-3-yl]pyrazine-2-carboxamide |
| 940 | N-{[3-(5-amino-6-{3-[(3S)-piperidin-3-yl]-1H-1,2,4-triazol-5-yl}pyrazin-2-yl)phenyl]methyl}-2-chlorobenzamide |
| 941 | N-{[3-(5-amino-6-{3-[(3S)-piperidin-3-yl]-1H-1,2,4-triazol-5-yl}pyrazin-2-yl)phenyl]methyl}-4-chlorobenzamide |
| 942 | N-{[3-(5-amino-6-{3-[(3S)-piperidin-3-yl]-1H-1,2,4-triazol-5-yl}pyrazin-2-yl)phenyl]methyl}-4-iodobenzamide |
| 943 | N-{[3-(5-amino-6-{3-[(3S)-piperidin-3-yl]-1H-1,2,4-triazol-5-yl}pyrazin-2-yl)phenyl]methyl}-3,5-difluorobenzamide |
| 944 | N-{[3-(5-amino-6-{3-[(3S)-piperidin-3-yl]-1H-1,2,4-triazol-5-yl}pyrazin-2-yl)phenyl]methyl}-4-bromo-2-fluorobenzamide |
| 945 | N-{[3-(5-amino-6-{3-[(3S)-piperidin-3-yl]-1H-1,2,4-triazol-5-yl}pyrazin-2-yl)phenyl]methyl}-4-bromo-2-chlorobenzamide |
| 946 | 3-[3-(2-aminopyridin-4-yl)-1H-1,2,4-triazol-5-yl]-5-(3-{[(1S)-2,3-dihydro-1H-inden-1-ylamino]methyl}phenyl)pyrazin-2-amine |
| 947 | 3-amino-N-azepan-3-yl-6-(3-{[(1S)-2,3-dihydro-1H-inden-1-ylamino]methyl}phenyl)pyrazine-2-carboxamide |
| 948 | 3-amino-N-[(3S)-piperidin-3-yl]-6-{3-[({[2-(2-thienyl)-1,3-thiazol-4-yl]carbonyl}amino)methyl]phenyl}pyrazine-2-carboxamide |
| 949 | 3-amino-N-[(3S)-piperidin-3-yl]-6-{3-[({[5-(2-thienyl)pyridin-3-yl]carbonyl}amino)methyl]phenyl}pyrazine-2-carboxamide |
| 950 | 3-amino-6-{3-[({[4-(1,1-dimethylethyl)phenyl]methyl}amino)carbonyl]phenyl}-N-[(3S)-piperidin-3-yl]pyrazine-2-carboxamide |
| 951 | 3-amino-6-[3-({[(2,4-dichloro-6-methylphenyl)methyl]amino}carbonyl)phenyl]-N-[(3S)-piperidin-3-yl]pyrazine-2-carboxamide |
| 952 | 3-amino-6-[3-({[(3,5-dichlorophenyl)methyl]amino}carbonyl)phenyl]-N-[(3S)-piperidin-3-yl]pyrazine-2-carboxamide |
| 953 | 3-amino-N-[(3S)-piperidin-3-yl]-6-(3-{[(2-thienylsulfonyl)amino]methyl}phenyl)pyrazine-2-carboxamide |
| 954 | 3-amino-N-[(3S)-piperidin-3-yl]-6-(3-{[(3-thienylsulfonyl)amino]methyl}phenyl)pyrazine-2-carboxamide |
| 955 | 3-amino-6-[3-({[(4-chlorophenyl)sulfonyl]amino}methyl)phenyl]-N-[(3S)-piperidin-3-yl]pyrazine-2-carboxamide |
| 956 | 3-amino-6-[3-({[(1,3-benzodioxol-5-ylamino)carbonyl]amino}methyl)phenyl]-N-[(3S)-piperidin-3-yl]pyrazine-2-carboxamide |
| 957 | 3-amino-6-(3-{[({[4-(methyloxy)phenyl]amino}carbonyl)amino]methyl}phenyl)-N-[(3S)-piperidin-3-yl]pyrazine-2-carboxamide |
| 958 | 3-amino-6-{3-[({[(4-fluorophenyl)amino]carbonyl}amino)methyl]phenyl}-N-[(3S)-piperidin-3-yl]pyrazine-2-carboxamide |
| 959 | 3-amino-6-(3-{[2-(diethylamino)ethyl]oxy}phenyl)-N-[(3S)-piperidin-3-yl]pyrazine-2-carboxamide |
| 960 | 3-amino-6-{3-[(2-morpholin-4-ylethyl)oxy]phenyl}-N-[(3S)-piperidin-3-yl]pyrazine-2-carboxamide |
| 961 | 3-amino-6-[3-(methyloxy)phenyl]-N-[(3S)-piperidin-3-yl]pyrazine-2-carboxamide |
| 962 | 3-amino-6-[3-(ethyloxy)phenyl]-N-[(3S)-piperidin-3-yl]pyrazine-2-carboxamide |
| 963 | 3-amino-N-[(3S)-piperidin-3-yl]-6-{3-[({[4-(1,2,3-thiadiazol-4-yl)phenyl]methyl}amino)carbonyl]phenyl}pyrazine-2-carboxamide |

TABLE 10-continued

| # | Name |
|---|---|
| 964 | 3-amino-6-(3-{[2-(ethylamino)ethyl]oxy}phenyl)-N-[(3S)-piperidin-3-yl]pyrazine-2-carboxamide |
| 965 | phenylmethyl 4-(2-{3-[3-(5-amino-6-{[(3S)-piperidin-3-ylamino]carbonyl}pyrazin-2-yl]phenyl]oxy}ethyl)piperazine-1-carboxylate |
| 966 | 3-amino-6-(3-{[({[4-(dimethylamino)phenyl]amino}carbonyl)amino]methyl}phenyl)-N-[(3S)-piperidin-3-yl]pyrazine-2-carboxamide |
| 967 | 3-amino-N-azepan-3-yl-6-(3-{[(1S)-2,3-dihydro-1H-inden-1-ylamino]carbonyl}phenyl)pyrazine-2-carboxamide |
| 968 | 3-amino-6-[3-({[[(1R,2S)-2-hydroxy-2,3-dihydro-1H-inden-1-yl]amino}methyl)phenyl]-N-[(3S)-piperidin-3-yl]pyrazine-2-carboxamide |
| 969 | 3-amino-6-[3-({[[(1S,2S)-2-hydroxy-2,3-dihydro-1H-inden-1-yl]amino}carbonyl)phenyl]-N-[(3S)-1-(phenylmethyl)azepan-3-yl]pyrazine-2-carboxamide |
| 970 | 3-amino-N-[(3S)-azepan-3-yl]-6-[3-({[(1S,2S)-2-hydroxy-2,3-dihydro-1H-inden-1-yl]amino}carbonyl)phenyl]pyrazine-2-carboxamide |
| 971 | 3-amino-6-{3-[({[(4-chlorophenyl)amino]carbonyl}amino)methyl]phenyl}-N-[(3S)-piperidin-3-yl]pyrazine-2-carboxamide |
| 972 | 3-amino-6-(3-{[(1S)-2,3-dihydro-1H-inden-1-ylamino]carbonyl}phenyl)-N-[(3S)-1-(phenylmethyl)azepan-3-yl]pyrazine-2-carboxamide |
| 973 | 3-amino-N-[(3S)-azepan-3-yl]-6-(3-{[(1S)-2,3-dihydro-1H-inden-1-ylamino]carbonyl}phenyl)pyrazine-2-carboxamide |
| 974 | 3-amino-N-[(3S)-azepan-3-yl]-6-(3-methylphenyl)pyrazine-2-carboxamide |
| 975 | 3-amino-6-(3-{[(2-methylphenyl)acetyl]amino}phenyl)-N-[(3S)-piperidin-3-yl]pyrazine-2-carboxamide |
| 976 | 3-amino-N-[(3S)-piperidin-3-yl]-6-[3-({[3-(trifluoromethyl)phenyl]acetyl}amino)phenyl]pyrazine-2-carboxamide |
| 977 | 3-amino-6-[3-({[4-(methyloxy)phenyl]acetyl}amino)phenyl]-N-[(3S)-piperidin-3-yl]pyrazine-2-carboxamide |
| 978 | 3-amino-6-(3-{[(6-methylpyridin-3-yl)carbonyl]amino}phenyl)-N-[(3S)-piperidin-3-yl]pyrazine-2-carboxamide |
| 979 | 3-amino-6-(3-{[(3-fluorophenyl)acetyl]amino}phenyl)-N-[(3S)-piperidin-3-yl]pyrazine-2-carboxamide |
| 980 | 3-amino-N-[(3S)-piperidin-3-yl]-6-{3-[(pyridin-3-ylacetyl)amino]phenyl}pyrazine-2-carboxamide |
| 981 | 3-amino-N-[(3S)-piperidin-3-yl]-6-{3-[(pyridin-3-ylcarbonyl)amino]phenyl}pyrazine-2-carboxamide |
| 982 | 3-amino-6-(3-{[(2,5-difluorophenyl)acetyl]amino}phenyl)-N-[(3S)-piperidin-3-yl]pyrazine-2-carboxamide |
| 983 | 3-amino-6-(3-{[(4-fluorophenyl)acetyl]amino}phenyl)-N-[(3S)-piperidin-3-yl]pyrazine-2-carboxamide |
| 984 | 3-amino-6-{3-[({[3-fluoro-5-(trifluoromethyl)phenyl]methyl}amino)carbonyl]phenyl}-N-[(3S)-piperidin-3-yl]pyrazine-2-carboxamide |
| 985 | 3-amino-6-[3-({[(3,4-dichlorophenyl)methyl]amino}carbonyl)phenyl]-N-[(3S)-piperidin-3-yl]pyrazine-2-carboxamide |
| 986 | 3-Amino-6-[3-({[5-(4-nitro-phenyl)-furan-2-carbonyl]-amino}-methyl)-phenyl]-pyrazine-2-carboxylic acid (3S)-piperidin-3-ylamide |
| 987 | 3-amino-6-[3-({[(3-hydroxypyridin-2-yl)carbonyl]amino}methyl)phenyl]-N-[(3S)-piperidin-3-yl]pyrazine-2-carboxamide |
| 988 | 3-amino-N-[(3S)-piperidin-3-yl]-6-[3-({[({4-[(trifluoromethyl)oxy]phenyl}oxy)acetyl]amino}methyl)phenyl]pyrazine-2-carboxamide |
| 989 | 3-amino-6-[3-({[(5-methylisoxazol-3-yl)carbonyl]amino}methyl)phenyl]-N-[(3S)-piperidin-3-yl]pyrazine-2-carboxamide |
| 990 | 3-amino-6-(3-{[(isoxazol-5-ylcarbonyl)amino]methyl}phenyl)-N-[(3S)-piperidin-3-yl]pyrazine-2-carboxamide |
| 991 | 3-amino-6-[3-({[(4-methyl-1,2,3-thiadiazol-5-yl)carbonyl]amino}methyl)phenyl]-N-[(3S)-piperidin-3-yl]pyrazine-2-carboxamide |
| 992 | 3-amino-6-[3-({[(2,5-dichloro-3-thienyl)carbonyl]amino}methyl)phenyl]-N-[(3S)-piperidin-3-yl]pyrazine-2-carboxamide |
| 993 | 3-amino-6-[3-({[(5-chloro-2-methylphenyl)methyl]amino}carbonyl)phenyl]-N-[(3S)-piperidin-3-yl]pyrazine-2-carboxamide |
| 994 | 3-amino-6-{3-[({[2-chloro-5-(trifluoromethyl)phenyl]methyl}amino)carbonyl]phenyl}-N-[(3S)-piperidin-3-yl]pyrazine-2-carboxamide |
| 995 | 3-amino-6-[3-({[(2-chloro-6-fluorophenyl)methyl]amino}carbonyl)phenyl]-N-[(3S)-piperidin-3-yl]pyrazine-2-carboxamide |
| 996 | 3-amino-N-[(3S)-azepan-3-yl]-6-[3-({[(4-chloro-2-fluorophenyl)methyl]amino}carbonyl)phenyl]pyrazine-2-carboxamide |
| 997 | 3-amino-6-[3-({[(3-chloro-2-fluorophenyl)methyl]amino}carbonyl)phenyl]-N-[(3S)-piperidin-3-yl]pyrazine-2-carboxamide |
| 998 | 3-amino-6-{3-[({[2-fluoro-5-(trifluoromethyl)phenyl]methyl}amino)carbonyl]phenyl}-N-[(3S)-piperidin-3-yl]pyrazine-2-carboxamide |
| 999 | 3-amino-6-[3-({[(2,4-difluorophenyl)methyl]amino}methyl)phenyl]-N-[(3S)-piperidin-3-yl]pyrazine-2-carboxamide |

TABLE 10-continued

| # | Name |
|---|------|
| 1000 | 3-amino-6-[3-({[(3-chloro-2,6-difluorophenyl)methyl]amino}carbonyl)phenyl]-N-[(3S)-piperidin-3-yl]pyrazine-2-carboxamide |
| 1001 | 3-amino-6-{3-[({[2-fluoro-4-(trifluoromethyl)phenyl]methyl}amino)carbonyl]phenyl}-N-[(3S)-piperidin-3-yl]pyrazine-2-carboxamide |
| 1002 | 3-amino-6-[3-({[(2-chloro-4-fluorophenyl)methyl]amino}carbonyl)phenyl]-N-[(3S)-piperidin-3-yl]pyrazine-2-carboxamide |
| 1003 | 3-amino-6-[3-({[(2,3-dichlorophenyl)methyl]amino}carbonyl)phenyl]-N-[(3S)-piperidin-3-yl]pyrazine-2-carboxamide |
| 1004 | 3-amino-N-[(3S)-piperidin-3-yl]-6-[3-({[(2,3,6-trifluorophenyl)methyl]amino}carbonyl)phenyl]pyrazine-2-carboxamide |
| 1005 | 3-amino-6-{3-[({[4-chloro-3-(trifluoromethyl)phenyl]methyl}amino)carbonyl]phenyl}-N-[(3S)-piperidin-3-yl]pyrazine-2-carboxamide |
| 1006 | 3-amino-6-[3-({[(3-chloro-4-fluorophenyl)methyl]amino}carbonyl)phenyl]-N-[(3S)-piperidin-3-yl]pyrazine-2-carboxamide |
| 1007 | 3-amino-N-[(3S)-azepan-3-yl]-6-[3-({[(2,3-difluorophenyl)methyl]amino}carbonyl)phenyl]pyrazine-2-carboxamide |
| 1008 | 3-amino-N-[(3S)-azepan-3-yl]-6-[3-({[(3,4-difluorophenyl)methyl]amino}carbonyl)phenyl]pyrazine-2-carboxamide |
| 1009 | 3-amino-N-[(3S)-azepan-3-yl]-6-[3-({[(3,5-difluorophenyl)methyl]amino}carbonyl)phenyl]pyrazine-2-carboxamide |
| 1010 | 3-amino-6-[3-({[(2,6-difluorophenyl)methyl]amino}carbonyl)phenyl]-N-[(3S)-piperidin-3-yl]pyrazine-2-carboxamide |
| 1011 | 3-amino-6-[3-({[(3,4-difluorophenyl)methyl]amino}carbonyl)phenyl]-N-[(3S)-piperidin-3-yl]pyrazine-2-carboxamide |
| 1012 | 3-amino-6-[3-({[(6-chloro-2-fluoro-3-methylphenyl)methyl]amino}carbonyl)phenyl]-N-[(3S)-piperidin-3-yl]pyrazine-2-carboxamide |
| 1013 | 3-amino-6-[3-({[(2-chloro-6-fluoro-3-methylphenyl)methyl]amino}carbonyl)phenyl]-N-[(3S)-piperidin-3-yl]pyrazine-2-carboxamide |
| 1014 | 3-amino-6-[3-({[(2-chloro-3,6-difluorophenyl)methyl]amino}carbonyl)phenyl]-N-[(3S)-piperidin-3-yl]pyrazine-2-carboxamide |
| 1015 | 3-amino-6-[3-({[(2,5-dichlorophenyl)methyl]amino}carbonyl)phenyl]-N-[(3S)-piperidin-3-yl]pyrazine-2-carboxamide |
| 1016 | 3-amino-N-[(3S)-piperidin-3-yl]-6-[3-({[(2,3,4-trifluorophenyl)methyl]amino}carbonyl)phenyl]pyrazine-2-carboxamide |
| 1017 | 3-amino-6-[3-({[(2,3-difluorophenyl)methyl]amino}carbonyl)phenyl]-N-[(3S)-piperidin-3-yl]pyrazine-2-carboxamide |
| 1018 | 3-amino-6-[3-({[(3-fluoro-4-methylphenyl)methyl]amino}carbonyl)phenyl]-N-[(3S)-piperidin-3-yl]pyrazine-2-carboxamide |
| 1019 | 3-amino-N-[(3S)-azepan-3-yl]-6-[3-({[(3-chloro-2,6-difluorophenyl)methyl]amino}carbonyl)phenyl]pyrazine-2-carboxamide |
| 1020 | 3-amino-N-[(3S)-azepan-3-yl]-6-(3-{[(2,3-dihydro-1,4-benzodioxin-6-ylmethyl)amino]carbonyl}phenyl)pyrazine-2-carboxamide |
| 1021 | 3-amino-N-[(3S)-azepan-3-yl]-6-[3-({[(2-chloro-6-fluorophenyl)methyl]amino}carbonyl)phenyl]pyrazine-2-carboxamide |
| 1022 | 3-amino-N-[(3S)-azepan-3-yl]-6-[3-({[(2,6-difluorophenyl)methyl]amino}carbonyl)phenyl]pyrazine-2-carboxamide |
| 1023 | 3-amino-N-[(3S)-azepan-3-yl]-6-[3-({[(3-chloro-4-fluorophenyl)methyl]amino}carbonyl)phenyl]pyrazine-2-carboxamide |
| 1024 | 3-amino-N-[(3S)-azepan-3-yl]-6-[3-({[(3-chloro-2-fluorophenyl)methyl]amino}carbonyl)phenyl]pyrazine-2-carboxamide |
| 1025 | 3-amino-6-[3-({[(3-chloro-2-methylphenyl)methyl]amino}carbonyl)phenyl]-N-[(3S)-piperidin-3-yl]pyrazine-2-carboxamide |
| 1026 | 3-amino-6-{3-[({[2,6-bis(methyloxy)phenyl]methyl}amino)carbonyl]phenyl}-N-[(3S)-piperidin-3-yl]pyrazine-2-carboxamide |
| 1027 | 3-amino-6-[3-({[(3-bromo-4-fluorophenyl)methyl]amino}carbonyl)phenyl]-N-[(3S)-piperidin-3-yl]pyrazine-2-carboxamide |
| 1028 | 3-amino-N-[(3S)-piperidin-3-yl]-6-[3-({[(3,4,5-trifluorophenyl)methyl]amino}carbonyl)phenyl]pyrazine-2-carboxamide |
| 1029 | 3-amino-6-[3-({[(4-fluoro-3-methylphenyl)methyl]amino}carbonyl)phenyl]-N-[(3S)-piperidin-3-yl]pyrazine-2-carboxamide |
| 1030 | 3-amino-N-[(3S)-piperidin-3-yl]-6-[3-({[(2,3,5-trifluorophenyl)methyl]amino}carbonyl)phenyl]pyrazine-2-carboxamide |
| 1031 | 3-amino-6-[3-({[(5-fluoro-2-methylphenyl)methyl]amino}carbonyl)phenyl]-N-[(3S)-piperidin-3-yl]pyrazine-2-carboxamide |
| 1032 | 3-amino-6-[3-({[(3-bromo-5-fluorophenyl)methyl]amino}carbonyl)phenyl]-N-[(3S)-piperidin-3-yl]pyrazine-2-carboxamide |
| 1033 | 3-amino-N-[(3S)-piperidin-3-yl]-6-{3-[({[4-(1H-pyrazol-1-yl)phenyl]methyl}amino)carbonyl]phenyl}pyrazine-2-carboxamide |
| 1034 | 3-amino-6-(3-{[(biphenyl-3-ylmethyl)amino]carbonyl}phenyl)-N-[(3S)-piperidin-3-yl]pyrazine-2-carboxamide |
| 1035 | 3-amino-6-[3-({[(2-methylphenyl)methyl]amino}carbonyl)phenyl]-N-[(3S)-piperidin-3-yl]pyrazine-2-carboxamide |

TABLE 10-continued

| # | Name |
|---|------|
| 1036 | 3-amino-6-[3-({[(2,5-dimethylphenyl)methyl]amino}carbonyl)phenyl]-N-[(3S)-piperidin-3-yl]pyrazine-2-carboxamide |
| 1037 | 3-amino-6-[3-({[(3,5-dimethylphenyl)methyl]amino}carbonyl)phenyl]-N-[(3S)-piperidin-3-yl]pyrazine-2-carboxamide |
| 1038 | 3-amino-6-[3-({[(2,4-dimethylphenyl)methyl]amino}carbonyl)phenyl]-N-[(3S)-piperidin-3-yl]pyrazine-2-carboxamide |
| 1039 | 3-amino-6-[3-({[(3-methoxyphenyl)methyl]amino}carbonyl)phenyl]-N-[(3S)-piperidin-3-yl]pyrazine-2-carboxamide |
| 1040 | 3-amino-6-{3-[({[phenyl]methyl}amino)carbonyl]phenyl}-N-[(3S)-piperidin-3-yl]pyrazine-2-carboxamide |
| 1041 | 3-amino-6-{3-[({[3,5-bis(methyloxy)phenyl]methyl}amino)carbonyl]phenyl}-N-[(3S)-piperidin-3-yl]pyrazine-2-carboxamide |
| 1042 | 3-amino-6-{3-[({[3,4-bis(methyloxy)phenyl]methyl}amino)carbonyl]phenyl}-N-[(3S)-piperidin-3-yl]pyrazine-2-carboxamide |
| 1043 | 3-amino-N-[(3S)-azepan-3-yl]-6-{3-[({[4-(1H-pyrazol-1-yl)phenyl]methyl}amino)carbonyl]phenyl}pyrazine-2-carboxamide |

Another aspect of the invention is a pharmaceutical composition comprising a compound according to any one of paragraphs [0039]-[0080] and a pharmaceutically acceptable carrier.

Another aspect of the invention is a metobolite of the compound or the pharmaceutical composition according to any one of paragraphs [0039]-[0081].

Another aspect of the invention is a method of modulating the in vivo activity of a kinase, the method comprising administering to a subject an effective amount of the compound or the pharmaceutical composition according to any of paragraphs [0039]-[0081].

Another aspect of the invention is a method according to paragraph [0083], wherein the kinase is Chk1.

Another aspect of the invention is a method according to paragraph [0084], wherein modulating the in vivo activity of the kinase comprises inhibition of said kinase.

Another aspect of the invention is a method of treating diseases or disorders associated with uncontrolled, abnormal, and/or unwanted cellular activities, the method comprising administering a therapeutically effective amount of to a mammal in need thereof and the compound as described in any one of paragraphs [0039]-[0080].

Another aspect of the invention is a method of inhibiting proliferation of cancerous cells, the method comprising contacting the cells or causing the cells to be contacted with a cancer therapeutic and the compound as described in any one of paragraphs [0039]-[0080].

Another aspect of the invention is a method according to paragraph [0087], wherein the cancer therapeutic is a DNA damaging agent.

Yet another aspect of the invention is a method of diminishing proliferation of cancerous cells in a patient, the method comprising administering to the patient the compound as described in any one of paragraphs [0039]-[0008] and one or more cancer therapeutic agents, preferably with a pharmaceutically acceptable carrier. Exemplary anti-cancer agents suitable for use (including analogs, pharmaceutically acceptable forms, such as salts and in liposomes) in this aspect of the invention are: 1. Topoisomerase I inhibitors: Camptothecin, Topotecan, 9-Nitrocamptothecin, 9-Aminocamptothecin, Karenitecin, Irinotecan, and the like; 2. Topoisomerase II inhibitors: Etoposide, Etoposide Phosphate, Teniposide, Amsacrine, Epipodophyllotoxin derivatives, Razoxane, Dexrazoxane (Zinecard), and the like; 3. Classical Alkylating agents: Nitrogen Mustards such as Mechlorethamine, Cyclophosphamide, Ifosfamide, Chlorambucil, Melphalan, and the like; Aziridines such as, Thiotepa, Trenimon, Triethylenemelamine, and the like; Epoxides such as Dianhydrogalactitol, Dibromodulcitol, and the like; Alkyl Alkane Sulfonates such as Busulfan, dimethylsulfate, and the like; Nitrosoureas such as Chlorothylnitrosourea, BCNU, CCNU (lomustine), Methyl-CCNU (semustine), Streptozotocin, Chlorozotocin, and the like; Alkylating agent-steroid conjugates such as Prednimustine (chlorambucil-prednisolone), Estramustine (nornitrogen mustard-estradiol), and the like; 4. Non-classical alkylating agents: Procarbazine, Dacarbazine, Hexamethylmelamine, Pentamethylmelamine, Temozolomide, and the like; 5. Other DNA damaging/binding agents: Cisplatins such as Cisplatin, Carboplatin, Oxaliplatin, Bleomycin, and the like; Antibiotics such as Dactinomycin, Mithramycin, Mitomycin C, and the like; Anthracyclines/Anthracenediones (note—also considered topo II inhibitors) such as Daunorubicin, Doxorubicin, Epirubicin, Idarubicin, and the like; 6. Antimetabolites: Antifolates such as Methotrexate, Edatrexate, Trimethoprim, Nolatrexed, Raltitrexed (Tomudex), Hydroxyurea, and the like; Nucleic acid analogs such as 5-fluorouracil, Ftorafur, Capecitabine, Furtulon, Eniluracil, ara-C (Cytosine arabinose), 5-azacytidine, Gemcitabine, Mercaptopurine, Thioguanine, Pentostatin, and the like; 7. Ribonucleic acid related: Antisense DNA, antisense RNA, antisense DNA/RNA hybrids, ribozymes, and the like; 8. Radiation: ultraviolet and/or other; 9. Vinca Alkaloids: Vincristine, Vinblastine, and the like; 10. Other anti-cancer agents: those having mechanisms of action that may or may not involve DNA damage; 11. Taxanes: Paclitaxel, Docetaxel, and the like; 12. Enzymes: L-Asparaginase and the like; 13. Natural Products; 14. Miscellaneous Agents: kinase inhibitors, Imatinib; 15. Mitotane; 16. Aminoglutethimide; 17. Hormones and Antagonists: Diethylstilbestrol, Ethinyl estradiol, Tamoxifen, Anastrozole, Testosterone propionate, Fluoxymesterone, Flutamide, Leuprolide, Prednisone, Hydroxyprogesterone caproate, Medroxyprogesterone aacetate, Megestrol acetate; 18. Biological Response Modifiers: Interferon-alfa, Interleukin, and the like.

Other agents suitable for use in combination with a compound of the invention are disclosed in "*Cancer Chemotherapy and Biotherapy: Principles and Practice,*" Third edition, B. A. Chabner and D. L. Longo, eds., 2001, Lippincott Williams and Wilkins, Philadelphia, U.S.A.; P. Calabresi and B. A. Chabner, "Chemotherapy of Neoplastic Diseases" in "*Goodman and Gilman's The Pharmcological Basis of Therapeutics,*" Tenth edition, J. G. Hardman and L. E. Limbird, eds., 2001, McGraw-Hill, New York, USA, pp. 1381-

1388; and B. A. Chabner, D. P. Ryan, L. Paz-Ares, R. Garcia-Carbonero, and P. Calabresi, "Antineoplastic Agents" in "Goodman and Gilman's The Pharmacological Basis of Therapeutics," Tenth edition, J. G. Hardman and L. E. Limbird, eds., 2001, McGraw-Hill, New York, USA, pp. 1389-1459.

Another aspect of the invention is a method of enhancing the efficacy of a disease therapy that inflicts DNA damage, the method comprising combining the disease therapy with administration of a compound or pharmaceutical composition as described in any one of paragraphs [0023]-[0066]. As an example, photochemotherapy of dermatological conditions such as psoriasis employs ultraviolet radiation in combination with psoralen type photosensitizers to cause DNA damage. In one embodiment of this aspect of the invention, such photochemotherapy is combined with administration of a compound or pharmaceutical composition as described in any one of paragraphs [0039]-[0081].

Definitions

As used in the present specification, the following words and phrases are generally intended to have the meanings as set forth below, except to the extent that the context in which they are used indicates otherwise or they are expressly defined to mean something different.

"Alkyl" is intended to include linear, branched, or cyclic hydrocarbon structures and combinations thereof, inclusively. For example, "$C_8$ alkyl" may refer to an n-octyl, isooctyl, cyclohexylethyl, and the like. Lower alkyl refers to alkyl groups of from one to eight carbon atoms. Examples of lower alkyl groups include methyl, ethyl, propyl, isopropyl, butyl, s-butyl, t-butyl, isobutyl, pentyl, cyclopentyl, hexyl, cyclohexyl, and the like. Higher alkyl refers to alkyl groups containing more that 6 carbon atoms. Exemplary alkyl groups are those of $C_{20}$ or below. Cycloalkyl is a subset of alkyl and includes cyclic hydrocarbon groups of from 3 to 13 carbon atoms. Examples of cycloalkyl groups include c-propyl, c-butyl, c-pentyl, norbornyl, adamantyl and the like. Cycloalkyl rings may have unsaturation but are not aromatic. In this application, alkyl refers to alkanyl, alkenyl, and alkynyl residues (and combinations thereof); it is intended to include cyclohexylmethyl, vinyl, allyl, isoprenyl, and the like. Thus when an alkyl residue having a specific number of carbons is named, all geometric isomers having that number of carbons are intended to be encompassed; thus either "butyl" or "$C_4$alkyl" is meant to include n-butyl, sec-butyl, isobutyl, t-butyl, isobutenyl and but-2-yne radicals, for example; "propyl" or "$C_3$alkyl" each include n-propyl, propenyl, and isopropyl, for example. Alkyls with variable numbers of carbons may be named by using number ranges as subscripts, as for example, lower alkyl is equivalent to $C_{1-8}$alkyl.

"Alkylene" refers to straight or branched chain divalent radical consisting solely of carbon and hydrogen atoms, containing no unsaturation and having from one to ten carbon atoms, e.g., methylene, ethylene, propylene, n-butylene and the like. Alkylene is a subset of alkyl, referring to the same residues as alkyl, but having two points of attachment and specifically fully saturated. Examples of alkylene include ethylene (—$CH_2CH_2$—), propylene (—$CH_2CH_2CH_2$—), 2-dimethylpropylene (—$CH_2C(CH_3)_2CH_2$—), cyclohexylpropylene (—$CH_2CH(C_6H_{13})CH_2$—).

"Alkylidene" refers to a straight or branched chain unsaturated divalent radical consisting solely of carbon and hydrogen atoms, having from two to ten carbon atoms, e.g., ethylidene, propylidene, n-butylidene, and the like. Alkylidene is a subset of alkyl, referring to the same residues as alkyl, but having two points of attachment and specifically double bond unsaturation. The unsaturation present includes at least one double bond and a double bond can exist between the first carbon of the chain and a carbon atom of the rest of the molecule to which it is attached.

"Alkylidyne" refers to a straight or branched chain unsaturated divalent radical consisting solely of carbon and hydrogen atoms having from two to ten carbon atoms, e.g., propylid-2-ynyl, n-butylid-1-ynyl, and the like. Alkylidyne is a subset of alkyl, referring to the same residues as alkyl, but having two points of attachment and specifically triple bond unsaturation. The unsaturation present includes at least one triple bond and a triple bond can exist between the first carbon of the chain and a carbon atom of the rest of the molecule to which it is attached.

Any of the above radicals, "alkylene," "alkylidene" and "alkylidyne," when optionally substituted, may contain alkyl substitution which itself contains unsaturation. For example, 2-(2-phenylethynyl-but-3-enyl)-naphthalene (IUPAC name) contains an n-butylid-3-ynyl radical with a vinyl substituent at the 2-position of said radical.

"Alkoxy" refers to the group —O-alkyl, for example including carbon atoms of a straight, branched, cyclic configuration, unsaturated chains, and combinations thereof attached to the parent structure through an oxygen atom. Examples include methoxy, ethoxy, propoxy, isopropoxy, cyclopropyloxy, cyclohexyloxy and the like. Lower-alkoxy refers to groups containing one to eight carbons.

"Substituted alkoxy" refers to the group —O-(substituted alkyl), the substitution on the alkyl group generally containing more than only carbon (as defined by alkoxy). One exemplary substituted alkoxy group is "polyalkoxy" or —O—(optionally substituted alkylene)-(optionally substituted alkoxy), and includes groups such as —$OCH_2CH_2OCH_3$, and glycol ethers such as polyethyleneglycol and —$O(CH_2CH_2O)_xCH_3$, where x is an integer of between about 2 and about 20, in another example, between about 2 and about 10, and in a further example between about 2 and about 5. Another exemplary substituted alkoxy group is hydroxyalkoxy or —$OCH_2(CH_2)_yOH$, where y is for example an integer of between about 1 and about 10, in another example y is an integer of between about 1 and about 4. Thus, where a group is defined as —OR, where "R" is optionally substituted alkyl, then such a group would include, but not be limited to, hydroxyalkoxy, polyalkoxy, and the like.

"Alkoxyl" refers to an alkoxy as a linking group, for example —$OCH_2$— and the like. Lower alkoxyl then refers to groups containing one to eight carbons and an oxygen.

"Substituted alkoxyl" refers to a linking group alkoxy, for example —$OCH_2CH_2OCH_2$—. Optionally substituted alkoxyl refers to both alkoxyl and substituted alkoxyls.

"Acyl" refers to groups of from one to ten carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to eight carbons.

"α-Amino Acids" refer to naturally occurring and commercially available amino acids and optical isomers thereof. Typical natural and commercially available α-amino acids are glycine, alanine, serine, homoserine, threonine, valine, norvaline, leucine, isoleucine, norleucine, aspartic acid, glutamic acid, lysine, omithine, histidine, arginine, cysteine, homocysteine, methionine, phenylalanine, homophenylalanine, phenylglycine, ortho-tyrosine, meta-tyrosine, para-tyrosine, tryptophan, glutamine, asparagine, proline and hydroxyproline. A "side chain of an α-amino acid" refers to the radical found on the α-carbon of an α-amino acid as defined above, for example, hydrogen (for glycine), methyl (for alanine), benzyl (for phenylalanine), and the like.

"Amino" refers to the group —NH$_2$. "Substituted amino," refers to the group —NHR or —NRR where each R is independently selected from the group: optionally substituted alkyl, optionally substituted alkoxy, optionally substituted aryl, optionally substituted heterocyclyl, acyl, carboxy, alkoxycarbonyl, sulfanyl, sulfinyl and sulfonyl, e.g., diethylamino, methylsulfonylamino, furanyl-oxy-sulfonamino.

"Aryl" refers to aromatic 6- to 14-membered carbocyclic rings include, e.g., benzene, naphthalene, indane, teralin, fluorene and the like.

"Arylene" refers to an "aryl" that is a linker between two other groups. For example, for G-V-B, "phenylene" for V refers to a benzene ring system that links G and B, that is, G and B are each attached to different carbons of V, leaving four potential sites for further substitution on V.

"Arylalkyl" refers to a residue in which an aryl moiety is attached to a parent structure via one of an alkylene, alkylidene, or alkylidyne radical. Examples include benzyl, phenethyl, phenylvinyl, phenylallyl and the like. The aryl, alkylene, alkylidene, or alkylidyne radical portion of an arylalkyl group may be optionally substituted. "Lower arylalkyl" refers to an arylalkyl where the "alkyl" portion of the group has one to eight carbons.

"Halogen" or "halo" refers to fluorine, chlorine, bromine or iodine. Dihaloaryl, dihaloalkyl, trihaloaryl etc. refer to aryl and alkyl substituted with a plurality of halogens, but not necessarily a plurality of the same halogen; thus 4-chloro-3-fluorophenyl is within the scope of dihaloaryl.

"Heteroatom" refers to O, S, N, or P.

"Heterocyclyl" refers to a stable 3- to 15-membered ring radical that consists of carbon atoms and from one to five heteroatoms selected from the group consisting of nitrogen, phosphorus, oxygen and sulfur. For purposes of this invention, the heterocyclyl ring radical may be a monocyclic, bicyclic or tricyclic ring system, which may include fused or bridged ring systems, either aromatic, saturated, or combinations thereof; and the nitrogen, phosphorus, carbon or sulfur atoms in the heterocyclyl ring radical may be optionally oxidized to various oxidation states, for example for the purposes of this invention and to negate undo repetition in the description, the corresponding N-oxide of pyridine derivatives, and the like, are understood to be included as compounds of the invention. In addition, the nitrogen atom may be optionally quaternized; and the ring radical may be partially or fully saturated or aromatic. Examples of such heterocyclyl ring radicals include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, indanyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothieliyl, thiamorpholinyl, thiamorpholinyl sulfoxide, thiamorpholinyl sulfone, dioxaphospholanyl, and oxadiazolyl.

"Heteroalicyclic" refers specifically to a non-aromatic heterocyclyl ring system radical. Heteroalicyclic ring systems include saturated and partially bridged ring systems having geometries [4.4.0], [4.3.0], [4.2.0], [4.1.0], [3.3.0], [3.2.0], [3.1.0], [3.3.3], [3.3.2], [3.3.1], [3.2.2], [3.2.1], [2.2.2], [2.2.1], and the like.

"Heteroaryl" refers specifically to an aromatic heterocyclyl ring system radical.

"Heteroarylene" refers to a "heteroaryl" that is a linker between two other groups. For example, for M-P-L, "pyridylene" for P refers to a pyridine ring system that links M and L, that is, M and L are each attached to different atoms of P, leaving four potential sites for further substitution on P.

"Heterocyclylalkyl" refers to a residue in which a heterocyclyl ring is attached to a parent structure via one of an alkylene, alkylidene, or alkylidyne radical. Examples include (4-methylpiperazin-1-yl)methyl, (morpholin-4-yl)methyl, 2-(oxazolin-2-yl)ethyl, 4-(4-methylpiperazin-1-yl)-2-butenyl, and the like. The heterocyclyl, alkylene, alkylidene, or alkylidyne radical portion of an arylalkyl group may be optionally substituted. "Lower heterocyclylalkyl" refers to an arylalkyl where the "alkyl" portion of the group has one to eight carbons.

The term "imino" refers to a substitution on a carbon atom, more specifically to a doubly bonded nitrogen. For example, an imine, an amidine, and an oxime, all contain the "imino" group.

"Optional" or "optionally" means that the subsequently described event or circumstance may or may not occur, and that the description includes instances where said event or circumstance occurs and instances in which it does not. It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. "Optionally substituted" refers to all subsequent modifiers in a term, for example in the term "optionally substituted $C_{1-8}$alkylaryl," optional substitution may occur on both the "$C_{1-8}$alkyl" portion and the "aryl" portion of the molecule; and for example, optionally substituted alkyl includes optionally substituted cycloalkyl groups, which in turn are defined as including optionally substituted alkyl groups, potentially ad infinitum. If a hetercyclic ring is "optionally substituted," then both the carbon and any heteroatoms in the ring may be substituted thereon. Examples of optional substitution include, but are not limited to alkyl, halogen, alkoxy, hydroxy, oxo, carbamyl, acylamino, sulfonamido, carboxy, alkoxycarbonyl, acyl, alkylthio, alkylsulfonyl, nitro, cyano, amino, alkylamino, cycloalkyl and the like. Thus, for example, if a group "—C(O)R" is described, where "R" is optionally substituted alkyl, then "R" would include, but not be limited to, —CH$_2$Ph, —CH$_2$CH$_2$OPh, —CH=CHPhCH$_3$, —C$_3$H$_4$CH$_2$N(H)Ph, and the like.

The term "ortho" is normally used in reference to relative position of two substituents on a benzene ring; however, in this application the term "ortho" is meant to apply to other aromatic ring systems where two substituents reside on adjacent carbons. For example, 3-bromo-4-fluoro-thiophene possesses a bromo group and a fluoro group which have an ortho, or 1,2-positional relationship, to each other.

The term "oxo" refers to a substitution on a carbon atom, more specifically to a doubly bonded oxygen. For example, an oxo-morpholine, a cyclohexanone, and an acyl group, all contain the "oxo" functionality.

"Saturated bridged ring system" refers to a bicyclic or polycyclic ring system that is not aromatic. Such a system may contain isolated or conjugated unsaturation, but not aromatic or heteroaromatic rings in its core structure (but may have aromatic substitution thereon). For example, 2,3,3a,4,7,7a-hexahydro-1H-indene and 1,2,3,4,4a,5,8,8a-octahydro-naphthalene are included in the class "saturated bridged ring system."

"Substituted" alkyl, aryl, and heterocyclyl, refer respectively to alkyl, aryl, and heterocyclyl, wherein one or more (for example up to about 5, in another example, up to about 3) hydrogen atoms are replaced by a substituent independently selected from the group: optionally substituted alkyl (e.g., fluoroalkyl), optionally substituted alkoxy, alkylenedioxy (e.g. methylenedioxy), optionally substituted amino (e.g., alkylamino and dialkylamino), optionally substituted amidino, optionally substituted aryl (e.g., phenyl), optionally substituted arylalkyl (e.g., benzyl), optionally substituted aryloxy (e.g., phenoxy), optionally substituted arylalkyloxy (e.g., benzyloxy), carboxy (—COOH), carboalkoxy (i.e., acyloxy or —OOCR), carboxyalkyl (i.e., esters or —COOR), carboxamido, aminocarbonyl, benzyloxycarbonylamino (CBZ-amino), cyano, carbonyl, halogen, hydroxy, optionally substituted heterocyclylalkyl, optionally substituted heterocyclyl, nitro, sulfanyl, sulfinyl, sulfonyl, and thio.

"Sulfanyl" refers to the groups: —S-(optionally substituted alkyl), —S-(optionally substituted aryl), and —S-(optionally substituted heterocyclyl).

"Sulfinyl" refers to the groups: —S(O)—H, —S(O)-(optionally substituted alkyl), —S(O)-optionally substituted aryl), and —S(O)-(optionally substituted heterocyclyl).

"Sulfonyl" refers to the groups: —S(O$_2$)—H, —S(O$_2$)-(optionally substituted alkyl), —S(O$_2$)-optionally substituted aryl), —S(O$_2$)-(optionally substituted heterocyclyl), —S(O$_2$)-(optionally substituted alkoxy), —S(O$_2$)-optionally substituted aryloxy), and —S(O$_2$)-(optionally substituted heterocyclyloxy).

The term "thiono" refers to a substitution on a carbon atom, more specifically to a doubly bonded sulfur. For example, a thioketone and a thioamide both contain the "thiono" functionality.

"Yield" for each of the reactions described herein is expressed as a percentage of the theoretical yield.

In some embodiments, as will be appreciated by those in the art, two adjacent groups on an aromatic system may be fused together to form a ring structure. The fused ring structure may contain heteroatoms and may be optionally substituted with one or more groups. It should additionally be noted that saturated carbons of such fused groups (i.e. saturated ring structures) may contain two substitution groups.

Some of the compounds of the invention may have imino, amino, oxo or hydroxy understood that such imino, amino, oxo or hydroxy substituents may exist in their corresponding tautomeric form, i.e., amino, imino, hydroxy or oxo, respectively. As well, tautomeric forms of ring conjugation, for example in a triazole, are understood to be within the scope of the invention, when formulae depict only one such tautomer.

Compounds of the invention are generally named using ACD/Name (available from Advanced Chemistry Development, Inc. of Toronto, Canada). This software derives names from chemical structures according to systematic application of the nomenclature rules agreed upon by the International Union of Pure and Applied Chemistry (IUPAC), International Union of Biochemistry and Molecular Biology (IUBMB), and the Chemical Abstracts Service (CAS).

The compounds of the invention, or their pharmaceutically acceptable salts, may have asymmetric carbon atoms, oxidized sulfur atoms or quaternized nitrogen atoms in their structure.

The compounds of the invention and their pharmaceutically acceptable salts may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention.

For linking groups, e.g. —OCH$_2$— or —C(=O)N(R)—, it is understood that either of the linking groups two partners may be bound to either end of the linking group. Put another way, linking groups are understood to describe both possible orientations between the A-OCH$_2$-B and A-CH$_2$O-B are described. In the case of substituted linking groups, e.g substituted alkoxyl, it is assumed that the substitution is in addition to the two groups to which the linking group is attached.

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. When desired, the R- and S-isomers may be resolved by methods known to those skilled in the art, for example by: formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents, or by converting on enantiomer to the other by asymmetric transformation. For a mixture of enantiomers, enriched in a particular enantiomer, the major component enantiomer may be further enriched (with concomitant loss in yield) by recrystallization.

The symbol "—" means a single bond, "=" means a double bond, "≡" means a triple bond, and "∿" refers to a group on a double-bond as occupying either position on the terminus of a double bond to which the symbol is attached. When a group is depicted removed from its parent formula, the "∿" symbol will be used at the end of the bond which was theoretically cleaved in order to separate the group from its parent structural formula.

When a group "R" is depicted as existing on a ring system, as for example in the formula

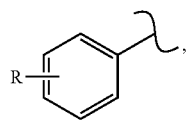

then a substituent "R" may reside on any atom of the ring system, assuming replacement of a depicted, implied, or expressly defined hydrogen from one of the ring atoms, so long as a stable structure is formed.

When a group "R" is depicted as existing on a fused ring system, as for example in the formula

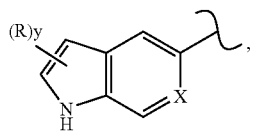

then a substituent "R" may reside on any atom of the fused ring system, assuming replacement of a depicted (e.g. the —NH— in the formula above), implied (e.g. as in the formula above, where the hydrogens are not shown but understood to be present), or expressly defined hydrogen (e.g. where in the formula above, "X" equals =CH—) from one of the ring atoms, so long as a stable structure is formed. In the example depicted, the "R" group may reside on either the 5-membered or the 6-membered ring of the fused ring system. In the formula depicted above, when y is 2 for example, then the two "R's" may reside on any two atoms of the ring system, again assuming each replaces a depicted, implied, or expressly defined hydrogen on the ring. When there are more than one such depicted "floating" groups, as for example in the formula

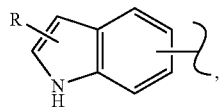

where there are two groups, namely, the "R" and the bond indicating attachment to a parent structure. In such cases, the "floating" groups may reside on any atoms of the ring system, again assuming each floating group replaces a depicted, implied, or expressly defined unique hydrogen on the ring.

"Substituted cycloalkyl," in this application, is meant to include bridged or fused ring systems wherein an all-carbon bridge portion of such ring systems, along with the two bridgehead carbons, is considered as a cycloalkyl. For example, the formula

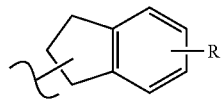

depicts a bridged ring system that has "R" substitution and is itself a substituent of a parent compound (as denoted by the "∼" symbol, supra). As mentioned above, either of the depicted "floating" groups may reside on either the alkyl bridge or the aromatic ring of the depicted bridged ring system. In this application, for such ring systems, when the parent compound is bonded to the alkyl bridge, as in

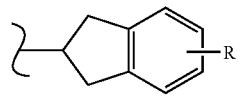

When a group "R" is depicted as existing on a saturated ring system, as for example in the formula

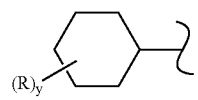

where "y" can be more than one, assuming each replaces a currently depicted, implied, or expressly defined hydrogen on the ring, then where the resulting structure is stable, two "R's" may reside on the same carbon. A simple example is when R is a methyl group, then in this instance there would exist a geminal dimethyl on a carbon of the depicted ring. In another example, two R's on the same carbon, including that carbon, may form a ring, thus creating a spirocyclic ring structure with the depicted ring.

implied (e.g. as in the formula above, where the hydrogens are not shown but understood to be present), or expressly defined hydrogen (e.g. where in the formula above, "X" equals =CH—) from one of the ring atoms, so long as a stable structure is formed. In the example depicted, the "R" group may reside on either the 5-membered or the 6-membered ring of the fused ring system. In the formula depicted above, when y is 2 for example, then the two "R's" may reside on any two atoms of the ring system, again assuming each replaces a depicted, implied, or expressly defined hydrogen on the ring. When there are more than one such depicted "floating" groups, as for example in the formula

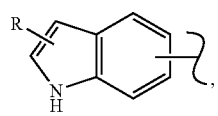

where there are two groups, namely, the "R" and the bond indicating attachment to a parent structure. In such cases, the "floating" groups may reside on any atoms of the ring system, again assuming each floating group replaces a depicted, implied, or expressly defined unique hydrogen on the ring.

"Substituted cycloalkyl," in this application, is meant to include bridged or fused ring systems wherein an all-carbon bridge portion of such ring systems, along with the two bridgehead carbons, is considered as a cycloalkyl. For example, the formula

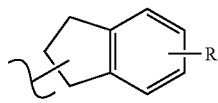

depicts a bridged ring system that has "R" substitution and is itself a substituent of a parent compound (as denoted by the "∼"symbol, supra). As mentioned above, either of the depicted "floating" groups may reside on either the alkyl bridge or the aromatic ring of the depicted bridged ring system. In this application, for such ring systems, when the parent compound is bonded to the alkyl bridge, as in

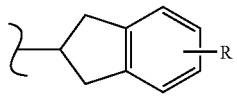

When a group "R" is depicted as existing on a saturated ring system, as for example in the formula

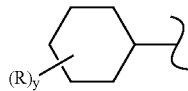

where "y" can be more than one, assuming each replaces a currently depicted, implied, or expressly defined hydrogen on the ring, then where the resulting structure is stable, two "R's" may reside on the same carbon. A simple example is when R is a methyl group, then in this instance there would exist a geminal dimethyl on a carbon of the depicted ring. In another example, two R's on the same carbon, including that carbon, may form a ring, thus creating a spirocyclic ring structure with the depicted ring.

"Patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

"Kinase-dependent diseases or conditions" refer to pathologic conditions that depend on the activity of one or more protein kinases. Kinases either directly or indirectly participate in the signal transduction pathways of a variety of cellular activities including proliferation, adhesion, migration, differentiation and invasion.

While not wishing to be bound to theory, phosphatases can also play a role in "kinase-dependent diseases or conditions" as cognates of kinases. That is, kinases phosphorylate and phosphates dephosphorylate, for example protein substrates. Therefore compounds of the invention, while modulating kinase activity as described herein, may also modulate, either directly or indirectly, phosphatase activity. This additional modulation, if present, may be synergistic (or not) to activity of compounds of the invention toward a related or otherwise interdependent kinase or kinase family. Thus, "kinase-dependent diseases or conditions" are those diseases that should be mitigated via treatment of a patient with compounds and/or formulations of the invention. Kinase-dependent diseases or conditions include diseases or disorders associated with uncontrolled, abnormal and/or unwanted cellular activities such as those set forth in paragraphs [0031]-[0038].

"Therapeutically effective amount" is an amount of a compound of the invention, that when administered to a patient, ameliorates a symptom of the disease. The amount of a compound of the in which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma, pancreas (ductal adenocarcinoma, insulinorna, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [neplrroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis defornians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal lands: neuroblastoma. Thus, the term "cancerous cell" as provided herein, includes a cell afflicted by any one of the above-identified conditions.

"Pharmaceutically acceptable acid addition salt" refers to those salts that retain the undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977;66:1-19 which is incorporated herein by reference.)

"Prodrug" refers to compounds that are transformed (typically rapidly) in vivo to Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about 1 and about 6 carbons) wherein the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about 1 and about 6 carbons). Amides and esters of the compounds of the present invention may be prepared according to conventional methods. Another example of a prodrug is a pyridine group; in many cases the pyridine group is oxidized to its corresponding N-oxide that may be a biologically active compound of the invention. Thus the "pyritline form" may be thought of as a prodrug. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference.

"Metabolite" refers to the break-down or end product of a compound or its salt produced by metabolism or biotransformation in the animal or human body; e.g., biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

In addition, it is intended that the present invention cover compounds made either using standard organic synthetic techniques, including combinatorial chemistry or by biological methods, such as bacterial digestion, metabolism, enzymatic conversion, and the like.

"Treating" or "treatment" as used herein covers the treatment of a disease-state in a human, which disease-state is characterized by uncontrolled, abnormal or unwanted cellular proliferation, differentiation, programmed cell death migration or chemoinvasion and invasion and includes at least one of: (i) preventing the disease-state from occurring in a human, in particular, when such human is predisposed to the disease-state but has not yet been diagnosed as having it; (ii) inhibiting the disease-state, i.e., arresting its development; and (iii) relieving the disease-state, i.e., causing regression of the disease-state. As is known in the art, adjustments for systemic versus localized delivery, age, body weight, general health, sex, diet, time of administration, drug interaction and the severity of the condition may be necessary, and will be ascertainable with routine General Administration Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

The compositions will include a conventional pharmaceutical carrier or excipient and a compound of the invention as the/an active agent, and, in addition, may include other medicinal agents, pharmaceutical agents, carriers, adjuvants, etc. Compositions of the invention may be used in combination with anticancer or other agents that are generally administered to a patient being treated for cancer. Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, etc.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to those skilled in the art.

Utility of Compounds of the Invention as Screening Agents

To employ the compounds of the invention in a method of screening for candidate agents that bind to, for example a Chk1 receptor kinase, the protein is bound to a support, and a compound of the invention is added to the assay. Alternatively, the compound of the invention is bound to the support and the protein is added. Classes of candidate agents among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate agent to, for example, a Chk1 protein may be done in a number of ways. In one example, the candidate agent (the compound of the invention) is labeled, for example, with a fluorescent or radioactive moiety and binding determined directly. For example, thus may be done by attaching all or a portion of the Chk1 protein to a solid support, adding a labeled agent (for example a compound of the invention in which at least one atom has been replaced by a detectable isotope), washing off excess reagent, and determining whether the amount of the label is that present on the solid support. Various blocking and washing steps may be utilized as is known in the art.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, a Chk1 protein may be labeled at tyrosine positions using $^{125}$I, or with fluorophores. Alternatively, more than one component may be labeled with different labels; using $^{125}$I for the proteins, for example, and a fluorophor for the candidate agents.

The compounds of the invention may also be used as competitors to screen for additional drug candidates. "Candidate bioactive agent" or "drug candidate" or grammatical equivalents as used herein describe any molecule, e.g., protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including both nucleic acid sequences and protein sequences. In other cases, alteration of cellular proliferation protein binding and/or activity is screened. In the case where protein binding or activity is screened, some embodiments exclude molecules already known to bind to that particular protein. Exemplary embodiments of assays described herein include candidate agents, which do not bind the target protein in its endogenous native state, termed herein as "exogenous" agents. In one example, exogenous agents further exclude antibodies to Chk1.

Candidate agents can encompass numerous chemical classes, though typically they are organic molecules having a molecular weight of more than about 100 and less than about 2,500 daltons. Candidate agents comprise functional groups necessary for structural interaction with proteins, particularly hydrogen bonding and lipophilic binding, and typically include at least an amine, carbonyl, hydroxyl, ether, or carboxyl group, for example at least two of the functional chemical groups. The candidate agents often comprise cyclical carbon or heterocyclyl structures and/or aromatic or polyaromatic structures substituted with one or more of the above functional groups. Candidate agents are also found among biomolecules including peptides, saccharides, fatty acids, steroids, purines, pyrimidines, derivatives, structural analogs, or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In one example, the binding of the candidate agent is determined through the use of competitive binding assays. In this example, the competitor is a binding moiety known to bind to Chk1, such as an antibody, peptide, binding partner, ligand, etc. Under certain circumstances, there may be competitive binding as between the candidate agent and the binding moiety, with the binding moiety displacing the candidate agent.

In some embodiments, the candidate agent is labeled. Either the candidate agent, or the competitor, or both, is added first to Chk1 for a time sufficient to allow binding, if present. Incubations may be performed at any temperature that facilitates optimal activity, typically between 4° C. and 40° C.

Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In one example, the competitor is added first, followed by the candidate agent. Displacement of the competitor is an indication the candidate agent is binding to Chk1 and thus is capable of binding to, and potentially modulating, the activity of the Chk1. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to Chk1 with a higher affinity. Thus, if the candidate agent is labeled, the presence of the label on the support, coupled with a lack of competitor binding, may indicate the candidate agent is capable of binding to Chk1.

It may be of value to identify the binding site of Chk1. This can be done in a variety of ways. In one embodiment, once Chk1 has been identified as binding to the candidate agent, the Chk1 is fragmented or modified and the assays repeated to identify the necessary components for binding.

Modulation is tested by screening for candidate agents capable of modulating the activity of Chk1 comprising the steps of combining a candidate agent with Chk1, as above, and determining an alteration in the biological activity of the Chk1. Thus, in this embodiment, the candidate agent should both bind to (although this may not be necessary), and alter its biological or biochemical activity as defined herein. The methods include both in vitro screening methods and in vivo screening of cells for alterations in cell viability, morphorlogy, and the like.

Alternatively, differential screening may be used to identify drug candidates that bind to native Chk1, but cannot bind to modified Chk1.

Positive controls and negative controls may be used in the assays. For example, all control and test samples are performed in at least triplicate to obtain statistically significant results. Incubation of samples is for a time sufficient for the binding of the agent to the protein. Following incubation, samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g., albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Abbreviations and Their Definitions

The following abbreviations and terms have the indicated meanings throughout:

Ac=acetyl
ATP=adenosine triphosphate
Boc=t-butyloxy carbonyl
br=broad
Bu=butyl
C=degrees Celsius
c-=cyclo
CBZ=carbobenzoxy=benzyloxycarbonyl
d=doublet
dd=doublet of doublet
dt=doublet of triplet
DBU=diazabicyclo[5.4.0]undec-7-ere
DCM=dichloromethane=methylene chloride=$CH_2Cl_2$
DCE=dichloroethylene
DEAD=diethyl azodicarboxylate
DIC=diisopropylcarbodiimide
DIEA=N,N-diisopropylethyl amine
DMAP=4-N,N-dimethylaminopyridine
DMF=N,N-dimethylfonnamide
DMSO=dimethyl sulfoxide
DVB=1,4-divinylbenzene
EEDQ=2-ethoxy-1-ethoxycarbonyl-1,2-dihydroquinoline
EI=Electron Impact ionization
Et=ethyl
Fmoc=9-fluorenylmethoxycarbonyl
g=gram(s)
GC=gas chromatography
h or hr=hour(s)
HATU=0-(7-Azabenzotriazol-1-yl)-1,1,3,3-tetramethyluronium hexafluorophosphate
HMDS=hexamethyldisilazane
HOAc=acetic acid
HOBt=hydroxybenzotriazole
HPLC=high pressure liquid chromatography
L=liter(s)
M=molar or molarity
m=multiplet
Me=methyl
mesyl=methanesulfonyl
mg=milligram(s)
MHz=megahertz (frequency)
min=minute(s)
mL=milliliter(s)
mM=millimolar
mmol=millimole(s)
mol=mole(s)
MS=mass spectral analysis
MTBE=methyl t-butyl ether
N=normal or normality
NBS=N-bromosuccinimide
NCS=N-chlorosuccinimide
nM=nanomolar
NMO=N-methylmorpholine oxide
NMR=nuclear magnetic resonance spectroscopy
PEG=polyethylene glycol
pEY=poly-glutamine, tyrosine
Ph=phenyl
PhOH=phenol
PfP=pentafluorophenol
PfPy=pentafluoropyridine
PPTS=pyridinium p-toluenesulfonate
PyBroP=bromo-tris-pyrrolidino-phosphonium hexafluorophosphate
q=quartet
RT=room temperature
Sat'd=saturated
s=singlet
s-=secondary
t-=tertiary
t or tr=triplet
TBDMS=t-butyldimethylsilyl
TES=triethylsilane
TFA=trifluoroacetic acid
TMOF=trimethyl orthoformate
TMS=trimethylsilyl
tosyl=p-toluenesulfonyl
Trt=triphenylmethyl
uL=microliter(s)
uM=micromole(s) or micromolar Synthesis of Compounds Scheme 1 depicts general synthetic routes for compounds of the invention and is not intended to be limiting. Specific examples are described subsequently to these general synthetic descriptions. In the generalizations below, specific reaction conditions, for example, reagents such as added bases, acids, solvents, temperature, and the like are not described so as not to confuse the discussion.

The general routes, in conjunction with the specific examples, contain sufficient information to allow one skilled in the art to synthesize compounds of the invention. In Scheme 1, some substituents are not defined described as taking part in the synthesis of compounds of the invention. This is done purely for simplification of description of syntheses. Such substituents in formula I may be appended to the scaffold of formula I at any time during synthesis or may pre-exist on intermediates or starting materials used to make compounds of the invention, as would be understood by one skilled in the art. More specific examples are presented below to more fully describe the invention.

Scheme 1 depicts examples of how compounds of the invention, consistent with formula I, are made (in these examples for simplicity of discussion, substituents $R^1$, $R^2$, and $R^3$ are —H, but this is not always the case). Generally, but not necessarily, a starting material will take the form of, for example, (i) or (ii). For example, (i) may take the form of a commercially available 3-amino-pyrazine (where Z is N). The group "$F_1$" represents functionality that can be converted to, or functionality that exists in, compounds of formula I. For example if $F_1$ represents a carboxylic acid group, then where A, of formula I, is a carbonyl, then (ii) may more appropriately represent the starting material. In other cases, A is introduced into (i) to make (ii). For example, if $F_1$ is a cyano group, then in some instances the cyano group in (i) is converted to a triazole ring system to produce A in (ii).

$F_2$ represents a functionality that is ultimately converted to, or used in the production or introduction of, E of formula I. For example, if $F_1$ is a carboxylic acid, then -A-$F_2$ can represent the esterified form of the carboxylic acid. If $F_1$ is a cyano group, then -A-$F_2$ can represent, for example, a triazole ring with appended functionality for subsequent transformation. Although not depicted, the functionality -A-E may exist in commercially available starting materials, or be introduced in a single step to (i).

$F_3$ represents a functionality that is ultimately converted to, or used in the production or introduction of, W of formula I. For example, intermediate (ii) is brominated selectively to afford (iii) where $F_3$ is —Br. Using aryl-aryl coupling reactions known to one skilled in the art, W is introduced, preferably with functionality $F_4$, into (iii) to make intermediate (v). $F_4$ represents a functionality that is ultimately converted to, or used in the production or introduction of, X of formula I. Alternatively, (iii) is converted to (iv) via introduction of E (for example an ester represented by -A-$F_2$ is converted to an amide represented by -A-E). Scheme 1 depicts only a subset of possible variations of making compounds of the invention.

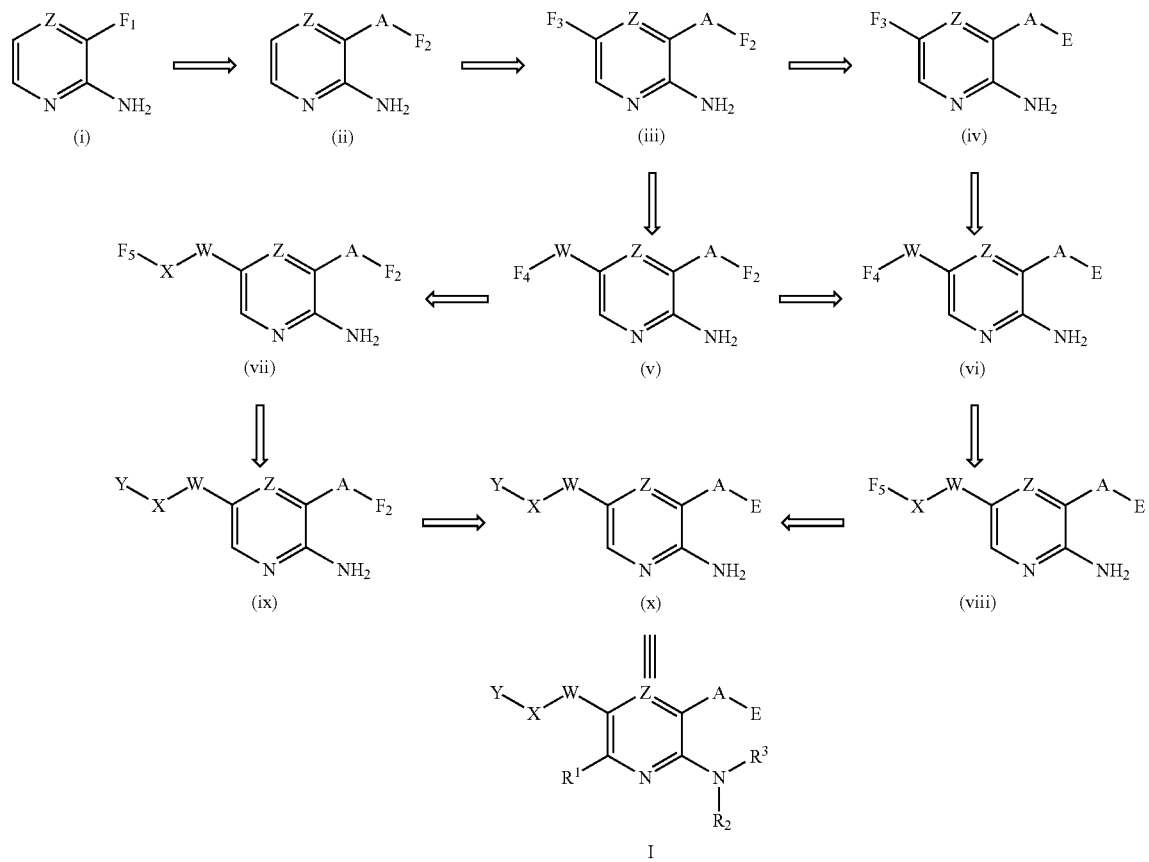

Scheme 1

Still referring to Scheme 1, intermediate (v) can be converted to intermediate (vi) via introduction of E (intermediate (vi) can also be made from (iv) via introduction of –W—$F_4$). Also from intermediate (v), X is introduced, preferably with functionality $F_5$, to make intermediate (vii). $F_5$ represents a functionality that is ultimately converted to, or used in the production or introduction of, Y of formula I. In many examples, —X—$F_5$ represents a linking group X with a reactive functionality, $F_5$, that is used to attach Y to X. In such cases, (vii) is converted to (ix). Alternatively, intermediate (vii) is converted, via introduction of —X—$F_5$, into (viii). Compounds of formula (x) are made from either intermediate (ix) or (viii). Compounds (x) are consistent with, and a subset of, formula I of the invention.

Thus compounds of the invention are generally made as depicted in Scheme 1. One skilled in the art would recognize that many variations of synthetic routes not included in Scheme 1 are possible, and thus are within the scope of the invention.

Scheme 2 depicts a general method of making 3-aminopyrazine-2-carboxamides of the invention. Commercially available methyl 3-amino-pyrazine-2-carboxylate was brominated using the procedure of Russ, T., Ried, W., Ullrich, F., and Mutschler, E. *Arch. Pharm.* (*Weinheim*) 1992, 375, 761-767 (by analogy, bromination of commercially available 2-aminonicotinic acid (for example as described in U.S. Pat. Nos. 3,950,160, and 4,361,700) affords 2-amino-5-bromopyridine-3-carboxylic acid. This intermediate can be used to make corresponding amino-pyridine analogues using similar methods similar to those described in Schemes 1-4 for 3-amino-pyrazine compounds.) The resulting bromo ester, (xi), was utilized, for example, in a Suzuki coupling with arylboronic acids by the method of W. J. Thompson, J. H. Jones, P. A. Lyle, and J. E. Thies *J. Org. Chem.* 1988, 53, 2052-2055 or a similar procedure. The resulting aryl substituted pyrazine ester, (xiv), was then hydrolyzed to the corresponding acid (xv). Acid (xv) was coupled with primary and secondary amines to give amides, (xvi), followed by removal of any protecting groups if necessary. Alternatively, aryl substituted pyrazine ester (xiv) was reacted directly with ammonia, methylamine, or other amines in a suitable solvent at elevated temperatures to afford amides (xvi). Again alternatively, bromopyrazine ester (xi) was converted (typically via hydrolysis) to bromopyrazine acid (xii), which was then coupled with amines to afford amides (xiii). The resulting bromo-pyrazine amides (xiii) were then, for example, coupled with arylboronic acids under Suzuki conditions to afford amides (xvi). In amides (xvi), the group —NR$_a$R$_b$ represents -E of formula I.

Alternatively, the ester moiety for example in intermediates (xi) and (xiv) were converted to an acid, amide, nitrile, aldehyde, hydroxymethyl, or other functional groups. These functional groups were then be elaborated into oximes, imines, hydrazones, or heterocycles such as triazoles, pyrimidines, oxadiazoles, and other heterocycles in accordance with group -A-E of formula I. More detailed descriptions of exemplary transformations are described below.

Typically, but not necessarily, the aryl groups (denoted Ar in Scheme 2, corresponding to W in formula I) contained functional groups such as an ester, aldehyde, hydroxymethyl, amine, hydroxyl, or other groups that were modified or functionalized either before or after the the aryl groups were coupled to, for example the bromo pyrazine. Schemes 3 and 4 depict a number of typical transformations that were carried out to form group —X—Y onto W, in cases where W was a meta-phenylene. These are presented as examples and are not intended to limit the scope of the invention.

Referring to Scheme 3, benzylic amine intermediate (xix) was formed, for example, either from benzylic alcohol intermediate (xvii) or aryl aldehyde intermediate (xviii) using standard synthetic techniques. For example, the —OH group of (xvii) was transformed into a leaving group and subsequently displaced with ammonia or an ammonia equivalent (such as a phthalimide) to form (xix). Alternatively, aldehyde (xviii) acylated, for example with acid chlorides, to form (xx) (according to formula I, W is meta-phenylene and X is —C(=O)NHCH$_2$—). Intermediate (xix) in many cases was, or otherwise could be, also reacted with sulfonyl chlorides, isocyanates, and other electrophiles. In another example, intermediate (xix) was subjected to reductive amination conditions to provide compounds (xxi).

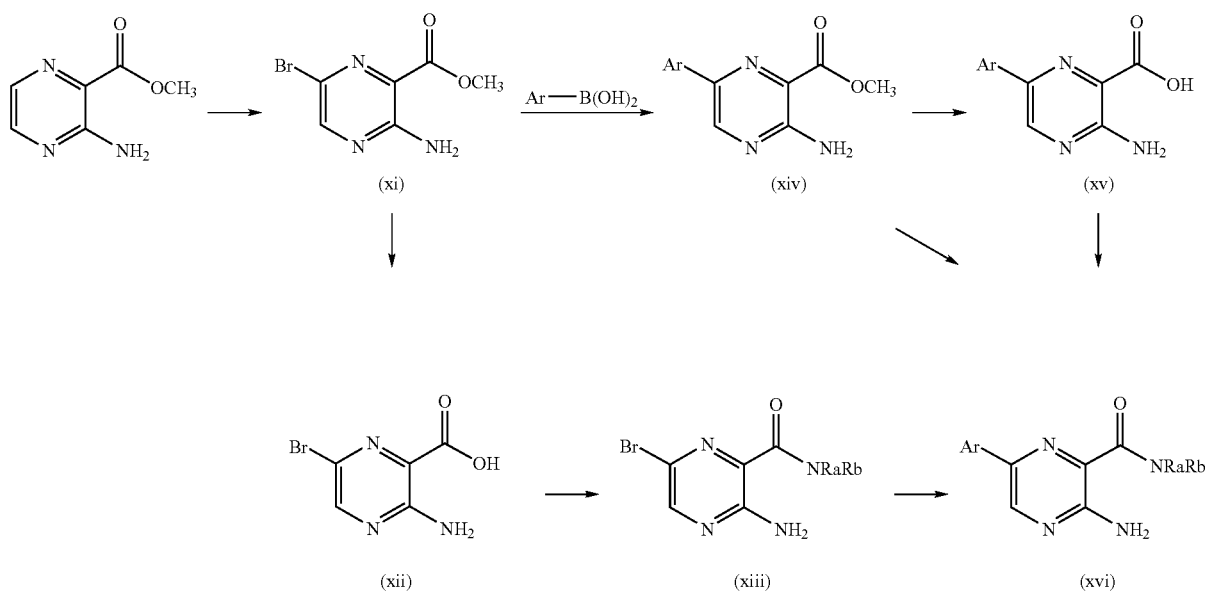

Scheme 2

Scheme 3

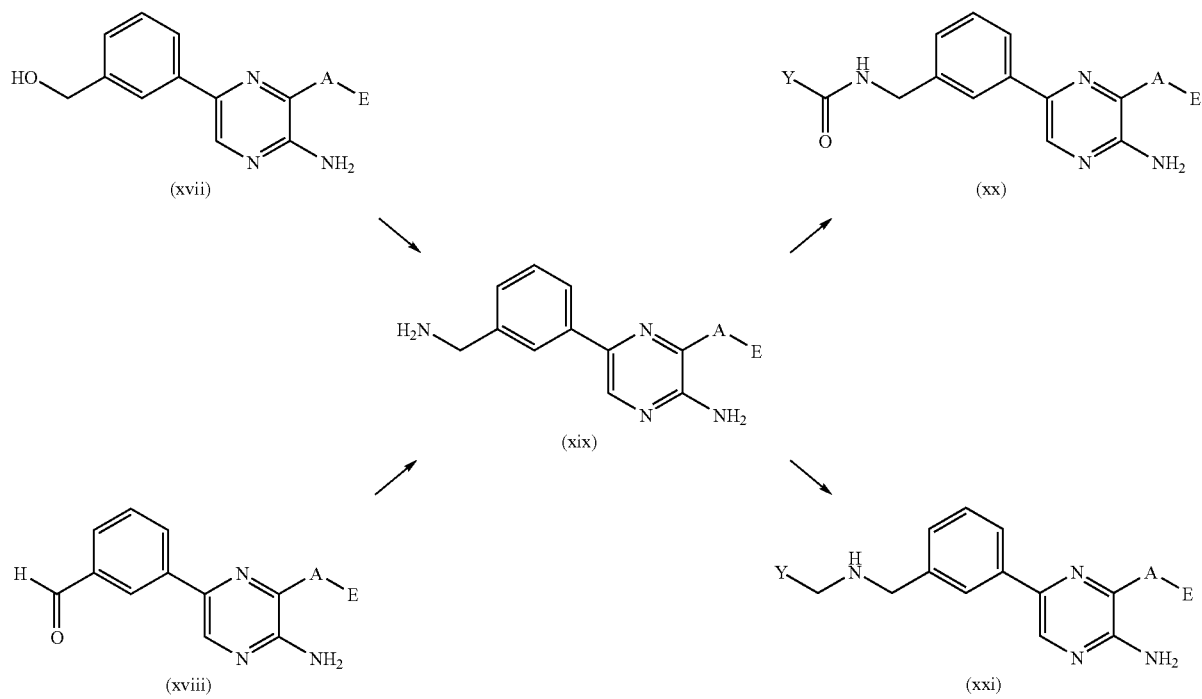

Scheme 4 shows additional transformations that were carried out to form group —X—Y onto W, in cases where W was a meta-phenylene. For example: esters (xxii) were converted to amides (xxiii), phenols (xxiv) were converted to ethers (xxv), and anilines (xxvi) were converted to amides (xxvii).

Scheme 4

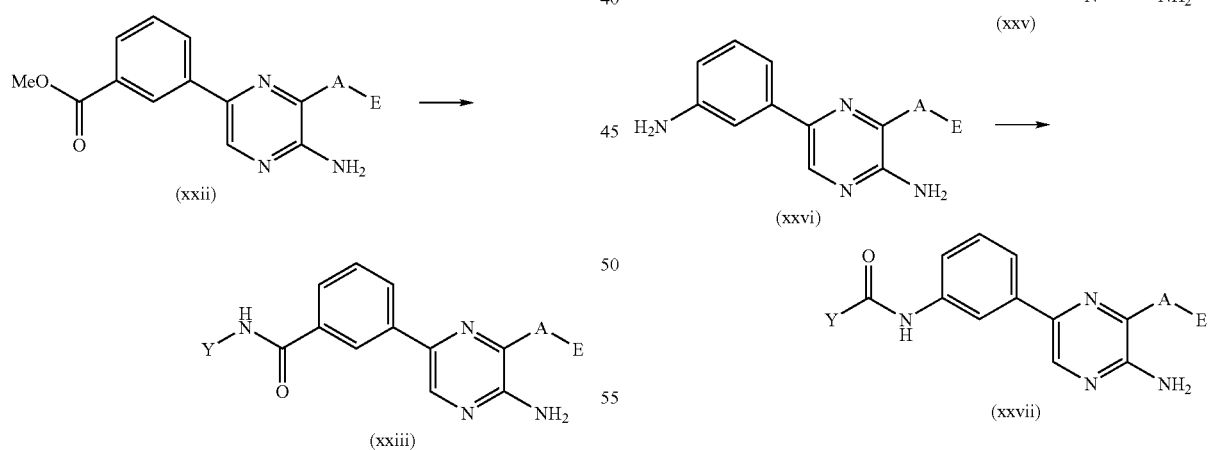

EXAMPLES

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

Generally, but not necessarily, each example set out below describes a multi-step synthesis as outlined above.

Example 1

3-amino-6-phenyl-N-(phenylmethyl)pyrazine-2-carboxamide

Methyl 3-amino-6-bromo-pyrazine-2-carboxylate: Commercially available methyl 3-amino-pyrazine-2-carboxylate (available from Aldrich Chemical Company) was brominated using a procedure similar to that of Russ, T., Ried, W., Ullrich, F., and Mutschler, E. *Arch. Pharm. (Weinheim)* 1992, 325, 761-767. To a solution of methyl 3-amino-2-pyrazine carboxylate (30.0 g, 200 mmol) in acetic acid (200 mL), bromine (11 mL) was added slowly via addition funnel. After complete addition of bromine, sodium carbonate powder was added slowly until precipitation occurred. The reaction mixture was allowed to stir at room temperature for 2 h. The reaction mixture was reduced to half-volume in vacuo and then diluted with water (500 mL). The reaction mixture was shaken vigorously and the resulting solid was collected using vacuum filtration. The solid was washed with ether to afford a pure yellow solid (91% yield).

Methyl 3-amino-6-phenylpyrazine-2-carboxylate: Methyl 3-amino-6-phenylpyrazine-2-carboxylate was prepared from methyl 3-amino-6-bromo-pyrazine-2-carboxylate using the procedure similar to that of W. J. Thompson, J. H. Jones, P. A. Lyle, and J. E. Thies *J. Org. Chem.* 1988, 53, 2052-2055.

3-amino-6-phenylpyrazine-2-carboxylic acid: To a solution of methyl 3-amino-6-phenylpyrazine-2-carboxylate (1.2 g, 5.26 mmol) in methanol (5 mL) was added 6.0 N aqueous sodium hydroxide (6 mL) at room temperature. The solution was stirred at 50 C. for 3 h. The reaction was neutralized slowly by adding 2.0 N hydrochloric acid until the pH of the solution became in the 2-3 range at 0° C. The solution was extracted with ethyl acetate (50 mL). The organic layer was washed with saturated aqueous sodium chloride (50 mL) and dried over magnesium sulfate. Filtration and concentration at reduced pressure afforded 3-amino-6-phenylpyrazine-2-carboxylic acid (0.59 g, 52% yield): MS (EI) for $C_{11}H_9O_2$: 216 (MH$^+$)

3-amino-6-phenyl-N-(phenylmethyl)pyrazine-2-carboxamide: To a solution of 3-amino-6-phenylpyrazine carboxylic acid (0.10 g, 0.47 mmol) in dichloromethane (3 mL) were added 1-ethyl-(3-dimethylaminopropyl)carbodiimide hydrochloride (EDCI, 0.11 g, 0.56 mmol), 1-hydroxybenzotriazole (HOBT, 75 mg, 0.56 mmol), and N-methylmorpholine (NMM, 56 mg, 0.56 mmol) at room temperature. The reaction was stirred for 15 min before benzylamine (0.56 mmol) was added. The reaction mixture was allowed to stir overnight. The reaction was diluted with ethyl acetate (200 mL) and washed with water (50 mL), saturated aqueous sodium bicarbonate (40 mL) and aqueous hydrochloric acid (30 mL), and saturated aqueous sodium chloride (25 mL). The organic layer was dried over magnesium sulfate, filtered and concentrated at reduced pressure to afford product (91 mg, 67% yield) as light yellow solid: $^1$H NMR (400 MHz, CDCl$_3$): δ 8.62 (s, 1H), 8.38 (br s, 1H), 7.84 (dd, 2H), 7.45 (m, 2H), 7.38 (m, 6H), 4.70 (d, 2H); MS (EI) for $C_{18}H_{16}N_4O$: 305 (MH$^+$).

Using the same or analogous synthetic techniques and/or substituting with alternative reagents, the following compounds of the invention were prepared:

3-amino-N,6-diphenylpyrazine-2-carboxamide: $^1$H NMR (400 MHz, CDCl$_3$): 9.92 (br s, 1H), 8.70 (s, 1H), 7.90 (dd, 2H), 7.72 (dd, 2H), 7.52 (m, 2H), 7.46 (m, 3H), 7.20 (t, 1H); MS (EI) for $C_{17}H_{14}N_4O$: 290(MH$^+$).

5-phenyl-3-(pyrrolidin-1-ylcarbonyl)pyrazin-2-amine: $^1$H NMR (400 MHz, CDCl$_3$): δ 8.58 (s, 1H), 7.82 (d, 2H), 7.45 (t, 2H), 7.40 (m, 1H), 6.40 (br s, 2H), 4.02 (m,1H), 4.70(m, 1H), 2.04 (m, 4H); MS (EI) for $C_{15}H_{16}N_4O$: 269 (MH$^+$).

3-amino-N-(cyclopropylmethyl)-6-phenylpyrazine-2-carboxamide: $^1$H NMR (400 MHz, CDCl$_3$): δ 8.62 (s, 1H), 8.10 (br s, 1H), 7.85 (dd, 2H), 7.50 (t, 2H), 7.40 (m, 1H), 3.30 (m, 2H), 1.10 (m, 1H), 0.80 (m, 2H), 0.30 (m, 2H); MS (EI) for $C_{15}H_{16}N_4O$: 269 (MH$^+$).

3-amino-6-phenyl-N-(tetrahydrofuran-2-ylmethyl)pyrazine-2-carboxamide: $^1$H NMR (400 MHz, CDCl$_3$): δ 8.60 (s, 1H), 8.30 (br s, 1H), 7.84 (d, 2H), 7.50 (t, 2H), 7.40 (m, 1H), 4.10 (m, 1H), 3.94 (m, 1H), 3.80 (m, 1H), 3.70 (m, 1H), 3.45 (m, 1H), 2.01 (m, 3H), 1.62 (m, 1H); MS (EI) for $C_{16}H_{18}N_4O_2$: 299 (MH$^+$).

3-amino-N-cyclohexyl-6-phenylpyrazine-2-carboxamide: $^1$H NMR (400 MHz, CDCl$_3$): δ 8.80 (s, 1H), 7.92 (br s, 1H), 7.82 (d, 2H), 7.45 (t, 2H), 7.40 (m, 2H), 3.90 (m, 1H), 2.01 (m, 2H), 1.90 (m, 2H), 1.85(m, 1H), 1.40 (m, 5H); MS (EI) for $C_{17}H_{20}N_4O$: 297 (MH$^+$).

3-amino-6-phenyl-N-(2-phenylethyl)pyrazine-2-carboxamide: $^1$H NMR (400 MHz, d$_6$-DMSO): 8.82 (m, 2H), 8.06 (m, 2H), 7.65 (br s, 2H), 7.49-7.20 (m, 8H), 3.58 (t, 2H), 2.90 (t, 2H); MS (EI) for $C_{19}H_{18}N_4$: 319.2 (MH$^+$).

3-amino-N-[(1R)-2,3-dihydro-1H-inden-1-yl]-6-phenylpyrazine-2-carboxamide: MS (EI) for $C_{20}H_{18}N_4O$: 331.2 (MH$^+$).

3-amino-N-[(1S)-2,3-dihydro-1H-inden-1-yl]-6-phenylpyrazine-2-carboxamide: $^1$H NMR (400 MHz, d$_6$-DMSO): 9.04 (d, 1H, 8.87 (s, 1H), 8.18 (m, 2H), 7.72 (br s, 2H), 7.49-7.18 (m, 7H), 5.60 (m, 1H), 3.02 (m, 1H), 2.86 (m, 1H), 2.44 (m, 1H), 2.21 (m, 1H); MS (EI) for $C_{20}H_{18}N_4O$: 331.2 (MH$^+$).

3-amino-N-(2,3-dihydro-1H-inden-2-yl)-6-phenylpyrazine-2-carboxamide: $^1$H NMR (400 MHz, d$_6$-DMSO): 9.04 (d, 1H), 8.87 (s, 1H), 8.18 (m, 2H), 7.72 (br s, 2H), 7.49-7.18 (m, 7H), 5.60 (m, 1H), 3.02 (m, 1H), 2.86 (m, 1H), 2.44 (m, 1H), 2.21 (m, 1H); MS (EI) for $C_{20}H_{18}N_4O$: 331.2 (MH$^+$).

3-amino-N-cyclopentyl-6-phenylpyrazine-2-carboxamide: $^1$H NMR (400 MHz, d$_6$-DMSO): 8.89 (d, 1H), 8.82 (s, 1H), 8.12 (m, 2H), 7.61 (br s, 2H), 7.46-7.15 (m, 7H), 4.79 (m, 1H), 3.28 (m, 2H), 3.11 (m, 2H); MS (EI) for $C_{16}H_{18}N_4O$: 283.2 (MH$^+$).

3-amino-N-cyclopropyl-6-phenylpyrazine-2-carboxamide: $^1$H NMR (400 MHz, d$_6$-DMSO): 8.83 (s, 1H), 8.65 (s, 1H), 8.13 (m, 2H), 7.65 (br s, 2H), 7.49-7.30 (m, 3H), 2.85 (m, 1H), 0.72 (m, 4H); MS (EI) for $C_{14}H_{14}N_4O$: 255.4 (MH$^+$).

Example 2

3-Amino-6-naphthalen-1-ylpyrazine-2-carboxamide

Methyl 3-amino-6-naphthalen-1-ylpyrazine-2-carboxylate: To a solution of methyl 3-amino-6-bromopyrazine-2-carboxylate (0.18 g, 0.74 mmol) in N,N-dimethylformamide (10 mL) were added [1,1'-bis(diphenylphosphino)ferrocene]dichloropalladium(II) complex with dichloromethane (1:1, 60 mg, 0.07 mmol), 1-naphthylboronic acid (0.32 g, 1.89 mmol), and triethylamine (0.15g, 1.52 mmol). The solution was degassed with nitrogen for 3-5 min. The reaction was then heated to 85-90° C. overnight. The reaction was cooled to room temperature and diluted with ethyl acetate (300 mL). The crude solution was passed through a pad of silica gel under vacuum. The filtrate was washed with saturated aqueous sodium bicarbonate (50 mL) and saturated aqueous sodium chloride (50 mL). The organic layer was dried over magnesium sulfate, filtered and concentrated at reduced pressure to afford impure product. Column purification on silica (8:2 hexanes/ethyl acetate) afforded methyl 3-amino-6-naphthalen-1-ylpyrazine-2-carboxylate (80 mg, 39% yield) as yellow solid: $^1$H NMR (400 MHz, CDCl$_3$): δ 8.52 (br s, 1H), 8.12 (br s, 1H), 7.92 (m, 2H), 7.52 (m, 5H), 4.02 (s, 3H); MS (EI) for C$_{16}$H$_{13}$N$_3$O$_2$: 280 (MHz).

3-amino-6-naphthalen-1-ylpyrazine-2-carboxamide: A solution of methyl 3-amino-6-naphthalen-1-ylpyrazine-2-carboxylate (80 mg, 0.29 mmol) in methanol (30 mL) was saturated with ammonia gas at 0° C. in a high-pressure test tube. The reaction tube was tightly sealed and heated to 80-90° C. for 4h. Reaction cooled to room temperature and evaporated at reduced pressure to afford 3-amino-6-naphthalen-1-ylpyrazine-2-carboxamide (59 mg, 79% yield) as yellow product: $^1$H NMR (400 MHz, CDCl$_3$): δ 8.80 (s, 1H), 8.10 (d, 1H), 7.90 (d, 2H), 7.58 (m, 6H); MS (EI) for C$_{15}$H$_{12}$N$_4$O: 265 (MH$^+$).

3-amino-6-(3-chlorophenyl)pyrazine-2-carboxamide: To a 15 mL sealed tube was added methyl 3-amino-6-(3-chlorophenyl)pyrazine-2-carboxylate (65 mg, 0.246 mmol) and methanol (8 mL). The suspension was cooled to 0° C. and NH$_3$ (g) was bubbled until saturation was achieved. The tube was sealed and heated at 85° C. overnight with stirring. During initial heating, the reaction mixture became homogeneous. The tube was removed from the heat and allowed to cool to room temperature. Upon cooling a yellow, needle-like precipitate formed. The precipitate was collected on filter paper to give 3-amino-6-(3-chlorophenyl)pyrazine-2-carboxamide (53.9 mg, 88% yield) as a yellow solid: $^1$H NMR (400 MHz, d6-DMSO): δ 8.88 (s, 1H), 8.42 (br s, 2H), 8.30 (t, 1H), 8.11 (d, 1H) 7.69 (br s, 2H), 7.46-7.40 (m, 2H); MS (EI) for C$_{11}$H$_9$N$_4$OCl: 249 (MH$^+$).

Using the same or analogous synthetic techniques and/or substituting with alternative reagents, the following compounds of the invention were prepared:

3-amino-6-naphthalen-2-ylpyrazine-2-carboxamide: $^1$H NMR (400 M&z, d$_6$-DMSO): δ 9.02 (s, 1H), 8.80 (s, 1H), 8.40 (m, 2H), 8.02 (m, 3H), 7.80 (br s, 1H), 7.50 (t, 2H); MS (EI) for C$_{15}$H$_{12}$N$_4$O: 265 (MH$^+$).

3-amino-6-biphenyl-4-ylpyrazine-2-carboxamide: $^1$H NMR (400 MHz, d$_6$-DMSO): δ 8.90 (s, 1H), 8.38 (br s, 1H), 8.30 (d, 2H), 7.70 (m, 5H), 7.50 (m, 2H), 7.34 (m, 1H); MS (EI) for C$_{17}$H$_{14}$N$_4$O: 291 (MH$^+$).

3-amino-6-(1-benzofuran-2-yl)pyrazine-2-carboxamide: $^1$H NMR (400 MHz, d$_6$-DMSO): δ 8.85 (s, 1H), 8.60 (br s, 1H), 7.80 (s, 1H), 7.60 (m, 3H), 7.30 (m, 2H); MS (EI) for C$_{13}$H$_{10}$N$_4$O: 255 (MH$^+$).

3-amino-6-biphenyl-3-ylpyrazine-2-carboxamide: $^1$H NMR (400 MHz, CDCl$_3$): v8.70 (s, 1H), 8.10 (s, 1H), 7.85 (d, 2H), 7.65 (t, 3H), 7.55 (t, 1H), 7.45 (t, 3H), 7.40 (t, 1H); MS (EI) for C$_{17}$H$_{14}$N$_4$O: 291 (MH$^+$).

3-[5-amino-6-(aminocarbonyl)pyrazin-2-yl]benzoic acid: $^1$H NMR (400 MHz, d$_6$-DMSO): δ 8.95 (s, 1H), 8.80 (br s, 2H), 8.50 (s, 1H), 8.30 (d, 1H), 7.98 (d, 1H), 7.60 (br t, 1H); MS (EI) for C$_{12}$H$_{10}$N$_4$O$_3$: 259 (MH$^+$).

3-amino-6-{4-[(phenylmethyl)oxy]phenyl}pyrazine-2-carboxamide: $^1$H NMR (400 MHz, d$_6$-DMSO): δ 8.80 (s, 1H), 8.30 (br s, 1H), 8.10 (d, 2H), 7.65 (br s, 1H), 7.49 (d, 2H), 7.40 (t, 2H), 7.35 (t, 1H), 7.10 (d, 2H), 5.20 (s, 2H); MS (EI) for C$_{18}$H$_{16}$N$_4$O$_2$: 321 (MH$^+$).

3-amino-6-(2-chlorophenyl)pyrazine-2-carboxamide: $^1$H NMR (400 MHz, d6-DMSO): δ 8.53 (s, 1H), 7.76-7.73 (m, 1H), 7.59-7.56 (m, 1H), 7.46-7.43 (m, 2H); MS (EI) for C$_{11}$H$_9$N$_4$OCl: 249 (MH$^+$).

3-amino-6-[3-(methyloxy)phenyl]pyrazine-2-carboxamide: $^1$H NMR (400 MHz, d6-DMSO): δ 8.82 (s, 1H), 7.69-7.65 (m, 4H), 7.33 (t, 1H), 6.91 (dd, 1H), 3.82 (s, 3H); MS (EI) for C$_{12}$H$_{12}$N$_4$O$_2$: 245 (MH$^+$).

3-amino-6-(2-methylphenyl)pyrazine-2-carboxamide: $^1$H NMR (400 MHz, d6-DMSO): δ 8.38 (s, 1H), 7.48-7.47 (m, 1H), 7.30-7.28 (m, 3H); MS (EI) for C$_{12}$H$_{12}$N$_4$O: 229 (MH$^+$)

3-amino-6-[2-(methyloxy)phenyl]pyrazine-2-carboxamide: $^1$H NMR (400 MHz, d6-DMSO): δ 8.72 (s, 1H), 7.94-7.91 (m, 1H), 7.36-7.34 (m, 1H), 7.14-7.12 (m, 1H), 7.07-7.05 (m, 1H), 3.86 (s, 3H); MS (EI) for C$_{12}$H$_{12}$N$_4$O$_2$: 245 (MH$^+$).

3-amino-6-(2,4-difluorophenyl)pyrazine-2-carboxamide: $^1$H NMR (400 MHz, d6-DMSO): δ 8.59 (s, 1H), 8.28-8.26 (m, 2H), 7.17 (br s, 2H), 7.38-7.37 (m, 1H), 7.20 (m, 1H); MS (EI) for C$_{11}$H$_8$N$_4$OF$_2$: 251 (MH$^+$).

3-amino-6-(3-fluorophenyl)pyrazine-2-carboxamide: $^1$H NMR (400 MHz, d6-DMSO): δ 8.89 (s, 1H), 8.11 (d, 1H), 7.98 (d, 1H), 7.48-7.46 (m, 1H), 7.17-7.16 (m, 1H); MS (EI) for C$_{11}$H$_9$N$_4$OF: 233 (MH$^+$).

3-amino-6-(3,4-difluorophenyl)pyrazine-2-carboxamide: $^1$H NMR (400 MHz, d6-DMSO): δ 8.88 (s, 1H), 8.41-8.35 (m, 1H), 8.02 (m, 1H), 7.52-7.45 (m, 1H); MS (EI) for C$_{11}$H$_8$N$_4$OF$_2$: 251 (MH$^+$).

3-amino-6-(4-fluorophenyl)-N-methylpyrazine-2-carboxamide: $^1$H NMR (400 MHz, d6-DMSO): δ 8.84 (m, 2H), 8.25-8.22 (m, 2H), 7.31-7.26 (m, 2H), 2.84 (d, 3H); MS (EI) for C$_{12}$H$_{11}$N$_4$OF: 247 (MH$^+$).

3-amino-6-{3-[(trifluoromethyl)oxy]phenyl}pyrazine-2-carboxamide: $^1$H NMR (400 MHz, d6-DMSO): δ 8.91 (s, 1H), 8.23 (s, 1H), 8.20-8.18 (m, 1H), 7.59-7.54 (t, 1H), 7.35-7.33 (d, 1H); MS (EI) for C$_{12}$H$_9$N$_4$O$_2$F$_3$: 299 (MH$^+$).

3-amino-6-(3-methylphenyl)pyrazine-2-carboxamide: $^1$H NMR (400 MHz, d6-DMSO): δ 8.82 (s, 1H), 8.00 (s, 1H), 7.93-7.91 (d, 1H), 7.34-7.31 (t, 1H), 7.18-7.16 (m, 1H), 2.38 (s, 3H), MS (EI) for C$_{12}$H$_{12}$N$_4$O: 229 (MH$^+$)

3-amino-6-{3-[(phenylmethyl)oxy]phenyl}pyrazine-2-carboxamide: $^1$H NMR (400 MHz, d6-DMSO): δ 8.84 (s, 1H), 7.78-7.77 (m, 1H), 7.71-7.70 (m, 2H), 7.50-7.59 (m, 2H), 7.43-7.39 (m, 2H), 7.38-7.31 (m, 2H), 7.02-6.99 (m, 1H), 5.21 (s, 2H); MS (EI) for C$_{18}$H$_{16}$N$_4$O$_2$: 321 (MH$^+$).

3-amino-6-(3-hydroxyphenyl)pyrazine-2-carboxamide: To a 25 mL recovery flask was added 3-amino-6-{3-[(phenylmethyl)oxy]phenyl}pyrazine-2-carboxamide (33 mg, 0.103 mmol) and ethyl acetate (10 mL). A catalytic amount of 10% Pd/C was added. The flask was sealed with a septum and fitted with an H$_2$ balloon. The reaction mixture was stirred overnight at room temperature. The reaction mixture was passed through a Celite pad. The filtrate was concentrated to give 3-amino-6-(3-hydroxyphenyl)pyrazine-2-carboxamide (23 mg, 96% yield) as a yeloow powder. $^1$H NMR (400 MHz, d6-DMSO): δ 9.47 (s, 1H), 8.74 (s, 1H), 7.55-7.53 (m, 1H), 7.46 (m, 1H), 7.25-7.22 (t, 1H), 6.78-6.76 (m, 1H); MS (EI) for C$_{11}$H$_{10}$N$_4$O$_2$: 231 (MH$^+$).

3-amino-N,N-dimethyl-6-phenylpyrazine-2-carboxamide: $^1$H NMR (400 MHz, CDCl$_3$): 8.54 (s, 1H), 7.89 (m, 2H), 7.48-7.33 (m, 3H), 5.88 (br s, 2H), 3.33 (s, 3H), 3.17 (s, 3H); MS (EI) for C$_{13}$H$_{14}$N$_4$O: 243.1 (MH$^+$).

3-amino-6-[4-(ethyloxy)phenyl]pyrazine-2-carboxamide: $^1$H NMR (400 MHz, d$_6$-DMSO): 8.78 (s, 1H), 8.28 (s, 1H), 8.08 (m, 2H), 7.66 (s, 1H), 7.56 (br s, 2H), 6.98 (m, 2H), 4.08 (q, 2H), 1.35 (t, 3H); MS (EI) for C$_{31}$H$_{14}$N$_4$O$_2$: 259.4 (MH$^+$).

3-amino-6-[3-(ethyloxy)phenyl]pyrazine-2-carboxamide: $^1$H NMR (400 MHz, d$_6$-DMSO): 8.85 (s, 1H), 8.30 (s, 1H), 7.96-7.28 (m, 6H), 6.92 (m, 1H), 4.13 (q, 2H), 1.35 (t, 3H); MS (EI) for C$_{13}$H$_{14}$N$_4$O$_2$: 259.4 (NH$^+$).

3-amino-6-(1,3-benzodioxol-5-yl)pyrazine-2-carboxamide: $^1$H NMR (400 MHz, d$_6$-DMSO): 8.78 (s, 1H), 8.36 (s, 1H), 7.85 (s, 1H), 7.79-7.37 (m, 4H), 6.96 (d, 1H), 6.07 (s, 2H); MS (EI) for $C_{12}H_{10}N_4O_3$: 259.4 (MH$^+$).

3-amino-6-[3-(aminocarbonyl)phenyl]pyrazine-2-carboxamide: $^1$H NMR (400 MHz, d$_6$-DMSO): 8.92 (s, 1H), 8.54 (s, 1H), 8.40 (s, 1H), 8.32 (d, 1H), 8.16 (s, 1H), 7.95 -7.42 (m, 6H); MS (EI) for $C_{12}H_{11}N_5O_2$: 258.4 (MH$^+$).

6-[3-(acetylamino)phenyl]-3-aminopyrazine-2-carboxamide: $^1$H NMR (400 MHz, d6-DMSO): 9.99 (s, 1H), 8.72 (s, 1H), 8.11 (m, 2H), 7.94-7.46 (m, 5H), 7.37 (m, 1H), 2.06 (s, 3H); MS (EI) for $C_{13}H_{13}N_5O_2$: 272.4 (MH$^+$).

3-amino-6-[4-(dimethylamino)phenyl]pyrazine-2-carboxamide: $^1$H NMR (400 MHz, d$_6$-DMSO): 8.73 (s, 1H), 8.21 (s, 1H), 7.97 (m, 2H), 7.64 (s, 1H), 7.45 (br s, 2H), 6.76 (m, 2H), 2.95 (s, 6H); MS (EI) for $C_{13}H_{15}N_5O$: 258.4 (MH$^+$).

methyl 3-[5-amino-6-(aminocarbonyl)pyrazin-2-yl]benzoate: $^1$H NMR (400 MHz, d$_6$-DMSO): 8.90 (s, 1H), 8.57 (s, 1H), 8.48 (m, 1H), 8.31 (s, 1H), 8.00-7.42 (m, 5H), 3.90 (s, 3H); MS (EI) for $C_{13}H_{12}N_4O_3$: 273.4 (MH$^+$).

3-amino-N-methyl-6-{3-[(phenylmethyl)oxy]phenyl}pyrazine-2-carboxamide: $^1$H NMR (400 MHz, d$_6$-DMSO): 8.82 (m, 2H), 7.92-7.19 (m, 10H), 7.03 (m, 1H), 5.22 (s, 2H), 2.85 (s, 3H); MS (EI) for $C_{19}H_{18}N_4O_2$: 335.4 (MH$^+$).

3-amino-6-(3-hydroxyphenyl)-N-methylpyrazine-2-carboxamide: $^1$H NMR (400 MHz, d$_6$-DMSO): 9.49 (s, 1H), 8.73 (m, 2H), 7.87-7.34 (m, 4H), 7.25 (m, 1H), 6.79 (m, 1H), 2.85 (d, 3H); MS (EI) for $C_{12}H_{12}N_4O_2$: 245.4 (MHz. MHz, d$_6$-DMSO): 8.85 (m, 2H), 8.15 (m, 2H), 7.68 (br s, 2H), 7.47 (m, 2H), 7.40 (m, 1H), 3.50 (m, 4H), 3.29 (s, 311); MS (EI) for $C_{14}H_{16}N_4O_2$: 273.4 (MH$^+$).

N-[2-(acetylamino)ethyl]-3-amino-6-phenylpyrazine-2-carboxamide: $^1$H NMR (400 MHz, 4-DMSO): 8.94 (t, 1H), 8.86 (s, 1H), 8.19 (m, 2H), 8.05 (t, 1H), 7.66 (br s, 1H), 7.46 (m, 2H), 7.38 (m, 1H), 3.38 (m, 2H), 3.27 (m, 2H), 1.83 (s, 3H); MS (EI) for $C_{15}H_{17}N_5O_2$: 300.4 (MH$^+$).

3-amino-6-phenylpyrazine-2-carbohydrazide: $^1$H NMR (400 MHz, d$_6$-DMSO): 10.02 (s, 1H), 8.82 (s, 1H), 8.19 (m, 2H), 7.58 (br s, 2H), 7.43 (m, 2H), 7.35 (m, 2H), 7.32 (m, 1H), 4.57 (m, 2H); MS (EI) for $C_{11}H_{11}N_5O$: 230.3 (MH$^+$).

3-amino-N-hydroxy-6-phenylpyrazine-2-carboxamide: $^1$H NMR (400 MHz, d$_6$-DMSO): 11.42 (s, 1H), 9.12 (s, 1H), 8.83 (s, 1H), 8.20 (m, 2H; 7.53 br s, 2H), 7.42 (m, 2H), 7.36 (m, 1H); MS (EI) for $C_{11}H_{10}N_4O_2$: 231.3 (MH$^+$).

3-amino-N-(2-hydroxyethyl)-6-(3-methylphenyl)pyrazine-2-carboxamide: A solution of 3-amino-6-bromo-2-carbomethoxypyrazine (100 mg, 0.4 mmol) and 2-aminoethanol (500 mg, 8.2 mmol) in THF (5 mL) was heated at reflux for 2 days. The reaction mixture was cooled, diluted with ethyl acetate (20 mL), washed with water then brine, dried over sodium sulfate, filtered, and concentrated. The oily residue was purified by flash chromatography (silica gel, eluted with ethyl acetate-hexanes gradient from 15% to 80% yield) to give 3-amino-N-(2-hydroxyethyl)-6-bromo-pyrazine-2-carboxamide, a pale yellow oil, (108 mg, 96% yield) MS (EI) for $C_7H_9BrN_4O_2$: 262 (MH$^+$).

The intermediate 3-amino-N-(2-hydroxyethyl)-6-bromopyrazine-2-carboxamide (108 mg, 0.4 mmole), [1,1'bis(diphenylphosphino)ferrocene]dichloropalladium(II)-dichloromethane complex (19 mg, 0.04 mmol), 3-methylphenylboronic acid (67 mg, 0.5 mmol) in DMF (2 mL) was de-gassed with nitrogen. Triethylamine (0.12 mL, 0.8 mmol) was then added and the resulting mixture was heated at 85° C. for 2.5 hours. The reaction mixture was cooled to room temperature, diluted with ethyl acetate (10 mL), filtered over silica gel, washed with saturated sodium bicarbonate solution (10 mL), dried over sodium sulfate, filtered, and concentrated. The oily residue was purified by flash chromatography (silica gel, eluted with ethyl acetate-hexanes gradient from 15% to 80% yield) to give methyl 3-amino-N-(2-hydroxyethyl)-6-(3-methylphenyl)pyrazine-2-carboxamide as a solid: (95 mg, 84% yield): $^1$H NMR (400 MHz, DMSO-d$_6$): 8.78 (s, 1H), 8.78-8.61 (b, 1H), 7.89 (s, 1H), 7.49-7.52 (t, 1H), 7.51-7.49 (d, 1H), 7.14-7.12 (d,1H), 3.50-3.35 (m, 2H), 2.89-70 (m, 2H), 2.51 (s, 3H): MS (EI) for $C_{14}H_{16}N_4O_2$: 273 (MH$^+$).

Example 3

3-amino-N-methyl-6-[4-(tetrahydro-2H-pyran-2-yloxy)phenyl]pyrazine-2-carboxamide 3-amino-6-bromo-N-methyl-2-pyrazinecarboxamide: An ice-cooled solution of 50 g of methyl 3-amino-6-bromo-pyrazine-2-carboxylate in 500 mL of MeOH was saturated with methylamine gas. The reaction was then heated at 85° C. in a sealed, stainless steel Parr pressure vessel for 2 h, and cooled to room temperature, and then on an ice water bath. The mixture was concentrated to an oil on a rotary evaporator under reduced pressure. The crude oil was dissolved in EtOAc and washed with water, dried (Na$_2$SO$_4$), filtered, and concentrated to give 43.9 g (88.0% yield) of product as a solid.

3-amino-N-methyl-6-[4-(tetrahydro-2H-pyran-2-yloxy)phenyl]pyrazine-2-carboxamide: A suspension of 3-amino-6-bromo-N-methyl-2-pyrazinecarboxamide (69.3 mg, 0.3 mmol), [4-(tetrahydro-2H-pyran-2-yloxy)phenyl boronic acid (111 mg, 0.5 mmol) [1,1-bis(diphenylphosphino)-ferrocene]dichloropalladium(II) complex with dichloromethane (1:1) (20.4 mg, 0.025 mmol), and triethylamine (121 mg,1.2 mmol) in DMF (20 mL) was stirred at 80° C. under nitrogen for 12 h. DMF was removed under vacuo. The residue was extracted with ethyl acetate (3×50 mL). The organic layers were washed with brine (10 mL) then dried over anhydrous sodium sulfate. Filtration, concentration and column chromatography on silica gave 3-amino-N-methyl-6-[4-(tetrahydro-2H-pyran-2-yloxy)phenyl]pyrazine-2-carboxamide (68.3 mg, 70% yield) as a yellow solid. $^1$H NMR (400 MHz, d$_6$-DMSO): 8.8 (m, 2H), 8.1 (d, 2H), 7.1 (d, 2H), 5.56 (s, 1H), 3.78 (m, 2H), 3.45 (m, 2H), 1.98-1.43 (m, 6H); MS (EI) for $C_{17}H_{20}N_4O_3$: 329 (MH+).

Using the same or analogous synthetic techniques and/or substituting with alternative reagents, the following compounds of the invention were prepared:

3-amino-6-[4-(ethyloxy)phenyl]-N-methylpyrazine-2-carboxamide: $^1$H NMR (400 MHz, CDCl$_3$): δ 8.52 (s, 1H), 8.02 (br s, 1H), 7.80 (d, 2H), 7.00 (br d, 2H), 7.55 (t, 2H), 412 (q, 2H), 3.02 (d, 3H), 1.43 (t, 3H); MS (EI) for $C_{14}H_{16}N_4O_2$: 273 (MH$^+$).

3-amino-N-methyl-6-(3-methylphenyl)pyrazine-2carboxamide: $^1$H NMR (400 MHz, CDCl$_3$): δ 8.60 (s, 1H), 8.01 (br s, 1H), 7.64 (br d, 2H), 7.38 (t, 1H), 7.25 (br d, 1H), 3.02 (d, 3H), 2.42 (s, 3H); MS (EI) for $C_{13}H_{14}N_4O$: 243 (MH$^+$).

3-amino-N-methyl-6-[4-(methyloxy)phenyl]pyrazine-2-carboxamide: $^1$H NMR (400 M, CDCl$_3$): δ 8.57 (s, 1H), 8.02 (br s, 1H), 7.80 (br d, 2H), 7.02 (br d, 2H), 3.84 (s, 3H), 3.10 (d, 3H); MS (EI) for $C_{13}H_{14}N_4O_2$: 259 (MH$^+$)

3-amino-N-methyl-6-[3-(methyloxy)phenyl]pyrazine-2-carboxamide: $^1$H NMR (400 MHz, CDCl$_3$): δ 8.60 (s, 1H), 8.02 (br s, 1H), 7.40 (m, 3H), 6.90 (br d, 1H), 3.92 (s, 3H, 3.02 (br s, 3H; MS (EI) for $C_{13}H_{14}N_4O_2$: 259 (MH$^+$).

3-amino-6-(4-fluoro-3-methylphenyl)-N-methylpyrazine-2-carboxamide: $^1$H NMR (400 MHz, CDCl$_3$): δ 8.52 (s, 1H), 7.94 (br s, 1H), 7.65 (m, 2H), 7.12 (t, 1H), 3.02 (d, 3H), 2.40 (s, 3H); MS (EI) for $C_{13}H_{13}N_4O$ F: 261 (MH$^+$).

3-amino-N-methyl-6-pyridin-3-ylpyrazine-2-carboxamide: $^1$H NMR (400 MHz, d$_6$-DMSO): δ 9.40 (br s, 1H), 8.94 (br s, 2H), 8.54 (m, 2H), 7.44 (t, 1H), 2.90 (br s, 3H), MS (EI) for C$_{11}$H$_{11}$N$_5$O: 230 (MH$^+$).

3-amino-6-[4-(dimethylamino)phenyl]-N-methylpyrazine-2-carboxamide: $^1$H NMR (400 M, CDCl$_3$): δ 8.58 (s, 1H), 8.12 (br s, 1H), 7.75 (br d, 2H), 6.80 (br d, 2H), 3.02 (m, 9H); MS (EI) for C$_{14}$H$_{17}$N$_5$O: 272 (MH$^+$).

3-amino-N-methyl-6-{4-[(methylsulfonyl)amino]phenyl}pyrazine-2-carboxamide: $^1$H NMR (400 MHz, d$_6$-DMSO): 9.80 (br s, 1H), 8.80 (br s, 2H), 8.15 (br d, 2H), 7.30 (br d, 2H), 3.02 (br s, 3H), 2.80 (br s, 3H); MS (EI) for C$_{13}$H$_{15}$N$_5$O$_3$S: 322 (MH$^+$).

3-amino-6-(3,5-dimethylphenyl)-N-methylpyrazine-2-carboxamide: $^1$H NMR (400 MHz, CDCl$_3$): 8.60 (s, 1H), 8.02 (br s, 1H), 7.45 (br d, 2H), 7.05 (br s, 1H), 3.02 (br s, 3H), 2.40 (br s, 6H); MS (EI) for C$_{14}$H$_{16}$N$_4$O: 257 (MH$^+$).

6-(4-acetylphenyl)-3-amino-N-methylpyrazine-2-carboxamide: $^1$H NMR (400 MHz, CDCl$_3$): 8.70 (br s, 1H), 8.05 (br d, 2H), 7.95 (br d, 3H, 3.10 (d, 3H), 2.60 (s, 3H); MS (EI) for C$_{14}$H$_{14}$N$_4$O$_2$: 271 (MH$^+$).

3-amino-6-[3,4-bis(methyloxy)phenyl]-methylpyrazine-2-carboxamide: $^1$H NMR (400 MHz, CDCl$_3$): 8.58 (s, 1H), 7.95 (br s, 1H), 7.40 (dd, 1H), 7.36 (d, 1H), 6.82 (d, 1H), 4.02(s, 3H), 3.92(s, 3H), 3.02 (d, 3H); MS (EI) for C$_{14}$H$_{16}$N$_4$O$_3$: 289 (MH$^+$).

3-amino-6-(3-cyanophenyl)-N-methylpyrazine-2-carboxamide: $^1$H NMR (400 MHz, d$_6$-DMSO): 8.89 (m, 2H), 8.70 (br s, 1H), 8.45 (d, 1H), 7.80 (d, 1H), 7.60 (t, 1H), 2.82 (br s, 3H); MS (EI) for C$_{13}$H$_{11}$N$_5$O: 254 (MH$^+$).

3-amino-N-methyl-6-[3-(1H-tetrazol-5-yl)phenyl]pyrazine-2-carboxamide: To a solution of 3-amino-6-(3-cyanophenyl)-N-methylpyrazine-2-carboxamide (93 mg, 0.37 mmol) in dry N,N-dimethylformamide (1 mL) were added sodium azide (27 mg, 0.41 mmol), and ammonium chloride (22 mg, 0.41 mmol). The reaction was heated to 100-110° C. overnight. Reaction cooled to room temperature and treated with saturated aqueous sodium bicarbonate (20 mL). The aqueous layer was washed with ethyl acetate (2×30 mL). The sodium bicarbonate layer was cooled to 0° C. and neutralized with 2.0 N hydrochloric acid until the pH of the solution became in the 2-3 range. The aqueous layer was extracted with ethyl acetate (100 mL) and washed with water (20 mL) and saturated aqueous sodium chloride (30 mL), dried over magnesium sulfate, filtered, and concentrated at reduced pressure to afford 3-amino-N-methyl-6-[3-(1H-tetrazol-5-yl)phenyl]pyrazine-2-carboxamide (25 mg, 23% yield) as light yellow solid. $^1$H NMR (400 MHz, d$_6$-DMSO): 8.92 (s, 1H), 8.84 (m, 1H), 8.70 (br s, 1H), 8.40 (br d, 1H), 8.12 (br d, 1H), 7.70 (t, 1H), 2.92 (br s, 3H); MS (EI) for C$_{13}$H$_{12}$N$_8$O: 297 (MH$^+$).

3-amino-6-[3-(ethyloxy)phenyl]-N-methylpyrazine-2-carboxamide: $^1$H NMR (400 MHz, d$_6$-DMSO): 8.83 (s, 1H), 8.81 (m, 1H), 7.70 (m, 2H), 7.62 (br s, 2H), 7.36 (m, 1H), 6.93 (m, 1H), 4.12 (q, 2H), 2.85 (d, 3H), 1.36 (t, 3H); MS (EI) for C$_{14}$H$_{16}$N$_4$O$_2$: 273.4 (MH$^+$).

3-amino-6-(3-aminophenyl)-N-methylpyrazine-2-carboxamide: $^1$H NMR (400 MHz, d$_6$-DMSO): 8.66 (m, 2H), 7.58 (br s, 2H), 7.27 (m, 2H), 7.11 (m, 1H), 6.59 (m, 1H), 5.09 (s, 2H), 2.85 (d, 3H); MS (EI) for C$_{12}$H$_{13}$N$_5$O: 244.4 (MH$^+$).

6-[3-(acetylamino)phenyl]-3-amino-N-methylpyrazine-2-carboxamide: $^1$H NMR (400 MHz, d$_6$-DMSO): 10.01 (s, 1H), 8.69 (m, 2H), 8.03 (m, 1H), 7.83 (m, 1H), 7.78 (m, 1H), 7.63 (br s, 2H), 7.38 (m, 1H), 2.85 (d, 3H), 2.08 (s, 3H); MS (EI) for C$_{12}$H$_{13}$N$_5$O: 286.4 (MH$^+$).

3-amino-6-[3-(hydroxymethyl)phenyl]-N-methylpyrazine-2-carboxamide: $^1$H NMR (400 MHz, d$_6$-DMSO): 8.82 (s, 1H), 8.78 (m, 1H), 8.04 (m, 2H), 7.64 (br s, 2H), 7.42 (m, 1H), 7.35 (m, 1H), 5.23 (t, 1H), 4.58 (d, 2H), 2.86 (d, 3H); MS (EI) for C$_{13}$H$_4$N$_4$O$_2$: 259.4 (MH$^+$).

3-amino-6-[4-(hydroxymethyl)phenyl]-N-methylpyrazine-2-carboxamide: $^1$H NMR (400 MHz, d$_6$-DMSO): 8.84 (s, 1H), 8.82 (m, 1H), 8.14 (d, 2H), 7.62 (br s, 2H), 7.40 (d, 2H), 5.24 (t, 1H), 4.55 (d, 2H), 2.85 (d, 3H); MS (EI) for C$_{13}$H$_{14}$N$_4$O$_2$: 259.4 (MH$^+$).

3-amino-N-methyl-6-{3-[(1E)-N-methylethanimidoyl]phenyl}pyrazine-2-carboxamide: $^1$H NMR (400 MHz, d$_6$-DMSO): 8.86 (s, 1H), 8.81 (m, 1H), 8.35 (m, 1H), 8.22 (m, 1H), 7.80 (m, 1H), 7.68 (br s, 2H), 7.48 (t, 1H), 3.29 (s, 3H), 2.85 (d, 3H), 2.30 (s, 3H); MS (EI) for C$_{15}$H$_{17}$N$_5$O: 284.4 (MH$^+$).

6-[4-(acetylamino)phenyl]-3-amino-N-methylpyrazine-2-carboxamide: $^1$H NMR (400 MHz, d$_6$DMSO): 10.06 (s, 1H), 8.80 (s, 1H), 8.11 (d, 2H), 7.67 (d, 2H), 7.60 (br s, 2H), 2.84 (d, 3H), 2.07 (s, 3H); MS (EI) for C$_{14}$H$_{15}$N$_5$O$_2$: 286.4 (MH$^+$).

3-amino-N-methyl-6-{3-[(methylamino)carbonyl]phenyl}pyrazine-2-carboxamide: $^1$H NMR (400 MHz, d$_6$-DMSO): 8.90 (s, (1H), 8.84 (m, 1H), 8.54 (m, 1H), 8.47 ((s, 1H), 8.34 (d, 1H), 7.82 (d, 1H), 7.72 (br s, 2H), 7.56 (t, 1H), 2.84 (d, 3H), 2.82 (d, 3H); MS (EI) for C$_{14}$H$_{15}$N$_5$O$_2$: 286.4 (MH$^+$).

6-(3-acetylphenyl)-3-amino-N-methylpyrazine-2-carboxamide: $^1$H NMR (400 MHz, d$_6$-DMSO): 8.94 (s, 1H), 8.87 (m, 1H), 8.57 (t, 1H), 8.48 (m, 1H), 7.93 (m, 1H), 7.75 (br s, 2H), 7.62 (t, 1H), 2.86 (d, 3H), 2.70 (s, 3H); MS (EI) for C$_{14}$H$_{14}$N$_4$O$_2$: 271.4 (MH$^+$).

3-amino-N-methyl-6-(3-{[(phenylmethyl)amino]carbonyl}phenyl)pyrazine-2-carboxamide, $^1$H NMR (400 MHz, d$_6$ DMSO), 9.14 (t, 1H), 8.91 (s, 1H), 8.84 (m, 1H), 8.54 (t, 1H), 8.39 (m, 1H), 7.89 (m, 1H), 7.70 (br s, 2H), 7.58 (t, 1H), 7.38-7.32 (m, 4H), 7.24 (m, 1H), 4.54 (d, 2H), 2.86 (d, 3H); MS (EI) for C$_{20}$H$_{19}$N$_5$O$_2$:362.1 (MH$^+$).

3-amino-6-[3-(aminocarbonyl)phenyl]-N-methylpyrazine-2carboxamide: $^1$H NMR (400 MHz, d$_6$-DMSO/CD$_3$OD): 8.90 (m, 1H), 8.57 (m, 1H), 8.32 (m, 1H), 7.91 (m, 1H), 7.57 (m, 1H), 2.90 (m, 3H); MS (EI) for C$_{13}$H$_{13}$N$_5$O$_2$: 272.0 (MH$^+$).

3-amino-6-{3-[(dimethylamino)carbonyl]phenyl}-N-methylpyrazine-2-carboxamide: $^1$H NMR (400 MHz, d$_6$-DMSO): 8.86 (m, 2H), 8.20 (m, 2H), 7.70 (br s, 2H), 7.49 (m, 1H), 7.34 (m, 1H), 3.02 (s, 3H), 2.92 (s, 3H), 2.83 (m, 3H); MS (EI) for C$_{15}$H$_{17}$N$_5$O$_2$: 300.4 (MH$^+$).

3-amino-N-methyl-6-[4-(methylsulfonyl)phenyl]pyrazine-2-carboxamide: $^1$H NMR (400 MHz, d$_6$-DMSO), 8.95 (m, 2H), 8.11 (br s, 2H), 7.96 (m, 2H), 3.26 (s, 3H), 2.85 (m, 3H); MS (EI) for C$_{13}$H$_{14}$N$_4$O$_3$S: 307.4 (MH$^+$).

3-amino-6-(3-aminophenyl)-N-ethylpyrazine-2-carboxamide: $^1$H NMR (400 MHz, d$_6$-DMSO): 8.71 (m, 1H), 8.65 (s, 1H), 7.60 (br s, 2H), 7.27 (m, 2H), 7.11 (m, 1H), 6.59 (m, 1H), 5.10 (s, 2H), 3.34 (m, 2H), 1.16 (m, 3H); MS (EI) for C$_{13}$H$_{15}$N$_5$O: 258.3 (MH$^+$).

3-amino-N-methyl-6-pyrimidin-5-ylpyrazine-2-carboxamide: $^1$H NMR (400 MHz, d$_6$-DMSO): 9.57 (m, 2H), 9.15 (s, 1H), 8.98 (m, 2H), 8.94 (s, 1H), 2.8 (d, 3H), MS (EI) for C$_{10}$H$_{10}$N$_6$O$_2$: 231 (MH$^+$).

3-amino-N-methyl-6-[3-(methylsulfonyl)phenyl]pyrazine-2-carboxamide: $^1$H NMR (400 MHz, d$_6$-DMSO): 8.98 (s, 1H), 8.84 (m, NH), 8.52 (m, 2H), 7.85 (d, 1H), 7.74 (t, 1H), 3.15 (s, 3H); 2.85 (d, 3H); MS (EI) for C$_{13}$H$_{14}$N$_4$O$_3$S: 307 (MH$^+$).

3-amino-N-methyl-6-[4-(tetrahydro-2H-pyran-2-yloxy)phenyl]pyrazine-2-carboxamide: Prepared as above.

3-amino-N-methyl-6-(4-hydroxyoxyphenyl)pyrazine-2-carboxamide: 3-amino-N-methyl-6-[4-(tetrahydro-2H-pyran-2-yloxy)phenyl]pyrazine-2-carboxamide (63 mg) was suspended in methanol followed by addition of aqueous hydrochloric acid (2 mL). The mixture was stirred for 15 min., poured into water (10 mL), and extracted with ethyl acetate (10 mL). The organic layer was washed with saturate aqueous sodium chloride then dried over anhydrous sodium sulfate. Filtration, concentration and column chromatography on silica followed by drying in vacuo afforded 3-amino-N-methyl-6-(4-hydroxyoxyphenyl)pyrazine-2-carboxamide (30 mg, 64% yield): $^1$H NMR (400 MHz; DMSO-D$_6$): 9.62 (s, 1H); 8.78 (m, 1H); 8.82 (m, 1H); 8.7 (s, 1H); 7.98 (d, 2H); 7.5 (br s, 1H); 6.8 (d, 2H); 2.85 (d, 3H); MS (EI) for $C_{12}H_{12}N_4O_2$:245 (MH$^+$).

3-amino-N-methyl-6-(3-thienyl)pyrazine-2-carboxamide: $^1$H NMR (400 MHz; DMSO-D$_6$): 8.85 (m, 1H); 8.76 (s, 1H); 8.25 (m, 1H); 7.92 (d, 1H); 7.64 (m, 1H); 2.82 (d, 3H); MS (EI) for $C_{10}H_{10}N_4OS$: 235 (MH$^+$).

3-amino-6-(1H-indol-5-yl)-N-methylpyrazine-2-carboxamide: $^1$H NMR (400 MHz; DMSO-D$_6$): 11.2 (s, 1H); 8.8 (s, 1H); 8.75 (m, 1H); 8.3 (s, 1H); 7.9 (d, 1H); 7.4 (d, 1H); 7.35 (t, 1H); 6.45 (s, 1H); 2.85 (d, 3H); MS (EI) for $C_{14}H_{13}N_5O$: 268 (MH$^+$).

3-amino-N-methyl-6-(2-thienyl)pyrazine-2-carboxamide: $^1$H NMR (400 MHz; DMSO-D$_6$): 8.7 (s, 1H); 8.48 (m, 1H); 7.75 (d, 1H); 7.62 (br s, 2H); 7.57 (d, 1H); 7.15 (t, 1H); 2.85 (d, 3H); MS (EI) for $C_{10}H_{10}N_4OS$: 235 (MH$^+$).

3-amino-N-methyl-6-pyridin-4-ylpyrazine-2-carboxamide: $^1$H NMR (400 MHz; CD$_3$OD): 8.82 (s, 1H); 8.55 (d, 2H); 8.1 (d, 2H); 2.85 (d, 3H); MS (EI) for $C_{11}H_{11}N_5O$: 230 (MH$^+$).

3-amino-N-methyl-6-naphthalen-2-ylpyrazine-2-carboxamide: $^1$H NMR (400 MHz, d$_6$-DMSO): 8.99 (s, 1H), 8.89 (m, 1H), 8.69 (s, 1H), 8.38 (d, 1H), 7.98 (d, 2H), 7.92 (d, 1H), 7.74 (br s, 2H), 7.52 (m, 2H), 2.88 (d, 3H); MS (EI) for $C_{16}H_{14}N_4O$: 279.2 (MH$^+$).

3-amino-N-methyl-6-quinolin-3-ylpyrazine-2-carboxamide: $^1$H NMR (400 MHz, d$_6$-DMSO): 9.76 (d, 1H), 9.05 (s, 2H), 8.99 (m, 1H), 8.02 (m, 2H), 7.89 (br s, 2H), 7.75 (m, 1H), 7.63 (m, 1H), 2.88 (d, 3H); MS (EI) for $C_{15}H_{13}N_5O$: 280.2 (MH$^+$).

Example 4

3-{5-amino-6-[(methylamino)carbonyl]pyrazin-2-yl}benzoic acid

N-methyl benzamides, where A is —C(=O)— and E is —N(H)CH$_3$ according to formula I, were prepared in analogous fashion as described above starting from 3-Amino-6-bromo-pyrazine-2-carboxylic acid methylamide.

Methyl 3-[5-amino-6-(methylamino)carbonyl)pyrazin-2-yl]benzoate: To a stirred mixture of 3-amino-6-bromo-pyrazine-2-carboxylic acid methylamide (2.29 g, 9.91 mmol, 1.00 equiv.), 3-methoxycarbonylphenylboronic acid (Digital Specialty Chemicals, Inc., 2.68 g, 14.9 mmol, 1.50 equiv.), triethylamine (2.90 g, 28.6 mmol, 2.88 equiv.) in 30 mL of DMF was added [1,1'-bis(diphenylphosphino)-ferrocene]dichloropalladium(II) complex with dichloromethane (1:1), (Aldrich Chemical Company, 405 mg, 0.496 mmol, 0.050 equiv.) The stirred mixture was warmed to 80-90° C. for 24 hr and then concentrated on a rotary evaporator under reduced pressure. The residue was dissolved in 250 mL of EtOAc, washed three times with 10 mL of 1 N aqueous NaOH, and then saturated aqueous NaCl. The organic solution was filtered through celite, and then concentrated on a rotary evaporator under reduced pressure. The crude product was purified by silica gel chromatography, using EtOAc as eluent, to afford the title compound (2.10 g, 74% yield).

3-{5-amino-6-[(methylamino)carbonyl]pyrazin-2-yl}benzoic acid: A flask was charged with methyl 3-[5-amino-6-(methylamino)carbonyl)pyrazin-2-yl]benzoate (2.86 g, 10 mmol) and 30 mL of a solution of 2 N aqueous NaOH. The mixture was refluxed for 15 min. and then allowed to cool to room temperature. The mixture was extracted with ethyl acetate (10 mL). The pH of the aqueous phase was adjusted to pH between 2-3 with 10% aqueous HCl with stirring. The resulting pale yellow solid product was collected by filtration, washed with water, arid dried, to afford 3-{5-amino-6-[(methylamino)carbonyl]pyrazin-2-yl}benzoic acid (2.30 g 84.5% yield): $^1$H NMR (400 MHz; DMSO-d$_6$): 8.83 (s, 1H); 8.80 (s, 1H); 8.51 (s, 1H); 8.41 (d, 1H); 7.93 (d, 1H); 7.93 (d, 1H); 7.65 (br s, 2H); 7.58 (m, 1H); 2.84 (s, 3H); MS (EI) for $C_{13}H_{12}N_4O_3$: 273 (MH$^+$).

3-amino-6-[3-({[(4-chlorophenyl)methyl]amino}carbonyl)phenyl]-N-methylpyrazine-2-carboxamide: A flask was charged with 3-{5-amino-6-[(methylamino)carbonyl]pyrazin-2-yl}benzoic acid (48.9 mg, 0.18 mmol), 1-hydroxybenzotriazole (HOBT, 39.7 mg, 0.294 mmol), 2.00 mL of tetrahydrofuran, 4-chlorobenzylamine (28.2 mg, 0.2 mmol) and 1-ethyl-(3-dimethylaminopropyl)carbodiimide hydrochloride (66.2 mg, 0.353 mmol). The reaction was stirred at room temperature for 2 h. The reaction was diluted with ethyl acetate, washed sequentially saturated aqueous NaCl, saturated aqueous sodium carbonate, 1.0 M aqueous hydrochloric acid, and saturated aqueous sodium bicarbonate The organic layer was dried over sodium sulfate, filtered, and concentrated on a rotary evaporator under reduced pressure. The crude product was purified by chromatography on silica gel using EtOAc as the eluent. After concentration, the product was triturated in 5% ethyl acetate in hexanes. The solid product was filtered, and after drying afforded 3-amino-6-[3-({[(4-chlorophenyl)methyl]amino}carbonyl)phenyl]-N-methylpyrazine-2-carboxamide (39.8 mg, 50% yield). $^1$H NMR (400 MHz; DMSO-d$_6$): 9.15 (m, 1H); 8.87 (s, 1H); 8.80 (m, 1H); 8.50 (s, 1H); 8.35 (d, 1H); 7.85 (d, 1H); 7.53 (d, 1H); 7.37 (m, 2H); 4.51 (d, 2H); 2.83 (s, 3H): MS (EI) for $C_{20}H_{18}N_5O_2Cl$: 396 (MH$^+$).

Using the same or analogous synthetic techniques and/or substituting with alternative reagents, the following compounds of the invention were prepared:

3-amino-6-[(2-oxo-2-phenyl-ethylcarbamoyl)-phenyl]-pyrazine-2-carboxylic acid methylamide: $^1$H NMR (400 MHz; DMSO-d$_6$): 9.13 (br s, 1H); 8.98 (br s, 1H); 8.90 (s, 1H); 8.65 (s, 1H); 8.38 (d, 1H); 8.07 (m, 2H); 7.84 (d, 1H); 7.64 (m, 1H); 6.60 (m, 3H);4.81 (d, 2H); 2.83 (s, 3H): MS (EI) for $C_{21}H_{19}N_5O_3$: 390 (MH$^+$).

3-amino-N-methyl-6-{3-[(4-methylpiperazin-1-yl)carbonyl]phenyl}pyrazine-2-carboxamide: MS (EI) for $C_{18}H_{22}N_6O_2$: 355 (MH$^+$).

3-amino-N-methyl-6-(3-{[(2-phenylethyl)amino]carbonyl}phenyl)pyrazine-2-carboxamide: MS (EI) for $C_{21}H_{21}N_5O_2$: 376 (MH$^+$).

3-amino-N-methyl-6-{3-[({[4-(methyloxy)phenyl]methyl}amino)carbonyl]phenyl}pyrazine-2-carboxamide: MS (EI) for $C_{21}H_{21}N_5O_3$: 392 (MH$^+$).

3-amino-6-(3-{[(1R)-2,3-dihydro-1H-inden-1-ylamino]carbonyl}phenyl)-N-methylpyrazine-2-carboxamide; MS (EI) for $C_{22}H_{21}N_5O_2$: 388 (MH$^+$).

3-amino-6-(3-{[(1S)-2,3-dihydro-1H-inden-1-ylamino]carbonyl}phenyl)-N-methylpyrazine-2-carboxamide: MS (EI) for $C_{22}H_{21}N_5O_2$: 388 (MH$^+$).

3-amino-6-[3-({[(4-chlorophenyl)methyl]amino}carbonyl)phenyl]-N-methylpyrazine-2-carboxamide: MS (EI) for $C_{20}H18N_5O_2Cl$: 396 (MH$^+$).

3-amino-N-methyl-6-(3-{[methyl(phenylmethyl)amino]carbonyl}phenyl)pyrazine-2-carboxamide: MS (EI) for $C_{21}H_{21}N_5O_2$: 376 (MH$^+$).

3-amino-6-[3-({[(2,4-dichlorophenyl)methyl]amino}carbonyl)phenyl]-N-methylpyrazine-2-carboxamide: MS (EI) for $C_{20}H17N_5O_2Cl_2$: 431 (MH$^+$).

3-amino-N-methyl-6-[3-({[(4-methylphenyl)methyl]amino)carbonyl)phenyl]pyrazine-2-carboxamide; MS (EI) for $C_{21}H_{21}N_5O_2$: 376 (MH$^+$).

3-amino-N-methyl-6-{3-[({[4-(trifluoromethyl)phenyl]methyl}amino)carbonyl]phenyl]pyrazine-2-carboxamide: MS (EI) for $C_{21}H_{18}N_5O_2F_3$: 430 (MH$^+$).

3-amino-6-[3-({[(4-fluorophenyl)methyl]amino}carbonyl)phenyl]-N-methylpyrazine-2-carboxamide: MS (EI) for $C_{20}H_{18}N_5O_2F$: 380 (MH$^+$).

3-amino-6-{3-[(2,3-dihydro-1H-inden-2-ylamino)carbonyl]phenyl}-N-methylpyrazine-2-carboxamide: $^1$H NMR (400 MHz; DMSO-d$_6$): 8.84 (s, 1H); 8.82 (m, 1H); 8.73(d, 1H); 8.47 (m, 1H); 8.31 (d, 1H); 7.82 (d, 1H); 7.52 (t, 1H); 7.12-7.22 (m, 3H); 4.76 (m, 1H); 3.20 (m, 2H); 3.0 (m, 2H) 2.82 (d, 3H); MS (EI) for $C_{22}H_{21}N_5O_2$: 388 (MH$^+$).

3-amino-N-methyl-6-{3-[{[3-methyloxy)phenyl]methyl}amino)carbonyl]phenyl}pyrazine-2-carboxamide: MS (EI) for $C_{21}H_{21}N_5O_3$: 392 (MH$^+$).

3-amino-N-methyl-6-{3-[({(1R)-1-[4-(methyloxy)phenyl]ethyl}amino)carbonyl]phenyl}pyrazine-2-carboxamide: $^1$H NMR (400 MHz; DMSO-d$_6$): 8.85 (s, 1H); 8.82 (m, 2H); 8.49(s, 1H); 8.38 (d, 1H); 7.80 (d, 1H); 7.65 (br s, 2H); 7.57 (t, 1H); 7.30 (d, 2H); 6.87 (d, 2H); 5.18 (m, 1H); 3.70 (m, 3H); 2.86 (s, 3H) 1.50 (d, 3H); MS (EI) for $C_{22}H_{23}N_5O_3$: 406 (MH$^+$).

3-amino-N-methyl-6-{3-[({[2-(trifluoromethyl)phenyl]methyl}amino)carbonyl]phenyl}pyrazine-2-carboxamide: MS (EI) for $C_{21}H_{18}N_5O_2F_3$: 430 (MH$^+$).

3-amino-6-[3-({[(3-fluorophenyl)methyl]amino}carbonyl)phenyl]-N-methylpyrazine-2-carboxamide: MS (EI) for $C_{20}H_{18}N_5O_2F$: 380 (MH$^+$)

3-amino-6-[3-({[1-(4-fluorophenyl)ethyl]amino}carbonyl)phenyl]-N-methylpyrazine-2-carboxamide: MS (EI) for $C_{21}H_{20}N_5O_2F$: 394 (MH$^+$)

3-amino-6-{3-[({[2,3-bis(methyloxy)phenyl]methyl}amino)carbonyl]phenyl}-N-methylpyrazine-2-carboxamide: MS (EI) for $C_{24}H_{25}N_3O_4$: 420 (MH$^+$)

3-amino-6-(3-{[bis(phenylmethyl)amino]carbonyl}phenyl)-N-methylpyrazine-2-carboxamide: MS (EI) for $C_{27}H_{25}N_5O_2$: 452 (MH$^+$)

3-amino-6-{3-[({[2,4-bis(methyloxy)phenyl]methyl}amino)carbonyl]phenyl}-N-methylpyrazine-2-carboxamide: MS (EI) for $C_{22}H_{23}N_5O_4$: 422 (MH$^+$)

3-amino-6-(3-{[ethyl(pyridin-4-ylmethyl)amino]carbonyl}phenyl)-N-methylpyrazine-2-carboxamide: MS (EI) for $C_{21}H_{22}N_6O_2$: 391 (MH$^+$)

3-amino-N-methyl-6-(3-{[4-(phenylmethyl)piperazin-1-yl]carbonyl}phenyl)pyrazine-2-carboxamide: MS (EI) for $C_{24}H_{26}N_6O_2$: 431 (MH$^+$)

3-amino-6-[3-({[1-(phenylmethyl)piperidin-4-yl]amino}carbonyl)phenyl]pyrazine-2-carboxamide: $^1$H NMR (400 MHz; DMSO-d$_6$): 8.84 (s, 1H); 8.82 (m, 1H); 8.42(s, 1H); 8.36 (br s, 1H); 7.80 (m, 1H); 7.65 (br s, 2H); 7.45 (t, 1H); 7.30 (m, 3H); 3.23 (m, 1H); 3.47 (s, 2H); 2.85 (s, 3H) 1.84-2.04 (m, 8H); MS (EI) for $C_{25}H_{28}N_6O_2$: 445 (MH$^+$)

3-amino-N-methyl-6-[3-({[(5-methylpyrazin-2-yl)methyl]amino}carbonyl)phenyl]pyrazine-2-carboxamide: MS (EI) for $C_{19}H_{19}N_7O_2$: 378 (MH$^+$)

3-amino-N-methyl-6-(3-{[(pyridin-2-ylmethyl)amino]carbonyl}phenyl)pyrazine-2-carboxamide: MS (EI) for $C_{19}H_{18}N_6O_2$: 363 (MH$^+$)

3-amino-N-methyl-6-(3-{[(pyridin-3-ylmethyl)amino]carbonyl}phenyl)pyrazine-2-carboxamide: MS (EI) for $C_{19}H_{18}N_6O_2$: 363 (MH$^+$)

3-amino-N-methyl-6-(3-{[(pyridin-4-ylmethyl)amino]carbonyl}phenyl)pyrazine-2-carboxamide: $^1$H NMR (400 MHz; DMSO-d$_6$): 9.21 (s, 1H); 8.89 (s, 1H); 8.26(s, 1H); 8.50 (m, 3H); 8.39 (d, 1H); 7.86 (d, 1H); 7.57 (t, 1H); 7.33 (s, 1H); 4.55 (s, 2H); 2.85 (s, 3H); MS (EI) for $C_{19}H_{18}N_6O_2$: 363 (MH$^+$)

3-amino-6-[3-({[(3-chlorophenyl)methyl]amino}carbonyl)phenyl]-N-methylpyrazine-2-carboxamide: MS (EI) for $C_{20}H_{18}N_5O_2Cl$: 396 (MH$^+$)

3-amino-6-(3-{[(cyclohexylmethyl)amino]carbonyl}phenyl)-N-methylpyrazine-2-carboxamide: MS (EI) for $C_{20}H_{25}N_5O_2$: 368 (MH$^+$)

3-amino-N-methyl-6-(3-{[(2-phenylpropyl)amino]carbonyl}phenyl)pyrazine-2-carboxamide: MS (EI) for $C_{22}H_{23}N_5O_2$: 390 (MH$^+$)

3-amino-6-[3-({[(2-chlorophenyl)methyl]amino}carbonyl)phenyl]-N-methylpyrazine-2-carboxamide: MS (EI) for $C_{20}H_{18}N_5O_2Cl$: 396 (H$^+$)

3-amino-6-[3-({[2-(2-chlorophenyl)ethyl]amino}carbonyl)phenyl]-N-methylpyrazine-2-carboxamide: MS (EI) for $C_{21}H_{20}N_5O_2Cl$: 410 (MH$^+$)

3-amino-N-methyl-6-{3-[({2-[2-(methyloxy)phenyl]ethyl}amino)carbonyl]phenyl}pyrazine-2-carboxamide: MS (EI) for $C_{22}H_{23}N_5O_3$: 406 (MH$^+$)

3-amino-6-[3-({[2-(4-fluorophenyl)ethyl]amino}carbonyl)phenyl]-N-methylpyrazine-2-carboxamide: MS (EI) for $C_{21}H_{20}N_5O_2F$: 394 (MH$^+$)

3-amino-N-methyl-6-[3-({[2-(2-thienyl)ethyl]amino}carbonyl)phenyl]pyrazine-2-carboxamide: MS (EI) for $C_{19}H_{19}N_5O_2S$: 382 (MH$^+$)

3-amino-6-{3-[(cyclohexylamino)carbonyl]phenyl}-3-N-methylpyrazine-2-carboxamide: MS (EI) for $C_{19}H_{23}N_5O_2$: 354 (MH$^+$)

1,1-dimethylethyl 4-({[(3-{5-amino-6-[(methylamino)carbonyl]pyrazin-2-yl}phenyl)carbonyl]amino}methyl)piperidine-1-carboxylate: MS (EI) for $C_{24}H_{32}N_6O_4$: 469 (MH$^+$)

3-amino-N-methyl-6-(3-{[(piperidin-4-ylmethyl)amino]carbonyl}phenyl)pyrazine-2-carboxamide: MS (EI) for $C_{19}H_{24}N_6O_2$: 369 (MH$^+$)

3-amino-N-methyl-6-[3-({[(3S)-1-(phenylmethyl)pyrrolidin-3-yl]amino}carbonyl)phenyl]pyrazine-2-carboxamide: $^1$H NMR (400 MHz; DMSO-d$_6$): 8.62 (s, 1H); 8.35 (s, 1H); 8.03 (br s, 1H); 7.98 (d, 1H); 7.52 (t, 1H); 7.3 (m, 5H); (m, 6.85 (d, 1H); 4.74 (m, 1H); 3.65 (d, 2H); 2.8-3.1 (m, 4H); 2.8 (m, 1H); 2.65 (m, 1H); 2.4 (m, 1H); 2.3 (m, 1H); 1.8 (m, 1H); MS (EI) for $C_{24}H_{26}N_6O_2$: 431 (MH$^+$)

3-amino-N-methyl-6-[3-({[(3R)-1-(phenylmethyl)pyrrolidin-3-yl]amino}carbonyl)phenyl]pyrazine-2-carboxamide: MS (EI) for $C_{24}H_{26}N_6O_2$: 431 (MH$^+$)

3-amino-N-methyl-6-[3-({[2-(phenyloxy)ethyl]amino}carbonyl)phenyl]pyrazine-2-carboxamide: $^1$H NMR (400 MHz; CDCl$_3$): 8.62 (s, 1H); 8.35 (m, 1H); 7.98(m, 2H); 7.72 (d, 1H); 7.54 (t, 1H); 7.3 (m, 1H); 6.92 (m, 2H); 6.75 (m, 1H); 4.2 (m, 2H); 3.97 (m, 2H); 3.0 (s, 3H); MS (EI) for $C_{21}H_{21}N_5O_3$: 392 (MH$^+$)

3-amino-N-methyl-6-{3-[({2-[4-(phenylmethyl)piperazin-1-yl]ethyl}amino)carbonyl]phenyl}pyrazine-2-carboxamide: MS (EI) for $C_{26}H_{31}N_7O_2$: 473(MH$^+$)

3-amino-N-methyl-6-{3-[({[1-(phenylmethyl)piperidin-4-yl]methyl}amino)carbonyl]phenyl}pyrazine-2-carboxamide: $^1$H NMR (400 MHz; CDCl$_3$): 8.62 (s, 1H); 8.35 (m, 1H);

7.98 (m, 2H); 7.68 (d, 1H); 7.54 (t, 1H); 7.3 (m, 5H); 6.25 (m, 1H); 3.5 (s, 2H); 3.4 (t, 2H); 3.05 (d, 3H); 2.92 (m, 2H); 1.98 (m, 2H); 1.78 (m, 2H); 1.38(m, 2H); MS (EI) for $C_{26}H_{30}N_6O_2$: 459 (MH$^+$)

3-amino-6-(3-{[(furan-3-ylmethyl)amino]carbonyl}phenyl)-N-methylpyrazine-2-carboxamide: $^1$H NMR (400 MHz; CDCl$_3$): 8.95 (m, 1H); 8.90 (s, 1H); 8.84 (m, 1H); 8.48 (s, 1H); 8.35 (d, 1H); 7.83 (d, 1H); 7.6 (m, 3H); 6.5 (s, 1H); 4.38 (d, 2H); 3.05 (d, 3H); 2.85 (d, 3H); MS (EI) for $C_{18}H_{17}N_5O_3$: 352 (MH$^+$)

3-amino-6-(3-{[(2,3-dihydro-1,4-benzodioxin-2-ylmethyl)amino]carbonyl}phenyl)-N-methylpyrazine-2-carboxamide: MS (EI) for $C_{22}H_{21}N_5O_4$: 420 (MH$^+$)

3-amino-6-(3-{[(furan-2-ylmethyl)amino]carbonyl}phenyl)-N-methylpyrazine-2-carboxamide: $^1$H NMR (400 MHz; CDCl$_3$): 9.05 (t, 1H); 8.88 (s, 1H); 8.82 (m, 1H); 8.48 (s, 1H); 8.38 (d, 1H); 7.85 (d, 1H); 7.55 (m, 2H); 6.39 (m, 1H); 6.35 (d, 1H); 3.5 (d, 2H); 2.85 (d, 3H); MS (EI) for $C_{18}H_{17}N_5O_3$: 352 (MH$^+$)

3-amino-N-methyl-6-{3-[({[4-(phenylmethyl)morpholin-2-yl]methyl}amino)carbonyl]phenyl}pyrazine-2-carboxamide: MS (EI) for $C_{25}H_{28}N_6O_3$: 461(MH$^+$)

3-amino-6-(3-{[(2,3-dihydro-1,4-benzodioxin-6-ylmethyl)amino]carbonyl}phenyl)-N-methylpyrazine-2-carboxamide: MS (EI) for $C_{22}H_{21}N_5O_2$: 420 (MH$^+$)

3-amino-6-(3-{[(2,3-dihydro-1-benzofuran-5-ylmethyl)amino]carbonyl}phenyl)-N-methylpyrazine-2-carboxamide: $^1$H NMR (400 MHz; DMSO-D$_6$): 9.07 (t, 1H); 8.88 (s, 1H); 8.85 (m, 1H); 8.52 (s, 1H); 8.38 (d, 1H); 7.88 (d, 1H); 7.58 (t, 1H); 7.58 (t, 1H); 8.88 (s, 7.08 (d, 1H); 6.7 (d, 1H); 4.5 (m, 2H); 3.2 (m, 2H); 2.85 (d, 3H); MS (EI) for $C_{22}H_{21}N_5O_3$: 404 (MH$^+$)

3-amino-6-[3-({[(6-fluoro-4H-1,3-benzodioxin-8-yl)methyl]amino}carbonyl)phenyl]-N-methylpyrazine: MS (EI) for $C_{22}H_{20}N_5O_4F$: 438 (MH$^+$)

3-amino-6-{3-[({[3,5-bis(methyloxy)phenyl]methyl}amino)carbonyl]phenyl}-N-methylpyrazine-2-carboxamide: $^1$H NMR (400 MHz; DMSO-D$_6$): 9.1 (t, 1H); 8.91 (s, 1H); 8.82(m, 1H); 8.52 (m, 1H); 8.39 (d, 1H); 7.88 (d, 1H); 7.58(t, 1H); 6.52 (m, 2H); 6.38 (m, 1H); 4.48 (d, 2H); 3.76 (s, 6H); 2.85 (d, 3H); MS (EI) for $C_{22}H_{23}N_5O_4$: 422 (MH$^+$)

3-amino-N-methyl-6-{3-[({[4-(methylsulfonyl)phenyl]methyl}amino)carbonyl]phenyl}pyrazine-2-carboxamide: $^1$H NMR (400 MHz; DMSO-D$_6$): 9.39 (t, 1H); 8.31 (s, 1H); 8.72 (m, 1H); 8.52 (s, 1H); 8.39 (d, 1H); 7.88-7.6 (m, 8H); 4.6 (d, 2H); 3.2 (s, 3H); 2.85 (d, 3H); MS (EI) for $C_{21}H_{21}N_5O_4S$: 440 (MH$^+$)

3-amino-6-[3-({[(5-bromo-2-fluorophenyl)methyl]amino}carbonyl)phenyl]-N-methylpyrazine-2-carboxamide: $^1$H NMR (400 MHz; DMSO-D$_6$): 9.19 (t, 1H); 8.84 (s, 1H); 8.82 (m, 1H); 8.52 (m, 1H); 8.38 (d, 1H); 7.86 (d, 1H); 7.54 (m, 2H); 7.5 (m, 3H); 7.2 (t, 1H); 4.54 (d, 2H); 2.84 (d, 3H); MS (EI) for $C_{20}H_{17}N_5O_2FBr$: 460 (MH$^+$)

3-amino-6-[3-({[(3-bromo4-fluorophenyl)methyl]amino}carbonyl)phenyl]-N-methylpyrazine-2-carboxamide: $^1$H NMR (400 MHz; DMSO-D$_6$): 9.29 (t, 1H); 8.91 (s, 1H); 8.84 (m, 1H); 8.52 (s, 1H, 8.39 (d, 1H); 7.88 (d, 1H); 7.58 (t, 1H); 7.4 (m, 1H); 7.35 (t, 1H); 4.48 (d, 2H); 2.85 (d, 3H); MS (EI) for $C_{20}H_{17}N_5O_2FBr$: 458 (MH$^+$)

3-amino-N-methyl-6-{3-[({[2,4,6-tris(methyloxy)phenyl]methyl}amino)carbonyl]phenyl}pyrazine-2-carboxamide: $^1$H NMR (400 MHz; DMSO-D$_6$): 8.88 (s, 1H); 8.84 (m, 1H); 8.42(s, 1H); 8.3 (d, 1H); 8.18 (m, 1H); 7.88 (d, 1H); 7.5 (t, 1H); 6.2 (s, 2H); 4.4 (d, 2H); 3.8 (s, 9H); 2.85(d, 3H); MS (EI) for $C_{23}H_{25}N_5O_5$: 452 (MH$^+$)

3-amino-N-methyl-6-[3-({[(3-methylphenyl)methyl]amino}carbonyl)phenyl]pyrazine-2-carboxamide: $^1$H NMR (400 MHz; DMSO-D$_6$): 9.1 (t, 1H); 8.91 (s, 1H); 8.84 (m, 1H); 8.54 (s, 1H); 8.39 (d, 1H); 7.88 (d, 1H); 7.59 (t, 1H); 7.26-7.05 (m, 4H); 4.5 (d, 2H); 2.85 (d, 3H); 2.35 (s, 3H); MS (EI) for $C_{21}H_{21}N_5O_2$: 376(MH$^+$)

3-amino-6-[3-({[(4-bromo-2-fluorophenyl)methyl]amino}carbonyl)phenyl]-N-methylpyrazine-2-carboxamide: $^1$H NMR (400 MHz; DMSO-D$_6$): 9.18 (t, 1H); 8.92 (s, 1H); 8.84 (m, 1H); 8.56 (s, 1H); 8.39 (d, 1H); 7.88 (d, 1H); 7.59 (m, 2H); 7.4 (m, 2H); 4.5 (d, 2H); 2.85 (t, 3H); MS (EI) for $C_{20}H_{17}N_5O_2FBr$: 460 (MH$^+$)

3-amino-6-[3-({[(2,5-dimethylphenyl)methyl]amino}carbonyl)phenyl]-N-methylpyrazine-2-carboxamide: $^1$H NMR (400 MHz; DMSO-D$_6$): 8.98 (t, 1H); 8.91 (s, 1H); 8.84 (m, 1H); 8.54 (s, 1H); 8.39 (d, 1H); 7.88 (d, 1H); 7.59 (t, 1H); 7.5 (m, 2H); 7.18 (d, 1H); 4.5 (d, 2H); 2.85 (d, 3H); 2.3 (s, 3H); 2.2 (s, 3H); MS (EI) for $C_{22}H_{23}N_5O_2$: 390 (MH$^+$)

3-amino-6-{3-[({[3,5-bis(trifluoromethyl)phenyl]methyl}amino)carbonyl]phenyl}-N-methylpyrazine-2-carboxamide: $^1$H NMR (400 MHz; DMSO-D$_6$): 9.3 (t, 1H); 8.91 (s, 1H); 8.84 (m, 1H); 8.54 (s, 1H); 8.39 (d, 1H); 8.05 (m, 3H); 7.85 (d, 1H); 7.6 (t, 2H); 4.7 (d, 2H); 2.85 (d, 3H); MS (EI) for $C_{22}H_{17}N_5O_2F6$: 498 (MH$^+$)

3-amino-6-(3-{[(2,2-diphenylethyl)amino]carbonyl}phenyl)-N-methylpyrazine-2-carboxamide: $^1$H NMR (400 MHz; DMSO-D$_6$): 8.2 (s, 1H); 8.15 (t, 1H); 8.64 (m, 1H); 8.34 (m, 2H); 7.7 (d, 1H); 7.5 (t, 1H); 7.39-7.21 (m, 10H); 7.2 (m, 2H); 4.46 (t, 1H); 3.95 (m, 2H); 2.85 (d, 3H); MS (EI) for $C_{27}H_{25}N_5O_2$: 452 (MH$^+$)

3-amino-6-[3-({[(4-ethylphenyl)methyl]amino}carbonyl)phenyl]-N-methylpyrazine-2-carboxamide: (400 MHz; DMSO-D$_6$): 9.8 (t, 1H); 8.88 (s, 1H); 8.82 (m, 1H); 8.5 (s, 1H); 8.36 (d, 1H); 7.86 (d, 1H); 7.56 (t, 2H); 7.25-7.14 (m, 4H); 4.4 (d, 2H); 2.85 (d, 3H); 2.6 (m, 2H); MS (EI) for $C_{222}H_{23}N_5O_2$: 390 (MH$^+$)

3-amino-N-methyl-6-[3-({[(4-propylphenyl)methyl]amino}carbonyl)phenyl]pyrazine-2-carboxamide: (400 MHz; DMSO-D$_6$): 9.08 (t, 1H); 8.88 (s, 1H); 8.81 (m, 1H); 8.5 (s, 1H); 8.38 (d, 1H); 7.86 (d, 1H); 7.55 (t, 1H); 7.18 (m, 4H); 4.5 (d, 2H); 2.85 (d, 3H); 2.55 (m, 2H); 1.5 (m, 2H); 1.08 (t, 3H); MS (EI) for $C_{23}H_{25}N_5O_2$: 404 (MH$^+$).

3-amino-6-(3-{[(1,1-dimethylethyl)amino]carbonyl}phenyl)-N-methylpyrazine-2-carboxamide: $^1$H NMR (400 MHz, d$_6$-DMSO): 8.92 (s, 1H), 8.88 (m, 1H), 8.38 (m, 2H), (m, 2H), 7.90 (m, 1H), 7.81 (m, 1H), 7.71 (br s, 2H), 7.53 (m, 1H), 2.87 (d, 3H), 1.43 (s, 9H); MS (EI) for $C_{17}H_{21}N_5O_2$: 328.5 (MH$^+$).

3-amino-6-[3-({[(1R,2S)-2-hydroxy-2,3-dihydro-1H-inden-1-yl]amino}carbonyl)phenyl]-N-methylpyrazine-2-carboxamide: $^1$H NMR (400 MHz, d$_6$-DMSO): 8.97 (m, 1H), 8.87 (m, 1H), 8.62 (m, 2H), 8.41 (m, 1H), 7.96 (m, 1H), 7.74 (br s, 2H), 7.59 (m, 1H), 7.26 (m, 4H), 5.52 (m, 1H), 5.14 (m, 1H), 4.55 (m, 1H), 3.14 (m, 1H), 2.93 (m, 1H), 2.85 (m, 3H); MS (EI) for $C_{22}H_{21}N_5O_3$: 404.5 (MH$^+$).

3-amino-6-[3-({[(1S,2R)-2-hydroxy-2,3-dihydro-1H-inden-1-yl]amino}carbonyl)phenyl]-N-methylpyrazine-2-carboxamide: $^1$H NMR (400 MHz, d$_6$-DMSO): 8.97 (m, 1H), 8.87 (m, 1H), 8.62 (m, 2H), 8.41 (m, 1H), 7.96 (m, 1H), 7.74 (br s, 2H), 7.59 (m, 1H), 7.26 (m, 4H), 5.52 (m, 1H), 5.14 (m, 1H), 4.55 (m, 3.14 (m, 1H), 2.93 (m, 1H), 2.85 (m, 3H); MS (EI) for $C_{22}H_{21}N_5O_3$: 404.5 (MH$^+$).

3-amino-N-methyl-6-{3-[(phenylamino)carbonyl]phenyl}pyrazine-2-carboxamide: $^1$H NMR (400 MHz, d$_6$-DMSO): 10.34 (m, 1H), 8.97 (m, 1H), 8.90 (m, 1H), 8.61 (m, 1H), 8.42 (m, 1H), 7.93 (m, 1H), 7.81 (m, 2H), 7.70 (br s, 2H), 7.63 (m, 1H), 7.38 (m, 2H), 7.13 (m, 1H), 2.87 (m, 3H); MS (EI) for $C_{19}H_{17}N_5O_2$: 348.4 (MH$^+$).

3-amino-6-[3-(1,3-dihydro-2H-isoindol-2-ylcarbonyl) phenyl]-N-methylpyrazine-2-carboxamide: ¹H NMR (400 MHz, d₆-DMSO): 8.92 (s, 1H), 8.86 (m, 1H), 8.33 (m, 2H), 7.67 (br s, 2H), 7.56 (m, 2H), 7.43 (m, 1H), 7.29 (m, 3H), 4.91 (s, 1H), 4.79 (s, 2H), 2.84 (m, 3H); MS (EI) for C₂₁H₁₉N₅O₂: 374.5 (MH⁺).

3-amino-N-methyl-6-[3-({[(1R)-1-phenylethyl] amino}carbonyl)phenyl]pyrazine-2-carboxamide: ¹H NMR (400 MHz, d₆-DMSO): 8.91 (s, 1H), 8.86 (m, 2H), 8.48 (s, 1H), 8.36 (m, 1H), 7.84 (m, 1H), 7.71 (br s, 2H), 7.54 (m, 1H), 7.40 (m, 2H), 7.32 (m, 2H), 7.21 (s, 1H), 5.20 (m, 1H), 2.85 (s, 3H), 1.53 (d, 3H); MS (EI) for C₂₁H₂₁N₅O₂: 376.5 (MH⁺).

3-amino-N-methyl-6-[3-({[(1S)-1-phenylethyl] amino}carbonyl)phenyl]pyrazine-2-carboxamide: ¹H NMR (400 MHz, d₆-DMSO): 8.91 (s, 1H), 8.86 (m, 2H), 8.48 (s, 1H), 7.21 (s, 1H), 5.20 (m, 1H), 2.85 (s, 3H), 1.53 (d, 3H); MS (EI) for C₂₁H₂₁N₅O₂: 376.5 (MH⁺)

3-amino-N-methyl-6-[3-({[(1R)-1-phenylpropyl] amino}carbonyl)phenyl]pyrazine-2-carboxamide: ¹H NMR (400 MHz, d₆-DMSO): 8.91 (s, 1H), 8.83 (m, 2H), 8.47 (s, 1H), 8.36 (m, 1H), 7.83 (m, 1H), 7.71 (br s, 2H), 7.54 (t, 1H), 7.39 (m, 2H), 7.32 (m, 2H), 7.21 (m, 1H), 4.94 (m, 1H), 2.85 (s, 3H), 1.86 (m, 2H), 0.94 (m, 3H); MS (EI) for C₂₂H₂₃N₅O₂: 390.5 (MH⁺).

3-amino-N-methyl-6-[3-({[(1S)-1-phenylpropyl] amino}carbonyl)phenyl]pyrazine-2-carboxamide: ¹H NMR (400 MHz, d₆-DMSO): 8.91 (s, 1H), 8.83 (m, 2H), 8.47 (s, 1H), 8.36 (m, 1H), 7.83 (m, 1H), 7.71 (br s, 2H), 7.54 (t, 1H), 7.39 (m, 2H), 7.32 (m, 2H), 7.21 (m, 1H), 4.94 (m, 1H), 2.85 (s, 3H), 1.86 (m, 2H), 0.94 (m, 3H); MS (EI) for 3-amino-N-methyl-6-[3-({[(1R,2S)-2-phenylcyclopropyl]amino}carbonyl)phenyl]pyrazine-2-carboxamide: ¹H NMR (400 MH, d₆-DMSO): 8.89 (s, 1H), 8.83 (m, 1H), 8.76 (d, 1H), 8.44 (s, 1H), 8.34 (d, 1H), 7.81 (d, 1H), 7.72 (br s, 2H), 7.54 (t, 1H), 7.27 (m, 2H), 7.17 (m, 3H), 3.06 (m, 1H), 2.85 (d, 3H), 2.12 (m, 1H), 1.39 (m, 1H), 1.26 (m, 1H); MS (EI) for C₂₂H₂₁N₅O₂: 388.5 (MH⁺).

3-amino-N-methyl-6-(3-{[(1R)-1,2,3,4-tetrahydronaphthalen-1-ylamino]carbonyl}phenyl)pyrazine-2-carboxamide: ¹H NMR (400 MHz, d₆-DMSO): 8.88 (s, 1H), 8.84 (m, 2H), 8.50 (s, 1H), 8.38 (d, 1H), 7.90 (d, 1H), 7.71 (brs, 2H), 7.56 (t, 1H), 7.22 (m, 1H), 7.16 (m, 3H), 5.29 (m, 1H), 2.84 (d, 3H), 2.79 (m, 2H), 2.02 (m, 2H), 1.84 (m, 2H); MS (EI) for C₂₃H₂₃N₅O₂: 402.5 (MH⁺)

3-amino-N-methyl-6-(3-{[(1S)-1,2,3,4-tetrahydronaphthalen-1-ylamino]carbonyl}phenyl)pyrazine-2-carboxamide: ¹H NMR (400 MHz, 6-DMSO): 8.88 (s, 1H), 8.84 (m, 2H), 8.50 (s, 1H), 8.38 (d, 1H), 7.90 (d, 1H), 7.71 (brs, 2H), 7.56 (t, 1H), 7.22 (m, 1H), 7.16 (m, 3H), 5.29 (m, 1H), 2.84 (d, 3H), 2.79 (m, 2H), 2.02 (m, 2H), 1.84 (m, 2H); MS (EI) for C₂₃H₂₃N₅O₂: 402.5 (MH⁺).

3-amino-N-methyl-6-{3-[({[3,4,5-tris(methyloxy)phenyl]methyl}amino)carbonyl]phenyl}pyrazine-2-carboxamide: ¹H NMR (400 MHz, d₆-DMSO): 9.05 (s, 1H), 8.89 (s, 1H), 8.82 (m, 1H), 8.50 (s, 1H), 8.36 (d, 1H), 7.87 (d, 1H), 7.71 (br s, 2H), 7.56 (m, 1H), 6.67 (s, 2H), 4.45 (s, 2H), 3.76 (s, 6H), 3.62 (s, 3H), 2.84 (s, 3H); MS (EI) for C₂₃H₂₅N₅O₅: 452.5 (MH⁺).

3-amino-N-methyl-6-{3-[({(1R,2R)-2-[(phenylmethyl) oxy]cyclopentyl}amino)carbonyl]phenyl}pyrazine-2-carboxamide: ¹H NMR (400 MHz, d₆-DMSO): 8.89 (s, 1H), 8.82 (m, 1H), 8.42 (m, 2H), 8.34 (d, 1H), 7.81 (m, 1H), 7.75 (br s, 2H), 7.55 (m, 1H), 7.30 (m, 4H), 7.23 (m, 1H), 4.57 (dd, 2H), 4.32 (m, 1H), 3.94 (m, 1H), 2.83 (d, 3H), 2.07 (m, 1H), 1.95 (m, 1H), 1.70 (m, 4H); MS (EI) for C₂₅H₂₇N₅O₃: 446.6 (MH⁺).

3-amino-N-methyl-6-{3-[({(1S,2S)-2-[(phenylmethyl) oxy]cyclopentyl}amino)carbonyl]phenyl}pyrazine-2-carboxamide: ¹H NMR (400 MHz, d₆-DMSO): 8.89 (s, 1H, 8.82 (m, 1H), 8.42 (m, 2H), 8.34 (d, 1H), 7.81 (m, 1H), 7.75 (br s, 2H), 7.55 (m, 1H), 7.30 (m, 4H), 7.23 (m, 1H), 4.57 (dd, 2H), 4.32 (m, 1H), 3.94 (m, 1H), 2.83 (d, 3H), 2.07 (m, 1H), 1.95 (m, 1H), 1.70 (m, 4H); MS (EI) for C₂₅H₂₇N₅O₃: 446.5 (MH⁺).

3-amino-6-(3-{[(biphenyl-2-ylmethyl)amino] carbonyl}phenyl)-N-methylpyrazine-2-carboxamide: ¹H NMR (400 MHz, d₆-DMSO): 9.02 (t, 1H), 8.90 (s, 1H), 8.84 (m, 1H), 8.49 (s, 1H), 8.38 (d, 1H), 7.86 (d, 1H), 7.74 (br s, 2H), 7.56 (t, 1H), 7.47 (m, 5H), 7.38 (m, 3H), 7.26 (m, 1H), 4.49 (d, 2H), 2.85 (d, 3H); MS (EI) for C₂₆H₂₃N₅O₂: 438.5 (MH⁺).

3-amino-6-(3-{[(biphenyl-4-ylmethyl)amino] carbonyl}phenyl)-N-methylpyrazine-2-carboxamide: ¹H NMR (400 MHz, d₆-DMSO): 9.19 (t, 1H), 8.92 (s, 1H), 8.84 (m, 1H), 8.55 (s, 1H), 8.40 (d, 1H), 7.91 (d, 1H), 7.75 (br s, 2H), 7.65 (m, 4H), 7.59 (t, 1H), 7.46 (m, 4H), 7.35 (m, 1H), 4.58 (d, 2H), 2.86 (d, 3H); MS (EI) for C₂₆H₂₃N₅O₂: 438.5 (MH⁺).

3-amino-N-methyl-6-{3-[({[4-(phenyloxy)phenyl] methyl}amino)carbonyl]phenyl}pyrazine-2-carboxamide: ¹H NMR (400 MHz, d₆-DMSO): 9.14 (t, 1H, 8.91 (s, 1H), 8.84 (m, 1H), 8.54 (s, 1H), 8.39 (d, 1H), 7.89 (d, 1H), 7.75 (br s, 2H), 7.58 (t, 1H), 7.38 (m, 4H), 7.12 (m, 1H), 6.99 (m, 4H), 2.87 (d, 3H),; MS (EI) for C₂₆H₂₃N₅O₃: 454.5 (MH⁺).

3-amino-N-methyl-6-{3-[({[3-(phenyloxy)phenyl] methyl}amino)carbonyl]phenyl}pyrazine-2-carboxamide: ¹H NMR (400 M, d₆-DMSO): 9.14 (t, 1H), 8.90 (s, 1H), 8.83 (m, 1H), 8.51 (s, 1H), 8.39 (d, 1H), 7.86 (d, 1H), 7.74 (br s, 2H), 7.57 (t, 1H), 7.37 (m, 3H), 7.13 (m, 2H), 7.01 (m, 3H), 6.88 (m, 1H), 4.52 (d, 2H), 2.86 (d, 3H); (d, 3H); MS (EI) for C₂₆H₂₃N₅O₃: 454.6 (MH⁺)

3-amino-6-(3-{[(biphenyl-3-ylmethyl)amino] carbonyl}phenyl)-N-methylpyrazine-2-carboxamide: ¹H NMR (400 MHz, d₆-DMSO): 9.19 (t, 1H), 8.92 (s, 1H), 8.84 (m, 1H), 8.56 (s, 1H), 8.39 (d, 1H), 7.90 (d, 1H), 7.69 (br s, 2H), 7.65 (m, 3H), 7.57 (m, 2H), 7.46 (m, 3H), 7.38 (m, 2H), 4.63 (d, 2H), 2.83 (d, 3H); MS (EI) for C₂₆H₂₃N₅O₂: 438.4 (MH⁺).

3-amino-N-methyl-6-(3-{[(1-methyl-1-phenylethyl) amino]carbonyl}phenyl)pyrazine-2-carboxamide: ¹H NMR (400 MHz, d₆-DMSO): 8.96 (s, 1H), 8.87 (m, 1H), 8.54 (s, 1H), 8.48 (s, 1H), 8.38 (d, 1H), 7.82 (d, 1H), 7.75 (br s, 2H), 7.55 (t, 1H), 7.42 (m, 2H), 7.30 (m, 2H), 7.18 (m, 1H), 2.85 (d, 3H), 1.71 (s, 6H); MS (EI) for C₂₂H₂₃N₅O₂: 390.4 (MH⁺).

3-amino-6-[3-({[(2,4-difluorophenyl)methyl] amino}carbonyl)phenyl]-N-methylpyrazine-2-carboxamide: ¹H NMR (400 MHz, d₆-DMSO): 9.13 (t, 1H), 8.91 (s, 1H), 8.84 (m, 1H), 8.52 (s, 1H), 8.40 (d, 1H), 7.87 (d, 1H), 7.73 (br s, 2H), 7.58 (t, 1H), 7.48 (m, 1H), 7.25 (m, 1H), 7.08 (m, 1H), 4.53 (d, 2H), 2.85 (d, 3H); MS (EI) for C₂₀H₁₇N₅O₂F₂: 398.3 (MH⁺).

3-amino-6-{3-[({[2-chloro-6-(phenyloxy)phenyl] methyl}amino)carbonyl]phenyl}-N-methylpyrazine-2-carboxamide: ¹H NMR (400 MHz, d₆-DMSO): 8.85 (s, 1H), 8.83 (m, 1H), 8.69 (t, 1H), 8.36 (s, 1H), 8.33 (d, 1H), 7.77 (d, 1H), 7.72 (br s, 2H), 7.51 (t, 1H), 7.34 (m, 4H), 7.05 (m, 3H), 6.85 (d, 1H), 4.67 (d, 2H), 2.83 (d, 3H); MS (EI) for C₂₆H₂₂N₅O₃Cl: 488.4 (MH⁺).

3-amino-6-[3-({[(2,5-dichlorophenyl)methyl] amino}carbonyl)phenyl]-N-methylpyrazine-2-carboxamide: ¹H NMR (400 MHz, d₆-DMSO): 9.18 (t, 1H), 8.92 (s, 1H), 8.84 (m, 1H), 8.56 (s, 1H), 8.41 (d, 1H), 7.91 (d, 1H), 7.74 (br s, 2H), 7.60 (t, 1H), 7.54 (d, 1H), 7.41 (m, 2H), 4.58 (d, 2H), 2.86 (d, 3H); MS (EI) for $C_{20}H_{17}N_5O_2Cl_2$: 430.4 (MH$^+$).

3-amino-6-{3-[({[2,6-bis(methyloxy)phenyl]methyl}amino)carbonyl]phenyl}-N-methylpyrazine-2-carboxamide: $^1$H NMR (400 MHz, d$_6$-DMSO): 8.90 (s, 1H), 8.86 (m, 1), 8.45 (s, 1H), 8.33 (d, 1H), 8.28 (t, 1H), 7.841 (d, 1H), 7.71 (br s, 2H), 7.53 (t, 1H), 7.27 (t, 1H), 6.69 (d, 2H), 4.50 (d, 2H), 3.80 (s, 6H), 2.85 (d, 3H); MS (EI) for $C_{22}H_{23}N_5O_4$: 422.4 (MH$^+$).

3-amino-6-[3-({[(2-chloro-6-methylphenyl)methyl]amino}carbonyl)phenyl]-N-methylpyrazine-2-carboxamide: $^1$H NMR (400 MHz, d$_6$-DMSO): 8.89 (s, 1H), 8.84 (m, 1H), 8.69 (m, 1H), 8.47 (s, 1H), 8.36 (d, 1H), 7.85 (d, 1H), 7.69 (br s, 2H), 7.54 (t, 1H), 7.32 (m, 1H), 7.24 (m, 2H), 4.65 (d, 2H), 2.85 (d, 3H), 2.45 (s, 3H); MS (EI) for $C_{21}H_{20}N_5O_2Cl$: 410.4 (MH$^+$).

3-amino-N-methyl-6-[3-({[(2,4,5-trifluorophenyl)methyl]amino}carbonyl)phenyl]pyrazine-2-carboxamide: $^1$H NMR (400 MHz, d$_6$-DMSO): 9.14 (t, 1H), 8.92 (s, 1H), 8.85 (m, 1H), 8.53 (s, 1H), 8.40 (d, 1H), 7.87 (d, 1H), 7.75 (br s, 2H), 7.58 (m, 2H), 7.50 (m, 1H), 4.52 (d, 2H), 2.86 (d, 3H); MS (EI) for $C_{20}H_{16}N_5O_2F_3$: 416.4 (MH$^+$).

3-amino-6-[3-({[(2,3-dichlorophenyl)methyl]amino}carbonyl)phenyl]-N-methylpyrazine-2-carboxamide: $^1$H NMR (400 MHz, d$_6$-DMSO): 9.22 (t, 1H), 8.93 (s, 1H), 8.86 (m, 1H), 8.57 (s, 1H), 8.42 (d, 1H), 7.90 (d, 1H), 7.76 (br s, 2H), 7.60 (m, 2H), 7.39 (m, 2H), 4.62 (d, 2H), 2.86 (d, 3H); MS (EI) for $C_{20}H_{17}N_5O_2Cl_2$: 430.32 (MH$^+$).

3-amino-6-[3-({[(4-chloro-2-fluorophenyl)methyl]amino}carbonyl)phenyl]-N-methylpyrazine-2-carboxamide: $^1$H NMR (400 MHz, d$_6$-DMSO): 9.16 (t, 1H), 8.91 (s, 1H), 8.84 (m, 1H), 8.53 (s, 1H), 8.40 (d, 1H), 7.87 (d, 1H), 7.80 (br s, 2H), 7.58 (t, 1H), 7.45 (m, 2H), 7.29 (d, 1H), 4.53 (d, 2H), 2.86 (d, 3H); MS (EI) for $C_{20}H_{17}N_5O_2FCl$: 414.4 (NH$^+$).

3-amino-6-[3-({[(3,5-dichlorophenyl)methyl]amino}carbonyl)phenyl]-N-methylpyrazine-2-carboxamide: $^1$H NMR (400 MHz, d$_6$-DMSO): 9.21 (t, 1H), 8.92 (s, 1H), 8.85 (m, 1H), 8.54 (s, 1H), 8.40 (d, 1H), 7.88 (d, 1H), 7.73 (br s, 2H), 7.59 (t, 1H), 7.52 (m, 1H), 7.42 (m, 2H), 4.54 (d, 2H), 2.86 (d, 3H); MS (EI) for $C_{20}H_{17}N_5O_2Cl_2$: 403.3 (MH$^+$).

3-amino-6-[3-({[(5-chloro-2-fluorophenyl)methyl]amino}carbonyl)phenyl]-N-methylpyrazine-2-carboxamide: $^1$H NMR (400 MHz, d$_6$-DMSO): 9.17 (t, 1H), 8.92 (s, 1H), 8.86 (m, 1h), 8.54 (s, 1H), 8.41 (d, 1H), 7.89 (d, 1H), 7.77 (br s, 2H), 7.59 (t, 1H), 7.46 (m, 1H), 7.41 (m, 1H), 7.28 (m, 1H), 4.55 (d, 2H), 2.86 (d, 3H); MS (EI) for $C_{20}H_{17}N_5O_2FCl$: 414.4 (MH$^+$).

3-amino-6-[3-({[(3,4-dichlorophenyl)methyl]amino}carbonyl)phenyl]-N-methylpyrazine-2-carboxamide: $^1$H NMR (400 MHz, d$_6$-DMSO): 9.21 (t, 1H), 8.91 (s, 1H), 8.85 (m, 1H), 8.53 (s, 1H), 8.40 (d, 1H), 7.88 (d, 1H), 7.72 (br s, 2H), 7.60 (m, 3H), 7.36 (d, 1H), 4.53 (d, 2H), 2.86 (d, 3H); MS (EI) for $C_{20}H_{17}N_5O_2Cl_2$: 430.3 (MH$^+$).

3-amino-6-[3-({[(4'-fluorobiphenyl-2-yl)methyl]amino}carbonyl)phenyl]-N-methylpyrazine-2-carboxamide: $^1$H NMR (400 MHz, d$_6$-DMSO): 9.03 (t, 1H), 8.90 (s, 1H), 8.84 (m, 1H), 8.49 (s, 1H), 8.38 (d, 1H), 7.85 (d, 1h), 7.71 (br s, 2H), 7.56 (t, 1H), 7.49 (m, 3H), 7.42-7.22 (m, 5H), 4.46 (d, 2H), 2.86 (d, 3H); MS (EI) for $C_{26}H_{22}N_5O_2F$: 456.4 (MH$^+$).

3-amino-6-[3-({[(4-fluoro-3-methylphenyl)methyl]amino}carbonyl)phenyl]-N-methylpyrazine-2-carboxamide: $^1$H NMR (400 MHz, d$_6$-DMSO): (9.12 (t, 1H), 8.91 (s, 1H), 8.84 (m, 1H), 8.53 (s, 1H), 8.39 (d, 1H), 7.89 (d, 1H), 7.73 (br s, 2H), 7.58 (t, 1H), 7.26 (m, 1H), 7.20 (m, 1H), 7.10 (m, 1H), 4.48 (d, 2H), 2.85 (d, 3H), 2.23 (s, 3H); MS (EI) for $C_{21}H_{20}N_5O_2F$: 394.4 (MH$^+$).

3-amino-6-[3-({[(3-chloro-2-fluorophenyl)methyl]amino}carbonyl)phenyl]-N-methylpyrazine-2-carboxamide: $^1$H NMR (400 MHz, d$_6$-DMSO): 9.19 (t, 1H), 8.92 (s, 1H), 8.84 (m, 1H), 8.54 (s, 1H), 8.40 (d, 1H), 7.88 (d, 1H), 7.76 (br s, 2H), 7.58 (t, 1H), 7.51 (t, 1H), 7.41 (t, 1H), 7.22 (t, 1H), 4.60 (d, 2H), 2.86 (d, 3H); MS (EI) for $C_{20}H_{17}N_5O_2FCl$: 414.4 (MH$^+$).

3-amino-6-[3-({[(6-chloro-2-fluoro-3-methylphenyl)methyl]amino}carbonyl)phenyl]-N-methylpyrazine-2-carboxamide: $^1$H NMR (400 MHz, d$_6$-DMSO): 8.89 (s, 1H), 8.84 (m, 1H), 8.48 (s, 1H), 8.37 (d, 2H), 7.85 (d, 1H), 7.74 (br s, 2H), 7.55 (t, 1H), 7.27 (m, 2H), 4.64 (d, 2H), 2.85 (d, 3H), 2.24 (s, 3H); MS (EI) for $C_{21}H_{19}N_5O_2FCl$: 428.4 (MH$^+$).

3-amino-6-[3-({[(4-iodophenyl)methyl]amino}carbonyl)phenyl]-N-methylpyrazine-2-carboxamide: $^1$H NMR (400 MHz, d$_6$-DMSO): 9.17 (t, 1H), 8.91 (s, 1H, 8.84 (m, 1H), 8.52 (s, 1H), 8.39 (d, 1H), 7.88 (d, 1H), 7.74 (br s, 7.71 (d, 2H), 7.58 (t, 1H), 7.18 (d, 2H), 4.49 (d, 2H), 2.86 (d, 3H); MS (EI) for $C_{20}H_{18}N_5O_2I$: 488.2 (MH$^+$).

3-amino-6-[3-({[(3-chloro-4-methylphenyl)methyl]amino}carbonyl)phenyl]-N-methylpyrazine-2-carboxamide: $^1$H NMR (400 MHz, d$_6$-DMSO): 9.16 (t, 1H), 8.92 (s, 1H), 8.85 (m, 1H), 8.53 (s, 1H), 8.39 (d, 1H), 7.88 (d, 1H), 7.75 (br s, 2H), 7.58 (t, 1H), 7.39 (s, 1H), 7.32 (d, 1H), 7.23 (d, 1H), 4.49 (d, 2H), 2.87 (d, 3H), 2.31 (s, 3H); MS (EI) for $C_{21}H_{20}N_5O_2Cl$: 410.4 (MH$^+$).

3-amino-6-[3-({[(2,5-difluorophenyl)methyl]amino}carbonyl)phenyl]-N-methylpyrazine-2-carboxamide: $^1$H NMR (400 MHz, d$_6$-DMSO): 9.13 (t, 1H), 8.89 (s, 1H), 8.82 (m, 1H), 8.52 (s, 1H), 8.38 (d, 1H), 7.86 (d, 1H), 7.71 (br s, 2H), 7.56 (t, 1H), 7.31-7.10 (m, 3H), 4.55 (d, 2H), 2.85 (d, 3H); MS (EI) for $C_{20}H_{17}N_5O_2F_2$: 398.5 (MH$^+$).

3-amino-6-[3-({[(2,6-difluorophenyl)methyl]amino}carbonyl)phenyl]-N-methylpyrazine-2-carboxamide: $^1$H NMR (400 MHz, d$_6$-DMSO): 8.95 (t, 1H), 8.86 (s, 1H), 8.80 (m, 1H), 8.45 (s, 1H), 8.34 (d, 1H), 7.81 (d, 1H), 7.71 (br s, 2H), 7.53 (t, 1H), 7.38 (m, 1H), 7.09 (m, 1H), 4.56 (d, 2H), 2.84 (d, 3H); MS (EI) for $C_{20}H_{17}N_5O_2F_2$: 398.4 (MH$^+$).

3-amino-6-[3-({[(3,5-difluorophenyl)methyl]amino}carbonyl)phenyl]-N-methylpyrazine-2-carboxamide: $^1$H NMR (400 MHz, d$_6$-DMSO): 9.18 (t, 1M), 8.89 (s, 1H), 8.82 (m, 1H), 8.52 (s, 1h), 8.37 (d, 1H), 7.86 (d, 1H), 7.71 (br s, 2H), 7.56 (t, 1H), 7.15-7.01 (m, 3H), 4.54 (d, 2H), 2.86 (d, 3H); MS (EI) for $C_{20}H_{17}N_5O_2F_2$: 398.5 (MH$^+$).

3-amino-6-[3-({[(3-iodophenyl)methyl]amino}carbonyl)phenyl]-N-methylpyrazine-2-carboxamide: $^1$H NMR (400 MHz, d$_6$-DMSO): 9.14 (t, 1H), 8.88 (s, 1H), 8.82 (m, 1H), 8.50 (s, 1h), 8.37 (d, 1H), 7.86 (d, 1H), 7.71 (br s, 1H), 7.67 (br s, 2H), 7.64-7.52 (m, 2H), 7.36 (d, 1H), 7.14 (t, 1H), 4.48 (d, 2H), 2.86 (d, 3H); MS (EI) for $C_{20}H_{18}N_5O_2I$: 488.4 (MH$^+$).

3-amino-N-methyl-6-[3-({[(2-piperidin-1-ylphenyl)methyl]amino}carbonyl)phenyl[pyrazine-2-carboxamide: $^1$H NMR (400 MHz, CDCl$_3$): 8.63 (s, 1H), 8.36 (m, 1H), 8.11 (m, 1H), 7.95 (m, 2H), 7.72 (d, 1H), 7.50 (t, 1H), 7.32 (m, 1H), 7.26 (m, 1h), 7.16 (d, 1H), 7.08 (t, 1H), 4.78 (d, 2H), 3.02 (d, 3H), 2.92 (m, 4H), 1.78-1.49 (m, 6H); MS (EI) for $C_{25}H_{28}N_6O_2$: 445.5 (MH$^+$).

3-amino-N-methyl-6-{3-[({[2-(methylthio)phenyl]methyl}amino)carbonyl]phenyl}pyrazine-2-carboxamide: $^1$H NMR (400 MHz, d$_6$-DMSO): 9.04 (t, 1H), 8.90 (s, 1H), 8.82 (m, 1H), 8.54 (m, 1H), 8.38 (d, 1H), 7.88 (d, 1H), 7.70 (br s, 2H), 7.57 (t, 1H), 7.28 (m, 3H), 7.15 (m, 1H), 4.52 (d, 2H), 2.85 (d, 3H), 2.51 (s, 3H); MS (EI) for $C_{21}H_{21}N_5O_2S$: 408.4 (MH$^+$).

3-amino-6-[3-({[(2-chloro-4-fluorophenyl)methyl] amino}carbonyl)phenyl]-N-methylpyrazine-2-carboxamide: $^1$H NMR (400 MHz, d$_6$-DMSO): 9.15 (t, 1H), 8.92 (s, 1H), 8.85 (m, 1H), 8.56 (m, 1H), 8.41 (d, 1H), 7.89 (d, 1H), 7.73 (br s, 2H), 7.59 (t, 1H), 7.48 (m, 2H), 7.24 (m, 1H), 4.57 (d, 2H), 2.85 (d, 3H); MS (EI) for $C_{20}H_{17}N_5O_2FCl$: 414.4 (MH$^+$).

3-amino-6-{3-[({(3,4-bis(methyloxy)phenyl] methyl}amino)carbonyl]phenyl}-N-methylpyrazine-2-carboxamide: $^1$H NMR (400 MHz, d$_6$-DMSO): 9.05 (t, 1H), 8.91 (s, 1H), 8.84 (m, 1H), 8.52 (m, 1H), 8.37 (d, 1H), 7.88 (d, 1H), 7.74 (br s, 2H), 7.57 (t, 1H), 6.98 (m, 1H), 6.89 (m, 2H), 4.47 (d, 2H), 3.74 (s, 3H), 3.73 (s, 3), 2.85 (d, 3H); MS (EI) for $C_{22}H_{23}N_5O_4$: 422.5 (MH$^+$).

3-amino-N-methyl-6-{3-[(phenylmethyl)amino] phenyl}pyrazine-2-carboxamide: $^1$H NMR (400 MHz, d$_6$-DMSO): 8.65 (s, 1H), 8.60 (m, 1H), 7.58 (br s, 2H), 7.42 (m, 1H), 7.37-7.19 (m, 6H), 7.13 (t, 1H), 6.60 (d, 1H), 6.23 (m, 1H), 4.57 (d, 2H), 2.85 (d, 3H); MS (EI) for $C_{19}H_{19}N_5O$: 334.4 (MH$^+$).

3-amino-6-[3-({[(2-amino-6-fluorophenyl)methyl] amino}carbonyl)phenyl]-N-methylpyrazine-2-carboxamide: $^1$H NMR (400 MHz, (4-DMSO): 9.01 (t, 1H), 8.88 (s, 1H), 8.82 (m, 1H), 8.48 (s, 1H), 8.36 (d, 1H), 7.86 (d, 1H), 7.71 (br s, 2H), 7.54 (t, 1H), 6.96 (m, 1H), 6.45 (d, 1H), 6.32 (t, 1H), 5.66 (s, 2H), 4.45 (d, 2H), 2.84 (d, 3H); MS (EI) for $C_{20}H_{19}N_6O_2F$: 395.4 (MH$^+$).

3-amino-6-{3-[({[4-fluoro-2-(trifluoromethyl)phenyl] methyl}amino)carbonyl]phenyl}-N-methylpyrazine-2-carboxamide: $^1$H NMR (400 MHz, d$_6$-DMSO): 9.23 (t, 1H), 8.93 (s, 1H), 8.84 (m, 1H), 8.57 (m, 1H), 8.42 (d, 1H), 7.91 (d, 1H), 7.76 (br s, 2H), 7.69-7.52 (m, 4H), 4.68 (d, 2H), 2.85 (d, 3H); MS (EI) for $C_{21}H_{17}N_5O_2F_4$: 448.4 (MH$^+$).

3-amino-N-methyl-6-{3-[({[6-(trifluoromethyl)pyridin-3-yl]methyl}amino) carbonyl]phenyl}pyrazine-2-carboxamide: $^1$H NMR (400 MHz, d$_6$-DMSO): 9.29 (t, 1H), 8.91 (s, 1H), 8.85 (m, 1H), 8.79 (s, 1H), 8.54 (s, 1H), 8.40 (d, 1H), 8.05 (d, 1H), 7.89 (m, 2H), 7.76 (br s, 2H), 7.59 (t, 1H), 4.65 (d, 2H), 2.85 (d, 3H); MS (EI) for $C_{20}H_{17}N_6O_2F_3$: 431.4 (MH$^+$).

3-amino-6-(3-{[2-(2,5-difluorophenyl)hydrazino] carbonyl}phenyl)-N-methylpyrazine-2-carboxamide: $^1$H NMR (400 MHz, d$_6$-DMSO): 10.52 (s, 1H), 8.93 (s, 1H), 8.84 (m, 1H), 8.59 (m, 1H), 8.42 (d, 1H), 8.20 (s, 1H), 7.88 (d, 1H), 7.74 (br s, 2H), 7.60 (t, 1H), 7.15 (m, 1H), 6.63 (m, 1H), 6.51 (m, 1H), 2.86 (d, 3H); MS (EI) for $C_{19}H_{16}N_6O_2F_2$: 399.4 (MH$^+$).

3-amino-N-methyl-6-(3-{[2-(2,3,5,6-tetrafluoro-4-methylphenyl)hydrazino]carbonyl}phenyl)pyrazine-2-carboxamide: $^1$H NMR (400 MHz, d$_6$-DMSO): 10.76 (s, 1H), 8.88 (s, 1H), 8.81 (m, 1H), 8.50 (s, 1H), 8.39 (d, 1H), 8.19 (s, 1H), 7.83 (d, 1H), 7.73 (br s, 2H), 7.57 (t, 1H), 2.87 (d, 3H), 2.15 (s, 3H); MS (EI) for $C_{20}H_{16}N_6O_2F_4$: 449.4 (MH$^+$).

3-amino-6-(3-{[2-(2-fluorophenyl)hydrazino] carbonyl}phenyl)-N-methylpyrazine-2-carboxamide: $^1$H NMR (400 MHz, d$_6$-DMSO): 10.50 (s, 1H), 8.92 (s, 1H), 8.84 (m, 1H), 8.58 (s, 1H), 8.41 (d, 1H), 7.88 (m, 2H), 7.74 (br s, 2H), 7.60 (t, 1H), 7.10 (m, 1H), 6.98 (m, 1H), 6.88 (m, 1H), 6.75 (m, 1H), 2.86 (d, 3H); MS (EI) for $C_{19}H_{17}N_6O_2F$: 381.4 (MH$^+$).

3-amino-6-(3-{[2-(2,4-difluorophenyl)hydrazino] carbonyl}phenyl)-N-methylpyrazine-2-carboxamide: $^1$H NMR (400 MHz, d$_6$-DMSO): 10.51 (s, 1H), 8.91 (s, 1H), 8.84 (m, 1H), 8.57 (s, 1H), 8.41 (d, 1H), 7.85 (m, 2H), 7.74 (br s, 2H), 7.59 (t, 1H), 7.17 (m, 1H), 6.89 (m, 2H), 2.87 (d, 3H); MS (EI) for $C_{19}H_{16}N_6O_2F_2$: 399.4 (MH$^+$).

3-amino-N-methyl-6-(3-{[2-(2,3,5,6-tetrafluorophenyl) hydrazino]carbonyl}phenyl)pyrazine-2-carboxamide: $^1$H NMR (400 MHz, d$_6$-DMSO): 10.80 (s, 1H), 8.88 (s, 1H), 8.81 (m, 1H), 8.50 (s, 1H), 8.40 (m, 2H), 7.84 (d, 1H), 7.73 (br s, 2H), 7.58 (t, 1H), 7.20 (m, 1H), 2.87 (d, 3H); MS (EI) for $C_{19}H_{14}N_6O_2F_4$: 435.4 (MH$^+$).

3-Amino-6-[3-({[(3,5-dimethylphenyl)methyl] amino}carbonyl)phenyl]-N-methylpyrazine-2-carboxamide: $^1$H NMR (400 MHz, d$_6$-DMSO): 9.08 (t, 1H), 8.91 (s, 1H), 8.84 (q, 1H), 8.54-8.52 (m, 1H), 8.39 (d, 1H), 7.58 (t, 1H), 6.95 (s, 2H), 6.88 (s, 1H), 4.46 (d, 2H), 4.10-3.70 (m, 2H), 2.85 (d, 3H), 2.25 (s, 6H); MS (EI) for $C_{22}H_{23}N_5O_2$: 390 MH$^+$).

3-amino-6-[3-({[(5-chloro-2-methylphenyl)methyl] amino}carbonyl)phenyl]-N-methylpyrazine-2-carboxamide: $^1$H NMR (400 MHz, d$_6$-DMSO): 9.06 (t, 1H), 8.91 (s, 1H), 8.84 (q, 1H), 8.56-8.53 (m, 1H), 8.40 (d, 1H), 8.00-7.30 (m, 2H), (m, 7.90 (d, 1H), 7.59 (t, 1H), 7.29 (s, 1H) 7.24-7.22 (m, 2H), 4.50 (d, 2H), 2.86 (d, 3H), 2.34 (s, 3H); MS (EI) for $C_{21}H_{20}N_5O_2Cl$: 410 (MH$^+$).

3-amino-6-[3-({[(2,4-dimethylphenyl)methyl] amino}carbonyl)phenyl]-N-methylpyrazine-2-carboxamide: $^1$H NMR (400 MHz, d$_6$-DMSO): 8.96 (t, 1H), 8.91 (s, 1H), 8.85 (q, 1H), 8.54-8.52 (m, 1H), 8.39 (d, 1H), 7.89 (d, 1H), 7.58 (t, 1H), 7.17 (d, 1H), 7.02-6.95 (m, 2H), 4.46 (d, 2H), 4.00-3.30 (m, 2), 2.85 (d, 3H), 2.31 (s, 3H), 2.25 (s, 3H); MS (EI) for $C_{22}H_{23}N_5O_2$: 390 (MH$^+$).

3-amino-6-[3-({[(2,3-difluorophenyl)methyl] amino}carbonyl)phenyl]-N-methylpyrazine-2-carboxamide: $^1$H NMR (400 MH, d$_6$-DMSO): 9.20 (t, 1H), 8.92 (s, 1H), 8.85 (q, 1H), 8.55-8.52 (m, 1H), 8.40 (d, 1H), 7.88 (d, 1H), 7.58 (t, 1H), 7.40-7.30 (m, 1H), 7.28-7.16 (m, 2H), 4.60 (d, 2H), 4.20-3.80 (m, 2H), 2.85 (d, 3H); MS (EI) for $C_{20}H_{17}N_5O_2F_2$: 398 (MH$^+$).

3-amino-N-methyl-6-{3-[({[4-(methylthio)phenyl] methyl}amino)carbonyl]phenyl}pyrazine-2-carboxamide: $^1$H NMR (400 MHz, d$_6$-DMSO): 9.13 (t, 1H), 8.91 (s, 1H), 8.84 (q, 1H), 8.53-8.51 (m, 1H), 8.39 (d, 1H), 8.00-7.30 (m, 2H), 7.88 (d, 1H), 7.58 (t, 1H), 7.31 (d, 2H), 7.24 (d, 2H), 4.49 (d, 2H), 2.85 (d, 3H), 2.45 (s, 3H); MS (EI) for $C_{21}H_{21}N_5O_2S$: 408 (MH$^+$).

3-amino-N-methyl-6-(3-{[(2-methylpropyl)amino] carbonyl}phenyl)pyrazine-2-carboxamide: $^1$H NMR (400 MHz, d$_6$-DMSO): 8.91 (s, 1H), 8.84 (q, 1H), 8.56 (t, 1H), 8.48-8.45 (m, 1H), 8.36 (dt, 1H), 8.20-7.30 (m, 2H), 7.83 (dt, 1H), 7.56 (t, 1H), 3.13 (dd, 2M), 2.86 (d, 3H), 1.94-1.82 (m, 1H), 0.92 (d, 6H); MS (EI) for $C_{17}H_{21}N_5O_2$: 328 (MH$^+$).

3-amino-N-methyl-6-(3-{[({3-[(trifluoromethyl)oxy] phenyl}methyl)amino]carbonyl}phenyl)pyrazine-2-carboxamide: $^1$H NMR (400 MHz, d$_6$-DMSO): 9.24 (t, 1H), 8.91 (s, 1H), 8.85 (q, 1H), 8.55-8.53 (m, 1H), 8.40 (d, 1H), 8.20-7.20 (m, 2H), 7.88 (d, 1H), 7.59 (t, 1H), 7.49 (t, 1H), 7.40 (d, 1H), 7.35 (s, 1H), 7.26 (d, 1H), 4.58 (d, 2H), 2.85 (d, 3H); MS (EI) for $C_{21}H_{18}N_5O_3F_3$: 446 (MH$^+$).

3-amino-6-(3-{[(cyclopropylmethyl)amino] carbonyl}phenyl)-N-methylpyrazine-2-carboxamide: $^1$H NMR (400 MHz, d$_6$-DMSO): 8.91 (s, 1H), 8.85 (q, 1H), 8.67 (t, 1H), 8.49-8.46 (m, 1H), 8.36 (dt, 1H), 8.10-7.20 (m, 2H), 7.85 (dt, 1H), 7.56 (t, 1H), 3.19 (dd, 2H), 2.86 (d, 3H), 1.12-1.01 (m, 1H), 0.49-0.43 (m, 2H), 0.29-0.23 (m, 2H); MS (EI) for $C_{17}H_{19}N_5O_2$: 326 (MH$^+$).

3-amino-6-{3-[(cyclopentylamino)carbonyl]phenyl}-N-methylpyrazine-2-carboxamide: $^1$H NMR (400 MHz, d$_6$-DMSO): 8.91 (s, 1H), 8.86 (q, 1H), 8.44-8.42 (m, 1H), 8.39-8.33 (m, 2H), 8.10-7.20 (m, 2H), 7.82 (dt, 1H), 7.54 (t, 1H), 4.31-4.21 (m, 1H), 2.85 (d, 3H), 1.99-1.86 (m, 2H), 1.79-1.66 (m, 2H), 1.62-1.50 (m, 4H); MS (EI) for $C_{18}H_{21}N_5O_2$: 340 (MH$^+$).

3-amino-N-methyl-6-(3-{[(4-methylphenyl)amino]carbonyl}phenyl)pyrazine-2-carboxamide: $^1$H NMR (400 MHz, d$_6$-DMSO): 10.3 (s, 1H), 8.95 (s, 1H), 8.89 (q, 1H), 8.59-8.57 (m, 1H), 8.40 (d, 1H), 8.00-7.30 (m, 2H), 7.90 (d, 1H), 7.69 (d, 2H), 7.62 (t, 1H), 7.18 (d, 1H), 2.86 (d, 3H), 2.30 (s, 3H); MS (EI) for $C_{20}H_{19}N_5O_2$: 362 (MH$^+$).

3-amino-N-methyl-6-[3-({[4-(methyloxy)phenyl]amino}carbonyl)phenyl]pyrazine-2-carboxamide: $^1$H NMR (400 M, d$_6$-DMSO): 10.2 (s, 1H), 8.95 (s, 1H), 8.89 (q, 1H), 8.59-8.57 (m, 1H), 8.40 (dt, 1H), 8.00-7.40 (m, 2H), 7.90 )dt, 1H), 7.73-7.68 (m, 2H), 7.61 (t, 1H), 6.98-6.93 (m, 2H), 3.76 (s, 3H), 2.86 (d, 3H); MS (EI) for $C_{20}H_{19}N_5O_3$: 378 (MH$^+$).

3-amino-6-(3-{[(2,2-dimethylpropyl)amino]carbonyl}phenyl)-N-methylpyrazine-2-carboxamide: $^1$H NMR (400 MHz, d$_6$-DMSO): 8.92 (s, 1H), 8.85 (q, 1H), 8.49-8.43 (m, 2H), 8.36 (dt, 1H), 8.00-7.40 (m, 2H), 7.83 (dt, 1H), 7.56 (t, 1H), 3.16 (d, 2H), 2.85 (d, 3H), 0.93 (s, 9H); MS (EI) for $C_{18}H_{23}N_5O_2$: 342 (MH$^+$).

3-amino-6-(3-{[(cyclopentylmethyl)amino]carbonyl}phenyl)-N-methylpyrazine-2-carboxamide: $^1$H NMR (400 MHz, d$_6$-DMSO): 8.91 (s, 1H), 8.85 (q, 1H), 8.57 (t, 1H), 8.47-8.44 (m, 1H), 8.36 (d, 1H), 8.00-7.30 (m, 2H), 7.82 (d, 1H), 7.55 (t, 1H), 3.26-3.21 (m, 2H), 2.86 (d, 3H), 2.23-2.12 (m, 1H), 1.72-1.45 (m, 6H), 1.33-1.22 (m, 2H); MS (EI) for $C_{19}H_{23}N_5O_2$: 354 (MH$^+$).

3-amino-6-{3-[(cyclopropylamino)carbonyl]phenyl}-N-methylpyrazine-2-carboxamide: $^1$H NMR (400 MHz, d$_6$-DMSO): 8.90 (s, 1H), 8.85 (q, 1H), 8.55-8.52 (m, 1H), 8.43-8.41 (m, 1H), 8.35 (d, 1H), 8.00-7.40 (m, 2H), 7.80 (d, 1H), 7.54 (t, 1H), 2.91-2.84 (m, 4H), 0.77-0.57 (m, 4H); MS (EI) for $C_{16}H_{17}N_5O_2$: 312 (MH$^+$).

3-amino-N-methyl-6-[3-({[(2,3,4-trifluorophenyl)methyl]amino}carbonyl)phenyl]pyrazine-2-carboxamide: $^1$H NMR (400 MHz, d$_6$-DMSO): 9.17 (t, 1H), 8.91 (s, 1H), 8.84 (q, 1H), 8.53-8.51 (m, 1H), 8.40 (d, 1H), 8.00-7.40 (m, 2H), 7.86 (d, 1H), 7.58 (t, 1H), 7.35-7.27 (m, 2H), 4.56 (d, 2H), 2.85 (d, 3H); MS (EI) for $C_{20}H_{16}N_5O_2F_3$: 416 (MH$^+$).

3-amino-6-[3-({[(3-chloro-2,6-difluorophenyl)methyl]amino}carbonyl)phenyl]-N-methylpyrazine-2-carboxamide: $^1$H NMR (400 MHz, d$_6$-DMSO): 9.05 (t, 1H), 8.89 (s, 1H), 8.83 (q, 1H), 8.48-8.46 (m, 1H), 8.37 (d, 1H), 7.90-7.20 (m, 2H), 7.83 (d, 1H), 7.66-7.58 (m, 1H), 7.55 (t, 1H), 7.20 (td, 1H), 4.59 (d, 2H), 2.84 (d, 3H); MS (EI) for $C_{20}H_{16}N_5O_2F_2Cl$: 432 (MH$^+$).

3-amino-6-{3-[(9H-fluoren-9-ylamino)carbonyl]phenyl}-N-methylpyrazine-2-carboxamide: $^1$H NMR (400 MHz, d$_6$-DMSO): 9.18 (d, 1H), 8.87 (s, 1H), 8.83 (q, 1H), 8.57-8.55 (m, 1H), 8.44 (d, 1H), 8.10-7.20 (m, 2H), 8.00 (d, 1H), 7.92 (d, 2H), 7.62-7.56 (m, 3H), 7.46 (t, 2H), 7.38-7.32 (m, 2H), 6.34 (d, 1H), 2.83 (d, 3H); MS (EI) for $C_{26}H_{21}N_5O_2$: 436 (MH$^+$).

3-amino-N-methyl-6-[3-({[(2-methylphenyl)methyl]amino}carbonyl)phenyl]pyrazine-2-carboxamide: $^1$H NMR (400 MHz, d$_6$-DMSO): 9.01 (t, 1H), 8.91 (s, 1H), 8.83 (q, 1H), 8.55-8.53 (m, 1H), 8.39 (d, 1H), 8.00-7.30 (m, 2H), 7.90 (d, 1H), 7.58 (t, 1H), 7.32-7.26 (m, 1H), 7.20-7.14 (m, 3H), 4.52 (d, 2H), 2.85 (d, 3H); MS (ED for $C_{21}H_{21}N_5O_2$: 376 (MH$^+$).

3-amino-6-(3-({[(3,4-dimethylphenyl)methyl]amino}carbonyl)phenyl]-N-methylpyrazine-2-carboxamide: $^1$H NMR (400 MHz, d$_6$-DMSO): 9.13 (t, 1H), 8.91 (s, 1H), 8.87 (q, 1H), 8.56-8.53 (m, 1H), 8.37 (dt, 1H), 8.20-7.30 (m, 2H), 7.88 (dt, 1H), 7.57 (t, 1H), 7.14-7.04 (m, 3H), 4.45 (d, 2H), 2.85 (d, 3H), 2.20 (s, 3H), 2.19 (s, 3H); MS (EI) for $C_{22}H_{23}N_5O_2$: 390 (MH$^+$).

3-amino-6-[3-({[(5-fluoro-2-methylphenyl)methyl]amino}carbonyl)phenyl]-N-methylpyrazine-2-carboxamide: $^1$H NMR (400 MHz, d$_6$-DMSO): 9.07 (t, 1H), 8.92 (s, 1H), 8.85 (q, 1H), 8.56-8.54 (m, 1H), 8.40 (d, 1H), 8.00-7.30 (m, 2H), 7.89 (dt, 1H), 7.59 (t, 1H), 7.22 (dd, 1H, 7.07 (dd, 1H), 7.00 (td, 1H), 4.49 (d, 2H), 2.85 (d, 3H), 2.32 (s, 3H); MS (EI) for $C_{21}H_{20}N_5O_2F$: 394 (MH$^+$).

3-amino-6-[3-({[(3,4-difluorophenyl)methyl]amino}carbonyl)phenyl]-N-methylpyrazine-2-carboxamide: $^1$H NMR (400 M, d$_6$-DMSO): 9.28 (t, 1H), 8.92 (s, 1H), 8.89 (q, 1H), 8.58-8.55 (m, 1H), 8.39 (d, 1H), 8.00-7.30 (m, 2H), 7.88 (d, 1H), 7.58 (t, 1H), 7.46-7.36 (m, 2H), 7.24-7.19 (m, 1H), 4.51 (d, 2H), 2.86 (d, 3H); MS (EI) for $C_{20}H_{17}N_5O_2F_2$: 398 (MH$^+$).

3-amino-6-[3-({[(2-fluorophenyl)methyl]amino}carbonyl)phenyl]-N-methylpyrazine-2-carboxamide: $^1$H NMR (400 M, d$_6$-DMSO): 9.13 (t, 1H), 8.91 (s, 1H), 8.84 (q, 1H), 8.55-8.52 (m, 1H), 8.40 (d, 1H), 8.00-7.10 (m, 2H), 7.89 (d, 1H), 7.58 (t, 1H), 7.43 (td, 1H), 7.36-7.29 (m, 1H), 7.24-7.15 (m, 2H), 4.57 (d, 2H), 2.86 (d, 3H); MS (EI) for $C_{20}H_{18}N_5O_2F$: 380 (MH$^+$).

3-amino-N-methyl-6-[3-({[(2,3,6-trifluorophenyl)methyl]amino}carbonyl)phenyl]pyrazine-2-carboxamide: $^1$H NMR (400 MHz, d$_6$-DMSO): 9.03 (t, 1H), 8.86 (s, 1H), 8.80 (q, 1H), 8.45 (t, 1H), 8.35 (dt, 1H), 8.00-7.28 (m, 2H), 7.81 (dt, 1H), 7.81 (dt, 1H), 7.53 (t, 1H), 7.50-7.39 (m, 1H), 7.17-7.09 (m, 1H), 4.58 (d, 2H), 2.84 (d, 3H); MS (EI) for $C_{20}H_{16}N_5O_2F_3$: 416 (MH$^+$).

3-amino-N-methyl-6-[3-({[(3,4,5-trifluorophenyl)methyl]amino}carbonyl)phenyl]pyrazine-2-carboxamide: $^1$H NMR (400 MHz, d$_6$-DMSO): 9.17 (t, 1H), 8.89 (s, 1H), 8.83 (q, 1H), 8.51 (t, 1H), 8.37 (dt, 1H), 8.00-7.00 (m, 2H), 7.85 (dt, 1H), 7.56 (t, 1H), 7.33-7.25 (m, 2H), 4.50 (d, 2H), 2.85 (d, 3H); MS (EI) for $C_{20}H_{16}N_5O_2F_3$: 416 (MH$^+$).

'3-amino-6-{3-[({[4-aminosulfonyl)phenyl]methyl}amino)carbonyl]phenyl}-N-methylpyrazine-2-carboxamide: $^1$H NMR (400 MHz, d$_6$-DMSO): 9.24 (t, 1H), 8.92 (s, 1H), 8.84 (q, 1H), 8.56 (s, 1H), 8.40 (d, 1H), 7.88 (d, 1H), 7.80 (d, 2H), 7.58 (dd, 1H), 7.54 (d, 2H), 7.34 (s, 2H), 4.60 (d, 2H), 2.83 (d, 3H); MS (EI) for $C_{20}H_{20}N_6O_4S$: 441 (MH$^+$).

'3-amino-6-[3-({[(2,3-dimethylphenyl)methyl]amino}carbonyl)phenyl]-N-methylpyrazine-2-carboxamide: $^1$H NMR (400 MHz, CDCl$_3$): 8.64 (s, 1H), 8.36 (s, 1H), 7.99 (m, 2H), 7.68 (d, 1H), 7.51 (dd, 1H), 7.17 (m, 3H), 7.23 (t, 1H), 4.70 (d, 2H), 3.03 (d, 3H), 2.35 (s, 3H), 2.29 (s, 3H); MS (EI) for $C_{22}H_{23}N_5O_2$: 390 (MH$^+$).

'3-amino-6-{3-[({[4-hydroxy-3-(methyloxy)phenyl]methyl}amino)carbonyl]phenyl}-N-methylpyrazine-2-carboxamide: $^1$H NMR (400 MHz, d$_4$-methanol): 8.76 (s, 1H), 8.54 (s, 1H), 8.20 (d, 1H), 7.86 (d, 1H), 7.57 (dd, 1H), 6.98 (s, 1H), 6.84 (d, 1H), 6.76 (d, 1H), 4.54 (s, 2H), 3.85 (s, 3H), 2.97 (s, 3H); MS (EI) for $C_{21}H_{21}N_5O_4$: 408 (MH$^+$).

'3-amino-6-[3-({[(4-chloro-2-methylphenyl)methyl]amino}carbonyl)phenyl]-N-methylpyrazine-2-carboxamide: $^1$H NMR (400 MHz, d$_4$-methanol): 8.76 (s, 1H), 8.55 (s, 1H), 8.22 (d, 1H), 7.86 (d, 1H), 7.58 (dd, 1H), 7.29 (d, 1H), 7.23 (s, 1H), 7.17 (d, 1H), 4.60 (s, 2H), 2.97 (s, 3H), 2.40 (s, 3H); MS(EI) for $C_{21}H_{20}N_5O_2Cl$: 410 (MH$^+$).

'3-amino-6-{3-[({[2-(ethyloxy)phenyl]methyl}amino)carbonyl]phenyl}-N-methylpyrazine-2-carboxamide: $^1$H NMR (400 MHz, d-chloroform): 8.64 (s, 1H), 8.36 (s, 1H), 7.99 (m, 2H), 7.68 (d, 1H), 7.51 (dd, 1H), 7.37 (d, 1H), 7.28

(dd, 1H), 6.94 (dd, 1H), 6.87 (d, 1H), 6.82 (t, 1H), 4.69 (d, 2H), 4.13 (q, 2H), 3.03 (d, 3H), 1.45 (t, 3H); MS(EI) for $C_{22}H_{23}N_5O_3$: 406 (MH+).

3-amino-N-methyl-6-(3-{[(naphtalen-2-ylmethyl)amino]carbonyl}phenyl) pyrazine-2-carboxamide: $^1$H NMR (400 MHz; d$_6$-DMSO): 9.17 (br s, 1H), 8.9 (s, 1H), 8.82 (s, 1H), 8.56 (s, 1H), 8.42-8.36 (d, 1H), 8.24-8.18 (d, 1H), 8-7.82 (td, 3H), 7.64-7.46 (m, 5H), 5.00 (s, 2H), 2.57 (s, 3H); MS (EI) for $C_{24}H_{21}N_5O_2$: 412 (MH+).

3-amino-N-methyl-6-(3-{[(tetrahydrofuran-2-ylmethyl)amino]carbonyl}phenyl)pyrazine-2-carboxamide: MS(EI) for $C_{18}H_{21}N_5O_3$: 356 (MH+).

3-amino-6-[3-({[(2-chloro-6-fluorophenyl)methyl]amino}carbonyl]phenyl}-N-methylpyrazine-2-carboxamide: $^1$H NMR (400 MHz, d$_6$-DMSO): 8.90 (s, 1H), 8.82 (s, 1H), 8.85 (s, 1H), 8.34-8.38 (d, 1H), 7.88-7.80 (d, 1H), 7.60-7.52 (t, 1H), 7.46-7.34 (m, 1H), 7.30-7.22 (t, 1H), 4.50 (s, 2H), 2.80 (s, 3H); MS (EI) for $C_{20}H_{17}N_5O_2FCl$: 414 (MH+).

3-amino-6-{3-[({[3-fluoro-5-(trifluoromethyl)phenyl]methyl}amino)carbonyl]phenyl}-N-methylpyrazine-2-carboxamide: $^1$H N (400 MHz, d$_6$-DMSO): 9.28 (br s, 1H), 8.90 (s, 1H), 8.82 (s, 1H), 8.54 (s, 1H), 8.44-8.36 (d, 2H), 7.94-7.84 (d, 1H), 7.68-7.48 (m, 4H); MS (EI) for $C_{21}H_{17}N_5O_2F_4$: 448 (MH+).

3-amino-6-{3-[({2-[3,5-bis(methyloxy)phenyl]ethyl}amino)carbonyl}phenyl}-N-methylpyrazine-2-carboxamide: $^1$H NMR (400 MHz, d$_6$-DMSO): 8.90 (s, 1H), 8.84 (d, 1H), 8.64 (s, 1H), 8.45 (s, 1H), 8.38-8.34 (d, 1H), 7.86-7.78 (d, 1H), 7.58-7.52 (t, 3H), 6.90-6.84 (d, 1H), 6.82-6.78 (d, 1H); MS (EI) for $C_{23}H_{25}N_5O_4$: 436 (MH+).

3-amino-6-(3-{[(1,3-benzodioxol-5-ylmethyl)amino]carbonyl}phenyl)-N-methylpyrazine-2-carboxamide: $^1$H NMR (400 MHz d$_6$-DMSO): 9.20 (s, 1H), 8.90 (s, 1H), 8.88-8.82 (d, 1H), 8.56 (s, 1H), 8.40-8.32 (d, 1H), 7.90-7.80 (d, 1H), 7.60-7.50 (t, 1H), 6.95 (s, 1H), 6.90-6.78 (q, 2H), 6.00 (s, 2H), 4.50-4.40 (d, 2H), 2.85 (s, 3H); MS (EI) for $C_{21}H_{19}N_5O_4$: 406 (MH+).

3-amino-N-methyl-6-(3-{[({4-[(trifluoromethyl)oxy]phenyl}methyl)amino]carbonyl]phenyl)pyrazine-2-carboxamide: $^1$H NMR (400 MHz, d$_6$-DMSO): 9.20 (t, 1H), 8.88 (s, 1H), 8.86-8.78 (d, 1H), 8.54 (s, 1H), 8.42-8.36 (d, 1H), 7.90-7.84 (d, 1H), 7.64-7.58 (t, 1H), 7.52-7.46 (d, 2H), 7.38-7.32 (d, 2H), 4.56-4.50 (d, 2H), 2.90-2.80 (t, 3H); MS (EI) for $C_{21}H_{18}N_5O_3F_3$: 446 (MH+).

3-amino-6-{3-[({[4-fluoro-3-(trifluoromethyl)phenyl]methyl}aminocarbonyl]phenyl}-N-methylpyrazine-2-carboxamide: $^1$H NMR (400 MHz, d$_6$-DMSO): 9.24-9.18 (t, 1H), 8.90 (s, 1H), 8.86-8.80 (d, 1H), 8.52 (s, 1H), 8.42-8.37 (d, 1H), 7.90-7.84 (d, 1H), 7.80-7.72 (m, 2H), 7.62-7.58 (q, 1H), 7.54-7.48 (t, 1H), 4.60-4.55 (d, 2H), 3.78-3.68 (d, 3H); MS (EI) for $C_{21}H_{17}N_5O_2F_4$ 448 (MH+).

3-amino-6-{3-[({[4-chloro-3-(trifluoromethyl)phenyl]methyl}amino)carbonyl]phenyl}-N-methylpyrazine-2-carboxamide: $^1$H NMR (400 MHz, d$_6$-DMSO): 9.28-9.22 (t, 1H), 8.90 (s, 1H), 8.88-8.82 (d, 1H), 8.52 (s, 1H), 8.44-8.36 (d, 1H), 7.90-7.82 (m, 2H), 7.74-7.66 (q, 2H), 7.60-7.54 (t, 1H); MS (EI) for $C_{21}H_{17}N_5O_2F_3Cl$: 464 (MH+).

Example 5

3-amino-6-[3-(hydroxy-benzylcarbamoyl)-phenyl]-pyrazine-2-carboxylic acid methylamide isomers Scheme 5 shows how 3-amino-6-[3-(hydroxy-benzylcarbamoyl)-phenyl]-pyrazine-2-carboxylic acid methylamide isomers were made. Methoxy benzylamines were demethylated via acidic hydrolysis to give the corresponding amine hydrobromide salts, (xxviii). These were used to make compounds (xxix) via amide forming reaction, for example using standard amide coupling reagents as depicted in Scheme 5. Exemplary details are set forth below.

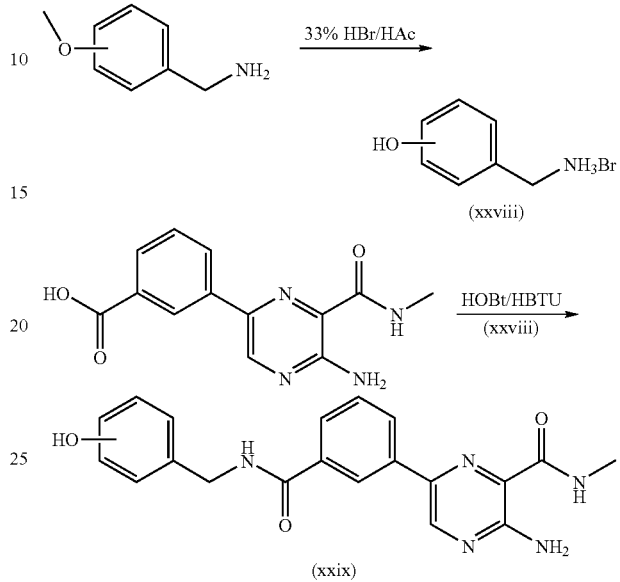

Scheme 5

3-amino-6-(3-{[(2-hydroxybenzyl)amino]carbonyl}phenyl)-N-methyl-2-pyrazine-carboxamide trifluoroacetate: A solution of 3.0 mL (0.023 mol) {[2-(methoxy)phenyl]methyl}amine was refluxed in 50 mL 33% HBr in glacial acetic acid until the full deprotection of the starting material. The solvent was evaporated to obtain 4.7 g 2-(aminomethyl)phenol hydrobromide: MS (EI) for $C_7H_9NO$: 124.1 (MH+).

To a solution of 54 mg (0.20 mmol) 3-{5-amino-6-[(methylamino)carbonyl]-2-pyrazinyl}benzoic acid in DMF (5 mL), 165 mg (1.20 mmol) 1-hydroxybenztriazol (HOBt), 380 mg (1.00 mmol) O-benzotriazol-1-yl-N,N,N',N'-tetramethyluronium hexafluorophosphate (HBTU) and 0.22 mL (2.00 mmol) 4-methylmorpholine was added and the reaction mixture was stirred for 30 minutes at room temperature, followed by the addition of 41 mg (0.20 mmol) 2-(aminomethyl)phenol hydrobromide The reaction mixture was stirred at room temperature for 18 h. The reaction was diluted with ethyl acetate washed sequentially with water, 1.0 M aqueous hydrochloric acid, water and saturated aqueous sodium chloride. The organic layer was dried over sodium sulfate, filtered, and concentrated on a rotary evaporator under reduced pressure. The crude product was purified by HPLC (reverse-phase, $CH_3CN/H_2O$ with 0.1% TFA). Upon removal of solvent, the product was taken up in methanol. Removal of solvent in vacuo provided 54 mg (55% yield) of title product: $^1$H NMR (400 M, d$_6$-DMSO): 9.02 (t, 1H), 8.84 (s, 1H), 8.78 (q, 1H), 8.50 (s, 1H), 8.36 (d, 1H), 7.78 (d, 1H), 7.54 (t, 1H), 7.22 (m, 2H), 6.94 (m, 2H), 4.86 (bs, 1H), 4.40 (d, 2H), 2.80 (d, 3H). MS (EI) for $C_{20}H_{19}N_5O_3$: 378.5 (MH+).

Using the same or analogous synthetic techniques and/or substituting with alternative reagents, the following compounds of the invention were prepared:

3-amino-6-(3-{[(3-hydroxybenzyl)amino]carbonyl}phenyl)-N-methyl-2-pyrazine-carboxamide trifluoroacetate: $^1$H NMR (400 MHz, d$_6$-DMSO): 9.02 (t, 1H), 8.86 (s, 1H), 8.80 (q, 1H), 8.54 (s, 1H), 8.36 (d, 1H), 7.86 (d, 1H), 7.58 (t, 1H), 7.15 (m, 2H), 6.94 (s, 1H), 6.76 (m, 1H), 4.94 (bs, 1H), 4.43 (d, 2H), 2.82 (d, 3H). MS (EI) for $C_{20}H_{19}N_5O_3$: 378.4 (MH+).

3-amino-6-(3-{[(4-hydroxybenzyl)amino]carbonyl}phenyl)-N-methyl-2-pyrazine-carboxamide trifluoroacetate: $^1$H NMR (400 MHz, $d_6$-DMSO) 9.04 (t, 1H), 8.88 (s, 1H), 8.84 (q, 1H), 8.54 (s, 1H), 8.40 (d, 1H), 7.86 (d, 1H), 7.60 (t, 1H), 7.18 (d, 2H), 6.86 (d, 2H), 5.02 (bs, 1H), 4.43 (d, 2H), 2.82 (d, 3H). MS (EI) for $C_{20}H_{19}N_5O_3$: 378.4 (MH+).

Example 6

3-amino-N-methyl-6-{3-[({2-[2-(4-morpholinyl)ethoxy]benzyl}amino)carbonyl]phenyl}-2-pyrazinecarboxamide Scheme 6 shows how 3-Amino-6-{3-[3-(morpholin-4-yl-ethoxy)-benzylcarbamoyl]-phe-nyl}-pyrazine-2-carboxylic acid methylamide isomers were made. Benzylamine hydrobromide salts (xxviii) (refer to Scheme 5) were converted to the corresponding Boc-protected derivatives (xxx). These were used to make compounds (xxxi), for example via Mitsinobu reaction. Intermediates (xxxi) were used to make compounds (xxxii) via amide forming reaction, for example using standard amide coupling reagents as depicted in Scheme 6. Exemplary details are set forth below.

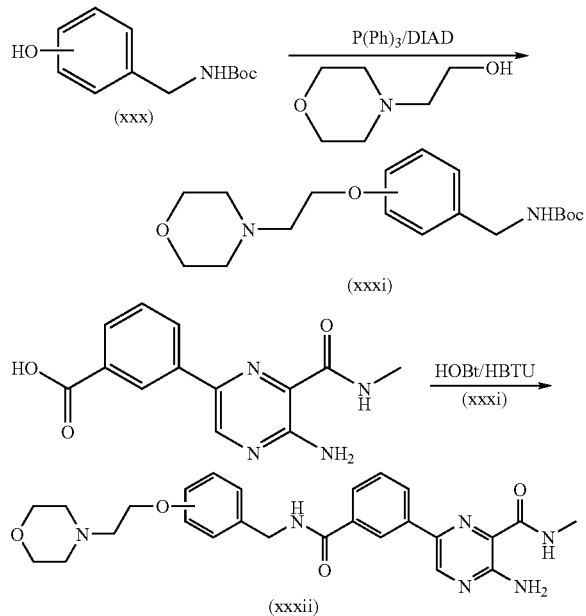

Scheme 5

3-amino-N-methyl-6-{3-[({2-[2-(4-morpholinyl)ethoxy]benzyl}amino)carbonyl]phe-nyl}-2-pyrazinecarboxamide:
To an ice-cold solution of 4.0 g (0.02 mol) 2-(aminomethyl)phenol hydrobromide was added 8.40 g (0.10 mol) sodium bicarbonate in 10% aqueous THF (150 mL) followed by 22 mL (0.022 mol) di-tert-butyl dicarbonate (1M in THF) and the reaction mixture was stirred at room temperature for 18 h. It was diluted with ethyl acetate and washed sequentially with water, 1.0 M aqueous hydrochloric acid, water and saturated aqueous sodium chloride. The organic layer was dried over sodium sulfate, filtered, and concentrated on a rotary evaporator under reduced pressure. The solvent was evaporated to obtain 4.2 g 1,1-dimethylethyl-[(2-hydroxyphenyl)-methyl]carbamate. MS (EI) for $C_{12}H_{17}NO_3$: 123.4 (M-Boc), 167.4 (M-tBu).

To an ice-cold solution of 3.30 g (0.015 mol) 1,1-dimethylethyl-[(2-hydroxyphenyl)-methyl]carbamate, 2.20 mL (0.018 mol) 2-morpholin-4-ylethanol and 4.80 g (0.019 mol) triphenylphosphine in a mixture of tetrahydrofuran-dichloromethane (2:1) (150 mL), 3.74 mL (0.019 mol) diisopropyl azodicarboxylate was added dropwise. The reaction mixture was stirred for 18 h. It was diluted with ethyl acetate and washed sequentially with water then saturated aqueous sodium chloride. The organic layer was dried over sodium sulfate, filtered and concentrated on a rotary evaporator under reduced pressure. The resulting crude material was purified by silca gel column chromatography to yield 3.6 g 1,1-dimethylethyl-({2-[(2-morpholin-4-ylethyl)oxy]pheny}methyl)carbamate, 71%. MS (EI) for $C_{18}H_{28}N_2O_4$: 337.4 (MH+), 236.4 (M-Boc).

Weight, 0.35g (1.0 mmol), of 1,1-dimethylethyl-({2-[(2-morpholin-4-ylethyl)oxy]pheny}methyl) carbamate was taken into dichloromethane (2 mL) and treated with 2.0 mL trifluoroacetic acid for 30 minutes at room temperature. The solvent was evaporated and the resulting crude ({2-[(2-morpholin-4-ylethyl)oxy]phenyl}methyl]trifluoroacetate, MS (EI) for $C_{13}H_{20}N_2O_2$: 337.4 (MH$^+$) was coupled with 0.27 g (1.00 mmol) 3-{5-amino-6-[(methylamino)carbonyl]-2-pyrazinyl}benzoic acid as described above. The reaction was diluted with ethyl acetate, washed sequentially with water, and saturated aqueous sodium chloride. The organic layer was dried over sodium sulfate, filtered and concentrated on a rotary evaporator under reduced pressure. The crude product was purified by HPLC (reverse-phase, $CH_3CN/H_2O$ with 0.1% TFA) Upon removal of solvent, the product was taken up in a mixture of 10% methanol in ethyl acetate (100 mL) and washed with saturated aqueous sodium bicarbonate (2×30 mL) then brine. The organic layer was dried over anhydrous sodium sulfate, filtered and concentrated in vacuo to provide 0.22 g title product, 44% yield. $^1$H NMR (400 MHz, $d_6$-DMSO): 9.04 (t, 1H), 8.84 (s, 1H), 8.80 (q, 1H), 8.54 (s, 1H), 8.38 (d, 1H), 7.82 (d, 1H), 7.60 (t, 1H), 7.18 (m, 2H), 6.96 (m, 2H), 4.44 (d, 2H), 4.04 (m, 2H), 3.85 (t, 4H), 2.84 (d, 3H) 2.78 (m, 2H), 2.37 (t, 4H). MS (EI) for $C_{26}H_{30}N_6O_4$: 491.5 (MH$^+$).

Using the same or analogous synthetic techniques and/or substituting with alternative reagents, the following compounds of the invention were prepared:

3-amino-N-methyl-6-{3-[({3-[2-(4-morpholinyl)ethoxy]benzyl}amino)carbonyl]phe-nyl}-2-pyrazinecarboxamide: $^1$H NMR (400 MHz, $d_6$-DMSO): 9.03 (t, 1H), 8.86 (s, 1H), 8.84 (q, 1H), 8.54 (s, 1H), 8.38 (d, 1H), 7.84 (d, 1H), 7.58 (t, 1H), 7.14 (m, 2H), 6.92 (s, 1H), 6.74 (m, 1H), 4.40 (d, 2H), 4.02 (m, 2H), 3.84 (t, 4H), 2.80 (d, 3H) 2.76 (m, 2H), 2.34 (t, 4H). MS (EI) for $C_{26}H_{30}N_6O_4$: 491.5 (MH+).

3-amino-N-methyl-6-{3-[({4-[2-(4-morpholinyl)ethoxy]benzyl}amino)carbonyl]phe nyl}-2-pyrazinecarboxamide: $^1$H NMR (400 MHz, $d_6$-DMSO): 9.02 (t, 1H), 8.88 (s, 1H), 8.84 (q, 1H), 8.52 (s, 1H), 8.37 (d, 1H), 7.82 (d, 1H), 7.58 (t, 1H), 7.16 (d, 2H), 6.84 (d, 2H), 4.42 (d, 2H), 4.06 (m, 2H), 3.82 (t, 4H), 2.82 (d, 3H) 2.78 (m, 2H), 2.36 (t, 4H). MS (EI) for $C_{26}H_{30}N_6O_4$: 491.5 (MH+).

3-amino-6-(3-{[(2-methoxybenzyl)amino]carbonyl}phenyl)-N-methyl-2-pyrazine-carboxamide: $^1$H NMR (400 MHz, $d_6$-DMSO): 9.03 (t, 1H), 8.86 (s, 1H), 8.84 (q, 1H), 8.52 (s, 1H), 8.40 (d, 1H), 7.82 (d, 1H), 7.56 (t, 1H), 7.20 (m, 2H), 6.96 (m, 2H), 4.44 (d, 2H), 3.64 (s, 3H), 2.84 (d, 3H). MS (EI) for $C_{21}H_{21}N_4O_3$: 392.4 (MH+).

3-amino-N-methyl-6-[3-({[4-(4-methyl-1-piperazinyl) benzyl]amino}carbonyl)phe-nyl]-2-pyrazinecarboxamide: ¹H NMR (400 MHz, d₆-DMSO): 9.04 (t, 1H), 8.86 (s, 1H), 8.82 (dd, 1H), 8.52 (s, 1H), 8.38 (d, 1H), 7.84 (d, 1H), 7.58 (t, 1H), 7.20 (d, 2H), 6.84 (d, 2H), 4.43 (d, 2H), 3.08 (t, 4H), 2.82 (d, 3H), 2.42 (t, 2.20 (s, 3H) MS (EI) for C₂₅H₂₉N₇O₂: 460.2 (MH+).

Example 7

3-amino-6-[3-({[(4-aminophenyl)methyl]amino}carbonyl) phenyl]-N-methylpyrazine-2-carboxamide A solution of 3-{5-amino-6-[(methylamino)carbonyl] pyrazin-2-yl}benzoic acid (0.10 g, 0.37 mmol), HOBt (0.055 g, 0.41 mmol) and HBTU (0.15 g, 0.41 mmol) in DMF (1.2 mL) was stirred at r.t. for 10 min. A solution of [4-(aminomethyl)phenyl]amine (0.050 mL, 0.44 mmol) in DMF (1.0 mL) was added and the resulting solution was stirred for 12 h at r.t. The solution was concentrated in vacuo and the crude mixture was partitioned between EtOAc (100 mL) and brine (50 mL). The organic layer was washed with brine (2×50 mL) and the organic layer was dried (Na₂SO₄), filtered and concentrated in vacuo. The residue was purified via column chromatography (SiO₂, 5% MeOH/CH₂Cl₂) and trituration of the product gave 0.035 g (39% yield) of product: ¹H NMR (400 MHz, d₆-DMSO): 8.95 (t, 1H), 8.91 (s, 1H), 8.84 (m, 1H), 8.50 (m, 1H), 8.37 (dt, 1H), 7.87 (dt, 1H), 7.56 (t, 1H), 7.01 (d, 2H), 6.52 (m, 2H), 4.97 (s, 2H), 4.35 (d, 2H), 2.85 (d, 3H); MS (EI) for C₂₀H₂₀N₆O₂: 377 (MH⁺).

Using the same or analogous synthetic techniques and/or substituting with alternative reagents, the following compounds of the invention were prepared:

3-amino-6-[3-({[(2-aminophenyl)methyl] amino}carbonyl)phenyl]-N-methylpyrazine-2-carboxamide. ¹H NMR (400 MHz, d₆-DMSO): 9.02 (t, 1H), 8.90 (s, 1H), 8.84 (m, 1H), 8.51 (m, 1H), 8.38 (dt, 1), 7.88 (dt, 1H); 7.58 (t; 1H); 7.07 (m, 1H), 6.97 (dt, 1H), 6.63 (dd, 1H), 6.52 (dt, 1H), 5.19 (s, 2H), 4.38 (d, 2H), 2.85 (d, 3H); MS (EI) for C₂₀H₂₀N₆O₂: 377 (MH⁺).

3-amino-6-[3-({[(3 -aminophenyl)methyl] amino}carbonyl)phenyl]-N-methylpyrazine-2-carboxamide. ¹H NMR (400 MHz, d₆-DMSO): 9.03 (t, 1H), 8.91 (s, 1H), 8.84 (m, 1H), 8.53 (m, 1H), 8.39 (dt, 1H), 7.89 (dt, 1H), 7.58 (t, 1H), 6.96 (t, 1H), 6.54 (m, 1H), 6.48 (d, 1H), 6.43 (m, 1H), 5.05 (s, 2H), 4.40 (d, 2H), 2.85 (d, 3H); MS (EI) for C₂₀H₂₀N₆O₂: 377 (MH⁺).

3-amino-6-{3-[({[4-(dimethylamino)phenyl] methyl}amino)carbonyl]phenyl}-N-methylpyrazine-2-carboxamide. ¹H NMR (400 MHz, d₆-DMSO): 9.01 (t, 1H), 8.91 (s, 1H), 8.85 (m, 1H), 8.51 (s, 1H), 8.37 (d, 1H), 7.87 (d, 1H), 7.56 (t, 1H), 7.18 (d, 2H), 6.70 (d, 2H), 4.41 (d, 2H), 2.85 (m, 9H); MS (EI) for C₂₂H₂₄N₆O₂: 405 (MH⁺).

3-amino-6-[3-({[(3-bromophenyl)methyl] amino}carbonyl)phenyl]-N-methylpyrazine-2-carboxamide. ¹H NMR (400 MHz, d₆-DMSO): 9.19 (t, 1H), 8.91 (s, 1H), 8.85 (m, 1H), 8.53 (m, 1H), 8.39 (dt, 1H), 7.89 (dt, 1H), 7.59 (t, 1H), 7.56 (s, 1H), 7.47 (m, 1H), 7.37 (d, 1H), 7.32 (t, 1H), 4.53 (d, 2H), 2.86 (d, 3H); MS (EI) for C₂₀H₁₈N₅O₂Br: 440 (M⁺).

3-amino-6-[3-({[(4-bromophenyl)methyl] amino}carbonyl)phenyl]-N-methylpyrazine-2-carboxamide. ¹H NMR (400 MHz, d₆-DMSO): 9.19 (t, 1H), 8.91 (m, 1H), 8.85 (m, 1H), 8.53 (m, 1H), 8.39 (m, 1H), 7.88 (m, 1H), 7.58 (t, 1H), 7.54 (d, 2H), 7.34 (d, 2H), 4.50 (d, 2H), 2.86 (d, 3H).

3-amino-6-[3-({[(2-bromophenyl)methyl] amino}carbonyl)phenyl]-N-methylpyrazine-2-carboxamide. ¹H NMR (400 MHz, d₆-DMSO): 9.20 (m, 1H), 8.93 (m, 1H), 8.86 (m, 1H), 8.58 (m, 1H), 8.41 (d, 1H), 7.91 (m, 1H), 7.64 (d, 1H), 7.60 (t, 1H), 7.39 (m, 2H), 7.24 (m, 1H), 4.57 (d, 2H), 2.85 (d, 3H); MS (EI) for C₂₀H₁₈N₅O₂Br: 442 (M⁺+2).

Example 8

3-amino-N-methyl-6-[3-({[(3-morpholin-4-ylphenyl)methyl]amino}methyl)phenyl]pyrazine-2-carboxamide Scheme 7 shows how 3-amino-N-methyl-6-[3-({[(3-morpholin-4-ylphenyl)methyl]amino}methyl)phenyl]pyrazine-2-carboxamide was made. (4-Morpholin-4-yl-phenyl)-methanol (xxxiii) was converted to the corresponding amine (xxxiv). Amine (xxxiv) was used to make compound (xxxv) via amide forming reaction, for example using standard amide coupling reagents as depicted in Scheme 7. Exemplary details and further analogous examples are set forth below.

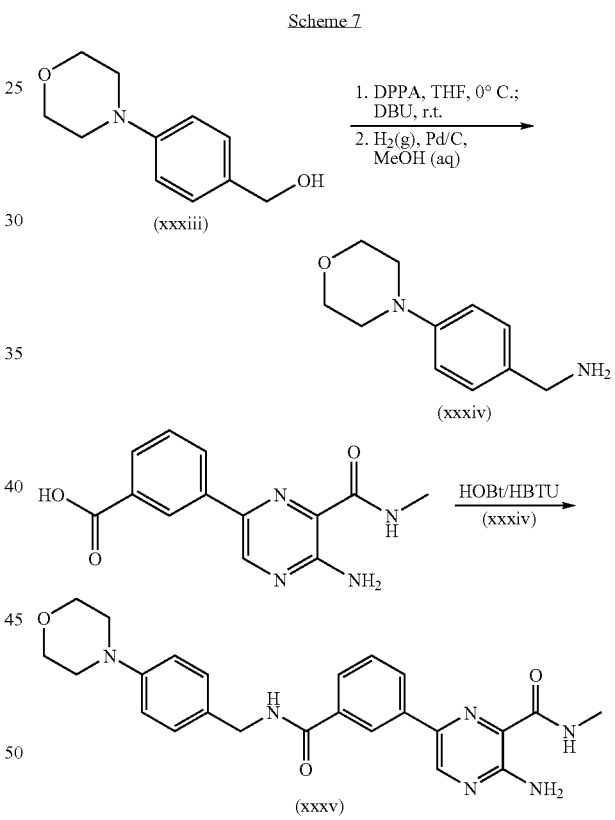

A solution of (3-morpholin-4-ylphenyl)methanol (0.10 g, 0.52 mmol), in THF (1.0 mL) was cooled to 0° C. and DPPA (0.13 mL, 0.62 mmol) was added, followed by DBU (0.093 mL, 0.62 mmol). The solution was allowed to warm to r.t. and stirred for 12 h. The solution was poured into EtOAc (100 mL) and this was washed with H₂O (50 mL) and 5% HCl(aq) (50 mL). The organic layer was dried (Na₂SO₄), filtered and concentrated in vacuo to give 0.16 g (>100% yield) of 4-[3-(azidomethyl)phenyl]morpholine, (TLC: UV active spot, R_f of 0.7 in 1:1 hexanes/EtOAc), which was used without further purification.

To a solution of 10% Pd/Carbon (0.030 g, 0.029 mmol) in 10% aqueous MeOH (4.2 mL) was added 4-[3-(azidomethyl)

phenyl]morpholine (0.16 g, 0.71 mmol) in MeOH (4.2 mL), and the solution was stirred vigorously under a H$_2$(g) balloon for 3 h. The solution was filtered through celite/fritted glass funnel and concentrated in vacuo. The crude residue was purified via HPLC (reverse-phase, CH$_3$CN/H$_2$O with 0.1% TFA) and fractions containing the desired product were concentrated in vacuo, to provide 0.064 g (29% yield) of [(3-morpholin-4-ylphenyl)methyl]amine trifluoroacetate.

A solution of 3-{5-amino-6-[(methylamino)carbonyl] pyrazin-2-yl}benzoic acid (0.081 g, 0.30 mmol), HOBt (0.048 g, 0.36 mmol) and HBTU (0.17 g, 0.45 mmol) in DMF (1.0 mL) was stirred at r.t. for 10 min. A solution of [(3-morpholin-4-ylphenyl)methyl]amine trifluoroacetate (0.13 g, 0.30 mmol) in DMF (1.0 mL) was added and the resulting solution was stirred for 12 h at r.t. The solution was concentrated in vacuo and the crude mixture was purified via HPLC (reverse-phase, CH$_3$CN/H$_2$O with 0.1% TFA). Upon removal of CH$_3$CN/H$_2$O, the product was taken up in EtOAc (100 mL) and washed with 1M NaOH(aq) (50 mL). The organic layer was dried (Na$_2$SO$_4$), filtered and concentrated in vacuo. Trituration and collection of a solid by vacuum filtration provided 11.6 mg (and treated with Bio-Rad AG 1-X8 resin (hydroxide form) until pH 8. The product was filtered and concentrated in vacuo, to provide 14.1 mg (9% yield) of 3-amino-N-methyl-6-[3-({[(3-morpholin-4-ylphenyl)methyl]amino}methyl) phenyl]pyrazine-2-carboxamide: $^1$H NMR (400 MHz, d$_6$-DMSO): 9.15 (t, 1H), 8.91 (s, 1H), 8.87 (m, 1H), 8.55 (s, 1H), 8.37 (d, 1H), 7.88 (d, 1H), 7.57 (t, 1H), 7.19 (t, 1H), 6.95 (s, 1H), 6.82 (m, 2H), 4.48 (d, 2H), 3.72 (t, 4H), 3.08 (t, 2H), 2.85 (d, 3H); MS (EI) for C$_{24}$H$_{26}$N$_6$O$_3$: 447 (MH$^+$).

Using the analogous synthetic techniques beginning from commercially available [(2-morpholin-4-ylphenyl)methyl] amine and [(4-morpholin-4-ylphenyl)methyl]amine, the following compounds of the invention were prepared:

3-amino-N-methyl-6-[3-({[(2-morpholin-4-ylphenyl)methyl]amino}methyl) phenyl]pyrazine-2-carboxamide: $^1$H NMR (400 MHz, d$_6$-DMSO): 9.06 (t, 1H), 8.92 (s, 1H), 8.85 (m, 1H), 8.56 (s, 1H), 8.39 (d, 1H), 7.91 (d, 1H), 7.58 (t, 1H), 7.31 (d, 1H), 7.25 (t, 1H), 7.15 (d, 1H), 7.09 (t, 1H), 4.65 (d, 2H), 3.77 (m, 4H), 2.89 (m, 2H), 2.85 (d, 3H); MS (EI) for C$_{24}$H$_{26}$N$_6$O$_3$: 447 (MH$^+$).

3-amino-N-methyl-6-[3-({[(4-morpholin-4-ylphenyl)methyl]amino}methyl)phenyl]pyrazine-2-carboxamide: $^1$H NMR (400 MHz, d$_6$-DMSO): 9.16 (t, 1H), 8.91 (s, 1H), 8.88 (m, 1H), 8.56 (s, 1H), 8.37 (dt, 1H), 7.88 dt, 1H), 7.56 (t, 1H), 7.23 (d, 2H), 6.91 (d, 2H), 4.43 (d, 2H), 3.72 (m, 4H), 3.06 (m, 2H), 2.85 (d, 3H); MS (EI) for C$_{24}$H$_{26}$N$_6$O$_3$: 447 (MH$^+$).

Methyl 3-{5-amino-6-[(cyclopropylamino)carbonyl] pyrazin-2-yl}benzoate: A mixture of 3-amino-6-bromopyrazine-2-cyclopropylcarboxamide (5.0 g, 19.4 mmole), [1,1'bis-(diphenylphosphino)ferrocene]dichloropalladium (II)-dichloromethane complex (0.88 g, 1.9 mmol), 3-carbomethoxyphenylboronic acid (4.2 g, 23.3 mmol) in DMF (30 mL) was de-gassed with nitrogen. Triethylamine (5.4 mL, 38.9 mmol) was then added and the resulting mixture was heated at 85° for 2.5 hours. The reaction mixture was cooled to room temperature, diluted with ethyl acetate (200 mL), filtered over silica gel, washed with saturated sodium bicarbonate solution (150 mL), dried over sodium sulfate, filtered, and concentrated. The oily residue was purified by flash chromatography (silica gel, eluted with ethyl acetate-hexanes gradient from 15% to 80% yield) to give methyl 3-{5-amino-6-[(cyclopropylamino)carbonyl]pyrazin-2-yl}benzoate (a tan color solid, 4.5 g, 74% yield): $^1$H NMR (400 MHz, DMSO-d$_6$): 8.67 (s, 1H), 8.50-8.49 (t, 1H), 8.07-8.03 (m, 2H), 7.57- 7.54 (t, 1M), 3.98 (s, 3H), 2.91-2.88 (m, 1H), 0.94-0.85 (m, 2H), 0.72-0.62 (m, 2H); MS (EI) for C$_{16}$H$_{16}$N$_4$O$_3$: 428 (MH$^+$).

Methyl 3-{5-amino-6-[(ethylamino)carbonyl]pyrazin-2-yl}benzoate: A mixture of 3-amino-6-bromopyrazine-2-ethylcarboxamide (5.0 g, 20.4 mmol), [1,1'bis-(diphenylphosphino)ferrocene]dichloropalladium(II)-dichloromethane complex (0.93 g, 2.04 mmol), 3-carbomethoxyphenylboronic acid (4.4 g, 24.4 mmol) in DMF (30 mL) was de-gassed with nitrogen. Triethylamine (5.7 mL, 40.1 mmol) was then added and the resulting mixture was heated at 85° for 2.5 hours. The reaction mixture was cooled to room temperature, diluted with ethyl acetate (200 mL), filtered over silica gel, washed with saturated sodium bicarbonate solution (150 mL), dried over sodium sulfate, filtered, and concentrated. The oily residue was purified by flash chromatography (silica gel, eluted with ethyl acetate-hexanes gradient from 15% to 80% yield) to give methyl 3-{5-amino-6-[(ethylamino)carbonyl] pyrazin-2-yl}benzoate (4.3 g, 70% yield): $^1$H NMR (400 MHz, CDCl$_3$): 8.66 (s, 1H), 8.53-8.52 (t, 1H), 8.08-8.06 (m, 2H), 8.00 (b, 1H), 3.5 (t, 1H), 3.97 (s, 3H), 2.91-2.88 (m, 1H), 0.94-0.85 (m, 2H), 0.72-0.62 (m, 2H); MS (EI) for C$_{15}$H$_{16}$N$_4$O$_3$: 301 (MH$^+$).

3-amino-N-ethyl-6-(3-{[(phenylmethyl)amino] carbonyl}phenyl)pyrazine-2-carboxamide: Methyl 3-{5-amino-6-[(ethylamino)carbonyl]pyrazin-2-yl}benzoate (480 mg, 1.6 mmol) was suspended in a 20 mL of 1:1 MeOH-5% aqueous sodium hydroxide and heated at 90-95° C. for 4 hours. The homogeneous reaction mixture was cooled to room temperature, concentrated to half the initial volume, cooled in an ice-bath, and acidified to pH of 4 with concentrated HCl. A white solid precipitated and was collected, washed with water and dried in vacuo to give 3-{5-amino-6-[(ethylamino)carbonyl]pyrazin-2-yl}benzoic acid (445 mg, 97% yield). The pyrazine acid (40 mg, 0.14 mmol) was dissolved in DMF (1 mL), and then 1-hydroxybenzotriazole (30 mg, 0.22 mmol), 1-[(3-dimethylamino)propyl]-3-ethylcarbodiimide hydrochloride (30 mg, 0.16 mmol), and 4-methylmorpholine (30 mg, 0.28 mol) were added sequentially. After one hour benzylamine (30 mg, 0.27 mmol) was added to the reaction mixture and stirring was continued at room temperature for 18 hours. The mixture was then diluted with ethyl acetate (10 mL), washed with water, saturated sodium bicarbonate solution then brine and dried over sodium sulfate, filtered, and concentrated. The oily residue was purified by flash chromatography (silica gel, eluted with ethyl acetate-hexanes gradient from 15% to 80% yield) to give 3-amino-N-ethyl-6-(3-{[(phenylmethyl)amino]carbonyl}phenyl) pyrazine-2-carboxamide (a tan color solid, 22 mg, 42% yield): $^1$H NMR (400 MHz, DMSO-d$_6$): 9.14 (s, 1H), 8.88 (s, 1H), 8.87-8.85 (b, 1H), 8.51 (s, 1H), 8.37-8.34 (d, 1H), 7.87-7.85 (d, 1H), 7.63-7.59 (b, 1H), 7.58-7.54 (t, 1), 7.34-7.23 (m, 4H), 4.53-4.52 (d, 2H), 3.38-3.29 (m, 2H), 1.17-1.14 (t, 3H); MS (EI) for C$_{21}$H$_{21}$N$_5$O$_2$: 376 (MH$^+$).

3-amino-6-[3-({[(2-chloro-6-fluorophenyl)methyl] amino}carbonyl)phenyl]-N-ethylpyrazine-2-carboxamide: Methyl 3-{5-amino-6-[(ethylamino)carbonyl]pyrazin-2-yl}benzoate (480 mg, 1.6 mmol) was suspended in a 20 mL of 1:1 MeOH-5% aqueous sodium hydroxide and heated at 90-95° C. for 4 hours. The homogeneous reaction mixture was cooled to room temperature, concentrated to half the initial volume, cooled in an ice-bath, and acidified to pH 4 with concentrated HCl. A white solid precipitated and was collected by filtration, washed with water and dried in vacuo to give 3-{5-amino-6-[(ethylamino)carbonyl]pyrazin-2-yl}benzoic acid (445 mg, 97% yield). The acid (40 mg, 0.14 mol) was dissolved in DMF (1 mL) and 1-hydroxybenzotriazole (30 mg, 0.22 mmol), 1-[(3-dimethylamino)propyl]-3-ethylcarbodiimide hydrochloride (30 mg, 0.16 mmol), and 4-methylmorpholine (30 mg, 0.28 mol) were added sequentially. After one hour, 2-chloro-6-fluorobenzylamine (30 mg, 0.19 mmol) was added to the reaction mixture and stirring was continued at room temperature for 18 hours. It was then diluted with ethyl acetate (10 mL), washed with water, saturated sodium bicarbonate solution, and brine, dried over sodium sulfate, filtered, and concentrated. The oily residue was purified by flash chromatography (silica gel, eluted with ethyl acetate-hexanes gradient from 15% to 80% yield) to give 3-amino-6-[3-({[(2-chloro-6-fluorophenyl)methyl]amino}carbonyl)phenyl]-N-ethylpyrazine-2-carboxamide (a tan color solid, 31 mg, 51% yield): $^1$H NMR (400 MHz, DMSO-$d_6$): 8.86 (s, 1H), 8.85-8.83 (b, 1H), 8.45 (s, 1H), 8.33-8.31 (d, 1H), 7.83-7.81 (d, 1H), 7.53-7.51 (t, 1H), 7.39-7.34 (m, 2H), 7.26-7.21 (t, 1H), 4.63-4.61 (d, 2H), 3.38-3.29 (m, 2H), 1.15-1.11 (t, 3H); MS (EI) for $C_{21}H_{19}ClFN_5O_2$: 428 (MH$^+$).

3-amino-N-cyclopropyl-6-(3-{[(phenylmethyl)amino]carbonyl}phenyl)pyrazine-2-carboxamide: Methyl 3-{5-amino-6-[(cyclopropylamino)carbonyl]pyrazin-2-yl}benzoate (480 mg, 1.5 mmol) was suspended in a 20 mL of 1:1 MeOH-5% aqueous sodium hydroxide and heated at 90-95° C. for 4 hours. The homogeneous reaction mixture was cooled to room temperature, concentrated to half the initial volume, cooled in an ice-bath, and acidified to pH 4 with concentrated HCl. A white solid precipitated and was collected by filtration, washed with water and dried in vacuo to give the intermediate 3-{5-amino-6[(cyclopropylamino)carbonyl]pyrazin-2-yl}benzoic acid. The acid (40 mg, 0.13 mmol) was dissolved in DMF (1 mL) and 1-hydroxybenzotriazole (30 mg, 0.22 mmol), 1-[(3-dimethylamino)propyl]-3-ethylcarbodiimide hydrochloride (30 mg, 0.16 mmol), and 4-methylmorpholine (30 mg, 0.28 mol) were added sequentially. After one hour benzylamine (30 mg, 0.27 mmol) was added to the reaction mixture and stirring was continued at room temperature for 18 hours. It was then diluted with ethyl acetate (10 mL), washed with water, saturated sodium bicarbonate solution, and brine, dried over sodium sulfate, filtered, and concentrated. The oily residue was purified by flash chromatography (silica gel, eluted with ethyl acetate-hexanes gradient from 15% to 80% yield) to give 3-amino-N-cyclopropyl-6-(3-{[(phenylmethyl)amino]carbonyl}phenyl)pyrazine-2-carboxamide (a tan color solid, 23 mg, 44% yield): $^1$H NMR (400 MHz, DMSO-$d_6$): 9.14 (t, 1H), 8.88 (s, 1H), 8.69-8.68 (d, 1H), 8.51 (s, 1H), 8.34-8.32 (d, 1H), 7.87-7.85 (d, 1H), 7.63-7.59 (b, 1H), 7.57-7.53 (t, 1H), 7.34-7.23 (m, 4H), 4.53-4.52 (d, 2H), 2.84-2.82 (m, 1H), 0.75-0.70 (m, 4H); MS (EI) for $C_{22}H_{21}N_5O_2$ 388 (MH$^+$).

3-amino-6-[3-({[(2-chloro-6-fluorophenyl)methyl]amino}carbonyl)phenyl]-N-cyclopropylpyrazine-2-carboxamide: Methyl 3-{5-amino-6-[(cyclopropylamino)carbonyl]pyrazin-2-yl}benzoate (480 mg, 1.5 mmol) was suspended in a 20 mL of 1:1 MeOH-5% aqueous sodium hydroxide and heated at 90-95° C. for 4 hours. The homogeneous reaction mixture was cooled to room temperature, concentrated to half the initial volume, cooled in an ice-bath, and acidified to pH 4 with concentrated HCl. A white solid precipitated and was collected by filtration, washed with water and dried in vacuo to give the intermediate 3-{5-amino-6-[(cyclopropylamino)carbonyl]pyrazin-2-yl}benzoic acid. The acid (40 mg, 0.13 mmol) was dissolved in DMF (1 mL) and 1-hydroxybenzotriazole (30 mg, 0.22 mmol), 1-[(3-dimethylamino)propyl]pyrazin-2-ethylcarbodiimide hydrochloride (30 mg, 0.16 mmol), and 4-methylmorpholine (30 mg, 0.28 mol) were added sequentially. After one hour 2-chloro-6-fluorobenzylamine (30 mg, 0.19 mmol) was added to the reaction mixture and stirring was continued at room temperature for 18 hours. It was then diluted with ethyl acetate (10 mL), washed with water, saturated sodium bicarbonate solution, and brine, dried over sodium sulfate, filtered, and concentrated. The oily residue was purified by flash chromatography (silica gel, eluted with ethyl acetate-hexanes gradient from 15% to 80% yield) to give 3-amino-6-[3-({[(2-chloro-6-fluorophenyl)methyl]amino}carbonyl)phenyl]-N-cyclopropyl-pyrazine-2-carboxamide (a tan color solid, 23 mg, 56% yield): $^1$H NMR (400 MHz, DMSO-$d_6$): 8.87-8.86 (t, 1H), 8.85-8.83 (b, 1H), 8.65-8.64 (d, 1H), 8.45 (s, 1H), 7.83-7.81 (d, 1H), 7.53-7.51 (t, 1H), 7.41-7.39 (m, 2H), 7.26-7.21 (t, 1H), 4.63-4.61 (d, 2H), 2.85-2.81 (m, 1H), 0.73-0.64 (m, 4H); MS (EI) for $C_{22}H_{19}ClFN_5O_2$: 440 (MH$^+$).

3-amino-N-methyl-6-{3-[(2-phenylhydrazino)carbonyl]phenyl}pyrazine-2-carboxamide: 3-{5-amino-6-[(methylamino)carbonyl]pyrazin-2-yl}benzoic acid (40 mg, 0.15 mmol) was dissolved in DMF (1 mL) and 1-hydroxybenzotriazole (30 mg, 0.22 mmol), 1-[(3-dimethylamino)propyl]-3-ethylcarbodiimide hydrochloride (30 mg, 0.16 mmol), and 4-methylmorpholine (30 mg, 0.28 mol) were added sequentially. After one hour phenylhydrazine (30 mg, 0.27 mmol) was added to the reaction mixture and stirring was continued at room temperature for 18 hours. It was then diluted with ethyl acetate (10 mL), washed with water, saturated sodium bicarbonate solution, and brine, dried over sodium sulfate, filtered, and concentrated. The oily residue was purified by flash chromatography (silica gel, eluted with ethyl acetate-hexanes gradient from 15% to 80% yield) to give 3-amino-N-methyl-6-{3-[(2-phenylhydrazino)carbonyl]phenyl}pyrazine-2-carboxamide (a tan color solid, 30 mg, 56% yield): $^1$H NMR (400 MHz, DMSO-$d_6$): 10.42 (b, 1H), 8.92 (s, 1H), 8.84-8.82 (b, 1H), 8.57-8.57 (s,1H0, 8.41-8.39 (d, 1H), 7.94-7.89(m, 1H), 7.89-7.86 (d, 1H), 7.61-7.57 (t, 1H), 7.17-7.13 (t, 1H), 6.83-6.80 (d, 1H), 6.73-6.69(m, 1H), 2.85 (s, 3H); MS (EI) for $C_{19}H_{18}N_6O_2$: 440 (MH$^+$).

Example 9

4-{5-amino-6-[(methylamino)carbonyl-]pyrazin-2-yl}benzoic acid

Phenylmethyl 4-{5-amino-6-[(methylamino)carbonyl]pyrazin-2-yl}benzoate: To a stirred mixture of 3-amino-6-bromo-N-methyl-2-pyrazinecarboxamide (0.577 g, 2.5 mmol), 4-benzyloxycarbonylphenylboronic acid (0.768 g, 3.0 mmol), triethylamine (1.01 g, 10 mmol) in 10 mL of DMF was added [1,1'-bis(diphenylphosphino)-ferrocene]dichloropalladium(II) complex with dichloromethane (1:1), (20.4 mg, 0.025 mmol). The stirred mixture was warmed to 80-90° C. for 12 h and then concentrated on a rotary evaporator under reduced pressure. The residue was dissolved in 50 mL of EtOAc, washed with brine (30 mL). The organic layer was filtered through celite, and then dried over anhydrous sodium sulfate. Filtration, concentration and column chromatography on silica EtOAc gave a solid (450 mg, 59.7% yield). $^1$H NMR (400 MHz; DMSO-$d_6$): 8.91 (s, 1H); 8.84 (br s, 1H); 8.33 (d, 2H); 8.02 (d, 2H); 7.30-7.48 (m, 5H); 5.38 (s, 2H); 2.86 (s, 3M); MS (EI) for $C_{20}H_{15}N_4O_3$: 363 (MH$^+$).

4-{5-amino-6-[(methylamino)carbonyl]pyrazin-2-yl}benzoic acid: A flask was charged with phenylmethyl 4-[5-amino-6-(methylamino)carbonyl) pyrazin-2-yl}benzoate (0.37 g, 1.01 mmol) and 10 mL of a solution of 1 N aqueous LiOH. The mixture was refluxed for 15 min. and then allowed to cool to room temperature. The mixture was extracted with ethyl acetate (10 mL). The pH of the aqueous phase was adjusted to pH of 2-3 with 10% aqueous HCl. The resulting solid product was collected by filtration, washed with water, and dried, to afford 4-{5-amino-6-[(methylamino)carbonyl]pyrazin-2-yl}benzoic acid (0.150 mg, 54.2% yield): $^1$H NMR (400 MHz; DMSO-$d_6$): 8.93 (s, 1H); 8.80 (br s, 1H); 8.30 (d, 2H); 8.41 (d, 1H); 8.0 (d, 2H); 2.86 (d, 3H); MS (EI) for $C_{13}H_{12}N_4O_3$: 273 (MH$^+$).

3-amino-N-methyl-6-(4-{[(phenylmethyl)amino]carbonyl}phenyl)pyrazine-2-carboxamide: $^1$H NMR (400 MHz; DMSO-$d_6$): 9.18 (m, 1H); 8.95 (s, 1H); 8.90 (m, 1H); 8.3 (d, 2H); 8.0 (d, 2H); 7.37 (m, 5H); 4.5 (d, 2H); 2.87 (d, 3H); MS (EI) for $C_{20}H_{19}N_5O_2$: 362 (MH$^+$).

3-amino-N-methyl-6-(4-{[(2-phenylethyl)amino]carbonyl}phenyl)pyrazine-2-carboxamide: MS (EI) for $C_{21}H_{21}N_5O_2$: 376 (MH$^+$)

3-amino-6-[4-({[(2,4-dichlorophenyl)methyl]amino}carbonyl)phenyl]-N-methylpyrazine-2-carboxamide: $^1$H NMR (400 MHz; DMSO-$d_6$): 9.18 (m, 1H); 8.97 (s, 1H); 8.90 (m, 1H); 8.3 (d, 2H); 8.0 (d, 2H); 7.62 (c, 1H); 7.4 (m, 2H); 4.53 (d, 2H); 2.87 (d, 3H); MS (EI) for $C_{20}H_{17}N_5O_2Cl_2$: 430 (MH$^+$)

3-amino-N-methyl-6-[4-({[(4-methylphenyl)methyl]amino}carbonyl)phenyl]pyrazine-2-carboxamide: $^1$H NMR (400 MHz; DMSO-$d_6$): 9.1 (m, 1H); 8.97 (s, 1H); 8.90 (m, 1H); 8.3 (d, 2H); 8.0 (d, 2H); 7.2-7.1 (m, 5H); 4.53 (d, 2H); 2.87 (d, 3H); 2.25 (s, 3H); MS (EI) for $C_{21}H_{21}N_5O_2$: 376 (MH$^+$)

3-amino-6-(4-{[(1S)-2,3-dihydro-1H-inden-1-ylamino]carbonyl}phenyl)-N-methylpyrazine-2-carboxamide: MS (EI) for $C_{22}H_{21}N_5O_2$: 388 (MH$^+$)

3-amino-N-methyl-6-[3-({[(2,4,6-trichlorophenyl)methyl]amino}carbonyl)phenyl]pyrazine-2-carboxamide: $^1$H NMR (400 MHz; DMSO-$D_6$): 8.86 (s, 1H); 8.8 (m, 1H); 8.68 (m, 1H); 8.42 (s, 1H); 8.34 (d, 1H); 7.8 (d, 1H); 7.54 (t, 1H); 7.46 (s, 1H); 7.34 (s, 1H); 4.6 (d, 2H); 2.85 (d, 3H); 2.43 (s, 3H); MS (EI) for $C_{20}H_{16}N_5O_2Cl_3$: 465 (MH$^+$)

3-amino-6-[3-({[(3-chloro-2-methylphenyl)methyl]amino}carbonyl)phenyl]-N-methylpyrazine-2-carboxamide: $^1$H NMR (400 MHz; DMSO-$D_6$): 9.25 (t, 1H); 8.88 (s, 1H); 8.82 (m, 1H); 8.5 (m, 1H); 8.38 (d, 1H); 7.86 (d, 1H); 7.56 (t, 1H); 1H); 7.34 (d, 1H); 7.28 (d, 1H); 7.2 (t, 1H); 4.5 (d, 2H); 2.85 (d, 3H); MS (EI) for $C_{21}H_{20}N_5O_2Cl$: 410 (MH$^+$)

3-amino-6-{3-[({[2,5-bis(methyloxy)phenyl]methyl}amino)carbonyl]phenyl}-N-methylpyrazine-2-carboxamide: $^1$H NMR (400 MHz; DMSO-$D_6$): 8.95 (t, 1H); 8.9 (s, 1H); 8.68 (m, 1H); 8.8 (m, 1H); 8.52 (s, 1H); 8.36 (d, 1H); 7.84 (d, 1H); 7.54 (t, 1H); 6.9 (d, 1H); 6.8 (m, 3H); 4.6 (d, 2H); 3.8 (s, 3H); 3.62 (s, 3H); 2.85 (d, 3H); MS (EI) for $C_{21}H_{21}N_5O_2$: 422 (MH$^+$)

3-amino-6-[3-({[(3-fluoro-4-methylphenyl)methyl]amino}carbonyl)phenyl]-N-methylpyrazine-2-carboxamide: $^1$H NMR (400 MHz; DMSO-$D_6$): 9.1 (t, 1H); 8.85 (s, 1H); 8.8 (m, 1H); 8.52 (s, 1H); 8.38 (d, 1H); 7.85 (d, 1H); 7.58 (t, 1H); 7.2 t, 1H); 4.45 (d, 2H); 2.85 (d, 3H); 2.2 (s, 3H); MS (EI) for $C_{21}H_{21}N_5O_2$: 394 (MH$^+$)

3-amino-6-[3-({[(2-chloro-6-fluoro-3-methylphenyl)methyl]amino}carbonyl)phenyl]-N-methylpyrazine-2-carboxamide: $^1$H NMR (400 MHz; DMSO-$D_6$): 8.85 (s, 1H); 8.8 (m, 1H); 8.53 (s, 1H); 8.38 (d, 1H); 7.8 (d, 1H); 7.56 (t, 1H); 7.2 (m, 1H); 7.15 (t, 1H); 4.6 (d, 2H); 2.85 (d, 3H); MS (EI) for $C_{21}H_{19}N_5O_2FCl$: 428 (MH$^+$)

3-amino-6-[3-({[(2-chloro-3,6-difluorophenyl)methyl]amino}carbonyl)phenyl]-N-methylpyrazine-2-carboxamide: $^1$H NMR (400 MHz; DMSO-$D_6$): 8.9 (t, 1H); 8.85 (s, 1H); 8.8 (m, 1H); 8.49 (s, 1H); 8.38 (d, 1H); 7.8 (d, 1H); 7.56 (t, 1H); 7.45 (m, 1H); 7.3 (m, 1H); 4.6 (d, 2H); 2.85 (d, 3H); 2.3 (s, 3H); MS (EI) for $C_{20}H_{16}N_5O_2F_2Cl$: 432 (MH$^+$)

3-amino-6-[3-({[(2,3-difluoro-4-methylphenyl)methyl]amino}carbonyl)phenyl]-N-methylpyrazine-2-carboxamide: $^1$H NMR (400 MHz; DMSO-$D_6$): 9.1 (t, 1H); 8.9 (s, 1H); 8.8 (m, 1H); 8.53 (s, 1H); 8.38 (d, 1H); 7.8 (d, 1H); 7.56 (t, 1H); 7.1 (m, 1H); 4.5 (d, 2H); 2.85 (d, 3H); 2.23 (s, 3H); MS (EI) for $C_{21}H_{19}N_5O_2F_2$: 412 (MH$^+$)

Example 10

3-Amino-N-methyl-6-{3-[(methylsulfonyl)amino]phenyl}pyrazine-2-carboxamide 3-amino-6-(3-aminophenyl)-N-methylpyrazine-2-carboxamide: To a solution of 3-amino-6-bromo-pyrazine-2-carboxylic acid methylamide (1.234 g, 5.30 mmol, 1.00 equiv.) in N,N-dimethylformamide (DMF, 30 mL) was added [1,1'-bis(diphenylphosphino)-ferrocene]dichloropalladium (II) complex with dichloromethane (1:1), (Aldrich Chemical Company, 433 mg, 0.530 mmol, 0.100 equiv.), 3-aminophenylboronic acid monohydrate (Aldrich Chemical Company, 1.149 g, 7.41 mmol, 1.40 equiv.), and triethylamine (TEA, 1.073 g, 10.6 mmol, 2.00 equiv.). Nitrogen was passed through the solution for 3-5 min. The reaction mixture was heated at 85-90° C. for 15 h with stirring. The reaction was allowed to cool to room temperature and diluted with 400 mL of EtOAc. The mixture was washed with saturated aqueous NaHCO$_3$ (2×50.0 mL), saturated aqueous NaCl (1×50.0 mL), dried over magnesium sulfate (MgSO$_4$), and filtered. The filtrate was concentrated on a rotary evaporator under reduced pressure. To the crude product was added 30 mL of a 4.0M solution of anhydrous HCl in dioxane. The resulting solid was filtered and rinsed with 20% methanol in diethyl ether to remove impurities. The solid was dissolved in methanol and neutralized with sufficient AG 1-X8 Resin (hydroxide form) that the pH of the solution became basic. The mixture was filtered, and the filtrate was concentrated on a rotary evaporator at reduced pressure to afford the title compound (0.695 g, 54% yield).

Example 11

3-amino-N-methyl-6-{3-[(methylsulfonyl)amino]phenyl}pyrazine-2-carboxamide 3-amino-N-methyl-6-{3-[(methylsulfonyl)amino]phenyl}pyrazine-2-carboxamide: To a solution of 3-amino-6-(3-aminophenyl)-N-methylpyrazine-2-carboxamide (26 mg, 0.11 mmol) in dry dichloromethane (2 mL) at 0° C. were added triethylamine (22 mg, 0.22 mmol) and methanesulfonyl chloride (20 mg, 0.17 mmol). The reaction was slowly warmed to room temperature and stirred overnight. Reaction was treated water (10 mL) and diluted with ethyl acetate (100 mL). The organic layer was washed with saturated aqueous sodium bicarbonate (40 mL) and saturated aqueous sodium chloride (30 mL), dried over magnesium sulfate, filtered, and concentrated to afford 3-amino-N-methyl-6-{3-[(methylsulfonyl)amino]phenyl}pyrazine-2-carboxamide (15 mg, 45% yield) as yellow solid. $^1$H NMR (400 MHz, CDCl$_3$): 8.62 (s, 1H), 7.94 (br s, 1H), 7.75 (br s, 1H), 7.68 (br d, 1H), 7.45 (t, 1H), 7.30 (br d, 1H), 7.25 (br s, 1H), 3.02 (m, 6H); MS (EI) for $C_{13}H_{15}N_5O_3S$: 322 (MH$^+$).

Example 12

3-Amino-N-methyl-6-[3-({[4-(methyloxy)phenyl]carbonyl}amino)phenyl]pyrazine-2-carboxamide To a solution of 3-amino-6-(3-aminophenyl)-N-methylpyrazine-2-carboxamide (20 mg, 0.07 mmol) and triethylamine (160 mg, 0.16 mmol) in tetrahydrofuran (1 mL) was added p-anisoyl chloride (20 mg, 0.12 mmol) slowly at room temperature. The mixture was allowed to stir overnight. The reaction was quenched with water (10 mL) at 0° C. and diluted with ethyl acetate (200 mL). The organic layer was washed with saturated aqueous sodium bicarbonate (30 mL), saturated aqueous sodium chloride, and dried over magnesium sulfate. The solution was filtered and concentrated at reduced pressure to afford 3-amino-N-methyl-6-[3-({[4-(methyloxy)phenyl]carbonyl}amino)phenyl]pyrazine-2-carboxamide (13 mg, 48% yield) as yellow solid. $^1$H NMR (400 MHz, d$_6$-DMSO): 10.10 (s, 1H), 8.85 (s, 2H), 8.30 (s, 1H), 8.02 (d, 2H), 7.90 (m, 2H), 7.40 (m, 1H), 7.02 (d, 2H), 3.80 (s, 3H), 2.82 (br s, 3H); MS (EI) for $C_{20}H_{19}N_5O_3$: 378 (MH$^+$).

Using the same or analogous synthetic techniques and/or substituting with alternative reagents as described above, the following compounds of the invention were prepared:

3-amino-N-methyl-6-{3-[(phenylcarbonyl)amino]phenyl}pyrazine-2-carboxamide: $^1$H NMR (400 MHz, d$_6$-DMSO): 10.60 (s, 1H), 8.72 (m, 2H), 8.30 (s, 1H), 8.05 (d, 2H), 7.92 (d, 1H), 7.82 (d, 1H), 7.60 (m, 3H), 7.45 (t, 1H), 2.86 (d, 3H); MS (EI) for $C_{19}H_{17}N_5O_2$: 348 (MH$^+$).

3-amino-N-methyl-6-[3-({[3-(methyloxy)phenyl]carbonyl}amino)phenyl]pyrazine-2-carboxamide: $^1$H NMR (400 MHz, d$_6$-DMSO): 10.50 (s, 1H), 8.72 (br s, 2H), 8.30 (s, 1H), 7.92 (d, 1H), 7.85 (d, 1H), 7.50 (m, 6H), 7.20 (d, 1H), 3.90 (s, 3H), 2.90 (s, 3H); MS (EI) for $C_{20}H_{19}N_5O_3$: 378 (MH$^+$).

3-Amino-6-(3-{[(4-chlorophenyl)carbonyl]amino}phenyl)-N-methylpyrazine-2-carboxamide: $^1$H NMR (400 MHz, d$_6$-DMSO): 10.35 (s, 1H), 8.70 (br s, 2H), 8.25 (br s, 1H), 8.02 (br d, 2H), 7.92 (br d, 1H), 7.82 (br d, 1H), 7.65 (m, 2H), 7.40 (t, 1H), 2.92 (s, 3H); MS (EI) for $C_{19}H_{16}N_5O_2Cl$: 382 (MH$^+$).

3-Amino-N-methyl-6-(3-{[(4-methylphenyl)carbonyl]amino}phenyl)pyrazine-2-carboxamide: $^1$H NMR (400 MHz, d$_6$-DMSO): 10.20 (s, 1H), 8.70 (br s, 2H), 8.25 (s, 1H), 7.82 (m, 4H), 7.40 (t, 1H), 7.15 (d, 2H), 2.80 (d, 3H), 2.40 (s, 3H); MS (EI) for $C_{20}H_{19}N_5O_2$: 362 (MH$^+$).

3-Amino-6-{3-[(furan-2-ylcarbonyl)amino]phenyl}-N-methylpyrazine-2-carboxamide: $^1$H NMR (400 MHz, d$_6$-DMSO): 10.20 (s, 1H), 8.70 (br s, 2H), 8.24 s, 1H), 7.95 (s, 1H), 7.92 (d, 1H), 7.80 (d, 1H), 7.40 (t, 1H), 7.26 (br s, 1H), 6.70 (br s, 1H), 2.80 (d, 3H); MS (EI) for $C_{17}H_{15}N_5O_3$: 338 (MH$^+$).

3-Amino-N-methyl-6-[3-({[3-(phenyloxy)phenyl]carbonyl}amino)phenyl]pyrazine-2-carboxamide: $^1$H NMR (400 MHz, d$_6$-DMSO): 8.75 (m, 2H), 8.28 (br s, 1H), 7.92 (d, 1H), 7.83 (br t, 2H), 7.64 (m, 1H), 7.58 (t, 1H), 7.45 (m, 4H), 7.26 (dd, 1H), 7.20 (br t, 1H), 7.12 (br d, 2H), 2.85 (d, 3H); MS (EI) for $C_{25}H_{21}N_5O_3$: 440 (MH$^+$).

3-Amino-6-{3-[(cyclopentylcarbonyl)amino]phenyl}-N-methylpyrazine-2-carboxamide: $^1$H NMR (400 MHz, d$_6$-DMSO): 9.92 (s, 1H), 8.70 (m, 2H), 8.10 (br s, 1H), 7.92 (d, 1H), 7.70 (d, 1H), 7.40 (t, 1H), 2.90 (m, 4H), 1.75 (br m, 8H); MS (EI) for $C_{18}H_{21}N_5O_2$: 340 (MH$^+$).

3-Amino-6-(3-{[(4-cyanophenyl)carbonyl]amino}phenyl)-N-methylpyrazine-2-carboxamide: $^1$H NMR (400 MHz, d$_6$-DMSO): 10.55 (br s, 1H), 8.70 (br s, 2H), 8.30 (br s, 1H), 8.15 (br d, 2H), 8.05 (br d, 2H), 7.92 (br d, 1H), 7.82 (br d, 1H), 7.40 (br t, 1H), 2.82 (br s, 3H); MS (EI) for $C_{20}H_{16}N_6O_2$: 373 (MH$^+$).

Example 13

3-Amino-N-methyl-6-[3-({[(phenylmethyl)amino]carbonyl}amino)phenyl]pyrazine-2-carboxamide 3-amino-N-methyl-6-[3-({[(phenylmethyl)amino]carbonyl}amino)phenyl]pyrazine-2-carboxamide: To a solution of 3-amino-6-(3-aminophenyl)-N-methylpyrazine-2-carboxamide (0.25 g, 1.03 mmol) in dry tetrahydrofuran (2 mL) was added benzyl isocyanate (0.15 g, 1.12 mmol). The mixture was allowed to stir overnight. The solid product was filtered from the reaction mixture and triturated with hexane/ethyl acetate (9:1). The solid was collected by filtration and dried to afford 3-amino-N-methyl-6-[3-({[(phenylmethyl)amino]carbonyl}amino)phenyl]pyrazine-2-carboxamide (0.26 g, 70% yield) as light yellow solid. $^1$H NMR (400 MHz, d$_6$-DMSO): 8.80 (m, 1H), 8.64 (s, 1H), 8.02 (s, 1H), 7.68 (d, 1H), 7.58 (d, 1H), 7.30 (m, 8H), 4.30 (d, 2H), 2.80 (d, 3H); MS (EI) for $C_{20}H_{20}N_6O_2$: 377 (MH$^+$).

Using the same or analogous synthetic techniques and/or substituting with alternative reagents as described above, the following compounds of the invention were prepared:

3-amino-6-[3-({[(4-fluorophenyl)amino]carbonyl}amino)phenyl]-N-methylpyrazine-2-carboxamide: $^1$H NMR (400 MHz, d$_6$-DMSO): 8.80 (br s, 1H), 8.75 (br m, 1H), 8.70 (br s, 1H), 8.65 (br s, 1H), 7.92 (br s, 1H), 7.54 (br d, 1H), 7.45 (m, 2H), 7.39 (t, 1H), 7.12 (br t, 3H), 2.86 (d, 3H); MS (EI) for $C_{19}H_{17}N_6O_2F$: 381 (MH$^+$).

3-amino-N-methyl-6-{3-[({[4-(methyloxy)phenyl]amino}carbonyl)amino]phenyl}pyrazine-2-carboxamide: $^1$H NMR (400 MHz, d$_6$-DMSO): 8.78 (br m, 1H), 8.70 (br s, 1H), 8.59 (br d, 2H), 7.92 (br s, 1H), 7.72 (br d, 1H), 7.56 (br d, 1H), 7.34 (m, 3H), 6.82 (br d, 2H), 3.70 (s, 3H), 2.80 (br d, 3H); MS (EI) for $C_{20}H_{20}N_6O_3$: 393 (MH$^+$).

According to the procedure described above, from 3-amino-6-(3-aminophenyl)-N-methylpyrazine-2-carboxamide and the corresponding acids, the following compounds of the invention were prepared:

3-amino-6-(3-{[[(4-chlorophenyl)acetyl]amino}phenyl)-N-methylpyrazine-2-carboxamide: $^1$H NMR (400 MHz, d$_6$-DMSO): 10.30 (s, 1H), 8.70 (m, 2H), 8.10 (br s, 1H), 7.85 (d, 1H), 7.70 (d, 1H), 7.40 (m, 5H), 3.64 (s, 2H), 2.82 (d, 3H); MS (EI) for $C_{20}H_{18}N_5O_2Cl$: 396 (MH$^+$).

3-amino-6-{3-[(diphenylacetyl)amino]phenyl}-N-methylpyrazine-2-carboxamide: $^1$H NMR (400 MHz, d$_6$-DMSO): 10.52 (s, 1H), 8.70 (m, 2H), 8.20 (br t, 1H), 7.85 (d, 1H), 7.72 (d, 1H), 7.32 (m, 11H), 5.20 (s, 1H), 2.82 (d, 3H); MS (EI) for $C_{26}H_{23}N_5O_2$: 438 (MH$^+$).

3-amino-N-methyl-6-{3-[(phenylacetyl)amino]phenyl}pyrazine-2-carboxamide: $^1$H NMR (400 MHz, d$_6$-DMSO): 8.72 (m, 1H), 8.68 (s, 1H), 8.02 (br s, 1H), 7.82 (d, 1H), 7.72 (d, 1H), 7.34 (m, 6H), 7.28 (m, 1H), 3.70 (s, 2H), 2.80 (d, 3H); MS (EI) for $C_{20}H_{19}N_5O_2$: 362 (MH$^+$).

3-amino-N-methyl-6-{3-[(3-phenylpropanoyl)amino]phenyl}pyrazine-2-carboxamide $^1$H NMR (400 MHz, d$_6$-DMSO): 8.68 (m, 2H), 8.08 (br s, 1H), 7.84 (d, 1H), 7.68 (d, 1H), 7.40 (t, 1H), 7.28 (m, 5H), 7.20 (m, 1H), 2.92 (t, 2H), 2.82 (d, 3H), 2.62 (t, 2H); MS (EI) for $C_{21}H_{21}N_5O_2$: 376 (MH$^+$).

3-amino-6-(3-{[(2,4-dichlorophenyl)acetyl]amino}phenyl)-N-methylpyrazine-2-carboxamide: $^1$H NMR (400 Nz, 4-DMSO): 10.30 (s, 1H), 8.62 (m, 2H), 8.10 (s, 1H), 7.82 (d, 1H), 7.62 (m, 3H), 7.40 (m, 4H), 3.92 (s, 2H), 2.82 (br s, 3H); MS (EI) for $C_{20}H_{17}N_5O_2Cl_2$: 430, 432 (MH$^+$).

3-amino-6-(3-{[(3,4-dichlorophenyl)acetyl]amino}phenyl)-N-methylpyrazine-2-carboxamide: $^1$H NMR (400 MHz, d$_6$-DMSO): 10.30 (s, 1H), 8.70 (m, 2H), 8.10 (s, 1H), 7.82 (d, 1H), 7.65 (m, 5H), 7.41 (m, 2H), 3.78 (s, 2H), 2.82 (d, 3H); MS (EI) for $C_{20}H_{17}N_5O_2Cl_2$: 430, 432 (MH$^+$).

3-amino-N-methyl-6-[3-({4-(trifluoromethyl)phenyl]acetyl}amino)phenyl]pyrazine-2-carboxamide: $^1$H NMR (400 MHz, d$_6$-DMSO): 10.40 (s, 1H), 8.80 (m, 2H), 8.10 (s, 1H), 7.90 (d, 1H), 7.70 (m, 4H), 7.60 (d, 2H), 7.40 (t, 1H), 3.80 (s, 2H), 2.84 (d, 3H); MS (EI) for $C_{21}H_{18}N_5O_2F_3$: 430 (MH$^+$).

3-amino-6-{3-[(1,3-benzodioxol-5-ylacetyl)amino]phenyl}-N-methylpyrazine-2-carboxamide: $^1$H NMR (400 MHz, d$_6$-DMSO): 10.20 (s, 1H), 8.70 (m, 2H), 8.10 (br s, 1H), 7.85 (d, 1H), 7.70 (d, 1H), 7.40 (t, 1H), 6.58 (m, 3H), 6.01 (s, 2H), 3.60 (s, 2H), 2.82 (d, 3H); MS (EI) for $C_{21}H_{19}N_5O_4$: 406 (MH$^+$).

9H-fluoren-9-ylmethyl (3-{5-amino-6-[(methylamino)carbonyl]pyrazin-2-yl}phenyl)carbamate: $^1$H NMR (400 MHz, d$_6$-DMSO): 9.73-9.67 (m, 1H), 8.68-8.61 (m, 2H), 8.00-7.20 (m, 21H), 8.00-7.96 (m, 1H), 7.90 (d, 2H), 7.86-7.26 (m, 9H), 4.49 (d, 2H), 4.32 (t, 1H), 2.84 (d, 3H); MS (EI) for $C_{27}H_{23}N_5O_3$: 466 (MH$^+$).

phenylmethyl (3-{5-amino-6-[(methylamino)carbonyl]pyrazin-2-yl}phenyl) carbamate: $^1$H NMR (400 MHz, d$_6$-DMSO): 9.76 (s, 1H), 8.68-8.61 (m, 2H), 8.03-7.98 (m, 1H), 8.00-7.00 (m, 2H), 7.82-7.76 (m, 1H), 7.54-7.47 (m, 1H), 7.46-7.30 (m, 4H), 5.18-5.14 (m, 2H), 4.50 (d, 2H), 2.87-2.82 (m, 3H); MS (EI) for $C_{20}H_{19}N_5O_3$: 378 (MH$^+$).

(1R,2S,5R)-5-methyl-2-(1-methylethyl)cyclohexyl (3-{5-amino-6-[(methylamino)carbonyl]pyrazin-2-yl}phenyl)carbamate: $^1$H NMR (400 MHz, d$_6$-DMSO): 9.56 (s, 1H), 8.67-8.61 (m, 2H), 8.01-7.99 (m, 1H), 7.90-7.20 (m, 2H), 7.77 (d, 1H), 7.54-7.49 (m, 1H), 7.37-7.32 (m, 1H), 4.56 (td, 1H), 2.85 (d, 3H), 1.72-0.68 (m, 18H); MS (EI) for $C_{23}H_{31}N_5O_3$: 426 (MH$^+$).

1,1-dimethylethyl (3-{5-amino-6-[(methylamino)carbonyl]pyrazin-2-yl}phenyl)carbamate: $^1$H NMR (400 MHz, d$_6$-DMSO): 9.29 (s, 1H), 8.68-8.61 (m, 2H), 7.99-7.96 (m, 1H), 8.00-7.20 (br, 2H), 7.77-7.72 (m, 1H), 7.52-7.47 (m, 1H), 7.35-7.30 (m, 1H), 2.83 (d, 3H), 1.47 (s, 9H); MS (EI) for $C_{17}H_{21}N_5O_3$: 344 (MH$^+$).

Example 14

Scheme 8 depicts a general synthetic route for compounds of the invention having substituents —W—X—Y according to formula I, wherein, for example, W is phenylene or pyridylene, X is —SO$_2$NH— or —C(=O)NH— wherein the phenylene or pyridylene is attached to the sulfur or the carbon atom of X, and Y is attached to the nitrogen of X. As described above, W, X, and Y all are optionally substituted, but for simplicity this is not shown here. As depicted, intermediate (xxxvi) is incorporated into a compound of the invention, (xxxviii), where Z is N or C, and L$_2$ is a substructure of X. In Scheme 8, L$_2$ represents either —SO$_2$— or —C(=O)—. The sequence of transformations regarding such intermediates may vary depending on the nature of each of W, X, and Y. For example, when L$_2$ is —SO$_2$—, the sulfonamide is typically generated prior to the conversion of the bromo group of (xxxvi) to the boronic ester group in intermediate (xxxvii). The same is true when L$_2$ is —C(=O)— and W is pyridylene. In cases where W is a substituted benzene, L$_2$ is —C(=O)—, and Y is an alkyl group, the amide bond is formed after the formation of (xxxviii) using synthetic steps known in the art. Conversion of (xxxvi) to (xxxvii) is carried out using bis (pinacolato)diboron based on procedures known to those skilled in the art. The transformation of (xxxvii) to (xxxviii) is accomplished using Suzuki coupling conditions, for example.

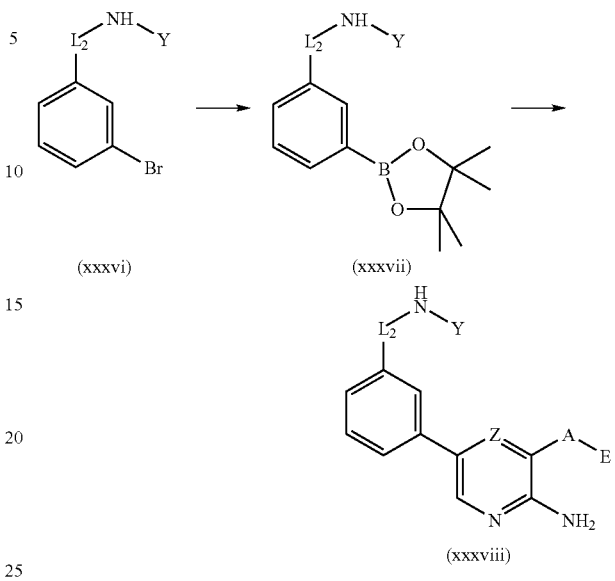

Scheme 8

3-Amino-6-(4-chloro-3-{[(phenylmethyl)amino]carbonyl}phenyl)-N-methylpyrazine-2-carboxamide Methyl 2-chloro-5-(4,4,5,5-tetramethyl-1,3,2-dioxaborolan-2-yl)benzoate: To a solution of methyl 5-bromo-2-chlorobenzoate (0.25 g, 1.01 mmol) in anhydrous dimethylsulfoxide (6 mL) were added bis(pinacolato)diboron (0.28 g, 1.10 mmol), potassium acetate (0.29 g, 3.01 mmol), and [1,1'-bis (diphenylphosphino)ferrocene]dichloropalladium (II) complex with dichloromethane (1:1, 25 mg, 0.03 mmol). The solution was degassed by passing nitrogen gas for 3-5 min and heated at 80-85° C. for 3 h. Reaction cooled to room temperature and diluted with ethyl acetate (250 mL). The organic layer was washed with saturated aqueous sodium bicarbonate (2×40 mL) and saturated aqueous sodium chloride (50 mL), dried over magnesium sulfate, filtered, and concentrated to afford methyl 2-chloro-5-(4,4,5,5-tetramethyl-1,3,2-dioxaborolan-2-yl)benzoate (0.12 g, 42% yield) as semi solid. 1H NMR (400 MHz, CDCl$_3$): 8.20 (br d, 1H), 7.80 (dd, 1H), 7.43 (d, 1H), 3.92 (s, 3H), 1.25 (s, 12H); MS (EI) for $C_{14}H_{18}N_4O_2BCl$: 297 (MH$^+$).

Methyl 5-{5-amino-6-[(methylamino)carbonyl]pyrazin-2-yl}-2-chlorobenzoate: To a solution of methyl 2-chloro-5-(4,4,5,5-tetramethyl-1,3,2-dioxaborolan-2-yl)benzoate (0.16 g, 0.55 mmol) in toluene (2 mL)) were added 3-amino-6-bromo-N-methyl-2-pyrazincarboxamide (0.13 g, 0.58 mmol), tetralds(triphenylphosphin)palladium(0) (64 mg, 0.06 mmol), ethanol (2 mL), and 2.0 N sodium carbonate (0.42 g, 4.00 mmol). The solution was degassed with nitrogen gas for 3-5 min and heated at 90-100° C. for 2 h. Reaction cooled to room temperature and diluted with ethyl acetate (200 mL). The organic layer was washed water (50 mL) and saturated aqueous sodium chloride (40 mL), dried over magnesium sulfate, filtered, and concentrated to afford crude product. Trituration with methanol (1 mL), filtration and drying gave methyl 5-{5-amino-6-[(methylamino)carbonyl]pyrazin-2-yl}-2-chlorobenzoate (96 mg, 56% yield) as yellow solid. $^1$H NMR (400 MHz, CDCl$_3$): 8.62 (br s, 1H), 8.28 (d, 1H), 7.92 (dd, 2H), 7.52 (d, 1H), 4.02 (s, 3H), 3.02 (s, 3H); MS (EI) for $C_{14}H_{13}N_4O_2Cl$: 321 (MH$^+$).

5-{5-Amino-6-[(methylamino)carbonyl]pyrazin-2-yl}-2-chlorobenzoic acid: To a solution of methyl 5-{5-amino-6-[(methylamino)carbonyl]pyrazin-2-yl}-2-chlorobenzoate (96 mg, 31 mmol) in methanol/tetrahydrofuran (1:1, 5.0 mL) was added 2.0 N aqueous sodium hydroxide (0.16 g, 4.00 mmol). The reaction was stirred overnight at room temperature. Reaction was neutralized with 2.0 N aqueous hydrochloric acid (4 mL) and diluted with ethyl acetate (100 mL). The organic layer was washed with water (20 mL), saturated aqueous sodium chloride (30 mL), dried over magnesium sulfate, filtered, and concentrated to afford 5-{5-amino-6-[(methylamino)carbonyl]pyrazin-2-yl}-2-chlorobenzoic acid (45 mg, 48% yield). $^1$H NMR (400 MHz, d$_6$-DMSO): 13.42 (br s, 1H), 8.90 (br s, 1H), 8.45 (d, 1H), 8.32 (dd, 1H), 7.85 (br s, 2H), 7.60 (d, 2H), 2.82 (s, 3H); MS (EI) for $C_{13}H_{11}N_4O_3Cl$: 307 (MH$^+$).

(d)-3-Amino-6-(4-chloro-3-{[(phenylmethyl)amino]carbony}phenyl)-N-methylpyrazine-2-carboxamide: The title compound was synthesized according to the procedure described above from 5-{5-amino-6-[(methylamino)carbonyl]pyrazin-2-yl}-2-chlorobenzoic acid and benzylamine. Yield 99%. $^1$H NMR (400 MHz, d$_6$-DMSO): 9.10 (t, 1H), 8.90 (s, 2H), 8.26 (m, 2H), 7.60 (d, 1H), 7.40 (m, 4H), 7.14 (t, 1H), 4.50 (d, 2H), 2.82 (d, 3H); MS (EI) for $C_{20}H_{18}N_5O_2Cl$: 396, 398 ). (MH$^+$).

Using the same or analogous synthetic techniques and/or substituting with alternative reagents as described above, the following compounds of the invention were prepared.

3-amino-6-(4-fluoro-3-{[(phenylmethyl)amino]carbonyl}phenyl)-N-methylpyrazine-2-carboxamide: $^1$H NMR (400 MHz, CDCl$_3$): 8.64 (m, 2H), 7.98 (m, 2H), 7.40 (m, 3H), 7.32 (m, 1H), 7.20 (m, 2H:), 7.15 (m, 1H), 4.70 (d, 2H), 3.02 (d, 3H), MS (EI) for $C_{20}H_{18}N_5O_2F$: 380 (MH$^+$).

3-amino-N-methyl-6-(4-(methyloxy)-3-{[(phenylmethyl)amino]carbonyl}phenyl)pyrazine-2-carboxamide: $^1$H NMR (400 MHz, CDCl$_3$): 8.80 (s, 1H), 8.60 (s, 1H), 8.20 (br s, 1H), 7.90 (m, 2H), 7.30 (m, 5H), 7.20 (d, 1H), 4.70 (d, 2H), 3.92 (s, 3H), 3.02 (d, 3H); MS (EI) for $C_{21}H_{21}N_5O_3$: 392 (MH$^+$).

3-amino-6-(2-fluoro-5-{[(phenylmethyl)amino]carbonyl}phenyl)-N-methylpyrazine-2-carboxamide: $^1$H NMR (400 MHz, CDCl$_3$): 8.62 (d, 1H), 8.30 (dd, 1H), 7.90 (br s, 1H), 7.70 (m, 1H), 7.30 (m, 4H), 7.26 (s, 1H), 7.20 (t, 1H), 6.50 (br s, 1H), 4.65 (d, 2H), 3.02 (d, 3H); MS (EI) for $C_{20}H_{18}N_5O_2F$: 380 (MH$^+$).

Example 15

3-Amino-N-methyl-6-(3-{[(phenylmethyl)amino]sulfonyl}phenyl)pyrazine-2-carboxamide 3-Bromo-N-(phenylmethyl)benzenesulfonamide: To a solution of 3-bromosulfonyl chloride (1.31 g, 5.14 mmol) in dry tetrahydrofuran (10 mmol) at 0° C. were added triethylamine (0.62 g, 6.17 mmol) and benzylamine (0.50 g, 4.57 mmol). The reaction was slowly warmed to room temperature and stirred overnight. Reaction was treated with 2.0 N aqueous hydrochloric acid (10 mL) and diluted with ethyl acetate (300 mmol). The organic layer was washed with water (30 mL), saturated aqueous sodium bicarbonate (40 mL), saturated aqueous sodium chloride (40 mL), dried over magnesium sulfate, filtered, and concentrated to afford 3-Bromo-N-(phenylmethyl)benzenesulfonamide (1.32 g, 78% yield). $^1$H NMR (400 MHz, CDCl$_3$): 7.34 (t, 1H1), 7.85 (s, 1H), 7.80 (m, 2H), 7.50 (t, 1H), 7.22 (m, 5H), 4.02 (d, 2H) MS (EI) for $C_{13}H_{12}NO_2SBr$: 326 (MH$^+$).

N-(phenylmethyl)-3-(4,4,5,5-tetramethyl-1,3,2-dioxaborolan-2-yl)benzenesulfonamide: The title compounds was synthesized according to the procedure described above. Yield 69%. $^1$H NMR (400 MHz, CDCl$_3$): 8.25 (s, 1H), 7.92 (m, 2H), 7.43 (t, 1H), 7.23 (m, 6H), 4.12 (d, 2H), 1.23 (s, 12H); MS (EI) for $C_{19}H_{24}NO_4SB$: 374 (MH$^+$).

3-Amino-N-methyl-6-(3-{[(phenylmethyl)amino]sulfonyl}phenyl)pyrazine-2-carboxamide was synthesized from N-(phenylmethyl)-3-(4,4,5,5-tetramethyl-1,3,2-dioxaborolan-2-yl)benzenesulfonamide and 3-amino-6-bromo-N-methyl-2-pyrazincarboxamide as yellow solid. Yield 20%. $^1$H NMR (400 MHz, d$_6$-DMSO): 8.84 (s, 1H), 8.80 (m, 1H), 8.46 (d, 1H), 8.38 (br s, 1H), 8.20 (t, 1H), 7.78 (d, 1H), 7.66 (t, 1H), 7.26 (m, 4H), 7.18 (m, 1H), 4.02 (d, 2H), 2.82 (d, 3H); MS (EI) for $C_{19}H_{19}N_5O_3S$: 398 (MH$^+$).

Example 16

3-Amino-N-methyl-6-(5-{[(phenylmethyl)amino]carbonyl}pyridin-3-yl)pyrazine-2-carboxamide 5-bromo-N-(phenylmethyl)pyridine-3-carboxamide was synthesized according to the procedure described above from 5-bromonicotinic acid and benzylamine. Yield 90%. $^1$H NMR (400 MHz, CDCl$_3$): 8.83 (d, 1H), 8.72 (d, 1H), 8.25 (t, 1H), 7.30 (m, 5H), 6.58 (br s, 1H), 4.62 (d, 2H); MS (EI) for $C_{13}H_{11}N_2OBr$: 291 (MH$^+$).

N-(phenylmethyl)-5-(4,4,5,5-tetramethyl-1,3,2-dioxaborolan-2-yl)pyridine-3-carboxamide was synthesized according to the procedure above from 5-bromo-N-(phenylmethyl)pyridine-3-carboxamide and bis(pinacolato)diboron. Yield 49%. $^1$H NMR (400 MHz, CDCl$_3$): 9.15 (br s, 1H), 9.02 (br s, 1H), 8.35 (br s, 1H), 7.32 (m, 5H), 6.42 (br, t, 1H), 4.62 (d, 2H), 1.29 (s, 12H); MS (EI) for $C_{19}H_{23}N_2O_3B$: 339 (MH$^+$).

3-amino-N-methyl-6-(5-{[(phenylmethyl)amino]carbonyl}pyridin-3-yl)pyrazine-2-carboxamide was synthesized according to the procedure described above from N-(phenylmethyl)-5-(4,4,5,5-tetramethyl-1,3,2-dioxaborolan-2-yl)pyridine-3-carboxamide and 3-amino-6-bromo-N-methyl-2-pyrazincarboxamide. Yield 38%. $^1$H NMR (400 MHz, d$_6$-DMSO): 9.58 (d, 1H), 9.36 (t, 1H), 9.02 (m, 3H), 8.86 (t, 1H), 7.34 (m, 4H), 7.24 (m, 1H), 4.50 (d, 2H), 2.83 (d, 3H); MS (EI) for $C_{19}H_{18}N_6O_2$: 363 (MH$^+$).

Using the same or analogous synthetic techniques and/or substituting with alternative reagents as described above, the following compounds of the invention were prepared:

3-amino-6-[5-({[(2,6-difluorophenyl)methyl]amino}carbonyl) pyridin-3-yl]-N-methylpyrazine-2-carboxamide: $^1$H NMR (400 MHz, d$_6$-DMSO): 9.54(d, 1H), 9.12 (t, 1H), 8.92 (m, 3H), 8.79 (t, 1H), 7.42 (m, 1H), 7.12 (t, 2H), 4.60 (d,2H), 2.82 (d, 3H); MS (EI) for $C_{19}H_{16}N_6O_2F_2$: 399 (MH$^+$).

3-amino-6-(5-{[(biphenyl-2-ylmethyl)amino]carbonyl}pyridin-3-yl)-N-methylpyrazine-2-carboxamide: $^1$H NMR (400 MHz, d$_6$-DMSO): 9.52 (d, 2H), 9.15 (t, 1H), 8.92 (m, 3H), 8.80 (t, 1H), 7.43 (m, 8H), 7.24 (br d, 1H), 4.50 (d, 2H), 2.82 (d, 3H), MS (EI) for $C_{25}H_{22}N_6O_2$: 439 ) (MH$^+$).

3-amino-6-(5-{[(2,3-dihydro-1,4-benzodioxin-6-ylmethyl)amino]carbonyl}pyridin-3-yl)-N-methylpyrazine-2-carboxamide: $^1$H NMR (400 MHz, d$_6$-DMSO): 9.52 (br t, 2H), 9.25 (t, 1H), 6.95 (t, 1H), 8.92 (m, 1H), 8.82 (m, 2H), 8.80 (m, 1H), 6.82 (br s, 2H), 4.40 (br s, 2H), 4.20 (s, 4H), 2.83 (d, 3H); MS (EI) for $C_{21}H_{20}N_6O_4$: 421 (MH$^+$)

Example 17

3-Amino-N-methyl-6-{3-[(2-phenylethyl)amino]phenyl}-pyrazine-2-carboxamide 3-bromo-N-(2-phenylethyl)aniline: To a solution of 3-bromoaniline (3.21 g, 18.60 mmol) in dry tetrahydrofuran (45 mL) were added triethylamine (2.82 g, 27.91 mmol) and phenylacetyl chloride 93.45 g, 22.30 mmol) at 0° C. The reaction warmed to room temperature and stirred for 4 h. The reaction mixture was treated with 2.0 N aqueous hydrochloric acid (20 mL) at 0° C. and diluted with ethyl acetate (300 mL). The organic layer was washed with water (20 mL), saturated aqueous sodium bicarbonate (50 mL) and saturated aqueous sodium chloride (50 mL), dried over magnesium sulfate, filtered, and concentrated to afford crude N-(3-bromophenyl)-2-phenylacetamide (4.84 g, 86% yield) which was used in the next step without any further purification.

To a solution of crude N-(3-bromophenyl)-2-phenylacetamide (3.02 g, 10.4 mmol) in dry tetrahydrofuran (25 mL) was added 1.0 N borane-tetrahydrofuran complex (1:1. 26 mL, 26.12 mmol) from an addition funnel at 0° C. The reaction was refluxed under nitrogen overnight. Reaction mixture was cooled to room temperature, treated with 2.0 N aqueous sodium hydroxide (30 mL) and then stirred for 20 min. The reaction was then cooled again at 0° C. and neutralized with 2.0 N aqueous hydrochloric acid (60 mL) and further stirred for 30 min. The aqueous layer was extracted with ethyl acetate (3×100 mL). The organic layer was washed with water (20 mL), saturated aqueous sodium chloride (50 mL), dried over magnesium sulfate, filtered, and concentrated to afford 3-Bromo-N-(2-phenylethyl)aniline (2.55 g, 85% yield) as brown oil with reasonable purity: $^1$H NMR (400 MHz, CDCl$_3$): 7.30 (t, 2H), 7.20 (m, 3H), 6.95 (t, 1H), 6.78 (br d, 1H), 6.70 (t, 1H), 6.45 (dd, 1H), 3.62 (br s, 1H), 3.40 (m, 2H), 2.92 (t, 2H); MS (EI) for $C_{14}H_{12}$NOBr: 290 MH$^+$).

N-(2-phenylethyl)-3-(4,4,5,5-tetramethyl-1,3,2-dioxaborolan-2-yl)aniline was synthesized according to the procedure described above from 3-bromo-N-(2-phenylethyl)aniline and bis(pinacolato)diboron. Yield 72%. $^1$H NMR (400 MHz, CDCl$_3$): 7.80 (m, 2H), 7.18 (m, 5H), 7.20 (br d, 1H), 6.70 (br t, 1H), 3.40(t, 2H), 2.85 (t, 2H), 1.23 (s, 12H1); MS (EI) for $C_{20}H_{26}NO_2B$: 324 (MH$^+$)

3-Amino-N-methyl-6-{3-[(2-phenylethyl)amino]phenyl}pyrazine-2-carboxamide was synthesized according to the procedure described above from N-(2-phenylethyl)-3-(4,4,5,5-tetramethyl-1,3,2-dioxaborolan-2-yl)aniline and 3-amino-6-bromo-N-methyl-2-pyrazincarboxamide. Yield 39%. $^1$H NMR (400 MHz, CDCl$_3$): 8.58 (s, 1H), 8.02 (br s, 1H), 7.32 (m, 3H), 7.26 (m, 3H), 7.18 (br d, 1H), 7.02 (br t, 1H), 6.64 (dd, 1H), 3.82 (br s, 1H), 3.51 (t, 2H), 3.02 (d, 3H), 2.94 (t, 2H); MS (EI) for $C_{20}H_{21}N_5O$: 348 (MH$^+$).

Using the same or analogous synthetic techniques and/or substituting with alternative reagents as described above, the following compounds of the invention were prepared:

3-amino-N-methyl-6-{1-[(phenylmethyl)amino]isoquinolin-7-yl}pyrazine-2-carboxamide: $^1$H NMR (400 MHz, d$_6$-DMSO): 11.15 (m, 1H), 9.64 (s, 1H), 9.30 (m, 1H), 9.15 (s, 1H), 8.84 (m, 1H), 8.03 (m, 1H), 7.58 (m, 1H), 7.50 (m, 2H), 7.37 (m, 2H), 7.28 (m, 2H), 5.08 (br s, 2H), 4.98 (d, 2H), 2.87 (d, 3H); MS (EI) for $C_{22}H_{20}N_6O$: 385.2 (MH$^+$).

3-amino-6-{1-[(1S)-2,3-dihydro-1H-inden-1-ylamino]isoquinolin-7-yl}-N-methylpyrazine-2-carboxamide: $^1$H NMR (400 MHz, d$_6$-DMSO): 9.07 (s, 1H), 8.89 (m, 2H), 8.59 (d, 1H), 7.90 (d, 1H), 7.79 (d, 2H), 7.66 (br s, 2H), 7.28 (m, 1H), 7.25 (m, 1H), 7.21 (t, 1H), 7.14 (t, 1H), 6.97 (d, 1H), 6.02 (m, 1H), 3.04 (m, 1H), 2.91 (m, 1H), 2.85 (d, 3H), 2.61 (m, 1H), 2.07 (m, 1H); MS (EI) for $C_{24}H_{22}N_6O$: 411.2 (MH$^+$).

3-amino-6-{3-[(1S)-2,3-dihydro-1H-inden-1-ylamino]-2,3-dihydro-1H-inden-5-yl}-N-methylpyrazine-2-carboxamide: 1H NMR (400 MHz, d$_6$-DMSO): 8.77 (s, 1H), 8.73 (m, 1H), 8.01 (m, 2H), 7.57 (br s, 2H), 7.48 (m, 1H), 7.37 (m, 1H), 7.29 (d, 1H), 7.21 (m, 1H), 7.15 (m, 2H), 4.34 (m, 2H), 2.97 (m, 2H), 2.84 (d, 3H), 2.77 (m, 2H), 2.44 (m, 1H), 2.34 (m, 1H), 1.83 (m, 2H); MS (EI) for $C_{24}H_{25}N_5O$: 400.2 (MH$^+$).

3-amino-N-methyl-6-[3-({[2-(phenylamino)ethyl]amino}carbonyl)phenyl]pyrazine-2-carboxamide was synthesized according to the procedure described in above from N-phenylethane-1,2-diamine and 3-{5-amino-6-[(methylamino)carbonyl]pyrazine-2-yl}benzoic acid. Yield 45%: 1H NMR (400 MHz, CDCl$_3$): 8.90 (s, 1H), 8.82 (br d, 1H), 8.70 (br t, 1H), 8.45 (br s, 1H), 8.32 (br d, 1H), 7.82 (br d, 1H), 7.52 (t, 1H), 7.02 (t, 2H), 6.62 (d, 2H), 6.50 (t, 1H), 5.72 (br t, 1H), 3.52 (d, 2H), 3.20 (d, 2H), 2.92 (d, 3H); MS (EI) for $C_{21}H_{22}N_6O_2$: 391 (MH$^+$)

6,6'-[(Oxomethanediyl)bis(iminobenzene-3,1-diyl)]bis(3-amino-N-methyl pyrazine-2-carboxamide: To a solution of 3-Amino-6-(3-aminophenyl)-N-methylpyrazine-2-carboxamide (0.10 g, 0.41 mmol) in dry tetrahydrofuran were added triethylamine (46 mg, 0.45 mmol) and 4-nitrophenyl chloroformate (91 mg, 0.45 mmol). The reaction of was allowed to stir overnight. A yellow solid material from the crude reaction was filtered and washed with diethyl ether (50 mL) and hexanes (50 mL) to yield 6,6'-[(oxomethanediyl)bis(iminobenzene-3,1-diyl)]bis(3-amino-N-methylpyrazine-2-carboxamide (0.11 g, 54% yield): $^1$H NMR (400 MHz, d$_6$-DMSO): 9.25 (br s, 2H), 8.75 (br d, 2H), 8.70 (s, 2H), 8.01 (s, 2H), 7.74 (br d, 2H), 7.60 (br d, 2H), 7.32 (t, 2H), 6.82 (br d, 2H), 2.80 (br s, 6H); MS (EI) for $C_{25}H_{24}N_{10}O_3$: 513 (MH$^+$).

3-Amino-6-biphenyl-3-yl-N-methylpyrazine-2-carboxamide was synthesized according to the procedure described in above. Yield 30%. $^1$H NMR (400 MHz, CDCl$_3$): 8.65 (br s, 1H), 8.03 (m, 1H), 8.01 (br s, 1H), 7.82 (dd, 1H), 7.65 (m, 3H), 7.50 (m, 3H), 7.40 (t, 1H), 3.02 (br s, 3H; MS (EI) for $C_{18}H_{16}N_4O$: 305 (MH$^+$)

Ethyl (3-{5-amino-6-[(methylamino)carbonyl]pyrazin-2-yl}phenyl)carbamate was synthesized according to the procedure described in above from 3-amino-6-(3-aminophenyl)-N-methylpyrazine-2-carboxamide and ethyl chloroformate. Yield 55%: $^1$H NMR (400 MHz, d$_6$-DMSO): 9.60 (br s, 1H), 8.68 (br s, 2H), 8.12 (br s, 1H), 7.80 (d, 1H), 7.52 (d, 1H), 7.39 (t, 1H), 4.06 (q, 2H), 2.85 (br s, 3H), 1.24 (t, 3H); MS (EI) for $C_{15}H_{17}N_5O_3$: 316 (MH$^+$)

3-Amino-6-(3-aminophenyl)-N-methylpyrazine-2-carboxamide. To a solution of 3-amino-6-bromo-N-methyl-2-pyrazinecarboxamide (1.23 g, 5.30 mmol) in N,N-dimethylformamide (30 mmol) were added [1,1'-bis(diphenylphosphino)-ferrocene]dichloropalladium(II) complex with dichloromethane (1:1, 433 mg, 0.53 mmol), 3-aminophenylboronic acid (1.15 g, 7.41 mmol), and triethylamine (1.07 g, 10.6mmol). The solution was degassed with nitrogen 3-5 min. The reaction was heated at 85-90° C. for 15 h with stirring. The reaction was allowed to cool to room temperature and diluted with ethyl acetate (400 mL). The organic layer was washed with saturated aqueous sodium bicarbonate (50 mL), saturated aqueous sodium chloride (50 mL), dried over magnesium sulfate, filtered, and concentrated to give crude product. To the crude product was added 4.0 N hydrochloric acid (1,4-dioxane solution, 30 mL). The resulting solid was filtered and washed with diethyl ether/methanol (4:1). The solid was dissolved in methanol and neutralized with sufficient AG 1-X8 Resin (hydroxide form) that the pH of the solution became basic. The mixture was filtered, and the filtrate was concentrated on a rotary evaporator at reduced pressure to afford 3-Amino-6-(3-aminophenyl)-N-methylpyrazine-2-carboxamide (0.70 g, 54% yield) as dark green solid. $^1$H NMR (400 MHz, d$_6$-DMSO): 8.70(br s, 1H), 8.62 (s, 1H), 7.60 (br s, 2H), 7.25 (m, 2H), 7.10 (t,. 1H), 6.15 (d, 1H), 5.06 (s, 2H), 2.8 (br s, 3H); MS (EID for C$_{12}$H$_{13}$N$_5$O: 244 ).

Example 18

Scheme 9 depicts a general synthetic route for compounds of the invention having substituents -W-X-Y according to formula I, wherein, for example, W is phenylene, X is —CH$_2$NH—, and Y is an indanyl group. Note, as defined above any of W, X, or Y are optionally substituted; this is only a set of examples. As depicted, intermediate (xxxix) is incorporated into a compound of the invention, (xliv). For example, optionally substituted indanone (xxxix) was to the corresponding alcohol (xl) using sodium borohydride or other appropriate reducing agent, depending upon, among other things, the substituent, R. The alcohol group in (xl) is transformed into an azide group in (xli) using diphenylphosphoryl azide and 1,8-diazabicyclo{5.4.0}undec-7-ene (DBU), for example. Reduction of azide (xli) is carried out typically, but not necessarily, using tin chloride give amine (xlii). Amine (xlii) is coupled to aldehyde (xliii), via reductive amination to afford (xliv). Amine (xlii) could also be coupled to a benzyl bromide, analogous to aldehyde (xxxxiii) to form (xliv), for example.

3-amino-N-methyl-6-[3-({[5-(2-thienyl)-2,3-dihydro-1H-inden-1-yl]amino methyl) phenyl]pyrazine-2-carboxamide 5-(2-thienyl)-2,3-dihydro-1H-inden-1-one. To a solution of 5-bromo-1-indanone (0.52g, 2.5 mmol) in toluene (5 mL) were added tetrakis(triphenylphosphine)-palladium(0) (29 mg, 0.03 mmol), thiophene-2-boronic acid (0.48 g, 3.7 mmol), ethanol (5 mL), and 2.0 N sodium carbonate (3 mL). The solution was flushed with nitrogen for 3 minutes. The reaction was heated at 110-120° C. for 4 h. Reaction cooled to room temperature and diluted with ethyl acetate (200 mL). The organic layer was washed with saturated aqueous sodium bicarbonate (2×50 mL), water (40 mL), saturated aqueous sodium chloride (50 mL), dried over magnesium sulfate, filtered and concentrated to afford 5-(2-thienyl)-2,3-dihydro-1H-inden-1-one (0.50g, 94% yield) as pure solid product. $^1$H NMR (400 MHz, CDCl$_3$) 7.80 (d, 1H), 7.70 (s, 1H), 7.62 (d, 1H), 7.43 (dd, 1H), 7.38 (dd, 1H), 7.12 (m, 1H), 3.20 (m, 2H), 2.66 (m, 2H).

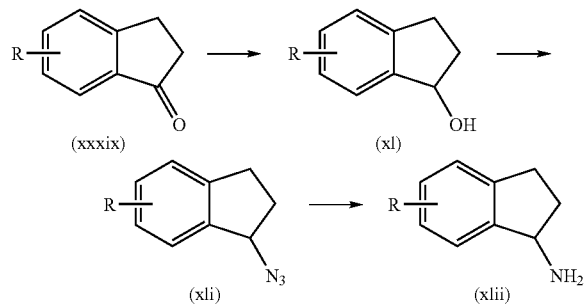

Scheme 9

(xxxix) (xl)

(xli) (xlii)

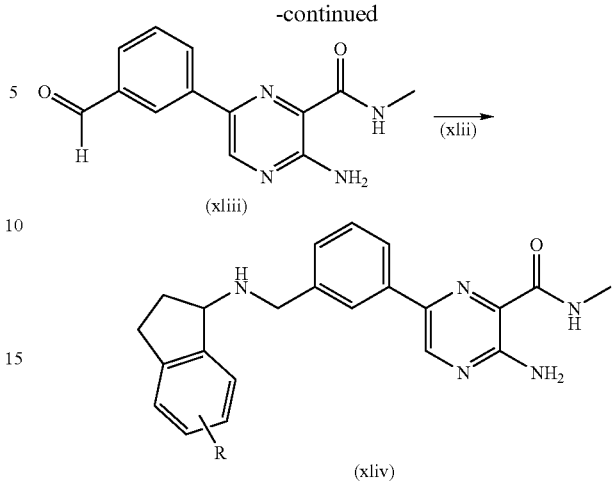

(xliii)

(xliv)

5-(2-thienyl)-2,3-dihydro-1H-inden-1-ol: To a slurry of sodium borohydride (0.22 g, 5.86 mmol) in methanol (6mL) at 0° C. was added a solution of 5-(2-thienyl)-2,3-dihydro-1H-inden-1-one (0.50 g, 2.34 mmol ) in methanol (2 mL). The reaction was slowly warmed to room temperature and stirred until the reaction was completed as monitored by thin layer chromatography (4 h). The reaction mixture was carefully quenched with 1.0 N aqueous hydrochloric acid at 0° C. until a clear solution was obtained. Diluted with ethyl acetate (200 mL), washed with saturated aqueous sodium bicarbonate, saturated aqueous sodium chloride (brine), and dried over anhydrous magnesium sulfate. Filtration, concentration and column chromatography on silica (7:3 hexanes/ethyl acetate) gave 5-(2-thienyl)-2,3-dihydro-1H-inden-1-ol (0.30 g, 59% yield) as solid. $^1$H NMR (400 MHz, CDCl$_3$): 7.48 (m, 2H), 7.38 (br d, 1H), 7.26 (m, 2H), 7.08 (dd, 1H), 5.21 (t, 1H), 3.04 (m, 1H), 2.80 (m, 1H), 2.50 (m, 1H), 2.10 (brs, 1H), 1.93 (m, 1H).

2-(1-azido-2,3-dihydro-1H-indene-5-yl)thiophene: To a solution of 5-(2-thienyl)-2,3-dihydro-1H-inden-1-ol (0.30 g, 1.39 mmol) in tetrahydrofuran (6 mL ) was added diphenylphosphoryl azide (0.58 g, 2.10 mmol) at 0° C. The reaction was stirred for 5 min prior to the addition of 1,8-diazabicyclo{5.4.0}undec-7-ene (DBU, 0.32 g, 2.10 mmol). The reaction was further stirred for 15 min at 0° C. before the reaction was allowed to warm to room temperature. The reaction was stopped after 1 h when the reaction was completed as monitored by thin layer chromatography. Diluted with ethyl acetate (200 mL), washed with water, saturated aqueous sodium chloride (brine), and dried over anhydrous magnesium sulfate. Filtration, concentration and column chromatography on silica (7:3 hexanes/ethyl acetate) gave 2-(1-azido-2,3-dihydro-1H-indene-5-yl)thiophene (0.24g, 72% yield) as oil. $^1$H NMR (400 MHz, CDCl$_3$) 7.54 (m, 2H), 7.40 (m, 2H), 7.24 (m, 1H), 7.08 (m, 1H), 5.85 (t, 1H), 3.12 (m, 1H), 2.90 (m, 1H), 2.45 (m, 1H), 2.19 (m, 1H).

5-(2-thienyl)-2,3-dihydro-1H-indene-1-yl)amine: To a solution of 2-(1-azido-2,3-dihydro-1H-inden-5-yl) thiophene (0.24 g, 0.99 mmol) in methanol (2mL) was added solid tin chloride dihydrate (0.45 g, 1.99 mmol) at room temperature under nitrogen. The reaction was stirred at room temperature overnight. The crude reaction mixture was poured into a separatory funnel and diluted with ethyl acetate (250 mL). The organic layer was washed with 2.0 N aqueous sodium hydroxide (50 mL), saturated aqueous sodium chloride (brine), and dried over anhydrous magnesium sulfate.

Filtration, concentration and column chromatography on silica (9:1 dichloromethane/methanol) gave [5-(2-thienyl)-2,3-dihydro-1H-indene-1-yl]amine (0.15 g, 72% yield) as semi-solid: $^1$H NMR (400 MHz, CDCl$_3$) 7.54 (m, 1H), 7.40 (d, 2H), 7.29 (m, 2H), 7.08 (m, 1H), 4.40 (t, 1H), 3.05 (m, 1H), 2.90 (m, 1H), 2.56 (m, 1H), 1.80 (m, 1H).

3-amino-N-methyl-6-[3-({[5-(2-thienyl)-2,3-dihydro-1H-inden-1-yl]amino}methyl)phenyl]pyrazine-2-carboxamide: To a solution of 5-(2-thienyl)-2,3-dihydro-1H-indene-1-yl]amine (73 mg, 0.34 mmol) in acetonitril (3 mL) were added 3-amino-6-[3-(bromomethyl)phenyl]-N-methylpyrazine-2-carboxamide (41 mg, 0.13 mmol) and N,N-diisopropylethylamine (22 mg, 0.17 mmol) at room temperature. The reaction was stirred overnight. Diluted with ethyl acetate (100 mL) and washed with water, saturated aqueous sodium chloride (brine), and dried over anhydrous magnesium sulfate. Filtration and concentration and column purification on silica (9:1 ethyl acetate/methanol) gave 3-amino-N-methyl-6-[3-({[5-(2-thienyl)-2,3-dihydro-1H-inden-1-yl]amino}methyl)phenyl]pyrazine-2-carboxamide (30 mg, 51% yield) as yellow solid. $^1$NMR (400 MHz, CD$_3$OD): 8.70 (s, 1H), 8.15 (br s, 1H), 7.86 (d, 1H), 7.49 (m, 6H), 7.32 (m, 2H), 7.05 (m, 1H), 4.35 (m, 1H), 3.92 (d, 2H), 3.10 (m, 4H), 2.95 (s, 3H), 2.85 (m, 1H), 2.45 (m, 1H), 2.10 (m, 1H); MS (EI) for C$_{26}$H$_{25}$N$_5$OS: 456 (MH$^+$).

Using the same or analogous synthetic techniques and/or substituting with alternative reagents as described above, the following compounds of the invention were prepared:

3-amino-6-(3-{[(5-bromo-2,3-dihydro-1H-inden-1-yl)amino]methyl}phenyl)-N-methylpyrazine-2-carboxamide: $^1$NMR (400 MHz, d$_6$-DMSO): 9.80 (br s, 2H), 9.40 (br S, 1H), 8.84 (s, 1H), 8.80 (s, 1H), 8.25 (d, 1H), 7.88 (br s, 1H), 7.80 (d, 1H), 7.48 (m, 4H), 4.82 (s, 1H), 4.24 (s, 2H), 3.25 (s, 3H), 3.20 (m, 1H), 2.80 (m, 1H), 2.50 (m, 1H), 2.40 (m, 1H); MS (EI) for C$_{22}$H$_{22}$N$_5$OBr: 453,455 (MH$^+$).

3-amino-6-(3-{[(5-furan-2-yl-2,3-dihydro-1H-inden-1-yl)amino]methyl}phenyl)-N-methylpyrazine-2-carboxamide: $^1$NMR (400 MHz, CD$_3$OD): 8.65 (s, 1H), 8.15 (s, 1H), 7.88 (d, 1H), 7.50 (m, 6H), 6.70 (d, 1H), 6.45 (m, 1H), 4.40 (m, 1H), 4.01 (d, 2H), 3.15 (m, 3H), 2.96 (s, 3H), 2.85 (m, 1H), 2.50 (m, 1H), 2.45 (m, 1H), 2.10 (m, 1H); MS (EI) for C$_{26}$H$_{25}$N$_5$O$_2$: 440 (MH$^+$).

3-amino-6-(3-{[(5-chloro-2,3-dihydro-1H-inden-1-yl)amino]methyl}phenyl)-N-methylpyrazine-2-carboxamide: $^1$NMR (400 MHz, CDCl$_3$): 8.58 (s, 1H), 8.20 (br s, 1H), 8.08 (br s, 1H), 7.70 (d, 1H), 7.40 (m, 3H), 7.20 (s, 1H), 7.15 (d, 1H), 4.40 (m, 1H), 3.80 (s, 2H), 3.10 (m, 4H), 2.80 (s, 1H), 2.45 (m, 1H), 2.20 (m, 1H); MS (EI) for C$_{22}$H$_{22}$N$_5$OCl: 408 (ME+).

3-amino-6-(3-{[(5-furan-3-yl-2,3-dihydro-1H-inden-1-yl)amino]methyl}phenyl)-N-methylpyrazine-2-carboxamide: $^1$NMR (400 MHz, CDCl$_3$): 8.62 (br s, 1H), 8.05 (br s, 1H), 7.89 (br s, 1H), 7.78 (m, 2H), 7.40 (m, 6H), 6.70 (br s, 1H), 4.35 (m, 1H), 4.01 (d, 1H), 3.10 (m, 4H), 2.95 (s, 3H), 2.85 (m, 1H), 2.50 (m, 1H), 1.85 (m, 1H); MS (EI) for C$_{26}$H$_{25}$N$_5$O$_2$: 440 (MH+).

3-amino-N-methyl-6-[3-({[5-(3-thienyl)-2,3-dihydro-1H-inden-1-yl]amino}methyl)phenyl]pyrazine-2-carboxamide: 1NMR (400 MHz, CDCl$_3$ ): 8.64 (s, 1H), 8.02 (br s, 1H), 7.90 (br s, 1H), 7.78 (m, 1H), 7.44 (m, 6H), 7.38 (m, 2H), 4.40 (m, 1H), 4.02 (d, 2H), 3.15 (m, 4H), 2.90 (m, 1H), 2.50 (m, 1), 1.90 (m, 1H); MS (EI) for C$_{26}$H$_{25}$N$_5$OS: 456 (MH+).

3-amino-N-methyl-6-(3-{[(5-phenyl-2,3-dihydro-1H-inden-1-yl)amino]methyl}phenyl)pyrazine-2-carboxamide: 1NMR (400 MHz, 46-DMSO ): 8.82 (m, 2H), 8.16 (br s, 1H), 8.05 (d, 1H), 7.62 (d, 2H), 7.45 (m, 7H), 7.34 (m, 1H), 4.24 (m, 1H), 3.90 (m, 2H), 3.01 (m, 1H), 2.80 (m, 4H), 2.38 (m, 1H), 1.90 (m, 1H); MS (EI) for C$_{28}$H$_{27}$N$_5$O: 450 (MH+).

3-amino-N-methyl-6-[3-({[6-(2-thienyl)-2,3-dihydro-1H-inden-1-yl]amino]methyl)phenyl]pyrazine-2-carboxamide: $^1$NMR (400 MHz, CDCl$_3$): 8.60 (s, 1H), 7.99 (br s, 1H), 7.88 (br s, 1H), 7.75 (m, 1H), 7.60 (s, 1H), 7.45 (m, 3H), 7.24 (m, 3H), 7.04 (m, 1H), 4.40 (m, 1H), 4.02 (d, 2H), 3.08 (m, 4H), 2.83 (m, 1H), 2.50 (m, 1H), 1.86 (m, 1H); MS (EI) for C$_{26}$H$_{25}$N$_5$O S: 456 (MH+).

3-amino-N-methyl-6-[3-({[5-(4-methyl-2-thienyl)-2,3-dihydro-1H-inden-1-yl]amino}methyl)phenyl]pyrazine-2-carboxamide: 1NMR (400 MHz, CDCl$_3$): 8.60 (s, 1H), 8.01 (br s, 1H), 7.88 (br s, 1H), 7.74 (m, 1H), 7.60 (s, 1H), 7.40 (m, 5H), 7.08 (br, s 1H), 6.80 (br s, 1H), 4.70 (m, 1H), 4.02 (d, 2H), 3.06 (m, 4H), 2.85 (m, 1H), 2.50 (s, 3H), 1.90 (m, 1H); MS (EI) for C$_{27}$H$_{27}$N$_5$OS: 470 (MH+).

3-amino-6-{3-[(2,3-dihydro-1-benzofuran-3-ylamino)methyl]phenyl}-N-methylpyrazine-2-carboxamide: 1NMR (400 M, CDCl$_3$): 8.60 (s, 1H), 8.15 (br s, 1H), 7.88 (br 1H), 7.65 (d, 1H), 7.40 (m, 3H), 7.26 (d, 1H), 6.96 (t, 1H), 6.90 (d, 1H), 4.60 (m, 3H), 3.90 (m, 2H), 3.01 (m, 3H); MS (EI) for C$_{21}$H$_{21}$N$_5$O$_2$: 376 (MH+).

3-amino -N-methyl-6-[3-({[5-(4-methylphenyl)-2,3-dihydro-1H-inden-1-yl]amino}miethyl)phenyl]pyrazine-2-carboxamide: $^1$H NMR (400 MHz, d$_6$-DMSO): 9.80 (br s, 1H), 9.02 (d, 1H), 8.82 (s, 1H), 8.60 (s, 1H), 8.21 (d, 1H), 7.50 (m, 7H), 7.25 (d, 1H), 4.82 (m, 1H), 4.30 (m, 2H), 3.20 (m, 1H), 2.92 (m, 1H), 2.80 (d, 3H), 2.50 (m, 1H), 2.30 (s, 3H), 2.40 (m, 1H); MS (EI) for C$_{29}$H$_{29}$N$_5$O: 464 (MH+).

Example 19

Scheme 10 depicts a general synthetic route for compounds of the invention having substituents —W—X—Y according to formula I, wherein, for example, W is phenylene, X is —CH$_2$NR$^4$—, and Y is various groups. Note, as defined above any of W, X, or Y are optionally substituted; this is only a set of examples. As depicted, primary amine (xlv), which in this example incorporates Y, is incorporated into a compound of the invention, (1). For example, amine (xlv), which has Y as part of its structure for example, is converted to 2,4-dinitrosulfonamide (xlvi). Sulfonanide (xlvi) is used to make sulfonamide (xlvii). The transformation (xlvi) to (xlvii) is carried out either under alkylation (R$^4$L$_3$, where -L$_3$ is a leaving group) or Mitsunobu (R$^4$OH) conditions. The sulfonamide bond is cleaved, typically but not necessarily via addition of a primary amine e.g. nt-propyl amidne, to free secondary amine (xlviii), which has Y and R$^4$ as part of its structure. Amine (xlviii) was then incorporated into compounds of the invention, typically but not necessarily, via coupling to a benzyl bromide, for example (xlix), to make compound (1).

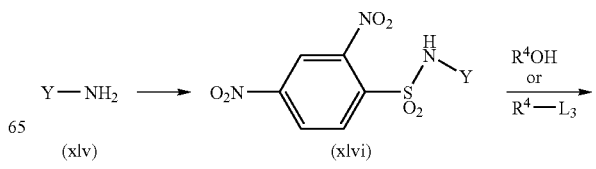

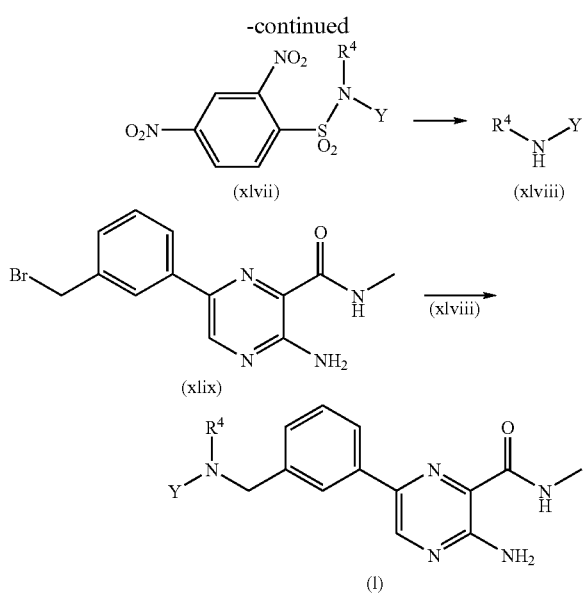

3-amino-6-[3-({[(2S)-6-bromo-1,2,34-tetrahydronaphthalen-2-yl]amino}methyl)phenyl]-N-methylpyrazine-2-carboxamide N-[(S)-6-bromo-1,2,3,4-tetrahydronaphthalen-2-yl]-2,4-dinitrobenzenesulfonamide: To a solution of (S)-6-bromo-2-aminotetraline (0.20 g, 0.9 mmol) in tetrahydrofuran (2 mL) was added N,N-diisopropylethylamine at 0° C. A solution of 2,4-dinitrobenzenesulfonyl chloride (0.29 g, 1.1 mmol) in tetrahydrofuran (2 mL) was added slowly via a syringe. The reaction was allowed to warm to room temperature and further stirred until the completion of the reaction (30 min) as monitored by thin layer chromatography. The crude reaction mixture was poured into a separatory funnel and diluted with ethyl acetate (250 mL) and washed with water (30 mL), saturated aqueous sodium chloride (40 mL), and dried over anhydrous magnesium sulfate. Filtration and concentration afforded the crude product. A pure N-[(2S)-6-bromo-1,2,3,4-tetrahydronaphthalen-2-yl]-2,4-dinitrobenzenesulfonamide (0.28 g, 70% yield) was separated from trituration with ether/hexane (5:1, 30 mL) as a yellow solid. $^1$NMR (400 MHz, CD$_3$OD): 8.75 (s, 1H), 8.60 (dd, 1H), 8.38 (d, 1H), 7.22 (br s, 1H), 7.20 (d, 1H), 6.90 (d, 1H), 3.65 (m, 1H), 2.65 (m, 4H), 1.90 (m, 1H), 1.75 (m, 1H).

3-Amino-6-[3-({[(2S)-6-bromo-1,2,3,4-tetrahydronaphthalen-2-yl]amino]methyl)phenyl]-N-methylpyrazine-2-carboxamide: To a solution of N-[(2S)-6-bromo-1,2,3,4-tetrahydronaphthalen-2-yl]-2,4-dinitrobenzenesulfonamide (68 mg, 0.15 mmol) in N,N-dimehtylformamide (1 mL) were added solid potassium carbonate (0.10 g, 0.75 mmol) and 3-amino-6-[3-(bromomethyl)phenyl]-N-methylpyrazine-2-carboxamide (70 mg, 0.22 mmol). The reaction stirred overnight at room temperature and diluted with ethyl acetate (50 mL). The organic layer was washed with water (30 mL) and saturated aqueous sodium chloride (30 mL), and dried over magnesium sulfate. Filtration and concentration gave crude product that was used in the next step without any purification.

To the dichloromethane solution (2 mmol) of the above product was added excess n-propylamine (0.5 mL) and stirred for 30 min. The organic solvent and excess reagent were removed at reduced pressure. Column purification on silica (9:1, ethyl acetate/methanol) gave an oily product.

To a solution of the above product in methanol (2 mL) was added 4.0 N hydrochloric acid (1,4-dioxane solution, 1.50 mL) and stirred for 40 min. Evaporation of the excess reagent and solvent, washing with diethyl ether afforded 3-amino-6-[3-(([(2S)-6-bromo-1,2,3,4-tetrahydronaphthalen-2-yl]amino}methyl)phenyl]-N-methylpyrazine-2-carboxamide (16 mg, 23% yield) as hydrochloric acid salt. $^1$NMR (400 MHz, CDCl$_3$): 8.62 (s, 1H), 8.02 (br s, 1H), 7.82 (br s, 1H), 7.75 (d, 1H), 7.40 (m, 2H), 7.20 (m, 2H), 6.74 (d, 1H), 4.01 (m, 2H), 2.90 (m, 6H), 2.60 (m, 2H), 2.12 (m, 1H), 1.70 (m, 1H); MS (EI) for C$_{23}$H$_{24}$N$_5$OBr: 466 (MH+).

Using the same or analogous synthetic techniques and/or substituting with alternative reagents as described above, the following compounds of the invention were prepared:

3-amino-6-[3-({[(2R)-6-bromo-1,2,3,4-tetrahydronaphthalen-2-yl]amino]methyl)phenyl]-N-methylpyrazine-2-carboxamide: $^1$NMR (400 MHz, CDCl$_3$): 8.60 (s, 1H), 8.05 (br s, 1H), 7.83 (br s, 1H), 7.75 (d, 1H), 7.42 (m, 2H), 7.20 (m, 2H), 6.72 (d, 1H), 4.01 (m, 2H), 3.10 (m, 4H), 2.84 (m, 2H), 2.60 (m, 1H), 2.10 (m, 1H), 1.70 (m, 2H); MS (EI) for C$_{23}$H$_{24}$N$_5$OBr: 466 (MH$^+$).

3-amino-6-{3-[(cyclopentylamino)methyl]phenyl}-N-methylpyrazine-2-carboxamide: $^1$NMR (400 MHz, CDCl$_3$): 8.70 (s, 1H), 8.48 (br s, 1H), 8.16 (d, 1H), 7.58 (m, 3H), 4.30 (s, 2H), 3.04 (br s, 3H), 2.20 (m, 2H), 1.72 (m, 7H); MS (EI) for C$_{18}$H$_{23}$N$_5$O: 326 (MH$^+$).

3-amino-N-methyl-6-{3-[({(1S,2S)-2-[(phenylmethyl)oxy]cyclopentyl}amino)methyl]phenyl}pyrazine-2-carboxamide: $^1$NMR (400 MHz, CDCl$_3$): 8.60 (s, 1H), 8.06 (br s, 1H), 7.80 (br s, 1H), 7.74 (d, 1H), 7.40 (t, 2H), 7.32 (m, 6H), 4.50 (q, 2H), 3.85 (m, 3H), 3.20 (m, 1H), 3.01 (d, 3H), 2.01 (m, 1H), 2.10 (m, 2H), 1.73 (m, 4H), 1.42 (m, 1H); MS (EI) for C$_{25}$H$_{29}$N$_5$O$_2$: 432 (MH$^+$).

3-amino-N-methyl-6-{3-[({(1R,2R)-2-[(phenylmethyl)oxy]cyclopentyl}amino)methyl]phenyl}pyrazine-2-carboxamide: $^1$NMR (400 MHz, CDCl$_3$): 8.65 (s, 1H), 8.40 (br s, 1H), 8.12 (d, 1H), 7.58 (t, 1H), 7.48 (d, 1H), 7.34 (m, 5H), 4.60 (q, 2H), 4.32 (s, 2H), 4.28 (m, 1H), 3.60 (m, 1H), 3.02 (s, 3H), 2.30 (m, 1H), 2.15 (m, 1H), 1.83 (m, 4H); MS (EI) for C$_{25}$H$_{29}$N$_5$O$_2$: 432 (MH$^+$).

Example 20

3-Amino-6-[3-({[2-(dimethylamino)-1-phenylethyl]amino}methyl)phenyl]-N-methylpyrazine-2-carboxamide To a solution of (2-amino-2-phenethyl)dimethyl amine (200 mg, 1.22 mmol) in acetonitril (15 mL) were added 3-amino-6-[3-(bromomethyl)phenyl]-N-methylpyrazine-2-carboxamide (0.11 g, 0.35 mmol) and N,N-diisopropylethyl amine (0.14 g, 1.05 mmol) at room temperature. The reaction was stirred overnight. Diluted with ethyl acetate (100 mL), washed with water (30 mL), saturated aqueous sodium chloride (brine), and dried over anhydrous magnesium sulfate. Filtration and concentration and reverse phase HPLC purification gave a trifluoro acetate salt. The fraction from the HPLC was neutralized with saturated aqueous sodium bicarbonate (50 mL) and diluted with ethyl acetate (200 mL). The organic layer was washed saturated aqueous sodium chloride (30 mL), dried over anhydrous magnesium sulfate, filtered, and concentrated to give the free amine. This free amine was converted into hydrochloric acid salt by treatment with 4.0 N hydrochloric acid (1,4-dioxane solution, 2.0 mL) in methanol solution (3 mL). Evaporation of the excess reagent and solvent gave 3-amino-6-[3-({[2-(dimethylamino)-1-phenylethyl]amino}methyl)phenyl]-N-methylpyrazine-2-carboxamide (88 mg, 18% yield) as yellow solid: 1NMR (400 MHz, CDCl$_3$): 8.61 (s, 1H), 8.05 (br s, 1H), 7.78 (br s, 1H), 7.74 (d, 1H), 7.35 (br m, 7H), 3.85 (d, 1H), 3.75 (dd, 1H), 3.60 (d, 1H), 3.04 (s, 3H), 2.65 (m, 2H), 2.20 (s, 6H); MS (EI) for C$_{23}$H$_{28}$N$_6$O: 405 (MH$^+$).

Using the same or analogous synthetic techniques and/or substituting with alternative reagents as described above, the following compounds of the invention were prepared:

3-amino-N-methyl-6-(3-{[(2-morpholin-4-yl-1-phenyl-ethyl)amino]methyl}phenyl)pyrazine-2-carboxamide: 1NMR (400 MHz, CDCl$_3$): 8.60 (s, 1H), 8.02 (br s, 1H), 7.74 (d, 1H), 7.70 (s, 1H), 7.39 (br m, 7H), 3.88 (d, 1H), 3.78 (dd, 1H), 3.65 (m, 3H), 3.58 (s, 1H), 3.05 (d, 3H), 2.55 (t, 1H), 2.45 (m, 2H), 2.30 (m, 3H); MS (EI) for C$_{25}$H$_{30}$N$_6$O$_2$: 447 (MH$^+$).

3-amino-N-methyl-6-(3-{[(1-phenyl-2-pyrrolidin-1-yl-ethyl)amino]methyl}phenyl)pyrazine-2-carboxamide: $^1$NMR (400 MHz, CDCl$_3$): 8.60 (s, 1H), 8.12 (br s, 1H), 7.80 (s, 1H), 7.74 (d, 1H), 7.40 (br m, 5H), 7.30 (m, 2H), 3.82 (d, 1H), 3.74 (d, 1H), 3.60 (d, 1H), 3.05 (d, 3H), 2.90 (m, 2H), 2.70 (br s, 1H), 2.50 (m, 1H), 2.40 (m, 1H), 2.25 (dd, 2H), 1.70 (m, 4H); MS (EI) for C$_{25}$H$_{30}$N$_6$O: 431 (MH$^+$).

Example 21

3-amino-6-(3-{[(1S)-2,3-dihydro-1H-inden-1-ylamino]methyl}phenyl)-N-(2-hydroxyethyl)pyrazine-2-carboxamide To a solution of methyl 3-amino-6-(3-{[(1S)-2,3-dihydro-1H-inden-1-ylamino]methyl}phenyl)-N-(2-hydroxyethyl) pyrazine-2-carboxylate (30 mg, 08 mmol) in methanol (1 mL) was added ethanolamine (20 mg, 0.32 mmol). The reaction was heated at 80-90° C. overnight. The reaction cooled to room temperature and diluted with ethyl acetate (150 mL). The organic layer was washed with saturated aqueous sodium bicarbonate and saturated aqueous sodium chloride, and dried over magnesium sulfate. Filtration, concentration, and column purification on silica (9.5:0.5, dichloromethane/methanol) afforded free amine product. To a solution of the amine in diethyl ether (2 mL) was added 4 N hydrochloric acid (1,4-dioxane solution, 1 mL) and stirred for 30 min. Concentration and washings with diethyl ether afforded 3-amino-6-(3-{[(1S)-2,3-dihydro-1H-inden-1-ylamino] methyl}phenyl)-N-(2-hydroxyethyl)pyrazine-2-carboxamide (13 mg, 38% yield) as yellow hydrochloric acid salt. 1NMR (400 MHz, CDCl$_3$): 8.58 (s, 1H), 8.40 (br s, 1H), 7.90 (br s, 1H), 7.68 (m, 1H), 7.38 (m, 3H), 7.20 (m, 3H), 4.35 (t, 1H), 3.90 (d, 2H), 3.80 (t, 2H), 3.60 (m, 2H), 3.06 (m, 1H), 2.84 (m, 1H), 2.48 (m, 3H), 1.92 (m, 1H); MS (EI) for C$_{23}$H$_{25}$N$_5$O$_2$: 404 (MH+).

Using the same or analogous synthetic techniques and/or substituting with alternative reagents as described above, the following compounds of the invention were prepared:

3-amino-N-cyclopropyl-6-(3-([(1S)-2,3-dihydro-1H-inden-1-ylamino]methyl}phenyl)pyrazine-2-carboxamide: 1NMR (400 MHz, CDCl$_3$): 8.60 (s, 1H), 8.05 (br s, 1H), 7.83 (br s, 1H), 7.70 (m, 1H), 7.40 (m, 3H), 7.20 (m, 3H), 4.35 (t, 1H), 4.02 (d, 2H), 3.02 (m, 1H), 2.85 (m, 2H), 2.50 (m, 1H), 1.92 (m, 1H), 1.13 (m, 1H), 0.90 (m, 2H), 0.70 (m, 1H); MS (EI) for C$_{24}$H$_{25}$N$_5$O: 400 (MH+).

5-(3-{[(1S)-2,3-dihydro-1H-inden-1-ylamino) methyl}phenyl)-3-(pyrrolidin-1-ylcarbonyl)pyrazin-2-amine: 1NMR (400 MHz, CDCl$_3$): 8.57 (s, 1H), 7.95 (br s, 1H), 7.78 (m, 1H), 7.42 (m, 3H), 7.24 (m, 3H), 4.35 (t, 1H), 4.02 (d, 4H), 3.70 (m, 2H), 3.05 (m, 1H), 2.85 (m, 1H), 2.48 (m, 1H), 1.94 (m, 5H); MS (EI) for C$_{25}$H$_{27}$N$_5$O: 414 (MH+).

3-amino-6-(3-{[(1S)-2,3-dihydro-1H-inden-1-ylamino] methyl}phenyl)-N-(3-hydroxypropyl)pyrazine-2-carboxamide: $^1$NMR (400 MHz, CDCl$_3$): 9.56 (s, 1H), 8.65 (m, 1H), 8.38 (br s, 1H), 7.72 (d, 1H), 7.38 (t, 2H), 7.50 (m, 4H), 4.40 (t, 1H), 4.01 (q, 2H), 3.60 (m, 3H), 3.40 (m, 1H), 3.08 (m, 1H), 2.90 (m, 1H), 2.50 (m, 1H), 2.00 (m, 1H), 1.75 (m, 2H); MS (EI) for C$_{24}$H$_{27}$N$_5$O$_2$: 418 (MH+).

Example 22

3-amino-6-(3-{(1S)-1-[(1S)-2,3-dihydro-1H-inden-1-ylamino]ethyl}phenyl)-N-methylpyrazine-2-carboxamide N-[(1S)-1-(3-bromophenyl)ethyl]-2,4-dinitrobenzenesulfonamide: To a stirred ice-cooled solution of (S)-(–)-3-bromo-α-methylbenzylamine (832 mg, 4.16 mmol, from Chiragene) in 15.6 mL of THF was added 1.33 g (4.99 mmol, 1.20 eq.) of 2,4-dinitrobenzenesulfonyl chloride, followed by 1.08 mL (6.20 mmol, 1.49 eq.) of N,N-diisopropylethylamine. The ice bath was removed, and the mixture was stirred at room temperature for 19 h and then concentrated. The residue was taken up in EtOAc, washed with 2×H$_2$O, dried over Na$_2$SO$_4$, filtered, and concentrated. The residue was sonicated in ca. 5 mL of EtOAc until a precipitate was formed. The mixture was diluted to ca. 25 mL with hexanes. Filtration afforded product as a tan solid (1.69 g, 94.4% yield).

N-[(1S)-1-(3-bromophenyl)ethyl]-N-[(1S)-2,3-dihydro-1H-inden-1-yl]-2,4-dinitrobenzenesulfonamide: A flask was charged with 500 mg (1.16 mmol) of N-[(1S)-1-(3-bromophenyl)ethyl]-2,4-dinitrobenzenesulfonamide, 625 mg (4.66 mmol, 4.02 eq.) of (R)-(–)-1-indanol (from Sigma-Aldrich), 305 mg (1.16 mmol, 1.0 eq.) of triphenylphosphine, 6.75 mL of benzene and the mixture cooled on an ice-water bath. To the mixture was added 0.183 mL (1.16 mmol, 1.0 eq.) of diethyl azodicarboxylate (DEAD). The ice bath was removed, and stirring was continued for 1 h. The mixture was cooled on an ice-water bath, followed by addition of 305 mg (1.16 mmol, 1.0 eq.) of triphenylphosphine and 0.183 mL (1.16 mmol, 1.0 eq.) of DEAD. The ice bath was removed, and stirring continued for 1 h. The mixture was cooled on an ice-water bath, followed by a third addition of 305 mg (1.16 mmol, 1.0 eq.) of triphenylphosphine and 0.183 mL (1.16 mmol, 1.0 eq.) of DEAD. The ice bath was removed, and stirring continued for 1 h. The mixture was diluted with EtOAc, washed with 2×sat. aqueous NaCl, dried (Na$_2$SO$_4$), filtered, and concentrated. The crude material was purified by silica gel chromatography on a 30 mm column (3.5 inches of silica) using EtOAc as eluent. The product was triturated in 10% EtOAc in hexanes and filtered affording 625 mg (98.5% yield) of product as a solid.

(1S)-1-(3-bromophenyl)ethyl](1S)-2,3-dihydro-1H-inden-1-ylamine: To a mixture of 625 mg (1.14 mmol) of N-[(1S)-1-(3-bromophenyl)ethyl]-N-[(1S)-2,3-dihydro-1H-inden-1-yl]-2,4-dinitrobenzenesulfonamide in 11.5 mmol of CH$_2$Cl$_2$ was added 1.44 mmol (17.5 mmol, 15.4 eq.) of n-propylamine. The reaction was stirred for 16 h at room temperature and concentrated. The crude material was purified by silica gel chromatography on a 25 mm column (3.5 inches of silica gel) using 10% EtOAc in hexanes as eluent. After concentration, 4.0 mL of Et$_2$O was added to the residue, followed by 4 N HCl in dioxane. The mixture was sonicated, filtered, and washed with Et$_2$O. The material was taken up in EtOAc, washed with 2×sat. aqueous NaHCO$_3$, dried (Na$_2$SO$_4$), filtered, and concentrated to afford 170 mg (47.2% yield) of product.

(1S)-N-{(1S)-1-[3-(4,4,5,5-tetramethyl-1,3,2-dioxaborolan-2-yl]ethyl}indane-1-amine was synthesized according to the procedure described in above from [(1S)-1-(3-bromophenyl)ethyl](1S)-2,3-dihydro-1H-indene-1-ylamine and bis(pinacolato)diboron. Yield 64%. $^1$H NMR (400 MHz, CDCl$_3$): 7.80 (br s, 1H), 7.72 (br d, 1H), 7.58 (br d, 1H), 7.35 (m, 2H), 7.18 (m, 3H), 4.12 (m, 2H), 2.90(m, 1H), 2.70 (m, 1H), 2.20 (m, 1H), 1.70 (m, 1H), 1.40 (d, 3H), 1.24 (s, 12H).

3-amino-6-(3-{(1S)-1-[(1S)-2,3-dihydro-1H-inden-1-ylamino]ethyl}phenyl)-N-methylpyrazine-2-carboxamide was prepared according to the procedure described above by coupling (1S)-N-{(1S)-1-[3-(4,4,5,5-tetramethyl-1,3,2-dioxaborolan-2-yl]ethyl}indane-1-amine and 3-amino-6-bromo-N-methyl-2-pyrazincarboxamide as hydrochloric acid salt. Yield 34%. $^1$H NMR (400 MHz, CDCl$_3$): 8.64 (s, 1H), 8.15 (br s, 1H), 8.02 (br s, 1H), 7.78 (m, 1H), 7.49 (m, 2H), 7.40 (m, 1H), 7.20 (m, 4H), 4.21 (m, 2H), 3.02 (m, 4H), 2.78 (m, 1H), 2.22 (m, 1H), 1.80 (br s, 1H), 1.42 (d, 3H); MS (EI) for C$_{23}$H$_{25}$N$_5$O: 388 (MH+).

Example 23

3-amino-6-(3-{[(1S)-2,3-dihydro-1H-inden-1-ylamino]sulfonyl}phenyl)pyrazine-2-carboxcamide 3-bromo-N-[(1S)-2,3-dihydro-1H-indene-1-yl]benzenesulfonamide was synthesized according to the procedure described above from (S)-1-aminoindan and 3-bromobenzensulfonyl chloride. Yield 52%. $^1$H NMR (400 MHz, CDCl$_3$): 7.20 (m, 1H), 7.90 (dd, 1H), 7.80 (dd, 1H), 7.50 (t, 1H), 7.20 (m, 2H), 7.15 (m, 1H), 7.02 br d, 1H), 4.80 (t, 1H), 2.90(m, 1H), 2.70 (m, 1H), 2.20 (m, 1H), 1.70 (m, 1H).

N-[(1S)-2,3-dihydro-1H-inden-1-yl)]-3-(4,4,5,5-tetramethyl-1,3,2-dioxaborolan)benzenesulfonamide was synthesized according to the procedure described above from 3-Bromo-N-[(1S)-2,3-dihydro-1H-indene-1-yl]benzenesulfonamide and bis(pinacolato)diboron. Yield 58%. $^1$H NMR (400 MHz, CDCl$_3$): 8.40 (br s, 1H), 8.02 (m, 2H), 7.54 (t, 1H), 7.16 (m, 4H), 4.90 (m, 1H), 4.70 (d, 1H), 2.90 (m, 1H), 2.78 (m, 1H), 2.30 (m, 1H), 1.70 (m, 1H), 1.24 (s, 12H).

3-amino-6-(3-{[(1S)-2,3-dihydro-1H-inden-1-ylamino]sulfonyl}phenyl)pyrazine-2-carboxamide was prepared according to the procedure described above by coupling N-[(1S)-2,3-dihydro-1H-inden-1-yl)]-3-(4,4,5,5-tetramethyl-1,3,2-dioxaborolan) benzenesulfonamide and 3-amino-6-bromo-N-methyl-2-pyrazincarboxamide. Yield 50%. $^1$H NMR (400 Mz, d$_6$-DMSO): 8.86 (s, 1H), 8.60 (br s, 1H), 8.45 (br d, 1H), 8.25 (br s, 1H), 8.20 (d, 1H), 7.85 (t, 2H), 7.70 (t, 1H), 7.19 (m, 4H), 4.80 (m, 1H), 2.80 (m, 1H), 2.62 (m, 1H), 2.00 (m, 1H), 1.60 (m, 1H); MS (EI) for C$_{20}$H$_{19}$N$_5$O$_3$S: 410 (MH+).

3-amino-6-(3-{[(1S)-2,3-dihydro-1H-inden-1-ylamino]sulfonyl}phenyl)-N-piperidin-3-ylpyrazine-2-carboxamide was prepared according to the procedure described above by coupling N-[(1S)-2,3-dihydro-1H-inden-1-yl)]-3-(4,4,5,5-tetramethyl-1,3,2-dioxaborolan)benzenesulfonamide and tert-butyl 3-[2-(3-amino-6-bromopyrazin-2-yl)-2-oxoethyl]piperidine-1-carboxylate followed by the deprotection of the boc group with 4.0 N hydrochloric acid(1,4-dioxane solution). Yield 50%. $^1$H NMR (400 MHz, CD$_3$OD): 8.78 (br s, 1H), 8.58 (br s, 1H), 8.35 (d, 1H), 7.95 (d, 1H), 7.75 (t, 1H), 7.18 (m, 2H), 7.10 (m, 2H), 4.85 (t, 1H), 4.30 (br s, 1H), 3.72 (m, 1H), 3.68 (m, 1H), 3.55 (m, 1H), 3.50 (br d, 1H), 3.35 (dr d, 1H), 3.15 (br t, 1H), 3.00 (br t, 1H), 2.90 (m, 1H), 2.70 (m, 1H), 2.10 (m, 2H), 1.78 (m, 1H), 1.70 (m, 1H); MS (EI) for C$_{25}$H$_{28}$N$_6$O$_3$S: 493 (MH+).

N-[3-(5-amino-6-{5-[(3S)-piperidin-3-yl]-4H-1,2,4-triazol-3-yl}pyrazin-2-yl)phenyl]-2-(2,4-dichlorophenyl)acetamide: $^1$H NMR (400 MHz, CD$_3$OD): 8.52 (br s, 1H), 8.48 (br s, 1H), 7.82 (br d, 1H), 7.48 (m, 6H), 7.35 (m, 1H), 3.92 (s, 3H), 3.70 (m, 1H), 3.42 (m, 2H), 3.05 (m, 1H), 2.30 (m, 1H), 2.02 (m, 3H); MS (EI) for C$_{25}$H$_{24}$N$_8$OCl$_2$: 524 (MH+).

1,1-dimethylethyl (3R)-3-{[(3-{5-amino-6-[(methylamino)carbonyl]pyrazin-2-yl}phenyl)carbonyl]amino}pyrrolidine-1-carboxylate: $^1$H NMR (400 MHz; DMSO-D$_6$): 8.91 (s, 1H); 8.86 (m, 1H); 8.63 (d 1H); 8.45 (s, 1H); 8.38 (d, 1H); 7.82 (d, 1H); 7.76 (t, 1H); 4.45 (m, 1H); 3.7-3.4 (m, 4H); 2.85 (d, 3H); 2.33 (m, 1H); 1.9 (m, 1H); 1.4 (s, 9H); MS (EI) for C$_{22}$H$_{28}$N$_6$O$_4$: 441 (MH$^+$)

Example 24

3-amino-N-methyl-6-(3-{[(3R)-pyrrolidin-3-ylamino]carbonyl}phenyl)pyrazine-2-carboxamide 1,1-dimethylethyl-3-{[(3-{5-amino-6[(methylamino)carbonyl )pyrazin-2-yl}phenyl}carbonyl}amino}pyrrolidine-1-carboxylate (0.7 g, mmol) was suspended in dichloromethane (4 mL) and TFA (3 mL) was added. The mixture was stirred at ambient temperature for 2 hr. After removal of volatiles under reduced pressure, the residue was partitioned between saturated solution K$_2$CO$_3$ (300 mg) and dichloromethane (10 mL). The organic layer was separated, dried (Na$_2$SO$_4$) and evaporated to dryness to afford 0.4 g (74% yield) of 3-amino-N-methyl-6-(3-{[(3R)-pyrrolidin-3-ylamino] carbonyl}phenyl) pyrazine-2-carboxamide. $^1$H NMR (400 MHz; DMSO-D$_6$): 8.9 (s, 1H); 8.85 (m, 1H); 8.71 (d, 1H); 8.48 (m, 1H); 7.4 (d, 1H); 7.84 (m, 1H); 7.6 (t, 1H); 4.54 (m, 2H); 3.6-3.18 (m, 4H); 2.85 (d, 3H); 2.25 (m, 1H); 2.1 (m, 1H); MS (EI) for C$_{17}$H$_{20}$N$_6$O$_2$: 341 (MH$^+$)

3-{[(4-chlorophenyl)methyl]amino}-6-{3-[({(3R)-1-[(4-chlorophenyl)methyl]pyrrolidin-3-yl}amino)carbonyl]phenyl}-N-methylpyrazine-2-carboxamide: To a solution of 3-amino-N-methyl-6-(3-{[(3R)-pyrrolidin-3-ylamino] carbonyl}phenyl)pyrazine-2-carboxamide (34.0 mg, 0.1 mmol) in acetonitrile was added K$_2$CO$_3$ (27.6 mg, 0.2 mmol) followed by 4-chlorobenzyl bromide (30.7 mg, 0.15 mmol). The mixture was allowed to stir at room temperature over 12 h and filtered. The acetonitrile solution was evaporated to dryness, the residue was chromatographed on silica gel using ethyl acetate/hexane 4:1 v/v and trituration of the resulting solid with hexane afforded 3-{[(4-chlorophenyl)methyl]amino}-6-{3-[({(3R)-1-[(4-chlorophenyl) methyl]pyrrolidin-3-yl}amino)carbonyl]phenyl}-N-methylpyrazine-2-carboxamide (28 mg, 47.6%yield): $^1$H NMR (400 MHz; DMSO-D$_6$): 8.9 (s, 1H); 8.85 (m, 1H); 8.75 (m, 1H); 8.38 (m, 2H); 7.78-7.5 (m, 1H); 4.63 (m, 5H); 3.9 (m, 1H); 3.6 (m, 2H); 3.4 (m, 1H); 2.85 (d, 3H); 2.5 (m, 1H); 2.2 (m, 1H); MS (EI) for C$_{31}$H$_{30}$N$_6$O$_2$Cl$_2$: 589 (MH$^+$)

The following compounds were prepared in an analogous manner as 3-{[(4-chlorophenyl)methyl]amino}-6-{3-[({(3R)-1-[(4-chlorophenyl)methyl]pyrrolidin-3-yl}amino)carbonyl]phenyl}-N-methylpyrazine-2-carboxamide.

3-amino-6-{3-[({(3R)-1-[(2,4-dichlorophenyl)methyl]pyrrolidin-3-yl}amino)carbonyl]phenyl}-N-methylpyrazine-2-carboxamide: $^1$H NMR (400 MHz; DMSO-D$_6$): 8.92 (s, 1H); 8.86 (m, 1H); 8.6 (d, 1H); 8.46 (m, 1H); 8.36 (d, 1H); 7.82 (d, 1H); 7.6-7.4 (m, 4H); 4.43 (m, 1H); 3.7 (m, 2H); 2.9 (m, 1H); 2.88 (d, 3H); 2.75 (m, 2H); 2.58 (m, 2H); 2.2 (m, 1H); 1.85 (m, 1H); MS (EI) for C$_{24}$H$_{24}$N$_6$O$_2$Cl$_2$: 4.99 (MH$^+$)

N-methyl-3-({[3-(methyloxy)phenyl]methyl}amino)-6-(3-{[((3R)-1-{[3-(methyloxy)phenyl]methyl}pyrrolidin-3-yl)amino]carbonyl}phenyl)pyrazine-2-carboxamide: 8.98

(m, 1H); 8.92 (m, 1H); 8.88 (s, 1H); 8.48 (m, 1H); 8.38 (d, 1H); 7.78 (d, 1H); 7.6-7.0 (m, 9H); 4.7 (m, 5H); 3.95 (m, 1H); 3.85 (s, 3H); 3.74 (s, 3H); 3.7 (m, 2H); 3.54 (m, 1H); 2.85 (s, 3H); 2.45(m, 1H); 2.28 (m, 1H); MS (EI) for $C_{33}H_{36}N_6O_4$; 581 (MH$^+$)

3-Amino-6-{3-[({(3R)-1-[(2,6-dichlorophenyl)methyl]pyrrolidin-3-yl}amino)carbonyl]phenyl}-N-methylpyrazine-2-carboxamide: $^1$H NMR (400 MHz; DMSO-D$_6$): 8.91 (s, 1H); 8.86 (m, 1H); 8.55 (d, 1H); 8.46 (m, 1H); 8.38 (d, 1H); 7.82 (d, 1H); 7.6-7.3 (m, 4H); 4.4 (m, 1H); 3.88 (s, 2H); 3.0 (m, 1H); 2.85 (d, 3H); 2.8-2.54 (m, 3H); 2.15 (m, 1H); 1.85 (m, 1H); MS (EI) for $C_{24}H_{24}N_6O_2C_2$: 499 (MH$^+$)

N-methyl-3-[(phenylmethyl)amino]-6-[3-({[(3R)-1-(phenylmethyl)pyrrolidin-3-yl]amino}carbonyl)phenyl]pyrazine-2-carboxamide: $^1$H NMR (400 MHz; DMSO-D$_6$): 8.92 (m, 2H); 8.86 (s, 1H); 8.45 (s, 1H); 8.36 (d, 1H); 7,76 (d, 1H); 7.7-7.46 (m, 11H); 4.65 (m, 5H); 3.91 (m, 1H); 3.62 (m, 2H); 3.45 (m, 1H); 2.85 (d, 3H); 2.49 (m, 1H); 1.22 (m, 1H); MS (EI) for $C_{31}H_{32}N_6O_2$: 521 (MH$^+$)

1,1-dimethylethyl 3-({[(3-{5-amino-6-[(methylamino)carbonyl]pyrazin-2-yl}phenyl)carbonyl]amino]methyl)pyrrolidine-1-carboxylate: $^1$H NMR (400 MHz; DMSO-D$_6$): 8.91 (s, 1H); 8.85 (m, 1H); 8.68 (m, 1H); 8.46 (s, 1H); 8.38 (d, 1H); 7.82 (d, 1H); 7.56 (t, 1H); 3.4 (m, 5H); 3.0 (m, 1H); 2.85 (d, 3H); 2.47 (m, 1H); 1.95 (m, 1H); 1.6 (m, 1H); 1.39 (s, 9H); MS (EI) for $C_{23}H_{30}N_6O_4$: 455 (MH$^+$)

1,1-dimethylethyl 2-({[(3-{5-amino-6-[(methylamino)carbonyl]pyrazin-2-yl}phenyl)carbonyl]amino}methyl)pyrrolidine-1-carboxylate: $^1$H NMR (400 MHz; DMSO-D$_6$): 8.91 (s, 1H); 8.85 (m, 1H); 8.5 (m, 1H); 8.46 (s, 1H); 8.38 (d, 1H);7.72 (d, 1H); 7.58 (t, 1H); 3.98 (m, 1H); 3.4 (m, 4H); 2.85 (d, 3H); 1.85 (m, 4H); 1.39 (s, 9H); MS (EI) for $C_{23}H_{30}N_6O_4$: 455 (MH$^+$)

3-amino-N-methyl-6-(3-{[(pyrrolidin-3-ylmethyl)amino]carbonyl]phenyl)pyrazine-2-carboxamide: $^1$H NMR (400 MHz; DMSO-D$_6$): 8.91 (s, 1H); 8.85 (m, 1H); 8.75 (m, 1H); 8.66 (br s, 2H); 8.48 (s, 1H); 8.38 (d, 1H); 7.84 (d, 1H); 7.58 (t, 1H); 3.6-3.2 (m, 5H); 3.1(m, 1H); 2.91 (m, 1H); 2.85 (d, 3H); 2.6 (m, 1H); 2.0 (m, 1H); 1.7 (m, 1H); MS (EI) for $C_{18}H_{22}N_6O_2$: 355 (MH$^+$)

3-amino-N-methyl-6-(3-{[(pyrrolidin-2-ylmethyl)amino]carbonyl}phenyl)pyrazine-2-carboxamide: $^1$H NMR (400 MHz; DMSO-D$_6$): 8.91 (s, 1H); 8.85 (m, 1H); 8.5 (s, 1H); 8.4 (d, 1H); 7.84 (d, 1H); 7.58 (t, 1H); 3.6-3.4(m, 3H); 3.1-3.2 (m, 2H); 2.85 (d, 3H); 2.0-1.6 (m, 4H); MS (EI) for $C_{21}H_{21}M_6O_2$: 355 (MH$^+$)

Example 25

Scheme 11 depicts a general synthetic route for compounds of the invention having substituents —W—X—Y according to formula I, wherein, for example, W is phenylene, X is —C(—O)NHCH$_2$—, and Y is a 3,4-dihydro-2H-benzo[1,4]oxazinyl group. As depicted, intermediate (li) is incorporated into a compound of the invention, (lvii). Nitro phenol (li) was reduced to aniline (lii). Then the aniline nitrogen was acylated to give intermediate (liii). A ring closure was effected to yield intermediate (liv). Reduction of the cyano group gave (lv), followed by reduction of the carbonyl giving primary amine (lvi). Amine (lvi) was coupled to an acid to yield compounds of the invention, for example (lvii) as depicted below.

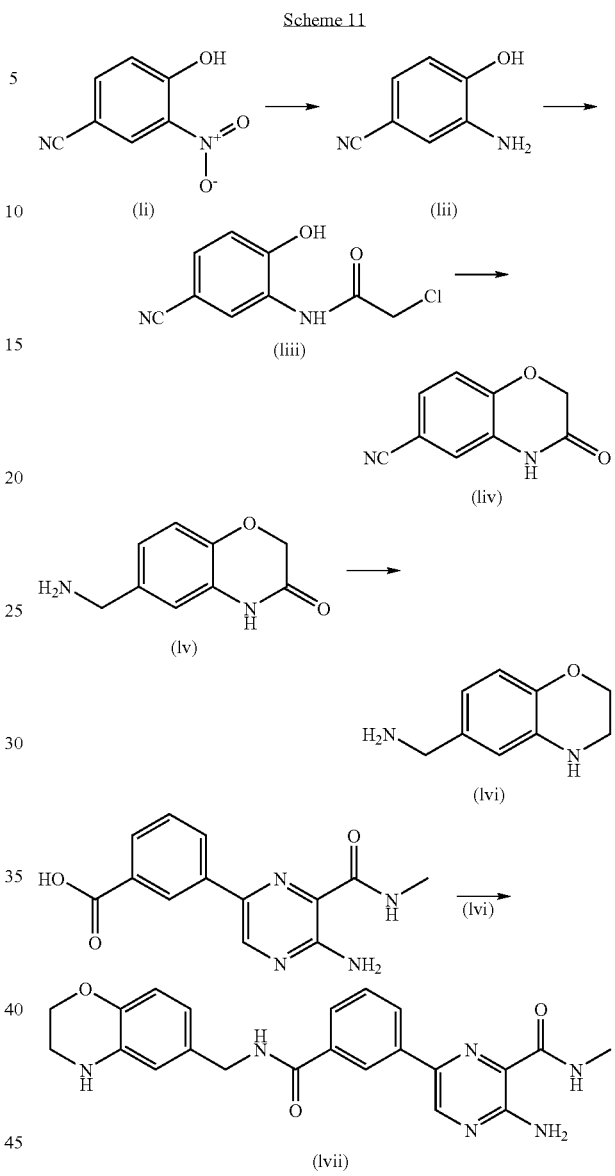

3-amino-6-(3-{[(3,4-dihydro-2H-1,4-benzoxazin-6-ylmethyl)amino]carbonyl}phenyl)-N-methyl pyrazine-2-carboxamide 3-Amino-4-hydroxybenzonitrile: To a solution of 3-nitro-4-hydroxybenzonitrile (3.28 g, 20 mmol) in ethyl acetate was hydrogenated over 5% Pd/C, at an initial pressure 20 psi in a Parr shaker. After 3 h the reaction mixture was filtered (Celite). The solvent was removed under reduced pressure and the residue oil 3-Amino-4-hydroxybenzonitrile (2.6 g, 97% yield) used in the next step without further purification: $^1$H NMR (400 MHz; DMSO-D$_6$): 6.85 (m, 2H); 6.73 (d, 1H); 5.0 (br s, NH).

3-Oxo-3,4-dihydro-2H-1,4-benzoxazin-6-carbonitrile: 3-amino-4-hydroxybenzonitrile (g, 10 mmol was dissolved in acetone (20 mL) and water (20 mL) containing sodium bicarbonate (4 g). 2-chloroacetyl chloride was added slowly and the mixture heated to reflux for 4 h and then allowed to stir overnight at 25° C. The layers were separated, and the water layer was extracted with ethyl acetate. The organic layers were combined and evaporated to give 3-oxo-3,4-dihydro-2H-1,4-benzoxazin-6-carbonitrile as an oil (1.3 g): $^1$H NMR (400 M ; DMSO-D$_6$): 7.4 (d, 1H); 7.2 (s, 1H); 7.1 (d, 1H).

3,4-Dihydro-2H-1,4-benzoxazine-6-ylmethyl)amine: a solution of 3-oxo-3,4-dihydro-2H-1,4-benzoxazin-6-carbonitrile (1.3 g ) in anhydrous TBF (20 mL) was slowly added to a stirred and ice -cooled solution of lithium aluminum hydride (30 mL, 1 M solution in THF). With continued cooling water (5 mmol) and sodium hydroxide (5 mL, 20% solution), water (20 mL) and ethyl acetate (30 mL) were added in succession. The organic solution was decanted from the white residue. The residue was washed twice with ether, all the organic solution were combined then dried over anhydrous sodium sulfate. Filtration and concentration followed by drying in vacuo afforded 3,4-dihydro-2H-1,4-benzoxazine-6-yl-methylamine (0.78 g,): $^1$H NMR (400 MHz; DMSO-D$_6$): 6.52 (d, 1H); 6.49 (s, 1H); 6.37 (d, 1H); 5.6 (br s, NH); 4.05 (t, 2H); 3.4 (m, 2H).

3-amino-6-(3-{[(3,4-dihydro-2H-1,4-benzoxazin-6-ylmethyl)amino]carbonyl}phenyl)-N-methylpyrazine-2-carboxamide: $^1$H NMR (400 MHz; DMSO-D$_6$): 8.96 (t, 1H); 8.79 (s, 1H); 8.81 (m, 1H); 8.5 (s, 1H); 8.35 (d, 1H)1 7.85 (d, 1H); 7.65 (br s, 2H); 7.55 (t, 1H); 6.55 (m, 2H); 6.44 (d, 1H); 5.77 (s, 1H); 4.4 (d, 2H); 4.15 (m, 2H); 3.2 (s, 1H); 2.85 (d, 3H); MS (EI) for C$_{22}$H$_{22}$N$_6$O$_3$: 419 (MH$^+$)

Example 26

3-amino-N-methyl-6-{3-[({[1-(phenylmethyl)pynolidin-2-yl]methyl amino)carbonyl]phenyl}pyrazine-2-carboxamide To a stirred solution of 3-amino-N-methyl-6-(3-{[(pyrrolidin-2-ylmethyl)amino]carbonyl}phenyl)pyrazine-2-carboxamide (35.4 mg, 0.01 mmol) and benzaldehyde (24.8 mg, 0.02 mmol) in methanol (3 mL) was added sodium cyanoborohydride (25 mg, 0.04 mmol). The mixture was stirred for 1 h and then acetic acid added until the pH of the solution was 7.0. The solution was stirred for an additional 6 h, solvent was removed and residue was partitioned with CHCl$_3$ and 2 M aqueous sodium hydroxide (5 mL). The aqueous phase was extracted with additional CHCl$_3$ (2×5 mL) and the combined organic layer were washed with saturated aqueous sodium chloride then dried over anhydrous sodium sulfate. Filtration, concentration and column chromatography provided 10 mg of 3-amino-N-methyl-6-{3-[({[1-(phenylmethyl)pyrrolidin-2-yl]methyl}amino)carbonyl]phenyl}pyrazine-2-carboxamide: $^1$H NMR (400 MHz; CDCl$_3$); 8.7 (s, 1H); 8.65 (s, 1H); 8.28 (br s, 1H); 7.95 (d, 1H); 7.22 (d, 1H); 7.53 (t, 1H); 7.2-7.4 (m, 5H); 4.3-3.5 (m, 7H); 2.95 (d, 3H); 2.35-1.8 (m, 4H); MS (EI) for C25H$_{28}$N$_6$O$_2$: 445 )

3-amino-N-methyl-6-{3-[({[1-(phenylmethyl)pyrrolidin-3-ylmethyl}amino)carbonyl]phenyl]pyrazine-2-carboxamide: $^1$H NMR (400 MHz; CDCl$_3$): 8.67 (s, 1H); 8.42 (s, 1H); 8.15 (m, 1H); 7.95 (d, 1H); 7.84 (d, 1H); 7.53 (t, 1H); 7.4 (m, 5H); 4.15 (m, 2H); 3.75 (m, 1H); 3.4 (m, 2H); 3.0 (m, 5H); 2.22 (m, 1H); 1.95 (m, 1H); MS (EI) for C$_{25}$H$_{28}$N$_6$O$_2$: 445 (MH$^+$)

3-amino-N-methyl-6-[3-({[(2-pyridin4-ylphenyl)methyl]amino}carbonyl]phenyl]pyrazine-2-carboxamide: $^1$H NMR (400 MHz; DMSO-D$_6$): 9.1 (t, 1H); 8.6 (s, 1H); 8.84 (m, 1H); 8.64 (m, 1H); 8.42 (m, 1H); 8.42 (m, 1H); 7.35 (d, 1H); 7.8 (d, 1H); 7.6-7.36 (m, 6H); 7.28 (d, 1H) 4.43 (d, 2H); 2.85 (d, 3H); MS (EI) for C$_{25}$H$_{22}$N$_6$O$_2$: 439 (+)

Example 27

Scheme 12 depicts a general synthetic route for compounds of the invention having substituents —W—X—Y according to formula I, wherein, for example, W is phenylene, X is —C(=O)NHCH$_2$—, and Y is a bis-aryl, aryl-heteroaryl, or heteroaryl-heteroaryl group. As depicted, intermediate (lvii), a compound of the invention, is converted to (lix), another compound of the invention, for example, via aromatic coupling reactions known in the art.

Scheme 12

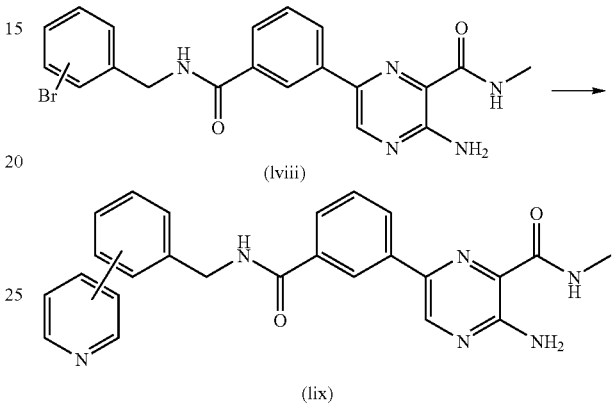

3-amino-N-methyl-6-[3-({[(2-pyridin-3-ylphenyl)methyl]amino}carbonyl)phenyl]pyrazine-2-carboxamide: $^1$H NMR (400 MHz; DMSO-D$_6$): 9.1 (t, 1H); 8.6 (s, 1H); 8.64 (m, 1H); 8.58 (m, 1H); 8.42 (s, 1H); 8.34 (d, 1H); 7.88 (m, 1H); 7.8 (d, 1H); 7.58-7.34 (m, 5H); 7.28 (d, 1H) 4.43 (d, 2H); 2.85 (d, 3H); MS (I) for C$_{25}$H$_{22}$N$_6$O$_2$: 439 (MH$^+$)

3-amino-N-methyl-6-[3-({[(4-pyridin-3-ylphenyl)methyl]amino}carbonyl)phenyl]pyrazine-2-carboxamide: (400 MHz; CD$_3$OD): 8.24 (t, 1H); 9.08 (m, 1H); 8.78 (s, 1H); 8.72 (m, 2H); 8.55 (m, 1H); 8.2 (d, 1H); 8.0 (m, 1H); 7.88 (d, 1H); 7.76 (m, 2H); 7.58 (m, 3H); 4.54 (d, 2H); 2.85 (s, 3H); MS (EI) for C$_{25}$H$_{22}$N$_6$O$_2$: 439 (MH$^+$)

Example 28

3-amino-6-[3-(1H-benzimidazol-2-yl)phenyl]-N-methylpyrazine-2-carboxamide

3-Amino-6-(3-formylphenyl)-N-methylpyrazine-2-carboxamide: Methyl 3-amino-6-(3-formylphenyl)pyrazine-2-carboxylate (0.6 g, mmol) was suspended in ammonia (30 mL, 2.0 M solution in methyl alcohol) and brought to reflux over 2 h, then water (100 mL) was added. The solid was collected, treated with 4 M HCl in 1,4-dioxane (10 mL) and stirred at 70° C. overnight. The solvent was removed and the residue was partitioned with ethyl acetate and saturated sodium bicarbonate. The organic layer was washed with brine then dried over sodium sulfate. Filtration, concentration and column chromatography on silica afforded 3-amino-6-(3-formylphenyl)-N-methylpyrazine-2-carboxamide (0.4 g).

3-amino-6-[3-(1H-benzimidazol-2-yl)phenyl]-N-methylpyrazine-2-carboxamide: A solution of 3-amino-6-(3-formylphenyl)-N-methylpyrazine-2-carboxamide (25.4 mg, 0.1 mmol) and 1,2-phenylendiamine in NMP (3 mL) was heated at 80° C. for 8 h. The solvent was removed and the residue was triturated with 0.1 M aquous hydrochloric acid.

Filtration and hplc purification of the precipitate afforded (24 mg, 57% yield) of product: (400 MHz; DMSO-D$_6$): 8.9 (s, 1H); 8.85 (m, 1H); 8.8 (s, 1H); 8.31 (d, 1H); 8.2 (d, 1H); 7.6 (m, 3H); 7.2 (m, 2H); 2.85 (d, 3H); MS (EI) for C$_{19}$H$_{16}$N$_6$O: 345 (MH$^+$)

Example 29

3-amino-N-methyl-6-[3-(4-phenyl-1H-imidazol-2-yl)phenyl]pyrazine-2-carboxamide 3-amino-6-{3-[amino(hydroxyimino)methyl]phenylpyrazine-2-carboxamide: 3-Amino-6-(3-cyanophenyl)-N-methylpyrazine-2-carboxamide (0.7 g, 2.76 mmol) and hydroxylamine (5 ml, 50% aqueous) were stirred in methanol/THF (5 mL, 1:1) at 80° C. for 8 h. The mixture was poured into water (30 mL). The solid was collected by filtration, washed with ethyl ether and dried to give 3-amino-6-{3-[amino(hydroxyimino)methyl]phenylpyrazine-2-carboxamide (0.75 g, 94.9% yield) as a white solid: $^1$H NMR (400 MHz; DMSO-d$_6$): 9.7 (s, 1H); 8.85 (m, 2H); 8.3 (s, 1H); 8.2 (d, 1H); 7.74 (d, 1H); 7.4 (t, 1H); 6.0 (s, 2H); 2.85 (d, 3H); MS (EI) for C$_{13}$H$_{14}$N$_6$O$_2$: 287 (MH$^+$).

3-amino-6-{3-[amino(imino)methyl]phenyl}-N-methylpyrazine-2-carboxamide: To a stirred solution of 3-amino-6-{3-[amino(hydroxyimino)methyl]phenylpyrazine-2-carboxamide (0.858 mg, 3 mmol) in pyridine (5 mL) was added acetic anhydride (4 mmol). The mixture was poured into water (50 mL) and extracted with ethyl acetate (30 mL). The extract was washed with brine, dried (Na$_2$CO$_3$), and concentrate to provide 6-{3-[(E,Z)-[(acetyloxy)imino](amino)methyl]phenyl}-3-amino-N-methylpyrazine-2-carboxamide: To a solution of this crude material (400 mg) in 950 mL of methanol was added Pd/C (5%, 20 mg) and the mixture was hydrogenated at 30 psi on a Parr shaker. The mixture was filtered through celite and the filtrate was evaporated, and concentrated to provide (300 mg, 37% yield) of 3-amino-6-{3-[amino(imino)methyl]phenyl}-N-methylpyrazine-2-carboxamide: MS (EI) for C$_{13}$H$_{14}$N$_6$O: 271 (MH$^+$).

3-amino-N-methyl-6-[3-(4-phenyl-1H-imidazol-2-yl)phenyl]pyrazine-2-carboxamide: To a stirred solution of 3-amino-6-{3-[amino(imino)methyl]phenyl}-N-methylpyrazine-2-carboxamide (0.13 6 mg, 0.5 mmol) in DMF (5 mL) was added bronoacetophenone (0.11 g, 0.55 mmol ) followed by K$_2$CO$_3$ (0.276 g). The resulting mixture was heated at 70 ° C. for 0.5 h. The mixture was poured into water (30 mL) and extracted with ethyl acetate (30 mL). The extract was washed with brine, dried (Na$_2$SO$_4$), and concentrated. The product was purified by hplc to provide 3-amino-N-methyl-6-[3-(4-phenyl-1H-imidazol-2-yl)phenyl]pyrazine-2-carboxamide (58 mg): $^1$H NMR (400 MHz; DMSO-d$_6$): 8.94 (s, 1H); 8.82 (m, 1H); 8.62 (s, 1H); 8.2 (d, 1H); 8.04 (d, 1H); 7.9-7.78 (m, 3H); 7.58 (t, 1H); 7.38 (m, 2H); 7.24 (t, 1H); 2.82 (d, 3H); MS (EI) for C$_{21}$H$_{18}$N$_6$O: 371 (MH$^+$).

Example 30

3-amino-N-methyl-6-[3-({[(4-propylphenyl)methyl]amino}methyl)phenyl]pyrazine-2-carboxamide 3-amino-N-methyl-6-[3-({[(4-propylphenyl)methyl]amino}methyl)phenyl]pyrazine-2-carboxamide: To a stirred solution of 3-amino-6-(3-formylphenyl)-N-methylpyrazine-2-carboxamide (50 mg, 0.19 mmol) and 4-propylbenzylamine (35.7 mg, 0.24 mmol) in TBF (5 mL) was added sodium cyanoborohydride (ca. 5 eq.) and the solution was stirred until refluxed for 1 h. The solvent was removed under reduced pressure. The residue was partitioned between ethyl acetate (50 mL) and saturated aqueous solution of Na$_2$CO$_3$ (10 mL). The phases were separated. The organic layer was washed with saturated aqueous sodium chloride then dried (Na2SO$_4$). Filtration and concentration followed by HPLC purification gave (24 mg, 32% yield) of 3-amino-N-methyl-6-[3-({[(4-propylphenyl)methyl]amino}methyl)phenyl]pyrazine-2-carboxamide: $^1$H NMR (400 MHz; DMSO-d$_6$): 9.7 (br s, 1H); 9.0 (m, 1H); 8.87 (s, 1H); 8.5 (s, 1H); 8.4 (d, 1H); 7.5 (m, 6H); 7.43 (m, 2H); 4.2 (d, 2H); 2.82 (d, 3H); 2.56 (m, 2H); 1.6 (m, 2H); 0.9 (m, 3H); MS (EI) for C$_{23}$H$_{27}$N$_5$O: 390 (MH$^+$).

Using the same or analogous synthetic techniques and/or substituting with alternative reagents, the following compounds of the invention were prepared:

3-amino-6-[3-({[(5-bromo-2-fluorophenyl)methyl]amino]methyl)phenyl]-N-methylpyrazine-2-carboxamide: $^1$H NMR (400 MH; DMSO-d$_6$): 9.8 (br s, 1H); 9.0 (m, 1H); 8.88 (s, 1H); 8.62 (s, 1H); 8.21 (m, 1H); 8.01 (m, 3H); 7.68 (m, 1H); 7.5 (m, 2H); 7.3 (t, 1H); 4.2 (d, 2H); 2.85 (t, 3H); MS (EI) for C$_{20}$H$_{19}$N$_5$OFBr: 446 (MH$^+$).

Example 31

Scheme 13 depicts a general synthetic route for compounds of the invention having substituents —W—X—Y according to formula I, wherein, for example, W is phenylene, X is —C(=O)NHCH$_2$—, and Y is an indanyl group. As depicted, intermediate (lx), is incorporated into (lxvii), a compound of the invention. 1-Amino-2,3-dihydro-R1,R2-substituted-1H-indene(s) were obtained from commercial sources or were prepared from cinnamic acids (or aryl propionic acids) by methods known to those skilled in the art as depicted in Scheme 13. Cinnamic acids (lx) were hydrogenated to afford acids (lxi). Acids (lxi) were converted to the corresponding acyl chlorides and subjected to electrophilic aromatic substitution conditions to afford ketones (lxiii). Ketones (lxiii) were reduced to the corresponding alcohols (lxiv), and the alcohols subsequently converted to the corresponding azides (lxv). Azides (lxv) were reduced to form the corresponding 1-aminoindanes (lxvi). Note, azides (lxv) with chloro- or bromo-substitution on phenyl ring portion were reduced to the 1-aminoindanes (lxvi) using SnCl$_2$ in ethyl acetate, typically. Aminoindanes (lxvi) were incorporated into compounds of the invention, e.g. (lxvii), via reductive amination, for example, as depicted. As mentioned, amines were also incorporated via coupling with corresponding benzyl bromides to give, for example, compounds (lxvii).

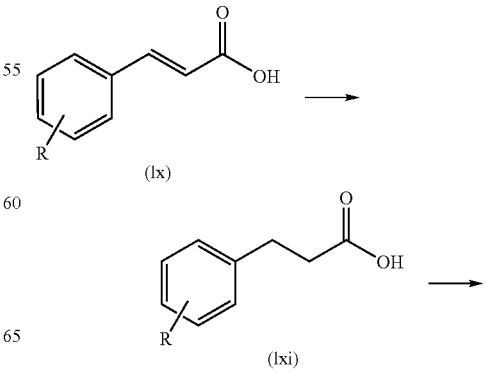

Scheme 13

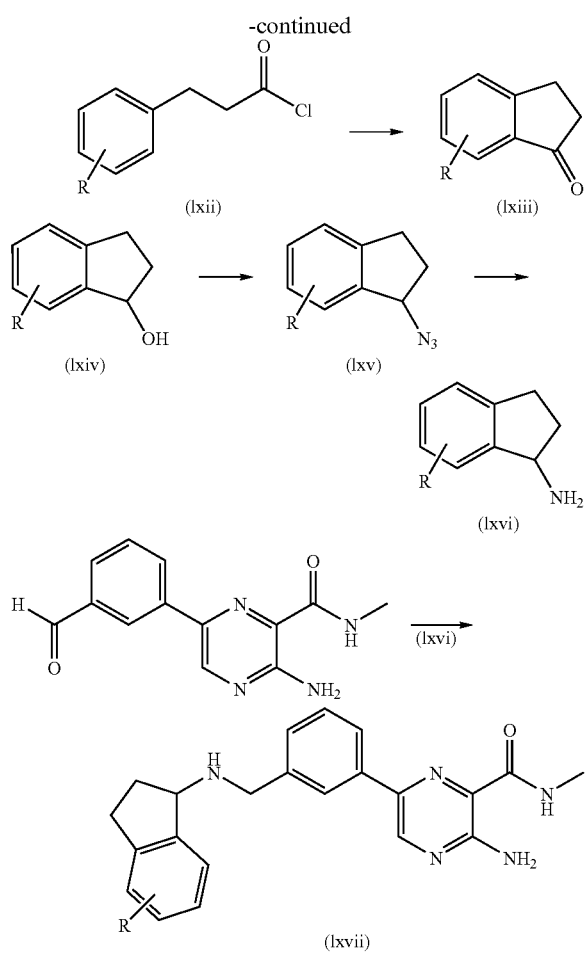

3-amino-6-(3-{[(4,7-difluoro-2,3-dihydro-1H-inden-1-yl)amino]methyl}phenyl)-N-methylpyrazine-2-carboxamide: To a stirred solution of 3-amino-6-(3-formylphenyl)-N-methylpyrazine-2-carboxamide (50 mg, 0.19 mmol) and 1-amino-4,7-difluoroindane (67.6 mg, 0.4 mmol) in THF (5 mL) was added sodium cyanoborohydride (62.8 mg, 1 mmol) and 1 drop of acetic acid. The solution was stirred overnight and solvent was removed under reduced pressure. The residue was partitioned between ethyl acetate (50 mL) and saturated aqueous solution of $Na_2CO_3$ (10 mL). The phases were separated. The organic layer was washed with HCl (5 mL 0.5 M) then saturated aqueous sodium chloride and dried ($Na_2SO_4$). Filtration and concentration follow by hplc purification gave (42.2 mg, 50% yield) of 3-amino-6-(3-{[(4,7-difluoro-3-methyl-2,3-dihydro-1H-inden-1-yl)amino]methyl}phenyl)-N-methylpyrazine-2-carboxamide. An excess of HCl in dioxane (0.2 mL, 4.0 M) was added to the solution and the solvent was removed to give hydrochloride: $^1$H NMR (400 MHz; DMSO-$d_6$): 10.1 (br s, 1H); 9.7 (br s, 1H); 9.0 (m, 1H); 8.85 (s, 1H); 8.2 (m, 1H); 7.5 (m, 2H); 7.3-7.2 (m, 2H); 5.0 (m, 1H); 4.6-4.15 (m, 3H); 3.4 (m, 1H); 2.95 (m, 1H); 2.85 (d, 3H); 2.6 (m, 1H); 2.46 (m, 1H); MS (EI) for $C_{22}H_{21}N_5OF_2$ HCl: 410 (MH$^+$).

3-amino-6-(3-{[(4,7-difluoro-3-methyl-2,3-dihydro-1H-inden-1-yl)amino]methyl)phenyl)-N-methylpyrazine-2-carboxamide: $^1$H NMR (400 MHz; DMSO-d6) 9.0 (m, NH); 8.88 (s, 1H); 8.6 (s, 1H); 8.2 (m, 1H); 7.5 (m, 2H); 7.4 (m, 2H); 4.5 (m, 1H); 4.2 (m, 2H); 2.85 (m, 3H); 2.8 (m, 1H); 2.2 (m, 2H); 1.3 (m, 3H); MS (EI) for $C_{23}H_{23}N_5OF_2$ HCl: 424 (MH$^+$).

3-amino-6-(3-{[(6-bromo4-fluoro-2,3-dihydro-1H-inden-1-yl)amino]methyl}phenyl)-N-methylpyrazine-2-carboxamide: $^1$H NMR (400 MHz; DMSO-$d_6$): 8.8 (s, 1H); 7.78 (m, 1H); 8.08 (s, 1H); 8.22 (m, 1H); 7.4-7.3 (m, 4H); 4.2 (m, 1H); 3.8 (m, 2H); 2.9 (m, 1H); 2.83 (d, 3H); 2.7 (m, 3H); 2.37 (m, 1H); 2.4 (m, 1H); MS (EI) for $C_{22}H_{21}N_5OFBr$: 470 (MH$^+$).

3-amino-6-(3-{[(4-fluoro-2,3-dihydro-1H-inden-1-yl)amino]methyl}phenyl)-N-methylpyrazine-2-carboxamide: $^1$H NMR (400 MHz; DMSO-$d_6$): 9.8 (br s, NM; 9.6 (br s, NH); 8.98 (m, 1H); 8.88 (s, 1H); 8.6 (s, 1H); 8.2 (m, 1H); 7.7-7.2 (m, 6H); 5.1-4.38 (m, 1H); 4.38 (m, 2H); 3.4 (m, 1H); 2.95 (m, 1H); 2.85 (d, 3H); 2.43-2.6 (m, 1H); MS (EI) for $C_{22}H_{22}N_5OF$ HCl: 392 (MH$^+$).

3-amino-6-(3-{[(4,6-difluoro-2,3-dihydro-1H-inden-1-yl)amino]methyl)phenyl)-N-methylpyrazine-2-carboxamide: $^1$H NMR (400 MH; CDCl$_3$): 9.1 (m, 1H); 8.8 (s, 1H); 8.6 (m, 1H); 8.4 (d, 1H); 8.74 (d, 1H); 7.5-7.2 (m, 3H); 4.6 (m, 1H); 3.9 (m, 2H); 3.4 (m, 1H); 3.0 (d, 3H); 2.9 (m, 1H); 2.5 (m, 1H); 1.3 (m, 1H); MS (EI) for $C_{22}H_{21}N_5OF_2$: 410 (MH$^+$).

3-amino-6-(3-{[(6-fluoro-2,3-dihydro-1H-inden-1-yl)amino]methyl}phenyl)-N-methylpyrazine-2-carboxamide; 1H NMR (400 MHz; CDCl$_3$): 8.6 (s, 1H); 8.0 (br s, 1H); 7.8 (s, 1H); 7.75 (m, 1H); 7.74 (m, 1H); 7.18-6.9 (m, 3H); 4.3 (m, 1H); 4.40 (m, 2H); 3.04 (d, 3H); 3.0 (m, 1H); 2.56 (m, 1H); 1.85 (m, 1H); MS (EI) for $C_{22}H_{22}N_5OFL$ 392 (MH$^+$).

3-amino-6-(3-{[(5,6-difluoro-2,3-dihydro-1H-inden-1-yl)amino]methyl}phenyl)-N-methylpyrazine-2-carboxamide: $^1$H NMR (400 MHz; DMSO-$d_6$): 8.6 (s, 1H); 8.0 (br s, 1H); 7.84 (s, 1H); 7.8 (d, 1H); 7.4 (m, 2H); 7.5 (m, 1H); 7.0 (m, 1H); 4.25 (t, 1H); 3.92 (m, 21); 3.08 (d, 3H); 3.0 (m, 1H); 2.8 (m, 1H); 2.5 (m, 1H); 1.9 (m, 1H); MS (EI) for $C_{22}H_{21}N_5OF_2$: 410 (MH$^+$).

3-amino-6-(3-{[(5,7-difluoro-2,3-dihydro-1H-inden-1-yl)amino]methyl}phenyl)-N-methylpyrazine-2-carboxamide: $^1$H NMR (400 M ; CDCl$_3$): 8.64 (s, 1H); 8.4 (m, 1H); 7.88 (s, 1H); 7.76 (d, 1H); 7.4 (m, 2H); 6.78 (d, 1H); 6.64 (t, 1H); 4.6 (m, 1H); 3.9 (m, 2H); 3.2 (m, 1H); 3.1 (d, 3H); 2.85 (m, 1H:); 2.4 (m, 1H); 2.1 (m, 1H); MS (EI) for $C_{22}H_{21}N_5OF_2$: 410 (MH$^+$).

3-amino-6-(3-{[(7-bromo-4-fluoro-2,3-dihydro -1H-inden-1-yl)amino]methyl]phenyl)-N-methylpyrazine-2-carboxamide: 1H NMR (400 MHz; DMSO-$d_6$): 8.81 (s, 1H); 8.78 (br s, 1H); 8.1 (m, 1H); 8.05 (m, 1H); 7.4 (m, 3H); 7.02 (t, 1H); 4.2 (m, 1H); 3.9 (m, 2H); 3.4 (m, 1H); 2.85 (d, 3H); 2.76 (m, 1H); 2.4 (m, 1H); 1.8 (m, 1H); MS (EI) for $C_{22}H_{21}N_5OFBr$: 472 (MH$^+$).

3-amino-6-(3-{[(6-chloro-2,3-dihydro-1H-inden-1-yl)amino]methyl}phenyl)-N-methylpyrazine-2-carboxamide: $^1$H NMR (400 MHz; DMSO-$d_6$): 8.84 (s, 1H); 8.80 (m, 1H); 8.17 (s, 1H); 8.08 (d, 1H); 7.4 (m, 4H); 7.25 (m, 2H); 4.25 (m, 1H); 3.87 (m, 2H); 2.9 (m, 1H); 2.85 (d, 3H); 2.7 (m, 1H); 2.4 (m, 1H); 1.8 (m, 1H); MS (EI) for $C_{22}H_{22}N_5OCl$: 408 (MH$^+$).

3-amino-6-(3-{[(4,6-dichloro-2,3-dihydro-1H-inden-1-yl)amino]methyl}phenyl)-N-methylpyrazine-2-carboxamide: $^1$H NMR (400 MHz; DMSO-$d_6$): 8.84 (s, 1H); 8.8 (m, 1H); 8.1 (s, 1H); 8.06 (d, 1H); 7.39 (m, 4H); 4.2 (m, 1H); 3.87 (m, 2H); 2.9 (m, 1H); 2.85 (d, 3H); 2.77 (m, 1H); 2.4 (m, 1H); 1.8 (m, 1H1); MS (EI) for $C_{22}H_{21}N_5OCl_2$: 442(MH$^+$).

3-amino-6-(3-{[(4-chloro-2,3-dihydro-1H-inden-1-yl)amino]methyl}phenyl)-N-methylpyrazine-2-carboxamide: $^1$H NMR (400 MHz; DMSO-$d_6$): 8.84 (s, 1H); 8.80 (m, 1H); 8.2 (s, 1H); 8.05 (d, 1H); 7.4-7.23 (m, 4H); 4.25 (m, 1H); 3.87 (m, 2H); 2.95 (m, 1H); 2.85 (d, 3H); 2.78 (m, 1H); 2.4 (m, 1H); 1.84 (m, 1H); MS (EI) for $C_{22}H_{22}N_5OCl$: 408 (MH$^+$).

3-amino-6-(3-{[(6-bromo-2,3-dihydro-1H-inden-1-yl) amino]methyl}phenyl)-N-methylpyrazine-2-carboxamide:
$^1$H NMR (400 MHz; DMSO-d$_6$): 9.9 (m, 2H); 9.05 (m, 1H); 8.9 (s, 1H); 8.7 (s, 1H); 8.2 (d, 1H); 8.15 (s, 1H); 7.5 (m, 3H); 7.3 (d, 1H); 4.85 (m, 1H); 4.25 (m, 2H); 3.18 (m, 1H); 2.86 (m, 1H); 2.81 (d, 3H); 2.65 (m, 1H); 2.4 (m, 1H); MS (EI) for C$_{22}$H$_{22}$N$_5$OBr HCl: 452 (MH$^+$).

3-amino-6-(3-{[(7-fluoro-2,3-dihydro-1H-inden-1-yl) amino]methyl}phenyl)-N-methylpyrazine-2-carboxamide:
MS (EI) for C$_{22}$H$_{22}$N$_5$OFHCl: 392 (MH$^+$).

3-amino-N-methyl-6-(3-{[(2R)-1,2,3,4-tetrahydronaphthalen-2-ylamino]methyl}phenyl)pyrazine-2-carboxamide:
$^1$H NMR (400 MHz, d$_6$-DMSO): 8.82 (s, 1H), 8.77 (dd, 1H), 8.08 (s, 1H), 8.02 (m, 1H), 7.62 (bs, 2H), 7.38 (m, 2H), 7.03 (s, 4H), 3.85 (s, 2H), 3.26 (m, 2H), 3.00 (dd, 1H), 2.86 (d, 3H), 2.81 (t, 1H), 2.68 (m, 1H), 2.56 (m, 1H), 2.02 (m, 1H), 1.56 (m, 1H); MS (EI) for C$_{23}$H$_{25}$N$_5$O: 388.4 (MH$^+$).

3-amino-N-methyl-6-(3-{[(2S)-1,2,3,4tetrahydronaphthalen-2-ylamino]methyl}phenyl)pyrazine-2-carboxamide:
$^1$H NMR (400 MHz, 46-DMSO): 8.82 (s, 1H), 8.77 (dd, 1H), 8.11 (s, 1H), 8.04 (m, 1H), 7.62 (bs, 2H), 7.39 (m, 2H), 7.02 (s, 4H), 3.86 (s, 2H), 3.25 (m, 2H), 3.00 (dd, 1H), 2.88 (d, 3H), 2.81 (t, 1H), 2.72 (m, 1H), 2.62 (m, 1H), 2.04 (m, 1H), 1.58 (m, 1H); MS (EI) for C$_{23}$H$_{25}$N$_5$O: 388.4 (MH$^+$).

Example 32

Scheme 14 shows, analogously to Scheme 13 above, that 2-aminoindan-1-ols were also prepared for incorporation into compounds of the invention. Ketones (lxiii) were converted to azides (lxviii), followed by reduction to 2-aminoindan-1-ols (lxix). These amino alcohols were used to make compounds of the invention, for example compounds (lxx), as depicted below.

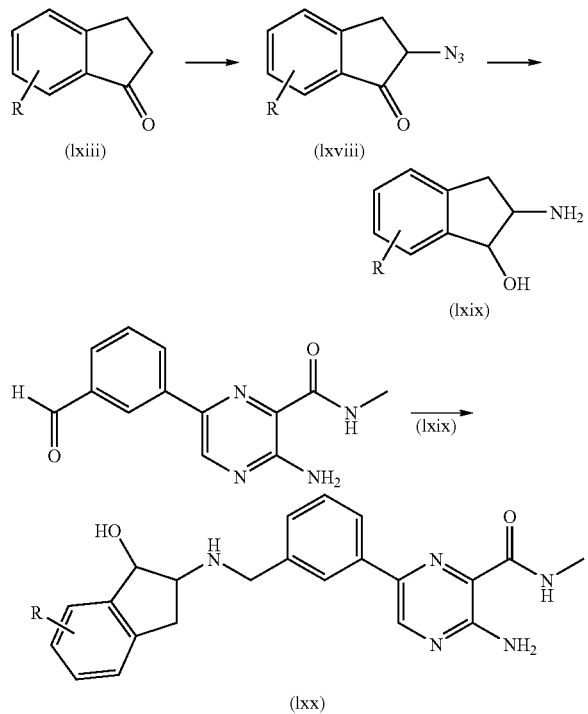

Scheme 14

3-amino-6-(3-{[(4-fluoro-1-hydroxy-2,3-dihydro-1H-inden-2-yl) amino]methyl}phenyl)-N-methylpyrazine-2-carboxamide A solution of 4-fluoro-2,3-dihydro-1H-inden-1-one (1.29 g, 9.34 mmol) and HNIB (5.02 g, 12.1 mmol) in CH$_3$CN (190.0 mL) was refluxed for 1.5 h, until the solution was clear yellow. Upon cooling to r.t., NaN$_3$ (1.21 g, 18.7 mmol) was added and the solution was stirred at r.t. for 12 h. Additional NaN$_3$ (0.50 g, 7.7 mmol) was added and the solution stirred further at r.t. for 4 h. The reaction mixture was concentrated in vacuo, and the residue was taken up in CH$_2$Cl$_2$ (100 mL). This solution was washed with H$_2$O (75 mL), dried (Na$_2$SO$_4$), filtered and concentrated in vacuo. The residue was purified via column chromatography (SiO$_2$, 5:1 hexanes/EtOAc) to give 1.61 g (96% yield) of 2-azido-4-fluoro-2,3-dihydro-1H-inden-1-one: $^1$H NMR (400 MHz, CDCl$_3$): 7.59 (d, 1H), 7.41 (m, 1H), 7.32 (t, 1H), 4.15 (dd, 1H), 3.55 (dd, 1H), 2.89 (dd, 1H).

To a solution of 2-azido-4-fluoro-2,3-dihydro-1H-inden-1-one (0.81 g, 4.5 mmol) in MeOH (15.0 mL), was added NaBH$_4$ (0.19 g, 4.5 mmol) in one portion. After stirring for 10 min at r.t., the solution was concentrated in vacuo. The residue was taken up in EtOAc (100 mL), and this solution was washed with saturated NaHCO$_3$ (aq) (50 mL), dried (Na$_2$SO$_4$), filtered and concentrated in vacuo to give 0.64 g (73% yield) of 2-azido-4-fluoro-2,3-dihydro-1H-inden-1-ol as a white solid, which was used without further purification: $^1$H NMR (400 MHz, CDCl$_3$): 7.23 (m, 2H), 6.97 (t, 1H), 5.15 (dd, 1H), 4.37 (q, 1H), 3.17 (d, 1H), 2.40 (d, 1H).

A solution of 10% Pd/Carbon (0.070 g, 0.50 mmol)), in EtOAc (7.0 mL) was stirred under a H$_2$ (g) balloon for 2 h, after which time a solution of 2-azido-4-fluoro-2,3-dihydro-1H-inden-1-ol (0.98 g, 5.1 mmol) and Boc$_2$O (1.3 g, 6.1 mmol) in EtOAc (3.0 mL) was added. The mixture was stirred under a H$_2$ (g) balloon at r.t. for 12 h. Filtration through celite/fritted glass funnel and concentration in vacuo gave a crude residue, which was purified via column chromatography (SiO$_2$, 3:1 hexanes/EtOAc) to give 0.62 g (46% yield) of 1,1-dimethylethyl (4-fluoro-1-hydroxy-2,3-dihydro-1H-inden-2-yl)carbamate: $^1$H NMR (400 MHz, CDCl$_3$): 7.18 (m, 2H), 6.94 (nm, 1H), 5.21 (bs, 0.5H), 5.03 (bs, 0.5H), 4.37 (bs, 0.5H), 4.10 (q, 0.5H), 3.24-3.40 (m, 1H), 2.59-2.86 (m, 1H), 1.44 (s, 9H).

To a solution of 1,1-dimethylethyl (4-fluoro-1-hydroxy-2,3-dihydro-1H-inden-2-yl)carbamate (0.30 g, 1.1 mmol) in CH$_2$Cl$_2$ (10 mL) was added TFA (1 mL), and the solution was heated to reflux. The solution was immediately cooled and concentrated in vacuo. The residue was taken up in MeOH and treated with Bio-Rad AG 1-X8 resin (hydroxide form) until pH 8. The product was filtered and concentrated in vacuo to give 0.12 g (64% yield) of 2-amino-4-fluoro-2,3-dihydro-1H-inden-1-ol, which was used without further purification for the subsequent reductive amination.

A solution of 3-amino-6-(3-forylphenyl)-N-methylpyrazine-2-carboxamide (0.15 g, 0.62 mmol), 2-amino-4-fluoro-2,3-dihydro-1H-inden-1-ol (0.12 g, 0.74 mmol), glacial AcOH (0.070 mL, 1.2 mmol) and NaBH(OAc)$_3$ (0.39 g, 1.8 mmol) in THF (2.5 mmol) was heated to 70° C. for 1 h. Upon cooling, saturated NaHCO$_3$ (aq) was added (25 mL). The aqueous layer was extracted with EtOAc (2×25 nm). The combined organic layers were dried (Na$_2$SO$_4$), filtered and concentrated in vacuo. The crude mixture was purified via HPLC (reverse-phase, CH$_3$CN/H$_2$O with 0.1% TFA). Upon removal of CH$_3$CN/H$_2$O, the product was taken up in MeOH and treated with Bio-Rad AG 1-X8 resin (hydroxide form) until pH 8. The product was filtered and concentrated in vacuo, to provide 14.1 mg (6% yield) of 3-amino-6-(3-{[(4-fluoro-1-hydroxy-2,3-dihydro-1H-inden-2-yl)amino]methyl}phenyl)-N-methylpyrazine-2-carboxamide: 1H NMR (400 MHz, $d_6$-DMSO): 8.81 (d, 1H), 8.77 (bs, 1H), 8.08 (d, 1H), 8.02 (d, 1H), 7.38 (m, 2H), 7.22 (m, 1H), 7.16 (d, 1H), 7.10 (d, 1H), 7.00 (q, 1H), 5.60 (d, 0.5H), 5.34 (bs, 0.5H), 4.91 (d, 0.5H), 4.84 (t, 0.5H), 3.84-4.02 (m, 2H), 3.18 (m, 1H), 2.98 (dd, 0.5H), 2.85 (d, 3H), 2.76 (dd, 0.5H), 2.52 (m, 2H); MS (EI) for $C_{22}H_{22}N_5O_2F$: 408 (MH$^+$).

Using the analogous synthetic techniques beginning from (4-fluoro-2,3-dihydro-1H-inden-2-yl)amine [Haadsma-svensson, S. R. et al. WO 9 504 713, 1995], the following compound of the invention was prepared:

3-amino-6-(3-{[(4-fluoro-2,3-dihydro-1H-inden-2-yl)amino]methyl}phenyl)-N-methylpyrazine-2-carboxamide: 1H NMR (400 Mz, $d_6$-DMSO): 8.81 (s, 1H), 8.75 (m, 1H), 8.06 (s, 1H), 8.02 (m, 1H), 7.37 (m, 2H), 7.14 (m, 1H), 7.02 (d, 1H), 6.91 (t, 1H), 3.83 (s, 2H), 3.60 (m, 1E), 3.11 (dd, 2H), 2.85 (d, 2H), 2.73-2.81 (m, 3H); MS (EI) for $C_{22}H_{22}N_5O$ F: 392 (MH$^+$).

Example 33

3-amino-N-methyl-6-{3-[(naphthalen-2-ylamino)methyl]phenyl}pyrazine-2-carboxamide. A solution of 3-amino-6-(3-formylphenyl)-N-methylpyrazine-2-carboxamide (0.075 g, 0.29 mmol), naphthalen-2-amine (0.21 g, 1.5 mmol), glacial AcOH (0.033 mL, 0.56 mmol) and NaBH(OAc)$_3$ (0.093 g, 0.44 mmol) in THF (1.1 mL) was heated to 80° C. for 12 h. Upon cooling, saturated NaHCO$_3$ (aq) was added (25 mL). The aqueous layer was extracted with EtOAc (2 x 25 mL). The combined organic layers were dried (Na$_2$SO$_4$), filtered and concentrated in vacuo. The crude mixture was purified via HPLC (reverse-phase, CH$_3$CN/H$_2$O with 0.1% TFA). Upon removal of CH$_3$CN/H$_2$O, the product was taken up in MeOH and treated with Bio-Rad AG 1-X8 resin (hydroxide form) until pH 8. The product was filtered and concentrated in vacuo, to provide 29.1 mg (26% yield) of 3-amino-N-methyl-6-{3-[(naphthalen-2-ylamino)methyl]phenyl}pyrazine-2-carboxamide: $^1$H NMR (400 MHz, 4-DMSO): 8.84 (s, 1H), 8.77 (d, 1H), 8.22 (s, 1H), 8.05 (dt, 1H), 7.62 (t, 2H), 7.51 (d, 1H), 7.41 (d, 2H), 7.27 (dt, 1H), 7.10 (dt, 2H), 6.77 (d, 1H), 6.57 (t, 1H), 4.46 (d, 2H), 2.85 (d, 3H); MS (EI) for $C_{23}H_{21}N_5O$: 384 (MH$^+$)

Using the same or analogous synthetic techniques and/or substituting with alternative reagents, the following compounds of the invention were prepared:

3-amino-N-methyl-6-{3-[(naphthalen-1-ylamino)methyl]phenyl}pyrazine-2-carboxamide: $^1$H NMR (400 MHz, $d_6$-DMSO): 8.78 (s, 1H), 8.70 (m, 1H), 8.25 (m, 1H), 8.20 (s, 1H), 7.99 (m, 2H), 7.73 (m, 1H), 7.42 (m, 2H), 7.36 (m, 2H), 7.16 (t, 1H), 7.05 (d, 1H), 6.96 (t, 1H), 6.42 (d, 1H), 4.57 (d, 2H), 2.84 (d, 3H); MS (EI) for $C_{23}H_{21}N_5O$: 384 (MH$^+$).

Example 34

3-amino-6-[3-({[(3-fluorobiphenyl-4-yl)methyl]amino}methyl)phenyl]-N-methylpyrazine-2-carboxamide A solution of 4-bromo-2-fluorobenzaldehyde (0.15 g, 0.74 mmol), tributyl(phenyl)stannane (0.27 mL, 0.81 mmol) and Pd(PPh$_3$)$_4$ (0.043 g, 0.037 mmol) in PhCH$_3$ (2.5 mL) was heated in a sealed reaction tube to 110° C. for 12 h. Additional tributyl(phenyl)stannane (0.20 mL, 0.61 mmol) and Pd(PPh$_3$)$_4$ (0.043 g, 0.037 mmol) were added and the solution was further heated to 110° C. for 2 h. The solvent was removed in vacuo. The residue was purified via column chromatography (SiO$_2$, 5:1 hexanes/EtOAc) to provide 0.23 g (>100% yield) of 3-fluorobiphenyl-4-carbaldehyde, which was used without further purification: MS (EI) for $C_{13}H_9OF$: 201 (MH$^+$).

A solution of 3-fluorobiphenyl-4-carbaldehyde (0.030 g, 0.15 mmol), 3-amino-6-[3-(aminomethyl)phenyl]-N-methylpyrazine-2-carboxamide (0.038 g, 0.15 mmol), glacial AcOH (0.010 mmol, 0.15 mmol) and NaBH(OAc)$_3$ (0.047 g, 0.22 mmol) in THF (0.6 mL) was stirred at r.t. for 12 h. Saturated NaHCO$_3$ (aq) was added (25 mL) and the aqueous layer was extracted with EtOAc (2×25 mL). The combined organic layers were dried (Na$_2$SO$_4$), filtered and concentrated in vacuo. The crude mixture was purified via HPLC (reverse-phase, CH$_3$CN/H$_2$O with 0.1% TFA). Upon removal of CH$_3$CN/H$_2$O, the product was taken up in MeOH and treated with Bio-Rad AG 1-X8 resin (hydroxide form) until pH 8. The product was filtered and concentrated in vacuo, to provide 13.4 mg (20% yield) of 3-amino-6-[3-({[(3-fluorobiphenyl4-yl)methyl]amino}methyl)phenyl]-N-methylpyrazine-2-carboxamide: $^1$H NMR (400 MHz, $d_6$-DMSO): 8.84 (s, 1H), 8.79 (d, 1H), 8.09 (bs, 1H), 8.05 (m, 1H), 7.70 (m, 2H), 7.61 (t, 1H), 7.36-7.53 (m, 8H), 3.80 (d, 4H), 2.86 (d, 3H); MS (EI) for $C_{26}H_{24}N_5OF$: 442 (MH$^+$).

Using the same or analogous synthetic techniques and/or substituting with alternative reagents, the following compounds of the invention were prepared:

3-amino-6-{3-[({[2-fluoro-4-(2-thienyl)phenyl]methyl}amino)methyl]phenyl}-N-methylpyrazine-2-carboxamide: $^1$H NMR (400 MHz, $d_6$-DMSO): 8.83 (s, 1H), 8.79 (m, 1H), 8.07 (bs, 1H), 8.05 (m, 1H), 7.58 (m, 2H), 7.54 (d, 1H), 7.37-7.50 (m, 4H), 7.15 (m, 1H), 3.78 (d, 4H), 3.17 (d, 1H), 2.86 (d, 3H); MS (EI) for $C_{24}H_{22}N_5OFS$: 448

3-amino-6-[3-({[(2-fluoro-4-furan-2-ylphenyl)methyl]amino}methyl)phenyl]-N-methylpyrazine-2-carboxamide: $^1$H NMR (400 M , $d_6$-DMSO): 8.81 (s, 1H), 8.77 (m, 1H), 8.06 (bs, 1H), 8.02 (m, 1H), 7.74 (d, 1H), 7.35-7.57 (m, 4H), 700 (d, 1H), 6.59 (m, 1H), 3.75 (d, 4H), 2.84 (d, 3H); MS (EI) for $C_{24}H_{22}N_5O_2F$: 432 (MH$^+$).

3-amino-6-{3-[({[2-fluoro-5-(2-thienyl)phenyl]methyl}amino)methyl]phenyl}-N-methylpyrazine-2-carboxamide: 1H NMR (400 MHz, $d_6$-DMSO): 8.80 (s, 1H), 8.75 (m, 1H), 8.07 (bs, 1H), 8.02 (m, 1H), 7.77 (dd, 1H), 7.55 (m, 1H), 7.50 (dd, 1H), 7.37-7.44 (m, 3H), 7.18 (dd, 1H), 7.10 (dd, 1H), 3.80 (d, 4H), 3.16 (d, 1H), 2.83 (d, 3H); MS (EI) for $C_{24}H_{22}N_5OFS$: 448 (MH$^+$).

3-amino-6-[3-({[(4-ethenyl-2-fluorophenyl)methyl]amino}methyl)phenyl]-N-methylpyrazine-2-carboxamide: 1H NMR (400 MHz, $d_6$-DMSO): 8.80 (s, 1H), 8.75 (m, 1H), 8.04 (bs, 1H), 8.01 (m, 1H), 7.25-7.48 (m, 5H), 6.69 (dd, 1H), 5.86 (d, 1H), 5.27 (d, 1H), 3.75 (d, 4H), 3.16 (d, 1H), 2.85 (d, 3H); MS (EI) for $C_{22}H_{22}N_5OF$: 392 (MH$^+$).

Example 35

2-amino-5-[3-hydroxymethyl)phenyl]-N-methylpyridine-3-carboxamide

2-Amino-5-bromopyridine-3-carboxylic acid was prepared by bromination, para- to the 2-amino group of commercially available 2-aminonicotinic acid as described in U.S. Pat. Nos. 3,950,160 and 4,361,700.

Methyl 2-amino-5-bromopyridine-3-carboxylate: A slurry of 2-amino-5-bromopyridine-3-carboxylic acid (7 g, 32.2 mmol) in methanol (150 mL) and H$_2$SO$_4$ (7 mmol) was heated to reflux for 48 h. The reaction mixture was concentrated to ca. 40 mL. Water (100 mmol) was added to the residual oil, and the mixture neutralized with sodium carbonate. Ethyl acetate (400 mL) was added and the organic layer was washed with saturated aqueous sodium chloride then dried (Na$_2$SO$_4$) and concentrated to give the title compound (5.5 g, 73.9% yield).

2-Amino-5-bromopyridine-N-methylpyridine-3-carboxamide: A slurry of the above methyl 2-amino-5-bromopyridine-3-carboxylate (3.0 g, 13 mmol) in methanol was cooled to 0° C., and methylamine gas was passed through the solution at a moderate rate for 5 min. The mixture was stirred in sealed tube at 50° C. for 24 h, and the methanol was removed in vacuo to provide 2-amino-5-bromopyridine-N-methylpyridine-3-carboxamide as a white solid (2.5 g, 80.6% yield): $^1$H NMR (400 MHz; DMSO-d$_6$): 8.54 (br s, 1H); 8.19 (d, 1H); 8.08 (d, 1H); 7.25 (s, 1H); 2.72 (d, 3H).

2-Amino-5-[3-hydroxymethyl)phenyl]-N-methylpyridine-3-carboxamide: To a solution of 2-amino-5-bromopyridine-N-methylpyridine-3-carboxamide (0.15 g, 0.66 mmol) in DMF (10 mL) was added 3-hydroxymethymphenyl boronic acid (129 mg, 0.85 mmol), Pd(dppf)$_2$Cl$_2$ (10 mol % yield) and sodium carbonate (0.3 g) and this mixture was stirred under a nitrogen atmosphere for 5 minutes. The mixture was heated at 85° C. for 4 h. The reaction mixture was cooled to room temperature. The mixture was extracted with ethyl acetate (3×10 mL) and the combined organic fractions were sequentially washed with aqueous ammonium chloride (2×5 mmol) and brine (2×5 mmol), dried over anhydrous sodium sulfate, filtered and evaporated in vacuo. The residue was triturated with diethyl ether/hexanes (2:1) and the solid was collected by vacuum filtration. Purification by column chromatography afforded a white solid (100 mg, 59% yield): $^1$H NMR (400 MHz; DMSO-d$_6$): 8.6 (br s, NH); 8.4 (d, 1H); 8.2 (d, 1H); 7.6 (s, 1H); 7.55 (d, 1H); 7.4 (t, 1H); 7.27 (d, 1H); 7.2 (br s, 2NH); 5.25 (t, 1H); 4.55 (d, 2H); 2.80 (d, 3H); MS (EI) for C$_{14}$H$_{15}$N$_3$O: 258 (MH$^+$).

Example 36

Scheme 15 depicts a general synthetic route for compounds of the invention having substituents —W—X—Y according to formula I, wherein, for example, W is phenylene, X is —CH$_2$NH—, and Y is various groups. Note, as defined above any of W, X, or Y are optionally substituted; this is only a set of examples. Analogous to Scheme 10, primary amine (xlv), which in this example incorporates Y, is incorporated into a compound of the invention, (lxxiii). For example, amine (xlv), which has Y as part of its structure for example, is converted to 2,4-dinitrosulfonamide (xlvi). Sulfonamide (xlvi) is used to make sulfonamide (lxxii). The transformation (xlvi) to (lxxii) is carried out under Mitsunobu conditions, in this case where the alcohol partner is intermediate, compound of the invention, (lxxi). As described above in relation to Scheme 10, the sulfonamide bond is cleaved, typically but not necessarily via addition of a primary amine e.g. n-propyl amine, to free secondary amine (lxxiii), which in this case is a compound of the invention.

Scheme 15

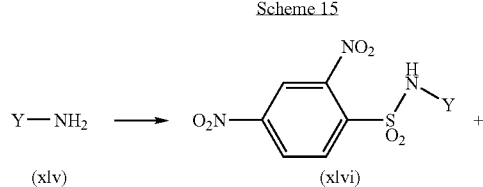

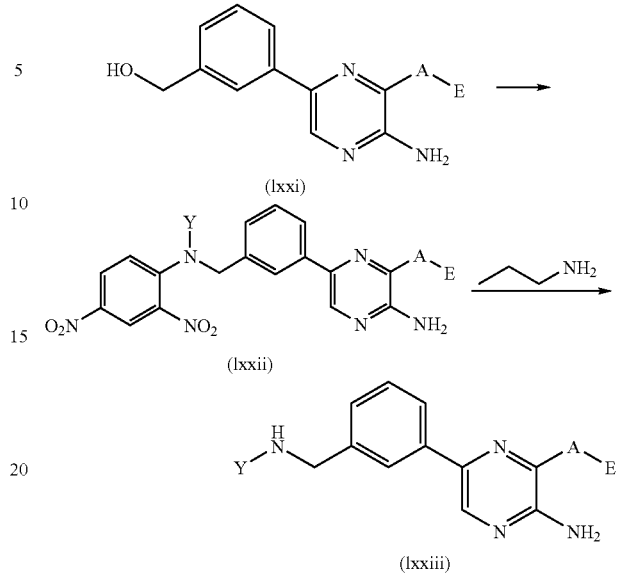

2-Amino-5-(3-{[[(2,4-dinitrophenyl)sulfonyl][(1S)-2,3-dihydro-1H-inden-1-yl]amino}methyl}phenyl]-N-methylpyridine-3-carboxamide N-[(1S)-2,3-dihydro-1H-inden-1-yl]-2,4-dinitrobenzenesulfonamide: To a stirred, ice-cooled solution of 4.00 g of (S)-(+)-1-aminoindan (30.0 mmol, from Sigma-Aldrich) in 113 mmol of THF was added 9.60 g (36.0 mmol, 1.20 eq.) of 2,4-dinitrobenzenesulfonyl chloride, followed by 7.80 mL (44.8 mmol, 1.49 eq.) of N,N-diisopropylethylamine. The ice bath was removed, and the mixture was stirred at room temperature for 19 h and then concentrated. The residue was taken up in EtOAc, washed with 2×H$_2$O, dried over Na$_2$SO$_4$, filtered, and concentrated. The residue was sonicated in ca. 30 mL of EtOAc until a precipitate was formed. The mixture was diluted to ca. 150 mL with hexanes. Filtration afforded pure product as a tan solid (8.59 g, 78.8% yield).

Triphenylphosphine (6.9 g, 26 mmol) was added to a stirred solution of 2-amino-5-[3-(hydroxymethyl)phenyl]-N-methylpyridine-3-carboxamide (5.16 g, 20 mmol) and N-[(1S)-2,3-dihydro-1H-inden-1-yl]-2,4-dinitrolbenzenesulfonamide (9.4 g, 26 mmol) in benzene (150 mL). Diethyl azodicarboxylate (4.5 g, 26 mmol) was then added drop wise and mixture was stirred at ambient temperature for 4 h. Ethyl acetate (400 mL) was added and the organic layer was washed with saturated aqueous sodium chloride then dried (Na$_2$SO$_4$). Filtration and concentration followed by column chromatography (ethyl acetate/hexane, 9:1) gave desired product (8.2 g, 50% yield).

2-amino-5-(3-{[(1S)-2,3-dihydro-1H-inden-1-ylamino]methyl}phenyl)-N-methylpyridine-3-carboxamide: 2-Amino-5-(3-{[[(2,4-dinitrophenyl)sulfonyl][(1S)-2,3-dihydro-1H-inden-1-yl]amino}methyl}phenyl]-N-methylpyridine-3-carboxamide was treated with excess n-propylamine (4 eq) in CH$_2$Cl$_2$ (150 mL). The mixture was diluted with additional ethyl acetate (200 mL). The mixture was subsequently washed with aqueous saturated sodium carbonate (3×30 mL) and brine (3×30 mL). The combined organic fractions were dried over anhydrous sodium sulfate, filtered and concentrated in vacuo. Purification of the residue by preparative HPLC (acetonitrile/water) gave desired product (5.8 g). The compound was converted to the hydrochloride salt using 4 M solution HCl in dioxane: $^1$H NMR (400 MHz; DMSO-d$_6$): 9.9 (br s, NH); 9.02 (s, 1H); 8.9 (s, 1H); 8.6 (s, 1H); 8.35 (br s, NH); 8.2 (s, 1H); 7.8 (d, 2H); 7.75 (m, 2H); 7.37 (m, 2H1); 7.29 (m, 1H); 4.85 (m, 1H); 4.25 (m, 2H); 3.4 (m, 1H); 2.9 (m, 1H); 2.80 (d, 3H); 2.43 (m, 1H); 2.4 (m, 1H); MS (EI) for C$_{23}$H$_{24}$N$_4$O HCl: 374 (MH$^+$).

2-amino-5-(3-{[(6-bromo-2,3-dihydro-1H-inden-1-yl) amino]methyl}phenyl)-N-methylpyridine-3-carboxamide: $^1$H NMR (400 MH; DMSO-d$_6$): 9.8 (br s, 2H); 9.15 (br s, 1H); 8.8 (s, 1H); 8.31 (s, 1H); 8.08 (s, 1H); 7.85 (d, 1H); 7.6 (m, 2H); 7.3 (d, 1H); 4.85 (m, 1H); 4.3 (m, 2H); 3.2 (m, 1H); 2.85 (m, 1H); 2.81 (d, 3H); 2.56 (m, 1H); 2.4 (m, 1H); MS (EI) for C$_{22}$H$_{23}$N$_4$OBr HCl: 451 (MH$^+$).

2-amino-5-(3-{[(4,6-difluoro-2,3-dihydro-1H-inden-1-yl)amino]methyl}phenyl)-N-methylpyridine-3-carboxamide: $^1$H NMR (400 MHz; DMSO-d$_6$): 10.0 (br s, 2H); 9.18 (m, 1H); 8.8 (s, 1H); 8.6 (s, 1H); 8.30 (br s, 2H); 8.25 (s, NH); 7.85-7.2 (m, 5H); 4.85 (m, 1H); 4.4 (m, 2H); 3.2 (m, 1H); 2.9 (m, 1H); 2.85 (d, 3H); 2.6-2.4 (m, 2H); MS (EI) for C$_{23}$H$_{22}$N$_4$OF$_2$ HCl: 409 (MH$^+$).

2-amino-5-(3-{[(7-bromo-4-fluoro-2,3-dihydro-1H-inden-1-yl)amino)methyl}phenyl)-N-methylpyridine-3-carboxamide: MS (EI) for C$_{23}$H$_{22}$N$_4$OFBr HCl: 469 (MH$^+$).

2-amino-5-(3-{[(4-chloro-2,3-dihydro-1H-inden-1-yl) amino]methyl}phenyl)-N-methylpyridine-3-carboxamide: $^1$H NMR (400 M ; DMSO-d$_6$): 9.4 (br s, NH); 8.9 (br s, 1H); 8.65 (br s, 1H); 8.6 (s, 1H); 8.2 (s, 1H); 7.75 (m, 2H); 7.6-7.48 (m, 3H); 7.7 (d, 1H); 4.85 (m, 1H); 4.3 (m, 2H); 3.8 (m, 1H); 3.18 (m, 1H); 2.85 (m, 3H); 2.59-2.4 (m, 2H); MS (EI) for C$_{23}$H$_{23}$N$_4$OCl HCl: 407 (MH$^+$).

2-amino-5-(3-{[(5,6-difluoro-2,3-dihydro-1H-inden-1-yl)amino]methyl}phenyl)-N-methylpyridine-3-carboxamide): $^1$H NMR (400 MHz; DMSO-d$_6$): 9.83 (br s, NH); 9.09 (br s, NH); 8.82 (s, 1H); 8.58 (s, 1H); 8.22 (s, 1H); 7.99 (m, 1H); 7.8 (m, 1H); 7.67-7.44 (m, 2H); 4.85 (m, 1H); 4.27 (m, 2H); 3.2 (m, 1H); 2.95 (m, 1H); MS (EI) for C$_{23}$H$_{22}$N$_4$OF$_2$: 408 (MH$^+$).

2-amino-5-(3-{[(5,7-difluoro-2,3-dihydro-1H-inden-1-yl)amino]methyl}phenyl)-N-methylpyridine-3-carboxamide: $^1$H NMR (400 MHz; DMSO-d$_6$): 9.7 (br s, NH); 9.4 (br s, 1H); 9.0 (br s, 1H); 8.7 (s, 1H); 8.57 (s, 1H); 8.1 (s, 1H); 7.8 (m, 1H); 7.5 (m, 1H); 7.2 (m, 2H); 4.85 (m, 1H); 4.3 (m, 2H); 3.89 (m, 1H); 3.18 (m, 1H); 2.85 (m, 3H); 2.69-2.5 (m, 2H); MS (EI) for C$_{23}$H$_{22}$N$_4$OF2 HCl: 409 (MH$^+$).

Using a strategy that combines synthetic technique as described in relation to both Scheme 14 and Scheme 15, the following compounds were made:

3-Amino-6-[3-({[6-(3-hydroxypropyl)-2,3-dihydro-1H-inden-1-yl]amino}methyl)phenyl]-N-methylpyrazine-2-carboxamide:

5-Bromo-2,3-dihydro-1H-inden-1-one (1.68 g, 7.99 mmol) was dissolved in DMF and treated with triethylamine (1.61 g, 15.98 mmol), copper iodide (152 mg, 0.79 mmol) and prop-2-yn-1-ol (2.24 g, 39.96 mmol) in the presence of Pd(PPh$_3$)$_4$ (462 mg, 0.39 mmol) at ambient temperature. After being refluxed for 16 h, the reaction mixture was extracted with ethyl acetate (100 mL×3) and washed with brine. The combined organic layers were dried over MgSO$_4$. Solvent removal under vacuum gave crude tan oil. Purification by preparative thin-layer chromatography afforded 5-(hydroxyprop-1-yn-1-yl)-2,3-dihydro-1H-indene-1-one (1.06 g, 72% yield): $^1$H NMR (400 MHz, CD$_3$OD): δ 7.63 (d, 1H), 7.59 (s, 1H), 7.42 (d, 1H), 4.45 (s, 2H), 3.18 (m, 2H), 2.69 (m, 2H); MS (EI) for C$_{12}$H$_{10}$O$_2$: 187.20 (MH$^+$).

To a solution of 5-(hydroxyprop-1-yn-1-yl)-2,3-dihydro-1H-indene-1-one (1.06 g, 5.71 mmol) in MeOH was added 10% Pd/C and hydrogenated by means of Pair shaker. After 12 h, the reaction mixture was filtered on Celite and concentrated in vacuo to give 5-(3-hydroxypropyl)-2,3-dihydro-1H-inden-1-one (1.03 g, 94% yield): MS (EI) for C$_{12}$H$_{14}$O$_2$: 191.24 (MH$^+$).

5-(Hydroxyprop-1-yn-1-yl)-2,3-dihydro-1H-indene-1-one (1.03 g, 5.42 mmol) was dissolved in DMF and treated with chloro-tert-butyldimethylsilane (981 mg, 6.51 mmol), imidazole (443 mg, 6.51 mmol) at 0° C. The reaction mixture was allowed to reach ambient temperature. After 10 h, the reaction mixture was extracted with ethyl acetate (100 mL×3), washed with water, brine and dried over MgSO$_4$. The organic layer was concentrated under vacuum and purified by flash column chromatography to yield the 5-(3-{[(1,1-dimethylethyl)(dimethyl)silyl]oxy}propyl)-2,3-dihydro-1H-inden-1-one (1.54 g, 94% yield): $^1$H NMR (400 MHz, CDCl$_3$): δ 7.63 (d, 1H), 7.59 (s, 1H), 7.42 (d, 1H), 4.45 (t, 2H), 3.10 (m, 2H), 2.78 (m, 2H), 2.64 (m, 2H), 1.82 (m, 2H), 0.95 (s, 9H), 0.06 (s, 6H).

5-(3-{[(1,1-Dimethylethyl)(dimethyl)silyl]oxy}propyl)-2,3-dihydro-1H-inden-1-one (1.54 g, 5.07 mmol) was dissolved in MeOH (20 mmol) and treated with NaBH$_4$ (231 mg, 6.10 mmol) at 0° C. After 1 h, the reaction mixture was quenched by slow addition of water at 0° C. The reaction mixture was extracted with ethyl acetate (100 mmol×3), washed with water, brine and dried over MgSO4. The organic layer was concentrated under vacuum and moved to the next reaction without further purification. To a solution of alcohol (1.56 g, 5.079 mmol) were added DPPA (1.81 g, 6.60 mmol), DBU (1.00 g, 6.60 mmol) at 0° C. The reaction mixture was allowed to reach ambient temperature and stirred for 10 h. The reaction mixture was concentrated in vacuo and purified by flash column chromatography to give 1-[5-(3-1{[(1,1-dimethylethyl)(dimethyl)silyl]oxyl}propyl)-2,3-dihydro-1H-inden-1-yl]-2-triaz-1-en-2-yne (1.05 g, 63%, two steps): $^1$H NMR (400 M, CDCl$_3$): δ 7.25 (d, 1H), 7.05 (m, 2H), 4.79 (m, 1H), 3.59 (t, 2H), 3.00 (m, 2H), 2.78 (m, 1H), 2.63 (m, 2H), 2.38 (m, 1H), 2.06 (m, 1H), 1.77 (m, 2H), 1.88 (s, 9H), 0.05 (s, 6H).

1-[5-(3-{[(1,1-Dimethylethyl)(dimethyl)silyl]oxyl}propyl)-2,3-dihydro-1H-1-yl]-2λ$^5$-triaz-1-en-2-yne was hydrogenated in MeOH on a Parr shaker (30 psi) overnight and filtered on Celite. The organic layer was concentrated and dissolved in THF (15 mL). To a solution of resulting amine were added 3,5-dinitrobenzenesulfonyl chloride (1.02 g, 3.81 mmol), diisopropylethylamine (616 mg, 4.76 mmol) at 0° C. The reaction mixture was allowed to reach to ambient temperature and stirred for 3 h to complete the reaction. The reaction mixture was concentrated in vacuo and purified by flash column chromatography to give N-[5-(3-{[(1,1-dimethylethyl) (dimethyl)silyl]oxy}propyl)-2,3-dihydro-1H-inden-1-yl]-3,5-dinitrobenzenesulfonamide (1.16 g, 68% yield, two steps).

To a solution of 3-amino-6-[3-(hydroxymethyl)phenyl]-N-methylpyrazine-2-carboxamide, 403 mg, 1.55 mmol) were added N-[5-(3-1[(1,1-dimethylethyl)(dimethyl)silyl] oxy}propyl)-2,3-dihydro-1H-inden-1-yl]-3,5-dinitro-benzenesulfonamide (950 mg, 1.77 mmol), triphenylphosphine (466 mg, 1.77 mmol), diethyl azodicarboxylate (309 mg, 1.77 mmol) at 0 ° C. and the reaction mixture was allowed to reach ambient temperature. After 10 h, the reaction mixture was extracted with ethyl acetate (100 mL×3), washed with water, brine and dried over MgSO$_4$. The organic layer was concentrated in vacuo and purified by flash column chromatography to yield 3-amino-6-[3-({[5-(3-{[(1,1-dimethylethyl)(dimethyl)silyl]oxy}propyl)-2,3-dihydro-1H-inden-1-yl][(3,5-dinitrophenyl)sulfonyl]amino}methyl)phenyl]-N-methylpyrazine-2-carboxamide (655 mg, 54% yield): $^1$H NMR (400 MHz, CDCl$_3$): δ 8.45 (s, 1H), 8.28 (d, 1H), 8.02 (m, 1H), 7.91 (m, 1H), 7.92 (d, 1H), 7.58 (m, 2H), 7.21 (m, 2H), 7.06 (m, 3H), 5.74 (t, 1H), 4.45 (d, 1H), 4.27 (d, 1H), 3.61 (m, 2H), 3.08 (d, 3H), 2.88 (m, 2H), 2.65 (m, 3H), 2.12 (m, 1H), 1.78 (m, 2H), 0.89 (s, 9H), 0.05 (s, 6H).

3-Amino-6-[3-({[5-(3-{[(1,1-dimethylethyl)(dimethyl)silyl]oxy}propyl)-2,3-dihydro-1H-inden-1-yl][(3,5-dinitrophenyl)sulfonyl]amino}methyl)phenyl]-N-methyl pyrazine-2-carboxamide (600 mg, 0.77 mmol) was dissolved in THF and refluxed for an hour in the presence of tetrabutylammonium fluoride in THBF. The reaction mixture was partitioned with water and extracted with ethyl acetate (10 mL×3) and dried over MgSO$_4$. Filteration and concentration under vacuum gave tan oil, which was subjected to the solution of dichloromethane and isopropylamine. After being stirred for 30 min, the solvent was removed in vacuo and purified by flash column chromatography to give the 3-amino-6-[3-({[6-(3-hydroxypropyl)-2,3-dihydro-1H-inden-1-yl]amino}methyl)phenyl]N-methylpyrazine-2-carboxamide (110 mg, 33% yield): $^1$H NMR (400 MHz, CD$_3$OD): δ 8.59 (s, 1H), 8.06 (bs, 1H), 7.91 (s, 1H), 7.52 (m, 1H), 7.40 (m, 2H), 7.11 (d, 1H), 7.08 (s, 1H), 7.03 (d, 1H), 4.32 (d, 1H), 3.66 (t, 2H), 3.02 (d, 3H), 2.99 (m, 1H), 2.81 (m, 1H), 2.69 (t, 2H), 2.44 (m, 1H), 1.90 (m, 4H), 1.32 (m, 3H), 0.82 (m, 2H); MS (EI) for $C_{25}H_{29}N_5O_2$: 432.23 (MH$^+$).

Using the same or analogous synthetic techniques and/or substituting with alternative reagents, the following compounds of the invention were prepared:

3-amino-6-(3-{[(1S)-2,3-dihydro-1H-inden-1-ylamino]methyl}phenyl)pyrazine-2-carbonitrile: $^1$H NMR (400 MHz, d$_6$-DMSO): 8.93 (s, 1H), 7.98 (s, 1H), 7.81 (d, 1H), 7.46 (br s, 2H), 7.44-7.38 (m, 3H), 7.22 (m, 1H), 7.17 (m, 2H), 4.16 (t, 1H), 3.86 (m, 2H), 2.94 (m, 1H), 2.73 (m, 1H), 2.32 (m, 1H), 1.82 (m, 1H); MS (EI) for $C_{21}H_{19}N_5$: 342.2 (MH$^+$).

Example 37

5-(3-{[(1S)-2.3-dihydro-1H-inden-1-ylamino]methyl}phenyl)-3-[5-(phenylmethyl)-4H-1,24-triazol-3-yl]pyrazin-2-amine N-{3-[5-amino-6-(5-benzyl-4H-1,2,4-triazole-3-yl)pyrazin-2-yl]benzyl}-2,4-dinitro-N-[(1S)-2,3-dihydro-1H-inden-1-yl]benzene sulfonamide: Triphenylphosphine (47 mg, 0.17 mmol) was added to a stirred solution of {3-[5-amino-6-(5-phenyl-4H-1,2,4-triazol-3-yl) pyrazin-2-yl]phenyl}methanol (50 mg, 0.14 mmol) and N-[(1S)-2,3-dihydro-1H-inden-1-yl]-2,4-dinitrobenzen sulfonamide (60 mg, 0.16 mmol) in THF. Diethyl azodicarboxylate (31 mg, 0.17 mmol) was then added and mixture was stirred at ambient temperature 4 h. Ethyl acetate (20 mL) was added, and the organic layer was washed with saturated aqueous sodium chloride, and then dried (Na$_2$SO$_4$). Filtration and concentration followed by chromatography on silica gel afforded the title compound: MS (EI) for $C_{35}H_{29}N_9O_6S$: 704 (MH$^+$).

The solution of crude benzene sulfonamide (50 mg) in dichloromethane (3 mL) was treated with excess n-propylamine (4 eq). The solvent was evaporated, and the residue chromatodraphed over silica gel with EtOAc-hexane (7:1) affording 5-(3-{[(1S)-2,3-dihydro-1H-inden-1-ylamino]methyl}phenyl)-3-[5-(phenylmethyl)-4H-1,2,4-triazol-3-yl]pyrazin-2-amine as a yellow solid (15 mg, 22% yield); $^1$H NMR (400 MHz; DMSO-d$_6$): 8.78 (s, 1H); 8.18 (s, 1H); 8.16 (d, 11H); 7.65 (br s, NH); 7.48-7.1 (m, 11H)l 4.2 (m, 3H); 3.8 (m, 2H); 2.9 (m, 1H); ); 2.7 (m, 1H); 2.3 (m, 1H); 1.8 (m, 1H); MS (EI) for $C_{29}H_{27}N_7$: 474 (MH$^+$).

5-(3-{[(1S)-2,3-dihydro-1H-inden-1-ylamino]methyl}phenyl)-3-(4H-1,2,4-triazol-3-yl)pyrazin-2-amine: $^1$H NMR (400 MHz; DMSO-d$_6$): 9.9 (m, 1H); 8.88 (s, 1H); 8.68 (s, 1H); 8.4 (br s, 1H); 8.24 (d, 1H); 7.85 (d, 1H); 7.6 (m, 2H); 7.4-7.2 (m, 3H); 4.8 (m, 1H); 4.4 (m, 2H); 3.2 (m, 1H); 2.9 (m, 1H); 2.55 (m, 1H); 2.4 (m, 1H); MS (EI) for $C_{22}H_{21}N_7$HCl: 384 (MH$^+$).

5-(3-{[(1S)-2,3-dihydro-1H-inden-1-ylamino]methyl}phenyl)-3-[5-(1,1-dimethylethyl)-4H-1,2,4-triazol-3-yl]pyrazin-2-amine): $^1$H NMR (400 MHz; DMSO-d$_6$): 8.8 (s, 1H); 8.6 (s, 1H); 8.4 (d, 1H); 7.8 (d, 1H); 7.6-7.25 (m, 5H); 4.48 (s, 1H); 4.4 (m, 2H); 3.2 (m, 1H); 2.9 (m, 1H); 2.5 (m, 1H); 2.35 (m, 1H); MS (EI) for $C_{26}H_{29}N_7$ HCl: 440 (MH$^+$).

(1S)-N-{[3-(6-{5-[(methyloxy)methyl]-4H-1,2,4-triazol-3-yl }pyrazin-2-yl)phenyl]methyl3-2,3-dihydro-1H-inden-1-amine: $^1$H NMR (400 M ; DMSO-d$_6$): 8. 8 (s, 1H); 8.15 (s, 1H); 8.07 (d, 1H); 7.7 (br s, 1H); 7.47(t, 1H); 7.4 (t, 1H); 7.4; (t, 1H); 5.25 (t, 1H); 4.6 (d, 2H); 3.1-2.9 (m, 3H); 2.4 (m, 2H); 2.2-1.9 (m, 3H); 1.8-1.6 (m, 3H); 1.04 (t, 3H); MS (EI) for $C_{20}H_{25}N_7O$: 380 (MH$^+$).

5-(3-{[(1S)-2,3-dihydro-1H-inden-1-ylamino]methyl}phenyl)-3-[5-(1-ethylpiperidin-3-yl)-4H-1,2,4-triazol-3-yl]pyrazin-2-amine: $^1$H NMR (400 MHz; DMSO-d$_6$): 10.4 (br s, NH); 9.98 (br s, NH); 8.9 (s, 1H); 8.77 (s, 1H); 8.3 (d, 1H); 7.84 (d, 1H); 7.8 (br s, 2NH); 7.5 (m, 2H); 7.3 (m, 3H); 4.8 (m, 1H); 4.3 (m, 2H); 3.8-3.6(m, 3H); 3.4-2.9 (m, 6H); 2.55-1.6 1 (m, 6H); 1.3 (t, 3H); MS (EI) for $C_{29}H_{34}N_8$ HCl: 495 (MH$^+$).

Example 38

3-Amino-6-(3-{[(1S)-2,3-dihydro-1H-inden-1-ylamino]methyl}phenyl)pyrazine-2-carboxamide A solution methyl 3-amino-6-[3-(hydroxymethyl)phenyl]pyrazine-2-carboxylate (37.4 mg, 0.1 mmol) in methanol (5 mL) was cooled to 0° C., and ammonia gas was passed through the solution at a moderate rate for 2 min. The mixture was stirred in sealed tube at 50 ° C. for 24 h then the methanol was removed in vacuo to provide 2-amino-5-N-methylpyrazine-3-carboxamide as a solid (20 mg, 55.7% yield): $^1$H NMR (400 MHz; DMSO-d$_6$): 8.8 (s, 1H); 8.3 (br s, 1H); 8.15 (s, 1H); 8.0 (d, 1H); 7.7 (s, 1H); 7.6 (br s, 2H); 7.4 (m, 3H); 7.2 (m, 3H); 4.2 (m, 1H); 3.89 (m, 2H); 2.9 (m, 1H); 2.7 (m, 1H); 2.3 (m, 1H); 1.8 (m, 1H); MS (EI) for $C_{21}H_{21}N_5O$: 360 (MH$^+$).

3-Amino-6-(3-{[(1S)-2,3-dihydro-1H-inden-1-ylamino]methyl}phenyl)-N-(2,2,2-trifluoroethyl)pyrazine-2-carboxamide was prepared from methyl 3-amino-6-[3-(hydrohymethyl)phenyl]pyrazine-2-carboxylate and 2,2,2-trifluoroethylamine in a manner analogous to that described in the previous example. $^1$H NMR (400 MHz; DMSO-d$_6$): 9.9 (br s, 1H); 9.88 (br s, 1H); 9.5 (t, 1H); 8.97 (s, 1H); 8.75 (s, 1H); 8.24 (m, 1H); 7.84 (d, 1H); 7.5 (m, 2H); 7.4-7.3 (m, 3H); 4.8 (m, 1H); 4.3 (m, 2H); 4.2 (m, 2H); 3.4 (m, 1H); 2.9 (m, 1H); 2.5 (m, 1H); 2.4 (m, 1H); MS (EI) for $C_{23}H_{22}N_5OF_3$ HCl: 422 (MH$^+$).

Example 39

3-Amino-6-bromopyrazine-2-carboxamide

A suspension of methyl 3-aminopyrazine-2-carboxylate (5 g, 32.6 mmol) and 150 mL of dry methanol saturated with anhydrous ammonia were heated in an autoclave at 110-115°

C. for 24 h. Concentration and filtration afforded 3-aminopyrazine-2-carboxamide (4.4 g, 97.7% yield) as a yellow solid.

To a solution 3-aminopyrazine-2-carboxamide (3 g, 22 mmol) in acetic acid (25 mL) was drop wise added bromine (4.2 g, 26.5 mmol) at room temperature the reaction mixture was stirred for 0.5 h and Na$_2$CO$_3$ (2 eq) was added slowly. Upon added of the reaction, the solvent was removed in vacuo, water (50 mL) was added to the residue and the precipitate was collected on a filter and washed with hexane (50 mL) to give 3-amino-6-bromopyrazine-2-carboxamide (4.5 g) as a yellow solid: MS (EI) for C$_5$H$_5$BrN$_4$O: 217 (MH$^+$).

3-Amino-6-bromopyrazine-2-carbonitrile: 3-Amino-6-bromopyrazine-2-carboxamide (1.5 g, 7 mmol) was dissolved in pyridine (15 mL). The solution was then cooled in an ice bath and POCl$_3$ (2 mL) was drop wise added. The resulting mixture was stirred at room temperature for 2.5 h. The solvent was removed and the residue was quenched by the careful addition of ice cooled Na$_2$CO$_3$ (5 mmol). Ethyl acetate was added (45 mL) and the organic layer was separated, washed with brine (5 mL), HCl (0.1 M aqueous solution, 1 mL) and water (5 mmol), dried with K$_2$CO$_3$ and concentrated. The crude matherial was triturated with hexane, and the resulting tan solid was filtered to provide 0.8 g (58% yield) of the title compound: $^1$H NMR (400 MHz; DMSO-d$_6$): 8.42 (s, 1H); 7.60 (br s, NH); MS (EI) for C$_5$H$_3$BrN$_4$: 199 (MH$^+$).

3-amino-6-[3-(hydroxymethyl)phenyl]pyrazine-2-carbonitrile: A mixture of 3-amino-6-bromopyrazine-2-carbonitrile (7.7 g, 37.9 mmol), 3-hydroxymetlhylphenyl boronic acid (7.4 g, 49.3 mmol), Pd(dppf)$_2$Cl$_2$ (10 mol % yield), and triethylamine (16.6 mL, 113 mmol) in DMF (50 mL) were heated at 85° C. for 12 h. The reaction was cooled to room temperature and water (50 mL), EtOAc (100 mL) was added. The organic layer was washed with brine (50 mL), dried (Na$_2$SO$_4$) and passed through a plug of Celite. The solvent was removed and the residue triturated with ether (40 mL) to give a title compound (6 g) as a white solid: $^1$H NMR (400 MHz; DMSO-d$_6$): 8.9 (s, 1H); 7.9 (s, 1H); 7.8 (d, 1H); 7.5-7.3 (m, 4H); 5.27 (t, 1H); 4.15 (d, 1H); MS (EI) for C$_{12}$H$_{10}$N$_4$O: 227 (MH$^+$).

Example 40

Preparation of Triazoles

{3-[5-amino-6-(5-phenyl-4H-1,2,4-triazol-3-yl)pyrazin-2-yl]phenyl}methanol: A mixture of 3-amino-6-[3-(hydroxymethyl)phenyl]pyrazine-2-carbonitrile (0.11 g, 0.5 mmol) and benzoic hydrazide (0.15 g, 1 mmol) were heated at 180-200° C. for 30 min. After cooling, the reaction mass was taken up with 5 mL DMF and the obtained solution was diluted with EtOAc and water, clarified with charcoal and filtered on Celite. The organic layer was separated. After drying over sodium sulfate, the ethyl acetate was evaporated under reduced pressure. Purification of the residue by preparative HPLC (Acetonitrile/water) gave desired product (50 mg): $^1$H NMR (400 MHz; DMSO-d$_6$): 8.3 (s, 1H); 8.1 (m, 2H); 7.6-7.3 (m, 7H); 5.45 (t, 1H); 4.6 (d, 2H); MS (EI) for C$_{23}$H$_{22}$N$_5$OF$_3$ HCl: 442 (MH$^+$).

1-ethyl piperidine-3-carbohydrazide: Using the procedure (as described in J. Med. Chem. (1990) 33 (1), 311-317), N-alkylation of ethyl nipecotate with 1-bromoethane in ethanol gave the ethyl 1-ethyl-3-piperidecarboxylate compound as a colorless liquid (85% yield). The ester (5 g, 27 mmol)) and hydrazine hydrate (5 mmol) were stirred under reflux for 4 h. Volatiles were stripped under reduced pressure. The solid was slurred in ether, filtered and dried, to give 1-ethyl piperidine-3-carbohydrazide (4.5 g, 94% yield).

(3-{5-amino-6-[5-(1-ethylpiperidin-3-yl)-4H-1,2,4-triazol-3-yl]pyrazin-2-yl}phenyl) methanol was prepared from 3-amino-6-[3-(hydroxymethyl) phenyl]pyrazine-2-carbonitrile and 1-ethyl piperidine-3-carbohydrazide in a manner analogous to that described in the previous example: $^1$H NMR (400 MHz; DMSO-d$_6$): 8.8 (s, 1H); 8.15 (s, 1H); 8.15 (s, 1H); 8.07 (d, 1H); 7.7 (br s, 1H); 7.47 (t, 1H); 7.4 (t, 1H); 5.25 (t, 1H); 4.6 (d, 2H); 3.1-2.9 (m, 3H); 2.4 (m, 2H); 2.2-1.9 (m, 3H); 1.8-1.6 1 (m, 3H); 1.04 (t, 3H); MS (EI) for C$_{20}$H$_{25}$N$_7$O: 380 (MH$^+$).

{3-[5-amino-6-(4H-1,2,4-triazol-3-yl)pyrazin-2-yl]phenyl}methanol: $^1$H NMR (400 MHz; DMSO-$_4$): 8.8 (s, 1H); 8.4 (m, 2H); 7.7-7.3 (m, 4H); 5.2 (t, 1H); 4.6 (d, 2H); MS (EI) for C$_{13}$H$_{12}$N$_6$O: 269 (MH$^+$).

{3-[5-amino-6-(5-methyl-4H-1,2,4-triazol-3-yl)pyrazin-2-yl]phenyl}methanol: $^1$H NMR (400 MHz; DMSO-d$_6$+TFA): 8.8 (s, 1H); 8.1 (s, 1H); 8.05 (d, 1H); 7.45 (t, 1H); 7.4 (d, 1H); 4.6 (s, 2H); 2.5 (s, 3H); MS (EI) for C$_{19}$H$_{16}$N$_6$O: 345 (MH$^+$).

(3-{5-amino-6-[5-(phenylmethyl)-4H-1,2,4-triazol-3-yl]pyrazin-2-yl}phenyl)methanol: $^1$HNMR (400 MHz; DMSO-d$_6$): 8.8 (s, 1H); 8.1 (m, 2H); 7.6 (m, 2H); 7.45-7.2 (m, 6H); 5.2 (m, 1H); 4.6 (d, 2H); 4.1 (s, 2H); MS (EI) for C$_{20}$H$_{18}$N$_6$O: 359 (MH$^+$).

(3-{5-amino-6-[5-(1,1-dimethylethyl)-4H-1,2,4-triazol-3-yl]pyrazin-2-yl}phenyl)methanol: $^1$H NMR (400 MHz; DMSO-d$_6$): 8. 8 (s, 1H); 8.1 (s, 1H); 7.4 (m, 3H); 5.2 (t, 1H); 4.6 (d, 2H); 1.4 (m, 9H); MS (EI) for C$_{17}$H$_{20}$N$_6$O: 325 (MH$^+$).

{3-[5-amino-6-(5-furan-2-yl-4H-1,2,4-triazol-3-yl) pyrazin-2-yl]phenyl}methanol: MS (EI) for C$_{17}$H$_{14}$N$_6$O$_2$: 335 (MH$^+$).

[3-(5-amino-6-{5-[3-(methyloxy)phenyl]-4H-1,2,4-triazol-3-yl}pyrazin-2-yl)phenyl]methanol): MS (EI) for C$_{20}$H$_{18}$N$_6$O$_2$: 375 (MH$^+$).

Example 41

Scheme 16 depicts a general synthetic route for exemplary compounds of the invention according to formula I, wherein —W—X—Y is first installed and then -A-R$^7$ is installed, specifically where A is a triazole. In this example, bromopyrazine (lxxiv) is coupled to boronic acid (lxxy) to afford intermediate (lxxyi). The cyano group of (lxxyi) is converted to, for example, a triazole to give (lxxyii), a compound according to formula I.

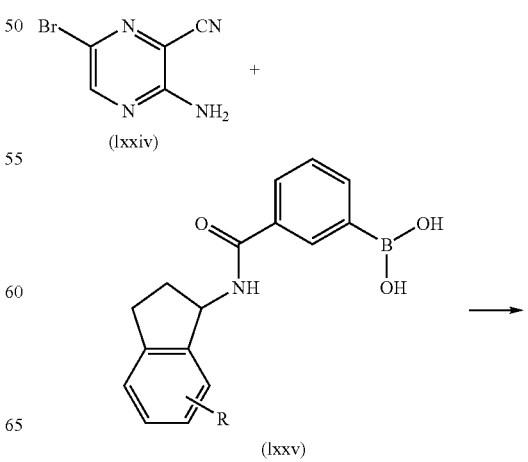

-continued

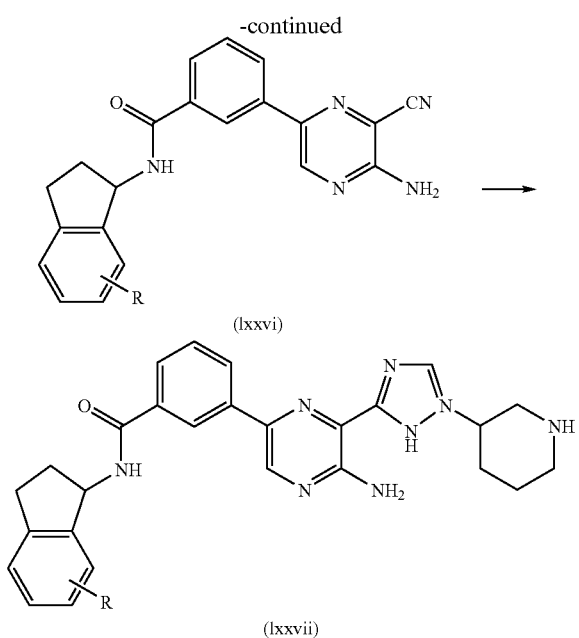
(lxxvi)
(lxxvii)

3-(5-amino-6-{5-[(3S)-piperidin-3-yl]-4H-1,2,4-triazol-3-yl pyrazin-2-yl)-N-[(1S)-2,3-dihydro-1H-inden-1-yl]benzamide (3-{(1S)-2.3-dihydro-1H-inden-1-ylamino]carbonyl}phenyl)boronic acid: To a suspension of 3-carboxybenzene boronic acid (7 g, 42.4 mmol) in dry methylene chloride (200 mL) were added thionyl chloride (50 mL) and 3 drops of DMF. The resulting mixture was stirred for 2 h at 50° C. The clear solution was evaporated to dryness to give the crude acid chloride. To that residue were added (S)-aminoindane (5.64 g, 42.4 mmol) and triethylamine (12.8 mL, 3 eq) in THF (50 mL). The reaction mixture was allowed to stir overnight and then poured into water (100 mL), extracted with EtOAc (3×50 mL). The combined organic extracts were washed with brine, HCl (0.1 M, 20 mL), dried (Na$_2$SO$_4$) and concentrated to give white solid. The solid was washed with hexane to give crude title compound (6.2 g): MS (EI) for C$_{16}$H$_{16}$BNO$_3$: 282 (MH$^+$).

To a mixture of (3-{(1S)-2.3-dihydro-1H-inden-1-ylamino]carbonyl}phenyl) boronic acid (6.2 g, 22.6 mmol) and 3-amino-6-bromopyrazine-2-carbonitrile (4.3 g, 21.8 mmol) in DMF (40 mL) was added triethylamine (9.2 mmol) and Pd(dppf)$_2$Cl$_2$ (10 mol % yield). The deep black mixture was stirred overnight at 85° C., cooled to room temperature and EtOAc (200 mL) was added. The organic layer was passed through a plug of Celite. The pale yellow solution was washed with brine (3×20 mmol), HCl (1 M aquous solution (10 mmol), sodium carbonate (30 mmol), dried (Na$_2$SO$_4$) and evaporated to dryness. The residue was recrystallized from hot EtOAc to give 3-(5-amino-6-cyanopyrazine-2-yl)-N-[(1S)-2,3-dihydro-1H-inden-1-yl]benzamide (2.4 g, 30.9% yield): $^1$H NMR (400 MHz; CD$_3$OD): 8.9 (m, 2H); 8.45 (s, 1H); 8.15 (d, 1H); 7.92 (d, 1H); 7.65-7.38 (m, 3H); 7.22 (m, 4H); 5.6 (m, 31); 3.03-2.85 (m, 2H); 2.42 (m, 1H); 2.0 (m, 1H); MS (EI) for C$_{21}$H$_{17}$N$_5$O: 356 (MH$^+$).

A solution of 3-(5-amino-6-cyanopyrazine-2-yl)-N-[(1S)-2,3-dihydro-1H-inden-1-yl]benzamide (2.4 g, 6.6 mmol) and 1,1-dimethyl (3S)-3-(hydrazinocarbonyl)piperidine-1-carboxylate (2.4 g, 10.1 mmol) in NMP (3 mL) was heated to 180-200° C. for 1 h. The solvent was removed under reduced pressure. The residue obtained was stirred with CH$_2$Cl$_2$/TFA (20% v/v)) for 30 min., concentrated and purified by hplc. The compound was converted to the hydrochloride salt using a 4 M solution of HCl in dioxane to afford 3-(5-amino-6-{5-[(3S)-piperidin-3-yl]-4H-1,2,4-triazol-3-yl}pyrazin-2-yl)-N-[(1S)-2,3-dihydro-1H-inden-1-yl]benzamide: $^1$H NMR (400 MHz; CD$_3$OD): 8.65 (s, 1H); 8.6 (d, 1H); 7.6 (t, 1H); 7.7-7.8 (m, 4H); 5.7 (t, 1H); 3.75-3.4 (m, 4H); 3.8-3.36 (m, 3H); 3.35-2.8 (m, 3H); 2.6 (m, 1H); 2.4 (m, 2H); 2.1-2.0(m, 4H); 1.3 (t, 3H); MS (EI) for C$_{27}$H$_{28}$N$_8$O: 481 (MH$^+$).

3-(5-amino-6-{5-[(3S)-piperidin-3-yl-4H]-1,2,4-triazol-3-yl}pyrazin-2-yl)-N-[(1R,2S)-2-hydroxy-2,3-dihydro-1H-inden-1-yl]benzamide: Using (1-R,2S)+cis-1-aminoindan-2-ol and 3-carboxybenzene boronic acid, the title compound was prepared according to the general scheme: $^1$H NMR (400 MHz; CD$_3$OD): 8.86 (s, 1H); 8.6 (s, 1H); 8.5 (d, 1H); 8.4 (d, 1H); 7.94 (d, 1H); 7.63 (m, NH); 7.6 (t, 1H); 7.25 (m, 3H); 5.52 (m, 1H); 4.55 (m, 1H); 3.2 (m, 4H); 2.93 (m, 4H); 2.75 (m, 1H); 2.11 (m, 11H); 1.68 (m, 2H); 1.5 (m, 2H); MS (EI) for C$_{27}$H$_{28}$N$_8$O$_2$: 497 (MH$^+$).

Using the same or analogous synthetic techniques and/or substituting with alternative reagents, the following compounds of the invention were prepared:

3-(5-amino-6-{3-[(3S)-piperidin-3-yl]-1H-1,2,4-triazol-5-yl }pyrazin-2-yl)-N-[2-chlorophenyl)methyl]benzamide: $^1$H NMR (400 MHz; DMSO-d$_6$): 9.3 (t, 1H); 9.0 (m, 2H); 8.8 (s, 1H); 8.73 (s, 1H); 8.45 (d, 1H); 7.8 (d, 1H); 7.75 (br s, 1H, NH); 7.6 (t, 1H): 7.49 (d, 1H); 7.41 (d, 1H); 7.3 (m, 2H); 4.6 (d, 2H); 3.6-2.9 (m, 4H); 2.2 (m, 1H); 1.8 (m, 4H); MS (EI) for C$_{25}$H$_{25}$N$_8$OCl HCl: 489 (MH$^+$).

3-(5-amino-6-{5-[(3S)-piperidin-3-yl]-4H-1,2,4-triazol-3-yl}pyrazin-2-N-[(2-fluorophenyl)methyl]benzamide: $^1$H NMR (400 MHz; DMSO-d$_6$): 9.5 (m, 1H); 9.3-9.1 (m, 2H); 8.85 (s, 1H); 8.78 (s, 1H); 8.43 (d, 1H); 7.9 (d, 1H); 7.6 (t, 1H); 7.42 (m, 4H); 4.5 (d, 2H); 3.58-2.8 (m, 5H); 2.12-1.83 (m, 4H); MS (EI) for C$_{25}$H$_{25}$N$_8$F HCl; 473 (MH$^+$).

3-(5-amino-6-{5-[(3S)-piperidin-3-yl]-4H-1,2,4-triazol-3-yl}pyrazin-2-yl)-N-[(3-fluorophenyl)methyl]benzamide: $^1$H NMR (400 MHz; DMSO-d$_6$): 9.4 (m, 1H); 9.0 (m, 2H); 8.9 (s, 1); 8.7 (s, 1H); 8.4 (d, 1H); 7.9 (m, 1H); 7.8 (br s, NH); 7.6 (t, 1H); 7.2 (m, 2H); 7.1 (m, 1H); 4.6 (d, 2H); 3.9-2.4 (m, 5H); 2.2-1.8 (m, 4H); MS (EI) for C$_{25}$H$_{25}$N$_8$F HCl: 473 (MH$^+$).

3-(5-amino-6-{5-[(3S)-piperidin-3-yl]-4H-1,2,4-triazol-3}pyrazin-2-yl)-N-[(4-fluorophenyl)methyl]benzamide: $^1$H NMR (400 MHz; DMSO-d$_6$): 9.5 (m, 1H); 9.35-9.1 (m, 2H); 8.9 (s, 1H); 8.8 (s, 1H); 8.4 (d, 1H); 7.9 (d, 1H); 7.6 (t, 1H); 7.4 (m, 4H); 4.5 (d, 2H); 3.6-2.9 (m, 5H); 2.2 (m, 1H); 1.8 (m, 3H); MS (EI) for C$_{25}$H$_{25}$N$_8$OF HCl; 473 (MH$^+$).

3-(5-amino-6-{5-[(3S)-piperidin-3-yl]-4H-1,2,4-triazol-3-yl}pyrazin-2-yl)-N-[(3-chlorophenyl)methyl]benzamide: $^1$H NMR (400 MHz; DMSO-d$_6$): 9.3 (t, 1H); 9.0 (m, 2H); 8.9 (s, 1H); 8.7 (s, 1H); 8.4 (d, 1H); 7.9 (d, 1H); 7.6 (t, 1H); 7.4 (m, 2H); 7.2 (m, 2H); 4.5 (d, 2H); 3.6-2.9 (m, 5H); 2.2 (m, 1H); 1.8 (m, 3H); MS (EI) for C$_{25}$H$_{25}$N$_8$OCl HCl: 489 (MH$^+$).

3-(5-amino-6-{5-[(3S)-piperidin-3-yl]-4H-1,2,4-triazol-3-yl}pyrazin-2-yl)-N-[(4-chlorophenyl)methyl]benzamide): $^1$H NMR (400 MHz; DMSO-d$_6$): 9.3 (t, 1H); 8.9 (m, 2H); 8.67 (s, 1H); 8.4 (d, 1H); 7.8 (d, 1H); 7.7 (m, NH); 7.6 (t, 1H);

7.2 (m, 4H); 4.5 (d, 2H); 3.6 (d, 1H); 3.4-3.1 (m, 3H); 3.0 (m, 1H); 2.1 (m, 1H); 1.8 (m, 3H); MS (EI) for $C_{25}H_{25}N_8OCl$ HCl: 489 (MH$^+$).

Example 42

3-(Methylamino)-6-phenylpyrazine-2-carboxamide

Methyl 3-chloro-6-phenylpyrazine-2-carboxylate: To a mixture of acetic acid/hydrochloric acid (1:1, 20 mL) at 0° C. was added methyl 3-amino-6-phenylpyrazine-2-carboxylate (1.02 g, 4.50 mmol). Aqueous solution of sodium nitrite (0.77 g, 11.2 mmol) was added drop wise. During the addition, the temperature of the reaction was controlled at 0-5° C. The reaction was slowly warmed to room temperature and stirred overnight. The reaction mixture was extracted with ethyl acetate (2×50 mL). The organic layer was washed with water (30 mL), saturated aqueous sodium chloride (30 mL), dried over magnesium sulfate, filtered and concentrated at reduced pressure to afford the crude methyl 3-hydroxy-6-phenylpyrazine-2-carboxylate which was used in the next step with out any purification. The crude product was treated with phosphorus oxychloride (30 mL) and heated to 90° C. for 2 h. The reaction was cooled to room temperature and poured into ice-water mixture and extracted with ethyl acetate (3×40 mL). The organic layer was washed with water (30 mL), saturated aqueous sodium chloride (30 mL), dried over magnesium sulfate, filtered, and concentrated to give crude product. Column purification on silica (8:2 hexanes/ethyl acetate) afforded methyl 3-chloro-6-phenylpyrazine-2-carboxylate (0.22 g, 20% yield) as yellow solid: 1H NMR (400 MHz, CDCl$_3$): δ 8.90 (s, 1H), 8.02 (t, 2H), 7.40 (t, 1H), 7.20 (br s, 2H), 3.90 (s, 3H): MS (EI) for $C_{12}H_9N_2O_2Cl$: 249 (MH$^+$).

3-(Methylamino)-6-phenylpyrazine-2-carboxamide: To a solution of methyl 3-chloro-6-phenylpyrazine-2-carboxylate (0.13 g, 0.53 mmol) in tetrahydrofuran (3 mL) was added 0.65 mL of 2.0 N methylamine in THF (1.30 mmol). The reaction was heated in a sealed high-pressure test tube to 90-95° C. overnight. The reaction was cooled to room temperature and diluted with ethyl acetate (100 mL). The organic layer was washed 2.0 N aqueous hydrochloric acid (20 mL), saturated aqueous sodium bicarbonate (30 mL), and saturated aqueous sodium chloride (30 mL). The organic layer was dried over magnesium sulfate, filtered and concentrated at reduced pressure to afford a yellowish product. Trituration with methanol (2 mL) gave a solid, which was filtered and washed with ether to afford afford methyl 3-(methylamino)-6-phenylpyrazine-2-carboxylate (31 mg, 24%) as yellow solid: MS (EI) for $C_{13}H_{13}N_3O_2$: 244 (MH$^+$). This intermediate ester was directly used in the next step.

A solution of of methyl 3-(methylamino)-6-phenylpyrazine-2-carboxylate (31 mg, 0.13 mmol) in methanol (5 ml) was saturated with ammonia at 0° C. The pressure tube was sealed and heated at 80-85° C. overnight. The reaction was cooled to room temperature and the solvent removed at reduced pressure to afford crude solid product. Reverse-phase BPLC purification gave 3-(methylamino)-6-phenylpyrazine-2-carboxamide (7 mg, 25% yield) as a yellow solid: $^1$H NM (400 MHz, CDCl$_3$): δ 8.42 (s, 1H), 8.50 (br s, 1H), 7.90 (d, 3H), 7.45 (m, 2H), 7.40 (m, 1H), 3.10 (br s, 3H); MS (EI) for $C_{12}H_{12}N_4O$: 229 (MH$^+$).

Using the same or analogous synthetic techniques and/or substituting with alternative reagents, the following compounds of the invention were prepared:

6-phenyl-3-[(phenylmethyl)amino]pyrazine-2-carboxamide: $^1$H NMR (400 MHz, CDCl$_3$): δ 9.01 (br t, 1H), 8.70 (s, 1H), 7.90 (m, 3H), 7.35 (m, 8H), 5.60 (br s, 1H), 4.80 (d, 2H); MS (EI) for C18H$_{16}$N$_4$O: 305 (MH$^+$).

6-phenyl-3-(propylamino)pyrazine-2-carboxamide: $^1$H NMR (400 MHz, CDCl$_3$): δ 8.70 (s, 1H), 8.70 (s, 1H), 8.60 (br s, 1H), 7.44 (t, 2H), 7.40 (t, 1H), 5.50 (br, s 1H), 3.50 (m, 2H), 1.70 (m, 2H), 1.02 (t, 3H); MS (EI) for $C_{14}H_{16}N_4O$: 257 (MH$^+$).

Example 43

3-Amino-N-methyl-6-(5-cyclopentyl-1,2,4-oxadiazol-3-yl)pyrazine-2-carboxamide 3-Amino-6-bromo-N-methylpyrazine-2-carboxamide (2.0 g, 8.7 mmol) and copper (I) cyanide (3.9 g, 43.5 mmol) were taken into DMF (20 mL) and the mixture was heated to reflux for two hours. The mixture was allowed to cool to room temperature then diluted with ethyl acetate (250 mL). The insoluble residue was removed by filtration and the filtrate partitioned with water. The organic layer was separated and washed with water (2×) then brine and dried over anhydrous magnesium sulfate. Filtration and concentration afforded 3-amino-6-cyano-N-methylpyrazine-2-carboxamide (500 mg, 33% yield) as a white solid: $^1$H NMR (400 MHz, d$_6$-DMSO): 8.84 (br m, 1H), 8.67 (br s, 1H), 8.65 (s, 1H), 2.77 (d, 3H).

3-Amino-6-cyano-N-methylpyrazine-2-carboxamide (839 mg, 4.7 mmol) was suspended in ethanol (25 mL) followed by addition of 50% aqueous hydroxylamine (2 mL, 31.3 mmol) and the mixture was stirred at room temperature for one hour. The suspension obtained was diluted with water (2 5mL) and the insoluble solid collected by filtration and washed with water. The solid was dried in vacuo to give 3-amino-6-[(hydroxyamino)(imino)methyl]-N-methylpyrazine-2-carboxamide (664 mg, 67% yield) as a white solid: MS (EI) for $C_7H_{10}N_6O_2$: 211 (MH$^+$).

3-Amino-6-[(hydroxyamino)(imino)methyl]-N-methylpyrazine-2-carboxamide (40 mg, 0.19 mmol) was taken into DMF (1.0 mL) followed by addition of PL-DIPAM (di-isopropylaminomethyl) resin (200 mg, 2.33 mmol/g), THF (1.0 ML) and cyclopentanecarbonyl chloride (23.1 uL, 0.19 mmol). The mixture was agitated for one hour then filtered and the resin rinsed with THF (1.0 mL). To the filtrate solution was added tetra-N-butylammonium fluoride (TBAF) (1.0 M in THF, 20 0 uL) and the solution was allowed to stir at room temperature over 12 hours. The mixture was concentrated and the residue partitioned with ethyl acetate and water. The organic layer was washed with water (1×), 1.0 M aqueous hydrochloric acid (1×) then brine and dried over anhydrous magnesium sulfate. The material was filtered and concentrated then the residue purified by silica gel flash chromatography using ethyl acetate:hexanes (1:1) as eluent. The pure fractions were combined, concentrated and dried in vacuo to give 3-amino-N-methyl-6-(5-cyclopentyl-1,2,4-oxadiazol-3-yl)pyrazine-2-carboxamide (23.3 mg, 43% yield) as a colorless amorphous residue: MS (EI) for $C_{13}H_{16}N_6O_2$: 289 (MH$^+$).

Using the same or analogous synthetic techniques and/or substituting with alternative reagents, the following compounds of the invention were prepared:

3-Amino-N-methyl-6-(5-pyridin-3-yl-1,2,4-oxadiazol-3-yl)pyrazine-2-carboxamide: MS (EI) for $C_{13}H_{11}N_7O_2$: 298 (MH$^+$).

3-Amino-N-methyl-6-(5-cyclohexyl-1,2,4-oxadiazol-3-yl)pyrazine-2-carboxamide: MS (EI) for $C_{14}H_{18}N_6O_2$: 303 (MH$^+$).

3-Amino-N-methyl-6-(5-phenyl-1,2,4-oxadiazol-3-yl)pyrazine-2-carboxamide: MS (EI) for $C_{14}H_{12}N_6O_2$: 297 (MH$^+$).

3-Amino-N-methyl-6-[5-(phenylmethyl)-1,2,4-oxadiazol-3-yl]pyrazine-2-carboxamide: MS (EI) for $C_{15}H_{14}N_6O_2$: 311 (MH$^+$).

3-Amino-N-methyl-6-(5-methyl-1,2,4-oxadiazol-3-yl)pyrazine-2-carboxamide: MS (EI) for $C_9H_{10}N_6O_2$: 235 (MH$^+$).

3-Amino-N-methyl-6-[5-(2-phenylethyl)-1,2,4-oxadiazol-3-yl]pyrazine-2-carboxamide: MS (EI) for $C_{16}H_{16}N_6O_2$: 325 (MH$^+$).

3-Amino-N-methyl-6-(5-pyridin-4-yl-1,2,4-oxadiazol-3-yl)pyrazine-2-carboxamide: MS (EI) for $C_{13}H_{11}N_7O_2$: 298 (MH$^+$).

3-Amino-N-methyl-6-[5-(1,1-dimethylethyl)-1,2,4-oxadiazol-3-yl]pyrazine-2-carboxamide: MS (EI) for $C_{12}H_{16}N_6O_2$: 276 (MH$^+$).

3-Amino-N-methyl-6-(5-furan-2-yl-1,2,4-oxadiazol-3-yl)pyrazine-2-carboxamide: MS (EI) for $C_{12}H_{10}N_6O_3$: 286 (MH$^+$).

Example 44

3-Amino-N-methyl-6-[3-(5-phenyl-1,2,4-oxadiazol-3-yl)phenyl]pyrazine-2-carboxamide 3-Amino-6-(3-cyanophenyl)-N-methylpyrazine-2-carboxamide (155 mg, 0.61 mmol) was suspended in ethanol (2 mL) followed by addition of 50% aqueous hydroxylamine (250 uL, 4.1 mmol) and the mixture was heated to reflux for 30 minutes then allowed to cool to room temperature. The suspension was diluted with water (2 mL) and the solid product collected by filtration and dried in vacuo to give crude 3-amino-N-methyl-6-{3-[(hydroxyamino)(imino)methyl]phenyl}pyrazine-2-carboxamide (125 mg, 72% yield) as a yellow solid which was carried forward without further purification: MS (EI) for $C_{13}H_{15}N_6O_2$: 287 (MH$^+$).

3-Amino-N-methyl-6-{3-[(hydroxyamino)(imino)methyl]phenyl}pyrazine-2-carboxamide (40 mg, 0.14 mmol) was suspended in DMF (750 uL) followed by addition of PL-DIPAM (diisopropylaminomethyl) resin (100 mg, 2.33 mmol/g) and benzoyl chloride (20 uL, 0.17 mmol). The mixture was agitated for one hour then diluted with ethyl acetate and the spent resin removed by filtration, The organic filtrate was washed with water (3×), brine then dried over anhydrous magnesium sulfate. The mixture was then filtered and concentrated and the solid residue suspended in TIF (1 mmol) followed by addition of tetra-N-butylammonium fluoride (TBAF) (1.0 M in THF, 100 uL) and the solution was allowed to stir at room temperature over 12 hours. The mixture was concentrated and the residue partitioned with ethyl acetate and water. The organic layer was washed with water (1×), 1.0 M aqueous hydrochloric acid (lx) then brine and dried over anhydrous magnesium sulfate. The material was filtered and concentrated then the residue purified by preparative reverse phase HPLC (water/acetonitrile/0.1% TFA eluent). The pure fractions were combined and lyophilized to afford 3-amino-N-methyl-6-[3-(5-phenyl-1,2,4-oxadiazol-3-yl)phenyl]pyrazine-2-carboxamide (10.4 mg, 20% yield) as a yellow solid: MS (EI) for $C_{20}H_{17}N_6O_2$: 372 (MH$^+$).

Using the same or analogous synthetic techniques and/or substituting with alternative reagents, the following compounds of the invention were prepared:

3-Amino-N-methyl-6-{3-[5-(phenylmethyl)-1,2,4-oxadiazol-3-yl]phenyl}pyrazine-2-carboxamide: MS (EI) for $C_{21}H_{19}N_6O_2$: 386 (MH$^+$).

3-Amino-N-methyl-6-t 3-[5-(2-phenylethyl)-1,2,4-oxadiazol-3-yl]phenyl]pyrazine-2-carboxamide: MS (EI) for $C_{21}H_{19}N_6O_2$: 400 (MH$^+$).

Example 45

3-Amino-N-methyl-6-1 3-[(2-phenylethyl)oxylphenyl}pyrazine-2-carboxamide

3-Amino-6-bromo-N-methylpyrazine-2-carboxamide (1.34 g, 5.8 mmol) and 3-hydroxyphenylboronic acid (1.2 g, 8.7 mmol) were taken into DMF (10 mL) followed by addition of [1,1'-bis(diphenylphosphinoferrocene]dichloropalladium (II) dichloromethane complex (440 mg, 0.54 mmol) and triethylamine (4.8 mL, 35 mmol). The mixture was heated to 95° C. for 12 hours then cooled to room temperature and diluted with an excess of ethyl acetate. The organic solution was washed with 0.5 M aqueous hydrochloric acid (1×), water (3×) then brine and dried over anhydrous magnesium sulfate. The mixture was then filtered and the organic solution concentrated and the residue purified by silica gel flash chromatography using ethyl acetate:hexanes (3:1) eluent. The pure fractions were combined and concentrated then dried in vacuo to give 3-amino-6-(3-hydroxyphenyl)-N-methylpyrazine-2-carboxamide (1.01 g, 71% yield) as a yellow solid: MS (EI) for $C_{12}H_{13}N_4O_2$: 245 (MH$^+$).

3-Amino-6-(3-hydroxyphenyl)-N-methylpyrazine-2-carboxamide (179 mg, 0.8 mmol) was taken into DMF (3 mL) followed by addition of cesium carbonate (1.3 g, 4 mmol) and 2-(bromoethyl)benzene (550 uL, 4 mmol). The mixture was heated to 85° C. for 12 hours then allowed to cool to room temperature. The mixture was diluted with an excess of ethyl acetate and washed with water (3×) then brine and dried over anhydrous magnesium sulfate. Filtration and concentration in vacuo followed by purification of the residue using silica gel flash chromatography using ethyl acetate:hexanes (2:3) as eluent. The pure fractions were combined and concentrated then dried in vacuo to give 3-amino-N-methyl-6-{3-[(2-phenylethyl)oxy]phenyl}pyrazine-2-carboxamide (86 mg, 31% yield) as a yellow solid. $^1$H NMR (400 MHz, d$_6$-DMSO): 8.83 (s, 1H), 8.82 (br m, 1H), 7.74 (d, 1H), 7.67 (tr, 1H), 7.38-7.31 (m, 6H), 7.26-7.22 (m, 1H), 6.95 (d tr, 1H), 4.31 (tr, 2H), 3.08 (tr, 2H), 2.85 (d, 3H); MS (EI) for $C_{20}H_{21}N_4O_2$: 349 (MH$^+$).

Example 46

3-Amino-N-methyl-6-(3-{[2-(4-methylpiperidin-1-yl)ethyl]oxy}phenyl)pyrazine-2-carboxamide 3-Amino-6-(3-hydroxyphenyl)-N-methylpyrazine-2-carboxamide (1.01 g, 4.1 mmol) was taken into DMF (10 mL) followed by addition of 1,2-dibromoethane (10 mL) and cesium carbonate (2.7 g, 8.2 mmol). The mixture was warmed to 85° C. over 5 days followed by addition of another aliquot of cesium carbonate and 1,2-dibromoethane and heating was continued an additional 4 hours. The mixture was diluted with an excess of ethyl acetate and washed with water (3×) then brine and dried over anhydrous magnesium sulfate. Filtration and concentration ill vacuo followed by purification of the residue using silica gel flash chromatography using ethyl acetate:hexanes (1:1) as eluent. The pure fractions were combined and concentrated then dried in vacuo to give 3-amino-6-{3-[(2-bromoethyl)oxy]phenyl}-N-methylpyrazine-2-carboxamide (486 mg, 34% yield) was a yellow solid: MS (EI) for $C_{14}H_{16}N_4O_2Br$: 351, 353 (MH$^+$).

3-Amino-6-{3-[(2-bromoethyl)oxy]phenyl}-N-methylpyrazine-2-carboxaamide (25 mg, 0.07 mmol) was taken into acetonitrile (1 mL) followed by addition of 4-methylpiperidine (58 mg, 0.58 mmol) and the mixture was stirred at room temperature over 12 hours. The crude reaction mixture was purified directly by preparative reverse phase HPLC (water/acetonitrile/0.1% TFA eluent). The pure fractions were combined and lyophilized to afford 3-amino-N-methyl-6-(3-{[2-(4-methylpiperidin-1-yl)ethyl]oxy}phenyl)pyrazine-2-carboxamide (20.2 mg, 60% yield) as an amorphous solid: MS (EI) for $C_{20}H_{28}N_5O_2$: 371 (MH$^+$).

Using the same or analogous synthetic techniques and/or substituting with alternative reagents, the following compounds of the invention were prepared:

3-Amino-6-[3-({2-[4-(2-hydroxyethyl)piperidin-1-yl]ethyl}oxy)phenyl]-N-methylpyrazine-2-carboxamide: MS (EI) for $C_{21}H_{30}N_5O_3$: 401 (MH$^+$).

3-Amino-6-(3-{[2-(3-hydroxypyrrolidin-1-yl)ethyl]oxy}phenyl)-N-methylpyrazine-2-carboxamide: MS (EI) for $C_{18}H_{24}N_5O_3$: 359 (MH$^+$).

3-Amino-N-methyl-6-[3-({2-[4-(phenylmethyl)piperidin-1-yl]ethyl}oxy)phenyl]pyrazine-2-carboxamide: MS (EI) for $C_{26}H_{32}N_5O_2$: 447 (MH$^+$).

3-Amino-N-methyl-6-{3-[(2-piperidin-1-ylethyl)oxy]phenyl}pyrazine-2-carboxamide: MS (EI) for $C_{19}H_{26}N_5O_2$: 357 (MH$^+$).

3-Amino-6-[3-({2-[ethyl(phenylmethyl)amino]ethyl}oxy)phenyl]-N-methylpyrazine-2-carboxamide: MS (EI) for $C_{23}H_{28}N_5O_2$: 407 (MH$^+$).

3-Amino-6-(3-{[2-(diethylamino)ethyl]oxy}phenyl)-N-methylpyrazine-2-carboxamide: MS (EI) for $C_{18}H_{26}N_5O_2$: 344 (MH$^+$).

3-Amino-N-methyl-6-(3-{[2-(4-phenylpiperazin-1-yl)ethyl]oxy}phenyl)pyrazine-2-carboxamide: MS (EI) for $C_{24}H_{30}N_6O_2$: 434 (MH$^+$).

3-Amino-6-[3-({2-[methyl(phenylmethyl)amino]ethyl}oxy)phenyl]-N-methylpyrazine-2-carboxamide: MS (EI) for $C_{22}H_{26}N_5O_2$: 393 (MH$^+$).

3-Amino-N-methyl-6-{3-[(2-morpholin-1-ylethyl)oxy]phenyl}pyrazine-2-carboxamide: MS (EI) for $C_{18}H_{24}N_5O_3$: 359 (MH$^+$).

3-Amino-6-[3-({2-[(cyclopropyl)(propyl)amino]ethyl}oxy)phenyl]-N-methylpyrazine-2-carboxamide: MS (EI) for $C_{21}H_{30}N_5O_2$: 384 (MH$^+$).

3-Amino-N-methyl-6-(3-{[2-(4-ethylpiperazin-1-yl)ethyl]oxy}phenyl)pyrazine-2-carboxamide: MS (EI) for $C_{20}H_{29}N_6O_2$: 385 (MH$^+$).

3-Amino-N-methyl-6-{3-[(2-pyrrolidin-1-ylethyl)oxy]phenyl}pyrazine-2-carboxamide: MS (EI) for $C_{18}H_{24}N_5O_2$: 343 (MH$^+$).

3-Amino-N-methyl-6-(3-{[2-(4-methylpiperazin-1-yl)ethyl]oxy}phenyl)pyrazine-2-carboxamide: MS (EI) for $C_{19}H_{27}N_6O_2$: 371 (MH$^+$).

3-Amino-6-[3-({2-[4-(2-hydroxyethyl)piperazin-1-yl]ethyl}oxy)phenyl]-N-methylpyrazine-2-carboxamide: MS (EI) for $C_{20}H_{29}N_6O_3$: 402 (MH$^+$).

3-Amino-6-(3-{[2-(3,4-dihydroisoquinolin-2(1H)-yl)ethyl]oxy}phenyl)-N-methylpyrazine-2-carboxamide: MS (EI) for $C_{23}H_{26}N_5O_2$: 405 (MH$^+$).

Ethyl 4-{2-[(3-{5-amino-6-[(methylamino)carbonyl]pyrazin-2-yl}phenyl)oxy]ethyl}piperazine-1-carboxylate: MS (EI) for $C_{21}H_{29}N_6O_4$: 430 (MH$^+$).

Example 47

3-Amino-N-methyl-6-(3-{[(phenylmethyl)thiolmethyl]phenyl)pyrazine-2-carboxamide

3-Amino-6-(3-hydroxymethylphenyl)-N-methylpyrazine-2-carboxamide (130 mg, 0.5 mmol) was suspended in THF (5 mL) followed by addition of pyridine (200 uL, 2.5 mmol) and the mixture was cooled to −78° C. Thionyl chloride (100 uL, 1.4 mmol) was added by syringe and the mixture was allowed to slowly warm to room temperature. An additional aliquot of thionyl chloride was added at room temperature and the mixture was allowed to stir an additional hour. The solvent was removed and the residue partitioned with ethyl acetate and 0.1 M aqueous hydrochloric acid. The organic layer was washed with saturated aqueous sodium bicarbonate then brine and dried over anhydrous magnesium sulfate. The mixture was filtered, concentrated and dried in vacuo to afford the crude benzyl chloride, which was taken on without further purification.

The above chloride was taken into acetonitrile (3 mL) followed by addition of benzyl mercaptan (100 uL, 0.86 mmol) then cesium carbonate (350 mg, 1.1 mmol) and the mixture was stirred at room temperature over one hour. The solvent was removed in vacuo and the residue partitioned with ethyl acetate and water. The organic layer was washed with brine and dried over anhydrous magnesium sulfate. The mixture was filtered, concentrated then dried in vacuo and the residue purified by silica gel flash chromatography using ethyl acetate:hexanes (1:1) as eluent. The pure fractions were combined, concentrated and dried in vacuo to give 3-amino-N-methyl-6-(3-{[(phenylmethyl)thio]methyl}phenyl)pyrazine-2-carboxamide (77.1 mg, 40% yield) as a yellow amorphous solid: $^1$H NMR (400 MHz, CDCl$_3$): 8.61 (s, 1H), 7.98 (br s, 1H), 7.76-7.74 (m, 2H), 7.42 (tr, 1H), 7.35-7.24 (m, 8H), 3.68 (s, 2H), 3.65 (s, 2H), 3.05 (d, 3H); MS (EI) for $C_{20}H_{21}N_4OS$: 366 (MH$^+$).

Example 48

3-Amino-N-methyl-6-(3-{[(phenylmethyl)sulfonyl]methyl}phenyl)pyrazine-2-carboxamide 3-Amino-N-methyl-6-(3-{[(phenylmethyl)thio]methyl}phenyl)pyrazine-2-carboxamide (73 mg, 0.2 mmol) was taken into dichloromethane (3 mL) followed by addition of m-CPBA (99 mg, 0.4 mmol) and the mixture was stirred for 30 minutes at room temperature. The solvent was removed and the residue partitioned with ethyl acetate and saturated aqueous sodium bicarbonate. The organic layer was washed with brine and dried over anhydrous magnesium sulfate. The mixture was filtered, concentrated and the residue suspended in a minimum of hot methanol to give a yellow solid. The material was collected by filtration and further purified by preparative reverse phase HPLC (water/acetonitrile/0.1% TFA eluent). The pure fractions were combined and lyophilized to afford 3-amino-N-methyl-6-(3-{[(phenylmethyl)sulfonyl]methyl}phenyl)pyrazine-2-carboxamide (35 mg, 44% yield) as a yellow solid: MS (EI) for $C_{20}H_{21}N_4O_3S$: 398 (MH$^+$).

Example 49

3-Amino-N-methyl-6-(3-{[(phenylmethyl)amino]methyl I phenyl)pyrazine-2-carboxamide Methyl 3-amino-6-(3-chloromethylphenyl)-N-methylpyrazine-2-carboxylate (30.6 mg, 0.11 mmol.) was taken into acetonitrile (2 mL) and THF (1 mL) followed by addition of benzylamine (12 uL, 0.11 mmol) then diisopropylethylamine (20 uL, 0.11 mmol) and the mixture was allowed to stir at room temperature over six days. The mixture was then concentrated in vacuo and the residue purified by silica gel flash chromatography initially using ethyl acetate as eluent followed by elution with 10% methanol in dichloromethane. The pure fractions were combined and concentrated then dried in vacuo to give methyl 3-amino-6-(3-{[(phenylmethyl)amino]methyl}phenyl)pyrazine-2-carboxylate (4.9 mg, 13% yield) as a yellow amorphous solid: MS (EI) for $C_{20}H_{21}N_4O_2$: 349 (MH+).

Methyl 3-amino-6-(3-{[(phenylmethyl)amino]methyl}phenyl)pyrazine-2-carboxylate (4.9 mg, 0.014 mmol) was taken into methanol (2 mL) and the solution was saturated with methylamine gas. The mixture was allowed to stir for two hours in a sealed vessel then concentrated and dried in vacuo to give 3-amino-N-methyl-6-(3-{[(phenylmethyl)amino]methyl}phenyl)pyrazine-2-carboxamide (4.9 mg, 100% yield) as a yellow amorphous solid: MS (EI) for $C_{20}H_{22}N_5O$: 348 (MH+).

Example 50

3-Amino-N-methyl-6-(3-{(phenylmethyl)oxylmethy}phenyl)pyrazine-2-carboxamide

Methyl 3-amino-6-(3-hydroxymethylphenyl)-N-methylpyrazine-2-carboxylate (75 mg, 0.3 mmol) was taken into THF (2 mL) followed by addition of pyridine (120 uL, 1.5 mmol) and the solution was cooled to 0° C. Thionyl chloride (42 uL, 0.6 mmol) was added to the mixture by syringe followed by warming to room temperature. The mixture was then stirred for two hours and partitioned with ethyl acetate and 1 M aqueous hydrochloric acid. The organic layer was washed with water (1x) then brine and dried over anhydrous sodium sulfate. The mixture was filtered and concentrated followed by silica gel flash chromatography using ethyl acetate:hexanes (1:1) as eluent. The pure fractions were combined and concentrated then dried in vacuo to give methyl 3-amino-6-(3-chloromethylphenyl)-N-methylpyrazine-2-carboxylate (30 mg, 37% yield) as a yellow solid: MS (EI) for $C_{13}H_{13}N_3O_2Cl$: 278, 280 (MH+).

Methyl 3-amino-6-(3-chloromethylphenyl)-N-methylpyrazine-2-carboxylate (18 mg, 0.06 mmol) and silver oxide (15 mg, 0.06 mmol) were added to benzyl alcohol (2 mL) and the mixture was heated to 110° C. over 15 hours. The benzyl alcohol was removed in vacuo and the residue purified by silica gel flash chromatography using ethyl acetate:hexanes (1:1) as eluent. The pure fractions were combined and concentrated then dried ill vacuo to give methyl 3-amino-6-(3-{[(phenylmethyl)oxy]methyl}phenyl)pyrazine-2-carboxylate (5.8 mg, 28% yield) as a yellow solid: MS (EI) for $C_{20}H_{20}N_3O_3$: 350 (MH+).

Methyl 3-amino-6-(3-{[(phenylmethyl)oxy]methyl}phenyl)pyrazine-2-carboxylate (5.8 mg, 0.017 mmol) was taken into methanol (2 mL) and the solution was saturated with methylamine gas, The mixture was allowed to stir for two hours in a sealed vessel then concentrated. The residue was purified by silica gel flash chromatography using ethyl acetate:hexanes (2:3) as eluent. The pure fractions were combined and concentrated then dried ill vacuo to give 3-amino-N-methyl-6-(3-{[(phenylmethyl)oxy]methyl}phenyl)pyrazine-2-carboxamide (4.1 mg, 69% yield) as a yellow amorphous solid: MS (EI) for $C_{20}H_{21}N_4O_2$: 349 (MH+).

Example 51

Scheme 17 shows that bromo-aromatic compounds were dimerized in some cases to make compounds according to formula I. In this example, bromo-pyrazine (lxxviii) is dimerized using boronic ester (lxxix), for example, to give (lxxx).

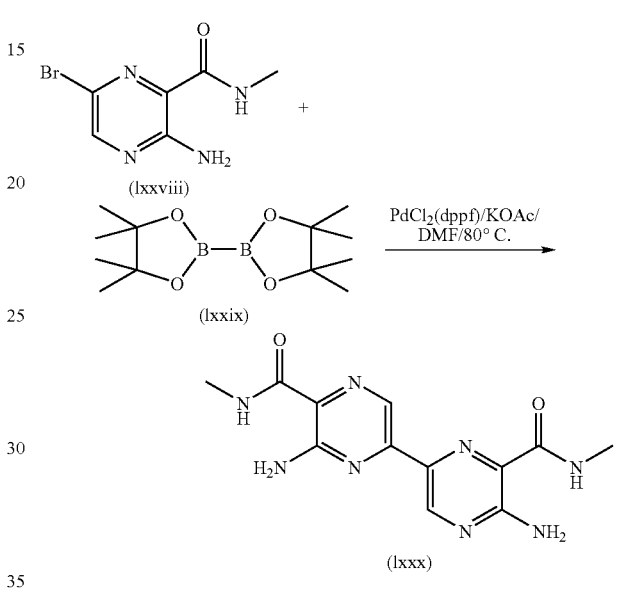

3-Amino-6-bromo-N-methylpyrazine-2-carboxamide: (50.0 mg, 0.22 mmol) was dissolved in DMNF followed by addition of bis(pinacolate)diborane (1.57 g, 0.43 mmol), KOAc (32.0 mg, 0.33 mmol) and PdCl$_2$(dppf) (10 mol %, 15.8 mg). This mixture was stirred at 80° C. under nitrogen for 12 hours. The reaction mixture was poured into water (10 mL), and extracted with ethyl acetate (3×20 mL). The organic layers were washed with brine (50 mL) then dried over anhydrous sodium sulfate. Filtration, concentration and purification by MPLC gave a solid that was dried to afford 8.45 mg (11.3% yield) of product: $^1$H NMR (400 MHz, CDCl$_3$): δ 8.20 (s, 1H), 7.80 (s, 1H), 7.45 (s, 1H), 3.00 (d, 6H); MS (EI) for $C_{12}H_{14}N_8O_2$: 303.45 (MH+).

Example 52

3-Amino-6-[3-(hydroxymethyl)phenyl]-N-methylpyrazine-2-carboxamide

3-Amino-6-bromo-N-methylpyrazine-2-carboxamide (2.00 g, 8.65 mmol) was dissolved in DMF followed by addition of 3-hydroxymethyl phenyl boronic acid (1.57 g, 10.32 mmol), K$_2$CO$_3$ (3.0 g, 21.7 mmol) and Pd(PPh$_3$)$_4$ (10 mol %, 1.0 g). This mixture was stirred at 90° C. under nitrogen for 12 hours. The reaction mixture was poured into water (150 mL), and extracted with ethyl acetate (3×50 mL). The organic layers were washed with brine (50 mL) then dried over anhydrous sodium sulfate. Filtration, concentration and column chromatography on silica (50% ethylacetate/hexanes) gave a solid which was dried to afforded 2.02 g (92% yield) of the title compound; $^1$H NMR (400 MHz, d6-DMSO): δ0 8.80 (s, 1H), 8.74 (br, 1H), 8.01(s, 2H), 7.45 (m, 4H), 5.21(t, 1H), 4.60 (d, 2H), 2.81(d, 3H); MS (EI) for $C_{13}H_{14}N_4O_2$: 259.38 (MH+).

3-Amino-6-[3-(bromomethyl)phenyl]-N-methylpyrazine-2-carboxamide 3-Amino-6-[3-(hydroxymethyl)phenyl]-N-methylpyrazine-2-carboxamide (1.00 g, 3.87 mmol) was dissolved in dichloromethane followed by addition of triphenylphosphine (1.83 g, 6.98 mmol) and carbon tetrabromide (2.13 g, 6.42 mmol). This mixture was stirred under nitrogen overnight. Concentration and column chromatography on silica (20% -50% ethylacetate/hexanes) gave a solid which was dried to afforded 0.42 g (39% yield) of intennediate 2. $^1$H NMR (400 MHz, CDCl$_3$): δ 8.60 (s, 1H), 7.45 (m, 5H), 4.60 (d, 2H), 3.05(d, 3H); MS (EI) for $C_{13}H_{13}BrN_4O$: 323.20 (M+2).

3-Amino-6-(3-{[5-methyl-pyrazine-2-ylmethyl)-amino]-methyl}-phenyl)-pyrazine-2-carboxylic acid methylamide: Intermediate 2 (31.0 mg, 1.12 mmol) was dissolved into acetonitrile (0.5 M solution) followed by addition of DIPEA (1.344 mmoL) and C-(5-methyl-pyrazin-2-yl)-methylanine (28.0 mg, 2.27 mmoL) and was stirred overnight at RT. This reaction was poured into water and brine mixture and extracted with ethylacetate (3×20 mL). The combined organic layer was dried over anhydrous sodium sulfate. Filteration, concentration and purified by MPLC and dried to give a yellow powder. $^1$H NMR (400 MHz, d6-DMSO): δ 8.80 (s, 1H), 8.45 (s, 2H), 8.10 (s, 1H), 7.98 (m, 1H), 7.40 (m, 1H), 7.38 (m, 1H), 3.98 (s, 2H), 3.96 (s, 2H), 3.00 (s, 3H), 2.50 (s, 3H); MS (EI) for $C_{19}H_{21}N_7O$: 364.47 (MH+).

Using the same or analogous synthetic techniques and/or substituting with alternative reagents {respective corresponding amines, etc.}, the following compounds of the invention were prepared.

3-amino-6-(3-{[(biphenyl-4-ylmethyl)amino]methyl}phenyl)-N-methylpyrazine-2-carboxamide: $^1$H NMR (400 MHz, d6-DMSO): δ 8.90 (m, 2H), 8.00 (m, 2H), 7.60 (m, 4H), 7.40 (m, 8H), 3.80 (d, 4H), 2.80 (m, 3H); MS (EI) for $C_{26}H_{25}NO_5$: 424.21 (MH+).

3-amino-6-(3-{[(biphenyl-2-ylmethyl)amino]methyl}phenyl)-N-methylpyrazine-2-carboxamide: $^1$H NMR (400 MHz, d4-MeOH): δ 8.60 (s, 1H), 7.80 (m, 2H), 7.35 (m, 1H), 3.75 (s, 2H), 3.65 (s, 2H), 3.30 (d, 3H); MS (EI) for $C_{26}H_{25}NO_5$: 424.48 (MH+).

3-amino-6-(3-{[(3,4-dihydro-2H-1,4-benzoxazin-6-ylmethyl)amino]methyl}phenyl)-N-methylpyrazine-2-carboxamide: $^1$H NMR (400 MHz, d6-DMSO): δ 8.90 (m, 2H), 8.03 (m, 2H), 7.40 (m, 2H), 6.60 (m, 3H), 5.70 (s, 1H), 4.11 (m, 2H), 3.80 (s, 2H), 3.60 (s, 2H), 3.20 (s, 2H), 2.80 (m, 3H); MS (EI) for $C_{22}H_{24}N_6O_2$: 405.39 (MH+).

3-amino-6-[3-({[(2,4-difluorophenyl)methyl]amino}methyl)phenyl]-N-methylpyrazine-2-carboxamide: $^1$H NMR (400 MHz, d6-DMSO): δ 9.40 (br, 2H), 8.80 (m, 2H), 8.21 (m, 2H), 7.40 (m, 4H), 4.38 (d, 4H), 2.83 (d, 3H); MS (EI) for $C_{20}H_{19}NO_5F_2$: 384.43 (MH+).

3-amino-6-[3-({[(2,5-difluorophenyl)methyl]amino}methyl)phenyl]-N-methylpyrazine-2-carboxamide: 1H NMR (400 MHz, d6-DMSO): δ 9.40 (br, 2H), 8.80 (m, 2H), 8.21 (m, 2H), 7.40 (m, 4H), 4.38 (d, 4H), 2.83 (d, 3H); MS (EI) for $C_{20}H_{19}NO_5F_2$: 384.41 (MH+).

3-amino-6-[3-({[(2,3-difluorophenyl)methyl]amino}methyl)phenyl]-N-methylpyrazine-2-carboxamide: $^1$H NMR (400 MHz, d6-DMSO): δ 8.80 (m, 2H), 8.05 (m, 2H), 7.35 (m, 6H), 3.80 (s, 4H), 2.80 (m, 3H); MS (EI) for $C_{20}H_{19}NO_5F_2$; 384.41 (MH+).

3-amino-N-methyl-6-{3-[({[4-(methylsulfonyl)phenyl]methyl}amino)methyl]phenyl}pyrazine-2-carboxamide: $^1$H NMR (400 MHz, d6-DMSO): δ 8.80 (m, 2H), 8.05 (m, 2H), 7.80 (m, 2H), 7.60 (m, 3H), 7.40 (m, 2H), 3.80 (d, 4H), 3.20 (s, 3H), 2.80 (d, 3H); MS (EI) for $C_{21}H_{23}N_5O_3S$: 426.42 (MH+).

3-amino-6-(3-{[(2,2-diphenylethyl)amino]methyl}phenyl)-N-methylpyrazine-2-carboxamide: $^1$H NMR (400 MHz, d6-DMSO): δ 8.80 (m, 2H), 8.05 (m, 2H), 7.60 (m, 2H), 7.22 (m, 11H), 4.20 (m, 1H), 3.80 (s, 4H), 2.80 (d, 3H); MS (EI) for $C_{27}H_{27}NO_5$: 438.48 (MH+).

3-amino-N-methyl-6-{3-[({[3-(phenyloxy)phenyl]methyl}amino)methyl]phenyl}pyrazine-2-carboxamide: $^1$H NMR (400 MHz, d4-MeOH): δ 8.70 (d, 2H), 8.11 (d, 2H), 7.90 (m, 2H), 7.60 (m, 1H), 7.40 (m, 3H), 7.00 (m, 4H), 3.80 (d, 4H), 2.92 (d, 3H); MS (EI) for $C_{26}H_{25}N_5O_2$: 440.47 (MH+).

3-amino-6-[3-({[(4-aminophenyl)methyl]amino]methyl)phenyl]-N-methylpyrazine-2-carboxamide: 1H NMR (400 MHz, d6-DMSO): δ 8.80 (m, 2H), 8.11 (d, 2H), 7.40 (m, 2H), 7.00 (m, 1H), 6.50 (m, 2H), 4.95(s, 2H), 3.80 (s, 2H), 3.60 (s, 2H), 2.80 (d, 3H); MS (EI) for $C_{20}H_{22}N_6O$: 363.44 (MH+).

3-amino-N-methyl-6-{3-[({[4-(phenyloxy)phenyl]methyl}amino)methyl]phenyl}pyrazine-2-carboxamide: $^1$H NMR (400 MHz, d4-MeOH): δ 8.65 (s, 2H), 8.11 (s, 1H), 7.96 (d, 1H), 7.40 (m, 5H), 6.92 (m, 6H), 3.80 (d, 4H), 2.92 (d, 3H); MS (EI) for $C_{26}H_{25}N_5O_2$: 440.47 (MH+).

3-amino-6-{3-[({[2,6-bis(methyloxy)phenyl]methyl}amino)methyl]pheny;}-N-methylpyrazine-2-carboxamide: $^1$H NMR (400 MHz, d4-MeOH): δ 8.70 (s, 1H), 8.11 (s, 1H), 7.90 (d, 1H), 7.40 (m, 1H), 7.20 (m, 2H), 6.60 (d, 2H), 3.85 (d, 4H), 3.80 (s, 6H), 2.95 (d, 3H); MS (EI) for $C_{22}H_{25}N_5O_3$: 408.47 (MH+).

3-amino-6-[3-({[(2-fluorophenyl)methyl]amino}methyl)phenyl]-N-methylpyrazine-2-carboxamide: 1H NMR (400 MHz, d4-MeOH): δ 8.70 (s, 1H), 8.11 (s, 1H), 7.90 (d, 1H), 7.40 (m, 6H), 3.85 (d, 4H), 2.95 (d, 3H); MS (EI) for $C_{20}H_{20}N_5OF$: 366.45 (MH+).

3-amino-6-(3-{[(2,6-difluorophenyl)methyl]amino}methyl)phenyl]-N-methylpyrazine-2-carboxamide: $^1$H NMR (400 MHz, d6-DMSO): δ 9.80 (s, 2H), 8.90 (m, 2H), 8.40 (s, 1H), 8.20 (s, 1H), 7.50 (m, 2H), 7.20 (m, 2H), 4.30 (d, 4H), 2.80 (d, 3H); MS (EI) for $C_{20}H_{19}N_5OF_2$: 384.42 (MH+).

3-amino-6-(3-{[(2,3-dihydro-1,4-benzodioxin-6-ylmethyl)amino]methyl}phenyl)-N-methylpyrazine-2-carboxamide: 1H NMR (400 MHz, d4-MeOE): δ 8.70 (s, 1H), 8.10 (s, 1H), 7.90 (d, 1H), 7.40 (m, 3H), 6.80 (m, 4H), 4.20 (s, 4H), 3.80 (s, 2H), 3.60 (s, 2H), 3.00 (d, 311); MS (EI) for $C_{22}H_{23}N_5O_3$: 406.49 (MH+).

3-amino-N-methyl-6-[3-({[(2-piperidin-1-ylphenyl)methyl]amino}methyl)phenyl]pyrazine-2-carboxamide: $^1$H NMR (400 MHz, d4-MeOH): δ 8.70 (s, 1H), 8.10 (s, 1H), 7.90 (d, 1H), 7.40 (m, 6H), 3.80 (d, 4H), 2.99 (d, 3H), 2.80 (d, 4H), 1.60 (m, 6H); MS (EI) for $C_{25}H_{30}N_6O$: 431.50 (MH+).

3-amino-6-[3-({[(2,5-dichlorophenyl)methyl]amino}methyl)phenyl]-N-methylpyrazine-2-carboxamide: $^1$H NMR (400 MHz, d6-DMSO): δ 8.90 (m, 2H), 8.10 (m, 2H), 7.40 (m, 6H), 3.80 (d, 4H), 2.80 (d, 3H); MS (EI) for $C_{20}H_{19}N_5OCl_2$: 416.29 (M+).

3-amino-6-[3-({[(3,5-dichlorophenyl)methyl]amino}methyl)phenyl]-N-methylpyrazine-2-carboxamide: $^1$H NMR (400 MHz, d6-DMSO): δ 8.90 (m, 2H), 8.10 (m, 2H), 7.40 (m, 6H), 3.80 (d, 4H), 2.80 (d, 3H); MS (EI) for $C_{20}H_{19}N_5OCl_2$: 416.32 (M+).

3-amino-6-{3-[(2,3-dihydro-1H-inden-2-ylamino)methyl]phenyl}-N-methylpyrazine-2-carboxamide: 1H NMR (400 MHz, d4-MeOH): δ 8.70 (s, 1H), 8.10 (s, 1H), 7.90 (d, 1H), 7.40 (m, 2H), 7.10 (m, 4H), 3.90 (s, 2H), 3.60 (m, 1H), 3.20 (m, 2H), 3.00 (s, 3H), 2.80 (m, 2H); MS (EI) for $C_{22}H_{23}N_5O$: 374.42 (MH+).

3-amino-6-[3-(1,3-dihydro-2H-isoindol-2-ylmethyl)phenyl]-N-methylpyrazine-2-carboxamide: $^1$H NMR (400 MHz, d6-DMSO): δ 8.80 (m, 2H), 8.10 (m, 2H), 7.40 (m, 2H), 7.20 (m, 4H), 3.98 (s, 2H), 3.82 (s, 4H), 2.80 (d, 3H); MS (EI) for $C_{21}H_{21}N_5O$: 360.45 (MH$^+$).

3-amino-6-(3-{[(1R)-2,3-dihydro-1H-inden-1-ylamino]methyl}phenyl)-N-methylpyrazine-2-carboxamide: $^1$H NMR (400 MHz, d6-DMSO): δ 8.70 (s, 1H), 8.10 (s, 1H), 7.90 (d, 1H), 7.40 (m, 3H), 7.10 (m, 3H), 4.40 (m, 1H), 3.97 (m, 2H), 3.10 (m, 1H), 3.00 (s, 3H), 2.94 (m, 1H), 2.40 (m, 1H), 2.00 (m, 1H); MS (EI) for $C_{22}H_{23}N_5O$: 374.45 (MH$^+$).

3-amino-6-(3-{[(1S)-2,3-dihydro-1H-inden-1-ylamino]methyl}phenyl)-N-methylpyrazine-2-carboxamide: $^1$H NMR (400 MHz, d6-DMSO): δ 8.70 (s, 1H), 8.10 (s, 1H), 7.90 (d, 1H), 7.40 (m, 3H), 7.10 (m, 3H), 4.40 (m, 1H), 3.97 (m, 2H), 3.10 (m, 1H), 3.00 (s, 3H), 2.94 (m, 1H), 2.40 (m, 1H), 2.00 (m, 1H); MS (EI) for $C_{22}H_{23}N_5O$: 374.46 (MH$^+$).

3-amino-N-methyl-6-[3-({[(3,4,5-trifluorophenyl)methyl]amino}methyl)phenyl]pyrazine-2-carboxamide: $^1$H NMR (400 MHz, d4-MeOH): δ 8.70 (s, 1H), 8.10 (s, 1H), 7.90 (d, 1H), 7.40 (m, 1H), 7.30 (m, 1H), 7.08 (m, 2H), 4.40 (m, 1H), 3.80 (d, 4H), 3.00 (s, 3H); MS (EI) for $C_{20}H_{18}N_{5}OF_{3}$: 402.40 (MH$^+$).

3-amino-N-methyl-6-[3-({[(1R)-1-phenylethyl]amino}methyl)phenyl]pyrazine-2-carboxamide: $^1$H NMR (400 MHz, d4-MeOH): δ 8.70 (s, 1H), 8.00 (s, 1H), 7.90 (d, 1H), 7.40 (m, 6H), 3.80 (m, 1H), 3.60 (m, 2H), 3.00 (s, 3H), 1.40 (d, 3H); MS (EI) for $C_{21}H_{23}N_5O$: 362.44 (MH$^+$).

3-amino-6-[3-({[(1R,2S)-2-hydroxy-2,3-dihydro-1H-inden-1-yl]amino]methyl)phenyl]-N-methylpyrazine-2-carboxamide: $^1$H NMR (400 MHz, d6-DMSO): δ 8.90 (m, 2H), 8.20 (s, 1H), 8.02 (d, 1H), 7.50 (m, 4H), 7.20 (m, 3H), 4.80 (br, 1H), 4.40 (m, 1H), 4.00 (m, 3H), 2.95 (m, 5H); MS (EI) for $C_{22}H_{23}N_5O_2$: 390.28 (MH$^+$).

3-amino-N-methyl-6-{3-[({[4-(2-thienyl)phenyl]methyl}amino)methyl]phenyl}pyrazine-2-carboxamide: $^1$H NMR (400 MHz, d4-MeOH): δ 8.90 (s, 1H), 8.15 (s, 1H), 7.90 (d, 1H), 7.60 (m, 2H), 7.40 (m, 6H), 7.10 (m, 1H), 3.80 (m, 4H), 3.00 (s, 3H); MS (EI) for $C_{24}H_{23}N_5OS$: 430.42 (MH$^{30}$).

3-amino-N-methyl-6-(3-[({[3-(1,2,3-thiadiazol-4-yl)phenyl]methyl}amino)methyl]phenyl}pyrazine-2-carboxamide: $^1$H NMR (400 MHz, d6-DMSO): δ 9.60 (s, 1H), 8.80 (m, 2H), 8.15 (m, 4H), 7.40 (m, 5H), 4.00 (s, 1), 3.80 (s, 3H), 2.80 (d, 3H); MS (EI) for $C_{22}H_{21}N_7OS$: 432.42 (MH$^+$).

3-amino-6-[3-({[(4-chloro-2-fluorophenyl)methyl]amino}methyl)phenyl]methylpyrazine-2-carboxamide: $^1$H NMR (400 MHz, d4-MeOH): δ 8.70 (s, 1H), 8.10 (s, 1H), 7.90 (m, 1H), 7.40 (m, 5H), 3.80 (d,4H), 2.95 (s, 3H); MS (EI) for $C_{20}H_{19}N_5OFCl$: 400.41 (Mh$^+$).

3-amino-N-methyl-6-{3-[({[3-(trifluoromethyl)phenyl]methyl}amino)methyl]phenyl}pyrazine-2-carboxamide: $^1$H NMR (400 MHz, d4-MeOH): δ 8.70 (s, 1H), 8.10 (s, 1H), 7.90 (m, 1H), 7.40 (m, 6H), 3.80 (d, 4H), 2.95 (s, 3H); MS (EI) for $C_{21}H_{20}N_5OF_3$: 416.44 (MH$^+$).

3-amino-N-methyl-6-[3-({[(1S)-1-phenylethyl]amino}methyl)phenyl]pyrazine-2-carboxamide: $^1$H NMR (400 MHz, d4-MeOH): δ 8.70 (s, 1H), 8.00 (s, 1H), 7.90 (d, 1H), 7.40 (m, 6H), 3.80 (m, 1H), 3.60 (m, 2H), 3.00 (s, 3H), 1.40 (d, 3H); MS (EI) for $C_{21}H_{23}N_5O$: 362.49 (MH$^+$).

3-amino-6-(3-{[[(1R)-2-hydroxy-1-phenylethyl]amino}methyl)phenyl]-N-methylpyrazine-2-carboxamide: $^1$H NMR (400 MHz, d4-MeOH): δ 8.70 (s, 1H), 8.00 (s, 1H), 7.90 (d, 1H), 7.40 (m, 7H), 3.80 (m, 3H), 3.60 (m, 3H), 3.00 (s, 3H); MS (EI) for $C_{21}H_{23}N_5O_2$: 378.48 (MH$^+$).

methyl (2S)-{[(3-{5-amino-6-[(methylamino)carbonyl]pyrazin-2-yl}phenyl)methyl]amino}(phenyl)ethanoate: $^1$H NMR (400 MHz, d4-MeOH): δ 8.70 (s, 1H), 8.00 (s, 1H), 7.90 (d, 1H), 7.40 (m, 7H), 3.80 (m, 6H), 3.00 (s, 3H); MS (EI) for $C_{22}H_{23}N_5O_3$: 406.49 (MH$^+$).

3-amino-N-methyl-6-[3-({[1-(phenylmethyl)pyrrolidin-3-yl]amino}methyl)phenyl]pyrazine-2-carboxamide: $^1$H NMR (400 MHz, d4-MeOH): δ 8.60 (s, 1H), 8.10 (s, 1H), 7.90 (d, 1H), 7.38 (m, 9H), 3.80 (d, 2H), 3.60 (s, 2H), 3.40 (m, 1H), 2.90 (s, 3H), 2.82 (m, 1H), 2.60 (m, 2H), 2.40 (m, 1H), 2.18 (m, 1H), 1.70 (m, 1H); MS (EI) for $C_{24}H_{28}N_6O$: 417.47 (MH$^+$).

3-amino-6-(3-{[ethyl(phenylmethyl)amino]methyl}phenyl)-N-methylpyrazine-2-carboxamide: $^1$H NMR (400 MHz, d4-MeOH): δ 8.60 (s, 1H), 7.90 (d, 1H), 7.82 (m, 1H), 7.30 (m, 8H), 3.61(d, 2H), 3.59 (d, 2H), 2.90 (s, 3H), 2.50 (q, 2H), 1.10 (t, 3H); MS (EI) for $C_{22}H_{25}N_5O$: 376.44 (MH$^+$).

3-amino-N-methyl-6-(3-({[(2S)-2-phenylcyclopropyl]amino}methyl)phenyl]pyrazine-2-carboxamide: 1H NMR (400 MHz, d4-MeOH): δ 8.60 (s, 1H), 7.99 (s, 1H), 7.85 (d, 1H), 7.40 (m, 2H), 7.15 (m, 5H), 6.90 (m, 2H), 3.90 (s, 2H), 2.90 (d, 3H), 2.38 (m, 1H), 1.85 (m, 1H), 1.10 (m, 1H), 1.00 (m, 1H); MS (EI) for $C_{22}H_{23}N_5O$: 374.43 (MH$^+$).

3-amino-N-methyl-6-(3-{[(1-methyl-1-phenylethyl)amino]methyl}phenyl) pyrazine-2-carboxamide: $^1$H NMR (400 MHz, d4-MeOH): δ 8.61 (s, 1H), 7.99 (s, 1H), 7.85 (d, 1H), 7.60 (m, 2H), 7.40 (m, 7H), 3.42 (s, 2H), 3.00 (s, 3H), 1.60 (s, 6H); MS (EI) for $C_{22}H_{25}N_5O$: 376.42 (MH$^+$).

3-amino-6-{3-[(9H-fluoren-9-ylamino)methyl]phenyl}-N-methylpyrazine-2-carboxamide: $^1$H NMR (400 MHz, d4-MeOH): δ 8.61 (s, 1H), 7.99 (s, 1H), 7.85 (d, 1H), 7.70 (m, 5H), 7.40 (m, 7H), 7.20 (d, 1H), 3.41 (s, 2H), 3.00 (s, 3H); MS (EI) for $C_{26}H_{23}N_5O$: 422.39 (MH$^+$).

3-amino-6-[3-({[(1S,2R)-2-hydroxy-2,3-dihydro-1H-inden-1-yl]amino}methyl)phenyl]-N-methylpyrazine-2-carboxamide: 1H NMR (400 MHz, d4-MeOH): δ 8.70 (s, 1H), 8.15 (s, 1H), 7.90 (d, 1H), 7.42 (m, 4H), 7.20 (m, 4H), 4.20 (m, 2H), 3.40 (s, 3H), 3.10 (m, 1H), 2.95 (m, 1H); MS (EI) for $C_{22}H_{23}N_5O_2$: 390.25 (MH$^+$).

3-amino-6-(3-{[(5-bromo-2,3-dihydro-1H-inden-2-yl)amino]methyl}phenyl)-N-methylpyrazine-2-carboxamide: 1H NMR (400 MHz, d4-MeOH): δ 8.70 (s, 1H), 8.15 (s, 1H), 7.90 (d, 1H), 7.42 (m, 7H), 3.85 (s, 2H), 3.61 (m, 1H), 3.20 (m, 2H), 2.95 (s, 3H), 2.80 (m, 2H); MS (EI) for $C_{22}H_{22}N_5OBr$: 452.10 (M+2).

3-amino-N-methyl-6-[3-({[(1S,2R)-2-(methyloxy)-2,3-dihydro-1H-inden-1-yl]amino}methyl)phenyl]pyrazine-2-carboxamide: $^1$H NMR (400 MHz, d4-MeOH): δ 8.70 (s, 1H), 8.15 (s, 1H), 7.90 (d, 1H), 7.42 (m, 4H), 7.20 (m, 4H), 4.20 (m, 2H), 3.40 (s, 3H), 3.40 (s, 3H), 3.10 (m, 1H), 3.00 (s, 3H), 2.95 (m, 1H); MS (EI) for $C_{23}H_{25}N_5O_2$: 404.27 (MH$^+$).

3-amino-6-(3-{[(5-fluoro-2,3-dihydro-1H-inden-1-yl)amino]methyl}phenyl)-N-methylpyrazine-2-carboxamide: 1H NMR (400 MHz, d4-MeOH): δ 8.70 (s, 1H), 8.15 (s, 1H), 7.90 (d, 1H), 7.42 (m, 4H), 7.10 (m, 3H), 4.40 (s, 2H), 3.40 (m, 2H), 3.10 (m, 1H), 2.75 (m, 1H), 2.40 (m, 1H); MS (EI) for $C_{22}H_{22}N_5OF$: 392.27 (MH$^+$).

3-amino-6-(3-({[(2S)-5-bromo-2,3-dihydro-1H-inden-2-yl]amino}methyl)phenyl]-N-methylpyrazine-2-carboxamide: $^1$H NMR (400 MHz, d6-DMSO): δ 8.80 (m, 2H), 8.15 (m, 2H), 7.35 (m, 6H), 3.80 (s, 2H), 3.58 (m, 1H), 3.16 (m, 2H), 2.82 (m, 3H), 2.70 (m, 2H); MS (EI) for $C_{22}H_{22}N_5OBr$: 454.14 (M+2).

3-amino-N-methyl-6-[3-({[(1R,2S)-2-(methyloxy)-2,3-dihydro-1H-inden-1-yl]amino}methyl)phenyl]pyrazine-2-carboxamide: $^1$H NMR (400 MHz, d4-MeOH): δ 8.70 (s, 1H), 8.15 (s, 1H), 7.90 (d, 1H), 7.42 (m, 4H), 7.20 (m, 4H), 4.20 (m, 2H), 3.40 (s, 3H), 3.10 (m, 1H), 3.00 (s, 3H), 2.95 (m, 1H); MS (EI) for $C_{23}H_{25}N_5O_2$: 404.27 (MH$^+$).

3-amino-N-methyl-6-(3-{[(3-oxo-2,3-dihydro-1H-inden-1-yl)amino]methyl}phenyl)pyrazine-2-carboxamide $^1$H NMR (400 MHz, d4-MeOH): δ 8.70 (s, 1H), 8.15 (s, 1H), 7.90 (d, 1H), 7.42 (m, 4H), 7.20 (m, 4H), 4.50 (m, 1H), 3.90 (s, 2H), 3.40 (m, 1H), 3.02 (m, 1H), 3.00 (s, 3H), 2.60 (m, 1H); MS (EI) for $C_{22}H_{21}N_5O_2$: 388.19 (MH$^+$).

3-amino-6-[3-({[(1S)-4-fluoro-2,3-dihydro-1H-inden-1-yl]amino}methyl)phenyl]-N-methylpyrazine-2-carboxamide $^1$H NMR (400 MHz, d4-MeOH): δ 8.64 (s, 1H), 8.10 (s, 1H), 7.85 (d, 1H), 7.40 (m, 3H), 7.20 (m, 3H), 6.90 (t, 1H), 4.40 (m, 1H), 3.90 (s, 2H), 3.10 (m, 1H), 2.98 (s, 3H), 2.80 (m, 1H), 2.42 (m, 1H), 2.10 (m, 1H); MS (ED) for $C_{22}H_{21}N_5OF$: 392.16 (MH$^+$).

3-amino-6-[3-({[(1S)-5,7-difluoro-2,3-dihydro-1H-inden-1-yl]amino}methyl)phenyl]-N-methylpyrazine-2-carboxamide: $^1$H NMR (400 MHz, d4-MeOH): δ 8.64 (s, 1H), 8.10 (s, 1H), 7.85 (d, 1H), 7.40 (m, 3H), 7.20 (m, 2H), 4.50 (m, 1H), 3.90 (m, 2H), 3.20 (m, 1H), 3.00 (s, 3H), 2.85 (m, 1H), 2.42 (m, 1H), 2.15 (m, 1H); MS (EI) for $C_{22}H_{21}N_5OF_2$: 410.20 (MH$^+$).

3-amino-N-methyl-6-[3-({[(1S)-5-(2-thienyl)-2,3-dihydro-1H-inden-1-yl]amino}methyl)phenyl]pyrazine-2-carboxamide: $^1$H NMR (400 MHz, d4-MeOH): δ 8.70 (s, 1H), 8.17 (s, 1H), 7.92 (d, 1H), 7.40 (m, 9H), 7.05 (m, 1H), 4.38 (m, 1H), 3.90 (m, 2H), 3.18 (m, 1H), 3.00 (s, 3H), 2.85 (m, 1H), 2.42 (m, 1H), 2.15 (m, 1H); MS (EI) for $C_{26}H_{25}N_5OS$: 456.14 (MH$^+$).

3-amino-6-(3-{[(4-bromo-2,3-dihydro-1H-inden-1-yl)amino]methyl}phenyl)-N-methylpyrazine-2-carboxamide: $^1$H NMR (400 MHz, d4-MeOH): δ 8.70 (s, 1H), 8.17 (s, 1H), 7.92 (d, 1H), 7.40 (m, 6H), 7.16 (m, 1H), 4.42 (m, 1H), 3.90 (m, 2H), 3.15 (m, 1H), 3.00 (s, 3H), 2.82 (m, 1H), 2.42 (m, 1H), 2.02 (m, 1H); MS (EI) for $C_{22}H_{22}N_5OBr$: 454.01 (M+2).

3-amino-N-methyl-6-(3-{[(4-phenyl-2,3-dihydro-1H-inden-1-yl)amino]methyl}phenyl)pyrazine-2-carboxamide: $^1$H NMR (400 MHz, d4-MeOH): δ 8.70 (s, 1H), 8.17 (s, 1H), 7.92 (d, 1H), 7.40 (m, 9H), 7.05 (m, 3H), 4.38 (m, 1H), 3.90 (m, 2H), 3.18 (m, 1H), 3.00 (s, 3H), 2.85 (m, 1H), 2.42 (m, 1H), 2.15 (m, 1H); MS (EI) for $C_{28}H_{27}N_5O$: 450.20 (MH$^+$).

3-amino-N-methyl-6-[3-({[4-(2-thienyl)-2,3-dihydro-1H-inden-1-yl]amino}methyl)phenyl]pyrazine-2-carboxamide: $^1$H NMR (400 MHz, d4-MeOH): δ 8.70 (s, 1H), 8.17 (s, 1H), 7.92 (d, 1H), 7.42 (m, 7H), 7.27 (m, 2H), 7.11 (m, 1H), 4.38 (m, 1H), 3.90 (m, 2H), 3.30 (m, 1H), 3.00 (m, 1H), 2.95 (s, 3H), 2.42 (m, 1H), 2.12 (m, 1H); MS (EI) for $C_{26}H_{25}N_5OS$: 456.15 (MH$^+$).

3-amino-N-methyl-6-[3-({[(2R)-6-phenyl-1,2,3,4-tetrahydronaphthalen-2-yl]amino}methyl)phenyl]pyrazine-2-carboxamide: $^1$H NMR (400 MHz, d4-MeOH): δ 8.70 (s, 1H), 8.17 (s, 1H), 7.92 (d, 1H), 7.60 (m, 2H), 7.30 (m, 10H), 4.70 (m, 1H), 4.00 (m, 2H), 3.18 (m, 1H), 3.11 (m, 1H), 2.99 (s, 3H), 2.85 (m, 1H), 2.70 (m, 1H), 2.12 (m, 1H), 1.70 (m, 1H); MS (EI) for $C_{29}H_{29}N_5O$: 464.21 (MH$^+$).

3-amino-N-methyl-6-{3-[({5-[(2-morpholin-4-ylethyl)oxy]-2,3-dihydro-1H-inden-1-yl}amino)methyl]phenyl}pyrazine-2-carboxamide: $^1$H NMR (400 MHz, d4-MeOH): δ 8.70 (s, 1H), 8.17 (s, 1H), 7.92 (d, 1H), 7.40 (m, 5H), 6.80 (m, 2H), 4.35 (m, 1H), 4.10 (m, 2H), 3.90 (m, 2H), 3.70 (m, 4H), 3.10 (m, 1H), 3.00 (s, 3H), 2.85 (m, 1H), 2.83 (m, 2H), 2.60 (m, 4H), 2.40 (m, 1H), 2.05 (m, 1H); MS (EI) for $C_{28}H_{34}N_6O_3$: 503.17 (MH$^+$).

3-amino-6-{3-[({5-[(cyanomethyl)oxy]-2,3-dihydro-1H-inden-1-yl}amino)methyl]phenyl}-N-methylpyrazine-2-carboxamide: 1H NMR (400 MHz, d4-MeOH): δ 8.70 (s, 1H), 8.17 (s, 1H), 7.92 (d, 1H), 7.40 (m, 5H), 6.90 (m, 2H), 4.95 (s, 2H), 4.35 (m, 1H), 3.90 (m, 2H), 3.10 (m, 1H), 3.00 (s, 3H), 2.85 (m, 1H), 2.40 (m, 1H), 2.05 (m, 1H); MS (EI) for $C_{24}H_{24}N_6O_2$: 429.17 (MH$^+$).

3-amino-N-methyl-6-[3-({[5-(1H-1,2,4-triazol-1-yl)-2,3-dihydro-1H-inden-1-yl]amino}methyl)phenyl]pyrazine-2-carboxamide: 1H NMR (400 MHz, d4-MeOH): δ 9.10 (s, 1H), 8.70 (s, 1H), 8.17 (s, 2H), 7.90 (d, 1H), 7.60 (m, 4), 7.40 (m, 3H), 4.40 (m, 1H), 3.95 (m, 2H), 3.16 (m, 1H), 3.00 (s, 3H), 2.92 (m, 1H), 2.50 (m, 1H), 2.03 (m, 1H); MS (EI) for $C_{24}H_{24}N_8O$: 441.17 (MH$^+$).

3-amino-6-(3-{[(4-hydroxy-2,3-dihydro-1H-inden-1-yl)amino]methyl}phenyl)-N-methylpyrazine-2-carboxamide: 1H NMR (400 MHz, d4-MeOH): δ 8.70 (s, 1H), 8.17 (s, 1H), 7.92 (d, 1H), 7.40 (m, 2H), 7.20 (m, 2H), 6.65 (m, 3H), 4.40 (br, OH, 1H), 4.21 (m, 1H), 3.90 (m, 2H), 3.10 (m, 1H), 3.00 (s, 3H), 2.85 (m, 1H), 2.40 (m, 1H), 2.05 (m, 1H); MS (EI) for $C_{22}H_{23}N_5O_2$: 390.16 (MH$^+$).

3-amino-N-methyl-6-{3-[({4-[(2-morpholin-4-ylethyl)oxy]-2,3-dihydro-1H-inden-1-yl}amino)methyl]phenyl}pyrazine-2-carboxamide: $^1$H NMR (400 MHz, d4-MeOH): δ 8.70 (s, 1H), 8.17 (s, 1H), 7.92 (d, 1H), 7.40 (m, 4H), 7.20 (m, 1H), 7.00 (m, 1H), 6.80 (m, 1H), 4.35 (m, 1H), 4.10 (m, 2H), 3.90 (m, 2H), 3.70 (m, 4H), 3.10 (m, 1H), 3.00 (s, 3H), 2.85 (m, 1H), 2.83 (m, 2H), 2.60 (m, 4H), 2.40 (m, 1H), 2.05 (m, 1H); MS (EI) for $C_{28}H_{34}N_6O_3$: 503.20 (MH$^+$).

3-amino-6-(3-{[(4-hydroxy-2,3-dihydro-1H-inden-1-yl)amino]methyl}phenyl)-N-methylpyrazine-2-carboxamide: $^1$H NMR (400 MHz, d4-MeOH): δ 8.70 (s, 1H), 8.17 (s, 1H), 7.92 (d, 1H), 7.42 (m, 4H), 7.10 (m, 1H), 6.95 (m, 1H), 6.61(m, 1H), 4.31 (m, 1H), 3.90 (m, 2H), 3.10 (m, 1H), 3.00 (s, 3H), 2.76 (m, 1H), 2.40 (m, 1H), 2.05 (m, 1H); MS (EI) for $C_{22}H_{23}N_5O_2$: 390.16 (MH$^+$).

3-amino-6-[3-(1H-imidazol-1-ylmethyl)phenyl]-N-methylpyrazine-2-carboxamide: $^1$H NMR (400 MHz, d$_6$-DMSO): δ 8.81 (s, 1H), 8.76 (m, 1H), 8.10 (m, 2H), 7.80 (s, 1H), 7.66 (br s, 2H), 7.41 (t, 1H), 7.24 (s, 1H), 7.17 (d, 1H), 6.89 (s, 1H), 5.24 (s, 2H), 2.86 (d, 3H); MS (EI) for $C_{16}H_{16}N_6O$: 309.2 (MH$^+$).

Example 53

Scheme 18 shows how alcohols were converted to amines to make compounds according to formula I. In this example, alcohol (lxxxi) is converted to the corresponding azide (lxxxii), which was reduced to the corresponding amine (lxxxiii). Amines (lxxxiii) were, for example, acylated, subjected to reductive amination, and the like to make compounds according to formula I.

Scheme 18

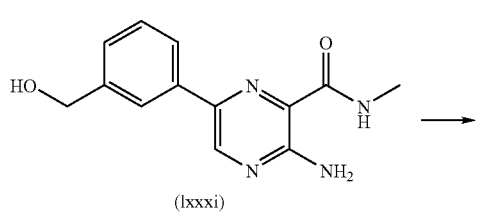

(lxxxi)

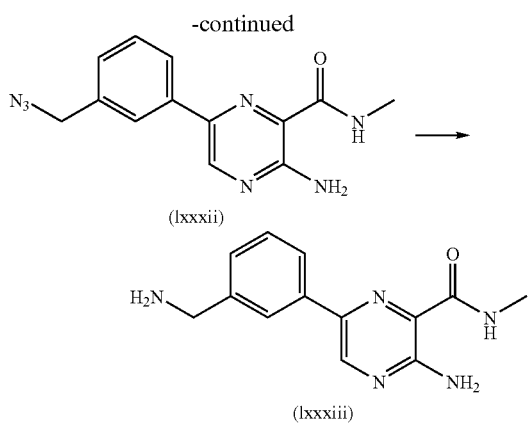

(lxxxii)

(lxxxiii)

3-Amino-6-[3-(aminomethyl)phenyl]-N-methylpyrazine-2-carboxamide

3-Amino-6-(3-hydroxymethyl-phenyl)-pyrazine-2-carboxylic acid methylamide (1.00 g, 3.87 mmol) was dissolved in THF (20 mL) followed by the addition of diphenylphosphoryl azide (0.63 mL, 5.42 mmol) and DBU (0.43 mL, 5.42 mmol). It was stirred at room temperature overnight. The reaction mixture was poured into water (100 mL), and extracted with ethyl acetate (2×50 mL) then dried over anhydrous sodium sulfate and filteration, concentration and purified by column chromatography (50% Ethylacetae/bexanes) to give 3-amino-6-(3-azidomethyl-phenyl)-pyrazine-2-carboxylic acid methylamide, 728 mg (66.4% yield): MS (EI) for $C_{13}H_{13}N_7O_0$: 284.12 (MH$^+$).

3-Amino-6-(3-azidomethyl-phenyl)-pyrazine-2-carboxylic acid methylamide was dissolved in the mixture of THF (15 mL) and H$_2$O (1.5 mL) followed by the addition of triphenylphosphine (1.07 g, 4.03 mmol) and it was stirred at room temperature overnight. The reaction mixture was poured into water (100 mL), and extracted with ethyl acetate (2×50 mL) then dried over anhydrous sodium sulfate and filtered, concentrated and purified by column chromatography (50% Ethylacetae/hexanes) to give 3-amino-6-(3-aminomethyl-phenyl)-pyrazine-2-carboxylic acid methylamide, 564 mg (85.0% yield): MS (EI) for $C_{13}H_{15}N_5O$: 258.13 (MH$^+$).

3-Amino-N-methyl-6-(3-{[(phenylcarbonyl)amino]methyl}phenyl)pyrazine-2-carboxamide 3-Amino-6-(3-aminomethyl-phenyl)-pyrazine-2-carboxylic acid methylamide (10.0 mg, 0.04 mmol) was dissolved in acetonitrile (2 mL) followed by the addition of TEA (11.2 μl, 0.08 mmol) and benzoyl chloride (3.50 μl, 0.04 mmol). It was stirred at room temperature overnight. The reaction mixture was poured into water (10 mL), and extracted with ethyl acetate (2×10 mL) then dried over anhydrous sodium sulfate and filteration, concentration and purified by column chromatography (50% Ethylacetae/hexanes) to give 3-amino-6-[3-(benzoylaminomethyl)-phenyl]-pyrazine-2-carboxylic acid methylamide, 8.70 mg (85.0% yield): $^1$H NMR (400 MHz, CDCl$_3$): δ 8.60 (s, 1H), 8.00 (br, 1H), 7.80 (m, 4H), 7.52 (m, 4H), 7.20 (s, 1H), 6.50 (br, 1H), 4.80 (m, 2H), 3.00 (d, 3H); MS (EI) for $C_{20}H_{19}N_5O_2$: 362.41 (MH$^+$).

Using the same or analogous synthetic techniques and/or substituting with alternative reagents {respective corresponding amines, etc.}, the following compounds of the invention were prepared.

3-Amino-6-[3-({[(4-chlorophenyl)carbonyl]amino}methyl)phenyl]-N-methylpyrazine-2-carboxamide: $^1$H NMR (400 MHz, CDCl$_3$): δ 8.60 (s, 1H), 8.00 (br, 1H), 7.80 (m, 3H), 7.52 (m, 4H), 7.20 (s, 1H), 6.42 (br, 1H), 4.78 (m, 2H), 3.00 (d, 3H); MS (EI) for $C_{20}H_{18}ClN_5O_2$: 396.36 (MH$^+$).

3-Amino-6-[3-({[(2,5-difluorophenyl)carbonyl]amino}methyl)phenyl]-N-methylpyrazine-2-carboxamide: $^1$H NMR (400 MHz, d6-DMSO): δ 9.10 (br, 1H), 8.80 (s, 1H), 8.20 (m,2H), 7.40 (m, 5H), 4.60 (m, 2H), 2.80 (d, 3H); MS (EI) for $C_{20}H_{17}F_2N_5O_2$: 398.43 (MH$^+$).

3-amino-N-methyl-6-(3-{[(naphthalen-2-ylcarbonyl)amino]methyl}phenyl)pyrazine-2-carboxamide: $^1$H NMR (400 MHz, d6-DMSO): δ 9.30 (br, 1H), 8.82 (s, 1H), 8.80 (br, 1H), 8.50 (s, 1H), 8.00 (m, 5H), 7.60 (m, 2H), 7.40 (m, 2H), 4.60 (m, 2H), 2.80 (d, 3H); MS (EI) for $C_{24}H_{21}N_5O_2$: 412.27 (MH$^+$).

3-amino-6-{3-[({[3,4-dichlorophenyl]carbonyl}amino)methyl]phenyl}-N-methylpyrazine-2-carboxamide: $^1$H NMR (400 MHz, d6-DMSO): δ 9.40 (br, 1H), 8.82 (s, 1H), 8.80 (br, 1H), 8.20 (s, 1H), 8.10 (m, 2H), 7.90 (d, 1H), 7.80 (d, 1H), 7.40 (m, 1H), 7.38 (m, 1H), 4.60 (m, 2H), 2.80 (d, 3H); MS (EI) for $C_{20}H_{17}Cl_2N_5O_2$: 430.36 (MH$^+$).

3-amino-N-methyl-6-(3-{[(phenylacetyl)amino]methyl}phenyl)pyrazine-2-carboxamide: $^1$H NMR (400 MHz, d6-DMSO): δ 8.80 (m, 2H), 8.71 (t, 1H), 8.01 (m, 3H), 7.40 (m, 1H), 7.22 (m,1H), 7.18 (m, 3H), 6.90 (m, 2H), 4.60 (d, 2H), 4.40 (d, 2H), 2.80 (d, 3H); MS (EI) for $C_{21}H_{21}N_5O_2$: 376.46 (MH$^+$).

3-amino-6-{3-({[(4-chlorophenyl)acetyl]amino}methyl)phenyl}-N-methylpyrazine-2-carboxamide: $^1$H NMR (400 MHz, d6-DMSO): δ 8.80 (m, 2H), 8.71 (t, 1H), 8.01 (m, 2H), 7.40 (m, 1H), 7.22 (m,1H), 7.18 (m, 3H), 6.90 (m, 2H), 4.60 (d, 2H), 4.40 (d, 2H), 2.80 (d, 3H); MS (ED) for $C_{21}H_{20}ClN_5O_2$: 410.45 (MH$^+$).

3-amino-6-(3-{[(biphenyl-4-ylcarbonyl)amino]methyl}phenyl)-N-methylpyrazine-2-carboxamide: $^1$H NMR (400 MHz, CDCl$_3$): δ 8.60 (s, 1H), 7.98 (br, 1H), 7.85 (m, 3H), 7.70 (m, 1H), 7.60 (m,4H), 7.40 (m, 3H), 7.22(s, 2H), 6.50 (br, 1H), 4.80 (d, 2H), 3.00 (d, 3H); MS (EI) for $C_{26}H_{23}N_5O_2$: 438.51 (MH$^+$).

3-amino-6-{3-[({[2-chloro-5-(trifluoromethyl)phenyl]carbonyl}amino)methyl]phenyl}-N-methylpyrazine-2-carboxamide: $^1$H NMR (400 MHz, CDCl$_3$): δ 8.60 (s, 1H), 7.80 (m, 3H), 7.40 (m, 3H), 7.22(s, 2H), 6.60 (br, 1H), 4.80 (d, 2H), 3.00 (d, 3H); MS (EI) for $C_{21}H_{17}ClF_3N_5O_2$: 464.42 (MH$^+$).

N-[(3-{5-amino-6-[(methylamino)carbonyl]pyrazin-2-yl}phenyl)methyl]-1H-indole-2-carboxamide: $^1$H NMR (400 MHz, d6-DMSO): δ 11.60 (s, 1H), 8.80 (s, 1H), 8.70 (m, 1H), 8.40 (m, 1H), 8.00 (m, 4H), 7.80 (m, 3H), 7.40 (m, 3H), 7.10 (m, 2H), 4.60 (d, 2H), 2.80 (d, 3H); MS (EI) for $C_{22}H_{20}N_6O_2$: 401.48 (MH$^+$).

3-amino-6-[3-({[(3-hydroxypyridin-2-yl)carbonyl]amino}methyl)phenyl]-N-methylpyrazine-2-carboxamide: $^1$H NMR (400 MHz, CDCl$_3$): δ 12.00 (s, 1H), 8.60 (s, 1H), 8.40 (br, 1H), 7.80 (m, 3H), 7.28 (m, 5H), 7.10 (m, 2H), 4.75 (d, 2H), 3.00 (d, 3H), 1.60 (br, 2H); MS (EI) for $C_{19}H_{18}N_6O_3$: 379.46 (MH$^+$).

3-amino-6-(3-({[(1H-indole-3-ylacetyl)amino]methyl}phenyl)-N-methylpyrazine-2-carboxamide: $^1$H NMR (400 MHz, CDCl$_3$): δ 10.85 (s, 1H), 8.80 (m, 1H), 8.40 (m, 1H), 8.00 (m, 2H), 7.50 (d, 2H), 7.40 (m, 3H), 7.00 (m, 2H), 4.40 (d, 2H), 3.60 (s, 3H), 3.40 (s, 2H); MS (EI) for $C_{23}H_{22}N_6O_2$: 414.18 (MH$^+$).

3-amino-N-methyl-6-{3-[({[4-(1-methylethyl)phenyl]methyl}amino)carbonyl]phenyl}pyrazine-2-carboxamide: $^1$H NMR (400 MHz, d6-DMSO): δ 9.12 (br, 1H), 8.90 (s, 1H), 8.80 (br, 1H), 8.50 (s, 1H), 8.38 (d, 1H), 7.80 (d, 1H), 7.50 (t, 1H), 7.20 (m, 4H), 4.50 (d, 2H), 2.80(d, 3H), 1.20(m, 6H), 0.80 (m, 1H); MS (EI) for $C_{23}H_{25}N_5O_2$: 404.52 (MH$^+$).

3-amino-N-methyl-6-(3-{[({[4-(1-methylethyl)phenyl]oxy}acetyl)amino]methyl}phenyl)pyrazine-2-carboxamide: $^1$H NMR (400 MHz, d6-DMSO): δ 8.90 (m, 2H), 8.72 (t, 1H), 8.05 (m, 2H), 7.40 (m, 1H), 7.20 (m, 3H), 6.90 (d, 2H), 4.60 (s, 2H), 4.40(d, 2H), 2.80(d, 3H), 1.20(m, 6H), 0.80 (m, 1H); MS (EI) for $C_{24}H_{27}N_5O_3$: 434.51 (MH$^+$).

3-amino-6-{3-[({[(4-aminophenyl)thio]acetyl}amino)methyl]phenyl}-N-methylpyrazine-2-carboxamide: $^1$H NMR (400 MHz, d6-DMSO): δ 8.90 (m, 2H), 8.70 (t, 1H), 8.00 (m, 2H), 7.40 (m, 1H), 7.18 (m, 3H), 6.50 (d, 2H), 5.20 (s, 2H), 4.40 (d, 2H), 2.80 (d, 3H); MS (EI) for $C_{21}H_{22}N_6O_2S$: 423.44 (MH$^+$).

3-amino-6-[3-({[(4-iodophenyl)carbonyl]amino}methyl)phenyl]-N-methylpyrazine-2-carboxamide: $^1$H NMR (400 MHz, d6-DMSO): δ 9.20 (m, 1H), 8.90 (m, 2H), 8.12 (m, 2H), 7.80 (m, 2H), 7.70 (m, 2H), 7.40 (m, 2H), 4.50 (d, 2H), 2.80 (d, 3H); MS (EI) for $C_{20}H_{18}N_5O_2I$: 488.35 (MH$^+$).

3-amino-N-methyl-6-[3-({[(4-pentylphenyl)carbonyl]amino}methyl)phenyl]pyrazine-2-carboxamide: $^1$H NMR (400 MHz, d6-DMSO): δ 9.00 (m, 1H), 8.90 (m, 2H), 8.12 (m, 2H), 7.80 (m, 2H), 7.40 (m, 4H), 4.60 (d, 2H), 3.40 (d, 3H), 1.60 (m, 2H), 1.20 (m, 5H), 0.80 (m, 4H); MS (EI) for $C_{25}H_{29}N_5O_2$: 432.55 (MH$^+$).

3-amino-6-(3-{[(1,3-benzodioxol-5-ylcarbonyl)amino]methyl}phenyl)-N-methylpyrazine-2-carboxamide: $^1$H NMR (400 MHz, d6-DMSO): δ 8.78 (m, 2H), 8.50 (br, 1H), 8.08 (d, 1H), 7.98 (s, 1H), 7.42 (t, 1H), 7.20 (d, 1H), 6.80 (m, 3H), 4.40 (d, 2H), 2.80 (d, 3H); MS (EI) for $C_{21}H_{19}N_5O_4$: 406.15 (MH$^+$).

3-amino-6-{3-[({[4-(1,1-dimethylethyl)phenyl]methyl}amino)carbonyl]phenyl}-N-methylpyrazine-2-carboxamide: $^1$H NMR (400 MHz, d6-DMSO): δ 9.10 (br, 1H), 8.90 (s, 1H), 8.80 (br, 1H), 8.50 (s, 1H), 8.40 (d, 1H), 7.82 (d, 1H), 7.60 (t, 1H), 7.35 (m, 4H), 4.50 (d, 2H), 2.80 (d, 3H); MS (EI) for $C_{24}H_{27}N_5O_2$: 418.52 (MH$^+$).

3-amino-N-methyl-6-(3-{[({1-[5-(trifluoromethyl)pyrimidin-2-yl]piperidin-4-yl}carbonyl)amino]methyl}phenyl)pyrazine-2-carboxamide: $^1$H NMR (400 MHz, d6-DMSO): δ 8.80 (m, 2H), 8.62 (m, 1H), 8.40 (t, 1H), 8.00 (m, 2H), 7.40 (t, 1H), 7.20 (d, 1H), 7.00 (d, 1H), 4.60 (d, 2H), 4.38 (d, 2H), 2.98 (t, 2H), 2.80 (d, 3H), 1.80 (m, 2H), 1.60 (m, 2H), 1.20 (m, 1H); MS (EI) for $C_{24}H_{25}N_8O_2F_3$: 515.51 (MH$^+$).

3-amino-N-methyl-6-{3-[({[4-(1-methylethyl)phenyl]carbonyl}amino)methyl]phenyl}pyrazine-2-carboxamide: $^1$H NMR (400 MHz, d6-DMSO): δ 9.00 (br, 1H), 8.90 (m, 2H), 8.12 (m, 2H), 7.82 (d, 1H), 7.35 (m, 4H), 4.60 (d, 2H), 2.90 (m, 1H), 2.80 (d, 3H), 1.20 (d, 6H); MS (EI) for $C_{23}H_{25}N_5O_2$: 404.50 (MH$^+$).

3-amino-6-[3-({[(4-butylphenyl)methyl]amino}carbonyl)phenyl]-N-methylpyrazine-2-carboxamide: $^1$H NMR (400 MHz, d6-DMSO): δ 9.10 (br, 1H), 8.90 (m, 2H), 8.50 (s, 1H), 8.40 (d, 1H), 7.82 (d, 1H), 7.60 (m, 1H), 7.20 (m, 4H), 4.60 (d, 2H), 2.80 (d, 3H), 2.60 (m, 2H), 1.60 (m, 2H), 1.32 (m, 2H), 0.90 (m, 3H); MS (EI) for $C_{24}H_{27}N_5O_2$: 418.49 (MH$^+$).

3-amino-N-methyl-6-{3-[({[4-(1,2,3-thiadiazol-4-yl)phenyl]methyl}amino)carbonyl]phenyl}pyrazine-2-carboxamide: $^1$H NMR (400 MHz, d6-DMSO): δ 9.60 (s, 1H), 9.20 (br, 1H), 8.90 (m, 2H), 8.60 (d, 1H), 8.18 (d, 2H), 7.98 (d, 1H), 7.58 (m, 3H), 4.60 (d, 2H), 2.80 (d, 3H); MS (EI) for $C_{22}H_{19}N_7O_2S$: 446.42 (MH$^+$).

3-amino-N-methyl-6-{3-[({[4-(2-thienyl)phenyl]methyl}amino)carbonyl]phenyl}pyrazine-2-carboxamide: $^1$H NMR (400 MHz, d6-DMSO): δ 9.20 (s, 1H), 8.90 (m, 2H), 8.60 (s, 1H), 8.40 (d, 1H), 7.98 (d, 1H), 7.58 (m, 7H), 7.18 (d, 1H), 4.60 (d, 2H), 2.80 (d, 3H); MS (EI) for $C_{24}H_{21}N_5O_2S$: 444.46 (MH$^+$).

3-amino-6-{3-[({[4-(1,1-dimethylethyl)phenyl]carbonyl}amino)methyl]phenyl}-N-methylpyrazine-2-carboxamide: $^1$H NMR (400 MHz, d6-DMSO): δ 9.10 (s, 1H), 8.90 (m, 2H), 8.00 (m, 4H), 7.40 (m, 4H), 4.60 (d, 2H), 2.80 (d, 3H); MS (EI) for $C_{24}H_{27}N_5O_2$: 418.51 (MH$^+$).

3-amino-N-methyl-6-{3-[({[4-(1H-pyrazol-1-yl)phenyl]methyl}amino)carbonyl]phenyl}pyrazine-2-carboxamide: $^1$H NMR (400 MHz, d6-DMSO): δ 9.20 (br, 1H), 8.90 (m, 2H), 8.50 (m, 3H), 7.60 (m, 7H), 6.50 (s, 1H), 4.60 (d, 2H), 2.80 (d, 3H); MS (EI) for $C_{23}H_{21}N_7O_2$: 428.48 (MH$^+$).

Example 54

Scheme 19 depicts a strategy for making exemplary compounds according to formula I where A is an oxazole. Compound (lxxxiv) is protected as the TBS-ether (lxxxv). The ester function of (lxxxv) is reduced to the corresponding alcohol, (lxxxvi), and reoxidized to the corresponding aldehyde, (lxxxvii). Aldehyde (lxxxvii) was converted to oxazole (lxxxviii) as described below.

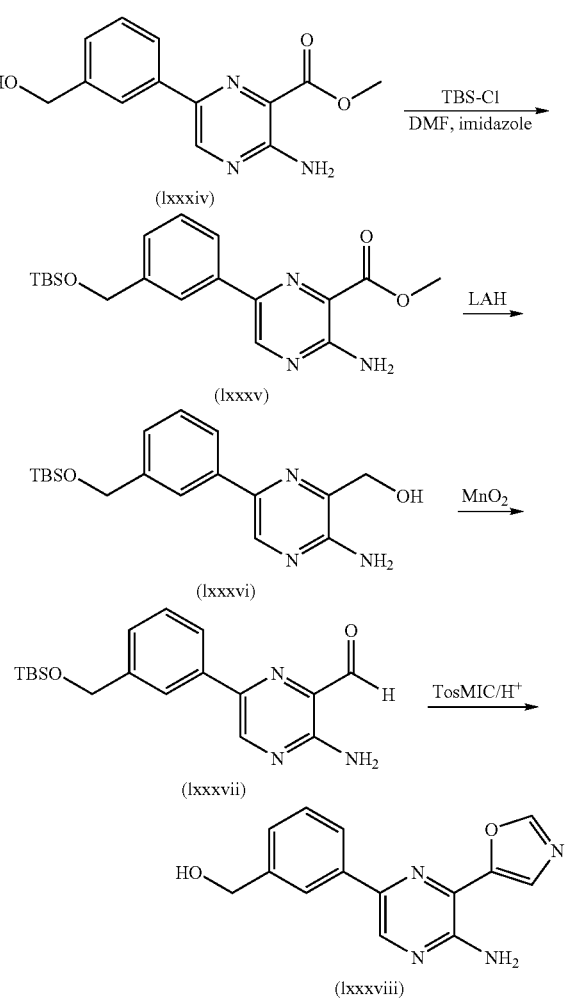

{3-[5-amino-6-(1,3-oxazol-5-yl)pyrazin-2-yl]phenyl}methanol: Methyl 3-amino-6-[3-(hydroxymethyl)

phenyl]pyrazine-2-carboxylate (200 mg, 0.77 mmol) was dissolved in DMF followed by addition of tert-butylsilyl chloride (0.14 g, 0.93 mmol) and imidazole (63 mg, 9.25 mmol). This mixture was stirred at room temperature under nitrogen for overnight. The reaction mixture was poured into water (75 mL), and extracted with ethyl acetate (2×50 mL) then dried over anhydrous sodium sulfate and filteration, concentration to give crude silyl ether product, 170 mg (59.0%). It was dissolve in THF followed by addition of lithium aluminum hydride (1.0 M solution in THF, 0.9 ml, about 2.0 equiv.) and it was stirred at room temperature for 5 hrs. It was directly subjected to oxidation reaction with $MnO_2$. Crude compounds was dissolved in acetone followd by the addition of $MnO_2$ (730 mg, 20 equiv.). It was refluxed for 1 hr then dried over anhydrous sodium sulfate and filteration, concentration to give crude aldehyde, 94.0 mg (66.0%). The aldehyde was dissolved in MeOH (20 ml), followed by tosylmethylisocyanide (56.0 mg, 2.87 mmol) and $K_2CO_3$ (40.0 mg, 2.87 mmol). This reaction mixture was refluxed for 4 hrs. and then followed usual aqeous work up and it was treated with HCl to give the desired oxazole, 62.0 mg (84.4%). $^1$H NMR (400 MHz, d4-MeOH): δ 8.70 (s, 1H), 8.01 (s, 1H), 7.80 (s, 1H), 7.20 (m, 4H), 4.70 (m, 2H); MS (EI) for $C_{14}H_{12}N_4O_2$: 267.14 (MH$^+$).

Example 55

5-(3-{[(1S)-2,3-dihydro-1H-inden-1-ylamino] methyl}phenyl)-3-(1,3-oxazol-5-yl)pyrazin-2-amine Using the {3-[5-Amino-6-(1,3-oxazol-5-yl)pyrazin-2-yl] phenyl}methanol, Mitsunobu reactions were carried out as outlined in Scheme 15 above to make compounds according to formula I.

To a solution of oxazole (lxxxviii) (1 (62.0 mg, 2.31 mmol) in benzene (0.5 M solution) was added N-[(1S)-2,3-dihydro-1H-inden-1-yl]2,4-dinitrobenzenesulfonamide (42.0 mg, 1.15 mmol), triphenylphosphine (57.7 mg, 2.19 mmol) and DEAD (0.034 mL, 2.31 mmol) and the mixture was allowed to stir at room temperature overnight. The solvent was removed and directly subjected to column chromatography purification (50% ethylacetate/hexanes) to give the intermediate sulfonamide, 123 mg (84.8% yield), which was treated with n-propylamine (20 equiv.) and purified by MPLC to give 5-(3-{[(1S)-2,3-dihydro-1H-inden-1-ylamino] methyl}phenyl)-3-(1,3-oxazol-5-yl)pyrazin-2-amine, 100 mg (81.3% yield): 1H NMR (400 MHz, d4-MeOH): δ 8.58 (s, 1H), 8.40 (s, 1H), 8.00 (s, 1H), 7.82 (d, 1H), 7.80 (s, 1H), 7.40 (m, 4H), 7.20 (4H), 4.35(m, 1H), 3.90 (m, 2H), 3.10 (m, 1H), 2.80 (m, 1H), 2.40 (m, 1H), 1.98 (m, 1H); MS (EI) for $C_{23}H_{21}N_5O$: 384.15 (MH$^+$).

Using the same or analogous synthetic techniques and/or substituting with alternative reagents {respective corresponding amines, etc.}, the following compounds of the invention were prepared.

1-[3-amino-6-(3-{[(1S)-2,3-dihydro-1H-inden-1-ylamino]methyl}phenyl)pyrazin-2-yl]ethanone: $^1$H NMR (400 MHz, d4-MeOH): δ 8.70 (s, 1H), 8.40 (s, 1H), 7.98 (d, 1H), 7.80 (m, 2H), 7.40 (m, 3H), 7.20 (m, 3H), 4.21 (m, 1H), 3.82 (m, 2H), 3.10 (m, 1H), 2.81 (m, 1H), 2.61 (m, 3H), 2.38 (m, 1H), 1.97 (m, 1H); MS (EI) for $C_{22}H_{22}N_4O$: 359.15 (MH$^+$).

[3-amino-6-(3-{[(1S)-2,3-dihydro-1H-inden-1-ylamino] methyl}phenyl)pyrazin-2-yl](phenyl)methanone: $^1$H NMR (400 MHz, d4-MeOH): δ 8.80 (s, 1H), 8.00 (d, 2H), 7.98 (s, 1H), 7.80 (m, 1H), 7.40 (m, 8H), 7.20 (m, 4H), 4.40 (m, 1H), 3.90 (m, 2H), 3.10 (m, 1H), 2.85 (m, 1H), 2.40 (m, 1H), 2.05 (m, 1H); MS (EI) for $C_{27}H_{24}N_4O$: 421.20 (MH$^+$).

5-(3-{[(1S)-2,3-dihydro-1H-inden-1-ylamino] methyl}phenyl)-3-(3-pyridin-3-yl-1H-1,2,4-triazol-5-yl) pyrazin-2-amine: $^1$H NMR (400 MHz, d4-MeOH): δ 10.1 (br, 1H), 9.00 (m, 3H), 8.70 (d, 1H), 8.30 (d, 1H), 7.91 (d, 1H), 7.40 (m, 7H), 4.81 (br, 1H), 4.35 (br, 1H), 4.71 (m, 1H), 3.21 (m, 1H), 2.91 (m, 1H), 2-.51 (m, 1H); MS (EI) for $C_{27}H_{24}N_8$: 461.16 (MH$^+$).

5-(3-{[(1S)-2,3-dihydro-1H-inden-1-ylamino] methyl}phenyl)-3-(3-piperidin-4-yl-1H-1,2,4-triazol-5-yl) pyrazin-2-amine: $^1$H NMR (400 MHz, d4-MeOH): δ 8.70 (s, 1H), 8.40 (br, 1H), 8.21 (m, 1H), 7.60 (m, 3H), 7.40 (m, 3H), 4.35 (s, 2H), 3.71 (m, 6H), 3.12 (m, 2H), 2.70 (m, 1H), 2.40 (m, 2H), 2.18 (m, 3H); MS (EI) for $C_{27}H_{30}N_8$: 467.41 (MH$^+$).

5-{3-[(2,3-dihydro-1H-inden-1-ylamino)methyl]phenyl}-3-(3-piperidin-3-yl-1H-1,2,4-triazol-5-yl)pyrazin-2-amine: $^1$H NMR (400 MHz, d4-MeOH): 6 8.60 (d, 2H), 8.18 (d, 1H), 7.79 (d, 1H), 7.60 (m, 2H), 7.40 (m, 3H), 4.40 (s, 2H), 3.60 (m, 6H), 3.12 (m, 1H), 3.05 (m, 1H), 2.67 (m, 1H), 2.42 (m, 1H), 2.18 (m, 1H), 2.10 (m, 3H); MS (EI) for $C_{27}H_{30}N_8$: 467.18 (MH$^+$).

5-(3-{[(1S)-2,3-dihydro-1H-inden-1-ylamino] methyl}phenyl)-3-{3-[(3S)-piperidin-3-yl]-1H-1,2,4-triazol-5-yl}pyrazin-2-amine: $^1$H NMR (400 MHz, d4-MeOH): δ 8.60 (d, 2H), 8.18 (d, 1H), 7.79 (d, 1H), 7.60 (m, 2H), 7.40 (m, 3H), 4.40 (s, 2H), 3.60 (m, 5H), 3.30 (m, 1H), 3.18 (m, 1H), 3.02 (m, 1H), 2.62 (m, 1H), 2.41 (m, 1H), 2.38 (m, 1H), 2.00 (m, 3H); MS (EI) for $C_{27}H_{30}N_8$: 467.33(MH$^+$).

5-(3-{[(1S)-2,3-dihydro-1H-inden-1-ylamino] methyl}phenyl)-3-{3-[(3R)-piperidin-3-yl]-1H-1,2,4-triazol-5-yl}pyrazin-2-amine: $^1$H NMR (400 MHz, d4-MeOH): δ 8.60 (d, 2H), 8.18 (d, 1H), 7.79 (d, 1H), 7.60 (m, 2H), 7.40 (m, 3H), 4.40 (s, 2H), 3.60 (m, 5H), 3.30 (m, 1H), 3.18 (m, 1H), 3.02 (m, 1H), 2.62 (m, 1H), 2.41 (m, 1H), 2.38 (m, 1H), 2.00 (m, 3H); MS (EI) for $C_{27}H_{30}N_8$: 467.33 (MH$^+$).

Example 56

Scheme 20 depicts a strategy for making exemplary compounds according to formula I where A is a triazole. Compound (lxxxix) is converted to the corresponding triazole, (xc), for example, as described below.

Scheme 20

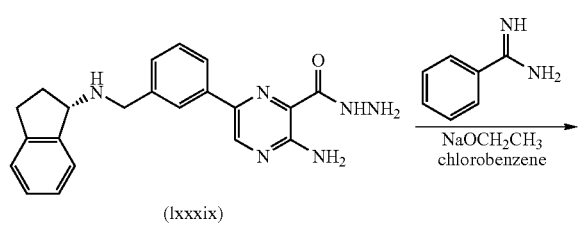

(lxxxix)

-continued

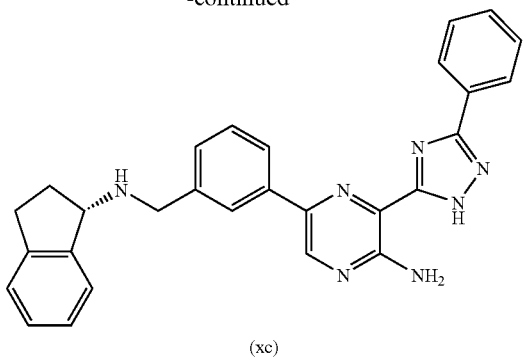

(xc)

5-(3-{[(1S)-2,3-dihydro-1H-inden-1-ylamino]methyl}phenyl)-3-(3-phenyl-1H-1,2,4-triazol-5-yl)pyrazin-2-amine: A solution of sodium ethoxide (19 mg, 0.27 mmol) in anhydrous ethanol (2 mL) was added to a solution of benzenecarboximidamide hydrochloride hydrate (31.35 mg, 0.2 mmol) in anhydrous ethanol (3 mL) at room temperature. The mixture was stirred at room temperature for 45 min. and filtered. To the ethanol filterate was added 3-amino-6-(3-{[(1S)-2,3-dihydro-1H-inden-1-ylamino]methyl}phenyl)pyrazine-2-carbohydrazide (50 mg, 0.13 mmol) and the resulting solution was heated to reflux overnight. The solvent was removed and purified by MPLC to give compound 1 (12.5 mg 21.3% yield): $^1$H NMR (400 MHz, d6-DMSO): δ 10.0 (s, 1H), 9.00 (m, 3H), 8.70 (d, 1H), 8.30 (d, 1H), 7.70 (d, 1H), 7.35 (m, 8H), 4.81 (br, 1H), 4.35 (br, 2H), 3.62 (m, 1H), 3.55 (m, 1H), 3.20 (m, 1H), 2.95 (m, 1H); MS (EI) for $C_{28}H_{25}N_7$: 460.10 (MH$^+$).

Using the same or analogous synthetic techniques and/or substituting with alternative reagents {respective corresponding amines, etc.}, the following compounds of the invention were prepared.

5-(3-{[(1S)-2,3-dihydro-1H-inden-1-ylamino]methyl}phenyl)-3-(3-pyridin-4-yl-1H-1,2,4-triazol-5-yl)pyrazin-2-amine: $^1$H NMR (400 MHz, d6-DMSO): δ 10.0 (br, 1H), 9.00 (m, 3H), 8.70 (d, 1H), 8.30 (d, 1H), 7.90 (d, 1H), 7.40 (m, 7H), 4.81 (br, 1H), 4.40 (br, 2H), 3.70 (m, 1H), 3.55 (m,1H), 3.25 (m, 1H), 2.95 (m, 1H), 2.50 (m, 1H); MS (EI) for $C_{27}H_{24}N_8$: 461.12 (MH$^+$).

Example 57

Scheme 21 depicts a strategy for making imidoates according to formula I. Nitrile (xci) is converted to the corresponding imidoate, (xcii), for example, as described below. Such imidoates are generally used as intermediates to make, for example, compounds according to formula I where A is a triazole, or oxadiazole, and the like as one skilled in the art could readily perform. For example addition of benzenecarboximidamide to imidoate (xcii) under appropriate conditions (e.g. heat and dehydrative conditions) would give the corresponding triazole derivative (xciii). Some exemplary compounds are listed in this example.

Scheme 21

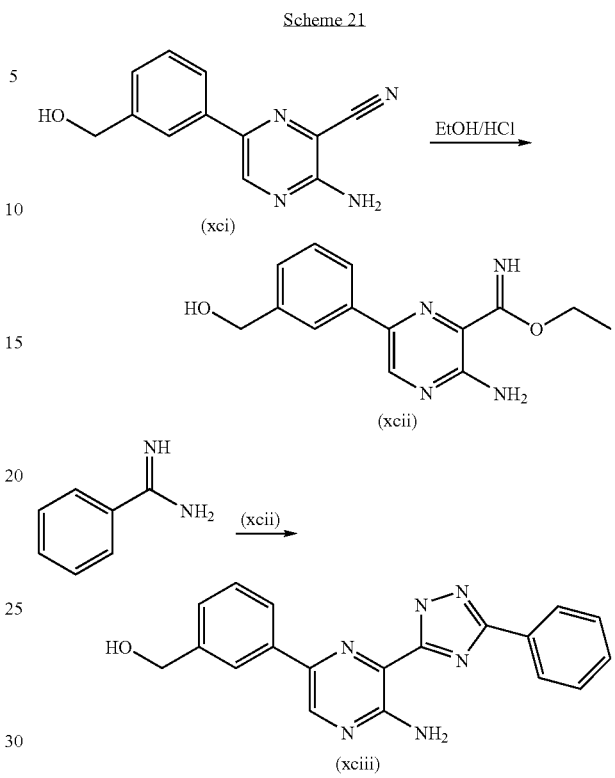

Ethyl 3-amino-6-[3-(hydroxymethyl)phenyl]pyrazine-2-carboximidoate: A suspension of 3-amino-6-[3-(hydroxymethyl)phenyl]pyrazine-2-carbonitrile (500 mg, 2.21 mmol) in ethanol was cooled by ice bath. Dry hydrogen chloride gas was bubbled into the reaction mixture for 2 or 3 hours. After gas addition was stopped, the solution was placed in a refrigerator overnight. The solution was filtered and evaporated to afforded compound 1 (452 mg, 75.3% yield): $^1$H NMR (400 MHz, d6-DMSO): δ 9.00 (s, 1H), 8.15 (s, 1H), 8.00 (m, 1H), 7.42 (m, 3H), 4.80 (q, 2H), 4.62 (s, 21H), 1.60 (t, 1H); MS (EI) for $C_{14}H_{16}N_4O$: 273.23 (MH$^+$).

Using the same or analogous synthetic techniques and/or substituting with alternative reagents {respective corresponding amines, etc.}, the following compounds of the invention were prepared.

2-({3-Amino-6-[3-(hydroxymethyl)phenyl]pyrazin-2-yl}carbonyl)-N-phenylhydrazine carboxamide: $^1$H NMR (400 MHz, d6-DMSO): δ 10.42 (s, 1H), 8.20 (m, 3H), 7.40 (m, 8H), 6.95 (m, 1H), 5.20 (t, 1H), 4.60 (m, 2H); MS (EI) for $C_{19}H_{18}N_6O_3$: 379.13 (MH$^+$).

3-Amino-N-hydroxy-6-[3-(hydroxymethyl)phenyl]pyrazine-2-carboximidamide: $^1$H NMR (400 MHz, d6-DMSO): δ 10.23 (s, 1H), 8.60 (s, 1H), 8.00 (m, 2H), 7.40 (m, 2H), 6.15 (s, 1H), 5.21 (t, 1H), 4.60 (m, 2H); MS (EI) for $C_{12}H_{13}N_5O_2$: 260.21 (MH$^+$).

{3-[5-Amino-6-(3-pyridin-3-yl-1H-1,2,4-triazol-5-yl)pyrazin-2-yl]phenyl}methanol: $^1$H NMR (400 MHz, d6-DMSO): δ 9.60 (s, 1H), 8.92 (m, 3H), 8.20 (m, 2H), 7.90 (m, 2H), 7.40 (m, 2H), 5.21 (t, 1H), 4.60 (m, 2H); MS (EI) for $C_{18}H_{15}N_7O$: 346.11 (MH$^+$).

(3-{5-Amino-6-[3-(4-chlorophenyl)-1H-1,2,4-triazol-5-yl]pyrazin-2-yl}phenyl)methanol: $^1$H NMR (400 MHz, d6-DMSO): δ 8.70 (s, 1H), 8.20 (m, 3H), 7.80 (m, 3H), 7.40

(m, 3H), 4.60 (m, 2H), 4.40 (s, 1H); MS (EI) for $C_{19}H_{15}N_6OCl$: 379.07 (MH$^+$).

{3-[5-amino-6-(3-pyridin-4-yl-1H-1,2,4-triazol-5-yl)pyrazin-2-yl]phenyl}methanol: $^1$H NMR (400 MHz, d4-MeOH): δ 8.80 (m, 5H), 8.10 (m, 3H), 7.50 (m, 2H), 7.40 (m, 3H), 4.72 (s, 2H) MS (EI) for $C_{18}H_{15}N_7O$: 346.24 (MH$^+$).

{3-[5-amino-6-(3-piperidin-4-yl-1H-1,2,4-triazol-5-yl)pyrazin-2-yl]phenyl}methanol: $^1$H NMR (400 MHz, d4-MeOH): δ 8.50 (s, 5H), 8.05 (s, 3H), 7.90 (m, 1H), 7.40 (m, 2H), 4.60 (s, 2H), 2.30 (m, 4H), 1.21 (m, 5H); MS (EI) for $C_{18}H_{12}N_7O$: 352.28 (MH$^+$).

{3-[5-amino-6-(3-piperidin-3-yl-1H-1,2,4-triazol-5-yl)pyrazin-2-yl]phenyl}methanol: $^1$H NMR (400 MHz, d6-DMSO): δ 9.50 (dd, 2H), 8.78 (s, 1H), 8.20 (m, 2H), 7.40 (m, 2H), 4.60 (s, 2H), 3.32 (m, 4H), 1.67 (m, 5H); MS (EI) for $C_{18}H_{12}N_7O$: 352.28 (MH$^+$).

{3-[5-amino-6-(3-pyrrolidin-3-yl-1H-1,2,4-triazol-5-yl)pyrazin-2-yl]phenyl}methanol: $^1$H NMR (400 MHz, d6-DMSO): δ 8.60 (s, 1H), 8.18 (s, 1H), 8.00 (d, 1H), 7.45 (m, 2H), 4.70 (s, 2H), 3.97 (m, 1H), 3.78 (m, 2H), 3.50 (m, 2H), 2.60 (m, 1H), 2.41 (m, 1H); MS (EI) for $C_{17}H_{19}N_7O$: 338.30 (MH$^+$).

{3-[5-amino-6-(3-pyridin-2-yl-1H-1,2,4-triazol-5-yl)pyrazin-2-yl]phenyl}methanol: $^1$H NMR (400 MHz, d6-DMSO): δ 8.91 (m, 2H), 8.56 (d, 1H), 8.40 (t, 1H), 8.18 (m, 2H), 7.81 (t, 1H), 7.42 (m, 2H), 4.70 (s, 2H); MS (EI) for $C_{18}H_{15}N_7O$: 346.22 (MH$^+$).

{3-[5-amino-6-(3-piperidin-2-yl-1H-1,2,4-triazol-5-yl)pyrazin-2-yl]phenyl}methanol: $^1$H NMR (400 MHz, d6-DMSO): δ 9.85 (m, 1H), 9.40 (m, 1H), 8.80 (s, 1H), 8.18 (m, 2H), 7.42 (m, 2H), 4.62 (s, 2H), 3.40 (m, 3H), 1.62 (m, 6H); MS (EI) for $C_{18}H_{21}N_7O$: 461.16 (MH$^+$).

{3-[5-amino-6-(3-morpholin-2-yl-1H-1,2,4-triazol-5-yl)pyrazin-2-yl]phenyl}methanol: $^1$H NMR (400 MHz, d6-DMSO): δ 9.85 (m, 1H), 9.60 (m, 1H), 8.80 (s, 1H), 8.18 (m, 2H), 7.42 (m, 2H), 5.12 (d, 1H), 4.62 (s, 2H); MS (EI) for $C_{17}H_{19}N_7O_2$: 354.15 (MH$^+$).

[3-(5-amino-6-{3-[(3R)-piperidin-3-yl]-1H-1,2,4-triazol-5-yl}pyrazin-2-yl)phenyl]methanol: $^1$H NMR (400 MHz, d4-MeOH): δ 9.60 (s, 1H), 8.20 (s, 1H), 8.10 (m, 2H), 4.72 (s, 2H), 3.62(m, 2H), 3.54 (m, 2H), 3.10 (m, 1H), 2.38 (m, 1H), 2.00 (m,3H); MS (EI) for $C_{18}H_{21}N_7O$: 352.17 (MH$^+$).

[3-(5-amino-6-{3-[(3S)-piperidin-3-yl]-1H-1,2,4-triazol-5-yl}pyrazin-2-yl)phenyl]methanol: $^1$H NMR (400 MHz, d4-MeOH): δ 9.60 (s, 1H), 8.20 (s, 1H), 8.10 (m, 2H), 4.72 (s, 2H), 3.62(m, 2H), 3.54 (m, 2H), 3.10 (m, 1H), 2.38 (m, 1H), 2.00 (m,3H); MS (EI) for $C_{18}H_{21}N_7O$: 352.17 (MH$^+$).

Example 58

Scheme 22 depicts another strategy for making exemplary compounds according to formula I where A is a triazole. Boronic acid-acyl chloride intermediate (xciv) is coupled with amine (xcv) to give amide (xcvi). Intermediate (xcvi) is coupled to a bromo-pyrazine, for example, to give intermediate (xcvii). The nitrile group of (xcvii) is converted to the corresponding triazole to yield (xcviii), for example, as more fully described below. Intermediate (xcvii) can also be used to make other heterocycles for A, according to formula I. Included in this example are other various triazole syntheses that generally start from a corresponding nitrile precursor.

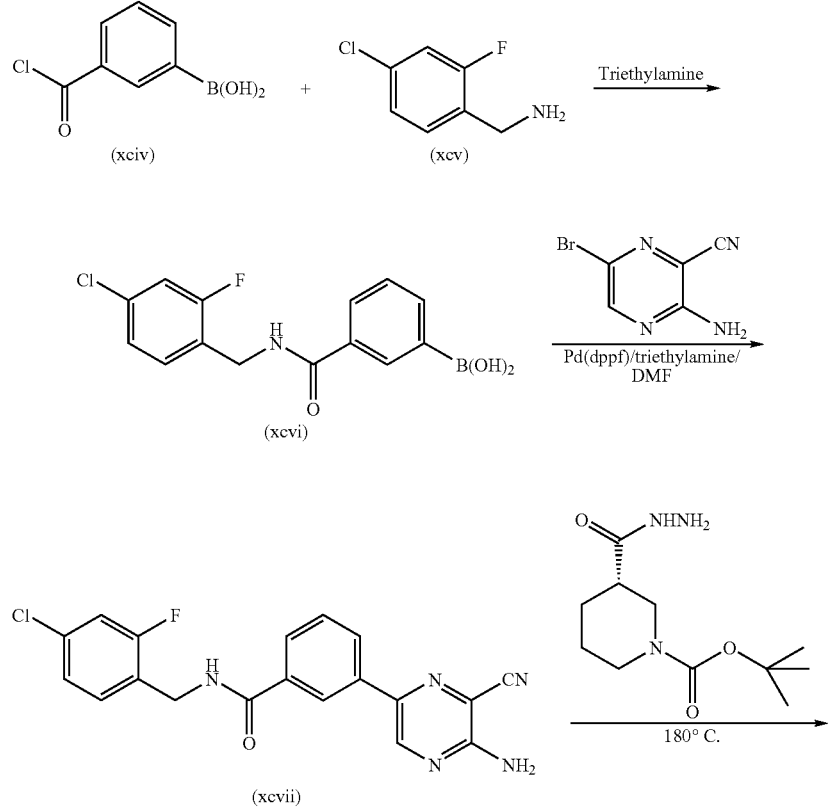

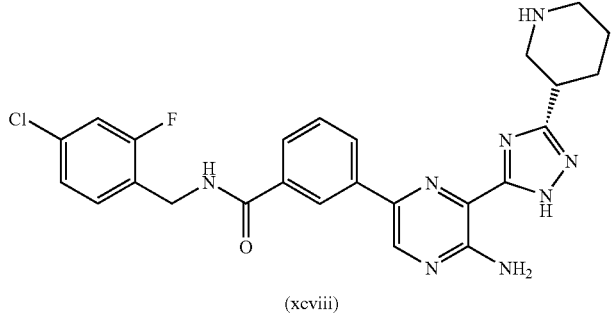

(xcviii)

3-(5-amin-6-cyano-pyrazin-2-yl)-N-[(4-chloro-2-fluorophenyl)methyl]benzamide 4-Carbonyl chloride phenylboronic aicd (35 0 mg, 1.90 mmol) was added to THF followed by addition of 4-chloro-2-fluoro benzylamine (466 mg, 2.37 mmol) and triethylamine (400 μl, 2.85 mmol). This mixture was stirred at room temperature under nitrogen overnight. The reaction mixture was poured into water (75 mL), and extracted with ethyl acetate (2×50 mL) then dried over anhydrous sodium sulfate and filteration, concentration to give crude reduction product, 525 mg (90.0% yield). Subsequently it was dissolved in DMF followed by addition of 3-amino-6-bromo-pyrazine-2-carbonitrile (169 mg, 0.85 mmol), Pd(dppf)CH$_2$Cl$_2$ (69.2 mg, 10 mol %) and triethylamine (118 μl, 2.12 mmol). It was heated to 80° C. for 16 hrs and quenched with H$_2$O and extracted with ethylacetate then dried over anhydrous sodium sulfate and filteration, concentration to give crude reduction product (275 mg, 85.0% yield): MS (EI) for C$_{19}$H$_{13}$ClFN$_5$O: 382.14 (MH$^+$).

3-(5-anmino-6{3-[(3S)-piperidin-3-yl]-1H-1,2,4-traiazol-5-yl}pyrazine-2-yl)-N[4-chloro-2-fluorophenyl)methyl]benzamide: 3-(5-Amino-6-cyano-pyrazin-2-yl)-N-(4-chloro-2-fluoro-benzyl)-benzamide (238.0 mg, 0.63 mmol) and 1,1-dimethylethyl (3S)-3-(hydrazinocarbonyl)piperidine-1-carboxylate (460 mg, 1.89 mmol) was combined together and it was heated to 180° C. for 1 or 2 hrs. The reaction mixture was poured into water (575 mL), and extracted with ethyl acetate (2×35 mL) then dried over anhydrous sodium sulfate and filteration, concentration and purified by MPLC to give 3-[5-amino-6-(5-piperidin-3-yl-2H-[1,2,4]triazol-3-yl)-pyrazin-2-yl]-N-(4-chloro-2-fluoro-benzyl)-benzamide (206.0 mg, 65.0% yield): $^1$H NMR (400 MHz, d4-MeOH): δ 8.60 (d, 2H), 8.20 (d, 1H), 7.82 (d, 1H), 7.58 (t, 1H), 7.38 (t, 1H), 7.15 (m, 2H), 4.60(s, 2H), 3.62 (m, 1H), 3.40(m, 3H), 2.99 (m, 1H), 2.37 (m, 1H), 1.98 (m, 3H); MS (EI) for C$_{25}$H$_{24}$N$_8$OFCl: 507.03 (MH$^+$).

1-(1,1-dimethylethyl) 3-ethyl (3S)-piperidine-1,3-dicarboxylate: To an ice-cooled, stirred solution of (S)-(+)-ethyl nipecotate (3.95 g, 25.1 mmnol, from Sigma-Aldrich) in 20 mL of THF, was added 8.21 g (37.6 mmol, 1.5 eq.) of di-tert-butyl dicarbonate. The ice bath was removed, and the reaction stirred at room temperature for 19 h and concentrated. The crude oil was purified by silica gel chromatography (55 mm column, 5 inches of silica gel) using 15% EtOAc in hexanes as eluent. Concentration afforded 6.28 g (97.2% yield) of product as an oil.

1,1-dimethylethyl (3S)-3-(hydrazinocarbonyl)piperidine-1-carboxylate: To a solution of 6.28 g (24.4 mmol) of 1-(1,1-dimethylethyl) 3-ethyl (3S)-piperidine-1,3-dicarboxylate in 25 mL of MeOH was added 7.11 mL of hydrazine monohydrate (146 mmol, 5.98 eq.). The mixture was refluxed for 2 h and concentrated. The reaction could be monitored by LC/MS on a reversed-phase column at 220 nm wavelength. The crude material was taken up in EtOAc, and washed with 2×H$_2$O, 1× sat. aqueous NaCl, and dried over Na$_2$SO$_4$. Filtration and concentration afforded 3.21 g of product (54.0% yield) as a viscous oil. The product was ca. 80% pure by hplc analysis and was used as such without further purification.

Using the same or analogous synthetic techniques and/or substituting with alternative reagents {respective corresponding amines, etc.}, the following compounds of the invention were prepared.

3-(5-amino-6-{3-[(3S)-piperidin-3-yl]-1H-1,2,4-triazol-5-yl}pyrazin-2-yl)-N-[(2,6-difluorophenyl)methyl]benzamide: $^1$H NMR (400 MHz, d4-MeOH): δ 8.60 (d, 2H), 8.38 (d, 1H), 7.88 (d, 1H), 7.60 (t, 1H), 7.38 (m, 2H), 7.15 (t, 1H), 4.80 (s, 2H), 3.78 (m, 1H), 3.50 (m, 3H), 3.15 (m, 1H), 2.37 (m, 1H), 1.98 (m, 3H); MS (EI) for C$_{25}$H$_{24}$N$_8$OF$_2$: 491.08 (MH$^+$).

3-(5-amino-6-{3-[(3S)-piperidin-3-yl]-1H-1,2,4-triazol-5yl}pyrazin-2-yl)-N-[(2-chloro-6-fluorophenyl)methyl]benzamide: $^1$H NMR (400 MHz, d4-MeOH): δ 8.60 (d, 2H), 8.32 (d, 1H), 7.82 (d, 1H), 7.60 (t, 1H), 7.40 (t, 1H), 7.00 (m, 2H), 4.70 (s, 2H), 3.78 (m, 1H), 3.50 (m, 3H), 3.05 (m, 1H), 2.37 (m, 1H), 2.00 (m, 3H); MS (EI) for C$_{25}$H$_{24}$N$_8$OFCl: 507.03 (MH$^+$).

3-(5-amino-6-{3-[(3S)-piperidin-3-yl]-1H-1,2,4-triazol-5-yl}pyrazin-2-yl)-N-[(2,5-dichlorophenyl)methyl]benzamide: $^1$H NMR (400 MHz, d4-MeOH): δ 8.75 (d, 2H), 8.38 (d, 1H), 7.95 (d, 1H), 7.62 (t, 1H), 7.40 (m, 2H), 7.25 (d, 1H), 4.62 (s, 2H), 3.78 (m, 1H), 3.50 (m, 3H), 3.05 (m, 1H), 2.41 (m, 1H), 2.00 (m, 3H); MS (EI) for C$_{25}$H$_{24}$N$_8$OCl$_2$: 523.19 (M$^+$).

3-(5-amino-6-{3-[(3S)-piperidin-3-yl]-1H-1,2,4-triazol-5-yl}pyrazin-2-yl)-N-[(3,4-dichlorophenyl)methyl]benzamide: $^1$H NMR (400 MHz, d4-MeOH): δ 8.70 (d, 2H), 8.38 (d, 1H), 7.95 (d, 1H), 7.62 (t, 1H), 7.58 (s, 1H), 7.42 (d, 2H), 7.38 (d, 1H), 4.60 (s, 2H), 3.72 (m, 1H), 3.50 (m, 3H), 3.05 (m, 1H), 2.38 (m, 1H), 2.00 (m, 3H); MS (EI) for C$_{25}$H$_{24}$N$_8$OCl$_2$: 523.19 (M$^+$).

(3-{5-Amino-6-[3-(2-thienyl)-1H-1,2,4-triazol-5-yl]pyrazin-2-yl}phenyl)methanol To a solution of 3-amino-6-[3-(hydroxymethyl)phenyl]pyrazine-2-carbonitrile (149 mg, 0.74 mmol) was added thiophene-2-carboxylic acid hydrazide (94 mg, 0.66 mmol), sodium methoxide (53 mg, 0.996 mmol) in MeOH (5 mL). After reflux for 4 days, the reaction mixture was extracted with ethyl acetate (10 mL×3) and dried over MgSO$_4$. Filtertion and concentration in vacuo gave a crude product, which was purified by preparative HPLC (0.1% TFA in water/ 0.1% TFA in CH$_3$CN). The product fractions were neutralized by aqueous saturated sodium bicarbonate solution and partitioned with ethyl acetate. The aqueous phase was extracted once with additional ethyl acetate. The combined organic layers were washed with saturated aqueous sodium chloride then dried over anhydrous magnesium sulfate. Filtration and concentration in vacuo gave the (3-{5-amino-6-[3-(2-thienyl)-1H-1,2,4-triazol-5-yl]pyrazin-2-yl } phenyl) methanol (14 mg, yield): $^1$H NMR (400 MHz, CD$_3$OD): δ 8.65 (s, 1H), 8.14 (s, 1H), 8.02 (d, 1H), 7.77 (m, 1H), 7.53 (m, 1H), 7.47 (m, 1H), 7.38 (m, 1H), 7.17 (m, 1H), 4.72 (s, 2H); MS (EI) for C$_{17}$H$_{14}$N$_6$O: 351.10 (MH$^+$).

(3-{5-Amino-6-[3-(2-aminopyridin-4-yl)-1H-1,2,4-triazol-5-yl]pyrazin-2-yl}phenyl)methanol: To a solution of of 3-amino-6-[3-(hydroxymethyl)phenyl]pyrazine-2-carbonitrile (250 mg, 1.11 mmol) was added 2-aminoisonicotinic acid hydrazide (311 mg, 2.04 mmol). After being heated at 180° C. for 90 min, the reaction mixture was dissolved in DMF and washed with water, ethyl acetate (10 mL×3). The aqueous phase was extracted once with additional ethyl acetate. The combined organic layers were washed with saturated aqueous sodium chloride then dried over anhydrous magnesium sulfate. Filtration and concentration in vacuo gave a crude oil, which was purified by preparative HPLC to yield (3-{5-amino-6-[3-(2-aminopyridin-4-yl)-1H-1,2,4-triazol-5-yl]pyrazin-2-yl}phenyl)methanol (23.2 mg, 5.7% yield): $^1$H NMR (400 MHz, DMSO-d6): δ 8.80 (s, 1H), 8.15 (s, 1H), 8.10 (m, 1H), 7.70 (m, 2H), 7.43 (m, 2H), 7.20 (m, 1H), 6.10 (s, 2H), 5.25 (m, 1H) 4.60 (m, 1H); MS (EI) for C$_{18}$H$_{16}$N$_8$O: 361.11 (MH$^+$).

Using the same or analogous synthetic techniques and/or substituting with alternative reagents, the following 1H-1,2, 4-triazole compounds of the invention were prepared:

5-{3-[(2,3-Dihydro-1H-inden-1-ylamino)methyl]phenyl}-3-{3-[3-(methyloxy)phenyl]-1H-1,2,4-triazol-5-yl}pyrazin-2-amine: $^1$H NMR (400 MHz, DMSO-d6): δ 8.82 (s, 1H), 8.38 (m, 2H), 7.82 (m, 1H), 7.76 (d, 1H), 7.62 (m, 2H), 7.52 (m, 1H), 7.43 (m, 1H), 7.35 (m, 3H), 7.11 (m, 1H), 4.75 (bs, 1H), 4.23 (m, 2H), 3.87 (s, 3H), 3.18 (m, 1H), 2.90 (m, 1H), 2.45 (m, 1H), 2.30 (m, 1H); MS (EI) for C$_{29}$H$_{27}$N$_7$O: 490.14 (MH$^+$).

3-{5-Amino-6-[3-(1-methylpiperidin-3-yl)-1H-1,2,4-triazol-5-yl]pyrazin-2-yl}-N-[(2-chloro-6-fluorophenyl)methyl]benzamide: $^1$H NMR (400 MHz, DMSO-d$_6$): δ 10.40 (s, 1H), 8.97 (m, 2H), 8.57 (s, 1H), 8.40 (m, 1H), 7.87 (m, 1H), 7.80 (bs, 1H), 7.55 (m, 1H), 7.37 (m, 2H), 7.22 (m, 1H), 4.63 (s, 2H), 3.78 (m, 1H), 3.43 (m, 2H), 3.23 (m, 1H), 3.00 (m, 1H), 2.97 (s, 3H), 2.22 (m, 1H), 2.01 (m, 2H), 1.61 (m, 1H); MS (EI) for C$_{26}$H$_{26}$N$_8$OFCl: 521.02 (MH$^+$).

3-(5-Amino-6-{3-[(3S)-piperidin-3-yl]-1H-1,2,4-triazol-5-yl}pyrazin-2-yl)-N-[(4-chloro-2-fluorophenyl)methyl] benzamide: $^1$H NMR (400 MHz, CD$_3$OD): δ 8.68 (s, 2H), 8.29 (d, 1H), 7.93 (d, 1h), 7.62 (t, 1H), 7.45 (t, 1H), 7.20 (m, 2H), 4.67 (s, 2H), 3.75 (m, 1H), 3.47 (m, 3H), 3.12 (m, 2H), 2.33 (m, 1H), 2.03 (m, 2H); MS (EI) for C$_{25}$H$_{24}$N$_8$OFCl: 507.02 (MH$^+$).

3-(5-Amino-6-{3-[(3S)-piperidin-3-yl]-1H-1,2,4-triazol-5-yl}pyrazin-2-yl)-N-[(2,4-difluorophenyl)methyl]benzamide: $^1$H NMR (400 MHz, DMSO-d$_6$): δ 9.23 (m, 1H), 8.89 (m, 2H), 8.65 (s, 1H), 8.42 (m, 1H), 7.89 (m, 1H), 7.78 (bs, 1H), 7.60 (m, 1H), 7.45 (m, 1H), 7.26 (m, 1H), 7.08 (m, 1H), 4.54 (d, 2H), 3.30 (m, 2H), 3.18 (m, 2H), 2.96 (m, 1H), 2.19 (m, 1H), 1.87 (m, 3H); MS (EI) for C$_{25}$H$_{24}$N$_8$OF$_2$: 491.08 (MH$^+$).

3-(5-Amino-6-{3-[(3S)-piperidin-3-yl]-1H-1,2,4-triazol-5-yl}pyrazin-2-yl)-N-[(3,4-difluorophenyl)methyl]benzamide: $^1$H NMR (400 MHz, DMSO-d6): δ 9.42 (m, 1H), 9.02 (m, 2H), 8.90 (s, 1H), 8.71 (s, 1H), 8.41 (m, 1H), 7.90 (m, 1H), 7.78 (m, 1H), 7.60 (m, 1H), 7.42 (m, 2H), 7.23 (m, 1H), 4.51 (d, 2H), 3.57 (m, 1H), 3.29 (m, 2H), 3.20 (m, 1H), 2.90 (m, 1H), 2.20 (m, 1H), 1.85 (m, 3H); MS (EI) for C$_{25}$H$_{24}$N$_8$OF$_2$: 491.08 (MH$^+$).

3-[3-(2-Aminopyridin-4-yl)-1H-1,2,4-triazol-5-yl]-5-(3-{[(1S)-2,3-dihydro-1H-inden-1-ylamino]methyl}phenyl) pyrazin-2-amine: $^1$H NMR (400 MHz, DMSO-d6): δ 8.99 (s, 1H), 8.85 (s, 1H), 7.31 (d, 2H), 8.07 (d, 1H), 7.85 (d, 1H), 7.73 (s, 1H), 7.55 (m, 2H), 7.37 (d, 1H), 7.31 (m, 1H), 4.83 (m, 1H), 4.32 (m, 2H), 3.25 (m, 1H), 2.91 (m, 1H), 2.43 (m, 1H); MS (EI) for C$_{27}$H$_{25}$N$_9$: 476.07 (MH$^+$).

(3-{5-amino-6-[3-(1-methylpiperidin-3-yl)-1H-1,2,4-triazol-5-yl]pyrazin-2-yl}phenyl)methanol: $^1$H NMR (400 MHz, d$_6$-DMSO): 10.34 (br s, 1H), 8.77 (s, 1H), 8.11 (s, 1H), 8.07 (d, 1H), 7.68 (br s, 2H), 7.42 (m, 1H), 7.34 (d, 1H), 4.58 (s, 2H), 3.75 (m, 1H), 3.45 (m, 1H), 3.38 (m, 1H), 3.22 (m, 1H), 2.99 (m, 1H), 2.82 (m, 3H), 2.19 (m, 1H), 1.95 (m, 2H), 1.68 (m, 1H); MS (EI) for C$_{19}$H$_{23}$N$_7$O: 366.2 (MH$^+$).

5-(3-{[(1S)-2,3-dihydro-1H-inden-1-ylamino]methyl}phenyl)-3-[3-(1-methylpiperidin-3-yl)-1H-1,2,4-triazol-5-yl]pyrazin-2-amine: $^1$H NMR (400 MHz, d$_6$-DMSO): 10.40 (br s, 1H), 9.76 (br s, 1H), 8.85 (s, 1H), 8.67 (s, 1H), 8.25 (m, 1H), 7.82 (d, 1H), 7.75 (br s, 2H), 7.53 (m, 2H), 7.36 (m, 2H), 7.30 (m, 1H), 4.83 (m, 1H), 4.27 (m, 2H), 3.76 (m, 1H), 3.46 (m, 1H), 3.40 (m, 1H), 3.20 (m, 2H), 2.94 (m, 2H), 2.82 (m, 3H), 2.38 (m, 1H, 2.20 (m, 1H), 1.96 (m, 2H), 1.67 (m, 1H); MS (EI) for C$_{28}$H$_{32}$N$_8$: 481.2 (MH$^+$).

Example 59

Scheme 23 depicts two exemplary compounds, (xcix) and (c), according to formula I, which are useful as intermediates to synthesize other compounds of the invention. Exemplary syntheses of such compounds follows, and generally can also be used to make other heterocycles (besides triazoles) for A, according to formula I.

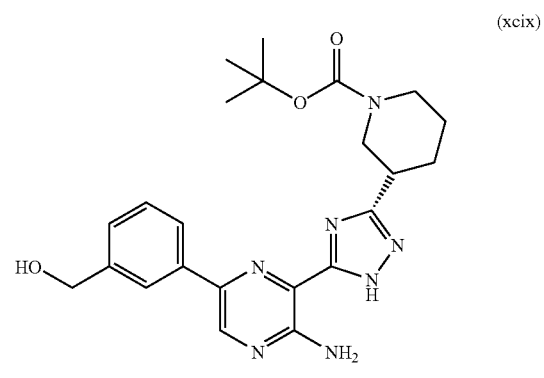

Scheme 23

(xcix)

-continued (c)

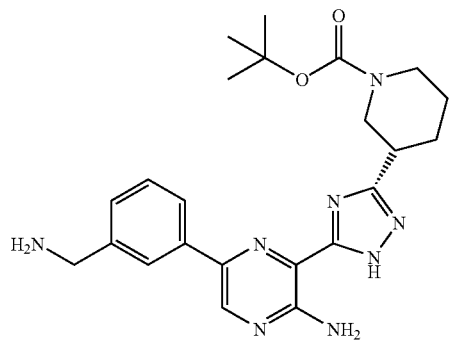

1,1-Dimethylethyl (3R)-3-(5-{3-amino-6-[3-(hydroxymethyl)phenyl]pyrazin-2-yl}-1H-1,2,4-triazol-3-yl)piperidine-1-carboxylate: 3-Amino-6-[3-(hydroxymethyl)phenyl]pyrazine-2-carbonitrile (514.0 mg, 2.27 mmol) and 1,1-dimethylethyl (3S)-3-(hydrazinocarbonyl)piperidine-1-carboxylate (1.66g, 6.83 mmol) were combined together and heated to 180° C. for 1-2 h. The reaction mixture was poured into water (100 mL), and extracted with ethyl acetate (2×35 mL) then dried over anhydrous sodium sulfate and filteration, concentration and purified by MPLC to give 1,1-dimethylethyl (3R)-3-(5-{3-amino-6-[3-(hydroxymethyl)phenyl]pyrazin-2-yl }-1H-1,2,4-triazol-3-yl)piperidine-1-carboxylate. (655.0 mg, 64.2% yield): MS (EI) for $C_{23}H_{29}N_7O_3$: 452.29 (MH+).

1,1-dimethylethyl(3R)-3-(5-{3-amino-6-[3-(aminomethyl)phenyl]pyrazin-2-yl}-1H-1,2,4-triazol-3-yl)piperidine-1-carboxylate: 1,1-dimethylethyl (3R)-3-(5-{3-amino-6-[3-(hydroxymethyl)phenyl]pyrazin-2-yl}-1H-1,2,4-triazol-3-yl)piperidine-1-carboxylate (655.0 mg, 1.45 mmol) was dissolved in THF (20 mL) followed by the addition of diphenylphosphoryl azide (0.45 mL, 2.03 mmol) and DBU (0.31 mL, 2.03 mmol). It was stirred at room temperature overnight. The reaction mixture was poured into water (100 mL), and extracted with ethyl acetate (2×50 mL) then dried over anhydrous sodium sulfate and filteration, concentration and purified by column chromatography (50% Ethylacetae/hexanes) to give the intermediate azide, 458.0 mg (66.4%, MS (EI) for $C_{23}H_{30}N_8O_2$: 451.27 (MH+), which was dissolved in the mixture of THF (15 mL) and $H_2O$ (1.5 mL) followed by the addition of triphenylphosphine (0.76g, 2.88 mmol) and it was stirred at room temperature overnight. The reaction mixture was poured into water (100 mL), and extracted with ethyl acetate (2×50 mL) then dried over anhydrous sodium sulfate. The extracts were filtered, concentrated, and purified by column chromatography (O to 100% MeOH in Ethyl acetate) to give 1,1-dimethylethyl(3R)-3-(5-{3-amino-6-[3-(aminomethyl)phenyl]pyrazin-2-yl}-1H-1,2,4-triazol-3-yl)piperidine-1-carboxylate, 368.0 mg (85.0% yield).

5-[3-(Aminomethyl)phenyl]-3-{3-[(3S)-piperidin-3-yl]-1H-1,2,4-triazol-5-yl}pyrazin-2-amine: To a solution of 1,1-dimethylethyl(3R)-3-(5-{3-amino-6-[3-(aminomethyl)phenyl]pyrazin-2-yl}-1H-1,2,4-triazol-3-yl)piperidine-1-carboxylate (50.0 mg, 0.11 mmol) in MeOH (3.0 mL) was added 4.0M HCl in dioxane (15 mL) and stirred it overnight at room temperature. All solvent was evaporated under vacuum to give compound 1, 28.0 mg (72.0% yield): $^1$H NMR (400 MHz, d4-MeOH): δ 8.62 (s, 1H), 8.38 (s, 1H), 8.21 (d, 1H), 7.60 (m, 1H), 4.22(s, 2H), 3.65 (m, 1H), 3.42 (m, 3H), 3.16 (m, 1H), 2.38 (m, 1H), 2.00 (m, 3H); MS (EI) for $C_{18}H_{22}N_8$: 351.27 (MH+).

Example 60

Generally, intermediates (xcix) and (c) (see Scheme 23 above) are used to attach Y (according to formula I) to make compounds of the invention, and thereby also establish X in many examples. Included in this example is description of such syntheses.

N-{[3-(5-amino-6-{3-[(3S)-piperidin-3-yl]-1H-1,2,4-triazol-5-yl}pyrazin-2-yl)phenyl]methyl}-2-chlorobenzamide HCl: Intermediate 2 (50.0 mg, 0.11 mmol) was dissolved in DMF (5mL) followed by the addition of HOBT (30.0 mg, 0.22 mmol) and EDCI (43.0 mg, 0.22 mmol). It was stirred at room temperature overnight. The reaction mixture was poured into water (100 mL), and extracted with ethyl acetate (2×50 mL) then dried over anhydrous sodium sulfate and filtered, concentrated and purified by column chromatography (50% Ethylacetae/hexanes) and subsequently it was treated with 4.0 M HCl in dioxane (20 mL) to give compound 1, 42.2 mg (78.0% yield).% yield). $^1$H NMR (400 MHz, d4-MeOH): δ 8.50 (s, 1H), 8.20 (s, 1H), 8.11 (s, 1H), 7.58 (m, 6H), 4.67(s, 2H), 3.73 (m, 1H), 3.45 (m, 3H), 3.18 (m, 1H), 2.38 (m, 1H), 2.00 (m, 3H); MS (EI) for $C_{25}H_{25}N_8OCl$: 489.24 (MH+).

Using the same or analogous synthetic techniques and/or substituting with alternative reagents {respective corresponding amines, etc.}, the following compounds of the invention were prepared.

N-{[3-(5-amino-6-{3-[(3S)-piperidin-3-yl]-1H-1,2,4-triazol-5-yl}pyrazin-2-yl)phenyl]methyl}-4-chlorobenzamide: 1H NMR (400 MHz, d4-MeOH): δ 8.52 (s, 1H), 8.14 (s, 1H), 8.00 (d, 1H), 7.84 (d, 2H), 7.42 (m, 4H), 4.62(s, 2H), 3.65 (m, 2H), 3.42 (m, 2H), 3.16 (m, 1H), 2.38 (m, 1H), 2.00 (m, 3H); MS (EI) for $C_{25}H_{25}N_8OCl$: 489.20 (MH+).

N-([3-(5-amino-6-{3-[(3S)-piperidin-3-yl]-1H-1,2,4-triazol-5-yl)phenyl]methyl}-4-iodobenzamide: $^1$H NMR (400 MHz, d4-MeOH): δ 8.58 (s, 1H), 8.18 (s, 1H), 7.98 (d, 1H), 7.81 (d, 2H), 7.62 (m, 2H), 7.40 (m, 2H), 4.62(s, 2H), 3.64 (m, 2H), 3.42 (m, 2H), 3.17 (m, 1H), 2.38 (m, 1H), 2.00 (m, 3H); MS (EI) for $C_{25}H_{25}N_8OI$: 581.16 (MH+).

N-{[3-(5-amino-6-{3-[(3S)-piperidin-3-yl]-1H-1,2,4-triazol-5-yl}pyrazin-2-yl)phenyl]methyl}-3,5-difluorobenzamide: $^1$H NMR (400 MHz, d4-MeOH): δ 8.55 (s, 1H), 8.18 (s, 1H), 7.98 (d, 1H), 7.42 (m, 4H), 7.18 (m, 1H), 4.62(s, 2H), 3.70 (m, 2H), 3.42 (m, 2H), 3.17 (m, 1H), 2.38 (m, 1H), 2.00 (m, 3H); MS (EI) for $C_{25}H_{24}N_8OF_2$: 491.21 (MH+).

N-{[3-(5-amino-6-{3-[(3S)-piperidin-3-yl]-1H-1,2,4-triazol-yl)phenyl]methyl}-4-bromo-2-fluorobenzamide: $^1$H NMR (400 MHz, d4-MeOH): δ 8.50 (s, 1H), 8.18 (s, 1H), 8.00 (d, 1H), 7.62 (t, 1H), 7.42 (m, 4H), 4.62(s, 2H), 3.63 (m, 2H), 3.42 (m, 2H), 3.17 (m, 1H), 2.38 (m, 1H), 2.00 (m, 3H); MS (EI) for $C_{25}H_{24}N_8OFBr$: 553.16 (M+2).

N-{[3-(5-amino-6-{3-[(3S)-piperidin-3-yl]-11-1,2,4-triazol-5-yl}pyrazin-2-yl)phenyl]methyl}4-bromo-2-chlorobenzamide: $^1$H NMR (400 MHz, d4-MeOH): δ 8.50 (s, 1H), 8.18 (s, 1H), 8.00 (d, 1H), 7.62 (s, 1H), 7.42 (m, 4H), 4.62(s, 2H), 3.63 (m, 2H), 3.42 (m, 2H), 3.17 (m, 1H), 2.38 (m, 1H), 2.00 (m, 3H); MS (EI) for $C_{25}H_{24}N_8OClBr$: 567.14 (M+).

3-amino-6-{3-[({[(4-chlorophenyl)amino]carbonyl}amino)methyl]phenyl}-N-[(3S)-piperidin-3-yl]pyrazine-2-carboxamide: $^1$H NMR (400 MHz, d6-DMSO): δ 9.42 (s, 1H), 9.30 (m, 1H), 9.12 (m, 1H), 8.71 (d, 1H), 8.15 (s, 1H), 8.00 (d, 1H), 7.42 (m, 3H), 7.38 (m, 3H), 4.80(br, 2H), 4.40 (s, 2H), 4.35 (m, 1H), 3.60 (m, 1H), 3.20 (m, 3H), 2.72 (m, 1H), 1.80 (m, 4H); MS (EI) for $C_{24}H_{26}N_7O_2Cl$: 480.19 (MH⁺).

Example 61

Scheme 24 depicts synthesis of amides of the invention according to formula I, from corresponding esters. In general, esters, for example pyrazine ester (ci), are combined with amines, for example as depicted, to give amides, for example (cii), according to formula I.

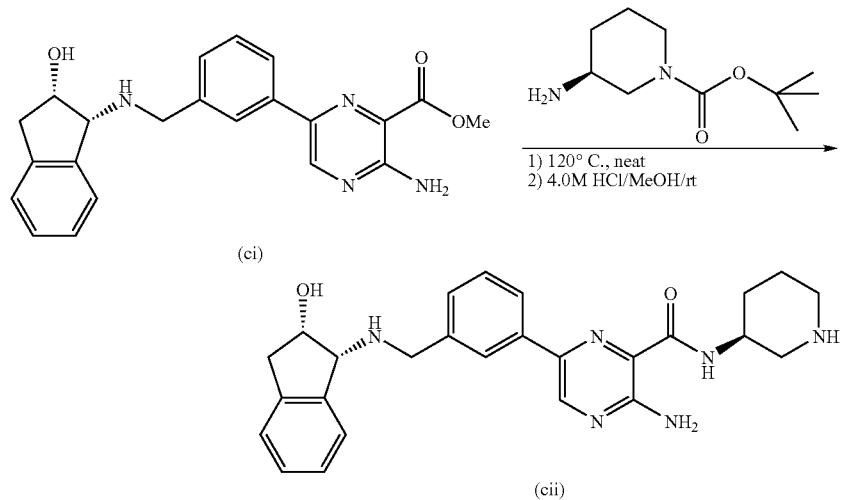

3-amino-6-[3-({[(1R,2S)-2-hydroxy-2,3-dihydro-1H-inden-1-yl]amino}methyl)phenyl]-N-[(3S)-piperidin-3-yl]pyrazine-2-carboxamide A mixture of 3-amino-6-{3-[(2-hydroxy-indan-1-ylamino)-methyl]-phenyl}-pyrazine-2-carboxylic acid methyl ester (400.0 mg, 1.02 mmol) and 1,1-dimethylethyl (3S)-3-aminopiperidine-1-carboxylate (970.0 mg, 4.84 mmol) was heated to 120° C. overnight. The reaction mixture was poured into water (100 mL), and extracted with ethyl acetate (2×50 mL) then dried over anhydrous sodium sulfate and filteration, concentration and purified by column chromatography (3% MeOH/Dichloromethane) and subsequently it was treated with 4.0 M HCl in dioxane (20 mL) to give 3-amino-6-[3-({[(1R,2S)-2-hydroxy-2,3-dihydro-1H-inden-1-yl]amino}methyl)phenyl]-N-[(3S)-piperidin-3-yl]pyrazine-2-carboxamide, 275.0 mg (58.7% yield). ¹H NMR (400 MHz, d4-MeOH): δ 8.72 (s, 2H), 8.18 (s, 1H), 7.80 (d, 1H), 7.60 (m, 2H), 7.38 (m, 3H), 4.80 (s, 1H), 4.50(s, 2H), 4.40 (m, 1H), 3.65 (m, 2H), 3.42 (m, 5H), 3.16 (m, 2H), 2.15 (m, 2H), 1.87 (m, 1H); MS (EI) for $C_{26}H_{30}N_6O_2$: 459.31 (MH⁺).

Example 62

3-Amino-6-(3-{[(1S)-2,3-dihydro-1H-inden-1-ylamino]methyl}phenyl)-N-ethylpyrazine-2-carboxamide To a solution of 3-amino-N-ethyl-6-[3-(hydroxymethyl)phenyl]pyrazine-2-carboxamide (566.1 mg, 1.0 eq) in dichloromethane (20 mL) were added carbon tetrabromide (749.8 mg, 1.1 eq), triphenylphosphine (600 mg, 1.1 eq) at ambient temperature. After being stirred for 7 h, the reaction mixture was partitioned with dichloromethane (10 mL×3), washed with brine. The organic layer was combined and dried over anhydrous magnesium sulfate. Filteration and concentration in vacuo gave a crude product. Purification by column chromatography afforded the 3-amino-6-[3-(bromomethyl)phenyl]-N-ethylpyrazine-2-carboxamide (534 mg, 77% yield):

¹H NMR (400 MHz, DMSO-d6): δ 8.87 (m, 2H), 8.84 (s, 2H), 8.23 (m, 1H), 7.61 (bs, 1H), 7.45 (m, 1H), 4.77 (s, 2H), 3.38 (m, 2H), 1.16 (m, 3H).

The 3-amino-6-[3-(bromomethyl)phenyl]-N-ethylpyrazine-2-carboxamide (112 mg, 1.0 eq) was dissolved in acetonitrile (5 mL) and treated with (1S)-2,3-dihydro-1H-inden-1-amine (133.8 mg, 3.0 eq), diisopropylethylamine (69.3 mg, 1.6 eq) at ambient temperature. After being stirred for 7 h, the white suspension was filtered on Celite and concentrated in vacuo. The resulting residue was purified by flash column chromatography to give the 3-amino-6-(3-{[(1S)-2,3-dihydro-1H-inden-1-ylamino]methyl}phenyl)-N-ethylpyrazine-2-carboxamide (50.2 mg, 39% yield): ¹H NMR (400 MHz, CD₃OD): δ 8.72 (s, 1H), 8.21 (s, 1H), 8.11 (d, 1H), 7.61 (d, 1H), 7.58 (t, 1H), 7.49 (d, 1H), 7.39 (d, 2H), 7.39 (d, 2H), 7.37 (m, 1H), 4.38 (s, 2H), 3.47 (m 1H), 3.23 (m, 1H), 3.01 (m, 1H), 2.64 (m, 1H), 2.39 (m, 1H); MS (EI) for $C_{23}H_{25}N_5O$: 388.22 (MH⁺).

3-Amino-6-(3-{[(5,7-difluoro-2,3-dihydro-1H-inden-1-yl)amino]methyl}phenyl)-N-ethylpyrazine-2-carboxamide: The 3-Amino-6-[3-(bromomethyl)phenyl]-N-ethylpyrazine-2-carboxamide (100 mg, 1.0 eq) was dissolved in acetonitrile (5 mL) and treated with [(1S)-5,7-difluoro-2,3-dihydro-1H-inden-1-yl]amine (151 mg, 3.0 eq), diisopropylethylamine (62 mg, 1.6 eq) at ambient temperature. After being stirred for 8 h, the white suspension was concentrated in vacuo and purified by flash column chromatography to give the title compound as colorless oil, which was dissolved in ethyl acetate (10 mL) and treated 1M HCl in ether. The resulting precipitate was filtered, washed with ether (2×2mL), and dried to afford 42mg (12% yield) of 3-amino-6-(3-{[(5,7- difluoro-2,3-dihydro-1H-inden-1-yl)amino]methyl}phenyl)-N-ethylpyrazine-2-carboxamide hydrochloride as a yellow solid: $^1$H NMR (400 MHz, CD$_3$OD): δ 8.71 (s, 1H), 8.22 (s, 1H), 8.13 (d, 1H), 7.57 (t, 1H), 7.51 (m, 1H), 7.06 (m, 1H), 6.98 (m, 1H), 5.08 (m, 1H), 4.38 (q, 2H), 3.45 (m, 2H), 3.39 (m, 1H), 3.05 (m, 1H), 2.84 (m, 1H), 2.53 (m, 1H); MS (FI) for C$_{23}$H$_{23}$NSOF$_2$: 424.16 (MH$^+$).

3-Amino-6-(3-{[(1S)-2,3-dihydro-1H-inden-1-ylamino]methyl}phenyl)-N-(naphthalen-2-ylmethyl)pyrazine-2-carboxamide: To a solution of methyl 3-amino-6-(3-{[(1S)-2,3-dihydro-1H-inden-1-ylaminomethyl}phenyl)pyrazine-2-carboxylate (1.0 eq) in methyl alcohol was added 2-aminonaphthalene (10.0 eq) and the reaction mixture was allowed to heat at 85° C. overnight. The solvent was removed followed by preparative HPLC (0.1% TFA in water/0.1% TFA in CH$_3$CN), which was neutralized by aqueous saturated sodium bicarbonate solution and partitioned with ethyl acetate. The aqueous phase was extracted once with additional ethyl acetate. The combined organic layers were washed with saturated aqueous sodium chloride then dried over anhydrous magnesium sulfate. Filtration and concentration to ca. 1 mL followed by addition of 1.0 M HCl in ether. The resulting precipitate was filtered and dried to give 3-amino-6-(3-{[(1S)-2,3-dihydro-1H-inden-1-ylamino]methyl}phenyl)-N-(naphthalen-2-ylmethyl)pyrazine-2-carboxamide hydrochloride as a yellow solid: $^1$H NMR (400 MHz, CD$_3$OD): δ 8.66 (s, 1H), 8.10 (d, 1H), 8.01 (m, 1H), 7.82 (d, 1H), 7.78 (d, 1H), 7.44 (m, 4H), 7.39 (m, 2H), 7.30 (m, 2H), 7.21 (m, 1H), 5.04 (s, 2H), 4.79 (m, 1H), 4.21 (s, 2H), 3.12 (m, 1H), 2.90 (m, 1H), 2.51 (m, 1H), 2.20 (m, 1H); MS (EI) for C$_{32}$H$_{29}$N$_5$O: 501.17 (MH$^+$).

3-Amino-N-cyclohexyl-6-(3-{[(1S)-2,3-dihydro-1H-inden-1-ylamino]methyl}phenyl)pyrazine-2-carboxamide: $^1$H NMR (400 MHz, CD$_3$OD): δ 8.70 (s, 1H), 8.11 (m, 2H), 7.62 (m, 2H), 7.53 (m, 1H), 7.41 (m, 2H), 7.33 (m, 1H), 4.40 (s, 2H), 3.93 (m, 1H), 3.15 (m, 1H), 2.75 (m, 1H), 2.41 (m, 1H), 2.00 (m, 2H), 1.84 (m, 2H), 1.75 (m, 1H), 1.50 (m, 2H); MS (EI) for C$_{27}$H$_{31}$N$_5$O: 442.24 (MH$^+$).

3-Amino-6-(3-{[(1S)-2,3-dihydro-1H-inden-1-ylamino]methyl}phenyl)-N-(pyridin-4-ylmethyl)pyrazine-2-carboxamide: $^1$H NMR (400 MHz, CD$_3$OD): δ 8.78 (m, 3H), 8.70 (m, 1H), 8.14 (m, 3H), 7.74 (d, 1H), 7.57 (t, 1H), 7.50 (m, 1H), 7.38 (m, 2H), 7.22 (m, 1H), 4.92 (s, 2H), 4.40 (s, 2H), 3.21 (m, 1H), 3.00 (m, 1H), 2.61 (m, 1H), 2.42 (m, 1H); MS (EI) for C$_{27}$H$_{31}$N$_5$O: 451.12 (MH$^+$).

3-Amino-6-(3-{[(1S)-2,3-dihydro-1H-inden-1-ylamino]methyl}phenyl)-N-(2-pyrrolidin-1-ylethyl)pyrazine-2-carboxamide: $^1$H NMR (400 MHz, CD$_3$OD): δ 8.83 (s, 1H), 8.78 (s, 1H), 8.15 (d, 1H), 7.91 (d, 1H), 7.56 (m, 2H), 7.41 (m, 2H), 7.38 (m, 1H), 4.41 (s, 2H), 3.82 (m, 4H), 3.54 (m, 2H), 3.24 (m, 1H), 3.18 (m, 1H), 3.05 (m, 1H), 2.83 (m, 1H) 2.43 (m, 1H), 2.17 (m, 2H), 2.10 (m, 2H); MS (EI) for C$_{27}$H$_{32}$N$_6$O: 457.21 (MH$^+$).

3-Amino-6-(3-{[(1S)-2,3-dihydro-1H-inden-1-ylamino]methyl}phenyl)-N-(2-piperidin-1-ylethyl)pyrazine-2-carboxamide: $^1$H NMR (400 MHz, CD$_3$OD): δ 8.88 (t, 1H), 8.76 (s, 1H), 8.09 (m, 1H), 7.79 (d, 1H), 7.54 (m, 2H), 7.38 (m, 2H), 7.31 (m, 1H), 4.92 (m, 1H), 4.42 (s, 1H), 4.4-3.8 (m, 4H), 3.83 (t, 1H), 3.72 (d, 1H), 3.44 (t, 1H), 3.40 (m,1H), 3.05 (m, 2H), 2.66 (m, 1H), 2.52 (m, 1H), 1.80 (m, 4H), 1.49 (m, 1); MS (EI) for C$_{28}$H$_{34}$N$_6$O: 471.20 (MH$^+$).

3-amino-6-(3-{[(1S)-2,3-dihydro-1H-inden-1-ylamino]methyl}phenyl)-N-(2-morpholin-4-ylethyl)pyrazine-2-carboxamide: $^1$H NMR (400 MHz, CD$_3$OD): δ 8.90 (s, 1H), 8.75 (s, 1H), 8.08 (m, 1H), 7.78 (d, 1H), 7.57 (d, 2H), 7.38 (m, 2H), 7.32 (m, 1H), 4.43 (s, 2H), 4.25 (m, 3H), 3.94 (t, 2H), 3.87 (m, 2H), 3.77 (m, 2H), 3.57 (t, 2H), 3.32 (m, 2H), 3.04 (m, 1H), 2.66 (m, 1H), 2.51 (m, 1H); MS (EI) for C$_{27}$H$_{32}$N$_6$O$_2$: 471.20 (MH$^+$).

3-amino-N-(cyclopropylmethyl)-6-(3-{[(1S)-2,3-dihydro-1H-inden-1-ylamino}methyl}phenyl)pyrazine-2-carboxamide: $^1$H NMR (400 MHz, CD$_3$OD): δ 8.58 (s, 1H), 8.13 (t, 1H), 7.91 (s, 1H), 7.72 (m, 1H), 7.40 (m, 3H), 7.17 (m, 2H), 4.32 (t, 1H), 3.45 (s, 2H), 3.33 (t, 2H), 3.02 (m, 1H), 2.72 (m, 1H), 2.46 (m, 1H1), 1.90 (m, 1H), 1.20 (m, 2H), 0.55 (m, 2H), 0.37 (m, 2H); MS (EI) for C$_{25}$H$_{27}$N$_5$O: 414.21 (MH$^+$).

3-Amino-6-(3-{[(1S)-2,3-dihydro-1H-inden-1-ylamino]methyl}phenyl)-N-(phenylmethyl)pyrazine-2-carboxamide: $^1$H NMR (400 MHz, CD$_3$OD): δ 8.70 (s, 1H), 8.39 (m, 1H), 8.14 (m, 1H), 7.66 (d, 1H), 7.54 (t, 1H), 7.52 (m, 1H), 7.40 (m, 3H), 7.11 (m, 1H), 7.24 (m, 1H), 4.66 (s, 2H), 4.39 (s, 2H), 3.23 (m, 1H), 3.02 (m, 1H), 2.61 (m, 1H), 2.41 (m, 1H); MS (EI) for C$_{28}$H$_{27}$N$_5$O: 451.20 (MH$^+$).

3-Amino-6-(3-{[(1S)-2,3-dihydro-1H-inden-1-ylamino]methyl}phenyl)-N-(2-phenylethyl)pyrazine-2-carboxamide: $^1$H NMR (400 MHz, CD$_3$OD): δ 8.68 (s, 1H0, 8.35 (m, 1H), 8.08 (m, 1H), 7.69 (d, 1H), 7.57 (m, 2H), 7.40 (m, 1H), 7.32 (m, 6H), 7.21 (m, 1H), 4.95 (m, 1H), 4.39 (s, 2H), 3.64 (q, 2H), 3.23 (m, 1H), 3.06 (m, 1H1), 3.92 (t, 2H), 2.65 (m, 1H), 2.42 (m, 1H); MS (EI) for C$_{29}$H$_{29}$N$_5$O: 464.20 (MH$^+$).

3-Amino-6-(3-{[(1S)-2,3-dihydro-1H-inden-1-ylamino]methyl}phenyl)-N-[2-(dimethylamino)ethyl]pyrazine-2-carboxamide: $^1$H NMR (400 MHz, CD$_3$OD): δ 8.708 (s, 1H), 8.74 (m, 1H), 8.13 (m, 1H), 7.58 (d, 1H), 7.59 (t, 1H), 7.48 (m, 1H), 7.40 (m, 2H), 7.35 (m, 1H), 4.40 (s, 2H), 3.78 (t, 2H), 3.50 (t, 2H), 3.59 (m, 1H), 3.02 (m, 7H), 2.65 (m, 1H), 2.45 (m, 1H); MS (EI) for C$_{25}$H$_{30}$N$_6$O: 431.22 (MH$^+$).

3-Amino-6-(3-{[(1S)-2,3-dihydro-1H-inden-1-ylamino]methyl}phenyl)-N-[2-(1H-imidazol-4-yl)ethyl]pyrazine-2-carboxamide: $^1$H NMR (400 MHz, CD$_3$OD): δ 8.81 (s, 1H), 8.65 (s, 1H), 8.63 (s, 1H), 8.10 (d, 1H), 7.73 (d, 1H), 7.56 (m, 2H), 7.41 (m, 2H), 7.38 (m, 1H), 4.41 (m, 2H), 3.80 (t, 2H), 3.28 (m, 1H), 3.17 (t, 2H), 3.04 (m, 1I1), 2.65 (m, 1H) 2.57 (m, 1H), 2.17 (m, 2H); MS (EI) for C$_{26}$H$_{27}$N$_7$O: 454.18 (MH$^+$).

3-Amino-6-(3-{[(1S)-2,3-dihydro-1H-inden-1-ylamino]methyl}phenyl)-N-[2-(methylamino)ethyl]pyrazine-2-carboxamide: $^1$H NMR (400 MHz, CD$_3$OD): δ 8.80 (s, 1H), 8.78 (s, 1H), 8.12 (d, 1H), 7.79 (d, 1H), 7.57 (m, 2H1), 7.39 (m, 2H), 7.33 (m, 1H), 4.40 (s, 2H), 3.82 (t, 2H), 3.27 (m, 1H), 3.17 (t, 21), 3.02 (m, 1H), 2.67 (m, 1H) 2.43 (m, 1H); MS (EI) for C$_{24}$H$_{28}$N$_6$O: 417.21 (MH$^+$).

3-Amino-6-(3-{[(1S)-2,3-dihydro-1H-inden-1-ylamino]methyl}phenyl)-N-[3-(dimethylamino)propyl]pyrazine-2-carboxamide: $^1$H NMR (400 MHz, CD$_3$OD): δ 8.80 (s, 1H), 8.72 (s, 1H), 8.11 (d, 1H), 7.79 (d, 1H), 7.58 (m, 2H), 7.39 (m, 2H), 7.32 (m, 1H), 4.40 (s, 2H), 3.61 (t, 2H), 3.52 (m, 5H), 3.05 (m, 1H), 2.71 (m, 1H) 2.49 (m, 1H), 2.12 (m, 2H); MS (E) for C$_{26}$H$_{32}$N$_6$O: 445.21 (MH$^+$).

3-Amino-6-(3-{[(1S)-2,3-dihydro-1H-inden-1-ylamino]methyl}phenyl)-N-[3-(1H-imidazol-1-yl)propyl]pyrazine-2-carboxamide: $^1$H NMR (400 MHz, CD$_3$OD): δ 9.10 (s, 1H), 8.68 (s, 1H), 8.03 (d, 2H), 7.51 (m, 2H), 7.46 (m, 3H), 7.30.(d, 1H), 7.22 (m, 2H), 4.31 (m, 4H), 3.48 (t, 2H), 3.41 (m, 1H), 2.93 (m, 1H), 2.52 (m, 1H) 2.38 (m, 1H), 2.23 (m, 1H); MS (EI) for C$_{27}$H$_{29}$N$_7$O: 468.18 (MH$^+$).

3-Amino-6-(3-{[(1S)-2,3-dihydro-1H-inden-1-ylamino]methyl}phenyl)-N-[3-(methylamino)propyl]pyrazine-2-carboxamide: $^1$H NMR (400 MHz, CD$_3$OD): δ 8.64 (s, 1H), 8.63 (s, 1H), 8.02 (d, 1H), 7.43 (m, 2H), 7.31 (m, 2H), 7.22 (m, 1H), 4.85 (m, 1H), 4.31 (s, 2H), 3.50 (t, 2H), 3.18 (m, 1H), 2.95 (m, 311), 2.62 (s, 2H) 2.53 (m, 1H), 2.37 (m, 1H), 1.98 (m, 1H); MS (EI) for C$_{25}$H$_{30}$N$_6$O: 431.22 (MH$^+$).

3-Amino-6-(3-{[(1S)-2,3-dihydro-1H-inden-1-ylamino]methyl}phenyl)-N-(3-pyrrolidin-1-ylpropyl)pyrazine-2-carboxamide: $^1$H NMR (400 MHz, CD$_3$OD): δ 8.83 (s, 1H), 8.73 (s, 1H), 8.10 (d, 1H), 7.79 (d, 1H), 7.59 (m, 211), 7.38 (m, 2H), 7.32 (m, 1H), 4.43 (s, 2H), 3.67 (m, 4H), 3.20 (m, 4H), 2.63 (m, 2H) 2.48 (m, 1H), 2.14 (m, 1H), 2.02 (m, 2H); MS (EI) for C$_{28}$H$_{34}$N$_6$O: 471.22 (MH$^+$).

3-Amino-N-1-azabicyclo[2.2.0]oct-3-yl-6-(3-{[(1S)-2,3-dihydro-ylamino]methyl}phenyl)pyrazine-2-carboxamide: $^1$H NMR (400 MHz, CD$_3$OD): δ 8.77 (s, 1H), 8.45 (m, 1H), 8.12 (d, 1H), 7.52 (d, 1H), 7.56 (t, 2H), 7.49 (d, 1H), 7.40 (d, 2H), 7.35 (m, 1H), 4.55 (m, 1H), 4.40 (s, 2H), 3.79 (d, 2H), 3.63 (d, 1H), 3.03 (m, 1H), 2.68 (m, 1H), 2.43 (m, 2H) 2.31 (m, 1H), 2.15 (m, 2H), 2.31 (m, 1H), 2.15 (m, 2H), 1.83 (m, 1H); MS (EI) for C$_{28}$H$_{32}$N$_6$O: 469.13 (MH$^+$).

3-Amino-N-[(3R)1-azabicyclo[2.2.0]oct-3-yl]-6-(3-{[(1S)-2,3-dihyddro-1H-inden-1-ylamino]methyl}phenyl)pyrazine-2-carboxamide: $^1$H NMR (400 MHz, DMSO-d6): δ 10.22 (bs, 1H), 10.10 (m, 1H), 9.95 (m, 1H), 9.08 (d, 1H), 8.93 (s, 2H), 8.12 (m, 1H), 7.91 (d, 1H), 7.70 (bs, 2H), 7.50 (d, 2H), 7.37 (d, 2H), 7.31 (m, 1H), 4.82 (bs, 1H), 4.49 (m, 1H), 4.38 (t, 2H), 4.02 (m, 1H), 3.60 (t, 1H), 3.21 (m, 4H), 2.90 (m, 1H), 2.44 (m, 2H), 2.13 (m, 1H), 1.94 (m, 2H), 1.73 (m, 1H); MS (EI) for C$_{28}$H$_{32}$N$_6$O: 469.15 (MH$^+$).

3-Amino-N-azepan-3-yl-6-(3-{[(1S)-2,3-dihydro-1H-inden-1-ylamino]methyl}phenyl)pyrazine-2-carboxamide: $^1$H NMR (400 MHz, DMSO-d6): δ 9.94 (bs, 2H), 9.58 (bs, 1H), 9.33 (bs, 1H), 9.10 (d, 1H), 8.91 (m, 2H), 8.09 (m, 1H), 7.88 (m, 1H), 7.47 (m, 2H), 7.42 (m, 2H), 7.27 (m, 2H), 4.82 (m, 1H), 4.49 (m, 1H), 4.36 (m, 2H), 3.48 (m, 1H), 3.30 (m, 3H), 3.05 (m, 1H), 2.82 (m, 1H), 2.48 (m, 2H), 2.10 (m, 1H), 2.00 (m, 1H), 1.85 (m, 3H), 1.62 (m, 1H) MS (EI) for C$_{27}$H$_{32}$N$_6$O: 457.12 (MH$^+$).

3-amino-6-(3-{[(1S)-2,3-dihydro-1H-inden-1-ylamino]methyl}phenyl)pyrazine-2-carbohydrazide: $^1$H NMR (400 MHz, d$_6$-DMSO): 9.96 (m, 1H), 8.80 (s, 1H), 8.16 (s, 1H), 8.01 (d, 1H), 7.56 (br s, 2H), 7.38 (m, 3H), 7.19 (m, 1H1), 7.15 (m, 2H), 4.57 (d, 2H), 4.16 (m, 1H), 3.86 (m, 2H), 2.92 (m, 1H), 2.72 (m, 1H), 2.53 (m, 1H), 2.31 (m, 1H), 1.81 (m, 1H); MS (EI) for C$_{21}$H$_{22}$N$_6$O: 375.2 (MH$^+$).

3-amino-6-(3-{[(1S)-2,3-dihydro-1H-inden-1-ylamino]methyl}phenyl)-N-(5-hydroxypentyl)pyrazine-2-carboxamide: $^1$H NMR (400 MHz, CDCl$_3$): 8.59 (s, 1H), 8.18 (t, 1H), 7.95 (s, 1H), 7.70 (d, 1H), 7.39 (m, 3H), 7.21 (m, 3H), 4.35 (t, 1H), 3.98 (m, 2H), 3.60 (m, 2H), 3.47 (m, 2H), 3.03 (m, 1H), 2.84 (m, 1H), 2.47 (m, 1H), 2.04 (br s, 3H), 1.93 (m, 1H), 1.68 (m, 2H), 1.60 (m, 2H), 1.51 (m, 2H); MS (EI) for C$_{26}$H$_{31}$N$_5$O$_2$: 446.2 (MH$^+$).

3-amino-6-(3-{[(1S)-2,3-dihydro-1H-inden-1-ylaminomethyl}phenyl)-N-(4-hydroxybutyl)pyrazine-2-carboxamide: $^1$H NMR (400 MHz, CDCl$_3$): 8.84 (m, 1H), 8.60 (s, 1H), 8.23 (s, 1H), 7.69 (d, 1H), 7.36 (m, 2H), 7.28 (m, 1H1), 7.24 (m, 1H), 7.21 (m, 2H), 4.37 (t, 1H), 3.96 (m, 2H), 3.47 (m, 4H), 3.05 (m, 1H), 2.85 (m, 1H), 2.63 (br s, 2H), 2.46 (m, 1H), 1.98 (m, 1H), 1.76 (m, 2H), 1.63 (m, 2H); MS (E1) for C$_{25}$H$_{29}$N$_5$O$_2$: 432.2 (MH$^+$).

3-amino-6-(3-{[(1S)-2,3-dihydro-1H-inden-1-ylamino]methyl}phenyl)-N'-methylpyrazine-2-carbohydrazide: $^1$H NMR (400 MHz, CDCl$_3$): 9.24 (s, 1H), 8.66 (s, 1H), 7.91 (s, 1H), 7.74 (m, 1H), 7.44 (m, 2H), 7.41 (m, 1H), 7.25 (m, 1h), 7.22 (m, 2H), 4.35 (t, 1H), 4.00 (m, 2H), 3.05 (m, 1H), 2.85 (m, 1H), 2.77 (s, 3H), 2.48 (m, 1H), 1.93 (m, 1H); MS (EI) for C$_{22}$H$_{24}$N$_6$O: 389.2 (MH$^+$).

3-amino-6-(3-{[(1S)-2,3-dihydro-1H-inden-1-ylamino]methyl}phenyl)-N,N-dimethylpyrazine-2-carboxamide: $^1$H NMR (400 MHz, CDCl$_3$): 8.51 (s, 1H), 7.89 (s, 1H), 7.74 (m, 1H), 7.40 (m, 3H), 7.22 (m, 3H), 5.86 (br s, 211), 4.32 (t, 1H), 3.98 (m, 2H), 3.31 (s, 3H), 3.17 (s, 3H), 3.03 (m, 1H), 2.83 (m, 1H), 2.45 (m, 1H), 1.91 (m, 1H); MS EI) for C$_{23}$H$_{25}$N$_5$O: 388.2 (MH$^+$).

Example 63

Synthesis of Compounds According to Formula I, Wherein A is —(C═O)— or —(C═NR$^6$)— Derived from methyl 3-amino-2-pyrazine carboxylate Methyl 3-amino-6-bromopyrazine-2-carboxylate. To a solution of methyl 3-amino-2-pyrazine carboxylate (30.0 g, 200 mmol) in acetic acid (200 mL), bromine (11 mL) was added slowly via addition funnel. After complete addition of bromine, sodium carbonate powder was added slowly until precipitation occurred. The reaction mixture was allowed to stir at room temperature for 2 h. The reaction mixture was reduced to half-volume in vacuo and then diluted with water (500 mL). The reaction mixture was shaken vigorously and the resulting solid was collected using vacuum filtration. The solid was washed with ether to afford a pure yellow solid (91% yield).

3-Amino-6-bromopyrazine-2-carboxylic acid. To a solution of methyl-3-amino-6-bromopyrazine carboxylate (10 g, 43 mmol) in THF:H$_2$O (3:1), lithium hydroxide (6.0 g, 140 mmol) was added. The reaction mixture was stirred at room temperature and monitored by LCMS. The reaction was complete after 1 h. The reaction mixture was poured into 1 N HCl (250 mL), extracted with ethyl acetate (3×, 200 mL), washed with brine (3×, 100 mL), dried over anhydrous sodium sulfate, filtered and concentrated to afford a yellow solid (100% yield).

3-Amino-6-(3-{[(biphenyl-2-ylmethyl)amino]carbonyl}phenyl)-N-[(3S)-piperidin-3-yl]pyrazine-2-carboxamide: To a solution of 3-amino-6-bromopyrazine-2-carboxylic acid (4.0 g, 18 mmol) in DMF, HATU (10.4 g, 27.5 mmol), N,N-diisopropylethylamine (8.5 mL, 27.5 mmol) and (S)-3-amino-1-N-Boc-piperidine (4.0 g, 20 mmol, commercially available from Astatech and Arch Corporation) were added. The reaction was allowed to stir at room temperature for 1 h. The reaction mixture was diluted with water (100 mL), extracted with ethyl acetate (3×, 200 mL), washed with 5% LiCl (3×, 100 mL) and brine (3×, 100 mL), dried over anhydrous sodium sulfate, filtered and concentrated in vacuo to afford a brown solid (MS (ESI-LCMS) for C$_{15}$H$_{22}$BrN$_5$O$_3$: 400 (MH$^+$). This material was taken up in ethylene glycol dimethyl ether (150 mL), and triethylamine (4.6 mL, 45 mmol), Pd(dppf)$_2$Cl$_2$ (2.3 g, 2.75 mmol), 3-carboxyphenyl-boronic acid (3.6 g, 21.8 mmol) and water (15 mL) were added. The reaction was refluxed at 85° C. and monitored by LCMS. The reaction was complete after 3 h. The solvent was removed under reduced pressure to afford a brown solid. The crude product was purified by silica gel chromatography to afford a yellow solid (MS (ESI-LCMS) for C$_{22}$H$_{27}$N$_5$O$_5$: 442 (MH$^+$). A portion of this intermediate (50 mg, 0.11 mmol) was dissolved in DMF (1 mL), and HATU (62.7 mg, 0.165 mmol), N,N-diisopropylethylamine (29 μL, 0.16 mmol) and 2-phenylbenzylamine (24.2 mg, 0.132 mmol) were added. The reaction was stirred at room temperature and monitored by LCMS. The reaction was complete after 1 h. The crude product was purified by preparative HPLC and lyophilized to afford a white solid (MS (ESI-LCMS) for C$_{35}$H$_{38}$N$_6$O$_4$: 607 (MH$^+$). This material was dissolved in methanol (2 mL), and 4M HCl in dioxane (2 mL) was added. The reaction was stirred at room temperature and monitored by LCMS. The reaction was complete after 1 h. The solvents were removed under reduced pressure to afford a yellow gel product. The yellow gel product was dissolved in acetonitrile-water (2 mL), frozen and lyophilized to afford a yellow solid: $^1$H NMR (400 MHz, d$_6$-DMSO): δ 9.25 (t, 1H), 9.05 (d, 1H), 8.95 (s, 1H), 8.9 (d, 1H), 8.85 (d, 1H), 8.6 (s, 1H), 8.35 (d, 1H), 7.9 (d, 1H), 7.6 (t, 1H), 7.5-7.3 (m, 8H), 7.25 (m, 1H), 4.5 (d, 2H), 4.35 (m, 1H), 3.25 (m, 2H), 3.05 (m, 1H), 2.75 (m, 1H), 1.95-1.7 (m, 4H). MS (EI) for C$_{30}$H$_{30}$N$_6$O$_2$: 507 (MH$^+$).

3-Amino-6-(3-{[(1S)-2,3-dihydro-1H-inden-1-ylamino] carbonyl}phenyl)-N-[(3S)-pyrrolidin-3-yl]pyrazine-2-carboxamide: To a solution of 3-carboxyphenyl boronic acid (20.0 g, 120 mmol) in thionyl chloride (120 mL) was added DMF (3 drops). The reaction mixture was allowed to stir at room temperature overnight. Excess thionyl chloride was removed under reduced pressure to afford a white solid. To a solution of this residue and triethylamine (33.4 mL, 240 mmol) in TBF (200 mL) at 0° C. was added slowly (S)-(+)-1-aminoindane (19.2 g, 144 mmol) in MeOH (100 mL) via addition funnel. After addition of (S)-(+)-1-aminoindane, the reaction mixture was stirred at room temperature and monitored by LCMS. The reaction was complete after 3 h. The reaction mixture was then concentrated under reduced pressure to afford a white solid. This material (33.72 g, 120 mmol) was added to a solution of methyl-3-amino-6-bromopyrazine carboxylate (23.2 g, 100 mmol) in DMF (200 mL), and triethylamine (28 mL, 200 mmol), Pd(dppf)$_2$Cl$_2$ (8.16 g, 10 mmol) and water (20 mL) were added. The reaction mixture was stirred at 80° C. overnight. The reaction mixture was cooled to room temperature. Water (800 mL) was added and the precipitated solid was collected via vacuum filtration and subsequently washed with water and ether. The desired product (80% pure) was carried to the next step without further purification (MS (ESI-LCMS) for C$_{22}$H$_{19}$N$_3$O$_3$: 375.2 (MH$^+$). To a solution of this material in TBF:H$_2$O (3:1), was added lithium hydroxide (13.85 g, 330 mmol). The reaction was stirred at room temperature and monitored by LCMS. The reaction was complete after 3 h. The reaction mixture was poured into 1N HCl (500 mL) and shaken vigorously. Vacuum filtration was used to collect the resulting yellow solid, which was confirmed by LCMS. Extraction of the aqueous layer with ethyl acetate (3×, 1L) was used to recover the remaining product. The combined organic layers were washed with brine (3×, 200 mL), dried over anhydrous sodium sulfate, filtered and concentrated in vacuo to afford a yellow solid (MS (ESI-LCMS) for C$_{21}$H$_{17}$N$_3$O$_3$: 360.2 (MH$^+$). To a portion of this yellow solid (2.0 g, 5.4 mmol) in DMF (50 mL) was added HATU (3.1 g, 8.1 mmol), N,N-diisopropylethylamine (2.8 mL, 16 mmol) and (S)-3-amino-1-N-Boc-pyrrolidine (1.5 g, 8.1 mmol). The reaction mixture was stirred at room temperature and monitored by LCMS. The reaction was complete after 1 h. The reaction mixture was diluted with water (200 mL), extracted with ethyl acetate (3×, 300 mL), washed with 5% LiCl (3×, 100 mL) and brine (3×, 200 mL), dried over anhydrous sodium sulfate, filtered and concentrated under reduced pressure. The material was purified by silica gel chromatography to afford a yellow solid (2.2 g, 92% yield) (MS (ESI-LCMS) for C$_{30}$H$_{34}$N$_6$O$_{34}$: 443.2 (MH$^+$). This material was dissolved in methanol (10 mL), and 4M HCl in dioxane (10 mL) was added. The reaction mixture was stirred at room temperature and monitored by LCMS. The reaction was complete after 2 h. The reaction mixture was concentrated in vacuo to afford a yellow solid as an HCl salt. $^1$H NMR (400 MHz, d$_6$-DMSO): δ 9.1 (d, 1H), 8.95 (s, 1H), 8.75 (d, 1H), 8.65 (s, 1H), 8.35 (d, 1H), 7.9 (d, 1H), 7.6 (t, 1H), 7.3-7.2 (m, 4H), 5.6 (q, 1H), 4.4 (m, 1H), 3.1-2.8 (m, 6H), 2.0 (m, 2H), 1.7 (m, 2H), 1.85 (m, 2H). MS (EI) for C$_{25}$H$_{26}$N$_6$O$_2$: 443 (MH$^+$).

3-Amino-6-{3-[(benzylamino)carbonyl]phenyl}-N-methoxy-N-methylpyrazine-2-carboxamide: 3-Carboxyphenylboronic acid (10 g, 61 mmol) was dissolved in thionyl chloride (60 mL) and DMF (catalytic), and the mixture was stirred at room temperature for 12 h. Thionyl chloride and DMF were removed under reduced pressure and the acid chloride was isolated as a white solid. A THF (100 mL) solution of the acid chloride was added dropwise to a MeOH (100 mL) solution of benzylamine (7 mL, 64 mmol) and triethylamine (18 mL), and the mixture was stirred at room temperature for 2 h. The solvent was removed under reduced pressure to give the benzamide as a white solid (MS (EI) for C$_{14}$H$_{14}$BN$_2$O$_3$: 256 (MH$^+$). A mixture containing this benzamide (15 g, 59 mmol), methyl-3-amino-6-bromopyrazine carboxylate (15 g, 66 mmol), tris(dibenzylideneactone)dipalladium (1.4 g, 1.5 mmol), 1,1'-bis(diphenylphosphine) ferrocene (1.0 g, 1.9 mmol), and triethylamine (100 mL, 720 mmol) in DMF (200 mL) and water (30 mL), was heated at 80° C. for 48 h. The reaction mixture was cooled to room temperature and diluted with water and ethyl acetate. The layers were separated and the organic layer was extracted 2× with 5% aqueous lithium chloride, dried over sodium sulfate, filtered, and concentrated under reduced pressure to give a brown solid. The product was purified by triturating the brown solid with dichloromethane (100 mL) and filtering the resultant mixture to give the methyl ester as a yellow solid (3.0 g, 15% yield). N,O-Dimethylyhdroxylamine was dissolved in anhydrous dichloromethane (15 mL). Trimethylaluminum (7 mL of a 2.0 M solution in hexanes) was added dropwise at 0° C. under N$_2$ and the solution was warmed to room temperature and stirred for 30 min. The previously prepared methyl ester (1.0 g, 2.8 mmol) was stirred in anhydrous dichloromethane (40 mL) and this solution was added in small portions to the reaction under N$_2$. The resulting solution was stirred at room temperature for 12 h. The reaction mixture was acidified with 0.5 N aqueous hydrochloric acid and extracted 3× with dichloromethane. The combined organic layers were washed with brine, dried over sodium sulfate, filtered, and concentrated under reduced pressure to give the product as a yellow solid (0.82 g, 76% yield). $^1$H NMR (400 MHz, d$_6$-DMSO): δ 9.23 (t, 1H), 8.50 (s, 1H), 8.16 (d, 1H), 7.93 (d, 1H), 7.62 (t, 1H), 7.43-7.38 (m, 5M), 7.35-7.30 (m, 1H), 6.82 (br s, 2H), 4.58 (d, 2H), 3.76 (s, 3H), 3.40 (s, 3H). MS (EI) for C$_{20}$H$_{21}$N$_5$O$_3$: 392 (MH$^+$).

3-{5-Amino-6-[(3-fluorophenyl)carbonyl]pyrazin-2-yl}-N-(phenylmethyl)benzamide: 3-Fluorophenylmagnesium bromide (1.5 mL of a 0.5 M solution in TBF, 0.75 mmol) was added dropwise to a THF (10 mL) solution of 3-amino-6-{3-[(benzylamino)carbonyl]phenyl}-N-methoxy-N-methylpyrazine-2-carboxamide (0.10 g, 0.25 mmol) at 0° C. under N$_2$. The reaction mixture was warmed to room temperature and stirred for 2 h. The mixture was diluted with water and extracted 3× with ethyl acetate. The combined organic layers were dried with magnesium sulfate, filtered, and concentrated under reduced pressure to give a yellow oil. The crude product was separated by preparative HPLC and lyophilized to give a yellow solid (4 mg, 4% yield). $^1$H NMR (400 MHz, d$_6$-DMSO): δ 9.10 (t, 1H), 9.05 (s, 1H), 8.42 (bs, 1H), 8.01 (m, 2H), 7.86-7.80 (m, 2H), 7.74 (d, 1H), 7.57-7.51 (m, 2H), 7.47-7.43 (m, 2H), 7.38-7.32 (m, 2H), 7.28-7.24 (m, 2H), 6.47-6.59 (m, 1H), 4.50 (d, 2H). MS (EI) for C$_{25}$H$_{19}$FN$_4$O$_2$: 427 (MH$^+$).

3-(5-Amino-6-{(1E)-N-[4-(methyloxy)phenyl] ethanehydrazonoyl}pyrazin-2-yl)-N-(phenylmethyl)benzamide: A solution of 3-amino-6-{3-[(benzylamino)carbonyl] phenyl}-N-methoxy-N-methylpyrazine-2-carboxamide (0.10 g, 0.25 mmol) in THF (5 mL) was cooled to 0° C., and a solution of CH₃MgCl (0.75 mL, 1 M in THF, 3.0 equiv.) was added slowly. The mixture was allowed to warm to room temperature over 1.5 hr. The mixture was then cooled to 0° C. and quenched slowly with saturated NH₄Cl solution. The mixture was extracted with ethyl acetate, washed with brine then water. The ethyl acetate extract was evaporated to afford the corresponding methyl ketone as a yellow solid. To a portion of this residue (35 mg, 0.1 mmol) in ethanol in a pressure tube (5 mL) was added 4-methoxyphenylhydrazine hydrochloride (52 mg, 3 mmol). This mixture was then heated to for 12 h. The solvent was removed under reduced pressure and the crude mixture was dissolved in a minimal amount of methanol and run through a plug of silica gel to give the product as a white solid (33 mg, 70% yield). $^1$H NMR (400 MHz, CDCl₃): δ 8.40 (m, 1H), 8.0 (m, 2H), 7.80 (m, 2H), 7.25 (m,1H), 7.2 (m, 4H), 6.9 (m, 4H), 4.8 (s, 2H), 3.8 (s, 3H), 2.6 (s, 3H). MS (EI) for $C_{27}H_{26}N_6O_2$: 467 (MH⁺).

3-(5-Amino-6-formylpyrazin-2-yl)-N-benzylbenzamide: A solution of 3-amino-6-{3-[(benzylamino)carbonyl]phenyl}-N-methoxy-N-methylpyrazine-2-carboxamide (2.5 g, 6.4 mmol) in THF (20 mL) was cooled to 0° C. Under N₂ lithium aluminum hydride (0.364g, 9.58 mmol) was added and the reaction was stirred at 0° C. for 1 h. The mixture was then quenched with H₂O at 0° C. Removal of solids via filtration, concentration of the filtrate and dissolution of the solid residue in H₂O followed by washing 3× with dichloromethane gave the product (1.90 g, 89% yield) with sufficient purity to be used without further purification.

3-[5-Amino-6-(morpholin-4-ylmethyl)pyrazin-2-yl]-N-(phenylmethyl)benzamiide: 3-(5-Amino-6-formylpyrazin-2-yl)-N-benzylbenzamide (1.27 g, 3.83 mmol) was dissolved in dichloroethane (30 mL) at 0° C. Morpholine (400 mg, 4.6 mmol), and NaBH(OAc)₃ (2.03 g, 9.58 mmol) were added and the reaction was stirred at room temperature for 20 h. The reaction mixture was diluted with saturated sodium carbonate and extracted 3× with ethyl acetate. The combined ethyl acetate layers were dried over sodium sulfate, filtered, and concentrated iii vacuo to afford the product (1.41 g, 88% yield). $^1$H NMR (400 MHz, d₄-CD₃OD): δ 8.60 (s, 1H), 8.47 (t, 1H), 8.12 (m, 1H), 7.84 (m, 1H), 7.55 (t, 1H), 7.31-7.89 (m, 4H), 7.23-7.26 (m, 1H), 4.61 (s, 2H), 4.43 (s, 2H), 3.32-4.16 (m, 8H). MS (EI) for $C_{23}H_{25}N_5O_2$: 404 (MH⁺).

Using the same or similar synthetic techniques, substituting with the appropriate reagents such as the respective amines, the following compounds of the invention were prepared:

3-{5-Amino-6-[(3,5-difluorophenyl)carbonyl]pyrazin-2-yl}-N-(phenylmethyl)benzamide: $^1$H NMR (400 MHz, d₆-DMSO): δ 9.25 (m, 2H), 8.45 (s, 1H), 8.08 (s, 1H), 8.05 (m, 1H), 8.02 (m, 1H), 7.67-7.53 (m, 5H), 7.35-7.24 (M, 5H), 4.51 (M, 2H). MS (EI) for $C_{25}H_{18}F_2N_4O_2$: 445 (MH⁺).

3-[5-Amino-6-(biphenyl-4-ylcarbonyl)pyrazin-2-yl]-N-(phenylmethyl)benzamide: $^1$H NMR (400 MHz, d₆-DMSO): δ 9.06 (t, 1H), 8.99 (s, 1H), 8.42 (s, 1H), 8.06-8.01 (m, 3H), 7.91 (s, 2H), 7.81-7.78 (m, 3H), 7.73-7.71 (m, 2H), 7.52-7.44 (m, 3H), 7.40-7.36 (m, 1H), 7.27-7.20 (m, 4H), 7.16-7.12 (m, 1H), 4.35 (d, 2H). MS (EI) for $C_{31}H_{24}N_4O_2$: 485 (MH⁺).

3-{5-Amino-6-[(4-chloro-3-fluorophenyl)carbonyl]pyrazin-2-yl}-N-(phenylmethyl)benzamide: $^1$H NMR (400 MHz, d₆-DMSO): δ 9.25 (m, 2H), 8.48 (s, 1H), 8.09 (s, 1H), 8.05 (m, 1H), 8.02 (m, 1H), 7.71-7.51 (m, 5H), 7.35-7.24 (m, 5H), 4.51 (m, 2H). MS (EI) for $C_{25}H_{19}ClFN_4O_2$: 461 (MH⁺).

3-(5-Amino-6-{[2,4-bis(methyloxy)phenyl]carbonyl}pyrazin-2-yl)-N-(phenylmethyl)benzamide: $^1$H NMR (400 MHz, d₆-DMSO): δ 9.11 (m, 1H), 8.95 (s, 1H), 8.36 (s, 1H), 7.91-7.83 (m, 4H), 7.53-7.23 (m, 7H), 6.68-6.62 (m, 2H), 4.50 (M, 2H). 3.85 (s, 3H), 3.65 (s, 3H). MS (EI) for $C_{27}H_{24}N_4O_4$: 469 (MH⁺).

3-(5-Amino-6-{[4-(dimethylamino)phenyl]carbonyl}pyrazin-2-yl)-N-(phenylmethyl)benzamide: $^1$H NMR (400 MHz, d₆-DMSO): δ 9.11 (t, 1H), 8.90 (s, 1H), 8.45 (s, 1H), 8.44 (d, 1H), 8.07 (d, 2H), 7.98 (d, 1H), 7.55 (t, 3H), 7.31-7.30 (m, 4H), 7.28-7.23 (m, 1H), 6.75 (d, 2H), 4.50 (d, 2H), 3.03 (s, 6H). MS (EI) for $C_{27}H_{25}N_5O_2$: 452 (MH⁺).

3-{5-Amino-6-[(4-methylphenyl)acetyl]pyrazin-2-yl}-N-(phenylmethyl)benzamide: $^1$H NMR (400 MHz, d6-DMSO): δ 9.18 (t, 1H), 9.02 (s, 1H), 8.59 (s, 1H), 8.26 (d, 1H), 7.91 (d, 2H), 7.61 (t, 1$), 7.38-7.29 (m, 4H), 7.24-7.17 (m, 3H), 7.08-7.06 (m, 3H), 4.53-4.51 (m, 4H), 2.23 (s, 3H). MS (EI) for $C_{27}H_{24}N_4O_2$: 437 (MH⁺).

1,1-Dimethylethyl 4-({[3-amino-6-(3-{[(phenylmethyl)amino]carbonyl}phenyl)-pyrazin-2-yl]carbonyl}amino)piperidine-1-carboxylate: $^1$H NMR (400 MHz, d₆-DMSO): δ 9.16 (t, 1H), 8.9 (s, 1H), 8.55 (d, 1H), 8.5 (s, 1H), 8.3 (d, 1H), 7.82 (d, 1H), 7.8-7.6 (m, 1H), 7.57 (t, 1H), 7.35-7.2 (m, 5H), 4.5 (d, 2H), 4.0 (m, 3H), 3.0-2.7 (m, 2H), 1.8 (d, 2H), 1.6 (q, 2H), 1.4 (s, 9H). MS(EI) for $C_{29}H_{34}N_6O_4$: 431 (MH⁺).

1,1-Dimethylethyl 4-[({[3-amino-6-(3-{[(phenylmethyl)amino]carbonyl}phenyl)-pyrazin-2-yl]carbonyl}amino)methyl]piperidine-1-carboxylate: $^1$H NMR (400 MHz, d₆-DMSO): δ 9.17 (t, 1H), 8.92 (t, 1H), 8.9 (s, 1H), 8.5 (s, 1I1), 8.35 (d, 1H), 7.35 (d, 1H), 7.57 (d, 1H), 7.35-7.2 (m, 5H), 4.5 (d, 2H), 3.9 (m, 2H), 3.2 (t, 2H), 2.65 (m, 2H), 1.8-1.6 (m, 3H), 1.4 (s, 9H), 1.05 (m, 2H). MS(EI) for $C_{30}H_{36}N_6O_4$: 445 (MH⁺).

3-Amino-6-(3-{[(phenylmethyl)amino]carbonyl}phenyl)-N-piperidin-4-ylpyrazine-2-carboxamide: $^1$H NMR (400 MHz, d₆-DMSO): δ 9.3 (t, 1H), 8.9 (s, 1H), 8.8 (d, 1H), 8.65 (m, 1H), 8.3 (d, 1H), 7.85 (d, 1H), 7.57 (t, 1H), 7.35-7.2 (m, 5H), 4.5 (d, 2H), 4.05 (m, 1H), 3.35 (m, 2H), 3.0 (m, 2H), 2.0-1.8 (m, 4H). MS (EI) for $C_{24}H_{26}N_6O_2$: 431 (MH⁺).

3-Amino-6-(3-{[(phenylmethyl)amino]carbonyl}phenyl)-N-(piperidin-4-ylmethyl)pyrazine-2-carboxamide: $^1$H NMR (400 MHz, d,-DMSO): δ 9.42 (t, 1H), 9.15 (t, 1H), 8.9 (s, 1H), 8.62 (s, 1H), 8.4 (d, 1H), 7.9 (d, 1H), 7.55 (t, 1H), 7.4-7.2 (m, 5H), 4.5 (d, 2H), 3.3-3.2 (m, 4H), 2.9-2.7 (m, 2H), 1.95-1.75 (m, 3H), 1.5-1.35 (m, 2H). MS (EI) for $C_{25}H_{28}N_6O_2$: 445 (MH⁺).

3-[5-Amino-6-(morpholin-4-ylcarbonyl)pyrazin-2-yl]-N-(phenylmethyl)benzamide: $^1$H NMR (400 MHz, d₆-DMSO): δ 9.18 (t, 1H), 8.78 (s, 1H), 8.42 (s, 1H), 8.1 (d, 1H), 7.88 (d, 1H), 7.55 (m, 1H), 7.38-7.24 (m, 5H), 4.55 (d, 2H), 3.78-3.4 (m, 8H). MS (EI) for $C_{23}H_{23}N_5O_3$: 418 (MH⁺).

3-(5-Aminopyrazin-2-yl)-N-(phenylmethyl)benzamide: $^1$H NMR (400 MHz, d₆-DMSO): δ 9.15 (t, 1H), 8.6 (s, 1H), 8.45 (s, 1H), 8.1 (d, 1H), 8.0 (s, 1H), 7.85 (d, 1H), 7.55 (t, 1H), 7.4-7.3 (m, 5H), 6.65 (s, 2H). MS (EI) for $C_{18}H_{16}N_4O$: 305 (MH⁺).

1,1-Dimethylethyl 3-({[3-amino-6-(3-{[(phenylmethyl)amino]carbonyl}phenyl)-pyrazin-2-yl]carbonyl}amino)pyrrolidine-1-carboxylate: $^1$H NMR (400 MHz, d₆-DMSO): δ 9.18 (t, 1H), 8.95 (s, 1H), 8.75 (m, 1H), 8.55 (s, 1H), 8.35 (d, 1H), 7.9 (d, 1H), 7.6 (t, 1H), 7.4-7.3 (m, 4H), 7.25 (m, 1H), 4.55 (m, 3H), 3.6 (m, 1H), 3.45 (m, 1H), 3.3 (m, 2H), 2.15-2.0 (m, 2H), 1.4 (s, 9H). MS (EI) for $C_{28}H_{32}N_6O_4$: 417 (MH⁺).

3-Amino-6-(3-{[(phenylmethyl)amino]carbonyl}phenyl)-N-[(3S)-pyrrolidin-3-yl]pyrazine-2-carboxamide: $^1$H NMR (400 MHz, d₆-DMSO): δ 9.55 (m, 2H), 9.3 (s, 1H), 8.95 (s, 1H), 8.75 (s, 1H), 8.35 (d, 1H), 7.95 (d, 1H), 7.55 (t, 1H), 7.4-7.3 (m, 4H), 7.25 (t, 1H), 4.7 (m, 1H), 4.5 (d, 2H), 3.4-3.2 (m, 2H) 2.3-2.1 (m, 2H), 1.1 (t, 2H). MS (EI) for $C_{23}H_{24}N_6O_2$: 417 (MH+).

3-{5-Amino-6-[(4-methylpiperazin-1-yl)carbonyl]pyrazin-2-yl}-N-(phenylmethyl)benzamide: $^1$H NMR (400 MHz, d$_6$-DMSO): δ 9.15 (t, 1H), 8.75 (s, 1H), 8.45 (s, 1H), 8.18 (d, 1H), 7.85 (d, 1H), 7.55 (t, 1H), 7.35-7.2 (m, 5H), 6.72 (s, 2H), 4,5 (d, 2H), 3.7 (t, 2H), 3.5 (t, 2H), 2.45 (t, 2H), 2.35 (t, 2H), 2.2 (s, 3H). MS (EI) for $C_{24}H_{26}N_6O_2$: 431 (MH+).

3-(5-Amino-6-{[4-(4-fluorophenyl)piperazin-1-yl]carbonyl}pyrazin-2-yl)-N-(phenylmethyl)benzamide: $^1$H NMR (400 MHz, d$_6$-DMSO): δ 9.15 (t, 1H), 8.75 (s, 1H), 8.45 (t, 1H), 8.18 (tt, 1H), 7.85 (m, 1H), 5.75 (m, 1H), 7.3 7.2 (m, 5H), 7.0 (m, 4H), 6.8 (s, 2H), 4.5 (d, 2H), 3.82 (t, 2H), 3.65 (t, 2H), 3.25 (t, 2H), 3.15 (t, 2H). MS (EI) for $C_{29}H_{27}N_6O_2F$: 511 (MH+).

3-(5-Amino-6-{[4-(phenylmethyl)piperazin-1-yl]carbonyl}pyrazin-2-yl)-N-(phenylmethyl)benzamide: $^1$H NMR (400 MHz, d$_6$-DMSO): δ 9.15 (t, 1H), 8.7 (s, 1H), 8.4 (t, 1H), 8.05 (d, 1H), 7.85 (d, 1H), 7.55 (t, 1H), 7.35-7.2 (m, 10H), 6.7 (s, 2H), 4.5 (d, 2H), 3.7 (t, 2H), 3.5 (m, 4H), 2.5-2.4 (m, 4H). MS (EI) for $C_{30}H_{30}N_6O_2$: 507 (MH+).

Methyl N-{[3-amino-6-(3-{[(phenylmethyl)amino]carbonyl}phenyl)pyrazin-2-yl]carbonyl}glycinate: $^1$H NMR (400 MHz, d$_6$-DMSO): δ 9.22 (t, 1H), 9.15 (t, 1H), 8.92 (s, 1H), 8.5 (s, 1H), 8.36 (d, 1H), 7.57 (t, 1H), 7.35-7.2 (m, 5H), 4.5 (d, 2H), 4.05 (d, 2H), 3.65 (s, 3H). MS (EI) for $C_{22}H_{21}N_5O_4$: 420 (MH+).

N-{[3-Amino-6-(3-{[(phenylmethyl)amino]carbonyl}phenyl)pyrazin-2-yl]carbonyl}glycine: $^1$H NMR (400 MHz, d$_6$-DMSO): δ 9.15 (t, 1H), 8.93 (s, 1H), 8.7 (s, 1H), 8.35 (d, 1H), 7.85 (d, 1H), 7.57 (t, 1H), 7.35-7.2 (m, 5H), 4.55 (d, 2H), 4.0 (d, 2H). MS (EI) for $C_{21}H_{19}N_5O_4$: 406 (MH+).

Methyl 1-{[3-amino-6-(3-{[(phenylmethyl)amino]carbonyl}phenyl)pyrazin-2-yl]carbonyl}-L-prolinate: $^1$H NMR (400 MHz, d$_6$-DMSO): δ 9.15 (m, 1H), 8.85-8.75 (s, 1H), 8.45-8.35 (s, 1H), 8.12-7.95 (d, 1H), 7.88 (d, 1H), 7.6 (m, 1H), 7.4-7.25 (m, 5H), 5.25 (m, 1H), 4.5 (m, 4H), 4.0 (t, 1H), 3.6 (s, 3H), 2.4-2.25 (m, 1H), 2.0-1.75 (m, 4H). MS (EI) for $C_{25}H_{25}N_5O_4$: 460 (MH+).

3-[(6aS)-6,11-dioxo-5,6a,7,8,9,11-hexahydro-6H-pyrazino[2,3-e]pyrrolo[1,2-a][1,4]diazepin-2-yl]-N-(phenylmethyl)benzamide: $^1$H NMR (400 MHz, d$_6$-DMSO): δ 11.3 (s, 1H), 9,3 (s, 1H), 9.2 (t, 1H), 8.7 (s, 1H), 8.3 (d, 1H), 8.0 (d, 1H), 7.7 (t, 1H), 6.4-6.2 (m, 5H), 4.5 (m, 3H), 3.7 (m, 1H), 3.5 (m, 1H), 3.0 (s, 1H), 2.0-1.8 (m, 3H). MS (EI) for $C_{24}H_{21}N_5O_3$: 428 (MH+).

Methyl 1-{[3-Amino-6-(3-{[(phenylmethyl)amino]carbonyl}phenyl)pyrazin-2-yl]carbonyl}piperidine-3-carboxylate: $^1$H NMR (400 MHz, d$_6$-DMSO): δ 9.15 (t, 1H), 8.75 (d, 1H), 8.42 (d, 1H), 8.08 (t, 1H), 7.85 (d, 1H), 7.55 (m, 1H), 7.35-7.25 (m, 5H), 6.72 (d, 2H), 4.5 (d, 2H), 4.1-3.9 (m, 1H), 3.65 (m, 2H), 3.45 (s, 2H), 3.25-3.05 (m, 2H), 2.75 (m, 1H), 2.0 (m, 1H), 1.8-1.5 (m, 3H). MS (EI) for $C_{26}H_{27}N_5O_4$: 474 (MH+).

1,1-Dimethylethyl 4-{[3-amino-6-(3-{[(phenylmethyl)amino]carbonyl}phenyl)-pyrazin-2-yl]carbonyl}piperazine-1-carboxylate: $^1$H NMR (400 MHz, d$_6$-DMSO): δ 9.15 (t, 1H), 8.72 (s, 1H), 8.6 (s, 1H), 8.05 (d, 1H), 7.85 (d, 1H), 7.57 (t, 1H), 7.35-7.2 (m, 5H), 6.75 (s, 2H), 4.5 (d, 2H), 3.65 (t, 2H), 3.5-3.35 (m, 6H), 1.4 (s, 9H). MS(EI) for $C_{28}H_{32}N_6O_4$: 417 (MH+).

3-[5-Amino-6-(piperazin-1-ylcarbonyl)pyrazin-2-yl]-N-(phenylmethyl)benzamide: $^1$H NMR (400 MHz, d$_6$-DMSO): δ 9.75 (br s, 2H), 9.1 (t, 1H), 8.8 (s, 1H), 8.45 (s, 1H), 8.05 (d, 1H), 7.86 (d, 1H), 7.55 (t, 1H), 7.35-7.2 (m, 5H), 4.5 (d, 2H), 3.95 (t, 2H), 3.8 (t, 2H), 3.25 (t, 2H), 3.15 (t, 2H). MS (EI) for $C_{23}H_{24}N_6O_2$: 417 (MH+).

3-(5-Amino-6-cyanopyrazin-2-yl)-N-(phenylmethyl)benzamide: $^1$H NMR (400 MHz, d$_6$-DMSO): δ 9.21-9.16 (m, 1H), 8.99 (s, 1H), 8.46-8.43 (m, 1H), 8.13-8.09 (m, 1H), 7.94-7.90 (m, 1H), 7.61-7.52 (m, 3H), 7.37-7.31 (m, 4H), 7.28-7.22 (m, 1H), 4.55-4.49 (m, 2H). MS (EI) for $C_{19}H_{15}N_5O$: 330 (MH+).

N-{[3-Amino-6-(3-{[(phenylmethyl)amino]carbonyl}phenyl)pyrazin-2-yl]carbonyl}-L-glutamic acid: $^1$H NMR (400 MHz, d$_6$-DMSO): δ 9.15 (t, 1H), 8.95 (s, 1H), 8.9 (d, 1H), 8.55 (s, 1H), 8.35 (d, 1H), 7.85 (d, 1H), 7.57 (t, 1H), 7.35-7.2 (m, 5H), 4.5 (d, 2H), 4.45 (t, 1H), 2.35 (m, 2H), 2.3-2.05 (m, 2H). MS (EI) for $C_{24}H_{23}N_5O_6$: 478 (MH+).

Ethyl N-{[3-amino-6-(3-{[(phenylmethyl)amino]carbonyl}phenyl)pyrazin-2-yl]carbonyl}-L-tyrosinate: $^1$H NMR (400 MHz, d$_6$-DMSO): δ 9.2 (t, 1H), 8.98 (s, 1H), 8.68 (d, 1H), 8.58 (s, 1H), 8.22 (d, 1H), 7.92 (d, 1H), 7.65 (t, 1H), 7.4-7.2 (m, 5H), 7.12 (d, 2H), 6.65 (d, 2H), 4.6 (m, 4H), 4.15 (m, 4H), 3.1 (d, 2H), 1.2 (t, 3H). MS (EI) for $C_{30}H_{29}N_5O_5$: 540 (MH+).

N-{[3-Amino-6-(3-{[(phenylmethyl)amino]carbonyl}phenyl)pyrazin-2-yl]carbonyl}tyrosine: $^1$H NMR (400 MHz, d$_6$-DMSO): δ 9.22 (t, 1H), 8.94 (s, 1H), 8.64 (d, 1H), 8.56 (s, 1H), 8.18 (d, 1H), 7.92 (d, 1H), 7.62 (t, 1H), 7.38-7.22 (m, 5H), 7.1 (d, 2H), 6.64 (d, 2H), 4.62-4.44 (m, 3H), 3.12 (d, 2H). MS (EI) for $C_{28}H_{25}N_5O_5$: 512 (MH+).

1,1-Dimethylethyl [3-({[3-amino-6-(3-{[(phenylmethyl)amino]carbonyl}phenyl)pyrazin-2-yl]carbonyl}amino)propyl]carbamate: $^1$H NMR (400 MHz, d$_6$-DMSO): δ 9.16 (t, 1H), 9.0 (t, 1H), 8.93 (s, 1H), 8.54 (s, 1H), 8.44 (d, 1H), 7.9 (d, 1H), 7.58 (t, 1H), 7.38-7.23 (m, 5H), 6.9 (t, 1H), 4.55 (d, 2H), 3.35 (m, 2H), 3.0 (q, 2H), 1.65 (q, 2H), 1.38 (s, 9H). MS (EI) for $C_{27}H_{32}N_6O_4$: 405 (MH+).

3-Amino-N-(3-aminopropyl)-6-(3-{[(phenylmethyl)amino]carbonyl}phenyl)pyrazine-2-carboxamide: $^1$H NMR (400 MHz, d$_6$-DMSO): δ 9.55 (t, 1H), 9.3 (t, 1H), 8.92 (s, 1H), 8.7 (s, 1H), 8.35 (m, 1H), 8.0 (s, 2H), 7.9 (m, 1H), 7.55 (t, 1H), 7.4-7.2 (m, 5H), 4.5 (d, 2H), 3.45 (m, 2H), 2.85 (m, 2H), 1.85 (m, 2H). MS (EI) for $C_{22}H_{24}N_6O_2$: 405 (MH+).

1-{[3-Amino-6-(3-{[(phenylmethyl)amino]carbonyl}phenyl)pyrazin-2-yl]carbonyl}piperidine-3-carboxylic acid: $^1$H NMR (400 MHz, d6-DMSO): δ 9.15 (t, 1H), 8.7 (s, 1H), 8.45 (s, 1H), 8.05 (d, 1H), 7.85 (d, 1H), 7.57 (t, 1H), 7.35-7.2 (m, 5H), 6.7 (s, 2H), 4.5 (d, 2H), 4.45-4.2 (m, 1H), 3.9-3.6 (m, 1H), 3.3 (m, 1H), 3.1 (m, 1H), 2.6 (m, 1H), 2.0 (m, 1H), 1.8-1.5 (m, 3H). MS(EI) for $C_{25}H_{25}N_5O_4$: 460 (MH+).

1,1-Dimethylethyl [2-({[3-amino-6-(3-{[(phenylmethyl)amino]carbonyl}phenyl)pyrazin-2-yl]carbonyl}amino)ethyl]carbamate: $^1$H NMR (400 MHz, d$_6$-DMSO): δ 9.15 (t, 1H), 8.95 (s, 1H), 8.95 (t, 1H), 8.55 (s, 1H), 8.42 (d, 1H), 7.9 (d, 1H), 7.57 (t, 1H), 7.35-7.2 (m, 5H), 7.02 (t, 1H), 4.5 (d, 2H), 3.4 (m, 2H), 3.2 (m, 2H), 1.4 (s, 9H). MS(EI) for $C_{26}H_{30}N_6O_4$: 391 (MH+).

3-Amino-N-(2-aminoethyl)-6-(3-{[(phenylmethyl)amino]carbonyl}phenyl)pyrazine-2-carboxamide: $^1$H NMR (400 MHz, d$_6$-DMSO): δ 9.6 (t, 1H), 9.3 (t, 1H), 8.95 (s, 1H), 8.75 (s, 1H), 8.37 (d, 1H), 7.9 (d, 1H), 7.57 (t, 1H), 7.35-7.2 (m, 5H), 4.5 (d, 2H), 3.62 (t, 2H), 3.04 (t, 2H). MS(EI) for $C_{21}H_{22}N_6O_2$: 391 (MH+).

1,1-Dimethylethyl (1-{[3-amino-6-(3-{[(phenylmethyl)amino]carbonyl}phenyl)pyrazin-2-yl]carbonyl}piperidin-4-yl)carbamate: $^1$H NMR (400 MHz, d$_6$-DMSO): δ 9.15 (t, 1H), 8.75 (s, 1H), 8.4 (s, 1H), 8.07 (d, 1H), 7.85 (d, 1H), 7.57 (t, 1H), 7.35-7.2 (m, 5H), 6.95 (d, 1H), 6.7 (s, 2H), 4.5 (d, 2H), 4.4 (m, 1H), 3.8 (mi, 1H), 3.6 (m, 1H), 3.2 (m, 1H), 3.05 (m, 1H), 1.9-1.7 (m, 2H), 1.5-1.3 (m, 2H), 1.4 (s, 9H). MS(EI) for $C_{29}H_{34}N_6O_4$: 431 (MH$^+$).

3-{5-Amino-6-[(4-aminopiperidin-1-yl)carbonyl]pyrazin-2-yl}-N-(phenylmethyl)benzamide: $^1$H NMR (400 MHz, d$_6$-DMSO): δ 9.23 (t, 1H), 8.75 (s, 1H), 8.42 (s, 1H), 8.25 (t, 3H), 8.05 (d, 1H), 7.95 (d, 1H), 7.57 (t, 1H), 7.4-7.2 (m, 5H), 4.5 (d, 2H), 3.9 (m, 1H), 3.7-3.5 (m, 1H), 3.35 (m, 1H), 3.2 (m, 1H), 2.95 (m, 1H), 2.1-1.9 (m, 2H), 1.7-1.5 (t, 2H). MS(EI) for $C_{24}H_{26}N_6O_2$: 431 (MH$^+$).

3-Amino-6-(3-{[(1S)-2,3-dihydro-1H-inden-1-ylamino]carbonyl}phenyl)-N-[(3R)-pyrrolidin-3-yl]pyrazine-2-carboxamide: $^1$H NMR (400 MHz, d$_6$-DMSO): δ 9.1 (d, 1H), 8.95 (s, 1H), 8.75 (d, 1H), 8.55 (s, 1H), 8.35 (d, 1H), 7.93 (d, 1H), 7.6 (t, 1H), 7.3-7.15 (m, 4H), 5.6 (q, 1H), 4.4 (m, 1H), 3.1-3.0 (m, 3H1), 2.9-2.8 (m, 3H), 2.15-2.0 (m, 2H), 1.8 (m, 2H). MS (EI) for $C_{25}H_{26}N_6O_2$: 443 (MH$^+$).

3-Amino-6-(3-{[(1S)-2,3-dihydro-1H-inden-1-ylamino]carbonyl}phenyl)-N-[(3S)-1-(furan-2-ylcarbonyl)pyrrolidin-3-yl]pyrazine-2-carboxamide: $^1$H NMR (400 MHz, d$_6$-DMSO): δ 8.96 (s, 1H), 8.9 (d, 1H), 8.85 (q, 1H), 8.6 (s, 1H), 8.35 (d, 1H), 7.95-7.85 (q, 2H), 7.6 (m, 1H), 7.3-7.15 (m, 4H), 6.65 (m, 1H), 5.6 (q, 1H), 4.65-4.5 (m, 1H), 4.15-3.95 (m, 1H), 3.8 (m, 2H), 3.6 (m, 1H), 3.05-2.8 (m, 2H), 2.3-2.0 (m, 4H). MS (EI) for $C_{30}H_{28}N_6O_4$: 537 (MH$^+$).

N-[3-(Acetylamino)propyl]-3-amino-6-(3-{[(phenylmethyl)amino]carbonyl}phenyl)pyrazine-2-carboxamide: $^1$H NMR (400 MHz, d$_6$-DMSO): δ 9.15 (t, 1H), 9.0 (t, 1H), 8.95 (s, 1H), 8.6 (s, 1H), 8.4 (d, 1H), 7.95 (t, 1H), 7.9 (d, 1H), 7.6 (t, 1H), 7.4-7.25 (m, 5H), 4.55 (d, 2H), 3.35 (q, 2H), 3.15 (q, 2H), 1.8 (s, 3H), 1.65 (m, 2H). MS (EI) for $C_{24}H_{26}N_6O_3$: 447 (MH$^+$).

3-Amino-N-{3-[(furan-2-ylcarbonyl)amino]propyl}-6-(3-{[phenylmethyl)amino]carbonyl}phenyl)pyrazine-2-carboxamide: $^1$H NMR (400 MHz, d$_6$-DMSO): δ 9.16 (t, 1H), 9.05 (t, 1H), 8.95 (s, 1H), 8.6 (s, 1H), 8.5 (t, 1H), 8.44 (d, 1H), 7.92 (d, 1H), 7.84 (s, 1H), 7.6 (t, 1H), 7.35-7.24 (m, 5H), 7.1 (d, 1H), 6.62 (m, 1H), 4.54 (d, 2H), 3.42-3.28 (m, 4H), 1.78 (m, 2H). MS (EI) for $C_{27}H_{26}N_6O_4$: 499 (MH$^+$).

3-Amino-6-(3-{[(1S)-2,3-dihydro-1H-inden-1-ylamino]carbonyl}phenyl)-N-[(3S)-1-(pyridin-4-ylcarbonyl)pyrrolidin-3-yl]pyrazine-2-carboxamide: $^1$H NMR (400 MHz, d$_6$-DMSO): δ 8.95-8.9 (m, 2H), 8.85-8.75 (dd, 1H), 8.7 (m, 2I1), 8.55 (d, 1H), 8.45 (s, 1H), 7.95 (t, 1H), 7.6 (t, 1H), 7.5 (d, 1H), 7.45 (d, 1H), 7.25 (m, 4I1), 5.6 (q, 1H), 4.55-4.5 (m, 1H), 3.9-3.4 (m, 3H), 3.1-2.9 (m, 3H), 2.25-1.95 (m, 3H), 1.35 (m, 21H). MS (EI) for $C_{31}H_{29}N_7O_3$: 548 (MH$^+$).

3-Amino-6-(3-{[(phenylmethyl)amino]carbonyl}phenyl)-N-{3-[(pyridin-4-ylcarbonyl)amino]propyl}pyrazine-2-carboxamide: $^1$H NMR (400 MHz, d$_6$-DMSO): δ 9.15 (t, 1H), 9.05 (t, 1H), 8.95 (s, 1H), 8.88 (t, 1H), 8.7 (d, 2H), 8.58 (s, 1H), 8.45 (d, 1H), 7.92 (d, 1H), 7.75 (d, 2H), 7.6 (t, 1H1), 7.35-7.25 (m, 5H), 4.55 (d, 2H), 3.4 (m, 4H), 1.85 (m, 2H). MS (EI) for $C_{28}H_{27}N_7O_3$: 510 (MH$^+$).

N-[3-({[3-Amino-6-(3-{[(phenylmethyl)amino]carbonyl}phenyl)pyrazin-2-yl]carbonyl}amino)propyl]quinoxaline-2-carboxamide: $^1$H NMR (400 MHz, d$_6$-DMSO): δ 9.45 (s, 1H), 9.2 (t, 1H), 9.1 (t, 1H), 9.05 (t, 1H), 8.9 (s, 1H), 8.5 (s, 1H), 8.4 (d, 1H), 8.15 (m, 2H), 7.95 (m, 2H), 7.85 (d, 1H), 7.55 (t, 1H), 7.35-7.15 (m, 5H), 4.5 (d, 2H), 3.5-3.4 (m, 4H), 1.85 (m, 2H). MS (EI) for $C_{31}H_{28}N_8O_3$: 561 (MH$^+$).

3-Amino-6-(3-{[(phenylmethyl)amino]carbonyl}phenyl)-N-[3-({[6-(trifluoromethyl)pyridin-3-yl]carbonyl}amino)propyl]pyrazine-2-carboxamide: $^1$H NMR (400 MHz, d$_6$-DMSO): δ 9.15 (t, 2H), 9.0 (t, 2H), 8.9 (s, 1H), 8.55 (s, 1H), 8.4 (m, 2H), 7.95 (d, 1H), 7.35 (d, 1H), 7.55 (t, 1H), 7.35-7.15 (m, 5H), 4.5 (d, 2H), 3.4 (m, 4H), 1.8 (m, 2H). MS (EI) for $C_{29}H_{26}N_7O_3F_3$: 578 (MH$^+$).

3-Amino-6-(3-{[(phenylmethyl)amino]carbonyl}phenyl)-N-{3-[(quinolin-8-ylsulfonyl)amino]propyl}pyrazine-2-carboxamide: $^1$H NMR (400 MHz, d$_6$-DMSO): δ 9.15 (t, 1H), 9.05 (m, 1H), 8.9 (s, 1H), 8.8 (t, 1H), 8.5 (m, 2H), 8.35 (q, 2H), 8.25 (d, 1H), 7.9 (d, 1H), 7.7 (m, 2H), 7.55 (t, 1H), 7.35-7.2 (m, 5H), 4.55 (d, 2H), 3.25 (q, 2H), 2.85 (q, 2H), 1.6 (q, 2H). MS (EI) for $C_{31}H_{29}N_7O_4S$: 596 (MH$^+$).

3-Amino-6-(3-{[(phenylmethyl)amino]carbonyl}phenyl)-N-{3-[(pyridin-2-ylsulfonyl)amino]propyl}pyrazine-2-carboxamide: $^1$H NMR (400 MHz, d$_6$-DMSO): δ 9.3 (t, 1H), 8.95 (m, 2H), 8.7 (d, 1H), 8.6 (s, 1H), 8.35 (d, 1H), 8.05 (t, 1H), 7.9 (m, 3H), 7.65-7.55 (m, 2H), 7.4-7.25 (m, 5H), 4.55 (d, 2H), 3.3 (q, 2H), 3.0 (q, 2H), 1.7 (q, 2H). MS (EI) for $C_{27}H_{27}N_7O_4S$: 546 (MH$^+$).

3-Amino-N-[3-({[(3,5-dimethylisoxazol-4-yl)amino]carbonyl}amino)propyl]-6-(3-{[(phenylmethyl)amino]carbonyl}phenyl)pyrazine-2-carboxamide: $^1$H NMR (400 MHz, d$_6$-DMSO): δ 9.15 (t, 1H), 9.05 (t, 1H), 8.95 (s, 1H), 8.55 (s, 1H), 8.4 (d, 1H), 7.9 (d, 1H), 7.6 (s, 1H), 7.5 (t, 1H), 7.35-7.2 (m, 5H), 6.35 (t, 1H), 4.55 (d, 2H1), 3.35 (m, 2H), 3.15 (q, 2H), 2.25 (s, 3H), 2.05 (s, 3H), 1.65 (q, 2H). MS (EI) for $C_{28}H_{30}N_8O_4$: 543 (MH$^+$).

3-Amino-6-(3-{[(phenylmethyl)amino]carbonyl}phenyl)-N-{2-[(pyridin-4-ylcarbonyl)amino]ethyl}pyrazine-2-carboxamide: $^1$H NMR (400 MHz, d$_6$-DMSO): δ 9.2 (t, 1H), 9.05 (t, 1H), 9.0 (t, 1H), 8.95 (s, 1H), 8.7 (d, 2H), 8.6 (s, 1H), 8.4 (d, 1H), 7.9 (d, 1H), 7.75 (d, 2H), 7.57 (t, 1H), 7.35-7.2 (m, 5H), 4.5 (d, 2H), 3.5 (t, 4H). MS(EI) for $C_{27}H_{29}N_7O_3$: 496 (MH$^+$).

3-Amino-N-{2-[(furan-2-ylcarbonyl)amino]ethyl}-6-(3-{[(phenylmethyl)amino]carbonyl}phenyl)pyrazine-2-carboxamide: $^1$H NMR (400 MHz, d$_6$-DMSO): δ 9.2 (t, 1H), 9.05 (t, 1H), 8.95 (s, 1H), 8.65 (t, 1H), 8.6 (s, 1H), 8.4 (d, 1H), 7.9 (d, 1H), 7.82 (d, 1H), 7.57 (t, 1H), 7.35-7.2 (m, 5H), 7.06 (d, 1H), 6.6 (d, 1H), 4.5 (d, 2H), 3.5 (t, 4H). MS(EI) for $C_{26}H_{24}N_6O_4$: 485 (MH$^+$).

N,N'-Cyclohexane-1,2-diylbis[3-amino-6-(3-{[(phenylmethyl)amino]carbonyl}phenyl)pyrazine-2-carboxamide]: $^1$H NMR (400 MHz, d$_6$-DMSO): δ 9.15 (d, 2H), 8.9 (s, 2H), 8.75 (d, 2H), 8.57 (s, 2H), 8.4 (d, 2H), 7.9 (d, 2H), 7.57 (t, 2H), 7.35-7.2 (m, 10H), 4.55 (d, 4H), 4.0 (m, 2H), 2.05 (d, 2H), 1.8 (d, 2H), 1.6 (m, 2H), 1.4 (t, 2H). MS(EI) for $C_{44}H_{42}N_{10}O_4$: 775 (MH$^+$).

N-[2-(Acetylamino)ethyl]-3-amino-6-(3-{[(phenylmethyl)amino]carbonyl}phenyl)pyrazine-2-carboxamide: $^1$H NMR (400 MHz, d$_6$-DMSO): δ 9.25 (t, 1H), 8.98 (t, 1H), 8.95 (s, 1H), 8.6 (s, 1H), 8.4 (d, 1H), 8.16 (t, 1H), 7.9 (d, 1H), 7.57 (t, 1H), 7.35-7.2 (m, 5H), 4.55 (d, 2H), 3.4 (t, 2H), 3.27 (t, 2H), 1.8 (s, 3H). MS(EI) for $C_{23}H_{24}N_6O_3$: 433 (MH$^+$).

3-Amino-6-(3-{[(phenylmethyl)amino]carbonyl}phenyl)-N-{2-[(quinolin-8-ylsulfonyl)amino]ethyl}pyrazine-2-carboxamide: $^1$H NMR (400 MHz, d$_6$-DMSO): δ 9.2 (t, 1H), 8.9 (s, 1H), 8.8 (d, 1H), 8.7 (t, 1H), 8.5 (s, 1H), 8.3 (m, 3H), 8.2 (d, 1H), 7.9 (d, 1H), 7.65 (t, 1H), 7.57 (t, 1H), 7.4-7.2 (m, 7H), 4.55 (d, 2H), 3.35 (t, 2H), 3.05 (t, 2H). MS(EI) for $C_{30}H_{27}N_7O_4S$: 582 (MH$^+$).

N-[2-({[3-Amino-6-(3-{[(phenylmethyl)amino]carbonyl}phenyl)pyrazin-2-yl]carbonyl}amino)ethyl]quinoxaline-2-carboxamide: $^1$H NMR (400 MHz, d$_6$-DMSO): δ 9.45 (s, 1H), 9.35 (t, 1H), 9.15 (t, 1H), 9.07 (t, 1H), 8.95 (s, 1H), 8.57 (s, 1H), 8.4 (d, 1H), 8.2 (d, 2H), 8.0 (d, 2H), 7.85 (d, 1H), 7.57 (t, 1H), 7.35-7.2 (m, 5H), 4.5 (d, 2H), 3.6 (t, 4H). MS(EI) for $C_{30}H_{26}N_8O_3$: 547 (MH$^+$).

3-Amino-N-(2-{[(2-chloropyridin-3-yl)carbonyl]amino}ethyl)-6-(3-{[(phenylmethyl)amino]carbonyl}phenyl)pyrazine-2-carboxamide: $^1$H NMR (400 MHz, d$_6$-DMSO): δ 9.2 (t, 1H), 9.0 (t, 1H), 8.95 (s, 1H), 8.8 (t, 1H), 8.6 (s, 1H), 8.45 (dd, 1H), 8.4 (d, 1H), 7.9 (m, 2H), 7.57 (t, 1H), 7.45 (m, 1H), 7.35-7.2 (m, 5H), 4.5 (d, 2H), 3.5 (t, 4ll). MS(EI) for C$_{27}$H$_{24}$N$_7$O$_3$Cl: 530 (MH$^+$).

3-Amino-6-(3-{[(phenylmethyl)amino]carbonyl}phenyl)-N-{2-[(pyridin-2-ylsulfonyl)amino]ethyl}pyrazine-2-carboxamide: $^1$H NMR (400 MHz, d$_6$-DMSO): δ 9.15 (t, 1H), 8.9 (s, 1H), 8.85 (t, 1H), 8.63 (d, 1H), 8.5 (s, 1l1), 8.37 (d, 1H), 8.1 (t, 1H), 8.0 (m, 2H), 7.9 (m, 2H), 7.57 (m, 2H), 7.35-7.2 (m, 5H), 4.55 (d, 2H), 3.4 (t, 2H), 3.2 (t, 2H). MS(EI) for C$_{26}$H$_{25}$N$_7$O$_4$S: 532 (MH$^+$).

3-Amino-N-[2-({[(3,5-dimethylisoxazol-4-yl)amino]carbonyl}amino)ethyl]-6-(3-{[(phenylmethyl)amino]carbonyl}phenyl)pyrazine-2-carboxamide: $^1$H NMR (400 MHz, d$_6$-DMSO): δ 9.15 (t, 1H), 9.05 (t, 1H), 8.95 (s, 1H, 8.6 (s, 1H), 8.4 (d, 1H1), 7.9 (d, 1H), 7.6 (s, 1H), 7.5 (t, 1H), 7.35-7.2 (m, 5H), 6.55 (t, 1H), 4.5 (d, 2H), 3.4 (t, 2H), 3.3 (t, 2H), 2.15 (s, 3H), 1.96 (s, 3H). MS(EI) for C$_{27}$H$_{28}$N$_8$O$_4$: 529 (MH$^+$).

3-Amino-6-(3-{[(phenylmethyl)amino]carbonyl}phenyl)pyrazine-2-carboxamide: $^1$H NMR (400 MHz, d$_6$-DMSO): δ 9.21-9.16 (m, 1H), 8.92 (s, 1H), 8.58-8.55 (m, 1H), 8.38-8.32 (m, 2H), 8.15-7.50 (bs, 2H), 7.79 (s, 1H), 7.60-7.54 (m, 1H), 7.38-7.31 (m, 4H), 7.28-7.22 (m, 1H), 4.58-4.53 (m, 2H). MS (EI) for C$_{19}$H$_{17}$N$_5$O$_2$: 348 (MH$^+$).

3-Amino-N-[3-({[4-(dimethylamino)phenyl]carbonyl}amino)propyl]-6-(3-{[(phenylmethyl)amino]carbonyl}phenyl)pyrazine-2-carboxamide: $^1$H NMR (400 MHz, d$_6$-DMSO): δ 9.15 (q, 2H), 8.95 (s, 1H), 8.6 (s, 1H), 8.45 (d, 1H), 8.25 (t, 1H), 7.9 (d, 1H), 7.7 (d, 2H), 7.6 (t, 1H), 7.35-7.2 (m, 5H), 6.65 (d, 2H), 4.45 (d, 2H), 3.35 (m, 4H), 2.95 (s, 6H), 1.75 (m, 2H). MS (EI) for C$_{31}$H$_{33}$N$_7$O$_3$: 552 (MH$^+$).

1,1-Dimethylethyl 4-[(3S)-3-({[3-amino-6-(3-{[(phenylmethyl)amino]carbonyl}phenyl)pyrazin-2-yl]carbonyl}amino)pyrrolidin-1-yl]piperidine-1-carboxylate: $^1$H NMR (400 MHz, d$_6$-DMSO): δ 9.2 (t, 1H), 8.95 (s, 1H), 8.65 (d, 1H), 8.55 (s, 1H), 8.3 (d, 1H), 7.9 (d, 1H), 7.7 (s, 1H), 7.55 (t, 1H), 7.35-7.2 (m, 5H), 4.55 (d, 2H), 4.5 (m, 1H), 3.8 (d, 2H), 2.9-2.7 (m, 3H), 2.55 (m, 1H), 2.25-2.1 (m, 2H), 1.9-1.75 (m, 3H), 1.4 (s, 9H), 1.25 (m, 2H). MS (EI) for C$_{33}$H$_{41}$N$_7$O$_4$: 600 (MH$^+$).

3-Amino-6-(3-{[(phenylmethyl)amino]carbonyl}phenyl)-N-[(3S)-1-piperidin-4-ylpyrrolidin-3-yl]pyrazine-2-carboxamide: $^1$H NMR (400 MHz, d$_6$-DMSO): δ 9.65-9.45 (t, 1H), 9.3 (m, 2H), 8.98 (d, 1H), 8.75 (m, 2H), 8.5-8.3 (dd, 1H), 7.9 (t, 1H), 7.55 (m, 1H), 7.4-7.25 (m, 4H), 4.95-4.7 (m, 1H), 4.55 (m, 2H), 3.4 (m, 6H), 3.1 (m, 1H), 2.9 (m, 2H), 2.35-1.9 (m, 6H). MS (EI) for C$_{28}$H$_{33}$N$_7$O$_2$: 500 (MH$^+$).

1,1-Dimethylethyl (2R)-2-{[(3S)-3-({[3-amino-6-(3-{[(phenylmethyl)amino]carbonyl}phenyl)pyrazin-2-yl]carbonyl}amino)pyrrolidin-1-yl]methyl}pyrrolidine-1-carboxylate: $^1$H NMR (400 MHz, d$_6$-DMSO): δ 9.2 (t, 1H), 8.93 (s, 1H), 8.6 (d, 1H), 8.55 (s, 1H), 8.25 (d, 1H), 7.9 (d, 1H), 7.57 (t, 1H), 7.35-7.2 (m, 5H), 4.55 (d, 2H), 4.4 (m, 1H), 3.8 (m, 1H), 3.2 (t, 2H), 2.8 (t, 2H), 2.6-2.4 (m, 4H), 2.2 (m, 1H), 1.9-1.7 (m, 5H), 1.4 (s, 9H). MS(EI) for C$_{33}$H$_{41}$N$_7$O$_4$: 600 (MH$^+$).

3-Amino-6-(3-{[(phenylmethyl)amino]carbonyl}phenyl)-N-{(3S)-1-[(2R)-pyrrolidin-2-ylmethyl]pyrrolidin-3-yl}pyrazine-2-carboxamide: $^1$H NMR (400 MHz, d$_6$-DMSO): δ 11.4 (m, 1H), 9.7-9.4 (m, 3H), 9.35 (d, 1H), 8.96 (s, 1H), 8.8-8.7 (m, 1H), 8.5-8.3 (m, 1H), 7.9 (d, 1H); 7.57 (t, 1H), 7.35-7.2 (m, 5H), 5.0-4.7 (m, 1H), 4.5 (d, 2H), 4.0-3.6 (m, 3H), 3.2 (m, 3H), 2.6 (m, 1H), 2.4-2.1 (m, 3H), 2.0-1.6 (m, 3H). MS(EI) for C$_{28}$H$_{33}$N$_7$O$_2$: 500 (MH$^+$).

3-Amino-N-((3S)-1-{[4-(dimethylamino)phenyl]methyl}pyrrolidin-3-yl)-6-(3-{[(phenylmethyl)amino]carbonyl}phenyl)pyrazine-2-carboxamide: $^1$H NMR (400 MHz, d$_6$-DMSO): δ 9.2 (t, 1H), 8.9 (s, 1H), 8.6 (d, 1H), 8.57 (s, 1H), 8.3 (d, 1H), 7.9 (d, 1H), 7.6 (t, 1H), 7.35-7.2 (m, 5H), 7.1 (d, 2H), 6.63 (d, 2H), 4.55 (d, 2H), 4.4 (m, 1H), 3.45 (m, 2H), 2.82 (s, 6H), 2.7 (t, 2H), 2.4 (m, 1H), 2.2 (m, 1H), 1.82 (m, 1H). MS(EI) for C$_{32}$H$_{35}$N$_7$O$_2$: 550 (MH$^+$).

3-Amino-N-{2-[({[4-(dimethylamino)phenyl]amino}carbonyl)amino]ethyl}-6-(3-{[(phenylmethyl)amino]carbonyl}phenyl)pyrazine-2-carboxamide: $^1$H NMR (400 MHz, d$_6$-DMSO): δ 9.15 (t, 1H), 9.05 (t, 1H), 8.95 (s, 1H), 8.6 (s, 1H), 8.42 (d, 1H), 7.9 (d, 1H), 7.57 (t, 1H), 7.45 (m, 2H), 7.35-7.2 (m, 5H), 6.57 (t, 1H), 4.5 (d, 2H), 3.4 (m, 4H), 3.05 (s, 6H). MS(EI) for C$_{30}$H$_{32}$N$_8$O$_3$: 553 (MH$^+$).

3-Amino-N-[2-({[4-(dimethylamino)phenyl]carbonyl}amino)ethyl]-6-(3-{[(phenylmethyl)amino]carbonyl}phenyl)pyrazine-2-carboxamide: $^1$H NMR (400 MHz, d$_6$-DMSO): δ 9.3 (t, 1H), 9.15 (t, 1H), 8.95 (s, 1H), 8.68 (s, 1H), 8.45 (m, 2H), 7.9 (d, 1H), 7.7 (d, 2H), 7.57 (t, 1H), 7.35-7.2 (m, 5H), 6.65 (d, 2H), 4.45 (d, 2H), 3.5 (t, 4H), 2.95 (s, 6). MS(EI) for C$_{30}$H$_{31}$N$_7$O$_3$: 538 (MH$^+$).

3-Amino-6-(3-{[(phenylmethyl)amino]carbonyl}phenyl)-N-[(3S)-1-(pyridin-2-ylmethyl)pyrrolidin-3-yl]pyrazine-2-carboxamide: $^1$H NMR (400 MHz, d$_6$-DMSO): δ 9.2 (t, 1H), 8.93 (s, 1H), 8.65 (d, 1H), 8.56 (s, 1H), 8.48 (m, 1H), 8.32 (d, 1H), 7.9 (d, 1H), 7.72 (m, 2H), 7.6 (t, 1H), 7.46 (d, 1H), 7.38-7.32 (m, 4H), 7.28-7.22 (m, 2H), 4.55 (d, 2H), 4.44 (m, 1H), 3.75 (s, 2H), 2.86-2.64 (m, 2H), 2.64-2.52 (m, 2H), 2.2 (m, 1H). MS (ESI-LCMS) for C$_{29}$H$_{29}$N$_7$O$_2$: 508 (MH$^+$).

Methyl N-{[3-amino-6-(3-{[(phenylmethyl)amino]carbonyl}phenyl)pyrazin-2-yl]carbonyl}threoninate: $^1$H NMR (400 MHz, d$_6$-DMSO): δ 9.17 (m, 1H), 9.00 (s, 1H), 8.64 (m, 1H), 8.52 (s, 1H), 8.19 (m, 1H), 7.93 (m, 1H), 7.74-7.62 (m, 3H), 7.37-7.25 (m, 5H), 5.41 (m, 1H), 4.55-4.50 (m, 3H), 4.32-4.29 (m, 1H), 3.70 (m, 3H), 1.16 (m, 2H). MS (EI) for C$_{24}$H$_{25}$N$_5$O$_5$: 464 (MH$^+$).

3-(Ethylamino)-N-[(3S)-1-ethylpyrrolidin-3-yl]-6-(3-{[(phenylmethyl)amino]carbonyl}phenyl)pyrazine-2-carboxamide: $^1$H NMR (400 MHz, d$_6$-DMSO): δ 12.0-10.0 (s, 1H), 9.25-9.15 (tt, 1H1), 9.05 (m, 1H), 9.0 (s, 1H), 8.65-8.55 (m, 1H), 8.3 (m, 1H), 7.9 (d, 1H), 7.55 (q, 1H), 7.35-7.2 (m, 5H), 4.75-4.5 (m, 1H1), 4.5 (d, 2H), 3.9-3.05 (m, 9H), 2.3-2.1 (m, 1H), 1.2 (q, 6H). MS (EI) for C$_{27}$H$_{32}$N$_6$O$_2$: 473 (MH$^+$).

3-Amino-N-[(3S)-1-ethylpyrrolidin-3-yl]-6-(3-{[(phenylmethyl)amino]carbonyl}phenyl)pyrazine-2-carboxamide: $^1$H NMR (400 MHz, d$_6$-DMSO): δ 9.2 (t, 1H), 8.9 (s, 1H), 8.6 (d, 1H), 8.53 (s, 1H), 8.3 (d, 1H), 7.88 (d, 1H), 7.56 (t, 1H), 7.38-7.2 (m, 5H), 4.55 (d, 2H), 4.35 (m, 1H), 2.65 (m, 2H), 2.55-2.35 (m, 4H), 2.15 (m, 1H), 1.8 (m, 1H), 1.0 (t, 3H). MS (EI) for C$_{25}$H$_{28}$N$_6$O$_2$: 445 (MH$^+$).

3-Amino-6-(3-{[(1S)-2,3-dihydro-1H-inden-1-ylamino]carbonyl}phenyl)-N-[(3S)-1-ethylpyrrolidin-3-yl]pyrazine-2-carboxamide: $^1$H NMR (400 MHz, d$_6$-DMSO): δ 8.95 (m, 2H), 8.6 (d, 1H), 8.55 (s, 1H), 8.3 (d, 1H), 7.9 (d, 1H), 7.55 (t, 1H), 7.3-7.15 (m, 4H), 5.6 (q, 1H), 4.4 (m, 1H), 3.0 (m, 1H), 2.85 (m, 1H1), 2.7 (m, 1H), 2.6 (m, 1H), 2.5-2.45 (m, 5H), 2.15 (m, 1H), 2.05 (m, 1H), 1.8 (m, 1H), 1.05 (t, 3H). MS (EI) for C$_{27}$H$_{30}$N$_6$O$_2$: 471 (MH$^+$).

6-(3-{[(1S)-2,3-Dihydro-1H-inden-1-ylamino]carbonyl}phenyl)-3-(ethylamino)-N-[(3S)-1-ethylpyrrolidin-3-yl]pyrazine-2-carboxamide: $^1$H NMR (400 MHz, d$_6$-DMSO): δ 9.0 (s, 2H), 8.75 (t, 1H), 8.7 (d, 1H), 8.6 (s, 1H), 8.3 (d, 1H), 7.9 (d, 1H), 7.6 (t, 1H), 7.3-7.15 (m, 1H), 5.6 (q, 1H), 4.4 (m, 1H), 3.5 (m, 4H), 3.05 (m, 1H), 2.9 (m, 2H), 2.8-2.4 (m, 5H), 2.2-2.0 (m, 2H), 1.8 (m, 1H), 1.2 (t, 3H), 1.05 (t, 3H). MS (EI) for $C_{29}H34N_6O_2$: 499 (MH$^+$).

3-Amino-6-[3-({[(1S,2R)-2-hydroxy-2,3-dihydro-1H-inden-1-yl]amino}carbonyl)phenyl]-N-[(3S)-pyrrolidin-3-yl]pyrazine-2-carboxamide: $^1$H NMR (400 MHz, d$_6$-DMSO): δ 9.5-9.2 (m, 2H), 9.0 (m, 2H), 8.7 (s, 1H), 8.55 (d, 1H), 8.4 (d, 1H), 7.95 (d, 1H), 7.55 (t, 1H), 7.3-7.15 (m, 4H), 5.5 (m, 1H), 4.6 (m, 1H), 4.55 (m, 1H), 3.3-3.05 (m, 5H), 2.95-2.9 (m, 1H), 2.2 5(m, 1H) and 2.1 (m, 1H). MS (EI) for $C_{25}H_{26}N_6O_3$: 459 (MH$^+$).

1,1-Dimethylethyl (3S)-3-({[3-amino-6-(3-{[(1S)-2,3-dihydro-ylamino]carbonyl}phenyl)pyrazin-2-yl]carbonyl}amino)pyrrolidine-1-carboxylate: $^1$H NMR (400 MHz, d$_6$-DMSO): δ 8.97 (s, 1H), 8.95 (d, 1H), 8.7 (d, 1H), 8.6 (s, 1H), 8.35 (d, 1H), 7.9 (d, 1H), 7.57 (t, 1H), 7.3-7.1 (m, 4H), 5.6 (t, 1H), 4.45 (t, 1H), 3.6-3.2 (m, 4H), 3.05-2.8 (m, 2H), 2.5 (m, 1H), 2.2-1.9 (m, 3H), 1.4 (s, 9H). MS(EI) for $C_{30}H_{34}N_6O_4$: 443 (MH$^+$).

1,1-Dimethylethyl (3S)-3-[({3-amino-6-[3-({[(1R)-1-phenylethyl]amino}carbonyl)phenyl]pyrazin-2-yl}carbonyl)amino]pyrrolidine-1-carboxylate: $^1$H NMR (400 MHz, d$_6$-DMSO): δ 8.98 (s, 1H), 8.95 (d, 1H), 8.78 (t, 1H), 8.57 (s, 1H), 8.35 (d, 1H), 7.85 (d, 1H), 7.57 (t, 1H), 7.42-7.2 (m, 5H), 5.2 (t, 1H), 4.5 (t, 1H), 3.65-3.25 (m, 4H), 2.2-2.0 (m, 2H), 1.5 (d, 3H), 1.4 (s, 9H). MS(EI) for $C_{29}H_{34}N_6O_4$: 431 (MH$^+$).

1,1-Dimethylethyl (3S)-3-[({3-amino-6-[3-(3,4-dihydroisoquinolin-2(1H)-ylcarbonyl)phenyl]pyrazin-2-yl}carbonyl)amino]pyrrolidine-1-carboxylate: $^1$H NMR (400 MHz, d$_6$-DMSO): δ 8.9 (t, 1H), 8.75 (t, 1H), 8.3-8.1 (m, 2H), 7.57 (t, 1H), 7.45 (m, 1H), 7.3-7.1 (m, 4H), 4.82 (t, 1H), 4.65-4.4 (m, 2H), 3.6-3.2 (m, 6H), 2.9 (m, 2H), 2.2-2.0 (m, 2H), 1.4 (s, 9H). MS(EI) for $C_{30}H_{34}N_6O_4$: 443 (MH$^+$).

1,1-Dimethylethyl (3S)-3-({[3-amino-6-(3-{[(2-phenylethyl)amino]carbonyl}phenyl)pyrazin-2-yl]carbonyl}amino)pyrrolidine-1-carboxylate: $^1$H NMR (400 MHz, d$_6$-DMSO): δ 8.95 (s, 1H), 8.7 (m, 2H), 8.45 (s, 1H), 8.35 (d, 1H), 7.85 (d, 1H), 7.57 (t, 1H), 7.35-7.2 (m, 5H), 4.5 (t, 1H), 3.6-3.45 (m, 4H), 3.4-3.25 (m, 2H), 2.9 (t, 2H), 2.2-2.0 (m, 2H), 1.4 (s, 9H). MS(EI) for $C_{29}H_{34}N_6O_4$: 431 (MH$^+$).

1,1-Dimethylethyl (3S)-3-[({3-amino-6-[3-({[(1S)-1-phenylethyl]amino}carbonyl)phenyl]pyrazin-2-yl}carbonyl)amino]pyrrolidine-1-carboxylate: $^1$H NMR (400 MHz, d$_6$-DMSO): δ 8.98 (s, 1H), 8.95 (d, 1H), 8.75 (t, 1H), 8.57 (s, 1H), 8.35 (d, 1H), 7.85 (d, 1H), 7.57 (t, 1H), 7.45-7.2 (m, 5H), 5.22 (t, 1H), 4.5 (t, 1H), 3.65-3.45 (m, 2H), 3.3 (m, 2H), 2.2-2.0 (m, 2H), 1.55 (s, 3H), 1.4 (s, 9H). MS(EI) for $C_{29}H_{34}N_6O_4$: 431 (MH$^+$).

3-Amino-6-[3-(3,4-dihydroisoquinolin-2(1H)-ylcarbonyl)phenyl]-N-[(3S)-pyrrolidin-3-yl]pyrazine-2-carboxamide: $^1$H NMR (400 MHz, d$_6$-DMSO): δ 9.6 (t, 1H), 9.35 (t, 1H), 9.0-8.9 (m, 2H), 8.4 (d, 1H), 8.2 (s, 1H), 7.57 (t, 1H), 7.42 (d, 1H), 7.35-7.0 (m, 4H), 4.8 (s, 1H), 4.6 (m, 2H), 3.9-3.6 (m, 2H), 3.4-3.1 (m, 4H), 2.9 (t, 2H), 2.25 (t, 1H), 2.05 (t, 1H). MS(EI) for $C_{25}H_{26}N_6O_2$: 443 (MH$^+$).

3-Amino-6-(3-{[(2-phenylethyl)amino]carbonyl}phenyl)-N-[(3S)-pyrrolidin-3-yl]pyrazine-2-carboxamide: $^1$H NMR (400 MHz, d$_6$-DMSO): δ 9.65 (t, 1H), 9.4 (t, 1H), 9.2 (d, 1H), 9.1 (t, 1H), 8.95 (s, 1H), 8.75 (s, 1H), 8.35 (d, 1H), 7.85 (d, 1H), 7.57 (t, 1H), 7.35-7.2 (m, 5H), 4.7 (t, 1H), 3.6-3.2 (m, 6H), 2.9 (t, 2H), 2.3 (t, 1H), 2.1 (t, 1H). MS(EI) for $C_{24}H_{26}N_6O_2$: 431 (MH$^+$).

3-Amino-6-[3-({[(1R)-1-phenylethyl]amino}carbonyl)phenyl]-N-[(3S)-pyrrolidin-3-yl]pyrazine-2-carboxamide: $^1$H NMR (400 MHz, d$_6$-DMSO): δ 9.75 (t, 1H), 9.55 (t, 1H), 9.3 (m, 2H), 8.99 (s, 1H), 8.8 (s, 1H), 8.4 (d, 1H), 7.9 (d, 1H), 7.57 (t, 1H), 7.45 (m, 3H), 7.38-7.2 (m, 3H), 5.25 (t, 1H), 4.7 (t, 1H), 3.6-3.2 (m, 411), 2.3 (t, 1H), 2.15 (t, 1H), 1.6 (s, 3H). MS(EI) for $C_{24}H_{26}N_6O_2$: 431(MH$^+$).

3-Amino-6-[3-({[(1S)-1-phenylethyl]amino}carbonyl)phenyl]-N-[(3S)-pyrrolidin-3-yl]pyrazine-2-carboxamide: $^1$H NMR (400 MHz, d$_6$-DMSO): δ 9.7 (t, 1H), 9.45 (t, 1H), 9.25 (m, 2H), 9.0 (s, 1H), 8.78 (s, 1H), 8.4 (d, 1H), 7.85 (d, 1H), 7.57 (t, 1H), 7.5 (m, 2H), 7.35-7.2 (m, 3H), 5.25 (t, 1H), 4.7 (t, 1H), 3.6-3.2 (m, 4H), 2.3 (t, 1H), 2.1 (t, 1H), 1.6 (s, 3H). MS(EI) for $C_{24}H_{26}N_6O_2$: 431 (MH$^+$).

3-(5-Amino-6-cyanopyrazin-2-yl)-N-[(1S)-2,3-dihydro-1H-inden-1-yl]benzamide: $^1$H NMR (400 MHz, d$_6$-DMSO): δ 8.99 (s, 1H), 8.96-8.89 (m, 1H), 8.48-8.43 (m, 1H), 8.13-8.07 (m, 1H), 7.98-7.92 (m, 1H), 7.63-7.48 (m, 3H), 7.32-7.16 (m, 4H), 5.66-5.56 (m, 1H), 3.07-2.96 (m, 1H), 2.94-2.80 (m, 1H), 2.54-2.43 (m, 1H), 2.08-1.95 (m, 1H). MS (EI) for $C_{21}H_{17}N_5O$: 356 (MH$^+$).

3-Amino-6-[3-({[(1R,2S)-2-hydroxy-2,3-dihydro-1H-inden-1-yl]amino}carbonyl)phenyl]-N-[(3S)-pyrrolidin-3-yl]pyrazine-2-carboxamide: $^1$H NMR (400 MHz, d$_6$-DMSO): δ 9.0 (s, 1H), 8.65-8.6 (m, 3H), 8.32 (d, 1H), 7.95 (d, 1H), 7.6 (t, 1H), 7.3-7.2 (m, 4H), 5.5 (m, 1H), 4.55 (m, 1H1), 4.35 (m, 1H), 3.1 (dd, 1H), 3.0-2.85 (m, 4H), 2.75 (m, 3H), 2.0 (m, 1H), and 1.7 (m, 1H). MS (EI) for $C_{25}H_{26}N_6O_3$: 459 (MH$^+$).

3-Amino-N-[(3S)-1-ethylpyrrolidin-3-yl]-6-[3-({[(1S,2R)-2-hydroxy-1H-inden-1-yl]amino}carbonyl)phenyl]pyrazine-2-carboxamide: $^1$H NMR (400 MHz, d$_6$-DMSO): δ 9.0 (s, 1H), 8.7-8.6 (m, 3H), 8.35 (d, 1H), 7.95 (d, 1H), 7.6 (t, 1H), 7.3-7.15 (m, 4H), 5.5 (m, 1H), 5.15 (s, 1H), 4.55 (m, 1H), 4.4 (m, 1H), 3.1 (dd, 1H), 2.95 (ss, 1H), 2.75 (m, 1H), 2.6 (s, 1H), 2.5 (m, 4H), 2.2 (m, 1H), 1.9 (m, 1H), 1.05 (t, 3H). MS (EI) for $C_{27}H_{30}N_6O_3$: 487 (MH$^+$).

1,1-Dimethylethyl 3-({[3-amino-6-(3-{[(1S)-2,3-dihydro-1H-inden-1-ylamino]carbonyl}phenyl)pyrazin-2-yl]carbonyl}amino)piperidine-1-carboxylate: $^1$H NMR (400 MHz, d$_6$-DMSO): δ 8.95 (m, 2H), 8.55 (m, 2H), 8.3 (d, 1H), 7.95 (d, 1H), 7.6 (t, 1H), 7.3-7.15 (m, 4H), 5.6 (q, 1H), 3.9-3.6 (m, 3H), 3.3 5(s, 3H), 3.1-2.85 (m, 4H), 2.0 (m, 1H), 1.85 (m, 1H), 1.7 (m, 2H), 1.3 (s, 9H). MS (EI) for $C_{31}H_{36}N_6O_4$: 457 (MH$^+$).

3-Amino-6-(3-{[(1S)-2,3-dihydro-1H-inden-1-ylamino]carbonyl}phenyl)-N-piperidin-3-ylpyrazine-2-carboxamide: $^1$H NMR (400 MHz, d$_6$-DMSO): δ 9.5-9.2 (m, 2H), 9.05 (m, 1H), 8.95 (s, 1H), 8.85 (t, 1H:), 8.55 (d, 1H), 8.35 (d, 1H), 7.95 (d, 1H), 7.6 (t, 1H), 7.25 (m, 4H), 5.6 (m, 1H), 5.0 (s, 1H), 4.3 (s 1H), 3.3-3.0 (m, 4H), 2.9 (m, 1H), 2.7 (m, 1H), 2.5 (m, 1H), 2.1 (m, 1H), 1.95-1.65 (m, 4H). MS (EI) for $C_{26}H_{28}N_6O_2$: 457 (MH$^+$).

3-Amino-6-(3-{[(1S)-2,3-dihydro-1H-inden-1-ylamino]carbonyl}phenyl)-N-(1-ethylpiperidin-3-yl)pyrazine-2-carboxamide: $^1$H NMR (400 MHz, d$_6$-DMSO): δ 8.95 (m, 2H), 8.55 (m, 2H), 8.25 (d, 1H), 7.92 (d, 1H), 7.6 (t, 1H), 7.25 (m, 4H), 5.6 (q, 1H), 4.0 (m, 1H), 3.05 (m, 1H), 2.9 (m, 1H), 2.7 (m, 1H), 2.35 (m, 2H), 2.2 (s, 2H), 2.05 (m, 1H), 1.7-1.5 (m, 4H), 1.25 (s, 1H), 1.0 (t, 3H). MS (EI) for $C_{28}H_{32}N_6O_2$: 485 (MH$^+$).

3-Amino-N-[(3S)-1-ethylpyrrolidin-3-yl]-6-[3-({[(1R,2S)-2-hydroxy-1H-inden-1-yl]amino}carbonyl)phenyl]pyrazine-2-carboxamide: $^1$H NMR (400 MH, d$_6$-DMSO): δ 8.97 (s, 1H), 8.65 (m, 3H), 8.3 (d, 1H), 7.96 (d, 1H), 7.7 (s, 1H), 7.6 (t, 1H), 7.25 (m, 4H), 5.5 (m, 1H), 5.2 (d, 1H), 4.55 (s, 1H), 4.4 (m, 1H), 3.1 (dd, 1H), 2.95 (s, 1H), 2.7 (m, 2H), 2.55-2.4 (m, 4H), 2.15 (m, 1H), 1.85 (m, 1H), 1.05 (t, 3H). MS (EI) for $C_{27}H_{30}N_6O_3$: 487 (MH$^+$).

3-Amino-6-(3-{[(1S)-2,3-dihydro-1H-inden-1-ylamino]carbonyl}phenyl)-N-pyrimidin-4-ylpyrazine-2-carboxamide: $^1$H NMR (400 MHz, d$_6$-DMSO): δ 10.9 (s, 1H), 9.2 (s, 2H), 9.04 (d, 1H), 8.9 (d, 1H), 8.65 (s, 1H), 8.4 (d, 2H), 8.05 (d, 1H), 7.7 (t, 1H), 7.3 (m, 4H), 5.7 (m, 1H), 3.15-2.9 (m, 2H), 2.1 (m, 1H). MS (EI) for $C_{25}HI_{21}N_7O_2$: 452 (MH$^+$).

3-Amino-6-[3-({[(1R,2S)-2-hydroxy-2,3-dihydro-1H-inden-1-yl]amino}carbonyl)phenyl]-N-[2-(1H-imidazol-4-yl)ethyl]pyrazine-2-carboxamide: $^1$H NMR 7.9 (d, 1H), 7.5 (t, 1H), 7.4 (s, 1H), 7.15 (m, 4H), 5.45 (m, 1H), 4.45 (t, 1H), 3.1 (m, 1H), 2.9 (m, 3H). MS (EI) for $C_{26}H_{25}N_7O_3$: 484 (MH$^+$).

1,1-Dimethylethyl (3S)-3-[({[3-amino-6-(3-{[(1S)-2,3-dihydro-1H-inden-1-ylamino]carbonyl}phenyl)pyrazin-2-yl]carbonyl}amino)methyl]pyrrolidine-1-carboxylate; $^1$H NMR (400 MHz, d$_6$-DMSO): δ 9.0 (m, 1H), 8.9 (d, 2H), 8.53 (s, 1H), 8.35 (d, 1H), 7.9 (d, 1H), 7.55 (t, 1H), 7.3-7.15 (m, 4H), 5.6 (q, 1H), 3.35 (d, 2H), 3.2 (m, 2H), 3.0 (m, 3H), 2.85 (m, 2H), 2.5 (m, 1H), 2.0 (m, 1H), 1.9 (m, 1H), 1.65 (m, 1H), 1.4 (s, 9H). MS (EI) for $C_{31}H_{36}N_6O_4$: 457 (MH$^+$).

3-Amino-6-(3-{[(1S)-2,3-dihydro-1H-inden-1-ylamino]carbonyl}phenyl)-N-[(3R)-pyrrolidin-3-ylmethyl]pyrazine-2-carboxamide: $^1$H NMR (400 MHz, d$_6$-DMSO): δ 9.4 (t, 2H), 9.22 (t, 1H), 9.05 (d, 1H), 8.95 (s, 1M), 8.6 (s, 1H), 8.5 (d, 1H), 7.95 (d, 1H), 7.6 (d, 1H), 7.45 (s, 2H), 7.3-7.15 (m, 4H), 5.6 (q, 1H), 3.4 (t, 2H), 3.25 (m, 2H), 3.15-2.8 (m, 4H), 2.6 (m, 1H), 2.45 (m, 2H), 2.1 (m, 1H), 2.0 (m, 1H), 1.7 (m, 1H). MS (EI) for $C_{26}H_{28}N_6O_2$: 457 (MH$^+$).

3-Amino-6-{3-[(2,3-dihydro-1H-inden-1-ylamino)carbonyl]phenyl}-N-piperidin-3-ylpyrazine-2-carboxamide: $^1$H NMR (400 MHz, d$_6$-DMSO): δ 8.96 (s, 1H), 8.89 (d, J=8.4 Hz, 1H), 8.72 (d, J=8.0 Hz, 1H), 8.54 (s, 1H), 8.35 (d, J=7.2 Hz, 1H), 7.93 (d, J=8.0 Hz, 1H), 7.60 (t, J=9.6 Hz, 1H), 7.30 (m, 1H), 7.25 (m, 1H), 5.61 (q, J=8 Hz, 1H), 4.20 (m, 1H), 3.29 (m, 1H), 3.01 (m, 2H), 2.89 (m, 1H), 2.03 (m, 1H), 1.90 (m, 1H), 1.74 (m, 2H). MS(E) for $C_{26}H_{28}N_6O_2$: 457 (MH$^+$).

3-Amino-6-(3-{[(1S)-2,3-dihydro-1H-inden-1-ylamino]carbonyl}phenyl)-N-[(3R)-piperidin-3-yl]pyrazine-2-carboxamide: $^1$H NMR (400 MHz, d$_6$-DMSO): δ 8.96 (s, 1H), 8.89 (d, J=8.2 Hz, 1H), 8.71 (m, 1H), 8.55 (s, 1H), 8.35 (d, J=7.6 Hz, 1H), 7.93 (d, J=8.0 Hz, 1H), 7.60 (t, J=8.0 Hz, 1H), 7.25 (m, 2H), 5.60 (q, J=8.4 Hz, 1H), 4.2 (m, 1H), 3.29 (m, 1H), 3.01 (m, 2H), 2.89 (m, 1H), 2.03 (m, 1H), 1.90 (m, 1H) 1.72 (m, 1H). MS(EI) for $C_{26}H_{28}N_6O_2$: 457 (MH$^+$).

3-Amino-6-[3-({[(1R,2S)-2-hydroxy-2,3-dihydro-1H-inden-1-yl]amino}carbonyl)phenyl]-N-piperidin-3-ylpyrazine-2-carboxamide: $^1$H NMR (400 MHz, d$_6$-DMSO): δ 9.2 (s, 1H), 8.75 (d, 1H), 8.65 (s, 1H), 8.5 (m, 1H), 8.35 (d, 1H), 8.0 (d, 1H), 7.6 (t, 1H), 7.25 (m, 4H), 5.5 (m, 1H), 4.55 (m, 1H), 4.25 (m, 1H), 3.5-2.7 (m, 7H), 1.9 (m, 2H), 1.7 (m, 2H). MS (EI) for $C_{26}H_{28}N_6O_3$: 473 (MH$^+$).

3-Amino-6-(3-{[(1S)-2,3-dihydro-1H-inden-1-ylamino]carbonyl}phenyl)-N-[2-(1H-imidazol-4-yl)ethyl]pyrazine-2-carboxamide: $^1$H NMR (400 MHz, d$_6$-DMSO): δ 9.05 (t, 2H), 8.9 (d, 2H), 8.55 (s, 1H), 8.35 (d, 1H), 7.95 (d, 11), 7.6 (t, 1H), 7.5 (s, 1H), 7.3-7.2 (m, 4H) 5.62 (q, 1H), 3.6 (q, 2H), 3.05-2.85 (m, 5H), 2.0 (m, 1H). MS (EI) for $C_{26}H_{25}N_7O_2$: 468 (MH$^+$).

3-Amino-N-azepan-4-yl-6-(3-{[(1S)-2,3-dihydro-1H-inden-1-ylamino]carbonyl}phenyl)pyrazine-2-carboxamide: $^1$H NMR (400 MHz, d$_6$-DMSO): δ 9.4 (s, 1H), 9.25 (s, 1H), 9.0 (m, 1H), 8.9 (s, 1H), 8.7 (d, 1H), 8.6 (s, 1H), 8.3 (d, 1H), 7.9 (d, 1H), 7.55 (t, 1H), 7.3-7.1 (m, 4H), 5.6 (q, 1H), 4.1 (s, 1H), 3.25 (m, 1H), 3.1-2.8 (m, 3H), 2.45 (m, 1H), 2.0-1.7 (m, 8H). MS (EI) for $C_{27}H_{30}N_6O_2$: 471 (MH$^+$).

1,1-Dimethylethyl (3S)-3-{[({3-amino-6-[3-({[(1R,2S)-2-hydroxy-2,3-dihydro-1H-inden-1-yl]amino}carbonyl)phenyl]pyrazin-2-yl}carbonyl)amino]methyl}pyrrolidine-1-carboxylate: $^1$H NMR (400 MHz, d$_6$-DMSO): δ 9.05 (m, 1H), 9.0 (s, 1H), 8.65 (s, 1H), 8.6 (d, 1H), 8.4 (d, 1H), 7.98 (d, 1H), 7.6 (t, 1H), 7.3-7.15 (m, 4H), 5.5 (m, 1H), 5.65 (d, 1H), 4.55 (m, 1H), 3.4 (m, 2H), 3.35 (m, 3H), 3.35-3.0 (m, 3H), 2.9 (d, 1H), 1.9 (m, 1H), 1.6 (m, 1H), 1.4 (m, 9H). MS (EI) for $C_{31}H_{36}N_6O_5$: 473 (MH$^+$).

1,1-Dimethylethyl 4-({[3-amino-6-(3-{[(1S)-2,3-dihydro-1H-inden-1-ylamino]carbonyl}phenyl)pyrazin-2-yl]carbonyl}amino)azepane-1-carboxylate: $^1$H NMR (400 MHz, d$_6$-DMSO): δ 8.95 (m, 2H), 8.65-8.55 (dd, 2H), 8.35 (d, 1H), 7.95 (d, 1H), 7.7 (s, 1H), 7.6 (t, 1H), 7.3-7.15 (m, 4H), 5.6 (q, 1H), 3.95 (m, 1H), 3.6-3.5 (m, 1H), 3.4-3.1 (m, 3H), 3.05 (m, 1H), 2.9 (m, 1H), 2.05-1.4 (m, 7H), 1.4 (s, 9H). MS (EI) for $C_{32}H_{38}N_6O_4$: 471 (MH$^+$).

1,1-Dimethylethyl (3S)-3-({[3-amino-6-(3-{[(1S)-2,3-dihydro-1H-inden-1-ylamino]carbonyl}phenyl)pyrazin-2-yl]carbonyl}amino)piperidine-1-carboxylate: $^1$H NMR (400 MHz, d$_6$-DMSO): δ 8.91 (s, 1H), 8.87 (d, J=8.0 Hz, 1H), 8.51 (m, 1H), 8.27 (d, J=6.4 Hz, 1H), 7.89 (d, J=7.2 Hz, 1H), 7.56 (t, J=8.0 Hz, 1H), 7.27 (m, 1H), 7.21 (m, 1H), 5.60 (q, J=8.8 Hz, 1H), 2.97 (m, 2H), 2.03 (m, 2H), 1.84 (m, 2H), 1.69 (m, 2H), 1.33 (s, 9H). MS (EI) for $C_{31}H_{36}N_6O_4$: 501 (M-$C_4H_9$).

1,1-Dimethylethyl (3S)-3-[({3-amino-6-[3-({[(1R,2S)-2-hydroxy-2,3-dihydro-1H-inden-1-yl]amino}carbonyl)phenyl]pyrazin-2-yl}carbonyl)amino]piperidine-1-carboxylate: $^1$H NMR (400 MHz, d$_6$-DMSO): δ 8.98 (s, 1H), 8.62 (s, 1H), 8.58 (m, 2H), 8.28 (d, J=6.40 Hz, 1H), 7.93 (d, J=8.0 Hz, 1H), 7.56 (t, 8.0 Hz, 1H), 7.22 (m, 4H), 5.48 (m, 1H), 4.54 (m, 1H), 3.85 (m, 2H), 3.71 (m, 2H), 3.10 (m, 2H), 2.91 (m, 2H), 1.86 (m, 1H), 1.71 (m, 2H), 1.36 (s, 9H). MS (EI) for $C_{31}H_{36}N_6O_5$: 517 (MH$^+$-$C_4H_9$).

3-Amino-6-[3-({[(1R,2S)-2-hydroxy-2,3-dihydro-1H-inden-1-yl]amino}carbonyl)phenyl]-N-[(3R)-pyrrolidin-3-ylmethyl]pyrazine-2-carboxamide: $^1$H NMR (400 MHz, d$_6$-DMSO): δ 9.1 (t, 1H), 8.95 (s, 1H), 8.65 (d, 2H), 8.5 (d, 1H), 7.95 (d, 1H), 7.55 (t, 1H), 7.25-7.15 (m, 4H), 5.5 (m, 1H), 5.0 (s, 1H1), 4.55 (m, 1H), 3.3 (m, 2H), 3.15-2.8 (m, 4H), 2.85 (m, 1H), 1.9 (m, 1H), 1.8 (s, 4H), 1.6 (m, 1H). MS (EI) for $C_{26}H_{28}N_6O_3$: 473 (MH$^+$).

1,1-Dimethylethyl 4-[({3-amino-6-[3-({[(1R,2S)-2-hydroxy-2,3-dihydro-1H-inden-1-yl]amino}carbonyl)phenyl]pyrazin-2-yl}carbonyl)amino]azepane-1-carboxylate: $^1$H NMR (400 MHz, d$_6$-DMSO): δ 8.95 (s, 1H), 8.7-8.65 (m, 3H), 8.45 (d, 1H), 7.95 (d, 1H), 7.6 (t, 1H), 7.3-7.15 (m, 4H), 5.5 (m, 1H), 4.55 (m, 1H), 3.95 (m, 1H), 3.6-3.1(m, 5H), 2.95 (d, 1H), 2.05-1.6 (m, 6H), 1.4 (s, 9H). MS (EI) for $C_{32}H_{38}N_6O_5$: 487 (MH$^+$).

3-Amino-N-azepan-4-yl-6-[3-({[(1R,2S)-2-hydroxy-2,3-dihydro-1H-inden-1-yl]amino}carbonyl)phenyl]pyrazine-2-carboxamide: $^1$H NMR (400 MHz, d$_6$-DMSO): δ 8.98 (s, 1H), 8.95 (d, 1H), 8.7 (s, 1H), 8.6 (d, 1H), 8.3 (d, 1H), 7.95 (d, 1H), 7.6 (t, 1H), 7.3-7.15 (m, 4H), 5.5 (m, 1H), 4.55 (m, 1H), 4.2 (m, 1H), 3.1 (dd, 1H), 3.0-2.7 (m, 4H), 1.95-1.55 (m, 9H). MS (EI) for $C_{27}H_{30}N_6O_3$: 487 (MH$^+$).

3-Amino-N-azepan-4-yl-6-{3-[(3aR,8aS)-8,8a-dihydro-3aH-indeno[1,2-d][1,3]oxazol-2-yl]phenyl}pyrazine-2-carboxamide: $^1$H NMR (400 MHz, d$_6$-DMSO): δ 9.4-9.25 (dd, 1H), 8.9 (s, 1H), 8.65 (s, 1H), 8.25 (d, 1H), 7.8 (m, 1H), 7.55 (t, 1H), 7.4 (m, 1H), 7.3 (m, 4H), 5.75 (d, 1H), 5.6 (t, 1H), 4.3 (m, 1H), 3.55 (dd, 1H), 3.3 (s, 1H), 3.2-2.9 (m, 4H), 2.7 (m, 1H), 1.9 (m, 2H), 1.65 (m, 311). MS (EI) for $C_{27}H_{28}N_6O_2$: 469 (MH$^+$).

1,1-Dimethylethyl (3R)-3-[({[3-amino-6-(3-{[(1S)-2,3-dihydro-ylamino]carbonyl}phenyl)pyrazin-2-yl]carbonyl}amino)methyl]pyrrolidine-1-carboxylate: $^1$H NMR (400 MHz, d$_6$-DMSO): δ 9.0 (m, 1H), 8.9 (d, 2H), 8.55 (s, 1H), 8.35 (d, 1H), 7.9 (d, 1H), 7.55 (t, 1H), 7.3-7.15 (m, 4H), 5.6 (q, 1H), 3.35 (m, 3H), 3.2 (m, 1H), 3.0 (m, 2H), 2.9 (m, 1H), 2.5 (m, 3H), 2.0 (m, 1H), 1.9 (m, 1H), 1.675 (m, 1H), 1.4 (s, 9H). MS (EI) for C$_{31}$H$_{36}$N$_6$O$_4$: 557 (MH$^+$).

3-Amino-6-(3-{[(1S)-2,3-dihydro-1H-inden-1-ylamino]carbonyl}phenyl)-N-[(3S)-pyrrolidin-3-ylmethyl]pyrazine-2-carboxamide: $^1$H NMR (400 MHz, d$_6$-DMSO): δ 9.35 (s, 2H), 9.15 (t, 1H), 9.0 (d, 1H), 8.85 (s, 1H), 8.6 (s, 1H), 8.4 (d, 1H), 7.9 (d, 1H), 7.55 (t, 1H), 7.3-7.15 (m, 4H), 5.6 (q, 1H), 4.9 (s, 1H), 3.4 (t, 2H), 3.15-2.85 (m, 4H), 2.65-2.45 (m, 4H), 2.15-1.9 (m, 2H), 1.7 (m, 1H). MS (EI) for C$_{26}$H$_{28}$N$_6$O$_2$: 457 (MH$^+$).

1,1-Dimethylethyl (3R)-3-{[({3-amino-6-[3-({[(1R,2S)-2-hydroxy-2,3-dihydro-1H-inden-1-yl]amino}carbonyl)phenyl]pyrazin-2-yl}carbonyl)amino]methyl}pyrrolidine-1-carboxylate: $^1$H NMR (400 MHz, d$_6$-DMSO): δ 9.0 (m, 1H), 8.95 (s, 1H), 8.65 (s, 1H), 8.57 (d, 1H), 8.4 (d, 1H), 7.95 (d, 1H), 7.55 (t, 1H), 7.3-7.15 (m, 4H), 5.5 (m, 1H), 5.1 (d, 1H), 4.55 (m, 1H), 3.35 (m, 5H), 3.25-3.05 (m, 3H), 2.9 (d, 1H), 2.5 (m, 1H), 1.9 (m, 1H), 1.65 (m, 1H), 1.4 (s, 9H). MS (EI) for C$_{31}$H$_{36}$N$_6$O$_5$: 473 (MH$^+$).

3-Amino-6-[3-({[(1R,2S)-2-hydroxy-2,3-dihydro-1H-inden-1-yl]amino}carbonyl)phenyl]-N-[(3S)-pyrrolidin-3-ylmethyl]pyrazine-2-carboxamide: $^1$H NMR (400 MHz, d$_6$-DMSO): δ 9.1 (m, 3H), 9.0 (s, 1H), 8.65 (d, 2H), 8.4 (d, 1H), 7.95 (d, 1H), 7.55 (t, 1H), 7.3-7.15 (m, 4H), 5.5 (m, 1H), 5.4 (s, 1H), 4.55 (t, 1H), 3.55 (s, 1H), 3.4 (m, 2H), 3.3-3.05 (m, 4H), 2.95 (d, 2H), 2.6 (m, 1H), 2.0 (m, 1H), 1.7 (m, 1H). MS (EI) for C$_{26}$H$_{28}$N$_6$O$_3$: 473 (MH$^+$).

1,1-Dimethylethyl (3R)-3-({[3-amino-6-(3-{[(1S)-2,3-dihydro-1H-inden-1-ylamino]carbonyl}phenyl)pyrazin-2-yl]carbonyl}amino)piperidine-1-carboxylate: $^1$H NMR (400 MH, d$_6$-DMSO): δ 8.91 (s, 1H), 8.87 (d, J=8.0 Hz, 1H), 8.51 (m, 1H), 8.27 (d, J=6.4 Hz, 1H), 7.89 (d, J=7.2 Hz, 1H), 7.56 (t, J=8.0 Hz, 1H), 7.27 (m, 1H), 7.21 (m, 1H), 5.60 (q, J=8.8 Hz, 1H), 2.97 (m, 2H), 2.03 (m, 2H), 1.84 (m, 2H), 1.69 (m, 2H), 1.33 (s, 9H). MS (EI) for C$_{31}$H$_{36}$N$_6$O$_4$: 501 (M-C$_4$H$_9$).

1,1-Dimethylethyl (3R)-3-[({3-amino-6-[3-({[(1R,2S)-2-hydroxy-2,3-dihydro-1H-inden-1-yl]amino}carbonyl)phenyl]pyrazin-2-yl}carbonyl)amino]piperidine-1-carboxylate: $^1$H NMR (400 MHz, d$_6$-DMSO): δ 8.91 (s, 2H), 8.72 (d, J=8.8 Hz, 1H), 8.51 (m, 1H), 8.28 (d, J=7.6 Hz, 1H), 7.90 (d, J=7.6 Hz, 1H), 7.56 (t, J=8.0 Hz, 1H), 7.27 (m, 2H), 7.19 (m, 2H), 5.60 (m, 4H), 3.81 (m, 2H), 3.71 (m, 2H), 3.00 (m, 2H), 2.91 (m, 2H), 2.01 (m, 1H), 1.86 (m, 1H), 1.71 (m, 2H), 1.36 (s, 9H). MS (EI) for C$_{31}$H$_{36}$N$_6$O$_5$: 473 (MH$^+$-C$_5$H$_9$O$_2$).

3-Amino-6-(3-{[(1S)-2,3-dihydro-1H-inden-1-ylamino]carbonyl}phenyl)-N-[(3S)-piperidin-3-yl]pyrazine-2-carboxamide: $^1$H NMR (400 MHz, d$_6$-DMSO): δ 9.02 (m, 1H), 8.91 (s, 1H), 8.87 (s, 1H), 8.85 (m, 1H), 8.73 (d, J=8.4 Hz, 1H), 8.65 (s, 1H), 8.57 (m, 1H), 8.52 (m, 1H), 8.43 (m, 1H), 8.35 (d, J=8.0 Hz, 1H), 7.95 (m, 1H), 7.91 (m, 1H), 7.62 (m, 2H), 7.36 (t, 8.4 Hz, 2H), 7.17 (m, 4H), 4.62 (d, J=6.0 Hz, 1H), 3.07 (m, 2H), 2.38 (m, 3H), 1.92 (m, 2H), 1.75 (m, 2H). MS (EI) C$_{23}$H$_{26}$N$_8$O$_2$: 447 (MH$^+$).

3-Amino-6-[3-({[(1R,2S)-2-hydroxy-2,3-dihydro-1H-inden-1-yl]amino}carbonyl)phenyl]-N-[(3S)-piperidin-3-yl]pyrazine-2-carboxamide: $^1$H NMR (400 MHz, d$_6$-DMSO): δ 9.01 (s, 1H), 8.76 (d, J=8.4 Hz, 1H), 8.67 (m, 1H), 8.62 (d, J=8.8 Hz, 1H), 8.10 (d, J=8.0 Hz, 1H), 7.97 (d, J=7.6 Hz, 1H), 7.60 (t, J=7.6 Hz, 1H), 7.28 (m, 2H), 7.22 (m, 2H), 5.51 (m, 1H), 5.18 (m, 1H), 4.56 (m, 1H), 4.23 (m, 1H), 3.15 (m, 2H), 2.96 (m, 2H), 2.72 (m, 1H), 1.88 (m, 2H), 1.71 (m, 2H), 1.23 (s, 1H). MS (EI) for C$_{26}$H$_{28}$N$_6$O$_3$: 473 (MH$^+$).

3-(5-Amino-6-{(1E)-N-[4-(1-methylethyl)phenyl]ethanehydrazonoyl}pyrazin-2-yl)-N-(phenylmethyl)benzamide: $^1$H NMR (400 MHz, CDCl$_3$): δ 8.40 (m, 1H), 8.0 (m, 2H), 7.80 (m, 2H), 7.25 (m,1H), 7.2 (m, 4H), 6.9 (m, 4H), 4.8 (s, 2H), 2.6 (s, 3H), 2.0 (s, 1H) 1.2 (m, 6H). MS (EI) for C$_{29}$H$_{30}$N$_6$O: 479 (MH$^+$).

3-{5-Amino-6-[(1E)-N-1,3-benzothiazol-2-ylethanehydrazonoyl]pyrazin-2-yl}-N-(phenylmethyl)benzamide: $^1$H NMR (400 MHz, d$_6$-DMSO): δ 8.40 (m, 1H), 8.0 (m, 2H), 7.80 (m, 2H), 7.25 (m, 1H), 7.2 (m, 4H), 6.9 (m, 4H), 4.5 (s, 2H), 2.8 (s, 3H). MS (EI) for C$_{27}$H$_{23}$N$_7$OS: 494 (MH$^+$).

3-{5-Amino-6-[(1E)-N-(4-methylphenyl)ethanehydrazonoyl]pyrazin-2-yl}-N-(phenylmethyl)benzamide: $^1$H NMR (400 MHz, d$_6$-DMSO): δ 9.90 (d, 1H), 9.80 (d, 1H), 9.20 (d, 1H), 8.50 (d, 2H), 8.20 (d, 1H), 7.90 (m, 1H), 7.75-7.0 (m, 7H), 4.50 (d, 2H), 2.6 (s, 3H), 1.30 (s, 3H). MS (EI) for C$_{27}$H$_{26}$N$_6$O: 451 (MH$^+$).

3-{5-Amino-6-[(1E)-N-(4-chlorophenyl)ethanehydrazonoyl]pyrazin-2-yl}-N-(phenylmethyl)benzamide: $^1$H NMR (400 MHz, d$_6$-DMSO): δ 9.80 (s, 1H), 9.10 (m, 1H), 8.65 (s, 1H), 8.55 (s, 1H), 8.2 (d, 1H), 7.90 (d, 1H), 7.60 (m, 1H), 7.4-7.1 (m, 8H), 4.50 (d, 2H), 3.2 (s, 3H), 2.6 (s, 3H). MS (EI) for C$_{27}$H$_{23}$ClN$_6$O: 472 (MH$^+$).

3-{5-Amino-6-[(1E)-N-methyl-N-phenylethanehydrazonoyl]pyrazin-2-yl}-N-(phenylmethyl)benzamide: $^1$H NMR (400 MHz, d$_6$-DMSO): δ 9.20 (m, 1H), 9.00 (d, 1H), 8.80 (d, 1H), 8.20 (dd, 2H), 7.95 (d, 2H), 7.60 (d, 1H), 7.45-7.0 (m, 6H), 4.50 (d, 2H), 3.2 (s, 3H), 2.6 (s, 3H). MS (EI) for C$_{27}$H$_{26}$N$_6$O: 451(MH$^+$).

3-{5-Amino-6-[(1E)-N-(2-hydroxyethyl)ethanehydrazonoyl]pyrazin-2-yl}-N-(phenylmethyl)benzamide: $^1$H NMR (400 MHz, d$_6$-DMSO): δ 9.20 (m, 1H), 8.45 (m, 2H), 8.15 (d, 1H), 7.80 (d, 1H), 7.45-7.15 (m, 5H), 4.50 (d, 2H), 3.6 (m, 2H), 3.3 (m, 2H), 2.2 (s, 3H). MS (EI) for C$_{22}$H$_{24}$N$_6$O$_2$: 405 (MH$^+$).

3-{5-Amino-6-[(1E)-N-morpholin-4-ylethanimidoyl]pyrazin-2-yl}-N-(phenylmethyl)benzamide: $^1$H NMR (400 MHz, d$_6$-DMSO): δ 9.20 (m, 1H), 8.8 (s, 1H), 8.65 (m, 1H), 8.2 (m,1H), 7.8 (m, 1H), 7.4 (m, 1H), 7.2 (m, 4H), 4.8 (s, 2H), 3.8 (m, 4H), 3.2 (m, 2H), 2.8 (m, 2H), 2.6 (s, 3H). MS (EI) for C$_{24}$H$_{26}$N$_6$O$_2$: 431 (MH$^+$).

4-((2E)-2-{1-[3-Amino-6-(3-{[(phenylmethyl)amino]carbonyl}phenyl)pyrazin-2-yl]ethylidene}hydrazino)benzoic acid: $^1$H NMR (400 MHz, d$_6$-DMSO): δ 10.0 (s, 1H), 9.2 (m, 1H), 8.8 (m, 1H), 8.5 (s, 1H1), 8.2 (m, 1H), 7.8 (m, 3H), 7.60 (m, 1H), 7.25 (m, 3H), 7.2 (m, 3H), 4.6 (s, 2H), 2.8 (s, 3H). MS (EI) for C$_{27}$H$_{24}$N$_6$O$_3$: 481 (MH$^+$).

Ethyl ((2E)-2-{1-[3-amino-6-(3-{[(phenylmethyl)amino]carbonyl}phenyl)pyrazin-2-yl]ethylidene}hydrazino)acetate: $^1$H NMR (400 MHz, d$_4$-MeOH): δ 8.40 (m, 1H), 8.2 (m, 2H), 7.9 (m, 1H), 7.80 (m, 1H), 7.35 (m, 1H), 7.2 (m, 4H), 4.6 (s, 2H), 4.2 (m, 2H), 3.8 (s, 2H), 2.4 (s, 3H), 1.2 (m, 3H). MS (EI) for C$_{24}$H$_{26}$N$_6$O$_3$: 447 (MH$^+$).

3-{5-Amino-6-[(1E)-N,N-dimethylethanehydrazonoyl]pyrazin-2-yl }-N-(phenylmethyl)benzamide: $^1$H NMR (400 MHz, CDCl$_3$): δ 9.2 (s, 1H), 9.0 (s, 1H), 8.40 (m, 1H), 8.2 (m, 1H), 7.80 (m, 2H), 7.25 (m, 1H), 7.2 (m, 3H), 4.8 (s, 2H), 3.3 (s, 6H), 2.6 (s, 3H). MS (EI) for C$_{22}$H$_{24}$N$_6$O: 389 (MH$^+$).

3-(5-Amino-6-{(1E)-N-[hydrazino(imino)methyl]ethanehydrazonoyl}pyrazin-2-yl)-N-(phenylmethyl)benzamide: $^1$H NMR (400 MHz, d$_4$-MeOH): δ 9.2 (s, 1H), 8.8 (s, 1H), 8.6 (m, 1H), 8.2 (m, 2H), 7.80 (m, 1H), 7.25 (m, 1H), 7.2 (m, 3H), 4.6 (s, 2H), 2.8 (s, 3H). MS (EI) for C$_{21}$H$_{23}$N$_9$O: 418 (MH$^+$).

3-(5-Amino-6-{(1E)-N-[4-(methylsulfonyl)phenyl] ethanehydrazonoyl}pyrazin-2-yl)-N-(phenylmethyl)benzamide: $^1$H NMR (400 MHz, d$_6$-DMSO): δ 10.0 (s, 1H), 9.2 (m, 1H), 8.8 (s, 1H), 8.5 (s, 1H), 8.2 (m, 1H), 7.8 (m, 2H), 7.6 (m, 1H), 7.25 (m, 3H), 7.2 (m, 3H), 4.6 (s, 2H), 3.2 (s, 3H), 2.8 (s, 3H). MS (EI) for C$_{27}$H$_{26}$N$_6$O$_3$S: 515 (MH$^+$).

3-{5-Amino-6-[(1E)-N-(4-cyanophenyl)ethanehydrazonoyl]pyrazin-2-yl}-N-(phenylmethyl)benzamide: $^1$H NMR (400 MHz, d$_6$-DMSO): δ 10.1 (s, 1H), 9.20 (m, 1H), 8.70 (s, 1H), 8.55 (s, 1H), 8.20 (d, 1H), 7.95 (d, 1H), 7.75 (d, 2H), 7.60 (m, 1H), 7.40-7.20 (m, 8H), 4.50 (d, 2H), 2.6 (s, 3H). MS (EI) for C$_{27}$H$_{23}$N$_7$O: 462 (MH$^+$).

3-{5-Amino-6-[(1E)-N-pyridin-2-ylethanehydrazonoyl]pyrazin-2-yl}-N-(phenylmethyl)benzamide: $^1$H NMR (400 MHz, d$_6$-DMSO): δ 9.20 (m, 1H), 8.75 (s, 1H), 8.55 (s, 1H), 8.20 (d, 2H), 7.95-7.85 (m, 3H), 7.60 (m, 1H), 7.40-7.20 (m, 5H), 4.50 (d, 2H), 2.6 (s, 3H). MS (EI) for C$_{25}$H$_{23}$N$_7$O: 438 (MH$^+$).

3-(5-Amino-6-{(1E)-N-[amino(imino)methyl]ethanehydrazonoyl}pyrazin-2-yl)-N-(phenylmethyl)benzamide: $^1$H NMR (400 MHz, d6-DMSO): δ 11.0 (m, 1H), 9.20 (m, 1H), 8.80 (s, 1H), 8.75 (s, 1H), 8.20 (d, 2H), 8.00-7.85 (m, 5H), 7.60 (m, 1H), 7.40-7.20 (m, 4H), 4.50 (d, 2H), 2.6 (s, 3H). MS (EI) for C$_{21}$H$_{22}$N$_8$O: 403 (MH$^+$).

3-[5-Amino-6-((1E)-N-{4-[(trifluoromethyl)oxy]phenyl}ethanehydrazonoyl)pyrazin-2-yl]-N-(phenylmethyl)benzamide: $^1$H NMR (400 MHz, d$_6$-DMSO): δ 10.1 (s, 1H), 9.90 (s, 1H), 9.20 (m, 1H), 8.70 (s, 1H), 8.55 (s, 1H), 8.20 (d, 1H), 7.95 (d, 2H), 7.60 (m, 2H), 7.40-7.20 (m, 6H), 4.50 (d, 2H), 2.6 (s, 3H). MS (EI) for C$_{27}$H23F$_3$N$_6$O$_2$: 522 (MH$^+$).

3-{5-Amino-6-[(1E)-N-(4-nitrophenyl)ethanehydrazanoyl]pyrazin-2-yl}-N-(phenylmethyl)benzamide: $^1$H NMR (400 MHz, d$_6$-DMSO): δ 10.5 (s, 1H), 9.20 (m, 1H), 8.70 (s, 1H), 8.55 (s, 1H), 8.20 (m, 3H), 7.95 (d, 2H), 7.60 (m, 1H), 7.40-7.20 (m, 7H), 4.50 (d, 2H), 2.6 (s, 3H). MS (EI) for C$_{26}$H$_{25}$N$_7$O$_3$: 483 (MH$^+$).

3-(5-Amino-6-{(1E)-N-[4-(trifluoromethyl)pyrimidin-2-yl]ethanehydrazonoyl}pyrazin-2-yl)-N-(phenylmethyl)benzamide: $^1$H NMR (400 MHz, d6-DMSO): δ 8.95 (m, 1H), 8.55 (s, 1H), 8.40 (s, 1H), 8.20 (d, 1H), 7.95 (d, 1H), 7.60 (m, 1H), 7.40-7.20 (m, 5H), 4.50 (s, 2H), 2.6 (s, 3H). MS (EI) for C$_{25}$H$_{21}$F$_3$N$_8$O: 507 (MH$^+$).

3-(5-Amino-6-{(1E)-N-[(dimethylamino)carbonothioyl]ethanehydrazonoyl}pyrazin-2-yl)-N-(phenylmethyl)benzamide: $^1$H NMR (400 MHz, d$_6$-DMSO): δ 9.90 (s, 1H), 9.20 (m, 1H), 8.70 (s, 1H), 8.55 (s, 1H), 8.20 (d, 1H), 7.95 (d, 1H), 7.60 (m, 1H), 7.40-7.20 (m, 6H), 4.50 (d, 2H), 3.4 (s, 6H), 2.6 (s, 3H). MS (EI) for C$_{23}$H$_{25}$N$_7$OS: 448 (MH$^+$).

3-{5-Amino-6-[(1E)-N-1H-1,2,3-benzotriazol-1-ylethanimidoyl]pyrazin-2-yl}-N-(phenylmethyl)benzamide: $^1$H NMR (400 MHz, d6-DMSO): δ 9.20 (m, 1H), 9.00 (s, 1H), 8.60 (s, 1H), 8.20 (d, 1H), 8.10 (s, 2H), 7.90 (dd, 2H), 7.70-7.60 (m, 2H), 7.50 (m, 1H), 7.40-7.20 (m, 6H), 4.50 (d, 2H), 2.95 (s, 3H). MS (EI) for C$_{26}$H$_{22}$N$_8$O: 463 (MH$^+$).

3-{5-Amino-6-[(1E)-N-methylethanehydrazonoyl]pyrazin-2-yl}-N-(phenylmethyl)benzamide: $^1$H NMR (400 MHz, d$_6$-DMSO): δ 8.50 (d, 1H), 8.30 (s, 1H), 8.20 (d, 1H), 7.90 (d, 1H), 7.65 (m, 1H), 7.40-7.20 (m, 5H:), 4.50 (d, 2H), 2.40 (s, 3H), 1.95 (s, 3H). MS (EI) for C$_{21}$H$_{22}$N$_6$O: 375 (MH$^+$).

3-(5-Amino-6-{(1E)-N-[4-(trifluoromethyl)phenyl]ethanehydrazonoyl}pyrazin-2-yl)-N-(phenylmethyl)benzamide: $^1$H NMR (400 MHz, d$_6$-DMSO): δ 10.0 (s, 1H), 9.2 (m, 1H), 8.8 (s, 1H), 8.5 (s, 1H), 8.2 (m, 1H), 7.8 (m, 2H), 7.6 (m, 1H), 7.25 (m, 3H), 7.2 (m, 3H), 4.6 (s, 2H), 2.8 (s, 3H). MS (EI) for C$_{27}$H$_{23}$N$_6$OF$_3$: 505 (MH$^+$).

3-{5-Amino-6-[(1E)-N-phenylethanehydrazonoyl]pyrazin-2-yl}-N-(phenylmethyl)benzamide: $^1$H NMR (400 MHz, d$_6$-DMSO): δ 10.0 (s, 1H), 9.2 (m, 1H), 8.8 (s, 1H), 8.5 (s, 1H), 8.2 (m, 1H), 7.8 (m, 2H), 7.6 (m, 1H), 7.25 (m, 4H), 7.2 (m, 3H), 4.6 (s, 2H), 2.8 (s, 3H). MS (EI) for C$_{26}$H$_{24}$N$_6$O: 437 (MH$^+$).

3-{5-Amino-6-[(1E)-N-(4-methylpiperazin-1-yl)ethanimidoyl]pyrazin-2-yl}-N-(phenylmethyl)benzamide: $^1$H NMR (400 MHz, d$_6$-DMSO): δ 9.20 (m, 1H), 8.8 (s, 1H), 8.65 (m, 1H), 8.2 (m, 1H), 7.8 (m, 1H), 7.4 (m, 1H), 7.2 (m, 4H), 4.8 (s, 2H), 3.6 (m, 2H), 3.4 (m, 2H), 3.2 (m, 2H), 3.0 (m, 2H), 2.8 (s, 3H), 2.6 (s, 3H). MS (EI) for C$_{25}$H$_{29}$N$_7$O: 444 (MH$^+$).

3-[5-Amino-6-((1E)-N-{(2R)-2-[(methyloxy)methyl]pyrrolidin-1-yl}ethanimidoyl)pyrazin-2-yl]-N-(phenylmethyl)benzamide: $^1$H NMR (400 MHz, d$_4$-MeOH): δ 8.65 (m, 1H), 8.3 (m,1H), 8.2 (m,1H), 7.8 (m, 1H), 7.6 (m, 1H), 7.4 (m, 4H), 7.2 (m, 1H), 4.8 (s, 2H), 3.6 (m, 2H), 3.4 (s, 3H), 3.2 (m, 2H), 3.1 (m, 1H), 2.6 (s, 3H), 2.0 (m, 4H). MS (EI) for C$_{26}$H$_{30}$N$_6$O$_2$: 459 (MH$^+$).

3-{5-Amino-6-[(1E)-N-azepan-1-ylethanimidoyl]pyrazin-2-yl}-N-(phenylmethyl)benzamide: $^1$H NMR (400 MHz, d$_4$-MeOH): δ 8.65 (m, 1H), 8.3 (m, 1H), 8.2 (m, 1H), 7.8 (m, 1H), 7.6 (m, 1H), 7.4 (m, 4H), 7.2 (m, 1H), 4.8 (s, 2H), 3.8 (m, 4H), 2.6 (s, 3H) 2.2 (m, 4H), 1.8 (m, 4H). MS (EI) for C$_2$6H$_{30}$N$_6$O: 443 (MH$^+$).

3-(5-Amino-6-{(E)-[(phenylmethyl)hydrazono]methyl}pyrazin-2-yl)-N-(phenylmethyl)benzamide: $^1$H NMR (400 MHz, d$_6$-DMSO): δ 9.20 (m, 1H), 8.55 (s, 1H), 8.40 (d, 1H), 8.30 (m, 1H), 8.10 (d, 1H), 7.80 (m, 2H ), 7.60-7.20 (m, 13H), 4.50-4.40 (dd, 4H). MS (EI) for C$_{26}$H$_{24}$N$_6$O: 437 (MH$^+$).

3-[5-Amino-6-((E)-{[amino(imino)methyl]hydrazono}methyl)pyrazin-2-yl]-N-(phenylmethyl)benzamide: $^1$H NMR (400 MHz, d$_6$-DMSO): δ 11.7 (s, 1H), 9.20 (m,1H), 8.80 (s, 1H), 8.50 (m, 1H), 8.40 (m, 1H), 8.15 (d, 1H), 7.95 (m, 3H), 7.60 (m, 1H), 7.40-7.20 (m, 6H), 4.50 (d, 2H). MS (ED for C$_{20}$H$_{20}$N$_8$O: 389 (MH$^+$).

3-(5-Amino-6-{(E)-[(2-hydroxyethyl)hydrazono]methyl}pyrazin-2-yl)-N-(phenylmethyl)benzamide: $^1$H NMR (400 MH, d$_6$-DMSO): δ 9.20 (m, 1H), 8.50 (m, 2H), 8.20 (d, 1H), 7.90 (m, 2H), 7.40-7.20 (m, 5H), 4.50 (d, 2H), 3.60 (m, 2H), 3.30 (m, 2H). MS (EI) for C$_{21}$H$_{22}$N$_6$O$_2$: 391 (MH$^+$).

3-{5-Amino-6-[(E)-(pyridin-2-ylhydrazono)methyl]pyrazin-2-yl}-N-(phenylmethyl)benzamide: $^1$H NMR (400 MHz, d$_6$-DMSO): δ 11.3 (s, 1H), 9.20 (m, 1H), 8.85 (s, 1H), 8.50 (s, 1H), 8.35 (s, 1H), 8.20 (dd, 2H), 7.75-7.50 (m, 3H), 7.40-7.20 (m, 5H), 7.10 (d, 1H), 6.95 (m, 1H), 4.50 (d, 2H). MS (EI) for C$_{24}$H$_{21}$N$_7$O: 424 (MH$^+$).

3-(5-Amino-6-{(E)-[(4-cyanophenyl)hydrazono]methyl}pyrazin-2-yl)-N-(phenylmethyl)benzamide: $^1$H NMR (400 MHz, d$_6$-DMSO): δ 11.5 (s, 1H), 9.20 (m,1H), 8.70 (s, 1H), 8.50 (s, 1H), 8.35 (s, 1H), 8.20 (d, 1H), 7.95 (d, 1H), 7.80-7.55 (m, 5H), 7.40-7.00 (m, 7H), 4.50 (d, 2H). MS (EI) for C$_{26}$H$_{21}$N$_7$O: 448 (MH$^+$).

3-(5-Amino-6-1{(E)-[(4-methylphenyl)hydrazono]methyl}pyrazin-2-yl)-N-(phenylmethyl)benzamide: $^1$H NMR (400 MHz, d$_6$-DMSO): δ 10.8 (s,1H), 9.20 (m,1H), 8.60 (s, 1H), 8.50 (s, 1H), 8.20 (m, 2H), 7.95 (d, 1H), 7.50 (m, 2H), 7.40-6.90 (m, 6H), 4.50 (d, 2H), 2.10 (s, 3H). MS (EI) for C$_{26}$H$_{42}$N$_6$O: 437 (MH$^+$).

3-{5-Amino-6-[(E)-(hydroxyimino)methyl]pyrazin-2-yl}-N-(phenylmethyl)benzamide: $^1$H NMR (400 MHz, d$_6$-DMSO): δ 11.9 (s, 1H), 9.20 (m, 1H), 8.75 (s, 1H), 8.55 (s, 1H), 8.30 (d, 1H), 8.10 (d, 1H), 7.90 (m, 1H), 7.65-7.15 (m, 7H), 4.50 (d, 2H). MS (EI) for C$_{19}$H$_{17}$N$_5$O$_2$: 348 (MH$^+$).

Ethyl 1-{[3-amino-6-(3-{[(phenylmethyl)amino]carbonyl}phenyl)pyrazin-2-yl]methyl}piperidine-4-carboxylate: $^1$H NMR (400 MHz, d$_4$-MeOH): δ 8.63 (s, 1H), 8.48 (s, 1H), 8.14 (m, 1H), 7.84 (m, 1H), 7.57 (t, 1H), 7.31-7.38 (m, 4H), 7.23-7.27 (m, 1H), 4.61 (s, 2H), 4.43 (s, 2H), 4.16-4.23 (m, 2H), 3.88-3.91 (m, 1H), 3.41-3.68 (m, 1H), 3.29-3.31 (m, 5H), 2.65-2.83 (m, 1H), 2.01-2.32 (m, 4H). MS (EI) for $C_{27}H_{31}N_5O_3$: 474 (MH$^+$).

3-[5-Amino-6-(hydroxymethyl)pyrazin-2-yl]-N-(phenylmethyl)benzamide: $^1$H NMR (400 MHz, d$_4$-MeOH): δ 8.40-8.47 (m, 1H), 8.34 (s, 1H1), 8.11-8.14 (m, 1H), 7.86-7.88 (m, 1H), 7.56 (m, 1H), 7.31-7.38 (m, 4H) 7.25-7.26 (m, 1H1), 4.82 (s, 2H), 4.61 (s, 2H). MS (EI) for $C_{19}H_{18}N_4O_2$: 432 (MH$^+$).

3-{5-Amino-6-[(4-pyridin-2-ylpiperazin-1-yl)methyl]pyrazin-2-yl}-N-(phenylmethyl)benzamide: $^1$H NMR (400 MHz, d$_4$-MeOH): δ 8.62 (s, 1H), 8.56 (s, 1H), 8.07-8.16 (m, 3H), 7.58-7.87 (m, 1H), 7.56 (t, 1H), 7.35-7.41 (m, 3H), 7.26-7.30 (m, 2H), 7.16-7.19 (m, 2H), 4.61 (s, 2H), 4.53 (s, 2H), 4.05 (s, 4H), 3.71-3.73 (m, 4H). MS (EI) for $C_{28}H_{29}N_7O$: 480(MH$^+$).

3-(5-Amino-6-{[3-(hydroxymethyl)piperidin-1-yl]methyl}pyrazin-2-yl)-N-(phenylmethyl)benzamide: $^1$H NMR (400 MHz, d$_4$-MeOH): δ 8.63 (s, 1H), 8.51 (t, 1H), 8.13-8.15 (m, 1H), 7.85-7.87 (m, 1H), 7.55-7.59 (m, 1H), 7.32-7.39 (m, 4H), 7.20-7.28 (m, 1H), 4.59-4.70 (m, 2H), 4.41 (s, 2H), 4.05-4.08 (m, 1H), 3.75-3.78 (m, 1H), 3.51-3.58 (m, 1H), 3.34-3.40 (m, 1H), 3.12-3.17 (m, 1H), 2.89 (t, 1H), 1.77-2.16 (m, 4H), 1.30-1.36 (m, 1H). MS (ESI-LCMS) for $C_{25}H_{29}N_5O_2$: 432 (MH$^+$).

1,1-Dimethylethyl (3S)-3-{[(3-amino-6-(3-[({[4-(methyloxy)phenyl]methyl}amino)carbonyl]phenyl}pyrazin-2-yl)carbonyl]amino}pyrrolidine-1-carboxylate: $^1$H NMR (400 MHz, d$_6$-DMSO): δ 9.06 (t, 1H), 8.95 (s, 1H), 8.7 (d, 1H), 8.5 (s, 1H), 8.3 (d, 1H), 7.85 (d, 1H), 7.57 (t, 1H), 7.25 (d, 2H), 6.85 (d, 2H), 4.5 (d, 2H), 3.7 (s, 3H), 3.6-3.2 (m, 4H), 2.2-2.0 (m, 2H), 1.4 (s, 9H). MS (EI) for $C_{29}H_{34}N_6O_5$: 447 (MH$^+$).

1,1-Dimethylethyl (3S)-3-({[3-amino-6-(3-{[({4-[(trifluoromethyl)oxy]phenyl}methyl)amino]carbonyl}phenyl)pyrazin-2-yl]carbonyl}amino)pyrrolidine-1-carboxylate: $^1$H NMR (400 MHz, d$_6$-DMSO): δ 9.23 (t, 1H), 8.95 (s, 1H), 8.75 (d, 1H), 8.55 (s, 1H), 8.35 (d, 1H), 7.9 (d, 1H), 7.57 (t, 1H), 7.48 (d, 2H), 7.37 (d, 2H), 4.57 (d, 2H), 4.5 (m, 1H), 3.6-3.2 (m, 4H), 2.2-2.0 (m, 2H), 1.4 (s, 9H). MS (EI) for $C_{29}H_{31}N_6O_5F_3$: 501 (MH$^+$).

1,1-Dimethylethyl (3S)-3-[({3-amino-6-[3-({[(2-chloro-6-fluorophenyl)methyl]amino}carbonyl)phenyl]pyrazin-2-yl}carbonyl)amino]pyrrolidine-1-carboxylate: $^1$H NMR (400 MHz, d$_6$-DMSO): δ 8.9 (s, 1H), 8.8 (d, 1H), 8.7 (t, 1H), 8.45 (s, 1H), 8.25 (d, 1H), 7.8 (d, 1H), 7.5 (t, 1H), 7.35-7.15 (m, 3H), 4.6 (d, 2H), 4.4 (m, 1H), 3.6-3.2 (m, 4H), 2.1-1.9 (m, 2H), 1.35 (s, 9H). MS (EI) for $C_{28}H_{30}N_6O_4Cl$: 469 (MH$^+$).

1,1-Dimethylethyl (3S)-3-{[(3-amino-6-{3-[({[4-(methylthio)phenyl]methyl}amino)carbonyl]phenyl pyrazin-2-yl) carbonyl]amino}pyrrolidine-1-carboxylate: $^1$H NMR (400 MHz, d$_6$-DMSO): δ 9.1 (t, 1H), 8.9 (s, 1H), 8.7 (d, 1H), 8.5 (s, 1H), 8.35 (d, 1H), 7.85 (d, 1H), 7.57 (t, 1H), 7.3 (d, 2H), 7.2 (d, 2H), 4.6-4.4 (m, 3H), 3.6-3.2 (m, 4H), 2.4 (s, 3H), 2.2-2.0 (m, 2H), 1.4 (s, 9H). MS (EI) for $C_{29}H_{34}N_6O_4S$: 463 (MH$^+$).

1,1-Dimethylethyl (3S)-3-{[(3-amino-6-{3-[(2,3-dihydro-1H-dien-2-ylamino)carbonyl]phenyl}pyrazin-2-yl)carbonyl]amino}pyrrolidine-1-carboxylate: $^1$H NMR (400 MHz, d$_6$-DMSO): δ 8.95 (s, 1H), 8.8-8.7 (m, 2H), 8.5 (s, 1H), 8.3 (d, 1H), 7.83 (d, 1H:), 7.57 (t, 1H), 7.2 (m, 2H), 7.15 (m, 2H1), 4.7 (m, 2H), 3.6-3.4 (m, 2H), 3.25 (m, 4H), 2.98 (m, 2H), 2.2-2.0 (m, 2H), 1.4 (s, 9H). MS (EI) for $C_{30}H_{34}N_6O_4$: 443 (MH$^+$).

3-Amino-6-{3-[({[4-(methyloxy)phenyl]methyl}amino)carbonyl]phenyl}-N-[(3S)-pyrrolidin-3-yl]pyrazine-2-carboxamide: $^1$H NMR (400 MHz, d$_6$-DMSO): δ 9.6-9.4 (m, 3H), 9.2 (d, 1H), 8.95 (s, 1H), 8.7 (s, 1H), 8.5 (d, 1H), 7.85 (d, 1H), 7.57 (t, 1H), 7.3 (d, 2H), 6.85 (d, 2H), 4.7 (m, 1H), 4.4 (d, 2H), 3.7 (s, 3H), 3.4-3.1 (m, 4H), 2.25 (t, 1H), 2.05 (t, 1H). MS (EI) for $C_{24}H_{26}N_6O_3$: 447 (MH$^+$).

3-Amino-N-[(3S)-pyrrolidin-3-yl]-6-(3-{[({4-[(trifluoromethyl)oxy]phenyl}methyl)amino]carbonyl}phenyl)pyrazine-2-carboxamide: $^1$H NMR (400 MHz, d$_6$-DMSO): δ 9.65 (t, 1H), 9.5 (m, 1H), 9.25 (m, 1H), 9.2 (d, 1H), 8.95 (s, 1H), 8.75 (s, 1H), 8.35 (d, 1H), 7.9 (d, 1H), 7.57 (t, 1H), 7.5 (d, 2H), 7.3 (d, 2H), 4.7 (m, 1H), 4.5 (d, 2H), 3.4-3.1 (m, 4H), 2.25 (t, 1H), 2.05 (t, 1H). MS (EI) for $C_{24}H_{23}N_6O_3F_3$: 501 (MH$^+$).

3-Amino-6-{3-[(2,3-dihydro-1H-inden-2-ylamino)carbonyl]phenyl}-N-[(3S)-pyrrolidin-3-yl]pyrazine-2-carboxamide: $^1$H NMR (400 MHz, d6-DMSO): δ 9.65 (m, 1H), 9.45 (m, 1H), 9.2 (m, 2H), 8.96 (s, 1H), 8.72 (s, 1H), 8.35 (d, 1H), 7.9 (d, 1H), 7.57 (t, 1H), 7.25 (t, 2H), 7.18 (d, 2H), 4.8-4.6 (m, 2H), 3.45-3.1 (m, 8H), 2.3 (t, 1H), 2.1 (t, 1H). MS (EI) for $C_{25}H_{26}N_6O_2$: 443 (MH$^+$).

3-Amino-6-[3-({[(2-chloro-6-fluorophenyl)methyl]amino)carbonyl]phenyl]-N-[(3S)-pyrrolidin-3-yl]pyrazine-2-carboxamide: $^1$H NMR (400 MHz, d$_6$-DMSO): δ 9.5 (m, 1H), 9.35 (m, 1H), 9.1 (m, 2H), 8.95 (s, 1H), 8.6 (s, 1H), 8.4 (d, 1H), 7.9 (d, 1H), 7.57 (t, 1H), 7.4-7.2 (m, 3H), 4.65 (s, 3H), 3.4-3.2 (m, 4H), 2.3 (m, 1H), 2.05 (m, 1H). MS (EI) for $C_{23}H_{22}N_6O_2FCl$: 469 (MH$^+$).

3-Amino-6-{3-[({[4-(methylthio)phenyl]methyl}amino)carbonyl]phenyl}-N-[(3S)-pyrrolidin-3-yl]pyrazine-2-carboxamide: $^1$H NMR (400 MHz, d$_6$-DMSO): δ 9.25 (t, 1H), 8.9 (s, 1H), 8.86 (d, 1H), 8.6 (s, 1H), 8.3 (d, 1H), 7.85 (d, 1H), 7.62 (d, 1H), 7.57 (t, 1H), 7.3 (d, 2H), 7.2 (d, 2H), 4.6 (t, 1H), 4.45 (d, 2H), 3.4-3.1 (m, 4H), 2.4 (s, 3H), 2.2 (m, 1H), 2.0 (m, 1H). MS (EI) for $C_{24}H_{26}N_6O_2S$: 463 (MH$^+$).

1,1-Dimethylethyl (3S)-3-[({3-amino-6-[3-({[(4-chlorophenyl)methyl]amino}carbonyl)phenyl]pyrazin-2-yl}carbonyl)amino]pyrrolidine-1-carboxylate: $^1$H NMR (400 MHz, d$_6$-DMSO): δ 9.2 (t, 1H), 8.95 (s, 1H), 8.75 (d, 1H), 8.55 (s, 1H), 8.4 (d, 1H), 7.85 (d, 1H), 7.57 (t, 1H), 7.4 (s, 4H), 4.5 (d, 2H), 4.47 (m, 1H), 3.6-3.2 (m, 4H), 2.2-2.0 (m 2H), 1.4 (s, 9H). MS (EI) for $C_{28}H_{31}N_6O_4Cl$: 451 (MH$^+$).

1,1-Dimethylethyl (3S)-3-({[3-amino-6-(3-{[(pyridin-2-ylmethyl)amino]carbonyl}phenyl)pyrazin-2-yl]carbonyl}amino)pyrrolidine-1-carboxylate: $^1$H NMR (400 MHz, d$_6$-DMSO): δ 9.4 (t, 1H), 8.95 (s, 1H), 8.7 (d, 2H), 8.6 (s, 1H), 8.4 (d, 1H), 8.2 (m, 1H), 7.9 (d, 1H), 7.75 (d, 1H), 7.65 (t, 1H), 7.6 (m, 2H), 4.75 (d, 2H), 4.5 (m, 1H), 3.6-3.2 (m, 4H), 2.2-2.0 (m, 2H), 1.4 (s, 9H). MS (EI) for $C_{27}H_{31}N_7O_4$: 462 (MH$^+$).

1,1-Dimethylethyl (3S)-3-({[3-amino-6-(3-([(pyridin-3-ylmethyl)amino]carbonyl}phenyl)pyrazin-2-yl]carbonyl}amino)pyrrolidine-1-carboxylate; $^1$H NMR (400 MHz, d$_6$-DMSO): δ 9.3 (t, 1H), 8.9 (s, 1H), 8.85 (m, 1H), 8.78 (d, 1H), 8.7 (d, 1H), 8.5 (s, 1H), 8.43 (d, 1H), 8.38 (d, 1H), 7.9 (m, 1H), 7.85 (d, 1H), 7.57 (t, 1H), 4.7 (d, 2H), 4.5 (m, 1H), 3.6-3.2 (m, 4H), 2.2-2.0 (m, 2H), 1.4 (s, 9H). MS (EI) for $C_{27}H_{31}N_7O_4$: 518 (MH$^+$).

1,1-Dimethylethyl (3S)-3-{[(3-amino-6-(3-[(3,4-dihydro-2H-chromen-4-ylamino)carbonyl]phenyl}pyrazin-2-yl)carbonyl]amino}pyrrolidine-1-carboxylate: $^1$H NMR (400 MHz, d$_6$-DMSO): δ 9.0 (m, 1H), 8.9 (s, 1H), 8.55 (s, 1H), 8.38 (d, 1H), 7.9 (d, 1H), 7.57 (t, 1H), 7.22 (d, 1H), 7.17 (t, 1H), 6.85 (t, 1H), 6.78 (d, 1H), 5.3 (m, 1H), 4.6-4.4 (m, 1H), 4.4-4.2 (m, 2H), 3.6-3.2 (m, 4H), 2.2-2.0 (m, 4H), 1.4 (s, 9H). MS (EI) for $C_{30}H_{34}N_6O_5$: 459 (MH$^+$).

3-Amino-6-[3-({[(4-chlorophenyl)methyl]amino}carbonyl)phenyl]-N-[(3S)-pyrrolidin-3-yl]pyrazine-2-carboxamide: $^1$H NMR (400 MHz, d$_6$-DMSO): δ 9.55 (t, 1H), 9.37 (m, 1H), 9.1 (m, 2H), 8.95 (s, 1H), 8.7 (s, 1H), 7.9 (d, 1H), 7.57 (t, 1H), 7.4 (s, 4H), 4.7 (m, 1H), 4.5 (d, 2H), 3.5-3.3 (m, 3H), 3.3-3.1 (m, 1H), 2.3 (m, 1H), 2.1 (m, 1H). MS (EI) for C$_{23}$H$_{23}$N$_6$O$_2$Cl: 451 (MH$^+$).

3-Amino-6-(3-{[(pyridin-2-ylmethyl)amino]carbonyl}phenyl)-N-[(3S)-pyrrolidin-3-yl]pyrazine-2-carboxamide: $^1$H NMR (400 MHz, d$_6$-DMSO): δ 10.15 (t, 1H), 9.55-9.4 (m, 2H), 9.26 (d, 1H), 8.95 (m, 2H), 8.82 (d, 1H), 8.5 (m, 1H), 8.35 (d, 1H), 8.0 (d, 1H), 7.9 (m, 2H), 7.57 (t, 1H), 4.9 (d, 2H), 4.75 (m, 1H), 3.4 (m, 3H), 3.2 (m, 1H), 2.3 (m, 1H), 2.1 (m, 1H). MS (EI) for C$_{22}$H$_{23}$N$_7$O$_2$: 418 (MH$^+$).

3-Amino-6-(3-{[(pyridin-3-ylmethyl)amino]carbonyl}phenyl)-N-[(3S)-pyrrolidin-3-yl]pyrazine-2-carboxamide: $^1$H NMR (400 MHz, d$_6$-DMSO): δ 10.15 (t, 1H), 9.6 (m, 2H), 9.3 (d, 1H), 9.03-8.83 (m, 4H), 8.65 (d, 1H), 8.3 (d, 1H), 8.07 (t, 1H), 7.9 (d, 1H), 7.57 (t, 1H), 4.78 (m, 3H), 3.42 (m, 3H), 3.2 (m, 1H), 2.3 (m, 1H), 2.1 (m, 1H). MS (EI) for C$_{22}$H$_{23}$N$_7$O$_2$: 418 (MH$^+$).

3-Amino-6-{3-[(3,4-dihydro-2H-chromen-4-ylamino)carbonyl]phenyl}-N-[(3)S-pyrrolidin-3-yl]pyrazine-2-carboxamide: $^1$H NMR (400 MHz, d$_6$-DMSO): δ 9.0 (m, 2H), 8.95-8.75 (m, 3H), 8.57 (s, 1H), 8.37 (d, 1H), 7.95 (d, 1H), 7.6 (t, 1H), 7.2 (m, 2H), 6.9 (t, 1H), 6.82 (d, 1H), 5.35 (m, 1H), 4.6 (m, 1H), 4.3 (m, 2H), 3.4 (m, 2H), 3.25 (m, 2H), 2.3-2.0 (m, 4H). MS (EI) for C$_{25}$H$_{26}$N$_6$O$_3$: 459 (MH$^+$).

3-Amino-6-{3-[(2,3-dihydro-1-benzofuran-3-ylamino)carbonyl]phenyl}-N-[(3S)-pyrrolidin-3-yl]pyrazine-2-carboxamide: $^1$H NMR (400 MHz, d$_6$-DMSO): δ 9.2 (d, 1H), 8.99 (m, 2H), 8.88 (d, 1H), 8.6 (s, 1H), 8.38 (d, 1H), 7.95 (d, 1H), 7.57 (t, 1H), 7.4 (d, 1H), 7.26 (t, 1H), 6.95 (m, 2H), 5.85 (m, 1H), 4.8-4.5 (m, 3H), 4.4-4.0 (m, 2H), 3.5-3.2 (m, 2H), 2.4-2.0 (m, 2H). MS (EI) for C$_{24}$H$_{24}$N$_6$O$_3$: 445 (MH$^+$).

1,1-Dimethylethyl (3S)-3-({[3-amino-6-(3-{[(1-methyl-1-phenylethyl)amino]carbonyl}phenyl)pyrazin-2-yl]carbonyl}amino)pyrrolidine-1-carboxylate: $^1$H NMR (400 MHz, d6-DMSO): δ 8.95 (s, 1H), 8.75 (m, 1H), 8.75 (s, 1H), 8.3 (d, 1H), 7.75 (d, 1H), 7.55 (t, 1H), 7.4 (d, 2H), 7.25 (t, 2H), 7.15 (m, 1H), 4.5 (m, 1H), 3.6-3.2 (m, 4H), 2.2-2.0 (m, 2H), 1.7 (s, 6H), 1.4 (s, 9H). MS (EI) for C$_{30}$H$_{36}$N$_6$O$_4$: 445 (MH$^+$).

3-Amino-6-(3-{[(1-methyl-1-phenylethyl)amino]carbonyl}phenyl)-N-[(3S)-pyrrolidin-3-yl]pyrazine-2-carboxamide: $^1$H NMR (400 MHz, d$_6$-DMSO): δ 9.1-8.9 (m, 2H), 9.0 (s, 1H), 8.95 (d, 1H), 8.6 (s, 1H), 8.35 (d, 1H), 7.85 (d, 1H), 7.57 (t, 1H), 7.4 (d, 2H), 7.3 (t, 2H), 7.2 (m, 1H), 4.6 (m, 1H), 3.5-3.2 (m, 4H), 2.3-2.1 (m, 2H), 1.7 (s, 6H). MS (EI) for C$_{25}$H$_{28}$N$_6$O$_2$: 445 (MH$^+$).

3-Amino-6-(3-{[(1 S)-2,3-dihydro-1H-inden-1-ylamino]carbonyl}phenyl)-N-[(3S)-1-methylpyrrolidin-3-yl]pyrazine-2-carboxamide: $^1$H NMR (400 MHz, d$_4$-MeOH): δ 8.81-8.75 (m, 1H), 8.59-8.54 (m, 1H), 8.26-8.18 (m, 1H), 7.90-7.85 (m, 1H), 7.61-7.54 (m, 1H), 7.34-7.16 (m, 4H), 5.73-5.66 (m, 1H), 4.71-4.61 (m, 1H), 4.05-3.85 (m, 2H), 3.50-3.41 (m, 1H), 3.29-2.87 (m, 6H), 2.76-2.56 (m, 2H), 2.44-2.23 (m, 1H), 2.09-2.01 (m, 1H). MS (EI) for C$_{26}$H$_{28}$N$_6$O$_2$: 457 (MH$^+$).

3-Amino-6-[3-({[(1R,2S)-2-hydroxy-2,3-dihydro-1H-inden-1-yl]amino}carbonyl)phenyl]-N-[(3S)-1-methylpyrrolidin-3-yl]pyrazine-2-carboxamide: $^1$H NMR (400 MHz, d$_4$-MeOH): δ 8.77-8.71 (m, 1H), 8.64-8.59 (m, 1H), 8.25-8.19 (m, 1H), 8.00-7.93 (m, 1H), 7.64-7.57 (m, 1H), 7.35-7.18 (m, 4H), 5.64-5.59 (m, 1H), 4.79-4.60 (m, 2H), 3.96-3.84 (m, 1H), 3.49-3.40 (m, 1H), 3.28-3.13 (m, 2H), 3.05-2.97 (m, 5H), 2.73-2.61 (m, 1H), 2.41-2.23 (m, 1H). MS (EI) for C$_{26}$H$_{28}$N$_6$O$_3$: 473 (MH$^+$).

3-Amino-N-[(3S)-pyrrolidin-3-yl]-6-[3-({[(3,4,5-trifluorophenyl)methyl]amino}carbonyl)phenyl]pyrazine-2-carboxamide: $^1$H NMR (400 MHz, d$_6$-DMSO): δ 9.8 (t, 1H), 9.5 (s, 1H), 9.3 (s, 1H), 9.2 (d, 1H), 8.95 (s, 1H), 8.8 (s, 1H), 8.35 (d, 1H), 7.9 (d, 1H), 7.55 (t, 1H), 7.35 (m, 2H), 4.75 (m, 1H), 4.5 (d, 2H), 3.4 (m, 3H), 3.2 (m, 1H), 2.3 (m, 1H), 2.15 (m, 1H). MS (EI) for C$_{23}$H$_{21}$N$_6$O$_2$F$_3$: 471 (MH$^+$).

3-Amino-N-[(3S)-pyrrolidin-3-yl]-6-[3-({[(2,3,6-trifluorophenyl)methyl]amino}carbonyl)phenyl]pyrazine-2-carboxamide: $^1$H NMR (400 MHz, d$_6$-DMSO): δ 9.55 (s, 1H), 9.45 (s, 1H), 9.35 (t, 1H), 9.1 (d, 1H), 8.9 (s, 1H), 8.35 (d, 1H), 7.85 (d, 1H), 7.55 (t, 1H), 7.45 (m, 1H), 7.12 (m, 1H), 5.0 (s, 1H), 4.65 (m, 1H), 4.55 (d, 2H), 3.45-3.15 (m, 4H), 2.25 (m, 1H), 2.1 (m, 1H). MS (EI) for C$_{23}$H$_{21}$N$_6$O$_2$F$_3$: 471 ).

3-Amino-N-[(3S)-pyrrolidin-3-yl]-6-[3-({[(2,3,5-trifluorophenyl)methyl]amino}carbonyl)phenyl]pyrazine-2-carboxamide: $^1$H NMR (400 MHz, d$_6$-DMSO): δ 9.8 (t, 1H), 9.55 (s, 1H), 9.4 (s, 1H), 9.25 (d, 1H), 8.95 (s, 1H), 8.85 (s, 1H), 8.35 (d, 1H), 7.9 (d, 1H), 7.55 (t, 1H), 7.45 (m, 1H), 7.15 (m, 1H), 4.75 (m, 1H), 4.55 (d, 2H), 3.4 (m, 3H), 3.2 (m, 1H), 2.3 (m, 1H), 2.15 (m, 1H). MS (EI) for C$_{23}$H$_{21}$N$_6$O$_2$F$_3$: 471 (MH$^+$).

3-Amino-6-[3-({[(3-bromo-4-fluorophenyl)methyl]amino}carbonyl)phenyl]-N-[(3S)-pyrrolidin-3-yl]pyrazine-2-carboxamide: $^1$H NMR (400 MHz, d$_6$-DMSO): δ 9.7 (t, 1H), 9.5 (s, 1H), 9.3 (s, 1H), 9.2 (d, 1H), 8.9 (s, 1H), 8.75 (s, 1H), 8.3 (d, 1H), 7.9 (d, 1H), 7.7 (d, 1H), 7.55 (t, 1H), 7.4 (m, 1H), 7.3 (t, 1H), 4.7 (m, 1H), 4.5 (d, 2H), 3.4 (m, 3H), 3.2 (m, 1H), 2.3 (m, 1H), 2.15 (m, 1H). MS (EI) for C$_{23}$H$_{22}$N$_6$O$_2$FBr: 515 (MH$^+$).

1,1-Dimethylethyl (3S)-3-[({3-amino-6-[3-({[(2,4-dichlorophenyl)methyl]amino}carbonyl)phenyl]pyrazin-2-yl}carbonyl)amino]pyrrolidine-1-carboxylate: $^1$H NMR (400 MHz, d$_6$-DMSO): δ 9.16 (t, 1H), 8.9 (s, 1H), 8.7 (d, 1H), 8.55 (s, 1H), 8.35 (d, 1H), 7.85 (d, 1H), 7.6 (s, 1H), 7.57 (t, 1H), 7.4 (m, 2H), 4.58 (d, 2H), 4.5 (m, 1H), 3.6-3.2 (m, 4H), 2.2-2.0 (m, 2H), 1.4 (s, 9H). MS (EI) for C$_{28}$H$_{30}$N$_6$O$_4$Cl$_2$: 485 (MH$^+$).

1,1-Dimethylethyl (3S)-3-[({3-amino-6-[3-({[(3,4-dichlorophenyl)methyl]amino}carbonyl)phenyl]pyrazin-2-yl}carbonyl)amino]pyrrolidine-1-carboxylate: $^1$H NMR (400 MHz, d$_6$-DMSO): δ 9.2 (t, 1H), 8.9 (s, 1H), 8.7 (d, 1H), 8.5 (s, 1H), 8.35 (d, 1H), 7.85 (d, 1H), 7.6 (m, 3H), 7.36 (d, 1H), 4.5 (m, 3H), 3.6-3.2 (m, 4H), 2.2-2.0 (m, 2H1), 1.4 (s, 9H). MS (EI) for C$_{28}$H$_{30}$N$_6$O$_4$Cl$_2$: 485 (MH$^+$).

3-Amino-6-[3-({[(2,4-dichlorophenyl)methyl]amino}carbonyl)phenyl]-N-[(3S)-pyrrolidin-3-yl]pyrazine-2-carboxamide: $^1$H NMR (400 MHz, d$_6$-DMSO): δ 9.7 (t, 1H), 9.5 (m, 1E), 9.3 (m, 1H), 9.2 (d, 1H), 8.95 (s, 1H), 8.8 (s, 1H), 8.35 (d, 1H), 7.9 (d, 1H), 7.6 (s, 1H), 7.57 (t, 1H), 7.4 (d, 2H), 4.7 (m, 1H), 4.55 (d, 2H), 3.5-3.1 (m, 4H), 2.4-2.0 (m, 2H). MS (EI) for C$_{23}$H$_{22}$N$_6$O$_2$Cl$_2$: 485 (MH$^+$).

3-Amino-6-[3-({[(3,4-dichlorophenyl)methyl]amino}carbonyl)phenyl]-N-[(3S)-pyrrolidin-3-yl]pyrazine-2-carboxamide: $^1$H NMR (400 MHz, d$_6$-DMSO): δ 9.78 (t, 1H), 9.5 (m, 1H), 9.35 (m, 1H), 9.23 (d, 1H), 8.95 (s, 1H), 8.8 (s, 1H), 8.53 (d, 1H), 7.9 (d, 1H), 7.6 (s, 1H), 7.6-7.5 (m, 2H), 7.4 (d, 1H), 4.7 (m, 1H), 4.5 (d, 2H), 3.5-3.1 (m, 4H), 2.4-2.1 (m, 2H). MS (EI) for C$_{23}$H$_{22}$N$_6$O$_2$Cl$_2$: 485 (MH$^+$).

3-Amino-6-{3-[({[4-(methyloxy)phenyl]methyl}amino)carbonyl]phenyl}-N-[(3S)-piperidin-3-yl]pyrazine-2-carboxamide: $^1$H NMR (400 MHz, d6-DMSO): δ 9.43 (t, 1H), 9.4 (m, 1H), 9.15 (m, 1H), 8.9 (s, 1H), 8.65 (s, 1H), 8.3 (d, 1H), 7.87 (d, 1H), 7.57 (t, 1H), 7.3 (d, 2H), 6.85 (d, 2H), 4.45 (d, 2H), 3.7 (s, 3l1), 3.3-3.1 (m, 3H), 2.75 (m, 1H), 1.9-1.7 (m, 4H). MS (EI) for C$_{25}$H$_{28}$N$_6$O$_3$: 461 (MH$^+$).

3-Amino-6-[3-({[(2,4-dichlorophenyl)methyl]amino}carbonyl)phenyl]-N-[(3S)-piperidin-3-yl]pyrazine-2-carboxamide: $^1$H NMR (400 MHz, d$_6$-DMSO): δ 9.65 (t, 1H), 9.3 (m, 1H), 9.05 (m, 1H), 9.0-8.9 (m, 2H), 8.75 (s, 1H), 8.3 (d, 1H), 7.9 (d, 1H), 7.6-7.5 (m, 2H), 7.4 (d, 2H), 4.6 (d, 2H), 3.3-3.1 (m, 3H), 2.75 (m, 1H), 1.9-1.7 (m, 4H). MS (EI) for C$_{24}$H$_{24}$N$_6$O$_2$Cl$_2$: 499 (MH$^+$).

3-Amino-6-[3-({[(4-fluorophenyl)methyl]amino}carbonyl)phenyl]-N-[(3S)-piperidin-3-yl]pyrazine-2-carboxamide: $^1$H NMR (400 MHz, d$_6$-DMSO): δ 9.4 (t, 1H), 9.05 (d, 1H), 8.95 (s, 1H), 8.85 (d, 2H), 8.65 (s, 11), 8.35 (d, 1H1), 7.9 (d, 1H), 7.6 (t, 1H), 7.4 (m, 2H), 7.15 (m, 2H), 4.5 (d, 2H), 4.25 (m, 1H), 3.25 (m, 2H), 3.1 (m, 1H), 2.75 (m, 1H), 1.95-1.7 (m, 4H). MS (EI) for C$_{24}$H$_{25}$N$_6$O$_2$F: 449 (MH$^+$).

3-Amino-N-[(3S)-piperidin-3-yl]-6-(3-{[({4-[(trifluoromethyl)oxy]phenyl}methyl)amino]carbonyl}phenyl)pyrazine-2-carboxamide: $^1$H NMR (400 MHz, d$_6$-DMSO): δ 9.55 (t, 1H), 9.15 (d, 1H), 8.95 (s, 1H), 8.0 (d, 2H), 8.7 (s, 1H), 8.35 (s, 1H), 7.9 (d, 1H), 7.6 (t, 1H), 7.5 (d, 2H), 7.35 (d, 2H), 4.55 (d, 2H), 4.3 (m, 1H), 3.3-3.1 (m, 3H), 2.75 (m, 1H), 1.95-1.7 (m, 4H). MS (EI) for C$_{25}$H$_{25}$N$_6$O$_3$F$_3$: 515 (MH$^+$).

3-Amino-6-(3-{[(biphenyl-4-ylmethyl)amino]carbonyl}phenyl)-N-[(3S)-piperidin-3-yl]pyrazine-2-carboxamide: $^1$H NMR (400 MHz, d$_6$-DMSO): δ 9.4 (t, 1H), 9.05 (d, 1H), 8.95 (s, 1H), 9.35 (d, 2H), 8.65 (s, 1H), 8.35 (d, 1H), 7.95 (d, 1H), 7.7-7.6 (m, 5H), 7.45 (m, 4H), 7.35 (m, 1H), 4.6 (d, 2H), 4.3 (m, 1H), 3.3-3.1 (m, 3H), 2.75 (m, 1H), 1.95-1.7 (m, 4H). MS (EI) for C$_{30}$H$_{30}$N$_6$O$_2$: 507 (MH$^+$).

3-Amino-N-[(3S)-piperidin-3-yl]-6-{3-[({[4-(1,2,3-thiadiazol-5-yl)phenyl]methyl}amino)carbonyl]phenyl}pyrazine-2-carboxamide: $^1$H NMR (400 MHz, d$_6$-DMSO): δ 9.6 (s, 1H), 9.25 (t, 1H), 8.95 (s, 1H), 8.75 (d, 2H1), 8.65 (m, 1H), 8.55 (s, 1H), 8.35 (d, 1H), 8.15 (d, 1H), 7.95 (d, 1H), 7.7 (s, 1H), 7.6 (t, 1H), 7.55 (d, 2H), 4.6 (d, 2H), 4.25 (m, 1H), 3.3 (m, 2H), 3.05 (m, 1H), 2.75 (m, 1H), 1.95-1.65 (m, 4H). MS (EI) for C$_{26}$H$_{26}$N$_8$O$_2$S: 515 (MH$^+$).

3-Amino-N-[(3S)-piperidin-3-yl]-6-(3-{[({2-[(trifluoromethyl)oxy]phenyl}methyl)amino]carbonyl}phenyl)pyrazine-2-carboxamide: $^1$H NMR (400 MHz, d$_6$-DMSO): δ 9.5 (t, 1H), 9.2 (s, 1H), 8.95 (s, 2H), 8.9 (d, 1H), 8.7 (s, 1H), 8.35 (d, 1H), 7.9 (d, 1H), 7.6 (t, 1H), 7.5 (d, 1H), 7.4 (m, 3H), 4.6 (d, 2H), 4.3 (m, 1H), 3.3-3.1 (m, 3H), 2.75 (m, 1H), 1.95-1.7 (m, 4H). MS (EI) for C$_{25}$H$_{25}$N$_6$O$_2$F$_3$: 515 (MH$^+$).

3-Amino-6-[3-({[(2,4-difluorophenyl)methyl]amino}carbonyl)phenyl]-N-[(3S)-piperidin-3-yl]pyrazine-2-carboxamide: $^1$H NMR (400 MHz, d$_6$-DMSO): δ 9.5 (t, 1H), 9.25 (m, 1H), 9.05 (m, 1H), 8.95 (s, 1H), 8.93 (d, 1H), 8.7 (s, 1H), 8.35 (d, 1H), 7.9 (d, 1H), 7.6 (t, 1H), 7.5 (m, 1H), 7.25 (m, 1H), 7.1 (m, 1H), 4.55 (d, 2H), 4.3 (m, 1H), 3.3-3.1 (m, 3H), 2.75 (m, 1H), 1.95-1.7 (m, 4H). MS (EI) for C$_{24}$H$_{24}$N$_6$O$_2$F$_2$: 467 (MH$^+$).

3-Amino-6-[3-({[(4-chloro-2-fluorophenyl)methyl]amino}carbonyl)phenyl]-N-[(3S)-piperidin-3-yl]pyrazine-2-carboxamide: $^1$H NMR (400 MHz, d$_6$-DMSO): δ 9.5 (t, 1H), 9.15 (d, 1H), 8.95 (s, 1H), 8.9 (d, 2H), 8.7 (s, 1H), 8.35 (d, 1H), 7.9 (d, 1H), 7.6 (t, 1H), 7.45 (m, 2H), 7.3 (m, 1H), 4.55 (d, 2H), 4.3 (m, 1H), 3.3-3.1 (m, 3H), 2.75 (m, 1H), 1.95-1.7 (m, 4H). MS (EI) for C$_{24}$H$_{24}$N$_6$O$_2$FCl: 483 (MH$^+$).

3-Amino-6-{3-[({[4-fluoro-3-(trifluoromethyl)phenyl]methyl}amino)carbonyl]phenyl}-N-[(3S)-piperidin-3-yl]pyrazine-2-carboxamide: $^1$H NMR (400 MHz, d$_6$-DMSO): δ 9.55 (m, 1H), 9.05 (d, 1H), 8.95 (s, 1H), 8.85 (m, 2H), 8.65 (s, 1H), 8.35 (d, 1H), 7.9 (d, 1H), 7.8 (m, 2H), 7.6 (t, 1H), 7.5 (t, 1H), 4.5 (d, 2H), 4.3 (m, 1H), 3.3-3.1 (m, 3H), 2.75 (m, 1H), 1.95-1.7 (m, 4H). MS (EI) for C$_{25}$H$_{24}$N$_6$O$_2$F$_4$: 517 (MH$^+$).

3-Amino-6-(3-{[(naphthalen-2-ylmethyl)amino]carbonyl}phenyl)-N-[(3S)-piperidin-3-yl]pyrazine-2-carboxamide: $^1$H NMR (400 MHz, d$_6$-DMSO): δ 9.55 (t, 1H), 9.3 (m, 1H), 9.1 (m, 1H), 9.0-8.9 (m, 2H), 8.75 (s, 1H), 8.4 (d, 1H), 8.3 (d, 1H), 8.0 (m, 2H), 7.9 (d, 1H), 7.7-7.5 (m, 5H), 5.05 (d, 2H), 4.3 (m, 1H), 3.3-3.1 (m, 3H), 2.8 (m, 1H), 2.0-1.7 (m, 4H). MS (EI) for C$_{28}$H$_{28}$N$_6$O$_2$: 481 (MH$^+$).

3-Amino-6-{3-[({[4-(dimethylamino)phenyl]methyl}amino)carbonyl]phenyl}-N-[(3S)-piperidin-3-yl]pyrazine-2-carboxamide: $^1$H NMR (400 MHz, d$_6$-DMSO): δ 9.05 (t, 1H), 8.9 (s, 1H), 8.8 (m, 1H), 8.7 (d, 1H), 8.65 (m, 1H), 8.5 (s, 1H), 8.3 (d, 1H), 7.9 (d, 1H), 7.57 (t, 1H), 7.25 (d, 2H), 6.85 (d, 2H), 4.4 (d, 2H), 4.25 (m, 1H), 3.4-3.0 (m, 3H), 2.9 (s, 6H), 2.9-2.7 (m, 1H), 2.0-1.7 (m, 4H). MS (EI) for C$_{26}$H$_{31}$N$_7$O$_2$: 474 (MH$^+$).

3-Amino-6-(3-{[(1,3-benzodioxol-5-ylmethyl)amino]carbonyl}phenyl)-N-[(3S)-piperidin-3-yl]pyrazine-2-carboxamide: $^1$H NMR (400 MHz, d$_6$-DMSO): δ 9.1 (t, 1H), 8.95 (s, 1H), 8.9 (m, 1H), 8.7 (d, 1H), 8.5 (s, 1H), 8.35 (d, 1H), 7.85 (d, 1H), 7.57 (t, 1H), 6.9 (s, 1H), 6.85 (m, 2H), 5.98 (s, 2H), 4.43 (d, 1H), 4.2 (m, 1H), 3.4-3.2 (m, 2H), 3.05 (q, 1H), 2.8 (m, 1H), 2.0-1.7 (m, 4H). MS (EI) for C$_{25}$H$_{26}$N$_6$O$_4$: 475 (MH$^+$).

3-Amino-N-[(3S)-piperidin-3-yl]-6-{3-[({[4-(2-thienyl)phenyl]methyl}amino)carbonyl]phenyl}pyrazine-2-carboxamide: $^1$H NMR (400 MH, d$_6$-DMSO): δ 9.3 (t, 1H), 9.0 (m, 1H), 8.95 (s, 1H), 8.8 (m, 1H), 8.78 (d, 1H), 8.6 (s, 1H), 8.35 (d, 1H), 7.9 (d, 1H), 7.64-7.56 (m, 2H), 7.51 (d, 1H), 7.6 (d, 1H), 7.4 (d, 2H), 7.1 (d, 1H), 4.55 (d, 2H), 4.25 (m, 1H), 3.3-3.0 (m, 3H), 2.8 (m, 1H), 2.0-1.7 (m, 4H). MS (EI) for C$_{28}$H$_{28}$N$_6$O$_2$S: 513 (MH$^+$).

3-Amino-6-{3-[({[2-(methyloxy)phenyl]methyl}amino)carbonyl]phenyl}-N-[(3S)-piperidin-3-yl]pyrazine-2-carboxamide: $^1$H NMR (400 MHz, d$_6$-DMSO): δ 9.26 (t, 2H), 9.03 (m, 1H), 8.95 (s, 1H), 8.87 (d, 1H), 8.65 (s, 1H), 8.3 (d, 1H), 7.9 (d, 1H), 7.57 (t, 1H), 7.2 (m, 2H), 7.0 (d, 1H), 6.9 (t, 1H), 4.5 (d, 2H), 4.3 (m, 1H), 3.8 (s, 3H), 3.3-3.0 (m, 3H), 2.74 (m, 1H), 1.9-1.7 (m,4H). MS (EI) for C$_{25}$H$_{28}$N$_6$O$_3$: 461 (MH$^+$).

3-Amino-6-{3-[({[2,4-bis(methyloxy)phenyl]methyl}amino)carbonyl]phenyl}-N-[(3S)-piperidin-3-yl]pyrazine-2-carboxamide: $^1$H NMR (400 MHz, d$_6$-DMSO): δ 9.3 (m, 1H), 9.1 (m, 2H), 8.95 (s, 1H), 8.9 (d, 1H), 8.65 (s, 1H), 8.35 (d, 1H), 7.9 (d, 1H), 7.57 (t, 1H), 7.1 (d, 1H), 6.6 (s, 1H), 6.5 (d, 1H), 4.5 (d, 2H), 4.3 (m, 1H), 3.8 (s, 6H), 3.3-3.0 (m, 3H), 2.75 (m, 1H), 2.0-1.7 (m, 4H). MS (EI) for C$_{26}$H$_{30}$N$_6$O$_4$: 491 (MH$^+$).

3-Amino-6-[3-({[(4-chloro-2-methylphenyl)methyl]amino}carbonyl)phenyl]-N-[(3S)-piperidin-3-yl]pyrazine-2-carboxamide: $^1$H NMR (400 MHz, d$_6$-DMSO): δ 9.4 (t, 1H), 9.3 (m, 1H), 9.07 (m, 1H), 8.95 (s, 1H), 8.94 (d, 1H), 8.7 (s, 1H), 8.3 (d, 1H), 7.9 (d, 1H), 7.57 (t, 1H), 7.3 (d, 1H), 7.25 (s, 1H), 7.2 (d, 1H), 4.45 (d, 2H), 4.3 (m, 1H), 3.3-3.1 (m, 3H), 2.75 (m, 1H), 2.4 (s, 3H), 2.0-1.7 (m, 4H). MS (EI) for C$_{25}$H$_{27}$N$_6$O$_2$Cl: 479 (MH$^+$).

3-Amino-6-[3-({[(2,3-difluoro-4-methylphenyl)methyl]amino}carbonyl)phenyl]-N-[(3S)-piperidin-3-yl]pyrazine-2-carboxamide: $^1$H NMR (400 MHz, d$_6$-DMSO): δ 9.5 (t, 1H), 9.3 (m, 1H), 9.05 (m, 1H), 8.95 (s, 1H), 8.94 (d, 1H), 8.7 (s, 1H), 8.34 (d, 1H), 7.9 (d, 1H), 7.57 (t, 1H), 7.17 (m, 1H), 7.04 (m, 1H), 4.55 (d, 2H), 4.3 (m, 1H), 3.3-3.1 (m, 3H), 2.78 (m, 1H), 2.25 (s; 3H), 2.0-1.7 (m, 4H). MS (EI) for C$_{25}$H$_{26}$N$_6$O$_2$F$_2$: 481 (MH$^+$).

3-Amino-6-{3-[({[4-(methylsulfonyl)phenyl]methyl}amino)carbonyl]phenyl}-N-[(3S)-piperidin-3-yl]pyrazine-2-carboxamide: $^1$H NMR (400 MHz, d$_4$-MeOH): δ 8.79 (s, 1H), 8.55 (m, 1H), 8.23-8.20 (m, 1H), 7.95-7.87 (m, 3H), 7.65-7.57 (m, 3H), 4.72 (s, 2H), 4.31-4.29 (m, 1H), 3.50-3.45 (m, 2H), 3.38-3.31 (m, 2H), 3.13-2.98 (m, 5H), 2.10-1.83 (m, 4H). MS (EI) for $C_{25}H_{28}N_6O_4S$: 510 (MH$^+$).

3-Amino-6-(3-{[(2,3-dihydro-1,4-benzodioxin-6-ylmethyl)amino]carbonyl}phenyl)-N-[(3S)-piperidin-3-yl]pyrazine-2-carboxamide: $^1$H NMR (400 MHz, d$_4$-MeOH): δ 8.78 (s, 1H), 8.53 (s, 1H), 8.19-8.17 (m, 1H), 7.85-7.83 (m, 1H), 7.58-7.55 (m, 1H), 6.86-6.77 (m, 3H), 4.49 (s, 2H), 4.31-4.28 (m, 1H), 4.20 (s, 4H), 3.51-3.46 (m, 1H), 3.37-3.29 (m, 1H), 3.16-3.10 (m, 1H), 2.99-2.97 (m, 1H), 2.10-1.83 (m, 4H). MS (EI) for $C_{26}H_{28}N_6O_4$: 489(MH$^+$).

3-Amino-6-[3-({[(4-chlorophenyl)methyl]amino}carbonyl)phenyl]-N-[(3S)-piperidin-3-yl]pyrazine-2-carboxamide: $^1$H NMR (400 MHz, d$_4$-MeOH): δ 8.76 (s, 1H), 8.60 (m, 1H), 8.23-8.21 (m, 1H), 7.92-7.89 (m, 1H), 7.62-7.59 (m, 1H), 7.39-7.32 (m, 4H), 4.60 (s, 2H), 4.31-4.29 (m, 1H), 3.50-3.46 (m, 2H), 3.37-3.30 (m, 2H), 2.10-1.83 (m, 4H). MS (EI) for $C_{24}H_{25}N_6O_2Cl$: 465 (MH$^+$).

3-Amino-6-[3-({[(5-chloro-2-fluorophenyl)methyl]amino}carbonyl)phenyl]-N-[(3S)-piperidin-3-ylpyrazine-2-carboxamide: $^1$H NMR (400 MHz, d$_4$-MeOH): δ 8.79 (s, 1H), 8.61 (m, 1H), 8.23-8.20 (m, 1H), 7.87-7.82 (m, 1H), 7.77-7.03 (m, 5H), 4.82 (s, 2H), 4.39-4.36 (m, 1H), 3.51-3.45 (m, 2H), 3.13-2.98 (m, 2H), 2.10-1.83 (m, 4H). MS (EI) for $C_{24}H_{24}N_6O_2FCl$: 483 (MH$^+$).

3-Amino-6-{3-[({[4-(methylthio)phenyl]methyl amino}carbonyl]phenyl}-N-[(3S)-piperidin-3-yl]pyrazine-2-carboxamide: $^1$H NMR (400 MHz, d6-DMSO): δ 9.26 (m, 1H), 8.95 (s, 1H), 8.79 (d, J=8.4 Hz, 1H), 8.58 (s, 1H), 8.34 (d, J=8.0 Hz, 1H), 7.90 (d, J=8.4 Hz, 1H), 7.94 (t, J=8.0 Hz, 1H), 7.31 (m, 2H), 7.24 (m, 2H), 4.48 (d, J=6.0 Hz, 2H), 4.24 (m, 1H), 3.72 (m, 1H), 3.68 (m, 1H), 3.59 (s, 2H), 3.08 (m, 2H), 2.75 (m, 2H), 2.67 (m, 2H), 1.91 (m, 2H), 1.76 (m, 2H). MS (EI) for $C_{25}H_{28}N_6O_2S$: 477 (MH$^+$).

3-Amino-6-(3-{[(1,2-diphenylethyl)amino]carbonyl}phenyl)-N-[(3S)-piperidin-3-yl]pyrazine-2-carboxamide: $^1$H NMR (400 MHz, d$_6$-DMSO): δ 9.02 (m, 1H), 8.99 (m, 1H), 8.93 (m, 1H), 8.75 (m, 2H), 8.41 (m, 1H), 8.31 (m, 1H), 7.78 (m, 1H), 7.54 (m, 1H), 7.50 (m, 1H), 7.35 (m, 4H), 7.25 (m, 4H), 7.15 (m, 2H), 5.32 (m, 2H), 2.67 (m, 2H), 2.46 (m, 2H), 2.33 (m, 2H), 1.92 (m, 2H), 1.73 (m, 2H). MS (EI) for $C_{31}H_{32}N_6O_2$: 521 (MH$^+$).

3-Amino-6-[3-({[(3,5-difluorophenyl)methyl]amino}carbonyl)phenyl]-N-[(3S)-piperidin-3-yl]pyrazine-2-carboxamide: $^1$H NMR (400 MHz, d$_6$-DMSO): δ 9.43 (m, 1H), 8.96 (s, 2H), 8.85 (m, 1H), 8.64 (m, 1H), 8.35 (m, 1H), 7.92 (m, 1H), 7.61 (m, 1H), 7.10 (m, 3H), 4.53 (m, 2H), 3.68 (m, 2H), 3.60 (m, 1H), 3.48 (m, 2H), 3.25 (m, 2H), 1.91 (m, 2H), 1.77 (m, 2H). MS (EI) for $C_{24}H_{24}F_2N_6O_2$: 467 (MH$^+$).

Methyl 4-[({[3-(5-amino-6-{[(3S)-piperidin-3-ylamino]carbonyl}pyrazin-2-yl)phenyl]carbonyl}amino)methyl]benzoate: $^1$H NMR (400 MHz, d$_6$-DMSO): δ 9.39 (m, 1H), 8.96 (s, 1H), 8.81 (d, J=8.8 Hz, 1H), 8.36 (d, J =8.0 Hz, 1H), 7.95 (d, J=8.4 Hz, 2H), 7.92 (d, J=7.6 Hz, 1H), 7.61 (t, J=7.6 Hz, 1H), 7.52 (d, J=8.4 Hz, 2H), 4.61 (d, J=6.0 Hz, 2H), 3.85 (s, 3H), 3.67 (m, 1H), 3.48 (m, 2H), 3.25 (m, 2H), 3.08 (m, 2H), 2.77 (m, 2H), 1.90 (m, 2H), 1.75 (m, 2H). MS (EI) for $C_{26}H_{28}N_6O_4$: 489 (MH$^+$).

3-Amino-6-[3-({[(4-bromophenyl)methyl]amino}carbonyl)phenyl]-N-[(3S)-piperidin-3-yl]pyrazine-2-carboxamide: $^1$H NMR (400 MHz, d$_6$-DMSO): δ 9.47 (m, 1H), 9.11 (m, 1H), 8.95 (s, 1H), 8.89 (d, J=8.8 Hz, 1H), 8.67 (s, 1H), 8.34 (d, 8.4 Hz, 1H), 7.90 (d, J=8.0 Hz, 1H), 7.59 (t, J=7.6 Hz, 1H), 7.52 (m, 2H), 7.34 (d, J=8.4 Hz, 2H), 4.49 (d, J=6.0 Hz, 2H), 3.69 (m, 2H), 3.48 (m, 2H), 3.24 (m, 2H), 2.77 (m, 1H), 1.86 (m,4H). MS (EI) for $C_{24}H_{25}N_6O_2Br$: 510 (MH$^+$).

3-Amino-6-[3-({[(4-bromo-2-fluorophenyl)methyl]amino}carbonyl)phenyl]-N-[(3S)-piperidin-3-yl]pyrazine-2-carboxamide: $^1$H NMR (400 MHz, d$_6$-DMSO): δ 9.45 (m, 1H), 9.14 (m, 1H), 8.95 (s, 1H), 8.67 (s, 1H), 8.35 (d, J=8.0 Hz, 1H), 7.90 (d, J=7.6 Hz, 1H), 7.58 (m, 2H), 7.41 (m, 2H), 4.51 (d, J=8.0 Hz, 2H), 4.28 (m, 1H), 3.60 (m, 1H), 3.24 (m, 2H), 2.77 (m, 2H), 1.89 (m, 2H), 1.81 (m, 2H). MS (EI) for $C_{24}H_{24}BrFN_6O_2$: 528 (MH$^+$).

3-Amino-6-[3-({[(2-bromophenyl)methyl]amino}carbonyl)phenyl]-N-[(3S)-piperidin-3-yl]pyrazine-2-carboxamide: $^1$H NMR (400 MHz, d$_6$-DMSO): δ 9.39 (t, J=5.6 Hz, 1H), 9.00 (m, 1H), 8.97 (s, 1H), 8.85 (m, 1H), 8.68 (s, 1H), 8.36 (m, 1H), 7.93 (m, 1H), 7.64 (m, 2H), 7.39 (m, 2H), 7.23 (m, 1H), 4.51 (d, J =6.0 Hz, 2H), 3.67 (m, 1H), 3.50 (m, 1H), 3.25 (m, 2H), 3.14 (m, 1H), 2.77 (m, 2H), 1.91 (m, 2H), 1.76 (m, 2H). MS (EI) for $C_{24}H_{25}BrN_6O_2$: 510 (MH$^+$).

3-Amino-6-{3-[({[4-fluoro-2-(trifluoromethyl)phenyl]methyl}amino)carbonyl]phenyl}-N-[(3S)-piperidin-3-yl]pyrazine-2-carboxamide: $^1$H NMR (400 MHz, d$_6$-DMSO): δ 9.2 (t, 1H), 8.9 (s, 1H), 8.55 (s, 1H), 8.45 (d, 1H) 8.3 (d, 1H), 7.9 (d, 1l1), 7.7-7.5 (m, 5H), 4.7 (d, 2H), 3.85 (m, 1H), 2.9 (m, 3H), 2.75 (m, 1H), 1.95-1.7 (m, 4H). MS (EI) for $C_{25}H_{24}N_6O_2F_4$: 517 (MH$^+$).

3-Amino-6-{3-[({[2-fluoro-3-(trifluoromethyl)phenyl]methyl}amino)carbonyl]phenyl}-N-[(3S)-piperidin-3-yl]pyrazine-2-carboxamide: $^1$H NMR (400 MHz, d$_6$-DMSO): δ 9.3 (t, 1H), 8.95 (s, 1H), 8.6 (d, 1H), 8.55 (s, 1H), 8.3 (d, 1H), 8.0-7.5 (m, 6H), 7.4 (t, 1H), 4.6 (d, 2H), 4.0 (m, 1H), 3.1-2.9 (m, 2H), 2.75 (t, 1H), 2.6 (t, 1H), 1.9-1.5 (m, 4). MS (EI) for $C_{25}H_{24}N_6O_2F_4$: 517 (MH$^+$).

3-Amino-N-[(3S)-piperidin-3-yl]-6-[3-({[(3R)-pyrrolidin-3-ylmethyl]amino}carbonyl)phenyl]pyrazine-2-carboxamide: $^1$H NMR (400 MHz, d$_4$-MeOH): δ 8.83 (s, 1H), 8.72 (s, 1H), 8.43 (m, 1H), 8.17 (m, 1H), 7.79 (m, 1H), 7.51 (m, 1H), 4.26 (m, 1H), 3.65 (m, 1H), 3.58 (m, 2H), 3.47 (m, 3H), 3.37 (m, 3H1), 3.12 (m, 1H), 2.99 (m, 2H), 2.68 (m, 1H), 2.13 (m, 1H), 2.00 (m, 2H), 1.83 (m, 3H). MS (EI) for $C_{22}H_{29}N_7O_2$: 424 (MH$^+$).

3-Amino-N-[(3S)-piperidin-3-yl]-6-(3-{[(3R)-pyrrolidin-3-ylamino]carbonyl}phenyl)pyrazine-2-carboxamide: $^1$H NMR (400 MHz, d$_4$-MeOH): δ 8.80 (s, 1H), 8.58 (s, 1H), 8.24 (d, J=8.0 Hz, 1H), 7.91 (d, J=8.4 Hz, 1H), 7.60 (t, J=8.0 Hz, 1H), 4.33 (m, 1H), 3.75 (m, 1H), 3.63 (m, 2H), 3.50 (m, 2H), 3.20 (m, 2H), 3.04 (m, 1H), 2.43 (m, 2H), 2.28 (m, 2H), 2.10 (m, 2H), 1.92 (m, 2H). MS (EI) for $C_{21}H_{27}N_7O_2$: 410 (MH$^+$).

3-Amino-N-[(3S)-piperidin-3-yl]-6-(3-{[(2-piperidin-1-ylethyl)amino]carbonyl}phenyl)pyrazine-2-carboxamide: $^1$H NMR (400 MHz, d$_4$-MeOH): δ 8.80 (s, 1H), 8.64 (s, 1H), 8.24 (d, J=7.6 Hz, 1H), 7.94 (d, J=7.6 Hz, 1H), 7.61 (t, J=7.6 Hz, 1H), 4.33 (m, 1H), 3.85 (m, 2H), 3.69 (m, 5H), 3.58 (m, 1H), 3.47 (m, 2H), 3.39 (m, 2H), 3.24 (m, 2H), 3.02 (m, 2H), 2.10 (m, 2H), 2.00 (m, 2H), 1.86 (m, 4H). MS (EI) for $C_{24}H_{33}N_7O_2$: 452 (MH$^+$).

3-Amino-6-(3-{[(2-phenylethyl)amino]carbonyl}phenyl)-N-[(3S)-piperidin-3-yl]pyrazine-2-carboxamide: $^1$H NMR (400 MHz, d$_4$-MeOH): δ 8.76 (s, 1H), 8.48 (s, 1H), 8.18 (d, J=7.6 Hz, 1H), 7.78 (d, J=7.6 Hz, 1H), 7.76 (t, J=7.6 Hz, 1H), 7.26 (m, 4H), 7.19 (m, 1H), 4.34 (m, 1H), 3.73 (m, 1H), 3.66 (m, 4H), 3.57 (m, 1H), 3.48 (m, 1H), 3.36 (m, 2H), 3.15 (m, 1H), 3.02 (m, 1H), 2.95 (m, 2H), 2.09 (m, 2H), 1.90 (m, 2H). MS (EI) for $C_{25}H_{28}N_6O_2$: 445 (MH$^+$).

3-Amino-6-(3-({[2-(methyloxy)ethyl]amino}carbonyl)phenyl]-N-[(3S)-piperidin-3-yl]pyrazine-2-carboxamide: $^1$H NMR (400 MHz, d$_4$-MeOH): δ 8.76 (s, 1H), 8.48 (s, 1H), 8.18 (d, J=7.6 Hz, 1H), 7.78 (d, J=7.6 Hz, 1H), 7.76 (t, J=7.6 Hz, 1H), 4.33 (m, 1H), 3.74 (m, 1H), 3.67 (m, 2H), 3.59 (m, 1H), 3.49 (m, 1H), 3.39 (m, 3H), 3.34 (m, 2H), 3.16 (m, 1H), 3.02 (m, 1H), 2.10 (m, 2H), 1.90 (m, 211). MS (EI) for $C_{20}H_{26}N_6O_3$: 399 (MH$^+$).

3-Amino-6-[3-({[(4-iodophenyl)methyl]amino}carbonyl)phenyl]-N-[(3S)-piperidin-3-yl]pyrazine-2-carboxamide: $^1$H NMR (400 MHz, d$_6$-DMSO): δ 8.74 (s, 1H), 8.58 (m, 1H), 8.24-8.21 (m, 1H), 7.90-7.88 (m, 1H), 7.62-7.59 (m, 1H), 7.39-7.32 (m, 4H), 4.60 (s, 2H), 4.31-4.29 (m, 1H), 3.50-3.46 (m, 2H), 3.37-3.30 (m, 2H), 2.10-1.83 (m, 4H). MS (EI) for $C_{24}H_{25}N_6O_2I$: 557 (MH$^+$).

3-Amino-6-[3-({[(2-chlorophenyl)methyl]amino}carbonyl)phenyl]-N-[(3S)-piperidin-3-yl]pyrazine-2-carboxamide: $^1$H NMR (400 MHz, d$_6$-DMSO): δ 8.78 (s, 1H), 8.57 (m, 1H), 8.23-8.21 (m, 1H), 7.92-7.89 (m, 1H), 7.62-7.59 (m, 1H), 7.37-7.30 (m, 4H), 4.60 (s, 2H), 4.31-4.28 (m, 1H), 3.50-3.46 (m, 2H), 3.37-3.30 (m, 2H), 2.10-1.83 (m, 4H). MS (EI) for $C_{24}H_{25}N_6O_2Cl$: 465(MH$^+$).

3-Amino-6-(3-{[(4-chlorophenyl)acetyl]amino}phenyl)-N-[(3S)-piperidin-3-yl]pyrazine-2-carboxamide: $^1$H NMR (400 MHz, d$_6$-DMSO): δ 10.8 (s, 1H), 9.2 (m, 1H), 9.03 (m, 1H), 8.78 (s, 1H), 8.7 (d, 1H), 8.42 (s, if), 7.8 (m, 2H), 7.4 (m, 5H), 4.3 (m, 1H), 3.7 (s, 2H), 3.3-3.2 (m, 3H), 2.8 (m, 1H), 2.0-1.7 (m, 4H). MS (EI) for $C_{24}H_{25}N_6O_2Cl$: 465 (MH$^+$).

3-Amino-6-(3-{[(2,6-dichlorophenyl)acetyl]amino}phenyl)-N-[(3S)-piperidin-3-yl]pyrazine-2-carboxamide: $^1$H NMR (400 MHz, d$_6$-DMSO): δ 10.8 (s, 1H), 9.2 (m, 1H), 9.0 (m, 1H), 8.78 (s, 1H), 8.7 (d, 1H), 8.4 (s, 1H), 7.85 (d, 1H), 7.72 (d, 1H), 7.5 (t, 1H), 7.4 (m, 3H), 4.3 (m, 1H), 4.1 (s, 2H), 3.3-3.1 (m, 3H), 2.8 (m, 1H), 2.0-1.7 (m, 4H). MS (EI) for $C_{24}H_{24}N_6O_2Cl_2$: 499 (MH$^+$).

3-Amino-6-(3-{[(pentafluorophenyl)acetyl]amino}phenyl)-N-[(3S)-piperidin-3-yl]pyrazine-2-carboxamide: $^1$H NMR (400 MHz, d6-DMSO): δ 10.95 (s, 1H), 9.2 (m, 1H), 9.05 (m, 1H), 8.78 (s, 1H), 8.65 (d, 1H), 8.4 (s, 1H), 7.85 (d, 1H), 7.75 (d, 1H), 7.4 (t, 1H), 4.3 (m, 1H), 3.96 (s, 2H), 3.3-3.1 (m, 3H), 2.8 (m, 1H), 2.0-1.7 (m, 4H). MS (EI) for $C_{24}H_{21}N_6O_2F_5$: 521 (MH$^+$).

3-Amino-6-(3-{[(2-chloro-4-fluorophenyl)acetyl]amino}phenyl)-N-[(3S)-piperidin-3-yl]pyrazine-2-carboxamide: $^1$H NMR (400 MHz, d$_6$-DMSO): δ 10.7 (s, 1H), 9.2 (m, 1H), 9.05 (m, 1H), 8.78 (s, 1H), 8.7 (d, 1H), 8.4 (s, 1H), 7.85 (d, 1H), 7.75 (d, 1H), 7.5 (t, 1H), 7.45 (m, 2H), 7.25 (m, 1H), 4.3 (m, 1H), 3.9 (s, 2H), 3.3-3.1 (m, 3H), 2.8 (m, 1H), 2.0-1.7 (m, 4H). MS (EI) for $C_{24}H_{24}N_6O_2FCl$: 483 (MH$^+$).

3-Amino-6-(3-({[4-(methylthio)phenyl]acetyl}amino)phenyl]-N-[(3S)-piperidin-3-yl]pyrazine-2-carboxamide: $^1$H NMR (400 MHz, d$_6$-DMSO): δ 10.7 (s, 1H), 9.2 (m, 1H), 9.0 (m, 1H), 8.78 (s, 1H), 8.7 (d, 1H), 8.4 (s, 1H), 7.8 (d, 2H), 7.4 (m, 3H), 7.2 (d, 2H), 4.3 (m, 1H), 3.7 (s, 2H), 3.3-3.1 (m, 3H), 2.8 (m, 1H), 2.45 (s, 3H), 2.0-1.7 (m, 4H). MS (EI) for $C_{25}H_{28}N_6O_2S$: 477 (MH$^+$).

3-Amino-6-(3-{[(2,4-dichlorophenyl)acetyl]amino}phenyl)-N-[(3S)-piperidin-3-yl]pyrazine-2-carboxamide: $^1$H NMR (400 MHz, d$_6$-DMSO): δ 10.8 (s, 1H), 9.25 (m, 1H), 9.1 (m, 1H), 8.78 (s, 1H), 8.7 (d, 1H), 8.43 (s, 1H), 7.85 (d, 1H), 7.8 (d, 1H), 7.6 (s, 1H), 7.5 (t, 1H), 7.4 (m, 2H), 4.3 (m, 1H), 3.9 (s, 2H), 3.3-3.1 (m, 3H), 2.8 (m, 1H), 2.0-1.7 (m, 4H). MS (EI) for $C_{24}H_{24}N_6O_2Cl_2$: 499 (MH$^+$).

3-Amino-6-[3-({[4-(4-chlorophenyl)-2-thienyl]carbonyl}amino)phenyl]-N-[(3S)-piperidin-3-yl]pyrazine-2-carboxamide: $^1$H NMR (400 MHz, d$_6$-DMSO): δ 10.85 (s, 1H), 9.2-9.1 (m, 2H), 9.0-8.8 (m, 4H), 8.27 (s, 1H), 8.05 (d, 1H), 7.9-7.8 (m, 3H), 7.57 (d, 2H), 7.45 (t, 1H), 4.4 (m, 1H), 3.3-3.1 (m, 3H), 2.8 (m, 1H), 2.0-1.7 (m, 4H). MS (EI) for $C_{27}H_{25}N_6O_2SCl$: 533 (MH$^+$).

3-Amino-6-(3-{[(2,4-difluorophenyl)acetyl]amino}phenyl)-N-[(3S)-piperidin-3-yl]pyrazine-2-carboxamide: $^1$H NMR (400 MHz, d$_6$-DMSO): δ 10.7 (s, 1H), 9.1 (m, 1H), 8.95 (m, 1H), 8.75 (s, 1H), 8.67 (d, 1H), 8.4 (s, 1H), 7.82 (d, 1H), 7.72 (d, 1H), 7.5 (q, 1H), 7.4 (t, 1H), 7.25 (m, 1), 7.1 (m, 1H), 4.5 (s, 1H), 4.3 (m, 1H), 3.8 (s, 2H), 3.2 (m, 3H), 2.75 (m, 1H), 1.95-1.7 (m, 4H). MS (EI) for $C_{24}H_{24}N_6O_2F_2$: 483 (MH$^+$).

3-Amino-6-(3-{[(2-fluorophenyl)acetyl]amino}phenyl)-N-[(3S)-piperidin-3-yl]pyrazine-2-carboxamide: $^1$H NMR (400 MHz, d$_6$-DMSO): δ 10.7 (s, 1H), 9.15 (m, 1H), 9.0 (m, 1H), 8.75 (s, 1H), 8.7 (d, 1H), 8.4 (s, 1H), 7.8 (d, 1H), 7.75 (d, 1H), 7.5-7.1 (m, 5H), 4.3 (m, 1H), 3.8 (s, 2H), 3.2 (m, 3H), 2.75 (s, 1H), 1.95-1.7 (m, 4H). MS (EI) for $C_{24}H_{25}N_6O_2F$: 449 (MH$^+$).

3-Amino-6-{3-[({5-[2-chloro-5-(trifluoromethyl)phenyl]furan-2-yl}carbonyl)amino]phenyl}-N-[(3S)-piperidin-3-yl]pyrazine-2-carboxamide: $^1$H NMR (400 MHz, d$_6$-DMSO): δ 10.75 (s. 1H), 9.05 (m, 1H), 8.9 (m, 1H1), 8.85 (s, 1H), 8.75 (d, 1H), 8.6 (s, 1H), 8.5 (s, 1H), 7.9 (t, 3H), 7.8 (m, 2H), 7.5 (m, 2H), 4.3 (m, 1H), 3.35 (m, 3H), 2.75 (q, 1H), 1.9 (m, 3H), 1.75 (m, 1H). MS (EI) for $C_{28}H_{24}N_6O_3F_3Cl$: 585 (MH$^+$).

3-Amino-6-[3-({[4-(dimethylamino)naphthalen-1-yl]carbonyl}amino)phenyl]-N-[(3S)-piperidin-3-yl]pyrazine-2-carboxamide: $^1$H NMR (400 MHz, d$_6$-DMSO): δ 10.7 (s, 1H), 9.2 (m, 1H), 9.05 (m, 1H), 8.8 (s, 1H), 8.7 (d, 1H), 8.55 (s, 1H), 8.3 (m, 2H), 7.9 (t, 2H), 7.8 (d, 1H), 7.6 (m, 2H), 7.5 (t, 1H), 4.3 (m 1H), 3.3-3.1 (m, 3H), 3.0 (s, 6H), 2.75 (m, 1H), 1.95-1.7 (m, 4H). MS (EI) for $C_{29}H_{31}N_7O_2$: 510 (MH$^+$).

3-Amino-N-[(3S)-piperidin-3-yl]-6-[3-({[4-(1,2,3-thiadiazol-5-yl)phenyl]carbonyl}amino)phenyl]pyrazine-2-carboxamide: $^1$H NMR (400 MHz, d$_6$-DMSO): δ 10.7 (s, 1H), 9.85 (s, 1H), 9.15 (m, 1H), 8.95 (m, 1H), 8.8 (d, 2H), 8.67 (s, 1H), 8.3 (q, 4H), 8.0 (d, 1H), 7.9 (d, 1H), 7.5 (t, 1H), 4.3 (m, 1H), 3.25 (m, 3H), 2.75 (m, 1H), 1.95-1.7 (m, 4H). MS (EI) for $C_{25}H_{24}N_8O_2S$: 501 (MH$^+$.

3-Amino-6-(3-{[(1,3-dimethyl-1H-pyrazol-5-yl)carbonyl]amino}phenyl)-N-[(3S)-piperidin-3-yl]pyrazine-2-carboxamide: $^1$H NMR (400 MHz, d$_6$-DMSO): δ 10.5 (s, 1H), 9.25 (m, 1H), 9.1 (m, 1H), 8.8 (m, 2H), 8.7 (s, 1H), 7.95 (d, 1H), 7.85 (d, 1H), 7.45 (t, 1H), 7.2 (s, 1H), 5.75 (s, 1H), 4.3 (m, 1H), 3.25 (m, 3H), 2.75 (m, 1H), 1.95-1.7 (m, 4H). MS (EI) for $C_{22}H_{26}N_8O_2$: 435 (MH$^+$).

3-Amino-6-(3-{[(4-bromo-2-fluorophenyl)carbonyl]amino phenyl)-N-[(3S)-piperidin-3-yl]pyrazine-2-carboxamide: $^1$H NMR (400 MHz, d$_6$-DMSO): δ 10.7(s, 1H), 9.1(m, 1H), 8.9(m, 1H), 8.78(s, 1H), 8.7(d, 1H), 8.4(s, 1H), 7.9(d, 1H), 7.8(m, 2H), 7.7(d, 1H), 7.58(d, 1H), 7.5(t, 1H), 4.3(m, 1H), 3.3-3.1(m, 3H), 2.8(m, 1H), 2.0-1.7(m, 4H). MS (EI) for $C_{23}H_{22}N_6O_2FBr$: 515 (MH$^+$).

N-[3-(5-Amino-6-{[(3S)-piperidin-3-ylamino]carbonyl}pyrazin-2-yl)phenyl]quinoline-3-carboxamide: $^1$H NMR (400 MHz, d$_6$-DMSO): δ 11.15 (s, 1H), 9.65 (s, 1H), 9.4 (s, 1H), 9.18 (m, 1H), 8.98 (m, 1H), 8.83 (s, 1H), 8.8 (m, 2H), 8.25 (d, 1H), 8.2 (m, 1H), 8.1 (d, 1H), 8.0 (t, 1H), 7.9 (d, 1H), 7.8 (t, 1H), 7.5 (t, 1H), 4.3 (m, 1H), 3.3-3.2 (m, 3H), 2.8 (m, 1H), 2.0-1.7 (m, 4H). MS (EI) for $C_{26}H25N_7O_2$: 468 (MH$^+$).

3-Amino-6-[3-({[6-(methyloxy)-1-benzofuran-3-yl]acetyl}amino)phenyl]-N-[(3S)-piperidin-3-yl]pyrazine-2-carboxamide: $^1$H NMR (400 MHz, d$_6$-DMSO): δ 10.6 (s, 1H), 8.9 (m, 1H), 8.8 (m, 1H), 8.78 (s, 1H), 8.7 (d, 1H), 8.35 (s, 1H), 7.8 (m, 2H), 7.73 (d, 1H), 7.6 (d, 1H), 7.4 (t, 1H), 7.2 (s, 1H), 6.9 (d, 1H), 4.3 (m, 1H), 3.8 (s, 2H), 3.78 (d, 2H), 3.3-3.1 (m, 3H), 2.8 (m, 1H), 2.0-1.7 (m, 4H). MS (EI) for $C_{27}H_{28}N_6O_4$: 501 (MH$^+$).

3-Amino-N-[(3S)-piperidin-3-yl]-6-[3-({[4'-(trifluoromethyl)biphenyl-2-yl]carbonyl}amino)phenyl]pyrazine-2-carboxamide: $^1$H NMR (400 MHz, d$_6$-DMSO): δ 10.5 (s, 1H), 9.05 (m, 1H), 8.9 (m, 1H), 8.67 (s, 1H), 8.6 (d, 1H), 8.2 (s, 1H), 7.85 (d, 1H), 7.75 (d, 2H), 7.7-7.5 (m, 7H), 7.4 (t, 1H), 4.3 (m, 1H), 4.05 (s, 1H), 3.25 (m, 2H), 3.05 (m, 1H), 2.75 (m, 1H), 1.95-1.7 (m, 4H). MS (EI) for $C_{30}H_{27}N_6O_2F_3$: 561 (MH$^+$).

3-Amino-6-[3-({[3,5-bis(trifluoromethyl)phenyl]acetyl}amino)phenyl]-N-[(3S)-piperidin-3-yl]pyrazine-2-carboxamide: $^1$H NMR (400 MHz, d$_6$-DMSO): δ 0.8 (s, 1H), 9.05 (m, 1H), 8.9 (m, 1H), 8.72 (s, 1H), 8.52 (d, 1H), 8.35 (s, 1H), 8.1 (s, 2H), 8.0 (s, 1H), 7.8 (d, 1H), 7.7 (d, 2H), 7.4 (t, 1H), 4.3 (m, 1H), 4.0 (s, 2H), 3.3-3.15 (m, 3H), 2.75 (m, 1H), 1.95-1.7 (m, 4H). MS (EI) for $C_{26}H_{24}N_6O_2F_6$: 567 (MH$^+$).

3-Amino-6-{3-[({[4-(4-methylpiperazin-1-yl)phenyl]methyl}amino)carbonyl]phenyl}-N-[(3S)-piperidin-3-yl]pyrazine-2-carboxamide: $^1$H NMR (400 MHz, d$_4$-MeOH): δ 8.72 (s, 1H), 8.60 (s, 1H), 8.23 (m, 1H), 7.90 (m, 1H), 7.61 (m, 1H), 7.36 (m, 2H), 7.06 (m, 2H), 4.56 (s, 2H), 4.39-4.37 (m, 1H), 3.86-3.83 (m, 2H), 3.67-3.61 (m, 2H), 3.51-3.48 (m, 2H), 3.38-3.35 (m, 1H), 3.31-2.97 (m, 8H), 2.09-1.96 (m, 4H). MS (EI) for $C_{29}H_{36}N_8O_2$: 529 (MH$^+$).

3-Amino-6-[3-({[2-(4-fluorophenyl)ethyl]amino}carbonyl)phenyl]-N-[(3S)-piperidin-3-yl]pyrazine-2-carboxamide: $^1$H NMR (400 MHz, d$_4$-MeOH): δ 8.74 (s, 1H), 8.50 (m, 1H), 8.21-8.19 (m, 1H), 7.81-7.78 (m, 1H), 7.59-7.55 (m, 1H), 7.30-7.26 (m, 2H), 7.03-6.99 (m, 2H), 4.35 (m, 1H), 3.69-2.93 (m, 8H), 2.11-1.91 (m, 4H). MS (EI) for $C_{25}H_{27}N_6O_2F$: 463 (MH$^+$).

3-Amino-6-(3-{[(2-morpholin-4-ylethyl)amino]carbonyl}phenyl)-N-[(3S)-piperidin-3-yl]pyrazine-2-carboxamide: $^1$H NMR (400 MHz, d$_4$-MeOH): δ 8.80 (s, 1H), 8.67 (s, 1H), 8.24 (m, 1H), 7.95 (m, 1H), 7.63-7.59 (m, 1H), 4.37-4.36 (m, 1H), 4.12-4.08 (m, 2H), 3.89-3.84 (m, 4H), 3.75-3.66 (m, 2H), 3.49-3.03 (m, 8H), 2.12-1.91 (m, 4H). MS (EI) for $C_{23}H_{31}N_7O_3$: 454 (MH$^+$).

3-Amino-N-[(3S)-piperidin-3-yl]-6-[3-({[(2R)-pyrrolidin-2-ylmethyl]amino}carbonyl)phenyl]pyrazine-2-carboxamide: $^1$H NMR (400 MHz, d$_4$-MeOH): δ 8.77 (s, 1H), 8.61 (s, 1H), 8.25-8.23 (m, 1H), 7.93-7.91 (m, 1H), 7.63-7.61 (m, 1H), 4.37 (m, 1H), 3.57-2.77 (m, 1H), 2.24-1.86 (m, 6H). MS (EI) for $C_{22}H_{29}N_7O_2$: 424 (MH$^+$).

3-Amino-N-[(3S)-piperidin-3-yl]-6-(3-{[(2S)-pyrrolidin-2-ylamino]carbonyl}phenyl)pyrazine-2-carboxamide: $^1$H NMR (400 MHz, d$_4$-MeOH): δ 8.77 (s, 1H), 8.61 (s, 1H), 8.25-8.23 (m, 1H), 7.92-7.89 (m, 1H), 7.64-7.62 (m, 1H), 4.78-4.75 (m, 1H), 4.39-4.37 (m, 1H), 3.57-2.77 (m, 8H), 2.44-1.93 (m, 6H). MS (EI) for $C_{21}H_{27}N_7O_2$: 410 (MH$^+$).

3-Amino-6-{3-[(cyclopentylamino)carbonyl]phenyl}-N-[(3S)-piperidin-3-yl]pyrazine-2-carboxamide: $^1$H NMR (400 MHz, d$_4$-MeOH): δ 8.73 (s, 1H), 8.53 (s, 1H), 8.24-8.22 (m, 1H), 7.88-7.86 (m, 1H), 7.62-7.58 (m, 1H), 4.99-4.89 (m, 2H), 3.59-3.49 (m, 1H), 3.39-3.30 (m, 1H) 3.24-3.21 (m, 1H) 3.09-3.01 (m, 1H), 2.37-1.67 (m, 1H). MS (EI) for $C_{22}H_{27}N_6O_2$: 409 (MH$^+$).

3-Amino-6-{3-[({[4-(1,1-dimethylethyl)phenyl]methyl}amino)carbonyl]phenyl}-N-[(3S)-piperidin-3-yl]pyrazine-2-carboxamide: $^1$H NMR (400 M , d$_4$-MeOH): δ 8.89 (s, 1H), 8.57 (m, 1H), 8.18 (m, 1H), 8.05 (m, 1H), 7.82 (m, 1H), 7.78 (m, 1H), 7.42-7.24 (m, 4H), 4.62 (m, 3H), 4.27 (m, 1H), 3.42-2.92 (m, 4H), 2.18-1.84 (m, 4H), 1.27 (s, 9H). MS (EI) for $C_{28}H_{34}N_6O_2$: 487 (MH$^+$).

3-Amino-6-[3-({[(2,4-dichloro-6-methylphenyl)methyl]amino}carbonyl)phenyl]-N-[(3S)-piperidin-3-yl]pyrazine-2-carboxamide: $^1$H NMR (400 MHz, d$_4$-MeOH): δ 8.78 (s, 1H), 8.65 (m, 1H), 8.18 (m, 1H), 7.82 (m, 1H), 7.57 (m, 1H), 7.39-7.23 (m, 2H), 4.68 (m, 3H), 4.26 (m, 1H), 3.42-2.92 (m, 4H), 2.44 (s, 3H), 2.19-1.86 (m, 4H). MS (EI) for $C_{25}H_{26}N_6O_2Cl_2$: 513 (MH$^+$).

3-Amino-6-[3-({[(3,5dichlorophenyl)methyl]amino}carbonyl)phenyl]-N-[(3S)-piperidin-3-yl]pyrazine-2-carboxamide: $^1$H NMR (400 MHz, d$_4$-MeOH): δ 8.82 (s, 1H), 8.63 (m, 1H), 8.57 (m, 1H), 8.22 (m, 1H), 7.59 (m, 1H), 7.26 (s, 3EI), 4.68 (m, 3H), 4.26 (m, 1H), 3.47-2.99 (m, 4H), 2.15-1.82 (m, 4H). MS (EI) for $C_{24}H_{24}N_6O_2Cl_2$: 499 (MH$^+$).

3-Amino-N-[(3S)-piperidin-3-yl]-6-{3-[({[4-(1,2,3-thiadiazol-4-yl)phenyl]methyl}amino)carbonyl]phenyl}pyrazine-2-carboxamide: $^1$H NMR (400 MHz, d$_6$-DMSO): δ 9.6 (s, 1H), 9.55 (t, 1H), 9.2 (m, 1H), 9.0-8.9 (m, 3H), 8.7 (s, 1H), 8.35 (d, 1H), 8.1 (d, 2H), 7.95 (d, 1H), 7.6-7.5 (m, 3H), 4.6 (d, 2H), 4.3 (m, 1H), 3.3-3.1 (m, 3H), 2.75 (m, 1H), 1.95-1.7 (m, 4H). MS (EI) for $C_{26}H_{26}N_8O_2S$: 515 (MH$^+$).

3-Amino-6-(3-{[(1S)-2,3-dihydro-1H-inden-1-ylamino]methyl}phenyl)-N-[(3S)-pyrrolidin-3-yl]pyrazine-2-carboxamide: $^1$H NMR (400 MHz, d$_6$-DMSO): δ 10.0 (s, 2H), 9.55 (s, 2H), 9.15 (d, 1H), 8.92 (s, 1H), 8.12 (d, 1H), 7.9 (d, 1H), 7.6-7.45 (m, 4H), 7.35-7.25 (m, 3H), 4.85-4.8 (m, 2H), 4.3 (s, 2H), 3.4 (m, 4H), 3.2 (m, 2H), 2.9 (m, 1H), 2.45 (m, 2H), 2.3-2.15 (m, 2H). MS (EI) for $C_{25}H_{28}N_6O$: 429 (MH$^+$).

3-Amino-6-[3-({[(1R,2S)-2-hydroxy-2,3-dihydro-1H-inden-1-yl]amino}methyl)phenyl]-N-[(3S)-pyrrolidin-3-yl]pyrazine-2-carboxamide: $^1$H NMR (400 MHz, d$_6$-DMSO): δ 10.2 (s, 1H), 9.6 (s, 2H), 9.3 (m, 1H), 9.1 (d, 1H), 8.9 (d, 1H), 8.15 (d, 1H), 7.9 (d, 1H), 7.58 (d, 1H), 7.45 (t, 1H), 7.3-7.2 (m, 3H), 4.8 (m, 2H), 4.6 (m, 1H), 4.45 (m, 2H), 3.55 (m, 3H), 3.25-3.1 (m, 2H), 3.0 (d, 1H), 2.3-2.15 (m, 2H). MS (EI) for $C_{25}H_{28}N_6O_2$: 445. (MH$^+$).

3-Amino-N-[(3S)-pyrrolidin-3-yl]-6-(3-{[(1S)-1,2,3,4-tetrahydronaphthalen-ylamino]methyl}phenyl)pyrazine-2-carboxamide: $^1$H NMR (400 MHz, CDCl$_3$): δ 8.63 (s, 1H), 8.24 (d, 1H), 7.75 (s, 1H), 7.72-7.75 (m, 1H), 7.38-7.46 (m, 3H), 7.14-7.18 (m, 2H), 7.08-7.11 (m, 1H), 4.52-4.56 (m, 1H), 3.94-4.06 (m, 2H), 3.09 (t, 1H), 2.96-3.03 (m, 2H), 2.68-2.88 (m, 5H), 2.21-2.29 (m, 1H), 1.94-2.06 (m, 3H1), 1.74-1.86 (m, 2H). MS (EI) for $C_{26}H_{30}N_6O$: 443 (MH$^+$).

3-Amino-6-(3-hydroxyphenyl)-N-[(3S)-pyrrolidin-3-yl]pyrazine-2-carboxamide: $^1$H NMR (400 MHz, d$_6$-DMSO): δ 9.36 (br s, 2H), 8.80 (d, 1H), 8.75 (s, 1H), 7.57-7.53 (m, 2H), 7.23 (t, 1H), 6.78 (d, 1H), 4.64-4.57 (m, 2H), 4.20 (br s, 1H), 3.44-3.34 (m, 2H), 3.29-3.17 (m, 2H), 2.28-2.19 (m, 1H), 2.10-2.03 (m, 1H). MS (EI) for $C_{15}H_{17}N_7O_2$: 300 (MH$^+$).

3-Amino-6-(3-hydroxyphenyl)-N-[(3S)-piperidin-3-yl]pyrazine-2-carboxamide: $^1$H NMR (400 MHz, d$_6$-DMSO): δ 9.54 (br s, 1H), 8.93 (m, 1H), 8.82-8.79 (m, 1H), 7.75 (s, 1H), 8.62 (d, 1H), 7.60 (br s, 1H), 7.59-7.46 (m, 2H), 7.24 (t, 1H), 6.81 (d, 1H), 4.21 (br s, 1H), 3.27-3.20 (m, 2H), 3.03 (q, 1H), 2.76-2.74 (m, 1H), 1.89-1.87 (m, 2H), 1.76-1.72 (m, 2H). MS (EI) for $C_{16}H_{19}N_5O_2$: 314 (MH$^+$).

5-(3-{[(1S)-2,3-dihydro-1H-inden-1-ylamino]methyl}phenyl)-3-(4-piperidin-3-yl-1,3-thiazol-2-yl)pyrazin-2-amine: $^1$H NMR (400 MHz, d$_6$-DMSO): δ 9.4 (t, 2H), 8.9 (d, 1H), 8.8 (s, 1H), 8.63 (d, 1H), 8.15 (s, 1H), 8.05 (d, 1H), 7.9 (m, 1H), 7.67 (m, 2H), 7.6-7.5 (m, 2H), 7.4-7.25 (m, 3H), 4.85 (m, 1H), 4.3 (d, 2H), 3.6 (d, 1H), 3.4-3.0 (m, 4H), 2.9 (t, 2H), 2.4-2.0 (m, 2H),20-1.7 (m, 3H). MS (EI) for $C_{28}H_{30}N_6S$: 483 (MH$^+$).

1,1-Dimethylethyl (3S)-3-{[(3-amino-6-{3-[({[(1,1-dimethylethyl)oxy]carbonyl}amino)methyl]phenyl}pyrazin-2-yl)carbonyl]amino}piperidine-1-carboxylate: $^1$H NMR (400 MHz, CDCl$_3$): δ 8.4 (s, 1H), 8.2 (m, 1H), 7.80 (m, 2H), 7.4 (m, 1H), 4.6 (s, 2H), 4.1 (m, 1H), 3.4 (m, 4H), 1.8 (m, 4H), 1.5-1.6 (m, 18H). MS (EI) for $C_{27}H_{38}N_6O_5$: 527 (MH$^+$).

3-Amino-6-[3-(aminomethyl)phenyl]-N-[(3S)-piperidin-3-yl]pyrazine-2-carboxamide: $^1$H NMR (400 MHz, d$_4$-MeOH): δ 8.4 (s, 1H), 8.2 (m, 1H), 7.80 (m, 2H), 7.4 (m, 1H), 4.6 (s, 2H), 4.1 (m, 1H), 3.4 (m, 4H), 1.8 (m, 4H). MS (EI) for C$_{17}$H$_{22}$N$_6$O: 327 (MH$^+$).

3-Amino-N-[(3S)-piperidin-3-yl]-6-{3-[({[2-(2-thienyl)-1,3-thiazol-4-yl]carbonyl}amino)methyl]phenyl}pyrazine-2-carboxamide: $^1$H NMR (400 MHz, d$_4$-MeOH): δ 8.4 (s, 1H), 8.2 (m, 1H), 7.80 (m, 2H), 7.6 (s, 1H), 7.4 (m, 3H), 7.2 (m, 1H), 4.6 (s, 2H), 4.1 (m, 1H), 3.4 (m, 4H), 1.8 (m, 4H). MS (EI) for C$_{25}$H$_{25}$N$_7$O$_2$S$_2$: 520 (MH$^+$).

3-Amino-N-[(3S)-piperidin-3-yl]-6-{3-[({[5-(2-thienyl)pyridin-3-yl]carbonyl}amino)methyl]phenyl}pyrazine-2-carboxamide: $^1$H NMR (400 MHz, d$_4$-MeOH): δ 8.4 (s, 1H), 8.2 (m, 1H), 7.80 (m, 2H), 7.6 (s, 1H), 7.4 (m, 3H), 7.3 (m, 2H), 7.2 (m, 1H) 4.6 (s, 2H), 4.1 (m, 1H), 3.4 (m, 4H), 1.8 (m, 4H). MS (EI) for C$_{27}$H$_{27}$N$_7$O$_2$S: 514 (MH$^+$).

1,1-Dimethylethyl (3S)-3-[({3-amino-6-[3-(aminomethyl)phenyl]pyrazin-2-yl}carbonyl)amino]piperidine-1-carboxylate: $^1$H NMR (400 MHz, d$_6$-DMSO): δ 8.95 (m, 1H), 8.50 (d, 1H), 8.40-8.10 (m, 4H), 7.60-7.40 (m, 2H), 4.10 (m, 2H), 3.90-3.60 (m, 3H), 3.30-3.00 (m, 2H), 1.90-1.60 (m, 4H), 1.40 (s, 9H). MS (EI) for C$_{22}$H$_{30}$N$_6$O$_3$: 427 (MH$^+$).

3-Amino-6-[3-({[(4-fluorophenyl)carbonyl]amino}methyl)phenyl]-N-[(3S)-piperidin-3-yl]pyrazine-2-carboxamide: $^1$H NMR (400 MH, d$_4$-MeOH): δ 8.72 (s, 1H), 8.02 (s, 1H), 7.90-7.95 (m, 3H), 7.40-7.46 (m, 2H), 7.21 (t, 2H), 4.66 (m, 2H), 3.37-3.73 (m, 2H), 2.91-3.13 (m, 3H), 1.76-2.06 (m, 4H). MS (EI) for C$_{24}$H$_{25}$N$_6$O$_2$F: 449 (MH$^+$).

3-Amino-N-[(3S)-piperidin-3-yl]-6-(3-{[({4-[(trifluoromethyl)oxy]phenyl}carbonyl)amino]methyl}phenyl)pyrazine-2-carboxamide: $^1$H NMR (400 MHz, d$_4$-MeOH): δ 9.14-9.20 (m, 1H), 8.72 (s, 1H), 8.58-8.59 (m, 1H), 8.03 (s, 1H), 7.97-7.99 (m, 1H), 7.91-7.93 (m, 1H), 7.41-7.48 (m, 1H), 7.38-7.39 (m, 1H), 4.62-4.71 (m, 2H), 4.27 (s, 1H), 3.47-3.50 (m, 1H), 3.32-3.49 (m, 1H), 3.06-3.12 (m, 2H), 2.94-2.99 (m, 1H), 2.03-2.06 (m, 2H), 1.79-1.87 (m, 2H). MS (EI) for C$_{25}$H$_{25}$N$_6$O$_3$F$_3$: 515 (MH$^+$).

3-Amino-6-[3-({[(4-chlorophenyl)carbonyl]amino}methyl)phenyl]-N-[(3S)-piperidin-3-yl]pyrazine-2-carboxamide: $^1$H NMR (400 MHz, d$_4$-MeOH): δ 8.72 (s, 1H), 8.02 (s, 1H), 7.90-7.92 (m, 2H), 7.85-7.87 (m, 2H), 7.44-7.51 (m, 3H), 7.38-7.39 (m, 1H), 4.64-4.66 (m, 2H), 4.27 (s, 1H), 3.46-3.73 (m, 2H), 2.96-3.09 (m, 3H), 1.77-2.05 (m, 4H). MS (EI) for C$_{24}$H$_{25}$N$_6$O$_2$Cl: 465 (MH$^+$).

3-Amino-6-[3-({[(4-bromophenyl)carbonyl]amino}methyl)phenyl]-N-[(3S)-piperidin-3-yl]pyrazine-2-carboxamide: $^1$H NMR (400 MHz, d$_4$-MeOH): δ 8.72 (s, 1H), 8.01 (s, 1H), 7.93-7.89 (m, 1H), 7.81-7.76 (m, 2H), 7.68-7.63 (m, 2H), 7.48-7.42 (m, 1H), 7.41-7.36 (m, 1H), 4.71-4.59 (m, 2H), 4.35-4.20 (m, 1H), 3.51-3.44 (m, 1H), 3.39-3.30 (m, 1H), 3.11-3.02 (m, 1H), 3.00-2.91 (m, 1H), 2.10-1.96 (m, 2H), 1.94-1.67 (m, 2H). MS (EI) for C$_{24}$H$_{25}$N$_6$O$_2$Br: 508 (MH$^+$).

3-Amino-6-{3-{[(naphthalen-2-ylcarbonyl)amino]methyl}phenyl)-N-[(3S)-piperidin-3-yl]pyrazine-2-carboxamide: $^1$H NMR (400 MHz, d$_4$-MeOH): δ 8.73 (s, 1H), 8.45 (s, 1H), 8.07 (s, 1H), 8.02-7.88 (m, 5H), 7.64-7.54 (m, 2H), 7.51-7.40 (m, 2H), 4.81-4.65 (m, 2H), 4.25-4.12 (m, 1H), 3.49-3.40 (m, 1H), 3.30-3.22 (m, 1H1), 3.02-2.93 (m, 1H), 2.84-2.74 (m, 1H), 1.95-1.65 (m, 3H), 1.63-1.50 (m, 1H). MS (EI) for C$_{28}$H$_{28}$N$_6$O$_2$: 481 (MH$^+$).

3-Amino-6-{3-[({[4-(dimethylamino)phenyl]carbonyl}amino)methyl]phenyl}-N-[(3S)-piperidin-3-yl]pyrazine-2-carboxamide: $^1$H NMR (400 MHz, d$_4$-MeOH): δ 8.70 (s, 1H), 8.55 (d, 1H), 8.00 (s, 1H), 7.90-7.70 (m, 3H), 7.50-7.30 (m, 2H), 6.80-6.70 (m, 2H), 4.65 (m, 2H), 3.50-2.80 (m, 10H), 2.00-1.60 (m, 4H). MS (EI) for C$_{26}$H$_{31}$N$_7$O$_2$: 474 (MH$^+$).

3-Amino-6-{3-[({[4-(methyloxy)phenyl]carbonyl}amino)methyl]phenyl}-N-[(3S)-piperidin-3-yl]pyrazine-2-carboxamide: $^1$H NMR (400 MHz, d$_4$-MeOH): δ 8.70 (s, 1H), 8.55 (d, 1H), 8.05 (s, 1H), 8.00-7.85 (m, 4H), 7.50-7.40 (m, 2H), 7.00 (m, 2H), 4.65 (m, 2H), 4.25 (m, 1H), 3.80 (s, 3H), 3.50 (m, 1H), 3.10 (m, 1H), 2.95 (m, 1H), 2.00 (m, 2H), 1.80 (m, 2H). MS (EI) for C$_{25}$H$_{28}$N$_6$O$_3$: 461(MH$^+$).

3-Amino-6-(3-{[(biphenyl-4-ylcarbonyl)amino]methyl}phenyl)-N-[(3S)-piperidin-3-yl]pyrazine-2-carboxamide: $^1$H NMR (400 MHz, d$_4$-MeOH): δ 8.70 (s, 1H), 8.55 (d, 1H), 8.05 (s, 1H), 8.00-7.85 (m, 3H), 7.80-7.60 (m, 4H), 7.50-7.30 (m, 5SE), 4.65 (m, 2H), 4.25 (m, 1H), 3.50 (m, 1H), 3.10 (m, 1H), 2.95 (m, 1H), 2.00 (m, 2H), 1.80 (m, 2H). MS (EI) for C$_{30}$H$_{30}$N$_6$O$_2$: 507 (MH$^+$).

3-Amino-6-(3-{[(furan-2-ylcarbonyl)amino]methyl}phenyl)-N-[(3S)-piperidin-3-yl]pyrazine-2-carboxamide: $^1$H NMR (400 MHz, d$_4$-MeOH): δ 8.70 (s, 1H), 8.55 (d, 1H), 8.10 (s, 1H), 8.00 (s, 1H), 7.95 (m, 1H), 7.60 (m, 1H), 7.45-7.25 (m, 2H), 6.80 (m, 1H), 4.65 (m, 2H), 4.25 (m, 1H), 3.50 (m, 1H), 2.95 (m, 1H), 2.00 (m, 2H), 1.80 (m, 2H). MS (EI) for C$_{22}$H$_{24}$N$_6$O$_3$: 421 (MH$^+$).

3-Amino-6-(3-{[(2,3-dihydro-1-benzofuran-5-ylcarbonyl)amino]methyl}phenyl)-N-[(3S)-piperidin-3-yl]pyrazine-2-carboxamide: $^1$H NMR (400 MHz, d$_4$-MeOH): δ 8.72 (s, 1H), 8.01 (s, 1H), 7.92-7.87 (m, 1H), 7.76 (s, 1H), 7.71-7.66 (m, 1H), 7.48-7.41 (m, 1H), 7.40-7.35 (m, 1H), 6.81-6.76 (m, 1H), 4.67-4.57 (m, 4H), 4.33-4.20 (m, 1H), 3.52-3.42 (m, 1H), 3.40-3.20 (m, 3H), 3.11-3.02 (m, 1H), 3.00-2.90 (m, 1H), 2.08-1.97 (m, 2H), 1.90-1.68 (m, 2H). MS (EI) for C$_{26}$H$_{28}$N$_6$O$_3$: 473 (MH$^+$).

3-Amino-N-[(3S)-piperidin-3-yl]-6-(3-{[(2-thienylcarbonyl)amino]methyl}phenyl)pyrazine-2-carboxamide: $^1$H NMR (400 MHz, d$_4$-MeOH): δ 8.70 (s, 1H), 8.55,d, 1H), 8.10 (s, 1H), 8.00 (s, 1H), 7.95 (m, 1H), 7.60, 7.35 (m, 5H), 4.65 (m, 2H), 4.25 (m, 1H), 3.50 (m, 1H), 2.95 (m, 3H), 2.00 (m, 2H), 1.80 (m, 2H). MS (EI) for C$_{22}$H$_{24}$N$_6$O$_2$S: 437 (MH$^+$).

3-Amino-6-(3-{[(2,3-dihydro-1,4-benzodioxin-2-ylcarbonyl)amino]methyl}phenyl)-N-[(3S)-piperidin-3-yl]pyrazine-2-carboxamide: $^1$H NMR (400 MHz, d$_4$-MeOH): δ 8.80 (m, 1H), 8.70 (m, 1H), 7.95-7.75 (m, 2H), 7.40 (m, 1H), 7.20 (m, 1H), 7.00 (m, 1H), 6.95-6.85 (m, 3H), 4.85 (m, 1H), 4.60 (m, 1H), 4.50-4.25 (m, 4H), 3.50 (m, 1H), 3.35 (m, 1H), 3.10 (m, 1H), 2.95 (m, 1H), 2.10 (m, 21), 1.95 (m, 2H). MS (EI) for C$_{26}$H$_{28}$N$_6$O$_4$: 489 (MH$^+$).

N-[(3-{5-Amino-6-[(3R)-piperidin-3-ylacetyl]pyrazin-2-yl}phenyl)methyl]-N'-(4-bromophenyl)urea: $^1$H NMR (400 MHz, d$_4$-MeOH): δ 8.72 (s, 1H), 7.99 (s, 1H), 7.92-7.86 (m, 1H), 7.48-7.42 (m, 1H), 7.41-7.32 (m, 5H), 4.57-4.38 (m, 2H), 4.34-4.20 (m, 1H), 3.50-3.42 (m, 1H), 3.37-3.30 (m, 1H), 3.11-3.00 (m, 1H), 2.95-2.82 (m, 1H), 2.07-1.91 (m, 2H), 1.89-1.66 (m, 2H). MS (EI) for C$_{24}$H$_{26}$N$_7$O$_2$Br: 523 (MH$^+$).

N-[(3-{5-Amino-6-[(3R)-piperidin-3-ylacetyl]pyrazin-2-yl}phenyl)methyl]-N'-naphthalen-2-ylurea: $^1$H NMR (400 MHz, d$_4$-MeOH): δ 8.62 (s, 1H), 7.95-7.87 (m, 2H), 7.81-7.75 (m, 1H), 7.70-7.59 (m, 3H), 7.39-7.20 (m, 5H), 4.55-4.33 (m, 2H), 4.16-4.04 (m, 1H), 3.35-3.27 (m, 1H), 3.10-3.01 (m, 1H), 2.92-2.83 (m, 1H), 2.61-2.51 (m, 1H), 1.86-1.76 (m, 1H), 1.65-1.46 (m, 3H). MS (EI) for C$_{28}$H$_{29}$N$_7$O$_2$: 496 (MH$^+$).

3-Amino-6-[3-({[(biphenyl-4-ylamino)carbonyl]amino}methyl)phenyl]-N-[(3S)-piperidin-3-yl]pyrazine-2-carboxamide: $^1$H NMR (400 MHz, d4-MeOH): δ 8.74 (s, 1H), 8.03 (s, 1H), 7.92-7.86 (m, 1H), 7.61-7.34 (m, 10H), 7.32-7.25 (m, 1H), 4.61-4.42 (m, 2H), 4.32-4.18 (m, 1H), 3.49-3.41 (m, 1H), 3.30-3.21 (m, 1H), 3.08-2.99 (m, 1H), 2.90-2.78 (m, 1H), 2.07-1.67 (m, 4H). MS (EI) for $C_{30}H_{31}N_7O_2$: 522 (MH$^+$).

3-Amino-6-{3-[({[(2,4-difluorophenyl)amino]carbonyl}amino)methyl]phenyl}-N-[(3S)-piperidin-3-yl]pyrazine-2-carboxamide: $^1$H NMR (400 MHz, d$_4$-MeOH): δ 8.63 (s, 1H), 7.89 (s, 1H), 7.78-7.83 (m, 2H), 7.36 (t, 1H), 7.26-7.28 (m, 1H), 6.88-6.93 (m, 1H), 6.78-6.83 (m, 1H), 4.34-4.43 (m, 2H), 4.13-4.25 (m, 1H), 3.36-3.40 (m, 1H), 3.24-3.27 (m, 1H), 2.97-3.03 (m, 1H), 2.79-2.89 (m, 1H), 1.92-1.98 (m, 2H), 1.71-1.75 (m, 2H). MS (EI) for $C_{24}H_{25}N_7O_2F_2$: 482 (MH$^+$).

3-Amino-N-[(3S)-piperidin-3-yl]-6-[3-({[({2-[(trifluoromethyl)oxy]phenyl}amino)carbonyl]amino}methyl)phenyl]pyrazine-2-carboxamide: $^1$H NMR (400 MHz, d$_4$-MeOH): δ 8.76 (s, 1H), 8.13-8.15 (m, 1H), 7.99 (s, 1H), 7.90-7.92 (d, 1H), 7.46 (t, 1H), 7.36-7.38 (m, 1H), 7.26-7.30 (m, 2H), 7.04-7.09 (m, 1H), 4.44-4.55 (m, 2H), 4.02-4.03 (m, 1H), 3.45-3.48 (m, 1H), 3.07-3.13 (m, 2H), 2.92-2.95 (m, 1H), 1.77-2.05 (m, 4H). MS (E) for $C_{25}H_{26}N_7O_3F_3$: 530 (MH$^+$).

3-Amino-6-(3-{[({[2-(methylthio)phenyl]amino}carbonyl)amino]methyl}phenyl)-N-[(3S)-piperidin-3-yl]pyrazine-2-carboxamide: $^1$H NMR (400 MHz, d$_4$-MeOH): δ 8.64 (s, 1H), 7.93 (s, 1H), 7.80 (d, 1H), 7.69-7.71 (m, 1H), 7.26-7.38 (m, 3H), 7.09-7.14 (m, 1H), 6.96-6.98 (m, 1H), 4.34-4.46 (m, 2H), 4.09-4.13 (m, 1H), 3.31-3.38 (m, 1H), 2.90-2.98 (m, 2H), 2.78-2.83 (m, 1H), 2.80 (s, 3H), 1.84-1.94 (m, 2H), 1.66-1.73 (m, 2H). MS (EI) for $C_{25}H_{29}N_7O_2S$: 492 (MH$^+$).

3-Amino-6-{3-[({[(3-bromo-5-methylphenyl)amino]carbonyl}amino)methyl]phenyl}-N-[(3S)-piperidin-3-yl]pyrazine-2-carboxamide: $^1$H NMR (400 MHz, d$_4$-MeOH): δ 8.73 (s, 1H), 8.01 (s, 1H), 7.89-7.91 (m, 1H), 7.54-7.57 (m, 1H), 7.45 (t, 1H), 7.34-7.37 (m, 2H), 7.26-7.29 (m, 1H), 4.42-4.54 (m, 2H), 4.21-4.30 (m, 1H), 3.45-3.48 (m, 1H), 2.86-3.15 (m, 3H), 2.21 (s, 3H), 1.99-2.02 (m, 2H), 1.78-1.82 (m, 2H). MS (EI) for $C_{25}H_{28}N_7O_2Br$: 539 (MH$^+$).

3-Amino-6-{3-[({[(2-bromophenyl)amino]carbonyl}amino)methyl]phenyl}-N-[(3S)-piperidin-3-yl]pyrazine-2-carboxamide: $^1$H NMR (400 MHz, d$_4$-MeOH): δ 8.64 (s, 1H), 7.92 (s, 1H), 7.81-7.88 (m, 2H), 7.45-7.47 (m, 1H), 7.39 (t, 1H), 7.27-7.29 (m, 1H), 7.18-7.22 (m, 1H), 6.84-6.88 (m, 1H), 4.81 (s, 1H), 4.35-4.46 (m, 2H), 4.12-4.23 (m, 1H), 3.35-3.39 (m, 1H), 2.94-2.99 (m, 1H), 2.78-2.82 (m, 1H), 1.67-1.96 (m, 4H). MS (EI) for $C_{24}H_{26}N_7O_2Br$: 525 (MH$^+$).

3-Amino-N-[(3S)-piperidin-3-yl]-6-[3-({[({4-[(trifluoromethyl)oxy]phenyl}amino)carbonyl]amino}methyl)phenyl]pyrazine-2-carboxamide: $^1$H NMR (400 MHz, d$_4$-MeOH): δ 8.73 (s, 1H), 7.99 (s, 1H), 7.89-7.91 (m, 1H), 7.44-7.49 (m, 3H), 7.40-7.38 (m, 1H), 7.16-7.18 (m, 2H), 4.43-4.55 (m, 2H), 4.21-4.32 (m, 1H), 3.46-3.48 (m, 1H), 3.29-3.34 (m, 1H), 3.05-3.13 (m, 1H), 2.86-2.94 (m, 1H), 1.79-2.03 (m, 4H). MS (EI) for $C_{25}H_{26}N_7O_3F_3$: 530 (MH$^+$).

3-Amino-N-[(3S)-piperidin-3-yl]-6-(3-{[({[4-(trifluoromethyl)phenyl]amino}carbonyl)amino]methyl}phenyl)pyrazine-2-carboxamide: $^1$H NMR (400 MHz, d$_4$-MeOH): δ 8.73 (s, 1H), 8.00 (s, 1H), 7.89-7.91 (m, 1H), 7.53-7.60 (m, 4H), 7.44-7.47 (m, 2H), 7.36-7.38 (m, 1H), 4.44-4.56 (m, 2H), 4.22-4.33 (m, 1H), 3.43-3.50 (m, 1H), 3.04-3.12 (m, 2H), 2.83-2.94 (m, 1H), 1.73-2.08 (m, 4H). MS (EI) for $C_{25}H_{26}N_7O_2F_3$: 514 (MH$^+$).

3-Amino-6-[3-({[(2,3-dihydro-1,4-benzodioxin-6-ylamino)carbonyl]amino}methyl)phenyl]-N-[(3S)-piperidin-3-yl]pyrazine-2-carboxamide: $^1$H NMR (400 MHz, d$_4$-MeOH): δ 8.73 (s, 1H), 8.01 (s, 1H), 7.90-7.85 (m, 1H), 7.47-7.41 (m, 1H), 7.37-7.32 (m, 1H), 7.02-6.98 (m, 1H), 6.73-6.70 (m, 2H), 4.55-4.37 (m, 2H), 4.33-4.22 (m, 1H), 4.23-4.15 (m, 4H), 3.50-3.43 (m, 1H), 3.36-3.30 (m, 1H), 3.11-3.02 (m, 1H), 2.96-2.85 (m, 1H), 2.09-1.71 (m, 4H). MS (EI) for $C_{26}H_{29}N_7O_4$: 504 (MH$^+$).

3-Amino-6-[3-({[(1,3-benzodioxol-5-ylamino)carbonyl]amino}methyl)phenyl]-N-[(3S)-piperidin-3-yl]pyrazine-2-carboxamide: $^1$H NMR (400 MHz, d$_4$-MeOH): δ 8.71 (s, 1H), 8.01 (s, 1H), 7.90-7.85 (m, 1H), 7.47-7.41 (m, 1H), 7.37-7.32 (m, 1H), 7.10-7.07 (m, 1H), 6.74-6.64 (m, 2H), 5.90 (s, 2H), 4.54-4.38 (m, 2H), 4.33-4.22 (m, 1H), 3.50-3.43 (m, 1H), 3.37-3.31 (m, 1H), 3.12-3.03 (m, 1H), 2.96-2.86 (m, 1H), 2.08-1.96 (m, 2H), 1.89-1.72 (m, 2H). MS (EI) for $C_{25}H_{27}N_7O_4$: 490 (MH$^+$).

3-Amino-6-(3-{[({[4-(methyloxy)phenyl]amino}carbonyl)amino]methyl}phenyl)-N-[(3S)-piperidin-3-yl]pyrazine-2-carboxamide: $^1$H NMR (400 MHz, d$_4$-MeOH): δ 8.72 (s, 1H), 8.00 (s, 1H), 7.91-7.86 (m, 1H), 7.47-7.41 (m, 1H), 7.38-7.33 (m, 1H), 7.29-7.24 (m, 2H), 6.88-6.82 (m, 2H), 4.55-4.39 (m, 2H), 4.33-4.19 (m, 1H), 3.75 (s, 3H), 3.50-3.41 (m, 1H), 3.34-3.26 (m, 1H), 3.10-3.00 (m, 1H), 2.93-2.82 (m, 1H), 2.08-1.91 (m, 2H), 1.89-1.78 (m, 2H). MS (EI) for $C_{25}H_{29}N_7O_3$: 476 (MH$^+$).

3-Amino-6-{3-[({[(4-fluorophenyl)amino]carbonyl}amino)methyl]phenyl}-N-[(3S)-piperidin-3-yl]pyrazine-2-carboxamide: $^1$H NMR (400 MHz, d$_4$-MeOH): δ 8.72 (s, 1H), 7.99 (s, 1H), 7.92-7.87 (m, 1H), 7.49-7.41 (m, 1H), 7.40-7.33 (m, 3H), 7.04-6.96 (m, 2H), 4.55-4.44 (m, 2H), 4.32-4.22 (m, 1H), 3.50-3.43 (m, 1H), 3.36-3.29 (m, 1H), 3.12-3.03 (m, 1H), 2.96-2.86 (m, 1H), 2.08-1.95 (m, 2H), 1.90-1.73 (m, 2H). MS (EI) for $C_4H_{26}N_7O_2F$: 464 (MH$^+$).

3-Amino-6-(3-{[({[4-(dimethylamino)phenyl]amino}carbonyl)amino]methyl}phenyl)-N-[(3S)-piperidin-3-yl]pyrazine-2-carboxamide: $^1$H NMR (400 MHz, d$_4$-MeOH): δ 8.72 (s, 1H), 7.99-7.90 (m, 2H), 7.65-7.58 (m, 2EI), 7.54-7.42 (m, 3H), 7.39-7.34 (m, 1H), 4.49 (s, 2H), 4.36-4.24 (m, 1H), 3.53-3.44 (m, 1H), 3.39-3.30 (m, 1H), 3.15-3.05 (m, 1H), 3.04-2.90 (m, 1H), 2.15-1.97 (m, 2H), 1.95-1.82 (m, 2H). MS (EI) for $C_{26}H_{32}N_8O_2$: 489 (MH$^+$).

3-Amino-6-(3-{[[(2,3-dihydro-1-benzofuran-5-ylsulfonyl)amino]methyl}phenyl)-N-[(3S)-piperidin-3-yl]pyrazine-2-carboxamide: $^1$H NMR (400 MHz, d$_4$-MeOH): δ 8.65 (s, 1H), 7.93 (s, 1H), 7.89-7.83 (m, 1H), 7.63-7.55 (m, 2H), 7.39-7.33 (m, 1H), 7.24-7.19 (m, 1H), 6.77-6.72 (m, 1H), 4.62-4.53 (m, 2H), 4.39-4.24 (m, 1H), 4.15 (s, 2H), 3.54-3.46 (m, 1H), 3.39-3.31 (m, 1H), 3.21-3.10 (m, 3H), 3.06-2.92 (m, 1H), 2.19-2.03 (m, 2H), 1.96-1.81 (m, 2H). MS (EI) for $C_{25}H_{28}N_6O_4S$: 509 (MH$^+$).

3-Amino-6-(3-{[[(3,4-dihydro-2H-1,5-benzodioxepin-7-ylsulfonyl)amino]methyl}phenyl)-N-[(3S)-piperidin-3-yl]pyrazine-2-carboxamide: $^1$H NMR (400 MHz, d$_4$-MeOH): δ 8.67 (s, 1H), 7.95 (s, 1H), 7.88-7.83 (m, 1H), 7.39-7.32 (m, 3H), 7.24-7.19 (m, 1H), 6.98-6.93 (m, 1H), 4.38-4.27 (m, 1H), 4.21-4.11 (m, 6H), 3.55-3.46 (m, 1H), 3.40-3.31 (m, 1H), 3.19-3.08 (m, 1H), 3.06-2.94 (m, 1H), 2.22-2.02 (m, 4H), 1.98-1.81 (m, 2H). MS (EI) for $C_{26}H_{30}N_6O_5S$: 539 (MH$^+$).

3-Amino-N-[(3S)-piperidin-3-yl]-6-(3-{[(quinolin-7-ylsulfonyl)amino]methyl}phenyl)pyrazine-2-carboxamide: $^1$H NMR (400 MHz, d$_4$-MeOH): δ 8.98-8.95 (m, 1H), 8.46 (s, 1H), 8.28-8.23 (m, 2H), 8.04-7.99 (m, 1H), 7.75 (s, 1H), 7.63-7.46 (m, 3H), 7.10-6.98 (m, 2H), 4.39-4.26 (m, 1H), 4.26 (s, 2H), 3.55-3.48 (m, 1H), 3.39-3.31 (m, 1H), 3.19-3.10 (m, 1H), 3.04-2.92 (m, 1H), 2.21-2.02 (m, 2H), 2.00-1.82 (m, 2H). MS (EI) for $C_{26}H_{27}N_7O_3S$: 518 (MH$^+$).

3-Amino-N-[(3S)-piperidin-3-yl]-6-{3-[({[2-(trifluoromethyl)phenyl]sulfonyl}amino)methyl]phenyl}pyrazine-2-carboxamide: $^1$H NMR (400 MHz, $d_4$-MeOH): δ 8.57 (s, 1H), 8.43 (d, 1H), 8.02-8.04 (m, 1H), 7.98 (s, 1H), 7.74-7.79 (m, 2H), 7.60-7.62 (m, 2H), 7.24-7.28 (m, 2H), 7.14 (d, 1H), 4.22 (s, 3H), 3.39-3.44 (m, 1H), 3.01-3.06 (m, 2H), 2.82-2.92 (m, 1H), 1.99-2.18 (m, 2H), 1.80-1.82 (m, 2H). MS (EI) for $C_{24}H_{25}N_6O_3F_3S$: 535 (MH$^+$).

3-Amino-N-[(3S)-piperidin-3-yl]-6-(3-{[({4-[(trifluoromethyl)oxy]phenyl}sulfonyl)amino]methyl}phenyl)pyrazine-2-carboxamide: $^1$H NMR (400 MHz, $d_4$-MeOH): δ 8.58 (s, 1H), 8.46 (d, 1H), 7.89 (s, 1H), 7.76-7.84 (m, 2H), 7.24-7.30 (m, 3H), 7.12 (d, 1H), 4.15-4.27 (m, 1H), 4.13 (s, 2H), 3.39-3.43 (m, 1H), 3.01-3.07 (m, 2H), 2.91-2.93 (m, 1H), 1.94-2.09 (m, 2H), 1.74-1.85 (m, 2H). MS (EI) for $C_{24}H_{25}N_6O_4F_3S$: 551 (MH$^+$).

3-Amino-N-[(3S)-piperidin-3-yl]-6-(3-{[({2-[(trifluoromethyl)oxy]phenyl}sulfonyl)amino]methyl}phenyl)pyrazine-2-carboxamide: $^1$H NMR (400 MHz, $d_4$-MeOH): δ 8.67 (s, 1H), 8.02 (s, 1H), 7.94-8.02 (m, 1H), 7.83-7.85 (m, 1H), 7.60-7.64 (m, 1H), 7.38-7.41 (m, 2H), 7.31-7.35 (m, 1H), 7.21-7.23 (m, 1H), 4.29 (s, 3H), 3.47-3.53 (m, 1H), 3.11-3.16 (m, 2H), 2.96-3.10 (m, 1H), 1.84-2.38 (m, 4H). MS (EI) for $C_{24}H_{25}N_6O_4F_3S$: 551 (MH$^+$).

3-Amino-N-[(3S)-piperidin-3-yl]-6-{3-[({[4-(trifluoromethyl)phenyl]sulfonyl}amino)methyl]phenyl}pyrazine-2-carboxamide: $^1$H NMR (400 MHz, $d_4$-MeOH): δ 8.56 (s, 1H), 8.88 (s, 2H), 7.84 (m, 1H), 7.76 (d, 1H), 8.67 (d, 2H), 7.25 (t, 1H), 7.12 (d, 1H), 4.18-4.27 (m, 1H), 4.14 (s, 2H), 3.38-3.41 (m, 1H), 3.01-3.06 (m, 2H), 2.87-2.92 (m, 1H), 1.80-2.06 (m, 4H). MS (EI) for $C_{24}H_{25}N_6O_3F_3S$: 535 (MH$^+$).

3-Amino-6-(3-{[(2,3-dihydro-1,4-benzodioxin-6-ylsulfonyl)amino]methyl}phenyl)-N-[(3S)-piperidin-3-yl]pyrazine-2-carboxamide: $^1$H NMR (400 MHz, $d_4$-MeOH): δ 8.67 (s, 1H), 7.96 (s, 1H), 7.88-7.84 (m, 1H), 7.39-7.33 (m, 1H), 7.30-7.25 (m, 2H), 7.24-7.19 (m, 1H), 6.90-6.86 (m, 1H), 4.38-4.27 (m, 1H), 4.26-4.19 (m, 4H), 4.16 (s, 2H), 3.54-3.46 (m, 1H), 3.39-3.31 (m, 1H), 3.18-3.10 (m, 1H), 3.05-2.95 (m, 1H), 2.20-2.05 (m, 2H), 1.97-1.83 (m, 2H). MS (EI) for $C_{25}H_{28}N_6O_5S$: 524 (MH$^+$).

3-Amino-N-[(3S)-piperidin-3-yl]-6-(3-{[(2-thienylsulfonyl)amino]methyl}phenyl)pyrazine-2-carboxamide: $^1$H NMR (400 MHz, $d_4$-MeOH): δ 8.70 (s, 1H), 8.07 (s, 1H), 7.91-7.86 (m, 1H), 7.77-7.74 (m, 1H), 7.63-7.59 (m, 1H), 7.42-7.36 (m, 1H), 7.28-7.23 (m, 1H), 7.14-7.10 (m, 1H), 4.37-4.25 (m, 1H), 4.23 (s, 2H), 3.54-3.45 (m, 1H), 3.39-3.31 (m, 1H), 3.19-3.08 (m, 1H), 3.05-2.94 (m, 1H), 2.19-2.02 (m, 2H), 1.97-1.81 (m, 2H). MS (EI) for $C_{21}H_{24}N_6O_3S_2$: 473 (MH$^+$).

3-Amino-N-[(3S)-piperidin-3-yl]-6-(3-{[((3-thienylsulfonyl)amino]methyl}phenyl)pyrazine-2-carboxamide: $^1$H NMR (400 MHz, $d_4$-MeOH): δ8.70 (s, 1H), 8.09-8.03 (m, 2H), 7.91-7.86 (m, 1H), 7.60-7.55 (m, 1H), 7.41-7.33 (m, 2H), 7.27-7.21 (m, 1H), 4.37-4.25 (m, 1H), 4.20 (s, 2H), 3.54-3.45 (m, 1H), 3.39-3.31 (m, 1H), 3.19-3.09 (m, 1H), 3.05-2.93 (m, 1H), 2.19-2.02 (m, 2), 1.98-1.81 (m, 2H). MS (EI) for $C_{21}H_{24}N_6O_3S_2$: 473 (MH$^+$).

3-Amino-6-[3-({[(4-chlorophenyl)sulfonyl]amino}methyl)phenyl]-N-[(3S)-piperidin-3-yl]pyrazine-2-carboxamide: $^1$H NMR (400 MHz, $d_4$-MeOH): δ 8.66 (s, 1H), 7.94 (s, 1H), 7.90-7.85 (m, 1H), 7.81-7.75 (m, 2H), 7.50-7.45 (m, 2H), 7.39-7.33 (m, 1H), 7.25-7.20 (m, 1H), 4.38-4.25 (m, 1H), 4.20 (s, 2H), 3.55-3.46 (m, 1H), 3.39-3.31 (m, 1H), 3.18-3.08 (m, 1H), 3.05-2.93 (m, 1H), 2.20-2.01 (m, 2H), 1.98-1.81 (m, 2H). MS (EI) for $C_{23}H_{25}N_6O_3SCl$: 501 (MH$^+$).

N-[(2,4-Dichlorophenyl)methyl]-N'-[(1S)-2,3-dihydro-1H-inden-1-yl]benzene-1,3-dicarboxamide: $^1$H NMR (400 MHz, $d_6$-DMSO): δ 9.20 (t, J=6.0 Hz, 1H), 8.93 (d, J=8.4 Hz, 1H), 8.43 (m, 1H), 8.05 (m, 2H), 7.64 (m, 1H), 7.59 (m, 1H), 7.42 (m, 2H), 7.25 (m, 4H), 5.59 (m, 1H), 4.53 (m, 2H), 3.00 (m, 1H), 2.86 (m, 1H), 2.47 (m, 1H), 2.01 (m, 1H). MS (EI) for $C_{24}H_{20}Cl_2N_2O_2$: 439 (MH$^+$).

Example 64

3-Amino-6-{3-[({[3-fluoro-5-(trifluoromethyl)phenyl]methyl}amino)carbonyl]phenyl}-N-[(3S)-piperidin-3-yl]pyrazine-2-carboxamide To a solution of 3-[5-amino-6-({(3S)-1-(tert-butoxycarbonyl)piperidine-3-yl]amino}carbonyl)pyrazin-2-yl]benzoic acid (80 mg, 0.18 mmol) in dry dichloromethane (1.0 mL) were added 1-ethyl-(3-dimethylaminopropyl)carbodiimide hydrochloride (EDC, 48 mg, 0.25 mmol) and 1-hydroxybenzotriazole (HOBT, 34 mg, 0.25 mmol). The reaction mixture was stirred for 10-15 min at room temperature. A solution of 3-fluoro-4-(triflouromethyl)benzylamine (52 mg, 0.27 mmol) in dichloromethane (1 mL) was added and stirring continued for 2-3 h. Reaction was diluted with ethyl acetate (150 mL), washed with saturated aqueous sodium bicarbonate (40 mL) and saturated aqueous sodium chloride (50 mL). Dried over anhydrous magnesium sulfate, filtered, concentrated, and purification on silica (7:3 hexanes/ethyl acetate) afforded the amide product. MS (EI) for $C_{28}H_{28}N_6O_2F_4$: 517 [(M-boc)H$^+$].

To a solution of the above amide in methanol (2 mL) was added 4.0 N hydrochloric acid (1,4-dioxane solution, 1 mL) and the reaction stirred until the deprotection (removal of Boc-protecting group) was completed as monitored by thin layer chromatography. The excess reagent and solvent was removed at reduced pressure to give a solid product which was washed further with ethyl acetate (50 mL) to afford the hydrochloric acid salt of 3-amino-6-{3-[({[3-fluoro-5-(trifluoromethyl)phenyl]methyl}amino)carbonyl]phenyl}-N-[(3S)-piperidin-3-yl]pyrazine-2-carboxamide (16 mg, 15% yield) as yellow solid. $^1$H NMR (400 MHz, $d_6$-DMSO): 9.90 (s, 1H), 9.25 (br s, 1H), 9.02 (m, 3H), 8.80 (s, 1H), 8.54 (d, 1H), 7.90 (d, 1H), 7.60 (m, 4H), 4.60 (br s, 2H), 4.30 (m, 1H), 3.20 (m, 3H), 2.70 (m, 1H), 1.92 (m, 4H); MS (EI) for $C_{25}H_{24}N_6O_2F_4$: 517 (MH$^+$).

Using the same or analogous synthetic techniques and/or substituting with alternative reagents as described above, the following compounds of the invention were prepared:

3-amino-6-[3-({[(3,4-dichlorophenyl)methyl]amino}carbonyl)phenyl]-N-[(3S)-piperidin-3-yl]pyrazine-2-carboxamide: $^1$H NMR (400 MHz, $d_6$-DMSO): 9.80 (t, 1H), 9.20 (br s, 1H), 8.93 (m, 3H), 8.70 (s, 1H), 8.58 (d, 1H), 7.90 (d, 1H), 7.60 (m, 3H), 7.40 (d, 1H), 4.50 (d, 2H), 4.30 (m, 1H), 3.20 (m, 3H), 2.80 (m, 1H), 1.90 (m, 4H); MS (EI) for $C_{24}H_{24}N_6O_2Cl_2$: 499, 501 (MH$^+$).

3-amino-6-[3-({[(5-chloro-2-methylphenyl)methyl]amino}carbonyl)phenyl]-N-[(3S)-piperidin-3-yl]pyrazine-2-carboxamide: $^1$H NMR (400 MHz, $d_6$-DMSO): 9.45 (t, 1H), 9.20 (br s, 1H), 9.01 (m, 3H), 8.70 (s, 1H), 8.35 (d, 1H), 7.90 (d, 1H), 7.30 (s, 1H), 7.20 (s, 2H), 4.50 (m, 2H), 4.30 (m, 1H), 3.20 (m, 3H), 2.70 (m, 1H), 2.38 (s, 3H), 1.90 (m, 4H); MS (EI) for $C_{25}H_{27}N_6O_2Cl$: 479, 480 (MH$^+$).

3-amino-6-{3-[({[2-chloro-5-(trifluoromethyl)phenyl]methyl}amino)carbonyl]phenyl}-N-[(3S)-piperidin-3-yl]pyrazine-2-carboxamide: $^1$H NMR (400 MHz, $d_6$-DMSO): 9.85 (t, 1H), 9.25 (br s, 1H), 9.02 (m, 3H), 8.80 (s, 1H), 8.40 (d, 1H), 7.90 (d, 1H), 7.70 (m, 3H), 7.60 (t, 1H), 4.64 (br s, 2H), 4.30 (m, 1H), 3.25 (m, 3H), 2.70 (m, 1H), 1.92 (m, 4H); MS (EI) for $C_{25}H_{24}N_6O_2F_3Cl$: 533, 534 (MH$^+$).

3-amino-6-[3-({[(2-chloro-6-fluorophenyl)methyl]amino}carbonyl)phenyl]-N-[(3S)-piperidin-3-yl]pyrazine-2-carboxamide: $^1$H NMR (400 MHz, $d_6$-DMSO): 9.30 (br s, 1H), 9.00 (br s, 1H), 9.01 (t, 1H), 8.95 (s, 1H), 8.80 (d, 1H), 8.73 (s, 1H), 8.30 (d, 1H), 7.85 (d, 1H), 7.60 (t, 1H), 7.40 (m, 2H), 7.30 (t, 1H), 4.60 (s, 2H), 4.45 (m, 1H), 3.30 (m, 1H), 3.12 (m, 1H), 2.70 (m, 1H), 1.92 (m, 4H); MS (EI) for $C_{24}H_{24}N_6O_2FCl$: 483 (MH$^+$).

3-amino-6-[3-({[(3-chloro-2-fluorophenyl)methyl]amino}carbonyl)phenyl]-N-[(3S)-piperidin-3-yl]pyrazine-2-carboxamide: $^1$H NMR (400 MHz, $d_6$-DMSO): 9.80 (t, 1H), 9.30 (br s, 1H), 9.02 (br s, 1H), 8.92 (m, 2H), 8.70 (s, 1H), 8.30 (d, 1H), 7.90 (d, 1H), 7.60 (t, 1H), 7.50 (m, 2H), 7.20 (t, 1H), 4.60 (br s, 2H), 4.30 (m, 1H), 3.20 (m, 3H), 2.90 (m, 1H), 1.92 (m, 4H); MS (EI) for $C_{24}H_{24}N_6O_2FCl$: 483 (MH$^+$).

3-amino-6-{3-[({[2-fluoro-5-(trifluoromethyl)phenyl]methyl}amino)carbonyl]phenyl}-N-[(3S)-piperidin-3-yl]pyrazine-2-carboxamide: $^1$H NMR (400 MHz, $d_6$-DMSO): 9.65 (t, 1H), 9.20 (br s, 1H), 9.00 (br s, 1H), 8.90 (m, 2H), 8.70 (s, 1H), 8.30 (d, 1H), 7.90 (d, 1H), 7.80 (m, 1H), 7.78 (m, 1H), 7.58 (t, 1H), 7.45 (t, 1H), 4.60 (br s, 2H), 4.32 (m, 1H), 3.20 (m, 3H), 2.70 (m, 1H), 1.92 (m, 4H); MS (EI) for $C_{25}H_{24}N_6O_2F_4$: 517 (MH$^+$).

Example 65

3-amino-6-[3-({[(3-chloro-2,6-difluorophenyl)methyl]amino}carbonyl)phenyl]-N-[(3S)-piperidin-3-yl]pyrazine-2-carboxamide To a solution of tert-butyl (3S)-3-[({3-amino-6-[3-(methoxycarbonyl)phenyl]pyrazin-2-yl}carbonyl)amino]piperidine-1-carboxylate (100 mg, 0.22 mmol) in tetrahydrofuran/water (4:1, 1.5 mL) was added 0.5 N aqueous lithium hydroxide (0.5 mL, 0.55 mmol) and the reaction was stirred at room temperature overnight. Reaction was diluted with dichloromethane (4 mL) and treated with 0.5 N aqueous hydrochloric acid (0.5 mL). The aqueous layer was discarded. The crude acid in dichloromethane solution was treated with 1-ethyl-(3-dimethylaminopropyl)carbodiimide hydrochloride (EDCI, 63 mg, 0.33 mmol) and 1-hydroxybenzotriazole (HOBT, 45 mg, 0.33 mmol). The reaction was stirred for 10-15 min and then a solution of 5-chloro-1,6-difluorobenzylamine (46 mg, 0.26 mmol) in dichloromethane (0.5 mL) was added. The reaction was stirred for 2-3 h and diluted with ethyl acetate (150 mL). The organic layer was washed with saturated aqueous sodium bicarbonate (40 mL), saturated aqueous sodium chloride (50 mL), and dried over anhydrous magnesium sulfate. Filtration, concentration, and purification on silica (3:7 hexanes/ethyl acetate) afforded the boc-protected intermediate. MS (EI) for $C_{24}H_{23}N_6O_2F_2Cl$: 501, 503 [(M-boc)H$^+$].

To a solution of the above intermediate in methanol (2 mL) was added 4.0 N hydrochloric acid (1,4-dioxane solution, 1 mL) and the reaction stirred until the deprotection was completed as monitored by thin layer chromatography. The excess reagent and solvent was removed at reduced pressure to give a solid product which was washed further with ethyl acetate (50 mL) to afford the hydrochloric acid salt of 3-amino-6-[3-({[(3-chloro-2,6-difluorophenyl)methyl]amino}carbonyl)phenyl]-N-[(3S)-piperidin-3-yl]pyrazine-2-carboxamide (76 mg, 69% yield) as yellow solid $^1$H NMR (400 MHz, $d_6$-DMSO): 9.26 (m, 2H), 9.10 (m, 1H), 8.90 (s, 1H), 8.80 (d, 1H), 8.60 (s, 1H), 8.35 (d, 1H), 7.60 (m, 2H), 7.20 (t, 1H), 7.20 (t, 1H), 4.60 (br s, 2H), 4.30 (m, 1H), 3.20 (m, 3H), 3.10 (m, 1H), 2.80 (m, 1H), 1.90 (m, 2H), 1.80 (m, 2H); MS (EI) for $C_{24}H_{23}N_6O_2F_2Cl$: 501, 503 (MH$^+$).

Using the same or analogous synthetic techniques and/or substituting with alternative reagents as described above, the following compounds of the invention were prepared:

3-amino-6-{3-[({[2-fluoro-4-(trifluoromethyl)phenyl]methyl}amino)carbonyl]phenyl}-N-[(3S)-piperidin-3-yl]pyrazine-2-carboxamide: $^1$H NMR (400 MHz, $d_6$-DMSO): 9.70 (t, 1H), 9.30 (br s, 1H), 9.10 (br s, 1H), 9.01 (m, 2H), 8.80 (s, 1H), 8.36 (d, 1H), 7.90 (d, 1H), 7.60 (m, 6H), 4.60 (br s, 2H), 4.30 (m, 1H), 3.20 (m, 3H), 2.78 (m, 1H), 1.90 (m, 4H); MS (EI) for $C_{25}H_{24}N_6O_2F_4$: 517 (MH$^+$).

3-amino-6-[3-({[(2-chloro-4-fluorophenyl)methyl]amino}carbonyl)phenyl]-N-[(3S)-piperidin-3-yl]pyrazine-2-carboxamide: $^1$H NMR (400 MHz, $d_6$-DMSO): 9.54 (m, 1H), 9.25 (br s, 1H), 9.02 (m, 3H), 8.74 (s, 1H), 8.34 (d, 1H), 7.90 (d, 1H), 7.50 (m, 4H), 7.20 (t, 1H), 4.58 (br s, 2H), 4.30 (m, 1H), 3.20 (m, 3H), 2.75 (m, 1H), 1.92 (m, 4H); MS (EI) for $C_{24}H_{24}N_6O_2F_2Cl$: 483, 485 (MH$^+$).

3-amino-6-[3-({[(2,3-dichlorophenyl)methyl]amino}carbonyl)phenyl]-N-[(3S)-piperidin-3-yl]pyrazine-2-carboxamide: $^1$H NMR (400 MHz, d6-DMSO): 9.80 (t, 1H), 9.20 (br s, 1H), 9.01 (m, 3H), 8.74 (s, 1H), 8.30 (d, 1H), 7.90 (d, 1H), 7.60 (m, 2H), 7.40 (m, 2H), 4.60 (d, 2H), 4.30 (m, 1H), 3.20 (m, 3H), 2.74 (m, 1H), 1.92 (m, 4H); MS (EI) for $C_{24}H_{24}N_6O_2Cl_2$: 499, 500 (MH$^+$).

3-amino-N-[(3S)-piperidin-3-yl]-6-[3-({[(2,3,6-trifluorophenyl)methyl]amino}carbonyl)phenyl]pyrazine-2-carboxamide: $^1$H NMR (400 MHz, d6-DMSO): 9.23 (m, 2H), 9.02 (br s, 1H), 8.90 (s, 1H), 8.80 (d, 1H), 8.32 (d, 1H), 7.60 (t, 1H), 7.50 (m, 1H), 7.20 (m, 1H), 4.60 (d, 2H), 4.34 (m, 1H), 3.30 (m, 2H), 3.10 (m, 1H), 2.80 (m, 1H), 1.90 (m, 2H), 1.80 (m, 2H); MS (EI) for $C_{24}H_{23}N_6O_2F_3$: 485 (MH$^+$).

3-amino-6-{3-[({[4-chloro-3-(trifluoromethyl)phenyl]methyl}amino)carbonyl]phenyl}-N-[(3S)-piperidin-3-yl]pyrazine-2-carboxamide: $^1$H NMR (400 MHz, $d_6$-DMSO): 9.80 (m, 2H), 9.30 (br s, 1H), 9.04 (m, 3H), 8.74 (s, 1H), 8.30 (d, 1H), 7.90 (m, 2H), 7.70 (s, 2H), 7.60 (t, 1H), 4.60 (d, 2H), 4.30 (m, 1H), 3.20 (m, 3H), 2.80 (m, 1H), 1.90 (m, 4H); MS (EI) for $C_{25}H_{24}N_6O_2F_3Cl$: 533, 534 (MH$^+$).

3-amino-6-[3-({[(3-chloro-4-fluorophenyl)methyl]amino}carbonyl)phenyl]-N-[(3S)-piperidin-3-yl]pyrazine-2-carboxamide: $^1$H NMR (400 MHz, $d_6$-DMSO): 9.82 (m, 1H), 9.30 (br s, 1H), 9.02 (m, 3H), 8.78 (s, 1H), 8.50 (d, 1H), 7.90 (m, 1H), 7.70 (s, 2H), 7.60 (m, 2H), 7.40 (m, 2H), 4.50 (d, 2H), 4.30 (m, 1H), 3.20 (m, 3H), 2.80 (m, 1H), 1.92 (m, 4H); MS (EI) for $C_{24}H_{24}N_6O_2FCl$: 483, 485 (MH$^+$).

3-amino-6-[3-({[(2,6-difluorophenyl)methyl]amino}carbonyl)phenyl]-N-[(3S)-piperidin-3-yl]pyrazine-2-carboxamide: $^1$H NMR (400 MHz, $d_6$-DMSO): 9.20 (br s, 1H), 9.10 (m, 1H), 8.95 (m, 2H), 8.80 (d, 1H), 8.74 (s, 1H), 8.30 (d, 1H), 7.84 (d, 1H), 7.60 (t, 1H), 7.40 (m, 1H), 7.10 (m, 2H), 4.60 (d, 2H), 4.30 (m, 1H), 3.30 (m, 2H), 3.06 (m, 1H), 2.78 (m, 1H), 1.90 (m, 2H), 1.74 (m, 2H); MS (EI) for $C_{24}H_{24}N_6O_2F$: 467 (MH$^+$).

3-amino-6-[3-({[(3,4-difluorophenyl)methyl]amino}carbonyl)phenyl]-N-[(3S)-piperidin-3-yl]pyrazine-2-carboxamide: $^1$H NMR (400 MHz, $d_6$-DMSO): 9.80 (m, 1H), 9.20 (br s, 1H), 8.99 (m, 3H), 8.70 (s, 1H), 8.30 (d, 1H), 7.90 (d, 1H), 7.60 (t, 1H), 7.40 (m, 2H), 7.20 (br s, 1H), 4.60 (br s, 2H), 4.30 (m, 1H), 3.20 (m, 3H), 2.80 (m, 1H), 1.92 (m, 4H); MS (EI) for $C_{24}H_{24}N_6O_2F_2$: 467 (MH$^+$).

3-amino-6-[3-({[(6-chloro-2-fluoro-3-methylphenyl)methyl]amino}carbonyl)phenyl]-N-[(3S)-piperidin-3-yl]pyrazine-2-carboxamide: $^1$H NMR (400 MHz, $d_6$-DMSO): 9.20 (br s, 1H), 8.90 (m, 3H), 8.75 (m, 1H), 8.50 (s, 1H), 8.30 (d, 1H), 7.86 (d, 1H), 7.60 (t, 1H), 7.40 (m, 2H), 7.20 (t, 1H), 4.60

(br s, 2H), 4.30 (m, 1H), 3.30 (m, 2H), 3.02 (m, 1H), 2.80 (m, 1H), 2.30 (s, 3H), 1.92 (m, 2H), 1.80 (m, 2H); MS (EI) for $C_{25}H_{26}N_6O_2F_1Cl$: 497,499 (MH$^+$).

3-amino-6-[3-({[(2-chloro-6-fluoro-3-methylphenyl)methyl]amino}carbonyl)phenyl]-N-[(3S)-piperidin-3-yl]pyrazine-2-carboxamide: $^1$H NMR (400 MHz, d$_6$-DMSO): 9.30 (m, 1H), 9.10 (m, 1H), 8.90 (m, 2H), 8.80 (d, 1H), 8.70 (s, 1H), 8.30 (d, 1H), 7.84 (d, 1H), 7.60 (t, 1H), 7.30 (m, 2H), 4.60 (br s, 2H), 4.30 (m, 1H), 3.30 (m, 2H), 3.02 (m, 1H), 2.80 (m, 1H), 2.30 (s, 3H), 1.92 (m, 2H), 1.74 (m, 2H); MS (EI) for $C_{25}H_{26}N_6O_2F_1Cl$: 497, 499 (MH$^+$).

3-amino-6-[3-({[(5-fluoro-2-methylphenyl)methyl]amino}carbonyl)phenyl]-N-[(3S)-piperidin-3-yl]pyrazine-2-carboxamide: $^1$H NMR (400 MHz, d$_6$-DMSO): 9.40 (m, 1H), 9.20 (br s, 1H), 8.94 (s, 1H), 8.85 (d, 1H), 8.72 (s, 1H), 8.57 (d, 1H), 7.90 (d, 1H), 7.60 (t, 1H), 7.24 (m, 1H), 7.15 (m, 1H), 7.02 (m, 1H), 4.50 (br s, 2H), 4.30 (m, 1H), 3.20 (m, 3H), 2.80 (m, 1H), 2.30 (s, 3H), 1.90 (m, 4H); MS (EI) for $C_{25}H_{27}N_6O_2F$: 463 (MH$^+$).

3-amino-6-[3-({[(3-chloro-2-methylphenyl)methyl]amino}carbonyl)phenyl]-N-[(3S)-piperidin-3-yl]pyrazine-2-carboxamide: $^1$H NMR (400 MHz, d$_6$-DMSO): 9.50 (m, 1H), 9.10 (br s, 1H), 8.94 (s, 1H), 8.90 (d, 1H), 8.70 (s, 1H), 8.40 (d, 1H), 7.90 (d, 1H), 7.60 (t, 1H), 7.40 (s, 1H), 7.25 (m, 2H), 4.50 (br s, 2H), 4.30 (m, 1H), 3.20 (m, 3H), 2.80 (m, 1H), 2.30 (s, 3H), 1.90 (m, 4H); MS (EI) for $C_{25}H_{27}N_6O_2FCl$: 479, 481 (MH$^+$).

3-amino-6-{3-[({[2,6-bis(methyloxy)phenyl]methyl}amino)carbonyl]phenyl}-N-[(3S)-piperidin-3-yl]pyrazine-2-carboxamide: $^1$H NMR (400 MHz, d$_6$-DMSO): 9.30 (br s, 1H), 9.10 (br s, 1H), 8.90 (s, 1H), 8.84 (d, 1H), 8.63 (s, 1H), 8.30 (m, 2H), 7.84 (d, 1H), 7.60 (t, 1H), 7.30 (t, 1H), 6.70 (d, 2H), 4.45 (br s, 2H), 4.20 (m, 1H), 3.80 (s, 6H), 3.20 (m, 2H), 2.90 (m, 1H), 2.70 (s, 1H), 1.80 (m, 4H); MS (EI) for $C_{26}H_{30}N_6O_4$: 491 (MH$^+$).

3-amino-6-[3-({[(3-bromo-4-fluorophenyl)methyl]amino}carbonyl)phenyl]-N-[(3S)-piperidin-3-yl]pyrazine-2-carboxamide: $^1$H NMR (400 MHz, d$_6$-DMSO): 9.80 (m, 1H), 9.30 (br s, 1H), 9.01 (m, 3H), 8.85 (s, 1H), 8.34 (d, 1H), 7.90 (d, 1H), 7.70 (d, 1H), 7.60 (t, 1H), 7.40 (m, 2H), 4.50 (br s, 2H), 4.30 (m, 1H), 3.20 (m, 3H), 2.80 (m, 1H), 1.90 (m, 4H); MS (EI) for $C_{24}H_{24}N_6O_2FBr$: 427, 429 (MH$^+$).

3-amino-6-[3-([{(3-bromo-5-fluorophenyl)methyl]amino)carbonyl]phenyl]-N-[(3S)-piperidin-3-yl]pyrazine-2-carboxamide: $^1$H NMR (400 MHz, d$_6$-DMSO): 9.50 (m, 1H), 9.20 (br s, 1H), 8.98 (m, 2H), 8.70 (s, 1H), 8.36 (d, 1H), 7.90 (d, 1H), 7.60 (m, 3H), 7.20 (t, 1H), 4.50 (br s, 2H), 4.30 (m, 1H), 3.20 (m, 3H), 2.70 (m, 1H), 1.90 (m, 4H); MS (EI) for $C_{24}H_{24}N_6O_2FBr$: 527, 529 (MH$^+$).

3-amino-6-{3-[({[(3-methyloxy)phenyl]methyl}amino)carbonyl]phenyl}-N-[(3S)-piperidin-3-yl]pyrazine-2-carboxamide: $^1$H NMR (400 MHz, d$_6$-DMSO): 9.50 (t, 1H), 9.30 (br s, 1H), 8.90 (m, 2H), 8.70 (s, 1H), 8.35 (d, 1H), 7.90 (d, 1H), 7.60 (m, 3H), 7.22 (t, 1H), 6.93 (br s, 1H), 6.80 (d, 1H), 4.50 (br s, 2H), 4.30 (m, 1H), 3.73 (s, 3H), 3.20 (m, 3H), 2.70 (m, 1H), 1.90 (m, 4H); MS (EI) for $C_{25}H_{28}N_6O_3$: 461 (MH$^+$).

3-amino-6-{3-[({[3,4-bis(methyloxy)phenyl]methyl}amino)carbonyl]phenyl}-N-[(3S)-piperidin-3-yl]pyrazine-2-carboxamide: $^1$H NMR (400 MHz, DMSO-d$_6$): 9.30 (s, 1H), 9.20 (br s, 1H), 8.95 (m, 2H), 8.86 (d, 1H), 8.60 (s, 1H), 8.30 (d, 1H), 7.86 (d, 1H), 7.58 (t, 1H), 7.02 (s, 1H), 6.87 (br s, 2H), 4.50 (d, 2H), 4.30 (m, 1H), 3.74 (s, 3H), 3.72 (s, 3H), 3.25 (m, 2H), 3.15 (m, 1H), 2.70 (m, 1H), 1.90 (m, 4H); MS (EI) for $C_{26}H_{30}N_6O_4$: 491 (MH$^+$).

3-amino-6-[3-({[(2-chloro-3,6-difluorophenyl)methyl]amino}carbonyl)phenyl]-N-[(3S)-piperidin-3-yl]pyrazine-2-carboxamide: $^1$H NMR (400 MHz, DMSO-d$_6$): 9.31 (s, 1H), 9.09 (s, 2H), 8.93 (s, 1H), 8.80 (d, 1H), 8.56 (s, 1H), 8.33 (d, 1H), 7.86 (d, 1H), 7.57 (t, 1H), 7.48 (m, 1H), 7.35 (m, 1H), 4.65 (m, 2H), 4.37 (m, 1H), 3.29 (m, 2H), 3.05 (m, 1H), 2.74 (m,1H), 1.99-1.72 (m, 4H); MS (EI) for $C_{24}H_{23}N_6O_2F_2Cl$: 501.04 (MH$^+$).

3-amino-6-[3-({[(2,5-dichlorophenyl)methyl]amino}carbonyl)phenyl]-N-[(3S)-piperidin-3-yl]pyrazine-2-carboxamide: $^1$H NMR (400 MHz, DMSO-d$_6$): 9.61 (t, 1H), 9.15 (m, 1H), 8.97 (s, 1H), 8.96 (s, 1H), 8.94 (s, 1H), 8.77 (s, 1H), 8.36 (d, 1H), 7.94 (d, 1H), 7.61 (t, 1H), 7.53 (d, 1H), 7.44-7.39 (m, 2H), 4.57 (m, 2H), 4.29 (m, 1H), 3.28-3.16 (m, 3H), 2.76 (m, 1H), 1.91-1.72 (m, 4H); MS (EI) for $C_{24}H_{24}N_6O_2Cl_2$: 500.98 (MH$^+$).

3-amino-N-[(3S)-piperidin-3-yl]-6-[3-({[(2,3,4-trifluorophenyl)methyl]amino}carbonyl)phenyl]pyrazine-2-carboxamide: $^1$H NMR (400 MHz, DMSO-d$_6$): 9.56 (s, 1H), 9.18 (s, 1H), 9.00 (s, 1H), 8.96 (s, 1H), 8.92 (d, 1H), 8.70 (s, 1H), 8.34 (d, 1H), 7.89 (d, 1H), 7.59 (t, 1H), 7.32 (m, 2H), 4.55 (d, 2H), 4.28 (m, 1H), 3.29-3.15 (m, 3H), 2.76 (m, 1H), 1.91-1.73 (m, 4H); MS (EI) for $C_{24}H_{23}N_6O_2F_3$: 485.06 (MH$^+$).

3-amino-6-[3-({[(2,3-difluorophenyl)methyl]amino}carbonyl)phenyl]-N-[(3S)-piperidin-3-yl]pyrazine-2-carboxamide: $^1$H NMR (400 MHz, DMSO-d$_6$): 9.60 (s, 1H), 9.28 (s, 1H), 9.06 (s, 1H), 8.96 (s, 1H), 8.94 (s, 1H), 8.73 (s, 1H), 8.34 (d, 1H), 7.90 (d, 1H), 7.59 (t, 1H), 7.37-7.16 (m, 3H), 4.60 (m, 2H), 4.30 (m, 1H), 3.27-3.15 (m, 3H), 2.77 (m, 1H), 1.92-1.73 (m, 4H); MS (EI) for $C_{24}H_{24}N_6O_2F_2$: 467.06 (MH$^+$).

3-amino-6-[3-({[(3-fluoro-4-methylphenyl)methyl]amino}carbonyl)phenyl]-N-[(3S)-piperidin-3-yl]pyrazine-2-carboxamide: $^1$H NMR (400 MHz, DMSO-d$_6$): 9.55 (s, 1H), 9.28 (s, 1H), 9.08 (s, 1H), 8.96 (m, 2H), 8.72 (s, 1H), 8.33 (d, 1H), 7.91 (d, 1H), 7.59 (t, 1H), 7.24 (t, 1H), 7.15-7.10 (m, 2H), 4.50 (m, 2H), 4.30 (m, 1H), 3.29-3.13 (m, 3H), 2.76 (m, 1H), 2.20 (s, 3H), 1.94-1.71 (m, 4H); MS (EI) for $C_{25}H_{27}N_6O_2F$: 463.12 (MH$^+$).

3-amino-N-[(3S)-piperidin-3-yl]-6-[3-({[(3,4,5-trifluorophenyl)methyl]amino}carbonyl)phenyl]pyrazine-2-carboxamide: $^1$H NMR (400 MHz, DMSO-d$_6$): 9.72 (m, 1H), 9.23 (s, 1H), 9.00 (m, 2H), 8.96 (s, 1H), 8.78 (s, 1H), 8.33 (d, 1H), 7.91 (d, 1H), 7.59 (t, 1H), 7.36 (m, 2H), 4.49 (m, 2H), 4.30 (m, 1H), 3.28-3.17 (m, 3H), 2.76 (m, 1H), 1.94-1.70 (m, 4H); MS (EI) for $C_{24}H_{23}N_6O_2F_3$: 485.28 (MH$^+$).

3-amino-6-[3-({[(4-fluoro-3-methylphenyl)methyl]amino}carbonyl)phenyl]-N-[(3S)-piperidin-3-yl]pyrazine-2-carboxamide: $^1$H NMR (400 MHz, DMSO-d$_6$): 9.51 (m, 1H), 9.29 (s, 1H), 9.08 (s, 1H), 8.94 (m, 2H), 8.70 (s, 1H), 8.33 (d, 1H), 7.91 (d, 1H), 7.58 (t, 1H), 7.25 (m, 2H), 7.09 (t, 1H), 4.46 (m, 2H), 4.29 (m, 1H), 3.30-3.13 (m, 3H), 2.76 (m, 1H), 2.22 (s, 1H), 1.94-1.70 (m, 4H); MS (EI) for $C_{25}H_{27}N_6O_2F$: 463.31 (MH$^+$).

3-amino-N-[(3S)-piperidin-3-yl]-6-[3-({[(2,3,5-trifluorophenyl)methyl]amino}carbonyl)phenyl]pyrazine-2-carboxamide: $^1$H NMR (400 MHz, DMSO-d$_6$): 9.67 (s, 2H), 9.21 (s, 1H), 8.99 (s, 2H), 8.75 (m, 1H), 8.34 (d, 1H), 7.90 (d, 1H), 7.59 (t, 1H), 7.46 (m, 1H), 7.16 (m, 1H), 4.58 (m, 2H), 4.29 (m, 1H), 3.22 (m, 3H), 2.75 (m, 1H), 1.95-1.68 (m, 4H); MS (EI) for $C_{24}H_{23}N_6O_2F_3$: 485.27 (MH$^+$).

3-amino-N-[(3S)-piperidin-3-yl]-6-{3-[({[4-(1H-pyrazol-1-yl)phenyl]methyl}amino)carbonyl]phenyl}pyrazine-2-carboxamide: $^1$H NMR (400 MHz, DMSO-d$_6$): 9.63 (s, 1H), 9.36 (s, 1H), 9.14 (s, 1H), 8.98 (m, 2H), 8.76 (s, 1H), 8.48 (d, 1H), 8.34 (d, 1H), 7.93 (m, 1H), 7.81 (d, 2H), 7.73 (d, 1H), 7.59 (t,1H), 7.51 (d, 2H), 6.54 (m, 1H), 4.56 (m, 2H), 4.31 (m, 1H), 3.32-3.12 (m, 3H), 2.75 (m, 1H), 1.94-1.69 (m, 4H); MS (EI) for $C_{27}H_{28}N_8O_2$: 497.06 (MH$^+$).

3-amino-6-(3-{[(biphenyl-3-ylmethyl)amino]carbonyl}phenyl)-N-[(3S)-piperidin-3-yl]pyrazine-2-carboxamide: $^1$H NMR (400 MHz, DMSO-d$_6$): 9.60 (t, 1H), 9.31 (s, 1H), 9.08 (s, 1H), 8.94 (m, 2H), 8.74 (s, 1H), 8.34 (d, 1H), 7.93 (d, 1H), 7.68-7.34 (m, 10H), 4.60 (m, 2H), 4.29 (m, 1H), 3.30-3.11 (m, 3H), 2.74 (m, 1H), 1.94.1.67 (m, 4H); MS (EI) for C$_{30}$H$_{30}$N$_6$O$_2$: 507.07 (MH$^+$).

3-amino-6-[3-({[(2-methylphenyl)methyl]amino}carbonyl)phenyl]-N-[(3S)-piperidin-3-yl]pyrazine-2-carboxamide: $^1$H NMR (400 MHz, DMSO-d$_6$): 9.33 (t, 2H), 9.11 (m, 1H), 8.96 (s, 1H), 8.92 (d, 1H), 8.71 (s, 1H), 8.34 (d, 1H), 7.92 (d, 1H), 7.59 (t, 1H), 7.32 (m, 1H), 7.17 (m, 3H), 4.50 (m, 2H), 4.29 (m, 1H), 3.30-3.06 (m, 3H), 2.74 (m, 1H), 2.36 (s, 1H), 1.94-1.66 (m, 4H); MS (EI) for C$_{25}$H$_{28}$N$_6$O$_2$: 445.08 (MH$^+$).

3-amino-6-[3-({[(2,5-dimethylphenyl)methyl]amino}carbonyl)phenyl]-N-[(3S)-piperidin-3-yl]pyrazine-2-carboxamide: $^1$H NMR (400 MHz, DMSO-d$_6$): 9.34 (s, 1H), 9.28 (m, 1H), 9.13 (s,1H), 8.96 (s, 1H), 8.91 (d, 1H), 8.69 (s, 1H), 8.34 (d, 1H), 7.92 (d, 1H), 7.59 (t, 1H), 7.11 (s, 1H), 7.06 (d, 1H), 6.97 (d,1H), 4.46 (m, 2H), 4.29 (m, 1H), 3.32-3.02 (m, 3H), 2.74 (m, 1H), 2.31 (s,3H), 2.24 (s,3H), 1.97-1.67 (m, 4H); MS (EI) for C$_{26}$H$_{30}$N$_6$O$_2$: 459.09 (MH$^+$).

3-amino-6-[3-({[(3,5-dimethylphenyl)methyl]amino}carbonyl)phenyl]-N-[(3S)-piperidin-3-yl]pyrazine-2-carboxamide: $^1$H NMR (400 MHz, DMSO-d$_6$): 9.39 (s, 1H), 9.28 (s, 1H), 9.06 (s,1H), 8.95 (s, 1H), 8.91 (d, 1H), 8.68 (s, 1H), 8.34 (d, 1H), 7.92 (d, 1H), 7.59 (t, 1H), 6.96 (s, 2H), 6.87 (s,1H), 4.44 (m, 2H), 4.28 (m, 1H), 3.31-3.08 (m, 3H), 2.74 (m, 1H), 2.31 (s, 6H), 1.95-1.66 (m, 4H); MS (EI) for C$_{26}$H$_{30}$N$_6$O$_2$: 459.09 (MH$^+$).

3-amino-6-[3-({[(2,4-dimethylphenyl)methyl]amino}carbonyl)phenyl]-N-[(3S)-piperidin-3-yl]pyrazine-2-carboxamide: $^1$H NMR (400 MHz, DMSO-d$_6$): 9.29 (s, 1H), 9.23 (t, 1H), 9.08 (m,1H), 8.95 (s, 1H), 8.91 (d, 1H), 8.66 (s, 1H), 8.33 (d, 1H), 7.91 (d, 1H), 7.58 (t, 1H), 7.20 (d,1H), 6.99 (s, 1H), 6.96 (d,1H), 4.45 (m, 2H), 4.28 (m, 1H), 3.27-3.05 (m, 3H), 2.74 (m, 1H), 2.32 (s, 3H), 2.24 (s, 3H), 1.96-1.67 (m, 4H); MS (EI) for C$_{26}$H$_{30}$N$_6$O$_2$: 459.09 (MH$^{30}$).

3-amino-6-{3-[({[phenyl]methyl}amino)carbonyl]phenyl}-N-[(3S)-piperidin-3-yl]pyrazine-2-carboxamide: $^1$H NMR (400 MHz, DMSO-d$_6$): 9.48 (t, 1H), 9.26 (m, 1H), 9.05 (m, 1H), 8.96 (s, 1H), 8.92 (d, 1H), 8.70 (s, 1H), 8.34 (d, 1H), 7.91 (d, 1H), 7.59 (t, 1H), 7.40-7.31 (m, 4H), 7.28-7.22 (m, 1H), 4.53 (m, 2H), 4.29 (m, 1H), 3.32-3.07 (m, 3H), 2.75 (m, 1H), 1.95-1.67 (m, 4H); MS (EI) for C$_{24}$H$_{26}$N$_6$O$_2$: 431.09 (MH$^+$).

3-amino-6-{3-[({[3,5-bis(methyloxy)phenyl]methyl}amino)carbonyl]phenyl}-N-[(3S)-piperidin-3-yl]pyrazine-2-carboxamide: $^1$H NMR (400 MHz, DMSO-d$_6$): 9.46 (t, 1H), 9.31 (m, 1H), 9.10 (m, 1H), 8.96 (s, 1H), 8.94 (d, 1H), 8.70 (s, 1H), 8.34 (d, 1H), 7.91 (d, 1H), 7.59 (t, 1H), 6.54 (d, 2H), 6.39 (t, 1H), 4.45 (m, 2H), 4.29 (m, 1H), 3.72 (s, 6H), 3.34-3.10 (m, 3H), 2.75 (m,1H), 1.96-1.66 (m, 4H); MS (EI) for C$_{26}$H$_{30}$N$_6$O$_4$: 491.06 (MH$^+$).

Example 66

3-amino-6-(3-{[(2-methylphenyl)acetyl]amino}phenyl)-N-[(3S)-piperidin-3-yl]pyrazine-2-carboxamide To a solution of 2-methylphenylacetic acid (45 mg, 0.30 mmol) in dry dichloromethane (1.0 mL) were added 1-ethyl-(3-dimethylaminopropyl)carbodiimide hydrochloride (EDCI, 72 mg, 0.38 mmol) and 1-hydroxybenzotriazole (HOBT, 51 mg, 0.38 mmol). The reaction mixture was stirred for 10-15 min at room temperature. A solution of tert-butyl (3S)-3-({[3-amino-6-(3-aminophenyl)pyrazin-2-yl]carbonyl}amino)piperidine-1-carboxylate (80 mg, 0.20 mmol) in dichloromethane (1 mL) was added and stirring continued for 2-3 h. Reaction was diluted with ethyl acetate (150 mL), washed with saturated aqueous sodium bicarbonate (40 mL) and saturated aqueous sodium chloride (50 mL). Dried over anhydrous magnesium sulfate, filtered, concentrated, and purification on silica (hexanes/ethyl acetate, 3:7) afforded the protected intermediate. MS (EI) for C$_{25}$H$_{28}$N$_6$O$_2$: 445 [(M-boc)H$^+$].

To a solution of the above intermediate in methanol (2 mL) was added 4.0 N hydrochloric acid (1,4-dioxane solution, 1 mL) and the reaction stirred until the deprotection was completed as monitored by thin layer chromatography. The excess reagent and solvent was removed at reduced pressure to give a solid product which was washed further with ethyl acetate (50 mL) to afford the hydrochloric acid salt of 3-amino-6-(3-{[(2-methylphenyl)acetyl]amino}phenyl)-N-[(3S)-piperidin-3-yl]pyrazine-2-carboxamide (56 mg, 63% yield) as yellow solid. $^1$NMR (400 MHz, d$_6$-DMSO): 10.72 (s, 1H), 9.20 (br s, 1H), 9.04 (br s, 1H), 8.80 (s, 1H), 8.70 (d, 1H), 8.45 (s, 1H), 7.80 (d, 1H), 7.40 (m, 2H), 7.18 (m, 3H), 4.32 (m, 1H), 3.80 (s, 2H), 3.25 (m, 3H), 2.80 (m, 1H), 2.3 (s, 3H), 1.80 (m, 4H); MS (EI) for C$_{25}$H$_{28}$N$_6$O$_2$: 445 (MH+).

Using the same or analogous synthetic techniques and/or substituting with alternative reagents as described above, the following compounds of the invention were prepared:

3-amino-N-[(3S)-piperidin-3-yl]-6-[3-({[3-(trifluoromethyl)phenyl]acetyl}amino)phenyl]pyrazine-2-carboxamide: $^1$NMR (400 MH, d$_6$-DMSO): 10.82 (s, 1H), 9.10 (br s, 1H), 8.92 (br s, 1H), 8.90 (s, 1H), 8.85 (d, 1H), 8.40 (s, 1H), 7.72 (m, 6H), 7.40 (t, 1H), 4.40 (m, 1H), 3.84 (s, 2H), 3.25 (m, 3H), 2.80 (m, 1H), 1.84 (m, 4H); MS (EI) for C$_{25}$H$_{25}$N$_6$O$_2$F$_3$: 499 (MH$^+$).

3-amino-6-[3-({[4-(methyloxy)phenyl]acetyl}amino)phenyl]-N-[(3S)-piperidin-3-yl]pyrazine-2-carboxamide: $^1$NMR (400 MHz, d$_6$-DMSO): 10.60 (s, 1H), 9.10 (br s, 1H), 9.01 (br s, 1H), 8.78 (s, 1H), 8.68 (d, 1H), 8.40 (s, 1H), 7.80 (t, 1H), 7.40 (t, 1H), 7.30 (d, 2H), 6.85 (d, 2H), 4.45 (m, 1H), 3.72 (s, 3H), 3.60 (s, 2H), 3.25 (m, 3H), 2.80 (m, 1H), 1.90 (m, 4H); MS (EI) for C$_{25}$H$_{28}$N$_6$O$_3$: 461 (MH$^+$).

3-amino-6-(3-{[(6-methylpyridin-3-yl)carbonyl]amino}phenyl)-N-[(3S)-piperidin-3-yl]pyrazine-2-carboxamide: $^1$NMR (400 MHz, d$_6$-DMSO): 11.40 (s, 1H), 9.60 (s, 1H), 9.50 (br s, 1H), 9.10 (m, 2H), 8.90 (m, 3H), 8.15 (d, 1H), 8.00 (d, 1H), 7.90 (d, 1H), 7.50 (t, 2H), 4.40 (m, 1H), 3.30 (m, 3H), 2.90 (m, 4H), 1.80 (m, 4H); MS (EI) for C$_{23}$H$_{25}$N$_7$O$_2$: 432 (MH$^+$).

3-amino-6-(3-{[(3-fluorophenyl)acetyl]amino}phenyl)-N-[(3S)-piperidin-3-yl]pyrazine-2-carboxamide: $^1$NMR (400 MHz, d$_6$-DMSO): 10.80 (s, 1H), 9.10 (br s, 1H), 8.95 (br s, 1H), 8.80 (s, 1H), 8.70 (d, 1H), 8.40 (s, 1H), 7.80 (m, 2H), 7.40 (m, 2H), 7.30 (m, 2H), 7.10 (t, 1H), 4.30 (m, 1H), 3.75 (s, 2H), 3.22 (m, 3H), 2.80 (m, 1H), 1.90 (m, 4H); MS (EI) for C$_{24}$H$_{25}$N$_6$O$_2$F: 449 (MH$^+$).

3-amino-N-[(3S)-piperidin-3-yl]-6-{3-[(pyridin-3-ylacetyl)amino]phenyl}pyrazine-2-carboxamide: $^1$NMR (400 MHz, d$_6$-DMSO): 11.15 (s, 1H), 9.28 (br s, 1H), 9.02 (m, 2H), 8.90 (d, 1H), 8.78 (s, 1H), 8.65 (d, 1H), 8.60 (d, 1H), 8.50 (s, 1H), 8.02 (m, 1H), 7.80 (m, 2H), 7.40 (t, 1H), 4.30 (m, 1H), 3.30 (m, 3H), 2.80 (m, 1H), 1.92 (m, 4H); MS (EI) for C$_{23}$H$_{25}$N$_7$O$_2$: 432 (MH$^+$).

3-amino-N-[(3S)-piperidin-3-yl]-6-{3-[(pyridin-3-ylcarbonyl)amino]phenyl}pyrazine-2-carboxamide: $^1$NMR (400 MHz, d$_6$-DMSO): 11.30 (s, 1H), 9.80 (s, 1H), 9.30 (br s, 1H), 9.02 (m, 3H), 8.80 (m, 3H), 8.10 (d, 1H), 8.01 (m, 1H), 7.90

(d, 1H), 7.45 (t, 1H), 4.30 (m, 1H), 3.35 (m, 3H), 2.78 (m, 1H), 1.90 (m, 4H); MS (EI) for $C_{22}H_{23}N_7O_2$: 418 (MH$^+$).

3-amino-6-(3-{[(2,5-difluorophenyl)acetyl]amino}phenyl)-N-[(3S)-piperidin-3-yl]pyrazine-2-carboxamide: $^1$NMR (400 MH, d$_6$-DMSO): 10.75 (s, 1H), 9.10 (br s, 1H), 9.01 (br s, 1H), 8.80 (s, 1H), 8.70 (d, 1H), 8.60 (s, 1H), 7.80 (m, 2H), 7.40 (t, 1H), 7.32 (m, 3H), 4.30 (m, 1H), 3.80 (s, 2H), 3.20 (m, 3H), 2.78 (m, 1H), 1.90 (m, 4H); MS (EI) for $C_{24}H_{24}N_6O_2F_2$: 467 (MH$^+$).

3-amino-6-(3-{[(4-fluorophenyl)acetyl]amino}phenyl)-N-[(3S)-piperidin-3-yl]pyrazine-2-carboxamide: $^1$NMR (400 MHz, d$_6$-DMSO): 10.72 (s, 1H), 9.18 (br s, 1H), 9.02 (br s, 1H), 8.80 (s, 1H), 8.70 (d, 1H), 7.80 (m, 2H), 7.40 (m, 3H), 7.20 (m, 2H), 4.24 (m, 1H), 3.73 (s, 2H), 3.30 (m, 3H), 2.80 (m, 1H), 1.92 (m, 4H); MS (EI) for $C_{24}H_{25}N_6O_2F$: 449 (MH+).

Example 67

Scheme 25 depicts three exemplary compounds, (ciii), (civ), and (cv), the latter two according to formula I, which are useful as intermediates to synthesize other compounds of the invention, particularly assembling —W—X—Y. The general methods described above are used in various combinations to make compounds, (ciii), (civ), and (cv). Exemplary syntheses of such compounds follows Scheme 25

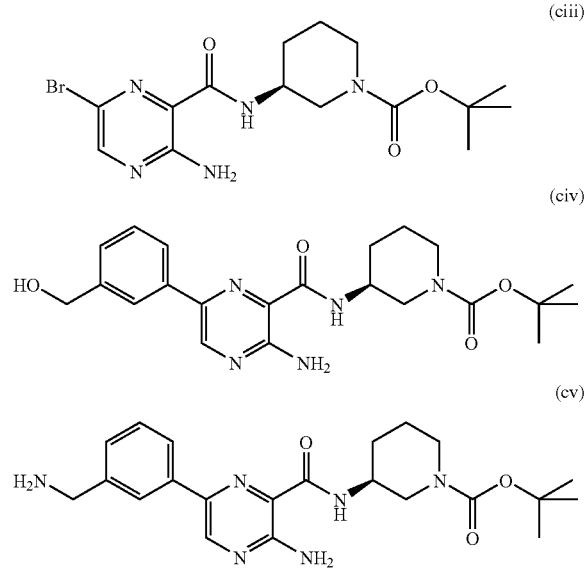

1,1-dimethylethyl (3S)-3-{[(3-amino-6-bromopyrazin-2-yl)carbonyl]amino}piperidine-1-carboxylate 3-amino-6-bromopyrazine-2-carboxylic acid (3.63 g, 16.65 mmol), HATU (9.49 g, 25.0 mg) and DIEA (4.35 mL, 25.0 mmol) was added to a solution of (s)-3-amino-piperidine-1-carboxylic acid tert-butyl ester (4.00 g, 19.97 mmol, commercially available from Astatech or Arch Corporation). It was stirred at room temperature overnight. The reaction mixture was poured into water (200 mL), and extracted with ethyl acetate (2×150 mL) then dried over anhydrous sodium sulfate and filteration, concentration and purified by column chromatography to give 1,1-dimethylethyl (3S)-3-{[(3-amino-6-bromopyrazin-2-yl)carbonyl]amino}piperidine-1-carboxylate 5.00 g (75.0% yield): MS (EI) for $C_{15}H_{22}BrN_5O_3$: 401.12 (MH$^+$).

1,1-dimethylethyl (3S)-3-[({3-amino-6-[3-(hydroxymethyl)phenyl]pyrazin-2yl}carbonyl)amino]piperidine-1-carboxylate 1,1-dimethylethyl (3S)-3-{[(3-amino-6-bromopyrazin-2-yl)carbonyl]amino}piperidine-1-carboxylate (765.0 mg, 1.91 mmol) was dissolved in DMF followed by addition of 3-hydroxymethyl phenylboronic acid (349.0 mg, 2.23 mmol), K$_2$CO$_3$ (660.0 mg, 4.77 mmol) and Pd(PPh$_3$)$_4$ (10 mol %, 220 mg). This mixture was stirred at 90° C. under nitrogen for 12 hours. The reaction mixture was poured into water (150 mL), and extracted with ethyl acetate (3×50 mL). The organic layers were washed with brine (50 mL) then dried over anhydrous sodium sulfate. Filteration, concentration and column chromatography on silica (50% ethylacetate/hexanes) gave a solid which was dried to afford 765.0 mg (92% yield) of 1,1-dimethylethyl (3S)-3-[({3-amino-6-[3-(hydroxymethyl)phenyl]pyrazin-2yl}carbonyl)amino]piperidine-1-carboxylate: MS (EI) for $C_{22}H_{29}N_5O_4$: 428.23 (MH$^+$).

1,1-dimethylethyl (3S)-3-[({3-amino-6-[3-(aminomethyl)phenyl]pyrazin-2-yl}carbonyl)amino]piperidine-1-carboxylate 1,1-Dimethylethyl (3S)-3-[({3-amino-6-[3-hydroxymethyl)phenyl]pyrazin-2yl}carbonyl)amino]piperidine-1-carboxylate (965.0 mg, 2.26 mmol) was dissolved in THF (20 mL) followed by the addition of diphenylphosphoryl azide (0.68 mL, 3.16 mmol) and DBU (0.50 mL, 3.16 mmol). It was stirred at room temperature overnight. The reaction mixture was poured into water (100 mL), and extracted with ethyl acetate (2×50 mL) then dried over anhydrous sodium sulfate and filteration, concentration and purified by column chromatography (20%→50% Ethylacetae/hexanes) to give the corresponding azide, 588.0 mg (57.6% yield) and then it was dissolved in the mixture of THF (20 mL) and H$_2$O (2.0 mL) followed by the addition of triphenylphosphine (1.02 g, 3.88 mmol) and it was stirred at room temperature overnight. The reaction mixture was poured into water (100 mL), and extracted with ethyl acetate (2×50 mL) then dried over anhydrous sodium sulfate and filteration, concentration and purified by column chromatography (100% Ethylacetate→100% MeON) to give 1,1-dimethylethyl (3S)-3-[({3-amino-6-[3-(amino-methyl)phenyl]pyrazin-2-yl}carbonyl)amino]piperidine-1-carboxylate, 435.0 mg (78.8% yield): MS (EI) for $C_{22}H_{30}N_6O_3$: 427.24 (MH$^+$).

Example 68

3-Amino-6-[3-({[(4-fluorophenyl)carbonyl]amino}methyl)phenyl]-N-[(3S)-piperidin-3-yl]pyrazine-2-carboxamide 1,1-dimethylethyl (3S)-3-[({3-amino-6-[3-(amino-methyl)phenyl]pyrazin-2-yl}carbonyl)amino]piperidine-1-carboxylate (150.0 mg, 0.35 mmol) and 4-fluorobenzoic acid (50.0 mg, 0.36 mmol) was dissolved in DMF (5 mL) followed by the addition of HOBT (95.5 mg, 0.70 mmol) and EDCI (135.4 mg, 0.70 mmol). It was stirred at room temperature overnight. The reaction mixture was poured into water (20 mL), and extracted with ethyl acetate (2×30 mL) then dried over anhydrous sodium sulfate and filteration, concentration and purified by column chromatography (50% Ethylacetae/hexanes) and subsequently it was treated with 4.0 M HCl in dioxane (20 mL) to give compound 3-Amino-6-[3-({[(4-fluorophenyl)carbonyl]amino}methyl)phenyl]-N-[(3S)-piperidin-3-yl]pyrazine-2-carboxamide: 70.0 mg (46.6% yield). $^1$H NMR (400 MHz, d4-MeOH): δ 8.62 (s, 1H), 8.16 (s, 1H), 7.98 (m, 3H), 7.48 (m, 2H), 7.20 (m, 3H), 4.67(s, 2H), 4.38 (m, 1H), 3.45 (m, 1H), 3.38 (m, 1H), 3.18 (m, 1H), 3.00 (m, 1H), 2.18 (m, 2H), 1.80 (m, 2H); MS (EI) for $C_{24}H_{25}N_6O_2F$: 449.32 (MH$^+$).

Using the same or analogous synthetic techniques and/or substituting with alternative reagents {respective corresponding amines, etc.}, the following compounds of the invention were prepared.

3-amino-6-[3-({[(4-chlorophenyl)carbonyl]amino}methyl)phenyl]-N-[(3S)-piperidin-3-yl]pyrazine-2-carboxamide: $^1$H NMR (400 MHz, d6-DMSO): δ 9.50 (m, 2H), 9.30 (br,1H), 8.78(d, 1H), 8.20 (s, 1H), 8.00 (m, 3H), 7.60 (m, 2H), 7.40 (m, 2H), 5.00 (br, 2H), 4.67(d, 2H), 4.38 (m, 1H), 3.20 (m, 3H), 2.80 (m, 1H), 1.80 (m, 4H); MS (EI) for $C_{24}H_{25}N_6O_2Cl$: 465.21 (MH$^+$).

3-amino-6-{3-[({[5-(4-nitrophenyl)furan-2-yl]carbonyl}amino)methyl]phenyl}-N-[(3S)-piperidin-3-yl]pyrazine-2-carboxamide: $^1$H NMR (400 MHz, d4-MeOH): δ 8.62 (s, 1H), 8.38 (d, 2H), 8.10(d, 3H), 7.98 (d, 1H), 7.50 (m, 2H), 7.30 (dd, 2H), 4.70 (s, 2H), 4.30 (br, 1H), 3.70 (m, 1H), 3.50 (m, 1H), 3.38 (m, 1H), 3.17 (m, 1H), 3.00 (m, 1H), 2.10 (m, 2H), 1.80 (m, 2H); MS (EI) for $C_{28}H_{28}N_7O_5$: 543.28 (MH$^+$).

3-amino-6-[3-({[(3-hydroxypyridin-2-yl)carbonyl]amino}methyl)phenyl]-N-[(3S)-piperidin-3-yl]pyrazine-2-carboxamide: $^1$H NMR (400 MHz, d4-MeOH): δ; 8.70 (s, 1H), 8.40 (d, 2H), 8.10(m, 1H), 8.00 (m, 1H), 7.40 (m, 1H), 7.30 (m, 1H), 4.80 (s, 1H), 4.40 (br, 1H), 4.08 (s, 2H), 3.70 (m, 1H), 3.50 (m, 1H), 3.40 (m, 1H), 3.20 (m, 1H), 3.10 (m, 1H), 2.10 (m, 2H), 1.80 (m, 2H); MS (EI) for $C_{23}H_{25}N_7O_3$: 448.28 (MH$^+$).

3-amino-N-[(3S)-piperidin-3-yl]-6-[3-({[({4-[(trifluoromethyl)oxy]phenyl}oxy)acetyl]amino}methyl)phenyl]pyrazine-2-carboxamide: $^1$H NMR (400 MHz, d6-DMSO): δ; 9.20 (m, 1H), 9.00 (m, 1H), 8.92 (m, 1H), 8.70 (d, 1H), 8.00 (m, 2H), 7.40 (m, 1H), 7.28 (m, 3H), 7.00 (m, 2H), 4.60 (s, 1H), 4.40 (d, 2H), 4.25 (m, 1H), 3.20 (m, 4H), 2.70 (m, 1H), 1.80 (m, 3H); MS (EI) for $C_{26}H_{27}N_6O_4F_3$: 545.26 (MH$^+$).

3-amino-6-[3-({[(5-methylisoxazol-3-yl)carbonyl]amino}methyl)phenyl]-N-[(3S)-piperidin-3-yl]pyrazine-2-carboxamide: $^1$H NMR (400 MHz, d6-DMSO): δ; 9.40 (m, 1H), 9.20 (m, 1H), 9.00 (m, 1H), 8.60 (d, 1H), 8.00 (m, 2H), 7.40 (m, 1H), 7.28 (m, 1H), 6.60 (s, 1H), 4.50 (d, 2H), 4.20 (m, 1H), 3.20 (m, 4H), 2.75 (m, 1H), 2.45 (s, 3H), 1.80 (m, 3H); MS (EI) for $C_{22}H_{25}N_7O_3$: 436.25 (MH$^+$).

3-amino-6-(3-{[(isoxazol-5-ylcarbonyl)amino]methyl}phenyl)-N-[(3S)-piperidin-3-yl]pyrazine-2-carboxamide: $^1$H NMR (400 MHz, d6-DMSO): δ; 9.70 (m, 1H), 9.20 (m, 1H), 9.00 (m, 1H), 8.70 (d, 1H), 8.68 (m, 1H), 8.15 (s, 1H), 8.00 (d, 1H), 7.40 (m, 1H), 7.30 (m, 1H), 7.20 (s, 1H), 4.50 (d, 2H), 4.20 (m, 1H), 3.20 (m, 4H), 2.75 (m, 1H), 1.80 (m, 3H); MS (EI) for $C_{21}H_{23}N_7O_3$: 422.23 (MH$^+$).

3-amino-6-[3-({[(4-methyl-1,2,3-thiadiazol-5-yl)carbonyl]amino}methyl)phenyl]-N-[(3S)-piperidin-3-yl]pyrazine-2-carboxamide: $^1$H NMR (400 MHz, d6-DMSO): δ; 9.60 (m, 1H), 9.20 (m, 1H), 9.00 (m, 1H), 8.70 (d, 2H), 8.15 (s, 1H), 8.00 (d, 1H), 7.40 (m, 2H), 4.50 (d, 2H), 4.20 (m, 1H), 3.20 (m, 4H), 2.80 (s, 3H), 2.75 (m, 1H), 1.80 (m, 3H); MS (EI) for $C_{21}H_{24}N_8O_2S$: 453.25 (MH$^+$).

3-amino-6-[3-({[(2,5-dichloro-3-thienyl)carbonyl]amino}methyl)phenyl]-N-[(3S)-piperidin-3-yl]pyrazine-2-carboxamide: $^1$H NMR (400 MHz, d6-DMSO): δ 9.40 (m, 1H), 9.20 (m, 1H), 9.80 (s, 1H), 8.70 (d, 1H), 8.20 (s, 1H), 8.00 (d, 1H), 7.60 (s, 1H), 7.40 (m, 2H), 4.50 (d, 2H), 4.30 (m, 1H), 3.70 (m, 1H), 3.50 (m, 1H), 3.20 (m, 2H), 2.80 (m, 1H), 1.80 (m, 3H); MS (EI) for $C_{22}H_{22}N_6O_2SCl_2$: 505.12 (MH$^+$).

3-amino-6-[3-({[(2,4-difluorophenyl)methyl]amino}methyl)phenyl]-N-[(3S)-piperidin-3-yl]pyrazine-2-carboxamide: $^1$H NMR (400 MHz, d6-DMSO): δ 10.30 (br, 1H), 9.50 (m, 1H), 9.28 (m, 1H), 8.90 (m, 2H), 8.15 (m, 1H), 7.90 (m, 1H), 7.50 (m, 2H), 7.38 (m, 1H), 7.20 9 m, 1H), 4.20 (m, 4H), 3.40 (m, 2H), 3.20 (m, 2H), 2.70 (m, 1H), 2.00 (m, 1H), 1.80 (m, 3H); MS (EI) for $C_{24}H_{26}N_6OF_2$: 453.25 (MH$^+$).

Example 69

Example 69 describes synthesis of azepan derivatives according to formula I. Generally, but not necessarily, the synthetic strategies follow those described above.

3-Amino-N-azepan-3-yl-6-(3-}[(1S)-2,3-dihydro-1H-inden-1-ylamino]carbonyl}phenyl)pyrazine-2-carboxamide To a solution of 3-amino-6-(3-{[(1R)-2,3-dihydro-1H-inden-1-ylamino]carbonyl}phenyl)pyrazine-2-carboxylic acid (409 mg, 1.09 mmol) were added azepan-3-amine (125 mg, 1.09 mmol), EDCI (252 mg, 1.31 mmol), HOBt (178 mg, 1.31 mmol) at ambient temperature. After being stirred for 2 h, the reaction mixture was quenched by addition of aqueous sodium bicarbonate followed by extraction with ethyl acetate (20 mL×3). The aqueous phase was extracted once with additional ethyl acetate. The combined organic layers were washed with saturated aqueous sodium chloride then dried over anhydrous magnesium sulfate. Filtration and concentration in vacuo gave a crude oil, which was purified by preparative HPLC to yield the 3-amino-N-azepan-3-yl-6-(3-{[(1S)-2,3-dihydro-1H-inden-1-ylamino]carbonyl}phenyl)pyrazine-2-carboxamide (22 mg, 4.2% yield): $^1$H NMR (400 MHz, CD$_3$OD): δ 8.70 (m, 1H), 8.67 (m, 1H), 8.27 (m, 1H) 7.97 (m, 1H), 7.62 (t, 1H), 7.25 (m, 4H), 5.70 (m, 1H), 4.99 (m, 1H), 4.43 (m, 1H), 3.46 (m, 2H), 3.38 (m, 1H), 3.15 (m, 2H), 2.94 (m, 1H), 2.61 (m, 1H), 2.17 (m, 2H), 1.95 (m, 4H), 1.62 (m, 1H); MS (EI) for $C_{27}H_{30}N_6O_2$: 471.32 (MH$^+$).

3-Amino-6-[3-({[(2S)-2-hydroxy-2,3-dihydro-1H-inden-1-yl]amino}carbonyl)phenyl]-N-[(3S)-1-(phenylmethyl)azepan-3-yl]pyrazine-2-carboxamide 3-Amino-6-[3-({[(1S,2S)-2-hydroxy-2,3-dihydro-1H-inden-1-yl]amino}carbonyl)phenyl]pyrazine-2-carboxylic acid (1.0 eq) was dissolved in DMF-THF and treated with (3S)-1-(phenylmethyl)azepan-3-amine (1.46 eq), EDCI (1.2 eq) and HOBt (1.2 eq) at ambient temperature. After being stirred overnight, the reaction mixture was quenched by addition of aqueous sodium bicarbonate followed by extraction with ethyl acetate (20 mL×3). The aqueous phase was extracted once with additional ethyl acetate. The combined organic layers were washed with saturated aqueous sodium chloride then dried over anhydrous magnesium sulfate. Filtration and concentration in vacuo gave a crude oil, which was purified by preparative HPLC to yield a crude oil, which was dissolved in ethyl acetate (10 mL), and treated with 1M HCl in ether (5 mL). The resulting precipitation was filtered, washed with methanol (2×20 mL), and dried to afford 122 mg (12% yield) of 3-amino-6-[3-({[(2S)-2-hydroxy-2,3-dihydro-1H-inden-1-yl]amino}carbonyl)phenyl]-N-[(3S)-1-

(phenylmethyl)azepan-3-yl]pyrazine-2-carboxamide (122 mg, 15% yield).: $^1$H NMR (400 MHz, DMSO-d6): δ 8.98 (s, 1H), 8.90 (m, 1H), 8.75 (s, 1H), 8.63 (m, 2H), 8.11 (m, 1H), 7.95 (m, 2H), 7.62 (m, 2H), 7.58 (m, 1H), 7.42 (m, 1H), 7.20 (m, 3H), 7.08 (m, 1H), 5.50 (m, 1H), 4.51 (m, 1H), 4.49 (m, 1H), 4.46 (m, 1H), 4.40 (m, 1H), 3.50 (m, 1H), 3.65 (m, 2H), 3.20 (m, 2H), 2.85 (m, 1H), 2.10 (m, 1H), 1.80 (m, 2H), 1.58 (m, 1H); MS (EI) for $C_{34}H_{36}N_6O_3$: 577.08 (MH$^+$).

3-Amino-N-[(3S)-azepan-3-yl]-6-[3-({[(2S)-2-hydroxy-2,3-dihydro-1H-inden-1-yl]amino}carbonyl)phenyl]pyrazine-2-carboxamide was prepared using the same synthetic procedure as above followed by hydrogenation (1 atm) with 10% palladium hydroxide in MeOH: $^1$H NMR (400 MHz, DMSO-d6): δ 9.18 (bs, 1H), 8.97 (m, 2H), 8.82 (m, 1H), 8.61 (m, 2H), 8.33 (m, 1H), 7.92 (m, 1H), 7.70 (bs, 2H), 7.59 (t, 1H), 7.27 (m, 2H), 7.20 (m, 1H), 5.50 (m, 1H), 4.53 (m, 1H), 4.35 (m, 1H), 3.27 (m, 1H), 3.09 (m, 2H), 1.98 (m, 1H), 1.84 (m, 4H), 1.57 (m, 2H); MS (EI) for $C_{27}H_{30}N_6O_3$: 487.07 (MH$^+$).

1,1-dimethylethyl (3S)-3-{[(3-amino-6-bromopyrazin-2-yl)carbonyl]amino}azepane-1-carboxylate: (3S)-3-aminoazepan-2-one is prepared by either the resolution of racemic α-amino-ε-caprolactam (Sigma-Aldrich) by the method of E. M. Rezler, R. R. Fenton, W. J. Esdale, M. J. McKeage, P. J. Russell, and T. W. Hambley J. Med. Chem. 1997, 40, 3508-3515, or by chiral synthesis from L-lysine using the method of R. Pellegata, M. Pinza, and G. Pifferi, Synthesis, 1978, 614-616. (3S)-3-[(Triphenylmethyl)amino]azepan-2-one and (3S)-N-(triphenylmethyl)azepan-3-amine were prepared using similar methods.

1,1-dimethylethyl (3S)-3-[(triphenylmethyl)amino] azepane-1-carboxylate: To an ice-cooled, stirred solution of (3S)-N-(triphenylmethyl)azepan-3-amine (30.0 mmol) in 60 mL of THF, was added 9.85 g (45.1 mmol, 1.5 eq.) of di-tert-butyl dicarbonate. The ice bath was removed, and the reaction stirred at room temperature for 19 h and concentrated. The crude oil was purified by silica gel chromatography (55 mm column, 7.5 inches of silica gel) using 10% EtOAc in hexanes as eluent. Concentration afforded 13.7 g (100% yield) of product as a solid.

1,1-dimethylethyl (3S)-3-aminoazepane-1-carboxylate: To 13.7 g (30 mmol) of 1,1-dimethylethyl (3S)-3-[(triphenylmethyl)amino]azepane-1-carboxylate was carefully added 100 mL MeOH, 75 mL EtOH, and 1.00 g of 10% Palladium on charcoal. The mixture was hydrogenated on a Parr shaker under 30 psi of hydrogen gas for 15 h. The mixture was filtered through a pad of celite, and the filtrate concentrated to afford a quantitative yield (6.43 g) of product. The product was used as such without further purification.

1,1-dimethylethyl (3S)-3-{[(3-amino-6-bromopyrazin-2-yl)carbonyl]amino}azepane-1-carboxylate: A flask was charged with 6.43 g (30 mmol) of 1,1-dimethylethyl (3S)-3-aminoazepane-1-carboxylate, 109 mL THF, 5.49 g of 3-amino-6-bromopyrazine-2-carboxylic acid (25.2 mmol, 0.84 eq.), 5.00 mL TEA (35.9 mmol, 1.20 eq.), 5.11 g (37.8 mmol, 1.26 eq.) of 1-hydroxybenzotriazole (HOBT), and 7.25 g (37.8 mmol, 1.26 eq.) of 1-[3-(dimethylamino)propyl]-3-ethylcarbodiimide hydrochloride (EDCI). The reaction was allowed to stir for 16 h. The reaction was diluted with EtOAc, washed with 2×sat. aqueous NaHCO$_3$, 1×sat. aqueous NaCl, dried (Na$_2$SO$_4$), filtered, and concentrated. The crude material was purified by silica gel chromatography on a 55 mm column (7.5 inches of silica gel) using 30-50% EtOAc in hexanes as eluent. Concentration afforded 4.57 g (43.8% yield) of product as a solid.

The 1,1-dimethylethyl (3S)-3-{[(3-amino-6-bromopyrazin-2-yl)carbonyl]amino}azepane-1-carboxylate could be used in a manner analogous to that used for 1,1-dimethylethyl (3S)-3-{[(3-amino-6-bromopyrazin-2-yl)carbonyl] amino}piperidine-1-carboxylate to prepare compounds that are part of the invention.

Using the same or analogous synthetic techniques and/or substituting with alternative reagents, the following azepan compounds of the invention were prepared:

3-Amino-6-{3-[(2,3-dihydro-1H-inden-1-ylamino)carbonyl]phenyl}-N-[(3S)-1-(phenylmethyl)azepan-3-yl]pyrazine-2-carboxamide: $^1$H NMR (400 MHz, DMSO-d6): δ 9.20 (d, 1H), 8.95 (m, 3H), 8.85 (s, 1H), 8.50 (d, 1H), 7.97 (m, 1H), 7.50 (m, 3H), 7.41 (m, 1H), 7.32 (m, 4H), 7.05 (m, 1H), 5.60 (m, 1H), 4.35 (m, 1H), 4.29 (m, 1H), 4.20 (m, 1H), 3.08 (m, 2H), 2.91 (m, 2H), 2.45 (m, 1H), 2.31 (m, 1H), 1.80 (m, 3H), 1.42 (m, 1H); MS (EI) for $C_{34}H_{36}N_6O_2$: 461.07 (MH$^+$).

3-Amino-N-[(3S)-azepan-3-yl]-6-{3-[(2,3-dihydro-1H-inden-1-ylamino)carbonyl]phenyl}pyrazine-2-carboxamide: $^1$H NMR (400 MHz, DMSO-d6): δ 9.64 (bs, 1H), 9.32 (bs, 1H), 9.21 (d, 1H), 8.98 (m, 2H), 8.70 (bs, 1H), 8.39 (d, 1H), 7.93 (d, 1H), 7.58 (t, 1H), 7.30 (m, 4H), 5.62 (m, 1H), 4.35 (m, 1H), 3.21 (m, 2H), 3.18 (m, 1H), 3.02 (m, 2H), 2.85 (m, 1H), 2.43 (m, 1H), 2.18 (m, 1H), 1.93 (m, 1H), 1.80 (m, 4H), 1.55 (m, 1H); MS (EI) for $C_{27}H_{30}N_6O_2$: 471.10 (MH$^+$).

3-Amino-N-[(3S)-azepan-3-yl]-6-(3-methylphenyl)pyrazine-2-carboxamide: $^1$H NMR (400 MHz, CD$_3$OD): δ 8.60 (s, 1H), 7.88 (m, 2H), 7.37 (m, 1H), 7.23 (m, 1H), 4.45 (m, 1H), 3.40 (m, 4H), 2.43 (s, 3H), 2.21 (m, 1H), 2.00 (m, 2H), 1.65 (m, 1H), 1.32 (m, 1H), 0.98 (m, 1H); MS (EI) for $C_{18}H_{23}N_5O$: 326.28 (MH$^+$).

3-Amino-N-[(3S)-azepan-3-yl]-6-[3-({[(4-chloro-2-fluorophenyl)methyl]amino}carbonyl)phenyl]pyrazine-2-carboxamide: $^1$H NMR (400 MHz, DMSO-d6): δ 9.50 (m, 2H), 9.15 (bs, 1H), 9.02 (d, 1H), 8.92 (s, 1H), 8.73 (s, 1H), 8.31 (d, 1H), 7.86 (d, 1H), 7.56 (t, 1H), 7.45 (m, 2H), 7.25 (m, 1H), 4.94 (bs, 2H), 4.49 (m, 2H), 4.40 (m, 1H), 3.33 (m, 2H), 3.23 (m, 1H), 3.00 (m, 1H), 2.08 (m, 1H), 1.80 (m, 3H), 1.55 (m, 1H); MS (EI) for $C_{25}H_{26}N_6O_2FCl$: 497.03 (MH$^+$).

3-Amino-N-[(3S)-azepan-3-yl]-6-[3-({[(2,3-difluorophenyl)methyl]amino}carbonyl)phenyl]pyrazine-2-carboxamide: $^1$H NMR (400 MHz, DMSO-d6): δ 9.30 (t, 1H), 8.98 (m, 2H), 8.70 (m, 2H), 8.59 (s, 1H), 8.32 (s, 1H), 7.89 (d, 1H), 7.72 (bs, 1H), 7.58 (t, 1H), 7.34 (m, 1H), 7.20 (m, 2H), 4.60 (m, 2H), 4.36 (m, 1H), 3.35 (m, 1H), 3.22 (m, 1H), 3.09 (m, 1H), 2.67 (m, 1H), 2.33 (m, 1H), 1.99 (m, 1H), 1.85 (m, 3H), 1.58 (m, 1H); MS (EI) for $C_{25}H_{26}N_6O_2F_2$: 481.08 (MH$^+$).

3-Amino-N-[(3S)-azepan-3-yl]-6-[3-({[(3,4-difluorophenyl)methyl]amino}carbonyl)phenyl]pyrazine-2-carboxamide: $^1$H NMR (400 MHz, DMSO-d6): δ 9.48 (m, 1H), 9.37 (m, 1H), 8.99 (m, 2H), 8.95 (s, 1H), 8.32 (d, 1H), 7.85 (d, 1H), 7.55 (t, 1H), 7.43 (m, 2H), 7.23 (m, 1H), 4.50 (m, 3H), 3.34 (m, 2H), 3.24 (m, 2H), 3.07 (m, 1H), 2.05 (m, 1H), 1.80 (m, 4H), 1.58 (m, 1H); MS (EI) for $C_{25}H_{26}N_6O_2F_2$: 481.08 (MH$^+$).

3-Amino-N-[(3S)-azepan-3-yl]-6-[3-({[(3,5-difluorophenyl)methyl]amino}carbonyl)phenyl]pyrazine-2-carboxamide: $^1$H NMR (400 MHz, DMSO-d6): δ 9.46 (t, 2H), 9.18 (bs, 1H), 8.95 (m, 3H), 8.68 (s, 1H), 8.33 (m, 1H), 7.91 (d, 1H), 7.70 (bs, 1H), 7.60 (t, 1H), 7.12 (m, 3H), 4.54 (m, 2H), 4.39 (m, 1H), 3.38 (m, 2H), 3.24 (m, 1H), 3.06 (m, 1H), 2.00 (m, 1H), 1.89 (m, 4H), 1.57 (m, 1H); MS (EI) for $C_{25}H_{26}N_6O_2F_2$: 481.07(MH$^+$).

3-Amino-N-[(3S)-azepan-3-yl]-6-[3-({[(3-chloro-2,6-difluorophenyl)methyl]amino}carbonyl)phenyl]pyrazine-2-carboxamide: $^1$H NMR (400 MHz, DMSO-d6): δ 9.58 (bs, 1H), 9.30 (m, 1H), 9.23 (m, 1H), 9.00 (d, 1H), 8.93 (s, 1H), 8.63 (s, 1H), 8.52 (bs, 2H), 8.33 (m, 1H), 7.86 (m, 1H), 7.79 (m, 1H), 7.60 (m, 2H), 7.32 (t, 1H), 7.18 (t, 1H), 4.58 (m, 2H), 4.41 (m, 1H), 4.06 (m, 2H), 3.31 (m, 1H), 3.22 (m, 2H), 3.01 (m, 1H), 2.00 (m, 1H), 1.90 (m, 2H), 1.80 (m, 2H), 1.59 (m, 1H); MS (EI) for $C_{25}H_{25}N_6O_2F_2Cl$: 515.03 (MH$^+$).

3-Amino-N-[(3S)-azepan-3-yl]-6-(3-{[(2,3-dihydro-1,4-benzodioxin-6-ylmethyl)amino]carbonyl}phenyl)pyrazine-2-carboxamide: $^1$H NMR (400 MHz, DMSO-d6): δ 9.48 (bs, 1H), 9.38 (m, 1H), 9.14 (bs, 1H), 9.10 (m, 1H), 8.95 (s, 1H), 8.69 (s, 1H), 8.32 (m, 1H), 7.89 (m, 1H), 7.57 (m, 1H), 6.83 (s, 3H), 4.41 (m, 2H), 3.45 (m, 4H), 3.17 (m, 1H), 2.00 (m, 1H), 1.89 (m, 3H), 1.59 (m, 1H); MS (EI) for $C_{27}H_{30}N_6O_4$: 503.10. (MH$^+$)

3-Amino-N-[(3S)-azepan-3-yl]-6-[3-({[(2-chloro-6-fluorophenyl)methyl]amino}carbonyl)phenyl]pyrazine-2-carboxamide: $^1$H NMR (400 MHz, DMSO-d6): δ 9.34 (bs, 1H), 9.09 (m, 1H), 8.97 (d, 1H), 8.92 (s, 1H), 8.60 (s, 2H), 8.55 (bs, 2H), 8.34 (m, 1H), 7.85 (m, 1H), 7.54 (m, 2H), 7.44 (m, 1H), 7.39 (m, 2H), 7.25 (m, 1H), 4.63 (m, 2H), 4.40 (m, 1H), 3.25 (m, 2H), 3.03 (m, 1H), 2.00 (m, 1H), 1.90 (m, 1H), 1.83 (m, 2H), 1.59 (m, 1H); MS (EI) for $C_{25}H_{26}N_6O_2FCl$: 497.31 (MH$^+$).

3-Amino-N-[(3S)-azepan-3-yl]-6-[3-({[(2,6-difluorophenyl)methyl]amino}carbonyl)phenyl]pyrazine-2-carboxamide: $^1$H NMR (400 MHz, DMSO-d6): δ 9.20 (bs, 1H), 9.05 (m, 1H), 8.97 (bs, 1H), 8.90 (s, 1H), 8.82 (m, 1H), 8.51 (s, 1H), 8.30 (m, 1H), 7.83 (m, 1H), 7.69 (bs, 1H), 7.53 (t, 1H), 7.36 (m, 1H), 7.10 (m, 2H), 4.55 (m, 2H), 4.34 (m, 1H), 3.25 (m, 3H), 3.06 (m, 2H), 1.90 (m, 1H), 1.83 (m, 3H), 1.57 (m, 1H); MS (EI) for $C_{25}H_{26}N_6O_2F_2$: 481.29 (MH$^+$).

3-Amino-N-[(3S)-azepan-3-yl]-6-[3-({[(3-chloro-4-fluorophenyl)methyl]amino}carbonyl)phenyl]pyrazine-2-carboxamide: $^1$H NMR (400 MHz, DMSO-d6): δ 9.46 (m, 1H), 9.27 (bs, 1H), 8.94 (m, 2H), 8.92 (s, 1H), 8.67 (m, 1H), 8.30 (d, 1H), 7.70 (bs, 1H), 7.60 (m, 2H), 7.56 (m, 2H), 7.36 (m, 2H), 4.50 (m, 3H), 3.32 (m, 2H), 3.22 (m, 2H), 3.03 (m, 1H), 2.01 (m, 1H), 1.85 (m, 3H), 1.59 (m, 1H); MS (EI) for $C_{25}H_{26}N_6O_2FCl$: 497.25 (MH$^+$).

3-Amino-N-[(3S)-azepan-3-yl]-6-[3-({[(3-chloro-2-fluorophenyl)methyl]amino}carbonyl)phenyl]pyrazine-2-carboxamide: $^1$H NMR (400 MHz, DMSO-d6): δ 9.36 (m, 1H), 9.14 (m, 1H), 8.92 (s, 1H), 8.87 (m, 2H), 8.62 (m, 1H), 8.10 (m, 1H), 7.88 (m, 2H), 7.57 (t, 1H), 7.48 (m, 1H), 7.39 (m, 1H), 7.19 (m, 1H), 4.57 (m, 1H), 4.36 (bs, 1H), 3.23 (m, 1H), 3.04 (m, 1H), 1.99 (m, 1H), 1.90 (m, 3H), 1.79 (m, 1H), 1.57 (m, 1H); MS (EI) for $C_{25}H_{26}N_6O_2FCl$: 497.04 (MH$^+$).

Example 70

Scheme 26 depicts another strategy for making exemplary compounds according to formula I where A is a triazole. Nitrile intermediates (cvi) were converted to aminoamidines (cvii), which were acylated and the intermediates cyclized to form 3-{5-Amino-6-[imino(2-methylhydrazino)methyl] pyrazin-2-yl}-N-(phenylmethyl)benzamide: $^1$H NMR (400 MHz, d$_6$-DMSO): δ 9.21-9.15 (m, 1H), 8.95-8.91 (m, 1H), 8.54 (s, 1H), 8.31 (bs, 1H), 7.93-7.88 (m, 1H), 7.93-7.42 (bs, 2H), 7.62-7.55 (m, 1H), 7.38-7.31 (m, 4H), 7.29-7.23 (m, 1H), 4.57-4.51 (m, 1H), 2.89 (bs, 3H); MS (EI) for $C_{20}H_{21}N_7O$: 376.16 (MH$^+$).

3-{5-Amino-6-[imino(2-phenylhydrazino)methyl] pyrazin-2-yl}-N-(phenylmethyl)benzamide: $^1$H NMR (400 MHz, d$_6$-DMSO): δ 9.21-9.15 (m, 1H), 8.74 (bs, 2H), 8.55-8.51 (m, 1H), 8.31-8.25 (m, 1H), 7.89-7.84 (m, 1H), 7.59-7.52 (m, 1H), 7.37-7.20 (m, 6H), 6.98-6.92 (m, 2H), 6.80-6.71 (m, 1H), 4.57-4.50 (m, 2H); MS (EI) for $C_{25}H_{23}N_7O$: 438.15 (MH$^+$).

3-{5-Amino-6-[imino(morpholin-4-ylamino)methyl] pyrazin-2-yl}-N-(phenylmethyl)benzamide: $^1$H NMR (400 MHz, d$_6$-DMSO): δ 9.21-9.14 (m, 1H), 8.90 (bs, 1H), 8.75 (s, 1H), 8.53-8.49 (m, 1H), 8.28-8.23 (m, 1H), 7.88-7.83 (m, 1H), 7.58-7.51 (m, 1H), 7.50-7.00 (m, 6H), 6.65 (bs, 2H), 4.56-4.49 (m, 2H), 3.80-3.71 (m, 4H), 2.80-2.65 (m, 4H); MS (EI) for $C_{23}H_{25}N_7O_2$: 432.15 (MH$^+$).

3-(5-Amino-6-{imino[(4-methylpiperazin-1-yl)amino] methyl}pyrazin-2-yl)-N-(phenylmethyl)benzamide: $^1$H NMR (400 MHz, d$_6$-DMSO): δ 9.80 (bs, 2H), 9.20-9.12 (m, 1H), 8.86 (bs, 1H), 8.50 (s, 1H), 8.22 (bs, 1H), 7.91-7.86 (m, 1H), 7.60-7.53 (m, 1H), 7.36-7.20 (m, 5H), 4.56-4.48 (m, 2H), 3.40-3.15 (m, 4H), 2.92-2.75 (m, 7H); MS (EI) for $C_{24}H_{28}N_8O$: 445.18 (MH$^+$).

3-{5-Amino-6-[imino(piperidin-1-ylamino)methyl] pyrazin-2-yl}-N-(phenylmethyl)benzamide: $^1$H NMR (400 MHz, d$_6$-DMSO): δ 9.21-9.14 (m, 1H), 8.98 (bs, 1H), 8.73 (s, 1H), 8.53-8.49 (m, 1H), 8.27-8.22 (m, 1H), 7.88-7.83 (m, 1H), 7.58-7.51 (m, 1H), 7.38-7.18 (m, 5H), 6.51 (bs, 2H), 4.56-4.49 (m, 2H), 2.74-2.60 (m, 4H), 1.74-1.62 (m, 4H), 1.50-1.38 (m, 2H); MS (EI) for $C_{24}H_{27}N_7O$: 430.18 (MH$^+$).

3-{5-Amino-6-[(azepan-1-ylamino)(imino)methyl] pyrazin-2-yl}-N-(phenylmethyl)benzamide: $^1$H NMR (400 MHz, d$_6$-DMSO): δ 11.23 (bs, 1H), 9.80 (bs, 1H), 9.17-9.08 (m, 2H), 8.92 (s, 1H), 8.49-8.43 (m, 1H), 8.16-8.08 (m, 1H), 7.92-7.86 (m, 1H), 7.60-7.53 (m, 1H), 7.38-7.05 (m, 6H), 4.57-4.47 (m, 2H), 3.15-2.95 (m, 4H), 1.85-1.55 (m, 8H); MS (EI) for $C_{25}H_{29}N_7O$: 444.20 (MH$^+$).

3-{5-Amino-6-[imino({(2R)-2-[(methyloxy)methyl]pyrrolidin-1-yl}amino)methyl]pyrazin-2-yl}-N-(phenylmethyl) benzamide: $^1$H NMR (400 MHz, d$_6$-DMSO): δ 9.79 (bs, 1H), 9.37 (bs, 1H), 9.16-9.10 (m, 1H), 8.95 (s, 1H), 8.50-8.46 (m, 1H), 8.17-8.10 (m, 1H), 7.92-7.87 (m, 1H), 7.61-7.54 (m, 1H), 7.38-7.18 (m, 5H), 7.04 (bs, 2H), 4.55-4.48 (m, 2H), 3.55-3.48 (m, 2H), 3.42-3.32 (m, 1H), 3.28 (s, 3H), 3.27-3.18 (m, 1H), 2.85-2.74 (m, 1H), 2.10-1.72 (m, 4H), 1.54-1.38 (m, 1H); MS (EI) for $C_{25}H_{29}N_7O_2$: 460.18 (MH$^+$).

3-[5-Amino-6-(imino{2-[4-(trifluoromethyl)pyrimidin-2-yl]hydrazino}methyl)pyrazin-2-yl]-N-(phenylmethyl)benzamide: $^1$H NMR (400 MHz, d$_6$-DMSO): δ 9.25-9.05 (m, 2H), 8.99 (s, 1H), 8.79 (bs, 1H), 8.47-8.43 (m, 1H), 8.14-8.08 (m, 1H), 7.95-7.90 (m, 1H), 7.62-7.41 (m, 4H), 7.39-7.21 (m, 6H), 6.91 (bs, 1H), 4.55-4.50 (m, 2H); MS (EI) for $C_{24}H_{20}N_9OF_3$: 508.09 (MH$^+$).

3-[5-Amino-6-(1,5-diphenyl-1H-1,2,4-triazol-3-yl) pyrazin-2-yl]-N-(phenylmethyl)benzamide: $^1$H NMR (400 MHz, d$_6$-DMSO): δ 9.20-9.13 (m, 1H), 8.84 (s, 1H), 8.56-8.52 (m, 1H), 8.25-8.20 (m, 1H), 7.91-7.85 (m, 1H), 7.60-7.38-7.30 (m, 5H), 7.28-7.22 (m, 1H), 4.55-4.50 (m, 2H); MS (EI) for $C_{32}H_{25}N_7O$: 524.12 (MH$^+$).

3-[5-Amino-6-(1,5-dimethyl-1H-1,2,4-triazol-3-yl) pyrazin-2-yl]-N-(phenylmethyl)benzamide: $^1$H NMR (400 MHz, d$_6$-DMSO): δ 9.21-9.14 (m, 1H), 8.75 (s, 1H), 8.54-8.50 (m, 1H), 8.22-8.17 (m, 1H), 7.90-7.85 (m, 1H), 7.62-7.55 (m, 2H), 7.40-7.20 (m, 6H), 4.57-4.50 (m, 2H), 3.94 (s, 3H), 2.55 (s, 3H); MS (EI) for $C_{22}H_{21}N_7O$: 400.16 (MH$^+$).

3-[5-Amino-6-(1-methyl-5-phenyl-1H-1,2,4-triazol-3-yl) pyrazin-2-yl]-N-(phenylmethyl)benzamide: $^1$H NMR (400 MHz, d$_6$-DMSO): δ 9.22-9.13 (m, 1H), 8.79 (s, 1H), 8.56-8.52 (m, 1H), 8.24-8.19 (m, 1H), 7.95-7.86 (m, 3H), 7.68-7.51 (m, 5H), 7.40-7.21 (m, 6H), 4.57-4.48 (m, 2H), 4.13 (s, 3H); MS (EI) for $C_{27}H_{23}N_7O$: 462.11 (MH$^+$).

3-{5-Amino-6-[imino(2-pyridin-2-ylhydrazino)methyl] pyrazin-2-yl}-N-(phenylmethyl)benzamide: $^1$H NMR (400 MHz, d$_6$-DMSO): δ 9.46 (bs, 1H), 9.26-9.19 (m, 1H), 8.74 (s, 1H), 8.59-8.55 (m, 1H), 8.36-8.30 (m, 1H), 8.16-8.12 (m, 1H), 7.91-7.86 (m, 1H), 7.70-7.62 (m, 1H), 7.60-7.53 (m, 1H), 7.40-7.32 (m, 4H), 7.30-7.22 (m, 1H), 6.90-6.82 (m, 1H), 6.79-6.70 (m, 3H), 4.59-4.53 (m, 2H); MS (EI) for $C_{24}H_{22}N_8O$: 439.15 (MH⁺).

3-[5-Amino-6-(1-methyl-5-piperidin-2-yl-1H-1,2,4-triazol-3-yl)pyrazin-2-yl]-N-(phenylmethyl)benzamide: ¹H NMR (400 MHz, d₆-DMSO): δ 9.42-9.23 (m, 2H), 9.21-9.13 (m, 1H), 8.79 (s, 1H), 8.52-8.48 (m, 1H), 8.20-8.14 (m, 1H), 7.92-7.86 (m, 1H), 7.68-7.54 (m, 2H), 7.39-7.31 (m, 4H), 7.30-7.22 (m, 1H), 4.92-4.81 (m, 1H), 4.57-4.49 (m, 2H), 4.06 (s, 3H), 3.22-3.02 (m, 2H), 2.23-2.14 (m, 1H), 1.95-1.60 (m, 5H); MS (EI) for $C_{26}H_{28}N_8O$: 469.17 (MH⁺).

3-[5-Amino-6-(5-methyl-1-pyridin-2-yl-1H-1,2,4-triazol-3-yl)pyrazin-2-yl]-N-(phenylmethyl)benzamide: ¹H NMR (400 MHz, d₆-DMSO): δ 9.22-9.15 (m, 1H), 8.82 (s, 1H), 8.66-8.61 (m, 1H), 8.56-8.53 (m, 1H), 8.25-8.20 (m, 1H), 8.17-8.11 (m,1H), 8.10-8.05 (m, 1H), 7.92-7.87 (m, 1H), 7.63-7.52 (m, 4H), 7.39-7.31 (m, 4H), 7.29-7.22 (m, 1H), 4.57-4.50 (m, 2H), 2.90 (s, 3H); MS (EI) for $C_{26}H_{22}N_8O$: 463.15 (MH⁺).

3-{5-Amino-6-[(2-ethylhydrazino)(imino)methyl]pyrazin-2-yl}-N-(2,3-dihydro-1H-inden-1-yl)benzamide: ¹H NMR (400 MHz, d₄-MeOH): δ 8.8 (s, 1H), 8.7 (s, 1H), 8.2 (m, 1H), 7.80 (m, 1H), 7.4 (m, 2H), 7.2 (m, 3H), 5.8 (m, 1H), 2.8 (m, 2.4 (m, 2H), 2.0 (m, 2H), 1.5 (m, 3H). MS (EI) for $C_{23}H_{25}N_7O$: 416 (MH⁺).

3-{5-Amino-6-[imino(2-methylhydrazino)methyl]pyrazin-2-yl}-N-[(1S)-2,3-dihydro-1H-inden-1-yl]benzamide: ¹H NMR (400 MHz, d₆-DMSO): δ 8.96-8.91 (m, 1H), 8.64 (s, 1H), 8.53-8.50 (m, 1H), 8.30-8.24 (m, 1H), 7.92-7.87 (m, 1H), 7.58-7.52 (m, 1H), 7.32-7.17 (m, 4H), 6.03 (s, 2H), 5.67-5.58 (m, 1H), 5.26 (s, 1H), 3.08-2.96 (m, 1H), 2.94-2.85 (m, 1H), 2.84 (s, 3H), 2.50-2.44 (m, 1H), 2.07-1.99 (m, 1H). MS (EI) for $C_{22}H_{23}N_7O$: 402 (MH⁺).

3-{5-Amino-6-[imino(2-phenylhydrazino)methyl]pyrazin-2-yl}-N-[(1S)-2,3-dihydro-1H-inden-1-yl]benzamide: ¹H NMR (400 MHz, d₆-DMSO): δ 9.00-8.91 (m, 1H), 8.78-8.68 (m, 1H), 8.57-8.53 (m, 1H), 8.36-8.30 (m, 1H), 7.95-7.89 (m, 1H), 7.61-7.52 (m, 1H), 7.33-7.14 (m, 5H), 6.99-6.93 (m, 2H), 6.78-6.71 (m, 1H), 6.50 (s, 2H), 5.68-5.57 (m, 1H), 3.08-2.96 (m, 1H), 2.95-2.82 (m, 1H), 2.56-2.46 (m, 1H), 2.10-1.97 (m, 1H). MS (EI) for $C_{27}H_{25}N_7O$: 464 (MH⁺).

Phenylmethyl 3-{3-[3-amino-6-(3-{[(1S)-2,3-dihydro-1H-inden-1-ylamino]carbonyl}phenyl)pyrazin-2-yl]-1-methyl-1H-1,2,4-triazol-5-yl}piperidine-1-carboxylate: ¹H NMR (400 MHz, d₆-DMSO): δ 8.93-8.88 (m, 1H), 8.74 (s, 1H), 8.53-8.49 (m, 1H), 8.20-8.14 (m, 1H), 7.93-7.85 (m, 1H), 7.61-7.54 (m, 1H), 7.42-7.15 (m, 11H), 5.67-5.57 (m, 1H), 5.10 (s, 2H), 4.18-3.88 (m, 6H), 2.12-1.93 (m, 2H), 1.88-1.70 (m, 2H), 1.64-1.42 (m, 2H). MS (EI) for $C_{36}H_{36}N_8O_3$: 629 (MH⁺).

Phenylmethyl 3-{3-[3-amino-6-(3-{[(1S)-2,3-dihydro-1H-inden-1-ylamino]carbonyl}phenyl)pyrazin-2-yl]-1-ethyl-1H-1,2,4-triazol-5-yl}piperidine-1-carboxylate: ¹H NMR (400 MHz, d₄-MeOH): δ 8.8 (s, 1H), 8.7 (s, 1H), 8.2 (m, 1H), 7.80 (m, 1H), 7.4 (m, 2H), 7.3 (m, 5H), 7.2 (m, 3H), 5.8 (m, 1H), 2.8 (m, 2H), 2.4 (m, 2H), 2.2-3.2 (m, 7H), 1.8-2.0 (m, 9H). MS (EI) for $C_{37}H_{38}N_8O_3$: 643 (MH⁺).

3-Amino-6-bromo-N'-pyridin-2-ylpyrazine-2-carboximidohydrazide: ¹H NMR (400 MHz, d₆-DMSO): δ 9.00 (s, 1H), 8.95 (m, 1H), 8.55 (s, 1H), 8.10 (d, 1H), 7.95 (d, 1H), 7.50 (m, 3H), 7.30-7.10 (m, 4H), 5.60 (m, 2H), 3.0-2.8 (m, 2H), 2.40 (m, 1H), 2.00 (m, 1H). MS (EI) for $C_{10}H_{10}BrN_7$: 356(MH⁺).

3-[5-Amino-6-(1-ethyl-5-piperidin-3-yl-1H-1,2,4-triazol-3-yl)pyrazin-2-yl]-N-(2,3-dihydro-1H-inden-1-yl)benzamide: ¹H NMR (400 MHz, d₄-MeOH): δ 8.8 (s, 1H), 8.7 (s, 1H), 8.2 (m, 1H), 7.80 (m, 1H), 7.4 (m, 2H), 7.2 (m, 3H), 5.8 (m, 1H), 2.8 (m, 2H), 2.4 (m, 2H), 2.2-3.2 (m, 5H), 1.8-2.0 (m, 9H). MS (EI) for $C_{29}H_{32}N_8O$: 509 (MH⁺).

3-[5-Amino-6-(1-methyl-5-piperidin-3-yl-1H-1,2,4-triazol-3-yl)pyrazin-2-yl]-N-[(1S)-2,3-dihydro-1H-inden-1-yl]benzamide: ¹H NMR (400 MHz, d₄-MeOH): δ 8.57-8.49 (m, 2H), 8.12-8.05 (m, 1H), 7.89-7.82 (m, 1H), 7.54-7.46 (m, 1H), 7.28-7.06 (m, 4H), 5.67-5.56 (m, 1H), 3.96 (s, 3H), 3.57-3.24 (m, 3H), 3.10-2.87 (m, 3H), 2.60-2.46 (m, 1H), 2.15-1.40 (m, 6H). MS (EI) for $C_{28}H_{30}N_8O$: 495 (MH⁺).

3-{5-Amino-6-[imino(2-pyridin-4-ylhydrazino)methyl]pyrazin-2-yl}-N-(2,3-dihydro-1H-inden-1-yl)benzamide: ¹H NMR (400 MHz, d₆-DMSO): δ 10.9 (s, 1H), 8.95 (m, 2H), 8.55 (s, 1H), 8.30-8.10 (m, 3H), 7.95-7.00 (m, 10H), 5.60 (m, 2H), 3.0-2.8 (m, 2H), 2.40 (m, 1H), 2.00 (m, 1H). MS (EI) for $C_{26}H_{24}N_8O$: 465 (MH⁺).

Phenylmethyl 3-[3-(3-amino-6-bromopyrazin-2-yl)-1-pyridin-2-yl-1H-1,2,4-triazol-5-yl]piperidine-1-carboxylate: ¹H NMR (400 MHz, d₄-MeOH): δ 8.20 (s, 1H), 7.40-7.20 (m, 9H), 5.10 (m, 2H), 4.00-3.60 (m, 4H), 3.2 (m, 1H), 2.0-1.40 (m, 4H). MS (EI) for $C_{24}H_{23}BrN_8O_8$: 536 (MH⁺).

Phenylmethyl (3R)-3-{3-[3-amino-6-(3-{[(1S)-2,3-dihydro-1H-inden-1-ylamino]carbonyl}phenyl)pyrazin-2-yl]-1-ethyl-1H-1,2,4-triazol-5-yl}piperidine-1-carboxylate: ¹H NMR (400 MHz, d₄-MeOH): δ 8.8 (s, 1H), 8.7 (s, 1H), 8.2 (m, 1H), 7.80 (m, 1H), 7.4 (m, 2H), 7.3 (m, 5H), 7.2 (m, 3H), 5.8 (m, 1H), 2.8 (m, 2H), 2.4 (m, 2H), 2.2-3.2 (m, 7H), 1.8-2.0 (m, 9H). MS (EI) for $C_{37}H_{38}N_8O_3$: 643 (MH⁺).

3-(5-Amino-6-(1-ethyl-5-[(3R)-piperidin-3-yl]-1H-1,2,4-triazol-3-yl}pyrazin-2-yl)-N-[(1S)-2,3-dihydro-1H-inden-1-yl]benzamide: ¹H NMR (400 MHz, d₄-MeOH): δ 8.8 (s, 1H), 8.7 (s, 1H), 8.2 (m, 1H), 7.80 (m, 1H), 7.4 (m, 2H), 7.2 (m, 3H), 5.8 (m, 1H), 2.8 (m, 2H), 2.4 (m, 2H), 2.2-3.2 (m, 5H), 1.8-2.0 (m, 9H). MS (EI) for $C_{29}H_{32}N_8O$: 509 (MH⁺).

Phenylmethyl (3R)-3-{3-[3-amino-6-(3-{[(1S)-2,3-dihydro-1H-inden-1-ylamino]carbonyl}phenyl)pyrazin-2-yl]-1-methyl-1H-1,2,4-triazol-5-yl}piperidine-1-carboxylate ¹H NMR (400 MHz, d₄-MeOH): δ 8.95 (m, 1H), 8.60 (m, 1H), 8.20 (d, 1H), 7.95 (d, 1H), 7.60 (m, 1H), 7.40-7.20 (m, 9H), 5.65 (m, 1H), 5.20 (m, 2H), 4.2-3.8 (m, 4H), 3.20-2.80 (m, 5H), 2.60, (m, 1H), 2.20-1.60 (m, 5H). MS (EI) for $C_{36}H_{36}N_8O_3$: 629 (MH⁺).

3-[5-Amino-6-(5-{2-[(phenylmethyl)oxy]ethyl}-1H-1,2,4-triazol-3-yl)pyrazin-2-yl]-N-[(1S)-2,3-dihydro-1H-inden-1-yl]benzamide: ¹H NMR (400 MHz, d₄-MeOH): δ 8.8 (s, 1H), 8.7 (s, 1H), 8.2 (m, 1H), 7.80 (m, 1H), 7.4 (m, 2H), 7.25 (m, 5H), 7.2 (m, 3H), 5.8 (m, 1H), 3.0 (m, 4H), 2.8 (m, 2H), 2.4 (m, 2H), 2.0 (m, 2H). MS (EI) for $C_{31}H_{29}N_7O_2$: 532 (MH⁺).

3-[5-Amino-6-(1-phenyl-5-piperidin-3-yl-1H-1,2,4-triazol-3-yl)pyrazin-2-yl]-N-[(1S)-2,3-dihydro-1H-inden-1-yl]benzamide: ¹H NMR (400 MHz, d₄-MeOH): δ 8.72-8.61 (m, 2H), 8.22-8.17 (m, 1H), 7.97-7.91 (m, 1H), 7.70-7.56 (m, 6H), 7.36-7.15 (m, 4H), 5.76-5.66 (m, 1H), 3.58-3.46 (m, 2H), 3.15-2.86 (m, 4H), 2.68-2.57 (m, 1H), 2.15-1.75 (m, 6H). MS (EI) for $C_{33}H_{32}N_8O$: 557 (MH⁺).

3-{5-Amino-6-[amino(imino)methyl]pyrazin-2-yl}-N-[(1S)-2,3-dihydro-1H-inden-1-yl]benzamide: ¹H NMR (400 MHz, d₆-DMSO): δ 8.95 (m, 2), 8.50 (s, 1H), 8.20 (d, 1H), 7.95 (d, 1H), 7.60 (m, 1H), 7.40-7.20 (m, 4H), 5.60 (m, 1H), 3.20-2.80 (m, 2H), 2.20-2.00 (m, 2H). MS (EI) for $C_{21}H_{20}N_6O$: 373 (MH⁺).

3-[5-Amino-6-(5-methyl-1-pyridin-4-yl-1H-1,2,4-triazol-3-yl)pyrazin-2-yl]-N-[(1S)-2,3-dihydro-1H-inden-1-yl]benzamide: ¹H NMR (400 MHz, d₆-DMSO): δ 9.00-8.90 (m, 3H), 8.50 (s, 1H), 8.20 (d, 1H), 7.95 (m, 2H), 7.60 (m, 2H), 7.40-7.20 (m, 4H), 5.60 (m, 1H), 3.20-2.80 (m, 2H), 2.75 (s, 3H), 2.20-2.00 (m, 2H). MS (EI) for $C_{28}H_{24}N_8O$: 489 (MH⁺).

3-[5-Amino-6-(1,5-dimethyl-1H-1,2,4-triazol-3-yl)pyrazin-2-yl]-N-[(1S)-2,3-dihydro-1H-inden-1-yl]benzamide: $^1$H NMR (400 MHz, d$_4$-MeOH): δ 8.75 (m, 2H), 8.20 (d, 1H), 7.95 (d, 1H), 7.60 (m, 1H), 7.40-7.20 (m, 4H), 5.70 (m, 1H), 4.00 (s, 3H), 3.20-2.80 (m, 2H), 2.60 (s, 3H), 2.20-2.00 (m, 2H). MS (EI) for C$_{24}$H$_{23}$N$_7$O: 426 (MH$^+$).

3-[5-Amino-6-(1-pyridin-4-yl-1H-1,2,4-triazol-3-yl)pyrazin-2-yl]-N-[(1S-2,3-dihydro-1H-inden-1-yl]benzamide: $^1$H NMR (400 MHz, d$_4$-MeOH): δ 9.00 (s, 1H), 8.95 (m, 1H), 8.60 (s, 1H), 8.25 (d, 1H), 8.20-8.00 (m, 3H), 7.90-7.60 (m, 4H), 7.40-7.00 (m, 3H), 5.80 (m, 1H), 3.20-2.60 (m, 3H), 2.20-2.00 (m, 1H). MS (EI) for C$_{27}$H$_{22}$N$_8$O: 475 (MH$^+$).

Example 71

Scheme 27 depicts another strategy for making exemplary compounds according to formula I where A is a pyrimidine. Weirireb's amide intermediates (cix) were converted to α,β-unsaturated intermediates (cx), which were coupled with amindines and the intermediates cyclized to form pyrimidines (cxi). Intermediate (cix) can also be used to make other heterocycles for A, according to formula I.

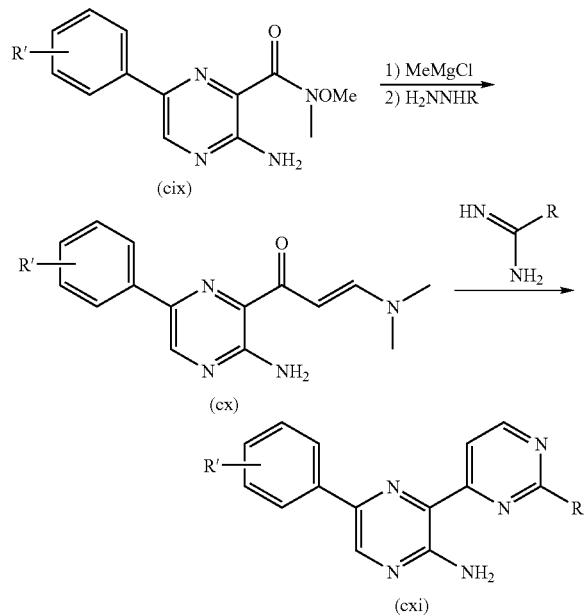

3-[5-Amino-6-(2-aminopyrimidin-4-yl)pyrazin-2-yl]-N-(phenylmethyl)benzamide: To a THF (50 mL) solution of 3-amino-6-{3-[(benzylamino)carbonyl]phenyl}-N-methoxy-N-methylpyrazine-2-carboxamide (1.0 g, 2.6 mmol) was added 3.0 M methylmagnesium chloride in THF (6.1 mL, 18 mmol) and the mixture was stirred for 3 h. Saturated ammonium chloride was added and the mixture was extracted 3× with ethyl acetate. The combined organic layers were dried over sodium sulfate, filtered, and concentrated under reduced pressure. The crude product was purified by silica gel chromatography to afford the pure methyl ketone (0.400 g, 45% yield). This material was dissolved in ethanol (20 mL), dimethylformamide dimethyl acetal (2 mL, 15 mmol) was added and the mixture was heated to reflux for 90 min. LCMS analysis showed desired product and complete consumption of starting material. The reaction mixture was concentrated under reduced pressure and redissolved in ethanol (10 mL). Guanidine (0.364 g, 2.0 mmol) was added followed by potassium carbonate (0.80 g, 5.8 mmol). The mixture was heated in a sealed tube at 80° C. overnight. The mixture was transferred to a round-bottomed flask and concentrated under reduced pressure. Water (100 mL) was added and the residue was extracted with ethyl acetate (3×100 mL). The combined organic fractions were washed with water, dried over anhydrous sodium sulfate, filtered and concentrated under reduced pressure to give the desired product (0.103 g, 45% yield). $^1$H NMR (400 MHz, d$_6$-DMSO): δ 9.22 (br s, 1H), 8.86 (s, 1H), 8.56 (m, 1H), 8.40 (d, 1H), 8.25 (d, 1H), 7.90 (d, 1H), 7.71 (d, 1H), 7.59 (t, 1H), 7.52 (br s, 1H), 7.36 (m, 4H), 7.26 (m, 1H), 7.01 (br s, 1H), 4.53 (m, 3H). MS (EI) for C$_{22}$H$_{19}$N$_7$O: 398 (MH$^+$).

Using the same or similar synthetic techniques, substituting with the appropriate reagents such as the respective amines, the following compounds of the invention were prepared:

3-{5-Amino-6-[2-(dimethylamino)pyrimidin-4-yl]pyrazin-2-yl}-N-(phenylmethyl)benzamide: $^1$H NMR (400 MHz, d$_6$-DMSO): δ 9.20 (t, 1H), 8.80 (s, 1H), 8.57 (s, 1H), 8.54 (d, 1H), 8.26 (d, 1H), 7.90 (d, 1H), 7.75 (d, 1H), 7.59 (t, 1H), 7.36 (m, 4H), 7.26 (m, 1H), 4.58 (m, 1H), 4.54 (d, 2H), 3.20 (s, 6H). MS (EI) for C$_{24}$H$_{23}$N$_7$O: 426 (MH$^+$).

3-[5-Amino-6-(2-methylpyrimidin-4-yl)pyrazin-2-yl]-N-(phenylmethyl)benzamide: $^1$H NMR (400 MHz, d$_6$-DMSO): δ 9.20 (t, 1H), 8.92 (s, 1H), 8.88 (d, 1H), 8.59 (s, 1H), 8.43 (d, 1H), 8.39, (m, 1H), 8.30 (d, 1H), 7.92 (d, 1H), 7.60 (t, 1H), 7.36 (m, 5H), 7.28 (m, 1H), 4.58 (t, 1H), 4.54 (d, 2H), 2.77 (s, 3H). MS (EI) for C$_{23}$H$_{20}$N$_6$O: 397 (MH$^+$).

3-{5-Amino-6-[2-(methylamino)pyrimidin-4-yl]pyrazin-2-yl}-N-(phenylmethyl)benzamide: $^1$H NMR (400 MHz, d$_6$-DMSO): δ 9.20 (br s, 1H), 8.86 (m, 1H), 8.56 (m, 1H), 8.45 (m, 1H), 8.25 (m, 1H), 7.89 (m, 1H), 7.72 (m, 1H), 7.60 (m, 1H), 7.35 (m, 4H), 7.27 (m, 2H), 4.54 (m, 3H), 2.87 (m, 3H). MS (EI) for C$_{23}$H$_{21}$N$_7$O: 412 (MH$^+$).

Example 72

Scheme 28 depicts another strategy for making exemplary compounds according to formula I where W is a substituted phenylene. Analogous to dimerization described in Example 51, Scheme 17, above, intermediates (cxiii) were prepared by coupling aryl halides such as (cxii) to appropriate pyrazines, as depicted. In this example, mono-saponification of the esters and thus selective amide formation gave compounds (cxiv). The saponification process was repeated to make compounds (cxv).

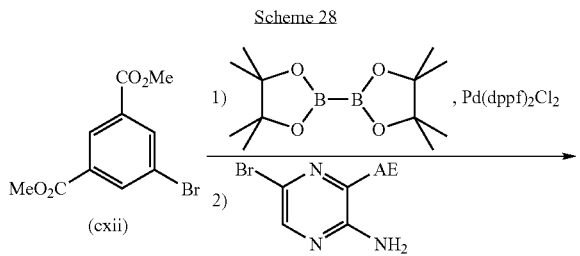

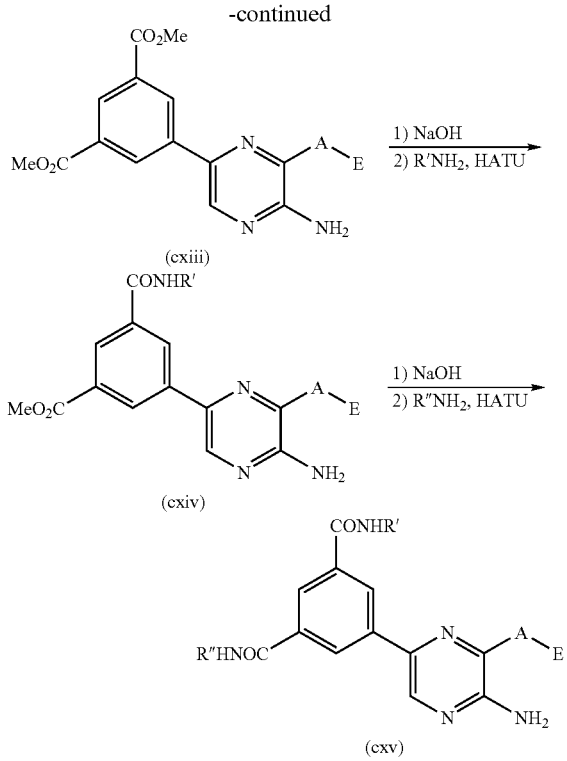

Dimethyl 5-{5-amino-6-[(methyloxy)carbonyl]pyrazin-2-yl}benzene-1,3-dicarboxylate: A mixture containing 5-bromoisophthalic acid dimethyl ester (0.20 g, 0.73 mmol), bispinacolatodiboron (0.21 g, 0.80 mmol), 1,1'-bis(diphenylphosphine)ferrocene palladium dichloride (0.029 g, 0.035 mmol), and potassium acetate (0.26 g, 2.3 mmol) in dioxane (5 mL) was heated at 80° C. for 1 h. The reaction mixture was cooled to room temperature and methyl 3-amino-6-bromo-pyrazine-2-carboxylate (0.17 mg, 0.70 mmol), 1,1'-bis(diphenylphosphine)ferrocene palladium dichloride (0.035 g, 0.042 mmol), sodium bicarbonate (320 mg, 3.8 mmol), and water (1 mL) were added. The mixture was heated at 80° C. for 12 h, after which time, the mixture was diluted with water and ethyl acetate. The layers were separated and the organic layer was extracted with 1 N hydrochloric acid (2×) and dried over sodium sulfate. Filtration, concentration, and silica gel chromatography gave the product as a yellow solid (23 mg, 12% yield). $^1$H NMR (400 MHz, $d_6$-DMSO): δ 9.04 (s, 1H), 8.74 (d, 2H), 8.44 (t, 1H), 7.62 (s, 2H), 3.32 (s, 3H), 2.49 (s, 3H), 2.48 (s, 3H). MS (EI) for $C_{16}H_{15}N_3O_6$: 346 (MH$^+$).

3-{5-Amino-6-[(methylamino)carbonyl]pyrazin-2-yl}-5-[(methyloxy)carbonyl]benzoic acid: A mixture containing dimethyl 5-{5-amino-6-[(methylamino)carbonyl]pyrazin-2-yl}benzene-1,3-dicarboxylate (1.1 g, 3.2 mmol) and aqueous sodium hydroxide (3 mL of a 1N solution) was heated in dioxane (100 mL) at 95° C. for 3 h. The mixture was diluted with 1 N aqueous hydrochloric acid (300 mL) and extracted with ethyl acetate (3×300 mL) and saturated ammonium chloride solution and dried over sodium sulfate. Filtration, concentration and purification by reverse phase HPLC gave the product as a yellow solid (0.39 g, 37% yield). $^1$H NMR (400 MHz, $d_6$-DMSO): δ 8.83 (s, 1H), 8.78 (d, 1H), 8.70 (d, 2H), 8.39 (t, 1H), 7.69 (br, 2H), 6.47 (br, 1H), 3.87 (s, 3H), 2.79 (d, 3H). MS (EI) for $C_{15}H_{14}N_4O_5$: 331 (MH$^+$).

Methyl 3-{5-amino-6-[(methylamino)carbonyl]pyrazin-2-yl}-5-{[(1S)-2,3-dihydro-1H-inden-1-ylamino]carbonyl}benzoate: A mixture containing 3-{5-amino-6-[(methylamino)carbonyl]pyrazin-2-yl}-5-[(methyloxy)carbonyl]benzoic acid (0.34 g, 1.0 mmol), O-(7-azabenzotriazol-1-yl)-N,N,N',N'-tetramethyluroniumhexafluorophosphate (0.51 g, 1.6 mmol), (S)-(+)-1-aminoindan (0.17 g, 1.3 mmol), diisopropylethylamine (0.6 mL, 3.4 mmol) and DMF (70 mL) were stirred at room temperature for 12 h. The reaction mixture was diluted with water and extracted 3' with ethyl acetate and 3× with 5% aqueous lithium chloride, and dried over sodium sulfate. Filtration, concentration, and purification by reverse phase HPLC gave the product as a yellow solid (0.41 g, 90% yield). $^1$H NMR (400 MHz, $d_6$-DMSO): δ 9.09 (d, 1H), 8.91 (s, 1H), 8.83 (d, 1H), 8.75 (t, 1H), 8.70 (t, 1H), 8.45 (t, 1H), 7.73 (br, 2H), 7.28 (d, 2H), 7.24-7.17 (m, 2H), 5.64-5.58 (q, 1H), 3.91 (s, 3H), 3.04-3.00 (m, 1H), 3.00-2.87 (m, 1H), 2.83 (d, 3H), 2.53-2.51 (m, 1H), 2.06-1.96 (m, 1H). MS (EI) for $C_{24}H_{23}N_5O_4$: 446 (MH$^+$).

3-Amino-6-{3-[(2,3-dihydro-1H-inden-1-ylamino)carbonyl]-4-fluorophenyl}-N-methylpyrazine-2-carboxamide: A solution of methyl 2-fluoro-5-iodobenzoate (0.41 g, 1.5 mmol), bispinacolatodiboron (0.41 g, 1.6 mmol), Pd(dppfCl$_2$).CH$_2$Cl$_2$ (180 mg, 0.22 mmol) and potassium acetate (0.43 g, 4.4 mmol) was heated at 80° C. in dioxane (50 mL) for 48 h. To this solution was added 3-amino-6-bromo-N-methylpyrazine-2-carboxamide (0.35 g, 1.5 mmol), additional Pd(dppfCl$_2$).CH$_2$Cl$_2$ (0.2 g, 0.2 mmol), sodium bicarbonate (0.5 g, 6 mmol), and water (5 mL) and the resulting solution was heated at 90° C. for an additional 16 h. The cooled solution was filtered through celite and concentrated under reduced pressure. Dichloromethane (100 mL) was added to the residue, which was washed with water, brine, and dried over anhydrous sodium sulfate. Filtration, concentration and silica gel chromatography gave the biaryl product (0.24 g, 54% yield) as a light yellow solid. A solution of this material and lithium hydroxide (160 mg, 3.8 mmol) in dioxane (60 mL) and water (5 mL) was heated at 70° C. for 6 h. To the cooled solution was added 1M aqueous HCl and the reaction was concentrated to approximately 10 mL. The resulting solid was filtered and dried to yield the carboxylic acid (0.22 g, 97% yield) as a yellow solid. To a solution of this material, (S)-(+)-aminoindane (107 mg, 0.8 mmol) and Hunig's base (0.7 mL, 4 mmol) in DMF (10 mL) was added HATU (0.38 g, 1.0 mmol) and the solution was stirred at room temperature for 4 h. Ethyl acetate (50 mL) was added to the solution and it was washed with a 5% aqueous solution of lithium chloride (3×50 mL) and brine, dried over anhydrous sodium sulfate, filtered, and concentrated under reduced pressure to yield a residue that was purified by silica gel chromatography to yield the desired product as a pale yellow solid (64 mg, 20% yield). $^1$H NMR (400 MHz, CDCl$_3$): δ 8.69-8.66 (m, 2H), 8.38 (m, 1H), 7.99-7.95 (m, 2H), 7.40-7.02 (m, 7H), 5.77-5.75 (m, 1H), 3.07-2.75 (m, 6H), 1.99-195 (m, 1H). MS (EI) for $C_{22}H_{20}FN_5O_2$: 406 (MH$^+$).

Using the same or similar synthetic techniques, substituting with the appropriate reagents such as the respective amines, the following compounds of the invention were prepared:

3-Amino-6-{3-[(2,3-dihydro-1H-inden-1-ylamino)carbonyl]-5-fluorophenyl}-N-methylpyrazine-2-carboxamide: $^1$H NMR (400 MHz, $d_6$-DMSO): δ 8.96-8.93 (m, 3H), 8.39-8.29 (m, 2H), 7.66-7.64 (m, 1H), 7.29-7.19 (m, 4H), 5.59 (m, 1H), 3.34-2.84 (m, 6H), 2.03-1.98 (m, 1H). MS (EI) for $C_{22}H_{20}FN_5O_2$: 406 (MH$^+$).

Dimethyl 5-{5-amino-6-[(methylamino)carbonyl]pyrazin-2-yl}benzene-1,3-dicarboxylate: $^1$H NMR (400 MHz, $d_6$-DMSO): δ 8.85 (s, 1H), 8.79 (d, 1H), 8.73-8.72 (m, 2H), 8.39-8.38 (m, 1H), 7.75 (br, 1H), 3.87 (s, 6H), 3.82 (br, 1H), 2.79 (d, 3H). MS (EI) for $C_{16}H_{16}N_4O_5$: 345 (MH$^+$).

1,1-Dimethylethyl (3S)-3-{[(3-amino-6-{3-[(2,3-dihydro-1H-inden-1-ylamino)sulfonyl]phenyl}pyrazin-2-yl)carbonyl]amino}pyrrolidine-1-carboxylate: $^1$H NMR (400 MHz, $d_6$-DMSO): δ 8.80 (s, 1H), 8.59 (d, 1H), 8.40-8.38 (m, 2H), 8.08 (br, 1H), 7.79 (t, 1H), 7.67 (br, 1H), 7.66-7.62 (m, 2H), 7.10-7.04 (m, 4H), 4.70 (t, 1H), 4.43-4.39 (m, 1H), 3.56-3.47 (m, 1H), 3.40-3.34 (m, 1H), 3.24-3.17 (m, 2H), 2.76-2.70 (m, 1H), 2.69-2.53 (m, 1H), 2.04-1.89 (m, 3H), 1.63-1.54 (m, 1H), 1.33 (s, 9H). MS (EI) for $C_{29}H_{34}N_6O_5S$: 577 (MH$^-$).

3-Amino-6-{3-[(2,3-dihydro-1H-inden-1-ylamino)sulfonyl]phenyl}-N-[(3S)-pyrrolidin-3-yl]pyrazine-2-carboxamide: $^1$H NMR (400 MHz, $d_6$-DMSO): δ 8.86 (s, 1H), 8.69-8.68 (m, 1H), 8.50-8.47 (m, 2H), 7.85 (d, 1H), 7.75 (br s, 1H), 7.70 (t, 2H), 7.14 (d, 4H), 4.77 (t, 1H), 4.41 (br s, 1H), 3.10-2.99 (m, 2H), 2.86-2.76 (m, 3H), 2.68-2.60 (m, 1H), 2.49 (s, 2H), 2.09-2.03 (m, 2H), 1.83-1.75 (m, 1H), 1.70-1.61 (m, 1H). MS (EI) for $C_{24}H_{26}N_6O_3S$: 477 (MH$^+$).

1,1-Dimethylethyl-3-{[[(3-{5-amino-6-[(methylamino)carbonyl]pyrazin-2-yl}-5-{[(1R)-2,3-dihydro-1H-inden-1-ylamino]carbonyl}phenyl)carbonyl]amino}pyrrolidine-1-carboxylate: $^1$H NMR (400 MHz, $d_6$-DMSO): δ 8.95 (d, 1H), 8.88 (s, 1H), 8.80 (d, 1H), 8.72 (d, 1H), 8.59 (d, 1H), 8.53 (s, 1H), 8.26 (s, 1H), 7.73 (br, 2H), 7.20-7.12 (m, 2H), 5.55 (q, 1H), 4.40 (m, 1H), 3.55-3.50 (m, 1H), 3.42-3.35 (m, 1H), 3.25-3.18 (m, 1H), 2.99-2.82 (m, 1H), 2.60 (m, 1H), 2.46-2.44 (m, 1H), 2.43 (s, 3H), 2.43-2.26 (m, 1H), 2.10-1.88 (m, 3H), 1.34 (s, 9H). MS (EI) for $C_{32}H_{37}N_7O_5$: 598 (MH$^-$).

5-{5-Amino-6-[(methylamino)carbonyl]pyrazin-2-yl}-N-[(1S)-2,3-dihydro-1H-inden-1-yl]-N'-pyrrolidin-3-ylbenzene-1,3-dicarboxamide: $^1$H NMR (400 MHz, $d_6$-DMSO): δ 9.02 (d, 1H), 8.93 (s, 1H), 8.84-8.80 (m, 4H), 8.67 (t, 1H), 8.60 (t, 1H), 8.33 (t, 1H), 7.77 (br s, 2H), 7.28 (d, 2H), 7.24-7.17 (m, 2H), 5.60 (q, 1H), 4.57-4.51 (m, 1H), 3.39 (m, 1H), 3.32-3.21 (m, 2H), 3.04-2.98 (m, 1H), 2.91-2.87 (m, 1H), 2.84 (d, 3H), 2.50 (m, 1H), 2.27-2.18 (m, 1H), 2.10-1.89 (s, 2H). MS (EI) for $C_{27}H_{29}N_7O_3$: 500 (MH$^+$).

5-{5-Amino-6-[(methylamino)carbonyl]pyrazin-2-yl}-N-(2,3-dihydro-1H-inden-1-yl)-N'-pyrrolidin-3-ylbenzene-1,3-dicarboxamide: $^1$H NMR (400 MHz, $d_6$-DMSO): δ 9.02 (d, 1H), 8.93 (s, 1H), 8.85-8.21 (m, 4H), 8.67 (t, 1H), 8.61 (t, 1H), 8.34 (t, 1H), 7.28 (d, 2H), 7.24-7.19 (m, 2H), 7.56 (br, 2H), 5.60 (q, 1H), 4.56-4.50 (m, 1H), 3.50-3.35 (m, 2H), 3.32-3.18 (m, 2H), 3.04-3.97 (m, 1H), 2.91-2.87 (m, 1H), 2.84 (d, 3H), 2.27-2.18 (m, 1H), 2.10-2.96 (m, 2H). MS (EI) for $C_{27}H_{29}N_7O_3$: 500 (MH$^+$).

Example 73

Scheme 29 depicts another strategy for making exemplary compounds according to formula I where W is a substituted phenylene, specifically where W possessed a phenolic group and it was desirable to selectively alkylate the phenolic oxygen. Compounds (cxvii) were prepared by coupling phenols with, for example, alkyl bromides, as depicted.

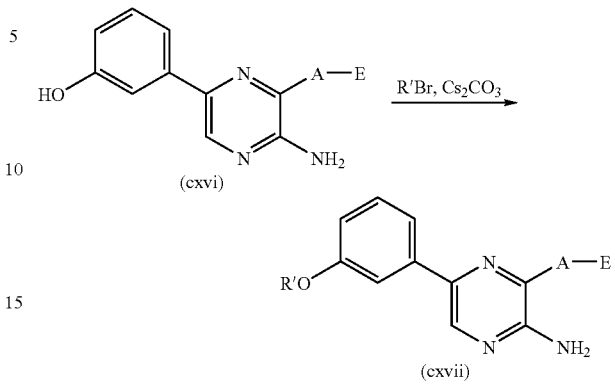

Scheme 29

3-Amino-6-(3-{[2-(4-phenylpiperazin-1-yl)ethyl]oxy}phenyl)-N-[(3S)-piperidin-3-yl]pyrazine-2-carboxamide: A mixture of 3-amino-6-(3-hydroxyphenyl)-N-[(3S)-piperidin-3-yl]pyrazine-2-carboxamide (0.11 g, 0.27 mmol), 1,2-dibromoethane (4 mL, 46 mmol), and cesium carbonate (0.35 g, 1.1 mmol) in DMF (2 mL) was heated at 80° C. for 12 h. The reaction mixture was cooled to room temperature, diluted with 1 N aqueous hydrochloric acid solution, and extracted 3× with ethyl acetate, 2× with 5% aqueous lithium chloride, and dried over sodium sulfate. Filtration, concentration, and silica gel chromatography gave the corresponding ether. A mixture of this ether intermediate (0.012 g, 0.023 mmol) and N-phenylpiperazine (4.4 mg, 0.027 mmol) was stirred in acetonitrile (5 mL) at room temperature for 3 h. Concentration followed by reverse phase HPLC gave the protected product as a yellow solid. This solid was added to 4 N hydrochloric acid in dioxane (5 mL) and the mixture was stirred at room temperature for 1 h. Removal of solvent under reduced pressure gave the desired product as a yellow solid (3.2 mg, 28% yield). 1H NMR (400 MHz, $d_6$-DMSO): δ 9.10 (br s, 1H), 8.88 (s, 1H), 8.71 (br, 1H), 7.78-7.67 (m, 2H), 7.65 (br s, 1H), 7.42 (t, 1H), 7.25 (t, 2H), 7.04-6.98 (m, 3H), 6.85 (t, 1H), 4.56 (br, 2H), 4.24 (br, 2H), 3.83 (d, 2H), 3.70-3.63 (m, 4H), 3.48-3.45 (m, 1H), 3.30-3.18 (m, 6H), 2.76 (br, 1H), 1.87-1.78 (m, 4H). MS (EI) for $C_{28}H_{35}N_7O_2$: 502 (MH$^+$).

Using the same or similar synthetic techniques, substituting with the appropriate reagents such as the respective amines, the following compounds of the invention were prepared:

3-Amino-6-{3-[(2-hydroxyethyl)oxy]phenyl}-N-[(3S)-piperidin-3-yl]pyrazine-2-carboxamide: $^1$H NMR (400 MHz, $d_6$-DMSO): δ 9.15-9.08 (m, 1H), 8.95-8.92 (m, 1H), 8.85 (s, 1H), 8.69 (d, 1H), 7.66 (br s, 1H), 7.69 (d, 1H), 7.63 (s, 1H), 7.36 (t, 1H), 6.95 (dd, 1H), 4.22 (br s, 1H), 4.07 (t, 2H), 3.23 (t, 2H), 3.05-3.02 (m, 1H), 2.76-2.74 (m, 1H), 1.97-1.88 (m, 2H), 1.76-1.74 (m, 2H), 1.26-1.13 (m, 2H), 0.87-0.81 (m, 1H). MS (EI) for $C_{18}H_{23}N_5O_3$: 358 (MH$^+$).

3-Amino-6-[3-(methyloxy)phenyl]-N-[(3S)-piperidin-3-yl]pyrazine-2-carboxamide: $^1$H NMR (400 MHz, $d_6$-DMSO): δ 9.02-8.99 (m, 1H), 8.86 (s, 1H), 8.85 (m, 1H), 8.68 (d, 1H), 7.70-7.65 (m, 3H), 7.37 (t, 1H), 6.95 (dd, 1H), 4.24 (m, 1H), 3.82 (s, 3H), 3.27-3.19 (m, 2H), 3.07-2.99 (m, 1H), 2.77-2.74 (m, 1H), 1.89-1.87 (m, 2H), 1.76-1.72 (m, 2H). MS (EI) for $C_{17}H_{21}N_5O_2$: 328 (MH$^+$).

3-Amino-6-[3-(ethyloxy)phenyl]-N-[(3S)-piperidin-3-yl]pyrazine-2-carboxamide: $^1$H NMR (400 MHz, $d_6$-DMSO): δ 9.03-9.00 (m, 1H), 8.87-8.82 (m, 1H), 8.81 (s, 1H), 8.64 (d, 1H), 7.64-7.57 (m, 3H), 7.31 (t, 1H), 6.89 (dd, 1H), 4.19-4.17 (m, 1H), 4.06 (q, 2H), 3.22-3.15 (m, 2H), 3.02-2.95 (m, 1H), 2.72-2.70 (m, 1H), 1.85-1.83 (m, 2H), 1.71-1.68 (m, 2H), 1.30 (t, 3H). MS (EI) for $C_{18}H_{23}N_5O_2$: 342 (MH$^+$).

3-Amino-6-(3-{[2-(diethylamino)ethyl]oxy}phenyl)-N-[(3S)-piperidin-3-yl]pyrazine-2-carboxamide: $^1$H NMR (400 MHz, d$_4$-MeOH): δ 8.63 (s, 1H), 7.64-7.62 (m, 2H), 7.36 (t, 1H), 6.98 (d, 1H), 4.40 (br s, 2H), 4.25 (br s, 1H), 3.66-3.63 (m, 2H), 3.59-3.51 (m, 9H), 3.50-3.47 (m, 2H), 1.95 (br s, 2H), 1.83 (br, 2H), 1.31 (m, 7H). MS (EI) for $C_{22}H_{32}N_6O_2$: 413 (MH$^+$).

3-Amino-6-{3-[(2-morpholin-4-ylethyl)oxy]phenyl}-N-[(3S)-piperidin-3-yl]pyrazine-2-carboxamide: $^1$H NMR (400 MHz, d$_4$-MeOH): δ 8.70 (br s, 1H), 7.80 (br s, 1H), 7.71 (d, 1H), 7.45 (m, 1H), 7.09 (d, 1H), 4.55 (m, 2H), 4.36 (m, 1H), 4.10-4.06 (m, 2H), 3.93 (m, 2H), 3.74-3.71 (m, 2H), 3.67-3.64 (m, 9H), 3.58-3.56 (m, 2H), 3.48-3.47 (m, 1H), 2.10-2.04 (m, 2H), 1.89 (m, 2H). MS (EI) for $C_{22}H_{30}N_6O_3$: 427 (MH$^+$).

3-Amino-6-(3-{[2-(ethylamino)ethyl]oxy}phenyl)-N-[(3S)-piperidin-3-yl]pyrazine-2-carboxamide: $^1$H NMR (400 MHz, d$_4$-MeOH): δ 8.70 (s, 1H), 7.73-7.70 (m, 2H), 7.44 (t, 1H), 7.08 (d, 1H), 4.41-4.34 (m, 2H), 3.75-3.72 (m, 2H), 3.70-3.63 (m, 5H), 3.58-3.56 (m, 1H), 3.50 (br s, 2H), 3.37-3.34 (m, 1H), 3.21-3.19 (m, 2H), 3.04 (m, 1H), 2.10-2.04 (m, 2H), 1.98-1.92 (m, 2H), 1.38 (t, 3H). MS (EI) for $C_{20}H_{28}N_6O_2$: 385 (MH$^+$).

Phenylmethyl 4-(2-{[3-(5-amino-6-{[(3S)-piperidin-3-ylamino]carbonyl}pyrazin-2-yl)phenyl]oxy}ethyl)piperazine-1-carboxylate: $^1$H NMR (400 MHz, d$_4$-MeOH): δ 8.69 (br s, 1H), 7.87 (br s, 1H), 7.70 (m, 1H), 7.45 (m, 1H), 7.37-7.31 (m, 4H), 7.10 (d, 1H), 5.16 (s, 2H), 4.56 (m, 2H), 4.37-4.28 (m, 4H), 3.74-3.70 (m, 4H), 3.69-3.62 (m, 4H), 3.58-3.56 (m, 2H), 3.34 (m, 4H), 3.05 (m, 2H), 2.08 (m, 2H), 1.89 (m, 2H). MS (EI) for $C_{30}H_{37}N_7O_4$: 560 (MH$^+$).

3-Amino-N-[(3S)-azepan-3-yl]-6-{3-[({[4-(1H-pyrazol-1-yl)phenyl]methyl}amino)carbonyl]phenyl}pyrazine-2-carboxamide: $^1$H NMR (400 MHz, DMSO-d$_8$): δ 9.59 (m, 2H), 9.25 (bs, 1H), 9.08 (d, 1H), 8.96 (s, 1H), 8.78 (m, 1H), 8.48 (d, 1H), 8.32 (m, 1H), 7.92 (m, 1H), 7.80 (m, 1H), 7.78 (m, 1H), 7.73 (m, 1H), 7.58 (t, 1H), 7.50 (d, 2H), 6.53 (m, 1H), 4.77 (bs, 2H), 4.53 (m, 2H), 4.43 (m, 1H), 3.34 (m, 2H), 3.24 (m, 1H), 2.99 (m, 1H), 2.01 (m, 2H), 1.80 (m, 3H), 1.54 (m, 1H); MS (EI) for $C_{28}H_{30}N_8O_2$ 511.36 (MH$^+$).

Assays

Chk1 and Chk2 assays were performed by measuring incorporation of γ-$^{33}$P ATP into immobilized myelin basic protein (MBP). High binding white 384 well plates (Greiner) were coated with MBP (Sigma #M-1891) by incubation of 60 ul/well of 20 μg/ml MBP in Tris-buffered saline (TBS; 50 mM Tris pH 8.0, 138 mM NaCl, 2.7 mM KCl) for 24 hours at 4° C. Plates were washed 3× with 100 μl TBS. Kinase reactions were carried out in a total volume of 34 μl in kinase buffer (5 mM Hepes pH 7.6, 15 mM NaCl, 0.01% bovine gamma globulin (Sigma #I-5506), 10 mM MgCl$_2$, 1 mM DTT, 0.02% TritonX-100). Compound dilutions were performed in DMSO and added to assay wells to a final DMSO concentration of 1%. Each data point was measured in duplicate, and at least two duplicate assays were performed for each individual compound determination. Chk1 and Chk2 enzymes (Upstate Biotechnology) were added to final concentrations of 10 nM (Chk1) or 20 nM (Chk2). A mixture of unlabeled ATP and γ-$^{33}$P ATP was added to start the reaction (2×10$^6$ cpm of γ-$^{33}$P ATP per well (3000 Ci/mmole) and either 10 μM or 30 μM unlabeled ATP (for Chk1 and Chk2 assays respectively). The reaction was carried out for 1 hour at room temperature with shaking. Plates were washed 7× with TBS, followed by the addition of 50 μl/well scintillation fluid (Wallac). Plates were read using a Wallac Trilux counter. This is only one format of such assays, various other formats are possible, as known to those skilled in the art.

The above assay procedure can be used to determine the IC$_{50}$ for inhibition and/or the inhibition constant K$_i$. The IC$_{50}$ is defined as the concentration of compound required to reduce the enzyme activity by 50% under the conditions of the assay. Exemplary compositions have IC$_{50}$'s of, for example, less than about 100 μM, less than about 10 μM, less than about 1 μM, and further for example having IC$_{50}$'s of less than about 100 nM, and still further, for example, less than about 10 nM. The K$_i$ for a compound may be determined from the IC$_{50}$ based on three assumptions. First, only one compound molecule binds to the enzyme and there is no cooperativity. Second, the concentrations of active enzyme and the compound tested are known (i.e., there are no significant amounts of impurities or inactive forms in the preparations). Third, the enzymatic rate of the enzyme-inhibitor complex is zero. The rate (i.e., compound concentration) data are fitted to the equation:

$$V = V_{max}E_0\left[1 - \frac{(E_0 + I_0 + K_d) - \sqrt{(E_0 + I_0 + K_d)^2 - 4E_0\,I_0}}{2E_0}\right]$$

Where V is the observed rate, V$_{max}$ is the rate of the free enzyme, I$_0$ is the inhibitor concentration, E$_0$ is the enzyme concentration, and K$_d$ is the dissociation constant of the enzyme-inhibitor complex.

Kinase Specificity Assays:

Kinase activity and compound inhibition are investigated using one or more of the three assay formats described below. The ATP concentrations for each assay are selected to be close to the Michaelis-Menten constant (K$_M$) for each individual kinase. Dose-response experiments are performed at 10 different inhibitor concentrations in a 384-well plate format. The data are fitted to the following four-parameter equation:

$$Y = Min + (Max - Min)/(1 + (X/IC_{50})^H)$$

where Y is the observed signal, X is the inhibitor concentration, Min is the background signal in the absence of enzyme (0% enzyme activity), Max is the signal in the absence of inhibitor (100% enzyme activity), IC$_{50}$ is the inhibitor concentration at 50% enzyme inhibition and H represents the empirical Hill's slope to measure the cooperativity. Typically H is close to unity.

$^{33}$P Phosphoryl Transfer Assay:

Greiner 384-well white, clear bottom, high binding plates are coated with 2 μg/well of protein or peptide substrate in a 50 μL volume overnight at ambient temperature. The coating buffer typically contains 40 μg/mL substrate, 22.5 mM Na$_2$CO$_3$, 27.5 mM NaHCO$_3$, 150 mM NaCl and 3 mM NaN$_3$. The coating solution is aspirated and the plates are washed once with 50 μL of assay buffer and padded dry. Subsequently compounds and enzymes are mixed with γ$^{33}$P-ATP (3.3 μCi/nmol) in a total volume of 20 uL in suitable assay buffers. The mixture is incubated at ambient temperature for 1.5-2.5 hrs and terminated by aspiration using a Molecular Devices EMBLA 96-head plate washer. The plates are subsequently washed 6-12 times with PBST or TBS buffer. Scintillation fluid (50 μl/well) is then added, the plates are sealed and activity assessed by liquid scintillation spectrometry using a Perkin Elmer MicroBeta TriLux.

Luciferase-Coupled Chemiluminescent Assay (LCCA)

In the LCCA assays, kinase activity is measured as the percent ATP consumed following the kinase reaction using luciferase-luciferin-coupled chemiluminescence. Greiner 384-well white, clear bottom, medium binding plates are used for LCCA. Briefly, the kinase reaction is initiated by mixing compounds, ATP and kinase in a 20 uL volume. The mixture is incubated at ambient temperature for 2-4 hrs. At the end of the kinase reaction, a 20 uL luciferase-luciferin mix is added and the chemiluminescent signal is read using a Wallac Victor$^2$ reader. The luciferase-luciferin mix consists of 50 mM HEPES, pH 7.8, 8.5 ug/mL oxalic acid (pH 7.8), 5 (or 50) mM DTT, 0.4% Triton X-100, 0.25 mg/mL coenzyme A, 63 uM AMP, 28 ug/mL luciferin and 40,000 units of light/mL luciferase. For the LCCA assays, total ATP consumption has been standardized to 25-45% and the $IC_{50}$ values correlates well with those determined by radiometric assays.

AlphaScreen

AlphaScreen technology is a proximity assay which utilizes the increase in fluorescent signal when donor and acceptor beads are close in proximity. Biotinylated poly(Glu,Tyr) 4:1 is used as the kinase substrate, in conjunction with streptavidin-coated donor beads and anti-phosphortyrosine antibody PY100-coated acceptor beads. Upon phosphorylation, the peptide substrate can bind to both donor and acceptor beads giving rise to an increase in fluorescence. Compounds, ATP, biotinylated poly(Glu, Tyr) and kinases are mixed in a volume of 20 uL for 1 hr at ambient temperature using Greiner 384-well white clear bottom medium binding plates. Following incubation a 10 uL solution containing 15-30 mg/mL AlphaScreen beads, 75 mM Hepes, pH 7.4, 300 mM NaCl, 120 mM EDTA, 0.3% BSA and 0.03% Tween-20 is added to each well. After 2-16 hr incubation of the beads, plates are read in a Perkin Elmer AlphaQuest reader. The $IC_{50}$ values correlates well with those of radiometric assays.

In order to assess the ability of the compound to abrogate the G2 checkpoint in cells (via Chk1 inhibition), a mitotic index assay can be performed. Mitotic index was determined by measuring accumulation of cells in mitosis in the presence of a DNA damaging agent (for example, Adriamycin; Adr). Nocodozole (Noc) was used to induce mitotic arrest. In the presence of Noc, cells accumulate in mitosis and are detected using an M-phase specific antibody. In the presence of Adr and Noc, cells undergo G2 arrest and do not proceed to M-phase. Addition of Chk1 inhibitors causes the G2 checkpoint to be bypassed, and M-phase cells are detected. HT-29 cells were cultured by 1:20 passaging in DMEM+10% fetal bovine serum (DMEM/FBS) at 37° C. and 5% $CO_2$. Prior to the assay, cells were plated at 6500 cells/well in 100 μl DMEM/FBS in black/clear bottom 96 well plates (BD Biocoat). After growing for 24 hours at 37° C./5% $CO_2$, Adr was added to a final concentration of 250 nM and cells were grown for a further 18-20 hrs. Medium was then aspirated from the plates and 70 μl of 0.7 μM Noc added in DMEM/FBS containing 0.55% v/v DMSO. Compounds were diluted in DMEM/FBS containing 0.55% v/v DMSO, and 30 μl of compound solution added to the assay plates. Control wells with Noc, compound/Noc and Noc/Adr alone were also set up. Cells were grown for a further 18-20 hrs and visually inspected before fixing with formaldehyde. The percentage of mitotic cells was determined by immunofluoresence using a M-phase specific anti-phosphohistoneH3 rabbit polyclonal antibody and a goat anti-rabbit secondary antibody conjugated to Alexa Fluor 488 dye. Cell nuclei were also stained using Hoechst dye. Staining and fluorescence detection was performed using a Cellomics Arrayscan instrument, using the manufacturer's mitotic index assay kit. This is only one format of such assays, various other formats are possible, as known to those skilled in the art.

Structure Activity Relationships

Table 11 shows structure activity relationship data for selected compounds of the invention with respect to Chk1 only. Inhibition is indicated as $IC_{50}$ with following key: A=$IC_{50}$ less than 50 nM, B=$IC_{50}$ greater than 50 nM but less than or equal to 1000 nM, C=$IC_{50}$ greater than 1000 nM but less than 10,000 nM, and D=$IC_{50}$ of 10,000 nM or greater.

TABLE 11

| # | Name | Chk1 $IC_{50}$ |
|---|------|----------------|
| 1 | 3-amino-6-phenyl-N-(2-phenylethyl)pyrazine-2-carboxamide | D |
| 2 | 3-amino-6-phenyl-N-(phenylmethyl)pyrazine-2-carboxamide | D |
| 3 | 3-amino-6-(3-chlorophenyl)pyrazine-2-carboxamide | D |
| 4 | 3-amino-N-[(1R)-2,3-dihydro-1H-inden-1-yl]-6-phenylpyrazine-2-carboxamide | D |
| 5 | 3-amino-N-[(1S)-2,3-dihydro-1H-inden-1-yl]-6-phenylpyrazine-2-carboxamide | D |
| 6 | 3-amino-N-(2,3-dihydro-1H-inden-2-yl)-6-phenylpyrazine-2-carboxamide | D |
| 7 | 3-amino-6-(2-chlorophenyl)pyrazine-2-carboxamide | D |
| 8 | 3-amino-N-cyclopentyl-6-phenylpyrazine-2-carboxamide | D |
| 9 | 3-amino-N,N-dimethyl-6-phenylpyrazine-2-carboxamide | C |
| 10 | 3-amino-6-[3-(methyloxy)phenyl]pyrazine-2-carboxamide | C |
| 11 | 5-phenyl-3-(pyrrolidin-1-ylcarbonyl)pyrazin-2-amine | D |
| 12 | 3-amino-N-(cyclopropylmethyl)-6-phenylpyrazine-2-carboxamide | D |
| 13 | 3-amino-6-phenyl-N-(tetrahydrofuran-2-ylmethyl)pyrazine-2-carboxamide | D |
| 14 | 3-amino-N-cyclohexyl-6-phenylpyrazine-2-carboxamide | D |
| 15 | 6-phenyl-N-propyl-3-(propylamino)pyrazine-2-carboxamide | D |
| 16 | 3-amino-6-(2-methylphenyl)pyrazine-2-carboxamide | D |
| 17 | 3-amino-6-[2-(methyloxy)phenyl]pyrazine-2-carboxamide | D |
| 18 | 3-amino-6-(2,4-difluorophenyl)pyrazine-2-carboxamide | D |
| 19 | 3-amino-6-(3-fluorophenyl)pyrazine-2-carboxamide | D |
| 20 | 3-amino-N-cyclopropyl-6-phenylpyrazine-2-carboxamide | D |
| 21 | 3-amino-6-(3,4-difluorophenyl)pyrazine-2-carboxamide | D |
| 22 | 3-amino-6-(4-fluorophenyl)-N-methylpyrazine-2-carboxamide | C |
| 23 | 3-amino-6-[4-(ethyloxy)phenyl]pyrazine-2-carboxamide | C |
| 24 | 3-amino-6-[3-(ethyloxy)phenyl]pyrazine-2-carboxamide | C |
| 25 | 3-amino-6-(1,3-benzodioxol-5-yl)pyrazine-2-carboxamide | D |
| 26 | 3-amino-6-naphthalen-1-ylpyrazine-2-carboxamide | D |

TABLE 11-continued

| # | Name | Chk1 IC$_{50}$ |
|---|---|---|
| 27 | 3-amino-6-naphthalen-2-ylpyrazine-2-carboxamide | D |
| 28 | 3-amino-6-{3-[(trifluoromethyl)oxy]phenyl}pyrazine-2-carboxamide | C |
| 29 | 3-amino-6-[3-(aminocarbonyl)phenyl]pyrazine-2-carboxamide | C |
| 30 | 6-[3-(acetylamino)phenyl]-3-aminopyrazine-2-carboxamide | C |
| 31 | 3-amino-6-biphenyl-4-ylpyrazine-2-carboxamide | D |
| 32 | 3-amino-6-[4-(dimethylamino)phenyl]pyrazine-2-carboxamide | C |
| 33 | 3-amino-6-(3-methylphenyl)pyrazine-2-carboxamide | C |
| 34 | methyl 3-[5-amino-6-(aminocarbonyl)pyrazin-2-yl]benzoate | C |
| 35 | 3-amino-6-{3-[(phenylmethyl)oxy]phenyl}pyrazine-2-carboxamide | B |
| 36 | 3-amino-6-(3-hydroxyphenyl)pyrazine-2-carboxamide | B |
| 37 | 3-amino-6-(1-benzofuran-2-yl)pyrazine-2-carboxamide | D |
| 38 | 3-(methylamino)-6-phenylpyrazine-2-carboxamide | D |
| 39 | 6-phenyl-3-[(phenylmethyl)amino]pyrazine-2-carboxamide | D |
| 40 | 6-phenyl-3-(propylamino)pyrazine-2-carboxamide | D |
| 41 | 3-amino-6-biphenyl-3-ylpyrazine-2-carboxamide | B |
| 42 | 3-[5-amino-6-(aminocarbonyl)pyrazin-2-yl]benzoic acid | D |
| 43 | 3-amino-6-{4-[(phenylmethyl)oxy]phenyl}pyrazine-2-carboxamide | D |
| 44 | 3-amino-N-methyl-6-{3-[(phenylmethyl)oxy]phenyl}pyrazine-2-carboxamide | C |
| 45 | 3-amino-6-(3-hydroxyphenyl)-N-methylpyrazine-2-carboxamide | B |
| 46 | 3-amino-N-[2-(methyloxy)ethyl]-6-phenylpyrazine-2-carboxamide | C |
| 47 | N-[2-(acetylamino)ethyl]-3-amino-6-phenylpyrazine-2-carboxamide | D |
| 48 | 3-amino-6-phenylpyrazine-2-carbohydrazide | C |
| 49 | 3-amino-N-hydroxy-6-phenylpyrazine-2-carboxamide | C |
| 50 | 3-amino-6-[3-(ethyloxy)phenyl]-N-methylpyrazine-2-carboxamide | C |
| 51 | 3-amino-6-(3-aminophenyl)-N-methylpyrazine-2-carboxamide | B |
| 52 | 3-amino-6-[4-(ethyloxy)phenyl]-N-methylpyrazine-2-carboxamide | C |
| 53 | 3-amino-N-methyl-6-(3-methylphenyl)pyrazine-2-carboxamide | B |
| 54 | 3-amino-N-methyl-6-[4-(methyloxy)phenyl]pyrazine-2-carboxamide | C |
| 55 | 3-amino-6-biphenyl-3-yl-N-methylpyrazine-2-carboxamide | B |
| 56 | 6-[3-(acetylamino)phenyl]-3-amino-N-methylpyrazine-2-carboxamide | B |
| 57 | 3-amino-6-[3-(hydroxymethyl)phenyl]-N-methylpyrazine-2-carboxamide | B |
| 58 | 3-amino-6-[4-(hydroxymethyl)phenyl]-N-methylpyrazine-2-carboxamide | C |
| 59 | 3-amino-N-methyl-6-{3-[(1E)-N-methylethanimidoyl]phenyl}pyrazine-2-carboxamide | C |
| 60 | 3-amino-N-methyl-6-[3-(methyloxy)phenyl]pyrazine-2-carboxamide | C |
| 61 | 3-amino-6-(4-fluoro-3-methylphenyl)-N-methylpyrazine-2-carboxamide | B |
| 62 | 3-amino-N-methyl-6-pyridin-3-ylpyrazine-2-carboxamide | C |
| 63 | 6-[4-(acetylamino)phenyl]-3-amino-N-methylpyrazine-2-carboxamide | C |
| 64 | 3-amino-N-methyl-6-{3-[(methylamino)carbonyl]phenyl}pyrazine-2-carboxamide | C |
| 65 | 6-(3-acetylphenyl)-3-amino-N-methylpyrazine-2-carboxamide | C |
| 66 | 3-amino-N-methyl-6-(5-pyridin-3-yl-1,2,4-oxadiazol-3-yl)pyrazine-2-carboxamide | D |
| 67 | 3-amino-6-(5-cyclopentyl-1,2,4-oxadiazol-3-yl)-N-methylpyrazine-2-carboxamide | D |
| 68 | 3-amino-6-(5-cyclohexyl-1,2,4-oxadiazol-3-yl)-N-methylpyrazine-2-carboxamide | D |
| 69 | 3-amino-N-methyl-6-(5-phenyl-1,2,4-oxadiazol-3-yl)pyrazine-2-carboxamide | D |
| 70 | 3-amino-N-methyl-6-[5-(phenylmethyl)-1,2,4-oxadiazol-3-yl]pyrazine-2-carboxamide | D |
| 71 | 3-amino-N-methyl-6-(5-methyl-1,2,4-oxadiazol-3-yl)pyrazine-2-carboxamide | C |
| 72 | 3-amino-N-methyl-6-[5-(2-phenylethyl)-1,2,4-oxadiazol-3-yl]pyrazine-2-carboxamide | D |
| 73 | 3-amino-N-methyl-6-(5-pyridin-4-yl-1,2,4-oxadiazol-3-yl)pyrazine-2-carboxamide | D |
| 74 | 3-amino-6-[5-(1,1-dimethylethyl)-1,2,4-oxadiazol-3-yl]-N-methylpyrazine-2-carboxamide | D |
| 75 | 3-amino-6-(5-furan-2-yl-1,2,4-oxadiazol-3-yl)-N-methylpyrazine-2-carboxamide | D |
| 76 | 3-amino-6-[4-(dimethylamino)phenyl]-N-methylpyrazine-2-carboxamide | C |
| 77 | 3-amino-N-methyl-6-{4-[(methylsulfonyl)amino]phenyl}pyrazine-2-carboxamide | C |
| 78 | 3-amino-6-(3,5-dimethylphenyl)-N-methylpyrazine-2-carboxamide | C |
| 79 | 6-(4-acetylphenyl)-3-amino-N-methylpyrazine-2-carboxamide | C |
| 80 | 3-amino-6-[3,4-bis(methyloxy)phenyl]-N-methylpyrazine-2-carboxamide | C |
| 81 | 3-amino-N-methyl-6-{3-[(phenylcarbonyl)amino]phenyl}pyrazine-2-carboxamide | B |
| 82 | 3-amino-N-methyl-6-{3-[(methylsulfonyl)amino]phenyl}pyrazine-2-carboxamide | C |
| 83 | 3-amino-N-methyl-6-[3-(1H-tetrazol-5-yl)phenyl]pyrazine-2-carboxamide | C |
| 84 | 3-amino-N-methyl-6-(3-{[(phenylmethyl)amino]carbonyl}phenyl)pyrazine-2-carboxamide | B |
| 85 | 3-amino-6-[3-(aminocarbonyl)phenyl]-N-methylpyrazine-2-carboxamide | C |
| 86 | 3-amino-6-{3-[(dimethylamino)carbonyl]phenyl}-N-methylpyrazine-2-carboxamide | C |

TABLE 11-continued

| # | Name | Chk1 IC$_{50}$ |
|---|------|----------------|
| 87 | 3-amino-N-methyl-6-[4-(methylsulfonyl)phenyl]pyrazine-2-carboxamide | C |
| 88 | 3-amino-6-(3-aminophenyl)-N-ethylpyrazine-2-carboxamide | C |
| 89 | 3-amino-6-[3-({[(4-fluorophenyl)amino]carbonyl}amino)phenyl]-N-methylpyrazine-2-carboxamide | B |
| 90 | 3-amino-N-methyl-6-{3-[({[4-(methyloxy)phenyl]amino}carbonyl)amino]phenyl}pyrazine-2-carboxamide | B |
| 91 | 6,6'-[(oxomethanediyl)bis(iminobenzene-3,1-diyl)]bis(3-amino-N-methylpyrazine-2-carboxamide) | A |
| 92 | 3-{5-amino-6-[(methylamino)carbonyl]pyrazin-2-yl}benzoic acid | D |
| 93 | 3-amino-N-methyl-6-{3-[(4-methylpiperazin-1-yl)carbonyl]phenyl}pyrazine-2-carboxamide | C |
| 94 | 3-amino-N-methyl-6-(3-{[(2-phenylethyl)amino]carbonyl}phenyl)pyrazine-2-carboxamide | B |
| 95 | 3-amino-N-methyl-6-{3-[({[4-(methyloxy)phenyl]methyl}amino)carbonyl]phenyl}pyrazine-2-carboxamide | B |
| 96 | 3-amino-6-(3-{[((1R)-2,3-dihydro-1H-inden-1-ylamino]carbonyl}phenyl)-N-methylpyrazine-2-carboxamide | C |
| 97 | 3-amino-6-(3-{[((1S)-2,3-dihydro-1H-inden-1-ylamino]carbonyl}phenyl)-N-methylpyrazine-2-carboxamide | B |
| 98 | 3-amino-6-[3-({[(4-chlorophenyl)methyl]amino}carbonyl)phenyl]-N-methylpyrazine-2-carboxamide | B |
| 99 | 3-amino-N-methyl-6-(3-{[methyl(phenylmethyl)amino]carbonyl}phenyl)pyrazine-2-carboxamide | C |
| 100 | 3-amino-6-[3-({[(2,4-dichlorophenyl)methyl]amino}carbonyl)phenyl]-N-methylpyrazine-2-carboxamide | B |
| 101 | 3-amino-N-methyl-6-[3-({[(4-methylphenyl)methyl]amino}carbonyl)phenyl]pyrazine-2-carboxamide | B |
| 102 | 3-amino-N-methyl-6-{3-[({[4-(trifluoromethyl)phenyl]methyl}amino)carbonyl]phenyl}pyrazine-2-carboxamide | B |
| 103 | 3-amino-6-[3-({[(4-fluorophenyl)methyl]amino}carbonyl)phenyl]-N-methylpyrazine-2-carboxamide | B |
| 104 | 3-amino-6-{3-[(2,3-dihydro-1H-inden-2-ylamino)carbonyl]phenyl}-N-methylpyrazine-2-carboxamide | B |
| 105 | 3-amino-N-methyl-6-[3-({[3-(methyloxy)phenyl]carbonyl}amino)phenyl]pyrazine-2-carboxamide | B |
| 106 | 3-amino-N-methyl-6-[3-({[4-(methyloxy)phenyl]carbonyl}amino)phenyl]pyrazine-2-carboxamide | B |
| 107 | 3-amino-N-methyl-6-{3-[({[3-(methyloxy)phenyl]methyl}amino)carbonyl]phenyl}pyrazine-2-carboxamide | B |
| 108 | 3-amino-N-methyl-6-{3-[({(1R)-1-[4-(methyloxy)phenyl]ethyl}amino)carbonyl]phenyl}pyrazine-2-carboxamide | C |
| 109 | 3-amino-N-methyl-6-{3-[({[2-(trifluoromethyl)phenyl]methyl}amino)carbonyl]phenyl}pyrazine-2-carboxamide | B |
| 110 | 3-amino-6-[3-({[(3-fluorophenyl)methyl]amino}carbonyl)phenyl]-N-methylpyrazine-2-carboxamide | B |
| 111 | 3-amino-6-(3-{[(4-chlorophenyl)carbonyl]amino}phenyl)-N-methylpyrazine-2-carboxamide | B |
| 112 | 3-amino-6-[3-({[1-(4-fluorophenyl)ethyl]amino}carbonyl)phenyl]-N-methylpyrazine-2-carboxamide | C |
| 113 | 3-amino-6-{3-[({[2,3-bis(methyloxy)phenyl]methyl}amino)carbonyl]phenyl}-N-methylpyrazine-2-carboxamide | B |
| 114 | 3-amino-6-(3-{[bis(phenylmethyl)amino]carbonyl}phenyl)-N-methylpyrazine-2-carboxamide | C |
| 115 | 3-amino-6-{3-[({[2,4-bis(methyloxy)phenyl]methyl}amino)carbonyl]phenyl}-N-methylpyrazine-2-carboxamide | B |
| 116 | 3-amino-6-(3-{[ethyl(pyridin-4-ylmethyl)amino]carbonyl}phenyl)-N-methylpyrazine-2-carboxamide | C |
| 117 | 3-amino-N-methyl-6-(3-{[4-(phenylmethyl)piperazin-1-yl]carbonyl}phenyl)pyrazine-2-carboxamide | C |
| 118 | 3-amino-N-methyl-6-[3-({[1-(phenylmethyl)piperidin-4-yl]amino}carbonyl)phenyl]pyrazine-2-carboxamide | B |
| 119 | 3-amino-N-methyl-6-(3-{[(4-methylphenyl)carbonyl]amino}phenyl)pyrazine-2-carboxamide | B |
| 120 | 3-amino-N-methyl-6-[3-({[(5-methylpyrazin-2-yl)methyl]amino}carbonyl)phenyl]pyrazine-2-carboxamide | C |
| 121 | 3-amino-N-methyl-6-(3-{[(pyridin-2-ylmethyl)amino]carbonyl}phenyl)pyrazine-2-carboxamide | B |
| 122 | 3-amino-N-methyl-6-(3-{[(pyridin-3-ylmethyl)amino]carbonyl}phenyl)pyrazine-2-carboxamide | B |
| 123 | 3-amino-N-methyl-6-(3-{[(pyridin-4-ylmethyl)amino]carbonyl}phenyl)pyrazine-2-carboxamide | B |
| 124 | 3-amino-6-{3-[(furan-2-ylcarbonyl)amino]phenyl}-N-methylpyrazine-2-carboxamide | B |
| 125 | 3-amino-6-[3-({[(3-chlorophenyl)methyl]amino}carbonyl)phenyl]-N-methylpyrazine-2-carboxamide | B |

TABLE 11-continued

| # | Name | Chk1 IC$_{50}$ |
|---|------|---------------|
| 126 | 3-amino-6-(3-{[(cyclohexylmethyl)amino]carbonyl}phenyl)-N-methylpyrazine-2-carboxamide | B |
| 127 | 3-amino-N-methyl-6-(3-{[(2-phenylpropyl)amino]carbonyl}phenyl)pyrazine-2-carboxamide | B |
| 128 | 3-amino-6-[3-({[(2-chlorophenyl)methyl]amino}carbonyl)phenyl]-N-methylpyrazine-2-carboxamide | B |
| 129 | 3-amino-6-[3-({[2-(2-chlorophenyl)ethyl]amino}carbonyl)phenyl]-N-methylpyrazine-2-carboxamide | B |
| 130 | 3-amino-N-methyl-6-{3-[({2-[2-(methyloxy)phenyl]ethyl}amino)carbonyl]phenyl}pyrazine-2-carboxamide | B |
| 131 | 3-amino-6-[3-({[2-(4-fluorophenyl)ethyl]amino}carbonyl)phenyl]-N-methylpyrazine-2-carboxamide | B |
| 132 | 3-amino-N-methyl-6-[3-({[2-(2-thienyl)ethyl]amino}carbonyl)phenyl]pyrazine-2-carboxamide | B |
| 133 | 3-amino-6-{3-[(cyclohexylamino)carbonyl]phenyl}-N-methylpyrazine-2-carboxamide | C |
| 134 | 1,1-dimethylethyl 4-({[(3-{5-amino-6-[(methylamino)carbonyl]pyrazin-2-yl}phenyl)carbonyl]amino}methyl)piperidine-1-carboxylate | B |
| 135 | 3-amino-N-methyl-6-(3-{[(piperidin-4-ylmethyl)amino]carbonyl}phenyl)pyrazine-2-carboxamide | B |
| 136 | 3-amino-N-methyl-6-[3-(5-phenyl-1,2,4-oxadiazol-3-yl)phenyl]pyrazine-2-carboxamide | C |
| 137 | 3-amino-N-methyl-6-{3-[5-(phenylmethyl)-1,2,4-oxadiazol-3-yl]phenyl}pyrazine-2-carboxamide | C |
| 138 | 3-amino-N-methyl-6-{3-[5-(2-phenylethyl)-1,2,4-oxadiazol-3-yl]phenyl}pyrazine-2-carboxamide | C |
| 139 | 3-amino-6-(3-{[(1,1-dimethylethyl)amino]carbonyl}phenyl)-N-methylpyrazine-2-carboxamide | C |
| 140 | 3-amino-6-[3-({[(1R,2S)-2-hydroxy-2,3-dihydro-1H-inden-1-yl]amino}carbonyl)phenyl]-N-methylpyrazine-2-carboxamide | B |
| 141 | 3-amino-6-[3-({[(1S,2R)-2-hydroxy-2,3-dihydro-1H-inden-1-yl]amino}carbonyl)phenyl]-N-methylpyrazine-2-carboxamide | C |
| 142 | 3-amino-N-methyl-6-{3-[(phenylamino)carbonyl]phenyl}pyrazine-2-carboxamide | C |
| 143 | 3-amino-6-[3-(1,3-dihydro-2H-isoindol-2-ylcarbonyl)phenyl]-N-methylpyrazine-2-carboxamide | C |
| 144 | 3-amino-N-methyl-6-[3-({[(1R)-1-phenylethyl]amino}carbonyl)phenyl]pyrazine-2-carboxamide | C |
| 145 | 3-amino-N-methyl-6-[3-({[(1S)-1-phenylethyl]amino}carbonyl)phenyl]pyrazine-2-carboxamide | B |
| 146 | 3-amino-N-methyl-6-[3-({[(1R)-1-phenylpropyl]amino}carbonyl)phenyl]pyrazine-2-carboxamide | C |
| 147 | 3-amino-N-methyl-6-[3-({[(1S)-1-phenylpropyl]amino}carbonyl)phenyl]pyrazine-2-carboxamide | C |
| 148 | 3-amino-N-methyl-6-[3-({[(1R,2S)-2-phenylcyclopropyl]amino}carbonyl)phenyl]pyrazine-2-carboxamide | B |
| 149 | phenylmethyl 4-{5-amino-6-[(methylamino)carbonyl]pyrazin-2-yl}benzoate | D |
| 150 | 3-amino-N-methyl-6-(4-{[(phenylmethyl)amino]carbonyl}phenyl)pyrazine-2-carboxamide | C |
| 151 | 3-amino-N-methyl-6-(4-{[(2-phenylethyl)amino]carbonyl}phenyl)pyrazine-2-carboxamide | B |
| 152 | 3-amino-6-[4-({[(2,4-dichlorophenyl)methyl]amino}carbonyl)phenyl]-N-methylpyrazine-2-carboxamide | B |
| 153 | 3-amino-N-methyl-6-[4-({[(4-methylphenyl)methyl]amino}carbonyl)phenyl]pyrazine-2-carboxamide | B |
| 154 | 3-amino-6-(4-{[(1S)-2,3-dihydro-1H-inden-1-ylamino]carbonyl}phenyl)-N-methylpyrazine-2-carboxamide | B |
| 155 | 3-amino-6-(3-{[(4-chlorophenyl)acetyl]amino}phenyl)-N-methylpyrazine-2-carboxamide | B |
| 156 | 3-amino-N-methyl-6-[3-({[3-(phenyloxy)phenyl]carbonyl}amino)phenyl]pyrazine-2-carboxamide | B |
| 157 | 3-amino-6-{3-[(diphenylacetyl)amino]phenyl}-N-methylpyrazine-2-carboxamide | B |
| 158 | 3-amino-N-methyl-6-{3-[(phenylacetyl)amino]phenyl}pyrazine-2-carboxamide | B |
| 159 | 3-amino-N-methyl-6-{3-[(3-phenylpropanoyl)amino]phenyl}pyrazine-2-carboxamide | B |
| 160 | 3-amino-N-methyl-6-(3-{[(1R)-1,2,3,4-tetrahydronaphthalen-1-ylamino]carbonyl}phenyl)pyrazine-2-carboxamide | C |
| 161 | 3-amino-N-methyl-6-(3-{[(1S)-1,2,3,4-tetrahydronaphthalen-1-ylamino]carbonyl}phenyl)pyrazine-2-carboxamide | B |
| 162 | 3-amino-N-methyl-6-{3-[({[3,4,5-tris(methyloxy)phenyl]methyl}amino)carbonyl]phenyl}pyrazine-2-carboxamide | B |
| 163 | 3-amino-N-methyl-6-{3-[({(1R,2R)-2-[(phenylmethyl)oxy]cyclopentyl}amino)carbonyl]phenyl}pyrazine-2-carboxamide | C |

TABLE 11-continued

| # | Name | Chk1 IC$_{50}$ |
|---|------|----------------|
| 164 | 3-amino-N-methyl-6-{3-[({(1S,2S)-2-[(phenylmethyl)oxy]cyclopentyl}amino)carbonyl]phenyl}pyrazine-2-carboxamide | B |
| 165 | 3-amino-6-(3-cyanophenyl)-N-methylpyrazine-2-carboxamide | C |
| 166 | 3-amino-6-{3-[(cyclopentylcarbonyl)amino]phenyl}-N-methylpyrazine-2-carboxamide | B |
| 167 | 3-amino-6-(3-{[(4-cyanophenyl)carbonyl]amino}phenyl)-N-methylpyrazine-2-carboxamide | B |
| 168 | 3-amino-N-methyl-6-[3-({[(phenylmethyl)amino]carbonyl}amino)phenyl]pyrazine-2-carboxamide | B |
| 169 | 3-amino-N-methyl-6-(3-{[(naphthalen-2-ylmethyl)amino]carbonyl}phenyl)pyrazine-2-carboxamide | B |
| 170 | 3-amino-N-methyl-6-(3-{[(tetrahydrofuran-2-ylmethyl)amino]carbonyl}phenyl)pyrazine-2-carboxamide | C |
| 171 | 3-amino-6-[3-({[(2-chloro-6-fluorophenyl)methyl]amino}carbonyl)phenyl]-N-methylpyrazine-2-carboxamide | B |
| 172 | 3-amino-6-{3-[({[3-fluoro-5-(trifluoromethyl)phenyl]methyl}amino)carbonyl]phenyl}-N-methylpyrazine-2-carboxamide | B |
| 173 | 3-amino-6-{3-[({2-[3,5-bis(methyloxy)phenyl]ethyl}amino)carbonyl]phenyl}-N-methylpyrazine-2-carboxamide | C |
| 174 | 3-amino-N-methyl-6-{3-[(2-phenylethyl)oxy]phenyl}pyrazine-2-carboxamide | B |
| 175 | 3-amino-N-methyl-6-(3-{[2-(4-methylpiperidin-1-yl)ethyl]oxy}phenyl)pyrazine-2-carboxamide | C |
| 176 | 3-amino-6-[3-({2-[4-(2-hydroxyethyl)piperidin-1-yl]ethyl}oxy)phenyl]-N-methylpyrazine-2-carboxamide | C |
| 177 | 3-amino-6-(3-{[2-(3-hydroxypyrrolidin-1-yl)ethyl]oxy}phenyl)-N-methylpyrazine-2-carboxamide | C |
| 178 | 3-amino-6-[3-({2-[ethyl(phenylmethyl)amino]ethyl}oxy)phenyl]-N-methylpyrazine-2-carboxamide | B |
| 179 | 3-amino-6-(3-{[2-(diethylamino)ethyl]oxy}phenyl)-N-methylpyrazine-2-carboxamide | B |
| 180 | 3-amino-6-(3-{[(biphenyl-2-ylmethyl)amino]carbonyl}phenyl)-N-methylpyrazine-2-carboxamide | A |
| 181 | 3-amino-N-methyl-6-(3-{[2-(4-phenylpiperazin-1-yl)ethyl]oxy}phenyl)pyrazine-2-carboxamide | B |
| 182 | 3-amino-6-(3-{[(biphenyl-4-ylmethyl)amino]carbonyl}phenyl)-N-methylpyrazine-2-carboxamide | A |
| 183 | 3-amino-N-methyl-6-[3-({2-[methyl(phenylmethyl)amino]ethyl}oxy)phenyl]pyrazine-2-carboxamide | B |
| 184 | 3-amino-N-methyl-6-{3-[({[4-(phenyloxy)phenyl]methyl}amino)carbonyl]phenyl}pyrazine-2-carboxamide | B |
| 185 | 3-amino-N-methyl-6-{3-[(2-morpholin-4-ylethyl)oxy]phenyl}pyrazine-2-carboxamide | C |
| 186 | 3-amino-6-[3-({2-[(cyclopropylmethyl)(propyl)amino]ethyl}oxy)phenyl]-N-methylpyrazine-2-carboxamide | B |
| 187 | 3-amino-N-methyl-6-[3-({2-[4-(phenylmethyl)piperidin-1-yl]ethyl}oxy)phenyl]pyrazine-2-carboxamide | B |
| 188 | 3-amino-N-methyl-6-{3-[(2-piperidin-1-ylethyl)oxy]phenyl}pyrazine-2-carboxamide | B |
| 189 | 3-amino-N-methyl-6-{3-[({[3-(phenyloxy)phenyl]methyl}amino)carbonyl]phenyl}pyrazine-2-carboxamide | B |
| 190 | 3-amino-6-(3-{[2-(4-ethylpiperazin-1-yl)ethyl]oxy}phenyl)-N-methylpyrazine-2-carboxamide | B |
| 191 | 3-amino-N-methyl-6-{3-[(2-pyrrolidin-1-ylethyl)oxy]phenyl}pyrazine-2-carboxamide | B |
| 192 | 3-amino-N-methyl-6-{3-{[2-(4-methylpiperazin-1-yl)ethyl]oxy}phenyl}pyrazine-2-carboxamide | B |
| 193 | 3-amino-6-[3-({2-[4-(2-hydroxyethyl)piperazin-1-yl]ethyl}oxy)phenyl]-N-methylpyrazine-2-carboxamide | B |
| 194 | 3-amino-6-(3-{[2-(3,4-dihydroisoquinolin-2(1H)-yl)ethyl]oxy}phenyl)-N-methylpyrazine-2-carboxamide | B |
| 195 | ethyl 4-{2-[(3-{5-amino-6-[(methylamino)carbonyl]pyrazin-2-yl}phenyl)oxy]ethyl}piperazine-1-carboxylate | C |
| 196 | 3-amino-N-methyl-6-[3-({[(3S)-1-(phenylmethyl)pyrrolidin-3-yl]amino}carbonyl)phenyl]pyrazine-2-carboxamide | B |
| 197 | 3-amino-N-methyl-6-[3-({[(3R)-1-(phenylmethyl)pyrrolidin-3-yl]amino}carbonyl)phenyl]pyrazine-2-carboxamide | B |
| 198 | 3-amino-N-methyl-6-[3-({[2-(phenyloxy)ethyl]amino}carbonyl)phenyl]pyrazine-2-carboxamide | B |
| 199 | 3-amino-N-methyl-6-{3-[({2-[4-(phenylmethyl)piperazine-1-yl]ethyl}amino)carbonyl]phenyl}pyrazine-2-carboxamide | B |
| 200 | 3-amino-N-methyl-6-{3-[({[1-(phenylmethyl)piperidin-4-yl]methyl}amino)carbonyl]phenyl}pyrazine-2-carboxamide | D |
| 201 | 3-amino-6-(3-{[(furan-3-ylmethyl)amino]carbonyl}phenyl)-N-methylpyrazine-2-carboxamide | B |

TABLE 11-continued

| # | Name | Chk1 IC$_{50}$ |
|---|---|---|
| 202 | 3-amino-6-(3-{[(2,3-dihydro-1,4-benzodioxin-2-ylmethyl)amino]carbonyl}phenyl)-N-methylpyrazine-2-carboxamide | B |
| 203 | 3-amino-6-(3-{[(furan-2-ylmethyl)amino]carbonyl}phenyl)-N-methylpyrazine-2-carboxamide | B |
| 204 | 3-amino-N-methyl-6-{3-[({[4-(phenylmethyl)morpholin-2-yl]methyl}amino)carbonyl]phenyl}pyrazine-2-carboxamide | B |
| 205 | 3-amino-6-(3-{[(2,3-dihydro-1,4-benzodioxin-6-ylmethyl)amino]carbonyl}phenyl)-N-methylpyrazine-2-carboxamide | A |
| 206 | 3-amino-6-(3-{[(2,3-dihydro-1,4-benzodioxin-6-ylmethyl)amino]carbonyl}phenyl)-N-methylpyrazine-2-carboxamide | A |
| 207 | 3-amino-6-(3-{[(2,3-dihydro-1-benzofuran-5-ylmethyl)amino]carbonyl}phenyl)-N-methylpyrazine-2-carboxamide | B |
| 208 | 3-amino-6-[3-({[(6-fluoro-4H-1,3-benzodioxin-8-yl)methyl]amino}carbonyl)phenyl]-N-methylpyrazine-2-carboxamide | B |
| 209 | 3-amino-6-(3-{[[(2,4-dichlorophenyl)acetyl]amino}phenyl)-N-methylpyrazine-2-carboxamide | A |
| 210 | 3-amino-6-(3-{[(3,4-dichlorophenyl)acetyl]amino}phenyl)-N-methylpyrazine-2-carboxamide | B |
| 211 | 3-amino-N-methyl-6-[3-({[4-(trifluoromethyl)phenyl]acetyl}amino)phenyl]pyrazine-2-carboxamide | B |
| 212 | 3-amino-6-[3-({[(3,5-dimethylphenyl)methyl]amino}carbonyl)phenyl]-N-methylpyrazine-2-carboxamide | B |
| 213 | 3-amino-6-[3-({[(5-chloro-2-methylphenyl)methyl]amino}carbonyl)phenyl]-N-methylpyrazine-2-carboxamide | B |
| 214 | 3-amino-6-[3-({[(2,4-dimethylphenyl)methyl]amino}carbonyl)phenyl]-N-methylpyrazine-2-carboxamide | B |
| 215 | 3-amino-6-[3-({[(2,3-difluorophenyl)methyl]amino}carbonyl)phenyl]-N-methylpyrazine-2-carboxamide | C |
| 216 | 3-amino-N-methyl-6-{3-[({[4-(methylthio)phenyl]methyl}amino)carbonyl]phenyl}pyrazine-2-carboxamide | A |
| 217 | 3-amino-N-methyl-6-(3-{[(2-methylpropyl)amino]carbonyl}phenyl)pyrazine-2-carboxamide | C |
| 218 | 3-amino-N-methyl-6-(3-{[({3-[(trifluoromethyl)oxy]phenyl}methyl)amino]carbonyl}phenyl)pyrazine-2-carboxamide | C |
| 219 | 3-amino-6-(3-{[(cyclopropylmethyl)amino]carbonyl}phenyl)-N-methylpyrazine-2-carboxamide | B |
| 220 | 3-amino-6-{3-[(cyclopentylamino)carbonyl]phenyl}-N-methylpyrazine-2-carboxamide | C |
| 221 | 3-amino-N-methyl-6-(3-{[(4-methylphenyl)amino]carbonyl}phenyl)pyrazine-2-carboxamide | C |
| 222 | 3-amino-N-methyl-6-[3-({[4-(methyloxy)phenyl]amino}carbonyl)phenyl]pyrazine-2-carboxamide | B |
| 223 | 3-amino-6-(3-{[(1,3-benzodioxol-5-ylmethyl)amino]carbonyl}phenyl)-N-methylpyrazine-2-carboxamide | B |
| 224 | 3-amino-6-(3-{[(biphenyl-3-ylmethyl)amino]carbonyl}phenyl)-N-methylpyrazine-2-carboxamide | B |
| 225 | 3-amino-N-methyl-6-(3-{[(1-methyl-1-phenylethyl)amino]carbonyl}phenyl)pyrazine-2-carboxamide | C |
| 226 | 3-amino-6-[3-({[(2,4-difluorophenyl)methyl]amino}carbonyl)phenyl]-N-methylpyrazine-2-carboxamide | B |
| 227 | 3-amino-N-methyl-6-(3-{[({4-[(trifluoromethyl)oxy]phenyl}methyl)amino]carbonyl}phenyl)pyrazine-2-carboxamide | B |
| 228 | 3-amino-6-{3-[({[4-fluoro-3-(trifluoromethyl)phenyl]methyl}amino)carbonyl]phenyl}-N-methylpyrazine-2-carboxamide | B |
| 229 | 3-amino-6-{3-[({[4-chloro-3-(trifluoromethyl)phenyl]methyl}amino)carbonyl]phenyl}-N-methylpyrazine-2-carboxamide | B |
| 230 | 3-amino-6-[3-({[(4-aminophenyl)methyl]amino}carbonyl)phenyl]-N-methylpyrazine-2-carboxamide | B |
| 231 | 3-amino-6-[3-({[(2-aminophenyl)methyl]amino}carbonyl)phenyl]-N-methylpyrazine-2-carboxamide | B |
| 232 | 3-amino-6-[3-({[(3-aminophenyl)methyl]amino}carbonyl)phenyl]-N-methylpyrazine-2-carboxamide | B |
| 233 | 3-amino-N-methyl-6-pyrimidin-5-ylpyrazine-2-carboxamide | D |
| 234 | 3-amino-N-methyl-6-[3-(methylsulfonyl)phenyl]pyrazine-2-carboxamide | C |
| 235 | 3-amino-N-methyl-6-[4-(tetrahydro-2H-pyran-2-yloxy)phenyl]pyrazine-2-carboxamide | B |
| 236 | 3-amino-6-(4-hydroxyphenyl)-N-methylpyrazine-2-carboxamide | B |
| 237 | 3-amino-6-{3-[({[4-(aminosulfonyl)phenyl]methyl}amino)carbonyl]phenyl}-N-methylpyrazine-2-carboxamide | B |
| 238 | 3-amino-6-{3-[({[4-(dimethylamino)phenyl]methyl}amino)carbonyl]phenyl}-N-methylpyrazine-2-carboxamide | B |
| 239 | 3-amino-6-[3-({[(3-bromophenyl)methyl]amino}carbonyl)phenyl]-N-methylpyrazine-2-carboxamide | B |

TABLE 11-continued

| # | Name | Chk1 IC$_{50}$ |
|---|---|---|
| 240 | 3-amino-6-(4-chloro-3-{[(phenylmethyl)amino]carbonyl}phenyl)-N-methylpyrazine-2-carboxamide | B |
| 241 | methyl 3-{5-amino-6-[(cyclopropylamino)carbonyl]pyrazin-2-yl}benzoate | D |
| 242 | methyl 3-{5-amino-6-[(ethylamino)carbonyl]pyrazin-2-yl}benzoate | C |
| 243 | 3-amino-6-[3-({[(2,3-dimethylphenyl)methyl]amino}carbonyl)phenyl]-N-methylpyrazine-2-carboxamide | B |
| 244 | 3-amino-6-{3-[({[4-hydroxy-3-(methyloxy)phenyl]methyl}amino)carbonyl]phenyl}-N-methylpyrazine-2-carboxamide | B |
| 245 | 3-amino-6-[3-({[(4-chloro-2-methylphenyl)methyl]amino}carbonyl)phenyl]-N-methylpyrazine-2-carboxamide | B |
| 246 | 3-amino-6-{3-[({[2-(ethyloxy)phenyl]methyl}amino)carbonyl]phenyl}-N-methylpyrazine-2-carboxamide | B |
| 247 | 3-amino-6-{3-[({[2-chloro-6-(phenyloxy)phenyl]methyl}amino)carbonyl]phenyl}-N-methylpyrazine-2-carboxamide | B |
| 248 | 3-amino-6-[3-({[(2,5-dichlorophenyl)methyl]amino}carbonyl)phenyl]-N-methylpyrazine-2-carboxamide | B |
| 249 | 3-amino-6-{3-[({[2,6-bis(methyloxy)phenyl]methyl}amino)carbonyl]phenyl}-N-methylpyrazine-2-carboxamide | C |
| 250 | 3-amino-6-[3-({[(2-chloro-6-methylphenyl)methyl]amino}carbonyl)phenyl]-N-methylpyrazine-2-carboxamide | B |
| 251 | 3-amino-N-methyl-6-[3-({[(2,4,5-trifluorophenyl)methyl]amino}carbonyl)phenyl]pyrazine-2-carboxamide | B |
| 252 | 3-amino-6-(3-{[(2,2-dimethylpropyl)amino]carbonyl}phenyl)-N-methylpyrazine-2-carboxamide | C |
| 253 | 3-amino-6-(3-{[(cyclopentylmethyl)amino]carbonyl}phenyl)-N-methylpyrazine-2-carboxamide | B |
| 254 | 3-amino-6-{3-[({[3,5-bis(methyloxy)phenyl]methyl}amino)carbonyl]phenyl}-N-methylpyrazine-2-carboxamide | B |
| 255 | 3-amino-N-methyl-6-{3-[({[4-(methylsulfonyl)phenyl]methyl}amino)carbonyl]phenyl}pyrazine-2-carboxamide | B |
| 256 | 3-amino-6-[3-({[(5-bromo-2-fluorophenyl)methyl]amino}carbonyl)phenyl]-N-methylpyrazine-2-carboxamide | B |
| 257 | 3-amino-6-[3-({[(3-bromo-4-fluorophenyl)methyl]amino}carbonyl)phenyl]-N-methylpyrazine-2-carboxamide | B |
| 258 | 3-amino-N-methyl-6-{3-[({[2,4,6-tris(methyloxy)phenyl]methyl}amino)carbonyl]phenyl}pyrazine-2-carboxamide | B |
| 259 | 3-amino-N-methyl-6-[3-({[(3-methylphenyl)methyl]amino}carbonyl)phenyl]pyrazine-2-carboxamide | B |
| 260 | 3-amino-6-[3-({[(4-bromo-2-fluorophenyl)methyl]amino}carbonyl)phenyl]-N-methylpyrazine-2-carboxamide | B |
| 261 | 3-amino-6-[3-({[(2,5-dimethylphenyl)methyl]amino}carbonyl)phenyl]-N-methylpyrazine-2-carboxamide | B |
| 262 | 3-amino-6-{3-[({[3,5-bis(trifluoromethyl)phenyl]methyl}amino)carbonyl]phenyl}-N-methylpyrazine-2-carboxamide | B |
| 263 | 3-amino-6-(3-{[(2,2-diphenylethyl)amino]carbonyl}phenyl)-N-methylpyrazine-2-carboxamide | B |
| 264 | 3-amino-N-methyl-6-(3-thienyl)pyrazine-2-carboxamide | B |
| 265 | 3-amino-N-methyl-6-(3-{[(phenylmethyl)amino]sulfonyl}phenyl)pyrazine-2-carboxamide | C |
| 266 | 5,5'-diamino-N,N'-dimethyl-2,2'-bipyrazine-6,6'-dicarboxamide | D |
| 267 | 3-amino-6-(1H-indol-5-yl)-N-methylpyrazine-2-carboxamide | B |
| 268 | 3-amino-N-methyl-6-(2-thienyl)pyrazine-2-carboxamide | B |
| 269 | 3-amino-N-methyl-6-pyridin-4-ylpyrazine-2-carboxamide | C |
| 270 | 3-amino-N-cyclopropyl-6-(3-{[(phenylmethyl)amino]carbonyl}phenyl)pyrazine-2-carboxamide | C |
| 271 | 3-amino-6-[3-({[(2-chloro-6-fluorophenyl)methyl]amino}carbonyl)phenyl]-N-cyclopropylpyrazine-2-carboxamide | D |
| 272 | 3-amino-N-ethyl-6-(3-{[(phenylmethyl)amino]carbonyl}phenyl)pyrazine-2-carboxamide | C |
| 273 | 3-amino-6-[3-({[(2-chloro-6-fluorophenyl)methyl]amino}carbonyl)phenyl]-N-ethylpyrazine-2-carboxamide | C |
| 274 | 3-amino-6-[3-({[(2,3-dichlorophenyl)methyl]amino}carbonyl)phenyl]-N-methylpyrazine-2-carboxamide | B |
| 275 | 3-amino-6-[3-({[(4-chloro-2-fluorophenyl)methyl]amino}carbonyl)phenyl]-N-methylpyrazine-2-carboxamide | A |
| 276 | 3-amino-6-[3-({[(3,5-dichlorophenyl)methyl]amino}carbonyl)phenyl]-N-methylpyrazine-2-carboxamide | B |
| 277 | 3-amino-6-[3-({[(5-chloro-2-fluorophenyl)methyl]amino}carbonyl)phenyl]-N-methylpyrazine-2-carboxamide | B |
| 278 | 3-amino-6-{3-[(cyclopropylamino)carbonyl]phenyl}-N-methylpyrazine-2-carboxamide | C |

TABLE 11-continued

| # | Name | Chk1 IC$_{50}$ |
|---|------|----------------|
| 279 | 3-amino-6-[3-({[(3,4-dichlorophenyl)methyl]amino}carbonyl)phenyl]-N-methylpyrazine-2-carboxamide | B |
| 280 | 3-amino-6-[3-({[(4'-fluorobiphenyl-2-yl)methyl]amino}carbonyl)phenyl]-N-methylpyrazine-2-carboxamide | B |
| 281 | 3-amino-N-methyl-6-[3-({[(2,3,4-trifluorophenyl)methyl]amino}carbonyl)phenyl]pyrazine-2-carboxamide | B |
| 282 | 3-amino-6-[3-({[(3-chloro-2,6-difluorophenyl)methyl]amino}carbonyl)phenyl]-N-methylpyrazine-2-carboxamide | B |
| 283 | 3-amino-6-[3-({[(3-chloro-2,6-difluorophenyl)methyl]amino}carbonyl)phenyl]-N-methylpyrazine-2-carboxamide | B |
| 284 | 3-amino-6-{3-[(9H-fluoren-9-ylamino)carbonyl]phenyl}-N-methylpyrazine-2-carboxamide | D |
| 285 | 3-amino-N-methyl-6-[3-({[(2-methylphenyl)methyl]amino}carbonyl)phenyl]pyrazine-2-carboxamide | B |
| 286 | 3-amino-6-[3-({[(3,4-dimethylphenyl)methyl]amino}carbonyl)phenyl]-N-methylpyrazine-2-carboxamide | B |
| 287 | 3-amino-6-[3-({[(5-fluoro-2-methylphenyl)methyl]amino}carbonyl)phenyl]-N-methylpyrazine-2-carboxamide | B |
| 288 | 3-amino-6-[3-({[(3,4-difluorophenyl)methyl]amino}carbonyl)phenyl]-N-methylpyrazine-2-carboxamide | B |
| 289 | 3-amino-6-[3-({[(2-fluorophenyl)methyl]amino}carbonyl)phenyl]-N-methylpyrazine-2-carboxamide | B |
| 290 | 3-amino-N-methyl-6-{3-[({[4-(4-methylpiperazin-1-yl)phenyl]methyl}amino)carbonyl]phenyl}pyrazine-2-carboxamide | C |
| 291 | 3-amino-6-(4-fluoro-3-{[(phenylmethyl)amino]carbonyl}phenyl)-N-methylpyrazine-2-carboxamide | B |
| 292 | 3-amino-N-methyl-6-[3-({[(2,4,6-trichlorophenyl)methyl]amino}carbonyl)phenyl]pyrazine-2-carboxamide | B |
| 293 | 3-amino-6-[3-({[(3-chloro-2-methylphenyl)methyl]amino}carbonyl)phenyl]-N-methylpyrazine-2-carboxamide | B |
| 294 | 3-amino-6-{3-[({[2,5-bis(methyloxy)phenyl]methyl}amino)carbonyl]phenyl}-N-methylpyrazine-2-carboxamide | B |
| 295 | 3-amino-6-[3-({[(3-fluoro-4-methylphenyl)methyl]amino}carbonyl)phenyl]-N-methylpyrazine-2-carboxamide | B |
| 296 | 3-amino-6-[3-({[(2-chloro-6-fluoro-3-methylphenyl)methyl]amino}carbonyl)phenyl]-N-methylpyrazine-2-carboxamide | B |
| 297 | 3-amino-6-[3-({[(2-chloro-3,6-difluorophenyl)methyl]amino}carbonyl)phenyl]-N-methylpyrazine-2-carboxamide | B |
| 298 | 3-amino-6-[3-({[(2,3-difluoro-4-methylphenyl)methyl]amino}carbonyl)phenyl]-N-methylpyrazine-2-carboxamide | B |
| 299 | 3-amino-6-[3-({[(4-fluoro-3-methylphenyl)methyl]amino}carbonyl)phenyl]-N-methylpyrazine-2-carboxamide | B |
| 300 | 3-amino-6-[3-({[(3-chloro-2-fluorophenyl)methyl]amino}carbonyl)phenyl]-N-methylpyrazine-2-carboxamide | B |
| 301 | 3-amino-6-[3-({[(6-chloro-2-fluoro-3-methylphenyl)methyl]amino}carbonyl)phenyl]-N-methylpyrazine-2-carboxamide | B |
| 302 | 3-amino-6-[3-({[(4-iodophenyl)methyl]amino}carbonyl)phenyl]-N-methylpyrazine-2-carboxamide | A |
| 303 | 3-amino-6-[3-({[(3-chloro-4-methylphenyl)methyl]amino}carbonyl)phenyl]-N-methylpyrazine-2-carboxamide | B |
| 304 | 3-amino-6-[3-({[(4-bromophenyl)methyl]amino}carbonyl)phenyl]-N-methylpyrazine-2-carboxamide | B |
| 305 | 3-amino-6-[3-({[(2-bromophenyl)methyl]amino}carbonyl)phenyl]-N-methylpyrazine-2-carboxamide | B |
| 306 | 3-amino-N-methyl-6-[3-({[(2,3,6-trifluorophenyl)methyl]amino}carbonyl)phenyl]pyrazine-2-carboxamide | B |
| 307 | 3-amino-N-methyl-6-[3-({[(2,3,6-trifluorophenyl)methyl]amino}carbonyl)phenyl]pyrazine-2-carboxamide | B |
| 308 | 3-amino-N-methyl-6-(3-{[(phenylcarbonyl)amino]methyl}phenyl)pyrazine-2-carboxamide | B |
| 309 | 3-amino-6-[3-({[(4-chlorophenyl)carbonyl]amino}methyl)phenyl]-N-methylpyrazine-2-carboxamide | B |
| 310 | 3-amino-6-[3-({[(2,5-difluorophenyl)carbonyl]amino}methyl)phenyl]-N-methylpyrazine-2-carboxamide | B |
| 311 | 3-amino-N-methyl-6-(3-{[(naphthalen-2-ylcarbonyl)amino]methyl}phenyl)pyrazine-2-carboxamide | B |
| 312 | 3-amino-N-methyl-6-(3-{[(phenylmethyl)thio]methyl}phenyl)pyrazine-2-carboxamide | B |
| 313 | 3-amino-N-methyl-6-(3-{[(phenylmethyl)sulfonyl]methyl}phenyl)pyrazine-2-carboxamide | B |

TABLE 11-continued

| # | Name | Chk1 IC$_{50}$ |
|---|---|---|
| 314 | 3-amino-N-methyl-6-(3-{[(phenylmethyl)oxy]methyl}phenyl)pyrazine-2-carboxamide | B |
| 315 | 3-amino-N-methyl-6-(3-{[(phenylmethyl)amino]methyl}phenyl)pyrazine-2-carboxamide | B |
| 316 | 3-amino-N-methyl-6-[3-({[(3,4,5-trifluorophenyl)methyl]amino}carbonyl)phenyl]pyrazine-2-carboxamide | B |
| 317 | 9H-fluoren-9-ylmethyl (3-{5-amino-6-[(methylamino)carbonyl]pyrazin-2-yl}phenyl)carbamate | C |
| 318 | phenylmethyl (3-{5-amino-6-[(methylamino)carbonyl]pyrazin-2-yl}phenyl)carbamate | B |
| 319 | ethyl (3-{5-amino-6-[(methylamino)carbonyl]pyrazin-2-yl}phenyl)carbamate | B |
| 320 | 3-amino-6-[3-({[(3,4-dichlorophenyl)carbonyl]amino}methyl)phenyl]-N-methylpyrazine-2-carboxamide | B |
| 321 | 1,1-dimethylethyl (3-{5-amino-6-[(methylamino)carbonyl]pyrazin-2-yl}phenyl)carbamate | C |
| 322 | (1R,2S,5R)-5-methyl-2-(1-methylethyl)cyclohexyl (3-{5-amino-6-[(methylamino)carbonyl]pyrazin-2-yl}phenyl)carbamate | D |
| 323 | 3-amino-6-[3-({[(4-hydroxyphenyl)methyl]amino}carbonyl)phenyl]-N-methylpyrazine-2-carboxamide | B |
| 324 | 3-amino-N-methyl-6-(3-{[({4-[(2-morpholin-4-ylethyl)oxy]phenyl}methyl)amino]carbonyl}phenyl)pyrazine-2-carboxamide | B |
| 325 | 3-amino-N-methyl-6-{3-[({[2-(methyloxy)phenyl]methyl}amino)carbonyl]phenyl}pyrazine-2-carboxamide | B |
| 326 | 3-amino-6-[3-({[(3-hydroxyphenyl)methyl]amino}carbonyl)phenyl]-N-methylpyrazine-2-carboxamide | B |
| 327 | 3-amino-6-[3-({[(2-hydroxyphenyl)methyl]amino}carbonyl)phenyl]-N-methylpyrazine-2-carboxamide | B |
| 328 | 3-amino-N-methyl-6-{3-[(2-phenylhydrazino)carbonyl]phenyl}pyrazine-2-carboxamide | A |
| 329 | 3-amino-N-(2-hydroxyethyl)-6-(3-methylphenyl)pyrazine-2-carboxamide | C |
| 330 | 3-amino-N-methyl-6-(3-{[(phenylacetyl)amino]methyl}phenyl)pyrazine-2-carboxamide | B |
| 331 | 3-amino-6-[3-({[(4-chlorophenyl)acetyl]amino}methyl)phenyl]-N-methylpyrazine-2-carboxamide | B |
| 332 | 3-amino-6-(3-{[(biphenyl-4-ylcarbonyl)amino]methyl}phenyl)-N-methylpyrazine-2-carboxamide | A |
| 333 | 3-amino-6-{3-[({[2-chloro-5-(trifluoromethyl)phenyl]carbonyl}amino)methyl]phenyl}-N-methylpyrazine-2-carboxamide | B |
| 334 | N-[(3-{5-amino-6-[(methylamino)carbonyl]pyrazin-2-yl}phenyl)methyl]-1H-indole-2-carboxamide | B |
| 335 | 3-amino-6-[3-({[(3-hydroxypyridin-2-yl)carbonyl]amino}methyl)phenyl]-N-methylpyrazine-2-carboxamide | B |
| 336 | 3-amino-6-(3-{[(1H-indol-3-ylacetyl)amino]methyl}phenyl)-N-methylpyrazine-2-carboxamide | B |
| 337 | 3-amino-6-[3-({[(2,5-difluorophenyl)methyl]amino}carbonyl)phenyl]-N-methylpyrazine-2-carboxamide | B |
| 338 | 3-amino-6-[3-({[(2,6-difluorophenyl)methyl]amino}carbonyl)phenyl]-N-methylpyrazine-2-carboxamide | B |
| 339 | 3-amino-6-[3-({[(3,5-difluorophenyl)methyl]amino}carbonyl)phenyl]-N-methylpyrazine-2-carboxamide | A |
| 340 | 3-amino-6-[3-({[(3-iodophenyl)methyl]amino}carbonyl)phenyl]-N-methylpyrazine-2-carboxamide | A |
| 341 | 3-amino-N-methyl-6-[3-({[(2-morpholin-4-ylphenyl)methyl]amino}carbonyl)phenyl]pyrazine-2-carboxamide | B |
| 342 | 3-amino-N-methyl-6-(3-{[({3-[(2-morpholin-4-ylethyl)oxy]phenyl}methyl)amino]carbonyl}phenyl)pyrazine-2-carboxamide | B |
| 343 | 3-amino-N-methyl-6-(3-{[({4-morpholin-4-ylphenyl)methyl]amino}carbonyl)phenyl]pyrazine-2-carboxamide | B |
| 344 | 3-amino-N-methyl-6-[3-({[(3-morpholin-4-ylphenyl)methyl]amino}carbonyl)phenyl]pyrazine-2-carboxamide | C |
| 345 | 3-amino-N-methyl-6-{3-[({[4-(1-methylethyl)phenyl]methyl}amino)carbonyl]phenyl}pyrazine-2-carboxamide | B |
| 346 | 3-amino-N-methyl-6-(3-{[({[4-(1-methylethyl)phenyl]oxy}acetyl)amino]methyl}phenyl)pyrazine-2-carboxamide | B |
| 347 | 3-amino-6-{3-[({[(4-aminophenyl)thio]acetyl}amino)methyl]phenyl}-N-methylpyrazine-2-carboxamide | B |
| 348 | 3-amino-N-methyl-6-(4-(methyloxy)-3-{[(phenylmethyl)amino]carbonyl}phenyl)pyrazine-2-carboxamide | B |
| 349 | 3-amino-N-methyl-6-(5-{[(phenylmethyl)amino]carbonyl}pyridin-3-yl)pyrazine-2-carboxamide | B |
| 350 | 3-amino-6-[3-({[(4-iodophenyl)carbonyl]amino}methyl)phenyl]-N-methylpyrazine-2-carboxamide | A |
| 351 | 3-amino-N-methyl-6-[3-({[(4-pentylphenyl)carbonyl]amino}methyl)phenyl]pyrazine-2-carboxamide | B |

TABLE 11-continued

| # | Name | Chk1 IC$_{50}$ |
|---|------|---------------|
| 352 | 3-amino-6-(3-{[(1,3-benzodioxol-5-ylcarbonyl)amino]methyl}phenyl)-N-methylpyrazine-2-carboxamide | B |
| 353 | 3-amino-6-{3-[({[4-(1,1-dimethylethyl)phenyl]methyl}amino)carbonyl]phenyl}-N-methylpyrazine-2-carboxamide | B |
| 354 | 3-amino-N-methyl-6-(3-{[({1-[5-(trifluoromethyl)pyrimidin-2-yl]piperidin-4-yl}carbonyl)amino]methyl}phenyl)pyrazine-2-carboxamide | B |
| 355 | 3-amino-N-methyl-6-[3-({[(2-piperidin-1-ylphenyl)methyl]amino}carbonyl)phenyl]pyrazine-2-carboxamide | B |
| 356 | 3-amino-N-methyl-6-{3-[({[2-(methylthio)phenyl]methyl}amino)carbonyl]phenyl}pyrazine-2-carboxamide | A |
| 357 | 1,1-dimethylethyl (3R)-3-{[(3-{5-amino-6-[(methylamino)carbonyl]pyrazin-2-yl}phenyl)carbonyl]amino}pyrrolidine-1-carboxylate | C |
| 358 | 3-amino-N-methyl-6-(3-{[(3R)-pyrrolidin-3-ylamino]carbonyl}phenyl)pyrazine-2-carboxamide | C |
| 359 | 3-{[(4-chlorophenyl)methyl]amino}-6-{3-[({(3R)-1-[(4-chlorophenyl)methyl]pyrrolidin-3-yl}amino)carbonyl]phenyl}-N-methylpyrazine-2-carboxamide | B |
| 360 | 3-amino-6-{3-[({(3R)-1-[(2,4-dichlorophenyl)methyl]pyrrolidin-3-yl}amino)carbonyl]phenyl}-N-methylpyrazine-2-carboxamide | B |
| 361 | N-methyl-3-({[3-(methyloxy)phenyl]methyl}amino)-6-(3-{[((3R)-1-{[3-(methyloxy)phenyl]methyl}pyrrolidin-3-yl)amino]carbonyl}phenyl)pyrazine-2-carboxamide | B |
| 362 | 3-amino-6-{3-[({(3R)-1-[(2,6-dichlorophenyl)methyl]pyrrolidin-3-yl}amino)carbonyl]phenyl}-N-methylpyrazine-2-carboxamide | B |
| 363 | N-methyl-3-[(phenylmethyl)amino]-6-(3-{[((3R)-1-(phenylmethyl)pyrrolidin-3-yl]amino}carbonyl)phenyl]pyrazine-2-carboxamide | B |
| 364 | 1,1-dimethylethyl 3-({[(3-{5-amino-6-[(methylamino)carbonyl]pyrazin-2-yl}phenyl)carbonyl]amino}methyl)pyrrolidine-1-carboxylate | B |
| 365 | 1,1-dimethylethyl 2-({[(3-{5-amino-6-[(methylamino)carbonyl]pyrazin-2-yl}phenyl)carbonyl]amino}methyl)pyrrolidine-1-carboxylate | C |
| 366 | 3-amino-N-methyl-6-(3-{[(pyrrolidin-3-ylmethyl)amino]carbonyl}phenyl)pyrazine-2-carboxamide | B |
| 367 | 3-amino-N-methyl-6-(3-{[(pyrrolidin-2-ylmethyl)amino]carbonyl}phenyl)pyrazine-2-carboxamide | B |
| 368 | 3-amino-6-(2-fluoro-5-{[(phenylmethyl)amino]carbonyl}phenyl)-N-methylpyrazine-2-carboxamide | B |
| 369 | 3-amino-6-{3-[(1,3-benzodioxol-5-ylacetyl)amino]phenyl}-N-methylpyrazine-2-carboxamide | B |
| 370 | 3-amino-6-[3-({[(2-chloro-4-fluorophenyl)methyl]amino}carbonyl)phenyl]-N-methylpyrazine-2-carboxamide | B |
| 371 | 3-amino-6-{3-[({[3,4-bis(methyloxy)phenyl]methyl}amino)carbonyl]phenyl}-N-methylpyrazine-2-carboxamide | B |
| 372 | 3-amino-N-methyl-6-{3-[(phenylmethyl)amino]phenyl}pyrazine-2-carboxamide | B |
| 373 | 3-amino-N-methyl-6-(3-{[({2-[(2-morpholin-4-ylethyl)oxy]phenyl}methyl)amino]carbonyl}phenyl)pyrazine-2-carboxamide | B |
| 374 | 3-amino-N-methyl-6-{3-[({[4-(1-methylethyl)phenyl]carbonyl}amino)methyl]phenyl}pyrazine-2-carboxamide | B |
| 375 | 3-amino-6-[3-({[(4-butylphenyl)methyl]amino}carbonyl)phenyl]-N-methylpyrazine-2-carboxamide | B |
| 376 | 3-amino-N-methyl-6-{3-[({[4-(1,2,3-thiadiazol-4-yl)phenyl]methyl}amino)carbonyl]phenyl}pyrazine-2-carboxamide | A |
| 377 | 3-amino-N-methyl-6-{3-[({[4-(2-thienyl)phenyl]methyl}amino)carbonyl]phenyl}pyrazine-2-carboxamide | A |
| 378 | 3-amino-6-{3-[({[4-(1,1-dimethylethyl)phenyl]carbonyl}amino)methyl]phenyl}-N-methylpyrazine-2-carboxamide | B |
| 379 | 3-amino-N-methyl-6-{3-[({[4-(1H-pyrazol-1-yl)phenyl]methyl}amino)carbonyl]phenyl}pyrazine-2-carboxamide | B |
| 380 | 3-amino-6-(3-{[(3,4-dihydro-2H-1,4-benzoxazin-6-ylmethyl)amino]carbonyl}phenyl)-N-methylpyrazine-2-carboxamide | B |
| 381 | 3-amino-6-[3-({[(2-amino-6-fluorophenyl)methyl]amino}carbonyl)phenyl]-N-methylpyrazine-2-carboxamide | B |
| 382 | 3-amino-6-(3-{[(biphenyl-4-ylmethyl)amino]methyl}phenyl)-N-methylpyrazine-2-carboxamide | B |
| 383 | 3-amino-6-(3-{[(biphenyl-2-ylmethyl)amino]methyl}phenyl)-N-methylpyrazine-2-carboxamide | B |
| 384 | 3-amino-6-(3-{[(biphenyl-3-ylmethyl)amino]methyl}phenyl)-N-methylpyrazine-2-carboxamide | B |
| 385 | 3-amino-N-methyl-6-{3-[({[1-(phenylmethyl)pyrrolidin-2-yl]methyl}amino)carbonyl]phenyl}pyrazine-2-carboxamide | B |
| 386 | 3-amino-6-(3-{[(3,4-dihydro-2H-1,4-benzoxazin-6-ylmethyl)amino]methyl}phenyl)-N-methylpyrazine-2-carboxamide | B |
| 387 | 3-amino-6-[3-({[(2,4-difluorophenyl)methyl]amino}methyl)phenyl]-N-methylpyrazine-2-carboxamide | A |

TABLE 11-continued

| # | Name | Chk1 IC$_{50}$ |
|---|---|---|
| 388 | 3-amino-6-[3-({[(2,5-difluorophenyl)methyl]amino}methyl)phenyl]-N-methylpyrazine-2-carboxamide | B |
| 389 | 3-amino-6-[3-({[(2,3-difluorophenyl)methyl]amino}methyl)phenyl]-N-methylpyrazine-2-carboxamide | B |
| 390 | 3-amino-N-methyl-6-[3-({[(2-pyridin-4-ylphenyl)methyl]amino}carbonyl)phenyl]pyrazine-2-carboxamide | B |
| 391 | 3-amino-N-methyl-6-[3-({[(2-pyridin-3-ylphenyl)methyl]amino}carbonyl)phenyl]pyrazine-2-carboxamide | B |
| 392 | 3-amino-N-methyl-6-{3-[({[4-(methylsulfonyl)phenyl]methyl}amino)methyl]phenyl}pyrazine-2-carboxamide | B |
| 393 | 3-amino-6-(3-{[(2,2-diphenylethyl)amino]methyl}phenyl)-N-methylpyrazine-2-carboxamide | B |
| 394 | 3-amino-N-methyl-6-{3-[({[1-(phenylmethyl)pyrrolidin-3-yl]methyl}amino)carbonyl]phenyl}pyrazine-2-carboxamide | B |
| 395 | 3-amino-N-methyl-6-{3-[({[3-(phenyloxy)phenyl]methyl}amino)methyl]phenyl}pyrazine-2-carboxamide | B |
| 396 | 3-amino-6-[3-({[(4-aminophenyl)methyl]amino}methyl)phenyl]-N-methylpyrazine-2-carboxamide | B |
| 397 | 3-amino-N-methyl-6-{3-[({[4-(phenyloxy)phenyl]methyl}amino)methyl]phenyl}pyrazine-2-carboxamide | B |
| 398 | 3-amino-6-{3-[({[2,6-bis(methyloxy)phenyl]methyl}amino)methyl]phenyl}-N-methylpyrazine-2-carboxamide | B |
| 399 | 3-amino-6-[3-({[(2-fluorophenyl)methyl]amino}methyl)phenyl]-N-methylpyrazine-2-carboxamide | A |
| 400 | 3-amino-6-[5-({[(2,6-difluorophenyl)methyl]amino}carbonyl)pyridin-3-yl]-N-methylpyrazine-2-carboxamide | B |
| 401 | 3-amino-6-(5-{[(biphenyl-2-ylmethyl)amino]carbonyl}pyridin-3-yl)-N-methylpyrazine-2-carboxamide | B |
| 402 | 3-amino-6-[3-({[(2,6-difluorophenyl)methyl]amino}methyl)phenyl]-N-methylpyrazine-2-carboxamide | B |
| 403 | 3-amino-6-(3-{[({2,3-dihydro-1,4-benzodioxin-6-ylmethyl)amino]methyl}phenyl)-N-methylpyrazine-2-carboxamide | B |
| 404 | 3-amino-N-methyl-6-[3-({[(2-piperidin-1-ylphenyl)methyl]amino}methyl)phenyl]pyrazine-2-carboxamide | B |
| 405 | 3-amino-6-{3-[({[4-fluoro-2-(trifluoromethyl)phenyl]methyl}amino)carbonyl]phenyl}-N-methylpyrazine-2-carboxamide | B |
| 406 | 3-amino-N-methyl-6-{3-[({[6-(trifluoromethyl)pyridin-3-yl]methyl}amino)carbonyl]phenyl}pyrazine-2-carboxamide | B |
| 407 | 3-amino-6-[3-(1H-benzimidazol-2-yl)phenyl]-N-methylpyrazine-2-carboxamide | B |
| 408 | 3-amino-6-[3-({[(2,5-dichlorophenyl)methyl]amino}methyl)phenyl]-N-methylpyrazine-2-carboxamide | B |
| 409 | 3-amino-6-[3-({[(3,5-dichlorophenyl)methyl]amino}methyl)phenyl]-N-methylpyrazine-2-carboxamide | A |
| 410 | 3-amino-N-methyl-6-{3-[(2-phenylethyl)amino]phenyl}pyrazine-2-carboxamide | B |
| 411 | 3-amino-6-(5-{[(2,3-dihydro-1,4-benzodioxin-6-ylmethyl)amino]carbonyl}pyridin-3-yl)-N-methylpyrazine-2-carboxamide | B |
| 412 | 3-amino-N-methyl-6-[3-({[2-(phenylamino)ethyl]amino}carbonyl)phenyl]pyrazine-2-carboxamide | B |
| 413 | 3-amino-6-[3-({[(4-ethylphenyl)methyl]amino}carbonyl)phenyl]-N-methylpyrazine-2-carboxamide | B |
| 414 | 3-amino-N-methyl-6-[3-({[(4-pyridin-3-ylphenyl)methyl]amino}carbonyl)phenyl]pyrazine-2-carboxamide | B |
| 415 | 3-amino-6-{3-[(2,3-dihydro-1H-inden-2-ylamino)methyl]phenyl}-N-methylpyrazine-2-carboxamide | A |
| 416 | 3-amino-6-[3-(1,3-dihydro-2H-isoindol-2-ylmethyl)phenyl]-N-methylpyrazine-2-carboxamide | B |
| 417 | 3-amino-6-(3-{[(1R)-2,3-dihydro-1H-inden-1-ylamino]methyl}phenyl)-N-methylpyrazine-2-carboxamide | B |
| 418 | 3-amino-6-(3-{[(1S)-2,3-dihydro-1H-inden-1-ylamino]methyl}phenyl)-N-methylpyrazine-2-carboxamide | A |
| 419 | 3-amino-N-methyl-6-[3-({[(3,4,5-trifluorophenyl)methyl]amino}methyl)phenyl]pyrazine-2-carboxamide | A |
| 420 | 3-amino-N-methyl-6-[3-({[(1R)-1-phenylethyl]amino}methyl)phenyl]pyrazine-2-carboxamide | B |
| 421 | 3-amino-6-[3-({[(1R,2S)-2-hydroxy-2,3-dihydro-1H-inden-1-yl]amino}methyl)phenyl]-N-methylpyrazine-2-carboxamide | A |
| 422 | 3-amino-N-methyl-6-{3-[({[4-(2-thienyl)phenyl]methyl}amino)methyl]phenyl}pyrazine-2-carboxamide | A |
| 423 | 3-amino-N-methyl-6-{3-[({[3-(1,2,3-thiadiazol-4-yl)phenyl]methyl}amino)methyl]phenyl}pyrazine-2-carboxamide | B |

TABLE 11-continued

| # | Name | Chk1 IC$_{50}$ |
|---|------|---|
| 424 | 3-amino-N-methyl-6-[3-({[(4-propylphenyl)methyl]amino}carbonyl)phenyl]pyrazine-2-carboxamide | B |
| 425 | 3-amino-6-[3-({[(4-chloro-2-fluorophenyl)methyl]amino}methyl)phenyl]-N-methylpyrazine-2-carboxamide | B |
| 426 | 3-amino-N-methyl-6-{3-[({[3-(trifluoromethyl)phenyl]methyl}amino)methyl]phenyl}pyrazine-2-carboxamide | B |
| 427 | 3-amino-N-methyl-6-[3-({[(1S)-1-phenylethyl]amino}methyl)phenyl]pyrazine-2-carboxamide | B |
| 428 | 3-amino-6-[3-({[(1R)-2-hydroxy-1-phenylethyl]amino}methyl)phenyl]-N-methylpyrazine-2-carboxamide | B |
| 429 | methyl (2S)-{[(3-{5-amino-6-[(methylamino)carbonyl]pyrazin-2-yl}phenyl)methyl]amino}(phenyl)ethanoate | C |
| 430 | 3-amino-6-(3-{[2-(2,5-difluorophenyl)hydrazino]carbonyl}phenyl)-N-methylpyrazine-2-carboxamide | B |
| 431 | 3-amino-N-methyl-6-(3-{[2-(2,3,5,6-tetrafluoro-4-methylphenyl)hydrazino]carbonyl}phenyl)pyrazine-2-carboxamide | B |
| 432 | 3-amino-6-(3-{[2-(2-fluorophenyl)hydrazino]carbonyl}phenyl)-N-methylpyrazine-2-carboxamide | B |
| 433 | 3-amino-6-(3-{[2-(2,4-difluorophenyl)hydrazino]carbonyl}phenyl)-N-methylpyrazine-2-carboxamide | B |
| 434 | 3-amino-N-methyl-6-(3-{[2-(2,3,5,6-tetrafluorophenyl)hydrazino]carbonyl}phenyl)pyrazine-2-carboxamide | B |
| 435 | 3-amino-N-methyl-6-[3-({[(5-methylpyrazin-2-yl)methyl]amino}methyl)phenyl]pyrazine-2-carboxamide | B |
| 436 | 3-amino-N-methyl-6-(3-{[(1S)-1,2,3,4-tetrahydronaphthalen-1-ylamino]methyl}phenyl)pyrazine-2-carboxamide | A |
| 437 | 3-amino-N-methyl-6-[3-({[(3S)-1-(phenylmethyl)pyrrolidin-3-yl]amino}methyl)phenyl]pyrazine-2-carboxamide | B |
| 438 | 3-amino-N-methyl-6-[3-({[(3R)-1-(phenylmethyl)pyrrolidin-3-yl]amino}methyl)phenyl]pyrazine-2-carboxamide | B |
| 439 | 3-amino-6-(3-{[ethyl(phenylmethyl)amino]methyl}phenyl)-N-methylpyrazine-2-carboxamide | B |
| 440 | 3-amino-N-methyl-6-[3-({[(1S,2S)-2-phenylcyclopropyl]amino}methyl)phenyl]pyrazine-2-carboxamide | B |
| 441 | 3-Amino-6-(3-benzylcarbamoyl-phenyl)-pyrazine-2-carboxylic acid methylamide | B |
| 442 | 3-amino-N-methyl-6-[3-(4-phenyl-1H-imidazol-2-yl)phenyl]pyrazine-2-carboxamide | B |
| 443 | 3-amino-N-methyl-6-[3-({[(4-propylphenyl)methyl]amino}methyl)phenyl]pyrazine-2-carboxamide | B |
| 444 | 3-amino-6-[3-({[(5-bromo-2-fluorophenyl)methyl]amino}methyl)phenyl]-N-methylpyrazine-2-carboxamide | B |
| 445 | 3-amino-N-methyl-6-(3-{[(2R)-1,2,3,4-tetrahydronaphthalen-2-ylamino]methyl}phenyl)pyrazine-2-carboxamide | A |
| 446 | 3-amino-N-methyl-6-(3-{[(1-methyl-1-phenylethyl)amino]methyl}phenyl)pyrazine-2-carboxamide | B |
| 447 | 3-amino-6-{3-[(9H-fluoren-9-ylamino)methyl]phenyl}-N-methylpyrazine-2-carboxamide | C |
| 448 | 3-amino-N-methyl-6-{3-[(naphthalen-1-ylamino)methyl]phenyl}pyrazine-2-carboxamide | B |
| 449 | 3-amino-6-[3-({[(3-fluorobiphenyl-4-yl)methyl]amino}methyl)phenyl]-N-methylpyrazine-2-carboxamide | B |
| 450 | 3-amino-6-{3-[({[2-fluoro-4-(2-thienyl)phenyl]methyl}amino)methyl]phenyl}-N-methylpyrazine-2-carboxamide | A |
| 451 | 3-amino-6-[3-({[(2-fluoro-4-furan-2-ylphenyl)methyl]amino}methyl)phenyl]-N-methylpyrazine-2-carboxamide | A |
| 452 | 3-amino-N-methyl-6-{3-[(naphthalen-2-ylamino)methyl]phenyl}pyrazine-2-carboxamide | B |
| 453 | 3-amino-6-[3-({[(1S,2R)-2-hydroxy-2,3-dihydro-1H-inden-1-yl]amino}methyl)phenyl]-N-methylpyrazine-2-carboxamide | A |
| 454 | 3-amino-N-methyl-6-(3-{[(2S)-1,2,3,4-tetrahydronaphthalen-2-ylamino]methyl}phenyl)pyrazine-2-carboxamide | A |
| 455 | methyl 3-amino-6-(3-{[(4,7-difluoro-2,3-dihydro-1H-inden-1-yl)amino]methyl}phenyl)pyrazine-2-carboxylate | B |
| 456 | 3-amino-6-(3-{[(5-bromo-2,3-dihydro-1H-inden-2-yl)amino]methyl}phenyl)-N-methylpyrazine-2-carboxamide | B |
| 457 | 3-amino-6-{3-[({[2-fluoro-5-(2-thienyl)phenyl]methyl}amino)methyl]phenyl}-N-methylpyrazine-2-carboxamide | B |
| 458 | 3-amino-6-[3-({[(4-ethenyl-2-fluorophenyl)methyl]amino}methyl)phenyl]-N-methylpyrazine-2-carboxamide | B |
| 459 | 3-amino-6-(3-{[(4,7-difluoro-3-methyl-2,3-dihydro-1H-inden-1-yl)amino]methyl}phenyl)-N-methylpyrazine-2-carboxamide | B |
| 460 | 3-amino-N-methyl-6-[3-({[(1S,2R)-2-(methyloxy)-2,3-dihydro-1H-inden-1-yl]amino}methyl)phenyl]pyrazine-2-carboxamide | B |
| 461 | 3-amino-6-(3-{[(5-bromo-2,3-dihydro-1H-inden-1-yl)amino]methyl}phenyl)-N-methylpyrazine-2-carboxamide | B |

TABLE 11-continued

| # | Name | Chk1 IC$_{50}$ |
|---|---|---|
| 462 | 3-amino-6-[3-({[(2S)-6-bromo-1,2,3,4-tetrahydronaphthalen-2-yl]amino}methyl)phenyl]-N-methylpyrazine-2-carboxamide | A |
| 463 | 3-amino-6-[3-({[(2R)-6-bromo-1,2,3,4-tetrahydronaphthalen-2-yl]amino}methyl)phenyl]-N-methylpyrazine-2-carboxamide | B |
| 464 | 3-amino-6-(3-{[(5-fluoro-2,3-dihydro-1H-inden-1-yl)amino]methyl}phenyl)-N-methylpyrazine-2-carboxamide | B |
| 465 | 3-amino-6-[3-({[(2S)-5-bromo-2,3-dihydro-1H-inden-2-yl]amino}methyl)phenyl]-N-methylpyrazine-2-carboxamide | A |
| 466 | 3-amino-6-(3-{[(4-fluoro-2,3-dihydro-1H-inden-2-yl)amino]methyl}phenyl)-N-methylpyrazine-2-carboxamide | A |
| 467 | 3-amino-6-(3-{[(4-fluoro-1-hydroxy-2,3-dihydro-1H-inden-2-yl)amino]methyl}phenyl)-N-methylpyrazine-2-carboxamide | B |
| 468 | 3-amino-N-methyl-6-[3-({[(1R,2S)-2-(methyloxy)-2,3-dihydro-1H-inden-1-yl]amino}methyl)phenyl]pyrazine-2-carboxamide | B |
| 469 | 3-amino-6-(3-{[(4,7-difluoro-2,3-dihydro-1H-inden-1-yl)amino]methyl}phenyl)-N-methylpyrazine-2-carboxamide | B |
| 470 | 3-amino-6-(3-{[(6-bromo-4-fluoro-2,3-dihydro-1H-inden-1-yl)amino]methyl}phenyl)-N-methylpyrazine-2-carboxamide | B |
| 471 | 3-amino-N-methyl-6-{3-[[(3-oxo-2,3-dihydro-1H-inden-1-yl)amino]methyl}phenyl]pyrazine-2-carboxamide | B |
| 472 | 3-amino-6-(3-{[(5-furan-2-yl-2,3-dihydro-1H-inden-1-yl)amino]methyl}phenyl)-N-methylpyrazine-2-carboxamide | A |
| 473 | 3-amino-6-(3-{[[(4-fluoro-2,3-dihydro-1H-inden-1-yl)amino]methyl}phenyl)-N-methylpyrazine-2-carboxamide | B |
| 474 | 3-amino-6-(3-{[(4,6-difluoro-2,3-dihydro-1H-inden-1-yl)amino]methyl}phenyl)-N-methylpyrazine-2-carboxamide | B |
| 475 | 3-amino-6-(3-{[[(6-fluoro-2,3-dihydro-1H-inden-1-yl)amino]methyl}phenyl)-N-methylpyrazine-2-carboxamide | A |
| 476 | 3-amino-6-(3-{[(5,6-difluoro-2,3-dihydro-1H-inden-1-yl)amino]methyl}phenyl)-N-methylpyrazine-2-carboxamide | B |
| 477 | 3-amino-6-(3-{[[(5-chloro-2,3-dihydro-1H-inden-1-yl)amino]methyl}phenyl)-N-methylpyrazine-2-carboxamide | A |
| 478 | 3-amino-N-methyl-6-[3-({[5-(2-thienyl)-2,3-dihydro-1H-inden-1-yl]amino}methyl)phenyl]pyrazine-2-carboxamide | A |
| 479 | 3-amino-6-(3-{[(5,7-difluoro-2,3-dihydro-1H-inden-1-yl)amino]methyl}phenyl)-N-methylpyrazine-2-carboxamide | B |
| 480 | 3-amino-6-(3-{[(5-furan-3-yl-2,3-dihydro-1H-inden-1-yl)amino]methyl}phenyl)-N-methylpyrazine-2-carboxamide | A |
| 481 | 3-amino-N-methyl-6-[3-({[5-(3-thienyl)-2,3-dihydro-1H-inden-1-yl]amino}methyl)phenyl]pyrazine-2-carboxamide | A |
| 482 | 3-amino-6-[3-({[(1S)-4-fluoro-2,3-dihydro-1H-inden-1-yl]amino}methyl)phenyl]-N-methylpyrazine-2-carboxamide | A |
| 483 | 3-amino-6-[3-({[(1S)-5,7-difluoro-2,3-dihydro-1H-inden-1-yl]amino}methyl)phenyl]-N-methylpyrazine-2-carboxamide | B |
| 484 | 3-amino-6-(3-{[(7-bromo-4-fluoro-2,3-dihydro-1H-inden-1-yl)amino]methyl}phenyl)-N-methylpyrazine-2-carboxamide | B |
| 485 | 3-amino-6-(3-{[[(6-chloro-2,3-dihydro-1H-inden-1-yl)amino]methyl}phenyl)-N-methylpyrazine-2-carboxamide | B |
| 486 | 3-amino-6-(3-{[(4,6-dichloro-2,3-dihydro-1H-inden-1-yl)amino]methyl}phenyl)-N-methylpyrazine-2-carboxamide | B |
| 487 | 3-amino-6-(3-{[[(4-chloro-2,3-dihydro-1H-inden-1-yl)amino]methyl}phenyl)-N-methylpyrazine-2-carboxamide | A |
| 488 | 3-amino-6-(3-{[(1S)-2,3-dihydro-1H-inden-1-ylamino]methyl}phenyl)-N-ethylpyrazine-2-carboxamide | B |
| 489 | 3-amino-6-(3-{[(5,7-difluoro-2,3-dihydro-1H-inden-1-yl)amino]methyl}phenyl)-N-ethylpyrazine-2-carboxamide | B |
| 490 | 3-amino-N-methyl-6-[3-({[(1S)-5-(2-thienyl)-2,3-dihydro-1H-inden-1-yl]amino}methyl)phenyl]pyrazine-2-carboxamide | A |
| 491 | 3-amino-N-methyl-6-(3-{[(5-phenyl-2,3-dihydro-1H-inden-1-yl)amino]methyl}phenyl)pyrazine-2-carboxamide | B |
| 492 | 3-amino-6-(3-{[[(4-bromo-2,3-dihydro-1H-inden-1-yl)amino]methyl}phenyl)-N-methylpyrazine-2-carboxamide | A |
| 493 | 3-amino-N-methyl-6-(3-{[(4-phenyl-2,3-dihydro-1H-inden-1-yl)amino]methyl}phenyl)pyrazine-2-carboxamide | A |
| 494 | 3-amino-N-methyl-6-[3-({[4-(2-thienyl)-2,3-dihydro-1H-inden-1-yl]amino}methyl)phenyl]pyrazine-2-carboxamide | A |
| 495 | 3-amino-N-methyl-6-[3-({[6-(2-thienyl)-2,3-dihydro-1H-inden-1-yl]amino}methyl)phenyl]pyrazine-2-carboxamide | B |
| 496 | 3-amino-N-methyl-6-[3-({[5-(4-methyl-2-thienyl)-2,3-dihydro-1H-inden-1-yl]amino}methyl)phenyl]pyrazine-2-carboxamide | A |
| 497 | 3-amino-N-methyl-6-[3-({[(2R)-6-phenyl-1,2,3,4-tetrahydronaphthalen-2-yl]amino}methyl)phenyl]pyrazine-2-carboxamide | B |
| 498 | 3-amino-N-methyl-6-naphthalen-2-ylpyrazine-2-carboxamide | B |
| 499 | 3-amino-N-methyl-6-{3-[({(1S,2S)-2-[(phenylmethyl)oxy]cyclopentyl}amino)methyl]phenyl}pyrazine-2-carboxamide | B |

TABLE 11-continued

| # | Name | Chk1 IC$_{50}$ |
|---|---|---|
| 500 | 3-amino-6-{3-[(cyclopentylamino)methyl]phenyl}-N-methylpyrazine-2-carboxamide | B |
| 501 | 3-amino-6-(3-{[(6-bromo-2,3-dihydro-1H-inden-1-yl)amino]methyl}phenyl)-N-methylpyrazine-2-carboxamide | B |
| 502 | 3-amino-6-(3-{[(7-fluoro-2,3-dihydro-1H-inden-1-yl)amino]methyl}phenyl)-N-methylpyrazine-2-carboxamide | B |
| 503 | 3-amino-N-methyl-6-quinolin-3-ylpyrazine-2-carboxamide | C |
| 504 | 3-amino-6-[3-(1H-imidazol-1-ylmethyl)phenyl]-N-methylpyrazine-2-carboxamide | B |
| 505 | 3-amino-N-methyl-6-{3-[({5-[(2-morpholin-4-ylethyl)oxy]-2,3-dihydro-1H-inden-1-yl}amino)methyl]phenyl}pyrazine-2-carboxamide | B |
| 506 | 3-amino-N-methyl-6-{3-[({(1R,2R)-2-[(phenylmethyl)oxy]cyclopentyl}amino)methyl]phenyl}pyrazine-2-carboxamide | B |
| 507 | 3-amino-6-{3-[(2,3-dihydro-1-benzofuran-3-ylamino)methyl]phenyl}-N-methylpyrazine-2-carboxamide | B |
| 508 | 3-amino-6-{3-[({5-[(cyanomethyl)oxy]-2,3-dihydro-1H-inden-1-yl}amino)methyl]phenyl}-N-methylpyrazine-2-carboxamide | B |
| 509 | 2-amino-5-(3-{[(1S)-2,3-dihydro-1H-inden-1-ylamino]methyl}phenyl)-N-methylpyridine-3-carboxamide | B |
| 510 | 3-amino-N-methyl-6-[3-({[5-(4-methylphenyl)-2,3-dihydro-1H-inden-1-yl]amino}methyl)phenyl]pyrazine-2-carboxamide | B |
| 511 | 3-amino-6-[3-({[2-(dimethylamino)-1-phenylethyl]amino}methyl)phenyl]-N-methylpyrazine-2-carboxamide | B |
| 512 | 3-amino-N-methyl-6-[3-({[5-(1H-1,2,4-triazol-1-yl)-2,3-dihydro-1H-inden-1-yl]amino}methyl)phenyl]pyrazine-2-carboxamide | B |
| 513 | 3-amino-6-(3-{[(5-hydroxy-2,3-dihydro-1H-inden-1-yl)amino]methyl}phenyl)-N-methylpyrazine-2-carboxamide | B |
| 514 | 3-amino-N-methyl-6-{3-[({4-[(2-morpholin-4-ylethyl)oxy]-2,3-dihydro-1H-inden-1-yl}amino)methyl]phenyl}pyrazine-2-carboxamide | B |
| 515 | 3-amino-6-(3-{[(4-hydroxy-2,3-dihydro-1H-inden-1-yl)amino]methyl}phenyl)-N-methylpyrazine-2-carboxamide | A |
| 516 | 3-amino-N-methyl-6-{1-[(phenylmethyl)amino]isoquinolin-7-yl}pyrazine-2-carboxamide | C |
| 517 | 3-amino-N-methyl-6-(3-{[(2-morpholin-4-yl-1-phenylethyl)amino]methyl}phenyl)pyrazine-2-carboxamide | C |
| 518 | 3-amino-N-methyl-6-(3-{[(1-phenyl-2-pyrrolidin-1-ylethyl)amino]methyl}phenyl)pyrazine-2-carboxamide | B |
| 519 | 2-amino-5-(3-{[(6-bromo-2,3-dihydro-1H-inden-1-yl)amino]methyl}phenyl)-N-methylpyridine-3-carboxamide | B |
| 520 | 2-amino-5-(3-{[(4,6-difluoro-2,3-dihydro-1H-inden-1-yl)amino]methyl}phenyl)-N-methylpyridine-3-carboxamide | B |
| 521 | 2-amino-5-(3-{[(7-bromo-4-fluoro-2,3-dihydro-1H-inden-1-yl)amino]methyl}phenyl)-N-methylpyridine-3-carboxamide | C |
| 522 | 2-amino-5-(3-{[(4-chloro-2,3-dihydro-1H-inden-1-yl)amino]methyl}phenyl)-N-methylpyridine-3-carboxamide | B |
| 523 | 2-amino-5-(3-{[(5,6-difluoro-2,3-dihydro-1H-inden-1-yl)amino]methyl}phenyl)-N-methylpyridine-3-carboxamide | B |
| 524 | 2-amino-5-(3-{[(5,7-difluoro-2,3-dihydro-1H-inden-1-yl)amino]methyl}phenyl)-N-methylpyridine-3-carboxamide | B |
| 525 | 3-amino-6-{1-[(1S)-2,3-dihydro-1H-inden-1-ylamino]isoquinolin-7-yl}-N-methylpyrazine-2-carboxamide | B |
| 526 | 3-amino-6-{3-[(1S)-2,3-dihydro-1H-inden-1-ylamino]-2,3-dihydro-1H-inden-5-yl}-N-methylpyrazine-2-carboxamide | A |
| 527 | 3-amino-6-[3-({[6-(3-hydroxypropyl)-2,3-dihydro-1H-inden-1-yl]amino}methyl)phenyl]-N-methylpyrazine-2-carboxamide | A |
| 528 | 5-(3-{[(1S)-2,3-dihydro-1H-inden-1-ylamino]methyl}phenyl)-3-(1,3-oxazol-5-yl)pyrazin-2-amine | C |
| 529 | 3-amino-6-(3-{[(1S)-2,3-dihydro-1H-inden-1-ylamino]methyl}phenyl)pyrazine-2-carbohydrazide | B |
| 530 | 3-amino-6-(3-{[(1S)-2,3-dihydro-1H-inden-1-ylamino]methyl}phenyl)pyrazine-2-carboxamide | B |
| 531 | 1-[3-amino-6-(3-{[(1S)-2,3-dihydro-1H-inden-1-ylamino]methyl}phenyl)pyrazin-2-yl]ethanone | B |
| 532 | 3-amino-6-{3-[(2,3-dihydro-1H-inden-1-ylamino)methyl]phenyl}-N-(naphthalen-2-ylmethyl)pyrazine-2-carboxamide | D |
| 533 | 3-amino-N-cyclohexyl-6-{3-[(2,3-dihydro-1H-inden-1-ylamino)methyl]phenyl}pyrazine-2-carboxamide | C |
| 534 | 3-amino-6-(3-{[(1S)-2,3-dihydro-1H-inden-1-ylamino]methyl}phenyl)-N-(pyridin-4-ylmethyl)pyrazine-2-carboxamide | C |
| 535 | {3-[5-amino-6-(4H-1,2,4-triazol-3-yl)pyrazin-2-yl]phenyl}methanol | C |
| 536 | 5-(3-{[(1S)-2,3-dihydro-1H-inden-1-ylamino]methyl}phenyl)-3-(4H-1,2,4-triazol-3-yl)pyrazin-2-amine | B |
| 537 | 3-amino-6-(3-{[(1S)-2,3-dihydro-1H-inden-1-ylamino]methyl}phenyl)-N-(2,2,2-trifluoroethyl)pyrazine-2-carboxamide | C |
| 538 | 3-amino-6-(3-{[(1S)-2,3-dihydro-1H-inden-1-ylamino]methyl}phenyl)-N-(5-hydroxypentyl)pyrazine-2-carboxamide | C |

TABLE 11-continued

| # | Name | Chk1 IC$_{50}$ |
|---|------|----------------|
| 539 | 3-amino-6-(3-{[(1S)-2,3-dihydro-1H-inden-1-ylamino]methyl}phenyl)-N-(4-hydroxybutyl)pyrazine-2-carboxamide | B |
| 540 | 3-amino-6-(3-{[(1S)-2,3-dihydro-1H-inden-1-ylamino]methyl}phenyl)-N-(2-pyrrolidin-1-ylethyl)pyrazine-2-carboxamide | B |
| 541 | 3-amino-6-(3-{[(1S)-2,3-dihydro-1H-inden-1-ylamino]methyl}phenyl)-N-(2-piperidin-1-ylethyl)pyrazine-2-carboxamide | C |
| 542 | 3-amino-6-(3-{[(1S)-2,3-dihydro-1H-inden-1-ylamino]methyl}phenyl)-N-(2-morpholin-4-ylethyl)pyrazine-2-carboxamide | C |
| 543 | 3-amino-N-(cyclopropylmethyl)-6-(3-{[(1S)-2,3-dihydro-1H-inden-1-ylamino}methyl]phenyl)pyrazine-2-carboxamide | B |
| 544 | 3-amino-6-(3-{[(1S)-2,3-dihydro-1H-inden-1-ylamino]methyl}phenyl)-N-(phenylmethyl)pyrazine-2-carboxamide | C |
| 545 | 3-amino-6-(3-{[(1S)-2,3-dihydro-1H-inden-1-ylamino]methyl}phenyl)-N-(2-phenylethyl)pyrazine-2-carboxamide | C |
| 546 | [3-amino-6-(3-{[(1S)-2,3-dihydro-1H-inden-1-ylamino]methyl}phenyl)pyrazin-2-yl](phenyl)methanone | B |
| 547 | 3-amino-6-(3-{[(1S)-2,3-dihydro-1H-inden-1-ylamino]methyl}phenyl)-N-(2-hydroxyethyl)pyrazine-2-carboxamide | B |
| 548 | 3-amino-N-cyclopropyl-6-(3-{[(1S)-2,3-dihydro-1H-inden-1-ylamino]methyl}phenyl)pyrazine-2-carboxamide | B |
| 549 | 5-(3-{[(1S)-2,3-dihydro-1H-inden-1-ylamino]methyl}phenyl)-3-(pyrrolidin-1-ylcarbonyl)pyrazin-2-amine | C |
| 550 | {3-[5-amino-6-(5-methyl-4H-1,2,4-triazol-3-yl)pyrazin-2-yl]phenyl}methanol | C |
| 551 | {3-[5-amino-6-(5-phenyl-4H-1,2,4-triazol-3-yl)pyrazin-2-yl]phenyl}methanol | B |
| 552 | (3-{5-amino-6-[5-(phenylmethyl)-4H-1,2,4-triazol-3-yl]pyrazin-2-yl}phenyl)methanol | C |
| 553 | 3-amino-6-(3-{[(1S)-2,3-dihydro-1H-inden-1-ylamino]methyl}phenyl)-N'-methylpyrazine-2-carbohydrazide | B |
| 554 | 3-amino-6-(3-{[(1S)-2,3-dihydro-1H-inden-1-ylamino]methyl}phenyl)-N,N-dimethylpyrazine-2-carboxamide | B |
| 555 | 5-(3-{[(1S)-2,3-dihydro-1H-inden-1-ylamino]methyl}phenyl)-3-[5-(phenylmethyl)-4H-1,2,4-triazol-3-yl]pyrazin-2-amine | B |
| 556 | 3-amino-6-(3-{[(1S)-2,3-dihydro-1H-inden-1-ylamino]methyl}phenyl)-N-[2-(dimethylamino)ethyl]pyrazine-2-carboxamide | B |
| 557 | 5-(3-{[(1S)-2,3-dihydro-1H-inden-1-ylamino]methyl}phenyl)-3-(3-phenyl-1H-1,2,4-triazol-5-yl)pyrazin-2-amine | A |
| 558 | 3-amino-6-(3-{[(1S)-2,3-dihydro-1H-inden-1-ylamino]methyl}phenyl)-N-[2-(1H-imidazol-4-yl)ethyl]pyrazine-2-carboxamide | A |
| 559 | 3-amino-6-(3-{[(1S)-2,3-dihydro-1H-inden-1-ylamino]methyl}phenyl)-N-[2-(methylamino)ethyl]pyrazine-2-carboxamide | A |
| 560 | 3-{5-amino-6-[(3-fluorophenyl)carbonyl]pyrazin-2-yl}-N-(phenylmethyl)benzamide | D |
| 561 | 3-amino-6-(3-{[(1S)-2,3-dihydro-1H-inden-1-ylamino]methyl}phenyl)-N-(3-hydroxypropyl)pyrazine-2-carboxamide | B |
| 562 | 1,1-dimethylethyl 4-({[3-amino-6-(3-{[(phenylmethyl)amino]carbonyl}phenyl)pyrazin-2-yl]carbonyl}amino)piperidine-1-carboxylate | D |
| 563 | 1,1-dimethylethyl 4-[({[3-amino-6-(3-{[(phenylmethyl)amino]carbonyl}phenyl)pyrazin-2-yl]carbonyl}amino)methyl]piperidine-1-carboxylate | D |
| 564 | 3-amino-6-(3-{[(phenylmethyl)amino]carbonyl}phenyl)-N-piperidin-4-ylpyrazine-2-carboxamide | B |
| 565 | 3-amino-6-(3-{[(phenylmethyl)amino]carbonyl}phenyl)-N-(piperidin-4-ylmethyl)pyrazine-2-carboxamide | B |
| 566 | 3-[5-amino-6-(morpholin-4-ylcarbonyl)pyrazin-2-yl]-N-(phenylmethyl)benzamide | C |
| 567 | 1,1-dimethylethyl 3-({[3-amino-6-(3-{[(phenylmethyl)amino]carbonyl}phenyl)pyrazin-2-yl]carbonyl}amino)pyrrolidine-1-carboxylate | D |
| 568 | 3-amino-6-(3-{[(phenylmethyl)amino]carbonyl}phenyl)-N-pyrrolidin-3-ylpyrazine-2-carboxamide | B |
| 569 | (3-{5-amino-6-[5-(1,1-dimethylethyl)-4H-1,2,4-triazol-3-yl]pyrazin-2-yl}phenyl)methanol | C |
| 570 | {3-[5-amino-6-(5-furan-2-yl-4H-1,2,4-triazol-3-yl)pyrazin-2-yl]phenyl}methanol | B |
| 571 | [3-(5-amino-6-{5-[3-(methyloxy)phenyl]-4H-1,2,4-triazol-3-yl}pyrazin-2-yl)phenyl]methanol | D |
| 572 | 2-({3-amino-6-[3-(hydroxymethyl)phenyl]pyrazin-2-yl}carbonyl)-N-phenylhydrazinecarboxamide | B |
| 573 | 3-{5-amino-6-[(4-methylpiperazin-1-yl)carbonyl]pyrazin-2-yl}-N-(phenylmethyl)benzamide | D |
| 574 | 3-(5-amino-6-{[4-(4-fluorophenyl)piperazin-1-yl]carbonyl}pyrazin-2-yl)-N-(phenylmethyl)benzamide | D |
| 575 | 3-(5-amino-6-{[4-(phenylmethyl)piperazin-1-yl]carbonyl}pyrazin-2-yl)-N-(phenylmethyl)benzamide | D |
| 576 | methyl N-{[3-amino-6-(3-{[(phenylmethyl)amino]carbonyl}phenyl)pyrazin-2-yl]carbonyl}glycinate | C |

TABLE 11-continued

| # | Name | Chk1 IC$_{50}$ |
|---|------|---------------|
| 577 | N-{[3-amino-6-(3-{[(phenylmethyl)amino]carbonyl}phenyl)pyrazin-2-yl]carbonyl}glycine | D |
| 578 | 3-{5-amino-6-[(3,5-difluorophenyl)carbonyl]pyrazin-2-yl}-N-(phenylmethyl)benzamide | D |
| 579 | 3-[5-amino-6-(biphenyl-4-ylcarbonyl)pyrazin-2-yl]-N-(phenylmethyl)benzamide | D |
| 580 | {3-[5-amino-6-(3-pyridin-3-yl-1H-1,2,4-triazol-5-yl)pyrazin-2-yl]phenyl}methanol | B |
| 581 | (3-{5-amino-6-[3-(4-chlorophenyl)-1H-1,2,4-triazol-5-yl]pyrazin-2-yl}phenyl)methanol | D |
| 582 | 5-(3-{[(1S)-2,3-dihydro-1H-inden-1-ylamino]methyl}phenyl)-3-[5-(1,1-dimethylethyl)-4H-1,2,4-triazol-3-yl]pyrazin-2-amine | B |
| 583 | (3-{5-amino-6-[3-(2-thienyl)-1H-1,2,4-triazol-5-yl]pyrazin-2-yl}phenyl)methanol | B |
| 584 | 5-(3-{[(1S)-2,3-dihydro-1H-inden-1-ylamino]methyl}phenyl)-3-{3-[3-(methyloxy)phenyl]-1H-1,2,4-triazol-5-yl}pyrazin-2-amine | B |
| 585 | 3-amino-6-(3-{[(1S)-2,3-dihydro-1H-inden-1-ylamino]methyl}phenyl)-N-[3-(dimethylamino)propyl]pyrazine-2-carboxamide | C |
| 586 | 3-amino-6-(3-{[(1S)-2,3-dihydro-1H-inden-1-ylamino]methyl}phenyl)-N-[3-(1H-imidazol-1-yl)propyl]pyrazine-2-carboxamide | B |
| 587 | 3-{5-amino-6-[(4-chloro-3-fluorophenyl)carbonyl]pyrazin-2-yl}-N-(phenylmethyl)benzamide | D |
| 588 | 3-(5-amino-6-{[2,4-bis(methyloxy)phenyl]carbonyl}pyrazin-2-yl)-N-(phenylmethyl)benzamide | D |
| 589 | 3-(5-amino-6-{[4-(dimethylamino)phenyl]carbonyl}pyrazin-2-yl)-N-(phenylmethyl)benzamide | D |
| 590 | methyl 1-{[3-amino-6-(3-{[(phenylmethyl)amino]carbonyl}phenyl)pyrazin-2-yl]carbonyl}-L-prolinate | D |
| 591 | methyl 1-{[3-amino-6-(3-{[(phenylmethyl)amino]carbonyl}phenyl)pyrazin-2-yl]carbonyl}piperidine-3-carboxylate | D |
| 592 | 1,1-dimethylethyl 4-{[3-amino-6-(3-{[(phenylmethyl)amino]carbonyl}phenyl)pyrazin-2-yl]carbonyl}piperazine-1-carboxylate | D |
| 593 | 3-[5-amino-6-(piperazin-1-ylcarbonyl)pyrazin-2-yl]-N-(phenylmethyl)benzamide | D |
| 594 | N-{[3-amino-6-(3-{[(phenylmethyl)amino]carbonyl}phenyl)pyrazin-2-yl]carbonyl}glutamic acid | C |
| 595 | 5-(3-{[(1S)-2,3-dihydro-1H-inden-1-ylamino]methyl}phenyl)-3-{5-[(methyloxy)methyl]-4H-1,2,4-triazol-3-yl}pyrazin-2-amine | C |
| 596 | 5-(3-{[(1S)-2,3-dihydro-1H-inden-1-ylamino]methyl}phenyl)-3-(3-pyridin-3-yl-1H-1,2,4-triazol-5-yl)pyrazin-2-amine | A |
| 597 | 3-amino-6-(3-{[(1S)-2,3-dihydro-1H-inden-1-ylamino]methyl}phenyl)-N-[3-(methylamino)propyl]pyrazine-2-carboxamide | A |
| 598 | 3-amino-6-(3-{[(1S)-2,3-dihydro-1H-inden-1-ylamino]methyl}phenyl)-N-(3-pyrrolidin-1-ylpropyl)pyrazine-2-carboxamide | C |
| 599 | 3-(5-amino-6-{(1E)-N-[4-(methyloxy)phenyl]ethanehydrazonoyl}pyrazin-2-yl)-N-(phenylmethyl)benzamide | C |
| 600 | 3-(5-amino-6-{(1E)-N-[4-(1-methylethyl)phenyl]ethanehydrazonoyl}pyrazin-2-yl)-N-(phenylmethyl)benzamide | C |
| 601 | 3-{5-amino-6-[(1E)-N-1,3-benzothiazol-2-ylethanehydrazonoyl]pyrazin-2-yl}-N-(phenylmethyl)benzamide | D |
| 602 | 3-{5-amino-6-[(1E)-N-(4-methylphenyl)ethanehydrazonoyl]pyrazin-2-yl}-N-(phenylmethyl)benzamide | D |
| 603 | 3-{5-amino-6-[(1E)-N-(4-chlorophenyl)ethanehydrazonoyl]pyrazin-2-yl}-N-(phenylmethyl)benzamide | D |
| 604 | 3-{5-amino-6-[(1E)-N-methyl-N-phenylethanehydrazonoyl]pyrazin-2-yl}-N-(phenylmethyl)benzamide | C |
| 605 | 3-{5-amino-6-[(1E)-N-(2-hydroxyethyl)ethanehydrazonoyl]pyrazin-2-yl}-N-(phenylmethyl)benzamide | B |
| 606 | {3-[5-amino-6-(3-pyridin-4-yl-1H-1,2,4-triazol-5-yl)pyrazin-2-yl]phenyl}methanol | A |
| 607 | {3-[5-amino-6-(3-piperidin-4-yl-1H-1,2,4-triazol-5-yl)pyrazin-2-yl]phenyl}methanol | C |
| 608 | 3-[5-amino-6-(2-aminopyrimidin-4-yl)pyrazin-2-yl]-N-(phenylmethyl)benzamide | C |
| 609 | 3-{5-amino-6-[2-(dimethylamino)pyrimidin-4-yl]pyrazin-2-yl}-N-(phenylmethyl)benzamide | D |
| 610 | ethyl N-{[3-amino-6-(3-{[(phenylmethyl)amino]carbonyl}phenyl)pyrazin-2-yl]carbonyl}-L-tyrosinate | D |
| 611 | N-{[3-amino-6-(3-{[(phenylmethyl)amino]carbonyl}phenyl)pyrazin-2-yl]carbonyl}-D-tyrosine | D |
| 612 | 1,1-dimethylethyl [3-({[3-amino-6-(3-{[(phenylmethyl)amino]carbonyl}phenyl)pyrazin-2-yl]carbonyl}amino)propyl]carbamate | D |
| 613 | 3-amino-N-(3-aminopropyl)-6-(3-{[(phenylmethyl)amino]carbonyl}phenyl)pyrazine-2-carboxamide | B |

TABLE 11-continued

| # | Name | Chk1 IC$_{50}$ |
|---|------|----------------|
| 614 | 1-{[3-amino-6-(3-{[(phenylmethyl)amino]carbonyl}phenyl)pyrazin-2-yl]carbonyl}piperidine-3-carboxylic | D |
| 615 | 1,1-dimethylethyl [2-({[3-amino-6-(3-{[(phenylmethyl)amino]carbonyl}phenyl)pyrazin-2-yl]carbonyl}amino)ethyl]carbamate | D |
| 616 | 3-amino-N-(2-aminoethyl)-6-(3-{[(phenylmethyl)amino]carbonyl}phenyl)pyrazine-2-carboxamide | B |
| 617 | 1,1-dimethylethyl (1-{[3-amino-6-(3-{[(phenylmethyl)amino]carbonyl}phenyl)pyrazin-2-yl]carbonyl}piperidin-4-yl)carbamate | D |
| 618 | 3-{5-amino-6-[(4-aminopiperidin-1-yl)carbonyl]pyrazin-2-yl}-N-(phenylmethyl)benzamide | D |
| 619 | 3-{5-amino-6-[imino(2-phenylhydrazino)methyl]pyrazin-2-yl}-N-(phenylmethyl)benzamide | C |
| 620 | 3-{5-amino-6-[imino(morpholin-4-ylamino)methyl]pyrazin-2-yl}-N-(phenylmethyl)benzamide | C |
| 621 | 3-(5-amino-6-{imino[(4-methylpiperazin-1-yl)amino]methyl}pyrazin-2-yl)-N-(phenylmethyl)benzamide | D |
| 622 | 3-{5-amino-6-[imino(piperidin-1-ylamino)methyl]pyrazin-2-yl}-N-(phenylmethyl)benzamide | D |
| 623 | 3-{5-amino-6-[(azepan-1-ylamino)(imino)methyl]pyrazin-2-yl}-N-(phenylmethyl)benzamide | C |
| 624 | 3-{5-amino-6-[imino({(2R)-2-[(methyloxy)methyl]pyrrolidin-1-yl}amino)methyl]pyrazin-2-yl}-N-(phenylmethyl)benzamide | D |
| 625 | {3-[5-amino-6-(3-piperidin-3-yl-1H-1,2,4-triazol-5-yl)pyrazin-2-yl]phenyl}methanol | B |
| 626 | 3-{5-amino-6-[(1E)-N-morpholin-4-ylethanimidoyl]pyrazin-2-yl}-N-(phenylmethyl)benzamide | C |
| 627 | 4-((2E)-2-{1-[3-amino-6-(3-{[(phenylmethyl)amino]carbonyl}phenyl)pyrazin-2-yl]ethylidene}hydrazino)benzoic acid | C |
| 628 | ethyl ((2E)-2-{1-[3-amino-6-(3-{[(phenylmethyl)amino]carbonyl}phenyl)pyrazin-2-yl]ethylidene}hydrazino)acetate | D |
| 629 | 3-{5-amino-6-[(1E)-N,N-dimethylethanehydrazonoyl]pyrazin-2-yl}-N-(phenylmethyl)benzamide | B |
| 630 | 3-(5-amino-6-{(1E)-N-[4-(methylsulfonyl)phenyl]ethanehydrazonoyl}pyrazin-2-yl)-N-(phenylmethyl)benzamide | D |
| 631 | 3-{5-amino-6-[(1E)-N-(4-cyanophenyl)ethanehydrazonoyl]pyrazin-2-yl}-N-(phenylmethyl)benzamide | D |
| 632 | 3-{5-amino-6-[(1E)-N-pyridin-2-ylethanehydrazonoyl]pyrazin-2-yl}-N-(phenylmethyl)benzamide | D |
| 633 | 3-(5-amino-6-{(1E)-N-[amino(imino)methyl]ethanehydrazonoyl}pyrazin-2-yl)-N-(phenylmethyl)benzamide | C |
| 634 | 3-[5-amino-6-((1E)-N-{4-[(trifluoromethyl)oxy]phenyl}ethanehydrazonoyl)pyrazin-2-yl]-N-(phenylmethyl)benzamide | D |
| 635 | 3-(5-Amino-6-{1-[(4-nitro-phenyl)-hydrazono]-ethyl}-pyrazin-2-yl)-N-benzyl-benzamide | D |
| 636 | 3-(5-amino-6-{(1E)-N-[4-(trifluoromethyl)pyrimidin-2-yl]ethanehydrazonoyl}pyrazin-2-yl)-N-(phenylmethyl)benzamide | C |
| 637 | 3-{5-amino-6-[(1E)-N-1H-1,2,3-benzotriazol-1-ylethanimidoyl]pyrazin-2-yl}-N-(phenylmethyl)benzamide | D |
| 638 | 3-{5-amino-6-[(1E)-N-methylethanehydrazonoyl]pyrazin-2-yl}-N-(phenylmethyl)benzamide | D |
| 639 | 5-(3-{[(1S)-2,3-dihydro-1H-inden-1-ylamino]methyl}phenyl)-3-(3-piperidin-4-yl-1H-1,2,4-triazol-5-yl)pyrazin-2-amine | B |
| 640 | 3-(5-amino-6-{(1E)-N-[4-(trifluoromethyl)phenyl]ethanehydrazonoyl}pyrazin-2-yl)-N-(phenylmethyl)benzamide | D |
| 641 | 3-{5-amino-6-[(1E)-N-phenylethanehydrazonoyl]pyrazin-2-yl}-N-(phenylmethyl)benzamide | C |
| 642 | 3-{5-amino-6-[(1E)-N-(4-methylpiperazin-1-yl)ethanimidoyl]pyrazin-2-yl}-N-(phenylmethyl)benzamide | B |
| 643 | {3-[5-amino-6-(3-pyrrolidin-3-yl-1H-1,2,4-triazol-5-yl)pyrazin-2-yl]phenyl}methanol | B |
| 644 | 3-amino-6-(3-{[(1S)-2,3-dihydro-1H-inden-1-ylamino]carbonyl}phenyl)-N-[(3S)-pyrrolidin-3-yl]pyrazine-2-carboxamide | A |
| 645 | 3-amino-6-(3-{[(1S)-2,3-dihydro-1H-inden-1-ylamino]carbonyl}phenyl)-N-[(3R)-pyrrolidin-3-yl]pyrazine-2-carboxamide | B |
| 646 | 3-amino-6-(3-{[(1S)-2,3-dihydro-1H-inden-1-ylamino]carbonyl}phenyl)-N-[(3S)-1-(furan-2-ylcarbonyl)pyrrolidin-3-yl]pyrazine-2-carboxamide | C |
| 647 | N-[3-(acetylamino)propyl]-3-amino-6-(3-{[(phenylmethyl)amino]carbonyl}phenyl)pyrazine-2-carboxamide | C |
| 648 | 3-amino-N-{3-[(furan-2-ylcarbonyl)amino]propyl}-6-(3-{[(phenylmethyl)amino]carbonyl}phenyl)pyrazine-2-carboxamide | C |

TABLE 11-continued

| # | Name | Chk1 IC$_{50}$ |
|---|------|----------------|
| 649 | 3-amino-6-(3-{[(1S)-2,3-dihydro-1H-inden-1-ylamino]carbonyl}phenyl)-N-[(3S)-1-(pyridin-4-ylcarbonyl)pyrrolidin-3-yl]pyrazine-2-carboxamide | D |
| 650 | 3-amino-6-(3-{[(phenylmethyl)amino]carbonyl}phenyl)-N-{3-[(pyridin-4-ylcarbonyl)amino]propyl}pyrazine-2-carboxamide | C |
| 651 | N-[3-({[3-amino-6-(3-{[(phenylmethyl)amino]carbonyl}phenyl)pyrazin-2-yl]carbonyl}amino)propyl]quinoxaline-2-carboxamide | D |
| 652 | 3-amino-6-(3-{[(phenylmethyl)amino]carbonyl}phenyl)-N-[3-({[6-(trifluoromethyl)pyridin-3-yl]carbonyl}amino)propyl]pyrazine-2-carboxamide | D |
| 653 | 3-amino-6-(3-{[(phenylmethyl)amino]carbonyl}phenyl)-N-{3-[(quinolin-8-ylsulfonyl)amino]propyl}pyrazine-2-carboxamide | D |
| 654 | 3-amino-6-(3-{[(phenylmethyl)amino]carbonyl}phenyl)-N-{3-[(pyridin-2-ylsulfonyl)amino]propyl}pyrazine-2-carboxamide | C |
| 655 | 3-amino-N-[3-({[(3,5-dimethylisoxazol-4-yl)amino]carbonyl}amino)propyl]-6-(3-{[(phenylmethyl)amino]carbonyl}phenyl)pyrazine-2-carboxamide | C |
| 656 | 3-[5-amino-6-(2-methylpyrimidin-4-yl)pyrazin-2-yl]-N-(phenylmethyl)benzamide | C |
| 657 | 3-{5-amino-6-[2-(methylamino)pyrimidin-4-yl]pyrazin-2-yl}-N-(phenylmethyl)benzamide | D |
| 658 | 3-amino-6-(3-{[(phenylmethyl)amino]carbonyl}phenyl)-N-{2-[(pyridin-4-ylcarbonyl)amino]ethyl}pyrazine-2-carboxamide | C |
| 659 | 3-amino-N-{2-[(furan-2-ylcarbonyl)amino]ethyl}-6-(3-{[(phenylmethyl)amino]carbonyl}phenyl)pyrazine-2-carboxamide | D |
| 660 | N,N'-cyclohexane-1,2-diylbis[3-amino-6-(3-{[(phenylmethyl)amino]carbonyl}phenyl)pyrazine-2-carboxamide] | D |
| 661 | N-[2-(acetylamino)ethyl]-3-amino-6-(3-{[(phenylmethyl)amino]carbonyl}phenyl)pyrazine-2-carboxamide | C |
| 662 | 3-amino-6-(3-{[(phenylmethyl)amino]carbonyl}phenyl)-N-{2-[(quinolin-8-ylsulfonyl)amino]ethyl}pyrazine-2-carboxamide | D |
| 663 | N-[2-({[3-amino-6-(3-{[(phenylmethyl)amino]carbonyl}phenyl)pyrazin-2-yl]carbonyl}amino)ethyl]quinoxaline-2-carboxamide | D |
| 664 | 3-amino-N-(2-{[(2-chloropyridin-3-yl)carbonyl]amino}ethyl)-6-(3-{[(phenylmethyl)amino]carbonyl}phenyl)pyrazine-2-carboxamide | C |
| 665 | 3-amino-6-(3-{[(phenylmethyl)amino]carbonyl}phenyl)-N-{2-[(pyridin-2-ylsulfonyl)amino]ethyl}pyrazine-2-carboxamide | D |
| 666 | 3-amino-N-[2-({[(3,5-dimethylisoxazol-4-yl)amino]carbonyl}amino)ethyl]-6-(3-{[(phenylmethyl)amino]carbonyl}phenyl)pyrazine-2-carboxamide | C |
| 667 | 3-amino-6-(3-{[(phenylmethyl)amino]carbonyl}phenyl)pyrazine-2-carboxamide | B |
| 668 | 3-[5-amino-6-(imino{2-[4-(trifluoromethyl)pyrimidin-2-yl]hydrazino}methyl)pyrazin-2-yl]-N-(phenylmethyl)benzamide | C |
| 669 | 3-{5-amino-6-[[2-(1,3-benzothiazol-2-yl)hydrazino](imino)methyl]pyrazin-2-yl}-N-(phenylmethyl)benzamide | D |
| 670 | 3-[5-amino-6-(1,5-diphenyl-1H-1,2,4-triazol-3-yl)pyrazin-2-yl]-N-(phenylmethyl)benzamide | D |
| 671 | 3-[5-amino-6-(1,5-dimethyl-1H-1,2,4-triazol-3-yl)pyrazin-2-yl]-N-(phenylmethyl)benzamide | C |
| 672 | 3-[5-amino-6-(1-methyl-5-phenyl-1H-1,2,4-triazol-3-yl)pyrazin-2-yl]-N-(phenylmethyl)benzamide | D |
| 673 | 3-[5-amino-6-((1E)-N-{(2R)-2-[(methyloxy)methyl]pyrrolidin-1-yl}ethanimidoyl)pyrazin-2-yl]-N-(phenylmethyl)benzamide | B |
| 674 | 3-{5-amino-6-[(1E)-N-azepan-1-ylethanimidoyl]pyrazin-2-yl}-N-(phenylmethyl)benzamide | B |
| 675 | 3-(5-amino-6-{(E)-[(phenylmethyl)hydrazono]methyl}pyrazin-2-yl)-N-(phenylmethyl)benzamide | D |
| 676 | 3-[5-amino-6-((E)-{[amino(imino)methyl]hydrazono}methyl)pyrazin-2-yl]-N-(phenylmethyl)benzamide | D |
| 677 | 3-(5-amino-6-{(E)-[(2-hydroxyethyl)hydrazono]methyl}pyrazin-2-yl)-N-(phenylmethyl)benzamide | C |
| 678 | 3-{5-amino-6-[(E)-(pyridin-2-ylhydrazono)methyl]pyrazin-2-yl}-N-(phenylmethyl)benzamide | D |
| 679 | 3-(5-amino-6-{(E)-[(4-cyanophenyl)hydrazono]methyl}pyrazin-2-yl)-N-(phenylmethyl)benzamide | D |
| 680 | 3-(5-amino-6-{(E)-[(4-methylphenyl)hydrazono]methyl}pyrazin-2-yl)-N-(phenylmethyl)benzamide | D |
| 681 | 3-{5-amino-6-[(E)-(hydroxyimino)methyl]pyrazin-2-yl}-N-(phenylmethyl)benzamide | C |
| 682 | {3-[5-amino-6-(3-pyridin-2-yl-1H-1,2,4-triazol-5-yl)pyrazin-2-yl]phenyl}methanol | C |
| 683 | 5-(3-{[(1R)-2,3-dihydro-1H-inden-1-ylamino]methyl}phenyl)-3-(3-piperidin-3-yl-1H-1,2,4-triazol-5-yl)pyrazin-2-amine | A |
| 684 | 3-amino-N-[3-({[4-(dimethylamino)phenyl]carbonyl}amino)propyl]-6-(3-{[(phenylmethyl)amino]carbonyl}phenyl)pyrazine-2-carboxamide | D |
| 685 | 3-amino-6-(3-{[(1S)-2,3-dihydro-1H-inden-1-ylamino]methyl}phenyl)-N-[(3S)-pyrrolidin-3-yl]pyrazine-2-carboxamide | A |
| 686 | 1,1-dimethylethyl 4-[(3S)-3-({[3-amino-6-(3-{[(phenylmethyl)amino]carbonyl}phenyl)pyrazin-2-yl]carbonyl}amino)pyrrolidin-1-yl]piperidine-1-carboxylate | C |

TABLE 11-continued

| # | Name | Chk1 IC$_{50}$ |
|---|------|----------------|
| 687 | 3-amino-6-(3-{[(phenylmethyl)amino]carbonyl}phenyl)-N-[(3S)-1-piperidin-4-ylpyrrolidin-3-yl]pyrazine-2-carboxamide | C |
| 688 | 1,1-dimethylethyl (2R)-2-{[(3S)-3-({[3-amino-6-(3-{[(phenylmethyl)amino]carbonyl}phenyl)pyrazin-2-yl]carbonyl}amino)pyrrolidin-1-yl]methyl}pyrrolidine-1-carboxylate | D |
| 689 | 3-amino-6-(3-{[(phenylmethyl)amino]carbonyl}phenyl)-N-{(3S)-1-[(2R)-pyrrolidin-2-ylmethyl]pyrrolidin-3-yl}pyrazine-2-carboxamide | C |
| 690 | 3-amino-N-((3S)-1-{[4-(dimethylamino)phenyl]methyl}pyrrolidin-3-yl)-6-(3-{[(phenylmethyl)amino]carbonyl}phenyl)pyrazine-2-carboxamide | C |
| 691 | 3-amino-N-{2-[({[4-(dimethylamino)phenyl]amino}carbonyl)amino]ethyl}-6-(3-{[(phenylmethyl)amino]carbonyl}phenyl)pyrazine-2-carboxamide | D |
| 692 | 3-amino-N-[2-({[4-(dimethylamino)phenyl]carbonyl}amino)ethyl]-6-(3-{[(phenylmethyl)amino]carbonyl}phenyl)pyrazine-2-carboxamide | D |
| 693 | 3-{5-amino-6-[imino(2-pyridin-2-ylhydrazino)methyl]pyrazin-2-yl}-N-(phenylmethyl)benzamide | D |
| 694 | 3-[5-amino-6-(morpholin-4-ylmethyl)pyrazin-2-yl]-N-(phenylmethyl)benzamide | D |
| 695 | ethyl 1-{[3-amino-6-(3-{[(phenylmethyl)amino]carbonyl}phenyl)pyrazin-2-yl]methyl}piperidine-4-carboxylate | D |
| 696 | 3-amino-6-(3-{[(phenylmethyl)amino]carbonyl}phenyl)-N-[(3S)-1-(pyridin-2-ylmethyl)pyrrolidin-3-yl]pyrazine-2-carboxamide | B |
| 697 | methyl N-{[3-amino-6-(3-{[(phenylmethyl)amino]carbonyl}phenyl)pyrazin-2-yl]carbonyl}threoninate | D |
| 698 | {3-[5-amino-6-(3-piperidin-2-yl-1H-1,2,4-triazol-5-yl)pyrazin-2-yl]phenyl}methanol | D |
| 699 | 3-(ethylamino)-N-[(3S)-1-ethylpyrrolidin-3-yl]-6-(3-{[(phenylmethyl)amino]carbonyl}phenyl)pyrazine-2-carboxamide | D |
| 700 | 3-amino-N-[(3S)-1-ethylpyrrolidin-3-yl]-6-(3-{[(phenylmethyl)amino]carbonyl}phenyl)pyrazine-2-carboxamide | B |
| 701 | 3-[5-amino-6-(1-methyl-5-piperidin-2-yl-1H-1,2,4-triazol-3-yl)pyrazin-2-yl]-N-(phenylmethyl)benzamide | D |
| 702 | 3-[5-amino-6-(5-methyl-1-pyridin-2-yl-1H-1,2,4-triazol-3-yl)pyrazin-2-yl]-N-(phenylmethyl)benzamide | C |
| 703 | {3-[5-amino-6-(3-morpholin-2-yl-1H-1,2,4-triazol-5-yl)pyrazin-2-yl]phenyl}methanol | B |
| 704 | 5-(3-{[(1S)-2,3-dihydro-1H-inden-1-ylamino]methyl}phenyl)-3-{3-[(3S)-piperidin-3-yl]-1H-1,2,4-triazol-5-yl}pyrazin-2-amine | A |
| 705 | 5-(3-{[(1S)-2,3-dihydro-1H-inden-1-ylamino]methyl}phenyl)-3-{3-[(3R)-piperidin-3-yl]-1H-1,2,4-triazol-5-yl}pyrazin-2-amine | A |
| 706 | 3-amino-6-(3-{[(1S)-2,3-dihydro-1H-inden-1-ylamino]carbonyl}phenyl)-N-[(3S)-1-ethylpyrrolidin-3-yl]pyrazine-2-carboxamide | B |
| 707 | 6-(3-{[(1S)-2,3-dihydro-1H-inden-1-ylamino]carbonyl}phenyl)-3-(ethylamino)-N-[(3S)-1-ethylpyrrolidin-3-yl]pyrazine-2-carboxamide | D |
| 708 | 3-amino-6-[3-({[(1S,2R)-2-hydroxy-2,3-dihydro-1H-inden-1-yl]amino}carbonyl)phenyl]-N-[(3S)-pyrrolidin-3-yl]pyrazine-2-carboxamide | B |
| 709 | 1,1-dimethylethyl (3S)-3-({[3-amino-6-(3-{[(1S)-2,3-dihydro-1H-inden-1-ylamino]carbonyl}phenyl)pyrazin-2-yl]carbonyl}amino)pyrrolidine-1-carboxylate | D |
| 710 | 1,1-dimethylethyl (3S)-3-[({3-amino-6-[3-({[(1R)-1-phenylethyl]amino}carbonyl)phenyl]pyrazin-2-yl}carbonyl)amino]pyrrolidine-1-carboxylate | D |
| 711 | 1,1-dimethylethyl (3S)-3-[({3-amino-6-[3-(3,4-dihydroisoquinolin-2(1H)-ylcarbonyl)phenyl]pyrazin-2-yl}carbonyl)amino]pyrrolidine-1-carboxylate | D |
| 712 | 1,1-dimethylethyl (3S)-3-({[3-amino-6-(3-{[(2-phenylethyl)amino]carbonyl}phenyl)pyrazin-2-yl]carbonyl}amino)pyrrolidine-1-carboxylate | D |
| 713 | 1,1-dimethylethyl (3S)-3-[({3-amino-6-[3-({[(1S)-1-phenylethyl]amino}carbonyl)phenyl]pyrazin-2-yl}carbonyl)amino]pyrrolidine-1-carboxylate | C |
| 714 | 3-amino-6-[3-(3,4-dihydroisoquinolin-2(1H)-ylcarbonyl)phenyl]-N-[(3S)-pyrrolidin-3-yl]pyrazine-2-carboxamide | B |
| 715 | 3-amino-6-(3-{[(2-phenylethyl)amino]carbonyl}phenyl)-N-[(3S)-pyrrolidin-3-yl]pyrazine-2-carboxamide | B |
| 716 | 3-amino-6-[3-({[(1R)-1-phenylethyl]amino}carbonyl)phenyl]-N-[(3S)-pyrrolidin-3-yl]pyrazine-2-carboxamide | C |
| 717 | 3-amino-6-[3-({[(1S)-1-phenylethyl]amino}carbonyl)phenyl]-N-[(3S)-pyrrolidin-3-yl]pyrazine-2-carboxamide | B |
| 718 | 3-{5-amino-6-[(2-ethylhydrazino)(imino)methyl]pyrazin-2-yl}-N-(2,3-dihydro-1H-inden-1-yl)benzamide | C |
| 719 | 3-{5-amino-6-[imino(2-methylhydrazino)methyl]pyrazin-2-yl}-N-[(1S)-2,3-dihydro-1H-inden-1-yl]benzamide | C |
| 720 | 3-{5-amino-6-[imino(2-phenylhydrazino)methyl]pyrazin-2-yl}-N-[(1S)-2,3-dihydro-1H-inden-1-yl]benzamide | D |
| 721 | phenylmethyl 3-{3-[3-amino-6-(3-{[(1S)-2,3-dihydro-1H-inden-1-ylamino]carbonyl}phenyl)pyrazin-2-yl]-1-methyl-1H-1,2,4-triazol-5-yl}piperidine-1-carboxylate | D |

TABLE 11-continued

| # | Name | Chk1 IC$_{50}$ |
|---|------|----------------|
| 722 | phenylmethyl 3-{3-[3-amino-6-(3-{[(1S)-2,3-dihydro-1H-inden-1-ylamino]carbonyl}phenyl)pyrazin-2-yl]-1-ethyl-1H-1,2,4-triazol-5-yl}piperidine-1-carboxylate | D |
| 723 | 5-(3-{[(1S)-2,3-dihydro-1H-inden-1-ylamino]methyl}phenyl)-3-(3-pyridin-4-yl-1H-1,2,4-triazol-5-yl)pyrazin-2-amine | A |
| 724 | [3-(5-amino-6{3-[(3R)-piperidin-3-yl]-1H-1,2,4-triazol-5-yl}pyrazin-2-yl)phenyl]methanol | B |
| 725 | [3-(5-amino-6-{3[(3S)-piperidin-3-yl]-1H-1,2,4-triazol-5-yl}pyrazin-2-yl)phenyl]methanol | B |
| 726 | 3-amino-6-[3-({[(1R,2S)-2-hydroxy-2,3-dihydro-1H-inden-1-yl]amino}carbonyl)phenyl]-N-[(3S)-pyrrolidin-3-yl]pyrazine-2-carboxamide | A |
| 727 | 3-amino-N-[(3S)-1-ethylpyrrolidin-3-yl]-6-[3-({[(1S,2R)-2-hydroxy-2,3-dihydro-1H-inden-1-yl]amino}carbonyl)phenyl]pyrazine-2-carboxamide | C |
| 728 | 1,1-dimethylethyl 3-({[3-amino-6-(3-{[(1S)-2,3-dihydro-1H-inden-1-ylamino]carbonyl}phenyl)pyrazin-2-yl]carbonyl}amino)piperidine-1-carboxylate | D |
| 729 | 3-amino-6-(3-{[(1S)-2,3-dihydro-1H-inden-1-ylamino]carbonyl}phenyl)-N-piperidin-3-ylpyrazine-2-carboxamide | A |
| 730 | 3-amino-6-(3-{[(1S)-2,3-dihydro-1H-inden-1-ylamino]carbonyl}phenyl)-N-(1-ethylpiperidin-3-yl)pyrazine-2-carboxamide | B |
| 731 | 3-amino-N-[(3S)-1-ethylpyrrolidin-3-yl]-6-[3-({[(1R,2S)-2-hydroxy-2,3-dihydro-1H-inden-1-yl]amino}carbonyl)phenyl]pyrazine-2-carboxamide | B |
| 732 | (3-{5-amino-6-[5-(1-ethylpiperidin-3-yl)-4H-1,2,4-triazol-3-yl]pyrazin-2-yl}phenyl)methanol | C |
| 733 | 5-(3-{[(1S)-2,3-dihydro-1H-inden-1-ylamino]methyl}phenyl)-3-[5-(1-ethylpiperidin-3-yl)-4H-1,2,4-triazol-3-yl]pyrazin-2-amine | B |
| 734 | 3-[5-amino-6-(1-ethyl-5-piperidin-3-yl-1H-1,2,4-triazol-3-yl)pyrazin-2-yl]-N-[(1R)-2,3-dihydro-1H-inden-1-yl]benzamide | B |
| 735 | 3-(5-amino-6-(1-methyl-5-piperidin-3-yl-1H-1,2,4-triazol-3-yl)pyrazin-2-yl]-N-[(1S)-2,3-dihydro-1H-inden-1-yl]benzamide | B |
| 736 | (3-{5-amino-6-[3-(1-methylpiperidin-3-yl)-1H-1,2,4-triazol-5-yl]pyrazin-2-yl}phenyl)methanol | C |
| 737 | 5-(3-{[(1S)-2,3-dihydro-1H-inden-1-ylamino]methyl}phenyl)-3-[3-(1-methylpiperidin-3-yl)-1H-1,2,4-triazol-5-yl]pyrazin-2-amine | B |
| 738 | 1,1-dimethylethyl (3S)-3-{[(3-amino-6-{3-[({[4-(methyloxy)phenyl]methyl}amino)carbonyl]phenyl}pyrazin-2-yl)carbonyl]amino}pyrrolidine-1-carboxylate | B |
| 739 | 1,1-dimethylethyl (3S)-3-({[3-amino-6-(3-{[({4-[(trifluoromethyl)oxy]phenyl}methyl)amino]carbonyl}phenyl)pyrazin-2-yl]carbonyl}amino)pyrrolidine-1-carboxylate | B |
| 740 | 1,1-dimethylethyl (3S)-3-[({3-amino-6-[3-({[(2-chloro-6-fluorophenyl)methyl]amino}carbonyl)phenyl]pyrazin-2-yl}carbonyl)amino]pyrrolidine-1-carboxylate | C |
| 741 | 1,1-dimethylethyl (3S)-3-{[(3-amino-6-{3-[({[4-(methylthio)phenyl]methyl}amino)carbonyl]phenyl}pyrazin-2-yl)carbonyl]amino}pyrrolidine-1-carboxylate | C |
| 742 | 1,1-dimethylethyl (3S)-3-{[(3-amino-6-{3-[(2,3-dihydro-1H-inden-2-ylamino)carbonyl]phenyl}pyrazin-2-yl)carbonyl]amino}pyrrolidine-1-carboxylate | B |
| 743 | 3-amino-6-{3-[({[4-(methyloxy)phenyl]methyl}amino)carbonyl]phenyl}-N-[(3S)-pyrrolidin-3-yl]pyrazine-2-carboxamide | B |
| 744 | 3-amino-N-[(3S)-pyrrolidin-3-yl]-6-(3-{[({4-[(trifluoromethyl)oxy]phenyl}methyl)amino]carbonyl}phenyl)pyrazine-2-carboxamide | A |
| 745 | 3-amino-6-{3-[(2,3-dihydro-1H-inden-2-ylamino)carbonyl]phenyl}-N-[(3S)-pyrrolidin-3-yl]pyrazine-2-carboxamide | B |
| 746 | 3-amino-6-[3-({[(2-chloro-6-fluorophenyl)methyl]amino}carbonyl)phenyl]-N-[(3S)-pyrrolidin-3-yl]pyrazine-2-carboxamide | B |
| 747 | 3-amino-6-{3-[({[4-(methylthio)phenyl]methyl}amino)carbonyl]phenyl}-N-[(3S)-pyrrolidin-3-yl]pyrazine-2-carboxamide | A |
| 748 | 3-{5-amino-6-[imino(2-pyridin-4-ylhydrazino)methyl]pyrazin-2-yl}-N-[(1R)-2,3-dihydro-1H-inden-1-yl]benzamide | C |
| 749 | phenylmethyl (3R)-3-{3-[3-amino-6-(3-{[(1S)-2,3-dihydro-1H-inden-1-ylamino]carbonyl}phenyl)pyrazin-2-yl]-1-ethyl-1H-1,2,4-triazol-5-yl}piperidine-1-carboxylate | D |
| 750 | 3-amino-6-(3-{(1S)-1-[(1S)-2,3-dihydro-1H-inden-1-ylamino]ethyl}phenyl)-N-methylpyrazine-2-carboxamide | B |
| 751 | 3-amino-6-[3-({[(1R,2S)-2-hydroxy-2,3-dihydro-1H-inden-1-yl]amino}carbonyl)phenyl]-N-[2-(1H-imidazol-4-yl)ethyl]pyrazine-2-carboxamide | B |
| 752 | 1,1-dimethylethyl (3S)-3-[({[3-amino-6-(3-{[(1S)-2,3-dihydro-1H-inden-1-ylamino]carbonyl}phenyl)pyrazin-2-yl]carbonyl}amino)methyl]pyrrolidine-1-carboxylate | D |
| 753 | 3-amino-6-(3-{[(1S)-2,3-dihydro-1H-inden-1-ylamino]carbonyl}phenyl)-N-[(3R)-pyrrolidin-3-ylmethyl]pyrazine-2-carboxamide | A |

TABLE 11-continued

| # | Name | Chk1 IC$_{50}$ |
|---|------|---|
| 754 | phenylmethyl (3R)-3-{3-[3-amino-6-(3-{[(1S)-2,3-dihydro-1H-inden-1-ylamino]carbonyl}phenyl)pyrazin-2-yl]-1-methyl-1H-1,2,4-triazol-5-yl}piperidine-1-carboxylate | C |
| 755 | 3-(5-amino-6-{5-[(3S)-piperidin-3-yl]-4H-1,2,4-triazol-3-yl}pyrazin-2-yl)-N-[(1S)-2,3-dihydro-1H-inden-1-yl]benzamide | A |
| 756 | 1,1-dimethylethyl (3S)-3-[({3-amino-6-[3-({[(4-chlorophenyl)methyl]amino}carbonyl)phenyl]pyrazin-2-yl}carbonyl)amino]pyrrolidine-1-carboxylate | B |
| 757 | 1,1-dimethylethyl (3S)-3-({[3-amino-6-(3-{[(pyridin-2-ylmethyl)amino]carbonyl}phenyl)pyrazin-2-yl]carbonyl}amino)pyrrolidine-1-carboxylate | C |
| 758 | 1,1-dimethylethyl (3S)-3-({[3-amino-6-(3-{[(pyridin-3-ylmethyl)amino]carbonyl}phenyl)pyrazin-2-yl]carbonyl}amino)pyrrolidine-1-carboxylate | C |
| 759 | 1,1-dimethylethyl (3S)-3-{[(3-amino-6-{3-[(3,4-dihydro-2H-chromen-4-ylamino)carbonyl]phenyl}pyrazin-2-yl)carbonyl]amino}pyrrolidine-1-carboxylate | C |
| 760 | 3-amino-6-[3-({[(4-chlorophenyl)methyl]amino}carbonyl)phenyl]-N-[(3S)-pyrrolidin-3-yl]pyrazine-2-carboxamide | A |
| 761 | 3-amino-6-(3-{[(pyridin-2-ylmethyl)amino]carbonyl}phenyl)-N-[(3S)-pyrrolidin-3-yl]pyrazine-2-carboxamide | B |
| 762 | 3-amino-6-(3-{[(pyridin-2-ylmethyl)amino]carbonyl}phenyl)-N-[(3S)-pyrrolidin-3-yl]pyrazine-2-carboxamide | B |
| 763 | dimethyl 5-{5-amino-6-[(methylamino)carbonyl]pyrazin-2-yl}benzene-1,3-dicarboxylate | C |
| 764 | 3-amino-6-(3-{[(1S)-2,3-dihydro-1H-inden-1-ylamino]carbonyl}phenyl)-N-[(3S)-piperidin-3-yl]pyrazine-2-carboxamide | A |
| 765 | 3-amino-6-(3-{[(1S)-2,3-dihydro-1H-inden-1-ylamino]carbonyl}phenyl)-N-[(3R)-piperidin-3-yl]pyrazine-2-carboxamide | A |
| 766 | 3-amino-6-[3-({[(1R,2S)-2-hydroxy-2,3-dihydro-1H-inden-1-yl]amino}carbonyl)phenyl]-N-piperidin-3-ylpyrazine-2-carboxamide | A |
| 767 | 3-amino-6-(3-{[(1S)-2,3-dihydro-1H-inden-1-ylamino]carbonyl}phenyl)-N-[2-(1H-imidazol-4-yl)ethyl]pyrazine-2-carboxamide | B |
| 768 | 3-amino-N-azepan-4-yl-6-(3-{[(1S)-2,3-dihydro-1H-inden-1-ylamino]carbonyl}phenyl)pyrazine-2-carboxamide | B |
| 769 | 1,1-dimethylethyl (3S)-3-{[({3-amino-6-[3-({[(1R,2S)-2-hydroxy-2,3-dihydro-1H-inden-1-yl]amino}carbonyl)phenyl]pyrazin-2-yl}carbonyl)amino]methyl}pyrrolidine-1-carboxylate | D |
| 770 | 1,1-dimethylethyl 4-({[3-amino-6-(3-{[(1S)-2,3-dihydro-1H-inden-1-ylamino]carbonyl}phenyl)pyrazin-2-yl]carbonyl}amino)azepane-1-carboxylate | D |
| 771 | 3-[5-amino-6-(5-{2-[(phenylmethyl)oxy]ethyl}-1H-1,2,4-triazol-3-yl)pyrazin-2-yl]-N-[(1S)-2,3-dihydro-1H-inden-1-yl]benzamide | C |
| 772 | 3-amino-6-(3-{[(1S)-2,3-dihydro-1H-inden-1-ylamino]carbonyl}-4-fluorophenyl)-N-methylpyrazine-2-carboxamide | B |
| 773 | 3-[5-amino-6-(1-phenyl-5-piperidin-3-yl-1H-1,2,4-triazol-3-yl)pyrazin-2-yl]-N-[(1S)-2,3-dihydro-1H-inden-1-yl]benzamide | B |
| 774 | 3-{5-amino-6-[amino(imino)methyl]pyrazin-2-yl}-N-[(1S)-2,3-dihydro-1H-inden-1-yl]benzamide | C |
| 775 | 3-(5-amino-6-{5-[(3S)-piperidin-3-yl]-4H-1,2,4-triazol-3-yl}pyrazin-2-yl)-N-[(1R,2S)-2-hydroxy-2,3-dihydro-1H-inden-1-yl]benzamide | A |
| 776 | 1,1-dimethylethyl (3S)-3-({[3-amino-6-(3-{[(1S)-2,3-dihydro-1H-inden-1-ylamino]carbonyl}phenyl)pyrazin-2-yl]carbonyl}amino)piperidine-1-carboxylate | B |
| 777 | 1,1-dimethylethyl (3S)-3-[({3-amino-6-[3-({[(1R,2S)-2-hydroxy-2,3-dihydro-1H-inden-1-yl]amino}carbonyl)phenyl]pyrazin-2-yl}carbonyl)amino]piperidine-1-carboxylate | A |
| 778 | 3-amino-6-{3-[(3,4-dihydro-2H-chromen-4-ylamino)carbonyl]phenyl}-N-[(3S)-pyrrolidin-3-yl]pyrazine-2-carboxamide | B |
| 779 | 3-amino-6-{3-[(2,3-dihydro-1-benzofuran-3-ylamino)carbonyl]phenyl}-N-[(3S)-pyrrolidin-3-yl]pyrazine-2-carboxamide | B |
| 780 | 3-amino-6-[3-({[(1R,2S)-2-hydroxy-2,3-dihydro-1H-inden-1-yl]amino}carbonyl)phenyl]-N-[(3R)-pyrrolidin-3-ylmethyl]pyrazine-2-carboxamide | A |
| 781 | 1,1-dimethylethyl 4-[({3-amino-6-[3-({[(1R,2S)-2-hydroxy-2,3-dihydro-1H-inden-1-yl]amino}carbonyl)phenyl]pyrazin-2-yl}carbonyl)amino]azepane-1-carboxylate | B |
| 782 | 3-amino-N-azepan-4-yl-6-[3-({[(1R,2S)-2-hydroxy-2,3-dihydro-1H-inden-1-yl]amino}carbonyl)phenyl]pyrazine-2-carboxamide | A |
| 783 | 3-amino-N-azepan-4-yl-6-{3-[(3aR,8aS)-8,8a-dihydro-3aH-indeno[1,2-d][1,3]oxazol-2-yl]phenyl}pyrazine-2-carboxamide | B |
| 784 | 1,1-dimethylethyl (3R)-3-[({[3-amino-6-(3-{[(1S)-2,3-dihydro-1H-inden-1-ylamino]carbonyl}phenyl)pyrazin-2-yl]carbonyl}amino)methyl]pyrrolidine-1-carboxylate | D |
| 785 | 3-amino-6-(3-{[(1S)-2,3-dihydro-1H-inden-1-ylamino]carbonyl}phenyl)-N-[(3S)-pyrrolidin-3-ylmethyl]pyrazine-2-carboxamide | A |

TABLE 11-continued

| # | Name | Chk1 IC$_{50}$ |
|---|---|---|
| 786 | 1,1-dimethylethyl (3R)-3-{[({3-amino-6-[3-({[(1R,2S)-2-hydroxy-2,3-dihydro-1H-inden-1-yl]amino}carbonyl)phenyl]pyrazin-2-yl}carbonyl)amino]methyl}pyrrolidine-1-carboxylate | D |
| 787 | 3-amino-6-[3-({[(1R,2S)-2-hydroxy-2,3-dihydro-1H-inden-1-yl]amino}carbonyl)phenyl]-N-[(3S)-pyrrolidin-3-ylmethyl]pyrazine-2-carboxamide | A |
| 788 | 3-amino-6-(3-{[(1S)-2,3-dihydro-1H-inden-1-ylamino]carbonyl}-5-fluorophenyl)-N-methylpyrazine-2-carboxamide | B |
| 789 | 3-{5-amino-6-[(methylamino)carbonyl]pyrazin-2-yl}-5-[(methyloxy)carbonyl]benzoic acid | C |
| 790 | methyl 3-{5-amino-6-[(methylamino)carbonyl]pyrazin-2-yl}-5-{[(1S)-2,3-dihydro-1H-inden-1-ylamino]carbonyl}benzoate | B |
| 791 | 5-{5-amino-6-[(methylamino)carbonyl]pyrazin-2-yl}-N-[(1S)-2,3-dihydro-1H-inden-1-yl]-N'-pyrrolidin-3-ylbenzene-1,3-dicarboxamide | B |
| 792 | 3-[5-amino-6-(5-phenyl-1-pyridin-2-yl-1H-1,2,4-triazol-3-yl)pyrazin-2-yl]-N-(phenylmethyl)benzamide | C |
| 793 | 3-[5-amino-6-(5-methyl-1-pyridin-4-yl-1H-1,2,4-triazol-3-yl)pyrazin-2-yl]-N-[(1S)-2,3-dihydro-1H-inden-1-yl]benzamide | C |
| 794 | 1,1-dimethylethyl (3R)-3-({[3-amino-6-(3-{[(1S)-2,3-dihydro-1H-inden-1-ylamino]carbonyl}phenyl)pyrazin-2-yl]carbonyl}amino)piperidine-1-carboxylate | C |
| 795 | 1,1-dimethylethyl (3R)-3-[({3-amino-6-[3-({[(1R,2S)-2-hydroxy-2,3-dihydro-1H-inden-1-yl]amino}carbonyl)phenyl]pyrazin-2-yl}carbonyl)amino]piperidine-1-carboxylate | D |
| 796 | 3-amino-6-(3-{[(1S)-2,3-dihydro-1H-inden-1-ylamino]carbonyl}phenyl)-N-[(3S)-piperidin-3-yl]pyrazine-2-carboxamide | A |
| 797 | 5-{5-amino-6-[(methylamino)carbonyl]pyrazin-2-yl}-N-[(1R)-2,3-dihydro-1H-inden-1-yl]-N'-[(3R)-pyrrolidin-3-yl]benzene-1,3-dicarboxamide | B |
| 798 | (3-{5-amino-6-[3-(2-aminopyridin-4-yl)-1H-1,2,4-triazol-5-yl]pyrazin-2-yl}phenyl)methanol | B |
| 799 | 3-[5-amino-6-(1,5-dimethyl-1H-1,2,4-triazol-3-yl)pyrazin-2-yl]-N-[(1S)-2,3-dihydro-1H-inden-1-yl]benzamide | D |
| 800 | 1,1-dimethylethyl (3S)-3-({[3-amino-6-(3-{[(1-methyl-1-phenylethyl)amino]carbonyl}phenyl)pyrazin-2-yl]carbonyl}amino)pyrrolidine-1-carboxylate | D |
| 801 | 3-amino-6-(3-{[(1-methyl-1-phenylethyl)amino]carbonyl}phenyl)-N-[(3S)-pyrrolidin-3-yl]pyrazine-2-carboxamide | B |
| 802 | 3-amino-6-(3-{[(1S)-2,3-dihydro-1H-inden-1-ylamino]sulfonyl}phenyl)pyrazine-2-carboxamide | C |
| 803 | 3-amino-6-(3-{[(1S)-2,3-dihydro-1H-inden-1-ylamino]sulfonyl}phenyl)-N-piperidin-3-ylpyrazine-2-carboxamide | B |
| 804 | 3-amino-6-(3-{[(1S)-2,3-dihydro-1H-inden-1-ylamino]carbonyl}phenyl)-N-[(3S)-1-methylpyrrolidin-3-yl]pyrazine-2-carboxamide | B |
| 805 | 3-amino-6-[3-({[(1R,2S)-2-hydroxy-2,3-dihydro-1H-inden-1-yl]amino}carbonyl)phenyl]-N-[(3S)-1-methylpyrrolidin-3-yl]pyrazine-2-carboxamide | B |
| 806 | 3-amino-6-[3-({[(1R,2S)-2-hydroxy-2,3-dihydro-1H-inden-1-yl]amino}methyl)phenyl]-N-[(3S)-pyrrolidin-3-yl]pyrazine-2-carboxamide | A |
| 807 | 3-amino-6-[3-({[(1R,2S)-2-hydroxy-2,3-dihydro-1H-inden-1-yl]amino}carbonyl)phenyl]-N-[(3S)-piperidin-3-yl]pyrazine-2-carboxamide | A |
| 808 | 3-amino-N-[(3S)pyrrolidin-3-yl]-6-(3-{[(1S)-1,2,3,4-tetrahydronaphthalen-1-ylamino]methyl}phenyl)pyrazine-2-carboxamide | A |
| 809 | N-[3-(5-amino-6-{5-[(3S)-piperidin-3-yl]-4H-1,2,4-triazol-3-yl}pyrazin-2-yl)phenyl]-2-(2,4-dichlorophenyl)acetamide | A |
| 810 | 1,1-dimethylethyl (3S)-3-({[3-amino-6-(3-{[(1R)-2,3-dihydro-1H-inden-1-ylamino]sulfonyl}phenyl)pyrazin-2-yl]carbonyl}amino)pyrrolidine-1-carboxylate | D |
| 811 | 3-amino-6-(3-hydroxyphenyl)-N-[(3S)-pyrrolidin-3-yl]pyrazine-2-carboxamide | B |
| 812 | 3-amino-6-(3-{[(1R)-2,3-dihydro-1H-inden-1-ylamino]sulfonyl}phenyl)-N-[(3S)-pyrrolidin-3-yl]pyrazine-2-carboxamide | B |
| 813 | 3-[5-amino-6-(1-pyridin-4-yl-1H-1,2,4-triazol-3-yl)pyrazin-2-yl]-N-[(1S)-2,3-dihydro-1H-inden-1-yl]benzamide | C |
| 814 | 3-amino-N-[(3S)-pyrrolidin-3-yl]-6-[3-({[(3,4,5-trifluorophenyl)methyl]amino}carbonyl)phenyl]pyrazine-2-carboxamide | A |
| 815 | 3-amino-N-[(3S)-pyrrolidin-3-yl]-6-[3-({[(2,3,6-trifluorophenyl)methyl]amino}carbonyl)phenyl]pyrazine-2-carboxamide | B |
| 816 | 3-amino-N-[(3S)-pyrrolidin-3-yl]-6-[3-({[(2,3,5-trifluorophenyl)methyl]amino}carbonyl)phenyl]pyrazine-2-carboxamide | B |
| 817 | 3-amino-6-[3-({[(3-bromo-4-fluorophenyl)methyl]amino}carbonyl)phenyl]-N-[(3S)-pyrrolidin-3-yl]pyrazine-2-carboxamide | A |
| 818 | 3-{5-amino-6-[3-(1-methylpiperidin-3-yl)-1H-1,2,4-triazol-5-yl]pyrazin-2-yl}-N-[(2-chloro-6-fluorophenyl)methyl]benzamide | C |
| 819 | 3-amino-N-1-azabicyclo[2.2.2]oct-3-yl-6-(3-{[(1S)-2,3-dihydro-1H-inden-1-ylamino]methyl}phenyl)pyrazine-2-carboxamide | B |
| 820 | 3-(5-amino-6-{3-[(3S)-piperidin-3-yl]-1H-1,2,4-triazol-5-yl}pyrazin-2-yl)-N-[(4-chloro-2-fluorophenyl)methyl]benzamide | A |

TABLE 11-continued

| # | Name | Chk1 IC$_{50}$ |
|---|---|---|
| 821 | 3-(5-amino-6-{3-[(3S)-piperidin-3-yl]-1H-1,2,4-triazol-5-yl}pyrazin-2-yl)-N-[(2-chlorophenyl)methyl]benzamide | A |
| 822 | 1,1-dimethylethyl (3S)-3-[({3-amino-6-[3-({[(2,4-dichlorophenyl)methyl]amino}carbonyl)phenyl]pyrazin-2-yl}carbonyl)amino]pyrrolidine-1-carboxylate | C |
| 823 | 1,1-dimethylethyl (3S)-3-[({3-amino-6-[3-({[(3,4-dichlorophenyl)methyl]amino}carbonyl)phenyl]pyrazin-2-yl}carbonyl)amino]pyrrolidine-1-carboxylate | C |
| 824 | 5-(3-{[(1S)-2,3-dihydro-1H-inden-1-ylamino]methyl}phenyl)-3-(4-piperidin-3-yl-1,3-thiazol-2-yl)pyrazin-2-amine | D |
| 825 | 3-amino-6-[3-({[(2,4-dichlorophenyl)methyl]amino}carbonyl)phenyl]-N-[(3S)-pyrrolidin-3-yl]pyrazine-2-carboxamide | A |
| 826 | 3-amino-6-[3-({[(3,4-dichlorophenyl)methyl]amino}carbonyl)phenyl]-N-[(3S)-pyrrolidin-3-yl]pyrazine-2-carboxamide | A |
| 827 | 3-(5-amino-6-{3-[(3S)-piperidin-3-yl]-1H-1,2,4-triazol-5-yl}pyrazin-2-yl)-N-[(2,6-difluorophenyl)methyl]benzamide | B |
| 828 | 3-(5-amino-6-{3-[(3S)-piperidin-3-yl]-1H-1,2,4-triazol-5-yl}pyrazin-2-yl)-N-[(2-chloro-6-fluorophenyl)methyl]benzamide | B |
| 829 | 3-(5-amino-6-{3-[(3S)-piperidin-3-yl]-1H-1,2,4-triazol-5-yl}pyrazin-2-yl)-N-[(2,5-dichlorophenyl)methyl]benzamide | B |
| 830 | 3-(5-amino-6-{3-[(3S)-piperidin-3-yl]-1H-1,2,4-triazol-5-yl}pyrazin-2-yl)-N-[(3,4-dichlorophenyl)methyl]benzamide | A |
| 831 | 3-amino-6-{3-[({[4-(methyloxy)phenyl]methyl}amino)carbonyl]phenyl}-N-[(3S)-piperidin-3-yl]pyrazine-2-carboxamide | A |
| 832 | 3-amino-6-[3-({[(2,4-dichlorophenyl)methyl]amino}carbonyl)phenyl]-N-[(3S)-piperidin-3-yl]pyrazine-2-carboxamide | A |
| 833 | 1,1-dimethylethyl (3S)-3-{[(3-amino-6-{3-[({[(1,1-dimethylethyl)oxy]carbonyl}amino)methyl]phenyl}pyrazin-2-yl)carbonyl]amino}piperidine-1-carboxylate | B |
| 834 | 3-(5-amino-6-{5-[(3S)-piperidin-3-yl]-4H-1,2,4-triazol-3-yl}pyrazin-2-yl)-N-[(2-fluorophenyl)methyl]benzamide | A |
| 835 | 3-(5-amino-6-{5-[(3S)-piperidin-3-yl]-4H-1,2,4-triazol-3-yl}pyrazin-2-yl)-N-[(3-fluorophenyl)methyl]benzamide | A |
| 836 | 3-(5-amino-6-{5-[(3S)-piperidin-3-yl]-4H-1,2,4-triazol-3-yl}pyrazin-2-yl)-N-[(4-fluorophenyl)methyl]benzamide | A |
| 837 | 3-(5-amino-6-{5-[(3S)-piperidin-3-yl]-4H-1,2,4-triazol-3-yl}pyrazin-2-yl)-N-[(3-chlorophenyl)methyl]benzamide | A |
| 838 | 3-(5-amino-6-{5-[(3S)-piperidin-3-yl]-4H-1,2,4-triazol-3-yl}pyrazin-2-yl)-N-[(4-chlorophenyl)methyl]benzamide | A |
| 839 | 3-amino-6-[3-(aminomethyl)phenyl]-N-[(3S)-piperidin-3-yl]pyrazine-2-carboxamide | A |
| 840 | 3-amino-6-(3-hydroxyphenyl)-N-[(3S)-piperidin-3-yl]pyrazine-2-carboxamide | A |
| 841 | 1,1-dimethylethyl (3S)-3-[({3-amino-6-[3-(aminomethyl)phenyl]pyrazin-2-yl}carbonyl)amino]piperidine-1-carboxylate | B |
| 842 | 3-amino-6-[3-({[(4-fluorophenyl)methyl]amino}carbonyl)phenyl]-N-[(3S)-piperidin-3-yl]pyrazine-2-carboxamide | A |
| 843 | 3-amino-N-[(3S)-piperidin-3-yl]-6-(3-{[({4-[(trifluoromethyl)oxy]phenyl}methyl)amino]carbonyl}phenyl)pyrazine-2-carboxamide | A |
| 844 | 3-amino-6-(3-{[(biphenyl-4-ylmethyl)amino]carbonyl}phenyl)-N-[(3S)-piperidin-3-yl]pyrazine-2-carboxamide | A |
| 845 | 3-amino-N-[(3S)-piperidin-3-yl]-6-{3-[({[4-(1,2,3-thiadiazol-5-yl)phenyl]methyl}amino)carbonyl]phenyl}pyrazine-2-carboxamide | A |
| 846 | 3-amino-N-[(3S)-piperidin-3-yl]-6-(3-{[({2-[(trifluoromethyl)oxy]phenyl}methyl)amino]carbonyl}phenyl)pyrazine-2-carboxamide | A |
| 847 | 3-amino-6-(3-{[(biphenyl-2-ylmethyl)amino]carbonyl}phenyl)-N-[(3S)-piperidin-3-yl]pyrazine-2-carboxamide | A |
| 848 | 3-amino-6-[3-({[(2,4-difluorophenyl)methyl]amino}carbonyl)phenyl]-N-[(3S)-piperidin-3-yl]pyrazine-2-carboxamide | A |
| 849 | 3-amino-6-[3-({[(4-chloro-2-fluorophenyl)methyl]amino}carbonyl)phenyl]-N-[(3S)-piperidin-3-yl]pyrazine-2-carboxamide | A |
| 850 | 3-amino-6-{3-[({[4-fluoro-3-(trifluoromethyl)phenyl]methyl}amino)carbonyl]phenyl}-N-[(3S)-piperidin-3-yl]pyrazine-2-carboxamide | A |
| 851 | 3-amino-6-(3-{[(naphthalen-2-ylmethyl)amino]carbonyl}phenyl)-N-[(3S)-piperidin-3-yl]pyrazine-2-carboxamide | A |
| 852 | 3-amino-6-{3-[({[4-(dimethylamino)phenyl]methyl}amino)carbonyl]phenyl}-N-[(3S)-piperidin-3-yl]pyrazine-2-carboxamide | A |
| 853 | 3-amino-6-(3-{[(1,3-benzodioxol-5-ylmethyl)amino]carbonyl}phenyl)-N-[(3S)-piperidin-3-yl]pyrazine-2-carboxamide | A |
| 854 | 3-amino-N-[(3S)-piperidin-3-yl]-6-{3-[({[4-(2-thienyl)phenyl]methyl}amino)carbonyl]phenyl}pyazine-2-carboxamide | A |
| 855 | 3-amino-6-{3-[({[2-(methyloxy)phenyl]methyl}amino)carbonyl]phenyl}-N-[(3S)-piperidin-3-yl]pyrazine-2-carboxamide | A |

TABLE 11-continued

| # | Name | Chk1 IC$_{50}$ |
|---|---|---|
| 856 | 3-amino-6-{3-[({[2,4-bis(methyloxy)phenyl]methyl}amino)carbonyl]phenyl}-N-[(3S)-piperidin-3-yl]pyrazine-2-carboxamide | A |
| 857 | 3-amino-6-[3-({[(4-chloro-2-methylphenyl)methyl]amino}carbonyl)phenyl]-N-[(3S)-piperidin-3-yl]pyrazine-2-carboxamide | A |
| 858 | 3-amino-6-[3-({[(2,3-difluoro-4-methylphenyl)methyl]amino}carbonyl)phenyl]-N-[(3S)-piperidin-3-yl]pyrazine-2-carboxamide | A |
| 859 | 3-amino-6-{3-[({[4-(methylsulfonyl)phenyl]methyl}amino)carbonyl]phenyl}-N-[(3S)-piperidin-3-yl]pyrazine-2-carboxamide | A |
| 860 | 3-amino-6-(3-{[(2,3-dihydro-1,4-benzodioxin-6-ylmethyl)amino]carbonyl}phenyl)-N-[(3S)-piperidin-3-yl]pyrazine-2-carboxamide | A |
| 861 | 3-amino-6-[3-({[(4-chlorophenyl)methyl]amino}carbonyl)phenyl]-N-[(3S)-piperidin-3-yl]pyrazine-2-carboxamide | A |
| 862 | 3-amino-6-[3-({[(5-chloro-2-fluorophenyl)methyl]amino}carbonyl)phenyl]-N-[(3S)-piperidin-3-yl]pyrazine-2-carboxamide | A |
| 863 | 3-amino-N-[(3R)-1-azabicyclo[2.2.2]oct-3-yl]-6-(3-{[(1S)-2,3-dihydro-1H-inden-1-ylamino]methyl}phenyl)pyrazine-2-carboxamide | B |
| 864 | 3-amino-6-{3-[({[4-(methylthio)phenyl]methyl}amino)carbonyl]phenyl}-N-[(3S)-piperidin-3-yl]pyrazine-2-carboxamide | A |
| 865 | 3-(5-amino-6-{3-[(3S)-piperidin-3-yl]-1H-1,2,4-triazol-5-yl}pyrazin-2-yl)-N-[(2,4-difluorophenyl)methyl]benzamide | A |
| 866 | 3-amino-6-(3-{[(1,2-diphenylethyl)amino]carbonyl}phenyl)-N-[(3S)-piperidin-3-yl]pyrazine-2-carboxamide | A |
| 867 | 3-(5-amino-6-{3-[(3S)-piperidin-3-yl]-1H-1,2,4-triazol-5-yl}pyrazin-2-yl)-N-[(3,4-difluorophenyl)methyl]benzamide | A |
| 868 | 3-amino-6-[3-({[(3,5-difluorophenyl)methyl]amino}carbonyl)phenyl]-N-[(3S)-piperidin-3-yl]pyrazine-2-carboxamide | A |
| 869 | methyl 4-[({[3-(5-amino-6-{[(3S)-piperidin-3-ylamino]carbonyl}pyrazin-2-yl)phenyl]carbonyl}amino)methyl]benzoate | A |
| 870 | 3-amino-6-[3-({[(4-bromophenyl)methyl]amino}carbonyl)phenyl]-N-[(3S)-piperidin-3-yl]pyrazine-2-carboxamide | A |
| 871 | 3-amino-6-[3-({[(4-bromo-2-fluorophenyl)methyl]amino}carbonyl)phenyl]-N-[(3S)-piperidin-3-yl]pyrazine-2-carboxamide | A |
| 872 | 3-amino-6-[3-({[(2-bromophenyl)methyl]amino}carbonyl)phenyl]-N-[(3S)-piperidin-3-yl]pyrazine-2-carboxamide | A |
| 873 | 3-amino-6-{3-[({[4-fluoro-2-(trifluoromethyl)phenyl]methyl}amino)carbonyl]phenyl}-N-[(3S)-piperidin-3-yl]pyrazine-2-carboxamide | A |
| 874 | 3-amino-6-{3-[({[2-fluoro-3-(trifluoromethyl)phenyl]methyl}amino)carbonyl]phenyl}-N-[(3S)-piperidin-3-yl]pyrazine-2-carboxamide | A |
| 875 | 3-amino-N-[(3S)-piperidin-3-yl]-6-[3-({[(3R)-pyrrolidin-3-ylmethyl]amino}carbonyl)phenyl]pyrazine-2-carboxamide | A |
| 876 | 3-amino-N-[(3S)-piperidin-3-yl]-6-(3-{[(3R)-pyrrolidin-3-ylamino]carbonyl}phenyl)pyrazine-2-carboxamide | A |
| 877 | 3-amino-N-[(3S)-piperidin-3-yl]-6-(3-{[(2-piperidin-1-ylethyl)amino]carbonyl}phenyl)pyrazine-2-carboxamide | A |
| 878 | 3-amino-6-(3-{[(2-phenylethyl)amino]carbonyl}phenyl)-N-[(3S)-piperidin-3-yl]pyrazine-2-carboxamide | A |
| 879 | 3-amino-6-[3-({[2-(methyloxy)ethyl]amino}carbonyl)phenyl]-N-[(3S)-piperidin-3-yl]pyrazine-2-carboxamide | B |
| 880 | 3-amino-6-[3-({[(4-iodophenyl)methyl]amino}carbonyl)phenyl]-N-[(3S)-piperidin-3-yl]pyrazine-2-carboxamide | A |
| 881 | 3-amino-6-[3-({[(2-chlorophenyl)methyl]amino}carbonyl)phenyl]-N-[(3S)-piperidin-3-yl]pyrazine-2-carboxamide | A |
| 882 | 3-amino-6-[3-({[(4-fluorophenyl)carbonyl]amino}methyl)phenyl]-N-[(3S)-piperidin-3-yl]pyrazine-2-carboxamide | A |
| 883 | 3-amino-N-[(3S)-piperidin-3-yl]-6-(3-[({[4-[(trifluoromethyl)oxy]phenyl}carbonyl)amino]methyl}phenyl)pyrazine-2-carboxamide | A |
| 884 | 3-amino-6-[3-({[(4-chlorophenyl)carbonyl]amino}methyl)phenyl]-N-[(3S)-piperidin-3-yl]pyrazine-2-carboxamide | A |
| 885 | 3-amino-6-(3-{[[(4-chlorophenyl)acetyl]amino}phenyl)-N-[(3S)-piperidin-3-yl]pyrazine-2-carboxamide | A |
| 886 | 3-amino-6-(3-{[(2,6-dichlorophenyl)acetyl]amino}phenyl)-N-[(3S)-piperidin-3-yl]pyrazine-2-carboxamide | A |
| 887 | 3-amino-6-(3-{[(pentafluorophenyl)acetyl]amino}phenyl)-N-[(3S)-piperidin-3-yl]pyrazine-2-carboxamide | A |
| 888 | 3-amino-6-(3-{[(2-chloro-4-fluorophenyl)acetyl]amino}phenyl)-N-[(3S)-piperidin-3-yl]pyrazine-2-carboxamide | A |
| 889 | 3-amino-6-(3-{[{[4-(methylthio)phenyl]acetyl}amino)phenyl]-N-[(3S)-piperidin-3-yl]pyrazine-2-carboxamide | A |
| 890 | 3-amino-6-(3-{[(2,4-dichlorophenyl)acetyl]amino}phenyl)-N-[(3S)-piperidin-3-yl]pyrazine-2-carboxamide | A |
| 891 | 3-amino-6-[3-({[4-(4-chlorophenyl)-2-thienyl]carbonyl}amino)phenyl]-N-[(3S)-piperidin-3-yl]pyrazine-2-carboxamide | A |

TABLE 11-continued

| # | Name | Chk1 IC$_{50}$ |
|---|------|----------------|
| 892 | 3-amino-6-[3-({[(4-bromophenyl)carbonyl]amino}methyl)phenyl]-N-[(3S)-piperidin-3-yl]pyrazine-2-carboxamide | A |
| 893 | 3-amino-6-(3-{[(naphthalen-2-ylcarbonyl)amino]methyl}phenyl)-N-[(3S)-piperidin-3-yl]pyrazine-2-carboxamide | A |
| 894 | 3-amino-6-(3-{[2-(4-phenylpiperazin-1-yl)ethyl]oxy}phenyl)-N-[(3S)-piperidin-3-yl]pyrazine-2-carboxamide | A |
| 895 | N-[(3-{5-amino-6-[(3R)-piperidin-3-ylacetyl]pyrazin-2-yl}phenyl)methyl]-N'-(4-bromophenyl)urea | A |
| 896 | N-[(3-{5-amino-6-[(3R)-piperidin-3-ylacetyl]pyrazin-2-yl}phenyl)methyl]-N'-naphthalen-2-ylurea | A |
| 897 | 3-amino-6-(3-{[(2,4-difluorophenyl)acetyl]amino}phenyl)-N-[(3S)-piperidin-3-yl]pyrazine-2-carboxamide | A |
| 898 | 3-amino-6-(3-{[(2-fluorophenyl)acetyl]amino}phenyl)-N-[(3S)-piperidin-3-yl]pyrazine-2-carboxamide | A |
| 899 | 3-amino-6-{3-[({5-[2-chloro-5-(trifluoromethyl)phenyl]furan-2-yl}carbonyl)amino]phenyl}-N-[(3S)-piperidin-3-yl]pyrazine-2-carboxamide | A |
| 900 | 3-amino-6-[3-({[4-(dimethylamino)naphthalen-1-yl]carbonyl}amino)phenyl]-N-[(3S)-piperidin-3-yl]pyrazine-2-carboxamide | A |
| 901 | 3-amino-N-[(3S)-piperidin-3-yl]-6-[3-({[4-(1,2,3-thiadiazol-5-yl)phenyl]carbonyl}amino)phenyl]pyrazine-2-carboxamide | A |
| 902 | 3-amino-6-(3-{[(1,3-dimethyl-1H-pyrazol-5-yl)carbonyl]amino}phenyl)-N-[(3S)-piperidin-3-yl]pyrazine-2-carboxamide | A |
| 903 | 3-amino-6-{3-[({[4-(dimethylamino)phenyl]carbonyl}amino)methyl]phenyl}-N-[(3S)-piperidin-3-yl]pyrazine-2-carboxamide | A |
| 904 | 3-amino-6-{3-[(2-hydroxyethyl)oxy]phenyl}-N-[(3S)-piperidin-3-yl]pyrazine-2-carboxamide | A |
| 905 | 3-amino-6-(3-{[(2,3-dihydro-1-benzofuran-5-ylsulfonyl)amino]methyl}phenyl)-N-[(3S)-piperidin-3-yl]pyrazine-2-carboxamide | A |
| 906 | 3-amino-6-(3-{[(3,4-dihydro-2H-1,5-benzodioxepin-7-ylsulfonyl)amino]methyl}phenyl)-N-[(3S)-piperidin-3-yl]pyrazine-2-carboxamide | A |
| 907 | 3-amino-N-[(3S)-piperidin-3-yl]-6-(3-{[(quinolin-7-ylsulfonyl)amino]methyl}phenyl)pyrazine-2-carboxamide | B |
| 908 | 3-amino-6-[3-({[(biphenyl-4-ylamino)carbonyl]amino}methyl)phenyl]-N-[(3S)-piperidin-3-yl]pyrazine-2-carboxamide | A |
| 909 | 3-amino-6-(3-{[(4-bromo-2-fluorophenyl)carbonyl]amino}phenyl)-N-[(3S)-piperidin-3-yl]pyrazine-2-carboxamide | A |
| 910 | N-[3-(5-amino-6-{[(3S)-piperidin-3-ylamino]carbonyl}pyrazin-2-yl)phenyl]quinoline-3-carboxamide | A |
| 911 | 3-amino-6-[3-({[6-(methyloxy)-1-benzofuran-3-yl]acetyl}amino)phenyl]-N-[(3S)-piperidin-3-yl]pyrazine-2-carboxamide | A |
| 912 | 3-amino-N-[(3S)-piperidin-3-yl]-6-[3-({[4'-(trifluoromethyl)biphenyl-2-yl]carbonyl}amino)phenyl]pyrazine-2-carboxamide | A |
| 913 | 3-amino-6-(3-{[[3,5-bis(trifluoromethyl)phenyl]acetyl]amino}phenyl)-N-[(3S)-piperidin-3-yl]pyrazine-2-carboxamide | A |
| 914 | 3-amino-6-{3-[({[(2,4-difluorophenyl)amino]carbonyl}amino)methyl]phenyl}-N-[(3S)-piperidin-3-yl]pyrazine-2-carboxamide | A |
| 915 | 3-amino-N-[(3S)-piperidin-3-yl]-6-{3-[({[2-(trifluoromethyl)phenyl]sulfonyl}amino)methyl]phenyl}pyrazine-2-carboxamide | B |
| 916 | 3-amino-N-[(3S)-piperidin-3-yl]-6-(3-{[({4-[(trifluoromethyl)oxy]phenyl}sulfonyl)amino]methyl}phenyl)pyrazine-2-carboxamide | B |
| 917 | 3-amino-N-[(3S)-piperidin-3-yl]-6-(3-{[({2-[(trifluoromethyl)oxy]phenyl}sulfonyl)amino]methyl}phenyl)pyrazine-2-carboxamide | B |
| 918 | 3-amino-N-[(3S)-piperidin-3-yl]-6-(3-{[({4-(trifluoromethyl)phenyl]sulfonyl}amino)methyl]phenyl}pyrazine-2-carboxamide | B |
| 919 | 3-amino-N-[(3S)-piperidin-3-yl]-6-[3-({[({2-[(trifluoromethyl)oxy]phenyl}amino)carbonyl]amino}methyl)phenyl]pyrazine-2-carboxamide | B |
| 920 | 3-amino-6-(3-{[({[2-(methylthio)phenyl]amino}carbonyl)amino]methyl}phenyl)-N-[(3S)-piperidin-3-yl]pyrazine-2-carboxamide | A |
| 921 | 3-amino-6-{3-[({[(3-bromo-5-methylphenyl)amino]carbonyl}amino)methyl]phenyl}-N-[(3S)-piperidin-3-yl]pyrazine-2-carboxamide | A |
| 922 | 3-amino-6-{3-[({[(2-bromophenyl)amino]carbonyl}amino)methyl]phenyl}-N-[(3S)-piperidin-3-yl]pyrazine-2-carboxamide | A |
| 923 | 5-[3-(aminomethyl)phenyl]-3-{3-[(3S)-piperidin-3-yl]-1H-1,2,4-triazol-5-yl}pyrazin-2-amine | A |
| 924 | 3-amino-6-{3-[({[4-(4-methylpiperazin-1-yl)phenyl]methyl}amino)carbonyl]phenyl}-N-[(3S)-piperidin-3-yl]pyrazine-2-carboxamide | A |

TABLE 11-continued

| # | Name | Chk1 IC$_{50}$ |
|---|------|----------------|
| 925 | 3-amino-6-[3-({[2-(4-fluorophenyl)ethyl]amino}carbonyl)phenyl]-N-[(3S)-piperidin-3-yl]pyrazine-2-carboxamide | A |
| 926 | 3-amino-6-(3-{[(2-morpholin-4-ylethyl)amino]carbonyl}phenyl)-N-[(3S)-piperidin-3-yl]pyrazine-2-carboxamide | B |
| 927 | 3-amino-N-[(3S)-piperidin-3-yl]-6-[3-({[(2R)-pyrrolidin-2-ylmethyl]amino}carbonyl)phenyl]pyrazine-2-carboxamide | A |
| 928 | 3-amino-N-[(3S)-piperidin-3-yl]-6-(3-{[(2S)-pyrrolidin-2-ylamino]carbonyl}phenyl)pyrazine-2-carboxamide | A |
| 929 | 3-amino-6-{3-[(cyclopentylamino)carbonyl]phenyl}-N-[(3S)-piperidin-3-yl]pyrazine-2-carboxamide | B |
| 930 | 3-amino-N-[(3S)-piperidin-3-yl]-6-(3-{[({4-[(trifluoromethyl)oxy]phenyl}amino)carbonyl]amino}methyl)phenyl]pyrazine-2-carboxamide | A |
| 931 | 3-amino-N-[(3S)-piperidin-3-yl]-6-(3-{[({4-(trifluoromethyl)phenyl]amino}carbonyl)amino]methyl}phenyl)pyrazine-2-carboxamide | A |
| 932 | 3-amino-6-{3-[({[4-(methyloxy)phenyl]carbonyl}amino)methyl]phenyl}-N-[(3S)-piperidin-3-yl]pyrazine-2-carboxamide | A |
| 933 | 3-amino-6-(3-{[(biphenyl-4-ylcarbonyl)amino]methyl}phenyl)-N-[(3S)-piperidin-3-yl]pyrazine-2-carboxamide | A |
| 934 | 3-amino-6-(3-{[(furan-2-ylcarbonyl)amino]methyl}phenyl)-N-[(3S)-piperidin-3-yl]pyrazine-2-carboxamide | A |
| 935 | 3-amino-6-(3-{[({[(2,3-dihydro-1,4-benzodioxin-6-ylamino)carbonyl]amino}methyl)phenyl]-N-[(3S)-piperidin-3-yl]pyrazine-2-carboxamide | A |
| 936 | 3-amino-6-(3-{[(2,3-dihydro-1-benzofuran-5-ylcarbonyl)amino]methyl}phenyl)-N-[(3S)-piperidin-3-yl]pyrazine-2-carboxamide | A |
| 937 | 3-amino-6-(3-{[(2,3-dihydro-1,4-benzodioxin-6-ylsulfonyl)amino]methyl}phenyl)-N-[(3S)-piperidin-3-yl]pyrazine-2-carboxamide | A |
| 938 | 3-amino-N-[(3S)-piperidin-3-yl]-6-(3-{[(2-thienylcarbonyl)amino]methyl}phenyl)pyrazine-2-carboxamide | A |
| 939 | 3-amino-6-(3-{[(2,3-dihydro-1,4-benzodioxin-2-ylcarbonyl)amino]methyl}phenyl)-N-[(3S)-piperidin-3-yl]pyrazine-2-carboxamide | A |
| 940 | N-{[3-(5-amino-6-{3-[(3S)-piperidin-3-yl]-1H-1,2,4-triazol-5-yl}pyrazin-2-yl)phenyl]methyl}-2-chlorobenzamide | A |
| 941 | N-{[3-(5-amino-6-{3-[(3S)-piperidin-3-yl]-1H-1,2,4-triazol-5-yl}pyrazin-2-yl)phenyl]methyl}-4-chlorobenzamide | A |
| 942 | N-{[3-(5-amino-6-{3-[(3S)-piperidin-3-yl]-1H-1,2,4-triazol-5-yl}pyrazin-2-yl)phenyl]methyl}-4-iodobenzamide | A |
| 943 | N-{[3-(5-amino-6-{3-[(3S)-piperidin-3-yl]-1H-1,2,4-triazol-5-yl}pyrazin-2-yl)phenyl]methyl}-3,5-difluorobenzamide | A |
| 944 | N-{[3-(5-amino-6-{3-[(3S)-piperidin-3-yl]-1H-1,2,4-triazol-5-yl}pyrazin-2-yl)phenyl]methyl}-4-bromo-2-fluorobenzamide | A |
| 945 | N-{[3-(5-amino-6-{3-[(3S)-piperidin-3-yl]-1H-1,2,4-triazol-5-yl}pyrazin-2-yl)phenyl]methyl}-4-bromo-2-chlorobenzamide | A |
| 946 | 3-[3-(2-aminopyridin-4-yl)-1H-1,2,4-triazol-5-yl]-5-(3-{[(1S)-2,3-dihydro-1H-inden-1-ylamino]methyl}phenyl)pyrazin-2-amine | A |
| 947 | 3-amino-N-azepan-3-yl-6-(3-{[(1S)-2,3-dihydro-1H-inden-1-ylamino]methyl}phenyl)pyrazine-2-carboxamide | A |
| 948 | 3-amino-N-[(3S)-piperidin-3-yl]-6-{3-[({[2-(2-thienyl)-1,3-thiazol-4-yl]carbonyl}amino)methyl]phenyl}pyrazine-2-carboxamide | A |
| 949 | 3-amino-N-[(3S)-piperidin-3-yl]-6-{3-[({[5-(2-thienyl)pyridin-3-yl]carbonyl}amino)methyl]phenyl}pyrazine-2-carboxamide | A |
| 950 | 3-amino-6-{3-[({[4-(1,1-dimethylethyl)phenyl]methyl}amino)carbonyl]phenyl}-N-[(3S)-piperidin-3-yl]pyrazine-2-carboxamide | A |
| 951 | 3-amino-6-[3-({[(2,4-dichloro-6-methylphenyl)methyl]amino}carbonyl)phenyl]-N-[(3S)-piperidin-3-yl]pyrazine-2-carboxamide | A |
| 952 | 3-amino-6-[3-({[(3,5-dichlorophenyl)methyl]amino}carbonyl)phenyl]-N-[(3S)-piperidin-3-yl]pyrazine-2-carboxamide | A |
| 953 | 3-amino-N-[(3S)-piperidin-3-yl]-6-(3-{[(2-thienylsulfonyl)amino]methyl}phenyl)pyrazine-2-carboxamide | A |
| 954 | 3-amino-N-[(3S)-piperidin-3-yl]-6-{3-{[(3-thienylsulfonyl)amino]methyl}phenyl)pyrazine-2-carboxamide | A |
| 955 | 3-amino-6-(3-{[{[(4-chlorophenyl)sulfonyl]amino}methyl)phenyl]-N-[(3S)-piperidin-3-yl]pyrazine-2-carboxamide | A |
| 956 | 3-amino-6-[3-({[(1,3-benzodioxol-5-ylamino)carbonyl]amino}methyl)phenyl]-N-[(3S)-piperidin-3-yl]pyrazine-2-carboxamide | A |
| 957 | 3-amino-6-(3-{[({[4-(methyloxy)phenyl]amino}carbonyl)amino]methyl}phenyl)-N-[(3S)-piperidin-3-yl]pyrazine-2-carboxamide | A |

TABLE 11-continued

| # | Name | Chk1 IC$_{50}$ |
|---|------|----------------|
| 958 | 3-amino-6-{3-[({[(4-fluorophenyl)amino]carbonyl}amino)methyl]phenyl}-N-[(3S)-piperidin-3-yl]pyrazine-2-carboxamide | A |
| 959 | 3-amino-6-(3-{[2-(diethylamino)ethyl]oxy}phenyl)-N-[(3S)-piperidin-3-yl]pyrazine-2-carboxamide | A |
| 960 | 3-amino-6-{3-[(2-morpholin-4-ylethyl)oxy]phenyl}-N-[(3S)-piperidin-3-yl]pyrazine-2-carboxamide | B |
| 961 | 3-amino-6-[3-(methyloxy)phenyl]-N-[(3S)-piperidin-3-yl]pyrazine-2-carboxamide | A |
| 962 | 3-amino-6-[3-(ethyloxy)phenyl]-N-[(3S)-piperidin-3-yl]pyrazine-2-carboxamide | A |
| 963 | 3-amino-N-[(3S)-piperidin-3-yl]-6-{3-[({[4-(1,2,3-thiadiazol-4-yl)phenyl]methyl}amino)carbonyl]phenyl}pyrazine-2-carboxamide | A |
| 964 | 3-amino-6-(3-{[2-(ethylamino)ethyl]oxy}phenyl)-N-[(3S)-piperidin-3-yl]pyrazine-2-carboxamide | A |
| 965 | phenylmethyl 4-(2-{[3-(5-amino-6-{[(3S)-piperidin-3-ylamino]carbonyl}pyrazin-2-yl)phenyl]oxy}ethyl)piperazine-1-carboxylate | A |
| 966 | 3-amino-6-(3-{[({[4-(dimethylamino)phenyl]amino}carbonyl)amino]methyl}phenyl)-N-[(3S)-piperidin-3-yl]pyrazine-2-carboxamide | A |
| 967 | 3-amino-N-azepan-3-yl-6-(3-{[(1S)-2,3-dihydro-1H-inden-1-ylamino]carbonyl}phenyl)pyrazine-2-carboxamide | A |
| 968 | 3-amino-6-[3-({[(1R,2S)-2-hydroxy-2,3-dihydro-1H-inden-1-yl]amino}methyl)phenyl]-N-[(3S)-piperidin-3-yl]pyrazin-2-carboxamide | A |
| 969 | 3-amino-6-[3-({[(1S,2S)-2-hydroxy-2,3-dihydro-1H-inden-1-yl]amino}carbonyl)phenyl]-N-[(3S)-1-(phenylmethyl)azepan-3-yl]pyrazine-2-carboxamide | C |
| 970 | 3-amino-N-[(3S)-azepan-3-yl]-6-[3-({[(1S,2S)-2-hydroxy-2,3-dihydro-1H-inden-1-yl]amino}carbonyl)phenyl]pyrazine-2-carboxamide | A |
| 971 | 3-amino-6-{3-[({[(4-chlorophenyl)amino]carbonyl}amino)methyl]phenyl}-N-[(3S)-piperidin-3-yl]pyrazine-2-carboxamide | A |
| 972 | 3-amino-6-(3-{[(1S)-2,3-dihydro-1H-inden-1-ylamino]carbonyl}phenyl)-N-[(3S)-1-(phenylmethyl)azepan-3-yl]pyrazine-2-carboxamide | B |
| 973 | 3-amino-N-[(3S)-azepan-3-yl]-6-(3{[(1S)-2,3-dihydro-1H-inden-1-ylamino]carbonyl}phenyl)pyrazine-2-carboxamide | A |
| 974 | 3-amino-N-[(3S)-azepan-3-yl]-6-(3-methylphenyl)pyrazine-2-carboxamide | A |
| 975 | 3-amino-6-(3-{[(2-methylphenyl)acetyl]amino}phenyl)-N-[(3S)-piperidin-3-yl]pyrazine-2-carboxamide | A |
| 976 | 3-amino-N-[(3S)-piperidin-3-yl]-6-[3-({[3-(trifluoromethyl)phenyl]acetyl}amino)phenyl]pyrazine-2-carboxamide | A |
| 977 | 3-amino-6-(3-{[{4-(methyloxy)phenyl]acetyl}amino)phenyl]-N-[(3S)-piperidin-3-yl]pyrazine-2-carboxamide | A |
| 978 | 3-amino-6-(3-{[(6-methylpyridin-3-yl)carbonyl]amino}phenyl)-N-[(3S)-piperidin-3-yl]pyrazine-2-carboxamide | A |
| 979 | 3-amino-6-(3-{[(3-fluorophenyl)acetyl]amino}phenyl)-N-[(3S)-piperidin-3-yl]pyrazine-2-carboxamide | A |
| 980 | 3-amino-N-[(3S)-piperidin-3-yl]-6-{3-[(pyridin-3-ylacetyl)amino]phenyl}pyrazine-2-carboxamide | A |
| 981 | 3-amino-N-[(3S)-piperidin-3-yl]-6-{3-[(pyridin-3-ylcarbonyl)amino]phenyl}pyrazine-2-carboxamide | A |
| 982 | 3-amino-6-(3-{[(2,5-difluorophenyl)acetyl]amino}phenyl)-N-[(3S)-piperidin-3-yl]pyrazine-2-carboxamide | A |
| 983 | 3-amino-6-(3-{[(4-fluorophenyl)acetyl]amino}phenyl)-N-[(3S)-piperidin-3-yl]pyrazine-2-carboxamide | A |
| 984 | 3-amino-6-{3-[({[3-fluoro-5-(trifluoromethyl)phenyl]methyl}amino)carbonyl]phenyl}-N-[(3S)-piperidin-3-yl]pyrazine-2-carboxamide | A |
| 985 | 3-amino-6-[3-({[(3,4-dichlorophenyl)methyl]amino}carbonyl)phenyl]-N-[(3S)-piperidin-3-yl]pyrazine-2-carboxamide | A |
| 986 | 3-Amino-6-[3-({[5-(4-nitro-phenyl)-furan-2-carbonyl]-amino}-methyl)-phenyl]-pyrazine-2-carboxylic acid (3S)-piperidin-3-ylamide | A |
| 987 | 3-amino-6-[3-({[(3-hydroxypyridin-2-yl)carbonyl]amino}methyl)phenyl]-N-[(3S)-piperidin-3-yl]pyrazine-2-carboxamide | A |
| 988 | 3-amino-N-[(3S)-piperidin-3-yl]-6-[3-({[({4-[(trifluoromethyl)oxy]phenyl}oxy)acetyl]amino}methyl)phenyl]pyrazine-2-carboxamide | A |
| 989 | 3-amino-6-[3-({[(5-methylisoxazol-3-yl)carbonyl]amino}methyl)phenyl]-N-[(3S)-piperidin-3-yl]pyrazine-2-carboxamide | A |
| 990 | 3-amino-6-(3-{[(isoxazol-5-ylcarbonyl)amino]methyl}phenyl)-N-[(3S)-piperidin-3-yl]pyrazine-2-carboxamide | A |
| 991 | 3-amino-6-[3-({[(4-methyl-1,2,3-thiadiazol-5-yl)carbonyl]amino}methyl)phenyl]-N-[(3S)-piperidin-3-yl]pyrazine-2-carboxamide | A |
| 992 | 3-amino-6-[3-({[(2,5-dichloro-3-thienyl)carbonyl]amino}methyl)phenyl]-N-[(3S)-piperidin-3-yl]pyrazine-2-carboxamide | A |
| 993 | 3-amino-6-[3-({[({5-chloro-2-methylphenyl)methyl]amino}carbonyl)phenyl]-N-[(3S)-piperidin-3-yl]pyrazine-2-carboxamide | A |

TABLE 11-continued

| # | Name | Chk1 IC$_{50}$ |
|---|------|---|
| 994 | 3-amino-6-{3-[({[(2-chloro-5-(trifluoromethyl)phenyl]methyl}amino)carbonyl]phenyl}-N-[(3S)-piperidin-3-yl]pyrazine-2-carboxamide | A |
| 995 | 3-amino-6-[3-({[(2-chloro-6-fluorophenyl)methyl]amino}carbonyl)phenyl]-N-[(3S)-piperidin-3-yl]pyrazine-2-carboxamide | A |
| 996 | 3-amino-N-[(3S)-azepan-3-yl]-6-[3-({[(4-chloro-2-fluorophenyl)methyl]amino}carbonyl)phenyl]pyrazine-2-carboxamide | A |
| 997 | 3-amino-6-[3-({[(3-chloro-2-fluorophenyl)methyl]amino}carbonyl)phenyl]-N-[(3S)-piperidin-3-yl]pyrazine-2-carboxamide | A |
| 998 | 3-amino-6-{3-[({[(2-fluoro-5-(trifluoromethyl)phenyl]methyl}amino)carbonyl]phenyl}-N-[(3S)-piperidin-3-yl]pyrazine-2-carboxamide | A |
| 999 | 3-amino-6-[3-({[(2,4-difluorophenyl)methyl]amino}methyl)phenyl]-N-[(3S)-piperidin-3-yl]pyrazine-2-carboxamide | A |
| 1000 | 3-amino-6-[3-({[(3-chloro-2,6-difluorophenyl)methyl]amino}carbonyl)phenyl]-N-[(3S)-piperidin-3-yl]pyrazine-2-carboxamide | A |
| 1001 | 3-amino-6-{3-[({[(2-fluoro-4-(trifluoromethyl)phenyl]methyl}amino)carbonyl]phenyl}-N-[(3S)-piperidin-3-yl]pyrazine-2-carboxamide | A |
| 1002 | 3-amino-6-[3-({[(2-chloro-4-fluorophenyl)methyl]amino}carbonyl)phenyl]-N-[(3S)-piperidin-3-yl]pyrazine-2-carboxamide | A |
| 1003 | 3-amino-6-[3-({[(2,3-dichlorophenyl)methyl]amino}carbonyl)phenyl]-N-[(3S)-piperidin-3-yl]pyrazine-2-carboxamide | A |
| 1004 | 3-amino-N-[(3S)-piperidin-3-yl]-6-[3-({[(2,3,6-trifluorophenyl)methyl]amino}carbonyl)phenyl]pyrazine-2-carboxamide | A |
| 1005 | 3-amino-6-{3-[({[(4-chloro-3-(trifluoromethyl)phenyl]methyl}amino)carbonyl]phenyl}-N-[(3S)-piperidin-3-yl]pyrazine-2-carboxamide | A |
| 1006 | 3-amino-6-[3-({[(3-chloro-4-fluorophenyl)methyl]amino}corbonyl)phenyl]-N-[(3S)-piperidin-3-yl]pyrazine-2-carboxamide | A |
| 1007 | 3-amino-N-[(3S)-azepan-3-yl]-6-[3-({[(2,3-difluorophenyl)methyl]amino}carbonyl)phenyl]pyrazine-2-carboxamide | A |
| 1008 | 3-amino-N-[(3S)-azepan-3-yl]-6-[3-({[(3,4-difluorophenyl)methyl]amino}carbonyl)phenyl]pyrazine-2-carboxamide | A |
| 1009 | 3-amino-N-[(3S)-azepan-3-yl]-6-[3-({[(3,5-difluorophenyl)methyl]amino}carbonyl)phenyl]pyrazine-2-carboxamide | A |
| 1010 | 3-amino-6-[3-({[(2,6-difluorophenyl)methyl]amino}carbonyl)phenyl]-N-[(3S)-piperidin-3-yl]pyrazine-2-carboxamide | A |
| 1011 | 3-amino-6-[3-({[(3,4-difluorophenyl)methyl]amino}carbonyl)phenyl]-N-[(3S)-piperidin-3-yl]pyrazine-2-carboxamide | A |
| 1012 | 3-amino-6-[3-({[(6-chloro-2-fluoro-3-methylphenyl)methyl]amino}carbonyl)phenyl]-N-[(3S)-piperidin-3-yl]pyrazine-2-carboxamide | A |
| 1013 | 3-amino-6-[3-({[(2-chloro-6-fluoro-3-methylphenyl)methyl]amino}carbonyl)phenyl]-N-[(3S)-piperidin-3-yl]pyrazine-2-carboxamide | A |
| 1014 | 3-amino-6-[3-({[(2-chloro-3,6-difluorophenyl)methyl]amino}carbonyl)phenyl]-N-[(3S)-piperidin-3-yl]pyrazine-2-carboxamide | A |
| 1015 | 3-amino-6-[3-({[(2,5-dichlorophenyl)methyl]amino}carbonyl)phenyl]-N-[(3S)-piperidin-3-yl]pyrazine-2-carboxamide | A |
| 1016 | 3-amino-N-[(3S)-piperidin-3-yl]-6-[3-({[(2,3,4-trifluorophenyl)methyl]amino}carbonyl)phenyl]pyrazine-2-carboxamide | A |
| 1017 | 3-amino-6-[3-({[(2,3-difluorophenyl)methyl]amino}carbonyl)phenyl]-N-[(3S)-piperidin-3-yl]pyrazine-2-carboxamide | A |
| 1018 | 3-amino-6-[3-({[(3-fluoro-4-methylphenyl)methyl]amino}carbonyl)phenyl]-N-[(3S)-piperidin-3-yl]pyrazine-2-carboxamide | A |
| 1019 | 3-amino-N-[(3S)-azepan-3-yl]-6-[3-({[(3-chloro-2,6-difluorophenyl)methyl]amino}carbonyl)phenyl]pyrazine-2-carboxamide | A |
| 1020 | 3-amino-N-[(3S)-azepan-3-yl]-6-(3-{[(2,3-dihydro-1,4-benzodioxin-6-ylmethyl)amino]carbonyl}phenyl)pyrazine-2-carboxamide | A |
| 1021 | 3-amino-N-[(3S)-azepan-3-yl]-6-[3-({[(2-chloro-6-fluorophenyl)methyl]amino}carbonyl)phenyl]pyrazine-2-carboxamide | A |
| 1022 | 3-amino-N-[(3S)-azepan-3-yl]-6-[3-({[(2,6-difluorophenyl)methyl]amino}carbonyl)phenyl]pyrazine-2-carboxamide | A |
| 1023 | 3-amino-N-[(3S)-azepan-3-yl]-6-[3-({[(3-chloro-4-fluorophenyl)methyl]amino}carbonyl)phenyl]pyrazine-2-carboxamide | A |
| 1024 | 3-amino-N-[(3S)-azepan-3-yl]-6-[3-({[(3-chloro-2-fluorophenyl)methyl]amino}carbonyl)phenyl]pyrazine-2-carboxamide | A |
| 1025 | 3-amino-6-[3-({[(3-chloro-2-methylphenyl)methyl]amino}carbonyl)phenyl]-N-[(3S)-piperidin-3-yl]pyrazine-2-carboxamide | A |
| 1026 | 3-amino-6-{3-[({[2,6-bis(methyloxy)phenyl]methyl}amino)carbonyl]phenyl}-N-[(3S)-piperidin-3-yl]pyrazine-2-carboxamide | B |
| 1027 | 3-amino-6-[3-({[(3-bromo-4-fluorophenyl)methyl]amino}carbonyl)phenyl]-N-[(3S)-piperidin-3-yl]pyrazine-2-carboxamide | A |

TABLE 11-continued

| # | Name | Chk1 IC$_{50}$ |
|---|------|----------------|
| 1028 | 3-amino-N-[(3S)-piperidin-3-yl]-6-[3-({[(3,4,5-trifluorophenyl)methyl]amino}carbonyl)phenyl]pyrazine-2-carboxamide | A |
| 1029 | 3-amino-6-[3-({[(4-fluoro-3-methylphenyl)methyl]amino}carbonyl)phenyl]-N-[(3S)-piperidin-3-yl]pyrazine-2-carboxamide | A |
| 1030 | 3-amino-N-[(3S)-piperidin-3-yl]-6-[3-({[(2,3,5-trifluorophenyl)methyl]amino}carbonyl)phenyl]pyrazine-2-carboxamide | A |
| 1031 | 3-amino-6-[3-({[(5-fluoro-2-methylphenyl)methyl]amino}carbonyl)phenyl]-N-[(3S)-piperidin-3-yl]pyrazine-2-carboxamide | A |
| 1032 | 3-amino-6-[3-({[(3-bromo-5-fluorophenyl)methyl]amino}carbonyl)phenyl]-N-[(3S)-piperidin-3-yl]pyrazine-2-carboxamide | A |
| 1033 | 3-amino-N-[(3S)-piperidin-3-yl]-6-{3-[({[4-(1H-pyrazol-1-yl)phenyl]methyl}amino)carbonyl]phenyl}pyrazine-2-carboxamide | A |
| 1034 | 3-amino-6-(3-{[(biphenyl-3-ylmethyl)amino]carbonyl}phenyl)-N-[(3S)-piperidin-3-yl]pyrazine-2-carboxamide | A |
| 1035 | 3-amino-6-[3-({[(2-methylphenyl)methyl]amino}carbonyl)phenyl]-N-[(3S)-piperidin-3-yl]pyrazine-2-carboxamide | A |
| 1036 | 3-amino-6-[3-({[(2,5-dimethylphenyl)methyl]amino}carbonyl)phenyl]-N-[(3S)-piperidin-3-yl]pyrazine-2-carboxamide | A |
| 1037 | 3-amino-6-[3-({[(3,5-dimethylphenyl)methyl]amino}carbonyl)phenyl]-N-[(3S)-piperidin-3-yl]pyrazine-2-carboxamide | A |
| 1038 | 3-amino-6-[3-({[(2,4-dimethylphenyl)methyl]amino}carbonyl)phenyl]-N-[(3S)-piperidin-3-yl]pyrazine-2-carboxamide | A |
| 1039 | 3-amino-6-[3-({[(3-methoxyphenyl)methyl]amino}carbonyl)phenyl]-N-[(3S)-piperidin-3-yl]pyrazine-2-carboxamide | A |
| 1040 | 3-amino-6-{3-[({[phenyl]methyl}amino)carbonyl]phenyl}-N-[(3S)-piperidin-3-yl]pyrazine-2-carboxamide | A |
| 1041 | 3-amino-6-{3-[({[3,5-bis(methyloxy)phenyl]methyl}amino)carbonyl]phenyl}-N-[(3S)-piperidin-3-yl]pyrazine-2-carboxamide | A |
| 1042 | 3-amino-6-{3-[({[3,4-bis(methyloxy)phenyl]methyl}amino)carbonyl]phenyl}-N-[(3S)-piperidin-3-yl]pyrazine-2-carboxamide | A |

Table 12 shows structure activity relationship data for selected compounds of the invention with respect to Chk1 and a number of other enzymes, thus indicating selectivity of exemplary compounds of the invention toward Checkpoint kinases, particularly Chk1. Inhibition is indicated as IC$_{50}$ with following key: A=IC$_{50}$ less than 50 nM, B=IC$_{50}$ greater than 50 nM but less than or equal to 1000 nM, C=IC$_{50}$ greater than 1000 nM but less than 10,000 nM, and D=IC$_{50}$ of 10,000 nM or greater (a blank cell in the table indicates lack of data only).

Abbreviations for human enzymes listed in Table 12 are defined as follows: EphB4 refers to ephrin-related receptor tyrosine kinase B4; Tie-2 refers to tyrosine kinase with immunoglobulin and EGF repeats; EGFR refers to epidermal growth factor receptor; FGFR1 refers to fibroblast growth factor receptor; KDR refers to kinase insert domain containing receptor; Flt1 refers to fms-like tyrosine kinase 1; fyn refers to proto-oncogene tyrosine-protein kinase fyn; and PDGFR-β refers to platlet derived growth factor receptor beta chain. Chk1 refers to checkpoint homologue 1 (*S. pombe*); Chk2 refers to checkpoint-like protein 2; Flt1 refers to fms-like tyrosine kinase 1, Flt4 refers to fms-like tyrosine kinase 4; fyn refers to proto-oncogene tyrosine protein kinase fyn; KDR refers to kinase insert domain containing receptor; MAP4K3 refers to mitogen-activated protein kinase kinase kinase 3; c-MET refers to the cellular homologue of the met proto-oncogene; CLK1 refers to CDC-like kinase1; EMK refers to ELKL motif kinase 1; ErbB2 refers to erythroblastic leukemia viral Oncogene homologue 2; IGFR1 refers to insulin-like growth factor receptor 1; IRK refers to insulin receptor kinase; MAPKAP2 refers to mitogen-activated protein kinase-activated protein kinase; PKA refers to protein kinase A; PKC refers to protein kinase C epsilon isoform; PLK refers to polo-like kinase; scr refers to the src proto-oncogene; ZAP70 refers to zeta-chain associated protein kinase, 70 kD; cdc2 refers to cell division cycle protein 2.

TABLE 12

| # | Compound | Chk1 | Chk2 | FGFR1 | Flt1 | Flt4 | Fyn | PDGFR-β | KDR | MAP4K3 | c-Met | CLK1 |
|---|----------|------|------|-------|------|------|-----|---------|-----|--------|-------|------|
| 1 | 3-amino-6-{3-[({[4-(methyloxy)phenyl]methyl}amino)carbonyl]phenyl}-N-[(3S)-piperidin-3-yl]pyrazine-2-carboxamide | A | A | C | B | B | C | B | B | B | | C |
| 2 | 3-amino-N-[(3S)-piperidin-3-yl]-6-(3-{[({4-[(trifluoromethyl)oxy]phenyl}methyl)amino]carbonyl}phenyl)pyrazine-2-carboxamide | A | A | C | B | A | C | B | B | A | | C |
| 3 | 3-amino-6-[3-({[(4-chloro-2-fluorophenyl)methyl]amino} | A | A | C | B | A | B | B | B | A | | C |

TABLE 12-continued

| | | | | | | | | | | | | |
|---|---|---|---|---|---|---|---|---|---|---|---|---|
| | carbonyl)phenyl]-N-[(3S)-piperidin-3-yl]pyrazine-2-carboxamide | | | | | | | | | | | |
| 4 | 3-amino-6-{3-[({[4-(dimethylamino)phenyl]methyl}amino)carbonyl]phenyl}-N-[(3S)-piperidin-3-yl]pyrazine-2-carboxamide | A | A | C | B | B | B | B | B | B | | C |
| 5 | 3-amino-6-[3-({[(2,3-difluoro-4-methylphenyl)methyl]amino}carbonyl)phenyl]-N-[(3S)-piperidin-3-yl]pyrazine-2-carboxamide | A | A | C | B | B | B | B | B | A | | B |
| 6 | 3-amino-6-(3-{[(2,3-dihydro-1,4-benzodioxin-6-ylmethyl)amino]carbonyl}phenyl)-N-[(3S)-piperidin-3-yl]pyrazine-2-carboxamide | A | A | C | B | A | C | A | B | B | C | C |
| 7 | 3-amino-6-[3-({[(4-chlorophenyl)methyl]amino}carbonyl)phenyl]-N-[(3S)-piperidin-3-yl]pyrazine-2-carboxamide | A | A | C | B | A | C | B | A | A | | C |
| 8 | 3-amino-6-[3-({[(4-fluorophenyl)carbonyl]amino}methyl)phenyl]-N-[(3S)-piperidin-3-yl]pyrazine-2-carboxamide | A | A | B | B | A | B | B | B | A | | D |
| 9 | 3-amino-6-[3-({[(4-chlorophenyl)carbonyl]amino}methyl)phenyl]-N-[(3S)-piperidin-3-yl]pyrazine-2-carboxamide | A | A | B | B | A | B | A | A | A | C | C |
| 10 | 3-amino-6-{3-[(4-chlorophenyl)acetyl]amino}phenyl)-N-[(3S)-piperidin-3-yl]pyrazine-2-carboxamide | A | A | B | A | A | B | A | A | A | C | C |
| 11 | 3-amino-6-(3-{[(pentafluorophenyl)acetyl]amino}phenyl)-N-[(3S)-piperidin-3-yl]pyrazine-2-carboxamide | A | A | B | B | A | B | B | A | A | | C |
| 12 | 3-amino-6-(3-{[(2,4-difluorophenyl)acetyl]amino}phenyl)-N-[(3S)-piperidin-3-yl]pyrazine-2-carboxamide | A | A | B | B | A | B | A | A | A | C | C |
| 13 | 3-amino-6-[3-({[[(biphenyl-4-ylamino)carbonyl]amino}methyl)phenyl]-N-[(3S)-piperidin-3-yl]pyrazine-2-carboxamide | A | A | B | B | A | B | A | A | A | | D |
| 14 | 3-amino-6-(3-{[(4-bromo-2-fluorophenyl)carbonyl]amino}phenyl)-N-[(3S)-piperidin-3-yl]pyrazine-2-carboxamide | A | A | B | A | B | A | A | A | A | C | C |
| 15 | N-[3-(5-amino-6-{[(3S)-piperidin-3-ylamino]carbonyl}pyrazin-2-yl)phenyl]quinoline-3-carboxamide | A | A | B | A | A | B | A | A | A | | B |
| 16 | 3-amino-6-(3-{[(biphenyl-4-ylcarbonyl)amino]methyl}phenyl)-N-[(3S)-piperidin-3-yl]pyrazine-2-carboxamide | A | A | B | B | A | B | A | A | A | C | C |

TABLE 12-continued

| # | Compound | | | | | | | | | | |
|---|---|---|---|---|---|---|---|---|---|---|---|
| 17 | 3-amino-N-[(3S)-piperidin-3-yl]-6-(3-{[(2-thienylcarbonyl)amino]methyl}phenyl)pyrazine-2-carboxamide | A | A | B | B | A | B | A | A | A | D |
| 18 | 3-amino-6-(3-{[2-(ethylamino)ethyl]oxy}phenyl)-N-[(3S)-piperidin-3-yl]pyrazine-2-carboxamide | A | A | B | B | A | B | B | B | B | C |
| 19 | 3-amino-6-[3-({[(1R,2S)-2-hydroxy-2,3-dihydro-1H-inden-1-yl]amino}methyl)phenyl]-N-[(3S)-piperidin-3-yl]pyrazine-2-carboxamide | A | A | B | B | A | B | A | A | A | D |

| # | EGFR | EMK | EphA2R | EphB4 | ErbB2 | IGFR1 | IRK | MAPKAP2 | PKA | PKCe | PLK | SRC | Tie-2 | ZAP70 | Cdc2 |
|---|---|---|---|---|---|---|---|---|---|---|---|---|---|---|---|
| 1 | D | D | D | C | D | | D | | C | D | D | | | | D |
| 2 | D | C | D | D | D | | D | | C | D | C | | | | D |
| 3 | D | C | D | C | D | | D | | C | D | D | | | | D |
| 4 | D | D | D | D | C | | D | | D | D | D | | | | D |
| 5 | D | C | D | C | D | | D | | C | D | D | | | | D |
| 6 | | D | C | C | D | D | D | C | D | D | D | C | C | C | D |
| 7 | D | C | D | C | D | | D | | C | D | D | | | | D |
| 8 | C | C | C | C | D | | D | | C | D | D | | | | |
| 9 | | C | C | C | D | D | D | C | C | C | D | B | B | C | C |
| 10 | | C | C | C | D | D | D | C | C | C | D | B | B | B | C |
| 11 | C | C | D | C | D | | D | | C | D | D | | | | |
| 12 | B | C | C | C | C | D | D | C | C | C | D | B | B | C | D |
| 13 | D | C | D | C | C | | D | | B | D | C | | | | |
| 14 | | C | C | C | D | D | D | C | C | C | C | C | C | B | D |
| 15 | C | C | D | C | D | | D | | C | D | D | | | | |
| 16 | | C | C | B | D | D | D | C | B | D | C | B | C | C | C |
| 17 | C | C | D | C | D | | D | | C | D | D | | | | |
| 18 | C | C | C | C | D | | D | | D | D | D | | | | |
| 19 | C | B | D | C | D | | D | | C | D | D | | | | |

What is claimed is:

1. A compound of Formula I,

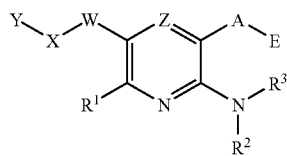

I or a pharmaceutically acceptable salt thereof, wherein, $R^1$ is H;

$R^2$ is H and $R^3$ is H or lower alkyl;

$R^4$ is —H or $R^5$;

$R^5$ is selected from (1) lower alkyl; (2) aryl; (3) lower arylalkyl; (4) heterocyclyl; and (5) lower heterocyclylalkyl; or $R^4$ and $R^5$, when taken together with a common nitrogen to which they are attached, form a five- to seven-membered heterocyclyl, said five- to seven-membered heterocyclyl optionally containing at least one additional heteroatom selected from N, O, S, and P;

Z is —N═;

A is selected from —C(═O)—, —C(═S)—, —C(═NR$^6$)—, and —R$^7$, when A is —R$^7$, E does not exist;

$R^6$ is selected from (1) —H; (2) —NO$_2$; (3) —N(R$^2$)R$^3$; (4) N(H)C(═NR$^2$)N(R$^2$)R$^3$; (5) —CN; (6) —OR$^4$; (7) lower alkyl; (8) heteroalicyclylalkyl; (10) arylalkyl; (11) alkoxy; and (12) heteroalicyclic;

$R^7$ is a five- to seven-membered heterocyclyl, said five- to seven-membered heterocyclyl optionally containing at least one additional heteroatom selected from N, O, S, and P;

E is selected from Table 2:

TABLE 2

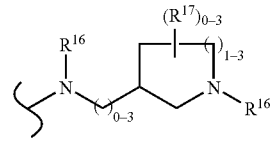

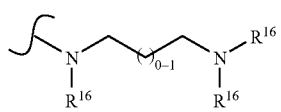

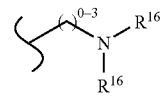

TABLE 2-continued

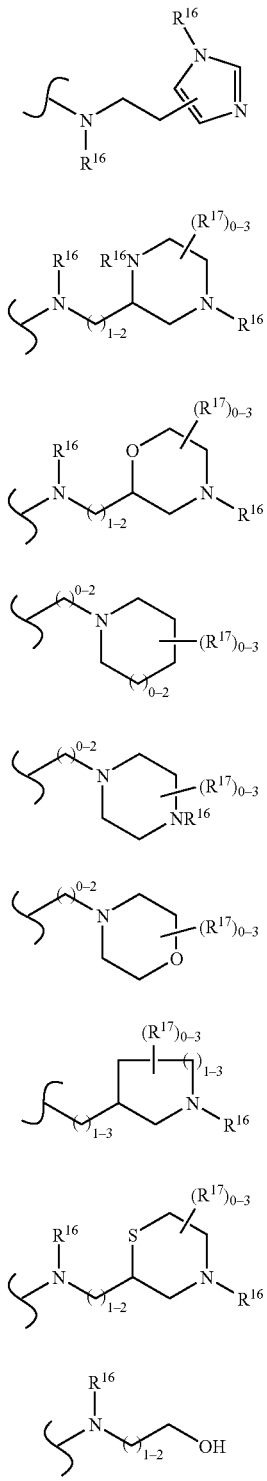

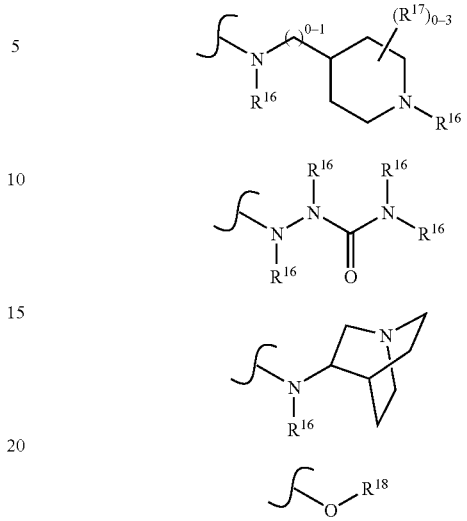

wherein each $R^{16}$ is independently selected from (1) —H, (2) lower alkyl; (3) —CO$_2$R$^4$, and (4) —C(=O)R$^4$; or two of $R^{16}$, together with the nitrogen or nitrogens to which they are attached, form a heterocyclic ring;

each $R^{17}$ is independently selected from (1) —H; (2) halogen; (3) oxo; (4) —CN; (5) —NH$_2$; (6) —CF$_3$; (7) —NO$_2$; (8) —OR$^4$; (9) —N(R$^4$)R$^5$; (10) —S(O)$_{0-2}$R$^5$; (11) —SO$_2$N(R$^4$)R$^5$; (12) —CO$_2$R$^4$; (13) —C(O)N(R$^4$)R$^5$; (14) —N(R$^4$)SO$_2$R$^5$; (15) —N(R$^4$)C(O)R$^5$; (16) —N(R$^4$)CO$_2$R$^5$; (17) —C(O)R$^4$; (18) lower alkyl; (20) arylalkyl; (21) heterocyclyl; and (22) lower heterocyclylalkyl; and $R^{18}$ is lower alkyl;

W is either (1) a six- to ten-membered arylene or (2) a five- to ten-membered heteroarylene;

X is selected from a single bond; —(CH$_2$)$_{0-3}$C(=O)N(R$^4$) (CH$_2$)$_{0-3}$—; —(CH$_2$)$_{0-3}$CO$_2$(CH$_2$)$_{0-3}$—; —(CH$_2$)$_{0-3}$SO$_2$N(R$^4$)(CH$_2$)$_{0-3}$—; —N(R$^4$)(CH$_2$)$_{2-3}$O—; —(CH$_2$)$_{0-3}$N(R$^4$)C(=O)N(R$^4$)(CH$_2$)$_{0-3}$—; —(CH$_2$)$_{0-3}$C(=O)N(R$^4$)(CH$_2$)$_{2-3}$O—; —(CH$_2$)$_{0-3}$S(O)$_{0-2}$(CH$_2$)$_{0-3}$—; —N(R$^4$)(CH$_2$)$_{2-3}$N(R$^4$)—; —(CH$_2$)$_{0-3}$C(=O)N(R$^4$)(CH$_2$)$_{1-3}$C(=O)—; —(CH$_2$)$_{0-3}$OC(=O)N(R$^4$)(CH$_2$)$_{0-3}$—; —C(=O)N(R$^4$)N(R$^4$)—; —(CH$_2$)$_{0-3}$CO$_2$(CH$_2$)$_{2-3}$N(R$^4$)—; —(CH$_2$)$_{0-3}$N(R$^4$)C(=O)(CH$_2$)$_{0-3}$O—; —(CH$_2$)$_{0-3}$N(R$^4$)(CH$_2$)$_{0-3}$—; —C(=O)N(R$^4$)(CH$_2$)$_{2-3}$N(R$^4$)—; —O(CH$_2$)$_{2-3}$O; —(CH$_2$)$_{0-3}$C(=O)N(R$^4$)(CH$_2$)$_{2-3}$S(O)$_{0-2}$—; —(CH$_2$)$_{0-3}$N(R$^4$)C(=O)(CH$_2$)$_{0-3}$S(O)$_{0-2}$—; —(CH$_2$)$_{0-3}$O(CH$_2$)$_{0-3}$—; alkoxyl; and lower alkylene; and Y is selected from (1) lower alkyl substituted with one or more aryl; (2) aryl; (3) and heterocyclyl or Y is selected from Table 1:

TABLE 1

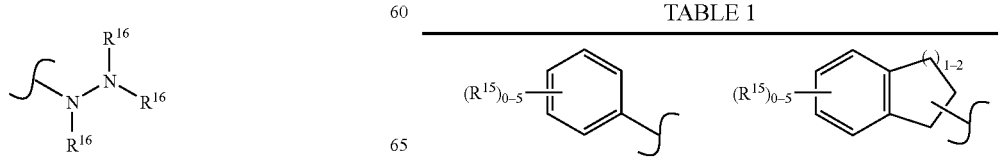

TABLE 1-continued

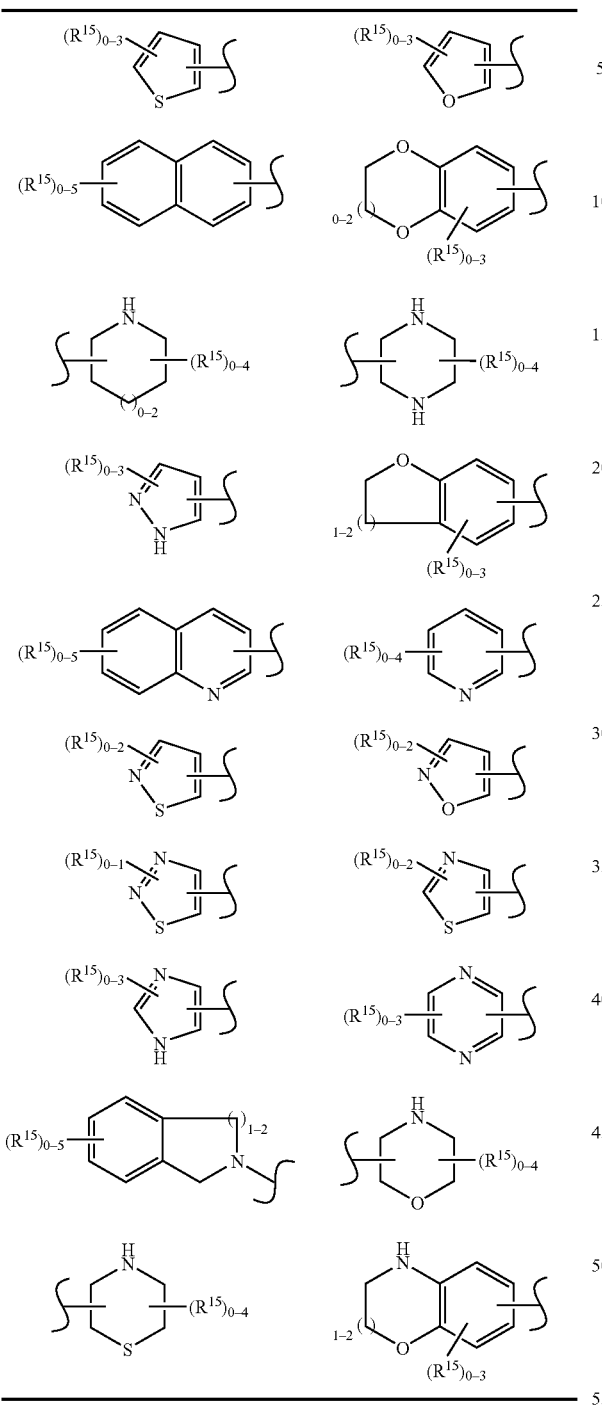

wherein each $R^{15}$ is independently selected from (1) —H; (2) halogen; (3) —CN; (4) —NH$_2$; (5) —CF$_3$; (6) —NO$_2$; (7) —OR$^4$; (8) —N(R$^4$)R$^5$; (9) —S(O)$_{0-2}$R$^5$; (10) —SO$_2$N(R$^4$)R$^5$; (11) —CO$_2$R$^4$; (12) —C(O)N(R$^4$)R$^5$; (13) —N(R$^4$)SO$_2$R$^5$; (14) —N(R$^4$)C(O)R$^5$; (15) —N(R$^4$)CO$_2$R$^5$; (16) —C(O)R$^4$; (17) lower alkyl; (18) aryl; (19) lower arylalkyl; (20) heterocyclyl; and (21) lower heterocyclylalkyl.

2. The compound according to claim 1, wherein R$^2$ and R$^3$ are —H.

3. The compound according to claim 2, wherein A is R$^7$, and R$^7$ is either

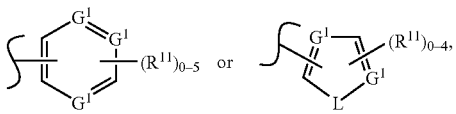

wherein each G$^1$ is independently =N— or =C(R$^{11}$)—, L is selected from —O—, —S(O)$_{0-2}$—, and —NR$^{11}$, wherein each R$^{11}$ is independently selected from (1) —H, (2) halogen, (3) —CN, (4) —NH$_2$, (5) —CF$_3$, (6) —NO$_2$, (7) —OR$^4$, (8) —N(R$^4$)R$^5$, (9) —S(O)$_{0-2}$R$^5$, (10) —SO$_2$N(R$^4$)R$^5$, (11) —CO$_2$R$^4$, (12) —C(O)N(R$^4$)R$^5$, (13) —N(R$^4$)SO$_2$R$^5$, (14) —N(R$^4$)C(O)R$^5$, (15) 2-N(R$^4$)CO$_2$R$^5$, (16) —C(O)R$^4$, (17) lower alkyl (18) aryl; (19) lower arylalkyl; (20) heterocyclyl; and (21) lower heterocyclylalkyl.

4. The compound according to claim 3, wherein R$^7$ is selected from

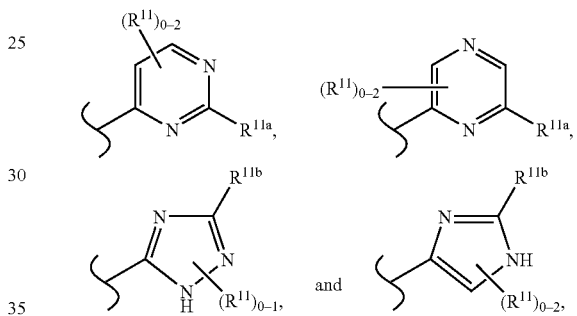

wherein R$^{11a}$ is selected from —H, lower alkyl;

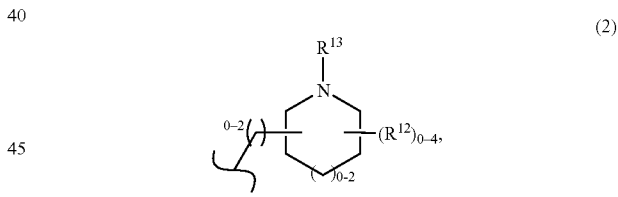

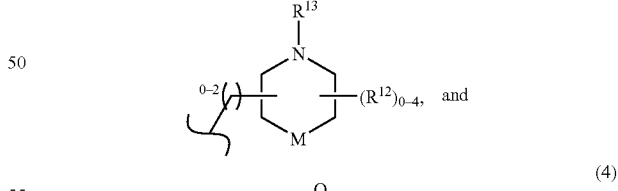

wherein each R$^{12}$ is independently selected from (1) —H, (2) halogen, (3) oxo, (4) —CN, (5) —NH$_2$, (6) —CF$_3$, (7) —NO$_2$, (8) —OR$^4$, (9) —N(R$^4$)R$^5$, (10) —S(O)$_{0-2}$R$^5$, (11) —SO$_2$N(R$^4$)R$^5$, (12) —CO$_2$R$^4$, (13) —C(O)N(R$^4$)R$^5$, (14) —N(R$^4$)SO$_2$R$^5$, (15) —N(R$^4$)C(O)R$^5$, (16) —N(R$^4$)CO$_2$R$^5$, (17) —C(O)R$^4$, (18) lower alkyl; (19) aryl; (20) lower arylalkyl; (21) Heterocyclyl; and (22) lower heterocyclylalkyl;

$R^{13}$ is selected from —H, and lower alkyl;

Q is either =N— or =C($R^{12}$)—; and

M is selected from —O—, —S(O)$_{0-2}$—, and —N$R^{13}$.

5. The compound according to claim 4, wherein W is

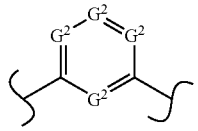

wherein each $G^2$ is independently =N— or =C($R^{14}$)—, and each $R^{14}$ is independently selected from (1) —H; (2) halogen; (3) —CN; (4) —NH$_2$; (5) —CF$_3$; (6) —NO$_2$; (7) —O$R^4$; (8) —N($R^4$)$R^5$; (9) —S(O)$_{0-2}$$R^5$; (10) —SO$_2$N($R^4$)$R^5$; (11) —CO$_2$$R^4$; (12) —C(O)N($R^4$)$R^5$; (13) —N($R^4$)SO$_2$$R^5$; (14) —N($R^4$)C(O)$R^5$; (15) —N($R^4$)CO$_2$$R^5$; (16) —C(O)$R^4$; (17) lower alkyl; (18) aryl; (19) lower arylalkyl; (20) heterocyclyl; and (21) lower heterocyclylalkyl.

6. The compound according to claim 5, wherein W is

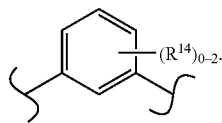

7. The compound according to claim 6, wherein X is selected from (1) —(CH$_2$)$_{0-3}$C(=O)N($R^4$)(CH$_2$)$_{0-3}$—; (2) —(CH$_2$)$_{0-3}$SO$_2$N($R^4$)(CH$_2$)$_{0-3}$—; (3) —N($R^4$)(CH$_2$)$_{2-3}$; (4) —(CH$_2$)$_{0-3}$N($R^4$)C(=O)N($R^4$)(CH$_2$)$_{0-3}$—; (5) —C(=O)N($R^4$)N($R^4$)—; (6) —(CH$_2$)$_{0-3}$C(=O)N($R^4$)(CH$_2$)$_{2-3}$O—; (7) —N($R^4$)(CH$_2$)$_{2-3}$N($R^4$)—; (8) —(CH$_2$)$_{0-3}$N($R^4$)(CH$_2$)$_{0-3}$; (9) —(CH$_2$)$_{0-3}$C(=O)N($R^4$)(CH$_2$)$_{1-3}$C(=O)—; (10) —O(CH$_2$)$_{2-3}$O—; (11) —(CH$_2$)$_{0-3}$OC(=O)N($R^4$)(CH$_2$)$_{0-3}$—; (12) —(CH$_2$)$_{0-3}$O(CH$_2$)$_{0-3}$—; (13) —(CH$_2$)$_{0-3}$CO$_2$(CH$_2$)$_{2-3}$N($R^4$)—; (14) —(CH$_2$)$_{0-3}$N($R^4$)C(=O)(CH$_2$)$_{0-3}$O—; (15) —C(=O)N($R^4$)(CH$_2$)$_{2-3}$N($R^4$)—; (16) alkoxyl and (17) lower alkylene.

8. The compound according to claim 7, wherein X is selected from (1) —C(=O)N(H)(CH$_2$)$_{1-2}$—; (2) —(CH$_2$)$_{1-2}$C(=O)N(H)—; (3) —C(=O)N(H)—; (4) —SO$_2$N(H)(CH$_2$)$_{1-2}$—; (5) —(CH$_2$)$_{1-2}$SO$_2$N(H)—; (6) —SO$_2$N(H)—; (7) —N(H)C(=O)N(H)(CH$_2$)$_{1-2}$—; (8) —N(H)C(=O)N(H)—; (9) —(CH$_2$)$_{0-2}$N($R^4$)(CH$_2$)$_{0-2}$—; (10) —(CH$_2$)$_{0-2}$O(CH$_2$)$_{0-2}$; (11) —C(=O)N(H)N(H)—; (12) —N($R^4$)(CH$_2$)$_{2-3}$N($R^4$)—; (13) —OCH$_2$C(=O)N(H)CH$_2$—; (14) —(CH$_2$)$_{1-2}$N(H)C(=O)N(H)—; (15) —OCH$_2$CH$_2$O—; —N($R^4$)CH$_2$C(=O)N(H)CH$_2$—; (16) —(CH$_2$)$_{0-1}$C(=O)N(H)(CH$_2$)$_{1-2}$C(=O)—; and (17) alkoxyl.

9. The compound according to claim 8, wherein Y is selected from phenyl; and a five- to six-membered heterocyclyl.

10. The compound according to claim 9, wherein $R^{11b}$ is selected from (1) alkyl; (2) phenyl; (3) pyridyl; (4) morpholinyl; (5) pyrrolidinyl; (6) piperidinyl; and (7) azepanyl.

11. The compound according to claim 10, wherein $R^7$ is

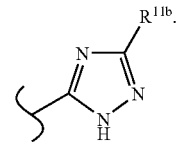

12. The compound according to claim 4, wherein $R^{11b}$ is

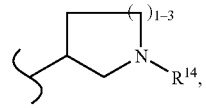

wherein $R^{14}$ is either —H or lower alkyl.

13. The compound according to claim 11, wherein $R^{11b}$ is a pyridyl group.

14. The compound according to claim 4, wherein $R^{11b}$ is a pyridyl group bearing a 2-amino group.

15. The compound according to claim 1, wherein A is —C(=O)— or —C(=N$R^6$)—.

16. The compound according to claim 15, wherein A is —C(=O)—.

17. The compound according to claim 16 wherein W is

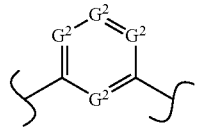

wherein each $G^2$ is independently =N— or =C($R^{14}$)—; wherein each $R^{14}$ is independently selected from (1) —H; (2) halogen; (3) —CN; (4) —NH$_2$; (5) —CF$_3$; (6) —NO$_2$; (7) —O$R^4$; (8) —N($R^4$)$R^5$; (9) —S(O)$_{0-2}$$R^5$; (10) —SO$_2$N($R^4$)$R^5$; (11) —CO$_2$$R^4$; (12) —C(O)N($R^4$)$R^5$; (13) —N($R^4$)SO$_2$$R^5$; (14) —N($R^4$)C(O)$R^5$; (15) —N($R^4$)CO$_2$$R^5$; (16) —C(O)$R^4$; (17) lower alkyl; (18) aryl; (19) lower arylalkyl; (20) heterocyclyl; and (21) lower heterocyclylalkyl.

18. The compound according to claim 17, wherein W is

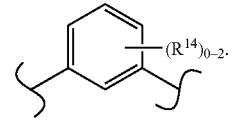

19. The compound according to claim 18, wherein X is selected from —(CH$_2$)$_{0-3}$C(=O)N($R^4$)(CH$_2$)$_{0-3}$—, —(CH$_2$)$_{0-3}$SO$_2$N($R^4$)(CH$_2$)$_{0-3}$, —N($R^4$)(CH$_2$)$_{2-3}$O, —(CH$_2$)$_{0-3}$N($R^4$)C(=O)N($R^4$)(CH$_2$)$_{0-3}$—, —C(=O)N($R^4$)N($R^4$)—, —(CH$_2$)$_{0-3}$C(=O)N($R^4$)(CH$_2$)$_{2-3}$O—, —N($R^4$)(CH$_2$)$_{2-3}$N($R^4$)—, —(CH$_2$)$_{0-3}$N($R^4$)(CH$_2$)$_{0-3}$—, —(CH$_2$)$_{0-3}$C(=O)N($R^4$)(CH$_2$)$_{1-3}$C(=O)—, —O(CH$_2$)$_{2-3}$O—, —(CH$_2$)$_{0-3}$OC(=O)N($R^4$)(CH$_2$)$_{0-3}$—, —(CH$_2$)$_{0-3}$O(CH$_2$)$_{0-3}$—, —(CH$_2$)$_{0-3}$CO$_2$(CH$_2$)$_{2-3}$N($R^4$)—, —(CH$_2$)$_{0-3}$N($R^4$)C(=O)(CH$_2$)$_{0-3}$O—, —C(=O)N($R^4$)(CH$_2$)$_{2-3}$N($R^4$)—, alkoxyl, and lower alkylene.

20. The compound according to claim 19, wherein X is selected from —C(=O)N(H)(CH$_2$)$_{1-2}$—, —(CH$_2$)$_{1-2}$C(=O)N(H)—, —C(=O)N(H)—, —SO$_2$N(H)(CH$_2$)$_{1-2}$, —(CH$_2$)$_{1-2}$SO$_2$N(H)—, —SO$_2$N(H)—, —N(H)C(=O)N(H)(CH$_2$)$_{1-2}$—, —N(H)C(=O)N(H)—, —(CH$_2$)$_{0-2}$N(R$^4$)(CH$_2$)$_{0-2}$—, —(CH$_2$)$_{0-2}$O(CH$_2$)$_{0-2}$, —C(=O)N(H)N(H)—, —N(R$^4$)(CH$_2$)$_{2-3}$N(R$^4$)—, —OCH$_2$C(=O)N(H)CH$_2$—, —(CH$_2$)$_{1-2}$N(H)C(=O)N(H)—, —OCH$_2$CH$_2$O—, —N(R$^4$)CH$_2$C(=O)N(H)CH$_2$—, —(CH$_2$)$_{0-1}$C(=O)N(H)(CH$_2$)$_{1-2}$C(=O)—, alkoxyl, and lower alkylene.

21. The compound according to claim 20, wherein E is either

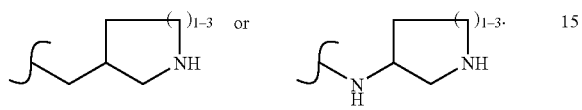

22. The compound according to claim 21, wherein E is either

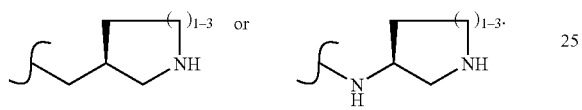

23. The compound according to claim 22, wherein R$^2$ and R$^3$ are —H.

24. The compound according to claim 15, wherein A is —C(=NR$^6$)—.

25. The compound according to claim 1, of formula II,

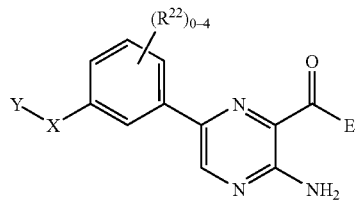

II wherein E is selected from Table 7, wherein each R$^{16}$ is independently selected from (1) —H, (2) lower alkyl; (3) —CO$_2$R$^4$, and (4) —C(=O)R$^4$; or two of R$^{16}$, together with the nitrogen or nitrogens to which they are attached, form a heterocyclic ring;

each R$^{17}$ is independently selected from (1) —H; (2) halogen; (3) oxo; (4) —CN; (5) —NH$_2$; (6) —CF$_3$; (7) —NO$_2$; (8) —OR$^4$; (9) —N(R$^4$)R$^5$; (10) —S(O)$_{0-2}$R$^5$; (11) —SO$_2$N(R$^4$)R$^5$; (12) —CO$_2$R$^4$; (13) —C(O)N(R$^4$)R$^5$; (14) —N(R$^4$)SO$_2$R$^5$; (15) —N(R$^4$)C(O)R$^5$; (16) —N(R$^4$)CO$_2$R$^5$; (17) —C(O)R$^4$; (18) lower alkyl; (19) aryl; (20) arylalkyl; (21) heterocyclyl; and (22) lower heterocyclylalkyl;

X is selected from —C(=O)N(H)(CH$_2$)$_{1-2}$—, —(CH$_2$)$_{1-2}$C(=O)N(H)—, —C(=O)N(H)—, —SO$_2$N(H)(CH$_2$)$_{1-2}$—, —(CH$_2$)$_{1-2}$SO$_2$N(H)—, —SO$_2$N(H)—, —N(H)C(=O)N(H)(CH$_2$)$_{1-2}$—, —N(H)C(=O)N(H)—, —(CH$_2$)$_{0-2}$N(R$^4$)(CH$_2$)$_{0-2}$—, —(CH$_2$)$_{0-2}$O(CH$_2$)$_{0-2}$, —C(=O)N(H)N(H)—, —N(R$^4$)(CH$_2$)$_{2-3}$N(R$^4$)—, —OCH$_2$C(=O)N(H)CH$_2$—, —(CH$_2$)$_{1-2}$N(H)C(=O)N(H)—, —OCH$_2$CH$_2$O, —N(R$^4$)CH$_2$C(=O)N(H)CH$_2$—, —(CH$_2$)$_{0-1}$C(=O)N(H)(CH$_2$)$_{1-2}$C(=O)—, alkoxyl, and lower alkylene;

each R$^{22}$ is independently selected from (1) —H; (2) halogen; (3) oxo; (4) —CN; (5) —NH$_2$; (6) —CF$_3$; (7) —NO$_2$; (8) —OR$^4$; (9) —N(R$^4$)R$^5$; (10) —S(O)$_{0-2}$R$^5$; (11) —SO$_2$N(R$^4$)R$^5$; (12) —CO$_2$R$^4$; (13) —C(O)N(R$^4$)R$^5$; (14) —N(R$^4$)SO$_2$R$^5$; (15) —N(R$^4$)C(O)R$^5$; (16) —N(R$^4$)CO$_2$R$^5$; (17) —C(O)R$^4$; (18) lower alkyl; (19) aryl; (20) lower arylalkyl; (21) heterocyclyl; and (22) lower heterocyclylalkyl;

Y is selected from Table 8,

TABLE 7

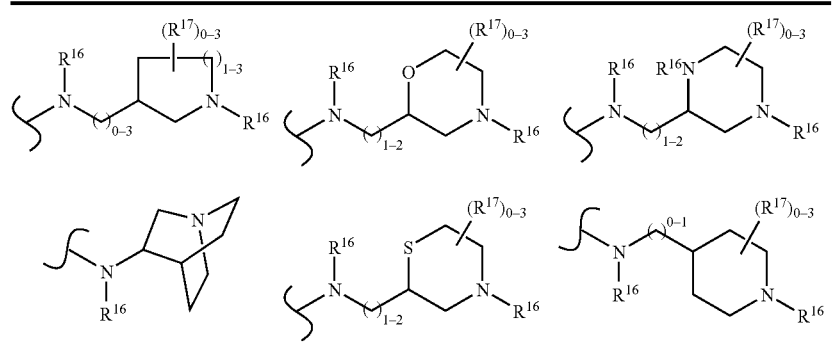

TABLE 8
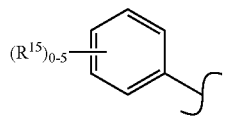 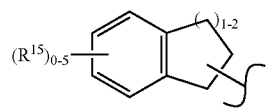 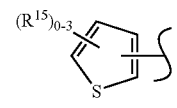
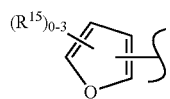 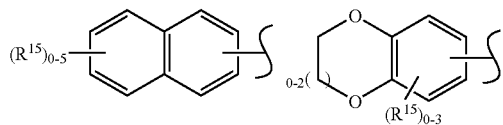
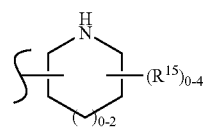 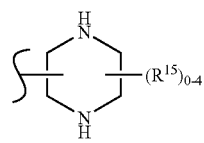 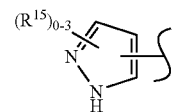
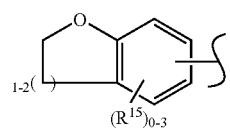 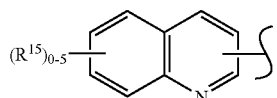 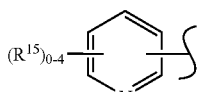
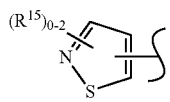 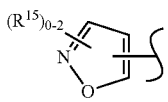 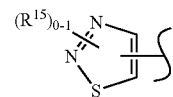
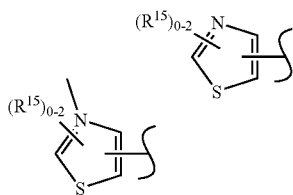 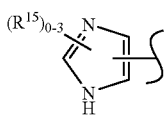 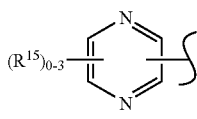
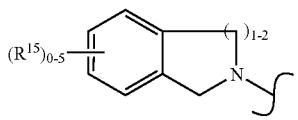 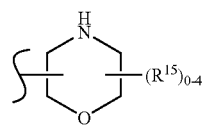 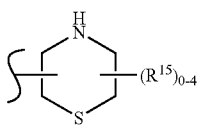
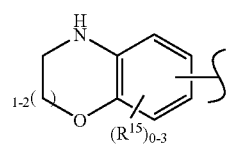

wherein each $R^{15}$ is independently selected from (1) —H; (2) halogen; (3) oxo; (4) —CN; (5) —NH$_2$; (6) —CF$_3$; (7) —NO$_2$; (8) —OR$^4$; (9) —N(R$^4$)R$^5$; (10) —S(O)$_{0-2}$R$^5$; (11) —SO$_2$N(R$^4$)R$^5$; (12) —CO$_2$R$^4$; (13) —C(O)N(R$^4$)R$^5$; (14) —N(R$^4$)SO$_2$R$^5$; (15) —N(R$^4$)C(O)R$^5$; (16) —N(R$^4$)CO$_2$R$^5$; (17) —C(O)R$^4$; (18) lower alkyl; (19) aryl; (20) lower arylalkyl; (21) heterocyclylalkyl and (22) heterocyclylalkyl.

26. The compound according to claim 1, of formula III,

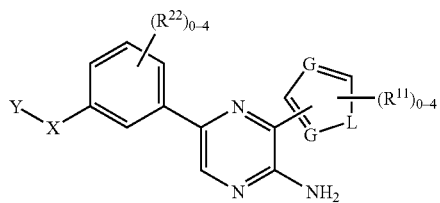

wherein,
each G is independently =N— or =C(R$^{11}$)—;
L is selected from —O—, —S(O)$_{0-2}$—, and —NR$^{11}$;
each $R^{11}$ is independently selected from (1) —H; (2) halogen; (3) —CN; (4) —NH$_2$; (5) —CF$_3$; (6) —NO$_2$; (7) —OR$^4$; (8) —N(R$^4$)R$^5$; (9) —S(O)$_{0-2}$R$^5$; (10) —SO$_2$N(R$^4$)R$^5$; (11) —CO$_2$R$^4$; (12) —C(O)N(R$^4$)R$^5$; (13) —N(R$^4$)SO$_2$R$^5$; (14) —N(R$^4$)C(O)R$^5$; (15) —N(R$^4$)CO$_2$R$^5$; (16) —C(O)R$^4$; (17) lower alkyl;
X is selected from (1) —C(=O)N(H)(CH$_2$)$_{1-2}$—; (2) —(CH$_2$)$_{1-2}$C(=O)N(H)—; (3) —C(=O)N(H)—; (4) —SO$_2$N(H)(CH$_2$)$_{1-2}$—; (5) —(CH$_2$)$_{1-2}$SO$_2$N(H)—; (6) —SO$_2$N(H)—; (7) —N(H)C(=O)N(H)(CH$_2$)$_{1-2}$—; (8) —N(H)C(=O)N(H)—; (9) —(CH$_2$)$_{0-2}$N(R$^4$)(CH$_2$)$_{0-2}$—; (10) —(CH$_2$)$_{0-2}$O(CH$_2$)$_{0-2}$; (11) —C(=O)N(H)N(H)—; (12) —N(R$^4$)(CH$_2$)$_{2-3}$N(R$^4$)—; (13) —OCH$_2$C(=O)N(H)CH$_2$—; (14) —(CH$_2$)$_{1-2}$N(H)C(=O)N(H)—; (15) —OCH$_2$CH$_2$O—; —N(R$^4$)CH$_2$C(=O)N(H)CH$_2$—; (16) —(CH$_2$)$_{0-1}$C(=O)N(H)(CH$_2$)$_{1-2}$C(O)—; (17) alkoxyl and (18) lower alkylene;
Y is selected from Table 9,

TABLE 9

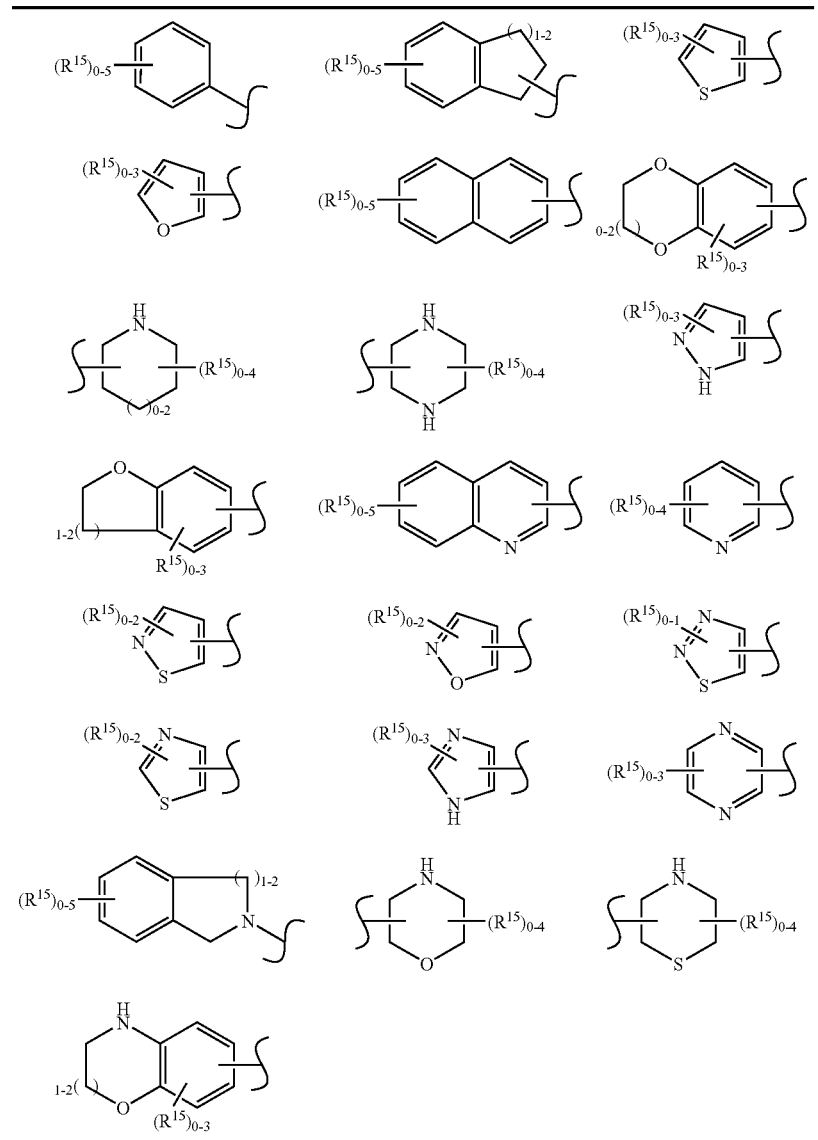

wherein each $R^{15}$ is independently selected from (1) —H; (2) halogen; (3) oxo; (4) —CN; (5) —NH$_2$; (6) —CF$_3$; (7) —NO$_2$; (8) —OR$^4$; (9) —N(R$^4$)R$^5$; (10) —S(O)$_{0-2}$R$^5$; (11) —SO$_2$N(R$^4$)R$^5$; (12) —CO$_2$R$^4$; (13) —C(O)N(R$^4$)R$^5$; (14) —N(R$^4$)SO$_2$R$^5$; (15) —N(R$^4$)C(O)R$^5$; (16) —N(R$^4$)CO$_2$R$^5$; (17) —C(O)R$^4$; (18) lower alkyl; (19) aryl; (20) lower arylalkyl; (21) heterocyclyl; and (22) lower heterocyclylalkyl; and each $R^{22}$ is independently selected from (1) —H; (2) halogen; (3) oxo; (4) —CN; (5) —NH$_2$; (6) —CF$_3$; (7) —NO$_2$; (8) —OR$^4$; (9) —N(R$^4$)R$^5$; (10) —S(O)$_{0-2}$R$^5$; (11) —SO$_2$N(R$^4$)R$^5$; (12) —CO$_2$R$^4$; (13) —C(O)N(R$^4$)R$^5$; (14) —N(R$^4$)SO$_2$R$^5$; (15) —N(R$^4$)C(O)R$^5$; (16) —N(R$^4$)CO$_2$R$^5$; (17) —C(O)R$^4$; (18) lower alkyl; (19) aryl; (20) lower arylalkyl; (21) heterocyclyl; and (22) lower heterocyclylalkyl.

27. A compound selected from Table 10, or a pharmaceutically acceptable salt thereof:

TABLE 10

| Name |
| --- |
| 3-amino-N,N-dimethyl-6-phenylpyrazine-2-carboxamide |
| 3-amino-6-[3-(methyloxy)phenyl]pyrazine-2-carboxamide |
| 3-amino-6-(4-fluorophenyl)-N-methylpyrazine-2-carboxamide |
| 3-amino-6-[4-(ethyloxy)phenyl]pyrazine-2-carboxamide |
| 3-amino-6-[3-(ethyloxy)phenyl]pyrazine-2-carboxamide |
| 3-amino-6-{3-[(trifluoromethyl)oxy]phenyl}pyrazine-2-carboxamide |
| 3-amino-6-[3-(aminocarbonyl)phenyl]pyrazine-2-carboxamide |
| 6-[3-(acetylamino)phenyl]-3-aminopyrazine-2-carboxamide |
| 3-amino-6-[4-(dimethylamino)phenyl]pyrazine-2-carboxamide |
| 3-amino-6-(3-methylphenyl)pyrazine-2-carboxamide |
| methyl 3-[5-amino-6-(aminocarbonyl)pyrazin-2-yl]benzoate |
| 3-amino-6-{3-[(phenylmethyl)oxy]phenyl}pyrazine-2-carboxamide |
| 3-amino-6-biphenyl-3-ylpyrazine-2-carboxamide |
| 3-amino-N-methyl-6-{3-[(phenylmethyl)oxy]phenyl}pyrazine-2-carboxamide |
| 3-amino-6-(3-hydroxyphenyl)-N-methylpyrazine-2-carboxamide |
| 3-amino-N-[2-(methyloxy)ethyl]-6-phenylpyrazine-2-carboxamide |
| N-[2-(acetylamino)ethyl]-3-amino-6-phenylpyrazine-2-carboxamide |
| 3-amino-6-phenylpyrazine-2-carbohydrazide |
| 3-amino-N-hydroxy-6-phenylpyrazine-2-carboxamide |
| 3-amino-6-[3-(ethyloxy)phenyl]-N-methylpyrazine-2-carboxamide |
| 3-amino-6-(3-aminophenyl)-N-methylpyrazine-2-carboxamide |
| 3-amino-6-[4-(ethyloxy)phenyl]-N-methylpyrazine-2-carboxamide |
| 3-amino-N-methyl-6-(3-methylphenyl)pyrazine-2-carboxamide |
| 3-amino-N-methyl-6-[4-(methyloxy)phenyl]pyrazine-2-carboxamide |
| 3-amino-6-biphenyl-3-yl-N-methylpyrazine-2-carboxamide |
| 6-[3-(acetylamino)phenyl]-3-amino-N-methylpyrazine-2-carboxamide |
| 3-amino-6-[3-(hydroxymethyl)phenyl]-N-methylpyrazine-2-carboxamide |
| 3-amino-6-[4-(hydroxymethyl)phenyl]-N-methylpyrazine-2-carboxamide |
| 3-amino-N-methyl-6-{3-[(1E)-N-methylethanimidoyl]phenyl}pyrazine-2-carboxamide |
| 3-amino-N-methyl-6-[3-(methyloxy)phenyl]pyrazine-2-carboxamide |
| 3-amino-6-(4-fluoro-3-methylphenyl)-N-methylpyrazine-2-carboxamide |
| 3-amino-N-methyl-6-pyridin-3-ylpyrazine-2-carboxamide |
| 6-[4-(acetylamino)phenyl]-3-amino-N-methylpyrazine-2-carboxamide |
| 3-amino-N-methyl-6-{3-[(methylamino)carbonyl]phenyl}pyrazine-2-carboxamide |
| 6-(3-acetylphenyl)-3-amino-N-methylpyrazine-2-carboxamide |
| 3-amino-N-methyl-6-(5-methyl-1,2,4-oxadiazol-3-yl)pyrazine-2-carboxamide |
| 3-amino-6-[4-(dimethylamino)phenyl]-N-methylpyrazine-2-carboxamide |
| 3-amino-N-methyl-6-{4-[(methylsulfonyl)amino]phenyl}pyrazine-2-carboxamide |
| 3-amino-6-(3,5-dimethylphenyl)-N-methylpyrazine-2-carboxamide |
| 6-(4-acetylphenyl)-3-amino-N-methylpyrazine-2-carboxamide |
| 3-amino-6-[3,4-bis(methyloxy)phenyl]-N-methylpyrazine-2-carboxamide |
| 3-amino-N-methyl-6-{3-[(phenylcarbonyl)amino]phenyl}pyrazine-2-carboxamide |
| 3-amino-N-methyl-6-{3-[(methylsulfonyl)amino]phenyl}pyrazine-2-carboxamide |
| 3-amino-N-methyl-6-[3-(1H-tetrazol-5-yl)phenyl]pyrazine-2-carboxamide |
| 3-amino-N-methyl-6-(3-{[(phenylmethyl)amino]carbonyl}phenyl)pyrazine-2-carboxamide |
| 3-amino-6-[3-(aminocarbonyl)phenyl]-N-methylpyrazine-2-carboxamide |
| 3-amino-6-{3-[(dimethylamino)carbonyl]phenyl}-N-methylpyrazine-2-carboxamide |
| 3-amino-N-methyl-6-[4-(methylsulfonyl)phenyl]pyrazine-2-carboxamide |
| 3-amino-6-(3-aminophenyl)-N-ethylpyrazine-2-carboxamide |
| 3-amino-6-[3-({[(4-fluorophenyl)amino]carbonyl}amino)phenyl]-N-methylpyrazine-2-carboxamide |
| 3-amino-N-methyl-6-{3-[({[4-(methyloxy)phenyl]amino}carbonyl)amino]phenyl}pyrazine-2-carboxamide |
| 6,6'-[(oxomethanediyl)bis(iminobenzene-3,1-diyl)]bis(3-amino-N-methylpyrazine-2-carboxamide) |
| 3-{5-amino-6-[(methylamino)carbonyl]pyrazin-2-yl}benzoic acid |
| 3-amino-N-methyl-6-{3-[(4-methylpiperazin-1-yl)carbonyl]phenyl}pyrazine-2-carboxamide |
| 3-amino-N-methyl-6-(3-{[(2-phenylethyl)amino]carbonyl}phenyl)pyrazine-2-carboxamide |

TABLE 10-continued

Name 3-amino-N-methyl-6-{3-[({4-(methyloxy)phenyl]methyl}amino)carbonyl]phenyl}pyrazine-2-carboxamide
3-amino-6-(3-{[(1R)-2,3-dihydro-1H-inden-1-ylamino]carbonyl}phenyl)-N-methylpyrazine-2-carboxamide
3-amino-6-(3-{[(1S)-2,3-dihydro-1H-inden-1-ylamino]carbonyl}phenyl)-N-methylpyrazine-2-carboxamide
3-amino-6-[3-({[(4-chlorophenyl)methyl]amino}carbonyl)phenyl]-N-methylpyrazine-2-carboxamide
3-amino-N-methyl-6-(3-{[methyl(phenylmethyl)amino]carbonyl}phenyl)pyrazine-2-carboxamide
3-amino-6-[3-({[(2,4-dichlorophenyl)methyl]amino}carbonyl)phenyl]-N-methylpyrazine-2-carboxamide
3-amino-N-methyl-6-[3-({[(4-methylphenyl)methyl]amino}carbonyl)phenyl]pyrazine-2-carboxamide
3-amino-N-methyl-6-{3-[({4-(trifluoromethyl)phenyl]methyl}amino)carbonyl]phenyl}pyrazine-2-carboxamide
3-amino-6-[3-({[(4-fluorophenyl)methyl]amino}carbonyl)phenyl]-N-methylpyrazine-2-carboxamide
3-amino-6-{3-[(2,3-dihydro-1H-inden-2-ylamino)carbonyl]phenyl}-N-methylpyrazine-2-carboxamide
3-amino-N-methyl-6-[3-({[3-(methyloxy)phenyl]carbonyl}amino)phenyl]pyrazine-2-carboxamide
3-amino-N-methyl-6-[3-({[4-(methyloxy)phenyl]carbonyl}amino)phenyl]pyrazine-2-carboxamide
3-amino-N-methyl-6-{3-[({[3-(methyloxy)phenyl]methyl}amino)carbonyl]phenyl}pyrazine-2-carboxamide
3-amino-N-methyl-6-{3-[({(1R)-1-[4-(methyloxy)phenyl]ethyl}amino)carbonyl]phenyl}pyrazine-2-carboxamide
3-amino-N-methyl-6-{3-[({[2-(trifluoromethyl)phenyl]methyl}amino)carbonyl]phenyl}pyrazine-2-carboxamide
3-amino-6-[3-({[(3-fluorophenyl)methyl]amino}carbonyl)phenyl]-N-methylpyrazine-2-carboxamide
3-amino-6-(3-{[(4-chlorophenyl)carbonyl]amino}phenyl)-N-methylpyrazine-2-carboxamide
3-amino-6-[3-({[1-(4-fluorophenyl)ethyl]amino}carbonyl)phenyl]-N-methylpyrazine-2-carboxamide
3-amino-6-{3-[({[2,3-bis(methyloxy)phenyl]methyl}amino)carbonyl]phenyl}-N-methylpyrazine-2-carboxamide
3-amino-6-(3-{[bis(phenylmethyl)amino]carbonyl}phenyl)-N-methylpyrazine-2-carboxamide
3-amino-6-{3-[({[2,4-bis(methyloxy)phenyl]methyl}amino)carbonyl]phenyl}-N-methylpyrazine-2-carboxamide
3-amino-6-(3-{[ethyl(pyridin-4-ylmethyl)amino]carbonyl}phenyl)-N-methylpyrazine-2-carboxamide
3-amino-N-methyl-6-(3-{[4-(phenylmethyl)piperazin-1-yl]carbonyl}phenyl)pyrazine-2-carboxamide
3-amino-N-methyl-6-[3-({[1-(phenylmethyl)piperidin-4-yl]amino}carbonyl)phenyl]pyrazine-2-carboxamide
3-amino-N-methyl-6-(3-{[(4-methylphenyl)carbonyl]amino}phenyl)pyrazine-2-carboxamide
3-amino-N-methyl-6-[3-({[(5-methylpyrazin-2-yl)methyl]amino}carbonyl)phenyl]pyrazine-2-carboxamide
3-amino-N-methyl-6-(3-{[(pyridin-2-ylmethyl)amino]carbonyl}phenyl)pyrazine-2-carboxamide
3-amino-N-methyl-6-(3-{[(pyridin-3-ylmethyl)amino]carbonyl}phenyl)pyrazine-2-carboxamide
3-amino-N-methyl-6-(3-{[(pyridin-4-ylmethyl)amino]carbonyl}phenyl)pyrazine-2-carboxamide
3-amino-6-{3-[(furan-2-ylcarbonyl)amino]phenyl}-N-methylpyrazine-2-carboxamide
3-amino-6-[3-({[(3-chlorophenyl)methyl]amino}carbonyl)phenyl]-N-methylpyrazine-2-carboxamide
3-amino-6-(3-{[(cyclohexylmethyl)amino]carbonyl}phenyl)-N-methylpyrazine-2-carboxamide
3-amino-N-methyl-6-(3-{[(2-phenylpropyl)amino]carbonyl}phenyl)pyrazine-2-carboxamide
3-amino-6-[3-({[(2-chlorophenyl)methyl]amino}carbonyl)phenyl]-N-methylpyrazine-2-carboxamide
3-amino-6-[3-({[2-(2-chlorophenyl)ethyl]amino}carbonyl)phenyl]-N-methylpyrazine-2-carboxamide
3-amino-N-methyl-6-{3-[({2-[2-(methyloxy)phenyl]ethyl}amino)carbonyl]phenyl}pyrazine-2-carboxamide
3-amino-6-[3-({[2-(4-fluorophenyl)ethyl]amino}carbonyl)phenyl]-N-methylpyrazine-2-carboxamide
3-amino-N-methyl-6-[3-({[2-(2-thienyl)ethyl]amino}carbonyl)phenyl]pyrazine-2-carboxamide
3-amino-6-{3-[(cyclohexylamino)carbonyl]phenyl}-N-methylpyrazine-2-

TABLE 10-continued

Name carboxamide
1,1-dimethylethyl 4-({[(3-{5-amino-6-[(methylamino)carbonyl]pyrazin-2-yl}phenyl)carbonyl]amino}methyl)piperidine-1-carboxylate
3-amino-N-methyl-6-(3-{[(piperidin-4-ylmethyl)amino]carbonyl}phenyl)pyrazine-2-carboxamide
3-amino-N-methyl-6-[3-(5-phenyl-1,2,4-oxadiazol-3-yl)phenyl]pyrazine-2-carboxamide
3-amino-N-methyl-6-{3-[5-(phenylmethyl)-1,2,4-oxadiazol-3-yl]phenyl}pyrazine-2-carboxamide
3-amino-N-methyl-6-{3-[5-(2-phenylethyl)-1,2,4-oxadiazol-3-yl]phenyl}pyrazine-2-carboxamide
3-amino-6-(3-{[(1,1-dimethylethyl)amino]carbonyl}phenyl)-N-methylpyrazine-2-carboxamide
3-amino-6-[3-({[(1R,2S)-2-hydroxy-2,3-dihydro-1H-inden-1-yl]amino}carbonyl)phenyl]-N-methylpyrazine-2-carboxamide
3-amino-6-[3-({[(1S,2R)-2-hydroxy-2,3-dihydro-1H-inden-1-yl]amino}carbonyl)phenyl]-N-methylpyrazine-2-carboxamide
3-amino-N-methyl-6-{3-[(phenylamino)carbonyl]phenyl}pyrazine-2-carboxamide
3-amino-6-[3-(1,3-dihydro-2H-isoindol-2-ylcarbonyl)phenyl]-N-methylpyrazine-2-carboxamide
3-amino-N-methyl-6-[3-({[(1R)-1-phenylethyl]amino}carbonyl)phenyl]pyrazine-2-carboxamide
3-amino-N-methyl-6-[3-({[(1S)-1-phenylethyl]amino}carbonyl)phenyl]pyrazine-2-carboxamide
3-amino-N-methyl-6-[3-({[(1R)-1-phenylpropyl]amino}carbonyl)phenyl]pyrazine-2-carboxamide
3-amino-N-methyl-6-[3-({[(1S)-1-phenylpropyl]amino}carbonyl)phenyl]pyrazine-2-carboxamide
3-amino-N-methyl-6-[3-({[(1R,2S)-2-phenylcyclopropyl]amino}carbonyl)phenyl]pyrazine-2-carboxamide
phenylmethyl 4-{5-amino-6-[(methylamino)carbonyl]pyrazin-2-yl}benzoate
3-amino-N-methyl-6-(4-{[(phenylmethyl)amino]carbonyl}phenyl)pyrazine-2-carboxamide
3-amino-N-methyl-6-(4-{[(2-phenylethyl)amino]carbonyl}phenyl)pyrazine-2-carboxamide
3-amino-6-[4-({[(2,4-dichlorophenyl)methyl]amino}carbonyl)phenyl]-N-methylpyrazine-2-carboxamide
3-amino-N-methyl-6-[4-({[(4-methylphenyl)methyl]amino}carbonyl)phenyl]pyrazine-2-carboxamide
3-amino-6-(4-{[(1S)-2,3-dihydro-1H-inden-1-ylamino]carbonyl}phenyl)-N-methylpyrazine-2-carboxamide
3-amino-6-(3-{[(4-chlorophenyl)acetyl]amino}phenyl)-N-methylpyrazine-2-carboxamide
3-amino-N-methyl-6-[3-({[3-(phenyloxy)phenyl]carbonyl}amino)phenyl]pyrazine-2-carboxamide
3-amino-6-{3-[(diphenylacetyl)amino]phenyl}-N-methylpyrazine-2-carboxamide
3-amino-N-methyl-6-{3-[(phenylacetyl)amino]phenyl}pyrazine-2-carboxamide
3-amino-N-methyl-6-{3-[(3-phenylpropanoyl)amino]phenyl}pyrazine-2-carboxamide
3-amino-N-methyl-6-(3-{[(1R)-1,2,3,4-tetrahydronaphthalen-1-ylamino]carbonyl}phenyl)pyrazine-2-carboxamide
3-amino-N-methyl-6-(3-{[(1S)-1,2,3,4-tetrahydronaphthalen-1-ylamino]carbonyl}phenyl)pyrazine-2-carboxamide
3-amino-N-methyl-6-{3-[({[3,4,5-tris(methyloxy)phenyl]methyl}amino)carbonyl]phenyl}pyrazine-2-carboxamide
3-amino-N-methyl-6-{3-[({(1R,2R)-2-[(phenylmethyl)oxy]cyclopentyl}amino)carbonyl]phenyl}pyrazine-2-carboxamide
3-amino-N-methyl-6-{3-[({(1S,2S)-2-[(phenylmethyl)oxy]cyclopentyl}amino)carbonyl]phenyl}pyrazine-2-carboxamide
3-amino-6-(3-cyanophenyl)-N-methylpyrazine-2-carboxamide
3-amino-6-{3-[(cyclopentylcarbonyl)amino]phenyl}-N-methylpyrazine-2-carboxamide
3-amino-6-(3-{[(4-cyanophenyl)carbonyl]amino}phenyl)-N-methylpyrazine-2-carboxamide
3-amino-N-methyl-6-[3-({[(phenylmethyl)amino]carbonyl}amino)phenyl]pyrazine-2-carboxamide
3-amino-N-methyl-6-(3-{[(naphthalen-2-ylmethyl)amino]carbonyl}phenyl)pyrazine-2-carboxamide
3-amino-N-methyl-6-(3-{[(tetrahydrofuran-2-ylmethyl)amino]carbonyl}phenyl)pyrazine-2-carboxamide
3-amino-6-[3-({[(2-chloro-6-fluorophenyl)methyl]amino}carbonyl)phenyl]-N-methylpyrazine-2-carboxamide
3-amino-6-{3-[({[3-fluoro-5-(trifluoromethyl)phenyl]methyl}amino)carbonyl]phenyl}-N-methylpyrazine-2-carboxamide
3-amino-6-{3-[({2-[3,5-bis(methyloxy)phenyl]ethyl}amino)carbonyl]phenyl}-N-methylpyrazine-2-carboxamide

TABLE 10-continued

Name 3-amino-N-methyl-6-{3-[(2-phenylethyl)oxy]phenyl}pyrazine-2-carboxamide
3-amino-N-methyl-6-(3-{[2-(4-methylpiperidin-1-yl)ethyl]oxy}phenyl)pyrazine-2-carboxamide
3-amino-6-[3-({2-[4-(2-hydroxyethyl)piperidin-1-yl]ethyl}oxy)phenyl]-N-methylpyrazine-2-carboxamide
3-amino-6-(3-{[2-(3-hydroxypyrrolidin-1-yl)ethyl]oxy}phenyl)-N-methylpyrazine-2-carboxamide
3-amino-6-[3-({2-[ethyl(phenylmethyl)amino]ethyl}oxy)phenyl]-N-methylpyrazine-2-carboxamide
3-amino-6-(3-{[2-(diethylamino)ethyl]oxy}phenyl)-N-methylpyrazine-2-carboxamide
3-amino-6-(3-{[[(biphenyl-2-ylmethyl)amino]carbonyl}phenyl)-N-methylpyrazine-2-carboxamide
3-amino-N-methyl-6-(3-{[2-(4-phenylpiperazin-1-yl)ethyl]oxy}phenyl)pyrazine-2-carboxamide
3-amino-6-(3-{[[(biphenyl-4-ylmethyl)amino]carbonyl}phenyl)-N-methylpyrazine-2-carboxamide
3-amino-N-methyl-6-[3-({2-[methyl(phenylmethyl)amino]ethyl}oxy)phenyl]pyrazine-2-carboxamide
3-amino-N-methyl-6-{3-[({[4-(phenyloxy)phenyl]methyl}amino)carbonyl]phenyl}pyrazine-2-carboxamide
3-amino-N-methyl-6-{3-[(2-morpholin-4-ylethyl)oxy]phenyl}pyrazine-2-carboxamide
3-amino-6-[3-({2-[(cyclopropylmethyl)(propyl)amino]ethyl}oxy)phenyl]-N-methylpyrazine-2-carboxamide
3-amino-N-methyl-6-[3-({2-[4-(phenylmethyl)piperidin-1-yl]ethyl}oxy)phenyl]pyrazine-2-carboxamide
3-amino-N-methyl-6-{3-[(2-piperidin-1-ylethyl)oxy]phenyl}pyrazine-2-carboxamide
3-amino-N-methyl-6-{3-[({[3-(phenyloxy)phenyl]methyl}amino)carbonyl]phenyl}pyrazine-2-carboxamide
3-amino-6-(3-{[2-(4-ethylpiperazin-1-yl)ethyl]oxy}phenyl)-N-methylpyrazine-2-carboxamide
3-amino-N-methyl-6-{3-[(2-pyrrolidin-1-ylethyl)oxy]phenyl}pyrazine-2-carboxamide
3-amino-N-methyl-6-(3-{[2-(4-methylpiperazin-1-yl)ethyl]oxy}phenyl)pyrazine-2-carboxamide
3-amino-6-[3-({2-[4-(2-hydroxyethyl)piperazin-1-yl]ethyl}oxy)phenyl]-N-methylpyrazine-2-carboxamide
3-amino-6-(3-{[2-(3,4-dihydroisoquinolin-2(1H)-yl)ethyl]oxy}phenyl)-N-methylpyrazine-2-carboxamide
ethyl 4-{2-[(3-{5-amino-6-[(methylamino)carbonyl]pyrazin-2-yl}phenyl)oxy]ethyl}piperazine-1-carboxylate
3-amino-N-methyl-6-[3-({[(3S)-1-(phenylmethyl)pyrrolidin-3-yl]amino}carbonyl)phenyl]pyrazine-2-carboxamide
3-amino-N-methyl-6-[3-({[(3R)-1-(phenylmethyl)pyrrolidin-3-yl]amino}carbonyl)phenyl]pyrazine-2-carboxamide
3-amino-N-methyl-6-[3-({[2-(phenyloxy)ethyl]amino}carbonyl)phenyl]pyrazine-2-carboxamide
3-amino-N-methyl-6-{3-[({2-[4-(phenylmethyl)piperazin-1-yl]ethyl}amino)carbonyl]phenyl}pyrazine-2-carboxamide
3-amino-N-methyl-6-{3-[({[1-(phenylmethyl)piperidin-4-yl]methyl}amino)carbonyl]phenyl}pyrazine-2-carboxamide
3-amino-6-(3-{[(furan-3-ylmethyl)amino]carbonyl}phenyl)-N-methylpyrazine-2-carboxamide
3-amino-6-(3-{[[(2,3-dihydro-1,4-benzodioxin-2-ylmethyl)amino]carbonyl}phenyl)-N-methylpyrazine-2-carboxamide
3-amino-6-(3-{[(furan-2-ylmethyl)amino]carbonyl}phenyl)-N-methylpyrazine-2-carboxamide
3-amino-N-methyl-6-{3-[({[4-(phenylmethyl)morpholin-2-yl]methyl}amino)carbonyl]phenyl}pyrazine-2-carboxamide
3-amino-6-(3-{[(2,3-dihydro-1,4-benzodioxin-6-ylmethyl)amino]carbonyl}phenyl)-N-methylpyrazine-2-carboxamide
3-amino-6-(3-{[(2,3-dihydro-1,4-benzodioxin-6-ylmethyl)amino]carbonyl}phenyl)-N-methylpyrazine-2-carboxamide
3-amino-6-(3-{[(2,3-dihydro-1-benzofuran-5-ylmethyl)amino]carbonyl}phenyl)-N-methylpyrazine-2-carboxamide
3-amino-6-[3-({[(6-fluoro-4H-1,3-benzodioxin-8-yl)methyl]amino}carbonyl)phenyl]-N-methylpyrazine-2-carboxamide
3-amino-6-(3-{[[(2,4-dichlorophenyl)acetyl]amino}phenyl)-N-methylpyrazine-2-carboxamide
3-amino-6-(3-{[[(3,4-dichlorophenyl)acetyl]amino}phenyl)-N-methylpyrazine-2-carboxamide
3-amino-N-methyl-6-[3-({[4-(trifluoromethyl)phenyl]acetyl}amino)phenyl]pyrazine-2-carboxamide
3-amino-6-[3-({[[(3,5-dimethylphenyl)methyl]amino}carbonyl)phenyl]-N-methylpyrazine-2-carboxamide TABLE 10-continued

| Name |
| --- |
| 3-amino-6-[3-({[(5-chloro-2-methylphenyl)methyl]amino}carbonyl)phenyl]-N-methylpyrazine-2-carboxamide |
| 3-amino-6-[3-({[(2,4-dimethylphenyl)methyl]amino}carbonyl)phenyl]-N-methylpyrazine-2-carboxamide |
| 3-amino-6-[3-({[(2,3-difluorophenyl)methyl]amino}carbonyl)phenyl]-N-methylpyrazine-2-carboxamide |
| 3-amino-N-methyl-6-{3-[({[4-(methylthio)phenyl]methyl}amino)carbonyl]phenyl}pyrazine-2-carboxamide |
| 3-amino-N-methyl-6-(3-{[(2-methylpropyl)amino]carbonyl}phenyl)pyrazine-2-carboxamide |
| 3-amino-N-methyl-6-(3-{[({3-[(trifluoromethyl)oxy]phenyl}methyl)amino]carbonyl}phenyl)pyrazine-2-carboxamide |
| 3-amino-6-(3-{[(cyclopropylmethyl)amino]carbonyl}phenyl)-N-methylpyrazine-2-carboxamide |
| 3-amino-6-{3-[(cyclopentylamino)carbonyl]phenyl}-N-methylpyrazine-2-carboxamide |
| 3-amino-N-methyl-6-(3-{[(4-methylphenyl)amino]carbonyl}phenyl)pyrazine-2-carboxamide |
| 3-amino-N-methyl-6-[3-({[4-(methyloxy)phenyl]amino}carbonyl)phenyl]pyrazine-2-carboxamide |
| 3-amino-6-(3-{[(1,3-benzodioxol-5-ylmethyl)amino]carbonyl}phenyl)-N-methylpyrazine-2-carboxamide |
| 3-amino-6-(3-{[(biphenyl-3-ylmethyl)amino]carbonyl}phenyl)-N-methylpyrazine-2-carboxamide |
| 3-amino-N-methyl-6-(3-{[(1-methyl-1-phenylethyl)amino]carbonyl}phenyl)pyrazine-2-carboxamide |
| 3-amino-6-[3-({[(2,4-difluorophenyl)methyl]amino}carbonyl)phenyl]-N-methylpyrazine-2-carboxamide |
| 3-amino-N-methyl-6-(3-{[({4-[(trifluoromethyl)oxy]phenyl}methyl)amino]carbonyl}phenyl)pyrazine-2-carboxamide |
| 3-amino-6-{3-[({[4-fluoro-3-(trifluoromethyl)phenyl]methyl}amino)carbonyl]phenyl}-N-methylpyrazine-2-carboxamide |
| 3-amino-6-{3-[({[4-chloro-3-(trifluoromethyl)phenyl]methyl}amino)carbonyl]phenyl}-N-methylpyrazine-2-carboxamide |
| 3-amino-6-[3-({[(4-aminophenyl)methyl]amino}carbonyl)phenyl]-N-methylpyrazine-2-carboxamide |
| 3-amino-6-[3-({[(2-aminophenyl)methyl]amino}carbonyl)phenyl]-N-methylpyrazine-2-carboxamide |
| 3-amino-6-[3-({[(3-aminophenyl)methyl]amino}carbonyl)phenyl]-N-methylpyrazine-2-carboxamide |
| 3-amino-N-methyl-6-pyrimidin-5-ylpyrazine-2-carboxamide |
| 3-amino-N-methyl-6-[3-(methylsulfonyl)phenyl]pyrazine-2-carboxamide |
| 3-amino-N-methyl-6-[4-(tetrahydro-2H-pyran-2-yloxy)phenyl]pyrazine-2-carboxamide |
| 3-amino-6-(4-hydroxyphenyl)-N-methylpyrazine-2-carboxamide |
| 3-amino-6-{3-[({[4-(aminosulfonyl)phenyl]methyl}amino)carbonyl]phenyl}-N-methylpyrazine-2-carboxamide |
| 3-amino-6-{3-[({[4-(dimethylamino)phenyl]methyl}amino)carbonyl]phenyl}-N-methylpyrazine-2-carboxamide |
| 3-amino-6-[3-({[(3-bromophenyl)methyl]amino}carbonyl)phenyl]-N-methylpyrazine-2-carboxamide |
| 3-amino-6-(4-chloro-3-{[(phenylmethyl)amino]carbonyl}phenyl)-N-methylpyrazine-2-carboxamide |
| methyl 3-{5-amino-6-[(cyclopropylamino)carbonyl]pyrazin-2-yl}benzoate |
| methyl 3-{5-amino-6-[(ethylamino)carbonyl]pyrazin-2-yl}benzoate |
| 3-amino-6-[3-({[(2,3-dimethylphenyl)methyl]amino}carbonyl)phenyl]-N-methylpyrazine-2-carboxamide |
| 3-amino-6-{3-[({[4-hydroxy-3-(methyloxy)phenyl]methyl}amino)carbonyl]phenyl}-N-methylpyrazine-2-carboxamide |
| 3-amino-6-[3-({[(4-chloro-2-methylphenyl)methyl]amino}carbonyl)phenyl]-N-methylpyrazine-2-carboxamide |
| 3-amino-6-{3-[({[2-(ethyloxy)phenyl]methyl}amino)carbonyl]phenyl}-N-methylpyrazine-2-carboxamide |
| 3-amino-6-{3-[({[2-chloro-6-(phenyloxy)phenyl]methyl}amino)carbonyl]phenyl}-N-methylpyrazine-2-carboxamide |
| 3-amino-6-[3-({[(2,5-dichlorophenyl)methyl]amino}carbonyl)phenyl]-N-methylpyrazine-2-carboxamide |
| 3-amino-6-{3-[({[2,6-bis(methyloxy)phenyl]methyl}amino)carbonyl]phenyl}-N-methylpyrazine-2-carboxamide |
| 3-amino-6-[3-({[(2-chloro-6-methylphenyl)methyl]amino}carbonyl)phenyl]-N-methylpyrazine-2-carboxamide |
| 3-amino-N-methyl-6-[3-({[(2,4,5-trifluorophenyl)methyl]amino}carbonyl)phenyl]pyrazine-2-carboxamide |

TABLE 10-continued

Name 3-amino-6-(3-{[(2,2-dimethylpropyl)amino]carbonyl}phenyl)-N-methylpyrazine-2-carboxamide
3-amino-6-(3-{[(cyclopentylmethyl)amino]carbonyl}phenyl)-N-methylpyrazine-2-carboxamide
3-amino-6-{3-[({[3,5-bis(methyloxy)phenyl]methyl}amino)carbonyl]phenyl}-N-methylpyrazine-2-carboxamide
3-amino-N-methyl-6-{3-[({[4-(methylsulfonyl)phenyl]methyl}amino)carbonyl]phenyl}pyrazine-2-carboxamide
3-amino-6-[3-({[(5-bromo-2-fluorophenyl)methyl]amino}carbonyl)phenyl]-N-methylpyrazine-2-carboxamide
3-amino-6-[3-({[(3-bromo-4-fluorophenyl)methyl]amino}carbonyl)phenyl]-N-methylpyrazine-2-carboxamide
3-amino-N-methyl-6-{3-[({[2,4,6-tris(methyloxy)phenyl]methyl}amino)carbonyl]phenyl}pyrazine-2-carboxamide
3-amino-N-methyl-6-[3-({[(3-methylphenyl)methyl]amino}carbonyl)phenyl]pyrazine-2-carboxamide
3-amino-6-[3-({[(4-bromo-2-fluorophenyl)methyl]amino}carbonyl)phenyl]-N-methylpyrazine-2-carboxamide
3-amino-6-[3-({[(2,5-dimethylphenyl)methyl]amino}carbonyl)phenyl]-N-methylpyrazine-2-carboxamide
3-amino-6-{3-[({[3,5-bis(trifluoromethyl)phenyl]methyl}amino)carbonyl]phenyl}-N-methylpyrazine-2-carboxamide
3-amino-6-(3-{[(2,2-diphenylethyl)amino]carbonyl}phenyl)-N-methylpyrazine-2-carboxamide
3-amino-N-methyl-6-(3-thienyl)pyrazine-2-carboxamide
3-amino-N-methyl-6-(3-{[(phenylmethyl)amino]sulfonyl}phenyl)pyrazine-2-carboxamide
5,5'-diamino-N,N'-dimethyl-2,2'-bipyrazine-6,6'-dicarboxamide
3-amino-6-(1H-indol-5-yl)-N-methylpyrazine-2-carboxamide
3-amino-N-methyl-6-(2-thienyl)pyrazine-2-carboxamide
3-amino-N-methyl-6-pyridin-4-ylpyrazine-2-carboxamide
3-amino-N-cyclopropyl-6-(3-{[(phenylmethyl)amino]carbonyl}phenyl)pyrazine-2-carboxamide
3-amino-6-[3-({[(2-chloro-6-fluorophenyl)methyl]amino}carbonyl)phenyl]-N-cyclopropylpyrazine-2-carboxamide
3-amino-N-ethyl-6-(3-{[(phenylmethyl)amino]carbonyl}phenyl)pyrazine-2-carboxamide
3-amino-6-[3-({[(2-chloro-6-fluorophenyl)methyl]amino}carbonyl)phenyl]-N-ethylpyrazine-2-carboxamide
3-amino-6-[3-({[(2,3-dichlorophenyl)methyl]amino}carbonyl)phenyl]-N-methylpyrazine-2-carboxamide
3-amino-6-[3-({[(4-chloro-2-fluorophenyl)methyl]amino}carbonyl)phenyl]-N-methylpyrazine-2-carboxamide
3-amino-6-[3-({[(3,5-dichlorophenyl)methyl]amino}carbonyl)phenyl]-N-methylpyrazine-2-carboxamide
3-amino-6-[3-({[(5-chloro-2-fluorophenyl)methyl]amino}carbonyl)phenyl]-N-methylpyrazine-2-carboxamide
3-amino-6-{3-[(cyclopropylamino)carbonyl]phenyl}-N-methylpyrazine-2-carboxamide
3-amino-6-[3-({[(3,4-dichlorophenyl)methyl]amino}carbonyl)phenyl]-N-methylpyrazine-2-carboxamide
3-amino-6-[3-({[(4'-fluorobiphenyl-2-yl)methyl]amino}carbonyl)phenyl]-N-methylpyrazine-2-carboxamide
3-amino-N-methyl-6-[3-({[(2,3,4-trifluorophenyl)methyl]amino}carbonyl)phenyl]pyrazine-2-carboxamide
3-amino-6-[3-({[(3-chloro-2,6-difluorophenyl)methyl]amino}carbonyl)phenyl]-N-methylpyrazine-2-carboxamide
3-amino-6-[3-({[(3-chloro-2,6-difluorophenyl)methyl]amino}carbonyl)phenyl]-N-methylpyrazine-2-carboxamide
3-amino-6-{3-[(9H-fluoren-9-ylamino)carbonyl]phenyl}-N-methylpyrazine-2-carboxamide
3-amino-N-methyl-6-[3-({[(2-methylphenyl)methyl]amino}carbonyl)phenyl]pyrazine-2-carboxamide
3-amino-6-[3-({[(3,4-dimethylphenyl)methyl]amino}carbonyl)phenyl]-N-methylpyrazine-2-carboxamide
3-amino-6-[3-({[(5-fluoro-2-methylphenyl)methyl]amino}carbonyl)phenyl]-N-methylpyrazine-2-carboxamide
3-amino-6-[3-({[(3,4-difluorophenyl)methyl]amino}carbonyl)phenyl]-N-methylpyrazine-2-carboxamide
3-amino-6-[3-({[(2-fluorophenyl)methyl]amino}carbonyl)phenyl]-N-methylpyrazine-2-carboxamide
3-amino-N-methyl-6-{3-[({[4-(4-methylpiperazin-1-yl)phenyl]methyl}amino)carbonyl]phenyl}pyrazine-2-carboxamide
3-amino-6-(4-fluoro-3-{[(phenylmethyl)amino]carbonyl}phenyl)-N-methylpyrazine-2-carboxamide
3-amino-N-methyl-6-[3-({[(2,4,6-trichlorophenyl)methyl]amino}carbonyl)phenyl]pyrazine-2-carboxamide

TABLE 10-continued

Name 3-amino-6-[3-({[(3-chloro-2-methylphenyl)methyl]amino}carbonyl)phenyl]-N-methylpyrazine-2-carboxamide
3-amino-6-{3-[({[2,5-bis(methyloxy)phenyl]methyl}amino)carbonyl]phenyl}-N-methylpyrazine-2-carboxamide
3-amino-6-[3-({[(3-fluoro-4-methylphenyl)methyl]amino}carbonyl)phenyl]-N-methylpyrazine-2-carboxamide
3-amino-6-[3-({[(2-chloro-6-fluoro-3-methylphenyl)methyl]amino}carbonyl)phenyl]-N-methylpyrazine-2-carboxamide
3-amino-6-[3-({[(2-chloro-3,6-difluorophenyl)methyl]amino}carbonyl)phenyl]-N-methylpyrazine-2-carboxamide
3-amino-6-[3-({[(2,3-difluoro-4-methylphenyl)methyl]amino}carbonyl)phenyl]-N-methylpyrazine-2-carboxamide
3-amino-6-[3-({[(4-fluoro-3-methylphenyl)methyl]amino}carbonyl)phenyl]-N-methylpyrazine-2-carboxamide
3-amino-6-[3-({[(3-chloro-2-fluorophenyl)methyl]amino}carbonyl)phenyl]-N-methylpyrazine-2-carboxamide
3-amino-6-[3-({[(6-chloro-2-fluoro-3-methylphenyl)methyl]amino}carbonyl)phenyl]-N-methylpyrazine-2-carboxamide
3-amino-6-[3-({[(4-iodophenyl)methyl]amino}carbonyl)phenyl]-N-methylpyrazine-2-carboxamide
3-amino-6-[3-({[(3-chloro-4-methylphenyl)methyl]amino}carbonyl)phenyl]-N-methylpyrazine-2-carboxamide
3-amino-6-[3-({[(4-bromophenyl)methyl]amino}carbonyl)phenyl]-N-methylpyrazine-2-carboxamide
3-amino-6-[3-({[(2-bromophenyl)methyl]amino}carbonyl)phenyl]-N-methylpyrazine-2-carboxamide
3-amino-N-methyl-6-[3-({[(2,3,6-trifluorophenyl)methyl]amino}carbonyl)phenyl]pyrazine-2-carboxamide
3-amino-N-methyl-6-[3-({[(2,3,6-trifluorophenyl)methyl]amino}carbonyl)phenyl]pyrazine-2-carboxamide
3-amino-N-methyl-6-(3-{[(phenylcarbonyl)amino]methyl}phenyl)pyrazine-2-carboxamide
3-amino-6-[3-({[(4-chlorophenyl)carbonyl]amino}methyl)phenyl]-N-methylpyrazine-2-carboxamide
3-amino-6-[3-({[[(2,5-difluorophenyl)carbonyl]amino}methyl)phenyl]-N-methylpyrazine-2-carboxamide
3-amino-N-methyl-6-(3-{[(naphthalen-2-ylcarbonyl)amino]methyl}phenyl)pyrazine-2-carboxamide
3-amino-N-methyl-6-(3-{[(phenylmethyl)thio]methyl}phenyl)pyrazine-2-carboxamide
3-amino-N-methyl-6-(3-{[(phenylmethyl)sulfonyl]methyl}phenyl)pyrazine-2-carboxamide
3-amino-N-methyl-6-(3-{[(phenylmethyl)oxy]methyl}phenyl)pyrazine-2-carboxamide
3-amino-N-methyl-6-(3-{[(phenylmethyl)amino]methyl}phenyl)pyrazine-2-carboxamide
3-amino-N-methyl-6-[3-({[(3,4,5-trifluorophenyl)methyl]amino}carbonyl)phenyl]pyrazine-2-carboxamide
9H-fluoren-9-ylmethyl (3-{5-amino-6-[(methylamino)carbonyl]pyrazin-2-yl}phenyl)carbamate
phenylmethyl (3-{5-amino-6-[(methylamino)carbonyl]pyrazin-2-yl}phenyl)carbamate
ethyl (3-{5-amino-6-[(methylamino)carbonyl]pyrazin-2-yl}phenyl)carbamate
3-amino-6-[3-({[(3,4-dichlorophenyl)carbonyl]amino}methyl)phenyl]-N-methylpyrazine-2-carboxamide
1,1-dimethylethyl (3-{5-amino-6-[(methylamino)carbonyl]pyrazin-2-yl}phenyl)carbamate
(1R,2S,5R)-5-methyl-2-(1-methylethyl)cyclohexyl (3-{5-amino-6-[(methylamino)carbonyl]pyrazin-2-yl}phenyl)carbamate
3-amino-6-[3-({[(4-hydroxyphenyl)methyl]amino}carbonyl)phenyl]-N-methylpyrazine-2-carboxamide
3-amino-N-methyl-6-(3-{[({4-[(2-morpholin-4-ylethyl)oxy]phenyl}methyl)amino]carbonyl}phenyl)pyrazine-2-carboxamide
3-amino-N-methyl-6-{3-[({[2-(methyloxy)phenyl]methyl}amino)carbonyl]phenyl}pyrazine-2-carboxamide
3-amino-6-[3-({[(3-hydroxyphenyl)methyl]amino}carbonyl)phenyl]-N-methylpyrazine-2-carboxamide
3-amino-6-[3-({[(2-hydroxyphenyl)methyl]amino}carbonyl)phenyl]-N-methylpyrazine-2-carboxamide
3-amino-N-methyl-6-{3-[(2-phenylhydrazino)carbonyl]phenyl}pyrazine-2-carboxamide
3-amino-N-(2-hydroxyethyl)-6-(3-methylphenyl)pyrazine-2-carboxamide
3-amino-N-methyl-6-(3-{[(phenylacetyl)amino]methyl}phenyl)pyrazine-2-carboxamide
3-amino-6-[3-({[(4-chlorophenyl)acetyl]amino}methyl)phenyl]-N-methylpyrazine-2-carboxamide
3-amino-6-(3-{[(biphenyl-4-ylcarbonyl)amino]methyl}phenyl)-N-methylpyrazine- TABLE 10-continued

| Name |
| --- |
| 2-carboxamide |
| 3-amino-6-{3-[({[2-chloro-5-(trifluoromethyl)phenyl]carbonyl}amino)methyl]phenyl}-N-methylpyrazine-2-carboxamide |
| N-[(3-{5-amino-6-[(methylamino)carbonyl]pyrazin-2-yl}phenyl)methyl]-1H-indole-2-carboxamide |
| 3-amino-6-[3-({[(3-hydroxypyridin-2-yl)carbonyl]amino}methyl)phenyl]-N-methylpyrazine-2-carboxamide |
| 3-amino-6-(3-{[(1H-indol-3-ylacetyl)amino]methyl}phenyl)-N-methylpyrazine-2-carboxamide |
| 3-amino-6-[3-({[(2,5-difluorophenyl)methyl]amino}carbonyl)phenyl]-N-methylpyrazine-2-carboxamide |
| 3-amino-6-[3-({[(2,6-difluorophenyl)methyl]amino}carbonyl)phenyl]-N-methylpyrazine-2-carboxamide |
| 3-amino-6-[3-({[(3,5-difluorophenyl)methyl]amino}carbonyl)phenyl]-N-methylpyrazine-2-carboxamide |
| 3-amino-6-[3-({[(3-iodophenyl)methyl]amino}carbonyl)phenyl]-N-methylpyrazine-2-carboxamide |
| 3-amino-N-methyl-6-[3-({[(2-morpholin-4-ylphenyl)methyl]amino}carbonyl)phenyl]pyrazine-2-carboxamide |
| 3-amino-N-methyl-6-(3-{[({3-[(2-morpholin-4-ylethyl)oxy]phenyl}methyl)amino]carbonyl}phenyl)pyrazine-2-carboxamide |
| 3-amino-N-methyl-6-[3-({[(4-morpholin-4-ylphenyl)methyl]amino}carbonyl)phenyl]pyrazine-2-carboxamide |
| 3-amino-N-methyl-6-[3-({[(3-morpholin-4-ylphenyl)methyl]amino}carbonyl)phenyl]pyrazine-2-carboxamide |
| 3-amino-N-methyl-6-{3-[({[4-(1-methylethyl)phenyl]methyl}amino)carbonyl]phenyl}pyrazine-2-carboxamide |
| 3-amino-N-methyl-6-(3-{[({[4-(1-methylethyl)phenyl]oxy}acetyl)amino]methyl}phenyl)pyrazine-2-carboxamide |
| 3-amino-6-{3-[({[(4-aminophenyl)thio]acetyl}amino)methyl]phenyl}-N-methylpyrazine-2-carboxamide |
| 3-amino-N-methyl-6-(4-(methyloxy)-3-{[(phenylmethyl)amino]carbonyl}phenyl)pyrazine-2-carboxamide |
| 3-amino-N-methyl-6-(5-{[(phenylmethyl)amino]carbonyl}pyridin-3-yl)pyrazine-2-carboxamide |
| 3-amino-6-[3-({[(4-iodophenyl)carbonyl]amino}methyl)phenyl]-N-methylpyrazine-2-carboxamide |
| 3-amino-N-methyl-6-[3-({[(4-pentylphenyl)carbonyl]amino}methyl)phenyl]pyrazine-2-carboxamide |
| 3-amino-6-(3-{[(1,3-benzodioxol-5-ylcarbonyl)amino]methyl}phenyl)-N-methylpyrazine-2-carboxamide |
| 3-amino-6-{3-[({[4-(1,1-dimethylethyl)phenyl]methyl}amino)carbonyl]phenyl}-N-methylpyrazine-2-carboxamide |
| 3-amino-N-methyl-6-(3-{[({1-[5-(trifluoromethyl)pyrimidin-2-yl]piperidin-4-yl}carbonyl)amino]methyl}phenyl)pyrazine-2-carboxamide |
| 3-amino-N-methyl-6-[3-({[(2-piperidin-1-ylphenyl)methyl]amino}carbonyl)phenyl]pyrazine-2-carboxamide |
| 3-amino-N-methyl-6-{3-[({[2-(methylthio)phenyl]methyl}amino)carbonyl]phenyl}pyrazine-2-carboxamide |
| 1,1-dimethylethyl (3R)-3-{[(3-{5-amino-6-[(methylamino)carbonyl]pyrazin-2-yl}phenyl)carbonyl]amino}pyrrolidine-1-carboxylate |
| 3-amino-N-methyl-6-(3-{[(3R)-pyrrolidin-3-ylamino]carbonyl}phenyl)pyrazine-2-carboxamide |
| 3-{[(4-chlorophenyl)methyl]amino}-6-{3-[({(3R)-1-[(4-chlorophenyl)methyl]pyrrolidin-3-yl}amino)carbonyl]phenyl}-N-methylpyrazine-2-carboxamide |
| 3-amino-6-{3-[({(3R)-1-[(2,4-dichlorophenyl)methyl]pyrrolidin-3-yl}amino)carbonyl]phenyl}-N-methylpyrazine-2-carboxamide |
| N-methyl-3-({[3-(methyloxy)phenyl]methyl}amino)-6-(3-{[((3R)-1-{[3-(methyloxy)phenyl]methyl}pyrrolidin-3-yl)amino]carbonyl}phenyl)pyrazine-2-carboxamide |
| 3-amino-6-{3-[({(3R)-1-[(2,6-dichlorophenyl)methyl]pyrrolidin-3-yl}amino)carbonyl]phenyl}-N-methylpyrazine-2-carboxamide |
| N-methyl-3-[(phenylmethyl)amino]-6-[3-({[(3R)-1-(phenylmethyl)pyrrolidin-3-yl]amino}carbonyl)phenyl]pyrazine-2-carboxamide |
| 1,1-dimethylethyl 3-({[(3-{5-amino-6-[(methylamino)carbonyl]pyrazin-2-yl}phenyl)carbonyl]amino}methyl)pyrrolidine-1-carboxylate |
| 1,1-dimethylethyl 2-({[(3-{5-amino-6-[(methylamino)carbonyl]pyrazin-2-yl}phenyl)carbonyl]amino}methyl)pyrrolidine-1-carboxylate |
| 3-amino-N-methyl-6-(3-{[(pyrrolidin-3-ylmethyl)amino]carbonyl}phenyl)pyrazine-2-carboxamide |
| 3-amino-N-methyl-6-(3-{[(pyrrolidin-2-ylmethyl)amino]carbonyl}phenyl)pyrazine-2-carboxamide |
| 3-amino-6-(2-fluoro-5-{[(phenylmethyl)amino]carbonyl}phenyl)-N-methylpyrazine-2-carboxamide |
| 3-amino-6-{3-[(1,3-benzodioxol-5-ylacetyl)amino]phenyl}-N-methylpyrazine-2- |

TABLE 10-continued

| Name |
| --- |
| carboxamide |
| 3-amino-6-[3-({[(2-chloro-4-fluorophenyl)methyl]amino}carbonyl)phenyl]-N-methylpyrazine-2-carboxamide |
| 3-amino-6-{3-[({[3,4-bis(methyloxy)phenyl]methyl}amino)carbonyl]phenyl}-N-methylpyrazine-2-carboxamide |
| 3-amino-N-methyl-6-{3-[(phenylmethyl)amino]phenyl}pyrazine-2-carboxamide |
| 3-amino-N-methyl-6-(3-{[({2-[(2-morpholin-4-ylethyl)oxy]phenyl}methyl)amino]carbonyl}phenyl)pyrazine-2-carboxamide |
| 3-amino-N-methyl-6-{3-[({[4-(1-methylethyl)phenyl]carbonyl}amino)methyl]phenyl}pyrazine-2-carboxamide |
| 3-amino-6-[3-({[(4-butylphenyl)methyl]amino}carbonyl)phenyl]-N-methylpyrazine-2-carboxamide |
| 3-amino-N-methyl-6-{3-[({[4-(1,2,3-thiadiazol-4-yl)phenyl]methyl}amino)carbonyl]phenyl}pyrazine-2-carboxamide |
| 3-amino-N-methyl-6-{3-[({[4-(2-thienyl)phenyl]methyl}amino)carbonyl]phenyl}pyrazine-2-carboxamide |
| 3-amino-6-{3-[({[4-(1,1-dimethylethyl)phenyl]carbonyl}amino)methyl]phenyl}-N-methylpyrazine-2-carboxamide |
| 3-amino-N-methyl-6-{3-[({[4-(1H-pyrazol-1-yl)phenyl]methyl}amino)carbonyl]phenyl}pyrazine-2-carboxamide |
| 3-amino-6-(3-{[(3,4-dihydro-2H-1,4-benzoxazin-6-ylmethyl)amino]carbonyl}phenyl)-N-methylpyrazine-2-carboxamide |
| 3-amino-6-[3-({[(2-amino-6-fluorophenyl)methyl]amino}carbonyl)phenyl]-N-methylpyrazine-2-carboxamide |
| 3-amino-6-(3-{[(biphenyl-4-ylmethyl)amino]methyl}phenyl)-N-methylpyrazine-2-carboxamide |
| 3-amino-6-(3-{[(biphenyl-2-ylmethyl)amino]methyl}phenyl)-N-methylpyrazine-2-carboxamide |
| 3-amino-6-(3-{[(biphenyl-3-ylmethyl)amino]methyl}phenyl)-N-methylpyrazine-2-carboxamide |
| 3-amino-N-methyl-6-{3-[({[1-(phenylmethyl)pyrrolidin-2-yl]methyl}amino)carbonyl]phenyl}pyrazine-2-carboxamide |
| 3-amino-6-(3-{[(3,4-dihydro-2H-1,4-benzoxazin-6-ylmethyl)amino]methyl}phenyl)-N-methylpyrazine-2-carboxamide |
| 3-amino-6-[3-({[(2,4-difluorophenyl)methyl]amino}methyl)phenyl]-N-methylpyrazine-2-carboxamide |
| 3-amino-6-[3-({[(2,5-difluorophenyl)methyl]amino}methyl)phenyl]-N-methylpyrazine-2-carboxamide |
| 3-amino-6-[3-({[(2,3-difluorophenyl)methyl]amino}methyl)phenyl]-N-methylpyrazine-2-carboxamide |
| 3-amino-N-methyl-6-[3-({[(2-pyridin-4-ylphenyl)methyl]amino}carbonyl)phenyl]pyrazine-2-carboxamide |
| 3-amino-N-methyl-6-[3-({[(2-pyridin-3-ylphenyl)methyl]amino}carbonyl)phenyl]pyrazine-2-carboxamide |
| 3-amino-N-methyl-6-{3-[({[4-(methylsulfonyl)phenyl]methyl}amino)methyl]phenyl}pyrazine-2-carboxamide |
| 3-amino-6-(3-{[(2,2-diphenylethyl)amino]methyl}phenyl)-N-methylpyrazine-2-carboxamide |
| 3-amino-N-methyl-6-{3-[({[1-(phenylmethyl)pyrrolidin-3-yl]methyl}amino)carbonyl]phenyl}pyrazine-2-carboxamide |
| 3-amino-N-methyl-6-{3-[({[3-(phenyloxy)phenyl]methyl}amino)methyl]phenyl}pyrazine-2-carboxamide |
| 3-amino-6-[3-({[(4-aminophenyl)methyl]amino}methyl)phenyl]-N-methylpyrazine-2-carboxamide |
| 3-amino-N-methyl-6-{3-[({[4-(phenyloxy)phenyl]methyl}amino)methyl]phenyl}pyrazine-2-carboxamide |
| 3-amino-6-{3-[({[2,6-bis(methyloxy)phenyl]methyl}amino)methyl]phenyl}-N-methylpyrazine-2-carboxamide |
| 3-amino-6-[3-({[(2-fluorophenyl)methyl]amino}methyl)phenyl]-N-methylpyrazine-2-carboxamide |
| 3-amino-6-[5-({[(2,6-difluorophenyl)methyl]amino}carbonyl)pyridin-3-yl]-N-methylpyrazine-2-carboxamide |
| 3-amino-6-(5-{[(biphenyl-2-ylmethyl)amino]carbonyl}pyridin-3-yl)-N-methylpyrazine-2-carboxamide |
| 3-amino-6-[3-({[(2,6-difluorophenyl)methyl]amino}methyl)phenyl]-N-methylpyrazine-2-carboxamide |
| 3-amino-6-(3-{[(2,3-dihydro-1,4-benzodioxin-6-ylmethyl)amino]methyl}phenyl)-N-methylpyrazine-2-carboxamide |
| 3-amino-N-methyl-6-[3-({[(2-piperidin-1-ylphenyl)methyl]amino}methyl)phenyl]pyrazine-2-carboxamide |
| 3-amino-6-{3-[({[4-fluoro-2-(trifluoromethyl)phenyl]methyl}amino)carbonyl]phenyl}-N-methylpyrazine-2-carboxamide |
| 3-amino-N-methyl-6-{3-[({[6-(trifluoromethyl)pyridin-3-yl]methyl}amino)carbonyl]phenyl}pyrazine-2-carboxamide |
| 3-amino-6-[3-(1H-benzimidazol-2-yl)phenyl]-N-methylpyrazine-2-carboxamide |
| 3-amino-6-[3-({[(2,5-dichlorophenyl)methyl]amino}methyl)phenyl]-N- |

TABLE 10-continued

Name methylpyrazine-2-carboxamide
3-amino-6-[3-({[(3,5-dichlorophenyl)methyl]amino}methyl)phenyl]-N-methylpyrazine-2-carboxamide
3-amino-N-methyl-6-{3-[(2-phenylethyl)amino]phenyl}pyrazine-2-carboxamide
3-amino-6-(5-{[(2,3-dihydro-1,4-benzodioxin-6-ylmethyl)amino]carbonyl}pyridin-3-yl)-N-methylpyrazine-2-carboxamide
3-amino-N-methyl-6-[3-({[2-(phenylamino)ethyl]amino}carbonyl)phenyl]pyrazine-2-carboxamide
3-amino-6-[3-({[(4-ethylphenyl)methyl]amino}carbonyl)phenyl]-N-methylpyrazine-2-carboxamide
3-amino-N-methyl-6-[3-({[(4-pyridin-3-ylphenyl)methyl]amino}carbonyl)phenyl]pyrazine-2-carboxamide
3-amino-6-{3-[(2,3-dihydro-1H-inden-2-ylamino)methyl]phenyl}-N-methylpyrazine-2-carboxamide
3-amino-6-[3-(1,3-dihydro-2H-isoindol-2-ylmethyl)phenyl]-N-methylpyrazine-2-carboxamide
3-amino-6-(3-{[(1R)-2,3-dihydro-1H-inden-1-ylamino]methyl}phenyl)-N-methylpyrazine-2-carboxamide
3-amino-6-(3-{[(1S)-2,3-dihydro-1H-inden-1-ylamino]methyl}phenyl)-N-methylpyrazine-2-carboxamide
3-amino-N-methyl-6-[3-({[(3,4,5-trifluorophenyl)methyl]amino}methyl)phenyl]pyrazine-2-carboxamide
3-amino-N-methyl-6-[3-({[(1R)-1-phenylethyl]amino}methyl)phenyl]pyrazine-2-carboxamide
3-amino-6-[3-({[(1R,2S)-2-hydroxy-2,3-dihydro-1H-inden-1-yl]amino}methyl)phenyl]-N-methylpyrazine-2-carboxamide
3-amino-N-methyl-6-{3-[({[4-(2-thienyl)phenyl]methyl}amino)methyl]phenyl}pyrazine-2-carboxamide
3-amino-N-methyl-6-{3-[({[3-(1,2,3-thiadiazol-4-yl)phenyl]methyl}amino)methyl]phenyl}pyrazine-2-carboxamide
3-amino-N-methyl-6-[3-({[(4-propylphenyl)methyl]amino}carbonyl)phenyl]pyrazine-2-carboxamide
3-amino-6-[3-({[(4-chloro-2-fluorophenyl)methyl]amino}methyl)phenyl]-N-methylpyrazine-2-carboxamide
3-amino-N-methyl-6-{3-[({[3-(trifluoromethyl)phenyl]methyl}amino)methyl]phenyl}pyrazine-2-carboxamide
3-amino-N-methyl-6-[3-({[(1S)-1-phenylethyl]amino}methyl)phenyl]pyrazine-2-carboxamide
3-amino-6-[3-({[(1R)-2-hydroxy-1-phenylethyl]amino}methyl)phenyl]-N-methylpyrazine-2-carboxamide
methyl (2S)-{[(3-{5-amino-6-[(methylamino)carbonyl]pyrazin-2-yl}phenyl)methyl]amino}(phenyl)ethanoate
3-amino-6-(3-{[2-(2,5-difluorophenyl)hydrazino]carbonyl}phenyl)-N-methylpyrazine-2-carboxamide
3-amino-N-methyl-6-(3-{[2-(2,3,5,6-tetrafluoro-4-methylphenyl)hydrazino]carbonyl}phenyl)pyrazine-2-carboxamide
3-amino-6-(3-{[2-(2-fluorophenyl)hydrazino]carbonyl}phenyl)-N-methylpyrazine-2-carboxamide
3-amino-6-(3-{[2-(2,4-difluorophenyl)hydrazino]carbonyl}phenyl)-N-methylpyrazine-2-carboxamide
3-amino-N-methyl-6-(3-{[2-(2,3,5,6-tetrafluorophenyl)hydrazino]carbonyl}phenyl)pyrazine-2-carboxamide
3-amino-N-methyl-6-[3-({[(5-methylpyrazin-2-yl)methyl]amino}methyl)phenyl]pyrazine-2-carboxamide
3-amino-N-methyl-6-(3-{[(1S)-1,2,3,4-tetrahydronaphthalen-1-ylamino]methyl}phenyl)pyrazine-2-carboxamide
3-amino-N-methyl-6-[3-({[(3S)-1-(phenylmethyl)pyrrolidin-3-yl]amino}methyl)phenyl]pyrazine-2-carboxamide
3-amino-N-methyl-6-[3-({[(3R)-1-(phenylmethyl)pyrrolidin-3-yl]amino}methyl)phenyl]pyrazine-2-carboxamide
3-amino-6-(3-{[ethyl(phenylmethyl)amino]methyl}phenyl)-N-methylpyrazine-2-carboxamide
3-amino-N-methyl-6-[3-({[(1S,2S)-2-phenylcyclopropyl]amino}methyl)phenyl]pyrazine-2-carboxamide
3-Amino-6-(3-benzylcarbamoyl-phenyl)-pyrazine-2-carboxylic acid methylamide
3-amino-N-methyl-6-[3-(4-phenyl-1H-imidazol-2-yl)phenyl]pyrazine-2-carboxamide
3-amino-N-methyl-6-[3-({[(4-propylphenyl)methyl]amino}methyl)phenyl]pyrazine-2-carboxamide
3-amino-6-[3-({[(5-bromo-2-fluorophenyl)methyl]amino}methyl)phenyl]-N-methylpyrazine-2-carboxamide
3-amino-N-methyl-6-(3-{[(2R)-1,2,3,4-tetrahydronaphthalen-2-ylamino]methyl}phenyl)pyrazine-2-carboxamide
3-amino-N-methyl-6-(3-{[(1-methyl-1-phenylethyl)amino]methyl}phenyl)pyrazine-2-carboxamide
3-amino-6-{3-[(9H-fluoren-9-ylamino)methyl]phenyl}-N-methylpyrazine-2-carboxamide TABLE 10-continued

| Name |
| --- |
| 3-amino-N-methyl-6-{3-[(naphthalen-1-ylamino)methyl]phenyl}pyrazine-2-carboxamide |
| 3-amino-6-[3-({[(3-fluorobiphenyl-4-yl)methyl]amino}methyl)phenyl]-N-methylpyrazine-2-carboxamide |
| 3-amino-6-{3-[({[2-fluoro-4-(2-thienyl)phenyl]methyl}amino)methyl]phenyl}-N-methylpyrazine-2-carboxamide |
| 3-amino-6-[3-({[(2-fluoro-4-furan-2-ylphenyl)methyl]amino}methyl)phenyl]-N-methylpyrazine-2-carboxamide |
| 3-amino-N-methyl-6-{3-[(naphthalen-2-ylamino)methyl]phenyl}pyrazine-2-carboxamide |
| 3-amino-6-[3-({[(1S,2R)-2-hydroxy-2,3-dihydro-1H-inden-1-yl]amino}methyl)phenyl]-N-methylpyrazine-2-carboxamide |
| 3-amino-N-methyl-6-(3-{[(2S)-1,2,3,4-tetrahydronaphthalen-2-ylamino]methyl}phenyl)pyrazine-2-carboxamide |
| methyl 3-amino-6-(3-{[(4,7-difluoro-2,3-dihydro-1H-inden-1-yl)amino]methyl}phenyl)pyrazine-2-carboxylate |
| 3-amino-6-(3-{[(5-bromo-2,3-dihydro-1H-inden-2-yl)amino]methyl}phenyl)-N-methylpyrazine-2-carboxamide |
| 3-amino-6-{3-[({[2-fluoro-5-(2-thienyl)phenyl]methyl}amino)methyl]phenyl}-N-methylpyrazine-2-carboxamide |
| 3-amino-6-[3-({[(4-ethenyl-2-fluorophenyl)methyl]amino}methyl)phenyl]-N-methylpyrazine-2-carboxamide |
| 3-amino-6-(3-{[(4,7-difluoro-3-methyl-2,3-dihydro-1H-inden-1-yl)amino]methyl}phenyl)-N-methylpyrazine-2-carboxamide |
| 3-amino-N-methyl-6-[3-({[(1S,2R)-2-(methyloxy)-2,3-dihydro-1H-inden-1-yl]amino}methyl)phenyl]pyrazine-2-carboxamide |
| 3-amino-6-(3-{[(5-bromo-2,3-dihydro-1H-inden-1-yl)amino]methyl}phenyl)-N-methylpyrazine-2-carboxamide |
| 3-amino-6-[3-({[(2S)-6-bromo-1,2,3,4-tetrahydronaphthalen-2-yl]amino}methyl)phenyl]-N-methylpyrazine-2-carboxamide |
| 3-amino-6-[3-({[(2R)-6-bromo-1,2,3,4-tetrahydronaphthalen-2-yl]amino}methyl)phenyl]-N-methylpyrazine-2-carboxamide |
| 3-amino-6-(3-{[(5-fluoro-2,3-dihydro-1H-inden-1-yl)amino]methyl}phenyl)-N-methylpyrazine-2-carboxamide |
| 3-amino-6-[3-({[(2S)-5-bromo-2,3-dihydro-1H-inden-2-yl]amino}methyl)phenyl]-N-methylpyrazine-2-carboxamide |
| 3-amino-6-(3-{[(4-fluoro-2,3-dihydro-1H-inden-2-yl)amino]methyl}phenyl)-N-methylpyrazine-2-carboxamide |
| 3-amino-6-(3-{[(4-fluoro-1-hydroxy-2,3-dihydro-1H-inden-2-yl)amino]methyl}phenyl)-N-methylpyrazine-2-carboxamide |
| 3-amino-N-methyl-6-[3-({[(1R,2S)-2-(methyloxy)-2,3-dihydro-1H-inden-1-yl]amino}methyl)phenyl]pyrazine-2-carboxamide |
| 3-amino-6-(3-{[(4,7-difluoro-2,3-dihydro-1H-inden-1-yl)amino]methyl}phenyl)-N-methylpyrazine-2-carboxamide |
| 3-amino-6-(3-{[(6-bromo-4-fluoro-2,3-dihydro-1H-inden-1-yl)amino]methyl}phenyl)-N-methylpyrazine-2-carboxamide |
| 3-amino-N-methyl-6-(3-{[(3-oxo-2,3-dihydro-1H-inden-1-yl)amino]methyl}phenyl)pyrazine-2-carboxamide |
| 3-amino-6-(3-{[(5-furan-2-yl-2,3-dihydro-1H-inden-1-yl)amino]methyl}phenyl)-N-methylpyrazine-2-carboxamide |
| 3-amino-6-(3-{[(4-fluoro-2,3-dihydro-1H-inden-1-yl)amino]methyl}phenyl)-N-methylpyrazine-2-carboxamide |
| 3-amino-6-(3-{[(4,6-difluoro-2,3-dihydro-1H-inden-1-yl)amino]methyl}phenyl)-N-methylpyrazine-2-carboxamide |
| 3-amino-6-(3-{[(6-fluoro-2,3-dihydro-1H-inden-1-yl)amino]methyl}phenyl)-N-methylpyrazine-2-carboxamide |
| 3-amino-6-(3-{[(5,6-difluoro-2,3-dihydro-1H-inden-1-yl)amino]methyl}phenyl)-N-methylpyrazine-2-carboxamide |
| 3-amino-6-(3-{[(5-chloro-2,3-dihydro-1H-inden-1-yl)amino]methyl}phenyl)-N-methylpyrazine-2-carboxamide |
| 3-amino-N-methyl-6-[3-({[5-(2-thienyl)-2,3-dihydro-1H-inden-1-yl]amino}methyl)phenyl]pyrazine-2-carboxamide |
| 3-amino-6-(3-{[(5,7-difluoro-2,3-dihydro-1H-inden-1-yl)amino]methyl}phenyl)-N-methylpyrazine-2-carboxamide |
| 3-amino-6-(3-{[(5-furan-3-yl-2,3-dihydro-1H-inden-1-yl)amino]methyl}phenyl)-N-methylpyrazine-2-carboxamide |
| 3-amino-N-methyl-6-[3-({[5-(3-thienyl)-2,3-dihydro-1H-inden-1-yl]amino}methyl)phenyl]pyrazine-2-carboxamide |
| 3-amino-6-[3-({[(1S)-4-fluoro-2,3-dihydro-1H-inden-1-yl]amino}methyl)phenyl]-N-methylpyrazine-2-carboxamide |
| 3-amino-6-[3-({[(1S)-5,7-difluoro-2,3-dihydro-1H-inden-1-yl]amino}methyl)phenyl]-N-methylpyrazine-2-carboxamide |
| 3-amino-6-(3-{[(7-bromo-4-fluoro-2,3-dihydro-1H-inden-1-yl)amino]methyl}phenyl)-N-methylpyrazine-2-carboxamide |
| 3-amino-6-(3-{[(6-chloro-2,3-dihydro-1H-inden-1-yl)amino]methyl}phenyl)-N-methylpyrazine-2-carboxamide |
| 3-amino-6-(3-{[(4,6-dichloro-2,3-dihydro-1H-inden-1-yl)amino]methyl}phenyl)-N- |

TABLE 10-continued

Name methylpyrazine-2-carboxamide
3-amino-6-(3-{[(4-chloro-2,3-dihydro-1H-inden-1-yl)amino]methyl}phenyl)-N-methylpyrazine-2-carboxamide
3-amino-6-(3-{[(1S)-2,3-dihydro-1H-inden-1-ylamino]methyl}phenyl)-N-ethylpyrazine-2-carboxamide
3-amino-6-(3-{[(5,7-difluoro-2,3-dihydro-1H-inden-1-yl)amino]methyl}phenyl)-N-ethylpyrazine-2-carboxamide
3-amino-N-methyl-6-[3-({[(1S)-5-(2-thienyl)-2,3-dihydro-1H-inden-1-yl]amino}methyl)phenyl]pyrazine-2-carboxamide
3-amino-N-methyl-6-(3-{[(5-phenyl-2,3-dihydro-1H-inden-1-yl)amino]methyl}phenyl)pyrazine-2-carboxamide
3-amino-6-(3-{[(4-bromo-2,3-dihydro-1H-inden-1-yl)amino]methyl}phenyl)-N-methylpyrazine-2-carboxamide
3-amino-N-methyl-6-(3-{[(4-phenyl-2,3-dihydro-1H-inden-1-yl)amino]methyl}phenyl)pyrazine-2-carboxamide
3-amino-N-methyl-6-[3-({[4-(2-thienyl)-2,3-dihydro-1H-inden-1-yl]amino}methyl)phenyl]pyrazine-2-carboxamide
3-amino-N-methyl-6-[3-({[6-(2-thienyl)-2,3-dihydro-1H-inden-1-yl]amino}methyl)phenyl]pyrazine-2-carboxamide
3-amino-N-methyl-6-[3-({[5-(4-methyl-2-thienyl)-2,3-dihydro-1H-inden-1-yl]amino}methyl)phenyl]pyrazine-2-carboxamide
3-amino-N-methyl-6-[3-({[(2R)-6-phenyl-1,2,3,4-tetrahydronaphthalen-2-yl]amino}methyl)phenyl]pyrazine-2-carboxamide
3-amino-N-methyl-6-naphthalen-2-ylpyrazine-2-carboxamide
3-amino-N-methyl-6-{3-[({(1S,2S)-2-[(phenylmethyl)oxy]cyclopentyl}amino)methyl]phenyl}pyrazine-2-carboxamide
3-amino-6-{3-[(cyclopentylamino)methyl]phenyl}-N-methylpyrazine-2-carboxamide
3-amino-6-(3-{[(6-bromo-2,3-dihydro-1H-inden-1-yl)amino]methyl}phenyl)-N-methylpyrazine-2-carboxamide
3-amino-6-(3-{[(7-fluoro-2,3-dihydro-1H-inden-1-yl)amino]methyl}phenyl)-N-methylpyrazine-2-carboxamide
3-amino-N-methyl-6-quinolin-3-ylpyrazine-2-carboxamide
3-amino-6-[3-(1H-imidazol-1-ylmethyl)phenyl]-N-methylpyrazine-2-carboxamide
3-amino-N-methyl-6-{3-[({5-[(2-morpholin-4-ylethyl)oxy]-2,3-dihydro-1H-inden-1-yl}amino)methyl]phenyl}pyrazine-2-carboxamide
3-amino-N-methyl-6-{3-[({(1R,2R)-2-[(phenylmethyl)oxy]cyclopentyl}amino)methyl]phenyl}pyrazine-2-carboxamide
3-amino-6-{3-[(2,3-dihydro-1-benzofuran-3-ylamino)methyl]phenyl}-N-methylpyrazine-2-carboxamide
3-amino-6-{3-[({5-[(cyanomethyl)oxy]-2,3-dihydro-1H-inden-1-yl}amino)methyl]phenyl}-N-methylpyrazine-2-carboxamide
2-amino-5-(3-{[(1S)-2,3-dihydro-1H-inden-1-ylamino]methyl}phenyl)-N-methylpyridine-3-carboxamide
3-amino-N-methyl-6-[3-({[5-(4-methylphenyl)-2,3-dihydro-1H-inden-1-yl]amino}methyl)phenyl]pyrazine-2-carboxamide
3-amino-6-[3-({[2-(dimethylamino)-1-phenylethyl]amino}methyl)phenyl]-N-methylpyrazine-2-carboxamide
3-amino-N-methyl-6-[3-({[5-(1H-1,2,4-triazol-1-yl)-2,3-dihydro-1H-inden-1-yl]amino}methyl)phenyl]pyrazine-2-carboxamide
3-amino-6-(3-{[(5-hydroxy-2,3-dihydro-1H-inden-1-yl)amino]methyl}phenyl)-N-methylpyrazine-2-carboxamide
3-amino-N-methyl-6-{3-[({4-[(2-morpholin-4-ylethyl)oxy]-2,3-dihydro-1H-inden-1-yl}amino)methyl]phenyl}pyrazine-2-carboxamide
3-amino-6-(3-{[(4-hydroxy-2,3-dihydro-1H-inden-1-yl)amino]methyl}phenyl)-N-methylpyrazine-2-carboxamide
3-amino-N-methyl-6-{1-[(phenylmethyl)amino]isoquinolin-7-yl}pyrazine-2-carboxamide
3-amino-N-methyl-6-(3-{[(2-morpholin-4-yl-1-phenylethyl)amino]methyl}phenyl)pyrazine-2-carboxamide
3-amino-N-methyl-6-{3-{[(1-phenyl-2-pyrrolidin-1-ylethyl)amino]methyl}phenyl)pyrazine-2-carboxamide
2-amino-5-(3-{[(6-bromo-2,3-dihydro-1H-inden-1-yl)amino]methyl}phenyl)-N-methylpyridine-3-carboxamide
2-amino-5-(3-{[(4,6-difluoro-2,3-dihydro-1H-inden-1-yl)amino]methyl}phenyl)-N-methylpyridine-3-carboxamide
2-amino-5-(3-{[(7-bromo-4-fluoro-2,3-dihydro-1H-inden-1-yl)amino]methyl}phenyl)-N-methylpyridine-3-carboxamide
2-amino-5-(3-{[(4-chloro-2,3-dihydro-1H-inden-1-yl)amino]methyl}phenyl)-N-methylpyridine-3-carboxamide
2-amino-5-(3-{[(5,6-difluoro-2,3-dihydro-1H-inden-1-yl)amino]methyl}phenyl)-N-methylpyridine-3-carboxamide
2-amino-5-(3-{[(5,7-difluoro-2,3-dihydro-1H-inden-1-yl)amino]methyl}phenyl)-N-methylpyridine-3-carboxamide
3-amino-6-{1-[(1S)-2,3-dihydro-1H-inden-1-ylamino]isoquinolin-7-yl}-N-methylpyrazine-2-carboxamide
3-amino-6-{3-[(1S)-2,3-dihydro-1H-inden-1-ylamino]-2,3-dihydro-1H-inden-5-yl}-

TABLE 10-continued

Name

N-methylpyrazine-2-carboxamide
3-amino-6-[3-({[6-(3-hydroxypropyl)-2,3-dihydro-1H-inden-1-yl]amino}methyl)phenyl]-N-methylpyrazine-2-carboxamide
5-(3-{[(1S)-2,3-dihydro-1H-inden-1-ylamino]methyl}phenyl)-3-(1,3-oxazol-5-yl)pyrazin-2-amine
3-amino-6-(3-{[(1S)-2,3-dihydro-1H-inden-1-ylamino]methyl}phenyl)pyrazine-2-carbohydrazide
3-amino-6-(3-{[(1S)-2,3-dihydro-1H-inden-1-ylamino]methyl}phenyl)pyrazine-2-carboxamide
1-[3-amino-6-(3-{[(1S)-2,3-dihydro-1H-inden-1-ylamino]methyl}phenyl)pyrazin-2-yl]ethanone
3-amino-6-{3-[(2,3-dihydro-1H-inden-1-ylamino)methyl]phenyl}-N-(naphthalen-2-ylmethyl)pyrazine-2-carboxamide
3-amino-N-cyclohexyl-6-{3-[(2,3-dihydro-1H-inden-1-ylamino)methyl]phenyl}pyrazine-2-carboxamide
3-amino-6-(3-{[(1S)-2,3-dihydro-1H-inden-1-ylamino]methyl}phenyl)-N-(pyridin-4-ylmethyl)pyrazine-2-carboxamide
{3-[5-amino-6-(4H-1,2,4-triazol-3-yl)pyrazin-2-yl]phenyl}methanol
5-(3-{[(1S)-2,3-dihydro-1H-inden-1-ylamino]methyl}phenyl)-3-(4H-1,2,4-triazol-3-yl)pyrazin-2-amine
3-amino-6-(3-{[(1S)-2,3-dihydro-1H-inden-1-ylamino]methyl}phenyl)-N-(2,2,2-trifluoroethyl)pyrazine-2-carboxamide
3-amino-6-(3-{[(1S)-2,3-dihydro-1H-inden-1-ylamino]methyl}phenyl)-N-(5-hydroxypentyl)pyrazine-2-carboxamide
3-amino-6-(3-{[(1S)-2,3-dihydro-1H-inden-1-ylamino]methyl}phenyl)-N-(4-hydroxybutyl)pyrazine-2-carboxamide
3-amino-6-(3-{[(1S)-2,3-dihydro-1H-inden-1-ylamino]methyl}phenyl)-N-(2-pyrrolidin-1-ylethyl)pyrazine-2-carboxamide
3-amino-6-(3-{[(1S)-2,3-dihydro-1H-inden-1-ylamino]methyl}phenyl)-N-(2-piperidin-1-ylethyl)pyrazine-2-carboxamide
3-amino-6-(3-{[(1S)-2,3-dihydro-1H-inden-1-ylamino]methyl}phenyl)-N-(2-morpholin-4-ylethyl)pyrazine-2-carboxamide
3-amino-N-(cyclopropylmethyl)-6-(3-{[(1S)-2,3-dihydro-1H-inden-1-ylamino]methyl}phenyl)pyrazine-2-carboxamide
3-amino-6-(3-{[(1S)-2,3-dihydro-1H-inden-1-ylamino]methyl}phenyl)-N-(phenylmethyl)pyrazine-2-carboxamide
3-amino-6-(3-{[(1S)-2,3-dihydro-1H-inden-1-ylamino]methyl}phenyl)-N-(2-phenylethyl)pyrazine-2-carboxamide
[3-amino-6-(3-{[(1S)-2,3-dihydro-1H-inden-1-ylamino]methyl}phenyl)pyrazin-2-yl](phenyl)methanone
3-amino-6-(3-{[(1S)-2,3-dihydro-1H-inden-1-ylamino]methyl}phenyl)-N-(2-hydroxyethyl)pyrazine-2-carboxamide
3-amino-N-cyclopropyl-6-(3-{[(1S)-2,3-dihydro-1H-inden-1-ylamino]methyl}phenyl)pyrazine-2-carboxamide
5-(3-{[(1S)-2,3-dihydro-1H-inden-1-ylamino]methyl}phenyl)-3-(pyrrolidin-1-ylcarbonyl)pyrazin-2-amine
{3-[5-amino-6-(5-methyl-4H-1,2,4-triazol-3-yl)pyrazin-2-yl]phenyl}methanol
{3-[5-amino-6-(5-phenyl-4H-1,2,4-triazol-3-yl)pyrazin-2-yl]phenyl}methanol
(3-{5-amino-6-[5-(phenylmethyl)-4H-1,2,4-triazol-3-yl]pyrazin-2-yl}phenyl)methanol
3-amino-6-(3-{[(1S)-2,3-dihydro-1H-inden-1-ylamino]methyl}phenyl)-N'-methylpyrazine-2-carbohydrazide
3-amino-6-(3-{[(1S)-2,3-dihydro-1H-inden-1-ylamino]methyl}phenyl)-N,N-dimethylpyrazine-2-carboxamide
5-(3-{[(1S)-2,3-dihydro-1H-inden-1-ylamino]methyl}phenyl)-3-[5-(phenylmethyl)-4H-1,2,4-triazol-3-yl]pyrazin-2-amine
3-amino-6-(3-{[(1S)-2,3-dihydro-1H-inden-1-ylamino]methyl}phenyl)-N-[2-(dimethylamino)ethyl]pyrazine-2-carboxamide
5-(3-{[(1S)-2,3-dihydro-1H-inden-1-ylamino]methyl}phenyl)-3-(3-phenyl-1H-1,2,4-triazol-5-yl)pyrazin-2-amine
3-amino-6-(3-{[(1S)-2,3-dihydro-1H-inden-1-ylamino]methyl}phenyl)-N-[2-(1H-imidazol-4-yl)ethyl]pyrazine-2-carboxamide
3-amino-6-(3-{[(1S)-2,3-dihydro-1H-inden-1-ylamino]methyl}phenyl)-N-[2-(methylamino)ethyl]pyrazine-2-carboxamide
3-{5-amino-6-[(3-fluorophenyl)carbonyl]pyrazin-2-yl}-N-(phenylmethyl)benzamide
3-amino-6-(3-{[(1S)-2,3-dihydro-1H-inden-1-ylamino]methyl}phenyl)-N-(3-hydroxypropyl)pyrazine-2-carboxamide
1,1-dimethylethyl 4-({[3-amino-6-(3-{[(phenylmethyl)amino]carbonyl}phenyl)pyrazin-2-yl]carbonyl}amino)piperidine-1-carboxylate
1,1-dimethylethyl 4-[({[3-amino-6-(3-{[(phenylmethyl)amino]carbonyl}phenyl)pyrazin-2-yl]carbonyl}amino)methyl]piperidine-1-carboxylate
3-amino-6-(3-{[(phenylmethyl)amino]carbonyl}phenyl)-N-piperidin-4-ylpyrazine-2-carboxamide
3-amino-6-(3-{[(phenylmethyl)amino]carbonyl}phenyl)-N-(piperidin-4-

TABLE 10-continued

Name ylmethyl)pyrazine-2-carboxamide
3-[5-amino-6-(morpholin-4-ylcarbonyl)pyrazin-2-yl]-N-(phenylmethyl)benzamide
1,1-dimethylethyl 3-({[3-amino-6-(3-{[(phenylmethyl)amino]carbonyl}phenyl)pyrazin-2-yl]carbonyl}amino)pyrrolidine-1-carboxylate
3-amino-6-(3-{[(phenylmethyl)amino]carbonyl}phenyl)-N-pyrrolidin-3-ylpyrazine-2-carboxamide
(3-{5-amino-6-[5-(1,1-dimethylethyl)-4H-1,2,4-triazol-3-yl]pyrazin-2-yl}phenyl)methanol
{3-[5-amino-6-(5-furan-2-yl-4H-1,2,4-triazol-3-yl)pyrazin-2-yl]phenyl}methanol
[3-(5-amino-6-{5-[3-(methyloxy)phenyl]-4H-1,2,4-triazol-3-yl}pyrazin-2-yl)phenyl]methanol
2-({3-amino-6-[3-(hydroxymethyl)phenyl]pyrazin-2-yl}carbonyl)-N-phenylhydrazinecarboxamide
3-{5-amino-6-[(4-methylpiperazin-1-yl)carbonyl]pyrazin-2-yl}-N-(phenylmethyl)benzamide
3-(5-amino-6-{[4-(4-fluorophenyl)piperazin-1-yl]carbonyl}pyrazin-2-yl)-N-(phenylmethyl)benzamide
3-(5-amino-6-{[4-(phenylmethyl)piperazin-1-yl]carbonyl}pyrazin-2-yl)-N-(phenylmethyl)benzamide
methyl N-{[3-amino-6-(3-{[(phenylmethyl)amino]carbonyl}phenyl)pyrazin-2-yl]carbonyl}glycinate
N-{[3-amino-6-(3-{[(phenylmethyl)amino]carbonyl}phenyl)pyrazin-2-yl]carbonyl}glycine
3-{5-amino-6-[(3,5-difluorophenyl)carbonyl]pyrazin-2-yl}-N-(phenylmethyl)benzamide
3-[5-amino-6-(biphenyl-4-ylcarbonyl)pyrazin-2-yl]-N-(phenylmethyl)benzamide
{3-[5-amino-6-(3-pyridin-3-yl-1H-1,2,4-triazol-5-yl)pyrazin-2-yl]phenyl}methanol
(3-{5-amino-6-[3-(4-chlorophenyl)-1H-1,2,4-triazol-5-yl]pyrazin-2-yl}phenyl)methanol
5-(3-{[(1S)-2,3-dihydro-1H-inden-1-ylamino]methyl}phenyl)-3-[5-(1,1-dimethylethyl)-4H-1,2,4-triazol-3-yl]pyrazin-2-amine
(3-{5-amino-6-[3-(2-thienyl)-1H-1,2,4-triazol-5-yl]pyrazin-2-yl}phenyl)methanol
5-(3-{[(1S)-2,3-dihydro-1H-inden-1-ylamino]methyl}phenyl)-3-{3-[3-(methyloxy)phenyl]-1H-1,2,4-triazol-5-yl}pyrazin-2-amine
3-amino-6-(3-{[(1S)-2,3-dihydro-1H-inden-1-ylamino]methyl}phenyl)-N-[3-(dimethylamino)propyl]pyrazine-2-carboxamide
3-amino-6-(3-{[(1S)-2,3-dihydro-1H-inden-1-ylamino]methyl}phenyl)-N-[3-(1H-imidazol-1-yl)propyl]pyrazine-2-carboxamide
3-{5-amino-6-[(4-chloro-3-fluorophenyl)carbonyl]pyrazin-2-yl}-N-(phenylmethyl)benzamide
3-(5-amino-6-{[2,4-bis(methyloxy)phenyl]carbonyl}pyrazin-2-yl)-N-(phenylmethyl)benzamide
3-(5-amino-6-{[4-(dimethylamino)phenyl]carbonyl}pyrazin-2-yl)-N-(phenylmethyl)benzamide
methyl 1-{[3-amino-6-(3-{[(phenylmethyl)amino]carbonyl}phenyl)pyrazin-2-yl]carbonyl}-L-prolinate
methyl 1-{[3-amino-6-(3-{[(phenylmethyl)amino]carbonyl}phenyl)pyrazin-2-yl]carbonyl}piperidine-3-carboxylate
1,1-dimethylethyl 4-{[3-amino-6-(3-{[(phenylmethyl)amino]carbonyl}phenyl)pyrazin-2-yl]carbonyl}piperazine-1-carboxylate
3-[5-amino-6-(piperazin-1-ylcarbonyl)pyrazin-2-yl]-N-(phenylmethyl)benzamide
N-{[3-amino-6-(3-{[(phenylmethyl)amino]carbonyl}phenyl)pyrazin-2-yl]carbonyl}glutamic acid
5-(3-{[(1S)-2,3-dihydro-1H-inden-1-ylamino]methyl}phenyl)-3-{5-[(methyloxy)methyl]-4H-1,2,4-triazol-3-yl}pyrazin-2-amine
5-(3-{[(1S)-2,3-dihydro-1H-inden-1-ylamino]methyl}phenyl)-3-(3-pyridin-3-yl-1H-1,2,4-triazol-5-yl)pyrazin-2-amine
3-amino-6-(3-{[(1S)-2,3-dihydro-1H-inden-1-ylamino]methyl}phenyl)-N-[3-(methylamino)propyl]pyrazine-2-carboxamide
3-amino-6-(3-{[(1S)-2,3-dihydro-1H-inden-1-ylamino]methyl}phenyl)-N-(3-pyrrolidin-1-ylpropyl)pyrazine-2-carboxamide
3-(5-amino-6-{(1E)-N-[4-(methyloxy)phenyl]ethanehydrazonoyl}pyrazin-2-yl)-N-(phenylmethyl)benzamide
3-(5-amino-6-{(1E)-N-[4-(1-methylethyl)phenyl]ethanehydrazonoyl}pyrazin-2-yl)-N-(phenylmethyl)benzamide
3-{5-amino-6-[(1E)-N-1,3-benzothiazol-2-ylethanehydrazonoyl]pyrazin-2-yl}-N-(phenylmethyl)benzamide
3-{5-amino-6-[(1E)-N-(4-methylphenyl)ethanehydrazonoyl]pyrazin-2-yl}-N-(phenylmethyl)benzamide
3-{5-amino-6-[(1E)-N-(4-chlorophenyl)ethanehydrazonoyl]pyrazin-2-yl}-N-(phenylmethyl)benzamide
3-{5-amino-6-[(1E)-N-methyl-N-phenylethanehydrazonoyl]pyrazin-2-yl}-N-(phenylmethyl)benzamide
3-{5-amino-6-[(1E)-N-(2-hydroxyethyl)ethanehydrazonoyl]pyrazin-2-yl}-N-(phenylmethyl)benzamide TABLE 10-continued

| Name |
| --- |
| {3-[5-amino-6-(3-pyridin-4-yl-1H-1,2,4-triazol-5-yl)pyrazin-2-yl]phenyl}methanol |
| {3-[5-amino-6-(3-piperidin-4-yl-1H-1,2,4-triazol-5-yl)pyrazin-2-yl]phenyl}methanol |
| 3-[5-amino-6-(2-aminopyrimidin-4-yl)pyrazin-2-yl]-N-(phenylmethyl)benzamide |
| 3-{5-amino-6-[2-(dimethylamino)pyrimidin-4-yl]pyrazin-2-yl}-N-(phenylmethyl)benzamide |
| ethyl N-{[3-amino-6-(3-{[(phenylmethyl)amino]carbonyl}phenyl)pyrazin-2-yl]carbonyl}-L-tyrosinate |
| N-{[3-amino-6-(3-{[(phenylmethyl)amino]carbonyl}phenyl)pyrazin-2-yl]carbonyl}-D-tyrosine |
| 1,1-dimethylethyl [3-({[3-amino-6-(3-{[(phenylmethyl)amino]carbonyl}phenyl)pyrazin-2-yl]carbonyl}amino)propyl]carbamate |
| 3-amino-N-(3-aminopropyl)-6-(3-{[(phenylmethyl)amino]carbonyl}phenyl)pyrazine-2-carboxamide |
| 1-{[3-amino-6-(3-{[(phenylmethyl)amino]carbonyl}phenyl)pyrazin-2-yl]carbonyl}piperidine-3-carboxylic |
| 1,1-dimethylethyl [2-({[3-amino-6-(3-{[(phenylmethyl)amino]carbonyl}phenyl)pyrazin-2-yl]carbonyl}amino)ethyl]carbamate |
| 3-amino-N-(2-aminoethyl)-6-(3-{[(phenylmethyl)amino]carbonyl}phenyl)pyrazine-2-carboxamide |
| 1,1-dimethylethyl (1-{[3-amino-6-(3-{[(phenylmethyl)amino]carbonyl}phenyl)pyrazin-2-yl]carbonyl}piperidin-4-yl)carbamate |
| 3-{5-amino-6-[(4-aminopiperidin-1-yl)carbonyl]pyrazin-2-yl}-N-(phenylmethyl)benzamide |
| 3-{5-amino-6-[imino(2-phenylhydrazino)methyl]pyrazin-2-yl}-N-(phenylmethyl)benzamide |
| 3-{5-amino-6-[imino(morpholin-4-ylamino)methyl]pyrazin-2-yl}-N-(phenylmethyl)benzamide |
| 3-(5-amino-6-{imino[(4-methylpiperazin-1-yl)amino]methyl}pyrazin-2-yl)-N-(phenylmethyl)benzamide |
| 3-{5-amino-6-[imino(piperidin-1-ylamino)methyl]pyrazin-2-yl}-N-(phenylmethyl)benzamide |
| 3-{5-amino-6-[(azepan-1-ylamino)(imino)methyl]pyrazin-2-yl}-N-(phenylmethyl)benzamide |
| 3-{5-amino-6-[imino({(2R)-2-[(methyloxy)methyl]pyrrolidin-1-yl}amino)methyl]pyrazin-2-yl}-N-(phenylmethyl)benzamide |
| {3-[5-amino-6-(3-piperidin-3-yl-1H-1,2,4-triazol-5-yl)pyrazin-2-yl]phenyl}methanol |
| 3-{5-amino-6-[(1E)-N-morpholin-4-ylethanimidoyl]pyrazin-2-yl}-N-(phenylmethyl)benzamide |
| 4-((2E)-2-{1-[3-amino-6-(3-{[(phenylmethyl)amino]carbonyl}phenyl)pyrazin-2-yl]ethylidene}hydrazino)benzoic acid |
| ethyl ((2E)-2-{1-[3-amino-6-(3-{[(phenylmethyl)amino]carbonyl}phenyl)pyrazin-2-yl]ethylidene}hydrazino)acetate |
| 3-{5-amino-6-[(1E)-N,N-dimethylethanehydrazonoyl]pyrazin-2-yl}-N-(phenylmethyl)benzamide |
| 3-(5-amino-6-{(1E)-N-[4-(methylsulfonyl)phenyl]ethanehydrazonoyl}pyrazin-2-yl)-N-(phenylmethyl)benzamide |
| 3-{5-amino-6-[(1E)-N-(4-cyanophenyl)ethanehydrazonoyl]pyrazin-2-yl}-N-(phenylmethyl)benzamide |
| 3-{5-amino-6-[(1E)-N-pyridin-2-ylethanehydrazonoyl]pyrazin-2-yl}-N-(phenylmethyl)benzamide |
| 3-(5-amino-6-{(1E)-N-[amino(imino)methyl]ethanehydrazonoyl}pyrazin-2-yl)-N-(phenylmethyl)benzamide |
| 3-[5-amino-6-((1E)-N-{4-[(trifluoromethyl)oxy]phenyl}ethanehydrazonoyl)pyrazin-2-yl]-N-(phenylmethyl)benzamide |
| 3-(5-Amino-6-{1-[(4-nitro-phenyl)-hydrazono]-ethyl}-pyrazin-2-yl)-N-benzyl-benzamide |
| 3-(5-amino-6-{(1E)-N-[4-(trifluoromethyl)pyrimidin-2-yl]ethanehydrazonoyl}pyrazin-2-yl)-N-(phenylmethyl)benzamide |
| 3-{5-amino-6-[(1E)-N-1H-1,2,3-benzotriazol-1-ylethanimidoyl]pyrazin-2-yl}-N-(phenylmethyl)benzamide |
| 3-{5-amino-6-[(1E)-N-methylethanehydrazonoyl]pyrazin-2-yl}-N-(phenylmethyl)benzamide |
| 5-(3-{[(1S)-2,3-dihydro-1H-inden-1-ylamino]methyl}phenyl)-3-(3-piperidin-4-yl-1H-1,2,4-triazol-5-yl)pyrazin-2-amine |
| 3-(5-amino-6-{(1E)-N-[4-(trifluoromethyl)phenyl]ethanehydrazonoyl}pyrazin-2-yl)-N-(phenylmethyl)benzamide |
| 3-{5-amino-6-[(1E)-N-phenylethanehydrazonoyl]pyrazin-2-yl}-N-(phenylmethyl)benzamide |
| 3-{5-amino-6-[(1E)-N-(4-methylpiperazin-1-yl)ethanimidoyl]pyrazin-2-yl}-N-(phenylmethyl)benzamide |
| {3-[5-amino-6-(3-pyrrolidin-3-yl-1H-1,2,4-triazol-5-yl)pyrazin-2- |

TABLE 10-continued

Name yl]phenyl}methanol
3-amino-6-(3-{[(1S)-2,3-dihydro-1H-inden-1-ylamino]carbonyl}phenyl)-N-[(3S)-pyrrolidin-3-yl]pyrazine-2-carboxamide
3-amino-6-(3-{[(1S)-2,3-dihydro-1H-inden-1-ylamino]carbonyl}phenyl)-N-[(3R)-pyrrolidin-3-yl]pyrazine-2-carboxamide
3-amino-6-(3-{[(1S)-2,3-dihydro-1H-inden-1-ylamino]carbonyl}phenyl)-N-[(3S)-1-(furan-2-ylcarbonyl)pyrrolidin-3-yl]pyrazine-2-carboxamide
N-[3-(acetylamino)propyl]-3-amino-6-(3-{[(phenylmethyl)amino]carbonyl}phenyl)pyrazine-2-carboxamide
3-amino-N-{3-[(furan-2-ylcarbonyl)amino]propyl}-6-(3-{[(phenylmethyl)amino]carbonyl}phenyl)pyrazine-2-carboxamide
3-amino-6-(3-{[(1S)-2,3-dihydro-1H-inden-1-ylamino]carbonyl}phenyl)-N-[(3S)-1-(pyridin-4-ylcarbonyl)pyrrolidin-3-yl]pyrazine-2-carboxamide
3-amino-6-(3-{[(phenylmethyl)amino]carbonyl}phenyl)-N-{3-[(pyridin-4-ylcarbonyl)amino]propyl}pyrazine-2-carboxamide
N-[3-({[3-amino-6-(3-{[(phenylmethyl)amino]carbonyl}phenyl)pyrazin-2-yl]carbonyl}amino)propyl]quinoxaline-2-carboxamide
3-amino-6-(3-{[(phenylmethyl)amino]carbonyl}phenyl)-N-[3-({[6-(trifluoromethyl)pyridin-3-yl]carbonyl}amino)propyl]pyrazine-2-carboxamide
3-amino-6-(3-{[(phenylmethyl)amino]carbonyl}phenyl)-N-{3-[(quinolin-8-ylsulfonyl)amino]propyl}pyrazine-2-carboxamide
3-amino-6-(3-{[(phenylmethyl)amino]carbonyl}phenyl)-N-{3-[(pyridin-2-ylsulfonyl)amino]propyl}pyrazine-2-carboxamide
3-amino-N-[3-({[(3,5-dimethylisoxazol-4-yl)amino]carbonyl}amino)propyl]-6-(3-{[(phenylmethyl)amino]carbonyl}phenyl)pyrazine-2-carboxamide
3-[5-amino-6-(2-methylpyrimidin-4-yl)pyrazin-2-yl]-N-(phenylmethyl)benzamide
3-{5-amino-6-[2-(methylamino)pyrimidin-4-yl]pyrazin-2-yl}-N-(phenylmethyl)benzamide
3-amino-6-(3-{[(phenylmethyl)amino]carbonyl}phenyl)-N-{2-[(pyridin-4-ylcarbonyl)amino]ethyl}pyrazine-2-carboxamide
3-amino-N-{2-[(furan-2-ylcarbonyl)amino]ethyl}-6-(3-{[(phenylmethyl)amino]carbonyl}phenyl)pyrazine-2-carboxamide
N,N'-cyclohexane-1,2-diylbis[3-amino-6-(3-{[(phenylmethyl)amino]carbonyl}phenyl)pyrazine-2-carboxamide]
N-[2-(acetylamino)ethyl]-3-amino-6-(3-{[(phenylmethyl)amino]carbonyl}phenyl)pyrazine-2-carboxamide
3-amino-6-(3-{[(phenylmethyl)amino]carbonyl}phenyl)-N-{2-[(quinolin-8-ylsulfonyl)amino]ethyl}pyrazine-2-carboxamide
N-[2-({[3-amino-6-(3-{[(phenylmethyl)amino]carbonyl}phenyl)pyrazin-2-yl]carbonyl}amino)ethyl]quinoxaline-2-carboxamide
3-amino-N-(2-{[(2-chloropyridin-3-yl)carbonyl]amino}ethyl)-6-(3-{[(phenylmethyl)amino]carbonyl}phenyl)pyrazine-2-carboxamide
3-amino-6-(3-{[(phenylmethyl)amino]carbonyl}phenyl)-N-{2-[(pyridin-2-ylsulfonyl)amino]ethyl}pyrazine-2-carboxamide
3-amino-N-[2-({[(3,5-dimethylisoxazol-4-yl)amino]carbonyl}amino)ethyl]-6-(3-{[(phenylmethyl)amino]carbonyl}phenyl)pyrazine-2-carboxamide
3-amino-6-(3-{[(phenylmethyl)amino]carbonyl}phenyl)pyrazine-2-carboxamide
3-[5-amino-6-(imino{2-[4-(trifluoromethyl)pyrimidin-2-yl]hydrazino}methyl)pyrazin-2-yl]-N-(phenylmethyl)benzamide
3-{5-amino-6-[[2-(1,3-benzothiazol-2-yl)hydrazino](imino)methyl]pyrazin-2-yl}-N-(phenylmethyl)benzamide
3-[5-amino-6-(1,5-diphenyl-1H-1,2,4-triazol-3-yl)pyrazin-2-yl]-N-(phenylmethyl)benzamide
3-[5-amino-6-(1,5-dimethyl-1H-1,2,4-triazol-3-yl)pyrazin-2-yl]-N-(phenylmethyl)benzamide
3-[5-amino-6-(1-methyl-5-phenyl-1H-1,2,4-triazol-3-yl)pyrazin-2-yl]-N-(phenylmethyl)benzamide
3-[5-amino-6-((1E)-N-{(2R)-2-[(methyloxy)methyl]pyrrolidin-1-yl}ethanimidoyl)pyrazin-2-yl]-N-(phenylmethyl)benzamide
3-{5-amino-6-[(1E)-N-azepan-1-ylethanimidoyl]pyrazin-2-yl}-N-(phenylmethyl)benzamide
3-(5-amino-6-{(E)-[(phenylmethyl)hydrazono]methyl}pyrazin-2-yl)-N-(phenylmethyl)benzamide
3-[5-amino-6-((E)-{[amino(imino)methyl]hydrazono}methyl)pyrazin-2-yl]-N-(phenylmethyl)benzamide
3-(5-amino-6-{(E)-[(2-hydroxyethyl)hydrazono]methyl}pyrazin-2-yl)-N-(phenylmethyl)benzamide
3-{5-amino-6-[(E)-(pyridin-2-ylhydrazono)methyl]pyrazin-2-yl}-N-(phenylmethyl)benzamide
3-(5-amino-6-{(E)-[(4-cyanophenyl)hydrazono]methyl}pyrazin-2-yl)-N-(phenylmethyl)benzamide
3-(5-amino-6-{(E)-[(4-methylphenyl)hydrazono]methyl}pyrazin-2-yl)-N-(phenylmethyl)benzamide
3-{5-amino-6-[(E)-(hydroxyimino)methyl]pyrazin-2-yl}-N-(phenylmethyl)benzamide
{3-[5-amino-6-(3-pyridin-2-yl-1H-1,2,4-triazol-5-yl)pyrazin-2-yl]phenyl}methanol
5-(3-{[(1R)-2,3-dihydro-1H-inden-1-ylamino]methyl}phenyl)-3-(3-piperidin-3-yl- TABLE 10-continued

| Name |
|---|
| 1H-1,2,4-triazol-5-yl)pyrazin-2-amine |
| 3-amino-N-[3-({[4-(dimethylamino)phenyl]carbonyl}amino)propyl]-6-(3-{[(phenylmethyl)amino]carbonyl}phenyl)pyrazine-2-carboxamide |
| 3-amino-6-(3-{[(1S)-2,3-dihydro-1H-inden-1-ylamino]methyl}phenyl)-N-[(3S)-pyrrolidin-3-yl]pyrazine-2-carboxamide |
| 1,1-dimethylethyl 4-[(3S)-3-({[3-amino-6-(3-{[(phenylmethyl)amino]carbonyl}phenyl)pyrazin-2-yl]carbonyl}amino)pyrrolidin-1-yl]piperidine-1-carboxylate |
| 3-amino-6-(3-{[(phenylmethyl)amino]carbonyl}phenyl)-N-[(3S)-1-piperidin-4-ylpyrrolidin-3-yl]pyrazine-2-carboxamide |
| 1,1-dimethylethyl (2R)-2-{[(3S)-3-({[3-amino-6-(3-{[(phenylmethyl)amino]carbonyl}phenyl)pyrazin-2-yl]carbonyl}amino)pyrrolidin-1-yl]methyl}pyrrolidine-1-carboxylate |
| 3-amino-6-(3-{[(phenylmethyl)amino]carbonyl}phenyl)-N-{(3S)-1-[(2R)-pyrrolidin-2-ylmethyl]pyrrolidin-3-yl}pyrazine-2-carboxamide |
| 3-amino-N-((3S)-1-{[4-(dimethylamino)phenyl]methyl}pyrrolidin-3-yl)-6-(3-{[(phenylmethyl)amino]carbonyl}phenyl)pyrazine-2-carboxamide |
| 3-amino-N-{2-[({[4-(dimethylamino)phenyl]amino}carbonyl)amino]ethyl}-6-(3-{[(phenylmethyl)amino]carbonyl}phenyl)pyrazine-2-carboxamide |
| 3-amino-N-[2-({[4-(dimethylamino)phenyl]carbonyl}amino)ethyl]-6-(3-{[(phenylmethyl)amino]carbonyl}phenyl)pyrazine-2-carboxamide |
| 3-{5-amino-6-[imino(2-pyridin-2-ylhydrazino)methyl]pyrazin-2-yl}-N-(phenylmethyl)benzamide |
| 3-[5-amino-6-(morpholin-4-ylmethyl)pyrazin-2-yl]-N-(phenylmethyl)benzamide |
| ethyl 1-{[3-amino-6-(3-{[(phenylmethyl)amino]carbonyl}phenyl)pyrazin-2-yl]methyl}piperidine-4-carboxylate |
| 3-amino-6-(3-{[(phenylmethyl)amino]carbonyl}phenyl)-N-[(3S)-1-(pyridin-2-ylmethyl)pyrrolidin-3-yl]pyrazine-2-carboxamide |
| methyl N-{[3-amino-6-(3-{[(phenylmethyl)amino]carbonyl}phenyl)pyrazin-2-yl]carbonyl}threoninate |
| {3-[5-amino-6-(3-piperidin-2-yl-1H-1,2,4-triazol-5-yl)pyrazin-2-yl]phenyl}methanol |
| 3-(ethylamino)-N-[(3S)-1-ethylpyrrolidin-3-yl]-6-(3-{[(phenylmethyl)amino]carbonyl}phenyl)pyrazine-2-carboxamide |
| 3-amino-N-[(3S)-1-ethylpyrrolidin-3-yl]-6-(3-{[(phenylmethyl)amino]carbonyl}phenyl)pyrazine-2-carboxamide |
| 3-[5-amino-6-(1-methyl-5-piperidin-2-yl-1H-1,2,4-triazol-3-yl)pyrazin-2-yl]-N-(phenylmethyl)benzamide |
| 3-[5-amino-6-(5-methyl-1-pyridin-2-yl-1H-1,2,4-triazol-3-yl)pyrazin-2-yl]-N-(phenylmethyl)benzamide |
| {3-[5-amino-6-(3-morpholin-2-yl-1H-1,2,4-triazol-5-yl)pyrazin-2-yl]phenyl}methanol |
| 5-(3-{[(1S)-2,3-dihydro-1H-inden-1-ylamino]methyl}phenyl)-3-{3-[(3S)-piperidin-3-yl]-1H-1,2,4-triazol-5-yl}pyrazin-2-amine |
| 5-(3-{[(1S)-2,3-dihydro-1H-inden-1-ylamino]methyl}phenyl)-3-{3-[(3R)-piperidin-3-yl]-1H-1,2,4-triazol-5-yl}pyrazin-2-amine |
| 3-amino-6-(3-{[(1S)-2,3-dihydro-1H-inden-1-ylamino]carbonyl}phenyl)-N-[(3S)-1-ethylpyrrolidin-3-yl]pyrazine-2-carboxamide |
| 6-(3-{[(1S)-2,3-dihydro-1H-inden-1-ylamino]carbonyl}phenyl)-3-(ethylamino)-N-[(3S)-1-ethylpyrrolidin-3-yl]pyrazine-2-carboxamide |
| 3-amino-6-[3-({[(1S,2R)-2-hydroxy-2,3-dihydro-1H-inden-1-yl]amino}carbonyl)phenyl]-N-[(3S)-pyrrolidin-3-yl]pyrazine-2-carboxamide |
| 1,1-dimethylethyl (3S)-3-({[3-amino-6-(3-{[(1S)-2,3-dihydro-1H-inden-1-ylamino]carbonyl}phenyl)pyrazin-2-yl]carbonyl}amino)pyrrolidine-1-carboxylate |
| 1,1-dimethylethyl (3S)-3-[({3-amino-6-[3-({[(1R)-1-phenylethyl]amino}carbonyl)phenyl]pyrazin-2-yl}carbonyl)amino]pyrrolidine-1-carboxylate |
| 1,1-dimethylethyl (3S)-3-[({3-amino-6-[3-(3,4-dihydroisoquinolin-2(1H)-ylcarbonyl)phenyl]pyrazin-2-yl}carbonyl)amino]pyrrolidine-1-carboxylate |
| 1,1-dimethylethyl (3S)-3-({[3-amino-6-(3-{[(2-phenylethyl)amino]carbonyl}phenyl)pyrazin-2-yl]carbonyl}amino)pyrrolidine-1-carboxylate |
| 1,1-dimethylethyl (3S)-3-[({3-amino-6-[3-({[(1S)-1-phenylethyl]amino}carbonyl)phenyl]pyrazin-2-yl}carbonyl)amino]pyrrolidine-1-carboxylate |
| 3-amino-6-[3-(3,4-dihydroisoquinolin-2(1H)-ylcarbonyl)phenyl]-N-[(3S)-pyrrolidin-3-yl]pyrazine-2-carboxamide |
| 3-amino-6-(3-{[(2-phenylethyl)amino]carbonyl}phenyl)-N-[(3S)-pyrrolidin-3-yl]pyrazine-2-carboxamide |
| 3-amino-6-[3-({[(1R)-1-phenylethyl]amino}carbonyl)phenyl]-N-[(3S)-pyrrolidin-3-yl]pyrazine-2-carboxamide |
| 3-amino-6-[3-({[(1S)-1-phenylethyl]amino}carbonyl)phenyl]-N-[(3S)-pyrrolidin-3-yl]pyrazine-2-carboxamide |
| 3-{5-amino-6-[(2-ethylhydrazino)(imino)methyl]pyrazin-2-yl}-N-(2,3-dihydro-1H-inden-1-yl)benzamide |
| 3-{5-amino-6-[imino(2-methylhydrazino)methyl]pyrazin-2-yl}-N-[(1S)-2,3-dihydro-1H-inden-1-yl]benzamide |

TABLE 10-continued

Name

3-{5-amino-6-[imino(2-phenylhydrazino)methyl]pyrazin-2-yl}-N-[(1S)-2,3-dihydro-1H-inden-1-yl]benzamide
phenylmethyl 3-{3-[3-amino-6-(3-{[(1S)-2,3-dihydro-1H-inden-1-ylamino]carbonyl}phenyl)pyrazin-2-yl]-1-methyl-1H-1,2,4-triazol-5-yl}piperidine-1-carboxylate
phenylmethyl 3-{3-[3-amino-6-(3-{[(1S)-2,3-dihydro-1H-inden-1-ylamino]carbonyl}phenyl)pyrazin-2-yl]-1-ethyl-1H-1,2,4-triazol-5-yl}piperidine-1-carboxylate
5-(3-{[(1S)-2,3-dihydro-1H-inden-1-ylamino]methyl}phenyl)-3-(3-pyridin-4-yl-1H-1,2,4-triazol-5-yl)pyrazin-2-amine
[3-(5-amino-6-{3-[(3R)-piperidin-3-yl]-1H-1,2,4-triazol-5-yl}pyrazin-2-yl)phenyl]methanol
[3-(5-amino-6-{3-[(3S)-piperidin-3-yl]-1H-1,2,4-triazol-5-yl}pyrazin-2-yl)phenyl]methanol
3-amino-6-[3-({[(1R,2S)-2-hydroxy-2,3-dihydro-1H-inden-1-yl]amino}carbonyl)phenyl]-N-[(3S)-pyrrolidin-3-yl]pyrazine-2-carboxamide
3-amino-N-[(3S)-1-ethylpyrrolidin-3-yl]-6-[3-({[(1S,2R)-2-hydroxy-2,3-dihydro-1H-inden-1-yl]amino}carbonyl)phenyl]pyrazine-2-carboxamide
1,1-dimethylethyl 3-({[3-amino-6-(3-{[(1S)-2,3-dihydro-1H-inden-1-ylamino]carbonyl}phenyl)pyrazin-2-yl]carbonyl}amino)piperidine-1-carboxylate
3-amino-6-(3-{[(1S)-2,3-dihydro-1H-inden-1-ylamino]carbonyl}phenyl)-N-piperidin-3-ylpyrazine-2-carboxamide
3-amino-6-(3-{[(1S)-2,3-dihydro-1H-inden-1-ylamino]carbonyl}phenyl)-N-(1-ethylpiperidin-3-yl)pyrazine-2-carboxamide
3-amino-N-[(3S)-1-ethylpyrrolidin-3-yl]-6-[3-({[(1R,2S)-2-hydroxy-2,3-dihydro-1H-inden-1-yl]amino}carbonyl)phenyl]pyrazine-2-carboxamide
(3-{5-amino-6-[5-(1-ethylpiperidin-3-yl)-4H-1,2,4-triazol-3-yl]pyrazin-2-yl}phenyl)methanol
5-(3-{[(1S)-2,3-dihydro-1H-inden-1-ylamino]methyl}phenyl)-3-[5-(1-ethylpiperidin-3-yl)-4H-1,2,4-triazol-3-yl]pyrazin-2-amine
3-[5-amino-6-(1-ethyl-5-piperidin-3-yl-1H-1,2,4-triazol-3-yl)pyrazin-2-yl]-N-[(1R)-2,3-dihydro-1H-inden-1-yl]benzamide
3-[5-amino-6-(1-methyl-5-piperidin-3-yl-1H-1,2,4-triazol-3-yl)pyrazin-2-yl]-N-[(1S)-2,3-dihydro-1H-inden-1-yl]benzamide
(3-{5-amino-6-[3-(1-methylpiperidin-3-yl)-1H-1,2,4-triazol-5-yl]pyrazin-2-yl}phenyl)methanol
5-(3-{[(1S)-2,3-dihydro-1H-inden-1-ylamino]methyl}phenyl)-3-[3-(1-methylpiperidin-3-yl)-1H-1,2,4-triazol-5-yl]pyrazin-2-amine
1,1-dimethylethyl (3S)-3-{[(3-amino-6-{3-[({4-(methyloxy)phenyl]methyl}amino)carbonyl]phenyl}pyrazin-2-yl)carbonyl]amino}pyrrolidine-1-carboxylate
1,1-dimethylethyl (3S)-3-({[3-amino-6-(3-{[({4-[(trifluoromethyl)oxy]phenyl}methyl)amino]carbonyl}phenyl)pyrazin-2-yl]carbonyl}amino)pyrrolidine-1-carboxylate
1,1-dimethylethyl (3S)-3-[({3-amino-6-[3-({[(2-chloro-6-fluorophenyl)methyl]amino}carbonyl)phenyl]pyrazin-2-yl}carbonyl)amino]pyrrolidine-1-carboxylate
1,1-dimethylethyl (3S)-3-{[(3-amino-6-{3-[({[4-(methylthio)phenyl]methyl}amino)carbonyl]phenyl}pyrazin-2-yl)carbonyl]amino}pyrrolidine-1-carboxylate
1,1-dimethylethyl (3S)-3-{[(3-amino-6-{3-[(2,3-dihydro-1H-inden-2-ylamino)carbonyl]phenyl}pyrazin-2-yl)carbonyl]amino}pyrrolidine-1-carboxylate
3-amino-6-{3-[({[4-(methyloxy)phenyl]methyl}amino)carbonyl]phenyl}-N-[(3S)-pyrrolidin-3-yl]pyrazine-2-carboxamide
3-amino-N-[(3S)-pyrrolidin-3-yl]-6-{3-{[({4-[(trifluoromethyl)oxy]phenyl}methyl)amino]carbonyl}phenyl)pyrazine-2-carboxamide
3-amino-6-{3-[(2,3-dihydro-1H-inden-2-ylamino)carbonyl]phenyl}-N-[(3S)-pyrrolidin-3-yl]pyrazine-2-carboxamide
3-amino-6-[3-({[(2-chloro-6-fluorophenyl)methyl]amino}carbonyl)phenyl]-N-[(3S)-pyrrolidin-3-yl]pyrazine-2-carboxamide
3-amino-6-{3-[({[4-(methylthio)phenyl]methyl}amino)carbonyl]phenyl}-N-[(3S)-pyrrolidin-3-yl]pyrazine-2-carboxamide
3-{5-amino-6-[imino(2-pyridin-4-ylhydrazino)methyl]pyrazin-2-yl}-N-[(1R)-2,3-dihydro-1H-inden-1-yl]benzamide
phenylmethyl (3R)-3-{3-[3-amino-6-(3-{[(1S)-2,3-dihydro-1H-inden-1-ylamino]carbonyl}phenyl)pyrazin-2-yl]-1-ethyl-1H-1,2,4-triazol-5-yl}piperidine-1-carboxylate
3-amino-6-(3-{(1S)-1-[(1S)-2,3-dihydro-1H-inden-1-ylamino]ethyl}phenyl)-N-methylpyrazine-2-carboxamide
3-amino-6-[3-({[(1R,2S)-2-hydroxy-2,3-dihydro-1H-inden-1-yl]amino}carbonyl)phenyl]-N-[2-(1H-imidazol-4-yl)ethyl]pyrazine-2-carboxamide
1,1-dimethylethyl (3S)-3-[({[3-amino-6-(3-{[(1S)-2,3-dihydro-1H-inden-1-ylamino]carbonyl}phenyl)pyrazin-2-yl]carbonyl}amino)methyl]pyrrolidine-1-carboxylate
3-amino-6-(3-{[(1S)-2,3-dihydro-1H-inden-1-ylamino]carbonyl}phenyl)-N-[(3R)-pyrrolidin-3-ylmethyl]pyrazine-2-carboxamide TABLE 10-continued

| Name |
| --- |
| phenylmethyl (3R)-3-{3-[3-amino-6-(3-{[(1S)-2,3-dihydro-1H-inden-1-ylamino]carbonyl}phenyl)pyrazin-2-yl]-1-methyl-1H-1,2,4-triazol-5-yl}piperidine-1-carboxylate |
| 3-(5-amino-6-{5-[(3S)-piperidin-3-yl]-4H-1,2,4-triazol-3-yl}pyrazin-2-yl)-N-[(1S)-2,3-dihydro-1H-inden-1-yl]benzamide |
| 1,1-dimethylethyl (3S)-3-[({3-amino-6-[3-({[(4-chlorophenyl)methyl]amino}carbonyl)phenyl]pyrazin-2-yl}carbonyl)amino]pyrrolidine-1-carboxylate |
| 1,1-dimethylethyl (3S)-3-({[3-amino-6-(3-{[(pyridin-2-ylmethyl)amino]carbonyl}phenyl)pyrazin-2-yl]carbonyl}amino)pyrrolidine-1-carboxylate |
| 1,1-dimethylethyl (3S)-3-({[3-amino-6-(3-{[(pyridin-3-ylmethyl)amino]carbonyl}phenyl)pyrazin-2-yl]carbonyl}amino)pyrrolidine-1-carboxylate |
| 1,1-dimethylethyl (3S)-3-{[(3-amino-6-{3-[(3,4-dihydro-2H-chromen-4-ylamino)carbonyl]phenyl}pyrazin-2-yl)carbonyl]amino}pyrrolidine-1-carboxylate |
| 3-amino-6-[3-({[(4-chlorophenyl)methyl]amino}carbonyl)phenyl]-N-[(3S)-pyrrolidin-3-yl]pyrazine-2-carboxamide |
| 3-amino-6-(3-{[(pyridin-2-ylmethyl)amino]carbonyl}phenyl)-N-[(3S)-pyrrolidin-3-yl]pyrazine-2-carboxamide |
| 3-amino-6-(3-{[(pyridin-3-ylmethyl)amino]carbonyl}phenyl)-N-[(3S)-pyrrolidin-3-yl]pyrazine-2-carboxamide |
| dimethyl 5-{5-amino-6-[(methylamino)carbonyl]pyrazin-2-yl}benzene-1,3-dicarboxylate |
| 3-amino-6-(3-{[(1S)-2,3-dihydro-1H-inden-1-ylamino]carbonyl}phenyl)-N-[(3S)-piperidin-3-yl]pyrazine-2-carboxamide |
| 3-amino-6-(3-{[(1S)-2,3-dihydro-1H-inden-1-ylamino]carbonyl}phenyl)-N-[(3R)-piperidin-3-yl]pyrazine-2-carboxamide |
| 3-amino-6-[3-({[(1R,2S)-2-hydroxy-2,3-dihydro-1H-inden-1-yl]amino}carbonyl)phenyl]-N-piperidin-3-ylpyrazine-2-carboxamide |
| 3-amino-6-(3-{[(1S)-2,3-dihydro-1H-inden-1-ylamino]carbonyl}phenyl)-N-[2-(1H-imidazol-4-yl)ethyl]pyrazine-2-carboxamide |
| 3-amino-N-azepan-4-yl-6-(3-{[(1S)-2,3-dihydro-1H-inden-1-ylamino]carbonyl}phenyl)pyrazine-2-carboxamide |
| 1,1-dimethylethyl (3S)-3-{[({3-amino-6-[3-({[(1R,2S)-2-hydroxy-2,3-dihydro-1H-inden-1-yl]amino}carbonyl)phenyl]pyrazin-2-yl}carbonyl)amino]methyl}pyrrolidine-1-carboxylate |
| 1,1-dimethylethyl 4-({[3-amino-6-(3-{[(1S)-2,3-dihydro-1H-inden-1-ylamino]carbonyl}phenyl)pyrazin-2-yl]carbonyl}amino)azepane-1-carboxylate |
| 3-[5-amino-6-(5-{2-[(phenylmethyl)oxy]ethyl}-1H-1,2,4-triazol-3-yl)pyrazin-2-yl]-N-[(1S)-2,3-dihydro-1H-inden-1-yl]benzamide |
| 3-amino-6-(3-{[(1S)-2,3-dihydro-1H-inden-1-ylamino]carbonyl}-4-fluorophenyl)-N-methylpyrazine-2-carboxamide |
| 3-[5-amino-6-(1-phenyl-5-piperidin-3-yl-1H-1,2,4-triazol-3-yl)pyrazin-2-yl]-N-[(1S)-2,3-dihydro-1H-inden-1-yl]benzamide |
| 3-{5-amino-6-[amino(imino)methyl]pyrazin-2-yl}-N-[(1S)-2,3-dihydro-1H-inden-1-yl]benzamide |
| 3-(5-amino-6-{5-[(3S)-piperidin-3-yl]-4H-1,2,4-triazol-3-yl}pyrazin-2-yl)-N-[(1R,2S)-2-hydroxy-2,3-dihydro-1H-inden-1-yl]benzamide |
| 1,1-dimethylethyl (3S)-3-({[3-amino-6-(3-{[(1S)-2,3-dihydro-1H-inden-1-ylamino]carbonyl}phenyl)pyrazin-2-yl]carbonyl}amino)piperidine-1-carboxylate |
| 1,1-dimethylethyl (3S)-3-[({3-amino-6-[3-({[(1R,2S)-2-hydroxy-2,3-dihydro-1H-inden-1-yl]amino}carbonyl)phenyl]pyrazin-2-yl}carbonyl)amino]piperidine-1-carboxylate |
| 3-amino-6-{3-[(3,4-dihydro-2H-chromen-4-ylamino)carbonyl]phenyl}-N-[(3S)-pyrrolidin-3-yl]pyrazine-2-carboxamide |
| 3-amino-6-{3-[(2,3-dihydro-1-benzofuran-3-ylamino)carbonyl]phenyl}-N-[(3S)-pyrrolidin-3-yl]pyrazine-2-carboxamide |
| 3-amino-6-[3-({[(1R,2S)-2-hydroxy-2,3-dihydro-1H-inden-1-yl]amino}carbonyl)phenyl]-N-[(3R)-pyrrolidin-3-ylmethyl]pyrazine-2-carboxamide |
| 1,1-dimethylethyl 4-[({3-amino-6-[3-({[(1R,2S)-2-hydroxy-2,3-dihydro-1H-inden-1-yl]amino}carbonyl)phenyl]pyrazin-2-yl}carbonyl)amino]azepane-1-carboxylate |
| 3-amino-N-azepan-4-yl-6-[3-({[(1R,2S)-2-hydroxy-2,3-dihydro-1H-inden-1-yl]amino}carbonyl)phenyl]pyrazine-2-carboxamide |
| 3-amino-N-azepan-4-yl-6-{3-[(3aR,8aS)-8,8a-dihydro-3aH-indeno[1,2-d][1,3]oxazol-2-yl]phenyl}pyrazine-2-carboxamide |
| 1,1-dimethylethyl (3R)-3-[({[3-amino-6-(3-{[(1S)-2,3-dihydro-1H-inden-1-ylamino]carbonyl}phenyl)pyrazin-2-yl]carbonyl}amino)methyl]pyrrolidine-1-carboxylate |
| 3-amino-6-(3-{[(1S)-2,3-dihydro-1H-inden-1-ylamino]carbonyl}phenyl)-N-[(3S)-pyrrolidin-3-ylmethyl]pyrazine-2-carboxamide |
| 1,1-dimethylethyl (3R)-3-{[({3-amino-6-[3-({[(1R,2S)-2-hydroxy-2,3-dihydro-1H-inden-1-yl]amino}carbonyl)phenyl]pyrazin-2-yl}carbonyl)amino]methyl}pyrrolidine-1-carboxylate |
| 3-amino-6-[3-({[(1R,2S)-2-hydroxy-2,3-dihydro-1H-inden-1-yl]amino}carbonyl)phenyl]-N-[(3S)-pyrrolidin-3-ylmethyl]pyrazine-2-carboxamide |
| 3-amino-6-(3-{[(1S)-2,3-dihydro-1H-inden-1-ylamino]carbonyl}-5-fluorophenyl)- |

TABLE 10-continued

Name

N-methylpyrazine-2-carboxamide
3-{5-amino-6-[(methylamino)carbonyl]pyrazin-2-yl}-5-[(methyloxy)carbonyl]benzoic acid
methyl 3-{5-amino-6-[(methylamino)carbonyl]pyrazin-2-yl}-5-{[(1S)-2,3-dihydro-1H-inden-1-ylamino]carbonyl}benzoate
5-{5-amino-6-[(methylamino)carbonyl]pyrazin-2-yl}-N-[(1S)-2,3-dihydro-1H-inden-1-yl]-N'-pyrrolidin-3-ylbenzene-1,3-dicarboxamide
3-[5-amino-6-(5-phenyl-1-pyridin-2-yl-1H-1,2,4-triazol-3-yl)pyrazin-2-yl]-N-(phenylmethyl)benzamide
3-[5-amino-6-(5-methyl-1-pyridin-4-yl-1H-1,2,4-triazol-3-yl)pyrazin-2-yl]-N-[(1S)-2,3-dihydro-1H-inden-1-yl]benzamide
1,1-dimethylethyl (3R)-3-({[3-amino-6-(3-{[(1S)-2,3-dihydro-1H-inden-1-ylamino]carbonyl}phenyl)pyrazin-2-yl]carbonyl}amino)piperidine-1-carboxylate
1,1-dimethylethyl (3R)-3-[({3-amino-6-[3-({[(1R,2S)-2-hydroxy-2,3-dihydro-1H-inden-1-yl]amino}carbonyl)phenyl]pyrazin-2-yl}carbonyl)amino]piperidine-1-carboxylate
3-amino-6-(3-{[(1S)-2,3-dihydro-1H-inden-1-ylamino]carbonyl}phenyl)-N-[(3S)-piperidin-3-yl]pyrazine-2-carboxamide
5-{5-amino-6-[(methylamino)carbonyl]pyrazin-2-yl}-N-[(1R)-2,3-dihydro-1H-inden-1-yl]-N'-[(3R)-pyrrolidin-3-yl]benzene-1,3-dicarboxamide
(3-{5-amino-6-[3-(2-aminopyridin-4-yl)-1H-1,2,4-triazol-5-yl]pyrazin-2-yl}phenyl)methanol
3-[5-amino-6-(1,5-dimethyl-1H-1,2,4-triazol-3-yl)pyrazin-2-yl]-N-[(1S)-2,3-dihydro-1H-inden-1-yl]benzamide
1,1-dimethylethyl (3S)-3-({[3-amino-6-(3-{[(1-methyl-1-phenylethyl)amino]carbonyl}phenyl)pyrazin-2-yl]carbonyl}amino)pyrrolidine-1-carboxylate
3-amino-6-(3-{[(1-methyl-1-phenylethyl)amino]carbonyl}phenyl)-N-[(3S)-pyrrolidin-3-yl]pyrazine-2-carboxamide
3-amino-6-(3-{[(1S)-2,3-dihydro-1H-inden-1-ylamino]sulfonyl}phenyl)pyrazine-2-carboxamide
3-amino-6-(3-{[(1S)-2,3-dihydro-1H-inden-1-ylamino]sulfonyl}phenyl)-N-piperidin-3-ylpyrazine-2-carboxamide
3-amino-6-(3-{[(1S)-2,3-dihydro-1H-inden-1-ylamino]carbonyl}phenyl)-N-[(3S)-1-methylpyrrolidin-3-yl]pyrazine-2-carboxamide
3-amino-6-[3-({[(1R,2S)-2-hydroxy-2,3-dihydro-1H-inden-1-yl]amino}carbonyl)phenyl]-N-[(3S)-1-methylpyrrolidin-3-yl]pyrazine-2-carboxamide
3-amino-6-[3-({[(1R,2S)-2-hydroxy-2,3-dihydro-1H-inden-1-yl]amino}methyl)phenyl]-N-[(3S)-pyrrolidin-3-yl]pyrazine-2-carboxamide
3-amino-6-[3-({[(1R,2S)-2-hydroxy-2,3-dihydro-1H-inden-1-yl]amino}carbonyl)phenyl]-N-[(3S)-piperidin-3-yl]pyrazine-2-carboxamide
3-amino-N-[(3S)-pyrrolidin-3-yl]-6-(3-{[(1S)-1,2,3,4-tetrahydronaphthalen-1-ylamino]methyl}phenyl)pyrazine-2-carboxamide
N-[3-(5-amino-6-{5-[(3S)-piperidin-3-yl]-4H-1,2,4-triazol-3-yl}pyrazin-2-yl)phenyl]-2-(2,4-dichlorophenyl)acetamide
1,1-dimethylethyl (3S)-3-({[3-amino-6-(3-{[(1R)-2,3-dihydro-1H-inden-1-ylamino]sulfonyl}phenyl)pyrazin-2-yl]carbonyl}amino)pyrrolidine-1-carboxylate
3-amino-6-(3-hydroxyphenyl)-N-[(3S)-pyrrolidin-3-yl]pyrazine-2-carboxamide
3-amino-6-(3-{[(1R)-2,3-dihydro-1H-inden-1-ylamino]sulfonyl}phenyl)-N-[(3S)-pyrrolidin-3-yl]pyrazine-2-carboxamide
3-[5-amino-6-(1-pyridin-4-yl-1H-1,2,4-triazol-3-yl)pyrazin-2-yl]-N-[(1S)-2,3-dihydro-1H-inden-1-yl]benzamide
3-amino-N-[(3S)-pyrrolidin-3-yl]-6-[3-({[(3,4,5-trifluorophenyl)methyl]amino}carbonyl)phenyl]pyrazine-2-carboxamide
3-amino-N-[(3S)-pyrrolidin-3-yl]-6-[3-({[(2,3,6-trifluorophenyl)methyl]amino}carbonyl)phenyl]pyrazine-2-carboxamide
3-amino-N-[(3S)-pyrrolidin-3-yl]-6-[3-({[(2,3,5-trifluorophenyl)methyl]amino}carbonyl)phenyl]pyrazine-2-carboxamide
3-amino-6-[3-({[(3-bromo-4-fluorophenyl)methyl]amino}carbonyl)phenyl]-N-[(3S)-pyrrolidin-3-yl]pyrazine-2-carboxamide
3-{5-amino-6-[3-(1-methylpiperidin-3-yl)-1H-1,2,4-triazol-5-yl]pyrazin-2-yl}-N-[(2-chloro-6-fluorophenyl)methyl]benzamide
3-amino-N-1-azabicyclo[2.2.2]oct-3-yl-6-(3-{[(1S)-2,3-dihydro-1H-inden-1-ylamino]methyl}phenyl)pyrazine-2-carboxamide
3-(5-amino-6-{3-[(3S)-piperidin-3-yl]-1H-1,2,4-triazol-5-yl}pyrazin-2-yl)-N-[(4-chloro-2-fluorophenyl)methyl]benzamide
3-(5-amino-6-{3-[(3S)-piperidin-3-yl]-1H-1,2,4-triazol-5-yl}pyrazin-2-yl)-N-[(2-chlorophenyl)methyl]benzamide
1,1-dimethylethyl (3S)-3-[({3-amino-6-[3-({[(2,4-dichlorophenyl)methyl]amino}carbonyl)phenyl]pyrazin-2-yl}carbonyl)amino]pyrrolidine-1-carboxylate
1,1-dimethylethyl (3S)-3-[({3-amino-6-[3-({[(3,4-dichlorophenyl)methyl]amino}carbonyl)phenyl]pyrazin-2-yl}carbonyl)amino]pyrrolidine-1-carboxylate
5-(3-{[(1S)-2,3-dihydro-1H-inden-1-ylamino]methyl}phenyl)-3-(4-piperidin-3-yl-1,3-thiazol-2-yl)pyrazin-2-amine

TABLE 10-continued

Name 3-amino-6-[3-({[(2,4-dichlorophenyl)methyl]amino}carbonyl)phenyl]-N-[(3S)-pyrrolidin-3-yl]pyrazine-2-carboxamide
3-amino-6-[3-({[(3,4-dichlorophenyl)methyl]amino}carbonyl)phenyl]-N-[(3S)-pyrrolidin-3-yl]pyrazine-2-carboxamide
3-(5-amino-6-{3-[(3S)-piperidin-3-yl]-1H-1,2,4-triazol-5-yl}pyrazin-2-yl)-N-[(2,6-difluorophenyl)methyl]benzamide
3-(5-amino-6-{3-[(3S)-piperidin-3-yl]-1H-1,2,4-triazol-5-yl}pyrazin-2-yl)-N-[(2-chloro-6-fluorophenyl)methyl]benzamide
3-(5-amino-6-{3-[(3S)-piperidin-3-yl]-1H-1,2,4-triazol-5-yl}pyrazin-2-yl)-N-[(2,5-dichlorophenyl)methyl]benzamide
3-(5-amino-6-{3-[(3S)-piperidin-3-yl]-1H-1,2,4-triazol-5-yl}pyrazin-2-yl)-N-[(3,4-dichlorophenyl)methyl]benzamide
3-amino-6-{3-[({[4-(methyloxy)phenyl]methyl}amino)carbonyl]phenyl}-N-[(3S)-piperidin-3-yl]pyrazine-2-carboxamide
3-amino-6-[3-({[(2,4-dichlorophenyl)methyl]amino}carbonyl)phenyl]-N-[(3S)-piperidin-3-yl]pyrazine-2-carboxamide
1,1-dimethylethyl (3S)-3-{[(3-amino-6-{3-[({[(1,1-dimethylethyl)oxy]carbonyl}amino)methyl]phenyl}pyrazin-2-yl)carbonyl]amino}piperidine-1-carboxylate
3-(5-amino-6-{5-[(3S)-piperidin-3-yl]-4H-1,2,4-triazol-3-yl}pyrazin-2-yl)-N-[(2-fluorophenyl)methyl]benzamide
3-(5-amino-6-{5-[(3S)-piperidin-3-yl]-4H-1,2,4-triazol-3-yl}pyrazin-2-yl)-N-[(3-fluorophenyl)methyl]benzamide
3-(5-amino-6-{5-[(3S)-piperidin-3-yl]-4H-1,2,4-triazol-3-yl}pyrazin-2-yl)-N-[(4-fluorophenyl)methyl]benzamide
3-(5-amino-6-{5-[(3S)-piperidin-3-yl]-4H-1,2,4-triazol-3-yl}pyrazin-2-yl)-N-[(3-chlorophenyl)methyl]benzamide
3-(5-amino-6-{5-[(3S)-piperidin-3-yl]-4H-1,2,4-triazol-3-yl}pyrazin-2-yl)-N-[(4-chlorophenyl)methyl]benzamide
3-amino-6-[3-(aminomethyl)phenyl]-N-[(3S)-piperidin-3-yl]pyrazine-2-carboxamide
3-amino-6-(3-hydroxyphenyl)-N-[(3S)-piperidin-3-yl]pyrazine-2-carboxamide
1,1-dimethylethyl (3S)-3-[({3-amino-6-[3-(aminomethyl)phenyl]pyrazin-2-yl}carbonyl)amino]piperidine-1-carboxylate
3-amino-6-[3-({[(4-fluorophenyl)methyl]amino}carbonyl)phenyl]-N-[(3S)-piperidin-3-yl]pyrazine-2-carboxamide
3-amino-N-[(3S)-piperidin-3-yl]-6-(3-{[({4-[(trifluoromethyl)oxy]phenyl}methyl)amino]carbonyl}phenyl)pyrazine-2-carboxamide
3-amino-6-(3-{[(biphenyl-4-ylmethyl)amino]carbonyl}phenyl)-N-[(3S)-piperidin-3-yl]pyrazine-2-carboxamide
3-amino-N-[(3S)-piperidin-3-yl]-6-{3-[({[4-(1,2,3-thiadiazol-5-yl)phenyl]methyl}amino)carbonyl]phenyl}pyrazine-2-carboxamide
3-amino-N-[(3S)-piperidin-3-yl]-6-(3-{[({2-[(trifluoromethyl)oxy]phenyl}methyl)amino]carbonyl}phenyl)pyrazine-2-carboxamide
3-amino-6-(3-{[(biphenyl-2-ylmethyl)amino]carbonyl}phenyl)-N-[(3S)-piperidin-3-yl]pyrazine-2-carboxamide
3-amino-6-[3-({[(2,4-difluorophenyl)methyl]amino}carbonyl)phenyl]-N-[(3S)-piperidin-3-yl]pyrazine-2-carboxamide
3-amino-6-[3-({[(4-chloro-2-fluorophenyl)methyl]amino}carbonyl)phenyl]-N-[(3S)-piperidin-3-yl]pyrazine-2-carboxamide
3-amino-6-{3-[({[4-fluoro-3-(trifluoromethyl)phenyl]methyl}amino)carbonyl]phenyl}-N-[(3S)-piperidin-3-yl]pyrazine-2-carboxamide
3-amino-6-(3-{[(naphthalen-2-ylmethyl)amino]carbonyl}phenyl)-N-[(3S)-piperidin-3-yl]pyrazine-2-carboxamide
3-amino-6-{3-[({[4-(dimethylamino)phenyl]methyl}amino)carbonyl]phenyl}-N-[(3S)-piperidin-3-yl]pyrazine-2-carboxamide
3-amino-6-(3-{[(1,3-benzodioxol-5-ylmethyl)amino]carbonyl}phenyl)-N-[(3S)-piperidin-3-yl]pyrazine-2-carboxamide
3-amino-N-[(3S)-piperidin-3-yl]-6-{3-[({[4-(2-thienyl)phenyl]methyl}amino)carbonyl]phenyl}pyrazine-2-carboxamide
3-amino-6-{3-[({[2-(methyloxy)phenyl]methyl}amino)carbonyl]phenyl}-N-[(3S)-piperidin-3-yl]pyrazine-2-carboxamide
3-amino-6-{3-[({[2,4-bis(methyloxy)phenyl]methyl}amino)carbonyl]phenyl}-N-[(3S)-piperidin-3-yl]pyrazine-2-carboxamide
3-amino-6-[3-({[(4-chloro-2-methylphenyl)methyl]amino}carbonyl)phenyl]-N-[(3S)-piperidin-3-yl]pyrazine-2-carboxamide
3-amino-6-[3-({[(2,3-difluoro-4-methylphenyl)methyl]amino}carbonyl)phenyl]-N-[(3S)-piperidin-3-yl]pyrazine-2-carboxamide
3-amino-6-{3-[({[4-(methylsulfonyl)phenyl]methyl}amino)carbonyl]phenyl}-N-[(3S)-piperidin-3-yl]pyrazine-2-carboxamide
3-amino-6-(3-{[(2,3-dihydro-1,4-benzodioxin-6-ylmethyl)amino]carbonyl}phenyl)-N-[(3S)-piperidin-3-yl]pyrazine-2-carboxamide
3-amino-6-[3-({[(4-chlorophenyl)methyl]amino}carbonyl)phenyl]-N-[(3S)-piperidin-3-yl]pyrazine-2-carboxamide TABLE 10-continued

| Name |
| --- |
| 3-amino-6-[3-({[(5-chloro-2-fluorophenyl)methyl]amino}carbonyl)phenyl]-N-[(3S)-piperidin-3-yl]pyrazine-2-carboxamide |
| 3-amino-N-[(3R)-1-azabicyclo[2.2.2]oct-3-yl]-6-(3-{[(1S)-2,3-dihydro-1H-inden-1-ylamino]methyl}phenyl)pyrazine-2-carboxamide |
| 3-amino-6-{3-[({[4-(methylthio)phenyl]methyl}amino)carbonyl]phenyl}-N-[(3S)-piperidin-3-yl]pyrazine-2-carboxamide |
| 3-(5-amino-6-{3-[(3S)-piperidin-3-yl]-1H-1,2,4-triazol-5-yl}pyrazin-2-yl)-N-[(2,4-difluorophenyl)methyl]benzamide |
| 3-amino-6-(3-{[(1,2-diphenylethyl)amino]carbonyl}phenyl)-N-[(3S)-piperidin-3-yl]pyrazine-2-carboxamide |
| 3-(5-amino-6-{3-[(3S)-piperidin-3-yl]-1H-1,2,4-triazol-5-yl}pyrazin-2-yl)-N-[(3,4-difluorophenyl)methyl]benzamide |
| 3-amino-6-[3-({[(3,5-difluorophenyl)methyl]amino}carbonyl)phenyl]-N-[(3S)-piperidin-3-yl]pyrazine-2-carboxamide |
| methyl 4-[({[3-(5-amino-6-{[(3S)-piperidin-3-ylamino]carbonyl}pyrazin-2-yl)phenyl]carbonyl}amino)methyl]benzoate |
| 3-amino-6-[3-({[(4-bromophenyl)methyl]amino}carbonyl)phenyl]-N-[(3S)-piperidin-3-yl]pyrazine-2-carboxamide |
| 3-amino-6-[3-({[(4-bromo-2-fluorophenyl)methyl]amino}carbonyl)phenyl]-N-[(3S)-piperidin-3-yl]pyrazine-2-carboxamide |
| 3-amino-6-[3-({[(2-bromophenyl)methyl]amino}carbonyl)phenyl]-N-[(3S)-piperidin-3-yl]pyrazine-2-carboxamide |
| 3-amino-6-{3-[({[4-fluoro-2-(trifluoromethyl)phenyl]methyl}amino)carbonyl]phenyl}-N-[(3S)-piperidin-3-yl]pyrazine-2-carboxamide |
| 3-amino-6-{3-[({[2-fluoro-3-(trifluoromethyl)phenyl]methyl}amino)carbonyl]phenyl}-N-[(3S)-piperidin-3-yl]pyrazine-2-carboxamide |
| 3-amino-N-[(3S)-piperidin-3-yl]-6-[3-({[(3R)-pyrrolidin-3-ylmethyl]amino}carbonyl)phenyl]pyrazine-2-carboxamide |
| 3-amino-N-[(3S)-piperidin-3-yl]-6-(3-{[(3R)-pyrrolidin-3-ylamino]carbonyl}phenyl)pyrazine-2-carboxamide |
| 3-amino-N-[(3S)-piperidin-3-yl]-6-(3-{[(2-piperidin-1-ylethyl)amino]carbonyl}phenyl)pyrazine-2-carboxamide |
| 3-amino-6-(3-{[(2-phenylethyl)amino]carbonyl}phenyl)-N-[(3S)-piperidin-3-yl]pyrazine-2-carboxamide |
| 3-amino-6-[3-({[(2-methyloxy)ethyl]amino}carbonyl)phenyl]-N-[(3S)-piperidin-3-yl]pyrazine-2-carboxamide |
| 3-amino-6-[3-({[(4-iodophenyl)methyl]amino}carbonyl)phenyl]-N-[(3S)-piperidin-3-yl]pyrazine-2-carboxamide |
| 3-amino-6-[3-({[(2-chlorophenyl)methyl]amino}carbonyl)phenyl]-N-[(3S)-piperidin-3-yl]pyrazine-2-carboxamide |
| 3-amino-6-[3-({[(4-fluorophenyl)carbonyl]amino}methyl)phenyl]-N-[(3S)-piperidin-3-yl]pyrazine-2-carboxamide |
| 3-amino-N-[(3S)-piperidin-3-yl]-6-(3-{[({4-[(trifluoromethyl)oxy]phenyl}carbonyl)amino]methyl}phenyl)pyrazine-2-carboxamide |
| 3-amino-6-[3-({[(4-chlorophenyl)carbonyl]amino}methyl)phenyl]-N-[(3S)-piperidin-3-yl]pyrazine-2-carboxamide |
| 3-amino-6-(3-{[(4-chlorophenyl)acetyl]amino}phenyl)-N-[(3S)-piperidin-3-yl]pyrazine-2-carboxamide |
| 3-amino-6-(3-{[(2,6-dichlorophenyl)acetyl]amino}phenyl)-N-[(3S)-piperidin-3-yl]pyrazine-2-carboxamide |
| 3-amino-6-(3-{[(pentafluorophenyl)acetyl]amino}phenyl)-N-[(3S)-piperidin-3-yl]pyrazine-2-carboxamide |
| 3-amino-6-(3-{[(2-chloro-4-fluorophenyl)acetyl]amino}phenyl)-N-[(3S)-piperidin-3-yl]pyrazine-2-carboxamide |
| 3-amino-6-[3-({[4-(methylthio)phenyl]acetyl}amino)phenyl]-N-[(3S)-piperidin-3-yl]pyrazine-2-carboxamide |
| 3-amino-6-(3-{[(2,4-dichlorophenyl)acetyl]amino}phenyl)-N-[(3S)-piperidin-3-yl]pyrazine-2-carboxamide |
| 3-amino-6-[3-({[4-(4-chlorophenyl)-2-thienyl]carbonyl}amino)phenyl]-N-[(3S)-piperidin-3-yl]pyrazine-2-carboxamide |
| 3-amino-6-[3-({[(4-bromophenyl)carbonyl]amino}methyl)phenyl]-N-[(3S)-piperidin-3-yl]pyrazine-2-carboxamide |
| 3-amino-6-(3-{[(naphthalen-2-ylcarbonyl)amino]methyl}phenyl)-N-[(3S)-piperidin-3-yl]pyrazine-2-carboxamide |
| 3-amino-6-(3-{[2-(4-phenylpiperazin-1-yl)ethyl]oxy}phenyl)-N-[(3S)-piperidin-3-yl]pyrazine-2-carboxamide |
| N-[(3-{5-amino-6-[(3R)-piperidin-3-ylacetyl]pyrazin-2-yl}phenyl)methyl]-N'-(4-bromophenyl)urea |
| N-[(3-{5-amino-6-[(3R)-piperidin-3-ylacetyl]pyrazin-2-yl}phenyl)methyl]-N'-naphthalen-2-ylurea |
| 3-amino-6-(3-{[(2,4-difluorophenyl)acetyl]amino}phenyl)-N-[(3S)-piperidin-3-yl]pyrazine-2-carboxamide |
| 3-amino-6-(3-{[(2-fluorophenyl)acetyl]amino}phenyl)-N-[(3S)-piperidin-3-yl]pyrazine-2-carboxamide |

TABLE 10-continued

Name 3-amino-6-{3-[({5-[2-chloro-5-(trifluoromethyl)phenyl]furan-2-yl}carbonyl)amino]phenyl}-N-[(3S)-piperidin-3-yl]pyrazine-2-carboxamide
3-amino-6-[3-({[4-(dimethylamino)naphthalen-1-yl]carbonyl}amino)phenyl]-N-[(3S)-piperidin-3-yl]pyrazine-2-carboxamide
3-amino-N-[(3S)-piperidin-3-yl]-6-[3-({[4-(1,2,3-thiadiazol-5-yl)phenyl]carbonyl}amino)phenyl]pyrazine-2-carboxamide
3-amino-6-(3-{[(1,3-dimethyl-1H-pyrazol-5-yl)carbonyl]amino}phenyl)-N-[(3S)-piperidin-3-yl]pyrazine-2-carboxamide
3-amino-6-{3-[({[4-(dimethylamino)phenyl]carbonyl}amino)methyl]phenyl}-N-[(3S)-piperidin-3-yl]pyrazine-2-carboxamide
3-amino-6-{3-[(2-hydroxyethyl)oxy]phenyl}-N-[(3S)-piperidin-3-yl]pyrazine-2-carboxamide
3-amino-6-(3-{[(2,3-dihydro-1-benzofuran-5-ylsulfonyl)amino]methyl}phenyl)-N-[(3S)-piperidin-3-yl]pyrazine-2-carboxamide
3-amino-6-(3-{[(3,4-dihydro-2H-1,5-benzodioxepin-7-ylsulfonyl)amino]methyl}phenyl)-N-[(3S)-piperidin-3-yl]pyrazine-2-carboxamide
3-amino-N-[(3S)-piperidin-3-yl]-6-(3-{[(quinolin-7-ylsulfonyl)amino]methyl}phenyl)pyrazine-2-carboxamide
3-amino-6-[3-({[(biphenyl-4-ylamino)carbonyl]amino}methyl)phenyl]-N-[(3S)-piperidin-3-yl]pyrazine-2-carboxamide
3-amino-6-(3-{[(4-bromo-2-fluorophenyl)carbonyl]amino}phenyl)-N-[(3S)-piperidin-3-yl]pyrazine-2-carboxamide
N-[3-(5-amino-6-{[(3S)-piperidin-3-ylamino]carbonyl}pyrazin-2-yl)phenyl]quinoline-3-carboxamide
3-amino-6-[3-({[6-(methyloxy)-1-benzofuran-3-yl]acetyl}amino)phenyl]-N-[(3S)-piperidin-3-yl]pyrazine-2-carboxamide
3-amino-N-[(3S)-piperidin-3-yl]-6-[3-({[4'-(trifluoromethyl)biphenyl-2-yl]carbonyl}amino)phenyl]pyrazine-2-carboxamide
3-amino-6-[3-({[3,5-bis(trifluoromethyl)phenyl]acetyl}amino)phenyl]-N-[(3S)-piperidin-3-yl]pyrazine-2-carboxamide
3-amino-6-{3-[({[(2,4-difluorophenyl)amino]carbonyl}amino)methyl]phenyl}-N-[(3S)-piperidin-3-yl]pyrazine-2-carboxamide
3-amino-N-[(3S)-piperidin-3-yl]-6-{3-[({[2-(trifluoromethyl)phenyl]sulfonyl}amino)methyl]phenyl}pyrazine-2-carboxamide
3-amino-N-[(3S)-piperidin-3-yl]-6-(3-{[({4-[(trifluoromethyl)oxy]phenyl}sulfonyl)amino]methyl}phenyl)pyrazine-2-carboxamide
3-amino-N-[(3S)-piperidin-3-yl]-6-(3-{[({2-[(trifluoromethyl)oxy]phenyl}sulfonyl)amino]methyl}phenyl)pyrazine-2-carboxamide
3-amino-N-[(3S)-piperidin-3-yl]-6-{3-[({[4-(trifluoromethyl)phenyl]sulfonyl}amino)methyl]phenyl}pyrazine-2-carboxamide
3-amino-N-[(3S)-piperidin-3-yl]-6-[3-({[({2-[(trifluoromethyl)oxy]phenyl}amino)carbonyl]amino}methyl)phenyl]pyrazine-2-carboxamide
3-amino-6-(3-{[({[2-(methylthio)phenyl]amino}carbonyl)amino]methyl}phenyl)-N-[(3S)-piperidin-3-yl]pyrazine-2-carboxamide
3-amino-6-{3-[({[(3-bromo-5-methylphenyl)amino]carbonyl}amino)methyl]phenyl}-N-[(3S)-piperidin-3-yl]pyrazine-2-carboxamide
3-amino-6-{3-[({[(2-bromophenyl)amino]carbonyl}amino)methyl]phenyl}-N-[(3S)-piperidin-3-yl]pyrazine-2-carboxamide
5-[3-(aminomethyl)phenyl]-3-{3-[(3S)-piperidin-3-yl]-1H-1,2,4-triazol-5-yl}pyrazin-2-amine
3-amino-6-{3-[({[4-(4-methylpiperazin-1-yl)phenyl]methyl}amino)carbonyl]phenyl}-N-[(3S)-piperidin-3-yl]pyrazine-2-carboxamide
3-amino-6-[3-({[2-(4-fluorophenyl)ethyl]amino}carbonyl)phenyl]-N-[(3S)-piperidin-3-yl]pyrazine-2-carboxamide
3-amino-6-(3-{[(2-morpholin-4-ylethyl)amino]carbonyl}phenyl)-N-[(3S)-piperidin-3-yl]pyrazine-2-carboxamide
3-amino-N-[(3S)-piperidin-3-yl]-6-[3-({[(2R)-pyrrolidin-2-ylmethyl]amino}carbonyl)phenyl]pyrazine-2-carboxamide
3-amino-N-[(3S)-piperidin-3-yl]-6-(3-{[(2S)-pyrrolidin-2-ylamino]carbonyl}phenyl)pyrazine-2-carboxamide
3-amino-6-{3-[(cyclopentylamino)carbonyl]phenyl}-N-[(3S)-piperidin-3-yl]pyrazine-2-carboxamide
3-amino-N-[(3S)-piperidin-3-yl]-6-[3-({[({4-[(trifluoromethyl)oxy]phenyl}amino)carbonyl]amino}methyl)phenyl]pyrazine-2-carboxamide
3-amino-N-[(3S)-piperidin-3-yl]-6-(3-{[({[4-(trifluoromethyl)phenyl]amino}carbonyl)amino]methyl}phenyl)pyrazine-2-carboxamide
3-amino-6-{3-[({[4-(methyloxy)phenyl]carbonyl}amino)methyl]phenyl}-N-[(3S)-piperidin-3-yl]pyrazine-2-carboxamide
3-amino-6-(3-{[(biphenyl-4-ylcarbonyl)amino]methyl}phenyl)-N-[(3S)-piperidin-3-yl]pyrazine-2-carboxamide TABLE 10-continued

| Name |
| --- |
| 3-amino-6-(3-{[(furan-2-ylcarbonyl)amino]methyl}phenyl)-N-[(3S)-piperidin-3-yl]pyrazine-2-carboxamide |
| 3-amino-6-[3-({[(2,3-dihydro-1,4-benzodioxin-6-ylamino)carbonyl]amino}methyl)phenyl]-N-[(3S)-piperidin-3-yl]pyrazine-2-carboxamide |
| 3-amino-6-(3-{[(2,3-dihydro-1-benzofuran-5-ylcarbonyl)amino]methyl}phenyl)-N-[(3S)-piperidin-3-yl]pyrazine-2-carboxamide |
| 3-amino-6-(3-{[(2,3-dihydro-1,4-benzodioxin-6-ylsulfonyl)amino]methyl}phenyl)-N-[(3S)-piperidin-3-yl]pyrazine-2-carboxamide |
| 3-amino-N-[(3S)-piperidin-3-yl]-6-(3-{[(2-thienylcarbonyl)amino]methyl}phenyl)pyrazine-2-carboxamide |
| 3-amino-6-(3-{[(2,3-dihydro-1,4-benzodioxin-2-ylcarbonyl)amino]methyl}phenyl)-N-[(3S)-piperidin-3-yl]pyrazine-2-carboxamide |
| N-{[3-(5-amino-6-{3-[(3S)-piperidin-3-yl]-1H-1,2,4-triazol-5-yl}pyrazin-2-yl)phenyl]methyl}-2-chlorobenzamide |
| N-{[3-(5-amino-6-{3-[(3S)-piperidin-3-yl]-1H-1,2,4-triazol-5-yl}pyrazin-2-yl)phenyl]methyl}-4-chlorobenzamide |
| N-{[3-(5-amino-6-{3-[(3S)-piperidin-3-yl]-1H-1,2,4-triazol-5-yl}pyrazin-2-yl)phenyl]methyl}-4-iodobenzamide |
| N-{[3-(5-amino-6-{3-[(3S)-piperidin-3-yl]-1H-1,2,4-triazol-5-yl}pyrazin-2-yl)phenyl]methyl}-3,5-difluorobenzamide |
| N-{[3-(5-amino-6-{3-[(3S)-piperidin-3-yl]-1H-1,2,4-triazol-5-yl}pyrazin-2-yl)phenyl]methyl}-4-bromo-2-fluorobenzamide |
| N-{[3-(5-amino-6-{3-[(3S)-piperidin-3-yl]-1H-1,2,4-triazol-5-yl}pyrazin-2-yl)phenyl]methyl}-4-bromo-2-chlorobenzamide |
| 3-[3-(2-aminopyridin-4-yl)-1H-1,2,4-triazol-5-yl]-5-(3-{[(1S)-2,3-dihydro-1H-inden-1-ylamino]methyl}phenyl)pyrazin-2-amine |
| 3-amino-N-azepan-3-yl-6-(3-{[(1S)-2,3-dihydro-1H-inden-1-ylamino]methyl}phenyl)pyrazine-2-carboxamide |
| 3-amino-N-[(3S)-piperidin-3-yl]-6-{3-[({[2-(2-thienyl)-1,3-thiazol-4-yl]carbonyl}amino)methyl]phenyl}pyrazine-2-carboxamide |
| 3-amino-N-[(3S)-piperidin-3-yl]-6-{3-[({[5-(2-thienyl)pyridin-3-yl]carbonyl}amino)methyl]phenyl}pyrazine-2-carboxamide |
| 3-amino-6-{3-[({[4-(1,1-dimethylethyl)phenyl]methyl}amino)carbonyl]phenyl}-N-[(3S)-piperidin-3-yl]pyrazine-2-carboxamide |
| 3-amino-6-[3-({[(2,4-dichloro-6-methylphenyl)methyl]amino}carbonyl)phenyl]-N-[(3S)-piperidin-3-yl]pyrazine-2-carboxamide |
| 3-amino-6-[3-({[(3,5-dichlorophenyl)methyl]amino}carbonyl)phenyl]-N-[(3S)-piperidin-3-yl]pyrazine-2-carboxamide |
| 3-amino-N-[(3S)-piperidin-3-yl]-6-(3-{[(2-thienylsulfonyl)amino]methyl}phenyl)pyrazine-2-carboxamide |
| 3-amino-N-[(3S)-piperidin-3-yl]-6-(3-{[(3-thienylsulfonyl)amino]methyl}phenyl)pyrazine-2-carboxamide |
| 3-amino-6-[3-({[(4-chlorophenyl)sulfonyl]amino}methyl)phenyl]-N-[(3S)-piperidin-3-yl]pyrazine-2-carboxamide |
| 3-amino-6-[3-({[(1,3-benzodioxol-5-ylamino)carbonyl]amino}methyl)phenyl]-N-[(3S)-piperidin-3-yl]pyrazine-2-carboxamide |
| 3-amino-6-(3-{[({[4-(methyloxy)phenyl]amino}carbonyl)amino]methyl}phenyl)-N-[(3S)-piperidin-3-yl]pyrazine-2-carboxamide |
| 3-amino-6-{3-[({[(4-fluorophenyl)amino]carbonyl}amino)methyl]phenyl}-N-[(3S)-piperidin-3-yl]pyrazine-2-carboxamide |
| 3-amino-6-(3-{[2-(diethylamino)ethyl]oxy}phenyl)-N-[(3S)-piperidin-3-yl]pyrazine-2-carboxamide |
| 3-amino-6-{3-[(2-morpholin-4-ylethyl)oxy]phenyl}-N-[(3S)-piperidin-3-yl]pyrazine-2-carboxamide |
| 3-amino-6-[3-(methyloxy)phenyl]-N-[(3S)-piperidin-3-yl]pyrazine-2-carboxamide |
| 3-amino-6-[3-(ethyloxy)phenyl]-N-[(3S)-piperidin-3-yl]pyrazine-2-carboxamide |
| 3-amino-N-[(3S)-piperidin-3-yl]-6-{3-[({[4-(1,2,3-thiadiazol-4-yl)phenyl]methyl}amino)carbonyl]phenyl}pyrazine-2-carboxamide |
| 3-amino-6-(3-{[2-(ethylamino)ethyl]oxy}phenyl)-N-[(3S)-piperidin-3-yl]pyrazine-2-carboxamide |
| phenylmethyl 4-(2-{[3-(5-amino-6-{[(3S)-piperidin-3-ylamino]carbonyl}pyrazin-2-yl)phenyl]oxy}ethyl)piperazine-1-carboxylate |
| 3-amino-6-(3-{[({[4-(dimethylamino)phenyl]amino}carbonyl)amino]methyl}phenyl)-N-[(3S)-piperidin-3-yl]pyrazine-2-carboxamide |
| 3-amino-N-azepan-3-yl-6-(3-{[(1S)-2,3-dihydro-1H-inden-1-ylamino]carbonyl}phenyl)pyrazine-2-carboxamide |
| 3-amino-6-[3-({[(1R,2S)-2-hydroxy-2,3-dihydro-1H-inden-1-yl]amino}methyl)phenyl]-N-[(3S)-piperidin-3-yl]pyrazine-2-carboxamide |
| 3-amino-6-[3-({[(1S,2S)-2-hydroxy-2,3-dihydro-1H-inden-1-yl]amino}carbonyl)phenyl]-N-[(3S)-1-(phenylmethyl)azepan-3-yl]pyrazine-2-carboxamide |
| 3-amino-N-[(3S)-azepan-3-yl]-6-[3-({[(1S,2S)-2-hydroxy-2,3-dihydro-1H-inden-1-yl]amino}carbonyl)phenyl]pyrazine-2-carboxamide |
| 3-amino-6-{3-[({[(4-chlorophenyl)amino]carbonyl}amino)methyl]phenyl}-N-[(3S)-piperidin-3-yl]pyrazine-2-carboxamide |

TABLE 10-continued

Name 3-amino-6-(3-{[(1S)-2,3-dihydro-1H-inden-1-ylamino]carbonyl}phenyl)-N-[(3S)-1-(phenylmethyl)azepan-3-yl]pyrazine-2-carboxamide
3-amino-N-[(3S)-azepan-3-yl]-6-(3-{[(1S)-2,3-dihydro-1H-inden-1-ylamino]carbonyl}phenyl)pyrazine-2-carboxamide
3-amino-N-[(3S)-azepan-3-yl]-6-(3-methylphenyl)pyrazine-2-carboxamide
3-amino-6-(3-{[(2-methylphenyl)acetyl]amino}phenyl)-N-[(3S)-piperidin-3-yl]pyrazine-2-carboxamide
3-amino-N-[(3S)-piperidin-3-yl]-6-[3-({[3-(trifluoromethyl)phenyl]acetyl}amino)phenyl]pyrazine-2-carboxamide
3-amino-6-[3-({[4-(methyloxy)phenyl]acetyl}amino)phenyl]-N-[(3S)-piperidin-3-yl]pyrazine-2-carboxamide
3-amino-6-(3-{[(6-methylpyridin-3-yl)carbonyl]amino}phenyl)-N-[(3S)-piperidin-3-yl]pyrazine-2-carboxamide
3-amino-6-(3-{[(3-fluorophenyl)acetyl]amino}phenyl)-N-[(3S)-piperidin-3-yl]pyrazine-2-carboxamide
3-amino-N-[(3S)-piperidin-3-yl]-6-{3-[(pyridin-3-ylacetyl)amino]phenyl}pyrazine-2-carboxamide
3-amino-N-[(3S)-piperidin-3-yl]-6-{3-[(pyridin-3-ylcarbonyl)amino]phenyl}pyrazine-2-carboxamide
3-amino-6-(3-{[(2,5-difluorophenyl)acetyl]amino}phenyl)-N-[(3S)-piperidin-3-yl]pyrazine-2-carboxamide
3-amino-6-(3-{[(4-fluorophenyl)acetyl]amino}phenyl)-N-[(3S)-piperidin-3-yl]pyrazine-2-carboxamide
3-amino-6-{3-[({[3-fluoro-5-(trifluoromethyl)phenyl]methyl}amino)carbonyl]phenyl}-N-[(3S)-piperidin-3-yl]pyrazine-2-carboxamide
3-amino-6-[3-({[(3,4-dichlorophenyl)methyl]amino}carbonyl)phenyl]-N-[(3S)-piperidin-3-yl]pyrazine-2-carboxamide
3-Amino-6-[3-({[5-(4-nitro-phenyl)-furan-2-carbonyl]-amino}-methyl)-phenyl]-pyrazine-2-carboxylic acid (3S)-piperidin-3-ylamide
3-amino-6-[3-({[(3-hydroxypyridin-2-yl)carbonyl]amino}methyl)phenyl]-N-[(3S)-piperidin-3-yl]pyrazine-2-carboxamide
3-amino-N-[(3S)-piperidin-3-yl]-6-[3-({[({4-[(trifluoromethyl)oxy]phenyl}oxy)acetyl]amino}methyl)phenyl]pyrazine-2-carboxamide
3-amino-6-[3-({[(5-methylisoxazol-3-yl)carbonyl]amino}methyl)phenyl]-N-[(3S)-piperidin-3-yl]pyrazine-2-carboxamide
3-amino-6-(3-{[(isoxazol-5-ylcarbonyl)amino]methyl}phenyl)-N-[(3S)-piperidin-3-yl]pyrazine-2-carboxamide
3-amino-6-[3-({[(4-methyl-1,2,3-thiadiazol-5-yl)carbonyl]amino}methyl)phenyl]-N-[(3S)-piperidin-3-yl]pyrazine-2-carboxamide
3-amino-6-[3-({[(2,5-dichloro-3-thienyl)carbonyl]amino}methyl)phenyl]-N-[(3S)-piperidin-3-yl]pyrazine-2-carboxamide
3-amino-6-[3-({[(5-chloro-2-methylphenyl)methyl]amino}carbonyl)phenyl]-N-[(3S)-piperidin-3-yl]pyrazine-2-carboxamide
3-amino-6-{3-[({[2-chloro-5-(trifluoromethyl)phenyl]methyl}amino)carbonyl]phenyl}-N-[(3S)-piperidin-3-yl]pyrazine-2-carboxamide
3-amino-6-[3-({[(2-chloro-6-fluorophenyl)methyl]amino}carbonyl)phenyl]-N-[(3S)-piperidin-3-yl]pyrazine-2-carboxamide
3-amino-N-[(3S)-azepan-3-yl]-6-[3-({[(4-chloro-2-fluorophenyl)methyl]amino}carbonyl)phenyl]pyrazine-2-carboxamide
3-amino-6-[3-({[(3-chloro-2-fluorophenyl)methyl]amino}carbonyl)phenyl]-N-[(3S)-piperidin-3-yl]pyrazine-2-carboxamide
3-amino-6-{3-[({[2-fluoro-5-(trifluoromethyl)phenyl]methyl}amino)carbonyl]phenyl}-N-[(3S)-piperidin-3-yl]pyrazine-2-carboxamide
3-amino-6-[3-({[(2,4-difluorophenyl)methyl]amino}methyl)phenyl]-N-[(3S)-piperidin-3-yl]pyrazine-2-carboxamide
3-amino-6-[3-({[(3-chloro-2,6-difluorophenyl)methyl]amino}carbonyl)phenyl]-N-[(3S)-piperidin-3-yl]pyrazine-2-carboxamide
3-amino-6-{3-[({[2-fluoro-4-(trifluoromethyl)phenyl]methyl}amino)carbonyl]phenyl}-N-[(3S)-piperidin-3-yl]pyrazine-2-carboxamide
3-amino-6-[3-({[(2-chloro-4-fluorophenyl)methyl]amino}carbonyl)phenyl]-N-[(3S)-piperidin-3-yl]pyrazine-2-carboxamide
3-amino-6-[3-({[(2,3-dichlorophenyl)methyl]amino}carbonyl)phenyl]-N-[(3S)-piperidin-3-yl]pyrazine-2-carboxamide
3-amino-N-[(3S)-piperidin-3-yl]-6-[3-({[(2,3,6-trifluorophenyl)methyl]amino}carbonyl)phenyl]pyrazine-2-carboxamide
3-amino-6-{3-[({[4-chloro-3-(trifluoromethyl)phenyl]methyl}amino)carbonyl]phenyl}-N-[(3S)-piperidin-3-yl]pyrazine-2-carboxamide
3-amino-6-[3-({[(3-chloro-4-fluorophenyl)methyl]amino}carbonyl)phenyl]-N-[(3S)-piperidin-3-yl]pyrazine-2-carboxamide
3-amino-N-[(3S)-azepan-3-yl]-6-[3-({[(2,3-difluorophenyl)methyl]amino}carbonyl)phenyl]pyrazine-2-carboxamide TABLE 10-continued

| Name |
| --- |
| 3-amino-N-[(3S)-azepan-3-yl]-6-[3-({[(3,4-difluorophenyl)methyl]amino}carbonyl)phenyl]pyrazine-2-carboxamide |
| 3-amino-N-[(3S)-azepan-3-yl]-6-[3-({[(3,5-difluorophenyl)methyl]amino}carbonyl)phenyl]pyrazine-2-carboxamide |
| 3-amino-6-[3-({[(2,6-difluorophenyl)methyl]amino}carbonyl)phenyl]-N-[(3S)-piperidin-3-yl]pyrazine-2-carboxamide |
| 3-amino-6-[3-({[(3,4-difluorophenyl)methyl]amino}carbonyl)phenyl]-N-[(3S)-piperidin-3-yl]pyrazine-2-carboxamide |
| 3-amino-6-[3-({[(6-chloro-2-fluoro-3-methylphenyl)methyl]amino}carbonyl)phenyl]-N-[(3S)-piperidin-3-yl]pyrazine-2-carboxamide |
| 3-amino-6-[3-({[(2-chloro-6-fluoro-3-methylphenyl)methyl]amino}carbonyl)phenyl]-N-[(3S)-piperidin-3-yl]pyrazine-2-carboxamide |
| 3-amino-6-[3-({[(2-chloro-3,6-difluorophenyl)methyl]amino}carbonyl)phenyl]-N-[(3S)-piperidin-3-yl]pyrazine-2-carboxamide |
| 3-amino-6-[3-({[(2,5-dichlorophenyl)methyl]amino}carbonyl)phenyl]-N-[(3S)-piperidin-3-yl]pyrazine-2-carboxamide |
| 3-amino-N-[(3S)-piperidin-3-yl]-6-[3-({[(2,3,4-trifluorophenyl)methyl]amino}carbonyl)phenyl]pyrazine-2-carboxamide |
| 3-amino-6-[3-({[(2,3-difluorophenyl)methyl]amino}carbonyl)phenyl]-N-[(3S)-piperidin-3-yl]pyrazine-2-carboxamide |
| 3-amino-6-[3-({[(3-fluoro-4-methylphenyl)methyl]amino}carbonyl)phenyl]-N-[(3S)-piperidin-3-yl]pyrazine-2-carboxamide |
| 3-amino-N-[(3S)-azepan-3-yl]-6-[3-({[(3-chloro-2,6-difluorophenyl)methyl]amino}carbonyl)phenyl]pyrazine-2-carboxamide |
| 3-amino-N-[(3S)-azepan-3-yl]-6-(3-{[(2,3-dihydro-1,4-benzodioxin-6-ylmethyl)amino]carbonyl}phenyl)pyrazine-2-carboxamide |
| 3-amino-N-[(3S)-azepan-3-yl]-6-[3-({[(2-chloro-6-fluorophenyl)methyl]amino}carbonyl)phenyl]pyrazine-2-carboxamide |
| 3-amino-N-[(3S)-azepan-3-yl]-6-[3-({[(2,6-difluorophenyl)methyl]amino}carbonyl)phenyl]pyrazine-2-carboxamide |
| 3-amino-N-[(3S)-azepan-3-yl]-6-[3-({[(3-chloro-4-fluorophenyl)methyl]amino}carbonyl)phenyl]pyrazine-2-carboxamide |
| 3-amino-N-[(3S)-azepan-3-yl]-6-[3-({[(3-chloro-2-fluorophenyl)methyl]amino}carbonyl)phenyl]pyrazine-2-carboxamide |
| 3-amino-6-[3-({[(3-chloro-2-methylphenyl)methyl]amino}carbonyl)phenyl]-N-[(3S)-piperidin-3-yl]pyrazine-2-carboxamide |
| 3-amino-6-{3-[({[2,6-bis(methyloxy)phenyl]methyl}amino)carbonyl]phenyl}-N-[(3S)-piperidin-3-yl]pyrazine-2-carboxamide |
| 3-amino-6-[3-({[(3-bromo-4-fluorophenyl)methyl]amino}carbonyl)phenyl]-N-[(3S)-piperidin-3-yl]pyrazine-2-carboxamide |
| 3-amino-N-[(3S)-piperidin-3-yl]-6-[3-({[(3,4,5-trifluorophenyl)methyl]amino}carbonyl)phenyl]pyrazine-2-carboxamide |
| 3-amino-6-[3-({[(4-fluoro-3-methylphenyl)methyl]amino}carbonyl)phenyl]-N-[(3S)-piperidin-3-yl]pyrazine-2-carboxamide |
| 3-amino-N-[(3S)-piperidin-3-yl]-6-[3-({[(2,3,5-trifluorophenyl)methyl]amino}carbonyl)phenyl]pyrazine-2-carboxamide |
| 3-amino-6-[3-({[(5-fluoro-2-methylphenyl)methyl]amino}carbonyl)phenyl]-N-[(3S)-piperidin-3-yl]pyrazine-2-carboxamide |
| 3-amino-6-[3-({[(3-bromo-5-fluorophenyl)methyl]amino}carbonyl)phenyl]-N-[(3S)-piperidin-3-yl]pyrazine-2-carboxamide |
| 3-amino-N-[(3S)-piperidin-3-yl]-6-{3-[({[4-(1H-pyrazol-1-yl)phenyl]methyl}amino)carbonyl]phenyl}pyrazine-2-carboxamide |
| 3-amino-6-(3-{[(biphenyl-3-ylmethyl)amino]carbonyl}phenyl)-N-[(3S)-piperidin-3-yl]pyrazine-2-carboxamide |
| 3-amino-6-[3-({[(2-methylphenyl)methyl]amino}carbonyl)phenyl]-N-[(3S)-piperidin-3-yl]pyrazine-2-carboxamide |
| 3-amino-6-[3-({[(2,5-dimethylphenyl)methyl]amino}carbonyl)phenyl]-N-[(3S)-piperidin-3-yl]pyrazine-2-carboxamide |
| 3-amino-6-[3-({[(3,5-dimethylphenyl)methyl]amino}carbonyl)phenyl]-N-[(3S)-piperidin-3-yl]pyrazine-2-carboxamide |
| 3-amino-6-[3-({[(2,4-dimethylphenyl)methyl]amino}carbonyl)phenyl]-N-[(3S)-piperidin-3-yl]pyrazine-2-carboxamide |
| 3-amino-6-[3-({[(3-methoxyphenyl)methyl]amino}carbonyl)phenyl]-N-[(3S)-piperidin-3-yl]pyrazine-2-carboxamide |
| 3-amino-6-{3-[({[phenyl]methyl}amino)carbonyl]phenyl}-N-[(3S)-piperidin-3-yl]pyrazine-2-carboxamide |
| 3-amino-6-{3-[({[3,5-bis(methyloxy)phenyl]methyl}amino)carbonyl]phenyl}-N-[(3S)-piperidin-3-yl]pyrazine-2-carboxamide |
| 3-amino-6-{3-[({[3,4-bis(methyloxy)phenyl]methyl}amino)carbonyl]phenyl}-N-[(3S)-piperidin-3-yl]pyrazine-2-carboxamide |
| 3-amino-N-[(3S)-azepan-3-yl]-6-{3-[({[4-(1H-pyrazol-1-yl)phenyl]methyl}amino)carbonyl]phenyl}pyrazine-2-carboxamide. |

28. A pharmaceutical composition comprising a compound according to claim 1 and a pharmaceutically acceptable carrier.

29. A compound according to the following name:
3-amino-6-[3-({[(2,4-difluorophenyl)methyl]amino}methyl)phenyl]-N-[(3S)-piperidin-3-yl]pyrazine-2-carboxamide, or a pharmaceutically acceptable salt thereof.

30. A method of diminishing proliferation of a plurality of cancerous cells in a patient, the method comprising administering to the patient the compound as described in claim 1, and one or more cancer therapeutic agents.

31. The method of claim 30, wherein the compound is combined with a pharmaceutically acceptable carrier.

32. The method of claim 30, wherein the cancer therpeutic agent is selected from the group consisting of a Topoisomerase I inhibitor, a Topoisomerase II inhibitor, an alkylating agent, a nitrogen mustard, an aziridine, an epoxide, an alkyl sulfonate, a nitrosourea, an alkylating agent-steroid conjugate, a DNA damaging/binding agent, a Cisplatin, an antibiotic, an anthracycline, an anthracenedione, an antimetabolite, an antifolate, a nucleic acid analog, a ribonucleic acid analog, a ribozyme, a Vinca alkaloid, a Taxane, an enzyme, a natural product, a kinase inhibitor, a hormone a hormones antagonist, and a biological response modifier.

33. The method of claim 30, wherein where the cancer therapeutic agent comprises at least one of: Camptothecin, Topotecan, 9-Nitrocamptothecin, 9-Aminocamptothecin, Karenitecin, Irinotecan, Etoposide, Etoposide Phosphate, Teniposide, Amsacrine, Razoxane, Dexrazoxane, Mechlorethamine, Cyclophosphamide, Ifosfamide, Chiorambucil, Melphalan, Thiotepa, Trenimon, Triethylenemelamine, Dianhydrogalactitol, Dibromodulcitol, Busulfan, dimethylsulfate, Chloroethylnitrosourea, BCNU, CCNU, Methyl-CCNU, Streptozotocin, Chlorozotocin, Prednimustine, Estramustine, Procarbazine, Dacarbazine, Hexamethylmelamine, Pentamethylmelamine, Temozolomide, Cisplatin, Carboplatin, Oxaliplatin, Bleomycin, Dactinomycin, Mithramycin, Mitomycin2 C, Daunorubicin, Doxorubicin, Epirubicin, Idarubicin, Methotrexate, Edatrexate, Trimethoprim, Nolatrexed, Raltitrexed, Hydroxyurea, 5-fluorouracil, Ftorafur, Capecitabine, Furtulon, Eniluracil, ara-C, 5-azacytidine, Gemeitabine, Mercaptopurine, Thioguanine, Pentostatin, antisense DNA, antisense RNA, an antisense DNAlRNA hybrid, a ribozyme, Vincristine, Vinblastine, Paclitaxel, Docetaxel, L-Asparaginase, a kinase inhibitor, Imatinib, Mitotane, Aminoglutethimide, Diethyistilbestrol, Ethinyl estradiol, Tamoxifen, Anastrozole, Testosterone propionate, Fluoxymesterone, Flutamide, Leuprolide, Prednisone, Hydroxyprogesterone caproate, Medroxyprogesterone acetate, Megestrol acetate and Interferon alfa.

34. The method of claim 33, wherein where the cancer therapeutic agent is Gemcitabine.

35. The method of claim 34, wherein where the compound is 3-amino-6-[3-({[(2,4-difluorophenyl)methyl]amino}methyl)phenyl]-N- [(3S)-piperidin-3-yl]pyrazine-2-carboxamide, or a pharmaceutically acceptable salt thereof.

\* \* \* \* \*

UNITED STATES PATENT AND TRADEMARK OFFICE
CERTIFICATE OF CORRECTION

| | | |
|---|---|---|
| PATENT NO. | : 7,704,995 B2 | |
| APPLICATION NO. | : 10/513081 | |
| DATED | : April 27, 2010 | |
| INVENTOR(S) | : Buhr et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1094 days.

Signed and Sealed this
Thirty-first Day of May, 2011

David J. Kappos
*Director of the United States Patent and Trademark Office*

UNITED STATES PATENT AND TRADEMARK OFFICE
CERTIFICATE OF CORRECTION

PATENT NO. : 7,704,995 B2  
APPLICATION NO. : 10/513081  
DATED : April 27, 2010  
INVENTOR(S) : Buhr et al.

Page 1 of 1

It is certified that error appears in the above-identified patent and that said Letters Patent is hereby corrected as shown below:

At claim 8, column 347, line 55, delete "(13) -OCH$_2$C(=O)N(H)CH$_2$-;".

At claim 8, column 347, line 57, delete "-N(R$^4$)CH$_2$C(=O)N(H)CH$_2$-;".

At claim 20, column 349, line 6, delete "-OCH$_2$C(=O)N(H)CH$_2$-,".

At claim 20, column 349, lines 8-9, delete "-N(R$^4$)CH$_2$C(=O)N(H)CH$_2$-,".

Signed and Sealed this  
Second Day of October, 2012

David J. Kappos  
*Director of the United States Patent and Trademark Office*